United States Patent
D'Angelo et al.

(10) Patent No.: US 8,362,241 B2
(45) Date of Patent: Jan. 29, 2013

(54) INHIBITORS OF PI3 KINASE AND/OR MTOR

(75) Inventors: Noel D'Angelo, Thousand Oaks, CA (US); Fang-Tsao Hong, Thousand Oaks, CA (US); Mark H. Norman, Thousand Oaks, CA (US); Adrian L. Smith, Simi Valley, CA (US); Seifu Tadesse, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 176 days.

(21) Appl. No.: 12/768,602

(22) Filed: Apr. 27, 2010

(65) Prior Publication Data

US 2010/0273764 A1 Oct. 28, 2010

Related U.S. Application Data

(60) Provisional application No. 61/258,532, filed on Nov. 5, 2009, provisional application No. 61/173,520, filed on Apr. 28, 2009.

(51) Int. Cl.
| | |
|---|---|
| C07D 401/14 | (2006.01) |
| C07D 403/14 | (2006.01) |
| A61K 31/4427 | (2006.01) |
| A61K 31/496 | (2006.01) |
| A61K 31/53 | (2006.01) |
| A61P 35/00 | (2006.01) |

(52) U.S. Cl. ......... 544/180; 544/194; 544/219; 514/241
(58) Field of Classification Search .................. 544/180, 544/194, 219; 514/241
See application file for complete search history.

(56) References Cited

U.S. PATENT DOCUMENTS

| 7,750,001 B2 | 7/2010 | Haruta et al. |
|---|---|---|
| 2003/0199511 A1 | 10/2003 | Qun Li et al. |
| 2007/0287708 A1 | 12/2007 | Cole et al. |
| 2010/0113523 A1 | 5/2010 | Alberte et al. |

FOREIGN PATENT DOCUMENTS

| EP | 1 277 738 A1 | 1/2003 |
|---|---|---|
| WO | WO 97/03967 A1 | 2/1997 |
| WO | WO 01/44172 A1 | 6/2001 |
| WO | WO 01/70734 A2 | 9/2001 |
| WO | WO 01/83456 A1 | 11/2001 |
| WO | WO 02/083654 A1 | 10/2002 |
| WO | WO 03/051366 A2 | 6/2003 |
| WO | WO 03/093297 A2 | 11/2003 |
| WO | WO 2004/000318 A2 | 12/2003 |
| WO | WO 2004/000820 A2 | 12/2003 |
| WO | WO 2004/099127 A1 | 11/2004 |
| WO | WO 2005/113494 A2 | 12/2005 |
| WO | WO 2006/005915 A1 | 1/2006 |
| WO | WO 2006/095906 A1 | 9/2006 |
| WO | WO 2006/123165 A2 | 11/2006 |
| WO | WO 2007/011721 A1 | 1/2007 |
| WO | WO 2007/042806 A1 | 4/2007 |
| WO | WO 2007/076092 A2 | 7/2007 |
| WO | WO 2007/084786 A1 | 7/2007 |
| WO | WO 2007/087276 A1 | 8/2007 |
| WO | WO 2008/032028 A1 | 3/2008 |
| WO | WO 2008/032033 A1 | 3/2008 |
| WO | WO 2008/032036 A1 | 3/2008 |
| WO | WO 2008/032041 A1 | 3/2008 |
| WO | WO 2008/032060 A1 | 3/2008 |
| WO | WO 2008/032064 A1 | 3/2008 |
| WO | WO 2008/032072 A1 | 3/2008 |
| WO | WO 2008/032077 A1 | 3/2008 |
| WO | WO 2008/032086 A | 3/2008 |
| WO | WO 2008/032089 A1 | 3/2008 |
| WO | WO 2008/032091 A1 | 3/2008 |
| WO | WO 2008/098058 A1 | 8/2008 |
| WO | WO 2009/007748 A2 | 1/2009 |
| WO | WO 2009/007750 A1 | 1/2009 |
| WO | WO 2009/007751 A2 | 1/2009 |
| WO | WO 2009/013348 A2 | 1/2009 |
| WO | WO 2009/055418 A1 | 4/2009 |
| WO | WO 2009/093981 A1 | 7/2009 |
| WO | WO 2009/115517 A2 | 9/2009 |
| WO | WO 2009/120094 A2 | 10/2009 |
| WO | WO 2009/143313 A1 | 11/2009 |
| WO | WO 2010/014939 A | 2/2010 |
| WO | WO 2010/051188 A1 | 5/2010 |
| WO | WO 2010/052569 A2 | 5/2010 |
| WO | WO 2010/061903 A1 | 6/2010 |
| WO | WO 2010/075380 A1 | 7/2010 |
| WO | WO 2010/093727 A1 | 8/2010 |
| WO | WO 2010/096314 A1 | 8/2010 |
| WO | WO 2010/100405 A1 | 9/2010 |
| WO | WO 2010/110685 A2 | 9/2010 |
| WO | WO 2010/110686 A1 | 9/2010 |
| WO | WO2010/144345 A | 12/2010 |

OTHER PUBLICATIONS

Cecil Textbook of Medicine, edited by Bennet, J.C., and Plum F., 20th edition,vol. 1, 1004-1010, 1996.* Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys. vol. 58(3): 932-940, 2004.*
Fabbro et al. Pharmacology & therapeutics 93, 79-98, 2002.*
Freshney et al.,Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Hayakawa, Bioorganic & Medicinal Chemistry Letters, 17(2007), 2438-2442.
International Search Report and Written Opinion PCT/US2010/032593.

* cited by examiner

Primary Examiner — Venkataraman Balasubramanian
(74) Attorney, Agent, or Firm — Todd M. Crissey

(57) ABSTRACT

The present invention relates to compounds of Formula I, or a pharmaceutically acceptable salt thereof;

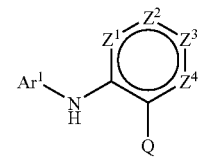

I methods of treating diseases or conditions, such as cancer, using the compounds; and
pharmaceutical compositions containing the compounds, wherein the variables are as defined herein.

8 Claims, No Drawings

INHIBITORS OF PI3 KINASE AND/OR MTOR

CROSS-REFERENCE TO RELATED APPLICATIONS

This application claims the benefit of U.S. Provisional Application No. 61/173,520, filed Apr. 28, 2009, and 61/258,532, filed Nov. 5, 2009, which are hereby incorporated by reference.

FIELD OF THE INVENTION

The present invention relates to compounds that inhibit phosphoinositide 3-kinase (PI3K) and/or mammalian target of rapamycin (mTOR); methods of treating diseases or conditions, such as cancer, using the compounds; and pharmaceutical compositions containing the compounds.

BACKGROUND OF THE INVENTION

PI3 kinases are a family of lipid kinases that have been found to play a key role in the regulation of many cellular processes including proliferation, survival, carbohydrate metabolism, and motility. PI3Ks are considered to have an important role in intracellular signal transduction. In particular, the PI3Ks generate and convey signals that have important roles in cancer. PI3Ks are ubiquitously expressed, are activated by a high proportion of cell surface receptors, especially those linked to tyrosine kinases, and influence a variety of cellular functions and events. Although some PI3K activity is likely to be essential for cellular health, PI3Ks are a diverse group of enzymes for which there is increasing evidence of functional specialization. This opens up the possibility of developing isoform-selective inhibitors that can be used to treat cancer.

The primary enzymatic activity of PI3K is the phosphorylation of inositol lipids (phosphoinositides) on the 3-position of the inositol headgroup. PI3 kinases catalyze the addition of phosphate to the 3'-OH position of the inositol ring of inositol lipids generating phosphatidyl inositol monophosphate, phosphatidyl inositol diphosphate and phosphatidyl inositol triphosphate.

There are a total of eight mammalian PI3Ks, which have been divided into three main classes on the basis of sequence homology, in vitro substrate preference, and method of activation and regulation. Enzymes of a first class (Class I) have a broad substrate specificity and phosphorylate phosphatidylinositiol (PtdIns), PtdIns(4)P and PtdIns(4,5)$P_2$. Class I PI3 kinases include mammalian p110α, p110β, p110δ and p110γ. Different members of the PI3-kinase family generate different lipid products. To date, four 3-phosphorylated inositol lipids have been identified in vivo. These lipids are bound by proteins that contain the appropriate lipid recognition module and which either act as effectors or transmit the PI3K signal onwards. The most familiar form of PI3K is a heterodimeric complex, consisting of a 110 kDa catalytic subunit now known as p110α and an 85 kDa regulatory/adapter subunit, p85α.

Phosphatidylinositol 3-kinase-alpha (PI3Kα), a dual specificity lipid and protein kinase, is composed of an 85 kDa regulatory subunit and a 110 kDa catalytic subunit. The protein includes a catalytic subunit, which uses ATP to phosphorylate PtdIns, PtdIns(4)P and PtdIns(4,5)$P_2$. PTEN, a tumor suppressor, can dephosphorylate phosphatidylinositol (3,4,5)-trisphosphate (PIP3), the major product of PI3 kinase Class I. PIP3, in turn, is required for translocation of protein kinase B (AKT1, PKB) to the cell membrane, where it is phosphorylated and activated by upstream kinases. The effect of PTEN on cell death is mediated through the PI3Kα/AKT1 pathway.

PI3Kα has been implicated in the control of cytoskeletal reorganization, apoptosis, vesicular trafficking and proliferation and differentiation processes. Increased copy number and expression of the p110α gene (PIK3CA) is associated with a number of cancers such as ovarian cancer, cervical cancer, breast cancer, colon cancer, rectal cancer, endometrial cancer, stomach cancer, liver cancer, lung cancer, thyroid cancer, acute myelogenous leukemia (AML), chronic myelogenous leukemia (CML), and glioblastomas. In view of the important role of PI3Kα in biological processes and disease states, inhibitors of this protein kinase are desirable. The present invention provides PI3K inhibitors, particularly PI3Kα inhibitors, which are useful for treating PI3Kα-mediated diseases and conditions.

Mammalian target of rapamycin (mTOR) is a serine/threonine kinase of approximately 289 kDa in size and a member of the evolutionary conserved eukaryotic TOR kinases. The mTOR protein is a member of the PI3 kinase like kinase (PIKK) family of proteins due to its C-terminal homology (catalytic domain) with PI3 kinase and the other family members, e.g. DNA dependent protein kinase (DNA-PKcs), Ataxia-telangiectasia mutated (ATM).

It has been demonstrated that mTOR kinase is a central regulator of cell growth and survival by mediating multiple important cellular functions including translation, cell cycle regulation, cytoskeleton reorganization, apoptosis and autophagy. mTOR resides in two biochemically and functionally distinct complexes that are conserved from yeast to human. The rapamycin sensitive mTOR-Raptor complex (mTORC1) regulates translation by activation of p70S6 kinase and inhibition of eIF4E binding protein 4EBP1 through phosphorylation, which is the best-described physiological function of mTOR signaling. mTORC1 activity is regulated by extracellular signals (growth factors and hormones) through the PI3K/AKT pathway, and by nutrient availability, intracellular energy status and oxygen through the regulators like LKB1 and AMPK. Rapamycin and its analogues inhibit mTORC1 activity by disrupting the interaction between mTOR and raptor. The rapamycin-insensitive complex, mTORC2, was discovered only recently. Unlike mTORC1 which contains raptor, the mTORC2 complex contains other proteins including Rictor and mSin1. mTORC2 phosphorylates AKT at the hydrophobic Ser473 site, and appears to be essential for AKT activity. Other substrates of mTORC2 include PKCα and SGK1. How mTORC2 activity is regulated is not well understood.

The mTORC1 pathway can be activated by elevated PI3K/AKT signaling or mutations in the tumor suppressor genes PTEN or TSC2, providing cells with a growth advantage by promoting protein synthesis. Cancer cells treated with the mTORC1 inhibitor rapamycin show growth inhibition and, in some cases, apoptosis. Three rapamycin analogues, CCI-779 (Wyeth), RAD001 (Novartis) and AP23573 (Ariad) are in clinical trials for the treatment of cancer. However response rates vary among cancer types from a low of less than 10% in patients with glioblastoma and breast cancer to a high of around 40% in patients with mantle cell lymphoma. Recent studies demonstrated that rapamycin can actually induce a strong AKT phosphorylation in tumors by attenuating the feedback inhibition on receptor tyrosine kinases mediated by p70S6K, one of the downstream effectors of mTORC1. For example, in Phase I clinical trials of RAD001, an increase in pAKT (+22.2 to 63.1% of initial values) was observed after dosing. If mTORC1 inhibition-induced phospho-AKT leads to increased cancer cell survival and acquisition of additional lesions, this could counteract the effects of growth inhibition by rapamycin analogues and explain the variable response rate. Therefore, identifying and developing small molecules that target the catalytic activity of mTOR (inhibiting both mTORC1 and mTORC2) will lead to more effective therapeutics to treat cancer patients by preventing the activation of AKT that is caused by mTORC1 specific inhibitors like rapamycin and its analogues. Dysregulated mTOR activity has been shown to associate with variety of human cancers such as breast, lung, kidney, brain, ovarian, colon, cervical, endometrial, prostate, liver, thyroid, GI tract, blood and lymphoma and other diseases such as hamartoma syndromes, rheumatoid arthritis, multiple sclerosis. In view of the important role of mTOR in biological processes and disease states, catalytic inhibitors of this protein kinase are desirable. The present invention provides kinase inhibitors, specifically PIK kinase inhibitors, more specifically, mTOR inhibitors, which are useful for treating diseases mediated by kinases, specifically PIK kinases, more specifically, mTOR.

SUMMARY OF THE INVENTION

In aspect 1, the present invention provides compounds of Formula I, or a pharmaceutically acceptable salt thereof,

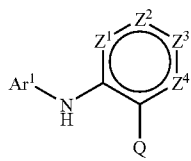

I wherein $Ar^1$ is a 5 to 10 membered monocyclic or bicyclic ring that can contain from zero to four heteroatoms independently selected from O, N or S, and which ring can be unsubstituted or substituted with groups independently selected from $C_{1-4}$haloalkyl, halo, oxo, —OCHF$_2$, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, or —C$_{2-6}$alkynyl, wherein —C$_{1-6}$alkyl, —C$_{2-6}$alkenyl, or —C$_{2-6}$alkynyl are substituted by 0, 1, 2 or 3 substituents independently selected from $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicyclic ring containing 0, 1, 2, 3 or 4 heteroatoms independently selected from N, O and S, which is substituted with 0, 1, or 2 substituents independently selected from $C_{1-8}$alkyl, $C_{2-6}$alkenyl, $C_{2-6}$alkynyl, $C_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O) NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each $R^a$ is independently hydrogen or $R^b$;

each $R^b$ is independently phenyl, benzyl, $C_{1-6}$alkyl, $C_{4-8}$heterocycloalkyl, or $C_{3-8}$cycloalkyl, wherein the phenyl, benzyl, $C_{1-6}$alkyl, $C_{4-8}$heterocycloalkyl or $C_{3-8}$cycloalkyl is substituted by 0, 1, 2 or 3 substituents independently selected from halo, —OH, —S(=O)$_2$R$^b$, —OC$_{2-6}$alkylOR$^a$, $C_{1-4}$alkyl, $C_{1-3}$haloalkyl, —OC$_{1-4}$alkyl, —NH$_2$, —CN, or —NR$^a$R$^a$;

each $R^c$ is independently hydrogen, —OR$^a$, —NR$^a$R$^a$, $C_{1-6}$alkyl, or the group CR$^c$R$^c$ can form a $C_{3-8}$cycloalkyl ring;

each n is independently 0, 1, 2, or 3;

each $Z^1$, $Z^2$, $Z^3$ or $Z^4$ is independently selected from N, NR or CR; or $Z^1$ and $Z^2$, $Z^2$ and $Z^3$, or $Z^3$ and $Z^4$, when NR or CR, can form a 5 or 6 membered ring when the two Rs are taken together with the carbon or nitrogen atoms to which they are attached, and the ring can contain from zero to three heteroatoms independently selected from O, N or S, and the ring can be unsubstituted or substituted with groups independently selected from $C_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —(CR$^c$R$^c$)$_n$NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —(CR$^c$R$^c$)$_n$C$_{4-8}$heterocycloalkyl, —(CR$^c$R$^c$)$_n$C$_{6-8}$aryl, —(CR$^c$R$^c$)$_n$C$_{5-8}$heteroaryl, —(CR$^c$R$^c$)$_n$O(CR$^c$R$^c$)$_n$C$_{6-8}$aryl, —(CR$^c$R$^c$)$_n$N(R$^a$)(CR$^c$R$^c$)$_n$C$_{6-8}$aryl, —(CH$_2$)$_n$N(R$^a$)(CR$^c$R$^c$)$_n$C$_{5-8}$heteroaryl, —(CR$^c$R$^c$)$_n$O(CR$^c$R$^c$)$_n$C$_{5-8}$heteroaryl, —C$_{1-6}$alkyl, —C$_{2-6}$alkenyl, or —C$_{2-6}$alkynyl, wherein the $C_{1-6}$alkyl, $C_{2-6}$alkenyl, $C_{2-6}$alkynyl, $C_{4-8}$heterocycloalkyl, $C_{6-8}$aryl or $C_{5-8}$heteroaryl are substituted by 0, 1, 2 or 3 substituents independently selected from $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

each R is independently selected from hydrogen, oxo, $C_{1-4}$haloalkyl, halo, —OCHF$_2$, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)

$R^b$, —S(=O)$_2R^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —(CR$^c$R$^c$)$_n$NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —(CR$^c$R$^c$)$_n$C$_{4-8}$heterocycloalkyl, —(CR$^c$R$^c$)$_n$C$_{6-8}$aryl, —(CR$^c$R$^c$)$_n$C$_{5-8}$heteroaryl, —(CR$^c$R$^c$)$_n$O(CR$^c$R$^c$)$_n$C$_{6-8}$aryl, —(CR$^c$R$^c$)$_n$C$_{3-8}$cycloalkyl, —(CR$^c$R$^c$)$_n$C$_{4-8}$heterocycloalkyl, —(CR$^c$R$^c$)$_n$O(CR$^c$R$^c$)$_n$CF$_3$, —(CR$^c$R$^c$)$_n$N(CR$^c$R$^c$)nOR$^a$, —(CR$^c$R$^c$)$_n$N(R$^a$)(CR$^c$R$^c$)$_n$C$_{6-8}$aryl, —(CR$^c$R$^c$)$_n$N(R$^a$)(CR$^c$R$^c$)$_n$C$_{5-8}$heteroaryl, —(CR$^c$R$^c$)$_n$O(CR$^c$R$^c$)$_n$C$_{5-8}$heteroaryl, —C$_{1-6}$alkyl, —C$_{2-6}$alkenyl, or —C$_{2-6}$alkynyl, wherein C$_{1-6}$alkyl, C$_{2-6}$alkenyl, C$_{2-6}$alkynyl, C$_{6-8}$aryl, C$_{4-8}$heterocycloalkyl, C$_{3-8}$cycloalkyl or C$_{5-8}$heteroaryl are substituted by 0, 1, 2 or 3 substituents independently selected from C$_{1-4}$haloalkyl, halo, oxo, C$_{1-6}$alkyl, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2R^b$, —OC$_{2-6}$alkylNR$^a$R$^a$, —OC$_{2-6}$alkylOR$^a$, —SR$^a$, —S(=O)R$^b$, —S(=O)$_2R^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, —(CR$^a$R$^a$)nC$_{3-8}$cycloalkyl, or —(CR$^a$R$^a$)$_n$OR$^a$;

Q is

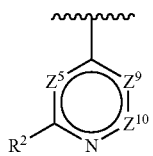

R$^2$ is methyl or ethyl;
Z$^5$ is N or CR$^c$;
Z$^9$ is N, NR or CR;
Z$^{10}$ is N, NR, or CR, or Z$^9$ and Z$^{10}$ can form a 5 or 6 membered ring when the two Rs are taken together with the carbon or nitrogen atoms to which they are attached, and the ring can contain from zero to three heteroatoms independently selected from O, N or S, and the ring can be unsubstituted or substituted with groups independently selected from C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2R^b$, —OC$_{2-6}$alkylNR$^a$R$^a$, —OC$_{2-6}$alkylOR$^a$, —SR$^a$, —S(=O)R$^b$, —S(=O)$_2R^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —(CR$^c$R$^c$)$_n$NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —(CR$^c$R$^c$)$_n$C$_{4-8}$heterocycloalkyl, —(CR$^c$R$^c$)$_n$C$_{6-8}$aryl, —(CR$^c$R$^c$)$_n$C$_{5-8}$heteroaryl, —(CR$^c$R$^c$)$_n$O(CR$^c$R$^c$)$_n$C$_{6-8}$aryl, —(CR$^c$R$^c$)$_n$N(R$^a$)(CR$^c$R$^c$)$_n$C$_{6-8}$aryl, —(CR$^c$R$^c$)$_n$N(R$^a$)(CR$^c$R$^c$)$_n$C$_{5-8}$heteroaryl, —(CR$^c$R$^c$)$_n$O(CR$^c$R$^c$)$_n$C$_{5-8}$heteroaryl, —C$_{1-6}$ alkyl, —C$_{2-6}$alkenyl, or —C$_{2-6}$alkynyl, wherein C$_{1-6}$alkyl, C$_{2-6}$alkenyl, C$_{2-6}$alkynyl, C$_{4-8}$heterocycloalkyl, C$_{6-8}$aryl or C$_{5-8}$heteroaryl are substituted by 0, 1, 2 or 3 substituents independently selected from C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2R^b$, —OC$_{2-6}$alkylNR$^a$R$^a$, —OC$_{2-6}$alkylOR$^a$, —SR$^a$, —S(=O)R$^b$, —S(=O)$_2R^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$; and the group NR$^a$R$^a$, either alone or a part of a larger group, can be a 4 to 6 membered heterocyclic ring wherein the two R$^a$s taken together with the nitrogen atom to which they are attached form a ring that can have from zero to one additional heteroatom selected from N, O or S, and the ring can be substituted or unsubstituted with from 1 to 3 substitutents independently selected from oxo, halo, —CN, nitro, —C(=O)R$^c$, —C(=O)OR$^c$, —OR$^c$, —OC(=O)R$^c$, —SR$^c$, —S(=O)R$^c$, —S(=O)$_2R^c$, —S(=O)$_2$NR$^c$R$^c$, —NR$^c$R$^c$, —C$_{1-6}$alkyl, —C$_{2-6}$alkenyl, or —C$_{2-6}$alkynyl.

In aspect 1a, the present invention provides compounds of Formula I, or a pharmaceutically acceptable salt thereof,

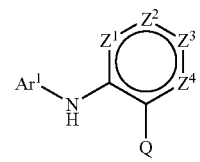

I wherein Ar$^1$ is a 5 to 10 membered monocyclic or bicyclic ring that can contain from zero to four heteroatoms independently selected from O, N or S, and which ring can be unsubstituted or substituted with groups independently selected from C$_{1-4}$haloalkyl, halo, oxo, —OCHF$_2$, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2R^b$, —OC$_{2-6}$alkylNR$^a$R$^a$, —OC$_{2-6}$alkylOR$^a$, —SR$^a$, —S(=O)R$^b$, —S(=O)$_2R^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, or —C$_{2-6}$alkynyl, wherein —C$_{1-6}$alkyl, —C$_{2-6}$alkenyl, or —C$_{2-6}$alkynyl are substituted by 0, 1, 2 or 3 substituents independently selected from C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2R^b$, —OC$_{2-6}$alkylNR$^a$R$^a$, —OC$_{2-6}$alkylOR$^a$, —SR$^a$, —S(=O)R$^b$, —S(=O)$_2R^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substitutents independently selected from $C_{1-8}$alkyl, $C_{2-6}$alkenyl, $C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O) N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN-$R^aR^a$ or —N$R^aC_{2-6}$alkylO$R^a$;

each $R^a$ is independently hydrogen or $R^b$;

each $R^b$ is independently phenyl, benzyl, $C_{1-6}$alkyl, $C_{4-8}$heterocycloalkyl, or $C_{3-8}$cycloalkyl, wherein the phenyl, benzyl, $C_{1-6}$alkyl, $C_{4-8}$heterocycloalkyl or $C_{3-8}$cycloalkyl is substituted by 0, 1, 2 or 3 substituents independently selected from halo, —OH, —S(=O)$_2R^b$, —OC$_{2-6}$alkylO$R^a$, $C_{1-4}$alkyl, $C_{1-3}$haloalkyl, —OC$_{1-4}$alkyl, —NH$_2$, —CN, or —N$R^aR^a$;

each $R^c$ is independently hydrogen, —O$R^a$, —N$R^aR^a$, —CF$_3$, $C_{1-6}$alkyl, or the group C$R^cR^c$ can form a $C_{3-8}$cycloalkyl ring;

each n is independently 0, 1, 2, or 3;

each $Z^1$, $Z^2$, $Z^3$ or $Z^4$ is independently selected from N, NR or CR; or $Z^1$ and $Z^2$, $Z^2$ and $Z^3$, or $Z^3$ and $Z^4$, when NR or CR, can form a 5 or 6 membered ring when the two Rs are taken together with the carbon or nitrogen atoms to which they are attached, and the ring can contain from zero to three heteroatoms independently selected from O, N or S, and the ring can be unsubstituted or substituted with groups independently selected from $C_{1-4}$haloalkyl, halo, —CN, nitro, —C(=O) N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—C$_{1-6}$alkylN($R^a$)C(=O)O$R^b$, —OC(=O)N($R^a$)S(=O)$_2R^b$, —OC$_{2-6}$alkylN$R^aR^a$, —OC$_{2-6}$alkylO$R^a$, —S$R^a$, —S(=O) $R^b$, —S(=O)$_2R^b$, —S(=O)$_2$N$R^aR^a$, —S(=O)$_2$N($R^a$)C (=O)$R^b$, —S(=O)$_2$N($R^a$)C(=O)O$R^b$, —S(=O)$_2$N($R^a$)C (=O)N$R^aR^a$, —(C$R^cR^c$)$_n$N$R^aR^a$, —N($R^a$)C(=O)$R^b$, —N($R^a$)C(=O)O$R^b$, —N($R^a$)C(=O)N$R^aR^a$, —N($R^a$)C (=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —(C$R^cR^c$)$_nC_{4-8}$heterocycloalkyl, —(C$R^cR^c$)$_nC_{6-8}$aryl, —(C$R^cR^c$)$_nC_{5-8}$heteroaryl, —(C$R^cR^c$)$_n$O(C$R^cR^c$)$_nC_{6-8}$aryl, —(C$R^cR^c$)$_n$N($R^a$)(C$R^cR^c$)$_nC_{6-8}$aryl, —(CH$_2$)$_n$N($R^a$)(C$R^cR^c$)$_nC_{5-8}$heteroaryl, —(C$R^cR^c$)$_n$O(C$R^cR^c$)$_nC_{5-8}$heteroaryl, —$C_{1-6}$alkyl, —$C_{2-6}$alkenyl, or —$C_{2-6}$alkynyl, wherein the $C_{1-6}$alkyl, $C_{2-6}$alkenyl, $C_{2-6}$alkynyl, $C_{4-8}$heterocycloalkyl, $C_{6-8}$aryl or $C_{5-8}$heteroaryl are substituted by 0, 1, 2 or 3 substituents independently selected from $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O) N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N ($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$) S(=O)$_2R^b$, —N($R^a$)S(=O)$_2$N$R^aR^a$, —N$R^aC_{2-6}$alkylN-$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$O$R^a$;

each R is independently selected from hydrogen, oxo, $C_{1-4}$haloalkyl, halo, —OCHF$_2$, —CN, nitro, —C(=O) N$R^aR^a$, —C(=O)$R^b$, —C(=O)O$R^b$, —C(=N$R^a$)N$R^aR^a$, —O$R^a$, —O—(C$R^aR^a$)$_n$O$R^a$, —OC(=O)$R^b$, —OC(=O)N $R^aR^a$, —O—C$_{1-6}$alkylN($R^a$)C(=O)O$R^b$, —OC(=O)N ($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —(C$R^cR^c$)$_n$N$R^aR^a$, —N($R^a$)C(=O)$R^b$, —N($R^a$)C(=O)O$R^b$, —N($R^a$)C(=O) N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$ alkylO$R^a$, —(C$R^cR^c$)$_nC_{4-8}$heterocycloalkyl, —(C$R^cR^c$)$_nC_{6-8}$aryl, —(C$R^cR^c$)$_nC_{5-8}$heteroaryl, —(C$R^c$ $R^c$)$_n$ O(C$R^cR^c$)$_n$ $C_{6-8}$aryl, —(C$R^cR^c$)$_nC_{3-8}$cycloalkyl, —(C$R^c$ $R^c$)$_nC_{4-8}$heterocycloalkyl, —(C$R^cR^c$)$_n$O(C$R^c$-C$R^c$)$_n$ CF$_3$, —(C$R^cR^c$)$_n$N(C$R^cR^c$)$_n$O$R^a$, —(C$R^cR^c$)$_n$N($R^a$) (C$R^cR^c$)$_n$ $C_{6-8}$aryl, —(C$R^c$ $R^c$)$_n$N($R^a$)(C$R^cR^c$)$_nC_{5-8}$heteroaryl, —(C$R^c$ $R^c$)$_n$O(C$R^cR^c$)$_n$ $C_{5-8}$heteroaryl, —$C_{1-6}$alkyl, —$C_{2-6}$alkenyl, or —$C_{2-6}$alkynyl, wherein $C_{1-6}$alkyl, $C_{2-6}$alkenyl, $C_{2-6}$alkynyl, $C_{6-8}$aryl, $C_{4-8}$heterocycloalkyl, $C_{3-8}$cycloalkyl or $C_{5-8}$heteroaryl are substituted by 0, 1, 2 or 3 substituents independently selected from $C_{1-4}$haloalkyl, halo, oxo, $C_{1-6}$alkyl, cyano, nitro, —C(=O)$R^b$, —C(=O)O$R^b$, —C(=O)N$R^aR^a$, —C(=N$R^a$)N$R^aR^a$, —O$R^a$, —OC(=O) $R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O) $R^b$, —S(=O)$_2R^b$, —S(=O)$_2$N$R^aR^a$, —S(=O)$_2$N($R^a$)C (=O)$R^b$, —S(=O)$_2$N($R^a$)C(=O)O$R^b$, —S(=O)$_2$N($R^a$)C (=O)N$R^aR^a$, —N$R^aR^a$, —N($R^a$)C(=O)$R^b$, —N($R^a$)C (=O)O$R^b$, —N($R^a$)C(=O)N$R^aR^a$, —N($R^a$)C(=N$R^a$) N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$) (C$R^aR^a$)$_n$—Y, —(C$R^aR^a$)$_n$Y, —(C$R^aR^a$)$_nC_{3-8}$cycloalkyl, or —(C$R^aR^a$)$_n$ O$R^a$;

Q is

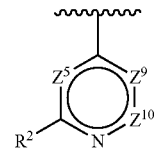

$R^2$ is methyl or ethyl;

$Z^5$ is N or CR$^c$;

$Z^9$ is N, NR or CR;

$Z^{10}$ is N, NR, or CR, or $Z^9$ and $Z^{10}$ can form a 5 or 6 membered ring when the two Rs are taken together with the carbon or nitrogen atoms to which they are attached, and the ring can contain from zero to three heteroatoms independently selected from O, N or S, and the ring can be unsubstituted or substituted with groups independently selected from $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—C$_{1-6}$alkylN($R^a$)C (=O)O$R^b$, —OC(=O)N($R^a$)S(=O)$_2R^b$, —OC$_{2-6}$alkylN-$R^aR^a$, —OC$_{2-6}$alkylO$R^a$, —S$R^a$, —S(=O)$R^b$, —S(=O)$_2$ $R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O) N$R^aR^a$, —(C$R^cR^c$)$_n$N$R^aR^a$, —N($R^a$)C(=O)$R^b$, —N($R^a$)C (=O)O$R^b$, —N($R^a$)C(=O)N$R^aR^a$, —N($R^a$)C(=N$R^a$) N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —(C$R^cR^c$)$_n$ $C_{4-8}$heterocycloalkyl, —(C$R^cR^c$)$_nC_{6-8}$aryl, —(C$R^cR^c$)$_nC_{5-8}$ heteroaryl, —(C$R^cR^c$)$_n$O(C$R^cR^c$)$_nC_{6-8}$aryl, —(C$R^cR^c$)$_n$N ($R^a$)(C$R^cR^c$)$_nC_{6-8}$aryl, —(C$R^cR^c$)$_n$N($R^a$)(C$R^cR^c$)$_nC_{5-8}$ heteroaryl, —(C$R^cR^c$)$_n$O(C$R^cR^c$)$_nC_{5-8}$heteroaryl, —$C_{1-6}$ alkyl, —$C_{2-6}$alkenyl, or —$C_{2-6}$alkynyl, wherein $C_{1-6}$alkyl, $C_{2-6}$alkenyl, $C_{2-6}$alkynyl, $C_{4-8}$heterocycloalkyl, $C_{6-8}$aryl or $C_{5-8}$heteroaryl are substituted by 0, 1, 2 or 3 substituents independently selected from $C_{1-4}$haloalkyl, halo, cyano, nitro, —C(=O)$R^b$, —C(=O)O$R^b$, —C(=O)N$R^aR^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$; and the group NR$^a$R$^a$, either alone or a part of a larger group, can be a 4 to 6 membered heterocyclic ring wherein the two R$^a$s taken together with the nitrogen atom to which they are attached form a ring that can have from zero to one additional heteroatom selected from N, O or S, and the ring can be substituted or unsubstituted with from 1 to 3 substituents independently selected from oxo, halo, —CN, nitro, —C(=O)R$^c$, —C(=O)OR$^c$, —OR$^c$, —OC(=O)R$^c$, —SR$^c$, —S(=O)R$^c$, —S(=O)$_2$R$^c$, —S(=O)$_2$NR$^c$R$^c$, —NR$^c$R$^c$, —C$_{1-6}$alkyl, —C$_{2-6}$alkenyl, or —C$_{2-6}$alkynyl.

In aspect 2, the present invention provides compounds of Formula I, or a pharmaceutically acceptable salt thereof,

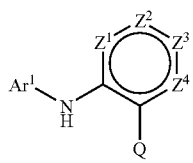

I wherein Ar$^1$ is a 5 to 10 membered monocyclic or bicyclic ring that can contain from zero to four heteroatoms independently selected from O, N or S, and which ring can be unsubstituted or substituted with groups independently selected from C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, or —C$_{2-6}$alkynyl, wherein C$_{1-6}$alkyl, C$_{2-6}$alkenyl, or C$_{2-6}$alkynyl are substituted by 0, 1, 2 or 3 substituents independently selected from C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicyclic ring containing 0, 1, 2, 3 or 4 heteroatoms independently selected from N, O and S, which is substituted with 0, 1, or 2 substituents independently selected from C$_{1-8}$alkyl, C$_{2-6}$alkenyl, C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R$^a$ is independently hydrogen or R$^b$;

each R$^b$ is independently phenyl, benzyl, C$_{1-6}$alkyl or C$_{3-8}$cycloalkyl, wherein the phenyl, benzyl, C$_{1-6}$alkyl or C$_{3-8}$cycloalkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, or —NR$^a$R$^a$;

each R$^c$ is independently hydrogen or C$_{1-6}$alkyl;

each n is independently 0, 1, 2, or 3;

each Z$^1$, Z$^2$, Z$^3$ or Z$^4$ is independently selected from N, NR or CR; or Z$^1$ and Z$^2$, Z$^2$ and Z$^3$, or Z$^3$ and Z$^4$, when NR or CR, can form a 5 or 6 membered ring when the two Rs are taken together with the carbon or nitrogen atoms to which they are attached, and the ring can contain from zero to three heteroatoms independently selected from O, N or S, and the ring can be unsubstituted or substituted with groups independently selected from C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —(CR$^c$R$^c$)$_n$NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —(CR$^c$R$^c$)$_n$C$_{3-8}$heterocycloalkyl, —(CR$^c$R$^c$)$_n$C$_{6-8}$aryl, —(CR$^c$R$^c$)$_n$C$_{5-8}$heteroaryl, —(CR$^c$R$^c$)$_n$O(CR$^c$R$^c$)$_n$C$_{6-8}$aryl, —(CR$^c$R$^c$)$_n$N(R$^a$)(CR$^c$R$^c$)$_n$C$_{6-8}$aryl, —(CH$_2$)$_n$N(R$^a$)(CR$^c$R$^c$)$_n$C$_{5-8}$heteroaryl, —(CR$^c$R$^c$)$_n$O(CR$^c$R$^c$)$_n$C$_{5-8}$heteroaryl, —C$_{1-6}$alkyl, —C$_{2-6}$alkenyl, or —C$_{2-6}$alkynyl, wherein the C$_{1-6}$alkyl, C$_{2-6}$alkenyl, C$_{2-6}$alkynyl, C$_{3-8}$heterocycloalkyl, C$_{6-8}$aryl or C$_{5-8}$heteroaryl are substituted by 0, 1, 2 or 3 substituents independently selected from C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

each R is independently selected from hydrogen C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —(CR$^c$R$^c$)$_n$NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —(CR$^c$R$^c$)$_n$C$_{3-8}$heterocycloalkyl, —(CR$^c$R$^c$)$_n$C$_{6-8}$aryl, —(CR$^c$R$^c$)$_n$C$_{5-8}$heteroaryl, —(CR$^c$R$^c$)$_n$O(CR$^c$R$^c$)$_n$C$_{6-8}$aryl, —(CR$^c$R$^c$)$_n$N(R$^a$)(CR$^c$R$^c$)$_n$C$_{6-8}$aryl, —(CR$^c$R$^c$)$_n$N(R$^a$)(CR$^c$R$^c$)$_n$C$_{5-8}$heteroaryl, —(CR$^c$R$^c$)$_n$O(CR$^c$R$^c$)$_n$C$_{5-8}$heteroaryl, —C$_{1-6}$alkyl, —C$_{2-6}$alkenyl, or —C$_{2-6}$alkynyl, wherein C$_{1-6}$alkyl, C$_{2-6}$alkenyl, C$_{2-6}$alkynyl, C$_{3-8}$heterocycloalkyl, C$_{6-8}$aryl or C$_{5-8}$heteroaryl are substituted by 0, 1, 2 or 3 substituents independently selected from C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Q is

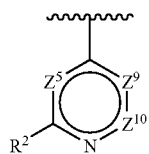

R$^2$ is methyl or ethyl;
Z$^5$ is N or CR$^c$;
Z$^9$ is N, NR or CR;
Z$^{10}$ is N, NR, or CR, or Z$^9$ and Z$^{10}$ can form a 5 or 6 membered ring when the two Rs are taken together with the carbon or nitrogen atoms to which they are attached, and the ring can contain from zero to three heteroatoms independently selected from O, N or S, and the ring can be unsubstituted or substituted with groups independently selected from C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —(CR$^a$R$^a$)$_n$NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —(CR$^c$R$^c$)$_n$C$_{3-8}$cycloalkyl —(CR$^c$R$^c$)$_n$C$_{3-8}$heterocycloalkyl, —(CR$^c$R$^c$)$_n$C$_{6-8}$aryl, —(CR$^c$R$^c$)$_n$C$_{5-8}$heteroaryl, —(CR$^c$R$^c$)$_n$O(CR$^c$R$^c$)$_n$C$_{6-8}$aryl, —(CR$^c$R$^c$)$_n$N(R$^a$)(CR$^c$R$^c$)$_n$C$_{6-8}$aryl, —(CR$^c$R$^c$)$_n$N(R$^a$)(CR$^c$R$^c$)$_n$C$_{5-8}$heteroaryl, —(CR$^c$R$^c$)$_n$O(CR$^c$R$^c$)$_n$C$_{5-8}$heteroaryl, —C$_{1-6}$alkyl, —C$_{2-6}$alkenyl, or —C$_{2-6}$alkynyl, wherein C$_{1-6}$alkyl, C$_{2-6}$alkenyl, C$_{2-6}$alkynyl, C$_{3-8}$cycloalkyl C$_{3-8}$heterocycloalkyl, C$_{6-8}$aryl or C$_{5-8}$heteroaryl are substituted by 0, 1, 2 or 3 substituents independently selected from C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$; and the group NR$^a$R$^a$, either alone or a part of a larger group, can be a 4 to 6 membered heterocyclic ring wherein the two R$^a$s taken together with the nitrogen atom to which they are attached form a ring that can have from zero to one additional heteroatom selected from N, O or S, and the ring can be substituted or unsubstituted with from 1 to 3 substituents independently selected from oxo, halo, —CN, nitro, —C(=O)R$^c$, —C(=O)OR$^c$, —OR$^c$, —OC(=O)R$^c$, —SR$^c$, —S(=O)R$^c$, —S(=O)$_2$R$^c$, —S(=O)$_2$NR$^c$R$^c$, —NR$^c$R$^c$, —C$_{1-6}$alkyl, —C$_{2-6}$alkenyl, or —C$_{2-6}$alkynyl.

In aspect 3, the present invention provides compounds in accordance with aspect 1 or 2, or a pharmaceutically acceptable salt thereof, wherein Q is

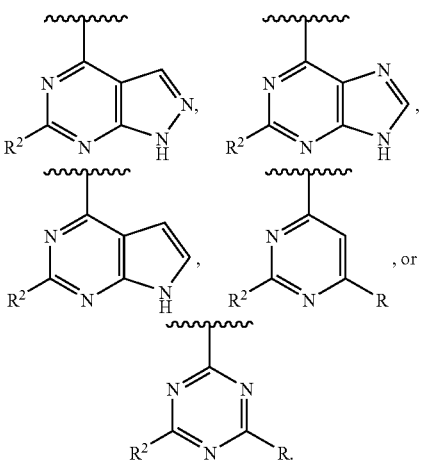

In aspect 4, the present invention provides compounds in accordance with aspect 1 or 2, or a pharmaceutically acceptable salt thereof, wherein Q is

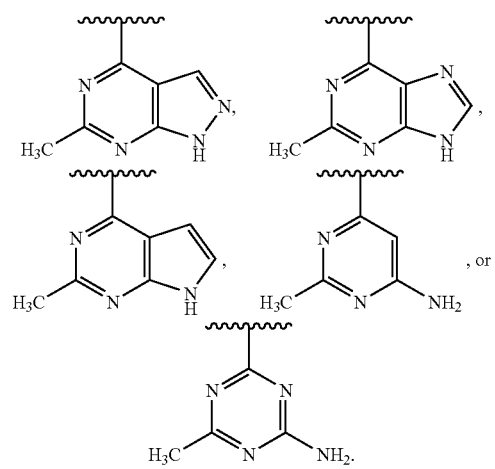

In aspect 5, the present invention provides compounds in accordance with any one of aspects 1 to 4, or a pharmaceutically acceptable salt thereof, wherein Z$^1$ is N; and Z$^2$, Z$^3$ and Z$^4$ are CR.

In aspect 6, the present invention provides compounds, in accordance with any one of aspects 1 to 4, or a pharmaceutically acceptable salt thereof, wherein Z$^1$ is N; and Z$^2$, Z$^3$ and Z$^4$ are CH.

In aspect 7, the present invention provides compounds in accordance with any one of aspects 1 to 4, or a pharmaceutically acceptable salt thereof, wherein $Z^1$, $Z^2$ and $Z^4$ are CR; and $Z^3$ is N.

In aspect 8, the present invention provides compounds in accordance with any one of aspects 1 to 4, or a pharmaceutically acceptable salt thereof, wherein $Z^1$ is N; $Z^2$ and $Z^3$ are CR; and $Z^4$ is N.

In aspect 9, the present invention provides compounds in accordance with any one of aspects 1 to 4, or a pharmaceutically acceptable salt thereof, wherein $Z^1$ is N; $Z^2$ and $Z^4$ are CH; and $Z^3$ is CR.

In aspect 10, the present invention provides compounds in accordance with any one of aspects 1 to 4, or a pharmaceutically acceptable salt thereof, wherein $Z^1$ is N; $Z^2$ and $Z^4$ are CH; $Z^3$ is CR; and R is selected from hydrogen, $C_{1-6}$alkyl, $C_{1-6}$substituted alkyl, halo, $C_{1-4}$haloalkyl, $-(CR^cR^c)_nC_{4-8}$heterocycloalkyl, $-(CR^cR^c)_nO(CR^cR^c)_nC_{6-8}$aryl, $-(CR^cR^c)_nN(R^a)(CR^cR^c)_nC_{6-8}$aryl, $-(CR^cR^c)_nN(R^a)(CR^cR^c)_nC_{5-8}$heteroaryl, $-(CR^cR^c)_n$substituted$C_{4-8}$heterocycloalkyl, $-(CR^cR^c)_nO(CR^cR^c)_n$substituted$C_{6-8}$aryl, $-(CR^cR^c)_nN(R^a)(CR^cR^c)_n$substituted$C_{6-8}$aryl, $-(CR^cR^c)_6N(R^a)(CR^cR^c)_n$substituted$C_{5-8}$heteroaryl, $C_{2-6}$alkenyl, or $-(CR^cR^c)_nNR^aR^a$. In a particular example of aspect 10, $Z^3$ is CR and R is $C_{1-6}$alkyl substituted with $-OR^a$.

In aspect 11, the present invention provides compounds in accordance with any one of aspects 1 to 10, or a pharmaceutically acceptable salt thereof, wherein $Ar^1$ is selected from pyrazolyl, indolyl, phenyl, pyridyl, pyrimidinyl, benzoxazolyl or indazolyl, which can be unsubstituted or substituted.

In aspect 12, the present invention provides compounds in accordance with any one of aspects 1 to 10, or a pharmaceutically acceptable salt thereof, wherein $Ar^1$ is selected from pyrazolyl, indolyl, phenyl, pyridyl, pyrimidinyl, benzoxazolyl or indazolyl, which can be unsubstituted or substituted with groups selected from $-OR^a$, halo, $-NR^aR^a$, $C_{1-4}$haloalkyl, $-N(R^a)C(=O)R^b$, or $-N(R^a)C(=O)NR^aR^a$.

In aspect 13, the present invention provides compounds in accordance with aspect 1 or 2, or a pharmaceutically acceptable salt thereof, wherein Q is

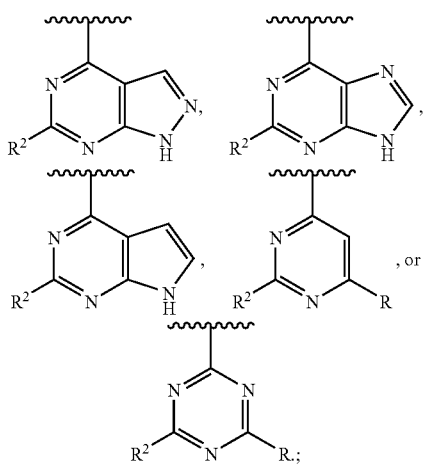

$Z^1$ is N; and $Z^2$, $Z^3$ and $Z^4$ are CR; and $Ar^1$ is selected from pyrazolyl, indolyl, phenyl, pyridyl, pyrimidinyl, benzoxazolyl or indazolyl, which can be unsubstituted or substituted.

In aspect 14, the present invention provides compounds of Formula I in accordance with aspect 1 or 2, or a pharmaceutically acceptable salt thereof, wherein Q is

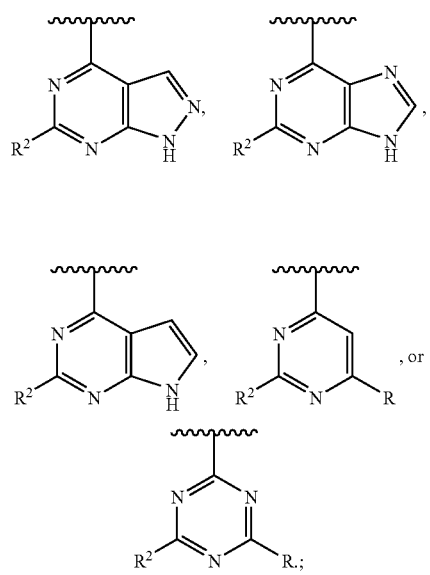

$Z^1$ is N; and $Z^2$, $Z^3$ and $Z^4$ are CH; and $Ar^1$ is selected from pyrazolyl, indolyl, phenyl, pyridyl, pyrimidinyl, benzoxazolyl or indazolyl, which can be unsubstituted or substituted.

In aspect 15, the present invention provides compounds in accordance with any one of aspects 1, 2 or 5 to 12, or a pharmaceutically acceptable salt thereof, wherein $R^2$ is methyl.

In aspect 16, the present invention provides compounds in accordance with any one of aspects 1, 2 or 5 to 12, or a pharmaceutically acceptable salt thereof, wherein Q is

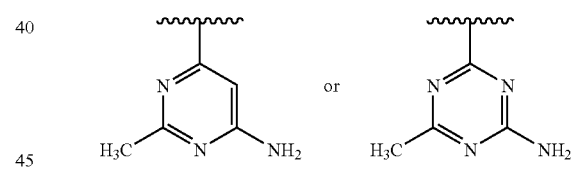

In aspect 17, the present invention provides compounds in accordance with aspect 1 or 2, or a pharmaceutically acceptable salt thereof, wherein Q is

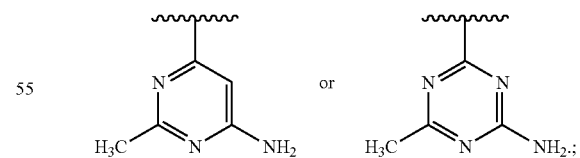

$Z^1$ is N; and $Z^2$, $Z^3$ and $Z^4$ are CR; and $Ar^1$ is selected from pyrazolyl, indolyl, phenyl, pyridyl, pyrimidinyl, benzoxazolyl or indazolyl, which can be unsubstituted or substituted.

In aspect 18, the present invention provides compounds in accordance with aspect 1 or 2, or a pharmaceutically acceptable salt thereof, wherein Q is

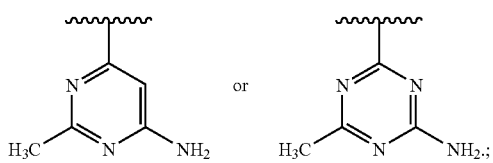

$Z^1$ is N;

$Z^2$ and $Z^4$ are CH;

$Ar^1$ is substituted pyridyl; and $Z^3$ is CR.

In aspect 19, the present invention provides compounds in accordance with any one of aspects 1 to 10, or a pharmaceutically acceptable salt thereof, wherein $Ar^1$ is selected from pyrazolyl, indolyl, phenyl, pyridyl, pyrimidinyl, benzoxazolyl, indazolyl, benzothiazolyl, quinolinyl, isoquinolinyl, benzimidazolyl, or benzothiadiazolyl, which can be unsubstituted or substituted.

In aspect 20, the present invention provides compounds in accordance with any of aspects 1 to 10, or a pharmaceutically acceptable salt thereof, wherein $Ar^1$ is selected from pyrazolyl, indolyl, phenyl, pyridyl, pyrimidinyl, benzoxazolyl, indazolyl, benzothiazolyl, quinolinyl, isoquinolinyl, benzimidazolyl, or benzothiadiazolyl, which can be unsubstituted or substituted with groups selected from —$OR^a$, halo, —$NR^aR^a$, $C_{1-4}$haloalkyl, —$N(R^a)C(=O)R^b$, —$N(R^a)S(=O)_2R^b$, —$N(R^a)S(=O)_2NR^aR^a$ or —$N(R^a)C(=O)NR^aR^a$.

In aspect 21, the present invention provides compounds of in accordance with aspect 1 or 2, or a pharmaceutically acceptable salt thereof, wherein Q is

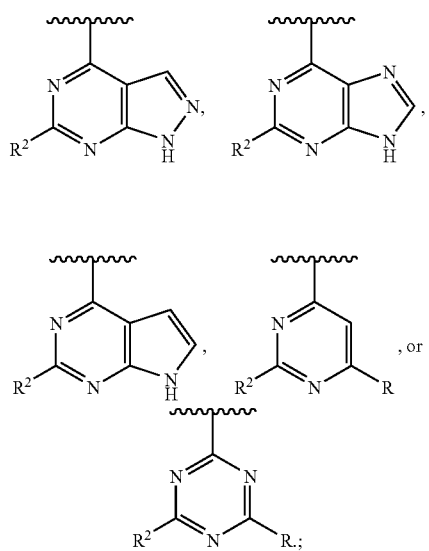

$Z^1$ is N; and $Z^2$, $Z^3$ and $Z^4$ are CR; and $Ar^1$ is selected from pyrazolyl, indolyl, phenyl, pyridyl, pyrimidinyl, benzoxazolyl, indazolyl, benzothiazolyl, quinolinyl, isoquinolinyl, benzimidazolyl, or benzothiadiazolyl.

In aspect 22, the present invention provides compounds of Formula I in accordance with aspect 1 or 2, or a pharmaceutically acceptable salt thereof, wherein Q is

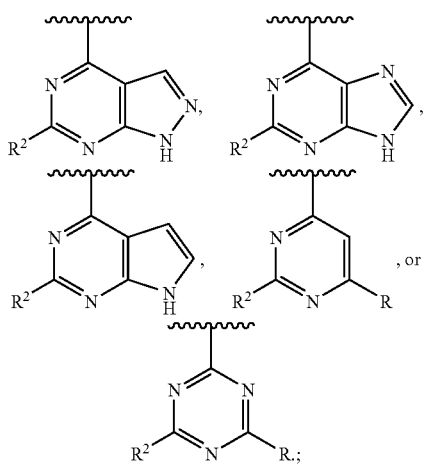

$Z^1$ is N; and $Z^2$, $Z^3$ and $Z^4$ are CH; and $Ar^1$ is selected from pyrazolyl, indolyl, phenyl, pyridyl, pyrimidinyl, benzoxazolyl, indazolyl, benzothiazolyl, quinolinyl, isoquinolinyl, benzimidazolyl, or benzothiadiazolyl.

In aspect 23, the present invention provides compounds in accordance with aspect 1 or 2, or a pharmaceutically acceptable salt thereof, wherein Q is

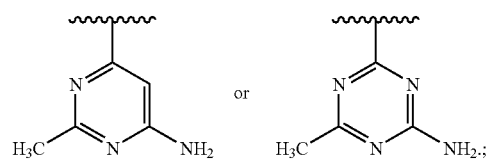

$Z^1$ is N; and $Z^2$, $Z^3$ and $Z^4$ are CR; and $Ar^1$ is selected from pyrazolyl, indolyl, phenyl, pyridyl, pyrimidinyl, benzoxazolyl, indazolyl, benzothiazolyl, quinolinyl, isoquinolinyl, benzimidazolyl, or benzothiadiazolyl, which can be unsubstituted or substituted.

In aspect 24, the present invention provides compounds, or a pharmaceutically acceptable salt thereof, selected from:

N-(3-(4-amino-6-methyl-1,3,5-triazin-2-yl)pyridin-2-yl)-1H-indol-4-amine;

3-(3-(4-amino-6-methyl-1,3,5-triazin-2-yl)pyridin-2-ylamino)phenol;

N-(3-(4-amino-6-methyl-1,3,5-triazin-2-yl)pyridin-2-yl)-1H-indazol-4-amine;

4-(2-(6-methoxypyridin-3-ylamino)pyridin-3-yl)-6-methyl-1,3,5-triazin-2-amine;

3-(3-(6-amino-2-methylpyrimidin-4-yl)pyridin-2-ylamino)phenol;

N-(3-(6-amino-2-methylpyrimidin-4-yl)pyridin-2-yl)-1H-indazol-4-amine;

N-(3-(6-amino-5-fluoro-2-methylpyrimidin-4-yl)pyridin-2-yl)-1H-indazol-4-amine;

3-(3-(4-amino-6-methyl-1,3,5-triazin-2-yl)-5-((4-(methylsulfonyl)piperazin-1-yl)methyl)pyridin-2-ylamino)phenol;

4-(2-(6-methoxypyridin-3-ylamino)-5-methylpyridin-3-yl)-6-methyl-1,3,5-triazin-2-amine;

methyl-6-(5-methyl-2-(pyridin-3-ylamino)pyridin-3-yl)-1,3,5-triazin-2-amine;

4-(5-methoxy-2-(6-methoxypyridin-3-ylamino)pyridin-3-yl)-6-methyl-1,3,5-triazin-2-amine;

N-(6-methoxypyridin-3-yl)-3-(4-methyl-1,3,5-triazin-2-yl)-5-((4-(methylsulfonyl)piperazin-1-yl)methyl)pyridin-2-amine;

4-(2-(6-methoxypyridin-3-ylamino)-5-((4-(methylsulfonyl)piperazin-1-yl)methyl)pyridin-3-yl)-6-methyl-1,3,5-triazin-2-amine;

N-(3-(4-amino-6-methyl-1,3,5-triazin-2-yl)-5-((4-(methylsulfonyl)piperazin-1-yl)methyl)pyridin-2-yl)-1H-indazol-4-amine;

4-methyl-6-(5-((4-(methylsulfonyl)piperazin-1-yl)methyl)-2-(6-(trifluoromethyl)pyridin-3-ylamino)pyridin-3-yl)-1,3,5-triazin-2-amine;

4-methyl-6-(5-((4-(methylsulfonyl)piperazin-1-yl)methyl)-2-(pyrimidin-5-ylamino)pyridin-3-yl)-1,3,5-triazin-2-amine;

N-(3-(4-amino-6-methyl-1,3,5-triazin-2-yl)-5-((4-(methylsulfonyl)piperazin-1-yl)methyl)pyridin-2-yl)benzo[d]oxazol-6-amine;

4-(2-(5-fluoro-6-methoxypyridin-3-ylamino)-5-((4-(methylsulfonyl)piperazin-1-yl)methyl)pyridin-3-yl)-6-methyl-1,3,5-triazin-2-amine;

4-(2-(6-methoxypyridin-3-ylamino)-5-(piperazin-1-ylmethyl)pyridin-3-yl)-6-methyl-1,3,5-triazin-2-amine;

4-(2-(6-methoxypyridin-3-ylamino)-5-(morpholinomethyl)pyridin-3-yl)-6-methyl-1,3,5-triazin-2-amine;

N-(3-(4-amino-6-methyl-1,3,5-triazin-2-yl)-5-methylpyridin-2-yl)-1H-indol-4-amine;

N-(3-(4-amino-6-methyl-1,3,5-triazin-2-yl)-5-methylpyridine-2-yl)-1H-indazol-4-amine;

4-(5-bromo-2-(4-methoxyphenylamino)pyridine-3-yl)-6-methyl-1,3,5-triazin-2-amine;

4-(2-(6-ethoxypyridin-3-ylamino)pyridine-3-yl)-6-methyl-1,3,5-triazin-2-amine;

N5-(3-(4-amino-6-methyl-1,3,5-triazin-2-yl)pyridin-2-yl)pyridine-2,5-diamine;

4-(2-(6-chloropyridin-3-ylamino)pyridin-3-yl)-6-methyl-1,3,5-triazin-2-amine;

N-(3-(6-methyl-1H-pyrazolo[3,4-d]pyrimidin-4-yl)pyridin-2-yl)-1H-indazol-4-amine;

N-(3-(2-methyl-9H-purin-6-yl)pyridin-2-yl)-1H-indol-4-amine;

N-(3-(2-methyl-9H-purin-6-yl)pyridin-2-yl)-1H-indazol-4-amine;

N-(6-methoxypyridin-3-yl)-3-(2-methyl-9H-purin-6-yl)pyridin-2-amine;

N-(5-chloro-3-(2-methyl-9H-purin-6-yl)pyridin-2-yl)-1H-indazol-4-amine;

N-(5-bromo-3-(2-methyl-9H-purin-6-yl)pyridine-2-yl)-1H-indazol-4-amine;

N-(3-(2-methyl-9H-purin-6-yl)-5-(trifluoromethyl)pyridine-2-yl)-1H-indazol-4-amine;

2-methoxy-N-(3-(2-methyl-9H-purin-6-yl)pyridin-2-yl)pyrimidin-5-amine;

N-(5-((4-methoxybenzyloxy)methyl)-3-(2-methyl-9H-purin-6-yl)pyridin-2-yl)-1H-indol-4-amine;

(6-(1H-indazol-4-ylamino)-5-(2-methyl-9H-purin-6-yl)pyridin-3-yl)methanol;

N-(6-methoxypyridin-3-yl)-3-(2-methyl-9H-purin-6-yl)-5-vinylpyridin-2-amine;

5-ethyl-N-(6-methoxypyridin-3-yl)-3-(2-methyl-9H-purin-6-yl)pyridin-2-amine;

2-(6-(6-methoxypyridin-3-ylamino)-5-(2-methyl-9H-purin-6-yl)pyridin-3-yl)ethanol;

(6-(6-methoxypyridin-3-ylamino)-5-(2-methyl-9H-purin-6-yl)pyridin-3-yl)methanol;

5-((4-methoxyphenylamino)methyl)-N-(6-methoxypyridin-3-yl)-3-(2-methyl-9H-purin-6-yl)pyridin-2-amine;

5-((3-methoxyphenylamino)methyl)-N-(6-methoxypyridin-3-yl)-3-(2-methyl-9H-purin-6-yl)pyridin-2-amine;

N-(6-methoxypyridin-3-yl)-3-(2-methyl-9H-purin-6-yl)-5-((pyridin-3-ylamino)methyl)pyridin-2-amine;

N-((6-(6-methoxypyridin-3-ylamino)-5-(2-methyl-9H-purin-6-yl)pyridin-3-yl)methyl)pyridazin-3-amine;

N-(6-methoxypyridin-3-yl)-3-(2-methyl-9H-purin-6-yl)-5-((pyridin-4-ylamino)methyl)pyridin-2-amine;

N-(6-methoxypyridin-3-yl)-3-(2-methyl-9H-purin-6-yl)-5-((pyridin-2-ylamino)methyl)pyridin-2-amine;

N-(6-methoxypyridin-3-yl)-3-(2-methyl-9H-purin-6-yl)-5-((phenylamino)methyl)pyridin-2-amine;

N-(6-methoxypyridin-3-yl)-3-(2-methyl-9H-purin-6-yl)-5-(piperazin-1-ylmethyl)pyridin-2-amine;

N-(6-methoxypyridin-3-yl)-3-(2-methyl-9H-purin-6-yl)-5-((4-(methylsulfonyl)piperazin-1-yl)methyl)pyridin-2-amine;

methyl 4-((6-(6-methoxypyridin-3-ylamino)-5-(2-methyl-9H-purin-6-yl)pyridin-3-yl)methyl)piperazine-1-carboxylate;

4-((6-(6-methoxypyridin-3-ylamino)-5-(2-methyl-9H-purin-6-yl)pyridin-3-yl)methyl)-N,N-dimethylpiperazine-1-carboxamide;

4-((6-(6-methoxypyridin-3-ylamino)-5-(2-methyl-9H-purin-6-yl)pyridin-3-yl)methyl)-N,N-dimethylpiperazine-1-sulfonamide;

1-(4-((6-(6-methoxypyridin-3-ylamino)-5-(2-methyl-9H-purin-6-yl)pyridin-3-yl)methyl)piperazin-1-yl)ethanone;

N5-(4-methoxyphenyl)-N2-(6-methoxypyridin-3-yl)-3-(2-methyl-9H-purin-6-yl)pyridine-2,5-diamine;

N5-benzyl-N2-(6-methoxypyridin-3-yl)-3-(2-methyl-9H-purin-6-yl)pyridine-2,5-diamine;

N2-(6-methoxypyridin-3-yl)-3-(2-methyl-9H-purin-6-yl)-N5-phenylpyridine-2,5-diamine;

N5-(2-methoxyethyl)-N2-(6-methoxypyridin-3-yl)-3-(2-methyl-9H-purin-6-yl)pyridine-2,5-diamine;

N5-ethyl-N2-(6-methoxypyridin-3-yl)-3-(2-methyl-9H-purin-6-yl)pyridine-2,5-diamine;

N5-(4-methoxybenzyl)-N2-(6-methoxypyridin-3-yl)-3-(2-methyl-9H-purin-6-yl)pyridine-2,5-diamine;

N5-(3-methoxyphenyl)-N2-(6-methoxypyridin-3-yl)-3-(2-methyl-9H-purin-6-yl)pyridine-2,5-diamine;

N-(3-(2-methyl-9H-purin-6-yl)-5-morpholinopyridin-2-yl)-1H-indazol-4-amine;

1-(6-(6-methoxypyridin-3-ylamino)-5-(2-methyl-9H-purin-6-yl)pyridin-3-yl)pyrrolidin-3-ol;

N-(6-methoxypyridin-3-yl)-3-(2-methyl-9H-purin-6-yl)-5-(4-(methylsulfonyl)piperazin-1-yl)pyridin-2-amine;

((2S)-1-(6-(6-methoxypyridin-3-ylamino)-5-(2-methyl-9H-purin-6-yl)pyridin-3-yl)pyrrolidin-2-yl)methanol;

((2R)-1-(6-(6-methoxypyridin-3-ylamino)-5-(2-methyl-9H-purin-6-yl)pyridin-3-yl)pyrrolidin-2-yl)methanol;

N-(4-(3-(2-methyl-9H-purin-6-yl)pyridin-2-ylamino)phenyl)acetamide;

N-(6-methoxypyridin-3-yl)-3-(2-methyl-9H-purin-6-yl)-5-(4-(methylsulfonyl)benzyl)pyridin-2-amine;

N-(3-(2-methyl-9H-purin-6-yl)-5-(4-(methylsulfonyl)benzyl)pyridin-2-yl)-1H-indazol-4-amine;

N-(5-(3-(2-methyl-9H-purin-6-yl)-5-(4-(methylsulfonyl)benzyl)pyridin-2-ylamino)pyridin-2-yl)acetamide;

N5-(3-(2-methyl-9H-purin-6-yl)-5-(4-(methylsulfonyl)benzyl)pyridin-2-yl)pyridine-2,5-diamine;

N-(3-(6-amino-2-methylpyrimidin-4-yl)pyridin-4-yl)-1H-indazol-4-amine;

N-(6-(4-(1H-indol-4-ylamino)pyridin-3-yl)-2-methylpyrimidin-4-yl)acetamide;

N-(3-(6-amino-2-methylpyrimidin-4-yl)pyridin-4-yl)-1H-indol-4-amine;

N-(3-(2-methyl-9H-purin-6-yl)pyridin-4-yl)-1H-indazol-4-amine;

6-methoxy-N-(3-(2-methyl-9H-purin-6-yl)pyridin-4-yl)pyridin-3-amine;

N-(3-(6-amino-2-methylpyrimidin-4-yl)pyrazin-2-yl)-1H-indazol-4-amine; or

N-(6-methoxypyridin-3-yl)-3-(2-methyl-9H-purin-6-yl)quinolin-2-amine

In aspect 25, the present invention provides compounds, or a pharmaceutically acceptable salt thereof, selected from:

4-(3-((6-methoxy-3-pyridinyl)amino)-2-pyrazinyl)-6-methyl-1,3,5-triazin-2-amine;

4-(3-((6-methoxy-3-pyridinyl)amino)-4-pyridinyl)-6-methyl-1,3,5-triazin-2-amine;

6-(3-((6-methoxy-3-pyridinyl)amino)-2-pyrazinyl)-2-methyl-4-pyrimidinamine;

4-(4-((6-methoxy-3-pyridinyl)amino)-5-pyrimidinyl)-6-methyl-1,3,5-triazin-2-amine;

5-(4-amino-6-methyl-1,3,5-triazin-2-yl)-N4-(6-methoxy-3-pyridinyl)-2,4-pyrimidinediamine;

4-(2-methoxy-4-((6-methoxy-3-pyridinyl)amino)-5-pyrimidinyl)-6-methyl-1,3,5-triazin-2-amine;

4-(4-((6-methoxy-3-pyridinyl)amino)-2-(4-morpholinyl)-5-pyrimidinyl)-6-methyl-1,3,5-triazin-2-amine;

5-(4-amino-6-methyl-1,3,5-triazin-2-yl)-N4-(6-methoxy-3-pyridinyl)-N2,N2-dimethyl-2,4-pyrimidinediamine;

4-(4-((6-methoxy-3-pyridinyl)amino)-2-(1-pyrrolidinyl)-5-pyrimidinyl)-6-methyl-1,3,5-triazin-2-amine;

4-(4-((6-methoxy-3-pyridinyl)amino)-2-(1-piperidinyl)-5-pyrimidinyl)-6-methyl-1,3,5-triazin-2-amine;

4-(4-((6-methoxy-3-pyridinyl)amino)-2-(4-pyridinyl)-5-pyrimidinyl)-6-methyl-1,3,5-triazin-2-amine;

4-(2-(4-fluorophenyl)-4-((6-methoxy-3-pyridinyl)amino)-5-pyrimidinyl)-6-methyl-1,3,5-triazin-2-amine;

5-(4-amino-6-methyl-1,3,5-triazin-2-yl)-N2-cyclopentyl-N4-(6-methoxy-3-pyridinyl)-2,4-pyrimidinediamine;

5-chloro-N-(6-methoxy-3-pyridinyl)-3-(2-methyl-9H-purin-6-yl)-2-pyridinamine;

N-(3-(4-amino-6-methyl-1,3,5-triazin-2-yl)-5-((4-(methylsulfonyl)-1-piperazinyl)methyl)-2-pyridinyl)-1,3-benzoxazol-5-amine;

N-(3-(4-amino-6-methyl-1,3,5-triazin-2-yl)-5-(4-morpholinylmethyl)-2-pyridinyl)-1,3-benzothiazol-5-amine;

4-(2-((5-fluoro-6-methoxy-3-pyridinyl)amino)-5-(4-morpholinylmethyl)-3-pyridinyl)-6-methyl-1,3,5-triazin-2-amine;

1-(6-((6-methoxy-3-pyridinyl)amino)-5-(2-methyl-9H-purin-6-yl)-3-pyridinyl)-2,2-dimethyl-1-propanol;

(1S)-1-(6-((6-methoxy-3-pyridinyl)amino)-5-(2-methyl-9H-purin-6-yl)-3-pyridinyl)-2,2-dimethyl-1-propanol;

(1R)-1-(6-((6-methoxy-3-pyridinyl)amino)-5-(2-methyl-9H-purin-6-yl)-3-pyridinyl)-2,2-dimethyl-1-propanol;

5-((tert-butylamino)methyl)-N-(6-methoxy-3-pyridinyl)-3-(2-methyl-9H-purin-6-yl)-2-pyridinamine;

N-(6-methoxy-3-pyridinyl)-5-(((1-methylethyl)amino)methyl)-3-(2-methyl-9H-purin-6-yl)-2-pyridinamine;

N-(6-methoxy-3-pyridinyl)-3-(2-methyl-9H-purin-6-yl)-5-(((2-pyridinylmethyl)amino)methyl)-2-pyridinamine;

N-(6-methoxy-3-pyridinyl)-3-(2-methyl-9H-purin-6-yl)-5-(((4-pyridinylmethyl)amino)methyl)-2-pyridinamine;

N-(6-methoxy-3-pyridinyl)-3-(2-methyl-9H-purin-6-yl)-5-(((3-pyridinylmethyl)amino)methyl)-2-pyridinamine;

(6-(((6-methoxy-3-pyridinyl)amino)-5-(2-methyl-9H-purin-6-yl)-3-pyridinyl)(4-(methylsulfonyl)phenyl)methanol;

N-(6-methoxy-3-pyridinyl)-3-(2-methyl-9H-purin-6-yl)-5-(1-(4-(methylsulfonyl)-1-piperazinyl)ethyl)-2-pyridinamine;

4-(2-((6-methoxy-3-pyridinyl)amino)-5-(4-(methylsulfonyl)benzyl)-3-pyridinyl)-6-methyl-1,3,5-triazin-2-amine;

4-(2-((5-fluoro-6-methoxy-3-pyridinyl)amino)-5-(4-(methylsulfonyl)benzyl)-3-pyridinyl)-6-methyl-1,3,5-triazin-2-amine;

4-(2-((5-fluoro-6-methoxy-3-pyridinyl)amino)-5-(1-(4-(methylsulfonyl)-1-piperazinyl)ethyl)-3-pyridinyl)-6-methyl-1,3,5-triazin-2-amine;

4-(2-((6-methoxy-3-pyridinyl)amino)-5-(1-(4-(methylsulfonyl)-1-piperazinyl)ethyl)-3-pyridinyl)-6-methyl-1,3,5-triazin-2-amine;

4-(2-((6-methoxy-3-pyridinyl)amino)-5-((1S)-1-(4-(methylsulfonyl)-1-piperazinyl)ethyl)-3-pyridinyl)-6-methyl-1,3,5-triazin-2-amine;

4-(2-((6-methoxy-3-pyridinyl)amino)-5-((1R)-1-(4-(methylsulfonyl)-1-piperazinyl)ethyl)-3-pyridinyl)-6-methyl-1,3,5-triazin-2-amine;

4-(2-((5-fluoro-6-methoxy-3-pyridinyl)amino)-5-((1S)-1-(4-(methylsulfonyl)-1-piperazinyl)ethyl)-3-pyridinyl)-6-methyl-1,3,5-triazin-2-amine;

4-(2-((5-fluoro-6-methoxy-3-pyridinyl)amino)-5-((1R)-1-(4-(methylsulfonyl)-1-piperazinyl)ethyl)-3-pyridinyl)-6-methyl-1,3,5-triazin-2-amine;

4-(2-((6-methoxy-3-pyridinyl)amino)-5-(1-(4-(methylsulfonyl)phenyl)ethyl)-3-pyridinyl)-6-methyl-1,3,5-triazin-2-amine;

4-(2-((5-fluoro-6-methoxy-3-pyridinyl)amino)-5-(1-(4-(methylsulfonyl)phenyl)ethyl)-3-pyridinyl)-6-methyl-1,3,5-triazin-2-amine;

4-(2-((6-methoxy-3-pyridinyl)amino)-5-(4-morpholinylcarbonyl)-3-pyridinyl)-6-methyl-1,3,5-triazin-2-amine;

4-(2-((5-fluoro-6-methoxy-3-pyridinyl)amino)-5-((4-(methylsulfonyl)-1-piperazinyl)carbonyl)-3-pyridinyl)-6-methyl-1,3,5-triazin-2-amine;

5-(4-amino-6-methyl-1,3,5-triazin-2-yl)-N-(2-methoxyethyl)-6-((6-methoxy-3-pyridinyl)amino)-3-pyridinecarboxamide;

4-((5-(4-amino-6-methyl-1,3,5-triazin-2-yl)-6-((6-methoxy-3-pyridinyl)amino)-3-pyridinyl)methyl)-3-morpholinone;

4-(2-((6-methoxy-3-pyridinyl)amino)-5-((1-(methylsulfonyl)-4-piperidinyl)methyl)-3-pyridinyl)-6-methyl-1,3,5-triazin-2-amine;

4-(5-benzyl-2-((6-methoxy-3-pyridinyl)amino)-3-pyridinyl)-6-methyl-1,3,5-triazin-2-amine;

4-(2-((6-methoxy-3-pyridinyl)amino)-5-((4-methyl-1-piperazinyl)methyl)-3-pyridinyl)-6-methyl-1,3,5-triazin-2-amine;

4-(2-((6-methoxy-3-pyridinyl)amino)-5-(((2R)-2-methyl-4-(methylsulfonyl)-1-piperazinyl)methyl)-3-pyridinyl)-6-methyl-1,3,5-triazin-2-amine;

4-((5-(4-amino-6-methyl-1,3,5-triazin-2-yl)-6-((5-fluoro-6-methoxy-3-pyridinyl)amino)-3-pyridinyl)methyl)-N,N-dimethyl-1-piperazinecarboxamide;

4-((5-(4-amino-6-methyl-1,3,5-triazin-2-yl)-6-((5-fluoro-6-hydroxy-3-pyridinyl)amino)-3-pyridinyl)methyl)-N,N-dimethyl-1-piperazinecarboxamide;

5-((3-(4-amino-6-methyl-1,3,5-triazin-2-yl)-5-((4-(methylsulfonyl)-1-piperazinyl)methyl)-2-pyridinyl)amino)-3-fluoro-2-pyridinol;

4-(2-((5-methoxy-3-pyridinyl)amino)-5-((4-(methylsulfonyl)-1-piperazinyl)methyl)-3-pyridinyl)-6-methyl-1,3,5-triazin-2-amine;

4-(2-((6-methoxy-3-pyridinyl)amino)-5-((4-(methylsulfonyl)-1-piperazinyl)methyl)-3-pyridinyl)-N,6-dimethyl-1,3,5-triazin-2-amine;
4-(2-((3-(difluoromethoxy)phenyl)amino)-3-pyridinyl)-6-methyl-1,3,5-triazin-2-amine;
N-(3-(4-amino-6-methyl-1,3,5-triazin-2-yl)-2-pyridinyl)-2-methyl-1,3-benzoxazol-5-amine;
4-(2-((3-fluoro-4-methoxyphenyl)amino)-3-pyridinyl)-6-methyl-1,3,5-triazin-2-amine;
4-(2-((4-fluoro-3-methoxyphenyl)amino)-3-pyridinyl)-6-methyl-1,3,5-triazin-2-amine;
4-(2-((2,2-difluoro-1,3-benzodioxol-5-yl)amino)-3-pyridinyl)-6-methyl-1,3,5-triazin-2-amine;
5-(4-amino-6-methyl-1,3,5-triazin-2-yl)-6'-methoxy-N-(6-methoxy-3-pyridinyl)-3,3'-bipyridin-6-amine;
4-(2-((3,4-dimethoxyphenyl)amino)-3-pyridinyl)-6-methyl-1,3,5-triazin-2-amine;
N-(3-(4-amino-6-methyl-1,3,5-triazin-2-yl)-2-pyridinyl)-2-methyl-6-quinolinamine;
5'-(4-amino-6-methyl-1,3,5-triazin-2-yl)-N-(6-methoxy-3-pyridinyl)-2,3'-bipyridin-6'-amine;
4-(2-((5-chloro-6-methoxy-3-pyridinyl)amino)-3-pyridinyl)-6-methyl-1,3,5-triazin-2-amine;
4-methyl-6-(2-((5-methyl-3-pyridinyl)amino)-3-pyridinyl)-1,3,5-triazin-2-amine;
5-(4-amino-6-methyl-1,3,5-triazin-2-yl)-N-(5-fluoro-6-methoxy-3-pyridinyl)-2,4'-bipyridin-6-amine;
1-((5-(4-amino-6-methyl-1,3,5-triazin-2-yl)-6-((5-fluoro-6-methoxy-3-pyridinyl)amino)-3-pyridinyl)carbonyl)-4-piperidinol;
6-(2-((6-methoxy-3-pyridinyl)amino)-5-((4-(methylsulfonyl)-1-piperazinyl)methyl)-3-pyridinyl)-2-methyl-4-pyrimidinamine;
(5-(4-amino-6-methyl-1,3,5-triazin-2-yl)-6-((6-methoxy-3-pyridinyl)amino)-3-pyridinyl)methanol;
3-(6-amino-2-methyl-4-pyrimidinyl)-N-1H-indazol-4-yl-2-quinoxalinamine;
N-(2-chloro-4-((3-(2-methyl-9H-purin-6-yl)-2-pyridinyl)amino)phenyl)acetamide;
N-(4-((3-(2-methyl-9H-purin-6-yl)-2-pyridinyl)amino)phenyl)cyclopropanecarboxamide;
N-(5-methoxy-3-pyridinyl)-3-(2-methyl-9H-purin-6-yl)-2-pyridinamine;
4-(5-chloro-2-((6-methoxy-3-pyridinyl)amino)-3-pyridinyl)-6-methyl-1,3,5-triazin-2-amine;
4-(5-fluoro-2-((5-fluoro-6-methoxy-3-pyridinyl)amino)-3-pyridinyl)-6-methyl-1,3,5-triazin-2-amine;
4-(5-fluoro-2-((5-fluoro-3-pyridinyl)amino)-3-pyridinyl)-6-methyl-1,3,5-triazin-2-amine;
5-(4-amino-6-methyl-1,3,5-triazin-2-yl)-6-((5-fluoro-6-methoxy-3-pyridinyl)amino)-3-pyridinecarbaldehyde;
4-(5-chloro-2-(tetrahydro-2H-pyran-4-ylamino)-3-pyridinyl)-6-methyl-1,3,5-triazin-2-amine;
4-(5-chloro-2-((5-fluoro-6-methoxy-3-pyridinyl)amino)-3-pyridinyl)-N-(2-methoxyethyl)-6-methyl-1,3,5-triazin-2-amine;
1-(5-((3-(4-amino-6-methyl-1,3,5-triazin-2-yl)-2-pyridinyl)amino)-2-pyridinyl)-3-phenylurea;
1-(5-((3-(4-amino-6-methyl-1,3,5-triazin-2-yl)-2-pyridinyl)amino)-2-pyridinyl)-3-(3-fluorophenyl)urea;
1-(5-((3-(4-amino-6-methyl-1,3,5-triazin-2-yl)-2-pyridinyl)amino)-2-pyridinyl)-3-(1-methylethyl)urea;
N-(5-((3-(4-amino-6-methyl-1,3,5-triazin-2-yl)-5-chloro-2-pyridinyl)amino)-2-pyridinyl)acetamide;
methyl (5-((3-(4-amino-6-methyl-1,3,5-triazin-2-yl)-5-chloro-2-pyridinyl)amino)-2-pyridinyl)carbamate;
1-(5-((3-(4-amino-6-methyl-1,3,5-triazin-2-yl)-5-chloro-2-pyridinyl)amino)-2-pyridinyl)-3-(4-(2-methoxyethoxy)phenyl)urea;
N-(5-((3-(4-amino-6-methyl-1,3,5-triazin-2-yl)-5-((4-(methylsulfonyl)-1-piperazinyl)methyl)-2-pyridinyl)amino)-2-pyridinyl)acetamide;
4-(2-((5-fluoro-6-methoxy-3-pyridinyl)amino)-6-methyl-3-pyridinyl)-6-methyl-1,3,5-triazin-2-amine;
4-(2-((5-fluoro-6-methoxy-3-pyridinyl)amino)-6-(4-morpholinylmethyl)-3-pyridinyl)-6-methyl-1,3,5-triazin-2-amine;
4-(2-((5-fluoro-6-methoxy-3-pyridinyl)amino)-6-((2,2,2-trifluoroethoxy)methyl)-3-pyridinyl)-6-methyl-1,3,5-triazin-2-amine;
4-(2-((5-fluoro-3-pyridinyl)amino)-6-methyl-3-pyridinyl)-6-methyl-1,3,5-triazin-2-amine;
4-(2-((6-methoxy-3-pyridinyl)amino)-5-(4-thiomorpholinylmethyl)-3-pyridinyl)-6-methyl-1,3,5-triazin-2-amine;
4-(2-((6-methoxy-3-pyridinyl)amino)-5-((1-oxido-4-thiomorpholinyl)methyl)-3-pyridinyl)-6-methyl-1,3,5-triazin-2-amine;
N-(3-(4-amino-6-methyl-1,3,5-triazin-2-yl)-5-((4-(methylsulfonyl)-1-piperazinyl)methyl)-2-pyridinyl)-3-methyl-3H-imidazo[4,5-b]pyridin-6-amine;
((3S)-1-(6-((6-methoxy-3-pyridinyl)amino)-5-(2-methyl-9H-purin-6-yl)-3-pyridinyl)-3-pyrrolidinyl)methanol;
(3S)-1-(6-((6-methoxy-3-pyridinyl)amino)-5-(2-methyl-9H-purin-6-yl)-3-pyridinyl)-3-pyrrolidinol;
(3R)-1-(6-((6-methoxy-3-pyridinyl)amino)-5-(2-methyl-9H-purin-6-yl)-3-pyridinyl)-3-pyrrolidinol;
4-(2-((2-methoxy-5-pyrimidinyl)amino)-5-((4-(methylsulfonyl)-1-piperazinyl)methyl)-3-pyridinyl)-6-methyl-1,3,5-triazin-2-amine;
4-((5-(4-amino-6-methyl-1,3,5-triazin-2-yl)-6-((6-methoxy-3-pyridinyl)amino)-3-pyridinyl)methyl)-N,N-dimethyl-1-piperazinesulfonamide;
1-((5-(4-amino-6-methyl-1,3,5-triazin-2-yl)-6-((6-methoxy-3-pyridinyl)amino)-3-pyridinyl)methyl)-4-piperidinol;
((3R)-1-((5-(4-amino-6-methyl-1,3,5-triazin-2-yl)-6-((6-methoxy-3-pyridinyl)amino)-3-pyridinyl)methyl)-3-pyrrolidinyl)methanol;
4-(2-((6-methoxy-3-pyridinyl)amino)-5-(((3S)-3-methyl-4-morpholinyl)methyl)-3-pyridinyl)-6-methyl-1,3,5-triazin-2-amine;
4-(5-(1-azetidinylmethyl)-2-((6-methoxy-3-pyridinyl)amino)-3-pyridinyl)-6-methyl-1,3,5-triazin-2-amine;
4-(2-((6-methoxy-3-pyridinyl)amino)-5-(1-pyrrolidinylmethyl)-3-pyridinyl)-6-methyl-1,3,5-triazin-2-amine;
4-(2-((6-methoxy-3-pyridinyl)amino)-5-(1-piperidinylmethyl)-3-pyridinyl)-6-methyl-1,3,5-triazin-2-amine;
4-(2-((6-methoxy-3-pyridinyl)amino)-5-((3-(methylsulfonyl)-1-azetidinyl)methyl)-3-pyridinyl)-6-methyl-1,3,5-triazin-2-amine;
4-(2-((6-methoxy-3-pyridinyl)amino)-5-((4-(methylsulfonyl)-1-piperidinyl)methyl)-3-pyridinyl)-6-methyl-1,3,5-triazin-2-amine;
2-(((5-(4-amino-6-methyl-1,3,5-triazin-2-yl)-6-((6-methoxy-3-pyridinyl)amino)-3-pyridinyl)methyl)amino)ethanol;
(2R)-2-(((5-(4-amino-6-methyl-1,3,5-triazin-2-yl)-6-((6-methoxy-3-pyridinyl)amino)-3-pyridinyl)methyl)amino)-1-propanol;
4-(5-(((2-methoxyethyl)amino)methyl)-2-((6-methoxy-3-pyridinyl)amino)-3-pyridinyl)-6-methyl-1,3,5-triazin-2-amine;

4-(2-((6-methoxy-3-pyridinyl)amino)-5-(((3R,S)-3-(methylsulfonyl)-1-pyrrolidinyl)methyl)-3-pyridinyl)-6-methyl-1,3,5-triazin-2-amine;

1-((5-(4-amino-6-methyl-1,3,5-triazin-2-yl)-6-((6-methoxy-3-pyridinyl)amino)-3-pyridinyl)methyl)-3-azetidinol;

2-((5-(4-amino-6-methyl-1,3,5-triazin-2-yl)-6-((6-methoxy-3-pyridinyl)amino)-3-pyridinyl)methyl)-2,5,7-triazaspiro[3.4]octane-6,8-dione;

4-(5-((3-amino-1-azetidinyl)methyl)-2-((6-methoxy-3-pyridinyl)amino)-3-pyridinyl)-6-methyl-1,3,5-triazin-2-amine;

N-(1-((5-(4-amino-6-methyl-1,3,5-triazin-2-yl)-6-((6-methoxy-3-pyridinyl)amino)-3-pyridinyl)methyl)-3-azetidinyl)methanesulfonamide;

4-(5-(5,6-dihydro[1,2,4]triazolo[1,5-a]pyrazin-7(8H)-ylmethyl)-2-((6-methoxy-3-pyridinyl)amino)-3-pyridinyl)-6-methyl-1,3,5-triazin-2-amine;

2-((5-(4-amino-6-methyl-1,3,5-triazin-2-yl)-6-((6-methoxy-3-pyridinyl)amino)-3-pyridinyl)(hydroxy)methyl)-4-bromo-N,N-dimethylbenzenesulfonamide;

4-((5-(4-amino-6-methyl-1,3,5-triazin-2-yl)-6-((6-methoxy-3-pyridinyl)amino)-3-pyridinyl)(hydroxy)methyl)-N,N-dimethylbenzenesulfonamide;

4-(amino(5-(4-amino-6-methyl-1,3,5-triazin-2-yl)-6-((6-methoxy-3-pyridinyl)amino)-3-pyridinyl)methyl)-N,N-dimethylbenzenesulfonamide;

3-(4-amino-6-methyl-1,3,5-triazin-2-yl)-N-(6-methoxy-3-pyridinyl)-2-quinolinamine;

4-(2-((6-methoxy-3-pyridinyl)amino)phenyl)-6-methyl-1,3,5-triazin-2-amine;

N-(3-(4-amino-6-methyl-1,3,5-triazin-2-yl)-5-((4-(methylsulfonyl)-1-piperazinyl)methyl)-2-pyridinyl)-1,3-benzothiazol-5-amine;

N-(3-(4-amino-6-methyl-1,3,5-triazin-2-yl)-5-((4-(methylsulfonyl)-1-piperazinyl)methyl)-2-pyridinyl)-1,3-benzothiazol-6-amine;

4-(2-((5-fluoro-3-pyridinyl)amino)-5-((4-(methylsulfonyl)-1-piperazinyl)methyl)-3-pyridinyl)-6-methyl-1,3,5-triazin-2-amine;

4-methyl-6-(5-((4-(methylsulfonyl)-1-piperazinyl)methyl)-2-(1H-pyrazol-4-ylamino)-3-pyridinyl)-1,3,5-triazin-2-amine;

4-methyl-6-(5-((4-(methylsulfonyl)-1-piperazinyl)methyl)-2-(1H-pyrazol-3-ylamino)-3-pyridinyl)-1,3,5-triazin-2-amine;

N-(3-(4-amino-6-methyl-1,3,5-triazin-2-yl)-5-((4-(methylsulfonyl)-1-piperazinyl)methyl)-2-pyridinyl)-6-fluoro-1H-indazol-4-amine;

4-(2-((5-fluoro-6-methoxy-3-pyridinyl)amino)-3-pyridinyl)-6-methyl-1,3,5-triazin-2-amine;

4-(2-((6-methoxy-3-pyridinyl)amino)-5-(1-methyl-1H-pyrazol-4-yl)-3-pyridinyl)-6-methyl-1,3,5-triazin-2-amine;

4-(2-((3,4-difluorophenyl)amino)-3-pyridinyl)-6-methyl-1,3,5-triazin-2-amine;

5-(4-amino-6-methyl-1,3,5-triazin-2-yl)-N-(6-methoxy-3-pyridinyl)-1',2',3',6'-tetrahydro-3,4'-bipyridin-6-amine;

4-(2-((6-methoxy-3-pyridinyl)amino)-5-(1H-pyrazol-4-yl)-3-pyridinyl)-6-methyl-1,3,5-triazin-2-amine;

5-(4-amino-6-methyl-1,3,5-triazin-2-yl)-N-(6-methoxy-3-pyridinyl)-6'-methyl-3,3'-bipyridin-6-amine;

4-(2-((6-methoxy-3-pyridinyl)amino)-5-(4-pyridazinyl)-3-pyridinyl)-6-methyl-1,3,5-triazin-2-amine;

5-(4-amino-6-methyl-1,3,5-triazin-2-yl)-5'-fluoro-N-(6-methoxy-3-pyridinyl)-3,3'-bipyridin-6-amine;

5-(4-amino-6-methyl-1,3,5-triazin-2-yl)-N-(6-methoxy-3-pyridinyl)-2,3'-bipyridin-6-amine;

5-(4-amino-6-methyl-1,3,5-triazin-2-yl)-N-(5-fluoro-6-methoxy-3-pyridinyl)-2,3'-bipyridin-6-amine;

4-(5-(3,6-dihydro-2H-pyran-4-yl)-2-((6-methoxy-3-pyridinyl)amino)-3-pyridinyl)-6-methyl-1,3,5-triazin-2-amine;

4-(5-chloro-2-((5-fluoro-3-pyridinyl)amino)-3-pyridinyl)-6-methyl-1,3,5-triazin-2-amine;

4-(2-((5-fluoro-3-pyridinyl)amino)-5-(1-methyl-1H-pyrazol-4-yl)-3-pyridinyl)-6-methyl-1,3,5-triazin-2-amine;

4-(2-((5-fluoro-6-methoxy-3-pyridinyl)amino)-6-(2-methoxyethoxy)-3-pyridinyl)-6-methyl-1,3,5-triazin-2-amine;

N-(3-(4-amino-6-methyl-1,3,5-triazin-2-yl)-5-((4-(methylsulfonyl)-1-piperazinyl)methyl)-2-pyridinyl)-1H-benzimidazol-5-amine;

N-(3-(4-amino-6-methyl-1,3,5-triazin-2-yl)-5-(1-piperazinylmethyl)-2-pyridinyl)-1H-benzimidazol-5-amine;

4-(5-(difluoromethoxy)-2-((6-methoxy-3-pyridinyl)amino)-3-pyridinyl)-6-methyl-1,3,5-triazin-2-amine;

4-((3-(4-amino-6-methyl-1,3,5-triazin-2-yl)-2-pyridinyl)amino)-2(1H)-pyridinone;

N-(5-((3-(4-amino-6-methyl-1,3,5-triazin-2-yl)-2-pyridinyl)amino)-2-chloro-3-pyridinyl)-4-fluorobenzenesulfonamide;

N5-(3-(4-amino-6-methyl-1,3,5-triazin-2-yl)-2-pyridinyl)-2-chloro-3,5-pyridinediamine;

N-(4-((3-(4-amino-6-methyl-1,3,5-triazin-2-yl)-5-chloro-2-pyridinyl)amino)-2-fluorophenyl)acetamide;

N-(4-((3-(4-amino-6-methyl-1,3,5-triazin-2-yl)-5-((4-(methylsulfonyl)-1-piperazinyl)methyl)-2-pyridinyl)amino)-2-fluorophenyl)acetamide;

N-(4-((3-(4-amino-6-methyl-1,3,5-triazin-2-yl)-5-((4-(methylsulfonyl)-1-piperazinyl)methyl)-2-pyridinyl)amino)phenyl)acetamide;

(1R,S)-1-(5-(4-amino-6-methyl-1,3,5-triazin-2-yl)-6-((6-methoxy-3-pyridinyl)amino)-3-pyridinyl)-2,2,2-trifluoroethanol;

4-(2-((5-fluoro-6-methoxy-3-pyridinyl)amino)-5-(((2S)-2-methyl-4-(methylsulfonyl)-1-piperazinyl)methyl)-3-pyridinyl)-6-methyl-1,3,5-triazin-2-amine;

4-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-6-methyl-1,3,5-triazin-2-amine;

4-(2-((5-fluoro-6-methoxy-3-pyridinyl)amino)-5-((1S)-1-((2S)-2-methyl-4-(methylsulfonyl)-1-piperazinyl)ethyl)-3-pyridinyl)-6-methyl-1,3,5-triazin-2-amine;

2-(5-(4-amino-6-methyl-1,3,5-triazin-2-yl)-6-((5-fluoro-6-methoxy-3-pyridinyl)amino)-3-pyridinyl)-2-propanol;

6-(2-((5-fluoro-6-methoxy-3-pyridinyl)amino)-5-((1S)-1-(4-morpholinyl)ethyl)-3-pyridinyl)-2-methyl-4-pyrimidinamine;

6-(2-((5-fluoro-6-methoxy-3-pyridinyl)amino)-5-((1R)-1-(4-morpholinyl)ethyl)-3-pyridinyl)-2-methyl-4-pyrimidinamine;

4-(5-(1-amino-1-methylethyl)-2-((6-methoxy-3-pyridinyl)amino)-3-pyridinyl)-6-methyl-1,3,5-triazin-2-amine;

4-(5-(1-amino-1-methylethyl)-2-((5-fluoro-6-methoxy-3-pyridinyl)amino)-3-pyridinyl)-6-methyl-1,3,5-triazin-2-amine;

4-(2-((6-methoxy-3-pyridinyl)amino)-5-(1-methyl-1-(4-(methylsulfonyl)-1-piperazinyl)ethyl)-3-pyridinyl)-6-methyl-1,3,5-triazin-2-amine;

4-(2-((5-fluoro-6-methoxy-3-pyridinyl)amino)-5-(1-methyl-1-(4-(methylsulfonyl)-1-piperazinyl)ethyl)-3-pyridinyl)-6-methyl-1,3,5-triazin-2-amine;

4-(2-((5-fluoro-6-methoxy-3-pyridinyl)amino)-5-(1-methyl-1-(4-morpholinyl)ethyl)-3-pyridinyl)-6-methyl-1,3,5-triazin-2-amine;

4-(2-((6-methoxy-3-pyridinyl)amino)-5-(1-(4-(methylsulfo-nyl)-1-piperazinyl)cyclopropyl)-3-pyridinyl)-6-methyl-1,3,5-triazin-2-amine;

4-(2-(6-methoxypyridin-3-ylamino)-5-(1-(4-(methylsulfo-nyl)piperazin-1-yl)ethyl)pyridin-3-yl)-6-methyl-1,3,5-triazin-2-amine;

(S)-4-(2-(6-methoxypyridin-3-ylamino)-5-(1-(4-(methylsul-fonyl)piperazin-1-yl)ethyl)pyridin-3-yl)-6-methyl-1,3,5-triazin-2-amine;

(R)-4-(2-(6-methoxypyridin-3-ylamino)-5-(1-(4-(methyl-sulfonyl)piperazin-1-yl)ethyl)pyridin-3-yl)-6-methyl-1,3,5-triazin-2-amine;

4-(2-(5-fluoro-6-methoxypyridin-3-ylamino)-5-(1-(4-(me-thylsulfonyl)piperazin-1-yl)ethyl)pyridin-3-yl)-6-methyl-1,3,5-triazin-2-amine; (s)-4-(2-(5-fluoro-6-methoxypyri-din-3-ylamino)-5-(1-(4-(methylsulfonyl)piperazin-1-yl)ethyl)pyridin-3-yl)-6-methyl-1,3,5-triazin-2-amine;

(R)-4-(2-(5-fluoro-6-methoxypyridin-3-ylamino)-5-(1-(4-(methylsulfonyl)piperazin-1-yl)ethyl)pyridin-3-yl)-6-me-thyl-1,3,5-triazin-2-amine;

(S)-4-(2-(5-fluoro-6-methoxypyridin-3-ylamino)-5-((2-me-thyl-4-(methylsulfonyl)piperazin-1-yl)methyl)pyridin-3-yl)-6-methyl-1,3,5-triazin-2-amine; or 4-(2-(5-fluoro-6-methoxypyridin-3-ylamino)-5-((R)-1-((S)-2-methyl-4-(methylsulfonyl)piperazin-1-yl)ethyl)pyri-din-3-yl)-6-methyl-1,3,5-triazin-2-amine.

In aspect 26, the present invention provides compounds, or a pharmaceutically acceptable salt thereof, selected from:

6-(3-(5-fluoro-6-methoxypyridin-3-ylamino)-6-(1-(4-(me-thylsulfonyl)piperazin-1-yl)ethyl)pyrazin-2-yl)-2-meth-ylpyrimidin-4-amine;

2-(6-(6-amino-2-methylpyrimidin-4-yl)-5-(5-fluoro-6-methoxypyridin-3-ylamino)pyrazin-2-yl)propan-2-ol;

1-(6-(6-amino-2-methylpyrimidin-4-yl)-5-(6-methoxypyri-din-3-ylamino)pyrazin-2-yl)ethanone;

6-(3-(6-methoxypyridin-3-ylamino)-6-(1-(4-(methylsulfo-nyl)piperazin-1-yl)ethyl)pyrazin-2-yl)-2-methylpyrimi-din-4-amine;

(R)-N-(3-(4-amino-6-methyl-1,3,5-triazin-2-yl)-5-(1-(4-(methylsulfonyl)piperazin-1-yl)ethyl)pyridin-2-yl)-5-fluoroquinolin-7-amine;

N-(3-(4-amino-6-methyl-1,3,5-triazin-2-yl)-5-(1-morpholi-noethyl)pyridin-2-yl)benzo[d]thiazol-5-amine;

4-(1-(5-(4-amino-6-methyl-1,3,5-triazin-2-yl)-6-(benzo[d]thiazol-5-ylamino)pyridin-3-yl)ethyl)-N,N-dimethylpip-erazine-1-carboxamide;

N-(3-(4-amino-6-methyl-1,3,5-triazin-2-yl)-5-(1-(4-(meth-ylsulfonyl)piperazin-1-yl)ethyl)pyridin-2-yl)benzo[d]thiazol-5-amine;

(R)-4-(2-(5-fluoro-6-methoxypyridin-3-ylamino)-5-(1-mor-pholinoethyl)pyridin-3-yl)-6-methyl-1,3,5-triazin-2-amine;

(S)-4-(2-(5-fluoro-6-methoxypyridin-3-ylamino)-5-(1-mor-pholinoethyl)pyridin-3-yl)-6-methyl-1,3,5-triazin-2-amine;

N-(3-(4-amino-6-methyl-1,3,5-triazin-2-yl)-5-((R)-1-((S)-2-methyl-4-(methylsulfonyl)piperazin-1-yl)ethyl)pyri-din-2-yl)benzo[d]thiazol-5-amine;

4-(1-(5-(4-amino-6-methyl-1,3,5-triazin-2-yl)-6-(5-fluoro-6-methoxypyridin-3-ylamino)pyridin-3-yl)ethyl)-N,N-dimethylpiperazine-1-carboxamide;

N-(5-fluoro-6-methoxypyridin-3-yl)-5-((R)-1-((S)-2-me-thyl-4-(methylsulfonyl)piperazin-1-yl)ethyl)-3-(2-me-thyl-9H-purin-6-yl)pyridin-2-amine;

N-(5-fluoro-6-methoxypyridin-3-yl)-5-((S)-1-((S)-2-me-thyl-4-(methylsulfonyl)piperazin-1-yl)ethyl)-3-(2-me-thyl-9H-purin-6-yl)pyridin-2-amine;

(R)-N-(5-fluoro-6-methoxypyridin-3-yl)-3-(2-methyl-9H-purin-6-yl)-5-(1-(4-(methylsulfonyl)piperazin-1-yl)ethyl)pyridin-2-amine;

1-(5-(4-amino-6-methyl-1,3,5-triazin-2-yl)-6-(5-fluoro-6-methoxypyridin-3-ylamino)pyridin-3-yl)cyclopropanol;

4-(2-(5-fluoro-6-methoxypyridin-3-ylamino)-5-(1-(isopro-pylamino)ethyl)pyridin-3-yl)-6-methyl-1,3,5-triazin-2-amine;

4-(5-(1-aminocyclopropyl)-2-(5-fluoro-6-methoxypyridin-3-ylamino)pyridin-3-yl)-6-methyl-1,3,5-triazin-2-amine;

4-(5-(3-aminopentan-3-yl)-2-(5-fluoro-6-methoxypyridin-3-ylamino)pyridin-3-yl)-6-methyl-1,3,5-triazin-2-amine;

(R)-4-(2-(5-isopropyl-6-methoxypyridin-3-ylamino)-5-(1-(4-(methylsulfonyl)piperazin-1-yl)ethyl)pyridin-3-yl)-6-methyl-1,3,5-triazin-2-amine;

4-(5-(ethylsulfonyl)-2-(5-fluoro-6-methoxypyridin-3-ylamino)pyridin-3-yl)-6-methyl-1,3,5-triazin-2-amine;

N-(5-((3-(6-amino-2-methyl-4-pyrimidinyl)-2-pyridinyl)amino)-2-chloro-3-pyridinyl)methanesulfonamide;

6-(2-((5-fluoro-6-methoxy-3-pyridinyl)amino)-5-((1R)-1-(4-(methylsulfonyl)-1-piperazinyl)ethyl)-3-pyridinyl)-2-methyl-4-pyrimidinamine;

6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-2-methyl-4-pyrimidinamine;

N-(5-((3-(6-amino-2-methyl-4-pyrimidinyl)-2-pyrazinyl)amino)-2-chloro-3-pyridinyl)methanesulfonamide;

4-(2-(6-methoxypyridin-3-ylamino)-5-(1-(3-(methylsulfo-nyl)azetidin-1-yl)ethyl)pyridin-3-yl)-6-methyl-1,3,5-tri-azin-2-amine;

(R)-4-(2-(6-chloropyridin-3-ylamino)-5-(1-(4-(methylsulfo-nyl)piperazin-1-yl)ethyl)pyridin-3-yl)-6-methyl-1,3,5-tri-azin-2-amine;

(R)-N-(3-(4-amino-6-methyl-1,3,5-triazin-2-yl)-5-(1-(4-(methylsulfonyl)piperazin-1-yl)ethyl)pyridin-2-yl)quino-lin-7-amine 2,2,2-trifluoroacetate;

2-(5-(4-amino-6-methyl-1,3,5-triazin-2-yl)-6-(5-fluoro-6-methoxypyridin-3-ylamino)pyridin-3-yl)-2-methylpro-pan-1-ol;

2-(5-(4-amino-6-methyl-1,3,5-triazin-2-yl)-6-(5-fluoro-6-methoxypyridin-3-ylamino)pyridin-3-yl)propan-1-ol;

4-(2-(5-fluoro-6-methoxypyridin-3-ylamino)-5-((4-(meth-ylsulfonyl)-2-(trifluoromethyl)piperazin-1-yl)methyl)py-ridin-3-yl)-6-methyl-1,3,5-triazin-2-amine;

1-(5-(4-amino-6-methyl-1,3,5-triazin-2-yl)-6-(5-fluoro-6-methoxypyridin-3-ylamino)pyridin-3-yl)-2,2,2-trifluoro-ethanolexample;

(S)-4-(2-(5-fluoro-6-methoxypyridin-3-ylamino)-5-((3-me-thylmorpholino)methyl)pyridin-3-yl)-6-methyl-1,3,5-tri-azin-2-amine;

(R)-4-(2-(5-fluoro-6-methoxypyridin-3-ylamino)-5-((2-me-thyl-4-(methylsulfonyl)piperazin-1-yl)methyl)pyridin-3-yl)-6-methyl-1,3,5-triazin-2-amine;

(S)-4-(2-(6-chloro-5-methoxypyridin-3-ylamino)-5-((2-me-thyl-4-(methylsulfonyl)piperazin-1-yl)methyl)pyridin-3-yl)-6-methyl-1,3,5-triazin-2-amine;

(S)-4-(2-(6-chloropyridin-3-ylamino)-5-((2-methyl-4-(me-thylsulfonyl)piperazin-1-yl)methyl)pyridin-3-yl)-6-me-thyl-1,3,5-triazin-2-amine;

(S)-4-(2-(2-methoxypyrimidin-5-ylamino)-5-((2-methyl-4-(methylsulfonyl)piperazin-1-yl)methyl)pyridin-3-yl)-6-methyl-1,3,5-triazin-2-amine;

2-(5-(4-amino-6-methyl-1,3,5-triazin-2-yl)-6-(6-methoxy-pyridin-3-ylamino)pyridin-3-yl)-1,1,1-trifluoropropan-2-ol;

4-(2-(6-methoxypyridin-3-ylamino)-5-(2,2,2-trifluoro-1-(4-(methylsulfonyl)piperazin-1-yl)ethyl)pyridin-3-yl)-6-methyl-1,3,5-triazin-2-amine;

(R)-1-(5-(4-amino-6-methyl-1,3,5-triazin-2-yl)-6-(6-methoxypyridin-3-ylamino)pyridin-3-yl)-2,2,2-trifluoroethanol;

(S)-1-(5-(4-amino-6-methyl-1,3,5-triazin-2-yl)-6-(6-methoxypyridin-3-ylamino)pyridin-3-yl)-2,2,2-trifluoroethanol;

4-(5-(1-amino-2,2,2-trifluoroethyl)-2-(6-methoxypyridin-3-ylamino)pyridin-3-yl)-6-methyl-1,3,5-triazin-2-amine;

4-(2-(5-fluoro-6-methoxypyridin-3-ylamino)-5-(2,2,2-trifluoro-1-(4-(methylsulfonyl)piperazin-1-yl)ethyl)pyridin-3-yl)-6-methyl-1,3,5-triazin-2-amine;

N-(3-(4-amino-6-methyl-1,3,5-triazin-2-yl)-5-((4-(methylsulfonyl)piperazin-1-yl)methyl)pyridin-2-yl)isoquinolin-7-amine;

4-(5-(1-aminoethyl)-2-(5-fluoro-6-methoxypyridin-3-ylamino)pyridin-3-yl)-6-methyl-1,3,5-triazin-2-amine;

N-(5-(3-(4-amino-6-methyl-1,3,5-triazin-2-yl)-5-(tetrahydro-2H-pyran-4-yl)pyridin-2-ylamino)-2-chloropyridin-3-yl)methanesulfonamide;

N-(5-(3-(4-amino-6-methyl-1,3,5-triazin-2-yl)-5-chloropyridin-2-ylamino)-2-methoxypyridin-3-yl)methanesulfonamide;

N-(5-(3-(4-amino-6-methyl-1,3,5-triazin-2-yl)-5-methoxypyridin-2-ylamino)-2-chloropyridin-3-yl)methanesulfonamide;

N'-(5-((3-(4-amino-6-methyl-1,3,5-triazin-2-yl)-5-methoxy-2-pyridinyl)amino)-2-chloro-3-pyridinyl)-N,N-dimethylsulfamide;

N-(5-(3-(4-amino-6-methyl-1,3,5-triazin-2-yl)-5-(morpholinomethyl)pyridin-2-ylamino)-2-chloropyridin-3-yl)methanesulfonamide;

N'-(5-((3-(4-amino-6-methyl-1,3,5-triazin-2-yl)-5-(4-morpholinylmethyl)-2-pyridinyl)amino)-2-chloro-3-pyridinyl)-N,N-dimethylsulfamide;

N-(5-(3-(4-amino-6-methyl-1,3,5-triazin-2-yl)-5-methoxypyridin-2-ylamino)-2-chloropyridin-3-yl)morpholine-4-sulfonamide;

N-(5-(3-(4-amino-6-methyl-1,3,5-triazin-2-yl)-5-(2-methoxyethoxy)pyridin-2-ylamino)-2-chloropyridin-3-yl)methanesulfonamide;

N-(5-(3-(4-amino-6-methyl-1,3,5-triazin-2-yl)-5-(2-methoxyethoxy)pyridin-2-ylamino)-2-methoxypyridin-3-yl)methanesulfonamide;

N-(5-(3-(4-amino-6-methyl-1,3,5-triazin-2-yl)-5-(morpholinomethyl)pyridin-2-ylamino)-2-methoxypyridin-3-yl)methanesulfonamide;

N-(2-chloro-5-(3-(2-methyl-9H-purin-6-yl)pyridin-2-ylamino)pyridin-3-yl)methanesulfonamide;

N-(2-chloro-5-(3-(2-methyl-9H-purin-6-yl)-5-(1-morpholinoethyl)pyridin-2-ylamino)pyridin-3-yl)methanesulfonamide;

N'-(2-chloro-5-((3-(2-methyl-9H-purin-6-yl)-5-(1-(4-morpholinyl)ethyl)-2-pyridinyl)amino)-3-pyridinyl)-n,n-dimethylsulfamide;

(R)-4-(2-(6-chloro-5-methoxypyridin-3-ylamino)-5-(1-(4-(methylsulfonyl)piperazin-1-yl)ethyl)pyridin-3-yl)-6-methyl-1,3,5-triazin-2-amine;

2-(5-(4-amino-6-methyl-1,3,5-triazin-2-yl)-6-(6-chloro-5-methoxypyridin-3-ylamino)pyridin-3-yl)propan-2-ol;

4-(5-(3,6-dihydro-2H-pyran-4-yl)-2-(5-fluoro-6-methoxypyridin-3-ylamino)pyridin-3-yl)-6-methyl-1,3,5-triazin-2-amine;

4-(2-(5-fluoro-6-methoxypyridin-3-ylamino)-5-(tetrahydro-2H-pyran-4-yl)pyridin-3-yl)-6-methyl-1,3,5-triazin-2-amine;

2-(5-(6-amino-2-methylpyrimidin-4-yl)-6-(5-fluoro-6-methoxypyridin-3-ylamino)pyridin-3-yl)propan-2-ol;

2-(5-(4-amino-6-methyl-1,3,5-triazin-2-yl)-6-(5-fluoro-6-methoxypyridin-3-ylamino)pyridin-3-yl)-2-methylpropanoic acid;

1-(5-(4-amino-6-methyl-1,3,5-triazin-2-yl)-6-(5-fluoro-6-methoxypyridin-3-ylamino)pyridin-3-yl)-2-methylpropane-1,2-diol;

2-(5-(4-amino-6-methyl-1,3,5-triazin-2-yl)-6-(6-methoxy-5-(trifluoromethyl)pyridin-3-ylamino)pyridin-3-yl)propan-2-ol;

1-(5-(4-amino-6-methyl-1,3,5-triazin-2-yl)-6-(5-fluoro-6-methoxypyridin-3-ylamino)pyridin-3-yl)ethanol;

2-(5-(4-amino-6-methyl-1,3,5-triazin-2-yl)-6-(5,6-dimethoxypyridin-3-ylamino)pyridin-3-yl)propan-2-ol;

1-(5-(4-amino-6-methyl-1,3,5-triazin-2-yl)-6-(5-fluoro-6-methoxypyridin-3-ylamino)pyridin-3-yl)-2-hydroxy-2-methylpropyl 3-chlorobenzoate;

2-(5-(4-amino-6-methyl-1,3,5-triazin-2-yl)-6-(5-fluoropyridin-3-ylamino)pyridin-3-yl)propan-2-ol;

2-(5-(4-amino-6-methyl-1,3,5-triazin-2-yl)-6-(5-methoxypyridin-3-ylamino)pyridin-3-yl)propan-2-ol;

2-(5-(4-amino-6-methyl-1,3,5-triazin-2-yl)-6-(6-methoxy-5-methylpyridin-3-ylamino)pyridin-3-yl)propan-2-ol;

2-(5-(4-amino-6-methyl-1,3,5-triazin-2-yl)-6-(5-(methylsulfonyl)pyridin-3-ylamino)pyridin-3-yl)propan-2-ol;

2-(5-(4-amino-6-methyl-1,3,5-triazin-2-yl)-6-(5-(phenylsulfonyl)pyridin-3-ylamino)pyridin-3-yl)propan-2-ol;

4-((5-(4-amino-6-methyl-1,3,5-triazin-2-yl)-6-(5-fluoro-6-methoxypyridin-3-ylamino)pyridin-3-yl)methyl)-N-isopropyl-N-methylpiperazine-1-carboxamide;

4-((5-(4-amino-6-methyl-1,3,5-triazin-2-yl)-6-(5-fluoro-6-methoxypyridin-3-ylaamino)pyridin-3-yl)methyl)-N-methyl-N-(2,2,2-trifluoroethyl)piperazine-1-carboxamide;

4-((5-(4-amino-6-methyl-1,3,5-triazin-2-yl)-6-(6-methoxypyridin-3-ylamino)pyridin-3-yl)methyl)-N-cyclopropyl-N-methylpiperazine-1-carboxamide;

4-(2-(5-fluoro-6-methoxypyridin-3-ylamino)-5-((R)-1-((R)-2-methyl-4-(methylsulfonyl)piperazin-1-yl)ethyl)pyridin-3-yl)-6-methyl-1,3,5-triazin-2-amine;

4-(2-(5-fluoro-6-methoxypyridin-3-ylamino)-5-((S)-1-((R)-2-methyl-4-(methylsulfonyl)piperazin-1-yl)ethyl)pyridin-3-yl)-6-methyl-1,3,5-triazin-2-amine;

4-(2-(2-methoxypyrimidin-5-ylamino)-5-((R)-1-((S)-2-methyl-4-(methylsulfonyl)piperazin-1-yl)ethyl)pyridin-3-yl)-6-methyl-1,3,5-triazin-2-amine;

4-(2-(6-chloropyridin-3-ylamino)-5-((R)-1-((S)-2-methyl-4-(methylsulfonyl)piperazin-1-yl)ethyl)pyridin-3-yl)-6-methyl-1,3,5-triazin-2-amine;

(R)-4-(2-(5-fluoro-6-methoxypyridin-3-ylamino)-5-((3-methyl-4-(methylsulfonyl)piperazin-1-yl)methyl)pyridin-3-yl)-6-methyl-1,3,5-triazin-2-amine;

N-(5-(3-(4-amino-6-methyl-1,3,5-triazin-2-yl)pyridin-2-ylamino)-2-chloropyridin-3-yl)cyclopropanesulfonamide;

N-(5-(3-(4-amino-6-methyl-1,3,5-triazin-2-yl)pyridin-2-ylamino)-2-chloropyridin-3-yl)morpholine-4-sulfonamide;

N-(5-(3-(4-amino-6-methyl-1,3,5-triazin-2-yl)pyridin-2-ylamino)-2-chloropyridin-3-yl)-N-isopropyl-N-methylaminosulfamide;

N-(5-(3-(4-amino-6-methyl-1,3,5-triazin-2-yl)-5-methoxypyridin-2-yl)-2-chloropyridine-3,5-diamine;

N-(5-(3-(4-amino-6-methyl-1,3,5-triazin-2-yl)-5-(1-morpholinoethyl)pyridin-2-ylamino)-2-chloropyridin-3-yl)methanesulfonamide;

N-(5-(3-(4-amino-6-methyl-1,3,5-triazin-2-yl)-5-(1-morpholinoethyl)pyridin-2-ylamino)-2-chloropyridin-3-yl)-N,N-dimethylaminosulfamide;

(R)-N-(5-(3-(4-amino-6-methyl-1,3,5-triazin-2-yl)-5-(1-morpholinoethyl)pyridin-2-ylamino)-2-chloropyridin-3-yl)methanesulfonamide;

(S)-N-(5-(3-(4-amino-6-methyl-1,3,5-triazin-2-yl)-5-(1-morpholinoethyl)pyridin-2-ylamino)-2-chloropyridin-3-yl)methanesulfonamide;

(R)-N-(5-(3-(4-amino-6-methyl-1,3,5-triazin-2-yl)-5-(1-morpholinoethyl)pyridin-2-ylamino)-2-chloropyridin-3-yl)-N,N-dimethylaminosulfamide;

(S)-N-(5-(3-(4-amino-6-methyl-1,3,5-triazin-2-yl)-5-(1-morpholinoethyl)pyridin-2-ylamino)-2-chloropyridin-3-yl)-N,N-dimethylaminosulfamide;

N-(5-(3-(6-amino-2-methylpyrimidin-4-yl)pyridin-2-ylamino)-2-chloropyridin-3-yl)-N,N-dimethylaminosulfamide;

N-(5-(3-(4-amino-6-methyl-1,3,5-triazin-2-yl)-5-(2-methoxyethoxy)pyridin-2-ylamino)-2-methylpyridin-3-yl)methanesulfonamide;

N-(5-(3-(4-amino-6-methyl-1,3,5-triazin-2-yl)pyridin-2-ylamino)-2-methylpyridin-3-yl)methanesulfonamide;

N-(5-(3-(4-amino-6-methyl-1,3,5-triazin-2-yl)-5-chloropyridin-2-ylamino)-2-methylpyridin-3-yl)methanesulfonamide;

N-(2-chloro-5-(3-(6-amino-2-methylpyrimidin-4-yl)-5-(1-morpholinoethyl)pyridin-2-ylamino)pyridin-3-yl)-N,N-dimethylaminosulfamide;

N-(5-(3-(6-amino-2-methylpyrimidin-4-yl)-5-vinylpyridin-2-ylamino)-2-chloropyridin-3-yl)methanesulfonamide;

(R)-N-(2-chloro-5-(3-(6-amino-2-methylpyrimidin-4-yl)-5-(1-morpholinoethyl)pyridin-2-ylamino)pyridin-3-yl)-N,N-dimethylaminosulfamide;

(S)-N-(2-chloro-5-(3-(6-amino-2-methylpyrimidin-4-yl)-5-(1-morpholinoethyl)pyridin-2-ylamino)pyridin-3-yl)-N,N-dimethylaminosulfamide;

4-(5-((1,1-dioxidohexahydro-5h-isothiazolo[2,3-a]pyrazin-5-yl)methyl)-2-((5-fluoro-6-methoxy-3-pyridinyl)amino)-3-pyridinyl)-6-methyl-1,3,5-triazin-2-amine; or N'-(5-((3-(4-amino-6-methyl-1,3,5-triazin-2-yl)-5-chloro-2-pyridinyl)amino)-2-chloro-3-pyridinyl)-n,n-dimethylsulfamide.

In aspect 27, the present invention provides compounds of Formula II, or a pharmaceutically acceptable salt thereof,

II

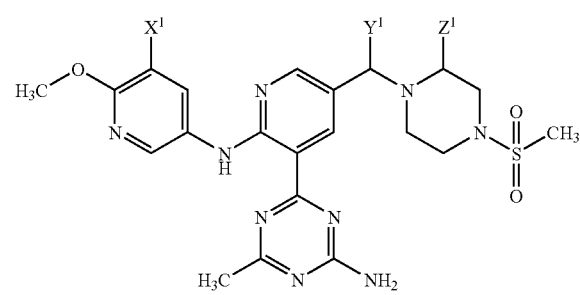

wherein $X^1$ is fluorine or hydrogen;
$Y^1$ is hydrogen or methyl; and
$Z^1$ is hydrogen or methyl.

In aspect 28, the present invention provides compounds in accordance with aspect 27, or a pharmaceutically acceptable salt thereof, wherein X1 is fluorine; Y1 is hydrogen or methyl; and Z1 is hydrogen or methyl.

In aspect 29, the present invention provides compounds of Formula IIa, or a pharmaceutically acceptable salt thereof, IIa

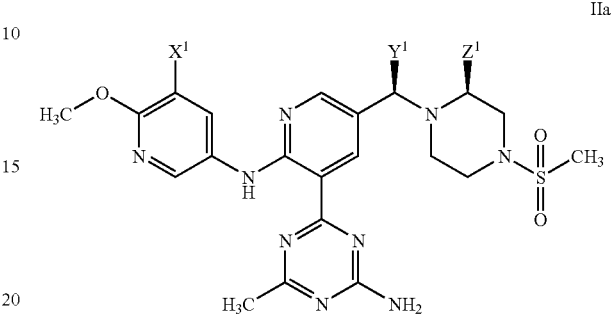

wherein $X^1$ is fluorine or hydrogen;
$Y^1$ is hydrogen or methyl; and
$Z^1$ is hydrogen or methyl.

In aspect 30, the present invention provides compounds in accordance with aspect 29, or a pharmaceutically acceptable salt thereof, wherein $X^1$ is fluorine; $Y^1$ is hydrogen or methyl; and $Z^1$ is hydrogen or methyl.

In aspect 31, the present invention provides pharmaceutical compositions comprising: a compound in accordance with any one of aspects 1 to 30, or a pharmaceutically acceptable salt thereof; and a pharmaceutically acceptable excipient.

In aspect 32, the present invention provides methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the method comprising administering to a patient in need thereof a therapeutically effective amount of a compound of any one of aspects 1 to 30, or a pharmaceutically acceptable salt thereof.

DETAILED DESCRIPTION OF THE INVENTION

The present invention provides compounds of Formula I, as defined above, or the pharmaceutically acceptable salts thereof. The present invention also provides pharmaceutical compositions comprising a compound of Formula I, or a pharmaceutically acceptable salt thereof, and methods of treating diseases or conditions, such as cancer, using a compound of Formula I, or a pharmaceutically acceptable salt thereof The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkly group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is $—CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 3 heteroatoms are particularly common It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, $—NR^xR^x$, nitro, cyano, halo or perhalo$C_{1-8}$alkyl, $C_{2-8}$alkenyl, $C_{2-8}$alkynyl, $—SR^x$, $—S(=O)_2R^x$, $—C(=O)OR^x$, $—C(=O)R^x$, wherein each $R^x$ is independently hydrogen or $C_1$-$C_8$ alkyl. It is noted that when the substituent is $—NR^xR^x$, the $R^x$ groups may be joined together with the nitrogen atom to form a ring.

The term "oxo", when used as a substitutent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$Cl_2$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N-($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O) $(OH)_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The compounds of the present invention are useful for the treatment of PI3K and/or mTOR mediated diseases and disorders including melanomas, carcinomas, and other cancers. In one embodiment of the invention, there is provided a method of modulating a PI3K and/or mTOR enzyme in a patient, the method comprising administering to a patient in need thereof a therapeutically effective amount of a compound of Formula I, or a pharmaceutically acceptable salt thereof The present invention also concerns the use of a compound of Formula I, or a pharmaceutically acceptable salt thereof, for the manufacture of a medicament for the treatment of a PI3K and/or mTOR mediated disease such as cancer. In another embodiment, more than one compound of the present invention may be administered to a patient. For example, a PI3K inhibitor and an mTOR inhibitor may be administered, or any combination thereof, including compounds that inhibit both PI3K and mTOR.

The term "patient in need thereof" means a patient who has or is at risk of having a PI3K and/or mTOR mediated disease or condition.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I, or a pharmaceutically acceptable salt thereof.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, chronic lyelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, athersoscleosis and Huntington's disease.

The compounds of Formula I, or a pharmaceutically acceptable salt thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta;

interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+ fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofiran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody(MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (Pfizer); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well known to those skilled in the art.

All patents and other publications recited herein are hereby incorporated by reference.

EXAMPLES

The examples presented below illustrate specific embodiments of the present invention. These examples are meant to be representative and are not intended to limit the scope of the claims in any manner. The starting materials for the specific examples below are generally available from commercial sources, unless otherwise specified. When helpful, commercial sources may be specifically indicated.

Analytical Methods:

Unless otherwise indicated, HPLC analyses and liquid chromatography-mass spectroscopy (LC-MS) procedures were run on a Agilent Model 1100 system utilizing one of the following two columns and methods:

(A) Using an Agilent Technologies Zorbax SB-$C_8$(5μ) reverse phase column (4.6×150 mm) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

(B) Using a Synergy MAX-RP, 5μ, 50×2.0 mm column with the same solvent system, a flow rate of 0.8 ml/min, and a gradient of 10% to 100% B for the first two minutes, then 100% B for 1.8 minutes, and then a return to 10% B over 0.2 minutes.

LC-MS Method:

Samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson (Gilson, Middleton, Wis.) workstation utilizing one of the following three columns and methods:

(A) Using a 50×100 mm column (Waters, Exterra, C18, 5μ, Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 min gradient from 40% to 100% solvent B followed by a 5 min flow of 100% solvent B. The gradient was followed by a 2 min return to 40% solvent B.

(B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

(C) Using a 100×50 mm column (Gemini, 10μ, C18, Phenomenex, Torrance, Calif.) at 100 ml/min. The mobile phase and solvent systems used were the same as in method B. The time gradient was 10% to 100% solvent B over 28 minutes, followed by a 2 min return to 10% solvent B.

Proton NMR Spectra:

Unless otherwise indicated, all $^1$H NMR spectra were run on a Varian series Mercury 300 MHz instrument (Varian, Palo Alto, Calif.) or a Bruker series 400 MHz instrument (Bruker, Bilerica, Mass.). Where so characterized, all observed protons are reported as parts-per-million (ppm) downfield from tetramethylsilane (TMS) or other internal reference in the appropriate solvent indicated.

Mass Spectra (MS):

Unless otherwise indicated, all mass spectral data for starting materials, intermediates and/or exemplary compounds are reported as mass/charge (m/z), having an (M+H$^+$) or (M−H⁻) molecular ion. The molecular ion reported was obtained by electrospray detection method. Compounds having an isotopic atom, such as bromine and the like, are reported according to the detected isotopic pattern, as appreciated by those skilled in the art.

The following abbreviations may be used herein:
~ about
+ve or pos. ion positive ion
Δ heat
Ac acetyl
Ac₂O acetic anhydride
ACN acetonitrile
A-phos, Am-Phos (bis[4-di-tert-butylphosphino)-N,N-dimethylaniline]palladium dichloride)
aq aqueous
ATP adenosine 5'-triphosphate
BOC tert-butyloxycarbonyl
Bu butyl
Bz benzyl
Calcd or Calc'd calculated
Conc. concentrated
DCM Dichloromethane
DEA Diethylamine
DIEA diisopropylethylamine
DMAP 4-dimethylaminopyridine
DME dimethoxyl ethyl ether
DMF N,N-dimethylformamide
DMSO dimethyl sulfoxide
DTT dithiothreitol
ESI or ES electrospray ionization
Et ethyl
Et₂O diethyl ether
Et₃N triethylamine
EtOAc ethyl acetate
EtOH ethyl alcohol
FBS fetal bovine serum
g grams
h hour
HCO₂H formic acid
Hex hexanes
HOAc acetic acid
HPLC high pressure liquid chromatography
IPA or iPrOH isopropyl alcohol
iPr₂NEt N-ethyl diisopropylamine
KOAc potassium acetate
LCMS, LC-MS or LC/MS liquid chromatography mass spectroscopy
LDA lithium diisopropylamide
LHMDS or LiHMDS lithium hexamethyldisilazide
LiTMP lithium tetramethylpiperidide
m/z mass divided by charge
mCPBA m-chloroperoxybenzoic acid
Me methyl
MeCN acetonitrile
MeI iodomethane
MeOH methyl alcohol
mg milligrams
min minutes
mL milliliters
MS mass spectra
MsCl mesylchloride
NaHMDS sodium hexamethyldisilazide
NaOtBu sodium tert-butoxide
NBS N-bromosuccinimide
NMO N-methylmorpholine-N-oxide
NMP 1-methyl-2-pyrrolidinone
NMR nuclear magnetic resonance
Pd₂dba₃ tris(dibenzylideneacetone)dipalladium(0)
PMB paramethoxybenzyl
RT or rt room temperature
Sat. or sat'd or satd saturated
SFC supercritical fluid chromatography
TFA Trifluoroacetic acid
TPAP Tetrapropylammonium perruthenate
Tris tris(hydroxymethyl)aminomethane
xantphos (9,9-dimethyl-9H-xanthene-4,5-diyl)bis(diphenylphosphine)
X-Phos 2-Dicyclohexylphosphino-2',4',6'-triisopropyl-1,1'-biphenyl Percents of solid reagents specified are percent by weight with respect to the total weight, and percents of solvents are specified by percent by volume with respect to the total volume, unless indicated otherwise.

Synthetic Schemes

SCHEME 1

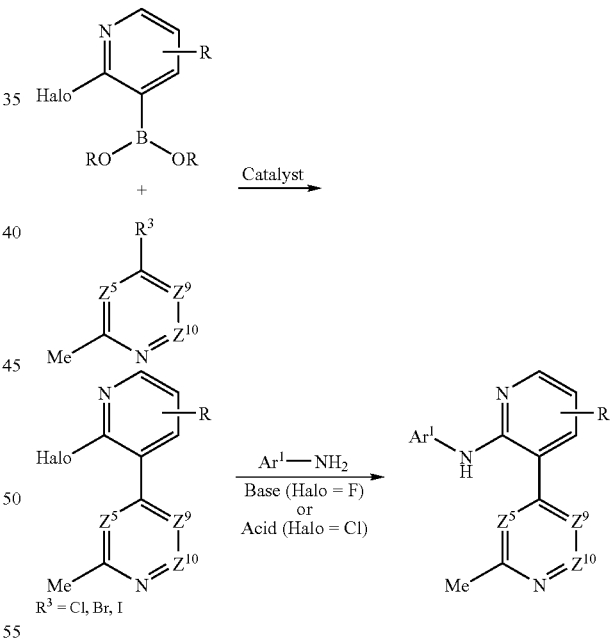

SCHEME 2

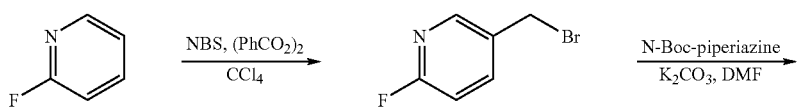

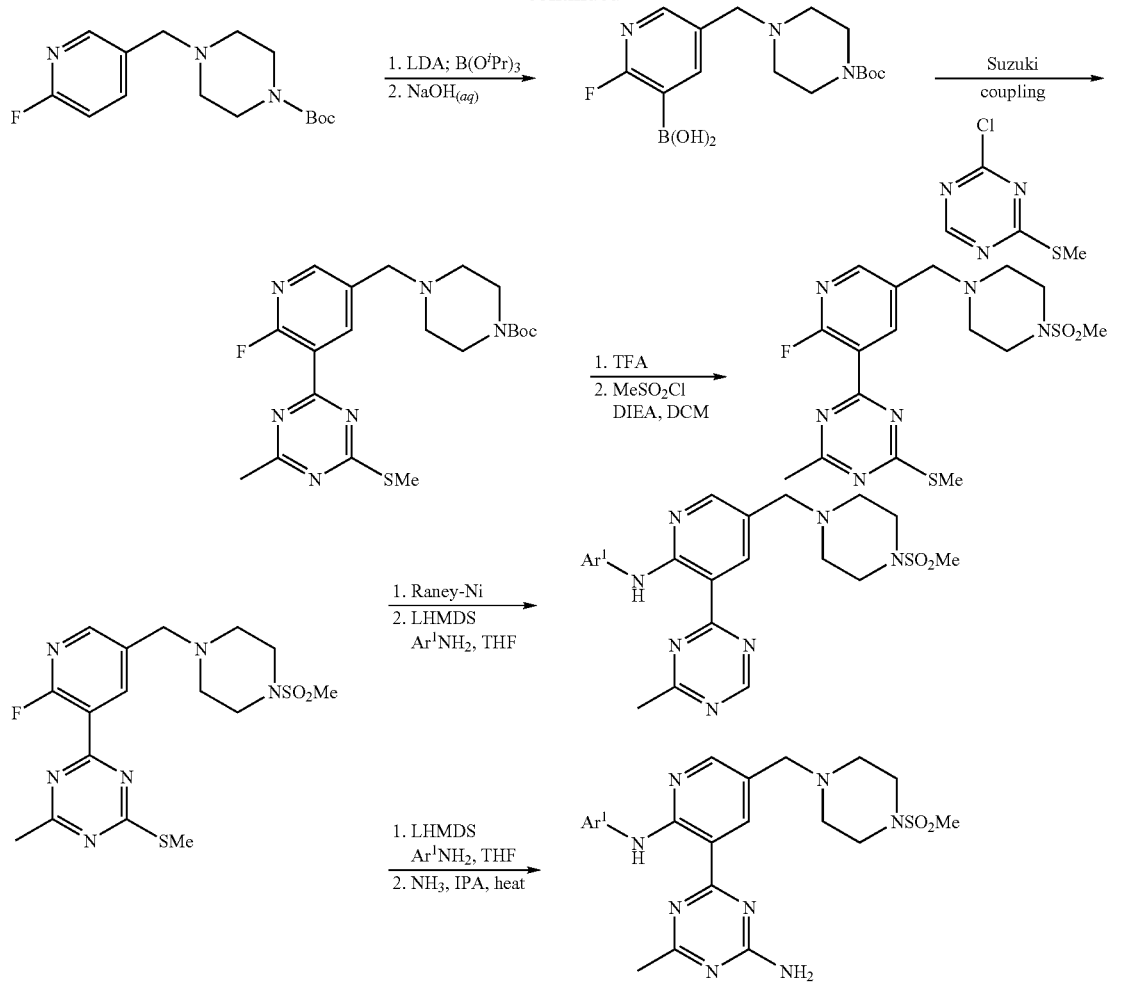
SCHEME 3
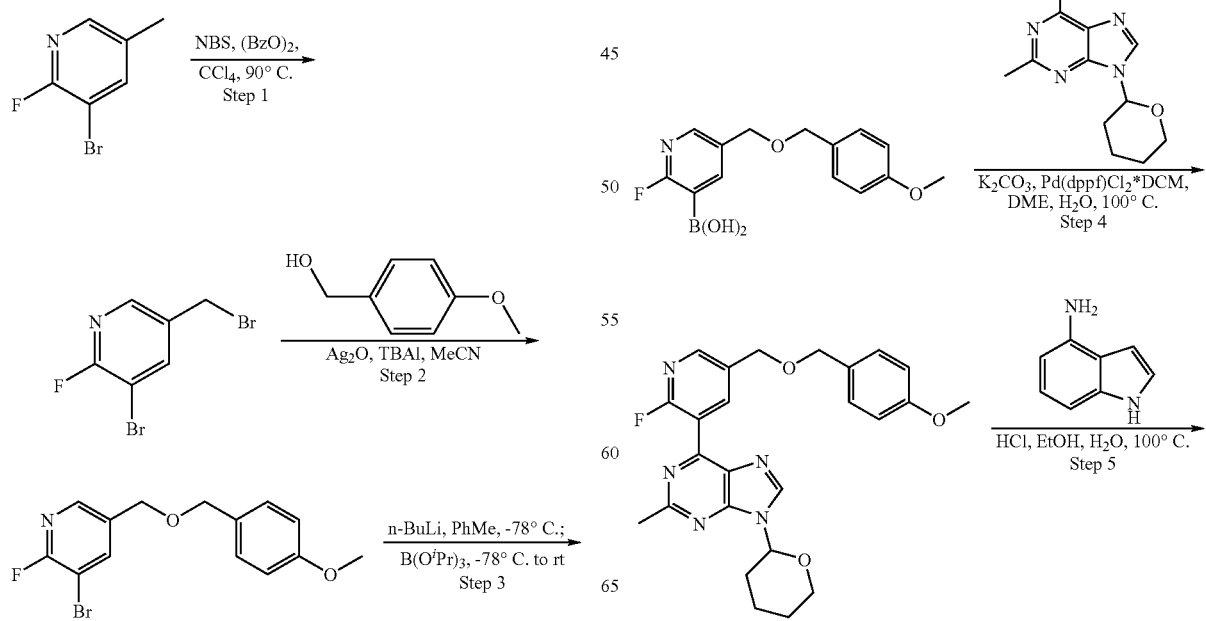

47
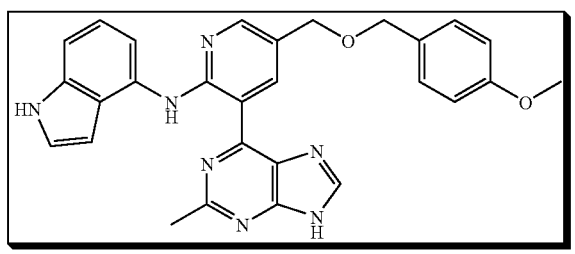
48
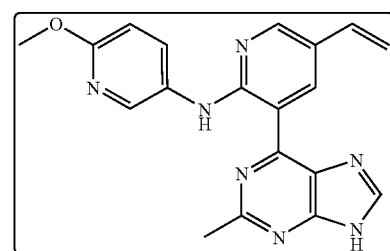
SCHEME 4
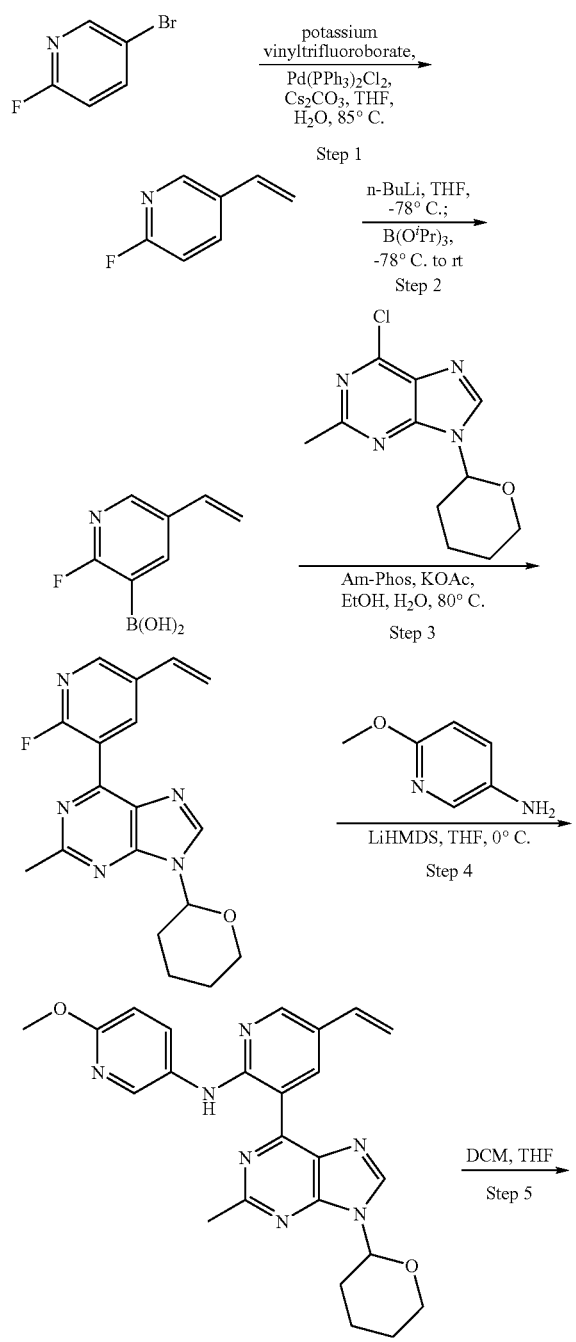
SCHEME 5
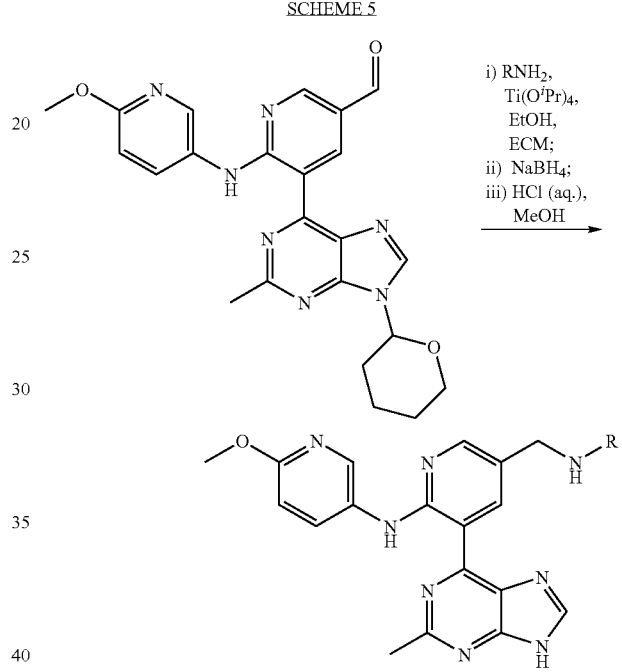
SCHEME 6
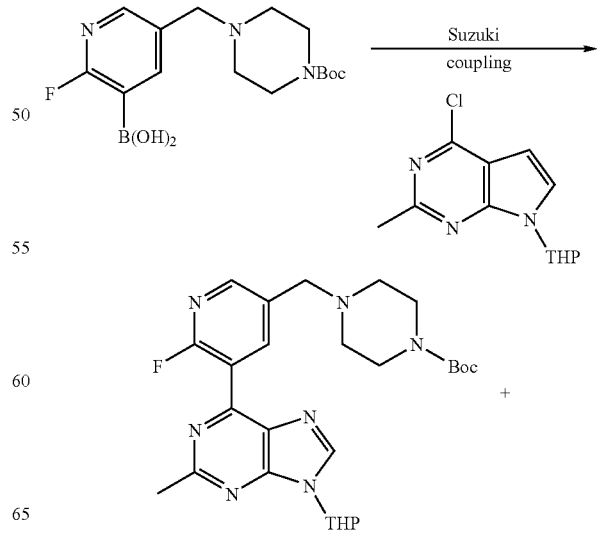

49
-continued
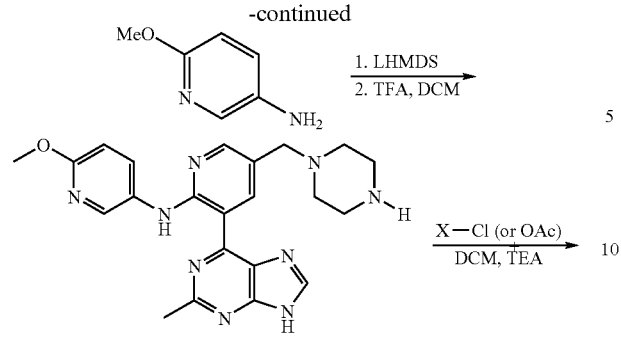
50
-continued
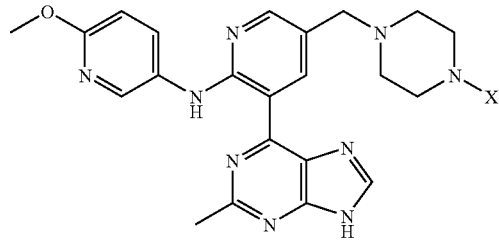
SCHEME 7
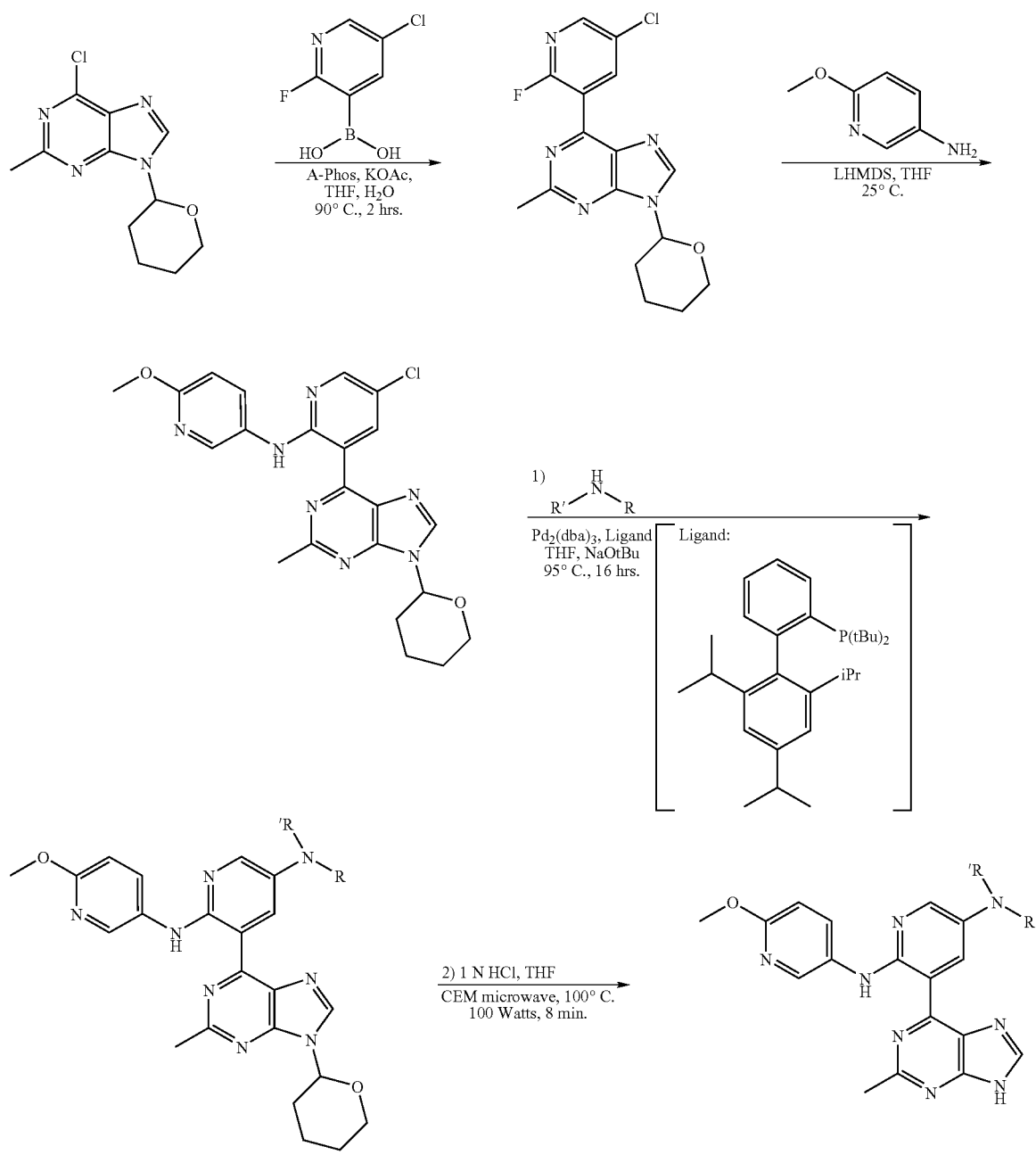

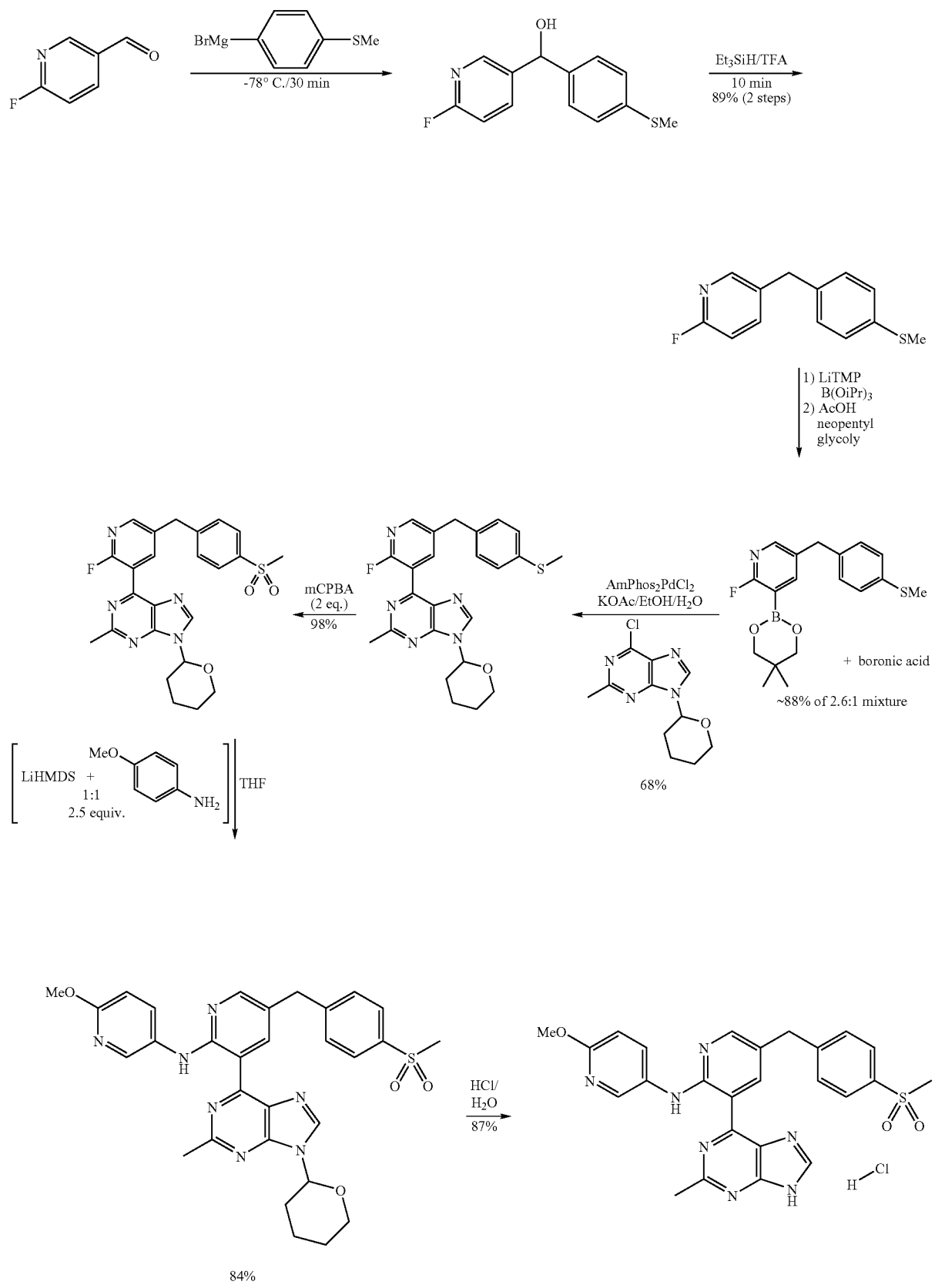

Example 1

6-chloro-9-(tetrahydro-2H-pyran-2-yl)-9H-purine

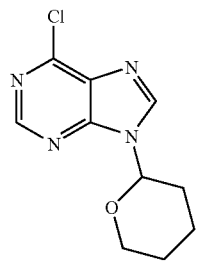 [SMILES: Clc1ncnc2c1ncn2C1CCCCO1]

A suspension of 6-chloro-9H-purine (25.36 g, 164 mmol) (Alfa Aesar, Ward Hill, Mass.) and 4-methylbenzenesulfonic acid (0.565 g, 3.28 mmol) in EtOAc (250 mL) was treated with 3,4-dihydro-2H-pyran (44.9 mL, 492 mmol). The mixture was heated at 90° C. and the solid slowly dissolved over 1 h. The flask was removed from the oil bath and the cloudy yellow solution was filtered and concentrated in vacuo.

The pale yellow residue was dissolved in DCM and purified by flash chromatography (50% EtOAc/hexane) (1 L silica/4 L solvent) to give 6-chloro-9-(tetrahydro-2H-pyran-2-yl)-9H-purine (38.90 g, 99% yield) as a colorless oil which slowly crystallized. $^1$H NMR (400 MHz, d6-DMSO) δ 8.91 (s, 1H), 8.82 (s, 1H), 5.80 (d, 1H), 4.04 (m, 1H), 3.75 (m, 1H), 2.35 (m, 1H), 2.01 (m, 2H), 1.76 (m, 1H), 1.62 (m, 2H).

Example 2

6-(2-fluoropyridin-3-yl)-9-(tetrahydro-2H-pyran-2-yl)-9H-purine

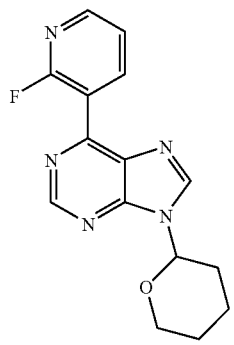 [SMILES: Fc1ncccc1-c1ncnc2c1ncn2C1CCCCO1]

A solution of 6-chloro-9-(tetrahydro-2H-pyran-2-yl)-9H-purine (1) (6.00 g, 25.1 mmol) in dioxane (54 mL) was sequentially treated with water (7.2 mL), 2-fluoropyridin-3-ylboronic acid (Asymchem Laboratories, Inc., Morrisville, N.C.) (5.31 g, 37.7 mmol), sodium carbonate monohydrate (9.35 g, 75.4 mmol) and PdCl$_2$(dppf) (Strem Chemicals, Inc., Newburyport, Mass.) (0.616 g, 0.754 mmol). The stirred mixture was degassed (alternating vacuum/nitrogen) and heated under nitrogen at 100° C. for 10 h. The mixture was cooled and extracted into EtOAc (500 mL) from water (400 mL). The aqueous layer was extracted with EtOAc (200 mL) and the combined organic extracts were dried (MgSO$_4$), filtered through Celite® (diatomaceous earth), and concentrated. The crude product was dissolved in a small volume of DCM and purified by flash chromatography (50% to 75% to 100% EtOAc/hexane) to give 6-(2-fluoropyridin-3-yl)-9-(tetrahydro-2H-pyran-2-yl)-9H-purine (3.96 g, 53% yield) as an off-white solid. $^1$H NMR (400 MHz, d6-DMSO) δ 9.11 (s, 1H), 8.91 (s, 1H), 8.58 (m, 1H), 8.49 (s, 1H), 7.62 (m, 1H), 5.85 (d, 1H), 4.05 (m, 1H), 3.75 (m, 1H), 2.38 (m, 1H), 2.05 (m, 2H), 1.79 (m, 1H), 1.61 (m, 2H).

Example 3

6-chloro-2-methyl-9-(tetrahydro-2H-pyran-2-yl)-9H-purine

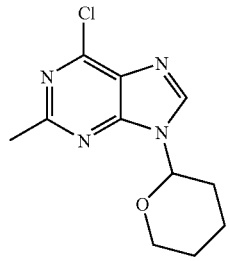 [SMILES: Cc1nc(Cl)c2ncn(C3CCCCO3)c2n1]

Step 1. 6-chloro-2-methylpyrimidine-4,5-diamine 2-methyl-4,6-dichloro-5-aminopyrimidine (Aldrich, 1.05 g) and ammonium hydroxide (3.0 mL, J.T. Baker, Phillipsburg, N.J., 28.0%-30.0%) were placed in a microwave vial. The vial was sealed and heated in a CEM microwave reactor (CEM Corporation, Matthews, N.C.) at 120° C. and 40 Watts for 25 minutes. The reaction was cooled to room temperature. This procedure was repeated a total of nine times using the following amounts of 2-methyl-4,6-dichloro-5-aminopyrimidine under the same reaction conditions:

Run 2: 1.027 g. 2.5 mL ammonium hydroxide.
Run 3: 1.034 g, 2.5 mL ammonium hydroxide.
Run 4: 1.118 g, 2.6 mL ammonium hydroxide.
Run 5: 1.117 g, 2.5 mL ammonium hydroxide.
Run 6: 1.149 g, 2.7 mL ammonium hydroxide.
Run 7: 1.264 g, 2.6 mL ammonium hydroxide.
Run 8: 1.106 g, 2.6 mL ammonium hydroxide.
Run 9: 1.075 g, 2.7 mL ammonium hydroxide.

All the runs were combined, concentrated, and taken on to Step 2. MS (ESI pos. ion) m/z: 159. Calculated exact mass for $C_5H_7ClN_4$: 158.

Step 2. 6-chloro-2-methyl-9H-purine

6-Chloro-2-methylpyrimidine-4,5-diamine (8.89 g, 56.1 mmol, the material from Step 1) was suspended in ethyl orthoformate (100 mL, 601 mmol) in a flask fitted with a reflux condenser and placed in a preheated oil bath (100° C.) and stirred for 75 minutes. Then, the reaction was cooled to room temperature, concentrated, treated with hexanes and filtered. The solid washed with hexanes, collected, and taken on to Step 3. MS (ESI pos. ion) m/z: 169. Calculated exact mass for $C_6H_5ClN_4$: 168.

Step 3. 6-chloro-2-methyl-9-(tetrahydro-2H-pyran-2-yl)-9H-purine

6-Chloro-2-methyl-9H-purine (9.45 g, 56 mmol, the material from Step 2) was suspended in DCM (100 mL) and p-toluenesulfonic acid (Acros Organics, Geel, Belgium, 12% in acetic acid, 0.90 mL, 5.6 mmol) and 2,3-dihydropyran (6.6 mL, 73 mmol) were added. The reaction flask was fitted with a reflux condenser and placed in a preheated oil bath (50° C.) and stirred under nitrogen for 30 minutes. Then, the reaction was cooled to room temperature and stirred overnight. After stirring overnight, the reaction was diluted with DCM and treated with saturated sodium bicarbonate (75 mL). The layers were separated, and the aqueous phase was extracted with DCM. The organic extracts were combined, dried over sodium sulfate, filtered, concentrated, and dried under high vacuum at 45° C. (in a water bath) and then at room temperature and then at 60° C. and finally at room temperature again to afford 6-chloro-2-methyl-9-(tetrahydro-2H-pyran-2-yl)-9H-purine (13.73 g, 97% over 3 steps). MS (ESI pos. ion) m/z: 253. Calculated exact mass for $C_{11}H_{13}ClN_4O$: 252. $^1$H NMR (CDCl$_3$, 400 MHz) δ 8.26 (s, 1H), 5.78 (d, J=10.56 Hz, 1H), 4.19 (d, J=11.93 Hz, 1H), 3.84-3.76 (m, 1H), 2.80 (s, 3H), 2.20-1.96 (m, 3H), 1.89-1.64 (m, 3H).

Example 4

6-(2-fluoropyridin-3-yl)-2-methyl-9-(tetrahydro-2H-pyran-2-yl)-9H-purine

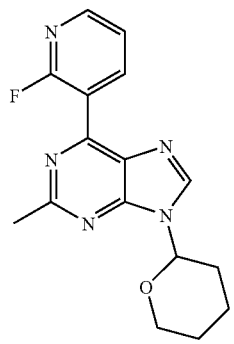

A mixture of 6-chloro-2-methyl-9-(tetrahydro-2H-pyran-2-yl)-9H-purine (3) (531.6 mg, 2104 μmol), 2-fluoropyridin-3-ylboronic acid (Asymchem Laboratories, Inc., Morrisville, N.C.) (596 mg, 4230 μmol), potassium acetate (629 mg, 6409 μmol) and bis(di-tert-butyl (4-dimethylaminophenyl)phosphine)dichloropalladium(II) (Aldrich, St. Louis, Mo.) (37.2 mg, 52.6 μmol) under a N$_2$ atmosphere was suspended in EtOH (5.0 mL) and H$_2$O (1.0 mL), degassed, and heated at gentle reflux for 2 h. LCMS indicated the reaction was complete. The mixture was poured into saturated aqueous NaHCO$_3$ and extracted into EtOAc. The EtOAc extracts were dried (MgSO$_4$), concentrated and purified by flash chromatography (EtOAc) to give 6-(2-fluoropyridin-3-yl)-2-methyl-9-(tetrahydro-2H-pyran-2-yl)-9H-purine (519 mg, 78.7% yield) as a pale yellow oil which crystallized to give a white solid upon trituration with Et$_2$O. $^1$H NMR (400 MHz, d6-DMSO) δ 8.79 (s, 1H); 8.46-8.53 (m, 1H); 8.43-8.46 (m, 1H); 7.55-7.62 (m, 1H); 5.78-5.85 (m, 1H); 4.00-4.08 (m, 1H); 3.70-3.80 (m, 1H); 2.78 (s, 3H); 2.26-2.40 (m, 1H); 1.95-2.06 (m, 2H); 1.72-1.87 (m, 1H); 1.56-1.67 (m, 2H). m/z (ESI, +ve) 314.0 (M+H)$^+$.

Example 5

4-chloro-6-methyl-1-(tetrahydro-2H-pyran-2-yl)-1H-pyrazolo[3,4-d]pyrimidine

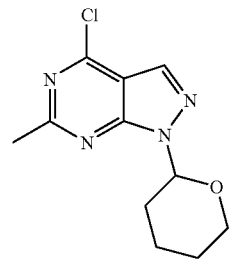 [SMILES: Cc1nc(Cl)c2cnn(C3CCCCO3)c2n1]

LDA was prepared by dropwise addition of n-butyllithium, 2.5 M solution in hexanes (Aldrich, St. Louis, Mo.) (14.7 mL, 36.8 mmol) to N,N-diisopropylamine (5.42 mL, 38.4 mmol) in THF (40 mL) cooled in an ice bath. The LDA solution was cooled to −78° C. and a solution of 4,6-dichloro-2-methylpyrimidine (Aldrich, St. Louis, Mo.) (5.448 g, 33.4 mmol) in THF (50 mL) was added dropwise over 1 h. A dark solution was obtained. A solution of N-methyl-N-(2-pyridyl)formamide (TCI Tokyo Kasei Kogyo Co., Ltd.) (4.80 mL, 40.1 mmol) in THF (20 mL) was added dropwise to the solution at −78° C. over 20 min. The resulting solution was stirred for 30 min and then quenched with a solution of acetic acid (2.10 mL, 36.8 mmol) in THF (20 mL) added dropwise at −78° C. over 10 min. The solution was stirred at −78° C. for 30 min.

The resulting solution of 4,6-dichloro-2-methylpyrimidine-5-carbaldehyde was treated dropwise with a solution of anhydrous hydrazine (1101 μL, 35071 μmol) at −78° C. The mixture was stirred for 15 min, and then the cooling bath was removed and the mixture stirred at RT for 1 h. The mixture was concentrated and partitioned between water (110 mL) and EtOAc (110 mL). The organic layer was washed with saturated aqueous NaHCO$_3$ (100 mL), separated, dried (MgSO$_4$), treated with activated charcoal and filtered through a plug of silica, washing with EtOAc. The filtrate was concentrated and purified by flash chromatography on silica eluting with 5% acetone/DCM to 25% EtOAc/hexane. The residue was suspended in DCM (3 mL), cooled in a freezer, and filtered to give 4-chloro-6-methyl-1H-pyrazolo[3,4-d]pyrimidine (330 mg, 5.86% yield) as a tan solid. $^1$H NMR (400 MHz, d6-DMSO) δ 14.25 (bs, 1H); 8.35 (s, 1H); 2.68 (s, 3H).

A suspension of the above 4-chloro-6-methyl-1H-pyrazolo [3,4-d]pyrimidine (325 mg, 1928 μmol) in EtOAc (3 mL) was treated with 3,4-dihydro-2H-pyran (528 μL, 5783 μmol) and MP-TsOH resin (Biotage) (72 mg, 4.3 mmol/g, 0.15 eq) and the resulting suspension was heated at 90° C. for 3 h, after which time LCMS indicated essentially complete conversion. The solution was filtered, washed with EtOAc, and concentrated to give a pale yellow oil. Purification by flash chromatography (EtOAc/hexane; 5% to 20%) gave 4-chloro-6-methyl-1-(tetrahydro-2H-pyran-2-yl)-1H-pyrazolo[3,4-d] pyrimidine (482 mg, 98.9% yield) as a colorless oil. $^1$H NMR (400 MHz, d6-DMSO) δ 8.44 (s, 1H); 5.91-6.02 (m, 1H);

3.91-3.99 (m, 1H); 3.67-3.77 (m, 1H); 2.72 (s, 3H); 2.36-2.48 (m, 1H); 1.96-2.08 (m, 1H); 1.87-1.95 (m, 1H); 1.32-1.84 (m, 3H).

Example 6

4-(2-fluoropyridin-3-yl)-6-methyl-1-(tetrahydro-2H-pyran-2-yl)-1H-pyrazolo[3,4-d]pyrimidine

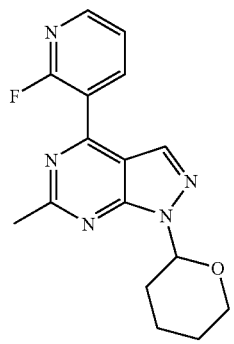 [SMILES: Cc1nc(-c2cccnc2F)c2cnn(C3CCCCO3)c2n1]

A mixture of 4-chloro-6-methyl-1-(tetrahydro-2H-pyran-2-yl)-1H-pyrazolo[3,4-d]pyrimidine (5) (107.8 mg, 427 µmol), 2-fluoropyridin-3-ylboronic acid (120 mg, 853 µmol) (Asymchem Laboratories, Inc., Morrisville, N.C.), and potassium acetate (105 mg, 1066 µmol) in EtOH (1.25 mL) and water (0.25 mL) was placed under vacuum for 5 min, then flushed with nitrogen for 5 min and treated with bis(di-tert-butyl (4-dimethylaminophenyl)phosphine)dichloropalladium(II) (8.0 mg, 11 µmol) (Aldrich, St. Louis, Mo.). The solution was then heated to 80° C. Reaction was complete by LCMS analysis after 60 min.

The reaction mixture was poured into EtOAc/saturated aqueous NaHCO₃ and extracted. The organic extract was dried (MgSO₄), filtered and concentrated. The residue was purified by flash chromatography (25% to 50% EtOAc/hexane) to give 4-(2-fluoropyridin-3-yl)-6-methyl-1-(tetrahydro-2H-pyran-2-yl)-1H-pyrazolo[3,4-d]pyrimidine (105 mg, 79% yield) as a pale yellow oil which slowly crystallized upon standing. $^1$H NMR (400 MHz, d6-DMSO) δ 8.46-8.57 (m, 2H); 8.41 (d, J=3.51 Hz, 1H); 7.64 (s, 1H); 6.04 (d, J=8.03 Hz, 1H); 3.92-4.02 (m, 1H); 3.68-3.79 (m, 1H); 2.82 (s, 3H); 2.41-2.48 (m, 1H); 2.00-2.10 (m, 1H); 1.88-1.99 (m, 1H); 1.72-1.87 (m, 1H); 1.59 (d, J=3.51 Hz, 2H).

Example 7

2,4-dichloro-6-methyl-1,3,5-triazine

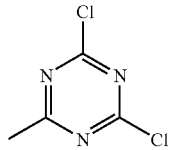

Methylmagnesium bromide, 3M in ether (Aldrich, St. Louis, Mo.) (10.0 mL, 30 mmol) was added slowly to a white suspension of 2,4,6-trichloro-1,3,5-triazine (Aldrich, St. Louis, Mo.) (3.68 g, 20 mmol) in DCM (25.0 mL, 389 mmol) at 0° C. and the resulting yellow suspension was warmed up to room temperature and stirring was continued until disappearance of starting material (TLC, KMnO₄ stain, 3H). The reaction was carefully quenched with NH₄Cl(aq) at 0° C. and then diluted with water and DCM (25.0 mL). The separated organic layer was dried, filtered and concentrated to give 2,4-dichloro-6-methyl-1,3,5-triazine as a yellow solid (2.94 g, 90%) which was used for further reaction without purification. $^1$H-NMR (CDCl₃, 400 MHz) δ 2.74 (s, 3H).

Example 8

2-chloro-4-methyl-6-(methylthio)-1,3,5-triazine

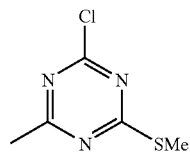

Sodium methanethiolate (0.49 g, 7.0 mmol) was added portionwise at 0° C. to a stirred cloudy solution of 2,4-dichloro-6-methyl-1,3,5-triazine (7) (1.04 g, 6.3 mmol) in toluene (10 mL, 94 mmol) over 15 min. After addition, the pale yellow mixture was stirred at the same temperature for another 1 h, and water (10 mL) was added. The separated aqueous layer was extracted with EtOAc (2×20 mL) and the combined organic layers were washed with brine, dried over Na₂SO₄, and concentrated to give the crude residue which was purified with flash column chromatography (hexanes to 70% DCM in hexanes) to give 2-chloro-4-methyl-6-(methylthio)-1,3,5-triazine (0.87 g, 78% yield) as a white solid. MS (API-ES) m/z 176 (M+H)⁺; $^1$H NMR (d6-DMSO, 400 MHz) δ 2.55 (s, 3H) 2.51 (br. s., 3H).

Example 9

4-chloro-6-methyl-1,3,5-triazin-2-amine

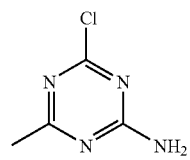

A solution of ammonia, 2.0M methyl alcohol (Aldrich, St. Louis, Mo.) (36.0 mL, 72 mmol) was added dropwise at room temperature (slightly exothermic) to a stirred yellow suspension of 2,4-dichloro-6-methyl-1,3,5-triazine (from Example 7) (2.94 g, 18 mmol) in toluene (20.0 mL, 188 mmol) over 1.5 h. The resulting mixture was stirred for an additional 2.5 h, concentrated and purified (ISCO, DCM to 10% MeOH in DCM) to give the desired product 4-chloro-6-methyl-1,3,5- triazin-2-amine (1.88 g, 73%) as a yellow solid. MS (API-ES) m/z 145 (M+H)+; $^1$H NMR (CD$_3$OD, 300 MHz) δ 2.32 (s, 3H).

Example 10

6-chloro-2-methylpyrimidin-4-amine

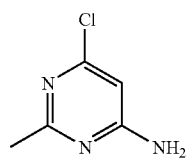

Ammonia, 2.0 M in methyl alcohol (6.0 mL, 12 mmol) was added to a stirred yellow suspension of 4,6-dichloro-2-methylpyrimidine (Aldrich) (0.487 g, 3 mmol) in 1,4-dioxane (10.0 mL) at room temperature. The resulting mixture was sealed and stirred at 70° C. overnight. After cooling, the reaction mixture was concentrated and the crude residue was dissolved in DCM/MeOH and mixed with SiO$_2$. The solvent was evaporated and the residue was purified by flash column chromatography (pure DCM to 10% MeOH in DCM) to give 6-chloro-2-methylpyrimidin-4-amine (0.25 g, 58%) as a white solid. MS (API-ES) m/z 144 (M+H)+.

Example 11

6-chloro-5-fluoro-2-methylpyrimidin-4-amine

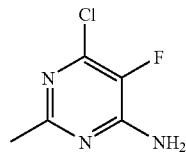

A mixture of 4,6-dichloro-5-fluoro-2-methylpyrimidine (1.55 g, 8.6 mmol) in aqueous ammonium hydroxide (10.00 mL, 90 mmol) and MeOH (1.00 mL, 25 mmol) was heated at 70° C. for 2 h (sealed tube). After cooling, 10 mL water was added and stirred for 30 min. The solid was isolated, washed with water, and dried to give the desired product 6-chloro-5-fluoro-2-methylpyrimidin-4-amine (0.9244 g, 67%) as a white solid. MS (API-ES) m/z 163 (M+H)+.

Example 12

2-methyl-4-(methylthio)-6-(tributylstannyl)pyrimidine

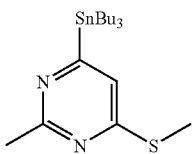

Step 1.
4-chloro-2-methyl-6-(tributylstannyl)pyrimidine n-Butyllithium solution, 1.6 M in hexane (0.184 mL, 2.200 mmol, Aldrich, St. Louis, Mo.) was added to a solution of diisopropylamine (0.314 mL, 2.200 mmol) in THF (5 mL) at 0° C. The reaction mixture was stirred at 0° C. for 15 min. Tributyltin hydride (0.527 mL, 2.000 mmol, Aldrich, St. Louis, Mo.) was added dropwisely. The solution was stirred at 0° C. for 15 min. The mixture was cooled down to −78° C., 4,6-dichloro-2-methylpyrimidine (326 mg, 2.000 mmol, Aldrich, St. Louis, Mo.) in THF (2 mL) was then added and the mixture was stirred at −78° C. for 8 h. The mixture was quenched by saturated aqueous KF (4 mL), and extracted with EtOAc (30 mL). The organic extract was washed with saturated NaCl (5 mL) and dried over Na$_2$SO$_4$. The solution was filtered and concentrated in vacuo to give 4-chloro-2-methyl-6-(tributylstannyl)pyrimidine as a light-yellow oil. The crude material was used directly in the next step without purification.

Step 2. 2-methyl-4-(methylthio)-6-(tributylstannyl)pyrimidine

Sodium thiomethoxide (140 mg, 2 mmol) was added to 4-chloro-2-methyl-6-(tributylstannyl)pyrimidine (835 mg, 2 mmol) in tetrahydrofuran (10 mL). The reaction mixture was stirred at room temperature for 48 h. The reaction mixture was diluted with water (20 mL) and extracted with EtOAc (2×30 mL). The organic extract was washed with saturated NaCl (5 mL) and dried over Na$_2$SO$_4$. The solution was filtered and concentrated in vacuo to give the crude material as an orange oil. The crude product was purified by silica gel chromatography, eluting with 5% EtOAc/hexanes to give 2-methyl-4-(methylthio)-6-(tributylstannyl)pyrimidine (256 mg, 30% yield). $^1$H NMR (300 MHz, CDCl$_3$) δ 7.07 (s, 1H); 2.62 (s, 3H); 2.51 (s, 3H); 1.44-1.70 (m, 6H); 1.21-1.42 (m, 6H); 0.98-1.21 (m, 6H); 0.91 (t, 9H).

Example 13

4-nitro-1-(tetrahydro-2H-pyran-2-yl)-1H-indazole (13A) and 4-nitro-2-(tetrahydro-2H-pyran-2-yl)-2H-indazole (13B)

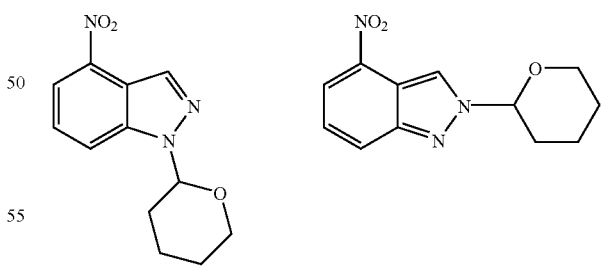

A suspension of 4-nitro-1H-indazole (Bionet Research, Cornwall, UK) (4.07 g, 24.9 mmol) in EtOAc (50 mL) was treated with 3,4-dihydro-2H-pyran (6.83 mL, 74.8 mmol) and MP-TsOH resin (Biotage, Uppsala, Sweden) (380 mg, 4.3 mmol/g, 0.06 eq.) and heated at gentle reflux for 2 h. The mixture was filtered, concentrated and purified by flash chromatography on silica (5% EtOAc/hexane to 10% EtOAc/10% DCM/Hexane) to give 4-nitro-1-(tetrahydro-2H-pyran-2-yl)-1H-indazole (3.040 g, 49.3% yield) as a pale yellow crystalline solid (recrystallized from EtOAc/hexane) followed by 4-nitro-2-(tetrahydro-2H-pyran-2-yl)-2H-indazole (2.336 g, 37.9% yield) as a pale yellow oil. Structural assignments were confirmed by NOESY (N—CH—O to aromatic protons).

4-Nitro-1-(tetrahydro-2H-pyran-2-yl)-1H-indazole (13a): $^1$H NMR (400 MHz, d6-DMSO) δ 8.57 (s, 1H); 8.32 (d, J=8.53 Hz, 1H); 8.21 (d, J=7.53 Hz, 1H); 7.69 (t, J=8.03 Hz, 1H); 6.04 (dd, J=9.54, 2.01 Hz, 1H); 3.84-3.93 (m, 1H); 3.74-3.83 (m, 1H); 2.36-2.46 (m, 1H); 1.98-2.12 (m, 2H); 1.70-1.84 (m, 1H); 1.56-1.67 (m, 2H). m/z (ESI, +ve). Found 270.0 (M+Na)$^+$.

4-Nitro-2-(tetrahydro-2H-pyran-2-yl)-2H-indazole (13b): $^1$H NMR (400 MHz, d6-DMSO) δ 8.92 (s, 1H); 8.22-8.26 (m, 2H); 7.54 (t, J=8.03 Hz, 1H); 5.93 (dd, J=9.54, 2.51 Hz, 1H); 4.01 (m., 1H); 3.71-3.83 (m, 1H); 2.18-2.30 (m, 1H); 2.15-1.34 (m, 5H). m/z (ESI, +ve). Found 270.0 (M+Na)$^+$.

Example 14

1-(tetrahydro-2H-pyran-2-yl)-1H-indazol-4-amine

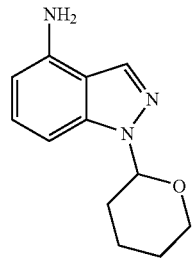 [SMILES: Nc1cccc2c1cnn2C1CCCCO1]

A solution of 4-nitro-1-(tetrahydro-2H-pyran-2-yl)-1H-indazole (1.05 g, 4247 μmol) in EtOAc (100 mL) was treated with 10% Pd/C (60 mg) and stirred under an atmosphere of H$_2$. The reaction was monitored by LCMS and found to be complete after 22 h. The reaction was filtered and concentrated (caution: tends to foam/bump). The residue was triturated with Et$_2$O to give 1-(tetrahydro-2H-pyran-2-yl)-1H-indazol-4-amine (892 mg, 96.7% yield) as an off-white solid. $^1$H NMR (400 MHz, d6-DMSO) δ 8.11 (s, 1H); 7.03 (t, J=7.82 Hz, 1H); 6.74 (d, J=8.22 Hz, 1H); 6.18 (d, J=7.43 Hz, 1H); 5.78 (s, 2H); 5.59-5.67 (m, 1H); 3.82-3.92 (m, 1H); 3.63-3.74 (m, 1H); 2.30-2.45 (m, 1H); 1.96-2.08 (m, 1H); 1.84-1.94 (m, 1H); 1.65-1.80 (m, 1H); 1.55 (br. s, 2H). m/z (ESI, +ve). Found 218 (M+H)$^+$.

Example 15

2-(tetrahydro-2H-pyran-2-yl)-2H-indazol-4-amine

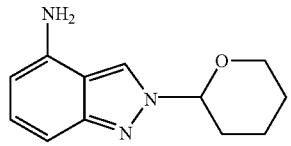

A solution of 4-nitro-2-(tetrahydro-2H-pyran-2-yl)-2H-indazole (2.336 g, 9448 μmol) was dissolved in EtOAc (100 mL) and treated with 10% Pd/C (100 mg). The resulting suspension was stirred under an atmosphere of H$_2$. for 16 h after which time reduction was complete. The reaction mixture was filtered, concentrated and purified by flash chromatography on silica (50% EtOAc/hexane) to give 2-(tetrahydro-2H-pyran-2-yl)-2H-indazol-4-amine (584 mg, 28.5% yield) as a dry orange foam. $^1$H NMR (400 MHz, d6-DMSO) δ 8.47 (s, 1H); 6.92 (t, J=7.82 Hz, 1H); 6.72 (d, J=8.61 Hz, 1H); 5.99 (d, J=7.04 Hz, 1H); 5.54-5.69 (m, 3H); 3.98 (d, J=11.74 Hz, 1H); 3.63-3.78 (m, 1H); 2.02-2.13 (m, 2H); 1.87-2.00 (m, 1H); 1.65-1.80 (m, 1H); 1.59 (br. s., 2H). m/z (ESI, +ve). Found 218.1 (M+H)$^+$.

Example 16

N-(5-(3-(9H-purin-6-yl)pyridin-2-ylamino)pyridin-2-yl)acetamide

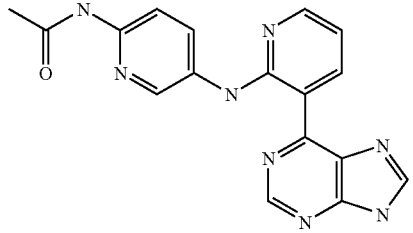 [SMILES: CC(=O)Nc1ccc(Nc2ncccc2-c2ncnc3[nH]cnc23)cn1]

Step 1. N-(5-(3-(9-(tetrahydro-2H-pyran-2-yl)-9H-purin-6-yl)pyridin-2-ylamino)pyridin-2-yl)acetamide A mixture of 6-(2-fluoropyridin-3-yl)-9-(tetrahydro-2H-pyran-2-yl)-9H-purine (300 mg, 1002 μmol) and 2-acetamido-5-aminopyridine (Aldrich, St. Louis, Mo.) (152 mg, 1002 μmol) was suspended in THF (2 mL) and treated with LiHMDS (1.0 M in THF, Aldrich, St. Louis, Mo.) (4009 μl, 4009 μmol). The mixture was stirred for 16 h and then poured into saturated aqueous NaHCO$_3$, extracting with EtOAc. Some dark orange insoluble material was observed. The EtOAc extract was dried (MgSO$_4$), filtered and concentrated to give N-(5-(3-(9-(tetrahydro-2H-pyran-2-yl)-9H-purin-6-yl)pyridin-2-ylamino)pyridin-2-yl)acetamide (324 mg, 75% yield) as an orange solid. $^1$H NMR (CDCl$_3$, 300 MHz) δ 12.35 (s, 1H), 9.73 (dd, 1H), 9.04 (s, 1H), 8.69 (bs, 1H), 8.37 (s, 1H), 8.35 (dd, 1H), 8.21 (bs, 2H), 8.00 (bs, 1H), 6.96 (dd, 1H), 5.89 (dd, 1H), 4.23 (m, 1H), 3.84 (m, 1H), 2.21 (s, 3H), 2.3-17 (m, 8H); m/z (API-ES) 431, (M+H)$^+$.

Step 2. N-(5-(3-(9H-purin-6-yl)pyridin-2-ylamino)pyridin-2-yl)acetamide

A suspension of N-(5-(3-(9-(tetrahydro-2H-pyran-2-yl)-9H-purin-6-yl)pyridin-2-ylamino)pyridin-2-yl)acetamide (19.6 mg, 46 μmol) in MeOH (about 0.2 mL) was treated with 2 M aqueous HCl (about 6 drops, excess) and gently heated. An almost clear solution was initially obtained, with a red solid crystallizing from solution. This was allowed to stand overnight and the solid collected by filtration, washing with a small quantity of MeOH. N-(5-(3-(9H-Purin-6-yl)pyridin-2-ylamino)pyridin-2-yl)acetamide hydrochloride (12 mg, 69% yield) was obtained as a dark solid. $^1$H NMR (d6-DMSO, 400 MHz) δ 12.61 (bs, 1H), 10.81 (bs, 1H), 9.76 (d, 1H), 9.14 (s, 1H), 8.86 (s, 1H), 8.73 (s, 1H), 8.36 (dd, 1H), 8.31 (dd, 1H), 7.97 (d, 1H), 7.10 (dd, 1H), 5.76 (s, 1H), 4.3 (bs, water+exchangeables); m/z (API-ES) 347, (M+H)⁺.

Example 17

N3-(3-(9H-purin-6-yl)pyridin-2-yl)pyridine-3,6-diamine

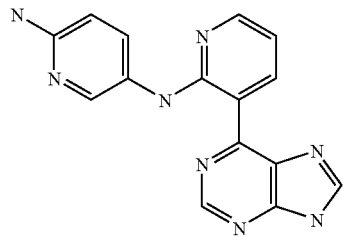 [SMILES: Nc1ccc(Nc2ncccc2-c2ncnc3[nH]cnc23)cn1]

A solution of N-(5-(3-(9-(tetrahydro-2H-pyran-2-yl)-9H-purin-6-yl)pyridin-2-ylamino)pyridin-2-yl)acetamide (18.8 mg, 44 µmol) in 5 N aqueous HCl (1 mL) was heated at 95° C. for 1 h, after which time LCMS indicated conversion to desired product. The solution was made slightly alkaline with 5 N aqueous NaOH (about pH 8) and the resulting precipitate was collected by filtration, washing with water, and dried to give N3-(3-(9H-purin-6-yl)pyridin-2-yl)pyridine-3,6-diamine (6.0 mg, 45% yield) as a dark solid. ¹H NMR (d6-DMSO, 400 MHz) δ 12.17 (bs, 1H), 9.74 (d, 1H), 8.98 (s, 1H), 8.55 (s, 1H), 8.21 (m, 2H), 7.77 (dd, 1H), 6.89 (dd, 1H), 6.49 (d, 1H), 5.65 (bs, 3H); m/z (API-ES) 305, (M+H)⁺.

Example 18

N-(3-(9H-purin-6-yl)pyridin-2-yl)-1H-indazol-4-amine

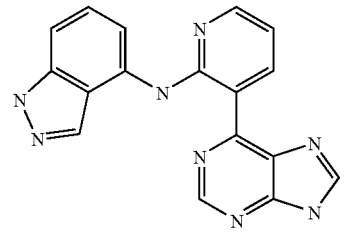 [SMILES: c1cnc(Nc2cccc3[nH]ncc23)c(-c2ncnc3[nH]cnc23)c1]

Step 1. 2-(tetrahydro-2H-pyran-2-yl)-N-(3-(9-(tetrahydro-2H-pyran-2-yl)-9H-purin-6-yl)pyridin-2-yl)-2H-indazol-4-amine A solution of 2-(tetrahydro-2H-pyran-2-yl)-2H-indazol-4-amine (37.4 mg, 172 µmol) and 6-(2-fluoropyridin-3-yl)-9-(tetrahydro-2H-pyran-2-yl)-9H-purine (51.5 mg, 172 µmol) in THF (1.0 mL) was cooled in an ice bath and treated dropwise with LHMDS (0.55 mL of a 1.0 M solution in THF, 3 equiv.). A deep red solution was obtained. The mixture was stirred for 60 min and then quenched with water (0.050 mL). The mixture was extracted with EtOAc from saturated aqueous NaHCO₃, dried (MgSO₄) and concentrated to give a dark residue. 2-(Tetrahydro-2H-pyran-2-yl)-N-(3-(9-(tetrahydro-2H-pyran-2-yl)-9H-purin-6-yl)pyridin-2-yl)-2H-indazol-4-amine (36.6 mg, 42.8% yield) was obtained by flash chromatography on silica (50% EtOAc/hexane) (yellow band on column) as a yellow oil which crystallized upon standing. ¹H NMR (400 MHz, CDCl₃) δ 12.75 (br. s., 1H); 9.77 (d, J=7.82 Hz, 1H); 9.12 (s, 1H); 8.44 (d, J=3.52 Hz, 1H); 8.38 (s, 2H); 8.06 (d, J=7.04 Hz, 1H); 7.41 (d, 1H); 7.35 (d, J=7.63 Hz, 1H); 6.92-7.03 (m, 1H); 5.88 (d, 1H); 5.73 (d, 1H); 4.13-4.30 (m, 2H); 3.84 (br. s., 2H); 2.17-2.35 (m, 3H); 2.00-2.16 (m, 3H); 1.79 (br. s., 6H). m/z (API-ES) 497.1 (M+H)⁺.

Step 2. N-(3-(9H-purin-6-yl)pyridin-2-yl)-1H-indazol-4-amine

A solution of 2-(tetrahydro-2H-pyran-2-yl)-N-(3-(9-(tetrahydro-2H-pyran-2-yl)-9H-purin-6-yl)pyridin-2-yl)-2H-indazol-4-amine (34.8 mg, 70 µmol) in DCM/MeOH (4 mL; 1:1) was treated with (+/−)-10-camphorsulfonic acid (8 mg, 0.5 equiv.) and the mixture stirred for 16 h. About 50% monodeprotection was observed in a clean reaction. An additional 20 mg of CSA was added (1.7 equiv. total). After 1 h, virtually complete monodeprotection observed and about 10% dideprotection. After 3 h, about 27% conversion to fully deprotected compound was observed in a clean reaction by LCMS. An additional 8 mg CSA was added (2.2 equiv. total) and the temperature of the reaction mixture was increased to 40° C. After a further 3 h, deprotection was essentially complete by LCMS. The volume of the reaction mixture was reduced by about 50% under a stream of N₂ in order to remove DCM, and the solution was triturated with Et₂O resulting in the formation of a precipitate which was collected by filtration washing with Et₂O and dried under vacuum to give N-(3-(9H-purin-6-yl)pyridin-2-yl)-1H-indazol-4-amine (+/−)-10-camphorsulfonate salt (33.7 mg, 86% yield) as a brown solid. ¹H NMR (400 MHz, DMSO-d6) δ 13.17 (br. s., 1H); 9.89 (d, 1H); 9.33 (s, 1H); 8.76 (s, 1H); 8.41-8.46 (m, 1H); 8.31 (s, 1H); 8.24 (d, 1H); 7.35 (t, 1H); 7.21 (d, 1H); 7.14 (t, 1H); 2.88 (d, 1H); 2.63-2.73 (m, 1H); 2.34-2.42 (d, 1H); 2.18-2.29 (m, 1H); 1.90-1.97 (m, 1H); 1.74-1.90 (m, 2H); 1.27 (m, 2H); 1.05 (s, 3H); 0.75 (s, 3H). m/z (ESI, +ve) 329.0 (M+H)⁺.

Example 19

N-(3-(9H-purin-6-yl)pyridin-2-yl)-1H-indol-4-amine 6-(2-Fluoropyridin-3-yl)-9-(tetrahydro-2H-pyran-2-yl)-9H-purine (115.0 mg, 0.3842 mmol) and 1H-indol-4-amine (Aldrich, St. Louis, Mo., 70.7 mg, 0.535 mmol) were suspended in EtOH (1.8 mL) and aqueous hydrochoric acid (5.0 M, 0.090 ml, 0.45 mmol) was added. The flask was fitted with a reflux condenser and placed in a preheated oil bath (100° C.), and the reaction was stirred for 3 hours. Then, the reaction was cooled to room temperature and diluted with DCM, 2 N ammonia in MeOH, EtOH, and MeOH and concentrated. The residue was treated with MeOH and filtered. Neither the filtrate nor the solid contained pure material, so they were combined, concentrated, treated with DMF, and filtered. The filtrate was concentrated and purified on HPLC (10% to 100% MeCN/water with 0.1% TFA over 30 minutes with a total flow rate of 100 mL/min). The fractions with product were collected, concentrated, and filtered through a silica gel plug (about 1 inch, 50:1 DCM/2 N ammonia in MeOH to 20:1 DCM/2 N ammonia in MeOH to 5:1 DCM/2 N ammonia in MeOH) to afford N-(3-(9H-purin-6-yl)pyridin-2-yl)-1H-indol-4-amine (6.9 mg, 5% yield). MS (ESI pos. ion) m/z: 328, (M+H)$^+$. $^1$H NMR (d6-DMSO, 400 MHz) δ 12.90 (s, 1H), 11.16 (s, 1H), 9.87 (d, J=7.82 Hz, 1H), 9.24 (s, 1H), 8.73 (s, 1H), 8.43 (dd, J=4.69 Hz, 1.96 Hz, 1H), 8.28 (dd, J=4.6 Hz, 3.81 Hz, 1H), 7.38-7.35 (m, 1H), 7.09 (s, 1H), 7.08-7.06 (m, 1H), 7.04 (dd, J=7.82 Hz, 4.69 Hz, 1H), 6.79-6.76 (m, 1H).

Example 20

N-(6-methoxypyridin-3-yl)-3-(9H-purin-6-yl)pyridin-2-amine

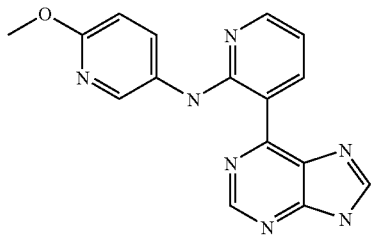 [SMILES: COc1ccc(Nc2ncccc2-c2ncnc3[nH]cnc23)cn1]

Step 1. 6-methoxy-N-(3-(9-(tetrahydro-2H-pyran-2-yl)-9H-purin-6-yl)pyridin-2-yl)pyridin-3-amine A solution of 6-(2-fluoropyridin-3-yl)-9-(tetrahydro-2H-pyran-2-yl)-9H-purine (196.6 mg, 657 µmol) and 3-amino-6-methoxypyridine (Aldrich, St. Louis, Mo.) (101.9 mg, 821 µmol) in THF (2.0 mL) was cooled in an ice bath and treated with LiHMDS (3.0 mL, 3.0 mmol). A blood-red solution was obtained. The mixture was stirred for 1 h, and then quenched with water (0.1 mL). The mixture was extracted into EtOAc from saturated aqueous NaHCO$_3$, concentrated and purified by flash chromatography on silica (50% EtOAc/hexane; yellow band from column) to give 6-methoxy-N-(3-(9-(tetrahydro-2H-pyran-2-yl)-9H-purin-6-yl)pyridin-2-yl)pyridin-3-amine (190 mg, 71.7% yield) as a yellow crystalline solid. $^1$H NMR (400 MHz, CDCl$_3$) δ 12.06 (s, 1H); 9.68 (dd, J=7.82, 1.76 Hz, 1H); 8.99 (s, 1H); 8.44 (d, J=2.54 Hz, 1H); 8.28 (dd, J=4.69, 1.76 Hz, 1H) 8.34 (s, 1H); 8.05 (dd, J=8.90, 2.64 Hz, 1H); 6.88 (dd, J=7.82, 4.69 Hz, 1H); 6.77 (d, J=8.80 Hz, 1H); 5.86 (dd, J=10.37, 2.35 Hz, 1H); 4.16-4.25 (m, 1H); 3.95 (s, 3H); 3.82 (s, 1H); 1.98-2.24 (m, 3H); 1.61-1.89 (m, 3H). m/z (ESI, +ve) 404.0 (M+H)$^+$.

Step 2. N-(6-methoxypyridin-3-yl)-3-(9H-purin-6-yl)pyridin-2-amine

A solution of 6-methoxy-N-(3-(9-(tetrahydro-2H-pyran-2-yl)-9H-purin-6-yl)pyridin-2-yl)pyridin-3-amine (190 mg, 471 µmol) in 2 N aqueous HCl (2.0 mL, 4 mmol) was heated briefly at 100° C. in an oil bath, and then the heater was turned off and the mixture allowed to slowly cool and stand overnight. An essentially clean conversion was observed. The solution was neutralized with aqueous ammonia, and the precipitated product was collected by filtration washing with a small volume of water and dried under vacuum. N-(6-methoxypyridin-3-yl)-3-(9H-purin-6-yl)pyridin-2-amine (120.4 mg, 80.1% yield) was obtained as an orange solid. $^1$H NMR (400 MHz, DMSO-d6) δ 13.80 (br. s., 1H); 12.33 (br. s., 1H); 9.73 (br. s., 1H); 9.10 (s, 1H); 8.70 (s, 1H); 8.50-8.58 (m, 1H); 8.25-8.34 (m, 1H); 8.08-8.20 (m, 1H); 6.95-7.07 (m, 1H); 6.79-6.90 (m, 1H); 3.85 (s, 3H). m/z (ESI, +ve) 320.0 (M+H)$^+$.

Example 21

N-(3-(6-amino-2-(trifluoromethyl)pyrimidin-4-yl)pyridin-2-yl)-1H-indazol-4-amine

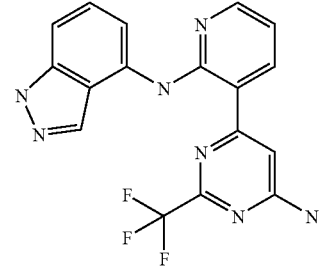 [SMILES: Nc1cc(-c2cccnc2Nc2cccc3[nH]ncc23)nc(C(F)(F)F)n1]

Step 1. 6-(2-fluoropyridin-3-yl)-2-(trifluoromethyl)pyrimidin-4-amine

The title compound was prepared in an analogous manner to that described above in Example 4 using 2-fluoropyridin-3-ylboronic acid and 6-chloro-2-(trifluoromethyl)pyrimidin-4-amine (SynChem Inc., Elk Grove Village, Ill.), and the desired product 6-(2-fluoropyridin-3-yl)-2-(trifluoromethyl)pyrimidin-4-amine was isolated as a white solid (34%). LCMS (API-ES) m/z 259 (M+H)$^+$; $^1$H NMR (400 MHz, d6-DMSO) δ 8.57 (t, J=8.80 Hz, 1H) 8.38 (d, J=3.91 Hz, 1H) 7.83 (br. s., 2H) 7.46-7.63 (m, 1H) 7.15 (s, 1H).

Step 2. N-(3-(6-amino-2-(trifluoromethyl)pyrimidin-4-yl)pyridin-2-yl)-1H-indazol-4-amine A mixture of 6-(2-fluoropyridin-3-yl)-2-(trifluoromethyl)pyrimidin-4-amine and 1H-indol-4-amine (1.2 equiv.) in 1,4-dioxane and 2 N HCl (aq) (10:1) was heated at 100° C. overnight in an analogous manner to that described in Example 22, Step 2. After cooling, the reaction mixture was concentrated and the crude residue was dissolved in DCM/MeOH and mixed with SiO$_2$. The solvent was evaporated and the residue purified by flash column chromatography (pure DCM to 5% MeOH in DCM) to give N-(3-(6-amino-2-(trifluoromethyl)pyrimidin-4-yl)pyridin-2-yl)-1H-indazol-4-amine as a yellow solid (13%). LCMS (API-ES) m/z 372 (M+H)$^+$; $^1$H NMR (400 MHz, d6-DMSO) δ ppm 13.06 (br. s., 1H) 10.82 (s, 1H) 8.36 (d, J=4.52 Hz, 1H) 8.11 (d, J=7.53 Hz, 1H) 7.99 (s, 1H) 7.89 (d, J=7.53 Hz, 1H) 7.81 (br. s., 2H) 7.29 (t, J=7.53 Hz, 1H) 7.14 (d, J=8.03 Hz, 1H) 7.07 (s, 1H) 6.95-7.05 (m, 1H).

Example 22

N-(3-(4-amino-6-methyl-1,3,5-triazin-2-yl)pyridin-2-yl)-1H-indol-4-amine

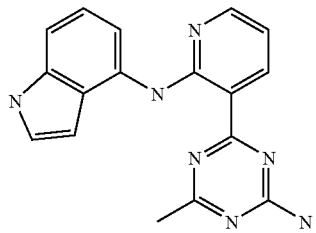 [SMILES: Cc1nc(N)nc(-c2cccnc2Nc2cccc3[nH]ccc23)n1]

Step 1. 4-(2-fluoropyridin-3-yl)-6-methyl-1,3,5-triazin-2-amine 1,4-Dioxane (6.00 mL, 2927 µmol) was added to a mixture of 4-chloro-6-methyl-1,3,5-triazin-2-amine (423.1 mg, 2927 µmol), 2-fluoropyridin-3-ylboronic acid (619 mg, 4390 µmol), bis(di-tert-butyl (4-dimethylaminophenyl)phosphine) dichloropalladium(II) (91.0 mg, 146 µmol) and potassium acetate (862 mg, 8780 µmol) and the mixture was heated at 100° C. overnight. After cooling, the mixture was passed through a short plug of Celite® (diatomaceous earth). The filter cake was washed with EtOAc (3×15 mL). The combined organic phases were concentrated to give a crude residue. Flash column chromatographic purification (short column, SiO$_2$, pure DCM to 3% MeOH in DCM) provided the title compound which was washed with MeOH to give 4-(2-fluoropyridin-3-yl)-6-methyl-1,3,5-triazin-2-amine (454 mg, 76%) as a pale brown powder. LCMS (API-ES) m/z 206 (M+H)$^+$; $^1$H NMR (400 MHz, d6-DMSO) δ 8.48 (ddd, J=9.91, 7.65, 2.01 Hz, 1H) 8.39 (d, J=5.02 Hz, 1H) 7.65 (br. s., 2H) 7.51 (ddd, J=7.15, 5.14, 1.76 Hz, 1H) 2.37 (s, 3H).

Step 2. N-(3-(4-amino-6-methyl-1,3,5-triazin-2-yl)pyridin-2-yl)-1H-indol-4-amine 2 N HCl (aq) (0.42 mL, 833 µmol) was added to a stirred mixture of 4-(2-fluoropyridin-3-yl)-6-methyl-1,3,5-triazin-2-amine (171 mg, 833 µmol) and 1H-indol-4-amine (132 mg, 1000 µmol) in 1,4-dioxane (4.00 mL, 46762 µmol) and the brown mixture was heated at 100° C. overnight. After cooling, the reaction mixture was concentrated and the crude residue was dissolved in DCM/MeOH and mixed with SiO$_2$. The solvent was evaporated and the residue was purified by flash column chromatography (pure DCM to 5% MeOH in DCM) followed by washing the eluent concentrates with EtOAc to give N-(3-(4-amino-6-methyl-1,3,5-triazin-2-yl) pyridin-2-yl)-1H-indol-4-amine (58 mg, 22%) as a yellow solid. LCMS (API-ES) m/z 318 (M+H)$^+$; $^1$H NMR (400 MHz, d6-DMSO) δ ppm 12.00 (s, 1H) 11.15 (br. s., 1H) 8.77 (dd, J=7.78, 1.76 Hz, 1H) 8.38 (dd, J=4.52, 1.51 Hz, 1H) 8.09 (d, J=6.02 Hz, 1H) 7.53-7.81 (m, 2H) 7.35 (t, J=2.76 Hz, 1H) 6.99-7.19 (m, 2H) 6.90 (dd, J=7.78, 4.77 Hz, 1H) 6.66 (br. s., 1H) 2.55 (s, 3H).

Example 23

3-(3-(4-amino-6-methyl-1,3,5-triazin-2-yl)pyridin-2-ylamino)phenol

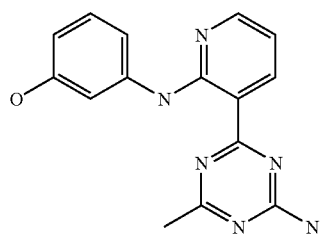 [SMILES: Cc1nc(N)nc(-c2cccnc2Nc2cccc(O)c2)n1]

The title compound was prepared in an analogous manner to that described in Example 22 using 4-(2-fluoropyridin-3-yl)-6-methyl-1,3,5-triazin-2-amine and 3-aminophenol, and isolated as a yellow solid (34%). LCMS (API-ES) m/z 295 (M+H)$^+$; $^1$H NMR (400 MHz, d6-DMSO) δ 11.97 (s, 1H) 9.27 (s, 1H) 8.76 (dd, J=7.78, 1.76 Hz, 1H) 8.35 (dd, J=4.77, 1.76 Hz, 1H) 7.64-7.92 (m, 2H) 7.51 (s, 1H) 6.99-7.28 (m, 2H) 6.89 (dd, J=7.53, 4.52 Hz, 1H) 6.40 (d, J=7.03 Hz, 1H) 2.45 (s, 3H).

Example 24

N-(3-(4-amino-6-methyl-1,3,5-triazin-2-yl)pyridin-2-yl)-1H-indazol-4-amine

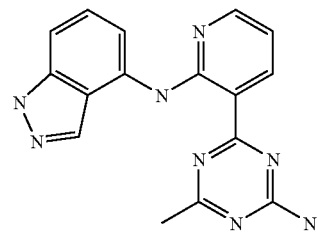 [SMILES: Cc1nc(N)nc(-c2cccnc2Nc2cccc3[nH]ncc23)n1]

The title compound was prepared in an analogous manner to that described in Example 22 using 4-(2-fluoropyridin-3-yl)-6-methyl-1,3,5-triazin-2-amine and 1H-indazol-4-amine, and isolated as a yellow solid (13%). LCMS (API-ES) m/z 319 (M+H)$^+$; $^1$H NMR (400 MHz, d6-DMSO) δ 13.10 (s, 1H) 12.26 (s, 1H) 8.80 (d, J=7.82 Hz, 1H) 8.42 (d, J=4.50 Hz, 1H)

8.19 (s, 1H) 8.13 (d, J=7.43 Hz, 1H) 7.75 (br. s., 2H) 7.31 (t, J=8.02 Hz, 1H) 7.16 (d, J=8.41 Hz, 1H) 6.89-7.07 (m, 1H) 2.56 (s, 3H).

Example 25

4-(2-(6-methoxypyridin-3-ylamino)pyridin-3-yl)-6-methyl-1,3,5-triazin-2-amine

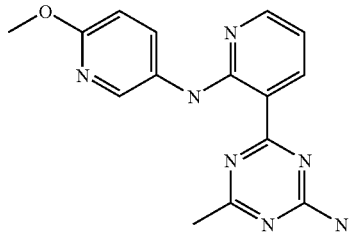 [SMILES: COc1ccc(Nc2ncccc2-c2nc(C)nc(N)n2)cn1]

The title compound was prepared in an analogous manner to that described in Example 22 using 4-(2-fluoropyridin-3-yl)-6-methyl-1,3,5-triazin-2-amine and 5-amino-2-methoxypyridine (Aldrich), and isolated as a yellow solid (80%). LCMS (API-ES) m/z 310 (M+H)+; 1H NMR (400 MHz, d6-DMSO) δ 11.74 (br. s., 1H) 8.77 (dd, J=5.02, 2.51 Hz, 1H) 8.53 (br. s., 1H) 8.29 (br. s., 1H) 8.08-8.23 (m, 1H) 7.84 (br. s., 1H) 7.71 (br. s., 1H) 6.88 (ddd, J=7.78, 4.27, 4.02 Hz, 1H) 6.82 (dd, J=8.78, 4.27 Hz, 1H) 3.84 (d, J=5.02 Hz, 3H) 2.42 (d, J=4.02 Hz, 3H).

Example 26

3-(3-(6-amino-2-methylpyrimidin-4-yl)pyridin-2-ylamino)phenol

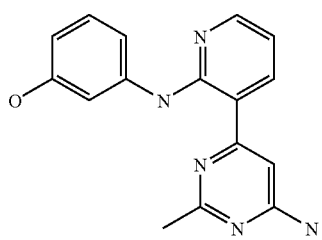 [SMILES: Cc1nc(N)cc(-c2cccnc2Nc2cccc(O)c2)n1]

The title compound was prepared in an analogous manner to that described in Example 22 using 6-chloro-2-methylpyrimidin-4-amine and 3-aminophenol, and was isolated as a yellow solid (3%). LCMS (API-ES) m/z 294 (M+H)+; 1H NMR (400 MHz, d6-DMSO) δ 12.23 (s, 1H) 9.25 (d, J=2.35 Hz, 1H) 8.18-8.35 (m, 1H) 8.02 (d, J=7.63 Hz, 1H) 7.36 (br. s., 1H) 6.95-7.16 (m, 4H) 6.84-6.93 (m, 1H) 6.74 (d, J=1.76 Hz, 1H) 6.35 (dd, J=6.65, 1.96 Hz, 1H) 2.51-2.62 (s, 3H).

Example 27

N-(3-(6-amino-2-methylpyrimidin-4-yl)pyridin-2-yl)-1H-indazol-4-amine

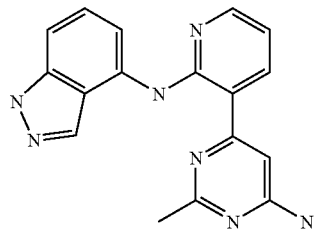 [SMILES: Cc1nc(N)cc(-c2cccnc2Nc2cccc3[nH]ncc23)n1]

The title compound was prepared in an analogous manner to that described in Example 22 using 6-chloro-2-methylpyrimidin-4-amine and 1H-indazol-4-amine, and was isolated as a yellow solid (17%). LCMS (API-ES) m/z 318 (M+H)+; 1H NMR (400 MHz, d6-DMSO) δ 13.09 (br. s., 1H) 12.29 (s, 1H) 8.35 (d, J=4.52 Hz, 1H) 7.89-8.22 (m, 3H) 7.29 (t, J=7.78 Hz, 1H) 6.86-7.20 (m, 4H) 6.79 (s, 1H) 2.62 (s, 3H).

Example 28

5-fluoro-6-(2-fluoropyridin-3-yl)-2-methylpyrimidin-4-amine

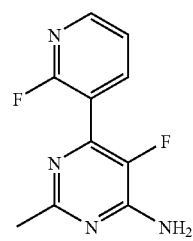 [SMILES: Cc1nc(N)c(F)c(-c2cccnc2F)n1]

DME (6.00 mL, 57722 μmol) and water (0.6 mL, 3152 μmol) were added to a mixture of 2-fluoropyridin-3-ylboronic acid (666 mg, 4728 μmol), 6-chloro-5-fluoro-2-methylpyrimidin-4-amine (0.5093 g, 3152 μmol), and Pd(Ph3P)4 (364 mg, 315 μmol) under nitrogen. The mixture was sealed and heated at 100° C. for 60 min under microwave irradiation. After cooling, the mixture was diluted with water and the precipitate was collected, washed with DCM, and 5-fluoro-6-(2-fluoropyridin-3-yl)-2-methylpyrimidin-4-amine (418 mg, 60%) was isolated as an off-white powder. LCMS (API-ES) m/z 223 (M+H)+; 1H NMR (400 MHz, d6-DMSO) δ 8.39

(d, J=4.02 Hz, 1H) 8.18 (t, J=8.03 Hz, 1H) 7.53 (t, J=5.27 Hz, 1H) 7.38 (br. s., 2H) 2.37 (s, 3H).

Example 29

N-(3-(6-amino-5-fluoro-2-methylpyrimidin-4-yl)pyridin-2-yl)-1H-indazol-4-amine

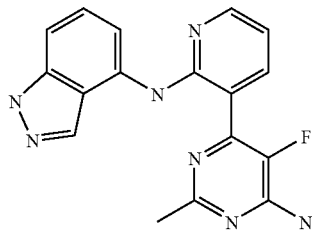 [SMILES: Cc1nc(N)c(F)c(-c2cccnc2Nc2cccc3[nH]ncc23)n1]

2 N Aqueous HCl (0.45 mL, 900 µmol) was added to a stirred mixture of 5-fluoro-4-(2-fluoropyridin-3-yl)-6-methylpyrimidin-2-amine (400 mg, 1800 µmol) and 1H-indazol-4-amine (360 mg, 2700 µmol) in 1,4-dioxane (3.00 mL, 1800 µmol) and the mixture was sealed and heated at 150° C. for 40 min under microwave irradiation. After cooling, the mixture was concentrated. Flash column chromatographic purification (short column, $SiO_2$, pure DCM to 10% MeOH in DCM) provided the title compound which was washed with MeOH to give N-(3-(6-amino-5-fluoro-2-methylpyrimidin-4-yl)pyridin-2-yl)-1H-indazol-4-amine (134 mg, 22% yield) as a yellow powder. LCMS (API-ES) m/z 336 (M+H)$^+$; $^1$H NMR (400 MHz, d6-DMSO) δ 13.07 (br. s., 1H) 10.87 (s, 1H) 8.34 (d, J=3.72 Hz, 1H) 7.82-8.18 (m, 3H) 7.47 (br. s., 2H) 7.19-7.36 (m, 1H) 7.11 (d, J=8.22 Hz, 1H) 6.75-7.05 (m, 1H) 2.56 (s, 3H).

Example 30

3-(3-(4-amino-6-methyl-1,3,5-triazin-2-yl)-5-((4-(methylsulfonyl)piperazin-1-yl)methyl)pyridin-2-ylamino)phenol

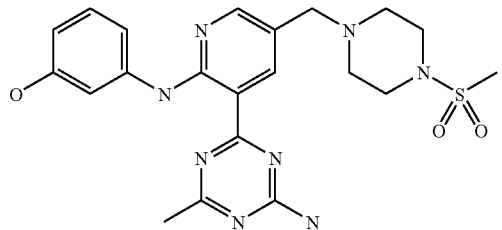 [SMILES: Cc1nc(N)nc(-c2cc(CN3CCN(S(C)(=O)=O)CC3)cnc2Nc2cccc(O)c2)n1]

Step 1. 5,6-dichloronicotinaldehyde

A mixture of 5,6-dichloro-3-pyridinemethanol (2.9967 g, 16.8 mmol) in DCM (3.00 mL, 46.6 mmol) was treated with Dess-Martin periodinane (7.14 g, 16.8 mmol) at room temperature and the mixture was stirred at room temperature overnight. The resulting reaction mixture was diluted with NaHCO$_3$(aq) and water (5 mL each) and diluted with DCM (5 mL). The separated aqueous layer was extracted with DCM (2×10 mL) and the combined organic layers were washed with brine, dried over Na$_2$SO$_4$, and concentrated to give a pale-yellow solid which was used directly for the next step.

Step 2. 1-((5,6-dichloropyridin-3-yl)methyl)-4-(methylsulfonyl)piperazine 1-methanesulfonylpiperazine (1.1 g, 6.8 mmol) followed by a catalytic amount of AcOH (0.020 mL, 0.34 mmol) were added to a stirred solution of 5,6-dichloronicotinaldehyde (1.20 g, 6.8 mmol) in EtOH (100 mL, 1713 mmol), the mixture was stirred at room temperature for 1 h (white precipitate formed), and the resulting suspension was treated portionwise with sodium cyanoborohydride (0.43 g, 6.8 mmol) (slightly exothermic) and stirred for another 2 h. The mixture was concentrated and quenched with 1 N HCl (aq), water (10 mL each) and EtOAc (50 mL). The separated aqueous layer was extracted with ethyl acetate (2×50 mL) and the combined organic layers were washed with brine, dried over Na$_2$SO$_4$, and concentrated to give a crude residue which was purified with flash column chromatography (ISCO Combiflash system, pure DCM to 3% 2 M NH$_3$/MeOH in DCM) to give 1-((5,6-dichloropyridin-3-yl)methyl)-4-(methylsulfonyl)piperazine (1.16 g, 52%) as a white solid. LCMS (API-ES) m/z 325 (M+H)$^+$; $^1$H NMR (400 MHz, CDCl$_3$) δ 8.23 (s, 1H) 7.78 (s, 1H) 3.54 (s, 2H) 3.26 (br. s., 4H) 2.80 (s, 3H) 2.57 (br. s., 4H).

Step 3. 3-(3-chloro-5-((4-(methylsulfonyl)piperazin-1-yl)methyl)pyridin-2-ylamino)phenol The title compound was prepared in an analogous manner to that described above in Example 22, Step 2 using 1-((5,6-dichloropyridin-3-yl)methyl)-4-(methylsulfonyl)piperazine and 3-aminophenol under microwave irradiation conditions (150° C., 30 min), and isolated as a pale yellow solid (70%). LCMS (API-ES) m/z 398 (M+H)$^+$.

Step 4. 3-(3-(4-amino-6-methyl-1,3,5-triazin-2-yl)-5-((4-(methylsulfonyl)piperazin-1-yl)methyl)pyridin-2-ylamino)phenol 1,4-Dioxane (4.00 mL, 46762 µmol) was added to a mixture of 3-(3-chloro-5-((4-(methylsulfonyl)piperazin-1-yl)methyl)pyridin-2-ylamino)phenol (390 mg, 983 µmol), bis(pinacolato)diboron (299 mg, 1179 µmol), X-Phos (46.8 mg, 98.3 µmol), tris(dibenzylideneacteone)dipalladium(0) (45.0 mg, 49.1 µmol) and potassium acetate (0.154 ml, 2457 µmol) and the mixture was stirred at 100° C. for 3 h. After cooling to room temperature, 4-chloro-6-methyl-1,3,5-triazin-2-amine (213 mg, 1474 µmol) and bis(di-tert-butyl (4-dimethylaminophenyl)phosphine)dichloropalladium(II) (Aldrich, St. Louis, Mo.) (61.1 mg, 98.3 µmol) was added and the mixture was resealed and continued heating at 100° C. overnight. The mixture was allowed to cool to room temperature, filtered through a short path of Celite® (diatomaceous earth), and the filter cake was washed with EtOAc (2×20 mL). The combined organic phases were concentrated with SiO$_2$ and purified by flash column chromatography (ISCO CombiFlash® system, Teledyne ISCO, Lincoln, Nebr.), pure DCM to 10% 2 M NH$_3$/MeOH in DCM) to give 3-(3-(4-Amino-6-methyl-1,3,5-triazin-2-yl)-5-((4-(methylsulfonyl)piperazin-1-yl)methyl)pyridin-2-ylamino)phenol (7 mg, 1.5%) as a yellow solid. LCMS (API-ES) m/z 471 (M+H)$^+$; $^1$H NMR (400 MHz, d6-DMSO) δ 11.98 (br. s., 1H) 9.27 (d, J=4.89 Hz, 1H) 8.59-8.78 (m, 1H) 8.26 (d, J=2.93 Hz, 1H) 7.61-7.92 (m, 1H)

7.50 (d, J=1.76 Hz, 1H) 6.81-7.26 (m, 2H) 6.24-6.50 (m, 1H) 3.49 (br. s., 2H) 3.11 (br. s., 4H) 2.87 (d, J=5.87 Hz, 3H) 2.37-2.48 (m, 7H).

Example 31

4-(2-(6-methoxypyridin-3-ylamino)-5-methylpyridin-3-yl)-6-methyl-1,3,5-triazin-2-amine

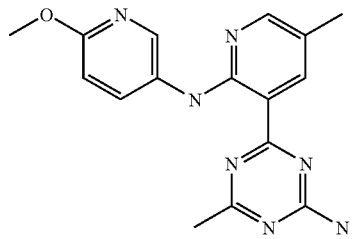 [SMILES: COc1ccc(Nc2ncc(C)cc2-c2nc(C)nc(N)n2)cn1]

Step 1. 2-fluoro-5-methylpyridin-3-ylboronic acid n-Butyllithium (2.5M solution in hexane, 9.6 mL, 24 mmol) was added to a mixture of diisopropylamine (3.4 mL, 24 mmol) in THF (5.00 mL, 61 mmol) at 0° C. and the resulting pale yellow solution was stirred at the same temperature for 30 min and then cooled down to −78° C. A suspension of 2-fluoro-5-methylpyridine (Aldrich, St. Louis, Mo.) (2.22 g, 20 mmol) in THF (5.00 mL, not complete dissolved) was slowly added. The resulting bright yellow solution was stirred at −78° C. for 1 h, treated with a solution of tri-i-propylborate (6.9 mL, 30 mmol) in THF (10.00 mL) and then allowed to warm up to room temperature. The yellow suspension was quenched with 1 N NaOH until basic (pH about 10) and the organic layer was separated. The aqueous layer was collected and carefully acidified with 6 N aqueous HCl until slightly acidic, and then extracted with EtOAc (×3). The combined organic layers were dried (Na$_2$SO$_4$), filtered and concentrated. The resulting white solid was washed with ether to give 2-fluoro-5-methylpyridin-3-ylboronic acid (2.9196 g, 94% yield) as a white solid. LCMS (API-ES) m/z 156 (M+H)$^+$.

Step 2. 4-(2-fluoro-5-methylpyridin-3-yl)-6-methyl-1,3,5-triazin-2-amine 1,4-Dioxane (3.00 mL, 8.5 mmol) was added to a mixture of bis(di-tert-butyl (4-dimethylaminophenyl)phosphine) dichloropalladium(II) (Aldrich, St. Louis, Mo.) (0.27 g, 0.43 mmol), 2-fluoro-5-methylpyridin-3-ylboronic acid (1.6 g, 10 mmol), 4-chloro-6-methyl-1,3,5-triazin-2-amine (1.24 g, 8.5 mmol) and potassium acetate (2.5 g, 26 mmol) and the mixture was sealed and heated at 120° C. for 30 min under microwave irradiation. After cooling, the mixture was passed through a short plug of Celite® (diatomaceous earth). The filter cake was washed with DCM (3×20 mL). The combined organic phases were concentrated. Flash column chromatographic purification (short column, SiO$_2$, pure DCM to 5% MeOH in DCM) provided 4-(2-fluoro-5-methylpyridin-3-yl)-6-methyl-1,3,5-triazin-2-amine (0.76, 41%) as a white solid which was used for the next step. LCMS (API-ES) m/z 220 (M+H)$^+$.

Step 3. di-tert-butyl 4-(2-fluoro-5-methylpyridin-3-yl)-6-methyl-1,3,5-triazin-2-yl-di-carbamate NaH (0.41 g, 10 mmol) was added to a solution of 4-(2-fluoro-5-methylpyridin-3-yl)-6-methyl-1,3,5-triazin-2-amine (0.9046 g, 4.1 mmol) in DMF (3.00 mL, 39 mmol) and the mixture was stirred at room temperature overnight. The resulting red-yellow solution was quenched with ice and the resulting yellow solid was washed with water to give the desired product as a yellow solid. LCMS (API-ES) m/z 420 (M+H)$^+$.

Step 4. 4-(2-(6-methoxypyridin-3-ylamino)-5-methylpyridin-3-yl)-6-methyl-1,3,5-triazin-2-amine LiHMDS, 1.0 M in THF (0.80 mL, 801 µmol) was added at room temperature to a stirred mixture of di-tert-butyl 4-(2-fluoro-5-methylpyridin-3-yl)-6-methyl-1,3,5-triazin-2-yl-di-carbamate (112 mg, 267 µmol) and 3-amino-6-methoxypyridine (Aldrich, St. Louis, Mo.) (50 mg, 401 µmol) in THF (3.00 mL, 36613 µmol) and the mixture was stirred at rt for 1 h. The reaction mixture was diluted with NH$_4$Cl (aq) and water (5 mL each) and diluted with ethyl acetate (10 mL). The separated aqueous layer was extracted with ethyl acetate (2×10 mL) and the combined organic layers were washed with brine, dried over Na$_2$SO$_4$, and concentrated to give a crude residue which was taken up in DCM (2.00 mL) and TFA (2.00 mL) was added. The mixture was stirred for 1 h. The reaction mixture was concentrated and re-diluted with DCM, NaHCO$_3$(aq), and water (10 mL each). The separated aqueous layer was extracted with DCM (2×10 mL) and the combined organic layers were washed with brine, dried over Na$_2$SO$_4$, and concentrated to give a crude residue which was purified by flash column chromatography (pure DCM to 5% MeOH in DCM) followed by another column chromatographic purification (hexanes to 80% ethyl acetate in hexanes) to give the desired product 4-(2-(6-methoxypyridin-3-ylamino)-5-methylpyridin-3-yl)-6-methyl-1,3,5-triazin-2-amine (11 mg, 13% yield) as a yellow solid. LCMS (API-ES) m/z 324 (M+H)$^+$; $^1$H NMR (400 MHz, d6-DMSO) δ 11.53 (br. s., 1H) 8.66 (br. s., 1H) 8.35 (br. s., 1H) 8.16 (br. s., 1H) 8.09 (d, J=10.37 Hz, 1H) 6.79 (d, J=9.19 Hz, 1H) 5.38 (br. s., 2H) 3.95 (s, 3H) 2.56 (s, 3H) 2.29 (s, 3H).

Example 32 methyl-6-(5-methyl-2-(pyridin-3-ylamino)pyridin-3-yl)-1,3,5-triazin-2-amine

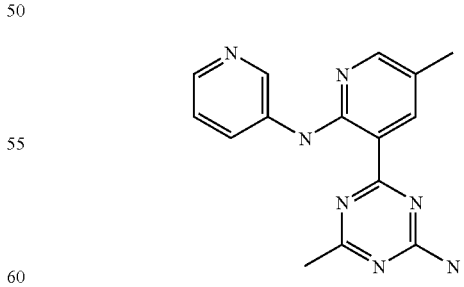

The title compound was prepared in an analogous manner to that described in Example 31, Step 4 using di-tert-butyl 4-(2-fluoro-5-methylpyridin-3-yl)-6-methyl-1,3,5-triazin-2-yl-di-carbamate and pyridin-3-amine (Aldrich, St. Louis, Mo.), and was isolated as a yellow solid (19%). LCMS (API-ES) m/z 294 (M+H)$^+$; $^1$H NMR (400 MHz, d6-DMSO) δ

12.29 (s, 1H) 9.36 (br. s., 1H) 8.69 (d, J=2.15 Hz, 1H) 8.65 (d, J=8.41 Hz, 1H) 8.36 (d, J=4.69 Hz, 1H) 8.30 (d, J=1.76 Hz, 1H) 7.95 (br. s., 1H) 7.84 (br. s., 1H) 7.71 (dd, J=7.34, 6.16 Hz, 1H) 2.46 (s, 3H) 2.32 (s, 3H).

Example 33

4-(5-methoxy-2-(6-methoxypyridin-3-ylamino)pyridin-3-yl)-6-methyl-1,3,5-triazin-2-amine

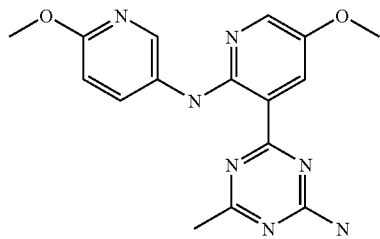

Step 1. 3-bromo-2-chloro-5-methoxypyridine

K$_2$CO$_3$ (0.50 g, 3.6 mmol) followed by methyl iodide (0.20 mL, 2.9 mmol) were added to a stirred mixture of 5-bromo-6-chloropyridin-3-ol (Asymchem Laboratories, Inc., Morrisville, N.C.) (0.50 g, 2.4 mmol) in DMF (3.00 mL) and the mixture was sealed and heated at 45° C. for 4 h and then allowed to stand at room temperature overnight. The resulting mixture was diluted with water and the precipitate was collected and dried to give the product as a tan solid. LCMS (API-ES) m/z 223 (M+H)$^+$; $^1$H NMR (400 MHz, CDCl$_3$) δ 8.04 (s, 1H) 7.49 (d, J=1.37 Hz, 1H) 3.86 (s, 3H).

Step 2. 2-chloro-5-methoxypyridin-3-ylboronic acid 2.5 M n-BuLi in hexane (3.7 mL, 9.3 mmol) was added slowly to a stirred premixed solution of 3-bromo-2-chloro-5-methoxypyridine (1.73 g, 7.8 mmol) and triisopropyl borate (2.1 mL, 9.3 mmol) in THF (10.0 mL, 122 mmol) at −78° C., and the resulting deep colored mixture was stirred at the same temperature for 1 h and then allowed to warm up to room temperature over 1 h. The reaction was quenched with 1 N NaOH(aq) and then some EtOAc. The separated aqueous layer was acidified with 5 N HCl until pH about 5 and then extracted with EtOAc (×2) and the combined organic layers were washed with brine, dried over Na$_2$SO$_4$, and concentrated to give 2-chloro-5-methoxypyridin-3-ylboronic acid (1.0276 g, 71%) as a brown solid. LCMS (API-ES) m/z 188 (M+H)$^+$.

Step 3. 4-(2-chloro-5-methoxypyridin-3-yl)-6-methyl-1,3,5-triazin-2-amine 1,4-dioxane (10.00 mL) and water (2.5 mL) were added to a stirred mixture of 2-chloro-5-methoxypyridin-3-ylboronic acid (1.03 g, 5.48 mmol), 4-chloro-6-methyl-1,3,5-triazin-2-amine (0.72 g, 4.98 mmol), Na$_2$CO$_3$ (1.32 g, 12.5 mmol), and Pd(PPh$_3$)$_4$ (0.576 g, 0.1 eq) and the mixture was sealed and heated at 90° C. overnight. After cooling, the mixture was concentrated. Flash column chromatographic purification (short column, SiO$_2$, pure DCM to 5% MeOH in DCM) provided 4-(2-chloro-5-methoxypyridin-3-yl)-6-methyl-1,3,5-triazin-2-amine (0.644 g, 51%) as a white solid. LCMS (API-ES) m/z 252 (M+H)$^+$; $^1$H NMR (400 MHz, d6-DMSO) δ 8.24 (d, J=1.17 Hz, 1H) 7.68 (br. s., 2H) 7.65 (d, J=1.17 Hz, 1H) 3.87 (s, 3H) 2.36 (s, 3H).

Step 4. 4-(5-methoxy-2-(6-methoxypyridin-3-ylamino)pyridin-3-yl)-6-methyl-1,3,5-triazin-2-amine 1,4-dioxane (0.1 mL, 1.169 mmol) and 2 N HCl (0.219 mL, 0.437 mmol) was added to a mixture of 4-(2-chloro-5-methoxypyridin-3-yl)-6-methyl-1,3,5-triazin-2-amine (110 mg, 0.437 mmol) and 5-amino-2-methoxypyridine (Aldrich, St. Louis, Mo.) (81 mg, 0.656 mmol) in a microwave reaction vessel and the mixture was sealed and heated at 140° C. for 60 min in a Personal Chemistry microwave unit under microwave irradiation. After cooling, the resulting dark mixture was concentrated. Flash column chromatographic purification (short column, SiO$_2$, pure DCM to 5% MeOH in DCM) provided the title compound mixed with starting material. This was washed with methanol several times and finally the solid was recrystallized from MeOH to give 4-(5-methoxy-2-(6-methoxypyridin-3-ylamino)pyridin-3-yl)-6-methyl-1,3,5-triazin-2-amine (21 mg, 0.062 mmol, 14.16% yield) as a yellow-green powder. LCMS (API-ES) m/z 340 (M+H)$^+$; $^1$H NMR (400 MHz, d6-DMSO) δ 11.47 (s, 1H) 8.52 (d, J=2.74 Hz, 1H) 8.39 (d, J=3.33 Hz, 1H) 8.13-8.18 (m, 1H) 8.12 (d, J=3.13 Hz, 1H) 7.86 (br. s., 1H) 7.73 (br. s., 1H) 6.79 (d, J=8.80 Hz, 1H) 3.83 (s, 3H) 3.82 (s, 3H) 2.44 (s, 3H).

Example 34

N-(6-methoxypyridin-3-yl)-3-(4-methyl-1,3,5-triazin-2-yl)-5-((4-(methylsulfonyl)piperazin-1-yl)methyl)pyridin-2-amine

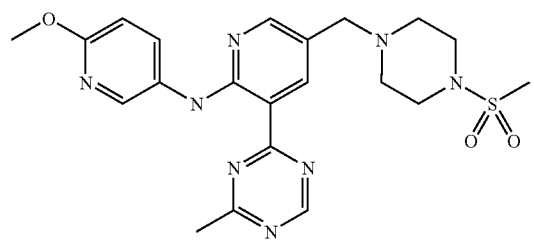

Step 1. 5-(bromomethyl)-2-fluoropyridine

Benzoyl peroxide (1.570 g, 6.48 mmol) and NBS (23.19 g, 130 mmol) was added to a stirred solution of 2-fluoro-5-methylpyridine (SynQuest Labs, Inc., Alachua, Fla., 14.4045 g, 130 mmol) in CCl$_4$ (125 mL) and the suspension was heated at reflux for 2 h. After cooling, the solution was filtered to remove solid and concentrated, and the residue was purified by flash column chromatography (ISCO Combiflash system, Teledyne ISCO, Lincoln, Nebr., hexanes to 10% ethyl acetate in hexanes) to give 5-(bromomethyl)-2-fluoropyridine (15.11 g, 80 mmol, 61.3% yield) as a yellow solid. LCMS (API-ES) m/z 191 (M+H)$^+$.

Step 2. tert-butyl 4-((6-fluoropyridin-3-yl)methyl)piperazine-1-carboxylate tert-Butyl piperazine-1-carboxylate (Aldrich, St. Louis, Mo., 17.77 g, 95 mmol) was added to a stirred solution of 5-(bromomethyl)-2-fluoropyridine (15.11 g, 80 mmol) in N,N-dimethylformamide (120 mL) at 0° C. and the suspension was stirred at room temperature overnight. The resulting thick reaction mixture was quenched with cold water (50 mL), the resulting suspension was stirred for 30 min, and the resulting solid was collected and washed with additional cold water (50 mL). The off-white precipitate was dried under vacuum to give the title compound tert-butyl 4-((6-fluoropyridin-3-yl)methyl)piperazine-1-carboxylate (19.7494 g, 66.9 mmol, 84% yield) as a white solid. LCMS (API-ES) m/z 296 (M+H)$^+$; $^1$H NMR (400 MHz, d6-DMSO) δ 8.13 (s, 1H) 7.90 (td, J=8.02, 1.37 Hz, 1H) 7.15 (dd, J=8.31, 2.05 Hz, 1H) 3.51 (s, 2H) 3.30 (br. s., 4H) 2.10-2.40 (m, 4H) 1.39 (s, 9H).

Step 3. 5-((4-(tert-butoxycarbonyl)piperazin-1-yl)methyl)-2-fluoropyridin-3-ylboronic acid n-Butyllithium (2.5 M in hexanes, 36.1 mL, 90 mmol) was added to a stirred solution of diisopropylamine (12.8 mL, 90 mmol) in tetrahydrofuran (150 mL, 75 mmol) at −40° C. and the slightly yellow solution was stirred at the same temperature for 1 h, and then cooled to −78° C. A solution of tert-butyl 4-((6-fluoropyridin-3-yl)methyl)piperazine-1-carboxylate (22.22 g, 75 mmol) in THF (100 mL) was cannulated slowly into the LDA solution over 30 min. The brown mixture was stirred at the same temperature for 1.5 h and then a solution of triisopropyl borate (25.9 mL, 113 mmol) in THF (50 mL) was added slowly. The resulting mixture was stirred at the same temperature for 30 min and then the cooling bath was removed. After the reaction mixture had warmed up to room temperature, the yellow heterogeneous mixture was quenched with 1.0 M NaOH(aq) (50 mL) and stirred for an additional 30 min. The separated aqueous layer was carefully acidified with 5 N aqueous HCl until acidic (pH 4 to about 5) and the resulting cloudy mixture was diluted with EtOAc (150 mL). The separated aqueous layer was extracted with EtOAc (2×150 mL) and the combined organic phases were dried (Na$_2$SO$_4$), filtered, and concentrated to give 5-((4-(tert-butoxycarbonyl)piperazin-1-yl)methyl)-2-fluoropyridin-3-ylboronic acid (21.93 g, 64.7 mmol, 86% yield) as a pale yellow solid. LCMS (API-ES) m/z 340 (M+H)$^+$.

Step 4. tert-butyl 4-((6-fluoro-5-(4-methyl-6-(methylthio)-1,3,5-triazin-2-yl)pyridin-3-yl)methyl)piperazine-1-carboxylate 1,4-dioxane (15 mL) and H$_2$O (3.00 mL) were added to a mixture of 2-chloro-4-methyl-6-(methylthio)-1,3,5-triazine (0.560 g, 3.19 mmol), 5-((4-(tert-butoxycarbonyl)piperazin-1-yl)methyl)-2-fluoropyridin-3-ylboronic acid (1.03 g, 3.04 mmol), Na$_2$CO$_3$ (0.805 g, 7.59 mmol), and Pd(Ph$_3$P)$_4$ (0.175 g, 0.152 mmol) and the stirred suspension was heated at 80° C. overnight. After cooling, the mixture was passed a short plug of Na$_2$SO$_4$, washed with EtOAc (×2) and concentrated. The residue was adsorbed onto a plug of silica gel and chromatographed through a RediSep®, Teledyne ISCO, Lincoln, Nebr., pre-packed silica gel column (hexanes to 30% ethyl acetate in hexanes) to give tert-butyl 4-((6-fluoro-5-(4-methyl-6-(methylthio)-1,3,5-triazin-2-yl)pyridin-3-yl)methyl)piperazine-1-carboxylate (0.9676 g, 74%) as a white solid. LCMS (API-ES) m/z 435 (M+H)$^+$; $^1$H NMR (400 MHz, CDCl$_3$) δ 8.57 (d, J=9.00 Hz, 1H) 8.30 (s, 1H) 3.58 (s, 2H) 3.44 (br. s., 4H) 2.66 (s, 3H) 2.64 (s, 3H) 2.43 (d, J=4.50 Hz, 4H) 1.46 (s, 9H).

Step 5. 2-(2-fluoro-5-((4-(methylsulfonyl)piperazin-1-yl)methyl)pyridin-3-yl)-4-methyl-6-(methylthio)-1,3,5-triazine TFA (4.00 mL, 51.9 mmol) was slowly added to a stirred solution of tert-butyl 4-((6-fluoro-5-(4-methyl-6-(methylthio)-1,3,5-triazin-2-yl)pyridin-3-yl)methyl)piperazine-1-carboxylate (0.853 g, 1.963 mmol) in DCM (5.00 mL, 78 mmol) cooled in an ice bath, and the mixture was then stirred at room temperature for 1 h. The mixture was concentrated, and the sticky residue was dissolved in DCM (10 mL) and cooled in an ice bath, and triethylamine (1.368 mL, 9.82 mmol) was added. Methanesulfonyl chloride (0.459 mL, 5.89 mmol) was slowly added to the mixture, which was then stirred at the same temperature for 1 h, concentrated, and the residue was adsorbed onto a plug of silica gel and chromatographed through a RediSep®, Teledyne ISCO, Lincoln, Nebr., pre-packed silica gel column (pure DCM to 10% MeOH in DCM) to give a solid which was washed with IPA to give 2-(2-fluoro-5-((4-(methylsulfonyl)piperazin-1-yl)methyl)pyridin-3-yl)-4-methyl-6-(methylthio)-1,3,5-triazine (0.64 g, 79%) as a white solid. LCMS (API-ES) m/z 413 (M+H)$^+$; $^1$H NMR (400 MHz, d6-DMSO) δ 8.58 (dd, J=9.29, 2.25 Hz, 1H) 8.37 (s, 1H) 3.67 (s, 2H) 3.01-3.19 (m, 4H) 2.87 (s, 3H) 2.61 (s, 3H) 2.60 (s, 3H) 2.47-2.49 (m, 4H).

Step 6. 2-(2-fluoro-5-((4-(methylsulfonyl)piperazin-1-yl)methyl)pyridin-3-yl)-4-methyl-1,3,5-triazine Raney nickel (76 mg, 1.297 mmol) water suspension was added to a mixture of 2-(2-fluoro-5-((4-(methylsulfonyl)piperazin-1-yl)methyl)pyridin-3-yl)-4-methyl-6-(methylthio)-1,3,5-triazine (107 mg, 0.259 mmol) in EtOH (5.00 mL, 86 mmol) and the mixture was heated under nitrogen at 70° C. for 1.5 h. The resulting mixture was passed through a short plug of Celite® (diatomaceous earth). The filter cake was washed with MeOH (3×10 mL). The combined organic phases were concentrated to give the crude product, which was used directly in the next step without purification.

Step 7. N-(6-methoxypyridin-3-yl)-3-(4-methyl-1,3,5-triazin-2-yl)-5-((4-(methylsulfonyl)piperazin-1-yl)methyl)pyridin-2-amine LiHMDS (1.0 M in THF, 557 µL, 0.557 mmol) was added to a stirred solution of 2-(2-fluoro-5-((4-(methylsulfonyl)piperazin-1-yl)methyl)pyridin-3-yl)-4-methyl-1,3,5-triazine (68.0 mg, 0.186 mmol) and 3-amino-6-methoxypyridine (Aldrich) (34.6 mg, 0.278 mmol) in THF (928 µL, 0.186 mmol) at 0° C. and the mixture was stirred at the same temperature for 1 h. The reaction mixture was quenched with water (10 mL) and diluted with ethyl acetate (10 mL). The separated aqueous layer was extracted with ethyl acetate (2×10 mL) and the combined organic layers were washed with brine, dried over Na$_2$SO$_4$, and concentrated. The crude product was adsorbed onto a plug of silica gel and chromatographed through a RediSep®, Teledyne ISCO, Lincoln, Nebr., pre-packed silica gel column (DCM to 5% MeOH in DCM) followed by washing with iPrOH to give N-(6-methoxypyridin-3-yl)-3-(4-methyl-1,3,5-triazin-2-yl)-5-((4-(methylsulfonyl)piperazin-1-yl)methyl)pyridin-2-amine (15 mg, 17%) as a yellow solid. LCMS (API-ES) m/z 471 (M+H)$^+$; $^1$H NMR (400 MHz, d6-DMSO) δ 11.44 (s, 1H) 9.29 (s, 1H) 8.81 (s, 1H) 8.51 (br. s., 1H) 8.29 (br. s., 1H) 8.11 (d, J=9.19 Hz, 1H) 6.85 (d, J=9.19 Hz, 1H) 3.85 (s, 3H) 3.53 (s, 2H) 3.11 (br. s., 4H) 2.87 (s, 3H) 2.75 (s, 3H) 2.34-2.49 (m, 4H).

Example 35

4-(2-(6-methoxypyridin-3-ylamino)-5-((4-(methylsulfonyl)piperazin-1-yl)methyl)pyridin-3-yl)-6-methyl-1,3,5-triazin-2-amine

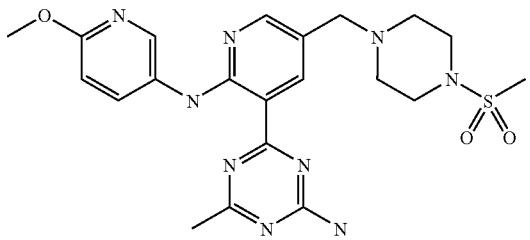

Step 1. N-(6-methoxypyridin-3-yl)-3-(4-methyl-6-(methylthio)-1,3,5-triazin-2-yl)-5-((4-(methylsulfonyl)piperazin-1-yl)methyl)pyridin-2-amine LiHMDS, 1.0 M in THF (0.754 mL, 0.754 mmol) was added dropwise to a stirred solution of 2-(2-fluoro-5-((4-(methylsulfonyl)piperazin-1-yl)methyl)pyridin-3-yl)-4-methyl-6-(methylthio)-1,3,5-triazine (0.311 g, 0.754 mmol) (Example 34, Step 5) and 3-amino-6-methoxypyridine (0.094 g, 0.754 mmol) in tetrahydrofuran (10 mL, 0.754 mmol) at −10° C. and the mixture was stirred at the same temperature for 1 h. The reaction mixture was diluted with NH$_4$Cl (aq) and water (10 mL each) and diluted with ethyl acetate (20 mL). The separated aqueous layer was extracted with ethyl acetate (2×20 mL) and the combined organic layers were washed with brine, dried over Na$_2$SO$_4$, concentrated and purified by flash column chromatography (ISCO Combiflash system, Teledyne ISCO, Lincoln, Nebr., DCM to 5% MeOH in DCM) to give N-(6-methoxypyridin-3-yl)-3-(4-methyl-6-(methylthio)-1,3,5-triazin-2-yl)-5-((4-(methylsulfonyl)piperazin-1-yl)methyl)pyridin-2-amine (237 mg, 0.459 mmol, 60.8% yield) as a yellow solid.

Step 2. 4-(2-(6-methoxypyridin-3-ylamino)-5-((4-(methylsulfonyl)piperazin-1-yl)methyl)pyridin-3-yl)-6-methyl-1,3,5-triazin-2-amine 2 M NH$_3$ in 2-propanol (2.00 mL, 92 mmol) was added to N-(6-methoxypyridin-3-yl)-3-(4-methyl-6-(methylthio)-1,3,5-triazin-2-yl)-5-((4-(methylsulfonyl)piperazin-1-yl)methyl)pyridin-2-amine (221 mg, 0.428 mmol) and the mixture was sealed and heated at 90° C. overnight. After cooling, the reaction mixture was concentrated, adsorbed onto a plug of silica gel and chromatographed through a RediSep®, Teledyne ISCO, Lincoln, Nebr., pre-packed silica gel column (DCM to 10% MeOH in DCM) followed by washing of the isolated solid with MeOH to give 4-(2-(6-methoxypyridin-3-ylamino)-5-((4-(methylsulfonyl)piperazin-1-yl)methyl)pyridin-3-yl)-6-methyl-1,3,5-triazin-2-amine (117 mg, 0.241 mmol, 56.3% yield) as a yellow solid. LCMS (API-ES) m/z 486 (M+H)$^+$; $^1$H NMR (400 MHz, d6-DMSO) δ 11.76 (br. s., 1H) 8.71 (br. s., 1H) 8.55 (br. s., 1H) 8.03-8.28 (m, 2H) 7.87 (br. s., 1H) 7.73 (br. s., 1H) 6.82 (d, J=7.63 Hz, 1H) 3.84 (br. s., 3H) 3.48 (br. s., 2H) 3.11 (br. s., 4H) 2.87 (br. s., 3H) 2.52-2.58 (m, 3H) 2.44 (br. s., 4H).

Example 36

N-(3-(4-amino-6-methyl-1,3,5-triazin-2-yl)-5-((4-(methylsulfonyl)piperazin-1-yl)methyl)pyridin-2-yl)-1H-indazol-4-amine

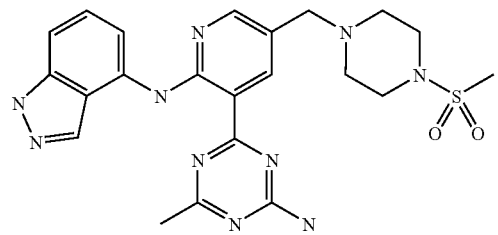 [SMILES: Cc1nc(N)nc(-c2cc(CN3CCN(S(C)(=O)=O)CC3)cnc2Nc2cccc3[nH]ncc23)n1]

Step 1. N-(3-(4-methyl-6-(methylthio)-1,3,5-triazin-2-yl)-5-((4-(methylsulfonyl)piperazin-1-yl)methyl)pyridin-2-yl)-1-(tetrahydro-2H-pyran-2-yl)-1H-indazol-4-amine The title compound was prepared in an analogous manner to that described above in Example 35, Step 1 using 1-(tetrahydro-2H-pyran-2-yl)-1H-indazol-4-amine, and isolated as a yellow solid (69%).

Step 2. N-(3-(4-amino-6-methyl-1,3,5-triazin-2-yl)-5-((4-(methylsulfonyl)piperazin-1-yl)methyl)pyridin-2-yl)-1H-indazol-4-amine 2 M NH$_3$ in 2-propanol (2.00 mL, 92 mmol) was added to N-(3-(4-methyl-6-(methylthio)-1,3,5-triazin-2-yl)-5-((4-(methylsulfonyl)piperazin-1-yl)methyl)pyridin-2-yl)-1-(tetrahydro-2H-pyran-2-yl)-1H-indazol-4-amine (97 mg, 0.159 mmol) and the mixture was sealed and heated at 90° C. overnight. After cooling, the precipitate was collected and dried to give a yellow solid which was dissolved in DCM (3.00 mL, 46.6 mmol) and then TFA (1.50 mL, 19.47 mmol) was slowly added. The mixture was stirred at rt for 1 h and then concentrated, adsorbed onto a plug of silica gel and chromatographed through a RediSep®, Teledyne ISCO, Lincoln, Nebr., pre-packed silica gel column (DCM to 10% MeOH in DCM) to give N-(3-(4-amino-6-methyl-1,3,5-triazin-2-yl)-5-((4-(methylsulfonyl)piperazin-1-yl)methyl)pyridin-2-yl)-1H-indazol-4-amine (18 mg, 0.036 mmol, 22.88% yield) as a yellow solid. LCMS (API-ES) m/z 495 (M+H)$^+$; $^1$H NMR (400 MHz, d6-DMSO) δ 13.10 (br. s., 1H) 12.27 (s, 1H) 8.75 (s, 1H) 8.32 (br. s., 1H) 8.19 (s, 1H) 8.13 (d, J=7.04 Hz, 1H) 7.78 (br. s., 2H) 7.31 (t, J=8.31 Hz, 1H) 7.15

(d, J=8.22 Hz, 1H) 3.53 (s, 2H) 3.12 (br. s., 4H) 2.87 (s, 3H) 2.57 (s, 3H) 2.37-2.49 (m, 4H).

Example 37

4-methyl-6-(5-((4-(methylsulfonyl)piperazin-1-yl)methyl)-2-(6-(trifluoromethyl)pyridin-3-ylamino)pyridin-3-yl)-1,3,5-triazin-2-amine

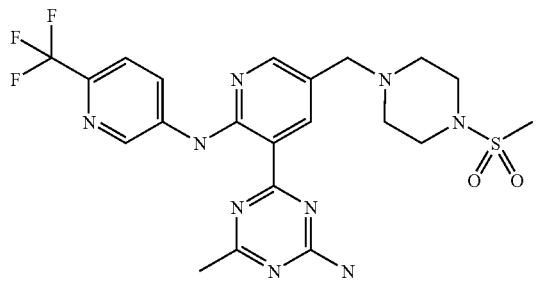 [SMILES: Cc1nc(N)nc(-c2cc(CN3CCN(S(C)(=O)=O)CC3)cnc2Nc2ccc(C(F)(F)F)nc2)n1]

The title compound was prepared in an analogous manner to that described above in Example 35, using 6-(trifluoromethyl)pyridin-3-amine in Step 1, and was isolated as a yellow solid (27%, two steps). LCMS (API-ES) m/z 524 (M+H)+; $^1$H NMR (400 MHz, d6-DMSO) δ 12.49 (s, 1H) 9.12 (d, J=2.54 Hz, 1H) 8.79 (d, J=2.15 Hz, 1H) 8.74 (dd, J=8.70, 2.05 Hz, 1H) 8.36 (d, J=2.15 Hz, 1H) 7.97 (br. s., 1H) 7.84 (d, J=8.61 Hz, 2H) 3.55 (s, 2H) 3.12 (br. s., 4H) 2.87 (s, 3H) 2.48-2.50 (m, 4H) 2.47 (s, 3H).

Example 38

4-methyl-6-(5-((4-(methylsulfonyl)piperazin-1-yl)methyl)-2-(pyrimidin-5-ylamino)pyridin-3-yl)-1,3,5-triazin-2-amine

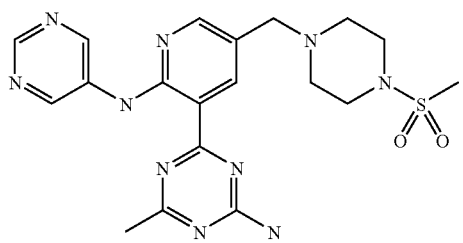 [SMILES: Cc1nc(N)nc(-c2cc(CN3CCN(S(C)(=O)=O)CC3)cnc2Nc2cncnc2)n1]

The title compound was prepared in an analogous manner to that described above in Example 35, using pyrimidin-5-amine in Step 1, and was isolated as a yellow solid (37%, two steps). LCMS (API-ES) m/z 457 (M+H)+; $^1$H NMR (400 MHz, d6-DMSO) δ 12.12 (s, 1H) 9.35 (s, 2H) 8.81 (s, 1H) 8.77 (d, J=2.35 Hz, 1H) 8.33 (d, J=2.15 Hz, 1H) 7.97 (br. s., 1H) 7.81 (br. s., 1H) 3.54 (s, 2H) 3.11 (br. s., 4H) 2.87 (s, 3H) 2.50 (m, 4H) 2.46 (s, 3H).

Example 39

N-(3-(4-amino-6-methyl-1,3,5-triazin-2-yl)-5-((4-(methylsulfonyl)piperazin-1-yl)methyl)pyridin-2-yl)benzo[d]oxazol-6-amine

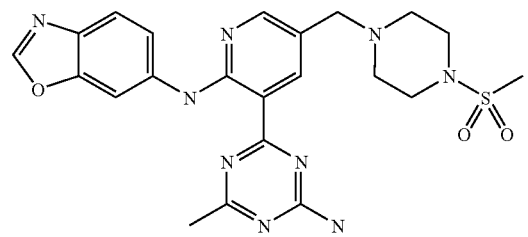 [SMILES: Cc1nc(N)nc(-c2cc(CN3CCN(S(C)(=O)=O)CC3)cnc2Nc2ccc3ncoc3c2)n1]

The title compound was prepared in an analogous manner to that described above in Example 35, using benzo[d]oxazol-6-amine (Bionet Research Intermediates, UK) in Step 1, and isolated as a yellow solid (35%, two steps). LCMS (API-ES) m/z 496 (M+H)+; $^1$H NMR (400 MHz, d6-DMSO) δ 12.30 (s, 1H) 8.75 (d, J=2.35 Hz, 1H) 8.65 (s, 1H) 8.61 (s, 1H) 8.33 (d, J=2.15 Hz, 1H) 7.89 (br. s., 1H) 7.78 (br. s., 1H) 7.67-7.75 (m, 1H) 7.59-7.67 (m, 1H) 3.52 (s, 2H) 3.30 (s, 3H) 3.12 (br. s., 4H) 2.87 (s, 3H) 2.47 (s, 4H).

Example 40

4-(2-(5-fluoro-6-methoxypyridin-3-ylamino)-5-((4-(methylsulfonyl)piperazin-1-yl)methyl)pyridin-3-yl)-6-methyl-1,3,5-triazin-2-amine

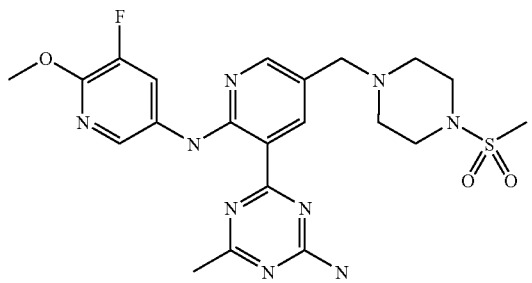

Step 1: tert-butyl 4-((5-(4-(bis(4-methoxybenzyl)amino)-6-methyl-1,3,5-triazin-2-yl)-6-fluoropyridin-3-yl)methyl)piperazine-1-carboxylate A mixture of 4-chloro-N,N-bis(4-methoxybenzyl)-6-methyl-1,3,5-triazin-2-amine (Example 51) (20 g, 52.0 mmol), 5-((4-(tert-butoxycarbonyl)piperazin-1-yl)methyl)-2-fluoropyridin-3-ylboronic acid (Example 34, Step 3) (21.15 g, 62.4 mmol), potassium acetate (8.12 mL, 130 mmol), and Amphos (bis(di-tert-butyl (4-dimethylaminophenyl)phosphine) dichloropalladium(II) (Aldrich, St. Louis, Mo.) (1.913 g, 2.70 mmol) in p-dioxane (300 mL, 3528 mmol) and water (60 mL, 52.0 mmol) contained in a 1 L 3 neck round-bottomed flask was stirred at 100° C. overnight. The solution was partitioned between water and EtOAc and the organic layer was separated, washed with water, dried over Na$_2$SO$_4$, filtered and concentrated in vacuo to give the crude product which was adsorbed onto silica gel and chromatographed through a Redi-Sep® pre-packed silica gel column (Teledyne ISCO, Lincoln, Nebr.) (330 g) eluting with a gradient of 10% to 50% EtOAc in hexane to give tert-butyl 4-((5-(4-(bis(4-methoxybenzyl)amino)-6-methyl-1,3,5-triazin-2-yl)-6-fluoropyridin-3-yl)methyl)piperazine-1-carboxylate (25.2 g, 39.1 mmol, 75% yield). m/z (ESI, positive ion) m/z 644 (M+H)$^+$.

Step 2: tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)piperazine-1-carboxylate A solution of tert-butyl 4-((5-(4-(bis(4-methoxybenzyl)amino)-6-methyl-1,3,5-triazin-2-yl)-6-fluoropyridin-3-yl)methyl)piperazine-1-carboxylate (25 g, 38.8 mmol) and 5-fluoro-6-methoxypyridin-3-amine (Anichem LLC, Monmouth N.J.) (8.28 g, 58.3 mmol) in tetrahydrofuran (400 mL, 38.8 mmol) contained in an oven dried 1 L 3-neck round-bottomed flask equipped with N$_2$ inlet was stirred at a temperature between −5° C. and −10° C. and treated dropwise with a 1.0 M solution of lithium bis(trimethylsilyl)amide in tetrahydrofuran (117 mL, 117 mmol). The dark pink solution was stirred between −5° C. and −10° C. for 1 h. The reaction was quenched with water (100 mL) and NH$_4$Cl (100 mL) and diluted with EtOAc (350 mL). The separated aqueous layer was extracted with EtOAc (2×300 mL) and the combined organic extracts were dried over Na$_2$SO$_4$, filtered and concentrated in vacuo to give the crude product which was adsorbed onto silica gel and chromatographed through a Redi-Sep® pre-packed silica gel column (Teledyne ISCO, Lincoln, Nebr.) (330 g) eluting with a gradient of 10% to 50% EtOAc in hexane to give tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)piperazine-1-carboxylate (26.8 g, 35.0 mmol, 90% yield). m/z (ESI, positive ion) m/z 766 (M+H)$^+$.

Step 3: 4-(2-(5-fluoro-6-methoxypyridin-3-ylamino)-5-(piperazin-1-ylmethyl)pyridin-3-yl)-N,N-bis(4-methoxybenzyl)-6-methyl-1,3,5-triazin-2-amine A solution of tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)piperazine-1-carboxylate (25 g, 32.6 mmol) in dichloromethane (150 mL, 32.6 mmol) and trifluoroacetic acid (150 mL, 2019 mmol) was stirred at room temperature for 1 h. The solution was concentrated and the residue was dissolved in DCM and carefully neutralized with saturated aqueous NaHCO$_3$. The aqueous layer was extracted with DCM and the organic extracts were dried over Na$_2$SO$_4$, filtered and concentrated in vacuo to give 4-(2-(5-fluoro-6-methoxypyridin-3-ylamino)-5-(piperazin-1-ylmethyl)pyridin-3-yl)-N,N-bis(4-methoxybenzyl)-6-methyl-1,3,5-triazin-2-amine (20 g, 30.0 mmol, 92% yield). The crude product was taken on to the next step without purification.

Step 4: 4-(2-(5-fluoro-6-methoxypyridin-3-ylamino)-5-((4-(methylsulfonyl)piperazin-1-yl)methyl)pyridin-3-yl)-N,N-bis(4-methoxybenzyl)-6-methyl-1,3,5-triazin-2-amine A 1 L 3-neck round-bottomed flask equipped with a thermometer was charged with 4-(2-(5-fluoro-6-methoxypyridin-3-ylamino)-5-(piperazin-1-ylmethyl)pyridin-3-yl)-N,N-bis(4-methoxybenzyl)-6-methyl-1,3,5-triazin-2-amine (25.1 g, 37.7 mmol) in dichloromethane (500 mL, 37.7 mmol). The suspension was stirred at −15° C. and treated with dropwise with triethylamine (52.4 mL, 377 mmol). The resulting solution was treated with methanesulfonyl chloride (8.92 mL, 113 mmol) and stirred at 0° C. for 1 h. The resulting mixture was sonicated and the solid was filtered, washed with water and dried in vacuo to give 4-(2-(5-fluoro-6-methoxypyridin-3-ylamino)-5-((4-(methylsulfonyl)piperazin-1-yl)methyl)pyridin-3-yl)-N,N-bis(4-methoxybenzyl)-6-methyl-1,3,5-triazin-2-amine (26.5 g, 35.6 mmol, 94% yield). m/z (ESI, positive ion) m/z 744 (M+H)$^+$.

Step 5: 4-(2-(5-fluoro-6-methoxypyridin-3-ylamino)-5-((4-(methylsulfonyl)piperazin-1-yl)methyl)pyridin-3-yl)-6-methyl-1,3,5-triazin-2-amine A 3 neck 500 mL flask equipped with overhead stirrer, thermocouple and nitrogen inlet was charged with 4-(2-(5-fluoro-6-methoxypyridin-3-ylamino)-5-((4-(methylsulfonyl)piperazin-1-yl)methyl)pyridin-3-yl)-N,N-bis(4-methoxybenzyl)-6-methyl-1,3,5-triazin-2-amine (26.9 g, 36.2 mmol) and TFA (175 mL). The dissolution of solids was exothermic. Upon complete dissolution, the solution was warmed to 45° C. and trifluoromethanesulfonic acid (16.06 mL, 181 mmol) was added dropwise. The reaction mixture was stirred for 1 h and then cooled to 20° C.

A separate 2 L flask equipped with overhead stirrer and thermocouple was charged with 500 mL 10 wt % trisodium citric acid (aq) and cooled to 0° C. The reaction mixture was added dropwise to the cooled aqueous solution. The product precipitated out of solution, DCM was added, and the slurry was stirred at 20° C. for 16 h. The solid was collected by filtration and washed with water then ethanol and dried under reduced pressure to give 4-(2-(5-fluoro-6-methoxypyridin-3-ylamino)-5-((4-(methylsulfonyl)piperazin-1-yl)methyl)pyridin-3-yl)-6-methyl-1,3,5-triazin-2-amine (15.06 g, 83%) as a yellow solid. m/z (ESI, positive ion) m/z 504 (M+H)$^+$. $^1$H NMR (400 MHz, d6-DMSO) δ 11.96 (s, 1H); 8.73 (d, J=2.15 Hz, 1H); 8.42 (d, J=2.15 Hz, 1H); 8.37 (dd, J=12.72, 2.15 Hz, 1H); 8.26 (d, J=2.15 Hz, 1H); 7.93 (br. s., 1H); 7.78 (br. s., 1H); 3.93 (s, 3H); 3.50 (s, 2H); 3.11 (br. s., 4H); 2.87 (s, 3H); 2.45-2.49 (m, 4H); 2.44 (s, 3H).

Example 41

4-(2-(6-methoxypyridin-3-ylamino)-5-(piperazin-1-ylmethyl)pyridin-3-yl)-6-methyl-1,3,5-triazin-2-amine

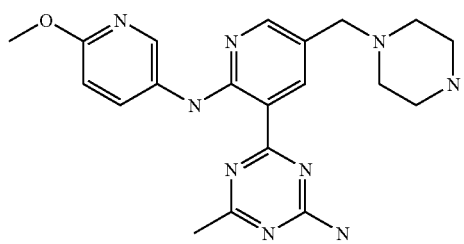 [SMILES: COc1ccc(Nc2ncc(CN3CCNCC3)cc2-c2nc(C)nc(N)n2)cn1]

Step 1. tert-butyl 4-((6-(6-methoxypyridin-3-ylamino)-5-(4-methyl-6-(methylthio)-1,3,5-triazin-2-yl)pyridin-3-yl)methyl)piperazine-1-carboxylate LiHMDS (1.519 mL, 1.0 M in THF, 1.519 mmol) was added to a stirred solution of tert-butyl 4-((6-fluoro-5-(4-methyl-6-(methylthio)-1,3,5-triazin-2-yl)pyridin-3-yl)methyl)piperazine-1-carboxylate (0.220 g, 0.506 mmol) and 5-amino-2-methoxypyridine (0.094 g, 0.759 mmol) in THF (3.00 mL, 36.6 mmol) at 0° C. and the mixture was stirred at the same temperature for 1 h. The reaction mixture was diluted with NH₄Cl (aq) and water (10 mL each) and diluted with ethyl acetate (10 mL). The separated aqueous layer was extracted with ethyl acetate (2×10 mL) and the combined organic layers were washed with brine, dried over Na₂SO₄, concentrated and purified by flash column chromatography (ISCO Combiflash system, Teledyne ISCO, Lincoln, Nebr., hexanes to 50% ethyl acetates in hexanes) to give tert-butyl 4-((6-(6-methoxypyridin-3-ylamino)-5-(4-methyl-6-(methylthio)-1,3,5-triazin-2-yl)pyridin-3-yl)methyl)piperazine-1-carboxylate (0.133 g, 49%) as a yellow solid. LCMS (API-ES) m/z 538 (M+H)⁺; ¹H NMR (400 MHz, CDCl₃) δ 11.42 (s, 1H) 8.81 (br. s., 1H) 8.36 (d, J=2.74 Hz, 1H) 8.27 (br. s., 1H) 8.10 (dd, J=8.71, 2.64 Hz, 1H) 6.79 (d, J=8.80 Hz, 1H) 3.95 (s, 3H) 3.50 (s, 2H) 3.43 (br. s., 4H) 2.67 (s, 3H) 2.66 (br. s., 3H) 2.42 (br. s., 4H) 1.45 (s, 9H).

Step 2. 4-(2-(6-methoxypyridin-3-ylamino)-5-(piperazin-1-ylmethyl)pyridin-3-yl)-6-methyl-1,3,5-triazin-2-amine TFA (2 mL, 26.0 mmol) was added to a stirred mixture of tert-butyl 4-((6-(6-methoxypyridin-3-ylamino)-5-(4-methyl-6-(methylthio)-1,3,5-triazin-2-yl)pyridin-3-yl)methyl)piperazine-1-carboxylate (66 mg, 0.123 mmol) in DCM (2. mL, 31.1 mmol) and the mixture was stirred at room temperature for 1 h. The reaction mixture was concentrated and re-diluted with DCM, NaHCO₃ (aq) and water (10 mL each). The separated aqueous layer was extracted with DCM (3×10 mL) and the combined organic layers were washed with brine, dried over Na₂SO₄, and concentrated. The crude product was treated with ammonia (2.0 M solution in 2-propanol, 2.00 mL, 92 mmol) and the mixture was sealed and heated at 90° C. overnight. After cooling, the reaction mixture was concentrated, adsorbed onto a plug of silica gel and chromatographed through a RediSep®, Teledyne ISCO, Lincoln, Nebr., pre-packed silica gel column (DCM to 10% MeOH in DCM) followed by washing the isolated solid with ether and ethyl acetate to give 4-(2-(6-methoxypyridin-3-ylamino)-5-(piperazin-1-ylmethyl)pyridin-3-yl)-6-methyl-1,3,5-triazin-2-amine (2.5 mg, 6.14 μmol, 13.45% yield) as a yellow solid. LCMS (API-ES) m/z 408 (M+H)⁺; ¹H NMR (400 MHz, d6-DMSO) δ 11.74 (br. s., 1H) 8.69 (br. s., 1H) 8.55 (br. s., 1H) 8.19 (br. s., 1H) 8.16 (br. s., 1H) 7.87 (br. s., 1H) 7.72 (br. s., 1H) 6.82 (d, J=8.41 Hz, 1H) 3.94-4.21 (m, 2H) 3.84 (br. s., 3H) 3.42 (d, J=13.50 Hz, 4H) 2.84 (br. s., 4H) 2.40-2.45 (m, 3H) 2.32 (br. s., 1H).

Example 42

5-(1,3-dioxolan-2-yl)-2-fluoropyridin-3-ylboronic acid

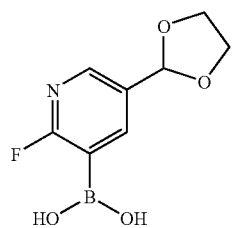 [SMILES: OB(O)c1cc(C2OCCO2)cnc1F]

Step 1. 5-(1,3-dioxolan-2-yl)-2-fluoropyridine

6-Fluoronicotinaldehyde (Asymchem Laboratories, Inc., Morrisville, N.C., 3.035 g, 24.26 mmol) was suspended in toluene (80 mL) and ethylene glycol (1.40 mL, 25.1 mmol) and p-toluenesulfonic acid (Acros Organics, Geel, Belgium, 12% in acetic acid, 0.15 mL) was added. The flask was fitted with a reflux condenser and placed in a preheated oil bath (120° C.) and stirred under nitrogen for 20 minutes. At this time, the reflux condenser was replaced with a Dean-Stark trap, and stirring was continued at 120° C. for 25 minutes. Then, the reaction was cooled and diluted with saturated sodium bicarbonate solution (20 mL) (before it had cooled to room temperature). The reaction was then diluted with water (20 mL) and EtOAc (30 mL). The layers were separated, and the aqueous phase was extracted with EtOAc. The organic extracts were combined, dried over sodium sulfate, filtered, concentrated, and purified on a silica gel filter (about 3 inches, 40:1 DCM/MeOH to 30:1 DCM/MeOH) to afford 5-(1,3-dioxolan-2-yl)-2-fluoropyridine (3.858 g), which was taken on to the next step. MS (ESI pos. ion) m/z 170 (M+H)⁺.

Step 2. 5-(1,3-dioxolan-2-yl)-2-fluoropyridin-3-ylboronic acid

Diisopropylamine (4.60 mL, 32.5 mmol) was dissolved in THF (80 mL) and cooled in an ice water bath. Then, n-butyllithium solution (1.6 M in hexanes, 21.0 mL, 33.6 mmol) was added via syringe. After 30 minutes, the reaction was cooled to −78° C. and 5-(1,3-dioxolan-2-yl)-2-fluoropyridine (3.73 g, 22.1 mmol) was added as a solution in THF (12 mL) dropwise over 5 minutes via syringe, followed by a THF (4 mL) rinse. The reaction was stirred at −78° C. under nitrogen for 1 hour, and then triisopropyl borate (Fluka 98+%, 8.0 mL, 34.9 mmol) was added via syringe, and the reaction was allowed to warm up to room temperature. After 4.5 hours, the reaction was quenched with 1 N NaOH (75 mL). The layers were separated, and the aqueous phase was treated with 5 N HCl to lower the pH to between 6 and 7. The aqueous phase was extracted with 10:1 DCM/MeOH. 5 N HCl was added to the aqueous phase to lower the pH to about 5, and extraction was continued with 10:1 DCM/MeOH. The organic extracts were combined, concentrated and dried under high vacuum to give 5-(1,3-dioxolan-2-yl)-2-fluoropyridin-3-ylboronic acid (3.165 g, 91% purity, 61% yield over 2 steps). MS (ESI pos. ion) m/z 214 (M+H)⁺.

Example 43

4-(2-(6-methoxypyridin-3-ylamino)-5-(morpholinomethyl)pyridin-3-yl)-6-methyl-1,3,5-triazin-2-amine

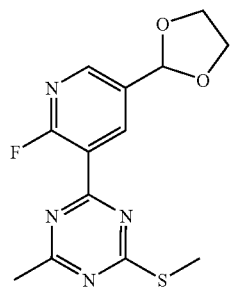 [SMILES: CSc1nc(C)nc(-c2cc(C3OCCO3)cnc2F)n1]

1,4-Dioxane (16 mL) and water (3.3 mL) were added to a mixture of 5-(1,3-dioxolan-2-yl)-2-fluoropyridin-3-ylboronic acid (0.715 g, 3.53 mmol), 2-chloro-4-methyl-6-(methylthio)-1,3,5-triazine (0.682 g, 3.88 mmol), Pd(PPh$_3$)$_4$ (0.408 g, 0.353 mmol), and Na$_2$CO$_3$ (0.935 g, 8.82 mmol) and the suspension was heated at 90° C. for 2 h. After cooling, the mixture was filtered, washed with EtOAc (2×20 mL), and the combined organic phases were concentrated. The crude product was adsorbed onto a plug of silica gel and chromatographed through a Redi-Sep pre-packed silica gel column (hexanes to 30% ethyl acetate in hexanes) to give 2-(5-(1,3-dioxolan-2-yl)-2-fluoropyridin-3-yl)-4-methyl-6-(methylthio)-1,3,5-triazine (0.5259 g, 1.706 mmol, 48.3% yield) as a white solid. LCMS (API-ES) m/z 309 (M+H)⁺.

Example 44

4-(2-(6-methoxypyridin-3-ylamino)-5-(morpholinomethyl)pyridin-3-yl)-6-methyl-1,3,5-triazin-2-amine

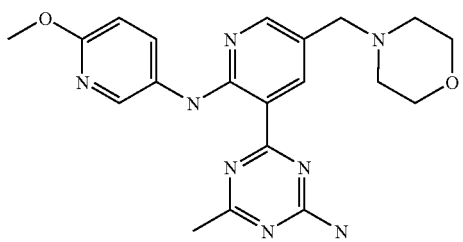 [SMILES: COc1ccc(Nc2ncc(CN3CCOCC3)cc2-c2nc(C)nc(N)n2)cn1]

Step 1. 5-(1,3-dioxolan-2-yl)-N-(6-methoxypyridin-3-yl)-3-(4-methyl-6-(methylthio)-1,3,5-triazin-2-yl)pyridin-2-amine LiHMDS (1.0 M in THF, 4.14 mL, 4.14 mmol) was added to a stirred solution of 2-(5-(1,3-dioxolan-2-yl)-2-fluoropyridin-3-yl)-4-methyl-6-(methylthio)-1,3,5-triazine (0.425 g, 1.379 mmol) and 5-amino-2-methoxypyridine (0.257 g, 2.068 mmol) in THF (3.00 mL, 36.6 mmol) at 0° C. and the mixture was stirred at the same temperature for 1 h. The reaction mixture was diluted with NH$_4$Cl (aq) and water (10 mL each) and diluted with ethyl acetate (10 mL). The separated aqueous layer was extracted with ethyl acetate (2×10 mL) and the combined organic layers were washed with brine, dried over Na$_2$SO$_4$, concentrated and the residue was purified by flash column chromatography (ISCO CombiFlash®, Teledyne ISCO, Lincoln, Nebr., hexanes to 50% ethyl acetates in hexanes) to give 5-(1,3-dioxolan-2-yl)-N-(6-methoxypyridin-3-yl)-3-(4-methyl-6-(methylthio)-1,3,5-triazin-2-yl)pyridin-2-amine (35 mg, 0.085 mmol, 6.15% yield) as a yellow solid. LCMS (API-ES) m/z 413 (M+H)⁺.

Step 2. 6-(6-methoxypyridin-3-ylamino)-5-(4-methyl-6-(methylthio)-1,3,5-triazin-2-yl)nicotinaldehyde 2 M Aqueous HCl (1.50 mL, 3.00 mmol) was added to a stirred solution of 5-(1,3-dioxolan-2-yl)-N-(6-methoxypyridin-3-yl)-3-(4-methyl-6-(methylthio)-1,3,5-triazin-2-yl)pyridin-2-amine (35 mg, 0.085 mmol) in THF (3.00 mL, 36.6 mmol) and the mixture was stirred at 25° C. for 2 h. A yellow precipitate gradually formed. The volatile solvents were minimized and the precipitate was collected and dried to give 6-(6-methoxypyridin-3-ylamino)-5-(4-methyl-6-(methylthio)-1,3,5-triazin-2-yl)nicotinaldehyde (27 mg, 0.073 mmol, 86% yield) as a yellow solid. LCMS (API-ES) m/z 369 (M+H)⁺.

Step 3. N-(6-methoxypyridin-3-yl)-3-(4-methyl-6-(methylthio)-1,3,5-triazin-2-yl)-5-(morpholinomethyl)pyridin-2-amine Morpholine (0.018 mL, 0.204 mmol) and a few drops of AcOH (3.88 µL, 0.068 mmol) were added to a stirred suspension of 6-(6-methoxypyridin-3-ylamino)-5-(4-methyl-6-(methylthio)-1,3,5-triazin-2-yl)nicotinaldehyde (25 mg, 0.068 mmol) in EtOH (3.00 mL, 51.4 mmol), the mixture was stirred at room temperature for 1 h, then treated with sodium cyanoborohydride (4.26 mg, 0.068 mmol) and stirred at room temperature overnight. The mixture was diluted with water and EtOAc (10mL each). The separated aqueous layer was extracted with ethyl acetate (2×10 mL) and the combined organic layers were washed with brine, dried over Na$_2$SO$_4$, and concentrated to give crude product which was purified by flash column chromatography (ISCO CombiFlash®, Teledyne ISCO, Lincoln, Nebr., DCM to 10% DCM in MeOH) to give N-(6-methoxypyridin-3-yl)-3-(4-methyl-6-(methylthio)-1,3,5-triazin-2-yl)-5-(morpholinomethyl)pyridin-2-amine (19 mg, 0.043 mmol, 63.7% yield) as a yellow solid. LCMS (API-ES) m/z 440 (M+H)⁺.

Step 4. 4-(2-(6-methoxypyridin-3-ylamino)-5-(morpholinomethyl)pyridin-3-yl)-6-methyl-1,3,5-triazin-2-amine A stirred mixture of N-(6-methoxypyridin-3-yl)-3-(4-methyl-6-(methylthio)-1,3,5-triazin-2-yl)-5-(morpholinomethyl)pyridin-2-amine (19 mg, 0.043 mmol) in 2.0 M NH$_3$/iPrOH (3.0 mL) was sealed and heated at 90° C. for 24 h. The reaction mixture was concentrated and the crude product was adsorbed onto a plug of silica gel and chromatographed through a RediSep®, Teledyne ISCO, Lincoln, Nebr., pre-packed silica gel column (DCM to 5% MeOH in DCM) to give 4-(2-(6-methoxypyridin-3-ylamino)-5-(morpholinomethyl)pyridin-3-yl)-6-methyl-1,3,5-triazin-2-amine (6.00 mg, 0.015 mmol, 34.0% yield) as a yellow solid. LCMS (API-ES) m/z 409 (M+H)+; 1H NMR (400 MHz, CDCl3, with one drop of d6-DMSO) δ 11.69 (br. s., 1H) 8.76 (br. s., 1H) 8.39 (br. s., 1H) 8.23 (br. s., 1H) 8.12 (br. s., 1H) 6.77 (d, J=9.00 Hz, 1H) 5.92 (br. s., 2H) 3.93 (br. s., 3H) 3.49 (br. s., 2H) 2.55 (br. s., 3H) 2.50 (br. s., 4H) 2.23 (br. s., 4H).

Example 45

4-(2-chloro-5-methylpyridin-3-yl)-6-methyl-1,3,5-triazin-2-amine

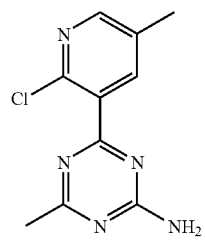 [SMILES: Cc1cnc(Cl)c(-c2nc(C)nc(N)n2)c1]

A glass microwave reaction vessel was charged with 4-chloro-6-methyl-1,3,5-triazin-2-amine (0.350 g, 2 mmol), 2-chloro-5-methylpyridin-3-ylboronic acid (combi-blocks catalog number BB-3511) (0.6 g, 3 mmol), sodium carbonate, monohydrate, crystal (J.T. Baker catalog number 3600-01) (0.450 g, 7 mmol), tetrakis(triphenylphosphine)palladium (0) (Strem chemicals catalog number 46-Z150) (0.3 g, 0.2 mmol). Degassed 1,2-dimethoxyethane (Aldrich catalog #255527) (11 mL, 109 mmol) and water (1 mL, 2 mmol) were added to the mixture. The reaction mixture was stirred and heated in a Smith Synthesizer® microwave reactor (Personal Chemistry, Inc., Upssala, Sweden) at 90° C. for 30 min. The mixture was filtered through Celite® (diatomaceous earth) and washed with ethyl acetate. The crude product was adsorbed onto a plug of silica gel and chromatographed through a RediSep®, Teledyne ISCO, Lincoln, Nebr., pre-packed silica gel column (40 g), eluting with a gradient of 5% to 10% 2 M NH3/MeOH in dichloromethane, to provide 4-(2-chloro-5-methylpyridin-3-yl)-6-methyl-1,3,5-triazin-2-amine (0.210 g, 36% yield).

Example 46

N-(3-(4-amino-6-methyl-1,3,5-triazin-2-yl)-5-methylpyridin-2-yl)-1H-indol-4-amine

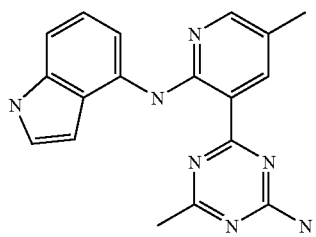 [SMILES: Cc1cnc(Nc2cccc3[nH]ccc23)c(-c2nc(C)nc(N)n2)c1]

The experimental procedure for this compound was the same as Example 22, Step 2 using 4-(2-chloro-5-methylpyridin-3-yl)-6-methyl-1,3,5-triazin-2-amine and 1H-indol-4-amine (Bionet Research, Cornwall, UK). LCMS (API-ES) m/z 332 (M+H)+. 1H NMR (400 MHz, d6-DMSO) δ 11.84 (s, 1H); 11.34 (s, 1H); 8.62 (d, J=1.17 Hz, 1H); 8.24 (d, J=0.59 Hz, 1H); 8.14 (d, J=0.59 Hz, 1H); 7.84 (d, J=0.59 Hz, 1H); 7.33 (br. s., 1H); 7.05 (s, 1H); 7.04 (d, J=3.33 Hz, 1H); 6.65 (d, J=1.17 Hz, 1H); 3.17 (d, J=2.74 Hz, 3H); 3.16 (br. s., 3H).

Example 47

N-(3-(4-amino-6-methyl-1,3,5-triazin-2-yl)-5-methylpyridine-2-yl)-1H-indazol-4-amine

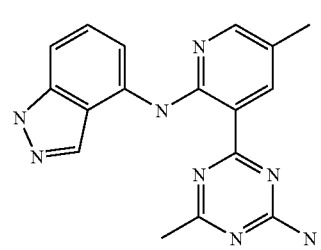 [SMILES: Cc1cnc(Nc2cccc3[nH]ncc23)c(-c2nc(C)nc(N)n2)c1]

The experimental procedure for this compound was the same as Example 22, Step 2 using 4-(2-chloro-5-methylpyridin-3-yl)-6-methyl-1,3,5-triazin-2-amine and 1H-indazol-4-amine. LCMS (API-ES) m/z 333 (M+H)+. 1H NMR (400 MHz, d6-DMSO) δ 13.08 (d, J=2.35 Hz, 1H); 12.12 (br. s., 1H); 8.64 (br. s., 1H); 8.28 (dd, J=3.81, 2.05 Hz, 1H); 8.14 (d, J=5.28 Hz, 2H); 7.74 (br. s., 2H); 7.31 (d, J=7.63 Hz, 1H); 7.32 (br. s., 1H); 7.13 (d, J=12.91 Hz, 1H); 3.32 (d, J=1.37 Hz, 6H).

Example 48

4-(5-bromo-2-(4-methoxyphenylamino)pyridine-3-yl)-6-methyl-1,3,5-triazin-2-amine

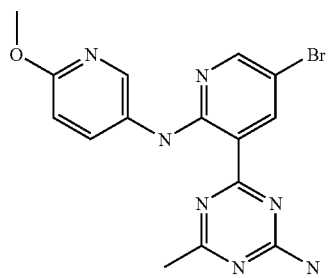 [SMILES: COc1ccc(Nc2ncc(Br)cc2-c2nc(C)nc(N)n2)cn1]

This compound was synthesized in 2 steps following the procedures of Example 45 and Example 31, Step 4 utilizing 5-bromo-2-fluoropyridin-3-ylboronic acid (Combi-Blocks, Inc.) and 4-chloro-6-methyl-1,3,5-triazin-2-amine in the first step. LCMS (API-ES) m/z 387/389 (M+H)+. 1H NMR (400 MHz, d6-DMSO) δ 11.70 (d, J=1.17 Hz, 1H); 8.84 (br. s., 1H); 8.49 (d, J=4.30 Hz, 1H); 8.37 (br. s., 1H); 8.07 (dd, J=4.21, 1.86 Hz, 1H); 7.81 (br. s., 1H); 6.84 (d, J=2.35 Hz, 1H); 3.84 (br. s., 3H); 2.50 (d, J=0.98 Hz, 3H).

Example 49

4-(2-(6-ethoxypyridin-3-ylamino)pyridine-3-yl)-6-methyl-1,3,5-triazin-2-amine

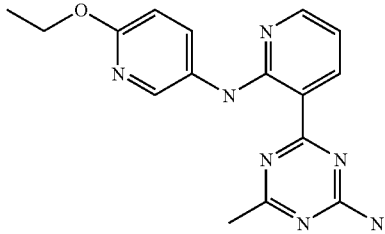 [SMILES: CCOc1ccc(Nc2ncccc2-c2nc(C)nc(N)n2)cn1]

4-(2-Fluoropyridin-3-yl)-6-methyl-1,3,5-triazin-2-amine (0.100 g, 0.49 mmol), 5-amino-2-ethoxypyridine (Combi-Blocks, Inc., San Diego, Calif.), 1,4-dioxane (0.75 mL, 8.8 mmol), (Aldrich, St. Louis, Mo.) and 2 N aqueous HCl (0.24 mL, 0.49 mmol) were added to a 50 mL round-bottomed flask. The suspension was stirred at 100° C. overnight. The crude product was adsorbed onto a plug of silica gel and purified by chromatography through a RediSep®, Teledyne ISCO, Lincoln, Nebr., pre-packed silica gel column (40 g), eluting with a gradient of 5% to 20% methanol in dichloromethane to give 4-(2-(6-ethoxypyridin-3-ylamino)pyridine-3-yl)-6-methyl-1,3,5-triazin-2-amine LCMS (API-ES) m/z 324 (M+H)$^+$. $^1$H NMR (400 MHz, d6-DMSO) δ 11.80 (br. s., 1H); 8.83 (br. s., 1H); 8.27 (d, J=4.11 Hz, 1H); 8.26 (d, J=4.11 Hz, 1H); 8.11 (br. s., 1H); 7.82 (dd, J=2.93, 1.56 Hz, 1H); 8.81 (d, J=4.11 Hz, 1H); 6.92 (br. s., 1H); 6.86 (d, J=9.39 Hz, 1H); 4.28-4.37 (m, 2H); 2.44 (br. s., 3H); 1.33 (t, J=7.04 Hz, 3H).

Example 50

N5-(3-(4-amino-6-methyl-1,3,5-triazin-2-yl)pyridin-2-yl)pyridine-2,5-diamine

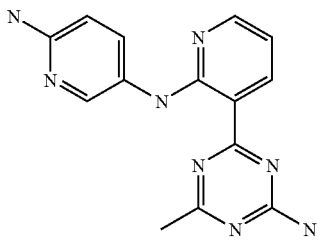 [SMILES: Cc1nc(N)nc(-c2cccnc2Nc2ccc(N)nc2)n1]

The title compound was prepared following the procedure of Example 49, utilizing 4-(2-fluoropyridin-3-yl)-6-methyl-1,3,5-triazin-2-amine and 2,5-diaminopyridine (Aldrich). LCMS (API-ES) m/z 295 (M+H)$^+$. $^1$H NMR (400 MHz, d6-DMSO) δ 11.52 (s, 1H); 8.75 (d, J=7.83 Hz, 1H); 8.74 (dt, J=7.83, 1.08 Hz, 1H); 8.34 (d, J=2.74 Hz, 1H); 8.27 (d, J=1.76 Hz, 1H); 8.26 (d, J=2.15 Hz, 1H); 7.87 (d, J=8.80 Hz, 1H); 7.88 (dt, J=9.00, 1.08 Hz, 1H); 7.68 (br. s., 1H); 6.83 (dd, J=7.82, 4.70 Hz, 1H); 6.62 (d, J=8.80 Hz, 1H); 2.42 (s, 3H).

Example 51

4-chloro-N,N-bis(4-methoxybenzyl)-6-methyl-1,3,5-triazin-2-amine

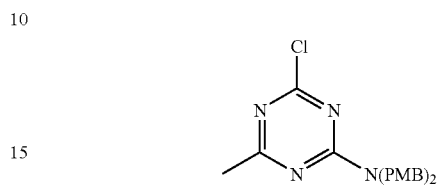

Cesium carbonate (0.860 mL, 10.74 mmol) was added to a mixture of 4-chloro-6-methyl-1,3,5-triazin-2-amine (1.10 g, 7.61 mmol) and 1-(chloromethyl)-4-methoxybenzene (1.10 mL, 8.11 mmol) in DMF (8.0 mL) at rt. After 40 min, more 1-(chloromethyl)-4-methoxybenzene (1.10 mL, 8.11 mmol) was added. After another 1 h, more cesium carbonate (0.860 mL, 10.74 mmol) was added. After another 30 min, the mixture was diluted with EtOAc (30 mL) and filtered through a pad of Celite® (diatomaceous earth). The filtrate was transferred to a separatory funnel, diluted with more EtOAc, and washed with water (3×20 mL). The organic layer was dried over Na$_2$SO$_4$ and concentrated. The resulting slurry was filtered and washed with 1:1 hexane-EtOAc. The filtrate was purified by chromatography on silica using 5 to 100% DCM in hexane to give the product as a soft white solid (1.8 g). LCMS (ES, pos.): cacld for C$_{20}$H$_{21}$ClN$_4$O$_2$: 384.1; found: 385.1 (M+H)$^+$. $^1$H NMR (400 MHz, CDCl$_3$) δ 7.16 (t, J=8.12 Hz, 4H); 6.81-6.95 (m, 4H); 4.74 (s, 2H); 4.69 (s, 2H); 3.81 (s, 6H); 2.45 (s, 3H).

Example 51

Alternative Procedure

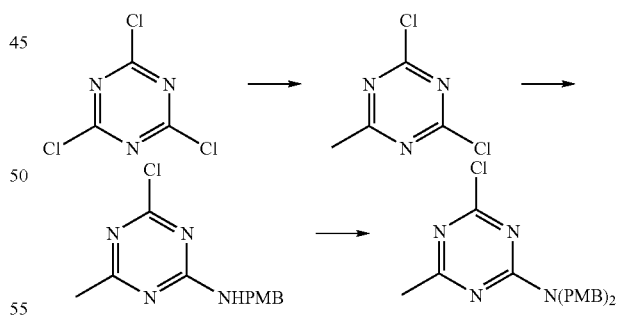

Step 1. 2,4-dichloro-6-methyl-1,3,5-triazine

To a 5-L reactor was added 2,4,6-trichloro-1,3,5-triazine (180 g, 976 mmol) and DCM (180 mL). To the solution cooled at 0° C. in a dry ice bath was added methylmagnesium bromide (390 mL, 1171 mmol) over 30 min while the reaction temperature was kept below rt. After the addition, the reaction mixture was placed in an ice-water bath to keep the internal temperature stable at 20° C. After the mixture was stirred overnight at rt, it was cooled to −20° C. and was slowly quenched with ice water (500 mL) (internal temperature was controlled below 0° C.). The mixture was allowed to warm to rt and was transferred to a separation funnel. The organic layer was washed with water (500 mL), and concentrated to afford 2,4-dichloro-6-methyl-1,3,5-triazine (127 g, 774 mmol, 79% yield) as a solid that was carried to the next step.

Step 2. 4-chloro-N-(4-methoxybenzyl)-6-methyl-1,3,5-triazin-2-amine

To a solution of 2,4-dichloro-6-methyl-1,3,5-triazine (190 g, 1159 mmol) in DMF (1500 mL) was added (4-methoxyphenyl)methanamine (159 g, 1159 mmol) slowly in 15 min while the temperature was controlled below 20° C. This was followed by the addition of N-ethyl-N-isopropylpropan-2-amine (222 mL, 1274 mmol) slowly over 15 min. After the completion of the reaction, EtOAc (2000 mL) was added and the mixture was washed with dilute brine (200 mL saturated NaCl plus 500 mL water), water (500 mL), saturated $NH_4Cl$ (250 mL), and finally water (250 mL). The organic layer was concentrated to afford 4-chloro-N-(4-methoxybenzyl)-6-methyl-1,3,5-triazin-2-amine as a solid (290.5 g, 1097 mmol, 95% yield). m/z 265.2 (M+H).

Step 3. 4-chloro-N,N-bis(4-methoxybenzyl)-6-methyl-1,3,5-triazin-2-amine

To a solution of 4-chloro-N-(4-methoxybenzyl)-6-methyl-1,3,5-triazin-2-amine (160 g, 604 mmol) in DMF (800 mL) at 0° C., was added sodium hydride (18.86 g, 786 mmol) slowly over 5 min. 1-(Chloromethyl)-4-methoxybenzene (91 mL, 665 mmol) was slowly added over 15 min. The reaction mixture was stirred at 0-5° C. for 30 min and allowed to warm to room temp 25° C. After 1 h, cold water (2.5 L) was added and the mixture was stirred overnight. The resulting slurry was filtered, washed with water (150 mL, ×2) and dried to afford 4-chloro-N,N-bis(4-methoxybenzyl)-6-methyl-1,3,5-triazin-2-amine as a solid (215.3 g, 559 mmol, 93% yield). LCMS (ES, pos.): Cacld for $C_{20}H_{21}ClN_4O_2$: 384.1; found: 385.1 $(M+H)^+$. $^1H$ NMR (400 MHz, $CDCl_3$) δ 7.16 (t, J=8.12 Hz, 4H); 6.81-6.95 (m, 4H); 4.74 (s, 2H); 4.69 (s, 2H); 3.81 (s, 6H); 2.45 (s, 3H).

Example 52

4-(2-fluoropyridin-3-yl)-N,N-bis(4-methoxybenzyl)-6-methyl-1,3,5-triazin-2-amine

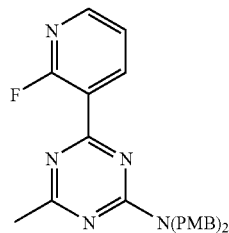

A mixture of potassium acetate (0.38 g, 3.87 mmol), 2-fluoro-3-pyridineboronic acid (0.28 g, 1.987 mmol) and 4-chloro-N,N-bis(4-methoxybenzyl)-6-methyl-1,3,5-triazin-2-amine (0.60 g, 1.559 mmol) in DCM (8.0 mL) was evaporated under nitrogen to dryness. THF (5.0 mL) was added followed by the addition of bis[4-(di-tert-butylphosphino)-N,N-dimethylaniline]palladium dichloride (Amphos) (0.060 g, 0.085 mmol). The mixture was heated in an oil bath at 80° C. After 1 h, EtOH (5 mL) was added and heating was continued overnight. The mixture was cooled to rt. Water (10 mL) and DCM (10 mL) were added. The organic layer was separated. The aqueous layer was extracted with $CH_2CL_2$ and the organic layer was dried over $MgSO_4$. The solution was filtered and concentrated in vacuo. The orange oil was adsorbed onto a plug of silica gel and purified by chromatography eluting with 2:1 hexane-acetone to provide 4-(2-fluoropyridin-3-yl)-N,N-bis(4-methoxybenzyl)-6-methyl-1,3,5-triazin-2-amine (80 mg, 0.180 mmol, 11.52% yield) as a white foam. LCMS (ES, pos.): calcd for $C_{25}H_{24}FN_5O_2$: 445.2; found: 446.2 $(M+H)^+$. $^1H$ NMR (400 MHz, $CDCl_3$) δ 8.49-8.62 (m, 1H); 7.86-7.99 (m, 1H); 7.27-7.36 (m, 1H); 7.23 (dd, J=8.31, 4.99 Hz, 4H); 6.87 (t, J=8.51 Hz, 4H); 3.81 (s, 3H) 4.81 (s, 4H); 3.80 (s, 3H); 2.55 (s, 3H).

Example 53

4-(2-(6-chloropyridin-3-ylamino)pyridin-3-yl)-N,N-bis(4-methoxybenzyl)-6-methyl-1,3,5-triazin-2-amine

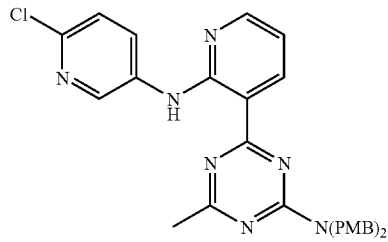

1.0 M LHMDS in THF (600 μL, 0.600 mmol) was added to a solution of 5-amino-2-chloropyridine (49 mg, 0.381 mmol) and 4-(2-fluoropyridin-3-yl)-N,N-bis(4-methoxybenzyl)-6-methyl-1,3,5-triazin-2-amine (80 mg, 0.180 mmol) in THF (4 mL) under nitrogen at rt. A dark orange mixture formed. After 1.5 h, the mixture was heated to about 50° C. After overnight, more 5-amino-2-chloropyridine (49 mg, 0.381 mmol) and LHMDS (600 μL, 0.600 mmol) were added. The reaction mixture was heated for another 2 h and cooled to rt. The mixture was neutralized with HCl (5 N, 0.3 mL) and diluted with EtOAc (10 mL) and water (10 mL). The aqueous layer was extracted with DCM twice and the combined organic was dried over $Na_2SO_4$ and concentrated. The residue was purified on silica (10-80% EtOAc in hexane) to give a yellow oil (70 mg). LCMS (ES, pos.): calcd for $C_{30}H_{28}FN_7O_2$: 553.2. found: 554.1 $(M+H)^+$. $^1H$ NMR (400 MHz, $CDCl_3$) δ 12.19 (s, 1H); 8.84 (dd, J=7.83, 1.76 Hz, 1H); 8.47 (d, J=2.74 Hz, 1H); 8.33 (dd, J=4.70, 1.76 Hz, 1H); 8.26 (dd, J=8.71, 2.84

Hz, 1H); 7.16-7.24 (m, 5H); 6.80-6.91 (m, 5H); 4.84 (s, 4H); 3.80 (d, J=5.87 Hz, 6H); 2.59 (s, 3H).

Example 54

4-(2-(6-chloropyridin-3-ylamino)pyridin-3-yl)-6-methyl-1,3,5-triazin-2-amine

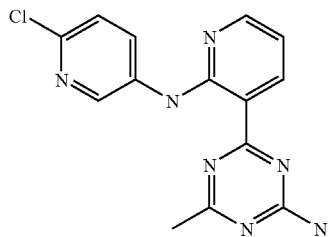 [SMILES: Cc1nc(N)nc(-c2cccnc2Nc2ccc(Cl)nc2)n1]

A solution of 4-(2-(6-chloropyridin-3-ylamino)pyridin-3-yl)-N,N-bis(4-methoxybenzyl)-6-methyl-1,3,5-triazin-2-amine (70 mg, 0.126 mmol) in TFA (10 mL) was heated to 80° C. After 24 h, the mixture was concentrated to a slurry. Water (5 mL) was added, followed by the addition of $Na_2CO_3$ in batches until the pH was basic. The mixture was filtered and the solid was washed with water, then MeOH, to give the product as a brown solid (39 mg). LCMS (ES, pos.): calcd for $C_{14}H_{12}ClN_7$: 313.1; found: 314.0 (M+H)$^+$. $^1$H NMR (400 MHz, d6-DMSO) δ 12.16 (s, 1H); 8.87 (d, J=2.74 Hz, 1H); 8.82 (dd, J=7.83, 1.76 Hz, 1H); 8.48 (dd, J=8.80, 2.74 Hz, 1H); 8.39 (dd, J=4.50, 1.76 Hz, 1H); 7.92 (br. s., 1H); 7.78 (br. s., 1H); 7.46 (d, J=8.61 Hz, 1H); 7.01 (dd, J=7.83, 4.70 Hz, 1H); 2.44 (s, 3H).

Example 55

N-(3-(6-methyl-1H-pyrazolo[3,4-d]pyrimidin-4-yl)pyridin-2-yl)-1H-indazol-4-amine

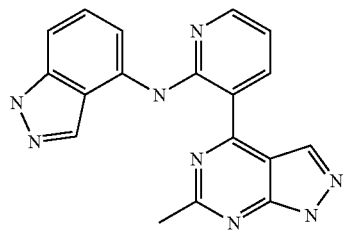 [SMILES: Cc1nc(-c2cccnc2Nc2cccc3[nH]ncc23)c2cn[nH]c2n1]

Step 1. N-(3-(6-methyl-1-(tetrahydro-2H-pyran-2-yl)-1H-pyrazolo[3,4-d]pyrimidin-4-yl)pyridin-2-yl)-2-(tetrahydro-2H-pyran-2-yl)-2H-indazol-4-amine A solution of 2-(tetrahydro-2H-pyran-2-yl)-2H-indazol-4-amine (80.2 mg, 369 µmol) and 4-(2-fluoropyridin-3-yl)-6-methyl-1-(tetrahydro-2H-pyran-2-yl)-1H-pyrazolo[3,4-d]pyrimidine (112.0 mg, 357 µmol) in THF (1.0 mL) was stirred in an ice bath and treated dropwise with LHMDS (1.0 M in THF, 1.1 mL, 3 equiv.). The mixture was stirred for 45 min and then quenched with water (0.1 mL). The mixture was extracted into EtOAc from saturated aqueous NaHCO$_3$, dried (MgSO$_4$) and concentrated to give a dark residue. The residue was purified by flash chromatography on silica (25-30% EtOAc/hexane) to give N-(3-(6-methyl-1-(tetrahydro-2H-pyran-2-yl)-1H-pyrazolo[3,4-d]pyrimidin-4-yl)pyridin-2-yl)-2-(tetrahydro-2H-pyran-2-yl)-2H-indazol-4-amine (56.9 mg, 31.2% yield) as a yellow oil. $^1$H NMR (400 MHz, CDCl$_3$) δ 11.97 (br. s, 1H); 8.43-8.53 (m, 1H); 8.30-8.42 (m, 3H); 7.96 (br. s., 1H); 7.38-7.48 (m, 1H); 7.34 (d, J=7.43 Hz, 1H); 6.94-7.03 (m, 1H); 6.16 (d, J=10.17 Hz, 1H); 5.71 (d, J=9.00 Hz, 1H); 4.14 (d, J=9.98 Hz, 2H); 3.73-3.95 (m, 2H); 3.04 (s, 3H); 2.58-2.76 (m, 1H); 2.26-2.39 (m, 1H); 1.94-2.25 (m, 4H); 1.59-1.93 (m, 6H). m/z (ESI, +ve) 511.1 (M+H)$^+$.

Step 2. N-(3-(6-methyl-1H-pyrazolo[3,4-d]pyrimidin-4-yl)pyridin-2-yl)-1H-indazol-4-amine A solution of N-(3-(6-methyl-1-(tetrahydro-2H-pyran-2-yl)-1H-pyrazolo[3,4-d]pyrimidin-4-yl)pyridin-2-yl)-2-(tetrahydro-2H-pyran-2-yl)-2H-indazol-4-amine (56.9 mg, 111 µmol) in DCM (1 mL) and MeOH (2 mL) was treated with (+/−)-10-camphorsulfonic acid (57 mg, 2.2 equiv.) and stirred for 16 h. LCMS indicated clean monodeprotection with only a small amount of the fully deprotected compound. Additional (+/−)-10-camphorsulfonic acid (57 mg, 2.2 equiv.) was added and the solution stirred at 60° C. for 1 h after which time reaction was complete. The mixture was concentrated and purified by SCX ion exchange chromatography washing with MeOH and eluting off with 2 N NH$_3$/MeOH to give N-(3-(6-methyl-1H-pyrazolo[3,4-d]pyrimidin-4-yl)pyridin-2-yl)-1H-indazol-4-amine (35 mg, 87% yield) as a brown solid. $^1$H NMR of free base thus obtained gives broad signals, so a small amount was converted to the HCl salt for better $^1$H NMR analysis by dissolving in MeOH containing 2 drops 2 M aqueous HCl followed by concentration to dryness. HCl salt: $^1$H NMR (400 MHz, d6-DMSO) δ 14.18 (br. s., 1H); 11.38 (s, 1H); 10.43 (s, 1H); 9.76 (s, 1H); 9.42 (d, 1H); 9.04 (s, 1H); 8.64 (d, 1H); 8.46 (s, 1H); 7.85-7.98 (m, 2H); 7.69 (d, J=9.54 Hz, 1H); 2.14 (s, 3H). m/z (ESI, +ve) 343.0 (M+H)$^+$.

Example 56

N-(3-(2-methyl-9H-purin-6-yl)pyridin-2-yl)-1H-indol-4-amine

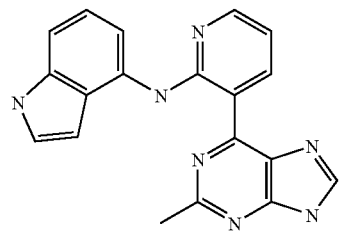 [SMILES: Cc1nc(-c2cccnc2Nc2cccc3[nH]ccc23)c2nc[nH]c2n1]

6-(2-Fluoropyridin-3-yl)-2-methyl-9-(tetrahydro-2H-pyran-2-yl)-9H-purine (270 mg, 0.862 mmol) and 4 aminoindole (159.3 mg, 1.205 mmol) were suspended in EtOH (5.0 mL) and then aqueous hydrochloric acid, (5 N, 0.21 mL, 1.1 mmol) was added. The reaction flask was fit with a reflux condenser, placed in a preheated oil bath (100° C.), and stirred for 3 hours. Then, the reaction was cooled to room temperature, diluted with 2 N ammonia in MeOH (4.0 mL), and allowed to stand overnight. Then, the material was concentrated, treated with DMF and filtered. The solid was washed with DCM, and the filtrate was concentrated and purified on prep HPLC (10% to 100% MeCN/water with 0.1% TFA over 30 minutes with a total flow rate of 100 mL/min). The fractions with product were collected, concentrated, and filtered through a silica gel plug (about 1 inch) with 10:1 DCM/2 N ammonia in MeOH to give N-(3-(2-methyl-9H-purin-6-yl)pyridin-2-yl)-1H-indol-4-amine (13.7 mg, 5%). MS (ESI pos. ion) m/z 342 (M+H)+. 1H NMR (d6-DMSO, 400 MHz) δ 13.60 (s, 1H), 12.44 (s, 1H), 11.16 (s, 1H), 9.77 (d, J=7.04 Hz, 1H), 8.61 (s, 1H), 8.37 (dd, J=4.69 Hz, 1.76 Hz, 1H), 8.05 (dd, J=6.85 Hz, 1.56 Hz, 1H), 7.37 (t, J=2.64 Hz, 1H), 7.11-7.04 (m, 2H), 7.01 (dd, J=7.82 Hz, 4.69 Hz, 1H), 6.72 (s, 1H), 2.92 (s, 3H).

Example 57

N-(3-(2-methyl-9H-purin-6-yl)pyridin-2-yl)-1H-indazol-4-amine

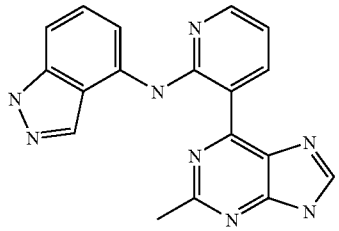 [SMILES: Cc1nc(-c2cccnc2Nc2cccc3[nH]ncc23)c2nc[nH]c2n1]

6-(2-Fluoropyridin-3-yl)-2-methyl-9-(tetrahydro-2H-pyran-2-yl)-9H-purine (24.9 mg, 0.079 mmol) and 1H-indazol-4-amine (Bionet Research, Cornwall, UK, 13.8 mg, 0.104 mmol) were suspended in EtOH (0.9 mL) and aqueous hydrochloric acid (5 M, 0.020 mL, 0.10 mmol) was added. The reaction flask was fitted with a reflux condenser and put in a preheated oil bath (100° C.), and the reaction was stirred for 90 minutes. Then, the reaction was cooled to room temperature and treated with 2 N ammonia in MeOH. In a separate flask, 6-(2-fluoropyridin-3-yl)-2-methyl-9-(tetrahydro-2H-pyran-2-yl)-9H-purine (295 mg, 0.943 mmol) and 1H-indazol-4-amine (Bionet Research, Cornwall, UK, 173.3 mg, 1.302 mmol) were suspended in EtOH (9.5 mL) and hydrochloric acid, (5 N, 0.23 mL, 1.2 mmol) was added. The reaction flask was fit with a reflux condenser and placed in a preheated oil bath (100° C.) and stirred for 75 minutes. Then, the reaction was cooled to room temperature and treated with 2 N ammonia in MeOH (4.8 mL).

The two reactions were combined, concentrated, diluted with DMF and DCM, and filtered. The filtrate was concentrated and purified by prep HPLC (10% to 100% MeCN/water with 0.1% TFA over 30 minutes with a total flow rate of 100 mL/min). The fractions with product were collected, concentrated, and filtered through a silica gel filter (about 1 inch, 10:1 DCM/2 N ammonia in MeOH) to give N-(3-(2-methyl-9H-purin-6-yl)pyridin-2-yl)-1H-indazol-4-amine (33.9 mg, 10% yield). MS (ESI pos. ion) m/z 343 (M+H)+. 1H NMR (d6-DMSO, 400 MHz) δ 13.12 (s, 1H), 12.72 (s, 1H), 9.78 (s, 1H), 8.62 (s, 1H), 8.41 (dd, J=4.50 Hz, 1.76 Hz, 1H), 8.27 (s, 1H), 8.10 (d, J=7.43 Hz, 1H), 7.33 (t, J=8.02 Hz, 1H), 7.17 (d, J=8.22 Hz, 1H), 7.09 (dd, J=7.83 Hz, 4.69 Hz, 1H), 2.94 (s, 3H).

Example 58

N-(6-methoxypyridin-3-yl)-3-(2-methyl-9H-purin-6-yl)pyridin-2-amine

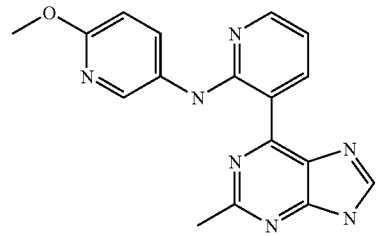 [SMILES: COc1ccc(Nc2ncccc2-c2nc(C)nc3[nH]cnc23)cn1]

Step 1. 6-methoxy-N-(3-(2-methyl-9-(tetrahydro-2H-pyran-2-yl)-9H-purin-6-yl)pyridin-2-yl)pyridin-3-amine A solution of 6-(2-fluoropyridin-3-yl)-2-methyl-9-(tetrahydro-2H-pyran-2-yl)-9H-purine (190 mg, 606 µmol) and 6-methoxypyridin-3-amine (94.1 mg, 758 µmol) (Aldrich, St. Louis, Mo.) in THF (2.0 mL) was cooled in an ice bath and treated with LiHMDS (3.0 mL, 3.0 mmol) (a 1.0 M in THF solution). A blood-red solution was obtained. The mixture was stirred for 1 h, and then quenched with water (0.1 mL). The mixture was extracted into EtOAc from saturated aqueous NaHCO3, concentrated and purified by flash chromatography on silica (25 to 50% EtOAc/hexane; yellow band from column) to give 6-methoxy-N-(3-(2-methyl-9-(tetrahydro-2H-pyran-2-yl)-9H-purin-6-yl)pyridin-2-yl)pyridin-3-amine (96.3 mg, 38.0% yield) as a yellow crystalline solid. 1H NMR (400 MHz, d6-DMSO) δ 12.50 (s, 1H); 9.72 (dd, J=7.82, 1.71 Hz, 1H); 8.87 (s, 1H); 8.53 (d, J=2.69 Hz, 1H); 8.32 (dd, J=4.65, 1.96 Hz, 1H); 8.18 (dd, J=8.93, 2.81 Hz, 1H); 7.01 (dd, J=7.82, 4.65 Hz, 1H); 6.85 (d, J=9.05 Hz, 1H); 5.80-5.89 (m, 1H); 3.97-4.12 (m, 1H); 3.85 (s, 3H); 3.67-3.82 (m, 1H); 2.89 (s, 3H); 2.27-2.38 (m, 1H); 1.93-2.12 (m, 2H); 1.72-1.88 (m, 1H); 1.55-1.70 (m, 2H). m/z (ESI, +ve) 418.1 (M+H)+.

Step 2. N-(6-methoxypyridin-3-yl)-3-(2-methyl-9H-purin-6-yl)pyridin-2-amine

A solution of 6-methoxy-N-(3-(2-methyl-9-(tetrahydro-2H-pyran-2-yl)-9H-purin-6-yl)pyridin-2-yl)pyridin-3-amine (95.3 mg, 228 µmol) in 2 N aqueous HCl (2.0 mL, 4 mmol) was heated briefly at 100° C. in an oil bath, and then the heater was turned off and the mixture allowed to slowly cool. The solution was concentrated and purified by SCX ion exchange chromatography washing with MeOH and eluting off with 2 N NH3/MeOH to give N-(6-methoxypyridin-3-yl)-3-(2-methyl-9H-purin-6-yl)pyridin-2-amine (72 mg, 95% yield) as an orange solid. 1H NMR (400 MHz, d6-DMSO) δ 13.60 (br. s., 1H); 12.68 (s, 1H); 9.80 (dd, J=7.82, 1.96 Hz, 1H); 8.60 (s, 1H); 8.54 (d, J=2.69 Hz, 1H); 8.31 (dd, J=4.65, 1.96 Hz, 1H); 8.20 (dd, J=8.92, 2.81 Hz, 1H); 7.00 (dd, J=7.95, 4.77 Hz, 1H); 6.85 (d, J=8.80 Hz, 1H); 3.85 (s, 3H); 2.86 (s, 3H). m/z (ESI, +ve) 334.0 (M+H)+.

Example 59

6-(5-chloro-2-fluoropyridin-3-yl)-2-methyl-9-(tetrahydro-2H-pyran-2-yl)-9H-purine

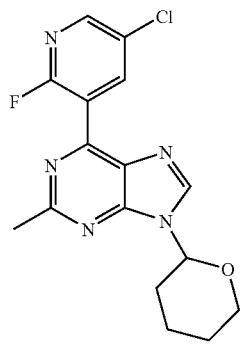 [SMILES: Cc1nc(-c2cc(Cl)cnc2F)c2ncn(C3CCCCO3)c2n1]

6-Chloro-2-methyl-9-(tetrahydro-2H-pyran-2-yl)-9H-purine (0.500 g, 1.979 mmol) and 5-chloro-2-fluoropyridin-3-ylboronic acid (1.388 g, 7.91 mmol) (Combi-Blocks, Inc., San Diego, Calif.) in THF (25 ml) were added to a 100 mL round-bottomed flask. Potassium acetate (0.583 g, 5.94 mmol) was added to the mixture, followed by water (1 mL). The mixture was evacuated, then backfilled with Nitrogen gas. Then bis(di-tert-butyl(4-dimethylaminophenyl)phosphine)dichloropalladium(II) (0.050 g) (Aldrich, St. Louis, Mo.) was added into the mixture. The mixture was evacuated, then backfilled with nitrogen gas. The flask was fitted with a reflux condenser, then placed into a pre-heated (90° C.) oil bath and allowed to stir under inert atmosphere for 2 h. The progress of the reaction was monitored by LCMS, which showed mostly desired product. The reaction mixture was allowed to cool to room temperature, diluted with water (10 mL) and extracted with CH$_2$Cl$_2$ (3×25 mL). The organic extracts were washed with satd aqueous Na$_2$CO$_3$ (1×20 mL) and dried over Na$_2$SO$_4$. The solution was filtered and concentrated in vacuo to give the crude material as a tan oil. The crude material was adsorbed onto a plug of silica gel and purified by chromatography through a Redi-Sep RediSep®, Teledyne ISCO, Lincoln, Nebr., pre-packed silica gel column (120 g), eluting with a gradient of 1% to 40% EtOAc in CH$_2$Cl$_2$, to give 6-(5-chloro-2-fluoropyridin-3-yl)-2-methyl-9-(tetrahydro-2H-pyran-2-yl)-9H-purine (0.502 g, 1.443 mmol, 73.0% yield) as yellow solid. $^1$H NMR (400 MHz, CDCl$_3$) δ 8.37-8.45 (m, 1H); 8.27-8.33 (m, 2H); 5.79-5.92 (m, 1H); 4.14-4.26 (m, 1H); 3.74-3.91 (m, 1H); 2.89 (s, 3H); 1.96-2.25 (m, 3H); 1.63-1.91 (m, 3H). m/z (ESI, +ve) 348 (M+H)+.

Example 60

N-(5-chloro-3-(2-methyl-9-(tetrahydro-2H-pyran-2-yl)-9H-purin-6-yl)pyridin-2-yl)-1-(tetrahydro-2H-pyran-2-yl)-1H-indazol-4-amine

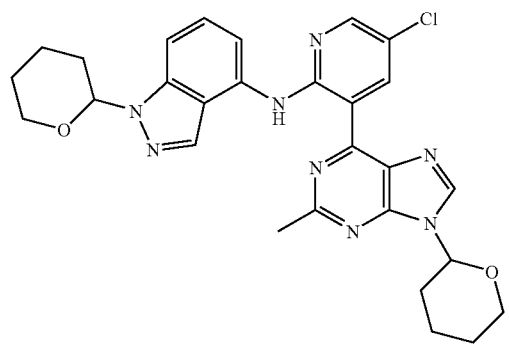 [SMILES: Cc1nc(-c2cc(Cl)cnc2Nc2cccc3c2cnn3C2CCCCO2)c2ncn(C3CCCCO3)c2n1]

A solution of 6-(5-chloro-2-fluoropyridin-3-yl)-2-methyl-9-(tetrahydro-2H-pyran-2-yl)-9H-purine (75.3 mg, 217 µmol) and 1-(tetrahydro-2H-pyran-2-yl)-1H-indazol-4-amine (49.4 mg, 227 µmol) in THF (1.0 mL) was cooled in an ice bath and treated dropwise with LiHMDS in THF (0.68 mL of 1.0 M solution, 3 equiv.) giving a deep red solution. The mixture was stirred for 45 min and then quenched with water (0.1 mL). Extraction into EtOAc from saturated aqueous NaHCO$_3$, drying (MgSO$_4$) and concentration gave a deep yellow oil. Purification by flash chromatography on silica eluting with 40% EtOAc/hexane gave N-(5-chloro-3-(2-methyl-9-(tetrahydro-2H-pyran-2-yl)-9H-purin-6-yl)pyridin-2-yl)-1-(tetrahydro-2H-pyran-2-yl)-1H-indazol-4-amine (96.8 mg, 82.0% yield) (yellow band on column) as a bright yellow solid. $^1$H NMR (400 MHz, CDCl$_3$) δ 12.70 (br. s., 1H); 9.82 (d, J=2.74 Hz, 1H); 8.21-8.40 (m, 3H); 8.06 (dd, J=7.53, 1.66 Hz, 1H); 7.42 (t, J=8.02 Hz, 1H); 7.20-7.30 (m, 1H); 5.87 (dd, J=10.47, 2.25 Hz, 1H); 5.72 (dd, J=9.59, 2.54 Hz, 1H); 4.15-4.28 (m, 1H); 4.02-4.12 (m, 1H); 3.70-3.88 (m, 2H); 3.00 (s, 3H); 2.52-2.71 (m, 1H); 1.98-2.27 (m, 5H); 1.58-1.92 (m, 6H). m/z (ESI, +ve) 545.1 (M+H)+.

Example 61

N-(5-chloro-3-(2-methyl-9H-purin-6-yl)pyridin-2-yl)-1H-indazol-4-amine

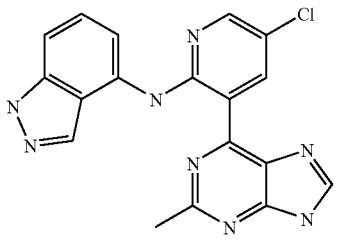 [SMILES: Cc1nc(-c2cc(Cl)cnc2Nc2cccc3[nH]ncc23)c2nc[nH]c2n1]

A solution of N-(5-chloro-3-(2-methyl-9-(tetrahydro-2H-pyran-2-yl)-9H-purin-6-yl)pyridin-2-yl)-1-(tetrahydro-2H-pyran-2-yl)-1H-indazol-4-amine (96.8 mg, 178 μmol) in DCM/MeOH (4.0 mL, 1:1) was treated with (+/−)-10-camphorsulfonic acid (91 mg, 391 μmol) and the stirred mixture placed in an oil bath at 40° C. The heater was turned off and the mixture stirred for 16 h. LCMS showed predominantly monodeprotection, so an additional 90 mg of CSA was added (4.4 equiv. total). The mixture was heated at 40° C. until LCMS indicated complete deprotection. The mixture was cooled and purified by ion exchange chromatography (washing with MeOH, eluting off with 2 N $NH_3$/MeOH). The product was concentrated, taken up in MeOH (3 mL), sonicated and allowed to stand. N-(5-Chloro-3-(2-methyl-9H-purin-6-yl)pyridin-2-yl)-1H-indazol-4-amine (55 mg, 82% yield) crystallized out and was collected by filtration as an orange solid. $^1$H NMR of free base thus obtained gives broad signals, so a small amount was converted to the HCl salt for better $^1$H NMR analysis by dissolving in MeOH containing 2 drops 2 M aqueous HCl followed by concentration to dryness. HCl salt: $^1$H NMR (400 MHz, d6-DMSO) δ 11.29 (br. s., 1H); 10.17 (br. s., 1H); 10.04 (s, 1H); 9.27 (d, J=2.69 Hz, 1H); 8.93 (s, 1H); 8.40 (s, 1H); 8.30 (d, J=2.69 Hz, 1H); 7.89 (d, J=9.54 Hz, 1H); 7.52 (d, J=9.54 Hz, 1H); 2.15 (s, 3H). m/z (ESI, +ve) 377.0 (M+H)$^+$.

Example 62

5-chloro-N-(6-methoxypyridin-3-yl)-3-(2-methyl-9-(tetrahydro-2H-pyran-2-yl)-9H-purin-6-yl)pyridin-2-amine

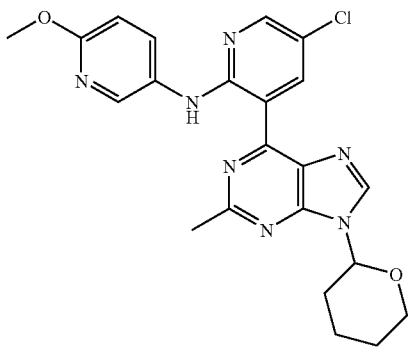 [SMILES: COc1ccc(Nc2ncc(Cl)cc2-c2nc(C)nc3c2ncn3C2CCCCO2)cn1]

A solution of 6-methoxypyridin-3-amine (0.357 g, 2.88 mmol) (Source: Aldrich) in THF (10 mL) was treated with lithium bis(trimethylsilyl)amide (5.03 mL, 5.03 mmol) (Source: Aldrich) and the mixture was stirred under an inert atmosphere for 20 minutes. Then 6-(5-chloro-2-fluoropyridin-3-yl)-2-methyl-9-(tetrahydro-2H-pyran-2-yl)-9H-purine (0.500 g, 1.438 mmol) was added to the mixture and the mixture was stirred overnight. The reaction mixture was diluted with DCM and brine solution. The organic layer was collected by extracting the aqueous layer with DCM (3×20 mL). The combined organic layers were dried over sodium sulfate, filtered and concentrated in vacuo. The crude was purified by ISCO Silica-Gel Chromatography, Teledyne ISCO, Lincoln, Nebr., (120 gram column), using a gradient of 10-60% EtOAc/DCM over 37 minutes. The fractions with desired material were combined and concentrated to give 5-chloro-N-(6-methoxypyridin-3-yl)-3-(2-methyl-9-(tetrahydro-2H-pyran-2-yl)-9H-purin-6-yl)pyridin-2-amine (0.590 g, 1.306 mmol, 91% yield) as a yellow solid. m/z (ESI, +ve) 452 (M+H)$^+$. $^1$H NMR (400 MHz, CDCl$_3$) δ 9.76 (s, 1H); 8.40 (s, 1H); 8.23 (s, 1H); 8.16 (s, 2H); 7.19 (s, 1H); 6.75 (d, J=8.80 Hz, 1H); 5.80 (d, 1H); 4.14 (d, 1H); 3.91 (s, 4H); 3.76 (t, 1H); 2.83 (s, 3H); 1.46-2.25 (m, 5H).

Example 63

6-(5-bromo-2-fluoropyridin-3-yl)-2-methyl-9-(tetrahydro-2H-pyran-2-yl)-9H-purine

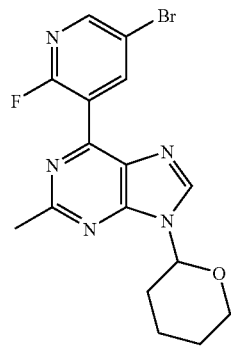 [SMILES: Cc1nc(-c2cc(Br)cnc2F)c2ncn(C3CCCCO3)c2n1]

A glass microwave reaction vessel was charged with 6-chloro-2-methyl-9-(tetrahydro-2H-pyran-2-yl)-9H-purine (0.525 g, 2 mmol), 5-bromo-2-fluoropyridine-3-boronic acid (0.5 g, 2 mmol) (Alfa Aesar, Ward Hill, Mass.), potassium carbonate (0.5 g, 9 mmol), (Aldrich, St. Louis, Mo.) dichloro [1,1'-bis(diphenylphosphino)ferrocene]dichloride palladium (II) dichloromethane adduct (0.2 g, 0.2 mmol) (Strem Chemicals, Inc., Newburyport, Mass.). A deoxygenated mixture of 1,2-dimethoxyethane (10 mL, 96 mmol) (Aldrich, St. Louis, Mo.) and water (1 mL) was added. The vial was deoxygenated for 5 minutes, capped, and the reaction mixture was stirred at 100° C. for 2 h. The crude product was adsorbed onto a plug of silica gel and chromatographed through a RediSep®, Teledyne ISCO, Lincoln, Nebr., pre-packed silica gel column (120 g), eluting with a gradient of 20% to 80% ethyl acetate in hexane to provide 6-(5-bromo-2-fluoropyridin-3-yl)-2-methyl-9-(tetrahydro-2-H-pyran-2-yl-9H-purine. m/z (ESI, +ve) 392/394 (M+H)$^+$.

Example 64

N-(5-bromo-3-(2-methyl-9H-purin-6-yl)pyridine-2-yl)-1H-indazol-4-amine

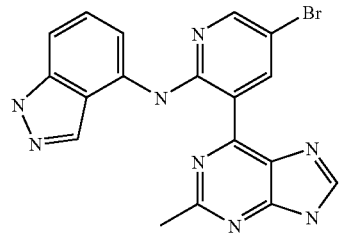

A solution of 6-(5-bromo-2-fluoropyridin-3-yl)-2-methyl-9-(tetrahydro-2H-pyran-2-yl)-9H-purine (0.250 g, 0.637 mmol) and 1-(tetrahydro-2H-pyran-2-yl)-1H-indazol-4- amine (0.138 g, 0.637 mmol) in THF (10 mL) was stirred at 0° C. and treated dropwise with lithium bis(trimethylsilyl)amide, 1.0 M solution in THF (1.912 mL, 1.912 mmol) (Aldrich catalog number 225770) and stirred at 0° C. for 30 minutes. The mixture was quenched with water (10 mL), diluted with water (50 mL) and extracted with dichloromethane. The crude material was adsorbed onto a plug of silica gel and purified by chromatography through a RediSep®, Teledyne ISCO, Lincoln, Nebr., pre-packed silica gel column (40 g), eluting with a gradient of 5% to 10% 2 M NH$_3$/MeOH in dichloromethane to give N-(5-bromo-3-(2-methyl-9-(tetrahydro-2H-pyran-2-yl)-9H-purin-6-yl)pyridin-2-yl)-1-(tetrahydro-2H-pyran-2-yl)-1H-indazol-4-amine as yellow crystals. This was treated with dichloromethane (5 mL) and trifluoroacetic acid (5 mL) (Aldrich, St. Louis, Mo.) to give N-(5-bromo-3-(2-methyl-9H-purin-6-yl)pyridin-2-yl)-1H-indazol-4-amine, m/z (ESI, +ve) 421/423 (M+H)$^+$. $^1$H NMR (400 MHz, d6-DMSO) δ 13.75 (br. s., 1H); 13.25 (br. s., 1H); 12.85 (br. s., 1H); 8.69 (br. s., 1H); 8.48 (br. s., 1H); 7.99 (br. s., 1H); 7.32 (br. s., 1H); 7.23 (br. s., 1H); 2.93 (s, 3H).

Example 65

N-(3-(2-methyl-9H-purin-6-yl)-5-(trifluoromethyl)pyridine-2-yl)-1H-indazol-4-amine

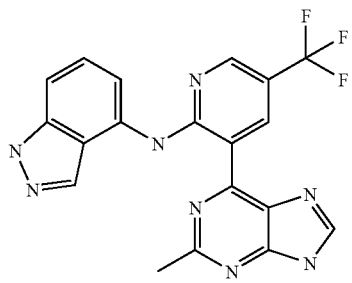 [SMILES: Cc1nc(-c2cc(C(F)(F)F)cnc2Nc2cccc3[nH]ncc23)c2nc[nH]c2n1]

This compound was synthesized following analogous procedures to those described in Example 63 and Example 64, substituting 2-fluoro-5-(trifluoromethyl)pyridine-3-ylboronic acid (Anichem, LLC., North Brunswick, N.J.) instead of 5-bromo-2-fluoropyridine-3-boronic acid in the first step. m/z (ESI, +ve) 411 (M+H)$^+$. $^1$H NMR (400 MHz, d6-DMSO) δ 13.24 (br. s., 1H); 10.26 (br. s., 1H); 8.72 (br. s., 1H); 8.28 (br. s., 1H); 7.96-8.05 (m, 1H); 7.37 (br. s., 1H); 7.30 (d, J=2.35 Hz, 1H); 7.31 (br. s., 1H); 2.93 (br. s., 3H).

Example 66

2-methoxy-N-(3-(2-methyl-9H-purin-6-yl)pyridin-2-yl)pyrimidin-5-amine

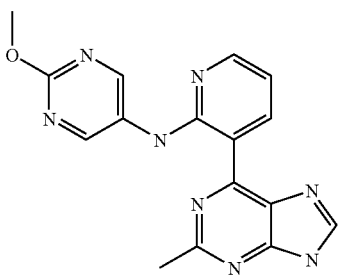 [SMILES: COc1ncc(Nc2ncccc2-c2nc(C)nc3[nH]cnc23)cn1]

The title compound was prepared following the procedure described in Example 58 substituting 5-amino-2-methoxypyrimidine (Ryan Scientific, Inc., Mt. Pleasant, S.C.) in the first step. m/z (ESI, +ve) 335 (M+H)$^+$. $^1$H NMR (400 MHz, d6-DMSO) δ 13.62 (br. s., 1H); 12.63 (br. s., 1H); 9.00 (s, 2H); 8.60 (s, 1H); 8.32 (dd, J=4.50, 1.76 Hz, 1H); 7.04 (dd, J=7.82, 4.69 Hz, 1H); 3.92 (s, 3H); 2.85 (s, 3H).

Example 67

3-bromo-5-(bromomethyl)-2-fluoropyridine

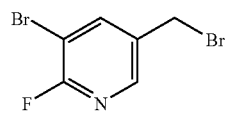

N-Bromosuccinimide (4.732 g, 26.59 mmol) and benzoyl peroxide (0.1356 g, 0.5598 mmol) were added to a solution of 3-bromo-2-fluoro-5-methylpyridine (Matrix Innovation Inc., Montreal, Quebec, Canada 5.318 g, 27.99 mmol) in CCl$_4$ (50 mL), and the mixture was heated at gentle reflux under a N$_2$ atmosphere for 16 h. The mixture was filtered, washing with CCl$_4$, and the residue concentrated and purified by flash chromatography on silica (1% to 1.5% EtOAc/hexane) to give 3-bromo-5-(bromomethyl)-2-fluoropyridine (1.593 g, 21.17% yield) as a white solid. $^1$H NMR (400 MHz, CDCl$_3$) δ 8.15 (s, 1H); 8.03 (dd, J=8.02, 2.15 Hz, 1H); 4.43 (s, 2H); $^{19}$F NMR (376 MHz, CDCl$_3$) δ −65.17 (br. s., 1 F). Sample did not ionize well in ESI+ mode.

Example 68

3-bromo-2-fluoro-5-((4-methoxybenzyloxy)methyl)pyridine

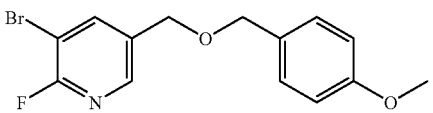 [SMILES: COc1ccc(COCc2cnc(F)c(Br)c2)cc1]

3-Bromo-5-(bromomethyl)-2-fluoropyridine (5.63 g, 20.9 mmol) was dissolved in MeCN (135 mL) and 4-methoxybenzyl alcohol (5.20 mL, 41.9 mmol), silver (I) oxide (7.169 g, 30.9 mmol), and tetrabutylammonium iodide (2.208 g, 5.98 mmol) were added. The reaction flask was covered with aluminum foil and the reaction was stirred under nitrogen at room temperature overnight. The reaction was filtered through a pad of Celite® (diatomaceous earth), washing with DCM, MeOH and MeCN. The filtrate was concentrated and purified on a silica gel column (3:1 to 2:1 to 3:2 hexanes/DCM to 3:2 DCM/hexanes to 2:1 DCM/hexanes to 3:1 DCM/ hexanes to DCM) to give 3-Bromo-2-fluoro-5-((4-methoxybenzyloxy)methyl)pyridine (1.62 g, 24%). MS (ESI pos. ion) m/z 326/328 (M+H)⁺.

Example 69

2-fluoro-5-((4-methoxybenzyloxy)methyl)pyridin-3-ylboronic acid

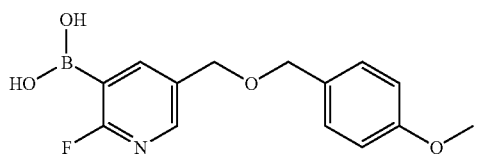 [SMILES: COc1ccc(COCc2cnc(F)c(B(O)O)c2)cc1]

3-Bromo-2-fluoro-5-((4-methoxybenzyloxy)methyl)pyridine (1.615 g, 4.952 mmol) was dissolved in PhMe (25.0 mL) and the reaction flask was cooled under nitrogen in a dry ice/acetone bath. Then, n-butyllithium solution (Fluka, Buchs, Switzerland, 1.6 M in hexane, 3.7 mL, 5.9 mmol) was added via syringe, turning the solution yellow. The reaction was stirred at −78° C. for 45 minutes and then triisopropyl borate (Alfa Aesar, Ward Hill, Mass. 98+%, 1.7 mL, 7.2 mmol) was added via syringe. The reaction was allowed to slowly warm up to room temperature, and after 90 minutes, the dry ice/acetone bath was removed. After another 25 minutes, the reaction was quenched with water and diluted with 10:1 DCM/MeOH. The biphasic solution was treated with 5 N HCl to lower the pH of the aqueous phase from 9 to about 4, and the aqueous phase extracted with 10:1 DCM/MeOH. The organic extracts were concentrated and dried under high vacuum in water bath (about 45° C.-60° C.), and then the solid was washed with Et₂O and dried again under high vacuum at room temperature over the weekend to afford 2-fluoro-5-((4-methoxybenzyloxy)methyl)pyridin-3-ylboronic acid (1.389 g, 68% purity, 66% yield). MS (ESI pos. ion) m/z 292 (M+H)⁺.

Example 70

6-(2-fluoro-5-((4-methoxybenzyloxy)methyl)pyridin-3-yl)-2-methyl-9-(tetrahydro-2H-pyran-2-yl)-9H-purine

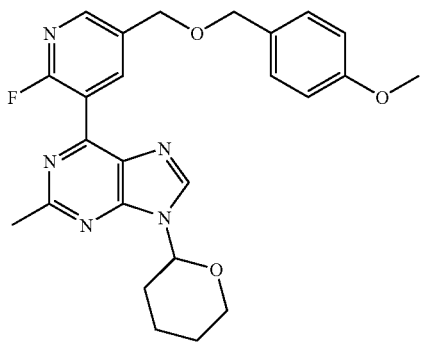 [SMILES: COc1ccc(COCc2cnc(F)c(-c3nc(C)nc4c3ncn4C3CCCCO3)c2)cc1]

6-Chloro-2-methyl-9-(tetrahydro-2H-pyran-2-yl)-9H-purine (38.7 mg, 0.153 mmol), 2-fluoro-5-((4-methoxybenzyloxy)methyl)pyridin-3-ylboronic acid (51.2 mg, 0.176 mmol), potassium carbonate (87.8 mg, 0.635 mmol), and [1,1'-bis(diphenylphosphino)ferrocene]-dichloropalladium (II), complex with dichloromethane (21.0 mg, 0.0257 mmol) were suspended in DME (1.0 mL) and water (0.30 mL). The flask was fitted with a reflux condenser and placed in a preheated oil bath (100° C.), stirred under nitrogen for 2 hours, and cooled to room temperature. In a separate flask, 6-chloro-2-methyl-9-(tetrahydro-2H-pyran-2-yl)-9H-purine (933 mg, 3.69 mmol), 2-fluoro-5-((4-methoxybenzyloxy)methyl)pyridin-3-ylboronic acid (1.338 g, 4.597 mmol), potassium carbonate (2.096 g, 1.517 µmol), and [1,1'-bis(diphenylphosphino)ferrocene]-dichloropalladium(II), complex with dichloromethane (360.9 mg, 0.4419 mmol) were suspended in DME (15 mL) and water (4.0 mL). Nitrogen was bubbled through the suspension for about 30 seconds, and then the flask was fitted with a reflux condenser and placed in a preheated oil bath (100° C.) and stirred under nitrogen, After 1 hour and 45 minutes, the reaction was cooled to room temperature. At this point, both reactions were combined, and the aqueous phase was removed via pipette. Then, the combined reactions were filtered through a Celite® (diatomaceous earth) pad, which was washed with DCM and MeOH. The filtrate was concentrated and treated with Et₂O. No precipitate was observed, so this was concentrated and the residue was purified on a silica gel filter (about 3 inches, 50:1 DCM/2 N ammonia in MeOH to 25:1 DCM/2 N ammonia in MeOH to 10:1 DCM/2 N ammonia in MeOH). Note: Product elutes with 50:1 DCM/2 N ammonia. The fractions with product were collected, concentrated, and dried under high vacuum overnight to give 6-(2-fluoro-5-((4-methoxybenzyloxy)methyl)pyridin-3-yl)-2-methyl-9-(tetrahydro-2H-pyran-2-yl)-9H-purine (1.688 g, 69% purity, 68% yield). MS (ESI pos. ion) m/z 464 (M+H)⁺.

Example 71

N-(5-((4-methoxybenzyloxy)methyl)-3-(2-methyl-9H-purin-6-yl)pyridin-2-yl)-1H-indol-4-amine

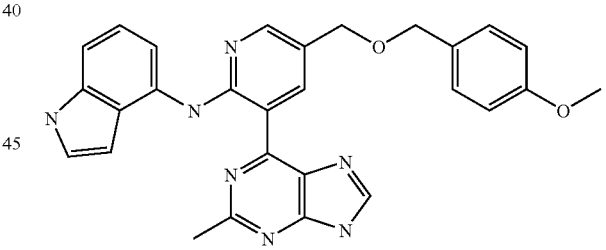

6-(2-Fluoro-5-((4-methoxybenzyloxy)methyl)pyridin-3-yl)-2-methyl-9-(tetrahydro-2H-pyran-2-yl)-9H-purine (171.2 mg, 0.3694 mmol) and 4-aminoindole (Aldrich, St. Louis, Mo., 69.2 mg, 0.524 mmol) were suspended in EtOH (2.0 mL) and hydrochloric acid (J.T. Baker, Phillipsburg, N.J., 5 N, 0.090 mL, 0.45 mmol) was added. The flask was fitted with a reflux condenser and placed in a preheated oil bath (100° C.) and stirred for about 105 minutes. Then, the reaction was cooled to room temperature and diluted with MeOH and 2 N ammonia in MeOH. The reaction was concentrated and treated with DMF and DCM and filtered. The filtrate was filtered again, and the solid was again washed with DCM. This filtrate was concentrated and purified by HPLC (10% to 100% MeCN/water with 0.1% TFA over 30 minutes with a total flow rate of 100 ml/min). The fractions with product were collected, concentrated, and filtered through a silica gel filter (about 1 inch, 10:1 DCM/2 N ammonia in MeOH) to give N-(5-((4-methoxybenzyloxy)methyl)-3-(2-methyl-9H-purin-6-yl)pyridin-2-yl)-1H-indol-4-amine (13.1 mg, 7% yield). MS (ESI pos. ion) m/z 492 (M+H)⁺. ¹H NMR (d6-DMSO, 400 MHz) δ 12.49 (s, 1H), 11.17 (s, 1H), 9.84 (s, 1H), 8.64 (s, 1H), 8.33 (s, 1H), 8.04 (d, J=6.85 Hz, 1H), 7.38-7.32 (m, 3H), 7.12-7.04 (m, 2H), 6.93 (d, J=8.80 Hz, 2H), 6.72 (s, 1H), 4.53 (s, 2H), 4.51 (s, 2H), 3.75 (s, 3H), 2.92 (s, 3H).

Example 72

(6-(1H-indazol-4-ylamino)-5-(2-methyl-9H-purin-6-yl)pyridin-3-yl)methanol

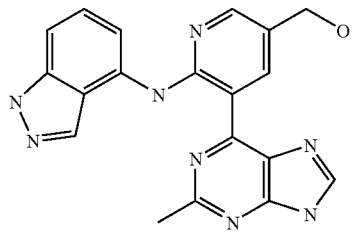 [SMILES: Cc1nc(-c2cc(CO)cnc2Nc2cccc3[nH]ncc23)c2nc[nH]c2n1]

Step 1. N-(5-((4-methoxybenzyloxy)methyl)-3-(2-methyl-9-(tetrahydro-2H-pyran-2-yl)-9H-purin-6-yl)pyridin-2-yl)-1-(tetrahydro-2H-pyran-2-yl)-1H-indazol-4-amine 6-(2-Fluoro-5-((4-methoxybenzyloxy)methyl)pyridin-3-yl)-2-methyl-9-(tetrahydro-2H-pyran-2-yl)-9H-purine (1.223 g, 2.634 mmol) and 1-(tetrahydro-2H-pyran-2-yl)-1H-indazol-4-amine (0.596 g, 2.74 mmol) were dissolved in THF (23.5 mL) and the flask was cooled in an ice water bath under nitrogen. Then, LiHMDS (1.0 M in THF, 7.8 mL, 7.8 mmol) was added via syringe, and the reaction was stirred under nitrogen at 0° C. for 35 minutes. Then, the reaction was quenched with water (40 mL) and diluted with water (40 mL), and then extracted with DCM and with 10:1 DCM/MeOH. Brine was added to break up emulsions. The organic extracts were combined, concentrated, and purified on a silica gel filter (about 3 inches, 50:1 DCM/2 N ammonia in MeOH to 40:1 DCM/2 N ammonia in MeOH) to afford N-(5-((4-methoxybenzyloxy)methyl)-3-(2-methyl-9-(tetrahydro-2H-pyran-2-yl)-9H-purin-6-yl)pyridin-2-yl)-1-(tetrahydro-2H-pyran-2-yl)-1H-indazol-4-amine (1.343 g, 54% purity, 43% yield). MS (ESI pos. ion) m/z 661 (M+H)⁺.

Step 2. (6-(1H-indazol-4-ylamino)-5-(2-methyl-9H-purin-6-yl)pyridin-3-yl)methanol N-(5-((4-methoxybenzyloxy)methyl)-3-(2-methyl-9-(tetrahydro-2H-pyran-2-yl)-9H-purin-6-yl)pyridin-2-yl)-1-(tetrahydro-2H-pyran-2-yl)-1H-indazol-4-amine (19.8 mg, 0.0300 mmol) was dissolved in DCM (1.0 mL) and TFA (0.10 mL) was added and the reaction was stirred at room temperature. After 2 hours, more TFA (0.15 mL) was added, and stirring was continued. After another hour, the reaction was quenched with saturated sodium bicarbonate (3.8 mL), and the reaction was stirred for about 10 minutes. In a separate flask, N-(5-((4-methoxybenzyloxy)methyl)-3-(2-methyl-9-(tetrahydro-2H-pyran-2-yl)-9H-purin-6-yl)pyridin-2-yl)-1-(tetrahydro-2H-pyran-2-yl)-1H-indazol-4-amine (178.5 mg, 0.2701 mmol) was dissolved in DCM (5.0 mL) and TFA (0.50 mL) was added. The reaction was stirred at room temperature for 3.5 hours, and then more TFA (0.75 mL) was added, and stirring was continued. After another hour, more TFA (0.80 mL) was added, and stirring was continued. After 45 minutes, the reaction was diluted with DCM (5 mL) and quenched with saturated sodium bicarbonate (30 mL). At this point, both reactions were combined and allowed to stand overnight. The layers were separated and brine was added to help break up emulsions. The aqueous phase was extracted with 10:1 DCM/MeOH. However, both the organic extracts and the aqueous phase were found by LCMS to contain product. So, they were combined, concentrated, and treated with 10:1 DCM/MeOH and filtered. The solid was washed with DCM and MeOH. The filtrate was concentrated and treated with DCM and MeOH and filtered again. The filtrate again was concentrated and dried briefly under high vacuum, then redissolved in DCM and MeOH and concentrated and dried on high vacuum over the weekend. The material was dissolved in MeOH and DMSO, concentrated, and washed repeatedly with Et₂O, and these washings were discarded. Then, the material was dissolved in EtOAc and MeOH, concentrated, treated with water, and filtered. The solid was washed with water, collected and set aside. The filtrate was filtered again (solid had precipitated out), and this solid was washed with water. The filtrate from this second filtration was discarded, and the two sets of solid were collected, treated with MeOH, and filtered. The solid was not pure by LCMS, so the filtrate and solid were combined, concentrated, and purified by HPLC (10% to 100% MeCN/water with 0.1% TFA over 30 minutes with a total flow rate of 100 mL/min). The fractions with product were collected, concentrated, and dried under high vacuum in a water bath (about 50° C.). Then, the solid was washed with DCM and repurified on HPLC (10% to 100% MeCN/water with 0.1% TFA over 30 minutes with a total flow rate of 100 mL/min) to give (6-(1H-indazol-4-ylamino)-5-(2-methyl-9H-purin-6-yl)pyridin-3-yl)methanol (16.8 mg, 17% yield). MS (ESI pos. ion) m/z 373 (M+H)⁺. ¹H NMR (d6-DMSO) δ 12.71 (s, 1H), 9.80 (s, 1H), 8.66 (s, 1H), 8.34 (d, J=1.96 Hz, 1H), 8.26 (s, 1H), 8.07 (d, J=7.82 Hz, 1H), 7.33 (t, J=8.4 Hz, 1H), 7.18 (d, J=8.41 Hz, 1H), 4.56 (s, 2H), 2.94 (s, 3H).

Example 73

N-(6-methoxypyridin-3-yl)-3-(2-methyl-9H-purin-6-yl)-5-vinylpyridin-2-amine

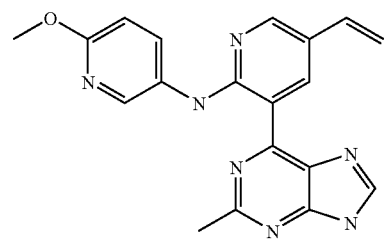 [SMILES: C=Cc1cnc(Nc2ccc(OC)nc2)c(-c2nc(C)nc3[nH]cnc23)c1]

Step 1. 2-fluoro-5-vinylpyridine

5-Bromo-2-fluoropyridine (Aldrich 99%, 5.14 g, 29.2 mmol) and potassium vinyltrifluoroborate (Aldrich, St. Louis, Mo., 4.23 g, 31.6 mmol) were suspended in THF (80 mL) and water (9.0 mL) and dichlorobis(triphenylphosphine)palladium (II) (0.627 g, 0.893 mmol) and cesium carbonate (28.5 g, 87.6 mmol) were added. The reaction flask was fitted with a reflux condenser and placed in a preheated oil bath (85° C.) and stirred overnight under nitrogen. Then, the reaction was cooled to room temperature and diluted with water (125 mL). The layers were separated, and the aqueous phase was extracted with DCM. The organic extracts were combined, dried over sodium sulfate, filtered, and concentrated (using an unheated water bath and a rotary evaporator pressure of 43-70 torr). The crude material was purified on a silica gel filter (about 3 inches) with DCM, and the fractions with product were collected, concentrated, and dried briefly under high vacuum. The material was triturated with $Et_2O$ and filtered, and the solid was washed with $Et_2O$. The filtrate was concentrated and dried on two separate occasions on the high vacuum for about 10 seconds each to afford 2-fluoro-5-vinylpyridine, which was taken to the next step.

Step 2. 2-fluoro-5-vinylpyridin-3-ylboronic acid

2-Fluoro-5-vinylpyridine (64.8 mg, 0.526 mmol) was dissolved in THF (2.0 mL) and the reaction flask was cooled in a dry ice/acetone bath. Then, n-butyllithium (1.6 M solution in hexanes, 0.40 mL, 0.64 mmol) was added via syringe dropwise, turning the solution red. The reaction was stirred at −78° C. for 45 minutes, and then triisopropyl borate (Aldrich, St. Louis, Mo. 98+%, 0.190 mL, 0.826 mmol) was added, and the reaction was allowed to slowly warm up to room temperature (the dry ice/acetone bath was removed after 80 minutes). The reaction was stirred at room temperature for 45 minutes, and then quenched with water. The layers were separated, and the organic phase was discarded. The aqueous phase was treated with 5 N HCl to lower the pH from 9 to 4. Then, the aqueous phase was extracted with 10:1 DCM/MeOH, and the organic extracts were combined and set aside. In a separate flask, 2-fluoro-5-vinylpyridine (4.15 g, 33.7 mmol) was decanted from a solid precipitate, which was washed with THF. The 2-fluoro-5-vinylpyridine was dissolved in THF (120 mL), and the reaction flask was cooled in a dry ice/acetone bath under nitrogen. Then, n-butyllithium solution (1.6 M in hexanes, 25.5 mL, 40.8 mmol) was added via syringe, turning the yellow solution into a deep red color. The reaction was stirred at −78° C. for 50 minutes, and then triisopropyl borate (Aldrich, St. Louis, Mo. 98+%, 11.5 mL, 50.0 mmol) was added via syringe, and the reaction was allowed to warm to room temperature (after 90 minutes, the dry ice/acetone bath was removed). Almost 5 hours after the addition of triisopropyl borate, the reaction was quenched with water (125 ml), slowly at first. The biphasic solution was stirred for 15 minutes, and then the layers were separated. The organic phase extracted one time with saturated sodium bicarbonate. This sodium bicarbonate washing was discarded. The organic phase was extracted two times with 1 N NaOH (60 mL and then 50 mL). These aqueous extractions were combined, treated with concentrated HCl to lower the pH to 4, and extracted with 10:1 DCM/MeOH. These organic extracts did not contain product, so they were discarded, along with these second aqueous extractions. The original aqueous phase (from the initial phase separation after quenching the reaction with water) was treated with 5 N HCl to lower the pH to around 3-4. This aqueous phase was extracted with 10:1 DCM/MeOH. These organic extracts were combined with the organic extracts from the first reaction, concentrated, and dried under high vacuum at room temperature to afford 2-fluoro-5-vinylpyridin-3-ylboronic acid (882 mg, 61% purity, 11% yield over 2 steps). MS (ESI pos. ion) m/z 168 $(M+H)^+$.

Step 3. 6-(2-fluoro-5-vinylpyridin-3-yl)-2-methyl-9-(tetrahydro-2H-pyran-2-yl)-9H-purine 6-Chloro-2-methyl-9-(tetrahydro-2H-pyran-2-yl)-9H-purine (984 mg, 3.89 mmol), 2-fluoro-5-vinylpyridin-3-ylboronic acid (882 mg, 5.28 mmol), bis(di-tert-butyl(4-dimethylaminophenyl)phosphino)dichloropalladium (138 mg, 0.195 mmol), and potassium acetate (1.212 g, 12.35 mmol) were suspended in ethanol (12.0 mL) and water (2.4 mL) and the flask was fitted with a reflux condenser and nitrogen was bubbled through the suspension for about 15 seconds. Then, the flask was put in a preheated oil bath (80° C.) and stirred under nitrogen for 1 h. The reaction was cooled to room temperature, diluted with water (20 mL), and extracted with DCM. The organic extracts were combined, dried over sodium sulfate, filtered, concentrated, and purified on a silica gel column (25:1 to 20:1 DCM/2 N ammonia in MeOH) to afford 6-(2-fluoro-5-vinylpyridin-3-yl)-2-methyl-9-(tetrahydro-2H-pyran-2-yl)-9H-purine, which was taken on to the next step. MS (ESI pos. ion) m/z 340 $(M+H)^+$.

Step 4. N-(6-methoxypyridin-3-yl)-3-(2-methyl-9-(tetrahydro-2H-pyran-2-yl)-9H-purin-6-yl)-5-vinylpyridin-2-amine 6-(2-Fluoro-5-vinylpyridin-3-yl)-2-methyl-9-(tetrahydro-2H-pyran-2-yl)-9H-purine (1.007 g, 2.967 mmol) and 5-amino-2-methoxypyridine (0.369 g, 2.97 mmol) were dissolved in THF (25 mL) and the reaction flask was cooled in an ice water bath. Then, LiHMDS (Aldrich, St. Louis, Mo., 1.0 M in THF, 9.0 mL, 9.0 mmol) was added via syringe, and the reaction was stirred under nitrogen for 35 minutes. Then, it was poured into water (50 mL), and the layers were separated. The aqueous phase was extracted with DCM, and the organic extracts were combined, dried over sodium sulfate, filtered, concentrated, and purified on a silica gel column (40:1 DCM/2 N ammonia in MeOH to 30:1 DCM/2 N ammonia in MeOH) to give N-(6-methoxypyridin-3-yl)-3-(2-methyl-9-(tetrahydro-2H-pyran-2-yl)-9H-purin-6-yl)-5-vinylpyridin-2-amine (410.3 mg, 85% purity, 20% yield over 2 steps). MS (ESI pos. ion) m/z 444 $(M+H)^+$.

Step 5: N-(6-methoxypyridin-3-yl)-3-(2-methyl-9H-purin-6-yl)-5-vinylpyridin-2-amine N-(6-methoxypyridin-3-yl)-3-(2-methyl-9-(tetrahydro-2H-pyran-2-yl)-9H-purin-6-yl)-5-vinylpyridin-2-amine (76.3 mg, 0.172 mmol) was dissolved in DCM (2.9 mL) and trifluoroacetic acid (Aldrich, St. Louis, Mo., hplc grade, 0.60 mL, 7.8 mmol) was added via syringe. The reaction was stirred at room temperature for 35 minutes, concentrated, treated with MeOH, and filtered. The solid was washed with $Et_2O$, but was not sufficiently (>95% by HPLC) pure. So, the solid and filtrate were combined, concentrated, treated with 2 N ammonia in MeOH, and concentrated again. The material was treated with $Et_2O$, but this did not precipitate product. So, it was concentrated, treated with water, and filtered. The solid was washed with water, but was still not 95% pure. So, the solid was collected and purified on HPLC (10% to 100% MeCN/water over 30 minutes using a total flow rate of 100 mL/min) to afford N-(6-methoxypyridin-3-yl)-3-(2-methyl-9H-purin-6-yl)-5-vinylpyridin-2-amine (68.6 mg). MS (ESI pos. ion) m/z 360 $(M+H)^+$. $^1H$ NMR (d6-DMSO) δ 12.70 (s, 1H), 9.98 (s, 1H), 8.65 (s, 1H), 8.55 (d, J=2.54 Hz, 1H), 8.40 (d, J=2.35 Hz, 1H), 8.19 (dd, J=8.8 Hz, 2.74 Hz, 1H), 6.86 (d, J=8.8 Hz, 1H), 6.79 (dd, J=17.5 Hz, 10.9 Hz, 1H), 5.78 (d, J=16.4 Hz, 1H), 5.26 (d, J=11.0 Hz, 1H), 3.85 (s, 3H), 2.86 (s, 3H).

Example 74

5-ethyl-N-(6-methoxypyridin-3-yl)-3-(2-methyl-9H-purin-6-yl)pyridin-2-amine

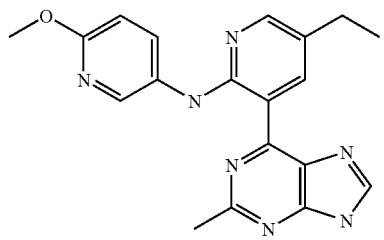 [SMILES: CCc1cnc(Nc2ccc(OC)nc2)c(-c2nc(C)nc3[nH]cnc23)c1]

N-(6-methoxypyridin-3-yl)-3-(2-methyl-9-(tetrahydro-2H-pyran-2-yl)-9H-purin-6-yl)-5-vinylpyridin-2-amine (62.0 mg, 0.140 mmol) and palladium on activated carbon (Aldrich, St. Louis, Mo. 10% Pd, 19.1 mg) were added to MeOH (2.0 mL) and TFA (0.30 mL). The reaction flask was evacuated and back-filled with hydrogen, and the reaction was stirred at room temperature for one hour. Then, the hydrogen balloon was removed, and stirring was continued at room temperature, without the balloon of hydrogen, for 90 minutes. Then, the reaction flask was fitted with a reflux condenser and put in a preheated oil bath (45° C.-50° C.), and stirring was continued under nitrogen overnight. The reaction was cooled to room temperature and filtered through a pad of Celite® (diatomaceous earth), which was washed with DCM and MeOH and a couple of drops of TFA. The filtrate was concentrated and purified on HPLC (10% to 100% MeCN/water with 0.1% TFA over 30 minutes with a total flow rate of 100 mL/min). The fractions with product were collected, concentrated, and dried under high vacuum in a water bath (50° C.). Then, the material was washed with Et$_2$O, MeOH, and Et$_2$O, collected, and dried under high vacuum overnight to give 5-ethyl-N-(6-methoxypyridin-3-yl)-3-(2-methyl-9H-purin-6-yl)pyridin-2-amine (17.8 mg, 35% yield). MS (ESI pos. ion) m/z 362 (M+H)$^+$. $^1$H NMR (400 MHz, d6-DMSO) δ 12.53 (s, 1H), 9.72 (s, 1H), 8.62 (s, 1H), 8.53 (d, J=2.54 Hz, 1H), 8.22-8.13 (m, 2H), 6.84 (d, J=8.8 Hz, 1H), 3.84 (s, 3H), 2.85 (s, 3H), 2.65 (q, J=7.37 Hz, 2H), 1.26 (t, J=7.53 Hz, 3H).

Example 75

2-(6-(6-methoxypyridin-3-ylamino)-5-(2-methyl-9H-purin-6-yl)pyridin-3-yl)ethanol

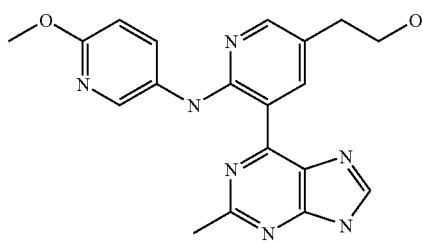 [SMILES: COc1ccc(Nc2ncc(CCO)cc2-c2nc(C)nc3[nH]cnc23)cn1]

Step 1. 2-(6-(6-methoxypyridin-3-ylamino)-5-(2-methyl-9-(tetrahydro-2H-pyran-2-yl)-9H-purin-6-yl)pyridin-3-yl)ethanol Tetrahydrofuran (2.0 mL) and cyclohexene (0.42 mL, 4.15 mmol) were cooled in an ice water bath under nitrogen, and borane-dimethyl sulfide complex (0.19 mL, 2.0 mmol) was added via syringe. The reaction was allowed to warm to room temperature while being stirred under nitrogen over 90 minutes, resulting in a suspension. In a separate flask, N-(6-methoxypyridin-3-yl)-3-(2-methyl-9-(tetrahydro-2H-pyran-2-yl)-9H-purin-6-yl)-5-vinylpyridin-2-amine (185.4 mg, 0.418 mmol) was dissolved in THF (6.0 mL), and to this solution was added 1.6 mL of the suspension generated in the first flask. The addition occurred via syringe dropwise, resulting in gas evolution. The reaction was stirred at room temperature under nitrogen for 40 minutes and then cooled in an ice/water bath and quenched with MeOH (4.0 mL), 2 N aqueous NaOH (4.8 mL), and 30% aqueous H$_2$O$_2$ (6.5 mL), all added via syringe. The reaction was stirred while being allowed to warm to room temperature. After 75 minutes, more 2 N aqueous NaOH (1.2 mL) and 30% aqueous hydrogen peroxide (3.5 mL) were added, and stirring was continued. Then, 3 hours after that, 5 N aqueous NaOH (1.60 mL) and 30% aqueous hydrogen peroxide (8.0 mL) were added, and stirring was continued for another hour. Then, the reaction was diluted with water (20 mL), DCM (20 mL), and MeOH (about 1 mL), and allowed to stand at room temperature overnight. Then, the layers were separated, and the aqueous phase was extracted with 10:1 DCM/MeOH. The organic extracts were combined, concentrated, and taken on to step 2.

Step 2. 2-(6-(6-methoxypyridin-3-ylamino)-5-(2-methyl-9H-purin-6-yl)pyridin-3-yl)ethanol The crude 2-(6-(6-methoxypyridin-3-ylamino)-5-(2-methyl-9-(tetrahydro-2H-pyran-2-yl)-9H-purin-6-yl)pyridin-3-yl)ethanol (193 mg, 0.418 mmol) was dissolved in MeOH (5.0 mL) and TFA (0.50 mL, 6.49 mmol) was added via syringe. The reaction was stirred at room temperature for 2.5 hours, and then more TFA (0.9 mL) was added, and stirring was continued overnight. Then, the flask was fitted with a reflux condenser and placed in a preheated oil bath (60° C.), stirring was continued for 75 minutes. (This 75 minute period was interrupted by an approximate 15 minute period where the flask was not in the oil bath.) The reaction was cooled to room temperature and filtered through a Celite® (diatomaceous earth) pad, which was washed with DCM and MeOH. The filtrate was concentrated and purified by prep HPLC (10% to 100% MeCN/water with 0.1% TFA over 30 minutes with a total flow rate of 100 mL/min) to give 2-(6-(6-methoxypyridin-3-ylamino)-5-(2-methyl-9H-purin-6-yl)pyridin-3-yl)ethanol (56.0 mg, 35% yield over 2 steps). MS (ESI pos. ion) m/z 378 (M+H)$^+$. $^1$H NMR (400 MHz, d6-DMSO) δ 12.50 (s, 1H), 9.66 (s, 1H), 8.62 (s, 1H), 8.53 (s, 1H), 8.20-

8.14 (m, 2H), 6.86 (d, J=8.8 Hz, 1H), 3.85 (s, 3H), 3.66 (t, J=6.86 Hz, 2H), 2.85 (s, 3H), 2.76 (t, J=6.86 Hz, 2H).

Example 76

(6-(6-methoxypyridin-3-ylamino)-5-(2-methyl-9H-purin-6-yl)pyridin-3-yl)methanol

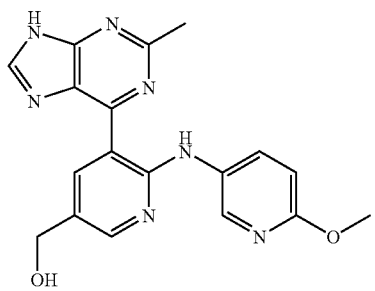 [SMILES: COc1ccc(Nc2ncc(CO)cc2-c2nc(C)nc3[nH]cnc23)cn1]

Step 1. 6-(5-(1,3-dioxolan-2-yl)-2-fluoropyridin-3-yl)-2-methyl-9-(tetrahydro-2H-pyran-2-yl)-9H-purine 6-Chloro-2-methyl-9-(tetrahydro-2H-pyran-2-yl)-9H-purine (3.200 g, 12.66 mmol), 5-(1,3-dioxolan-2-yl)-2-fluoropyridin-3-ylboronic acid (3.165 g, 14.86 mmol), bis(di-tert-butyl(4-dimethylaminophenyl)phosphino)dichloropalladium (514.9 mg, 0.7272 mmol), and potassium acetate (4.180 g, 42.59 mmol) were suspended in EtOH (50 mL) and water (10 mL) and nitrogen was bubbled through the suspension for about 15 seconds. Then, the flask was fitted with a reflux condenser and placed in a preheated oil bath (80° C.), and stirred under nitrogen for 1 hour. The reaction was cooled to room temperature, poured into water (125 mL), and extracted with DCM. The organic extracts were combined, dried over sodium sulfate, filtered, concentrated, and purified on a silica gel filter (600 mL fritted filter with about 3 inches of silica gel, 40:1 DCM/2 N ammonia in MeOH). The fractions with product were collected, concentrated, and washed repeatedly with hexanes and dried to give 6-(5-(1,3-dioxolan-2-yl)-2-fluoropyridin-3-yl)-2-methyl-9-(tetrahydro-2H-pyran-2-yl)-9H-purine (4.557 g), which was used for the next step. MS (ESI pos. ion) m/z 386 (M+H)$^+$.

Step 2. 5-(1,3-dioxolan-2-yl)-N-(6-methoxypyridin-3-yl)-3-(2-methyl-9-(tetrahydro-2H-pyran-2-yl)-9H-purin-6-yl)pyridin-2-amine 6-(5-(1,3-Dioxolan-2-yl)-2-fluoropyridin-3-yl)-2-methyl-9-(tetrahydro-2H-pyran-2-yl)-9H-purine (4.557 g, 11.82 mmol) and 5-amino-2-methoxypyridine (1.507 g, 12.14 mmol) were dissolved in tetrahydrofuran (80 mL) and cooled in an ice water bath. Then, LiHMDS (Aldrich 1.0 M in THF, 36.0 mL, 36.0 mmol) was added via syringe over about 10 minutes. The reaction was stirred under nitrogen at 0° C. for 40 minutes, and then the reaction was treated with water (100 mL) and warmed to room temperature. The layers were separated, and the aqueous phase was extracted with DCM. The aqueous phase was diluted with brine and extraction with DCM was continued. The combined organic extracts were combined, dried over sodium sulfate, filtered, concentrated, and purified on a silica gel filter (600 mL fritted filter, about 3 inches of silica gel, 80:1 DCM/2 N ammonia in MeOH to 50:1 DCM/2 N ammonia in MeOH) to give 5-(1,3-dioxolan-2-yl)-N-(6-methoxypyridin-3-yl)-3-(2-methyl-9-(tetrahydro-2H-pyran-2-yl)-9H-purin-6-yl)pyridin-2-amine (4.500 grams, 71% purity, 52% yield over two steps). MS MS (ESI pos. ion) m/z 446. Calculated exact mass for $C_{23}H_{23}N_7O_3$: 445 (M+—$C_2H_4O$). $^1$H NMR (CDCl$_3$, 400 MHz) δ 12.69 (s, 1H), 9.91 (s, 1H), 8.44 (d, J=2.74 Hz, 1H), 8.41 (d, J=2.15 Hz, 1H), 8.29 (s, 1H), 8.23 (dd, J=8.80 Hz, 2.74 Hz, 1H), 6.79 (d, J=8.80 Hz, 1H), 5.94 (s, 1H), 5.87 (dd, J=10.56 Hz, 2.15 Hz, 1H), 4.24-4.17 (m, 3H), 4.12-4.05 (m, 2H), 3.96 (s, 3H), 3.88-3.79 (m, 1H), 2.91 (s, 3H), 2.19-2.00 (m, 3H), 1.93-1.77 (m, 3H).

Step 3. 6-(6-methoxypyridin-3-ylamino)-5-(2-methyl-9-(tetrahydro-2H-pyran-2-yl)-9H-purin-6-yl)nicotinaldehyde 5-(1,3-Dioxolan-2-yl)-N-(6-methoxypyridin-3-yl)-3-(2-methyl-9-(tetrahydro-2H-pyran-2-yl)-9H-purin-6-yl)pyridin-2-amine (3.042 g, 6.21 mmol) was dissolved in tetrahydrofuran (50 mL) and then 2.0 M hydrochloric acid (15.5 mL, 31.0 mmol) was added via syringe, followed by a THF rinse (1.5 mL). The reaction was stirred at room temperature for 20 minutes, diluted with water (20 mL), and filtered. The solid was washed with water, collected, and dried under high vacuum over the weekend to afford 6-(6-methoxypyridin-3-ylamino)-5-(2-methyl-9-(tetrahydro-2H-pyran-2-yl)-9H-purin-6-yl)nicotinaldehyde (1.7 g, 61% yield). MS (ESI pos. ion) m/z 446 (M+H)$^+$. $^1$H NMR (CDCl$_3$, 400 MHz) δ 13.33 (s, 1H), 10.29 (d, J=2.15 Hz, 1H), 10.00 (s, 1H), 8.78 (d, J=1.96 Hz, 1H), 8.48 (d, J=2.74 Hz, 1H), 8.35 (s, 1H), 8.25 (dd, J=8.8 Hz, 2.74 Hz, 1H), 6.84 (d, J=8.8 Hz, 1H), 5.89 (dd, J=10.47 Hz, 2.05 Hz, 1H), 4.23 (d, J=11.74 Hz, 1H), 3.98 (s, 3H), 3.88-3.82 (m, 1H), 2.93 (s, 3H), 2.23-2.03 (m, 3H), 1.90-1.65 (m, 3H).

Step 4. (6-(6-methoxypyridin-3-ylamino)-5-(2-methyl-9H-purin-6-yl)pyridin-3-yl)methanol 6-(6-methoxypyridin-3-ylamino)-5-(2-methyl-9-(tetrahydro-2H-pyran-2-yl)-9H-purin-6-yl)nicotinaldehyde (157 mg, 0.352 mmol) was dissolved in methanol (5.0 mL) and sodium borohydride (21.6 mg, 0.571 mmol) was added. The reaction was stirred at room temperature for 75 minutes, and then more NaBH$_4$ (26 mg, 0.69 mmol) was added, along with DCM (3 mL). After 40 more minutes, 5 N aqueous HCl (0.50 mL, 2.5 mmol) was added, along with a MeOH rinse (about 1 mL), and stirring was continued at room temperature overnight. Then, the reaction was diluted with water (20 mL), and the suspension was filtered. The filtration was sluggish, so the filtrate was discarded, and the solid was collected, and the unfiltered material was extracted with 10:1 DCM/MeOH. These organic extracts were combined with the solid that was collected, while the aqueous suspension was again filtered. The solid from this filtration was combined with the solid and organic extracts collected earlier. The resultant solution was concentrated, treated with EtOAc, and filtered. The solid was washed with EtOAc and MeOH, but the solid was not 95% pure by HPLC, so the filtrate and solid were collected, concentrated, treated with DCM, and filtered again. The solid was washed with DCM. The product was still not 95% pure by HPLC, so the filtrate and solid were again collected, concentrated, and this time purified on HPLC (10% to 100% MeCN/water with 0.1% TFA over 30 minutes with a total flow rate of 100 mL/min) to give (6-(6-methoxypyridin-3-ylamino)-5-(2-methyl-9H-purin-6-yl)pyridin-3-yl)methanol (91.1 mg, 71% yield). MS (ESI pos. ion) m/z 364 (M+H)$^+$. $^1$H NMR (d6-

DMSO, 400 MHz) δ 12.62 (s, 1H), 9.79 (s, 1H), 8.62 (s, 1H), 8.54 (s, 1H), 8.24 (s, 1H), 8.17 (d, J=8.41 Hz, 1H), 6.86 (d, J=8.61 Hz, 1H), 4.52 (s, 2H), 3.85 (s, 3H), 2.86 (s, 3H).

Example 77

5-((4-methoxyphenylamino)methyl)-N-(6-methoxypyridin-3-yl)-3-(2-methyl-9H-purin-6-yl)pyridin-2-amine

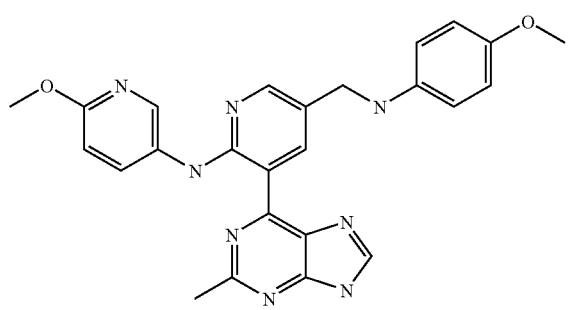

6-(6-methoxypyridin-3-ylamino)-5-(2-methyl-9-(tetrahydro-2H-pyran-2-yl)-9H-purin-6-yl)nicotinaldehyde (187.1 mg, 0.4200 mmol) was suspended in EtOH (3.8 mL) and tetraisopropoxytitanium (Fluka, Buchs, Switzerland, 0.25 mL, 0.84 mmol) and 4-methoxyaniline (Aldrich, St. Louis, Mo., 81.9 mg, 0.665 mmol) were added. DCM (2 mL) was added about 15 minutes later, and the reaction was stirred under nitrogen at room temperature overnight. Then, sodium borohydride (36 mg, 0.95 mmol) was added along with DCM (3 mL), and stirring was continued at room temperature, resulting in precipitation. After stirring for 1 hour, the suspension was treated with MeOH (1.5 mL) and 5 N HCl (0.60 mL). Stirring was continued at room temperature overnight. Then, the reaction was treated with water (20 mL) and filtered, and the solid was washed with water. The solid and unfiltered material were combined, concentrated, and treated with MeOH, and filtered. The filtration was sluggish, so instead the suspension was concentrated, treated with TFA and DMSO, and filtered with DCM and MeOH. This filtration was also sluggish, so the suspension was filtered instead through a Celite® (diatomaceous earth) pad. The filtrate was concentrated, but could not be filtered for HPLC purification despite treatment with DMSO, TFA, MeOH, and DCM. So, this solution was concentrated, and the fine suspension was filtered through a Celite® (diatomaceous earth) pad. This filtrate was purified by prep HPLC (10% to 100% MeCN/water with 0.1% TFA over 30 minutes with a total flow rate of 100 mL/min) to give 5-((4-methoxyphenylamino)methyl)-N-(6-methoxypyridin-3-yl)-3-(2-methyl-9H-purin-6-yl)pyridin-2-amine (149.4 mg, 76% yield). MS (ESI pos. ion) m/z 469 (M+H)+. 1H NMR (d6-DMSO, 400 MHz) δ 12.60 (s, 1H), 9.72 (s, 1H), 8.62 (s, 1H), 8.53 (d, J=2.54 Hz, 1H), 8.27 (s, 1H), 8.14 (dd, J=9.10 Hz, 2.45 Hz, 1H), 7.22 (s, 1H), 7.09 (s, 1H), 6.97 (s, 2H), 6.90-6.80 (m 3H), 4.38 (s, 2H), 3.85 (s, 3H), 3.67 (s, 3H), 2.85 (s, 3H).

Example 78

5-((3-methoxyphenylamino)methyl)-N-(6-methoxypyridin-3-yl)-3-(2-methyl-9H-purin-6-yl)pyridin-2-amine

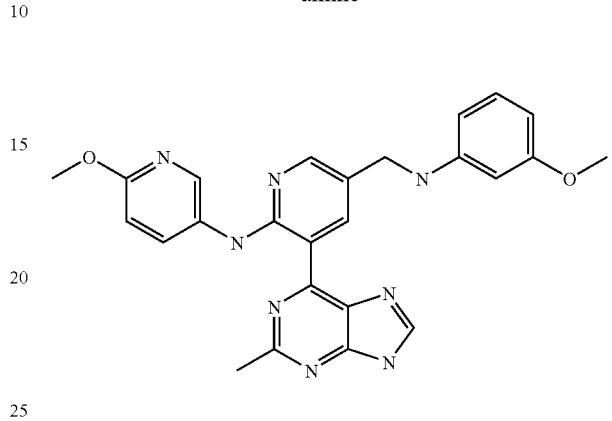

6-(6-methoxypyridin-3-ylamino)-5-(2-methyl-9-(tetrahydro-2H-pyran-2-yl)-9H-purin-6-yl)nicotinaldehyde (191.7 mg, 0.4303 mmol) was suspended in ethanol (4.0 mL) and tetraisopropoxytitanium (0.26 mL, 0.878 mmol) and 3-methoxyaniline (0.080 mL, 0.716 mmol) were added. The reaction was stirred under nitrogen at room temperature overnight, and then more DCM (about 3 mL) was added, along with more Ti(OiPr4) (0.13 mL, 0.44 mmol) and 3-methoxyaniline (0.050 mL, 0.45 mmol). Stirring was continued overnight, and then sodium borohydride (32.3 mg, 0.854 mmol) was added, along with MeOH (1 mL). The reaction was stirred at room temperature for 35 minutes and then quenched with 5 N HCl (0.60 mL), which was added dropwise. Stirring was continued at room temperature over the weekend. Then, the suspension was diluted with DCM and MeOH and filtered through a pad of Celite® (diatomaceous earth). The Celite® (diatomaceous earth) pad was washed with DCM and MeOH, and the filtrate was concentrated, treated with water, and filtered again through a fritted filter (no Celite® (diatomaceous earth)). The solid was washed with water, collected, and dried under high vacuum in a water bath at 50° C., and then at room temperature overnight, to give 5-((3-methoxyphenylamino)methyl)-N-(6-methoxypyridin-3-yl)-3-(2-methyl-9H-purin-6-yl)pyridin-2-amine (162.8 mg, 81% yield). MS (ESI pos. ion) m/z 469 (M+H)+. 1H NMR (d6-DMSO, 400 MHz) δ 12.53 (s, 1H), 9.74 (s, 1H), 8.62 (s, 1H), 8.51 (d, J=2.54 Hz, 1H), 8.27 (d, J=2.15 Hz, 1H), 8.13 (dd, J=8.80 Hz, 2.74 Hz, 1H), 7.00 (t, J=8.12 Hz, 1H), 6.87 (d, J=8.80 Hz, 1H), 6.38-6.17 (m, 3H), 4.29 (s, 2H), 3.85 (s, 3H), 3.66 (s, 3H), 2.84 (s, 3H).

Example 79

N-(6-methoxypyridin-3-yl)-3-(2-methyl-9H-purin-6-yl)-5-((pyridin-3-ylamino)methyl)pyridin-2-amine

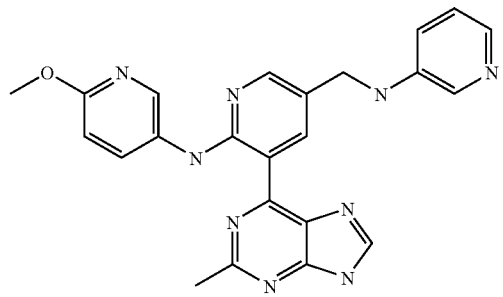 [SMILES: COc1ccc(Nc2ncc(CNc3cccnc3)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (153.3 mg, 0.3441 mmol) was suspended in ethanol (3.0 mL) and dichloromethane (3.0 mL), 3-aminopyridine (65.9 mg, 0.700 mmol) and tetraisopropoxytitanium (0.15 mL, 0.51 mmol) were added. The flask was fitted with a reflux condenser and placed in a preheated oil bath (50° C.-60° C.) and stirred under nitrogen for 6 hours. Then, the reaction was cooled to room temperature and allowed to stir overnight. After stirring overnight, sodium borohydride (26.7 mg, 0.706 mmol) was added, and stirring was continued at room temperature. After 35 minutes, the reaction was treated with 5 N HCl (0.60 mL) added dropwise, as gas evolution occurs. The reaction was diluted with MeOH (about 1 mL, both before and after adding the HCl) and stirred at room temperature for 5 hours. Then, the reaction flask was fitted with a reflux condenser and put in an oil bath which was heated to 50° C. Stirring was continued at this temperature for 1 hour, and then the reaction was cooled to room temperature. The suspension was diluted with DCM and MeOH and filtered through a Celite® (diatomaceous earth) pad, which was washed with DCM and MeOH. The filtrate was concentrated and treated with water and filtered. The solid was collected and purified on HPLC (10% to 100% MeCN/water with 0.1% TFA over 30 minutes with a total flow rate of 100 mL/min) to give N-(6-methoxypyridin-3-yl)-3-(2-methyl-9H-purin-6-yl)-5-((pyridin-3-ylamino)methyl)pyridin-2-amine (27.3 mg, 18%). MS (ESI pos. ion) m/z 440 (M+H)+. $^1$H NMR (d6-DMSO, 400 MHz) δ 13.63 (br s, 1H), 12.59 (s, 1H), 9.79 (s, 1H), 8.57 (s, 1H), 8.54 (d, J=2.74 Hz, 1H), 8.35 (d, J=2.35 Hz, 1H), 8.19-8.10 (m, 2H), 8.04 (d, J=1.56 Hz, 1H), 7.75-7.68 (m, 2H), 7.57 (br s, 1H), 6.85 (d, J=8.80 Hz, 1H), 4.45 (s, 2H), 3.85 (s, 3H), 2.85 (s, 3H).

Example 80

N-((6-(6-methoxypyridin-3-ylamino)-5-(2-methyl-9H-purin-6-yl)pyridin-3-yl)methyl)pyridazin-3-amine

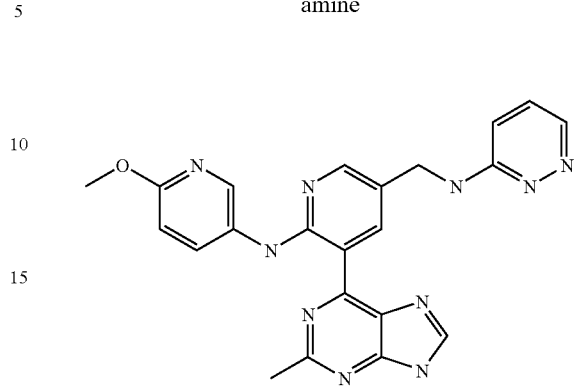

6-(6-methoxypyridin-3-ylamino)-5-(2-methyl-9-(tetrahydro-2H-pyran-2-yl)-9H-purin-6-yl)nicotinaldehyde (106.1 mg, 0.2382 mmol) was suspended in ethanol (1.5 mL) and dichloromethane (1.5 mL) and pyridazin-3-amine (39.2 mg, 0.412 mmol) and tetraisopropoxytitanium (0.11 mL, 0.37 mmol) were added. The reaction was stirred overnight at room temperature, and then more DCM (1 mL), 3-aminopyridazine (40.4 mg, 0.425 mmol), and Ti(OiPr)$_4$ (0.12 mL, 0.41 mmol) were added. The flask was fitted with a reflux condenser and placed in a preheated oil bath (50° C.) and stirred for 5 hours. Then, the temperature was raised to 70° C., and stirring was continued overnight. More DCM was added, along with more 3-aminopyridazine (35.2 mg, 0.370 mmol) and Ti(OiPr)$_4$ (0.10 mL, 0.34 mmol) and stirring was continued at 65° C. for 6 hours. Then, the oil bath temperature was raised to 70° C., and stirring was continued. More DCM was added 45 minutes later, and stirring was continued at 70° C. overnight. Then, the reaction was cooled to room temperature, and MeOH (1 mL) was added, followed by sodium borohydride (25.8 mg, 0.682 mmol). The reaction was stirred at room temperature for 75 minutes, and then 5 N HCl (0.50 mL) was added dropwise via syringe and the flask, with a reflux condenser attached, was put in a preheated oil bath (50° C.) and the reaction was stirred for 4.5 hours. The reaction was then cooled to room temperature, diluted with DCM and MeOH, and filtered through a Celite® (diatomaceous earth) pad. The Celite® (diatomaceous earth) pad was washed with DCM, MeOH, and a 1:1 mixture of DCM and MeOH. The filtrate was concentrated and again filtered (no Celite® (diatomaceous earth) pad this time). This filtrate was concentrated and again filtered through Celite® (diatomaceous earth). The filtrate was purified by prep HPLC (10% to 100% MeCN/water with 0.1% TFA over 30 minutes with a total flow rate of 100 mL/min) to give N-((6-(6-methoxypyridin-3-ylamino)-5-(2-methyl-9H-purin-6-yl)pyridin-3-yl)methyl)pyridazin-3-amine (17.4 mg, 17% yield). MS (ESI pos. ion) m/z 441 (M+H)+. $^1$H NMR (d6-DMSO, 400 MHz) δ 13.65 (br s, 1H), 12.63 (br s, 1H), 9.60 (br s, 1H), 9.16 (br s, 1H), 8.61 (d, J=3.33 Hz, 1H), 8.57 (s, 1H), 8.55 (d, J=2.74 Hz, 1H), 8.38 (d, J=2.35 Hz, 1H), 8.16 (dd, J=8.90 Hz, 2.84 Hz, 1H), 7.78 (dd, J=9.39 Hz, 4.30 Hz, 1H), 7.51 (d, J=9.19 Hz, 1H), 6.86 (d, J=9.0 Hz, 1H), 4.62 (d, J=5.09 Hz, 2H), 3.85 (s, 3H), 2.85 (s, 3H).

Example 81

N-(6-methoxypyridin-3-yl)-3-(2-methyl-9H-purin-6-yl)-5-((pyridin-4-ylamino)methyl)pyridin-2-amine

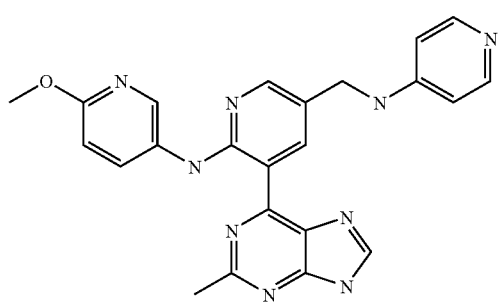 [SMILES: COc1ccc(Nc2ncc(CNc3ccncc3)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (88.7 mg, 0.199 mmol) was suspended in dichloromethane (1.5 mL) and EtOH (1.5 mL) and 4-aminopyridine (47.9 mg, 0.509 mmol) and tetraisopropoxytitanium (0.12 mL, 0.41 mmol) were added. The flask fitted with a reflux condenser and placed in a preheated oil bath (50° C.) and stirred overnight under nitrogen. Then, more 4-aminopyridine (45.9 mg, 0.488 mmol) and Ti(OiPr)$_4$ (0.12 mL, 0.41 mmol) were added, along with more DCM, and stirring was continued at 70° C. over the weekend.

The reaction was cooled to room temperature, diluted with DCM (1 mL) and MeOH (1 mL), and sodium borohydride (25.3 mg, 0.669 mmol) was added. The reaction was stirred at room temperature for 45 minutes, diluted with DCM and MeOH, and treated with 5 N HCl (0.55 mL). The reaction flask was placed in a preheated oil bath (50° C.), and stirred for 1 hour, and then the reaction was cooled to room temperature. The suspension was diluted with DCM and MeOH and filtered through a Celite® (diatomaceous earth) pad, which was washed with DCM and MeOH and a 1:1 mixture of these two solvents. The filtrate was concentrated, diluted with DMF (about 0.5 mL), and filtered through another Celite® (diatomaceous earth) pad, which was washed with DCM and MeOH. This filtrate was concentrated, diluted with DMSO, and filtered through Celite® (diatomaceous earth) again, and the filtrate was purified on HPLC (10% to 100% MeCN/water with 0.1% TFA over 30 minutes with a total flow rate of 100 mL/min). The fractions with product were combined, concentrated and purified by prep HPLC (10% to 100% MeCN/water with 0.1% TFA over 30 minutes with a total flow rate of 100 mL/min) a second time to give N-(6-methoxypyridin-3-yl)-3-(2-methyl-9H-purin-6-yl)-5-((pyridin-4-ylamino)methyl)pyridin-2-amine (33.3 mg, 38% yield). MS (ESI pos. ion) m/z 440 (M+H)$^+$. $^1$H NMR (d6-DMSO, 400 MHz) δ 13.16 (br s, 1H), 12.64 (br s, 1H), 9.79 (br s, 1H), 9.06 (t, J=4.89 Hz, 1H), 8.60 (s, 1H), 8.55 (d, J=2.74 Hz, 1H), 8.36 (d, J=2.35 Hz, 1H), 8.27 (t, J=5.97 Hz, 1H), 8.16 (dd, J=9.00 Hz, 2.74 Hz, 1H), 8.12 (t, J=6.26 Hz, 1H), 7.04 (d, J=7.04 Hz, 1H), 6.95 (d, J=8.80 Hz, 1H), 6.86 (d, J=8.80 Hz, 1H), 4.59 (d, J=5.48 Hz, 2H), 3.85 (s, 3H), 2.86 (s, 3H).

Example 82

N-(6-methoxypyridin-3-yl)-3-(2-methyl-9H-purin-6-yl)-5-((pyridin-2-ylamino)methyl)pyridin-2-amine

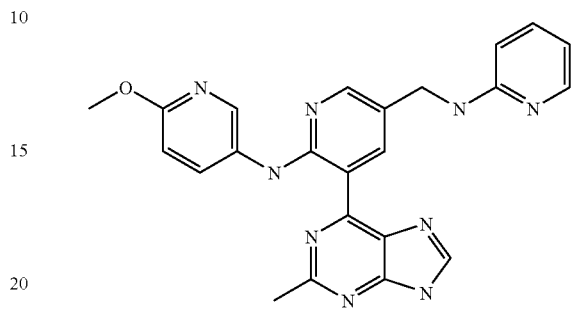

6-(6-methoxypyridin-3-ylamino)-5-(2-methyl-9-(tetrahydro-2H-pyran-2-yl)-9H-purin-6-yl)nicotinaldehyde (121.8 mg, 0.2734 mmol) and 2-aminopyridine (72.0 mg, 0.765 mmol) were suspended in dichloromethane (1.5 mL) and ethanol (1.5 mL) and tetraisopropoxytitanium (0.16 mL, 0.54 mmol) was added. The flask was fit with a reflux condenser and put in a preheated oil bath (70° C.) and stirred under nitrogen. After 5 hours, the reaction was diluted with DCM, and stirring was continued overnight. Then, more 2-aminopyridine (63.6 mg, 0.676 mmol) and Ti(OiPr)$_4$ (0.18 mL, 0.61 mmol), and DCM were added, and stirring was continued at 70° C. for about 6 hours. Then, the reaction was cooled to room temperature, and sodium borohydride (38.9 mg, 1.028 mmol) was added. The reaction was stirred at room temperature for 25 minutes, and then aqueous 5 N HCl (0.55 mL) was added. The flask was put in a preheated oil bath (50° C.) and stirring was continued overnight. Then, the reaction was cooled to room temperature, diluted with DCM and MeOH, and filtered through a Celite® (diatomaceous earth) pad, which was washed with a 1:1 mixture of DCM and MeOH. The filtrate was concentrated, treated with water, and filtered. The solid was washed with water, collected, treated with DMSO (about 1 mL), diluted with DCM, and filtered. The solid was washed with DCM, collected, and purified by prep HPLC (10% to 100% MeCN/water with 0.1% TFA over 30 minutes with a total flow rate of 100 mL/min) to give N-(6-methoxypyridin-3-yl)-3-(2-methyl-9H-purin-6-yl)-5-((pyridin-2-ylamino)methyl)pyridin-2-amine (62.7 mg, 52% yield). MS (ESI pos. ion) m/z 440 (M+H)$^+$. $^1$H NMR (d6-DMSO, 400 MHz) δ 13.60 (br s, 1H), 12.63 (s, 1H), 9.80 (s, 1H), 9.01 (br s, 1H), 8.56 (s, 1H), 8.55 (d, J=2.54 Hz, 1H), 8.36 (d, J=2.35 Hz, 1H), 8.15 (dd, J=8.80 Hz, 2.74 Hz, 1H), 7.98 (d, J=6.26 Hz, 1H), 7.92 (t, J=7.43 Hz, 1H), 7.11 (d, J=9.0 Hz, 1H), 6.90 (t, J=6.46 Hz, 1H), 6.86 (d, J=9.0 Hz, 1H), 4.61 (s, 2H), 3.85 (s, 3H), 2.85 (s, 3H).

Example 83

N-(6-methoxypyridin-3-yl)-3-(2-methyl-9H-purin-6-yl)-5-((phenylamino)methyl)pyridin-2-amine

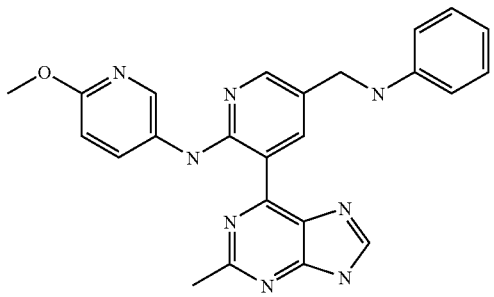 [SMILES: COc1ccc(Nc2ncc(CNc3ccccc3)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (122 mg, 0.274 mmol) was suspended in dichloromethane (1.5 mL) and ethanol (1.5 mL), and aniline (0.080 mL, 0.88 mmol) and tetraisopropoxytitanium (0.25 mL, 0.84 mmol) were added. The flask was fitted with a reflux condenser and placed in a preheated oil bath (70° C.-74° C.) and stirred under nitrogen for 45 minutes. Then, the reaction was cooled to room temperature and treated with sodium borohydride (39.8 mg, 1.05 mmol), along with MeOH (about 1 mL). The reaction was stirred at room temperature for 45 minutes, and then MeOH (about 1 mL) and aqueous 5 N HCl (0.55 mL) were added. The reaction flask was put in a preheated oil bath (50° C.-61° C.), stirred for 3.5 hours, and then cooled to room temperature. The resulting suspension was diluted with DCM and MeOH and filtered through a Celite® (diatomaceous earth) pad, which was washed with DCM, MeOH, and a 1:1 mixture of these 2 solvents. The filtrate was concentrated, treated with water, and filtered, and the solid was washed with water, collected, and washed with DCM. The solid was then purified by prep HPLC (10% to 100% MeCN/water with 0.1% TFA over 30 minutes with a total flow rate of 100 mL/min) to give N-(6-methoxypyridin-3-yl)-3-(2-methyl-9H-purin-6-yl)-5-((phenylamino)methyl)pyridin-2-amine (92.0 mg, 77% yield). MS (ESI pos. ion) m/z 439 (M+H)$^+$. $^1$H NMR (d6-DMSO, 400 MHz) δ 12.56 (br s, 1H), 9.77 (s, 1H), 8.62 (s, 1H), 8.52 (d, J=2.54 Hz, 1H), 8.29 (d, J=1.56 Hz, 1H), 8.15 (dd, J=8.90 Hz, 2.64 Hz, 1H), 7.10 (t, J=7.82 Hz, 2H), 6.85 (d, J=9.00 Hz, 1H), 6.71 (d, J=7.63 Hz, 2H), 6.60 (t, J=6.85 Hz, 1H), 4.29 (s, 2H), 3.85 (s, 3H), 2.85 (s, 3H).

Example 84

N-(6-methoxypyridin-3-yl)-3-(2-methyl-9H-purin-6-yl)-5-(piperazin-1-ylmethyl)pyridin-2-amine

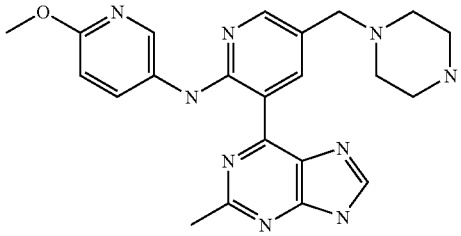 [SMILES: COc1ccc(Nc2ncc(CN3CCNCC3)cc2-c2nc(C)nc3[nH]cnc23)cn1]

Step 1. tert-butyl 4-((6-fluoro-5-(2-methyl-9-(tetrahydro-2H-pyran-2-yl)-9H-purin-6-yl)pyridin-3-yl)methyl)piperazine-1-carboxylate A mixture of 5-((4-(tert-butoxycarbonyl)piperazin-1-yl)methyl)-2-fluoropyridin-3-ylboronic acid (655 mg, 1.931 mmol), 6-chloro-2-methyl-9-(tetrahydro-2H-pyran-2-yl)-9H-purine (586 mg, 2.317 mmol), bis(di-tert-butyl(4-dimethylaminophenyl)phosphine)dichloropalladium(II) (Aldrich) (25.6 mg, 0.097 mmol) and potassium acetate (285 mg, 4.83 mmol) in ethanol (6.00 mL, 103 mmol) and H$_2$O (1.00 mL, 55.5 mmol) was heated at 80° C. for 2 h. After cooling, the reaction mixture was concentrated and the crude product was adsorbed onto a plug of silica gel and chromatographed through a RediSep®, Teledyne ISCO, Lincoln, Nebr., prepacked silica gel column (pure hexanes to 50% ethyl acetate in hexane) to give the tert-butyl 4-((6-fluoro-5-(2-methyl-9-(tetrahydro-2H-pyran-2-yl)-9H-purin-6-yl)pyridin-3-yl)methyl)piperazine-1-carboxylate as a pale yellow foam (0.877 g, 89%). LCMS (API-ES) m/z 512 (M+H)$^+$.

Step 2. tert-butyl 4-((6-(6-methoxypyridin-3-ylamino)-5-(2-methyl-9-(tetrahydro-2H-pyran-2-yl)-9H-purin-6-yl)pyridin-3-yl)methyl)piperazine-1-carboxylate LiHMDS (1.0 M in THF, 3.75 mL, 3.75 mmol) was slowly added to a stirred mixture of tert-butyl 4-((6-fluoro-5-(2-methyl-9-(tetrahydro-2H-pyran-2-yl)-9H-purin-6-yl)pyridin-3-yl)methyl)piperazine-1-carboxylate (0.6397 g, 1.250 mmol) and 3-amino-6-methoxypyridine (Aldrich, St. Louis, Mo.; 186 mg, 1.50 mmol) in tetrahydrofuran (10 mL, 1.250 mmol) at 0° C. and the mixture was stirred at the same temperature for 1 h before being quenched with NH$_4$Cl(aq) (10 mL) and water (10 mL). The separated aqueous layer was extracted with EtOAc (3×15 mL) and the combined organic layers were washed with brine, dried over Na$_2$SO$_4$, concentrated and purified by flash column chromatograph (hexanes to 50% ethyl acetate/hexanes) to give tert-butyl 4-((6-(6-methoxypyridin-3-ylamino)-5-(2-methyl-9-(tetrahydro-2H-pyran-2-yl)-9H-purin-6-yl)pyridin-3-yl)methyl)piperazine- 1-carboxylate (0.577 g, 0.937 mmol, 74.9% yield) as a yellow foam. LCMS (API-ES) m/z 616 (M+H)+.

Step 3. N-(6-methoxypyridin-3-yl)-3-(2-methyl-9H-purin-6-yl)-5-(piperazin-1-ylmethyl)pyridin-2-amine TFA (2.00 mL) was added to a stirred mixture of tert-butyl 4-((6-(6-methoxypyridin-3-ylamino)-5-(2-methyl-9-(tetrahydro-2H-pyran-2-yl)-9H-purin-6-yl)pyridin-3-yl)methyl)piperazine-1-carboxylate (112 mg, 0.182 mmol) in DCM (2.00 mL) and the mixture was stirred at room temperature for 1 h. The mixture was concentrated and re-diluted with DCM, NaHCO$_3$(aq) and water (10 mL each). The separated aqueous layer was extracted with DCM (4×20 mL) and the combined organic layers were washed with brine, dried over Na$_2$SO$_4$, concentrated and purified by flash column chromatography (DCM to 10% MeOH in DCM) to give N-(6-methoxypyridin-3-yl)-3-(2-methyl-9H-purin-6-yl)-5-(piperazin-1-ylmethyl)pyridin-2-amine (15 mg, 0.035 mmol, 19.11% yield) as a yellow solid. LCMS (API-ES) m/z 432 (M+H)+; $^1$H NMR (400 MHz, d6-DMSO) δ 12.63 (br. s., 1H) 9.69 (br. s., 1H) 8.60 (br. s., 1H) 8.54 (br. s., 1H) 7.86-8.30 (m, 3H) 6.85 (d, J=9.19 Hz, 1H) 3.85 (s, 3H) 3.52 (br. s., 2H) 2.90 (br. s., 4H) 2.85 (br. s., 3H) 2.37-2.49 (m, 4H).

Example 85

N-(6-methoxypyridin-3-yl)-3-(2-methyl-9H-purin-6-yl)-5-((4-(methylsulfonyl)piperazin-1-yl)methyl)pyridin-2-amine

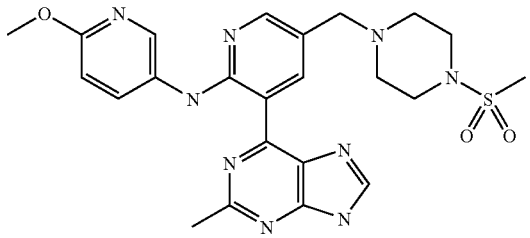

Step 1. N-(6-methoxypyridin-3-yl)-3-(2-methyl-9H-purin-6-yl)-5-(piperazin-1-ylmethyl)pyridin-2-amine TFA (3.00 mL, 38.9 mmol) was added to a stirred mixture of tert-butyl 4-((6-(6-methoxypyridin-3-ylamino)-5-(2-methyl-9-(tetrahydro-2H-pyran-2-yl)-9H-purin-6-yl)pyridin-3-yl)methyl)piperazine-1-carboxylate (155 mg, 0.252 mmol) in DCM (3 mL, 46.6 mmol) and the mixture was stirred at room temperature for 1 h. The reaction mixture was concentrated and then diluted with DCM, NaHCO$_3$(aq) and water (10 mL each). The separated aqueous layer was extracted with DCM (3×10 mL) and the combined organic layers were washed with brine, dried over Na$_2$SO$_4$, and concentrated to give crude N-(6-methoxypyridin-3-yl)-3-(2-methyl-9H-purin-6-yl)-5-(piperazin-1-ylmethyl)pyridin-2-amine Step 2. N-(6-methoxypyridin-3-yl)-3-(2-methyl-9H-purin-6-yl)-5-((4-(methylsulfonyl)piperazin-1-yl)methyl)pyridin-2-amine The crude residue from Step 1 was taken up in DCM (3 mL, 46.6 mmol), cooled to 0° C. and then DIEA (0.132 mL, 0.755 mmol) and methanesulfonyl chloride (0.029 mL, 0.378 mmol) were added. The mixture was stirred at the same temperature for 1 h and then diluted with NH$_4$Cl(aq) and water (10 mL each) and diluted with DCM (10 mL). The separated aqueous layer was extracted with DCM (2×15 mL) and the combined organic layers were washed with brine, dried over Na$_2$SO$_4$, concentrated and chromatographed through a Redi-Sep pre-packed silica gel column (DCM to 10% MeOH in DCM) to give N-(6-methoxypyridin-3-yl)-3-(2-methyl-9H-purin-6-yl)-5-((4-(methylsulfonyl)piperazin-1-yl)methyl)pyridin-2-amine (21 mg, 16%) as a yellow solid. LCMS (API-ES) m/z 510 (M+H)+; $^1$H NMR (400 MHz, d6-DMSO) δ 13.58 (br. s., 1H) 12.62 (br. s., 1H) 9.73 (br. s., 1H) 8.62 (s, 1H) 8.54 (d, J=2.54 Hz, 1H) 8.22 (d, J=1.56 Hz, 1H) 8.18 (dd, J=8.90, 2.45 Hz, 1H) 6.85 (d, J=8.80 Hz, 1H) 3.85 (s, 3H) 3.56 (s, 2H) 3.01-3.18 (m, 4H) 2.86 (s, 3H) 2.86 (s, 3H) 2.53 (br. s., 4H).

Example 86 methyl 4-((6-(6-methoxypyridin-3-ylamino)-5-(2-methyl-9H-purin-6-yl)pyridin-3-yl)methyl)piperazine-1-carboxylate

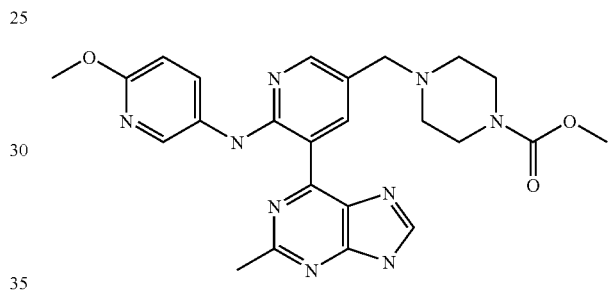

The title compound was isolated in 55% yield as a yellow solid following an analogous procedure to Example 85, Step 2 using N-(6-methoxypyridin-3-yl)-3-(2-methyl-9H-purin-6-yl)-5-(piperazin-1-ylmethyl)pyridin-2-amine and methyl chloroformate (Aldrich, St. Louis, Mo.). LCMS (API-ES) m/z 490 (M+H)+; $^1$H NMR (400 MHz, d6-DMSO) δ 13.60 (br. s., 1H) 12.62 (s, 1H) 9.74 (s, 1H) 8.62 (s, 1H) 8.54 (d, J=2.54 Hz, 1H) 8.21 (br. s., 1H) 8.19 (dd, J=9.19, 2.35 Hz, 1H) 6.85 (d, J=8.80 Hz, 1H) 3.85 (s, 3H) 3.58 (s, 3H) 3.52 (s, 2H) 3.34-3.45 (m, 4H) 2.86 (s, 3H) 2.40 (br. s., 4H).

Example 87

4-((6-(6-methoxypyridin-3-ylamino)-5-(2-methyl-9H-purin-6-yl)pyridin-3-yl)methyl)-N,N-dimethylpiperazine-1-carboxamide

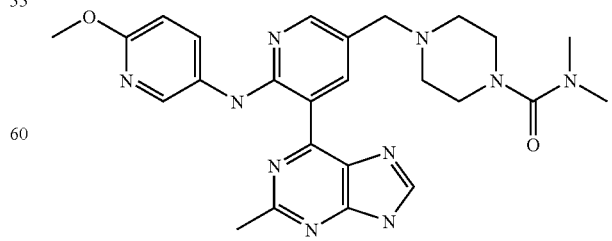

The title compound was isolated in 86% yield as a yellow solid following an analogous procedure to Example 85, Step 2 using N-(6-methoxypyridin-3-yl)-3-(2-methyl-9H-purin-6-yl)-5-(piperazin-1-ylmethyl)pyridin-2-amine and dimethylcarbamoyl chloride (Aldrich, St. Louis, Mo.). LCMS (API-ES) m/z 503 (M+H)+; 1H NMR (400 MHz, d6-DMSO) δ 13.62 (br. s., 1H) 12.65 (br. s., 1H) 9.75 (br. s., 1H) 8.63 (s, 1H) 8.54 (br. s., 1H) 7.93-8.32 (m, 2H) 6.86 (s, 1H) 3.85 (s, 3H) 3.52 (br. s., 2H) 3.11 (br. s., 4H) 2.86 (s, 3H) 2.72 (s, 6H) 2.42 (br. s., 4H).

Example 88

4-((6-(6-methoxypyridin-3-ylamino)-5-(2-methyl-9H-purin-6-yl)pyridin-3-yl)methyl)-N,N-dimethylpiperazine-1-sulfonamide

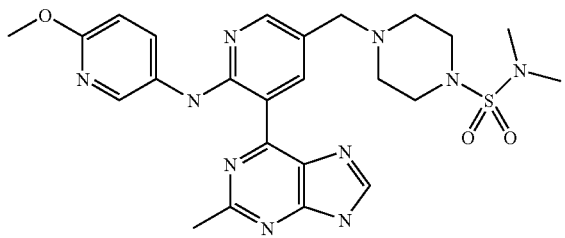

The title compound was isolated in 8% yield as a yellow solid following an analogous procedure to Example 85, Step 2 using N-(6-methoxypyridin-3-yl)-3-(2-methyl-9H-purin-6-yl)-5-(piperazin-1-ylmethyl)pyridin-2-amine and dimethylsulfamoyl chloride (Aldrich, St. Louis, Mo.). LCMS (API-ES) m/z 539 (M+H)+; 1H NMR (400 MHz, d6-DMSO) δ 13.62 (br. s., 1H) 12.64 (br. s., 1H) 9.74 (br. s., 1H) 8.63 (br. s., 1H) 8.54 (br. s., 1H) 8.22 (br. s., 1H) 8.19 (d, J=9.39 Hz, 1H) 6.85 (d, J=8.41 Hz, 1H) 3.85 (br. s., 3H) 3.54 (br. s., 2H) 3.17 (br. s., 4H) 2.86 (br. s., 3H) 2.75 (br. s., 6H) 2.37-2.48 (m, 4H).

Example 89

1-(4-((6-(6-methoxypyridin-3-ylamino)-5-(2-methyl-9H-purin-6-yl)pyridin-3-yl)methyl)piperazin-1-yl)ethanone

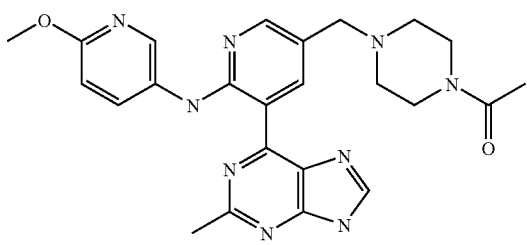 [SMILES: COc1ccc(Nc2ncc(CN3CCN(C(C)=O)CC3)cc2-c2nc(C)nc3[nH]cnc23)cn1]

Triethylamine (42.2 mg, 0.417 mmol) and Ac2O (0.013 mL, 0.139 mmol) were added to a stirred solution of N-(6-methoxypyridin-3-yl)-3-(2-methyl-9H-purin-6-yl)-5-(piperazin-1-ylmethyl)pyridin-2-amine (60 mg, 0.139 mmol) in DCM (3 mL, 46.6 mmol) and DMF (0.5 mL, to improve solubility) at room temperature. The mixture was stirred for 1 h and then diluted with NH4Cl(aq), water (10 mL) and EtOAc (10 mL each). The separated aqueous layer was extracted with EtOAc (3×15 mL) and the combined organic layers were washed with brine, dried over Na2SO4, and concentrated. The residue was heated at 60° C. with excess of Na2CO3 (50 mg) in CH3CN (5 mL) and water (1 mL) for 2 h. The resulting suspension was concentrated and washed with a minimal amount of cold MeOH to give 1-(4-((6-(6-methoxypyridin-3-ylamino)-5-(2-methyl-9H-purin-6-yl)pyridin-3-yl)methyl)piperazin-1-yl)ethanone (37 mg, 56%) as a yellow solid. LCMS (API-ES) m/z 474 (M+H)+; 1H NMR (400 MHz, d6-DMSO) δ 13.63 (br. s., 1H) 12.64 (br. s., 1H) 9.73 (br. s., 1H) 8.60 (s, 1H) 8.54 (br. s., 1H) 8.03-8.30 (m, 2H) 6.85 (d, J=8.61 Hz, 1H) 3.85 (s, 3H) 3.53 (br. s., 2H) 3.39-3.49 (m, 4H) 2.85 (s, 3H) 2.25-2.46 (m, 4H) 1.97 (s, 3H).

Example 90

N5-(4-methoxyphenyl)-N2-(6-methoxypyridin-3-yl)-3-(2-methyl-9H-purin-6-yl)pyridine-2,5-diamine

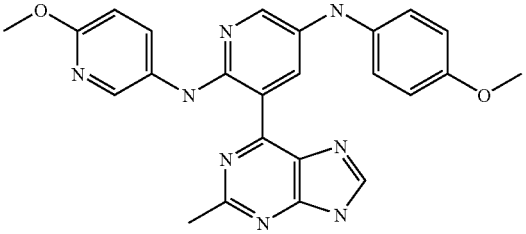

A mixture of 5-chloro-N-(6-methoxypyridin-3-yl)-3-(2-methyl-9-(tetrahydro-2H-pyran-2-yl)-9H-purin-6-yl)pyridin-2-amine (0.115 g, 0.254 mmol) and 4-anisidine (0.117 mL, 1.018 mmol) (Aldrich, St. Louis, Mo.) in THF (10 mL) was treated with sodium tert-butoxide (0.073 g, 0.763 mmol) (Aldrich, St. Louis, Mo.) and 2-di-t-butylphosphino-2',4',6'-tri-isopropyl-1,1'-biphenyl (0.025 g) (Strem Chemicals, Inc., Newburyport, Mass.). The mixture was deoxygenated and Pd2(dba)3 (0.023 g, 0.025 mmol) (Strem Chemicals, Inc., Newburyport, Mass.) was added under N2. The flask was fitted with a reflux condenser, then placed into a pre-heated bath at 90° C. and stirred overnight. The reaction mixture was allowed to cool to room temperature, diluted with water (10 mL) and extracted with 4:1 CH2Cl2/MeOH (5×25 mL) and from brine. The combined organic extracts were washed with saturated aqueous NaHCO3 (20 mL) and dried over Na2SO4. The solution was filtered and concentrated in vacuo to give the crude material as tan oil. This was adsorbed onto a plug of silica gel and purified by chromatography through a RediSep®, Teledyne ISCO, Lincoln, Nebr., pre-packed silica gel column (80 g), eluting with a gradient of 1% to 5% MeOH in CH2Cl2 over 30 minutes to give N5-(4-methoxyphenyl)-N2-(6-methoxypyridin-3-yl)-3-(2-methyl-9-(tetrahydro-2H-pyran-2-yl)-9H-purin-6-yl)pyridine-2,5-diamine as a tan oil. This was diluted with methanol (3 mL) and TFA (1.5 mL) and placed into a pre-heated (60° C.) bath. The mixture was allowed to stir under inert atmosphere for 2 h. The reaction mixture was allowed to cool to room temperature, concentrated in-vacuo, then diluted with DCM. The mixture was made basic with 10 N aqueous NaOH, diluted with water (15 mL) and extracted with CH2Cl2 (3×15 mL). The organic extract was washed with water (1×10 mL) and dried over Na2SO4. The solution was filtered and concentrated in vacuo to give a tan oil. This was adsorbed onto a plug of silica gel and purified by chromatography through a Redi-Sep pre-packed silica gel column (40 g), eluting with a gradient of 1% to 8% MeOH in CH$_2$Cl$_2$ over 25 minutes, to give N5-(4-methoxyphenyl)-N2-(6-methoxypyridin-3-yl)-3-(2-methyl-9H-purin-6-yl)pyridine-2,5-diamine (0.009 g, 0.020 mmol, 7.78% yield) as tan solid. MS (ESI pos. ion) m/z 455 (M+H)$^+$. $^1$H NMR (400 MHz, d6-DMSO) δ 9.62 (s, 1H); 8.59 (s, 1H); 8.51 (s, 1H); 8.14 (m, 2H); 7.00 (d, J=8.80 Hz, 2H); 6.84 (d, J=8.80 Hz, 3H); 3.84 (s, 3H); 3.70 (s, 3H); 2.86 (s, 3H).

Example 91

N5-benzyl-N2-(6-methoxypyridin-3-yl)-3-(2-methyl-9H-purin-6-yl)pyridine-2,5-diamine

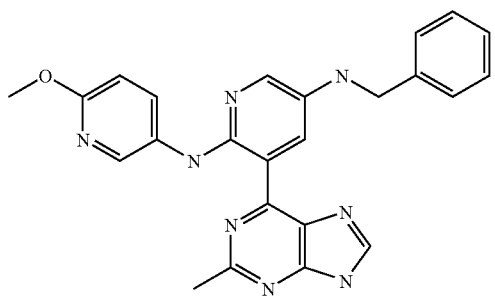 [SMILES: COc1ccc(Nc2ncc(NCc3ccccc3)cc2-c2nc(C)nc3[nH]cnc23)cn1]

A solution of 5-chloro-N-(6-methoxypyridin-3-yl)-3-(2-methyl-9-(tetrahydro-2H-pyran-2-yl)-9H-purin-6-yl)pyridin-2-amine (0.160 g, 0.354 mmol) and benzylamine (0.155 mL, 1.416 mmol) (Source: Aldrich) in THF (10 mL) was treated with sodium tert-butoxide (0.102 g, 1.062 mmol) and 2-di-t-butylphosphino-2',4',6'-tri-isopropyl-1,1'-biphenyl (0.030 g). The mixture was deoxygenated and treated with Pd$_2$(dba)$_3$ (0.032 g, 0.035 mmol) under N$_2$. The flask was fitted with a reflux condenser, then placed into a pre-heated bath at 90° C. and stirred overnight. The reaction mixture was diluted with saturated aqueous NaHCO$_3$ (10 mL) and extracted with CH$_2$Cl$_2$ (2×25 mL). The combined organic extracts were washed with NaHCO$_3$ (20 mL) and dried over Na$_2$SO$_4$. The solution was filtered and concentrated in vacuo to give a tan oil. This was adsorbed onto a plug of silica gel and purified by chromatography through a Redi-Sep pre-packed silica gel column (40 g), eluting with a gradient of 1% to 5% MeOH in CH$_2$Cl$_2$ over 25 minutes to give N5-benzyl-N2-(6-methoxypyridin-3-yl)-3-(2-methyl-9-(tetrahydro-2H-pyran-2-yl)-9H-purin-6-yl)pyridine-2,5-diamine as a tan solid. This material was added to a glass microwave reactor vial along with 1 N aqueous HCl (1 mL) and THF (3 mL). The mixture was stirred and heated in a Discover model microwave reactor (CEM, Matthews, N.C.) at 100° C. for 10 min (100 watts, Powermax feature on). The mixture was concentrated in-vacuo and diluted with DCM and 1 N aqueous NaOH. The mixture was extracted and the organic layer was dried over sodium sulfate, filtered and concentrated. The residue was diluted with ethyl ether and the precipitate was collected by filtration and washed with diethyl ether (5×25 mL). This gave N5-benzyl-N2-(6-methoxypyridin-3-yl)-3-(2-methyl-9H-purin-6-yl)pyridine-2,5-diamine (0.065 g, 0.148 mmol, 41.9% yield) as a tan solid. MS (ESI pos. ion) m/z 439 (M+H)$^+$. $^1$H NMR (400 MHz, CD$_3$OD) δ 8.56 (s, 1H); 8.21 (s, 1H); 8.11 (s, 1H); 7.80 (d, 1H); 7.59 (s, 1H); 7.35 (d, 2H); 7.22 (t, 2H); 7.12 (m, 1H); 6.64 (d, 1H); 4.31 (s, 2H); 3.76 (s, 3H); 2.69 (s, 3H).

Example 92

N2-(6-methoxypyridin-3-yl)-3-(2-methyl-9H-purin-6-yl)-N5-phenylpyridine-2,5-diamine

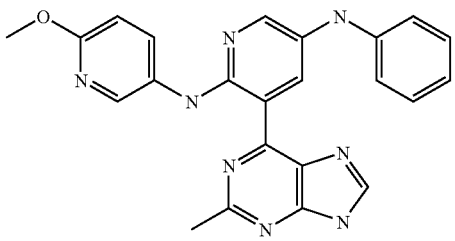 [SMILES: COc1ccc(Nc2ncc(Nc3ccccc3)cc2-c2nc(C)nc3[nH]cnc23)cn1]

A solution of 5-chloro-N-(6-methoxypyridin-3-yl)-3-(2-methyl-9-(tetrahydro-2H-pyran-2-yl)-9H-purin-6-yl)pyridin-2-amine (0.200 g, 0.443 mmol) and aniline (0.161 mL, 1.770 mmol) (Fluka, Buchs, Switzerland) in THF (10 mL) was treated with sodium tert-butoxide (0.128 g, 1.328 mmol) and 2-di-t-butylphosphino-2',4',6'-tri-isopropyl-1,1'-biphenyl (0.030 g). The mixture was deoxygenated and treated with Pd$_2$(dba)$_3$ (0.041 g, 0.044 mmol) under N$_2$. The flask was fitted with a reflux condenser, then placed into a pre-heated bath at 80° C. and stirred overnight. The reaction mixture was diluted with saturated aqueous NaHCO$_3$ (15 mL) and extracted with CH$_2$Cl$_2$ (2×25 mL). The combined organic extracts were washed with NaHCO$_3$ (20 mL) and dried over Na$_2$SO$_4$. The solution was filtered and concentrated in vacuo to give a tan oil. A glass microwave reaction vessel was charged with the crude oil and 1 N aqueous HCl (1.5 mL) in THF (2.5 mL). The reaction mixture was stirred and heated in a Discover model microwave reactor (CEM, Matthews, N.C.) at 100° C. for 8 min (100 watts, Powermax feature on). The mixture was diluted with methanol and then concentrated. The mixture was triturated with acetonitrile and allowed to stir 5 minutes. The precipitate was collected by filtration and washed with diethyl ether (3×25 mL). This gave N2-(6-methoxypyridin-3-yl)-3-(2-methyl-9H-purin-6-yl)-N5-phenylpyridine-2,5-diamine (0.180 g, 0.424 mmol, 96% yield) as a tan solid. MS (ESI pos. ion) m/z 425 (M+H)$^+$. $^1$H NMR (400 MHz, CD$_3$OD) δ 9.85 (s, 1H); 8.52 (s, 1H); 8.41 (s, 1H); 7.87 (s, 1H); 7.52 (d, J=7.43 Hz, 2H); 7.39 (d, J=7.43 Hz, 1H); 7.21-7.29 (m, 2H); 7.10 (s, 2H); 7.00 (d, 1H); 6.88 (s, 1H); 3.98 (s, 3H); 2.83 (s, 3H).

Example 93

N5-(2-methoxyethyl)-N2-(6-methoxypyridin-3-yl)-3-(2-methyl-9H-purin-6-yl)pyridine-2,5-diamine

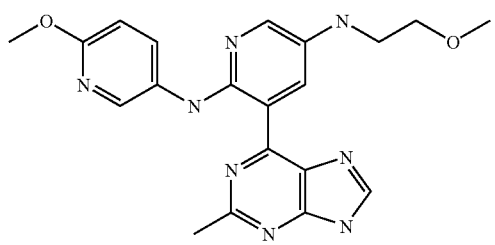

A solution of 5-chloro-N-(6-methoxypyridin-3-yl)-3-(2-methyl-9-(tetrahydro-2H-pyran-2-yl)-9H-purin-6-yl)pyridin-2-amine (0.150 g, 0.332 mmol) and 2-methoxyethylamine (0.114 mL, 1.328 mmol) (Aldrich, St. Louis, Mo.) in THF (10 mL) was treated with sodium tert-butoxide (0.096 g, 0.996 mmol) and 2-di-t-butylphosphino-2',4',6'-tri-isopropyl-1,1-biphenyl (0.030 g). The mixture was deoxygenated and treated with Pd$_2$(dba)$_3$ (0.030 g, 0.033 mmol) under N$_2$. The flask was fitted with a reflux condenser, then placed into a pre-heated bath at 80° C. and stirred overnight. The reaction mixture was diluted with water (10 mL) and extracted with 4:1 CHCl$_3$/isopropanol (2×20 mL). The combined organic extracts were washed with NaHCO$_3$ (20 mL) and dried over Na$_2$SO$_4$. The solution was filtered and concentrated in vacuo to give a tan oil. A glass microwave reaction vessel was charged with the crude oil and 1 N aqueous HCl (1.5 mL) in THF (3 mL). The reaction mixture was stirred and heated in a Discover model microwave reactor (CEM, Matthews, N.C.) at 100° C. for 8 min (100 watts, Powermax feature on). The mixture was diluted with methanol and then concentrated. The mixture was triturated with acetonitrile and allowed to stir 5 minutes. The precipitate was collected by filtration and washed with diethyl ether (3×25 mL). The solid was neutralized with 1 N aqueous sodium hydroxide and extracted with chloroform/isopropanol (4:1). The organic layer was dried over sodium sulfate, filtered and concentrated. The residue was diluted with diethyl ether and the precipitate was collected by filtration, washing with diethyl ether (3×20 ml) and finally with hexanes. This gave N5-(2-methoxyethyl)-N2-(6-methoxypyridin-3-yl)-3-(2-methyl-9H-purin-6-yl)pyridine-2,5-diamine (0.035 g, 0.086 mmol, 25.9% yield) as a tan solid. MS (ESI pos. ion) m/z 407 (M+H)$^+$. $^1$H NMR (400 MHz, d6-DMSO) δ 12.06 (s, 1H); 9.20 (s, 1H); 8.60 (s, 1H); 8.47 (s, 1H); 8.12 (d, 1H); 7.90 (d, J=2.35 Hz, 1H); 6.82 (d, 1H); 5.42 (s, 1H); 3.82 (s, 6H); 3.58 (t, J=5.58 Hz, 2H); 3.26 (s, 3H); 2.85 (s, 3H).

Example 94

N5-ethyl-N2-(6-methoxypyridin-3-yl)-3-(2-methyl-9H-purin-6-yl)pyridine-2,5-diamine

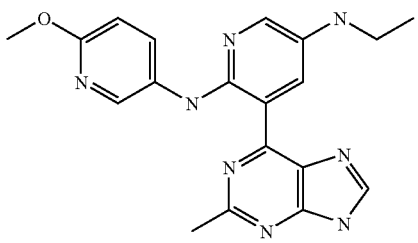 [SMILES: CCNc1cnc(Nc2ccc(OC)nc2)c(-c2nc(C)nc3[nH]cnc23)c1]

A solution of 5-chloro-N-(6-methoxypyridin-3-yl)-3-(2-methyl-9-(tetrahydro-2H-pyran-2-yl)-9H-purin-6-yl)pyridin-2-amine (0.200 g, 0.443 mmol) and ethylamine (0.553 mL, 1.106 mmol) (Aldrich, St. Louis, Mo.) in THF (10 mL) was treated with sodium tert-butoxide (0.128 g, 1.328 mmol) and 2-di-t-butylphosphino-2',4',6'-tri-isopropyl-1,1'-biphenyl (0.030 g). The mixture was deoxygenated and treated with Pd$_2$(dba)$_3$ (0.041 g, 0.044 mmol) under N$_2$. The flask was fitted with a reflux condenser, then placed into a pre-heated bath at 80° C. and stirred overnight. The reaction mixture was diluted with saturated aqueous NaHCO$_3$ (10 mL) and extracted with CH$_2$Cl$_2$ (2×25 mL). The combined organic extracts were washed with NaHCO$_3$ (20 mL) and dried over Na$_2$SO$_4$. The solution was filtered and concentrated in vacuo to give a tan oil. A glass microwave reaction vessel was charged with the crude oil and 1 N aqueous HCl (1.5 mL) in THF (3 mL). The reaction mixture was stirred and heated in a Discover model microwave reactor (CEM, Matthews, N.C.) at 100° C. for 8 min (100 watts, Powermax feature on). The mixture was concentrated and neutralized with SiliCycle Si-Carbonate Silica Gel (SiliCycle Inc., Quebec City, Canda) (0.800 g). The mixture was diluted with THF (5 mL) and allowed to stir under inert atmosphere overnight. The mixture was concentrated, diluted with DCM (10 mL) and filtered. The desired product was released from the silica by rinsing with methanol (20 mL). The filtrate was concentrated and triturated with diethyl ether to give N5-ethyl-N2-(6-methoxypyridin-3-yl)-3-(2-methyl-9H-purin-6-yl)pyridine-2,5-diamine (0.065 g, 0.173 mmol, 39.0% yield) as a tan solid. MS (ESI pos. ion) m/z 377 (M+H)$^+$. $^1$H NMR (400 MHz, CD$_3$OD) δ 8.65 (d, 1H); 8.35 (d, 1H); 8.20 (s, 1H); 7.92 (d, 1H); 7.76 (s, 1H); 6.75 (d, 1H); 3.87 (s, 3H); 3.20 (m, 2H); 2.80 (s, 3H); 1.29 (s, 3H).

Example 95

N5-(4-methoxybenzyl)-N2-(6-methoxypyridin-3-yl)-3-(2-methyl-9H-purin-6-yl)pyridine-2,5-diamine

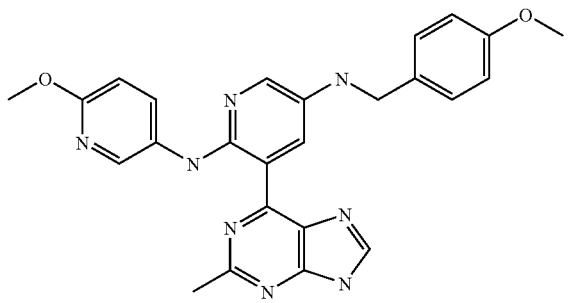

A solution of 5-chloro-N-(6-methoxypyridin-3-yl)-3-(2-methyl-9-(tetrahydro-2H-pyran-2-yl)-9H-purin-6-yl)pyridin-2-amine (0.150 g, 0.332 mmol) and 4-methoxybenzylamine (0.108 mL, 0.830 mmol) (Source: Aldrich) in THF (10 mL) was treated with sodium tert-butoxide (0.096 g, 0.996 mmol) and 2-di-t-butylphosphino-2',4',6'-tri-isopropyl-1,1-biphenyl (0.030 g). The mixture was deoxygenated and treated with Pd$_2$(dba)$_3$ (0.030 g, 0.033 mmol) under N$_2$. The flask was fitted with a reflux condenser, then placed into a pre-heated bath at 80° C. and stirred overnight. The reaction mixture was diluted with saturated aqueous NaHCO$_3$ (15 mL) and extracted with CH$_2$Cl$_2$ (2×25 mL). The combined organic extracts were washed with NaHCO$_3$ (20 mL) and dried over Na$_2$SO$_4$. The solution was filtered and concentrated in vacuo to give a tan oil. A glass microwave reaction vessel was charged with the crude oil and 1 N aqueous HCl (1.5 mL) in THF (2.5 mL). The reaction mixture was stirred and heated in a Discover model microwave reactor (CEM, Matthews, N.C.) at 100° C. for 8 min (100 watts, Powermax feature on). The mixture was diluted with MeOH, concentrated and neutralized with SiliCycle Si-Carbonate Silica Gel (SiliCycle Inc., Quebec City, Canda) (0.800 g). The mixture was diluted with THF/DCM (1:1) and allowed to stir under inert atmosphere overnight. The mixture was filtered and concentrated. The crude material was adsorbed onto a plug of silica gel and purified by chromatography through a RediSep®, Teledyne ISCO, Lincoln, Nebr., pre-packed silica gel column (40 g), eluting with a gradient of 1% to 15% isopropanol in dichloromethane to give N5-(4-methoxybenzyl)-N2-(6-methoxypyridin-3-yl)-3-(2-methyl-9H-purin-6-yl)pyridine-2,5-diamine (0.020 g, 0.043 mmol, 12.86% yield) as a tan solid. MS (ESI pos. ion) m/z 469 (M+H)+. 1H NMR (400 MHz, d6-DMSO) δ 13.58 (s, 1H); 12.06 (s, 1H); 9.26 (s, 1H); 8.59-8.65 (m, 1H); 8.44 (d, J=2.15 Hz, 1H); 8.09 (dd, J=8.80, 2.35 Hz, 1H); 7.81 (d, J=2.54 Hz, 1H); 7.38 (d, J=8.41 Hz, 2H); 6.88 (d, J=8.61 Hz, 2H); 6.78 (d, J=8.80 Hz, 1H); 5.75 (s, 1H); 4.26 (s, 2H); 3.76-3.88 (m, 3H); 3.71 (s, 3H); 2.80-2.90 (m, 3H).

Example 96

N5-(3-methoxyphenyl)-N2-(6-methoxypyridin-3-yl)-3-(2-methyl-9H-purin-6-yl)pyridine-2,5-diamine

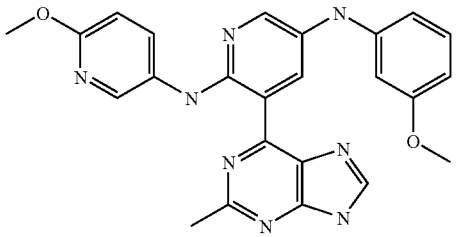

A solution of 5-chloro-N-(6-methoxypyridin-3-yl)-3-(2-methyl-9-(tetrahydro-2H-pyran-2-yl)-9H-purin-6-yl)pyridin-2-amine (0.230 g, 0.509 mmol) and 3-methoxyaniline (0.142 mL, 1.272 mmol) (Aldrich, St. Louis, Mo.) in THF (10 mL) was treated with sodium tert-butoxide (0.147 g, 1.527 mmol) and 2-di-t-butylphosphino-2',4',6'-tri-isopropyl-1,1'-biphenyl (0.040 g). The mixture was deoxygenated and treated with Pd2(dba)3 (0.030 g, 0.033 mmol) under N2. The flask was fitted with a reflux condenser, then placed into a pre-heated bath at 80° C. and stirred overnight. The reaction mixture was diluted with saturated aqueous NaHCO3 (15 mL) and extracted with CH2Cl2 (2×25 mL). The combined organic extracts were washed with NaHCO3 (20 mL) and dried over Na2SO4. The solution was filtered and concentrated in vacuo to give a tan oil. A glass microwave reaction vessel was charged with the crude oil and 1 N aqueous HCl (1.5 mL) in THF (2.5 mL). The reaction mixture was stirred and heated in a Discover model microwave reactor (CEM, Matthews, N.C.) at 100° C. for 8 min (100 watts, Powermax feature on). The mixture was diluted with MeOH, concentrated and triturated with THF. The precipitate was collected by filtration and washed with diethyl ether (3×25 ml). The solid (0.178 g) was neutralized with SiliCycle Si-Carbonate Silica Gel (SiliCycle Inc., Quebec City, Canda) (1.8 g) in a mixture of THF/DCM (1:1; 10 mL) and allowed to stir under inert atmosphere overnight. The mixture was filtered with a fine-fitted funnel The desired material which was still attached to the Silica-polymer, was released by washing the silica with methanol (2×10 mL) and concentrated. The residue was triturated with diethyl ether and the precipitate was collected by filtration to give N5-(3-methoxyphenyl)-N2-(6-methoxypyridin-3-yl)-3-(2-methyl-9H-purin-6-yl)pyridine-2,5-diamine (0.040 g, 0.088 mmol, 17.29% yield) as a tan solid. MS (ESI pos. ion) m/z 456 (M+H)+. 1H NMR (400 MHz, d6-DMSO) δ 12.50 (s, 1H); 9.75 (s, 1H); 8.54 (s, 2H); 8.17 (s, 2H); 8.08 (s, 1H); 7.08 (s, 1H); 6.83 (d, J=8.80 Hz, 1H); 6.51-6.59 (m, 2H); 6.32 (s, 1H); 3.84 (s, 3H); 3.71 (s, 3H); 2.86 (s, 3H).

Example 97

N-(3-(2-methyl-9H-purin-6-yl)-5-morpholinopyridin-2-yl)-1H-indazol-4-amine

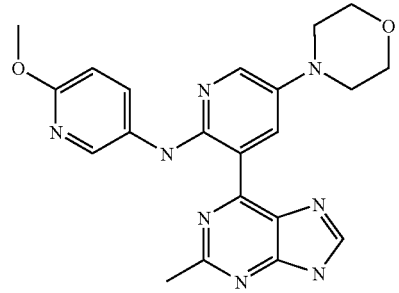 [SMILES: COc1ccc(Nc2ncc(N3CCOCC3)cc2-c2nc(C)nc3[nH]cnc23)cn1]

A mixture of 5-bromo-N-(6-methoxypyridin-3-yl)-3-(2-methyl-9-(tetrahydro-2H-pyran-2-yl)-9H-purin-6yl)pyridin-2-amine (0.310 g, 0.625 mmol) (Example 64 intermediate), morpholine (0.054 g, 0.625 mmol) (Aldrich, St. Louis, Mo.), sodium tert-butoxide (0.090 g, 0.937 mmol) (Aldrich, St. Louis, Mo.), tris(dibenzylideneacetone)dipalladium (0) (0.011 g, 0.012 mmol) (Aldrich, St. Louis, Mo.) and 9,9-dimethyl-4,5-bis(diphenylphosphino)xanthene (0.022 g, 0.037 mmol) (Strem Chemicals, Inc., Newburyport, Mass.) in dioxane (100 mL, 941 mmol) was deoxygenated and stirred at 95-100° C. under N2 for three hours. The reaction mixture was diluted with ethyl acetate and washed with water (3×). The organic layer was concentrated, adsorbed onto a plug of silica gel and chromatographed through a RediSep®, Teledyne ISCO, Lincoln, Nebr., pre-packed silica gel column (120 g), eluting with a gradient of 10% to 50% ethyl acetate in hexane to give N-(6-methoxypyridin-3-yl)-3-(2-methyl-9-(tetrahydro-2H-pyran-2-yl)-9H-purin-6yl)-5-morpholinopyridin-2amine (0.105 g, 33% yield). The residue was treated with trifluoroacetic acid (Aldrich, St. Louis, Mo.) and dichloromethane to give N-(3-(2-methyl-9H-purin-6-yl)-5-morpholinopyridin-2-yl)-1H-indazol-4-amine MS (ESI pos. ion) m/z 419 (M+H)+. 1H NMR (400 MHz, d6-DMSO) δ 12.46 ((br. s., 1H); 9.56 ((br. s., 1H); 8.56 (d, J=0.39 Hz, 1H); 8.51-8.53 (m, 1H); 8.12 (d, J=1.37 Hz, 2H); 6.82 (d, J=9.00 Hz, 1H); 3.78-3.86 (m, 7H); 3.11 (br. s., 2H); 3.12 (t, J=4.89 Hz, 2H); 2.84 (s, 3H).

Example 98

1-(6-(6-methoxypyridin-3-ylamino)-5-(2-methyl-9H-purin-6-yl)pyridin-3-yl)pyrrolidin-3-ol

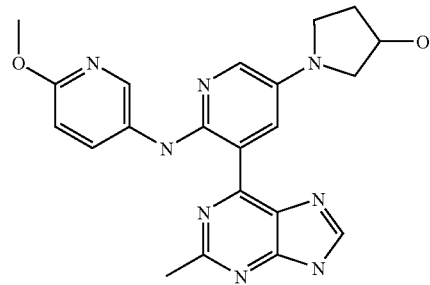 [SMILES: COc1ccc(Nc2ncc(N3CCC(O)C3)cc2-c2nc(C)nc3[nH]cnc23)cn1]

The title compound was synthesized following an analogous procedure to Example 97, substituting pyrrolidin-3-ol (Aldrich) for morpholine. MS (ESI pos. ion) m/z 419 (M+H)⁺. ¹H NMR (400 MHz, d6-DMSO) δ 13.57 (d, J=4.11 Hz, 1H); 12.13 (br. s., 1H); 8.65 (br. s., 1H); 8.49 (br. s., 1H); 8.35 (br. s., 1H); 7.80 (br. s., 1H); 6.79 (d, J=9.39 Hz, 1H); 5.12 (br. s., 1H); 4.45 (d, J=4.50 Hz, 1H); 3.83 (d, J=1.96 Hz, 3H); 3.51 (dd, J=4.60, 2.84 Hz, 1H); 3.50 (br. s., 1H); 3.41 (d, J=7.82 Hz, 2H); 3.15 (br. s., 1H); 2.85 (br. s., 3H).

Example 99

N-(6-methoxypyridin-3-yl)-3-(2-methyl-9H-purin-6-yl)-5-(4-(methylsulfonyl)piperazin-1-yl)pyridin-2-amine

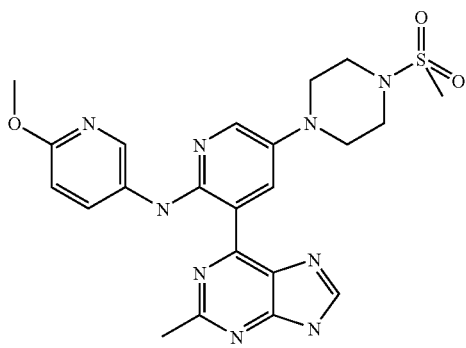 [SMILES: COc1ccc(Nc2ncc(N3CCN(S(C)(=O)=O)CC3)cc2-c2nc(C)nc3[nH]cnc23)cn1]

The title compound was synthesized following an analogous procedure to Example 97, substituting 1-methylsulfonylpiperazine (Apollo Chemical Company, LLC., Burlington, N.C.) for morpholine. MS (ESI pos. ion) m/z 496 (M+H)⁺. ¹H NMR (400 MHz, d6-DMSO) δ 13.66 (br. s., 1H); 12.35 (d, J=2.15 Hz, 1H); 9.63 (br. s., 1H); 8.63 (d, J=2.35 Hz, 1H); 8.52 (br. s., 1H); 8.15 (d, J=0.78 Hz, 2H); 6.83 (d, J=0.98 Hz, 1H); 3.84 (d, J=0.78 Hz, 3H); 3.33 (d, J=0.59 Hz, 3H); 3.23 (d, J=5.48 Hz, 3H); 2.97 (br. s., 1H); 2.96 (d, J=0.78 Hz, 3H); 2.85 (s, 3H); 1.04 (dd, J=6.46, 1.17 Hz, 1H).

Example 100

((2S)-1-(6-(6-methoxypyridin-3-ylamino)-5-(2-methyl-9H-purin-6-yl)pyridin-3-yl)pyrrolidin-2-yl)methanol

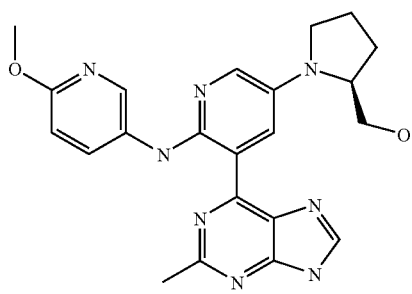 [SMILES: COc1ccc(Nc2ncc(N3CCC[C@H]3CO)cc2-c2nc(C)nc3[nH]cnc23)cn1]

The title compound was synthesized following an analogous procedure to Example 97, substituting (S)-pyrrolidin-2-methanol (Aldrich, St. Louis, Mo.) for morpholine. MS (ESI pos. ion) m/z 433 (M+H)⁺.

Example 101

((2R)-1-(6-(6-methoxypyridin-3-ylamino)-5-(2-methyl-9H-purin-6-yl)pyridin-3-yl)pyrrolidin-2-yl)methanol

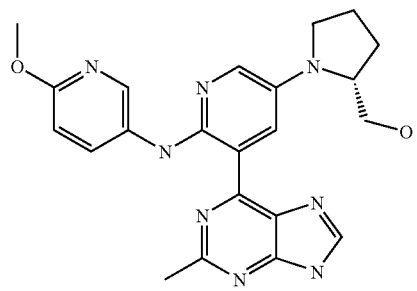 [SMILES: COc1ccc(Nc2ncc(N3CCC[C@@H]3CO)cc2-c2nc(C)nc3[nH]cnc23)cn1]

The title compound was synthesized following an analogous procedure to Example 97, substituting (R)-pyrrolidin-2-methanol (Aldrich, St. Louis, Mo.) for morpholine. MS (ESI pos. ion) m/z 433 (M+H)⁺.

Example 102

N-(4-(3-(2-methyl-9H-purin-6-yl)pyridin-2-ylamino)phenyl)acetamide

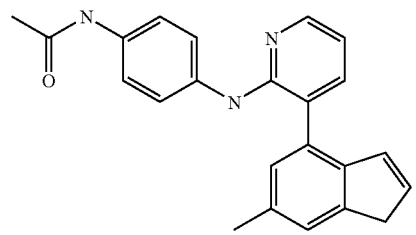 [SMILES: CC(=O)Nc1ccc(Nc2ncccc2-c2cc(C)cc3c2C=CC3)cc1]

Step 1. N-(4-(3-(2-methyl-9-(tetrahydro-2H-pyran-2-yl)-9H-purin-6-yl)pyridin-2-ylamino)phenyl)acetamide A glass microwave reaction vessel was charged with 4'-aminoacetanilide (69.0 mg, 0.460 mmol, Aldrich, St. Louis, Mo.) and 6-(2-fluoropyridin-3-yl)-2-methyl-9-(tetrahydro-2H-pyran-2-yl)-9H-purine (120 mg, 0.383 mmol) in THF (5 mL), Ar was bubbled in for 2 minutes and the reaction was sealed. The reaction mixture was cooled to 0° C., lithium bis(trimethylsilyl)amine (1 N in THF, 1.2 mL, 1.2 mmol) was added dropwise and the solution was stirred at 0° C. for 1h. After warming to room temperature, the reaction mixture was diluted with saturated NH₄Cl (10mL) and extracted with EtOAc (3×). The organic extracts were washed with brine and dried over Na₂SO₄. The solution was filtered and concentrated in vacuum. The crude material was purified by chromatography through a RediSep®, Teledyne ISCO, Lincoln, Nebr., pre-packed silica gel column (25 g), eluting with a gradient of 2% to 10% 2 M NH₃/MeOH in CH₂Cl₂, to provide N-(4-(3-(2-methyl-9-(tetrahydro-2H-pyran-2-yl)-9H-purin-6-yl)pyridin-2-ylamino)phenyl)acetamide (115 mg, 0.259 mmol, 67.7% yield) as a yellow solid. MS (ESI positive ion) m/z 444 (M+H)⁺. ¹H NMR (400 MHz, d6-DMSO) δ 12.68 (s, 1H); 9.86 (s, 1H); 9.72 (d, J=8.02 Hz, 1H); 8.86 (s, 1H); 8.34 (d, J=2.15 Hz, 1H); 7.75 (d, J=7.82 Hz, 2H); 7.56 (d, J=7.63 Hz, 2H); 6.98 (s, 1H); 5.84 (d, J=10.95 Hz, 1H); 3.92-4.22 (m, 1H); 3.64-3.87 (m, 1H); 2.90 (s, 3H); 2.30-2.33 (m, 1H); 2.03 (s, 3H); 1.99-2.01 (m, 2H); 1.79-1.82 (m, 1H); 1.48-1.71 (m, 2H).

Step 2. N-(4-(3-(2-methyl-9H-purin-6-yl)pyridin-2-ylamino)phenyl)acetamide

A solution of N-(4-(3-(2-methyl-9-(tetrahydro-2H-pyran-2-yl)-9H-purin-6-yl)pyridin-2-ylamino)phenyl)acetamide from Step 1 (90 mg, 0.203 mmol) in DCM (5 mL) was treated with trifluoroacetic acid (5 mL, 67.3 mmol). The solution was stirred for 30 minutes at room temperature. The mixture was cooled to 0° C. and neutralized with aqueous NaOH (10 N). The suspension was diluted with water and extracted with DCM (50 mL). The aqueous layer was concentrated under high vacuum to get a suspension and filtered to provide 300 mg of yellow solid. The crude material was purified by chromatography through a RediSep®, Teledyne ISCO, Lincoln, Nebr., pre-packed silica gel column (40 g) eluting with a gradient of 2% to 10% 2M NH₃/MeOH in DCM to provide N-(4-(3-(2-methyl-9H-purin-6-yl)pyridin-2-ylamino)phenyl)acetamide (20 mg, 0.056 mmol, 27.4% yield) as a yellow solid. MS (ESI positive ion) m/z 360 (M+H)⁺. ¹H NMR (400 MHz, d6-DMSO) δ 13.75 (s, 1H); 10.03 (d, J=7.43 Hz, 1H); 9.81 (s, 1H); 8.18 (s, 1H); 7.77 (d, J=7.82 Hz, 2H); 7.52 (d, J=8.22 Hz, 2H); 6.85-6.92 (m, 1H); 2.74 (s, 3H); 2.02 (s, 3H).

Example 103

N-(6-methoxypyridin-3-yl)-3-(2-methyl-9H-purin-6-yl)-5-(4-(methylsulfonyl)benzyl)pyridin-2-amine

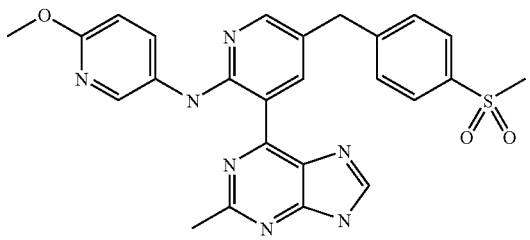

Step 1. (6-fluoropyridin-3-yl)(4-(methylthio)phenyl)methanol

Magnesium turnings (0.214 g, 8.79 mmol) in a minimal amount of THF were treated with 1,2-dibromoethane (50 µL, cat.) and the mixture was allowed to stand until effervescence was observed (1 min) A solution of 4-bromothioanisole (Aldrich) (1.705 g, 8.39 mmol) in THF (20 mL) was added dropwise and the mixture stirred for 2 h, occasionally heating to gentle reflux with a heat gun, to give a cloudy pale yellow solution. The resulting Grignard solution was added dropwise over 10 min to a solution of 6-fluoronicotinaldehyde (Frontier Scientific) (1.000 g, 7.99 mmol) in THF (10 mL) cooled in a dry ice/acetone bath. The mixture was stirred at −78° C. for 30 min, and then quenched by dropwise addition of 2 N aqueous HCl (9.0 mL, 2 equiv.). The cooling bath was removed and the mixture was allowed to warm to ambient temperature. The mixture was extracted into EtOAc from water, dried (MgSO₄) and concentrated to give (6-fluoropyridin-3-yl)(4-(methylthio)phenyl)methanol (1.856 g, 7.44 mmol, 93% yield) as a colorless oil. ¹H NMR (400 MHz, d6-DMSO) δ 8.23 (s, 1H); 7.87 (t, J=8.22 Hz, 1H); 7.32 (d, J=8.02 Hz, 2H); 7.22 (d, J=7.82 Hz, 2H); 7.11 (d, J=8.41 Hz, 1H); 6.11 (br. s., 1H); 5.78 (s, 1H); 2.44 (s, 3H). m/z (ESI, +ve) 250.0 (M+H)⁺.

Step 2. 2-fluoro-5-(4-(methylthio)benzyl)pyridine

A solution of (6-fluoropyridin-3-yl)(4-(methylthio)phenyl)methanol (1.716 g, 6.88 mmol) in DCM (3.0 mL) was treated with trifluoroacetic acid (2.56 mL, 34.4 mmol) resulting in a green solution. The mixture was stirred for 5 min, and then triethylsilane (3.30 mL, 20.65 mmol) was added dropwise. The green color dissipated rapidly to give a straw colored solution, and a brief exotherm was observed (DCM started refluxing). The mixture was stirred for 30 min, and then extracted into DCM from saturated aqueous NaHCO₃. The DCM extracts were dried (MgSO₄) and purified by flash chromatography (5% to 7.5% EtOAc/hexane) to give 2-fluoro-5-(4-(methylthio)benzyl)pyridine (89% over 2 steps) as a colorless oil. ¹H NMR (400 MHz, d6-DMSO) δ 8.15 (s, 1H); 7.81 (t, J=8.22 Hz, 1H); 7.20 (s, 4H); 7.10 (d, J=8.41 Hz, 1H); 3.94 (s, 2H); 2.44 (s, 3H). ¹⁹F NMR (376 MHz, d6-DMSO) δ-72.37 (s, 1 F). m/z (ESI, +ve ion) 234.0 (M+H)⁺.

Step 3. 3-(5,5-dimethyl-1,3,2-dioxaborinan-2-yl)-2-fluoro-5-(4-(methylthio)benzyl)pyridine and 2-fluoro-5-(4-(methylthio)benzyl)pyridin-3-ylboronic acid A solution of LiTMP was generated by dropwise addition of n-BuLi (1.6 M in hexanes) (1.653 mL, 2.65 mmol) to a solution of 2,2,6,6-tetramethylpiperidine (0.467 mL, 2.77 mmol) in THF (5.0 mL) cooled in an ice bath. The resulting yellow solution was stirred for 15 min. A solution of 2-fluoro-5-(4-(methylthio)benzyl)pyridine (561.1 mg, 2.405 mmol) and triisopropyl borate (1.110 mL, 4.81 mmol) in THF (5.0 mL) was cooled in a dry ice/acetone cooling bath and treated dropwise with the above LiTMP solution over 15 min to give a yellow/brown solution. The solution was stirred at −78° C. for 1 h, and then slowly allowed to warm up to 20° C. over 1.5 h. The solution was stirred for an additional 1 h at 20° C. before being quenched with acetic acid (159 mg, 2.65 mmol). The resulting pale yellow solution was treated with 2,2-dimethylpropane-1,3-diol (376 mg, 3.61 mmol) and stirred at 20° C. After 1 h, LCMS indicated 12% unreacted starting material and 88% of a peak whose m/z corresponded to 2-fluoro-5-(4-(methylthio)benzyl)pyridin-3-ylboronic acid. No change was observed by LCMS after stirring at 20° C. for a further 16 h. The mixture was extracted into EtOAc (2×) from water. LCMS indicated product was still in the aqueous layer, so the aqueous layer was acidified (2 M HCl) and re-extracted with EtOAc (2×) (successfully, by LCMS). The combined organic extracts were dried (MgSO₄) and concentrated to give an orange oil which partially crystallized (about 1.1 g). The mixture was re-extracted into EtOAc from 2 M aqueous HCl, dried (MgSO₄) and concentrated to give crude product (775 mg) as an orange/brown oil which crystallized to give a waxy solid. ¹H NMR and ¹⁹F NMR indicated 12% unreacted SM, 63% 3-(5,5-dimethyl-1,3,2-dioxaborinan-2-yl)-2-fluoro-5-(4-(methylthio)benzyl)pyridine (63.5% yield) and 24%

2-fluoro-5-(4-(methylthio)benzyl)pyridin-3-ylboronic acid (24.5% yield). The crude product was used in the next step with further purification.

3-(5,5-dimethyl-1,3,2-dioxaborinan-2-yl)-2-fluoro-5-(4-(methylthio)benzyl)pyridine: $^1$H NMR (400 MHz, d6-DMSO) δ 8.20 (d, J=2.15 Hz, 1H); 7.91-7.96 (m, 1H); 7.18-7.22 (m, 4H); 3.93 (s, 2H); 3.74 (s, 4H); 2.44 (s, 3H); 0.94 (s, 6H). $^{19}$F NMR (377 MHz, d6-DMSO) δ-63.56 (s, 1 F).

2-fluoro-5-(4-(methylthio)benzyl)pyridin-3-ylboronic acid: $^1$H NMR (400 MHz, d6-DMSO) δ 8.40 (br. s., 2H); 8.11-8.14 (m, 1H); 7.85-7.90 (m, 1H); 7.20 (s, 4H); 3.91 (s, 2H); 2.44 (s, 3H). $^{19}$F NMR (377 MHz, d6-DMSO) δ-64.21 (s, 1 F).

Step 4. 6-(2-fluoro-5-(4-(methylthio)benzyl)pyridin-3-yl)-2-methyl-9-(tetrahydro-2H-pyran-2-yl)-9H-purine A mixture of the boronate ester product mix from Step 3 (549.5 mg; about 1.74 mmol), 6-chloro-2-methyl-9-(tetrahydro-2H-pyran-2-yl)-9H-purine (463 mg, 1.831 mmol), potassium acetate (513 mg, 5.23 mmol) and bis(di-tert-butyl(4-dimethylaminophenyl)phosphine)dichloropalladium(II) (Aldrich, St. Louis, Mo.) (30.9 mg, 0.044 mmol) was placed under a $N_2$ atmosphere and suspended in EtOH (15 mL) and water (3.0 mL). The mixture was degassed and placed under $N_2$, and heated at 80° C. for 2.5 h. The mixture was cooled, extracted into EtOAc from saturated aqueous $NaHCO_3$, dried ($MgSO_4$) and concentrated. The product was purified by flash chromatography (50% EtOAc/hexane) to give 6-(2-fluoro-5-(4-(methylthio)benzyl)pyridin-3-yl)-2-methyl-9-(tetrahydro-2H-pyran-2-yl)-9H-purine (532.9 mg, 1.185 mmol, 68.0% yield) as a white foam. $^1$H NMR (400 MHz, CDCl$_3$) δ 8.28 (s, 1H); 8.18 (s, 1H); 8.14 (d, J=8.61 Hz, 1H); 7.16-7.23 (m, 2H); 7.09-7.16 (m, 2H); 5.84 (d, J=10.37 Hz, 1H); 4.18 (br. s., 1H); 4.04 (s, 2H); 3.82 (t, J=11.15 Hz, 1H); 2.88 (s, 3H); 2.45 (s, 3H); 2.05-2.22 (m, 3H); 1.63-1.89 (m, 3H). $^{19}$F NMR (376 MHz, CDCl$_3$) δ-70.26 (s, 1 F). m/z (ESI, +ve ion) 450.0 (M+H)$^+$.

Step 5. 6-(2-fluoro-5-(4-(methylsulfonyl)benzyl)pyridin-3-yl)-2-methyl-9-(tetrahydro-2H-pyran-2-yl)-9H-purine A solution of 6-(2-fluoro-5-(4-(methylthio)benzyl)pyridin-3-yl)-2-methyl-9-(tetrahydro-2H-pyran-2-yl)-9H-purine (532.9 mg, 1.185 mmol) in DCM (10 mL) was cooled in an ice bath and treated with mCPBA (Aldrich, St. Louis, Mo.; dried) (532 mg, 3.08 mmol) added portionwise over 5 min. The mixture was stirred for 2.5 h, after which time LCMS indicated completion. Saturated aqueous $NaHCO_3$ containing excess sodium thiosulfate (2 mL) was added and the mixture stirred for 10 min. The product was then extracted into EtOAc from saturated aqueous $NaHCO_3$, dried ($MgSO_4$) and concentrated to give 6-(2-fluoro-5-(4-(methylsulfonyl)benzyl)pyridin-3-yl)-2-methyl-9-(tetrahydro-2H-pyran-2-yl)-9H-purine (559.7 mg, 1.162 mmol, 98% yield) as a pale yellow foam. $^1$H NMR (400 MHz, CDCl$_3$) δ 8.28 (s, 1H); 8.22 (s, 1H); 8.16 (d, J=8.61 Hz, 1H); 7.88 (d, J=7.63 Hz, 2H); 7.43 (d, J=7.83 Hz, 2H); 5.84 (d, J=10.17 Hz, 1H); 4.12-4.24 (m, 3H); 3.82 (t, J=11.35 Hz, 1H); 3.03 (s, 3H); 2.88 (s, 3H); 1.98-2.23 (m, 3H); 1.63-1.90 (m, 3H). $^{19}$F NMR (376 MHz, CDCl$_3$) δ-69.21 (s, 1 F). m/z (ESI, +ve ion) 481.9 (M+H)$^+$.

Step 6. N-(6-methoxypyridin-3-yl)-3-(2-methyl-9-(tetrahydro-2H-pyran-2-yl)-9H-purin-6-yl)-5-(4-(methylsulfonyl)benzyl)pyridin-2-amine 6-methoxy-3-aminopyridine (Aldrich) (214 μL, 2.00 mmol) was dissolved in THF (1.80 mL) and cooled in an ice bath. LiHMDS (2.00 mL, 1.0 M in THF, 2.0 mmol) was added dropwise over 5 min. The resulting dark brown solution was stirred for 30 min prior to use. A solution of 6-(2-fluoro-5-(4-(methylsulfonyl)benzyl)pyridin-3-yl)-2-methyl-9-(tetrahydro-2H-pyran-2-yl)-9H-purine (92.6 mg, 0.192 mmol) in THF (1.0 mL) was cooled in an ice bath and treated dropwise with 0.85 mL of the above anilide solution (0.425 mmol) over 15 min, resulting in a deep red solution. 85% Conversion to desired product was observed by LCMS (215 nm) 5 min after completion of addition in a clean reaction. The reaction was checked after another 30 min and appeared to have stalled, so an additional 0.20 mL of the anilide solution was added dropwise. The mixture was stirred for 10 min, and then quenched by the addition of water (0.2 mL). The product was extracted into EtOAc from saturated aqueous $NaHCO_3$, dried ($MgSO_4$), concentrated and purified by flash chromatography (50% to 60% to 70% EtOAc/hexane) to give N-(6-methoxypyridin-3-yl)-3-(2-methyl-9-(tetrahydro-2H-pyran-2-yl)-9H-purin-6-yl)-5-(4-(methylsulfonyl)benzyl)pyridin-2-amine (94.5 mg, 0.161 mmol, 84% yield) as a dark yellow foam. $^1$H NMR (400 MHz, CDCl$_3$) δ 12.44 (s, 1H); 9.61 (d, J=2.15 Hz, 1H); 8.41 (d, J=2.74 Hz, 1H); 8.25 (s, 1H); 8.19 (dd, J=8.80, 2.74 Hz, 1H); 8.14 (d, J=2.15 Hz, 1H); 7.86 (d, J=8.22 Hz, 2H); 7.47 (d, J=8.02 Hz, 2H); 6.77 (d, J=8.80 Hz, 1H); 5.86 (d, J=10.37 Hz, 1H); 4.20 (d, J=11.35 Hz, 1H); 4.10 (s, 2H); 3.95 (s, 3H); 3.77-3.85 (m, 1H); 3.01 (s, 3H); 2.89 (s, 3H); 1.97-2.23 (m, 3H); 1.62-1.91 (m, 3H). m/z (ESI, +ve ion) 586.1 (M+H)$^+$.

Step 7. N-(6-methoxypyridin-3-yl)-3-(2-methyl-9H-purin-6-yl)-5-(4-(methylsulfonyl)benzyl)pyridin-2-amine N-(6-methoxypyridin-3-yl)-3-(2-methyl-9-(tetrahydro-2H-pyran-2-yl)-9H-purin-6-yl)-5-(4-(methylsulfonyl)benzyl)pyridin-2-amine (94.5 mg, 0.161 mmol) was suspended in a mixture of 2 M aqueous HCl (2.0 mL) and water (6 mL). The mixture was heated at reflux for 1 h and then allowed to cool and stand at room temperature over the weekend. The resulting solid was collected by filtration, washed with water, and dried to give N-(6-methoxypyridin-3-yl)-3-(2-methyl-9H-purin-6-yl)-5-(4-(methylsulfonyl)benzyl)pyridin-2-amine hydrochloride (75.7 mg, 0.141 mmol, 87% yield) as a yellow solid. $^1$H NMR (400 MHz, d6-DMSO) δ 12.50 (br. s., 1H); 9.66 (br. s., 1H); 8.60 (s, 1H); 8.52 (d, J=2.54 Hz, 1H); 8.26 (d, J=1.96 Hz, 1H); 8.16 (dd, J=8.80, 2.74 Hz, 1H); 7.87 (d, J=8.22 Hz, 2H); 7.57 (d, J=8.22 Hz, 2H); 6.85 (d, J=8.80

Hz, 1H); 4.13 (s, 2H); 3.85 (s, 3H); 3.17 (s, 3H); 2.84 (s, 3H). m/z (ESI, +ve ion) 502.0 (M+H)+.

Example 104

N-(3-(2-methyl-9H-purin-6-yl)-5-(4-(methylsulfonyl)benzyl)pyridin-2-yl)-1H-indazol-4-amine

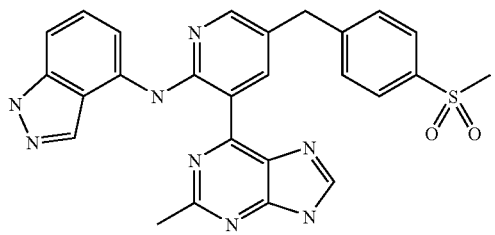 [SMILES: Cc1nc(-c2cc(Cc3ccc(S(C)(=O)=O)cc3)cnc2Nc2cccc3[nH]ncc23)c2nc[nH]c2n1]

Step 1. N-(3-(2-methyl-9-(tetrahydro-2H-pyran-2-yl)-9H-purin-6-yl)-5-(4-(methylsulfonyl)benzyl)pyridin-2-yl)-1-(tetrahydro-2H-pyran-2-yl)-1H-indazol-4-amine A mixture of 6-(2-fluoro-5-(4-(methylsulfonyl)benzyl)pyridin-3-yl)-2-methyl-9-(tetrahydro-2H-pyran-2-yl)-9H-purine (78.5 mg, 0.163 mmol) and 1-(tetrahydro-2H-pyran-2-yl)-1H-indazol-4-amine (45.5 mg, 0.209 mmol) in THF (1.0 mL) was cooled in an ice/salt bath and treated dropwise with LiHMDS (0.627 mL of a 1.0 M solution in THF). The mixture was stirred for 20 min and then quenched with water (0.1 mL). The mixture was stirred for 3 min and then extracted into EtOAc from saturated aqueous NaHCO$_3$. The EtOAc extracts were dried (MgSO$_4$) and concentrated to give a dark yellow solid (128 mg). This was taken on to the next step without further purification.

Step 2. N-(3-(2-methyl-9H-purin-6-yl)-5-(4-(methylsulfonyl)benzyl)pyridin-2-yl)-1H-indazol-4-amine A solution of N-(3-(2-methyl-9-(tetrahydro-2H-pyran-2-yl)-9H-purin-6-yl)-5-(4-(methylsulfonyl)benzyl)pyridin-2-yl)-1-(tetrahydro-2H-pyran-2-yl)-1H-indazol-4-amine (111 mg, 0.164 mmol) in DCM (3.0 mL) was treated with TFA (1.0 mL) and allowed to stand for 2 h. The mixture was concentrated, azeotroped with toluene, purified by prep HPLC, and the pure fractions were concentrated and triturated with MeOH to give pure N-(3-(2-methyl-9H-purin-6-yl)-5-(4-(methylsulfonyl)benzyl)pyridin-2-yl)-1H-indazol-4-amine trifluoroacetate (8.4 mg, 0.013 mmol, 8.22% yield) as an orange crystalline solid. $^1$H NMR (400 MHz, d6-DMSO) δ 13.12 (br. s., 1H); 12.61 (br. s., 1H); 9.68 (br. s., 1H); 8.63 (s, 1H); 8.36 (d, J=2.15 Hz, 1H); 8.26 (s, 1H); 8.08 (d, J=7.63 Hz, 1H); 7.87 (d, J=8.22 Hz, 2H); 7.59 (d, J=8.22 Hz, 2H); 7.31 (t, J=8.02 Hz, 1H); 7.16 (d, J=8.41 Hz, 1H); 4.17 (s, 2H); 3.16 (s, 3H); 2.93 (s, 3H). m/z (ESI, +ve ion) 511.0 (M+H)+.

Examples 105 and 106

N-(5-(3-(2-methyl-9H-purin-6-yl)-5-(4-(methylsulfonyl)benzyl)pyridin-2-ylamino)pyridin-2-yl)acetamide (105) and N5-(3-(2-methyl-9H-purin-6-yl)-5-(4-(methylsulfonyl)benzyl)pyridin-2-yl)pyridine-2,5-diamine (106)

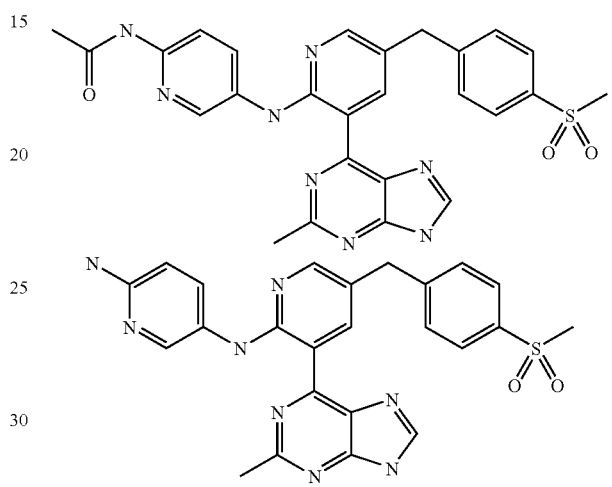

Step 1. N-(5-(3-(2-methyl-9-(tetrahydro-2H-pyran-2-yl)-9H-purin-6-yl)-5-(4-(methylsulfonyl)benzyl)pyridin-2-ylamino)pyridin-2-yl)acetamide A mixture of 6-(2-fluoro-5-(4-(methylsulfonyl)benzyl)pyridin-3-yl)-2-methyl-9-(tetrahydro-2H-pyran-2-yl)-9H-purine (59.9 mg, 0.124 mmol) and N-(5-aminopyridin-2-yl)acetamide (Aldrich, St. Louis, Mo.) (18.80 mg, 0.124 mmol) was dissolved/suspended in benzene (1.0 mL) in a 25 mL flask, frozen and lyophilized. The solid was dissolved in THF (1.0 mL), cooled in an ice bath, and treated dropwise with LiHMDS (0.50 mL of a 1.0 M solution in THF, 0.50 mmol) to give a deep red solution. The solution was stirred for 3 h. The mixture was poured into saturated aqueous NaHCO$_3$ and extracted in DCM followed by EtOAc. The combined organic extracts were dried (MgSO$_4$), filtered and concentrated to give a yellow solid (50 mg) which was soluble in DCM but poorly soluble in EtOAc. The product was purified by flashing through a plug of silica eluting with 5% MeOH/DCM to give N-(5-(3-(2-methyl-9-(tetrahydro-2H-pyran-2-yl)-9H-purin-6-yl)-5-(4-(methylsulfonyl)benzyl)pyridin-2-ylamino)pyridin-2-yl)acetamide (24.5 mg, 0.040 mmol, 32.1% yield) as a yellow solid. $^1$H NMR (400 MHz, CDCl$_3$) δ 12.71 (br. s., 1H); 9.64 (s, 1H); 8.69 (br. s., 1H); 8.13-8.31 (m, 5H); 7.87 (d, J=7.63 Hz, 2H); 7.48 (d, J=7.63 Hz, 2H); 5.86 (d, J=10.37 Hz, 1H); 4.20 (d, J=11.35 Hz, 1H); 3.83 (t, J=11.35 Hz, 1H) 4.12 (s, 2H); 3.02 (s, 3H); 2.92 (s, 3H); 2.22 (s, 3H); 1.94-2.18 (m, 3H); 1.60-1.91 (m, 3H). m/z (ESI, +ve ion) 613.1 (M+H)+.

Step 2. N-(5-(3-(2-methyl-9H-purin-6-yl)-5-(4-(methylsulfonyl)benzyl)pyridin-2-ylamino)pyridin-2-yl)acetamide and N5-(3-(2-methyl-9H-purin-6-yl)-5-(4-(methylsulfonyl)benzyl)pyridin-2-yl)pyridine-2,5-diamine A solution of N-(5-(3-(2-methyl-9-(tetrahydro-2H-pyran-2-yl)-9H-purin-6-yl)-5-(4-(methylsulfonyl)benzyl)pyridin-2-ylamino)pyridin-2-yl)acetamide (24.5 mg, 0.040 mmol) in DCM (3 mL) was treated with TFA (0.5 mL). The reaction was monitored by LCMS and, upon completion, some hydrolyzed acetamide was also observed. The mixture was concentrated and purified by prep HPLC to give N5-(3-(2-methyl-9H-purin-6-yl)-5-(4-(methylsulfonyl)benzyl)pyridin-2-yl)pyridine-2,5-diamine bis(trifluoroacetate) (3.2 mg, 4.48 µmol, 11.20% yield) followed by N-(5-(3-(2-methyl-9H-purin-6-yl)-5-(4-(methylsulfonyl)benzyl)pyridin-2-ylamino)pyridin-2-yl)acetamide trifluoroacetate (8.4 mg, 0.013 mmol, 32.7% yield).

N5-(3-(2-methyl-9H-purin-6-yl)-5-(4-(methylsulfonyl)benzyl)pyridin-2-yl)pyridine-2,5-diamine bis(trifluoroacetate): $^1$H NMR (400 MHz, CD$_3$OD) δ 9.63 (br. s., 1H); 8.92 (br. s., 1H); 8.43 (s, 1H); 8.25 (br. s., 1H); 8.00 (d, J=9.78 Hz, 1H); 7.92 (d, J=7.82 Hz, 2H); 7.60 (d, J=7.83 Hz, 2H); 7.07 (d, J=9.39 Hz, 1H); 4.19 (br. s., 2H); 3.11 (s, 3H); 2.90 (s, 3H). m/z (ESI, +ve ion) 487.0 (M+H)$^+$.

N-(5-(3-(2-methyl-9H-purin-6-yl)-5-(4-(methylsulfonyl)benzyl)pyridin-2-ylamino)pyridin-2-yl)acetamide trifluoroacetate: $^1$H NMR (400 MHz, d8-THF) δ 12.99 (br. s., 1H); 12.46 (br. s., 1H); 10.00 (br. s., 1H); 9.61 (br. s., 1H); 8.82 (br. s., 1H); 8.34 (s, 1H); 8.27 (br. s., 3H); 7.88 (d, J=8.02 Hz, 2H); 7.58 (d, J=7.82 Hz, 2H); 4.17 (s, 2H); 2.99 (s, 3H); 2.92 (s, 3H); 2.11 (s, 3H). m/z (ESI, +ve ion) 529.0 (M+H)$^+$.

Example 107

N-(3-(6-amino-2-methylpyrimidin-4-yl)pyridin-4-yl)-1H-indazol-4-amine

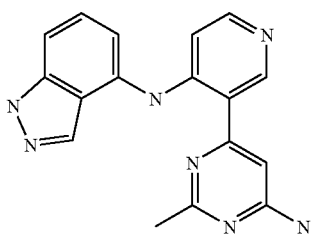 [SMILES: Cc1nc(N)cc(-c2cnccc2Nc2cccc3[nH]ncc23)n1]

Step 1.
6-(4-chloropyridin-3-yl)-2-methylpyrimidin-4-amine

A mixture of 4-chloro-3-(4,4,5,5-tetramethyl-1,3,2-dioxaborolan-2-yl)pyridine (239 mg, 998 µmol, Combi-Blocks, Inc., San Diego, Calif.), 6-chloro-2-methylpyrimidin-4-amine (143 mg, 998 µmol), dichloro 1,1'-bis(diphenylphosphino)ferrocene palladium (II) (81 mg, 100 µmol), cesium carbonate (160 µl, 1996 µmol) in dioxane (2 mL) and water (0.5 mL) was stirred at 100° C. for 10 min. The mixture was cooled down to room temperature. The reaction mixture was diluted with saturated NH$_4$Cl (5 mL) and extracted with EtOAc (2×30 mL). The organic extract was washed with saturated NaCl (5 mL), dried over Na$_2$SO$_4$, filtered, concentrated in vacuo and the residue was purified by silica gel chromatography, eluting with THF to give 6-(4-chloropyridin-3-yl)-2-methylpyrimidin-4-amine (32 mg, 15% yield). $^1$H NMR (300 MHz, MeOH) δ 8.66 (s, 1H); 8.57 (d, J=5.41 Hz, 1H); 7.66 (d, J=5.26 Hz, 1H); 6.64 (s, 1H); 2.04 (s, 3H). m/z (ESI, +ve ion) 221 (M+H)$^+$.

Step 2. N-(3-(6-amino-2-methylpyrimidin-4-yl)pyridin-4-yl)-1H-indazol-4-amine

A glass microwave reaction vessel was charged with 6-(4-chloropyridin-3-yl)-2-methylpyrimidin-4-amine (22 mg, 100 µmol), 1H-indazol-4-amine (27 mg, 199 µmol, Bionet) and EtOH (1 mL). The reaction mixture was stirred and heated in a Smith Synthesizer® microwave reactor (Personal Chemistry, Inc., Upssala, Sweden) at 160° C. for 30 min. The reaction mixture was diluted with saturated NaHCO$_3$ (2 mL) and extracted with EtOAc (3×20 mL). The organic extract was washed with saturated NaCl (2 mL), dried over Na$_2$SO$_4$, filtered, concentrated and the residue was purified by silica gel chromatography, eluting with 10% MeOH/CH$_2$Cl$_2$/1% NH$_4$OH to give N-(3-(6-amino-2-methylpyrimidin-4-yl)pyridin-4-yl)-1H-indazol-4-amine (14 mg, 44% yield). $^1$H NMR (300 MHz, CD$_3$OD) δ 8.71 (s, 1H); 8.19 (d, J=6.14 Hz, 1H); 7.34-7.53 (m, 2H); 7.29 (d, J=7.02 Hz, 1H); 7.18 (d, J=6.28 Hz, 1H); 6.90 (s, 1H); 2.59 (s, 3H). m/z (ESI, +ve ion) 318 (M+H)$^+$.

Examples 108 and 109

N-(6-(4-(1H-indol-4-ylamino)pyridin-3-yl)-2-methylpyrimidin-4-yl)acetamide (108) and N-(3-(6-amino-2-methylpyrimidin-4-yl)pyridin-4-yl)-1H-indol-4-amine (109)

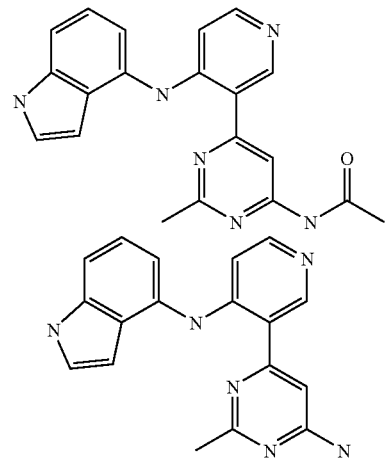

Step 1.
N-(6-chloro-2-methylpyrimidin-4-yl)acetamide

A mixture of 6-chloro-2-methylpyrimidin-4-amine (500 mg, 3483 µmol), pyridine (568 µl, 6965 µmol), and acetic anhydride (493 µl, 5224 µmol) was stirred at 40° C. for 24 h. The mixture was cooled down to rt. The reaction mixture was diluted with saturated NaHCO$_3$ (30 mL) and extracted with EtOAc (2×40 mL). The organic extract was washed with saturated NaCl (about2 mL), dried over Na$_2$SO$_4$, filtered, concentrated in vacuo and the residue was purified by silica gel chromatography eluting with 40% EtOAc/hexanes to give N-(6-chloro-2-methylpyrimidin-4-yl)acetamide (458 mg, 71% yield). $^1$H NMR (300 MHz, CDCl$_3$) δ 8.03 (s, 1H); 7.90 (s, 1H); 2.58 (s, 3H); 2.23 (s, 3H). m/z (ESI, +ve ion) 186 (M+H)$^+$.

Step 2. N-(6-(4-chloropyridin-3-yl)-2-methylpyrimidin-4-yl)acetamide

A mixture of N-(6-chloro-2-methylpyrimidin-4-yl)acetamide (228 mg, 1228 μmol), 3-chloro-4-(4,4,5,5-tetramethyl-1,3,2-dioxaborolan-2-yl)pyridine (294 mg, 1228 μmol, Combi-Blocks, Inc., San Diego, Calif.), dichloro 1,1'-bis(diphenylphosphino)ferrocene palladium (II) (100 mg, 123 μmol), cesium carbonate (197 μl, 2457 μmol), dioxane (4 mL) and water (0.5 mL) was stirred at 100° C. for 30 min. The mixture was cooled down to room temperature. The reaction mixture was diluted with saturated NH$_4$Cl (5 mL) and extracted with EtOAc (2×30 mL). The organic extract was washed with saturated NaCl (5 mL), dried over Na$_2$SO$_4$, filtered, concentrated in vacuo and the residue was purified by silica gel chromatography eluting with EtOAc to give N-(6-(3-chloropyridin-4-yl)-2-methylpyrimidin-4-yl)acetamide (102 mg, 31.6% yield). $^1$H NMR (300 MHz, CDCl$_3$) δ 8.80 (s, 1H); 8.56 (d, J=5.41 Hz, 1H); 8.34 (s, 1H); 7.94 (s, 1H); 7.44 (d, J=5.26 Hz, 1H); 2.69 (s, 3H); 2.25 (s, 3H). m/z (ESI, +ve ion) 263 (M+H)$^+$.

Step 3. N-(6-(4-(1H-indol-4-ylamino)pyridin-3-yl)-2-methylpyrimidin-4-yl)acetamide and N-(3-(6-amino-2-methylpyrimidin-4-yl)pyridin-4-yl)-1H-indol-4-amine A mixture of N-(6-(4-chloropyridin-3-yl)-2-methylpyrimidin-4-yl)acetamide (50 mg, 190 μmol) and 4-aminoindole (50 mg, 381 μmol, Alfa Aesar) in EtOH (2 mL) was stirred and heated in a Smith Synthesizer® microwave reactor (Personal Chemistry, Inc., Upssala, Sweden) at 160° C. for 30 min. The reaction mixture was diluted with saturated NaHCO$_3$ (3 mL) and extracted with EtOAc (3×20 mL). The organic extract was washed with saturated NaCl (2 mL), dried over Na$_2$SO$_4$, filtered, concentrated in vacuo and the residue was purified by silica gel chromatography eluting with 10% MeOH/EtOAc to give N-(6-(4-(1H-indol-4-ylamino)pyridin-3-yl)-2-methylpyrimidin-4-yl)acetamide (24 mg, 35% yield) and N-(3-(6-amino-2-methylpyrimidin-4-yl)pyridin-4-yl)-1H-indol-4-amine (22 mg, 37% yield).

N-(6-(4-(1H-indol-4-ylamino)pyridin-3-yl)-2-methylpyrimidin-4-yl)acetamide: $^1$H NMR (300 MHz, CDCl$_3$) δ 11.60 (s, 1H); 8.94 (s, 1H); 8.56 (s, 1H); 8.33 (s, 1H); 8.21 (d, J=5.85 Hz, 1H); 7.14 (s, 2H); 6.60 (s, 1H); 3.49 (s, 2H); 2.69 (s, 3H); 2.27 (s, 3H). m/z (ESI, +ve ion) 359 (M+H)$^+$.

N-(3-(6-amino-2-methylpyrimidin-4-yl)pyridin-4-yl)-1H-indol-4-amine: $^1$H NMR (300 MHz, d6-DMSO) δ 11.69 (s, 1H); 11.27 (s, 1H); 8.65 (s, 1H); 8.16 (d, J=5.85 Hz, 1H); 7.38 (s, 1H); 7.14-7.26 (m, 2H); 7.10 (t, J=7.75 Hz, 1H); 6.93-7.05 (m, 3H); 6.45 (s, 1H) 6.78 (s, 1H); 2.47 (s, 3H). m/z (ESI, +ve ion) 317 (M+H)$^+$.

Example 110

N-(3-(2-methyl-9H-purin-6-yl)pyridin-4-yl)-1H-indazol-4-amine

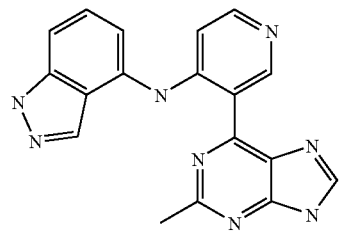 [SMILES: Cc1nc(-c2cnccc2Nc2cccc3[nH]ncc23)c2nc[nH]c2n1]

Step 1. 6-(4-chloropyridin-3-yl)-2-methyl-9-(tetrahydro-2H-pyran-2-yl)-9H-purine A mixture of 6-chloro-2-methyl-9-(tetrahydro-2H-pyran-2-yl)-9H-purine (506 mg, 2.004 mmol), 4-chloro-3-(4,4,5,5-tetramethyl-1,3,2-dioxaborolan-2-yl)pyridine (480 mg, 2.004 mmol, Combi-Blocks, Inc., San Diego, Calif.), dichloro 1,1'-bis(diphenylphosphino)ferrocene palladium (II) (164 mg, 0.200 mmol), and cesium carbonate (0.321 mL, 4.01 mmol) in dioxane (4 mL) and water (0.5 mL) was stirred at 100° C. for 30 min. The mixture was cooled down to room temperature. The reaction mixture was diluted with water (5 mL) and extracted with EtOAc (2×30 mL), The organic extract was washed with saturated NaCl (2 mL) and dried over Na$_2$SO$_4$. The solution was filtered and concentrated in vacuo to give a yellow solid. The crude material was adsorbed onto a plug of silica gel and purified by flash chromatography eluting with 10% MeOH in CH$_2$Cl$_2$ to provide 6-(4-chloropyridin-3-yl)-2-methyl-9-(tetrahydro-2H-pyran-2-yl)-9H-purine (98 mg, 15% yield) as light-yellow glass. $^1$H NMR (300 MHz, CDCl$_3$) δ 8.83 (s, 1H); 8.61 (d, J=5.41 Hz, 1H); 8.27 (s, 1H); 7.50 (d, J=5.41 Hz, 1H); 5.87 (d, J=10.08 Hz, 1H); 4.20 (d, J=11.25 Hz, 1H); 3.84 (t, J=11.33 Hz, 1H); 3.48 (d, J=5.41 Hz, 1H); 2.90 (s, 3H); 1.99-2.29 (m, 3H); 1.64-1.95 (m, 3H). m/z (ESI, +ve ion) 330 (M+H)$^+$.

Step 2

N-(3-(2-methyl-9H-purin-6-yl)pyridin-4-yl)-1H-indazol-4-amine

A glass microwave reaction vessel was charged with 6-(4-chloropyridin-3-yl)-2-methyl-9-(tetrahydro-2H-pyran-2-yl)-9H-purine (33 mg, 0.100 mmol) and 1H-indazol-4-amine (26.6 mg, 0.200 mmol, Bionet Research, Cornwall, UK) in Ethanol (1 mL) and a drop of 5 N HCl. The reaction mixture was stirred and heated in a Emrys Optmizer microwave reactor (Personal Chemistry, Biotage AB, Inc., Upssala, Sweden) at 160° C. for 30 min. The reaction mixture was diluted with saturated NaHCO$_3$ (5 mL) and extracted with EtOAc (2×30 mL). The combined organic extracts were washed with saturated NaCl (3 mL) and dried over Na$_2$SO$_4$. The solution was filtered and concentrated in vacuo to give a yellow solid. The crude material was adsorbed onto a plug of silica gel and purified by chromatography through a silica gel column, eluting with 10% MeOH/CH$_2$Cl$_2$ to provide N-(3-(2-methyl-9H-purin-6-yl)pyridin-4-yl)-1H-indazol-4-amine (23 mg, 67% yield) as yellow solid. $^1$H NMR (300 MHz, d6-DMSO) δ 13.27 (s, 1H); 12.54 (s, 1H); 10.22 (s, 1H); 8.64 (s, 1H); 8.30 (d, J=5.85 Hz, 1H); 8.16 (s, 1H); 7.30-7.43 (m, 3H); 7.18 (d, J=6.87 Hz, 1H); 2.82 (s, 3H). m/z (ESI, +ve ion) 343 (M+H)$^+$.

Example 111

6-methoxy-N-(3-(2-methyl-9H-purin-6-yl)pyridin-4-yl)pyridin-3-amine

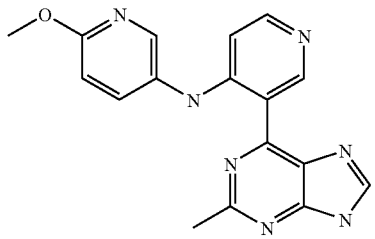 [SMILES: COc1ccc(Nc2ccncc2-c2nc(C)nc3[nH]cnc23)cn1]

A glass microwave reaction vessel was charged with 6-(4-chloropyridin-3-yl)-2-methyl-9-(tetrahydro-2H-pyran-2-yl)-9H-purine (36 mg, 0.109 mmol) and 5-amino-2-methoxypyridine (27.1 mg, 0.218 mmol, Aldrich) in ethanol (1 mL) and a drop of 5 N HCl. The reaction mixture was stirred and heated in a Emrys Optmizer microwave reactor (Personal Chemistry, Biotage AB, Inc., Upssala, Sweden) at 160° C. for 30 min. The reaction mixture was diluted with NaHCO$_3$ (5 mL) and extracted with EtOAc (2×30 mL). The organic extract was washed with saturated NaCl (3 mL) and dried over Na$_2$SO$_4$. The solution was filtered and concentrated in vacuo to give a yellow solid. The crude material was adsorbed onto a plug of silica gel and purified by chromatography through a silica gel column eluting with 10% MeOH/CH$_2$Cl$_2$ to provide 6-methoxy-N-(3-(2-methyl-9H-purin-6-yl)pyridin-4-yl)pyridin-3-amine (21 mg, 58% yield) as a yellow solid. $^1$H NMR (300 MHz, CD$_3$OD) δ 9.98 (s, 1H); 8.42 (s, 1H); 8.07-8.24 (m, 2H); 7.72 (d, J=8.92 Hz, 1H); 6.85-7.00 (m, 2H); 3.96 (s, 3H); 2.83 (s, 3H). m/z (ESI, +ve ion) 334 (M+H)$^+$.

Example 112

N-(3-(6-amino-2-methylpyrimidin-4-yl)pyrazin-2-yl)-1H-indazol-4-amine

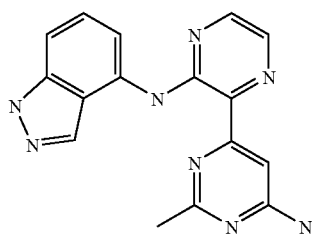 [SMILES: Cc1nc(N)cc(-c2nccnc2Nc2cccc3[nH]ncc23)n1]

Step 1. 4-(3-chloropyrazin-2-yl)-2-methyl-6-(methylthio)pyrimidine

A mixture of 2,3-dichloropyrazine (0.034 mL, 0.228 mmol, Aldrich, St. Louis, Mo.), 2-methyl-4-(methylthio)-6-(tributylstannyl)pyrimidine (98 mg, 0.228 mmol) and tetrakis(triphenylphosphine)palladium (26.4 mg, 0.023 mmol, Strem Chemicals, Inc., Newburyport, Mass.) in toluene (2 mL) was stirred at 110° C. for 48 h. The solvent was removed in vacuo and the residue was purified by silica gel chromatography eluting with 20% EtOAc/CH$_2$Cl$_2$ to give 4-(3-chloropyrazin-2-yl)-2-methyl-6-(methylthio)pyrimidine (12 mg, 21% yield). $^1$H NMR (300 MHz, CDCl$_3$) δ 8.63 (d, J=2.05 Hz, 1H); 8.47 (d, J=2.19 Hz, 1H); 7.44 (s, 1H); 2.77 (s, 3H); 2.56 (s, 3H). m/z (ESI, +ve ion) 253 (M+H)$^+$.

Step 2. N-(3-(2-methyl-6-(methylthio)pyrimidin-4-yl)pyrazin-2-yl)-1H-indazol-4-amine A glass microwave reaction vessel was charged with 4-(3-chloropyrazin-2-yl)-2-methyl-6-(methylthio)pyrimidine (60 mg, 0.237 mmol) and 1H-indazol-4-amine (63.2 mg, 0.475 mmol, Bionet) in ethanol (2 mL). The reaction mixture was stirred and heated in an Emrys Optmizer microwave reactor (Personal Chemistry, Biotage AB, Inc., Upssala, Sweden) at 160° C. for 30 min. The reaction mixture was diluted with saturated NaHCO$_3$ (5 mL) and extracted with EtOAc (2×30 mL). The combined organic extracts were washed with saturated NaCl (5 mL) and dried over Na$_2$SO$_4$. The solution was filtered and concentrated in vacuo to give a yellow solid. The crude material was adsorbed onto a plug of silica gel and purified by chromatography through a silica gel column eluting with 40% EtOAc/hexanes to provide N-(3-(2-methyl-6-(methylthio)pyrimidin-4-yl)pyrazin-2-yl)-1H-indazol-4-amine (38 mg, 46% yield) as yellow solid. $^1$H NMR (300 MHz, d8-dioxane) δ 12.49 (s, 1H); 11.68 (s, 1H); 10.69 (s, 1H); 8.24 (s, 2H); 8.10 (d, J=7.60 Hz, 1H); 8.02 (s, 1H); 7.23 (t, J=7.97 Hz, 1H); 7.07 (d, J=8.18 Hz, 1H); 2.83 (s, 3H); 2.53 (s, 3H). m/z (ESI, +ve ion) 350 (M+H)$^+$.

Step 3. N-(3-(2-methyl-6-(methylsulfinyl)pyrimidin-4-yl)pyrazin-2-yl)-1H-indazol-4-amine A mixture of N-(3-(2-methyl-6-(methylthio)pyrimidin-4-yl)pyrazin-2-yl)-1H-indazol-4-amine (20 mg, 0.057 mmol) and 3-chloroperoxybenzoic acid (14.82 mg, 0.086 mmol, Aldrich, St. Louis, Mo.—77%) in dioxane (1 mL) was stirred at room temperature for 2 h. LCMS showed no starting material left. The reaction mixture was used for the next step of reaction without purification.

Step 4. N-(3-(6-amino-2-methylpyrimidin-4-yl)pyrazin-2-yl)-1H-indazol-4-amine

The mixture from Step 3 was treated with ammonia (30% in water) in a sealed tube. The mixture was stirred at 100° C. overnight. The solvent was removed in vacuo and the residue was purified by silica gel chromatography eluting with 50% THF/CH$_2$Cl$_2$ to give N-(3-(6-amino-2-methylpyrimidin-4-yl)pyrazin-2-yl)-1H-indazol-4-amine (7 mg, 39% yield) as a yellow solid. $^1$H NMR (300 MHz, d6-DMSO) δ 13.17 (s, 1H); 12.95 (s, 1H); 8.37 (d, J=2.05 Hz, 1H); 8.25 (s, 1H); 8.18

(d, J=2.05 Hz, 1H); 8.10 (d, J=7.75 Hz, 1H); 7.45 (s, 1H); 7.33 (t, J=8.11 Hz, 1H); 7.19 (d, J=7.31 Hz, 1H); 2.65 (s, 3H). m/z (ESI, +ve ion) 319 (M+H)+.

Example 113

N-(6-methoxypyridin-3-yl)-3-(2-methyl-9H-purin-6-yl)quinolin-2-amine

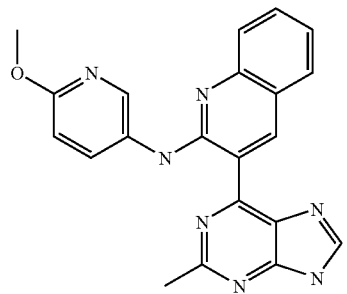 [SMILES: COc1ccc(Nc2nc3ccccc3cc2-c2nc(C)nc3[nH]cnc23)cn1]

Step 1: 2-chloro-3-(2-methyl-9-(tetrahydro-2H-pyran-2-yl)-9H-purin-6-yl)quinoline A mixture of 6-chloro-2-methyl-9-(tetrahydro-2H-pyran-2-yl)-9H-purine (0.55 g, 2.18 mmol), 2-chloroquinolin-3-ylboronic acid (0.90 g, 4.35 mmol, Aldrich, St. Louis, Mo.) and tetrakis(triphenylphosphine)palladium(0) (0.13 g, 0.11 mmol, Strem Chemicals, Inc., Newburyport, Mass.) in dioxane (3 mL) and water (1 mL) was sealed and purged with argon for several minutes. The reaction mixture was stirred at 90° C. for 6 h and then allowed to cool to room temperature. The organic phase was taken and the solvents removed under vacuum. Purification of the crude reaction mixture by silica gel chromatography (0 to 3% MeOH/CH$_2$Cl$_2$) provided the title compound as an orange solid. m/z (ESI, +ve ion) 380 (M+H)+.

Step 2: N-(6-methoxypyridin-3-yl)-3-(2-methyl-9-(tetrahydro-2H-pyran-2-yl)-9H-purin-6-yl)quinolin-2-amine A solution of 5-amino-2-methoxypyridine (50 mg, 0.41 mmol, Aldrich, St. Louis, Mo.) and 2-chloro-3-(2-methyl-9-(tetrahydro-2H-pyran-2-yl)-9H-purin-6-yl)quinoline (77 mg, 0.20 mmol) in dioxane (4 mL) at 0° C. was treated with LiHMDS (1 M in THF, 0.51 mL, 0.51 mmol). The reaction mixture was stirred at 0° C. for 1 h and 18 h at room temperature. Then an additional amount of LiHMDS (1 M in THF, 0.51 mL, 0.51 mmol) was added and the reaction mixture stirred at room temperature for 2 h. The reaction was quenched by the addition of MeOH (2 mL) and the solvents were removed under vacuum. Purification of the crude reaction mixture by silica gel chromatography (2 to 3% MeOH/CH$_2$Cl$_2$) provided the title compound as a dark orange solid. m/z (ESI, +ve ion) 468 (M+H)+.

Step 3: N-(6-methoxypyridin-3-yl)-3-(2-methyl-9H-purin-6-yl)quinolin-2-amine

A solution of N-(6-methoxypyridin-3-yl)-3-(2-methyl-9-(tetrahydro-2H-pyran-2-yl)-9H-purin-6-yl)quinolin-2-amine (21 mg, 0.045 mmol) in DCM (1 mL) and TFA (1 mL) was stirred at room temperature for 30 min. The solvents were removed under vacuum and the residue was dissolved in DCM, washed with saturated aqueous sodium bicarbonate (2×), water, and brine. The organic layer was dried over Na$_2$SO$_4$. The crude material was adsorbed onto a plug of silica gel and purified by silica gel chromatography (1 to 4% MeOH/CH$_2$Cl$_2$). The title compound was obtained as a yellow solid. m/z (ESI, +ve ion) 384 (M+H)+. $^1$H NMR (400 MHz, d6-DMSO) δ 13.71 (s, 1H); 12.73 (s, 1H); 10.24 (s, 1H); 8.86 (s, 1H); 8.71 (s, 1H); 8.40 (d, J=7.0 Hz, 1H); 7.92 (d, J=7.8 Hz, 1H); 7.71 (br. s., 2H); 7.37 (br. s., 1H); 6.92 (d, J=8.6 Hz, 1H); 3.88 (s, 3H); 2.91 (s, 3H).

Example 114

4-(3-(6-methoxypyridin-3-ylamino)pyrazin-2-yl)-6-methyl-1,3,5-triazin-2-amine

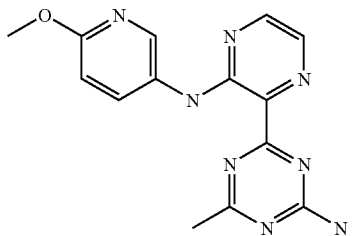 [SMILES: COc1ccc(Nc2nccnc2-c2nc(C)nc(N)n2)cn1]

Step 1: 2-iodo-4-methyl-6-(methylthio)-1,3,5-triazine

A mixture of 2-chloro-4-methyl-6-(methylthio)-1,3,5-triazine (2110 mg, 12.01 mmol) and 67% hydriodic acid solution (2.260 mL, 30.0 mmol) in CH$_2$Cl$_2$ (4 mL) was stirred at room temperature for 3 h. The solid was filtered off and washed with CH$_2$Cl$_2$. The solid was treated with sat. aqueous NaHCO$_3$ (10 mL) and extracted with EtOAc (2×30 mL). The organic extract was washed with saturated NaCl (10 mL) and dried over Na$_2$SO$_4$. The solution was filtered and concentrated in vacuo to give crude product as a yellow solid. This was purified by silica gel chromatography eluting with 50% CH$_2$Cl$_2$/hexanes to give 2-iodo-4-methyl-6-(methylthio)-1,3,5-triazine (2.1 g, 7.86 mmol, 65.4% yield). $^1$H NMR (300 MHz, CDCl$_3$) δ 2.53 (s, 3H); 2.51 (s, 3H). m/z (ESI, +ve ion) 267.8 (M+H)+.

Step 2: 2-fluoro-3-(tributylstannyl)pyrazine n-Butyllithium (1.6 M in hexane, 0.920 mL, 10.99 mmol) was added to 2,2,6,6-tetramethylpiperidine (2.024 mL, 11.99 mmol) in THF (50 mL) at −50° C. Following the addition, the mixture was stirred at 0° C. for 20 min and then cooled down to −100° C. 2-Fluoropyrazine (980 mg, 9.99 mmol) in THF (5 mL) was then added dropwisely. After 5 min, tributyltin chloride (3.25 mL, 11.99 mmol) in THF (5 mL) was added dropwisely and stirring was continued for 1 h. The reaction was quenched with a solution of 35% aqueous HCl, ethanol, THF (1:4:5) and allowed to warm to 20° C. The reaction mixture was diluted with sat. aqueous NaHCO$_3$ (30 mL) and extracted with EtOAc (2×50 mL). The organic extract was washed with saturated aqueous NaCl (30 mL) and dried over Na$_2$SO$_4$. The solution was filtered and concentrated in vacuo to give the crude material as orange oil. The crude material was adsorbed onto a plug of silica gel and purified by chromatography through a silica gel column eluting with 50% CH$_2$Cl$_2$/hexanes to give 2-fluoro-3-(tributylstannyl)pyrazine (2980 mg, 7.70 mmol, 77% yield) as colorless oil. $^1$H NMR (300 MHz, CDCl$_3$) δ 8.63 (s, 1H); 8.02 (s, 1H); 1.46-1.68 (m, 6H); 1.12-1.42 (m, 12H); 0.88 (t, J=7.23 Hz, 9H).

Step 3: 2-(3-fluoropyrazin-2-yl)-4-methyl-6-(methylthio)-1,3,5-triazine

A mixture of 2-iodo-4-methyl-6-(methylthio)-1,3,5-triazine (100 mg, 0.374 mmol), 2-fluoro-3-(tributylstannyl)pyrazine (145 mg, 0.374 mmol) and tetrakis(triphenylphosphine)palladium(0) (43.3 mg, 0.037 mmol) in toluene (2 mL) was stirred at 110° C. for 18 h. The mixture was cooled down to room temperature. The solvent was removed in vacuo and the residue was purified by silica gel chromatography eluting with 40% EtOAc/hexanes to give 2-(3-fluoropyrazin-2-yl)-4-methyl-6-(methylthio)-1,3,5-triazine (42 mg, 0.177 mmol, 47.3% yield). $^1$H NMR (300 MHz, CDCl$_3$) δ 8.73 (s, 1H); 8.42 (s, 1H); 2.73 (s, 3H); 2.65 (s, 3H). m/z (ESI, +ve ion) 238.0 (M+H)$^+$.

Step 4: N-(6-methoxypyridin-3-yl)-3-(4-methyl-6-(methylthio)-1,3,5-triazin-2-yl)pyrazin-2-amine A glass microwave reaction vessel was charged with 2-(3-fluoropyrazin-2-yl)-4-methyl-6-(methylthio)-1,3,5-triazine (61 mg, 0.257 mmol), 5-amino-2-methoxypyridine (0.038 mL, 0.309 mmol), copper(I) iodide (5 mg, 0.026 mmol) and N,N-diisopropylethylamine (0.089 mL, 0.514 mmol) in dioxane (1 mL). The reaction mixture was stirred and heated at 100° C. for 24 h. The solvent was removed in vacuo and the residue was purified by silica gel chromatography eluting with 20% EtOAc/CH$_2$Cl$_2$ to give N-(6-methoxypyridin-3-yl)-3-(4-methyl-6-(methylthio)-1,3,5-triazin-2-yl)pyrazin-2-amine (67 mg, 0.196 mmol, 76% yield) as a yellow solid. $^1$H NMR (300 MHz, CDCl$_3$) δ 11.34 (s, 1H); 8.36 (d, J=1.90 Hz, 1H); 8.26 (s, 2H); 8.00 (dd, J=8.99, 2.56 Hz, 1H); 6.80 (d, J=8.77 Hz, 1H); 3.96 (s, 3H); 2.77 (s, 3H); 2.68 (s, 3H). m/z (ESI, +ve ion) 342.0 (M+H)$^+$.

Step 5: 4-(3-(6-methoxypyridin-3-ylamino)pyrazin-2-yl)-6-methyl-1,3,5-triazin-2-amine A glass microwave reaction vessel was charged with N-(6-methoxypyridin-3-yl)-3-(4-methyl-6-(methylthio)-1,3,5-triazin-2-yl)pyrazin-2-amine (44 mg, 0.129 mmol) and ammonia (1 mL, 37% in water) in dioxane (1 mL). The reaction mixture was stirred and heated at 100° C. for 16 h. The solvent was removed in vacuo and the residue was purified by silica gel chromatography eluting with 10% MeOH/EtOAc to give 4-(3-(6-methoxypyridin-3-ylamino)pyrazin-2-yl)-6-methyl-1,3,5-triazin-2-amine (34 mg, 0.110 mmol, 85% yield) as a yellow solid. $^1$H NMR (300 MHz, CDCl$_3$) δ 11.83 (s, 1H); 8.37 (d, J=2.05 Hz, 1H); 8.24 (s, 1H); 8.20 (s, 1H); 8.04 (dd, J=8.92, 2.48 Hz, 1H); 6.80 (d, J=8.77 Hz, 1H); 5.71 (s, 2H); 3.95 (s, 3H); 2.62 (s, 3H). m/z (ESI, +ve ion) 311.0 (M+H)$^+$.

Example 115

4-(3-(6-methoxypyridin-3-ylamino)pyridin-4-yl)-6-methyl-1,3,5-triazin-2-amine

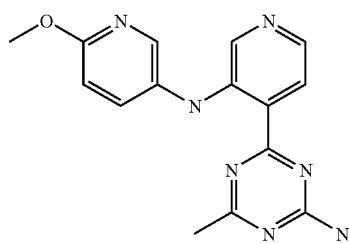 [SMILES: COc1ccc(Nc2cnccc2-c2nc(C)nc(N)n2)cn1]

Step 1: 4-iodo-N,N-bis(4-methoxybenzyl)-6-methyl-1,3,5-triazin-2-amine

A mixture of 4-chloro-N,N-bis(4-methoxybenzyl)-6-methyl-1,3,5-triazin-2-amine (1020 mg, 2.65 mmol) and 67% hydriodic acid solution (0.499 mL, 6.63 mmol) in CH$_2$Cl$_2$ (10 mL) was stirred at room temperature for 19 h. The reaction mixture was diluted with NaHCO$_3$ (30 mL) and extracted with EtOAc (2×40 mL). The organic extract was washed with saturated NaCl (20 mL) and dried over Na$_2$SO$_4$. The solution was filtered and concentrated in vacuo to give the crude material as a light-yellow solid. The solvent was removed in vacuo and the residue was purified by silica gel chromatography eluting with 50% CH$_2$Cl$_2$/hexanes to give 4-iodo-N,N-bis(4-methoxybenzyl)-6-methyl-1,3,5-triazin-2-amine (826 mg, 1.734 mmol, 65.4% yield) as a mixture of product and starting material (3:1).

Step 2: 4-(3-chloropyridin-4-yl)-N,N-bis(4-methoxybenzyl)-6-methyl-1,3,5-triazin-2-amine A mixture of 4-iodo-N,N-bis(4-methoxybenzyl)-6-methyl-1,3,5-triazin-2-amine (306 mg, 0.642 mmol), 3-chloropyridine-4-boronic acid (101 mg, 0.642 mmol), dichloro 1,1'-bis(diphenylphosphino)ferrocene palladium (II) (52.4 mg, 0.064 mmol) and cesium carbonate (251 mg, 0.770 mmol) in dioxane (6 mL) and water (1 mL) was stirred at 90° C. for 1 h. The mixture was cooled down to room temperature. The reaction mixture was diluted with water (20 mL) and extracted with EtOAc (2×30 mL). The organic extract was washed with saturated NaCl (10 mL) and dried over Na$_2$SO$_4$. The solution was filtered and concentrated in vacuo to give the crude material as a light-yellow glass. The crude product was purified by silica gel chromatography eluting with 50% EtOAc/hexanes to give the product as a glass. $^1$H NMR (300 MHz, CDCl$_3$) δ 8.69 (s, 1H); 8.58 (d, J=4.97 Hz, 1H); 7.71 (d, J=4.82 Hz, 1H); 7.10-7.26 (m, 4H); 6.86 (t, J=8.77 Hz, 4H); 4.80 (s, 4H); 3.81 (s, 3H); 3.80 (s, 3H); 2.56 (s, 3H). m/z (ESI, +ve ion) 462.0 (M+H)$^+$.

Step 3: N,N-bis(4-methoxybenzyl)-4-(3-(6-methoxypyridin-3-ylamino)pyridin-4-yl)-6-methyl-1,3,5-triazin-2-amine A glass microwave reaction vessel was charged with 4-(3-chloropyridin-4-yl)-N,N-bis(4-methoxybenzyl)-6-methyl-1,3,5-triazin-2-amine (32 mg, 0.069 mmol), 5-amino-2-methoxypyridine (0.017 mL, 0.139 mmol), Brett precatalyst ((SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium) (2 mg) and sodium 2-methylpropan-2-olate (16.64 mg, 0.173 mmol) and dioxane (1 mL). The reaction mixture was stirred and heated in an oil bath at 100° C. for 16 h. The reaction mixture was diluted with saturated NH$_4$Cl (10 mL) and extracted with EtOAc (2×20 mL). The organic extract was washed with saturated NaCl (5 mL) and dried over Na$_2$SO$_4$. The solution was filtered and concentrated in vacuo to give the crude material as orange oil. The crude product was purified by silica gel chromatography eluting with 20% THF/CH$_2$Cl$_2$ to give N,N-bis(4-methoxybenzyl)-4-(3-(6-methoxypyridin-3-ylamino)pyridin-4-yl)-6-methyl-1,3,5-triazin-2-amine (9 mg, 0.016 mmol, 24% yield). $^1$H NMR (300 MHz, CDCl$_3$) δ 10.32 (s, 1H); 8.49-8.68 (m, 1H); 8.33 (s, 1H); 8.24 (d, J=5.12 Hz, 2H); 8.03 (d, J=5.12 Hz, 2H); 7.95 (d, J=1.61 Hz, 1H); 7.38 (dd, J=8.70, 2.41 Hz, 2H); 7.21 (d, J=8.33 Hz, 2H); 7.14 (d, J=8.33 Hz, 2H); 6.98 (s, 1H); 6.87 (d, J=8.33 Hz, 2H); 6.79

(d, J=8.33 Hz, 2H); 6.72 (d, J=8.77 Hz, 1H); 4.86 (s, 2H); 4.79 (s, 2H); 3.81 (s, 3H); 3.76 (s, 3H); 2.56 (s, 3H). m/z (ESI, +ve ion) 550.0 (M+H)$^+$.

Step 4: 4-(3-(6-methoxypyridin-3-ylamino)pyridin-4-yl)-6-methyl-1,3,5-triazin-2-amine A glass microwave reaction vessel was charged with N,N-bis(4-methoxybenzyl)-4-(3-(6-methoxypyridin-3-ylamino)pyridin-4-yl)-6-methyl-1,3,5-triazin-2-amine (7 mg, 0.013 mmol) and trifluoromethane sulfonic acid (3.38 µL, 0.038 mmol) in TFA (0.1 mL). The reaction mixture was stirred and heated in an oil bath at room temperature for 2 h. The reaction mixture was diluted with saturated NaHCO$_3$ (5 mL) and extracted with EtOAc (2×20 mL). The organic extract was washed with saturated NaCl (5 mL) and dried over Na$_2$SO$_4$. The solution was filtered and concentrated in vacuo to give the crude material as a light-yellow solid. The crude product was purified by silica gel chromatography eluting with EtOAc to give 4-(3-(6-methoxypyridin-3-ylamino)pyridin-4-yl)-6-methyl-1,3,5-triazin-2-amine (3.2 mg, 10.35 µmol, 81% yield). $^1$H NMR (300 MHz, CDCl$_3$) δ 10.38 (s, 1H); 8.38 (s, 1H); 8.24 (d, J=5.12 Hz, 1H); 8.13 (s, 1H); 8.07 (d, J=4.97 Hz, 1H); 7.58 (dd, J=8.77, 2.05 Hz, 1H); 6.81 (d, J=8.77 Hz, 1H); 5.41 (s, 2H); 3.96 (s, 3H); 2.54 (s, 3H). m/z (ESI, +ve ion) 310.0 (M+H)$^+$.

Example 116

6-(3-(6-methoxypyridin-3-ylamino)pyrazin-2-yl)-2-methylpyrimidin-4-amine

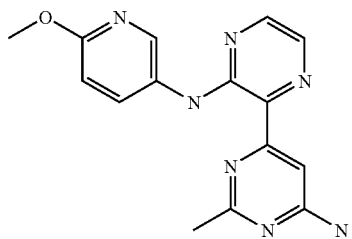 [SMILES: COc1ccc(Nc2nccnc2-c2cc(N)nc(C)n2)cn1]

Step 1: 4-(3-fluoropyrazin-2-yl)-2-methyl-6-(methylthio)pyrimidine

A glass microwave reaction vessel was charged with 4-iodo-2-methyl-6-(methylthio)pyrimidine (266 mg, 1.000 mmol), 2-fluoro-3-(tributylstannyl)pyrazine (387 mg, 1.000 mmol) and tetrakis(triphenylphosphine)palladium(0) (116 mg, 0.100 mmol) in toluene (3 mL). The reaction mixture was stirred and heated in an Emrys Optimizer microwave reactor (Personal Chemistry, Biotage AB, Inc., Upssala, Sweden) at 140° C. for 40 min. The solvent was removed in vacuo and the residue was purified by silica gel chromatography eluting with 40% EtOAc/hexanes to give 4-(3-fluoropyrazin-2-yl)-2-methyl-6-(methylthio)pyrimidine (28 mg, 0.119 mmol, 12% yield). $^1$H NMR (300 MHz, CDCl$_3$) δ 8.68 (s, 1H); 8.32 (s, 1H); 7.67 (s, 1H); 2.79 (s, 3H); 2.63 (s, 3H). m/z (ESI, +ve ion) 237.1 (M+H)$^+$.

Step 2: N-(6-methoxypyridin-3-yl)-3-(2-methyl-6-(methylthio)pyrimidin-4-yl)pyrazin-2-amine A glass microwave reaction vessel was charged with 4-(3-fluoropyrazin-2-yl)-2-methyl-6-(methylthio)pyrimidine (21 mg, 0.089 mmol), 5-amino-2-methoxypyridine (0.022 mL, 0.178 mmol), copper(I) iodide (2 mg, 8.89 µmol) and N-ethyl-N-isopropylpropan-2-amine (22.97 mg, 0.178 mmol) in dioxane (1 mL). The reaction mixture was stirred and heated in an oil bath at 100° C. for 24 h. The reaction mixture was diluted with water (5 mL) and extracted with EtOAc (2×20 mL). The organic extract was washed with saturated NaCl (5 mL) and dried over Na$_2$SO$_4$. The solution was filtered and concentrated in vacuo to give the crude material as a light-yellow solid. The crude product was purified by silica gel chromatography, eluting with 30% EtOAc/hexanes to give N-(6-methoxypyridin-3-yl)-3-(2-methyl-6-(methylthio)pyrimidin-4-yl)pyrazin-2-amine (14 mg, 0.041 mmol, 46.3% yield). $^1$H NMR (300 MHz, CDCl$_3$) δ 12.20 (s, 1H); 8.42 (d, J=2.05 Hz, 1H); 8.22 (s, 1H); 8.18 (s, 1H); 8.09 (dd, J=8.92, 2.63 Hz, 1H); 8.02 (d, J=1.90 Hz, 1H); 6.79 (d, J=8.77 Hz, 1H); 3.95 (s, 3H); 2.78 (s, 3H); 2.63 (s, 3H). m/z (ESI, +ve ion) 341.0 (M+H)$^+$.

Step 3: N-(6-methoxypyridin-3-yl)-3-(2-methyl-6-(methylsulfinyl)pyrimidin-4-yl)pyrazin-2-amine A glass microwave reaction vessel was charged with N-(6-methoxypyridin-3-yl)-3-(2-methyl-6-(methylthio)pyrimidin-4-yl)pyrazin-2-amine (11 mg, 0.032 mmol) and 3-chloroperoxybenzoic acid (11.15 mg, 0.065 mmol) in dioxane (1 mL). The reaction mixture was stirred at room temperature for 1 h. The reaction mixture was used for the next step reaction without purification.

Step 4: 6-(3-(6-methoxypyridin-3-ylamino)pyrazin-2-yl)-2-methylpyrimidin-4-amine A glass microwave reaction vessel was charged with N-(6-methoxypyridin-3-yl)-3-(2-methyl-6-(methylsulfinyl)pyrimidin-4-yl)pyrazin-2-amine (11.40 mg, 0.032 mmol) (crude product from the last step) and ammonium hydroxide, 28.0-30.0% (0.5 mL, 12.84 mmol) in dioxane (1 mL). The reaction mixture was stirred and heated in an oil bath at 100° C. for 2 h. The solvent was removed in vacuo and the residue was purified by silica gel chromatography eluting with 80% EtOAc/hexanes to give 6-(3-(6-methoxypyridin-3-ylamino)pyrazin-2-yl)-2-methylpyrimidin-4-amine (8.2 mg, 0.027 mmol, 83% yield). $^1$H NMR (300 MHz, CDCl$_3$) δ 12.46 (s, 1H); 8.42 (s, 1H); 8.15 (s, 1H); 8.10 (dd, J=8.77, 2.48 Hz, 1H); 7.98 (d, J=1.32 Hz, 1H); 7.47 (s, 1H); 6.78 (d, J=8.62 Hz, 1H); 4.95 (s, 2H); 3.95 (s, 3H); 2.64 (s, 3H). m/z (ESI, +ve ion) 310.1 (M+H)$^+$.

Example 117

4-(4-(6-methoxypyridin-3-ylamino)pyrimidin-5-yl)-6-methyl-1,3,5-triazin-2-amine

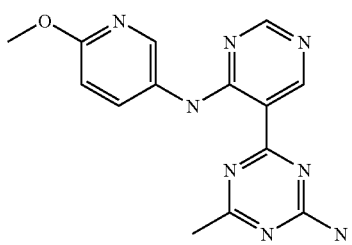 [SMILES: COc1ccc(Nc2ncncc2-c2nc(C)nc(N)n2)cn1]

Step 1: 5-bromo-N-(6-methoxypyridin-3-yl)pyrimidin-4-amine

A mixture of 5-bromopyrimidin-4-amine (344 mg, 1.977 mmol), 6-methoxypyridin-3-ylboronic acid (907 mg, 5.93 mmol), N,N-diisopropylethylamine (1.376 mL, 7.91 mmol) and anhydrous copper (II) acetate (539 mg, 2.97 mmol) in dichloromethane (2 mL) was stirred at room temperature overnight. The solid was filtered off and washed with $CH_2Cl_2$. The solvent was removed in vacuo and the residue was purified by silica gel chromatography eluting with 50% EtOAc/hexanes to give 5-bromo-N-(6-methoxypyridin-3-yl)pyrimidin-4-amine (36 mg, 0.128 mmol, 6.48% yield). $^1H$ NMR (300 MHz, $CDCl_3$) δ 8.55 (s, 1H); 8.46 (s, 1H); 8.28 (s, 1H); 7.85 (dd, J=8.77, 2.48 Hz, 1H); 6.98 (s, 1H); 6.80 (d, J=8.92 Hz, 1H); 3.95 (s, 3H). m/z (ESI, +ve ion) 281.0 (M+H)$^+$.

Step 2: N-(6-methoxypyridin-3-yl)-5-(4-methyl-6-(methylthio)-1,3,5-triazin-2-yl)pyrimidin-4-amine A glass microwave reaction vessel was charged with 5-bromo-N-(6-methoxypyridin-3-yl)pyrimidin-4-amine (23 mg, 0.082 mmol), 2-methyl-4-(methylthio)-6-(tributylstannyl)-1,3,5-triazine (35.2 mg, 0.082 mmol), copper(I) iodide (15 mg, 0.082 mmol), cesium fluoride (206 mg, 0.82 mmol) and tetrakis(triphenylphosphine)palladium(0) (9.45 mg, 8.18 μmol) and THF (1 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (10 mL) and extracted with EtOAc (2×30 mL). The organic extract was washed with saturated NaCl (5 mL) and dried over $Na_2SO_4$. The solution was filtered and concentrated in vacuo to give the crude product as a light-yellow solid. The crude product was purified by silica gel chromatography eluting with 60% EtOAc/hexanes to give N-(6-methoxypyridin-3-yl)-5-(4-methyl-6-(methylthio)-1,3,5-triazin-2-yl)pyrimidin-4-amine (15 mg, 0.044 mmol, 53.7% yield). $^1H$ NMR (300 MHz, $CDCl_3$) δ 11.58 (s, 1H); 9.65 (s, 1H); 8.74 (s, 1H); 8.35 (d, J=2.19 Hz, 1H); 8.07 (dd, J=8.84, 2.56 Hz, 1H); 6.82 (d, J=8.92 Hz, 1H); 3.96 (s, 3H); 2.67 (s, 3H); 2.65 (s, 3H). m/z (ESI, +ve ion) 342.0 (M+H)$^+$.

Step 3: 4-(4-(6-methoxypyridin-3-ylamino)pyrimidin-5-yl)-6-methyl-1,3,5-triazin-2-amine A glass microwave reaction vessel was charged with N-(6-methoxypyridin-3-yl)-5-(4-methyl-6-(methylthio)-1,3,5-triazin-2-yl)pyrimidin-4-amine (14 mg, 0.041 mmol), ammonium hydroxide, 28.0-30.0% (0.5 mL, 12.84 mmol) and dioxane (1 mL). The reaction mixture was stirred and heated at reflux in an oil bath for 1 h. The solid formed was filtered off and washed with EtOAc to give 4-(4-(6-methoxypyridin-3-ylamino)pyrimidin-5-yl)-6-methyl-1,3,5-triazin-2-amine (10 mg, 0.032 mmol, 79% yield). $^1H$ NMR (300 MHz, d6-DMSO) δ 11.78 (s, 1H); 9.37 (s, 1H); 8.65 (s, 1H); 8.48 (s, 1H); 8.10 (d, J=8.33 Hz, 1H); 7.94 (s, 1H); 7.79 (s, 1H); 6.88 (d, J=8.77 Hz, 1H); 3.87 (s, 3H); 2.43 (s, 3H). m/z (ESI, +ve ion) 311.1 (M+H)$^+$.

Example 118

5-(4-amino-6-methyl-1,3,5-triazin-2-yl)-N4-(6-methoxypyridin-3-yl)pyrimidine-2,4-diamine

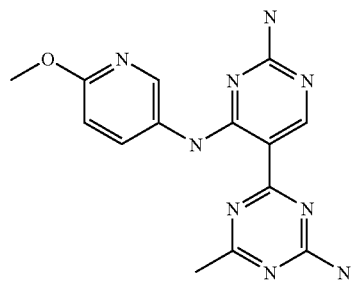 [SMILES: COc1ccc(Nc2nc(N)ncc2-c2nc(C)nc(N)n2)cn1]

Step 1: 2-chloro-5-iodo-N-(6-methoxypyridin-3-yl)pyrimidin-4-amine

A mixture of 2,4-dichloro-5-iodopyrimidine (274 mg, 0.997 mmol), 5-amino-2-methoxypyridine (0.247 mL, 1.994 mmol), N,N-diisopropylethylamine (0.347 mL, 1.994 mmol) and copper(I) iodide (38 mg, 0.199 mmol) in dioxane (2 mL) was stirred at 100° C. for 3 h. The mixture was cooled down to room temperature. The reaction mixture was diluted with water (10 mL) and extracted with EtOAc (2×30 mL). The organic extract was washed with saturated NaCl (10 mL) and dried over $Na_2SO_4$. The solution was filtered and concentrated in vacuo to give the crude material as orange oil. The crude product was purified by silica gel chromatography eluting with 40% EtOAc/hexanes to give 2-chloro-5-iodo-N-(6-methoxypyridin-3-yl)pyrimidin-4-amine (242 mg, 0.667 mmol, 67.0% yield). $^1H$ NMR (300 MHz, $CDCl_3$) δ 8.44 (s, 1H); 8.28 (d, J=1.90 Hz, 1H); 7.83 (dd, J=8.84, 2.56 Hz, 1H); 7.01 (s, 1H); 6.81 (d, J=8.77 Hz, 1H); 3.96 (s, 3H). m/z (ESI, +ve ion) 362.9 (M+H)$^+$.

Step 2: 2-chloro-N-(6-methoxypyridin-3-yl)-5-(4-methyl-6-(methylthio)-1,3,5-triazin-2-yl)pyrimidin-4-amine A glass microwave reaction vessel was charged with 2-chloro-5-iodo-N-(6-methoxypyridin-3-yl)pyrimidin-4-amine (181 mg, 0.499 mmol), 2-methyl-4-(methylthio)-6-(tributylstannyl)-1,3,5-triazine (215 mg, 0.499 mmol), copper(I) iodide (19 mg, 0.100 mmol), cesium fluoride (250 mg, 0.998 mmol), tetrakis(triphenylphosphine)palladium(0) (57.7 mg, 0.050 mmol) and dioxane (3 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (20 mL) and extracted with EtOAc (2×30 mL). The organic extract was washed with saturated NaCl (10 mL) and dried over $Na_2SO_4$. The solution was filtered and concentrated in vacuo to give the crude material as a yellow solid. The crude product was purified by silica gel chromatography eluting with 40% EtOAc/hexanes to give 2-chloro-N-(6-methoxypyridin-3-yl)-5-(4-methyl-6-(methylthio)-1,3,5-triazin-2-yl)pyrimidin-4-amine (87 mg, 0.231 mmol, 46.4% yield). ¹H NMR (300 MHz, CDCl₃) δ 11.82 (s, 1H); 9.48 (s, 1H); 8.37 (s, 1H); 8.08 (dd, J=9.28, 1.97 Hz, 1H); 6.83 (d, J=9.06 Hz, 1H); 3.96 (s, 3H); 2.67 (s, 3H); 2.64 (s, 3H). m/z (ESI, +ve ion) 376.0 (M+H)⁺.

Step 3: 5-(4-amino-6-methyl-1,3,5-triazin-2-yl)-N4-(6-methoxypyridin-3-yl)pyrimidine-2,4-diamine A glass microwave reaction vessel was charged with 2-chloro-N-(6-methoxypyridin-3-yl)-5-(4-methyl-6-(methylthio)-1,3,5-triazin-2-yl)pyrimidin-4-amine (32 mg, 0.085 mmol), ammonia (0.5 mL, 23.11 mmol) (30% in water) and dioxane (1 mL). The reaction mixture was stirred and heated in an oil bath at 100° C. for 16 h. The solvent was removed in vacuo and the residue was purified by silica gel chromatography eluting with 5% MeOH/EtOAc to give 5-(4-amino-6-methyl-1,3,5-triazin-2-yl)-N4-(6-methoxypyridin-3-yl)pyrimidine-2,4-diamine (21 mg, 0.065 mmol, 76% yield). ¹H NMR (300 MHz, d6-DMSO) δ 11.87 (s, 1H); 9.09 (s, 1H); 8.74 (s, 1H); 8.20 (d, J=9.35 Hz, 1H); 7.61 (s, 1H); 7.46 (s, 1H); 7.01 (s, 2H); 6.81 (d, J=8.04 Hz, 1H); 3.85 (s, 3H); 2.35 (s, 3H). m/z (ESI, +ve ion) 326.1 (M+H)⁺.

Example 119

4-(2-methoxy-4-(6-methoxypyridin-3-ylamino)pyrimidin-5-yl)-6-methyl-1,3,5-triazin-2-amine

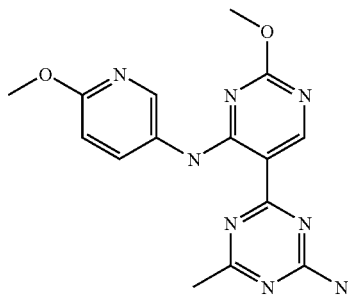 [SMILES: COc1ccc(Nc2nc(OC)ncc2-c2nc(C)nc(N)n2)cn1]

Step 1: 5-iodo-2-methoxy-N-(6-methoxypyridin-3-yl)pyrimidin-4-amine

A glass microwave reaction vessel was charged with 2-chloro-5-iodo-N-(6-methoxypyridin-3-yl)pyrimidin-4-amine (181 mg, 0.499 mmol), sodium methoxide (0.5 M solution in methanol, 0.043 mL, 0.749 mmol) and methanol (1 mL). The reaction mixture was stirred and heated in a Emrys Optimizer microwave reactor (Personal Chemistry, Biotage AB, Inc., Upssala, Sweden) at 140° C. for 15 min. The reaction mixture was diluted with water (10 mL) and extracted with EtOAc (2×20 mL). The organic extract was washed with saturated NaCl (5 mL) and dried over Na₂SO₄. The solution was filtered and concentrated in vacuo to give the crude material as a white solid. The crude product was purified by silica gel chromatography eluting with 50% EtOAc/hexanes to give 5-iodo-2-methoxy-N-(6-methoxypyridin-3-yl)pyrimidin-4-amine (162 mg, 0.452 mmol, 91% yield). ¹H NMR (300 MHz, CDCl₃) δ 8.35 (s, 1H); 8.26 (d, J=2.05 Hz, 1H); 7.83 (dd, J=8.84, 2.56 Hz, 1H); 6.87 (s, 1H); 6.78 (d, J=8.77 Hz, 1H); 3.94 (s, 3H); 3.89 (s, 3H). m/z (ESI, +ve ion) 359.0 (M+H)⁺.

Step 2: 2-methoxy-N-(6-methoxypyridin-3-yl)-5-(4-methyl-6-(methylthio)-1,3,5-triazin-2-yl)pyrimidin-4-amine A glass microwave reaction vessel was charged with 5-iodo-2-methoxy-N-(6-methoxypyridin-3-yl)pyrimidin-4-amine (120 mg, 0.335 mmol), 2-methyl-4-(methylthio)-6-(tributylstannyl)-1,3,5-triazine (144 mg, 0.335 mmol), copper(I) iodide (13 mg, 0.067 mmol), cesium fluoride (102 mg, 0.670 mmol), tetrakis(triphenylphosphine)palladium(0) (38.7 mg, 0.034 mmol) and dioxane (2 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (10 mL) and extracted with EtOAc (2×30 mL). The organic extract was washed with saturated NaCl (5 mL) and dried over Na₂SO₄. The solution was filtered and concentrated in vacuo to give the crude material as orange solid. The crude product was purified by silica gel chromatography eluting with 60% EtOAc/hexanes to give 2-methoxy-N-(6-methoxypyridin-3-yl)-5-(4-methyl-6-(methylthio)-1,3,5-triazin-2-yl)pyrimidin-4-amine (86 mg, 0.232 mmol, 69.1% yield). ¹H NMR (300 MHz, CDCl₃) δ 11.78 (s, 1H); 9.53 (s, 1H); 8.39 (s, 1H); 8.06 (dd, J=8.77, 1.90 Hz, 1H); 6.80 (d, J=8.92 Hz, 1H); 4.01 (s, 3H); 3.96 (s, 3H); 2.63 (s, 6H). m/z (ESI, +ve ion) 372.0 (M+H)⁺.

Step 3: 4-(2-methoxy-4-(6-methoxypyridin-3-ylamino)pyrimidin-5-yl)-6-methyl-1,3,5-triazin-2-amine A glass microwave reaction vessel was charged with 2-methoxy-N-(6-methoxypyridin-3-yl)-5-(4-methyl-6-(methylthio)-1,3,5-triazin-2-yl)pyrimidin-4-amine (41 mg, 0.110 mmol), ammonia (0.5 mL, 23.11 mmol) (30% in water) and dioxane (2 mL). The reaction mixture was stirred and heated in an oil bath at 100° C. for 16 h. The solid formed was filtered off and washed with EtOAc to give 4-(2-methoxy-4-(6-methoxypyridin-3-ylamino)pyrimidin-5-yl)-6-methyl-1,3,5-triazin-2-amine (28 mg, 0.082 mmol, 74.5% yield). ¹H NMR (300 MHz, d6-DMSO) δ 11.98 (s, 1H); 9.25 (s, 1H); 8.53 (s, 1H); 8.16 (dd, J=8.84, 2.56 Hz, 1H); 7.84 (s, 1H); 7.68 (s, 1H); 6.88 (d, J=8.77 Hz, 1H); 5.76 (s, 1H); 3.89 (s, 3H); 3.86 (s, 3H); 2.40 (s, 3H). m/z (ESI, +ve ion) 341.0 (M+H)⁺.

Example 120

4-(4-(6-methoxypyridin-3-ylamino)-2-morpholinopyrimidin-5-yl)-6-methyl-1,3,5-triazin-2-amine

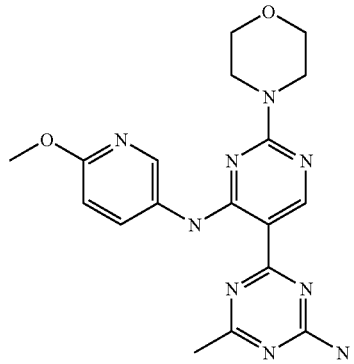 [SMILES: COc1ccc(Nc2nc(N3CCOCC3)ncc2-c2nc(C)nc(N)n2)cn1]

Step 1: 5-iodo-N-(6-methoxypyridin-3-yl)-2-morpholinopyrimidin-4-amine

A glass microwave reaction vessel was charged with 2-chloro-5-iodo-N-(6-methoxypyridin-3-yl)pyrimidin-4-amine (160 mg, 0.441 mmol), morpholine (0.077 mL, 0.883 mmol) and ethanol (3 mL). The reaction mixture was stirred and heated in a Emrys Optimizer microwave reactor (Personal Chemistry, Biotage AB, Inc., Upssala, Sweden) at 140° C. for 20 min. The reaction mixture was diluted with water (10 mL) and extracted with EtOAc (2×30 mL). The organic extract was washed with saturated NaCl (10 mL) and dried over $Na_2SO_4$. The solution was filtered and concentrated in vacuo to give the crude material as an off-white solid. The crude product was purified by silica gel chromatography eluting with 50% EtOAc/hexanes to give 5-iodo-N-(6-methoxypyridin-3-yl)-2-morpholinopyrimidin-4-amine (162 mg, 0.392 mmol, 89% yield). $^1$H NMR (300 MHz, CDCl$_3$) δ 8.26 (d, J=1.90 Hz, 1H); 8.20 (s, 1H); 7.72 (dd, J=8.77, 2.34 Hz, 1H); 6.75 (d, J=8.92 Hz, 1H); 6.67 (s, 1H); 3.95 (s, 3H); 3.68 (d, J=5.26 Hz, 8H). m/z (ESI, +ve ion) 414.0 (M+H)$^+$.

Step 2: N-(6-methoxypyridin-3-yl)-5-(4-methyl-6-(methylthio)-1,3,5-triazin-2-yl)-2-morpholinopyrimidin-4-amine A glass microwave reaction vessel was charged with 5-iodo-N-(6-methoxypyridin-3-yl)-2-morpholinopyrimidin-4-amine (118 mg, 0.286 mmol), 2-methyl-4-(methylthio)-6-(tributylstannyl)-1,3,5-triazine (123 mg, 0.286 mmol), copper(I) iodide (11 mg, 0.057 mmol), cesium fluoride (87 mg, 0.571 mmol), tetrakis(triphenylphosphine)palladium(0) (33.0 mg, 0.029 mmol) and dioxane (2 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (10 mL) and extracted with EtOAc (2×30 mL). The organic extract was washed with saturated NaCl (5 mL) and dried over $Na_2SO_4$. The solution was filtered and concentrated in vacuo to give the crude material as an orange solid. The crude product was purified by silica gel chromatography eluting with 60% EtOAc/hexanes to give N-(6-methoxypyridin-3-yl)-5-(4-methyl-6-(methylthio)-1,3,5-triazin-2-yl)-2-morpholinopyrimidin-4-amine (43 mg, 0.101 mmol, 35.3% yield). $^1$H NMR (300 MHz, CDCl$_3$) δ 11.63 (s, 1H); 9.41 (s, 1H); 8.38 (d, J=1.90 Hz, 1H); 7.90 (dd, J=8.77, 2.34 Hz, 1H); 6.78 (d, J=8.77 Hz, 1H); 3.96 (s, 3H); 3.88 (s, 4H); 3.65-3.81 (m, 4H); 2.60 (s, 3H); 2.58 (s, 3H). m/z (ESI, +ve ion) 427.1 (M+H)$^+$.

Step 3: 4-(4-(6-methoxypyridin-3-ylamino)-2-morpholinopyrimidin-5-yl)-6-methyl-1,3,5-triazin-2-amine A glass microwave reaction vessel was charged with N-(6-methoxypyridin-3-yl)-5-(4-methyl-6-(methylthio)-1,3,5-triazin-2-yl)-2-morpholinopyrimidin-4-amine (34 mg, 0.080 mmol), ammonia (0.5 mL, 23.11 mmol) (30% in water) and dioxane (1 mL). The reaction mixture was stirred and heated in an oil bath at 100° C. for 16 h. The solvent was removed in vacuo and the residue was purified by silica gel chromatography eluting with EtOAc to give 4-(4-(6-methoxypyridin-3-ylamino)-2-morpholinopyrimidin-5-yl)-6-methyl-1,3,5-triazin-2-amine (22 mg, 0.056 mmol, 69.8% yield). $^1$H NMR (300 MHz, d6-DMSO) δ 11.91 (s, 1H); 9.16 (s, 1H); 8.50 (s, 1H); 8.08 (d, J=4.97 Hz, 1H); 7.67 (s, 1H); 7.51 (s, 1H); 6.85 (d, J=8.77 Hz, 1H); 3.85 (s, 3H); 3.74 (s, 4H); 3.66 (s, 4H); 2.36 (s, 3H). m/z (ESI, +ve ion) 396.0 (M+H)$^+$.

Example 121

5-(4-amino-6-methyl-1,3,5-triazin-2-yl)-N4-(6-methoxypyridin-3-yl)-N2,N2-dimethylpyrimidine-2,4-diamine

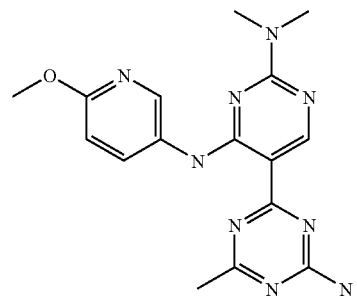 [SMILES: COc1ccc(Nc2nc(N(C)C)ncc2-c2nc(C)nc(N)n2)cn1]

Step 1: 5-iodo-N4-(6-methoxypyridin-3-yl)-N2,N2-dimethylpyrimidine-2,4-diamine A glass microwave reaction vessel was charged with 2-chloro-5-iodo-N-(6-methoxypyridin-3-yl)pyrimidin-4-amine (150 mg, 0.414 mmol), dimethylamine (2.0 M solution in tetrahydrofuran) (0.044 mL, 0.827 mmol) and ethanol (2 mL). The reaction mixture was stirred and heated in a Emrys Optimizer microwave reactor (Personal Chemistry, Biotage AB, Inc., Upssala, Sweden) at 140° C. for 20 min. The solvent was removed in vacuo and the residue was purified by silica gel chromatography eluting with 50% EtOAc/hexanes to give 5-iodo-N4-(6-methoxypyridin-3-yl)-N2,N2-dimethylpyrimidine-2,4-diamine (123 mg, 0.331 mmol, 80% yield). $^1$H NMR (300 MHz, CDCl$_3$) δ 8.30 (s, 1H); 8.18 (s, 1H); 7.84 (dd, J=8.92, 2.48 Hz, 1H); 6.75 (d, J=8.92 Hz, 1H); 6.65 (s, 1H); 3.94 (s, 3H); 3.09 (s, 6H). m/z (ESI, +ve ion) 371.9 (M+H)$^+$.

Step 2: N4-(6-methoxypyridin-3-yl)-N2,N2-dimethyl-5-(4-methyl-6-(methylthio)-1,3,5-triazin-2-yl)pyrimidine-2,4-diamine A glass microwave reaction vessel was charged with 5-iodo-N4-(6-methoxypyridin-3-yl)-N2,N2-dimethylpyrimidine-2,4-diamine (98 mg, 0.264 mmol), 2-methyl-4-(methylthio)-6-(tributylstannyl)-1,3,5-triazine (114 mg, 0.264 mmol), cesium fluoride (80 mg, 0.528 mmol), copper(I) iodide (10 mg, 0.053 mmol), tetrakis(triphenylphosphine)palladium(0) (30.5 mg, 0.026 mmol) and dioxane (2 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (5 mL) and extracted with EtOAc (2×30 mL). The organic extract was washed with saturated NaCl (10 mL) and dried over $Na_2SO_4$. The solution was filtered and concentrated in vacuo to give the crude material as an orange solid. The crude product was purified by silica gel chromatography eluting with 60% EtOAc/hexanes to give N4-(6-methoxypyridin-3-yl)-N2,N2-dimethyl-5-(4-methyl-6-(methylthio)-1,3,5-triazin-2-yl)pyrimidine-2,4-diamine (32 mg, 0.083 mmol, 31.5% yield). $^1$H NMR (300 MHz, CDCl₃) δ 11.66 (s, 1H); 9.43 (s, 1H); 8.42 (s, 1H); 8.05 (dd, J=8.70, 2.27 Hz, 1H); 6.77 (d, J=8.92 Hz, 1H); 3.95 (s, 3H); 3.25 (s, 6H); 2.59 (s, 3H); 2.57 (s, 3H). m/z (ESI, +ve ion) 385.1 (M+H)⁺.

Step 3: 5-(4-amino-6-methyl-1,3,5-triazin-2-yl)-N4-(6-methoxypyridin-3-yl)-N2,N2-dimethylpyrimidine-2,4-diamine A glass microwave reaction vessel was charged with N4-(6-methoxypyridin-3-yl)-N2,N2-dimethyl-5-(4-methyl-6-(methylthio)-1,3,5-triazin-2-yl)pyrimidine-2,4-diamine (16 mg, 0.042 mmol), ammonia (0.5 mL, 23.11 mmol) (30% in water) and dioxane (1 mL). The reaction mixture was stirred and heated in an oil bath at 100° C. for 16 h. The solvent was removed in vacuo and the residue was purified by silica gel chromatography eluting with 5% MeOH/EtOAc to give 5-(4-amino-6-methyl-1,3,5-triazin-2-yl)-N4-(6-methoxypyridin-3-yl)-N2,N2-dimethylpyrimidine-2,4-diamine (11 mg, 0.031 mmol, 74.8% yield). ¹H NMR (300 MHz, CDCl₃) δ 11.94 (s, 1H); 9.29 (s, 1H); 8.42 (s, 1H); 8.07 (dd, J=8.92, 2.34 Hz, 1H); 6.76 (d, J=8.77 Hz, 1H); 5.29 (s, 2H); 3.95 (s, 3H); 3.23 (s, 6H); 2.48 (s, 3H). m/z (ESI, +ve ion) 354.0 (M+H)⁺.

Example 122

4-(4-(6-methoxypyridin-3-ylamino)-2-(pyrrolidin-1-yl)pyrimidin-5-yl)-6-methyl-1,3,5-triazin-2-amine

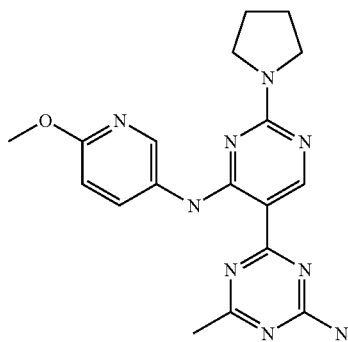 [SMILES: COc1ccc(Nc2nc(N3CCCC3)ncc2-c2nc(C)nc(N)n2)cn1]

Step 1: 5-iodo-N-(6-methoxypyridin-3-yl)-2-(pyrrolidin-1-yl)pyrimidin-4-amine

A glass microwave reaction vessel was charged with 2-chloro-5-iodo-N-(6-methoxypyridin-3-yl)pyrimidin-4-amine (181 mg, 0.499 mmol), pyrrolidine (0.084 mL, 0.998 mmol) and ethanol (2 mL). The reaction mixture was stirred and heated in a Emrys Optimizer microwave reactor (Personal Chemistry, Biotage AB, Inc., Upssala, Sweden) at 140° C. for 20 min. The reaction mixture was diluted with water (5 mL) and extracted with EtOAc (2×40 mL). The organic extract was washed with saturated NaCl (20 mL) and dried over Na₂SO₄. The solution was filtered and concentrated in vacuo to give the crude material as a white solid. The crude product was purified by silica gel chromatography eluting with 50% EtOAc/hexanes to give 5-iodo-N-(6-methoxypyridin-3-yl)-2-(pyrrolidin-1-yl)pyrimidin-4-amine (172 mg, 0.433 mmol, 87% yield). ¹H NMR (300 MHz, CDCl₃) δ 8.19 (s, 1H); 7.89 (dd, J=8.33, 2.34 Hz, 1H); 6.74 (d, J=8.92 Hz, 1H); 6.67 (s, 1H); 3.94 (s, 3H); 3.50 (s, 4H); 1.95 (s, 4H). m/z (ESI, +ve ion) 398.0 (M+H)⁺.

Step 2: N-(6-methoxypyridin-3-yl)-5-(4-methyl-6-(methylthio)-1,3,5-triazin-2-yl)-2-(pyrrolidin-1-yl)pyrimidin-4-amine A glass microwave reaction vessel was charged with 5-iodo-N-(6-methoxypyridin-3-yl)-2-(pyrrolidin-1-yl)pyrimidin-4-amine (141 mg, 0.355 mmol), 2-methyl-4-(methylthio)-6-(tributylstannyl)-1,3,5-triazine (153 mg, 0.355 mmol), copper(I) iodide (14 mg, 0.071 mmol), cesium fluoride (108 mg, 0.710 mmol), tetrakis(triphenylphosphine)palladium(0) (41.0 mg, 0.035 mmol) and dioxane (3 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (10 mL) and extracted with EtOAc (2×30 mL). The organic extract was washed with saturated NaCl (10 mL) and dried over Na₂SO₄. The solution was filtered and concentrated in vacuo to give the crude material as brown oil. The crude product was purified by silica gel chromatography eluting with 60% EtOAc/hexanes to give N-(6-methoxypyridin-3-yl)-5-(4-methyl-6-(methylthio)-1,3,5-triazin-2-yl)-2-(pyrrolidin-1-yl)pyrimidin-4-amine (28 mg, 0.068 mmol, 19.22% yield). ¹H NMR (300 MHz, CDCl₃) δ 11.74 (s, 1H); 9.45 (s, 1H); 8.49 (s, 1H); 8.13 (dd, J=8.92, 2.34 Hz, 1H); 6.77 (d, J=8.77 Hz, 1H); 3.95 (s, 3H); 3.58-3.76 (m, 4H); 2.59 (s, 3H); 2.57 (s, 3H); 1.93-2.09 (m, 4H). m/z (ESI, +ve ion) 411.0 (M+H)⁺.

Step 3: 4-(4-(6-methoxypyridin-3-ylamino)-2-(pyrrolidin-1-yl)pyrimidin-5-yl)-6-methyl-1,3,5-triazin-2-amine A glass microwave reaction vessel was charged with N-(6-methoxypyridin-3-yl)-5-(4-methyl-6-(methylthio)-1,3,5-triazin-2-yl)-2-(pyrrolidin-1-yl)pyrimidin-4-amine (18 mg, 0.044 mmol), ammonia (0.5 mL, 23.11 mmol) (30% in water) and dioxane (1 mL). The reaction mixture was stirred and heated in an oil bath at 100° C. for 18 h. The solvent was removed in vacuo and the residue was purified by silica gel chromatography eluting with EtOAc to give 4-(4-(6-methoxypyridin-3-ylamino)-2-(pyrrolidin-1-yl)pyrimidin-5-yl)-6-methyl-1,3,5-triazin-2-amine (12 mg, 0.032 mmol, 72.1% yield). ¹H NMR (300 MHz, CDCl₃) δ 12.03 (s, 1H); 9.30 (s, 1H); 8.48 (s, 1H); 8.15 (dd, J=8.92, 2.48 Hz, 1H); 6.76 (d, J=9.06 Hz, 1H); 5.24 (s, 2H); 3.95 (s, 3H); 3.66 (dd, J=5.85, 4.09 Hz, 4H); 2.49 (s, 3H); 2.00 (t, J=6.43 Hz, 4H). m/z (ESI, + ve ion) 380.1 (M+H)⁺.

Example 123

4-(4-(6-methoxypyridin-3-ylamino)-2-(piperidin-1-yl)pyrimidin-5-yl)-6-methyl-1,3,5-triazin-2-amine

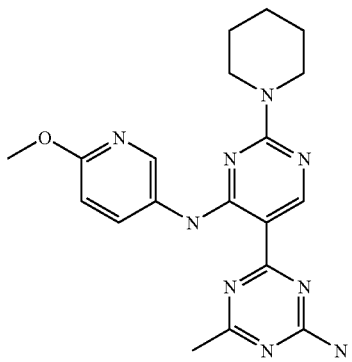 [SMILES: COc1ccc(Nc2nc(N3CCCCC3)ncc2-c2nc(C)nc(N)n2)cn1]

Step 1: 5-iodo-N-(6-methoxypyridin-3-yl)-2-(piperidin-1-yl)pyrimidin-4-amine A glass microwave reaction vessel was charged with 2-chloro-5-iodo-N-(6-methoxypyridin-3-yl)pyrimidin-4-amine (181 mg, 0.499 mmol), piperidine (0.099 mL, 0.998 mmol) and ethanol (2 mL). The reaction mixture was stirred and heated in a Emrys Optimizer microwave reactor (Personal Chemistry, Biotage AB, Inc., Upssala, Sweden) at 140° C. for 20 min. The reaction mixture was diluted with water (20 mL) and extracted with EtOAc (2×30 mL). The organic extract was washed with saturated NaCl (10 mL) and dried over $Na_2SO_4$. The solution was filtered and concentrated in vacuo to give the crude material as orange oil. The crude product was purified by silica gel chromatography eluting with 40% EtOAc/hexanes to give 5-iodo-N-(6-methoxypyridin-3-yl)-2-(piperidin-1-yl)pyrimidin-4-amine (189 mg, 0.460 mmol, 92% yield). $^1$H NMR (300 MHz, $CDCl_3$) δ 8.24 (s, 1H); 8.17 (s, 1H); 7.79 (dd, J=8.84, 2.56 Hz, 1H); 6.75 (d, J=8.77 Hz, 1H); 6.63 (s, 1H); 3.94 (s, 3H); 3.57-3.73 (m, 4H); 1.47-1.69 (m, J=4.68 Hz, 6H). m/z (ESI, +ve ion) 412.0 $(M+H)^+$.

Step 2: N-(6-methoxypyridin-3-yl)-5-(4-methyl-6-(methylthio)-1,3,5-triazin-2-yl)-2-(piperidin-1-yl)pyrimidin-4-amine A glass microwave reaction vessel was charged with 5-iodo-N-(6-methoxypyridin-3-yl)-2-(piperidin-1-yl)pyrimidin-4-amine (161 mg, 0.391 mmol), 2-methyl-4-(methylthio)-6-(tributylstannyl)-1,3,5-triazine (168 mg, 0.391 mmol), cesium fluoride (119 mg, 0.783 mmol), copper(I) iodide (15 mg, 0.078 mmol), tetrakis(triphenylphosphine)palladium(0) (45.2 mg, 0.039 mmol) and dioxane (2 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (10 mL) and extracted with EtOAc (2×30 mL). The organic extract was washed with saturated NaCl (10 mL) and dried over $Na_2SO_4$. The solution was filtered and concentrated in vacuo to give the crude material as an orange solid. The crude product was purified by silica gel chromatography eluting with 40% EtOAc/Hexanes to give N-(6-methoxypyridin-3-yl)-5-(4-methyl-6-(methylthio)-1,3,5-triazin-2-yl)-2-(piperidin-1-yl)pyrimidin-4-amine (36 mg, 0.085 mmol, 21.66% yield). $^1$H NMR (300 MHz, $CDCl_3$) δ 11.61 (s, 1H); 9.41 (s, 1H); 7.99 (d, J=8.48 Hz, 1H); 6.77 (d, J=8.77 Hz, 1H); 3.95 (s, 3H); 3.78-3.91 (m, 4H); 2.59 (s, 3H); 2.56 (s, 3H); 1.56-1.78 (m, J=2.63 Hz, 6H). m/z (ESI, +ve ion) 425.0 $(M+H)^+$.

Step 3: 4-(4-(6-methoxypyridin-3-ylamino)-2-(piperidin-1-yl)pyrimidin-5-yl)-6-methyl-1,3,5-triazin-2-amine A glass microwave reaction vessel was charged with N-(6-methoxypyridin-3-yl)-5-(4-methyl-6-(methylthio)-1,3,5-triazin-2-yl)-2-(piperidin-1-yl)pyrimidin-4-amine (22 mg, 0.052 mmol), ammonia (0.5 mL, 30% in water) and dioxane (2 mL). The reaction mixture was stirred and heated in an oil bath at 100° C. for 23 h. The solvent was removed in vacuo and the residue was purified by silica gel chromatography eluting with EtOAc to give 4-(4-(6-methoxypyridin-3-ylamino)-2-(piperidin-1-yl)pyrimidin-5-yl)-6-methyl-1,3,5-triazin-2-amine (18 mg, 0.046 mmol, 88% yield). $^1$H NMR (300 MHz, $CDCl_3$) δ 11.88 (s, 1H); 9.27 (s, 1H); 8.35 (s, 1H); 7.97-8.06 (m, J=8.18, 1.46 Hz, 1H); 6.76 (d, J=8.92 Hz, 1H); 5.21 (s, 2H); 3.95 (s, 3H); 3.83 (s, 4H); 2.48 (s, 3H); 1.57-1.76 (m, 6H). m/z (ESI, +ve ion) 394.1 $(M+H)^+$.

Example 124

4-(4-(6-methoxypyridin-3-ylamino)-2-(pyridin-4-yl)pyrimidin-5-yl)-6-methyl-1,3,5-triazin-2-amine

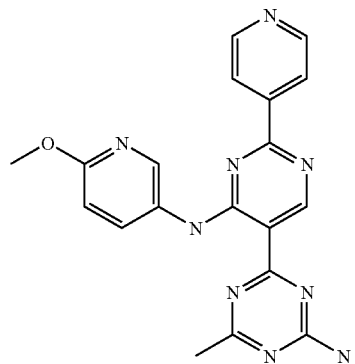 [SMILES: COc1ccc(Nc2nc(-c3ccncc3)ncc2-c2nc(C)nc(N)n2)cn1]

Step 1: N-(6-methoxypyridin-3-yl)-5-(4-methyl-6-(methylthio)-1,3,5-triazin-2-yl)-2-(pyridin-4-yl)pyrimidin-4-amine A mixture of 2-chloro-N-(6-methoxypyridin-3-yl)-5-(4-methyl-6-(methylthio)-1,3,5-triazin-2-yl)pyrimidin-4-amine (38 mg, 0.101 mmol), pyridine-4-boronic acid (14.91 mg, 0.121 mmol), dichloro 1,1'-bis(diphenylphosphino)ferrocene palladium(II) (8.26 mg, 10.11 µmol) and cesium carbonate (39 mg, 0.121 mmol) in dioxane (1 mL) was stirred at 100° C. for 1 h. The mixture was cooled down to room temperature. The reaction mixture was diluted with saturated $NH_4Cl$ (10 mL) and extracted with EtOAc (2×20 mL). The organic extract was washed with saturated NaCl (5 mL) and dried over $Na_2SO_4$. The solution was filtered and concentrated in vacuo to give the crude product as an orange solid. The crude product was purified by silica gel chromatography eluting with 10% MeOH/EtOAc to give N-(6-methoxypyridin-3-yl)-5-(4-methyl-6-(methylthio)-1,3,5-triazin-2-yl)-2-(pyridin-4-yl)pyrimidin-4-amine (11 mg, 0.026 mmol, 26.0% yield). $^1$H NMR (300 MHz, $CDCl_3$) δ 11.69 (s, 1H); 9.78 (s, 1H); 8.62-9.02 (m, 2H); 8.46 (s, 1H); 8.29-8.43 (m, 1H); 8.24 (d, J=4.53 Hz, 1H); 8.04-8.14 (m, 1H); 6.79-6.93 (m, 1H); 5.30 (s, 2H); 4.00 (s, 3H); 2.69 (s, 3H); 2.67 (s, 3H). m/z (ESI, +ve ion) 419.1 $(M+H)^+$.

Step 2: 4-(4-(6-methoxypyridin-3-ylamino)-2-(pyridin-4-yl)pyrimidin-5-yl)-6-methyl-1,3,5-triazin-2-amine A glass microwave reaction vessel was charged with N-(6-methoxypyridin-3-yl)-5-(4-methyl-6-(methylthio)-1,3,5-triazin-2-yl)-2-(pyridin-4-yl)pyrimidin-4-amine (8 mg, 0.019 mmol), ammonia (0.5 mL, 23.11 mmol) (30% in water) and dioxane (1 mL). The reaction mixture was stirred and heated in a Emrys Optimizer microwave reactor (Personal Chemistry, Biotage AB, Inc., Upssala, Sweden) at 100° C. for 18 h. The solvent was removed in vacuo and the residue was purified by silica gel chromatography eluting with 10% MeOH/EtOAc to give 4-(4-(6-methoxypyridin-3-ylamino)-2-(pyridin-4-yl)pyrimidin-5-yl)-6-methyl-1,3,5-triazin-2-amine (4 mg, 10.33 µmol, 54.0% yield). $^1$H NMR (300 MHz, d6-DMSO) δ 11.96 (s, 1H); 8.77 (d, J=5.12 Hz, 1H); 8.59 (s, 1H); 8.21 (dd, J=9.06, 2.34 Hz, 1H); 8.15 (d, J=5.12 Hz, 1H); 7.99 (s, 1H); 7.82 (s, 1H); 6.96 (d, J=8.77 Hz, 1H); 3.90 (s, 2H); 2.45 (s, 3H). m/z (ESI, +ve ion) 388.1 (M+H)$^+$.

Example 125

4-(2-(4-fluorophenyl)-4-(6-methoxypyridin-3-ylamino)pyrimidin-5-yl)-6-methyl-1,3,5-triazin-2-amine

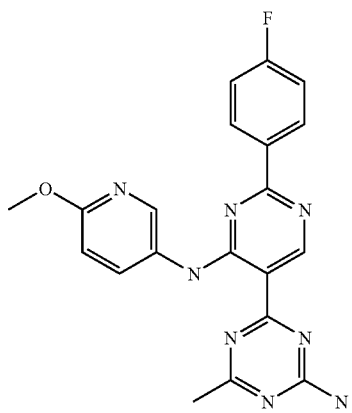 [SMILES: COc1ccc(Nc2nc(-c3ccc(F)cc3)ncc2-c2nc(C)nc(N)n2)cn1]

Step 1: 2-(4-fluorophenyl)-N-(6-methoxypyridin-3-yl)-5-(4-methyl-6-(methylthio)-1,3,5-triazin-2-yl)pyrimidin-4-amine A mixture of 2-chloro-N-(6-methoxypyridin-3-yl)-5-(4-methyl-6-(methylthio)-1,3,5-triazin-2-yl)pyrimidin-4-amine (38 mg, 0.101 mmol), 4-fluorobenzeneboronic acid (16.98 mg, 0.121 mmol), dichloro 1,1'-bis(diphenylphosphino)ferrocene palladium(II) (8.26 mg, 10.11 µmol) and cesium carbonate (66 mg, 0.202 mmol) in dioxane (3 mL) and water (0.5 mL) was stirred at 100° C. for 1 h. The mixture was cooled down to room temperature. The reaction mixture was diluted with saturated NH$_4$Cl (5 mL) and extracted with EtOAc (2×30 mL). The organic extract was washed with saturated NaCl (5 mL) and dried over Na$_2$SO$_4$. The solution was filtered and concentrated in vacuo to give the crude material as an orange solid. The crude product was purified by silica gel chromatography eluting with 30% EtOAc/hexanes to give 2-(4-fluorophenyl)-N-(6-methoxypyridin-3-yl)-5-(4-methyl-6-(methylthio)-1,3,5-triazin-2-yl)pyrimidin-4-amine (23 mg, 0.053 mmol, 52.2% yield). $^1$H NMR (300 MHz, CDCl$_3$) δ 11.64 (s, 1H); 9.73 (s, 1H); 8.39-8.50 (m, 3H); 8.11 (dd, J=8.77, 2.48 Hz, 1H); 7.16 (t, J=8.62 Hz, 2H); 6.87 (d, J=8.92 Hz, 1H); 4.00 (s, 3H); 2.67 (d, J=4.38 Hz, 6H). m/z (ESI, +ve ion) 436.1 (M+H)$^+$.

Step 2: 4-(2-(4-fluorophenyl)-4-(6-methoxypyridin-3-ylamino)pyrimidin-5-yl)-6-methyl-1,3,5-triazin-2-amine A glass microwave reaction vessel was charged with 2-(4-fluorophenyl)-N-(6-methoxypyridin-3-yl)-5-(4-methyl-6-(methylthio)-1,3,5-triazin-2-yl)pyrimidin-4-amine (12 mg, 0.028 mmol), ammonia (0.5 mL, 30% in water) and dioxane (1 mL). The reaction mixture was stirred and heated in a oil bath at 100° C. for 17 h. The solvent was removed in vacuo and the residue was purified by silica gel chromatography eluting with 80% EtOAc/hexanes to give 4-(2-(4-fluorophenyl)-4-(6-methoxypyridin-3-ylamino)pyrimidin-5-yl)-6-methyl-1,3,5-triazin-2-amine $^1$H NMR (300 MHz, CDCl$_3$) δ 9.60 (s, 1H); 8.35-8.54 (m, 3H); 8.12 (dd, J=8.84, 2.41 Hz, 1H); 7.15 (t, J=8.62 Hz, 2H); 6.86 (d, J=8.92 Hz, 1H); 5.44 (s, 2H); 3.99 (s, 3H); 2.56 (s, 3H). m/z (ESI, +ve ion) 405.0 (M+H)$^+$.

Example 126

5-(4-amino-6-methyl-1,3,5-triazin-2-yl)-N2-cyclopentyl-N4-(6-methoxypyridin-3-yl)pyrimidine-2,4-diamine

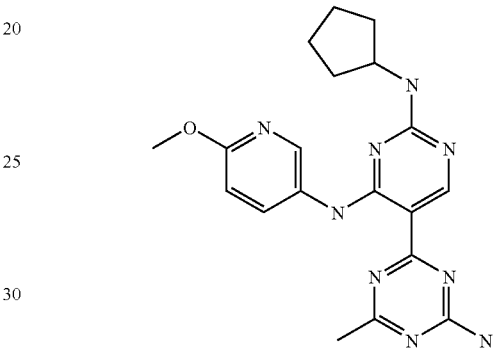

Step 1: N2-cyclopentyl-5-iodo-N4-(6-methoxypyridin-3-yl)pyrimidine-2,4-diamine

A glass microwave reaction vessel was charged with 2-chloro-5-iodo-N-(6-methoxypyridin-3-yl)pyrimidin-4-amine (181 mg, 0.499 mmol), cyclopentylamine (85 mg, 0.998 mmol) and ethanol (3 mL). The reaction mixture was stirred and heated in a Emrys Optimizer microwave reactor (Personal Chemistry, Biotage AB, Inc., Upssala, Sweden) at 140° C. for 30 min. The solvent was removed in vacuo and the residue was purified by silica gel chromatography eluting with 50% EtOAc/hexanes to give N2-cyclopentyl-5-iodo-N4-(6-methoxypyridin-3-yl)pyrimidine-2,4-diamine (188 mg, 0.457 mmol, 92% yield). $^1$H NMR (300 MHz, CDCl$_3$) δ 8.30 (s, 1H); 8.14 (s, 1H); 7.82 (d, J=10.38 Hz, 1H); 6.75 (d, J=8.92 Hz, 1H); 6.66 (s, 1H); 4.79-4.96 (m, 1H); 4.10 (dd, J=13.15, 4.53 Hz, 1H); 3.94 (s, 3H); 1.97 (dd, J=11.62, 5.19 Hz, 2H); 1.56-1.78 (m, 4H); 1.35-1.50 (m, 2H). m/z (ESI, +ve ion) 412.0 (M+H)$^+$.

Step 2: N2-cyclopentyl-N4-(6-methoxypyridin-3-yl)-5-(4-methyl-6-(methylthio)-1,3,5-triazin-2-yl)pyrimidine-2,4-diamine A glass microwave reaction vessel was charged with N2-cyclopentyl-5-iodo-N4-(6-methoxypyridin-3-yl)pyrimidine-2,4-diamine (145 mg, 0.353 mmol), 2-methyl-4-(methylthio)-6-(tributylstannyl)-1,3,5-triazine (152 mg, 0.353 mmol), copper(I) iodide (14 mg, 0.071 mmol), cesium fluoride (107 mg, 0.705 mmol), tetrakis(triphenylphosphine)palladium(0) (40.7 mg, 0.035 mmol) and dioxane (3 mL). The reaction mixture was stirred and heated in a Emrys Optimizer microwave reactor (Personal Chemistry, Biotage AB, Inc., Upssala, Sweden) at 140° C. for 20 min. The reaction mixture was diluted with water (10 mL) and extracted with EtOAc (2×30 mL). The organic extract was washed with saturated NaCl (5 mL) and dried over Na$_2$SO$_4$. The solution was filtered and concentrated in vacuo to give the crude material as a black solid. The crude product was purified by silica gel chromatography eluting with 50% EtOAc/hexanes to give N2-cyclopentyl-N4-(6-methoxypyridin-3-yl)-5-(4-methyl-6-(methylthio)-1,3,5-triazin-2-yl)pyrimidine-2,4-diamine (52 mg, 0.122 mmol, 34.7% yield) as a white solid. $^1$H NMR (300 MHz, CDCl3) δ 11.46-11.87 (m, 1H); 9.15-9.62 (m, 1H); 8.26-8.63 (m, 1H); 7.84-8.26 (m, 1H); 6.77 (d, J=8.77 Hz, 1H); 5.11-5.52 (m, 1H); 4.12-4.56 (m, 1H); 3.95 (s, 3H); 2.59 (d, J=6.87 Hz, 6H); 1.87-2.21 (m, 2H); 1.56-1.87 (m, 4H). m/z (ESI, +ve ion) 425.1 (M+H)$^+$.

Step 3: 5-(4-amino-6-methyl-1,3,5-triazin-2-yl)-N2-cyclopentyl-N4-(6-methoxypyridin-3-yl)pyrimidine-2,4-diamine A glass microwave reaction vessel was charged with N2-cyclopentyl-N4-(6-methoxypyridin-3-yl)-5-(4-methyl-6-(methylthio)-1,3,5-triazin-2-yl)pyrimidine-2,4-diamine (36 mg, 0.085 mmol), ammonia (0.5 mL, 23.11 mmol) and dioxane (2 mL). The reaction mixture was stirred and heated in an oil bath at 100° C. for 24 h. The solvent was removed in vacuo and the residue was purified by silica gel chromatography eluting with EtOAc to give 5-(4-amino-6-methyl-1,3,5-triazin-2-yl)-N2-cyclopentyl-N4-(6-methoxypyridin-3-yl)pyrimidine-2,4-diamine (28 mg, 0.071 mmol, 84% yield). $^1$H NMR (300 MHz, CDCl$_3$) δ 11.99 (s, 1H); 9.21 (s, 1H); 8.29-8.56 (m, 1H); 8.19 (s, 1H); 6.76 (d, J=8.92 Hz, 1H); 5.26 (s, 3H); 4.25 (s, 1H); 3.95 (s, 3H); 2.49 (s, 3H); 2.04 (s, 2H); 1.34-1.87 (m, 6H). m/z (ESI, +ve ion) 394.1 (M+H)$^+$.

Example 127

5-chloro-N-(6-methoxypyridin-3-yl)-3-(2-methyl-9H-purin-6-yl)pyridin-2-amine

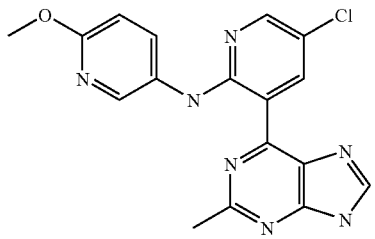 [SMILES: COc1ccc(Nc2ncc(Cl)cc2-c2nc(C)nc3[nH]cnc23)cn1]

The title compound was prepared following the procedure described in Example 62, with the deprotection of the purine performed as follows. A glass microwave reaction vessel was charged with 5-chloro-N-(6-methoxypyridin-3-yl)-3-(2-methyl-9-(tetrahydro-2H-pyran-2-yl)-9H-purin-6-yl)pyridin-2-amine (0.100 g, 0.221 mmol) and 1.0 M hydrochloric acid (1.106 mL, 1.106 mmol) in THF (2 ml). The reaction mixture was stirred and heated in a Discover model microwave reactor (CEM, Matthews, N.C.) at 100° C. for 10 minutes (100 watts, Powermax feature on). The mixture was diluted with DCM, made basic (pH about 12) with 1 N NaOH and allowed mixture to stir for 10 min. The precipitate was collected by filtration and washed with diethyl ether to give 5-chloro-N-(6-methoxypyridin-3-yl)-3-(2-methyl-9H-purin-6-yl)pyridin-2-amine (0.060 g, 0.163 mmol, 73.7% yield) as a yellow solid. $^1$H NMR (400 MHz, d6-DMSO) δ 13.83 (s, 1H); 10.24 (s, 1H); 8.54 (s, 1H); 8.18 (s, 2H); 8.06 (s, 1H); 3.85 (s, 3H); 2.73 (s, 3H); 1.62 (s, 2H). m/z (ESI, +ve ion) 367.9 (M+H)$^+$.

Example 128

N-(3-(4-amino-6-methyl-1,3,5-triazin-2-yl)-5-((4-(methylsulfonyl)piperazin-1-yl)methyl)pyridin-2-yl)benzo[d]oxazol-5-amine

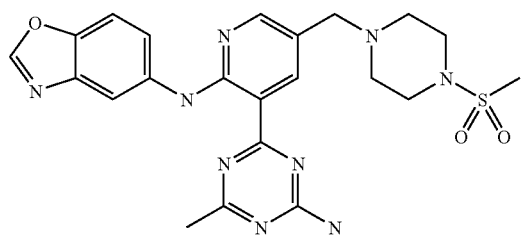 [SMILES: Cc1nc(N)nc(-c2cc(CN3CCN(S(C)(=O)=O)CC3)cnc2Nc2ccc3ocnc3c2)n1]

Step 1: tert-butyl 4-((5-(4-(bis(4-methoxybenzyl)amino)-6-methyl-1,3,5-triazin-2-yl)-6-fluoropyridin-3-yl)methyl)piperazine-1-carboxylate A microwave vial (80 mL) was charged with 4-chloro-N,N-bis(4-methoxybenzyl)-6-methyl-1,3,5-triazin-2-amine (2.496 g, 6.49 mmol), 5-((4-(tert-butoxycarbonyl)piperazin-1-yl)methyl)-2-fluoropyridin-3-ylboronic acid (2.000 g, 5.90 mmol), potassium acetate (1.777 g, 18.10 mmol), Am-Phos (0.403 g, 0.649 mmol), dioxane (20 mL) and water (3.00 mL, 167 mmol). The vial was heated in a CEM Voyager Microwave (Large-Scale Unit) for 25 minutes at 120° C. while 100 Watts of energy was supplied via Powermax (Simultaneous heating while cooling technology). The reaction mixture was diluted with water (15 mL) and extracted with Chloroform (3×50 mL). The organic extracts were combined and dried over Na$_2$SO$_4$. The solution was filtered and concentrated in vacuo to give the crude product as a yellow oil. The crude product was adsorbed onto a plug of silica gel and purified by chromatography through a SiliCycle SiliaSep pre-packed silica gel column (220 g) with a gradient of 10% to 100% ethyl acetate/hexanes over 45 min to give tert-butyl 4-((5-(4-(bis(4-methoxybenzyl)amino)-6-methyl-1,3,5-triazin-2-yl)-6-fluoropyridin-3-yl)methyl)piperazine-1-carboxylate (3.000 g, 4.66 mmol, 79% yield) as a yellow oil. $^1$H NMR (400 MHz, d6-DMSO) δ 8.50 (dd, J=9.39, 2.35 Hz, 1H); 8.28 (d, J=1.37 Hz, 1H); 7.25 (d, J=8.61 Hz, 4H); 6.89 (dd, J=11.15, 8.61 Hz, 4H); 6.70-6.81 (m, 1H); 4.77 (d, J=4.69 Hz, 4H); 3.65-3.82 (m, 6H); 3.58 (s, 2H); 3.24-3.37 (m, 4H); 2.47 (s, 3H); 2.28-2.38 (m, 4H); 1.33-1.50 (m, 9H). m/z (ESI, +ve ion) 644.2 (M+H)$^+$.

Step 2: 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine A glass microwave reaction vessel (80 mL) was charged with tert-butyl 4-((5-(4-(bis(4-methoxybenzyl)amino)-6-methyl-1,3,5-triazin-2-yl)-6-fluoropyridin-3-yl)methyl)piperazine-1-carboxylate (3.000 g, 4.66 mmol) and trifluoroacetic acid (5.39 mL, 69.9 mmol) in 1,2-dichloroethane (20 mL). The reaction mixture was stirred and heated in a CEM Voyager Model (Large-Scale Unit) Microwave at 80° C. for 5 min (100 watts, Powermax feature on). The mixture was concentrated in vacuo to remove as much residual TFA as possible.

The crude mixture (3.4 g) was dissolved in THF (30 mL), cooled to −20° C., then sodium carbonate (4.94 g, 46.6 mmol) was added to the mixture. After 10 min, methanesulfonyl chloride (3.63 mL, 46.6 mmol) was added dropwise. Following addition, the mixture was allowed to slowly warm to ambient temperature overnight. The mixture was diluted with DCM and water (30 ml). The reaction mixture was extracted with $CH_2Cl_2$ (3×20 mL). The combined organic extracts were dried over $Na_2SO_4$. The solution was filtered and concentrated in vacuo to give crude product as a tan oil. This was purified by chromatography through a SiliCycle SiliaSep pre-packed silica gel column (120 gram) eluting with a gradient of 10% to 100% EtOAc in hexane over 30 min, followed by a gradient of 1% to 15% MeOH in DCM over 20 minutes to give 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (1.702 g, 2.74 mmol, 58.7% yield) as light-yellow solid. $^1$H NMR (400 MHz, $CDCl_3$) δ 8.46 (dd, J=9.00, 2.15 Hz, 1H); 8.24 (d, J=1.37 Hz, 1H); 7.23 (dd, J=8.51, 6.94 Hz, 4H); 6.86 (t, J=8.71 Hz, 4H); 4.81 (d, J=1.96 Hz, 4H); 3.81 (d, J=6.26 Hz, 6H); 3.60 (s, 2H); 3.23 (s, 4H); 2.74-2.80 (m, 3H); 2.56-2.61 (m, 4H); 2.55 (s, 3H). m/z (ESI, +ve ion) 622.1 (M+H)$^+$.

Step 3: N-(3-(4-amino-6-methyl-1,3,5-triazin-2-yl)-5-((4-(methylsulfonyl)piperazin-1-yl)methyl)pyridin-2-yl)benzo[d]oxazol-5-amine A mixture of 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (0.900 g, 1.448 mmol) and benzo[d]oxazol-5-amine (0.388 g, 2.90 mmol) in THF (20 mL) was cooled to −20° C. and treated with 1.0 M lithium bis(trimethylsilyl)amide in THF (5.07 mL, 5.07 mmol) added dropwise. The mixture was allowed to slowly warm to ambient temperature. The reaction mixture was diluted with water (50 mL) and extracted with $CH_2Cl_2$ (3×50 mL). The combined organic extracts were dried over $Na_2SO_4$. The solution was filtered and concentrated to give the crude product as a tan solid. This was purified by chromatography through a SiliCycle SiliaSep pre-packed silica gel column (120 gram), eluting with a gradient of 0% to 10% MeOH in $CH_2Cl_2$ over 30 min to give N-(3-(4-(bis(4-methoxybenzyl)amino)-6-methyl-1,3,5-triazin-2-yl)-5-((4-(methylsulfonyl)piperazin-1-yl)methyl)pyridin-2-yl)benzo[d]oxazol-5-amine as a tan oil. This was treated with trifluoromethanesulfonic acid (0.916 mL, 10.32 mmol) in trifluoroacetic acid (7.75 mL, 101 mmol) and heated at 70° C. for 20 min. The mixture was cooled to ambient temperature and concentrated in vacuo. The crude residue was diluted with DCM (20 mL) and neutralized with sodium bicarbonate (10 g). The mixture was stirred vigorously for 10 min. Then water (10 mL) was added dropwise and allowed to stir for 5 min. The mixture was filtered through a fine-fritted funnel The collected solid was rinsed with water to wash away sodium bicarbonate. The yellow solid was washed with diethyl ether and recrystallized from hot DMF to give N-(3-(4-amino-6-methyl-1,3,5-triazin-2-yl)-5-((4-(methylsulfonyl)piperazin-1-yl)methyl)pyridin-2-yl)benzo[d]oxazol-5-amine (0.300 g, 0.605 mmol, 46.9% yield) as a light-yellow solid. $^1$H NMR (400 MHz, d6-DMSO) δ 12.11 (s, 1H); 8.68 (s, 2H); 8.50 (s, 1H); 8.29 (s, 1H); 7.90 (s, 1H); 7.72 (d, J=11.35 Hz, 3H); 3.51 (s, 2H); 3.12 (s, 4H); 2.87 (s, 3H); 2.50 (m, 7H). m/z (ESI, +ve ion) 496.1 (M+H)$^+$.

Example 129

N-(3-(4-amino-6-methyl-1,3,5-triazin-2-yl)-5-(morpholinomethyl)pyridin-2-yl)benzo[d]thiazol-5-amine

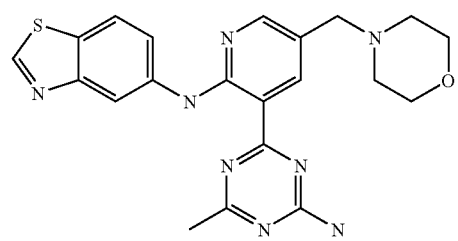 [SMILES: Cc1nc(N)nc(-c2cc(CN3CCOCC3)cnc2Nc2ccc3scnc3c2)n1]

Step 1: 5-(bromomethyl)-2-fluoropyridine

A mixture of 2-fluoro-5-methyl-pyridine (15.00 mL, 135 mmol), N-bromosuccinimide (24.03 g, 135 mmol) and benzoyl peroxide (1.635 g, 6.75 mmol) in carbon tetrachloride (100 mL) was heated at reflux for 2.5 h. The mixture was cooled and filtered through a medium-fritted funnel The solid was rinsed with DCM (3×50 ml). The filtrate was concentrated to give 5-(bromomethyl)-2-fluoropyridine (25.7 g, 135 mmol, 100% yield) as an orange oil. m/z (ESI, +ve ion) 191.9 (M+H)$^+$. The mixture was immediately carried into the next step of the synthesis without further purification.

Step 2: 4-((6-fluoropyridin-3-yl)methyl)morpholine

A solution of 5-(bromomethyl)-2-fluoropyridine (26.000 g, 137 mmol) in THF (30 mL) was cooled to −30° C. and morpholine (17.88 mL, 205 mmol) was slowly added. After 5 min, triethylamine (57.2 mL, 410 mmol) was slowly added. Following addition, the cooling bath was removed and the mixture was allowed to warm to ambient temperature. After 30 min, the mixture was filtered through a fine-fritted funnel and the filtrate was concentrated to give an orange oil. The crude material was purified by chromatography through a Thompson Instruments pre-packed silica gel (330 gram) column eluting with a gradient of 0% to 100% EtOAc in hexane over 50 min to give 4-((6-fluoropyridin-3-yl)methyl)morpholine (15.767 g, 80 mmol, 58.7% yield) as an orange oil. $^1$H NMR (400 MHz, $CDCl_3$) δ 8.13 (s, 1H); 7.79 (td, J=8.07, 2.45 Hz, 1H); 6.90 (dd, J=8.31, 2.84 Hz, 1H); 3.67-3.72 (m, 4H); 3.49 (s, 2H); 2.39-2.48 (m, 4H). m/z (ESI, +ve ion) 197.1 (M+H)$^+$.

Step 3: 2-fluoro-5-(morpholinomethyl)pyridin-3-ylboronic acid

A solution of diisopropylamine (13.51 mL, 96 mmol) in tetrahydrofuran (66 mL) was treated with 2.0 M n-butyl lithium in hexane (48.2 mL, 96 mmol) at −40° C. and stirred for 1 h. The resulting LDA solution was cooled to −78° C. and a solution of 4-((6-fluoropyridin-3-yl)methyl)morpholine (15.767 g, 80 mmol) in THF (50 mL) was added via cannula over 20 min. The deep-red mixture was stirred at −78° C. for 1.5 h. A solution of triisopropyl borate (27.7 mL, 121 mmol) in THF (22 mL) was added slowly. The resulting mixture was stirred at −78° C. for 30 min and then the cooling bath was removed and the reaction mixture was allowed to warm to room temperature. The mixture was quenched with 1 N NaOH$_{(aq)}$ (50 mL) and stirred. The aqueous layer was separated and the organic layer was extracted with 1 N NaOH (2×20 mL). The combined aqueous layers were carefully acidified with 5 N HCl until acidic (pH 5 to about 6) and the resulting cloudy mixture was extracted with EtOAc (3×100 mL). The aqueous layer was lyophilized. The resulting residue was diluted with 1:1 MeOH/DCM and placed into a sonicator for 5 min. The mixture was filtered through a fine-fritted funnel The filtrate was concentrated to give 2-fluoro-5-(morpholinomethyl)pyridin-3-ylboronic acid (19.000 g, 79 mmol, 99% yield) as a tan oil. $^1$H NMR (400 MHz, d4-MeOH) δ 8.46 (s, 1H); 8.32 (d, J=6.06 Hz, 1H); 4.42 (s, 2H); 3.82-4.00 (m, 4H); 3.23-3.36 (m, 4H); 2.01 (s, 1H). m/z (ESI, +ve ion) 241.1 (M+H)$^+$.

Step 4: 4-(2-fluoro-5-(morpholinomethyl)pyridin-3-yl)-N,N-bis(4-methoxybenzyl)-6-methyl-1,3,5-triazin-2-amine A mixture of 4-chloro-N,N-bis(4-methoxybenzyl)-6-methyl-1,3,5-triazin-2-amine (8.82 g, 22.91 mmol), 2-fluoro-5-(morpholinomethyl)pyridin-3-ylboronic acid (5.000 g, 20.83 mmol), potassium acetate (6.28 g, 63.9 mmol), and Am-Phos (1.036 g, 1.666 mmol) in dioxane (40 mL) and water (3.00 mL, 167 mmol) was heated in a CEM Voyager Microwave (Large-Scale Unit) for 25 min at 120° C. while 100 Watts of energy was supplied via Powermax (Simultaneous heating while cooling technology). The reaction mixture was diluted with saturated aqueous sodium bicarbonate solution (50 mL) and extracted with CHCl$_3$ (3×100 mL). The organic extracts were combined and dried over Na$_2$SO$_4$. The solution was filtered and concentrated to give crude product as a yellow oil. This was purified by chromatography through a SiliCycle SiliaSep pre-packed silica gel column (330 gram) using a gradient of 0-100% ethyl acetate/hexanes over 40 min, followed by a gradient of 1-20% methanol/dichloromethane over 30 min to give a tan oil. This was triturated with DCM and diethyl ether and the mixture was filtered. The filtrate was concentrated to give 4-(2-fluoro-5-(morpholinomethyl)pyridin-3-yl)-N,N-bis(4-methoxybenzyl)-6-methyl-1,3,5-triazin-2-amine (2.615 g, 4.80 mmol, 23% yield) as a light-yellow oil. $^1$H NMR (400 MHz, CDCl$_3$) δ 8.13 (d, J=1.56 Hz, 1H); 7.79 (td, J=7.97, 2.05 Hz, 1H); 7.22 (dd, J=8.61, 7.04 Hz, 4H); 6.81-6.92 (m, 4H); 4.82 (d, J=3.33 Hz, 2H); 3.76-3.86 (m, 4H); 3.70 (ddd, J=9.54, 4.99, 4.84 Hz, 4H); 3.45-3.57 (m, 6H); 2.55 (s, 3H); 2.46 (dq, J=12.79, 4.41 Hz, 4H). m/z (ESI, +ve ion) 545.2 (M+H)$^+$.

Step 5: N-(3-(4-amino-6-methyl-1,3,5-triazin-2-yl)-5-(morpholinomethyl)pyridin-2-yl)benzo[d]thiazol-5-amine A mixture of 4-(2-fluoro-5-(morpholinomethyl)pyridin-3-yl)-N,N-bis(4-methoxybenzyl)-6-methyl-1,3,5-triazin-2-amine (0.500 g, 0.918 mmol) and benzo[d]thiazol-5-amine (0.276 g, 1.836 mmol) in THF (10 mL) was cooled to −20° C. and treated dropwise with 1.0 M lithium bis(trimethylsilyl)amide in THF (3.21 mL, 3.21 mmol). The mixture was allowed to slowly warm to ambient temperature while stirring under inert atmosphere for 1 h. The reaction mixture was diluted with water (50 mL) and extracted with CHCl$_3$ (3×50 mL). The combined organic extracts were dried over Na$_2$SO$_4$. The solution was filtered and concentrated to give the crude product as a tan solid. This was purified by chromatography through a SiliCycle SiliaSep pre-packed silica gel column (80 gram) eluting with a gradient of 10% to 100% EtOAc in hexane over 30 minutes, followed by a gradient of 1-20% MeOH/DCM over 25 min to give the bis-PMB protected material (0.437 g) as a tan oil. This was treated with a mixture of trifluoroacetic acid (1.8 mL, 23.36 mmol) and trifluoromethanesulfonic acid (0.2 mL, 2.252 mmol) and the resulting solution was heated at 70° C. 20 min. The mixture was cooled to ambient temperature and concentrated to give a tan oil. The mixture was dissolved in DCM (10 mL) and allowed to stir 5 min, then sodium carbonate (2.5 grams) was slowly added to the mixture and allowed to stir vigorously for 20 min. The solid was collected by filtration and rinsed with dichloromethane (2×30 mL) followed by water (3×20 mL). The solid was dried to give N-(3-(4-amino-6-methyl-1,3,5-triazin-2-yl)-5-(morpholinomethyl)pyridin-2-yl)benzo[d]thiazol-5-amine (0.155 g, 0.357 mmol, 38.9% yield) as a tan solid. $^1$H NMR (400 MHz, d6-DMSO) δ 12.25 (s, 1H); 9.36 (s, 1H); 8.91 (s, 1H); 8.76 (s, 1H); 8.33 (s, 1H); 8.06 (d, J=8.80 Hz, 1H); 7.94 (s, 1H); 7.80 (s, 2H); 3.58 (s, 4H); 3.46 (s, 2H); 2.44-2.54 (m, 3H); 2.39 (s, 4H). m/z (ESI, +ve ion) 435 (M+H)$^+$.

Example 130

4-(2-(5-fluoro-6-methoxypyridin-3-ylamino)-5-(morpholinomethyl)pyridin-3-yl)-6-methyl-1,3,5-triazin-2-amine

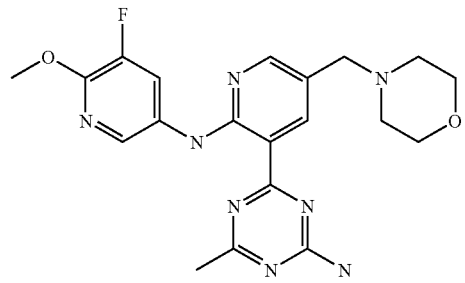 [SMILES: COc1ncc(Nc2ncc(CN3CCOCC3)cc2-c2nc(C)nc(N)n2)cc1F]

A mixture of 4-(2-fluoro-5-(morpholinomethyl)pyridin-3-yl)-N,N-bis(4-methoxybenzyl)-6-methyl-1,3,5-triazin-2-amine (0.500 g, 0.918 mmol) and 5-fluoro-6-methoxypyridin-3-amine (0.261 g, 1.836 mmol) in THF (20 mL) was cooled to −20° C. and treated with a 1.0 M solution of lithium bis(trimethylsilyl)amide (3.21 mL, 3.21 mmol) added dropwise. The mixture was allowed to slowly warm to ambient temperature over 1 h. The reaction mixture was diluted with water (50 mL) and extracted with CH$_2$Cl$_2$ (3×50 mL). The combined organic extracts were dried over sodium sulfate and concentrated to give the crude product as a tan solid. This was purified by chromatography through a SiliCycle SiliaSep pre-packed silica-gel column (80 gram) eluting with a gradient of 0% to 100% EtOAc in hexane over 30 min to give 4-(2-(5-fluoro-6-methoxypyridin-3-ylamino)-5-(morpholinomethyl)pyridin-3-yl)-N,N-bis(4-methoxybenzyl)-6-methyl-1,3,5-triazin-2-amine (0.095 g) as a tan oil. This was treated with trifluoroacetic acid (1.8 mL, 23.36 mmol) and trifluoromethanesulfonic acid (0.2 mL, 2.252 mmol) and heated at 70° C. for 20 min. The mixture was cooled to ambient temperature and concentrated to give a tan oil. This was dissolved in DCM (10 mL) and allowed to stir for 5 min, then sodium carbonate (1.6 g) was slowly added to the mixture and stirred vigorously for 20 min. The mixture was filtered and concentrated. The mixture was diluted with ethyl acetate and filtered. The filtrate was concentrated and the residue was diluted with diethyl ether (20 mL) and placed in a sonicator for 2 min. The precipitate was collected by filtration. The solid was recrystallized from hot ethyl acetate to give 4-(2-(5-fluoro-6-methoxypyridin-3-ylamino)-5-(morpholinomethyl)pyridin-3-yl)-6-methyl-1,3,5-triazin-2-amine (0.025 g, 0.059 mmol, 6.39% yield) as a tan solid. $^1$H NMR (400 MHz, d6-DMSO) δ 11.94 (s, 1H); 8.72 (s, 1H); 8.41 (s, 1H); 8.36 (d, J=12.91 Hz, 1H); 8.24 (s, 1H); 7.90 (s, 1H); 7.75 (s, 1H); 3.93 (s, 3H); 3.57 (s, 4H); 3.43 (s, 2H); 2.44 (s, 7H). m/z (ESI, +ve ion) 427 (M+H)$^+$.

Example 131

1-(6-(6-methoxypyridin-3-ylamino)-5-(2-methyl-9-(tetrahydro-2H-pyran-2-yl)-9H-purin-6-yl)pyridin-3-yl)-2,2-dimethylpropan-1-ol

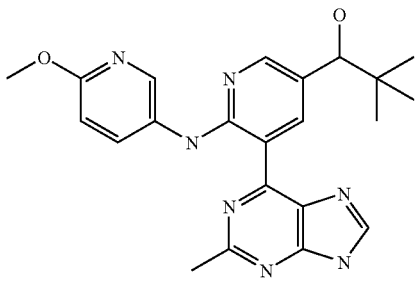 [SMILES: COc1ccc(Nc2ncc(C(O)C(C)(C)C)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (95.0 mg, 0.213 mmol) was dissolved in THF (2.5 mL) and the flask was cooled in an ice water bath. Then, tert-butylmagnesium chloride (1.0 M solution in tetrahydrofuran, 0.60 mL, 0.60 mmol) was added via syringe, turning the reaction red. The reaction was stirred under nitrogen while being warmed to room temperature, and after 70 min the reaction was treated with MeOH (1.0 mL) and 5 N HCl (0.50 mL). The flask was fitted with a reflux condenser and put in a preheated oil bath (about 50° C.), and stirring was continued for 1 h. Then, the reaction was cooled to room temperature, diluted with MeOH, concentrated, and purified by prep HPLC (10% to 100% MeCN/water with 0.1% TFA over 28 min using a total flow rate of 100 mL/min) to give 1-(6-(6-methoxypyridin-3-ylamino)-5-(2-methyl-9-(tetrahydro-2H-pyran-2-yl)-9H-purin-6-yl)pyridin-3-yl)-2,2-dimethylpropan-1-ol (45.9 mg, 97.4% purity, 52% yield). $^1$H NMR (d6-DMSO, 400 MHz) δ 12.62 (br s, 1H), 9.61 (s, 1H), 8.63 (s, 1H), 8.53 (d, J=2.74 Hz, 1H), 8.21-8.14 (m, 2H), 6.88 (d, J=9.0 Hz, 1H), 4.31 (s, 1H), 3.86 (s, 3H), 2.85 (s, 3H), 0.91 (s, 9H). m/z (ESI, pos. ion) 420 (M+H)$^+$.

Examples 132 and 133

(1S)-1-(6-(6-methoxypyridin-3-ylamino)-5-(2-methyl-9-(tetrahydro-2H-pyran-2-yl)-9H-purin-6-yl)pyridin-3-yl)-2,2-dimethylpropan-1-ol and (1R)-1-(6-(6-methoxypyridin-3-ylamino)-5-(2-methyl-9-(tetrahydro-2H-pyran-2-yl)-9H-purin-6-yl)pyridin-3-yl)-2,2-dimethylpropan-1-ol

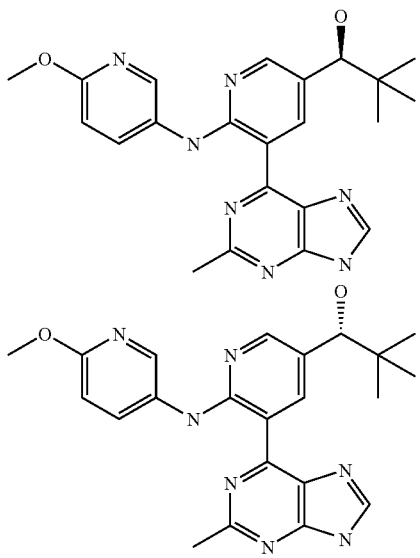

A mixture of isomers of 1-(6-(6-methoxypyridin-3-ylamino)-5-(2-methyl-9-(tetrahydro-2H-pyran-2-yl)-9H-purin-6-yl)pyridin-3-yl)-2,2-dimethylpropan-1-ol (Example 131) was purified using chiral SFC preparative chromatography. The following conditions were used:

Column: IC (250×21 mm, 5 μm)×2
Mobile Phase: 65:35 (A:B)
A: Liquid CO$_2$
B: Methanol (0.2% DEA)
Flow Rate: 50 mL/min
Oven/column temp: 40° C.
about 2 mg/injection The two separate peaks containing the two enantiomers were collected, concentrated, and dried under high vacuum to afford the two enantiomers.

First Eluting Peak (Example 132):
$^1$H NMR (d6-DMSO, 400 MHz) δ 12.80 (s, 1H), 9.80 (s, 1H), 8.54 (d, J=2.74 Hz, 1H), 8.48 (s, 1H), 8.21 (dd, J=8.90 Hz, 2.84 Hz, 1H), 8.17 (d, J=2.35 Hz, 1H), 6.84 (8.80 Hz, 1H), 5.24 (d, J=3.72 Hz, 1H), 4.29 (d, J=3.52 Hz, 1H), 3.84 (s, 3H), 2.83 (s, 3H), 0.90 (s, 9H). m/z (ESI, pos. ion) 420 (M+H)$^+$.

Second Eluting Peak (Example 133):
$^1$H NMR (d6-DMSO, 400 MHz) δ 12.65 (s, 1H), 9.78 (s, 1H), 8.57 (s, 1H), 8.54 (d, J=2.15 Hz, 1H), 8.22 (d, J=2.35 Hz, 1H), 8.19 (s, 1H), 6.84 (d, J=8.80 Hz, 1H), 5.26 (s, 1H), 4.29 (s, 1H), 3.84 (s, 3H), 2.85 (s, 3H), 0.90 (s, 9H). m/z (ESI, +ve ion) 420 (M+H)$^+$.

Example 134

5-((tert-butylamino)methyl)-N-(6-methoxypyridin-3-yl)-3-(2-methyl-9H-purin-6-yl)pyridin-2-amine

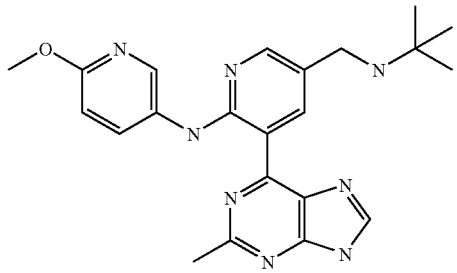 [SMILES: COc1ccc(Nc2ncc(CNC(C)(C)C)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (99.5 mg, 0.223 mmol) was suspended in CH$_2$Cl$_2$ (1.5 mL) and ethanol (1.5 mL), and tert-butylamine (0.075 mL, 0.71 mmol) and tetraisopropoxytitanium (0.20 mL, 0.68 mmol) were added. The reaction was stirred under nitrogen at room temperature for 20 min, and then was fitted with a reflux condenser and put in a preheated oil bath (about 50° C.) and stirred for 90 min. Then, the reaction was cooled to room temperature and sodium borohydride (28.7 mg, 0.759 mmol) and MeOH (1.0 mL) were added. The reaction was stirred at room temperature for 45 minutes, and then more MeOH and 5 N HCl (0.50 mL) were added, and stirring was continued overnight at room temperature. Then, the reaction was diluted with DCM and MeOH and filtered through a Celite® (diatomaceous earth) pad, which was washed with DCM, MeOH, and a 1:1 mixture of these 2 solvents. The filtrate was concentrated and diluted with DCM and MeOH and filtered through another Celite® (diatomaceous earth) pad, which was washed with DCM and MeOH. The filtrate was concentrated and purified by prep HPLC to give 5-((tert-butylamino)methyl)-N-(6-methoxypyridin-3-yl)-3-(2-methyl-9H-purin-6-yl)pyridin-2-amine (51.1 mg, 98.3% purity, 43% yield) as a TFA salt. $^1$H NMR (d6-DMSO, 400 MHz) δ 12.74 (br s, 1H), 9.81 (br s, 1H), 8.70 (s, 1H), 8.65 (br s, 2H), 8.59 (d, J=2.74 Hz, 1H), 8.42 (d, J=2.35 Hz, 1H), 8.14 (dd, J=8.80 Hz, 2.74 Hz, 1H), 6.89 (d, J=8.80 Hz, 1H), 4.18 (br s, 2H), 3.86 (s, 3H), 2.87 (s, 3H), 1.39 (s, 9H). m/z (ESI, +ve ion) 419 (M+H)$^+$.

Example 135

5-((isopropylamino)methyl)-N-(6-methoxypyridin-3-yl)-3-(2-methyl-9H-purin-6-yl)pyridin-2-amine

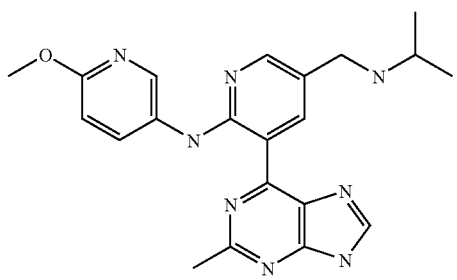 [SMILES: COc1ccc(Nc2ncc(CNC(C)C)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (90.6 mg, 0.203 mmol) was suspended in ethanol (1.2 mL) and DCM (1.2 mL), and isopropylamine (0.060 mL, 0.70 mmol) and tetraisopropoxytitanium (0.20 mL, 0.68 mmol) were added. The reaction was stirred at room temperature for 75 min, and then sodium borohydride (26.8 mg, 0.708 mmol) was added, along with MeOH (1 mL), and stirring was continued at room temperature. After 2 h, more MeOH and 5 N HCl (0.50 mL) were added, and stirring was continued overnight. The suspension was diluted with DCM and MeOH and filtered through a Celite® (diatomaceous earth) pad, which was washed with DCM and MeOH. The filtrate was concentrated and purified by prep HPLC to give 5-((isopropylamino)methyl)-N-(6-methoxypyridin-3-yl)-3-(2-methyl-9H-purin-6-yl)pyridin-2-amine (79.5 mg, 97.1% purity, 76% yield) as a TFA salt. $^1$H NMR (d6-DMSO, 400 MHz) δ 12.71 (br s, 1H), 9.80 (br s, 1H), 8.69 (s, 1H), 8.65 (br s, 2H), 8.58 (d, J=2.74 Hz, 1H), 8.42 (d, J=2.15 Hz, 1H), 8.14 (dd, J=9.00 Hz, 2.74 Hz, 1H), 6.89 (d, J=9.00 Hz, 1H), 4.24-4.18 (m, 2H), 3.86 (s, 3H), 3.48-3.38 (m, 1H), 2.87 (s, 3H), 1.31 (d, J=6.46 Hz, 6H). m/z (ESI, +ve ion) 405 (M+H)$^+$.

Example 136

N-(6-methoxypyridin-3-yl)-3-(2-methyl-9H-purin-6-yl)-5-((pyridin-2-ylmethylamino)methyl)pyridin-2-amine

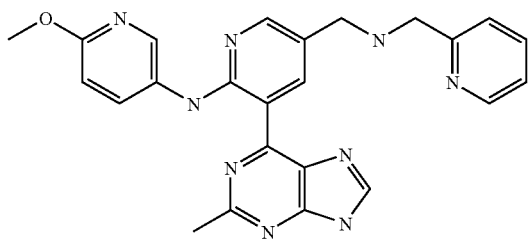 [SMILES: COc1ccc(Nc2ncc(CNCc3ccccn3)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (73.8 mg, 0.166 mmol) was suspended in CH$_2$Cl$_2$ (1.5 mL) and EtOH (1.5 mL), and 2-(aminomethyl)pyridine (0.050 mL, 0.49 mmol) and tetraisopropoxytitanium (0.15 ml, 0.51 mmol) were added via syringe. The reaction was stirred under nitrogen at room temperature for 90 min, and then sodium borohydride (26.3 mg, 0.695 mmol) and MeOH (1.0 mL) were added, and stirring was continued. After 70 min, more MeOH and 5 N aqueous HCl (0.50 mL) were added, and stirring was continued overnight. The suspension was diluted with DCM and MeOH and filtered through a Celite® (diatomaceous earth) pad, which was washed with DCM and MeOH. The filtrate was concentrated, treated with DMSO and TFA, and purified by prep HPLC (10% to 100% MeCN/water with 0.1% TFA over 28 min using a total flow rate of 100 mL/min) to give N-(6-methoxypyridin-3-yl)-3-(2-methyl-9H-purin-6-yl)-5-((pyridin-2-ylmethylamino)methyl)pyridin-2-amine (52.1 mg, 55% yield) as a TFA salt. $^1$H NMR (d6-DMSO, 400 MHz) δ 12.69 (br s, 1H), 9.81 (br s, 1H), 9.46 (br s, 2H), 8.68 (s, 1H), 8.66 (d, J=4.30 Hz, 1H), 8.56 (d, J=2.74 Hz, 1H), 8.41 (d, J=2.35 Hz, 1H), 8.14 (dd, J=9.00 Hz, 2.74 Hz, 1H), 7.89 (dt, J=7.73 Hz, 1.76 Hz, 1H), 7.51 (d, J=7.82 Hz, 1H), 7.46-7.41 (m, 1H), 6.88 (d, J=8.80 Hz, 1H), 4.41 (s, 2H), 4.29 (s, 2H), 3.85 (s, 3H), 2.86 (s, 3H). m/z (ESI, pos. ion) 454 (M+H)+.

Example 137

N-(6-methoxypyridin-3-yl)-3-(2-methyl-9H-purin-6-yl)-5-((pyridin-4-ylmethylamino)methyl)pyridin-2-amine

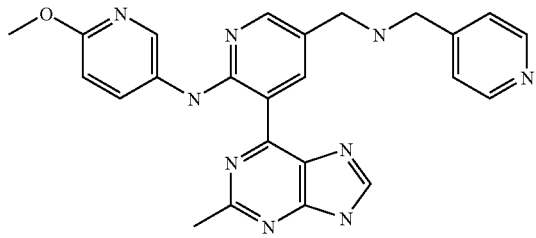

6-(6-methoxypyridin-3-ylamino)-5-(2-methyl-9-(tetrahydro-2H-pyran-2-yl)-9H-purin-6-yl)nicotinaldehyde (102.5 mg, 0.230 mmol) was suspended in dichloromethane (1.3 mL) and EtOH (1.3 mL), and 4-(aminomethyl)pyridine (0.070 mL, 0.69 mmol) and tetraisopropoxytitanium (0.20 mL, 0.68 mmol) were added. The reaction was stirred under nitrogen at room temperature. After 50 min, sodium borohydride (30.8 mg, 0.814 mmol) and MeOH (1 mL) were added, and stirring was continued at room temperature. After 1 h, more MeOH and 5 N aqueous HCl (0.60 mL) were added, and stirring was continued at room temperature over the weekend. Then, the reaction was treated with DCM and MeOH and was filtered through a Celite® (diatomaceous earth) pad, which was washed with DCM and MeOH. The filtrate was concentrated and treated with DCM and TFA and some DMSO (about 1 mL) and concentrated. The material was dissolved in water and partially concentrated resulting in the formation of a precipitate. The suspension was filtered, and the solid was washed with MeOH. The solid was set aside. The filtrate was concentrated and filtered again. The solid was combined with the solid collected from the first filtration. The filtrate was concentrated and purified by prep HPLC (10% to 100% MeCN/water with 0.1% TFA over 28 minutes with a total flow of 100 mL/min). The fractions with product were combined with the solid that had been collected, concentrated, and dried under high vacuum, first at about 50° C., and then at room temperature overnight to afford N-(6-methoxypyridin-3-yl)-3-(2-methyl-9H-purin-6-yl)-5-((pyridin-4-ylmethylamino)methyl)pyridin-2-amine (126.6 mg, 96.7% purity, 97% yield) as a TFA salt. 1H NMR (D2O, 400 MHz) δ 8.83-8.77 (m, 4H), 8.43 (s, 1H), 8.21 (dd, J=8.41 Hz, 2.35 Hz, 2H), 8.08-8.03 (m, 3H), 7.82 (dd, J=9.00 Hz, 2.74 Hz, 1H), 6.95 (dd, J=9.00 Hz, 1H), 4.63 (s, 2H), 4.51 (s, 2H), 4.42 (s, 2H), 3.91 (s, 3H), 2.69 (s, 3H). m/z (ESI, pos. ion) 454 (M+H)+.

Example 138

N-(6-methoxypyridin-3-yl)-3-(2-methyl-9H-purin-6-yl)-5-((pyridin-3-ylmethylamino)methyl)pyridin-2-amine

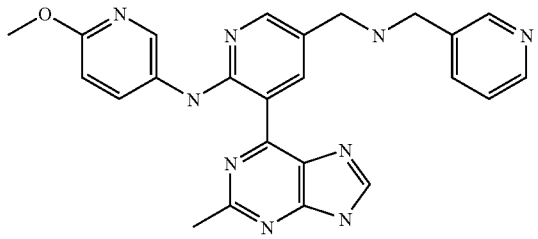 [SMILES: COc1ccc(Nc2ncc(CNCc3cccnc3)cc2-c2nc(C)nc3[nH]cnc23)cn1]

6-(6-methoxypyridin-3-ylamino)-5-(2-methyl-9-(tetrahydro-2H-pyran-2-yl)-9H-purin-6-yl)nicotinaldehyde (113.7 mg, 0.255 mmol) was suspended in dichloromethane (1.3 mL) and ethanol (1.3 mL), and 3-(aminomethyl)pyridine (0.080 mL, 0.79 mmol) and tetraisopropoxytitanium (0.23 mL, 0.78 mmol) were added. The reaction was stirred under nitrogen at room temperature. After 85 min, sodium borohydride (33.8 mg, 0.893 mmol) and MeOH (1 mL) were added, and stirring was continued at room temperature. After another 70 min, 5 N HCl (0.50 mL) was added, along with MeOH, and stirring was continued at room temperature for 3 days. More 5 N HCl (0.20 mL) and MeOH were added, and stirring was continued at room temperature overnight. The suspension was diluted with DCM and MeOH and filtered through a Celite® (diatomaceous earth) pad, which was washed with DCM and MeOH. The filtrate was concentrated, treated with DCM, MeOH, TFA, and concentrated again. The material was dissolved with water and MeOH and purified by prep HPLC (10% to 100% MeCN/water with 0.1% TFA over 28 min with a total flow rate of 100 mL/min). The HPLC fractions with product were collected, concentrated, and dried under high vacuum, first in a water bath at 50° C., and then at room temperature overnight to give N-(6-methoxypyridin-3-yl)-3-(2-methyl-9H-purin-6-yl)-5-((pyridin-3-ylmethylamino)methyl)pyridin-2-amine (117.1 mg, 81% yield) as a TFA salt. 1H NMR (D2O, 400 MHz) δ 8.94 (s, 1H), 8.92-8.87 (m, 1H), 8.83 (d, J=5.87 Hz, 1H), 8.69 (d, J=8.22 Hz, 1H), 8.47 (s, 1H), 8.37 (s, 1H), 8.26 (d, J=2.15 Hz, 1H), 8.13-8.06 (m, 1H), 7.98 (dd, J=9.19 Hz, 2.54 Hz, 1H), 7.11 (d, J=9.19

Hz, 1H), 4.61 (s, 2H), 4.44 (s, 2H), 3.99 (s, 3H), 2.73 (s, 3H). m/z (ESI, +ve ion) 454 (M+H)+.

Example 139

(6-(6-methoxypyridin-3-ylamino)-5-(2-methyl-9H-purin-6-yl)pyridin-3-yl)(4-(methylsulfonyl)phenyl)methanol

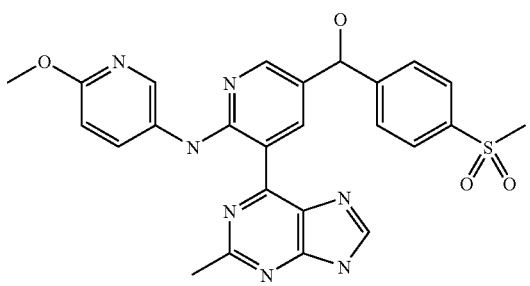

Step 1: (6-(6-methoxypyridin-3-ylamino)-5-(2-methyl-9-(tetrahydro-2H-pyran-2-yl)-9H-purin-6-yl)pyridin-3-yl)(4-(methylthio)phenyl)methanol 6-(6-methoxypyridin-3-ylamino)-5-(2-methyl-9-(tetrahydro-2H-pyran-2-yl)-9H-purin-6-yl)nicotinaldehyde (209.2 mg, 0.470 mmol) was suspended in THF (5.0 mL) and the reaction flask was cooled in an ice water bath under nitrogen. Then, 4-thioanisolemagnesium bromide (0.5 M solution in tetrahydrofuran, 2.5 mL, 1.3 mmol) was added via syringe, and the reaction was allowed to slowly warm up to room temperature. After 1 h, the reaction was quenched with saturated ammonium chloride and diluted with water. The reaction was extracted with 10:1 DCM/MeOH. These organic extracts were combined, concentrated, and purified on a silica gel filter (about 1 inch in a 30 ml fritted filter with 50:1 DCM/2 N ammonia in MeOH to 20:1 DCM/2 N ammonia in MeOH to 5:1 DCM/2 N ammonia in MeOH). The fractions with product were collected, concentrated, and dried under high vacuum to give (6-(6-methoxypyridin-3-ylamino)-5-(2-methyl-9-(tetrahydro-2H-pyran-2-yl)-9H-purin-6-yl)pyridin-3-yl)(4-(methylthio)phenyl)methanol (241 mg). 1H NMR (CDCl3) δ 12.51 (s, 1H), 9.80 (s, 1H), 8.39 (s, 1H), 8.26-8.18 (m, 3H), 7.43-7.38 (m, 2H), 7.26-7.20 (m, 2H), 6.77 (d, J=8.41 Hz, 1H), 5.90 (s, 1H), 5.85 (d, J=10.17 Hz, 1H), 4.20 (d, J=11.35 Hz, 1H), 3.95 (s, 3H), 3.83 (t, J=11.25 Hz, 1H), 2.89 (s, 3H), 2.74 (s, 1H), 2.47 (s, 3H), 2.17-1.65 (m, 6H). m/z (ESI, +ve ion) 570 (M+H)+.

Step 2: (6-(6-methoxypyridin-3-ylamino)-5-(2-methyl-9-(tetrahydro-2H-pyran-2-yl)-9H-purin-6-yl)pyridin-3-yl)(4-(methylsulfonyl)phenyl)methanol (6-(6-methoxypyridin-3-ylamino)-5-(2-methyl-9-(tetrahydro-2H-pyran-2-yl)-9H-purin-6-yl)pyridin-3-yl)(4-(methylthio)phenyl)methanol (241 mg, 0.423 mmol) was dissolved in DCM (4.0 mL) and the reaction flask was cooled in an ice water bath under nitrogen. Then, mCPBA (180.5 mg, 1.046 mmol) was added as a solution in DCM (5 mL) via syringe, and the reaction was warmed to room temperature and stirred. After 45 min, more mCPBA (58 mg, 0.34 mmol) was added, and stirring was continued. After 25 min, more mCPBA (27.3 mg, 0.158 mmol) was added, and stirring was continued. After 15 minutes, the reaction was treated with a solution made of 10 mL saturated sodium bicarbonate and 2 mL saturated sodium thiosulfate. The mixture was stirred at room temperature for 30 min. Then, the layers were separated and the aqueous phase was extracted with DCM and then with 10:1 DCM/MeOH. The organic extracts were combined, washed with brine, concentrated, and dried under high vacuum in a water bath (about 40° C.) to give (6-(6-methoxypyridin-3-ylamino)-5-(2-methyl-9-(tetrahydro-2H-pyran-2-yl)-9H-purin-6-yl)pyridin-3-yl)(4-(methylsulfonyl)phenyl)methanol, which was taken on directly to the next step. 1H NMR (CDCl3, 400 MHz) δ 12.54 (s, 1H), 9.75 (s, 1H), 8.40 (s, 1H), 8.27-8.21 (m, 2H), 8.17 (d, J=8.22 Hz, 1H), 7.95-7.89 (m, 2H), 7.74-7.68 (m, 2H), 6.78 (d, J=10.17 Hz, 1H), 6.01 (s, 1H), 5.85 (d, J=11.93 Hz, 1H), 4.21 (d, J=13.11 Hz, 1H), 3.95 (s, 3H), 3.87-3.77 (m, 1H), 3.03 (s, 3H), 2.97-2.89 (m, 1H), 2.89 (s, 3H), 2.19-1.95 (m, 3H), 1.93-1.65 (m, 3H). m/z (ESI, +ve ion) 602 (M+H)+.

Step 3: (6-(6-methoxypyridin-3-ylamino)-5-(2-methyl-9H-purin-6-yl)pyridin-3-yl)(4-(methylsulfonyl)phenyl)methanol (6-(6-methoxypyridin-3-ylamino)-5-(2-methyl-9-(tetrahydro-2H-pyran-2-yl)-9H-purin-6-yl)pyridin-3-yl)(4-(methylsulfonyl)phenyl)methanol (the crude material from the previous step) was suspended in MeOH (5.0 mL) and aqueous hydrochloric acid (5 N, 0.50 mL, 2.5 mmol) was added. The reaction was stirred at room temperature for about 2 h, and then was diluted with DCM and MeOH. After 3.5 h, the suspension was filtered. Neither solid nor filtrate was >95% pure by HPLC, so they were combined, concentrated, treated with water, and filtered. The solid was collected, treated with DMSO and TFA, and filtered through a Celite® (diatomaceous earth) pad. The filtrate was purified by prep HPLC (10% to 100% MeCN/water with 0.1% TFA over 28 min with a total flow rate of 100 mL/min.) to give (6-(6-methoxypyridin-3-ylamino)-5-(2-methyl-9H-purin-6-yl)pyridin-3-yl)(4-(methylsulfonyl)phenyl)methanol (122.4 mg, 56% yield over two steps). 1H NMR (d6-DMSO, 400 MHz) includes δ 12.62 (br s, 1H), 9.84 (br s, 1H), 8.62 (s, 1H), 8.52 (d, J=2.54 Hz, 1H), 8.29 (d, J=2.15 Hz, 1H), 8.16 (dd, J=8.71 Hz, 2.64 Hz, 1H), 7.90 (d, J=8.22 Hz, 2H), 7.73 (d, J=8.22 Hz, 2H), 6.84 (d, J=8.80 Hz, 1H), 5.91 (s, 1H), 3.84 (s, 3H), 3.17 (s, 3H), 2.84 (s, 3H). m/z (ESI, pos. ion) 518 (M+H)+.

Example 140

N-(6-methoxypyridin-3-yl)-3-(2-methyl-9H-purin-6-yl)-5-(1-(4-(methylsulfonyl)piperazin-1-yl)ethyl)pyridin-2-amine

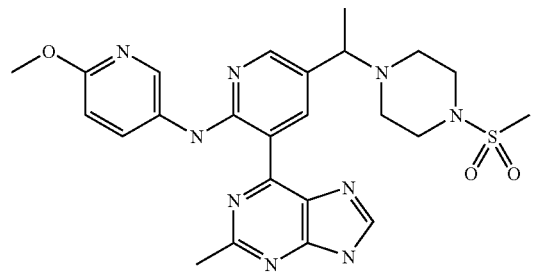

Step 1: 1-(6-(6-methoxypyridin-3-ylamino)-5-(2-methyl-9-(tetrahydro-2H-pyran-2-yl)-9H-purin-6-yl)pyridin-3-yl)ethanol 6-(6-methoxypyridin-3-ylamino)-5-(2-methyl-9-(tetrahydro-2H-pyran-2-yl)-9H-purin-6-yl)nicotinaldehyde (641.5 mg, 1.440 mmol) was suspended in THF (14 mL) and the reaction was cooled in an ice bath under nitrogen. Then, methylmagnesium bromide (3.0 M solution in diethyl ether, 1.65 mL, 4.95 mmol) was added via syringe, and the reaction was allowed to warm up to room temperature. After 1 h and 45 min, the reaction was cooled in an ice bath and the reaction was treated with saturated ammonium chloride, dropwise at first as gas evolution was observed. Then, the reaction was warmed to room temperature and diluted with water (15 mL). The layers were separated, and the aqueous phase was extracted with 10:1 DCM/MeOH. The organic layer and the organic extracts were combined, concentrated, and dried under high vacuum to give 1-(6-(6-methoxypyridin-3-ylamino)-5-(2-methyl-9-(tetrahydro-2H-pyran-2-yl)-9H-purin-6-yl)pyridin-3-yl)ethanol (725 mg). $^1$H NMR (CDCl$_3$, 400 MHz) δ 12.52 (s, 1H), 9.81 (s, 1H), 8.43 (s, 1H), 8.36-8.19 (m, 3H), 6.83-6.77 (m, 1H), 5.88 (d, J=9.00 Hz, 1H), 5.01 (d, J=5.87 Hz, 1H), 4.21 (d, J=10.95 Hz, 1H), 3.89-3.81 (m, 1H), 2.91 (s, 3H), 2.21-1.65 (m, 6H), 1.63-1.61 (m, 3H). m/z (ESI, pos. ion) 462 (M+H)$^+$.

Step 2: N-(6-methoxypyridin-3-yl)-3-(2-methyl-9H-purin-6-yl)-5-(1-(4-(methylsulfonyl)piperazin-1-yl)ethyl)pyridin-2-amine 1-(6-(6-methoxypyridin-3-ylamino)-5-(2-methyl-9-(tetrahydro-2H-pyran-2-yl)-9H-purin-6-yl)pyridin-3-yl)ethanol (14.2 mg, 0.031 mmol) was dissolved in DCM (1 mL) and triethylamine (Aldrich 99.5%, 0.020 mL, 0.14 mmol) was added. The reaction was cooled in an ice bath under nitrogen, and methanesulfonyl chloride (0.010 mL, 0.13 mmol) was added. The reaction was stirred under nitrogen at 0° C. for 15 min, and then 1-methanesulfonylpiperazine (35 mg, 0.21 mmol) was added. The reaction was warmed to room temperature, and stirring was continued. After 90 min, the reaction was diluted with MeOH (1 mL) and 5 N aqueous HCl (0.20 mL) was added. Stirring was continued at room temperature for 3.5 h. Water was also added.

Separately, 1-(6-(6-methoxypyridin-3-ylamino)-5-(2-methyl-9-(tetrahydro-2H-pyran-2-yl)-9H-purin-6-yl)pyridin-3-yl)ethanol (231 mg, 0.501 mmol) was dissolved in DCM (10 mL) and triethylamine (Aldrich 99.5%, 0.28 ml, 2.0 mmol) was added. The reaction was cooled in an ice water bath, and methanesulfonyl chloride (0.15 mL, 1.9 mmol) was added. The reaction was stirred at 0° C. for 15 min, and then 1-methanesulfonylpiperazine (474.4 mg, 2.89 mmol) was added, causing precipitation. The reaction was warmed to room temperature and stirring was continued. After 2 h, the reaction was diluted with MeOH (10 mL) and 5 N HCl (2.0 mL) was added. Stirring was continued at room temperature. After another hour, this reaction was combined with the other reaction, treated with 5 N NaOH and 5 N HCl to adjust the pH to around 6, and allowed to stand at room temperature over the weekend. The resultant suspension was filtered, and the solid was washed with DCM and MeOH. The filtrate was concentrated and treated with water and filtered. The solid was washed with water. The filtrate was discarded. The solid was collected and purified by prep HPLC (10% to 100% MeCN/water with 0.1% TFA over 28 min using a total flow rate of 100 mL/min.) to give N-(6-methoxypyridin-3-yl)-3-(2-methyl-9H-purin-6-yl)-5-(1-(4-(methylsulfonyl)piperazin-1-yl)ethyl)pyridin-2-amine (81.0 mg, 24% yield) as a TFA salt. $^1$H NMR (d6-DMSO, 400 MHz) δ 12.61 (br s, 1H), 9.78 (s, 1H), 8.67 (s, 1H), 8.54 (d, J=2.54 Hz, 1H), 8.40 (d, J=2.35 Hz, 1H), 8.16 (dd, J=9.0 Hz, 2.74 Hz, 1H), 6.87 (d, J=8.80 Hz, 1H), 4.69 (br, s, 1H), 3.85 (s, 3H), 3.45-3.00 (m, 6H), 2.98 (s, 3H), 2.86 (s, 3H), 1.76 (d, J=7.04 Hz, 3H). m/z (ESI, pos. ion) 524 (M+H)$^+$.

Example 141

4-(2-(6-methoxypyridin-3-ylamino)-5-(4-(methylsulfonyl)benzyl)pyridin-3-yl)-6-methyl-1,3,5-triazin-2-amine

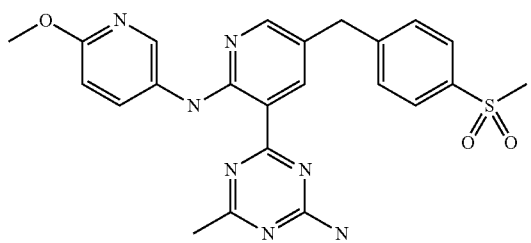

Step 1: 4-(2-fluoro-5-(4-(methylthio)benzyl)pyridin-3-yl)-N,N-bis(4-methoxybenzyl)-6-methyl-1,3,5-triazin-2-amine 4-Chloro-N,N-bis(4-methoxybenzyl)-6-methyl-1,3,5-triazin-2-amine (2.37 g, 6.15 mmol), 2-fluoro-5-(4-(methylthio)benzyl)pyridin-3-ylboronic acid (1.89 g, 6.83 mmol), Am-Phos (224 mg, 0.316 mmol), and potassium acetate (2.72 g, 27.7 mmol) were suspended in EtOH (30 mL) and water (7.5 mL). Nitrogen was bubbled through the suspension for about 20 seconds, and then the flask was fitted with a reflux condenser and put in a preheated oil bath (80° C.-88° C.) and the reaction was stirred under nitrogen for 2 hours and 45 minutes. Then, the reaction was cooled to room temperature, treated with water (90 mL) and extracted with DCM. The organic extracts were combined, dried over sodium sulfate, filtered, and concentrated. The residue was washed with hexanes, but the hexanes rinsings still contained product. So, these rinsings were combined with the residue and concentrated. The material was purified on a silica gel filter (600 mL fritted filter funnel with about 3 inches of silica gel; 5:1 DCM/hexanes to DCM to 40:1 DCM/MeOH to 30:1 DCM/MeOH) to give 4-(2-fluoro-5-(4-(methylthio)benzyl)pyridin-3-yl)-N,N-bis (4-methoxybenzyl)-6-methyl-1,3,5-triazin-2-amine (2.843 g). $^1$H NMR (CDCl$_3$, 400 MHz) δ 8.32 (dd, J=9.00 Hz, 2.35 Hz, 1H), 8.14 (dd, J=1.56 Hz, 1H), 7.24-7.18 (m, 6H), 7.13-7.09 (m, 2H), 6.90-6.83 (m, 4H), 4.81 (s, 2H), 4.78 (s, 2H), 3.99 (s, 2H), 3.82 (s, 3H), 3.80 (s, 3H), 2.53 (s, 3H), 2.46 (s, 3H). m/z (ESI, pos. ion) 582 (M+H)$^+$.

Step 2: 4-(2-fluoro-5-(4-(methylsulfonyl)benzyl)pyridin-3-yl)-N,N-bis(4-methoxybenzyl)-6-methyl-1,3,5-triazin-2-amine 4-(2-Fluoro-5-(4-(methylthio)benzyl)pyridin-3-yl)-N,N-bis(4-methoxybenzyl)-6-methyl-1,3,5-triazin-2-amine (624.5 mg, 1.074 mmol) was dissolved in DCM (11 mL) and the flask was cooled in an ice water bath. Then, mCPBA (557 mg, 3.23 mmol) was added as a solution in DCM (17.5 mL) and the reaction was warmed to room temperature and stirred under nitrogen. After 35 min, the reaction was treated with a mixture of saturated sodium bicarbonate (25 mL) and saturated sodium thiosulfate (6 mL), and stirring was continued at room temperature. After 50 minutes, the layers were separated, and the aqueous phase was extracted with DCM. The organic phase was dried over sodium sulfate, filtered, concentrated, and purified on a silica gel filter (30 mL fritted filter with about 1 inch of silica gel; DCM to 50:1 DCM/MeOH) to give 4-(2-fluoro-5-(4-(methylsulfonyl)benzyl)pyridin-3-yl)-N,N-bis(4-methoxybenzyl)-6-methyl-1,3,5-triazin-2-amine (539.6 mg, 75% yield based on 91% purity). $^1$H NMR (CDCl$_3$, 400 MHz) δ 8.34 (dd, J=8.90 Hz, 2.45 Hz, 1H), 8.16 (d, J=1.76 Hz, 1H), 7.89 (d, J=8.41 Hz, 2H), 7.40 (d, J=8.22 Hz, 2H), 7.21 (d, J=8.61 Hz, 4H), 6.90-6.82 (m, 4H), 4.82 (s, 2H), 4.79 (s, 2H), 4.13 (s, 2H), 3.82 (s, 3H), 3.80 (s, 3H), 3.03 (s, 3H), 2.54 (s, 3H). m/z (ESI, +ve ion) m/z 614 (M+H)$^+$.

Step 3: N,N-bis(4-methoxybenzyl)-4-(2-(6-methoxypyridin-3-ylamino)-5-(4-(methylsulfonyl)benzyl)pyridin-3-yl)-6-methyl-1,3,5-triazin-2-amine 4-(2-Fluoro-5-(4-(methylsulfonyl)benzyl)pyridin-3-yl)-N,N-bis(4-methoxybenzyl)-6-methyl-1,3,5-triazin-2-amine (503 mg, 0.820 mmol) and 5-amino-2-methoxypyridine (112 mg, 0.905 mmol) were dissolved in THF (8.0 mL) and the flask was cooled in an ice water bath while the reaction was stirred under nitrogen. Then, lithium bis(trimethylsilyl)amide (1.0 M solution in tetrahydrofuran (2.5 mL, 2.500 mmol) was added via syringe, and the reaction was stirred for 40 min. Then, the reaction was treated with ice water (0.60 mL) and the reaction was diluted with DCM, dried over sodium sulfate, filtered, concentrated, and purified on a silica gel filter (150 mL fritted filter with about 2 inches of silica gel; DCM to 100:1 DCM/MeOH to 50:1 DCM/MeOH). The pure fractions were set aside, while the impure ones were collected, concentrated, and purified on another silica gel filter (30 mL fritted filter with about 1 inch of silica gel; DCM to 100:1 DCM/MeOH). The fractions with product were combined with the pure fractions from the first column and concentrated to give N,N-bis(4-methoxybenzyl)-4-(2-(6-methoxypyridin-3-ylamino)-5-(4-(methylsulfonyl)benzyl)pyridin-3-yl)-6-methyl-1,3,5-triazin-2-amine (412 mg). $^1$H NMR (CDCl$_3$, 400 MHz) δ 11.58 (s, 1H), 8.61 (d, J=2.35 Hz, 1H), 8.26 (d, J=2.54 Hz, 1H), 8.13 (d, J=2.35 Hz, 1H), 7.87 (dd, J=8.90 Hz, 2.64 Hz, 1H), 7.81 (d, J=8.22 Hz, 2H), 7.37 (d, J=8.22 Hz, 2H), 7.21 (d, J=8.61 Hz, 2H), 7.15 (d, J=8.61 Hz, 2H), 6.87 (d, J=8.61 Hz, 2H), 6.82 (d, J=8.41 Hz, 2H), 6.70 (d, J=8.80 Hz, 1H), 4.85 (s, 2H), 4.77 (s, 2H), 4.00 (s, 2H), 3.93 (s, 3H), 3.82 (s, 3H), 3.80 (s, 3H), 2.98 (s, 3H), 2.57 (s, 3H). m/z (ESI, +ve ion) 718 (M+H)$^+$.

Step 4: 4-(2-(6-methoxypyridin-3-ylamino)-5-(4-(methylsulfonyl)benzyl)pyridin-3-yl)-6-methyl-1,3,5-triazin-2-amine N,N-bis(4-methoxybenzyl)-4-(2-(6-methoxypyridin-3-ylamino)-5-(4-(methylsulfonyl)benzyl)pyridin-3-yl)-6-methyl-1,3,5-triazin-2-amine (412 mg, 0.574 mmol) was suspended in trifluoroacetic acid (Aldrich redistilled 99+%, 6.0 mL, 78 mmol) and the flask was fitted with a reflux condenser and put in a preheated oil bath (75° C.) and the reaction was stirred overnight. Then, the reaction was cooled to room temperature and concentrated and diluted with saturated sodium bicarbonate and then with 5 N NaOH to raise the pH to about 8-9. The suspension was filtered, and the solid was washed with water. The filtrate was discarded, and the solid was collected with DCM and MeOH, concentrated, treated with MeOH, and filtered. The solid was washed with MeOH. The solid was not >95% pure by HPLC, so the filtrate and solid were combined, concentrated, and purified on a silica gel column (30:1 to 20:1 DCM/MeOH). The fractions with product were collected, concentrated, treated with MeOH, and filtered. The yellow solid was washed with MeOH, collected, and dried under high vacuum at room temperature overnight to give 4-(2-(6-methoxypyridin-3-ylamino)-5-(4-(methylsulfonyl)benzyl)pyridin-3-yl)-6-methyl-1,3,5-triazin-2-amine (126.1 mg, 46% yield) as a yellow powder. $^1$H NMR (CDCl$_3$, 400 MHz) δ 11.64 (s, 1H), 8.65 (d, J=2.15 Hz, 1H), 8.36 (d, J=2.35 Hz, 1H), 8.17 (d, J=1.56 Hz, 1H), 8.11 (dd, J=8.90 Hz, 2.25 Hz, 1H), 7.88 (d, J=8.22 Hz, 2H), 7.42 (d, J=7.82 Hz, 2H), 6.78 (d, J=8.80 Hz, 1H), 5.36 (br s, 2H), 4.04 (s, 2H), 3.95 (s, 3H), 3.04 (s, 3H), 2.56 (s, 3H). m/z (ESI, +ve ion) 478 (M+H)$^+$.

Example 142

4-(2-(5-fluoro-6-methoxypyridin-3-ylamino)-5-(4-(methylsulfonyl)benzyl)pyridin-3-yl)-6-methyl-1,3,5-triazin-2-amine

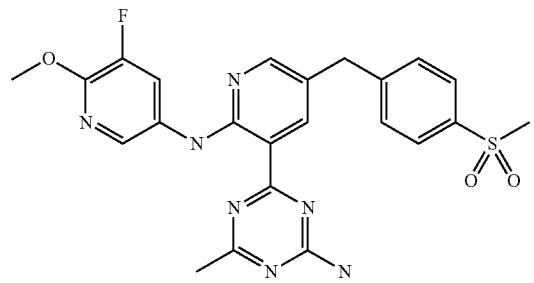

Step 1: 4-(2-(5-fluoro-6-methoxypyridin-3-ylamino)-5-(4-(methylsulfonyl)benzyl)pyridin-3-yl)-N,N-bis(4-methoxybenzyl)-6-methyl-1,3,5-triazin-2-amine 4-(2-Fluoro-5-(4-(methylsulfonyl)benzyl)pyridin-3-yl)-N,N-bis(4-methoxybenzyl)-6-methyl-1,3,5-triazin-2-amine (602.4 mg, 0.9816 mmol) and 5-fluoro-6-methoxypyridin-3-amine (159.0 mg, 1.119 mmol) were dissolved in THF (10 mL) and the reaction flask was cooled in an ice water bath. Then, lithium bis(trimethylsilyl)amide (1.0 M solution in tetrahydrofuran, 3.0 mL, 3.0 mmol) was added via syringe, and the reaction was stirred under nitrogen for 35 min. Then, the reaction was diluted with water (20 mL) and then extracted with DCM. Brine was added to the biphasic mixture and extraction with DCM was continued. Water and MeOH were also added to the aqueous phase to help break up emulsions. The organic extracts (about 350 mL total) were combined and washed with brine (50 mL). The brine layer was extracted with DCM, and all of the organic extracts were combined, dried over sodium sulfate, filtered, concentrated, and purified on a silica gel filter (150 mL fritted funnel with about 2 inches of silica gel; 100:1 DCM/MeOH) to give 4-(2-(5-fluoro-6-methoxypyridin-3-ylamino)-5-(4-(methylsulfonyl)benzyl)pyridin-3-yl)-N,N-bis(4-methoxybenzyl)-6-methyl-1,3,5-triazin-2-amine (384.7 mg). $^1$H NMR (CDCl$_3$, 400 MHz) δ 11.82 (br s, 1H), 8.63 (d, J=1.96 Hz, 1H), 8.17 (d, J=2.15 Hz, 1H), 8.00 (d, J=12.32 Hz, 1H), 7.95 (d, J=2.15 Hz, 1H), 7.82 (d, J=8.02 Hz, 2H), 7.37 (d, J=8.22 Hz, 2H), 7.21 (d, J=8.41 Hz, 2H), 7.15 (d, J=8.41 Hz, 2H), 6.90-6.81 (m, 4H), 4.86 (s, 2H), 4.77 (s, 2H), 4.01 (s, 5H), 3.82 (s, 3H), 3.80 (s, 3H), 2.96 (s, 3H), 2.58 (s, 3H). m/z (ESI, pos. ion) 736 (M+H)+.

Step 2: 4-(2-(5-fluoro-6-methoxypyridin-3-ylamino)-5-(4-(methylsulfonyl)benzyl)pyridin-3-yl)-6-methyl-1,3,5-triazin-2-amine 4-(2-(5-Fluoro-6-methoxypyridin-3-ylamino)-5-(4-(methylsulfonyl)benzyl)pyridin-3-yl)-N,N-bis(4-methoxybenzyl)-6-methyl-1,3,5-triazin-2-amine (384.7 mg, 0.5228 mmol) was dissolved in trifluoroacetic acid (Aldrich redistilled 99+%, 5.0 mL, 65 mmol) and the reaction flask was fitted with a reflux condenser and placed in a preheated oil bath (75° C.) and stirred overnight. Then, the reaction was cooled to room temperature, concentrated, and treated with saturated sodium bicarbonate and 5 N NaOH and then with 5 N HCl to adjust the pH to 6. Then, DCM was added and the layers were separated. The aqueous phase was filtered, and the collected solid was combined with the organic phase. The aqueous phase was extracted with DCM, and these organic extracts were combined with the organic phase, concentrated, and purified on a silica gel column (30:1 DCM/2 N ammonia in MeOH to 10:1 DCM/2 N ammonia in MeOH). The solvent polarity was increased after most of the product had eluted. The fractions with product were collected, concentrated, treated with MeOH, and filtered. The solid was washed with MeOH, collected, and dried under high vacuum. The material was <95% pure by HPLC, so the solid was washed with EtOAc, filtered, collected, and dried under high vacuum in a water bath (40° C.) and then at room temperature overnight to give 4-(2-(5-fluoro-6-methoxypyridin-3-ylamino)-5-(4-(methylsulfonyl)benzyl)pyridin-3-yl)-6-methyl-1,3,5-triazin-2-amine (61.3 mg, 24% yield) as a yellow powder. $^1$H NMR (d6-DMSO, 400 MHz) δ 11.89 (s, 1H), 8.65 (d, J=2.15 Hz, 1H), 8.40 (d, J=2.15 Hz, 1H), 8.38-8.30 (m, 2H), 7.86 (d, J=8.22 Hz, 2H), 7.90-7.84 (m, 1H), 7.74 (br s, 1H), 7.53 (d, J=8.22 Hz, 2H), 4.09 (s, 2H), 3.93 (s, 3H), 3.17 (s, 3H), 2.41 (s, 3H). m/z (ESI, +ve ion) 496 (M+H)+.

Example 143

4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine

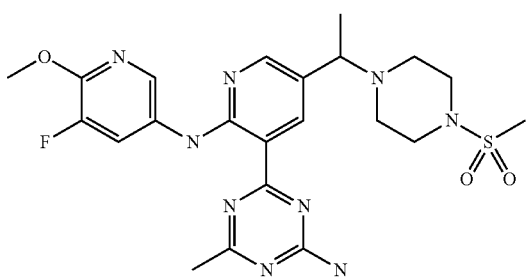

Step 1: 4-(5-(1,3-dioxolan-2-yl)-2-fluoropyridin-3-yl)-N,N-bis(4-methoxybenzyl)-6-methyl-1,3,5-triazin-2-amine 4-Chloro-N,N-bis(4-methoxybenzyl)-6-methyl-1,3,5-triazin-2-amine (Example 51; (2.102 g, 5.462 mmol), 5-(1,3-dioxolan-2-yl)-2-fluoro-3-(4,4,5,5-tetramethyl-1,3,2-dioxaborolan-2-yl)pyridine (Example 234; 1.901 g, 6.442 mmol), Am-Phos (200.6 mg, 0.2833 mmol), and potassium acetate (1.51 g, 15.4 mmol) were suspended in water (4 mL) and 1,4-dioxane (20 mL) and nitrogen was bubbled through the suspension for 30 s. Then, the flask was fitted with a reflux condenser and placed in a preheated oil bath (100° C.) and stirred under nitrogen for 4 h. Then, the reaction was cooled to room temperature, treated with water (40 mL), and extracted with EtOAc. The organic extracts were combined, dried over sodium sulfate, filtered through a Celite® (diatomaceous earth) pad, and concentrated. The crude material was purified on a silica gel filter (600 mL fritted funnel with about 3 inches of silica gel; DCM to 100:1 DCM/MeOH to 50:1 DCM/MeOH) to give 4-(5-(1,3-dioxolan-2-yl)-2-fluoropyridin-3-yl)-N,N-bis(4-methoxybenzyl)-6-methyl-1,3,5-triazin-2-amine (3.175 g). $^1$H NMR (CDCl$_3$, 400 MHz) δ 8.65 (dd, J=8.90 Hz, 2.45 Hz, 1H), 8.42 (d, J=1.37 Hz, 1H), 7.23 (dd, J=8.41 Hz, 5.87 Hz, 4H), 6.87 (dd, J=10.27 Hz, 8.71 Hz, 4H), 5.93 (s, 1H), 4.83 (s, 2H), 4.81 (s, 2H), 4.17-4.04 (m, 4H), 3.82 (s, 3H), 3.80 (s, 3H), 2.55 (s, 3H). m/z (ESI, +ve ion) 518 (M+H)+.

Step 2: 5-(4-(bis(4-methoxybenzyl)amino)-6-methyl-1,3,5-triazin-2-yl)-6-(5-fluoro-6-methoxypyridin-3-ylamino)nicotinaldehyde 4-(5-(1,3-Dioxolan-2-yl)-2-fluoropyridin-3-yl)-N,N-bis(4-methoxybenzyl)-6-methyl-1,3,5-triazin-2-amine (1.688 g, 3.262 mmol) and 5-fluoro-6-methoxypyridin-3-amine (0.477 g, 3.36 mmol) were dissolved in THF (28 mL) and the reaction flask was cooled in an ice water bath under nitrogen. Then, lithium bis(trimethylsilyl)amide (1.0 M solution in tetrahydrofuran, 9.5 mL, 9.5 mmol) was added, and the reaction was stirred under nitrogen for 35 min. Then, aqueous HCl (5.0 M, 4.5 mL, 22.50 mmol) and MeOH (5.8 mL) were added, and the reaction was warmed to room temperature and stirred. After 10 min, the reaction was treated with water (20 mL) and extracted with DCM. The organic extracts were combined, dried over sodium sulfate, filtered, concentrated, and purified on a silica gel filter (150 mL fritted filter with about 2 inches of silica gel; DCM to 100:1 DCM/MeOH). The fractions with product were collected, concentrated, and dried under high vacuum. LCMS showed mostly product, but some unhydrolyzed acetonide was also present. The material was dissolved in THF (20 mL) and MeOH (4.0 mL) and aqueous HCl (5.0 M, 2.0 mL, 10 mmol) was added, and the solution was stirred at room temperature. After 25 min, the reaction was diluted with water (20 mL) and DCM. The layers were separated, and the aqueous phase was extracted with DCM. The organic extracts were combined, dried over sodium sulfate, filtered, concentrated, and dried under high vacuum overnight to give 5-(4-(bis(4-methoxybenzyl)amino)-6-methyl-1,3,5-triazin-2-yl)-6-(5-fluoro-6-methoxypyridin-3-ylamino)nicotinaldehyde (1.098 g). $^1$H NMR (CDCl$_3$, 400 MHz) δ 12.58 (s, 1H), 9.92 (s, 1H), 9.25 (d, J=2.35 Hz, 1H), 8.75 (d, J=2.15 Hz, 1H), 8.03-7.97 (m, 2H), 7.21 (dd, J=15.06 Hz, 8.41 Hz, 4H), 6.87 (dd, J=11.15 Hz, 8.61 Hz, 4H), 4.89 (s, 2H), 4.85 (s, 2H), 4.04 (s, 3H), 3.82 (s, 3H), 3.79 (s, 3H), 2.61 (s, 3H). m/z (ESI, pos. ion) 596 (M+H)+.

Step 3: 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol 5-(4-(Bis(4-methoxybenzyl)amino)-6-methyl-1,3,5-triazin-2-yl)-6-(5-fluoro-6-methoxypyridin-3-ylamino)nicotinaldehyde (1.0538 g, 1.769 mmol) was suspended in THF (16 mL) and the reaction flask was cooled in an ice water bath. Then, methylmagnesium bromide (3.0 M in diethyl ether, 1.80 mL, 5.40 mmol) was added via syringe, and the reaction was stirred at 0° C. for 25 min. Then, the reaction was treated with saturated ammonium chloride (3 mL, dropwise at first as gas evolution is observed) and water (20 mL). The reaction was diluted with EtOAc and the layers were separated. The aqueous phase was extracted with EtOAc. The organic extracts were combined, dried over sodium sulfate, filtered, concentrated, and purified on a silica gel filter (150 mL fritted filter with about 2 inches of silica gel; 100:1 DCM/MeOH (to elute non-polar impurities) to 40:1 (to elute product)) to give 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol (893.8 mg). $^1$H NMR (400 MHz, CDCl$_3$) δ 11.86 (s, 1H), 8.83 (d, J=2.35 Hz, 1H), 8.32 (d, J=2.35 Hz, 1H), 8.01 (dd, J=12.13 Hz, 2.15 Hz, 1H), 7.96 (d, J=2.35 Hz, 1H), 7.21 (dd, J=10.76 Hz, 8.61 Hz, 4H), 6.87 (dd, J=12.13 Hz, 8.80 Hz, 4H), 4.94-4.81 (m, 5H), 4.02 (s, 3H), 3.82 (s, 3H), 3.79 (s, 3H), 2.59 (s, 3H), 1.73 (d, J=3.72 Hz, 1H), 1.53 (d, J=6.46 Hz, 3H). m/z (ESI, pos. ion) 612 (M+H)$^+$.

Step 4: 4-(2-(5-fluoro-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine 1-(5-(4-(Bis(4-methoxybenzyl)amino)-6-methyl-1,3,5-triazin-2-yl)-6-(5-fluoro-6-methoxypyridin-3-ylamino)pyridin-3-yl)ethanol (867.1 mg, 1.418 mmol) was dissolved in DCM (22 mL) and the flask was cooled in an ice water bath. Then, triethylamine (0.90 mL, 6.5 mmol) and methanesulfonyl chloride (0.41 mL, 5.3 mmol) were added, and the reaction was stirred under nitrogen. After 20 min, the reaction was diluted with DCM (125 mL) and treated with water (25 mL). The layers were separated, and the aqueous phase was extracted with DCM. The organic extracts were combined, dried over sodium sulfate, filtered, concentrated, and dissolved in DCM (15 mL). Triethylamine (0.90 mL, 6.5 mmol) and 1-methanesulfonylpiperazine (753.9 mg, 4.591 mmol) were added and the reaction was stirred under nitrogen at room temperature overnight. Then, the reaction was treated with water (20 mL) and diluted with DCM. The layers were separated, and the aqueous phase was extracted with DCM. The organic extracts were combined, dried over sodium sulfate, filtered, concentrated, and purified on a silica gel filter (150 mL fritted filter with about 2 inches of silica gel; DCM to 50:1 DCM/MeOH to 30:1 DCM/2 N ammonia in MeOH to 15:1 DCM/2 N ammonia in MeOH to 10:1 DCM/2 N ammonia in MeOH). The product eluted with 50:1 DCM/MeOH. The fractions with product were collected, concentrated, and repurified on a silica gel filter (150 mL fritted filter with about 2 inches of silica gel; 100:1 DCM/MeOH, to elute impurities to 40:1 DCM/MeOH, to elute product) to give 4-(2-(5-fluoro-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (456.7 mg). $^1$H NMR (CDCl$_3$, 400 MHz) δ 11.87 (s, 1H), 8.72 (d, J=2.35 Hz, 1H), 8.25 (d, J=2.35 Hz, 1H), 8.07 (d, J=12.32 Hz, 2.15 Hz, 1H), 7.97 (d, J=2.35 Hz, 1H), 7.22 (t, J=8.51 Hz, 4H), 6.91-6.82 (m, 4H), 4.93-4.76 (m, 4H), 4.02 (s, 3H), 3.82 (s, 3H), 3.79 (s, 3H), 3.55 (q, J=6.78 Hz, 1H), 3.16 (t, J=4.60 Hz, 4H), 2.69 (s, 3H), 2.60 (s, 3H), 2.58-2.49 (m, 4H), 1.38 (d, J=6.65 Hz, 3H). m/z (ESI, pos. ion) 758 (M+H)$^+$.

Step 5: 4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine 4-(2-(5-Fluoro-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (456.7 mg, 0.6026 mmol) was dissolved in trifluoroacetic acid (9.5 mL) and the reaction flask was fitted with a reflux condenser and put in a preheated oil bath (75-77° C.) and stirred for 16 h. The reaction was cooled to room temperature and concentrated. The reaction was diluted with DCM (40 mL) and treated with saturated sodium bicarbonate and 5 N NaOH to raise the pH of the aqueous phase to about 8. Then, the layers were separated and the aqueous phase was extracted with DCM and 10:1 DCM/MeOH. The organic extracts were combined, dried over sodium sulfate, filtered, concentrated, treated with MeOH, and filtered. The solid was washed with MeOH. The solid was not >95% pure by HPLC, so the filtrate and solid were combined, concentrated, and purified on a silica gel column according to the procedure described by Still et al. (Journal of Organic Chemistry, 1978, 43, 2923-2925) using this eluent system: 30:1 DCM/2 N ammonia in MeOH to 20:1 DCM/2 N ammonia in MeOH to 15:1 DCM/2 N ammonia in MeOH to 5:1 DCM/2 N ammonia in MeOH. The fractions with product were collected, concentrated, treated with MeOH, and filtered. The solid was washed with MeOH, collected, and dried under high vacuum to give 4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (194.7 mg, 62% yield) as a yellow powder. $^1$H NMR (CDCl$_3$, 400 MHz) δ 11.93 (s, 1H), 8.71 (d, J=2.54 Hz, 1H), 8.31 (t, J=2.25 Hz, 1H), 8.27 (d, J=2.35 Hz, 1H), 8.05 (d, J=2.15 Hz, 1H), 5.42 (br s, 2H), 4.04 (s, 3H), 3.56 (quartet, J=6.65 Hz, 1H), 3.24 (t, J=4.69 Hz, 4H), 2.78 (s, 3H), 2.68-2.54 (m, 7H), 1.44 (t, J=6.85 Hz, 3H). m/z (ESI, pos. ion) 518 (M+H)$^+$.

Example 144

4-(2-(6-methoxypyridin-3-ylamino)-5-(1-(4-(methylsulfonyl)piperazin-1-yl)ethyl)pyridin-3-yl)-6-methyl-1,3,5-triazin-2-amine

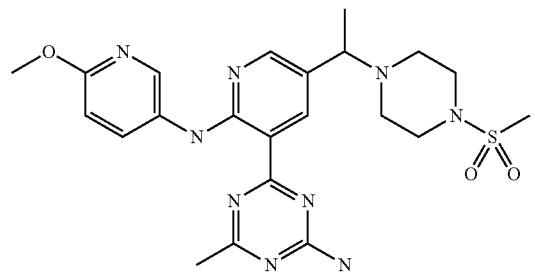

Step 1: 5-(4-(bis(4-methoxybenzyl)amino)-6-methyl-1,3,5-triazin-2-yl)-6-(6-methoxypyridin-3-ylamino)nicotinaldehyde A stock solution of 4-(5-(1,3-dioxolan-2-yl)-2-fluoropyridin-3-yl)-N,N-bis(4-methoxybenzyl)-6-methyl-1,3,5-triazin-2-amine (Example 143, Step 1) (5.85 g, 11.30 mmol) in benzene (50 mL) contained in a 250 mL round-bottomed flask with stir bar was frozen and lyophilized overnight (pale yellow solid obtained). The flask was opened to $N_2$ and THF (50 mL) was added followed by 6-methoxypyridin-3-amine (1.332 mL, 12.43 mmol). The solution was cooled in an ice bath and LiHMDS (44 mL of a 1.0 M solution in THF, 44 mmol) was added. The mixture was stirred for 40 min and then quenched with water (3 mL) and concentrated to dryness. The residue was taken up in a mixture of DCM and 2 N aqueous HCl and stirred for 30 min. The product was extracted into DCM from 2 N HCl, washed with saturated aqueous $NaHCO_3$, dried ($MgSO_4$) and concentrated to give a brown solid. This was dissolved in DCM and purified by flash chromatography (30% EtOAc, 10% DCM, 60% hexane) to give 5-(4-(bis(4-methoxybenzyl)amino)-6-methyl-1,3,5-triazin-2-yl)-6-(6-methoxypyridin-3-ylamino)nicotinaldehyde (3.98 g, 6.89 mmol, 61.0% yield) as a yellow solid. $^1$H NMR (400 MHz, d6-DMSO) δ 12.09 (s, 1H); 9.90 (s, 1H); 9.14 (d, J=2.35 Hz, 1H); 8.77 (d, J=2.35 Hz, 1H); 8.31 (d, J=2.74 Hz, 1H); 7.87 (dd, J=8.80, 2.74 Hz, 1H); 7.28 (d, J=8.61 Hz, 2H); 7.21 (d, J=8.80 Hz, 2H); 6.87-6.94 (m, 2H); 6.78-6.87 (m, 3H); 4.83 (d, J=7.24 Hz, 4H); 3.85 (s, 3H); 3.74 (s, 3H); 3.69 (s, 3H); 2.58 (s, 3H). m/z (ESI, +ve ion) 578 (M+H)$^+$.

Step 2: 1-(5-(4-(bis(4-methoxybenzyl)amino)-6-methyl-1,3,5-triazin-2-yl)-6-(6-methoxypyridin-3-ylamino)pyridin-3-yl)ethanol 5-(4-(Bis(4-methoxybenzyl)amino)-6-methyl-1,3,5-triazin-2-yl)-6-(6-methoxypyridin-3-ylamino)nicotinaldehyde (877.5 mg, 1.519 mmol) was suspended in THF (15 mL) and methylmagnesium bromide (3.0 M in diethyl ether, 1.5 mL, 4.5 mmol) was added. More THF (2.5 mL) was added after about 10 min. After 40 additional min, the reaction was quenched with saturated ammonium chloride and diluted with water (20 mL). The layers were separated, and the aqueous phase was extracted with EtOAc. The organic extracts were combined, dried over sodium sulfate, filtered, concentrated, and purified on a silica gel filter (150 mL fritted filter with about 2 inches of silica gel; 100:1 DCM/MeOH to 40:1 DCM/MeOH) to afford 1-(5-(4-(bis(4-methoxybenzyl)amino)-6-methyl-1,3,5-triazin-2-yl)-6-(6-methoxypyridin-3-ylamino)pyridin-3-yl)ethanol (878.2 mg). $^1$H NMR ($CDCl_3$, 400 MHz) δ 11.62 (s, 1H), 8.82 (d, J=2.54 Hz, 1H), 8.30 (d, J=2.54 Hz, 1H), 8.26 (d, J=2.74 Hz, 1H), 7.88 (dd, J=8.80 Hz, 2.74 Hz, 1H), 7.21 (dd, J=12.91 Hz, 8.61 Hz, 4H), 6.90-6.82 (m, 4H), 6.71 (d, J=8.80 Hz, 1H), 4.93-4.86 (m, 3H), 4.82 (d, J=6.26 Hz, 2H), 3.93 (s, 3H), 3.82 (s, 3H), 3.79 (s, 3H), 2.58 (s, 3H), 1.72 (d, J=3.91 Hz, 1H), 1.52 (d, J=6.46 Hz, 3H). m/z (ESI, +ve ion) 594 (M+H)$^+$.

Step 3: N,N-bis(4-methoxybenzyl)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine 1-(5-(4-(bis(4-methoxybenzyl)amino)-6-methyl-1,3,5-triazin-2-yl)-6-(6-methoxypyridin-3-ylamino)pyridin-3-yl)ethanol (732.1 mg, 1.233 mmol) was dissolved in dichloromethane (22 mL) and the reaction flask was cooled in an ice water bath. The reaction was stirred under nitrogen, and triethylamine (0.77 mL, 5.5 mmol) and methanesulfonylchloride (0.37 mL, 4.8 mmol) were added via syringe. The reaction was stirred at 0° C. under nitrogen for 15 min and then was diluted with dichloromethane (125 mL) and treated with water (20 mL). The layers were separated, and the aqueous phase was extracted with dichloromethane. The organic extracts were combined, dried over sodium sulfate, filtered, concentrated, and dissolved in dichloromethane (13 mL). To this solution were added triethylamine (0.77 ml, 5.5 mmol) and 1-methanesulfonylpiperazine (648 mg, 3.95 mmol). The reaction was stirred under nitrogen at room temperature overnight and then concentrated and purified on a silica gel filter (150 mL fritted filter with about 2 inches of silica gel; 100:1 DCM/MeOH to elute impurities to 50:1 DCM/MeOH to elute product). The fractions with product were collected, concentrated, and washed with hexanes. The material dried under high vacuum at room temperature to give N,N-bis(4-methoxybenzyl)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (501.6 mg,). $^1$H NMR ($CDCl_3$, 400 MHz) δ 11.63 (s, 1H), 8.70 (d, J=2.54 Hz, 1H), 8.28 (d, J=2.54 Hz, 1H), 8.22 (d, J=2.54 Hz, 1H), 7.92 (dd, J=9.00 Hz, 2.74 Hz, 1H), 7.22 (t, J=9.29 Hz, 4H), 6.86 (dd, J=18.58 Hz, 8.61 Hz, 4H), 6.72 (d, J=8.80 Hz, 1H), 4.93-4.76 (m, 4H), 3.93 (s, 3H), 3.82 (s, 3H), 3.79 (s, 3H), 3.54 (quartet, J=6.78 Hz, 1H), 3.16 (t, J=4.40 Hz, 4H), 2.68 (s, 3H), 2.61-2.49 (m, 7H), 1.38 (d, J=6.65 Hz, 3H). m/z (ESI, +ve ion) 740 (M+H)$^+$.

Step 4: 4-(2-(6-methoxypyridin-3-ylamino)-5-(1-(4-(methylsulfonyl)piperazin-1-yl)ethyl)pyridin-3-yl)-6-methyl-1,3,5-triazin-2-amine N,N-Bis(4-methoxybenzyl)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (499.0 mg, 0.6744 mmol) was dissolved in trifluoroacetic acid (10.4 mL, 140 mmol) and the flask was fitted with a reflux condenser, placed in a preheated oil bath (75° C.) and stirred overnight. Then, the reaction was cooled to room temperature, concentrated, diluted with DCM (40 mL) and treated with saturated sodium bicarbonate, water, and 5 N NaOH until the pH of the aqueous phase was about 7. Then, the layers were separated, and the aqueous phase was extracted with DCM and 10:1 DCM/MeOH. During these extractions, 5 N NaOH was added to the aqueous phase to raise the pH from about 5 to about 11. The organic extracts were combined, dried over sodium sulfate, filtered, concentrated, and purified on a silica gel filter (150 mL fritted filter with about 2 inches of silica gel; 75:1 DCM/MeOH to 50:1 DCM/MeOH to 35:1 DCM/2 N ammonia in MeOH to 20:1 DCM/2 N ammonia in MeOH to 10:1 DCM/2 N ammonia in MeOH) to give 4-(2-(6-methoxypyridin-3-ylamino)-5-(1-(4-(methylsulfonyl)piperazin-1-yl)ethyl)pyridin-3-yl)-6-methyl-1,3,5-triazin-2-amine (241.9 mg, 72% yield) as a yellow powder. $^1$H NMR ($CDCl_3$, 400 MHz) δ 11.68 (s, 1H), 8.71 (s, 1H), 8.36 (d, J=2.74 Hz, 1H), 8.27 (d, J=2.35 Hz, 1H), 8.13 (dd, J=8.80 Hz, 2.74 Hz, 1H), 6.79 (d, J=8.80 Hz, 1H), 5.42 (br s, 2H), 3.95 (s, 3H), 3.60-

3.52 (m, 1H), 3.30-3.20 (m, 4H), 2.77 (s, 3H), 2.70-2.53 (m, 7H), 1.45 (d, J=6.06 Hz, 3H). m/z (ESI, +ve ion) 500 (M+H)+.

Examples 145 and 146

(S)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (Example 145) and (R)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (Example 146)

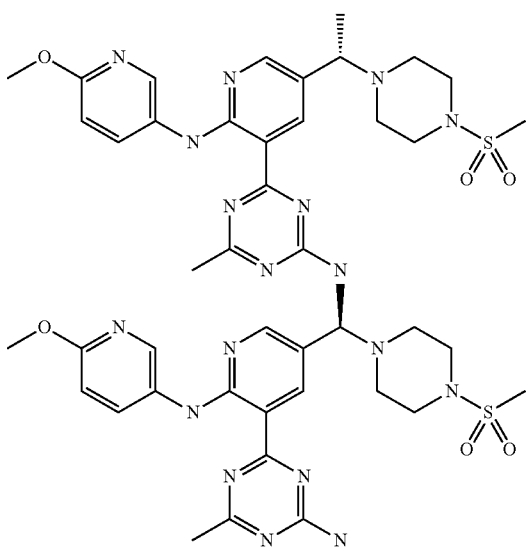

A mixture of isomers of 4-(2-(6-methoxypyridin-3-ylamino)-5-(1-(4-(methylsulfonyl)piperazin-1-yl)ethyl)pyridin-3-yl)-6-methyl-1,3,5-triazin-2-amine (Example 144) (235 mg) was separated using chiral SFC preparative chromatography. The following conditions were used:
Column: Chiralcel OJ-H (250×21 mm, 5 µm)
Mobile Phase: 76:24 (A:B)
A: Supercritical $CO_2$
B: Methanol (with about 0.2% diethylamine)
Flow Rate: 70 mL/min
Oven/column temp: 40° C.

The two resulting peaks were separately collected, concentrated in vacuo, and dried under high vacuum to give the two enantiomers. The absolute stereochemistries of the enantiomers were determined by X-ray crystallographic analysis of the compound from the second eluting peak (Example 146) in complex with PI3Kγ at 2.9 Å resolution.

(S)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (from the first eluting peak) was isolated as a yellow powder. $^1$H NMR (CDCl$_3$, 400 MHz) δ 11.66 (s, 1H), 8.70 (d, J=2.35 Hz, 1H), 8.36 (d, J=2.54 Hz, 1H), 8.27 (d, J=2.35 Hz, 1H), 8.13 (dd, J=8.80 Hz, 2.74 Hz, 1H), 6.79 (d, J=8.80 Hz, 1H), 5.38 (br s, 2H), 3.95 (s, 3H), 3.55 (q, J=6.78 Hz, 1H), 3.23 (t, J=4.89 Hz, 4H), 2.77 (s, 3H), 2.66-2.54 (m, 4H), 2.58 (s, 3H), 1.44 (d, J=6.65 Hz, 3H). m/z (ESI, +ve ion) 500 (M+H)+.

(R)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (from the second eluting peak) was isolated as a yellow powder. $^1$H NMR (CDCl$_3$, 400 MHz) δ 11.66 (s, 1H), 8.70 (d, J=2.35 Hz, 1H), 8.36 (d, J=2.54 Hz, 1H), 8.27 (d, J=2.35 Hz, 1H), 8.13 (dd, J=8.80 Hz, 2.74 Hz, 1H), 6.79 (d, J=8.80 Hz, 1H), 5.38 (br s, 2H), 3.95 (s, 3H), 3.55 (q, J=6.78 Hz, 1H), 3.23 (t, J=4.89 Hz, 4H), 2.77 (s, 3H), 2.66-2.54 (m, 4H), 2.58 (s, 3H), 1.44 (d, J=6.65 Hz, 3H). m/z (ESI, +ve ion) 500 (M+H)+.

Example 146 was also prepared by the following sequence of reaction conditions:

Step 1. 1-(6-fluoropyridin-3-yl)ethanol

A clear solution (prepared by filtration of a slightly cloudy suspension) of 6-fluoronicotinaldehyde (Frontier Scientific, Logan, Utah; 9.88 g, 79 mmol) in THF (100 mL) was added dropwise via addition funnel to a solution of methylmagnesium bromide (3.0 M in diethyl ether; 31.6 mL, 95 mmol) in THF (280 mL) at −6° C. (Addition was completed over about 20 min; reaction temperature kept below −5° C. during addition.) MeOH (10 mL) was then added (dropwise), followed by saturated aqueous NH$_4$Cl (300 mL) and sufficient water to dissolve the precipitate. EtOAc (200 mL) was then added, and the organic layer was separated. The aqueous layer was extracted with DCM (2×150 mL), and all organic extracts were combined, dried over sodium sulfate, filtered, and concentrated in vacuo to provide 1-(6-fluoropyridin-3-yl)ethanol (10.55 g, 95% yield) as a light-yellow oil. $^1$H NMR (400 MHz, CDCl$_3$) δ 8.18 (d, J=2.0 Hz, 1H) 7.85 (td, J=8.1, 2.5 Hz, 1H) 6.92 (dd, J=8.5, 2.8 Hz, 1H) 4.98 (q, J=6.5 Hz, 1H) 2.21 (br. s., 1H) 1.53 (d, J=6.5 Hz, 3H).

Step 2. 5-(1-bromoethyl)-2-fluoropyridine

Thionyl bromide (11.60 mL, 149 mmol) was added (dropwise over 15 min; gas evolution) to a solution of 1-(6-fluoropyridin-3-yl)ethanol (10.55 g, 74.7 mmol) in DCM (300 mL) at 25° C., and the resulting orange solution was stirred at 25° C. for 3 h. Excess SOBr$_2$ was then carefully quenched with water (150 mL) at 0° C. with vigorous stirring, and 5.0 N aqueous NaOH (100 mL) was then carefully added at 0° C. (over about 10 min) to neutralize HBr and SO$_2$ (Yellow mixture results; final pH about 9; adjust with saturated aqueous NaHCO$_3$, to a pH of about 9 as necessary.) The resulting mixture was vigorously stirred at 0° C. for 5 min to ensure complete quench of acidic species, and the resulting mixture was then partitioned between DCM (200 mL) and half saturated aqueous NaHCO$_3$ to a pH of about 9 (600 mL). The organic layer was separated, and the aqueous layer was extracted with DCM (300 mL). The combined organic extracts were sequentially washed with saturated aqueous NaHCO$_3$ (500 mL) and brine (500 mL), dried over sodium sulfate, filtered, and concentrated in vacuo to provide 5-(1-bromoethyl)-2-fluoropyridine (14.58 g, 96% yield) as a yellow oil (71% LCAP; m/z (ESI, +ve) 204.0 (M+H)+), which was used directly in Step 3.

Step 3. (R)-tert-butyl 4-(1-(6-fluoropyridin-3-yl)ethyl)piperazine-1-carboxylate tert-Butyl piperazine-1-carboxylate (Aldrich, St. Louis, Mo.; 13.31 g, 71.5 mmol), potassium iodide (2.37 g, 14.29 mmol), and potassium carbonate (11.85 g, 86 mmol) were sequentially added to a solution of 5-(1-bromoethyl)-2-fluoropyridine (14.58 g, 71.5 mmol) in acetonitrile (300 mL) at 25° C., and the resulting mixture was heated at 80° C. for 1 h. The reaction mixture was then partially concentrated in vacuo (final volume: about 80 mL), diluted with EtOAc (600 mL), and sequentially washed with 4:1 water:brine (2×600 mL)

and brine (600 mL). The organic layer was dried over sodium sulfate, filtered, and concentrated in vacuo. Chromatographic purification of the residue (silica gel, 0 to 100% EtOAc/Hexanes) furnished tert-butyl 4-(1-(6-fluoropyridin-3-yl)ethyl)piperazine-1-carboxylate (16.9 g, 73% yield over (2 steps) as a yellow oil. $^1$H NMR (300 MHz, CDCl$_3$) δ 8.12 (d, J=1.8 Hz, 1H), 7.78 (td, J=8.1, 2.3 Hz, 1H), 6.90 (dd, J=8.4, 2.9 Hz, 1H), 3.47 (q, J=6.7 Hz, 1H), 3.39 (t, J=4.8 Hz, 4H), 2.37-2.49 (m, 2H), 2.25-2.36 (m, 2H), 1.44 (s, 9H), 1.36 (d, J=6.7 Hz, 3H). $^{19}$F NMR (377 MHz, CDCl$_3$) δ −70.50 (dd, J=8.0, 2.3 Hz, 1 F). m/z (ESI, +ve) 310.3 (M+H)$^+$.

tert-Butyl 4-(1-(6-fluoropyridin-3-yl)ethyl)piperazine-1-carboxylate was separated into its constituent enantiomers by super-critical fluid chromatography (SFC) using the following conditions:

Column: Chiralpak® AD-H (250×30 mm, 5 μm)
Mobile Phase: 75:25(A:B)
A: Supercritical CO$_2$
B: Methanol (+0.2% diethylamine)
Flow Rate: 120 mL/min
Oven/column temperature: 40° C.
Sample dissolved at 70 mg/mL in methanol; 50 mg/injection (repeat injection). Injection cycle time: 1.2 min/injection The first peak to elute from the column under these conditions was collected, concentrated in vacuo, and dried under high vacuum to provide (R)-tert-butyl 4-(1-(6-fluoropyridin-3-yl)ethyl)piperazine-1-carboxylate (6.86 g, 22.2 mmol) as a light-yellow solid (>99% ee).

Step 4. (R)-5-(1-(4-(tert-butoxycarbonyl)piperazin-1-yl)ethyl)-2-fluoropyridin-3-ylboronic acid n-Butyllithium (2.5 M in hexanes, Aldrich; 20.0 mL, 50.0 mmol) was added (dropwise over 20 min) to a solution of (R)-tert-butyl 4-(1-(6-fluoropyridin-3-yl)ethyl)piperazine-1-carboxylate (10.0 g, 32.3 mmol) in THF (150 mL) at −78° C., and the resulting mixture was stirred at −78° C. for 20 min. Triisopropyl borate (15.0 mL, 65.2 mmol) was then added (dropwise over 10 min), followed by additional THF (20 mL) to rinse solidified triisopropyl borate from the side of the flask. The resulting mixture was stirred at −78° C. for 15 min, and the cooling bath was then removed. The reaction mixture was stirred for 1 h, and 1 N aq. NaOH (100 mL) and water (40 mL) were then sequentially added. The resulting mixture was stirred for 10 min, and the organic layer was separated. The organic layer was extracted with 1 N aq. NaOH (40 mL), and the aqueous layers were then combined and pH-adjusted with 5 N aqueous HCl to a final pH of about 5. The resulting mixture was extracted with EtOAc (3×200 mL), and the combined organic extracts were dried over sodium sulfate, filtered, and concentrated in vacuo to provide (R)-5-(1-(4-(tert-butoxycarbonyl)piperazin-1-yl)ethyl)-2-fluoropyridin-3-ylboronic acid (9.27 g, 81% yield) as a white solid. $^1$H NMR (400 MHz, d$_4$-MeOH) δ 8.39 (br. s., 1H), 8.26 (d, J=6.5 Hz, 1H), 4.54-4.63 (m, 1H), 3.31 (br. s., 4H; masked by MeOH), 3.13 (br. s., 4H), 1.80 (d, J=6.8 Hz, 3H), 1.45 (s, 9H). $^{19}$F NMR (377 MHz, d$_4$-MeOH) δ −60.93 (br. s., 1 F). m/z (ESI, +ve) 354.2 (M+H)$^+$.

Step 5. (R)-tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (R)-5-(1-(4-(tert-butoxycarbonyl)piperazin-1-yl)ethyl)-2-fluoropyridin-3-ylboronic acid (9.27 g, 26.2 mmol), 4-chloro-N,N-bis(4-methoxybenzyl)-6-methyl-1,3,5-triazin-2-amine (Example 51) (11.47 g, 29.8 mmol), bis-(di-tert-butyl(4-dimethylaminophenyl)phosphine)dichloropalladium(II) (Aldrich, St. Louis, Mo.) (1.820 g, 2.57 mmol), and potassium acetate (8.17 g, 83.0 mmol) were suspended in a mixture of 1,4-dioxane (150 mL) and water (30 mL). The resulting mixture was sparged with nitrogen (for about 30 sec) and then stirred at 100° C. for 3.5 h. The reaction mixture was then allowed to cool to 25° C., water (150 mL) was added, and the resulting mixture was extracted with EtOAc (3×300 mL). The organic extracts were combined, dried over sodium sulfate, filtered, and concentrated in vacuo. Chromatographic purification of the residue (silica gel, 3% MeOH/DCM) furnished (R)-tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (13.63 g, 79% yield) as a colorless oil. $^1$H NMR (400 MHz, CDCl$_3$) δ 8.44 (dd, J=9.0, 2.3 Hz, 1H), 8.25 (d, J=1.8 Hz, 1H), 7.24 (d, J=5.7 Hz, 2H), 7.22 (d, J=5.5 Hz, 2H), 6.86 (t, J=8.9 Hz, 4H), 4.83 (s, 2H), 4.80 (s, 2H), 3.81 (s, 3H), 3.79 (s, 3H), 3.54-3.61 (m, 1H), 3.40 (d, J=3.7 Hz, 4H), 2.55 (s, 3H), 2.44 (d, J=2.7 Hz, 2H), 2.27-2.39 (m, 2H), 1.44 (s, 9H), 1.40 (d, J=6.7 Hz, 3H). $^{19}$F NMR (377 MHz, CDCl$_3$) δ −67.83 (d, J=9.2 Hz, 0.7 F), −70.47 (d, J=5.7 Hz, 0.3 F). m/z (ESI, +ve) 658.4 (M+H)$^+$.

Step 6. (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine 2,2,2-Trifluoroacetic acid (45.9 mL, 596 mmol) was added (over about 10 min) to a solution of (R)-tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (7.00 g, 10.64 mmol) in DCM (106 mL) at 0° C., and the resulting mixture was stirred at 25° C. for 2 h. The reaction mixture was then concentrated in vacuo (5 torr, 25° C.) to provide a viscous oil, which was taken up in DCM (100 mL) and cooled to 0° C. Ice (20 mL) was added, followed by solid sodium bicarbonate (added in portions to the rapidly stirred mixture until gas evolution ceased). Water (300 mL) and DCM (50 mL) were then added. The organic layer was separated, and the aqueous layer was extracted with DCM (2×150 mL). All organic extracts were then combined, dried over sodium sulfate, and filtered through a 0.45 μM ZAPCAP filter (Sigma-Aldrich Corp., St. Louis, Mo.). The clear filtrate was partially concentrated in vacuo (final volume, 100 mL) and cooled to 0° C. Triethylamine (5.93 mL, 42.6 mmol) and methanesulfonyl chloride (1.647 mL, 21.28 mmol) (added dropwise) were then sequentially added, and the resulting mixture was stirred at 0° C. for 1 h. Saturated aqueous NaHCO$_3$ (50 mL) was added, and the resulting mixture was partitioned between DCM (150 mL) and water (200 mL). The organic layer was separated, and the aqueous layer was extracted with DCM (3×100 mL). All organic layers were then combined, dried over sodium sulfate, filtered, and concentrated in vacuo. Chromatographic purification of the residue (silica gel, 20 to 100% (10% MeOH/EtOAc)/hexane) provided (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (6.28 g, 9.88 mmol, 93% yield) as a white foam. $^1$H NMR (400 MHz, CDCl$_3$) δ 8.45 (dd, J=9.0, 2.3 Hz, 1H), 8.27 (s, 1H), 7.23 (t, J=8.0 Hz, 4H), 6.87 (t, J=8.6 Hz, 4H), 4.82 (s, 2H), 4.81 (s, 2H), 3.81 (s, 3H), 3.80 (s, 3H), 3.63 (q, J=6.8 Hz, 1H), 3.20 (br. s., 4H), 2.73 (s, 3H), 2.59-2.67 (m, 2H), 2.55 (s, 3H), 2.49-2.54 (m, 2H), 1.41 (d, J=6.7 Hz, 3H). $^{19}$F NMR (377 MHz, CDCl$_3$) δ −67.44 (d, J=9.2 Hz, 0.92 F), −70.10 (br. s., 0.08 F). m/z (ESI, +ve) 636.2 (M+H)$^+$.

Step 7. (R)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (19.64 g, 30.9 mmol) and 5-amino-2-methoxypyridine (4.13 mL, 33.3 mmol) were dissolved in THF (300 mL) in a 2-necked round bottomed flask equipped with a stirbar and a dropping funnel. To the dropping funnel was added lithium bis(trimethylsilyl)amide, 1.0 M solution in tetrahydrofuran/ethylbenzene (Acros; 96.0 mL, 96 mmol) via cannula, and the reaction flask was cooled in an ice water bath under nitrogen. Then, the LiHMDS solution was added to the reaction mixture dropwise over 20 min. The reaction mixture was subsequently stirred for 30 min and saturated ammonium chloride (40 mL) was then added dropwise via the dropping funnel, followed by water (200 mL). The reaction was warmed to room temperature and diluted with EtOAc (150 mL). The organic layer was separated, and the aqueous layer was extracted with EtOAc. The combined organic layers were then dried over sodium sulfate, filtered, and concentrated in vacuo. Chromatogtraphic purification of the residue (silica gel, 75:1 DCM/MeOH to 50:1 DCM/MeOH to 50:1 DCM/2 N ammonia in MeOH to 40:1 DCM/2 N ammonia in MeOH) provided (R)-N,N-bis(4-methoxybenzyl)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (18.47 g).

(R)-N,N-bis(4-methoxybenzyl)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (18.47 g, 24.96 mmol) was dissolved in trifluoroacetic acid (200 mL, 2596 mmol) and the flask was fitted with a reflux condensor and put in a pre-heated oil bath (75-85° C.). The reaction was stirred under nitrogen overnight. The reaction mixture was then cooled to room temperature and concentrated in vacuo. The concentrate was diluted with DCM and saturated aqueous sodium bicarbonate was added, followed by aqueous 5 N NaOH (to raise the pH of the aqueous phase to about 14) and then 5 N HCl (to lower the aqueous pH to about 5). Finally, saturated aqueous sodium bicarbonate was added to raise the pH to about 6 to 7. The organic layer was separated and combined with the residual solid that did not dissolve in the organic phase. The aqueous phase was treated with brine and extracted with 10:1 DCM/MeOH. All of the organic extracts and undissolved solid were then combined and concentrated in vacuo.

The residue was taken up in DCM and filtered. The solid was washed with DCM. The filtrate was concentrated, treated with MeOH, and filtered. The combined solids were then washed with MeOH and DCM and set aside (SOLID A).

The combined filtrates were concentrated in vacuo and purified by column chromatography (silica gel, 50:1 DCM/MeOH to 40:1 DCM/MeOH to 30:1 DCM/MeOH to 20:1 DCM/MeOH to 20:1 DCM/2 N ammonia in MeOH to 15:1 DCM/MeOH to 10:1 DCM/2 N ammonia in MeOH). Product-containing fractions were combined and concentrated in vacuo, and the resulting solid was combined with SOLID A. The combined solids were then suspended in Et$_2$O and filtered. The collected solid was washed with Et$_2$O, and the filtrate was discarded. The solid was washed with MeOH and Et$_2$O, then with DCM, MeOH, and Et$_2$O. The solid was set aside (SOLID B), and the filtrate was concentrated in vacuo and purified by column chromatography (silica gel, 100:1 DCM/MeOH to 50:1 DCM/MeOH to 20:1 DCM/MeOH to 20:1 DCM/2 N ammonia in MeOH to 15:1 DCM/2 N ammonia in MeOH to 10:1 DCM/2 N ammonia in MeOH). Product-containing fractions were combined and concentrated in vacuo, and the resulting solid was combined with SOLID B and dried.

The resulting solid was dissolved in DMSO (about 50 mL) and partially concentrated in vacuo until a solid started to form. Sufficient DMSO was added to dissolve the precipitated solid, and the solution was poured into water (about 400 mL). Water was added to bring the final volume to about 600 mL (only a small amount of precipitate was formed). Brine (100 mL) was added, and a yellow solid was precipitated. The resulting suspension was filtered, and the collected solid (SOLID C) was washed with water. Solid sodium chloride was added to the filtrate to give a saturated solution, which was allowed to stand at room temperature overnight, resulting in additional precipitated solid. This precipitate was collected by filtration, washed with water, combined with SOLID C, and dried in vacuo. The dried solid was treated with water (200 mL) and saturated sodium bicarbonate (50 mL) and mixed for 10 min. The resulting suspension was then filtered and sequentially washed with water and EtOH. The collected solid was then dried in vacuo to give (R)-4-(2-(6-methoxypyridin-3-ylamino)-5-(1-(4-(methylsulfonyl)piperazin-1-yl)ethyl)pyridin-3-yl)-6-methyl-1,3,5-triazin-2-amine (8.46 g, 55% over 2 steps) as a yellow solid. $^1$H NMR (CDCl$_3$, 400 MHz) δ 11.66 (s, 1H), 8.70 (d, J=2.35 Hz, 1H), 8.36 (d, J=2.54 Hz, 1H), 8.27 (d, J=2.35 Hz, 1H), 8.13 (dd, J=8.80 Hz, 2.74 Hz, 1H), 6.79 (d, J=8.80 Hz, 1H), 5.38 (br s, 2H), 3.95 (s, 3H), 3.55 (q, J=6.78 Hz, 1H), 3.23 (t, J=4.89 Hz, 4H), 2.77 (s, 3H), 2.66-2.54 (m, 4H), 2.58 (s, 3H), 1.44 (d, J=6.65 Hz, 3H). m/z (ESI, +ve ion) 500 (M+H)$^+$.

Examples 147 and 148

(S)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (Example 147) and (R)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (Example 148)

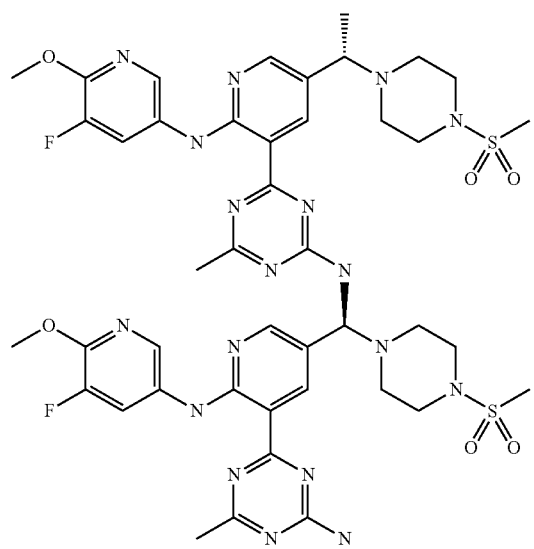

A mixture of isomers of 4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (Example 143) (187 mg) was separated using chiral SFC preparative chromatography. The following conditions were used:
Column: Chiralcel OJ-H (250×20 mm, 5 μm)
Mobile Phase: 78:22 (A:B)
A: Liquid $CO_2$
B: Methanol (with about 1% diethylamine)
Flow Rate: 70 mL/min
Oven/column temp: 40° C.

The two resulting peaks were separately collected, concentrated in vacuo, and dried under high vacuum to give the two enantiomers.

(S)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (from the first-eluting peak) was isolated as a yellow powder. $^1$H NMR (CDCl$_3$, 400 MHz) δ 11.93 (s, 1H), 8.71 (d, J=2.35 Hz, 1H), 8.32-8.26 (m, 2H), 8.05 (d, J=2.35 Hz, 1H), 5.40 (br s, 2H), 4.03 (s, 3H), 3.56 (q, J=7.04 Hz, 1H), 3.24 (t, J=4.89 Hz, 4H), 2.78 (s, 3H), 2.68-2.53 (m, 4H), 2.59 (s, 3H), 1.44 (d, J=6.65 Hz, 3H). m/z (ESI, pos. ion) 518 (M+H)$^+$.

(R)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (from the second-eluting peak) was isolated as a yellow powder. $^1$H NMR (CDCl$_3$, 400 MHz) δ 11.93 (s, 1H), 8.71 (d, J=2.35 Hz, 1H), 8.32-8.26 (m, 2H), 8.05 (d, J=2.15 Hz, 1H), 5.41 (br s, 2H), 4.04 (s, 3H), 3.56 (q, J=6.39 Hz, 1H), 3.24 (t, J=4.50 Hz, 4H), 2.78 (s, 3H), 2.68-2.53 (m, 4H), 2.59 (s, 3H), 1.44 (d, J=6.65 Hz, 3H). m/z (ESI, pos. ion) 518 (M+H)$^+$.

Example 148 was also prepared by the following sequence of reaction conditions, thus confirming the absolute stereochemistries assigned for the two enantiomers above:

Step 1. (R)-4-(2-(5-fluoro-6-methoxypyridin-3-ylamino)-5-(1-(4-(methylsulfonyl)piperazin-1-yl)ethyl)pyridin-3-yl)-N,N-bis (4-methoxybenzyl)-6-methyl-1,3,5-triazin-2-amine Lithium bis(trimethylsilyl)amide (1.0 M in hexane; 31.9 mL, 31.9 mmol) was added (dropwise over 10 min) to a mixture of (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (Example 146, Step 6; 6.75 g, 10.62 mmol) and 5-fluoro-6-methoxypyridin-3-amine (Anichem, North Brunswick, N.J.; 2.264 g, 15.93 mmol) in THF (100 mL) at 0° C., and the resulting solution was stirred at 0° C. for 1 h. Excess LiHMDS was then quenched with saturated aqueous NH$_4$Cl (140 mL) and the reaction mixture was partitioned between EtOAc (500 mL) and half-saturated aqueous NH$_4$Cl (200 mL). The organic layer was separated, and the aqueous layer was extracted with EtOAc (2×200 mL). The combined organic extracts were sequentially washed with brine (300 mL), dried over sodium sulfate, filtered, and concentrated in vacuo. Chromatographic purification of the residue (silica gel, 0 to 100% EtOAc/hexanes) furnished (R)-4-(2-(5-fluoro-6-methoxypyridin-3-ylamino)-5-(1-(4-(methylsulfonyl)piperazin-1-yl)ethyl)pyridin-3-yl)-N,N-bis (4-methoxybenzyl)-6-methyl-1,3,5-triazin-2-amine (7.25 g, 90% yield) as a yellow solid. $^1$H NMR (400 MHz, CDCl$_3$) δ 11.88 (1H, s), 8.72 (1H, d, J=2.0 Hz), 8.25 (1H, d, J=2.2 Hz), 8.06 (1H, dd, J=12.3, 1.6 Hz), 7.96 (1H, d, J=2.0 Hz), 7.21 (4H, t, J=8.2 Hz), 6.86 (4H, dd, J=14.1, 8.4 Hz), 4.70-4.96 (4H, m), 4.01 (3H, s), 3.81 (3H, s), 3.78 (3H, s), 3.55 (1H, q, J=6.7 Hz), 3.15 (4H, br s), 2.68 (3H, s), 2.59 (3H, s), 2.48-2.57 (4H, m), 1.38 (3H, d, J=6.7 Hz). $^{19}$F NMR (376 MHz, CDCl$_3$) δ −139.13 (1 F, d, J=13.0 Hz). m/z (ESI, +ve) 758.3 (M+H)$^+$.

Step 2. (R)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine A solution of (R)-4-(2-(5-fluoro-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (9.94 g, 13.12 mmol) and trifluoromethanesulfonic acid (6.5 mL, 73.2 mmol) in TFA (65 mL) was stirred at 70° C. for 2 h. The mixture was subsequently cooled to 25° C. and concentrated in vacuo. The residue was cooled over a 0° C. bath, and ice (about 250 g), NaOH (1N, aqueous; 220 mL), and saturated aqueous NaHCO$_3$ (110 mL) were sequentially added to bring the pH of the resulting mixture to about 9. The resulting yellow-brown slurry was extracted with DCM (3×400 mL), and the combined organic extracts were dried over sodium sulfate and concentrated onto silica gel. Chromatographic purification (silica gel, 0 to 10% MeOH/EtOAc) furnished a yellow solid. This solid was purified by preparative SFC chromatography (column: Chiralcel OD-H (250×20 mm, 5 μm), mobile phase: 77:23 (A:B), A: liquid $CO_2$, B: methanol (+1% diethylamine), flow rate: 70 mL/min, oven/column temp: 40° C.) to provide a yellow solid, which was then suspended in MeOH plus 0.2% diethylamine (175 mL). The resulting mixture was sonicated for 2 min, centrifuged (3000×g, 5 min), and the pelleted material was collected. This wash process was then repeated, and the collected material was subsequently suspended in isopropanol plus 0.2% 2M NH$_3$ in MeOH (175 mL). The resulting mixture was sonicated for 2 min, centrifuged (3000×g, 5 min), and the pelleted material was collected. This wash process was repeated, and the collected material was then dried in vacuo to provide (R)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine (3.50 g, 52% yield) as a yellow solid. $^1$H NMR (400 MHz, CDCl$_3$) δ 11.90 (s, 1H), 8.70 (d, J=1.6 Hz, 1H), 8.30 (d, J=2.2 Hz, 1H), 8.27 (dd, J=12.5, 2.0 Hz, 1H), 8.04 (d, J=2.3 Hz, 1H), 5.41 (br. s., 2H), 4.03 (s, 3H), 3.55 (q, J=6.4 Hz, 1H), 3.23 (br. s., 4H), 2.77 (s, 3H), 2.60-2.68 (m, 2H), 2.58 (s, 5H), 1.44 (d, J=6.7 Hz, 3H). $^{19}$F NMR (377 MHz, CDCl$_3$) δ −138.85 (d, J=12.6 Hz, 1 F). m/z (ESI, +ve) 518.2 (M+H)$^+$.

Example 149

4-(2-(6-methoxypyridin-3-ylamino)-5-(1-(4-(methylsulfonyl)phenyl)ethyl)pyridin-3-yl)-6-methyl-1,3,5-triazin-2-amine

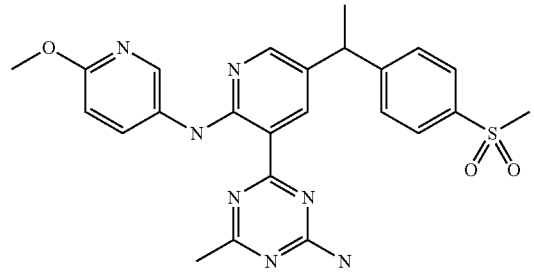

Step 1: (6-fluoropyridin-3-yl)(4-(methylthio)phenyl) methanone (6-Fluoropyridin-3-yl)(4-(methylthio)phenyl)methanol (Example 103) (1.5304 g, 6.1387 mmol) was dissolved in DCM (60 mL) and manganese(IV) oxide (Aldrich less than 5 micron, activated, 2.546 g, 29.28 mmol) was added. The reaction was stirred at room temperature for 90 minutes, and then more activated manganese (IV) oxide (2.736 g, 31.47 mmol) was added. The reaction was stirred overnight and then was filtered through a Celite® (diatomaceous earth) pad, which was washed with DCM. The filtrate was concentrated, and dried under high vacuum to give (6-fluoropyridin-3-yl) (4-(methylthio)phenyl)methanone (1.334 g). $^1$H NMR (CDCl$_3$, 400 MHz) δ 8.64 (d, J=2.35 Hz, 1H), 8.26 (td, J=8.07 Hz, 2.45 Hz, 1H), 7.75 (d, J=8.61 Hz, 2H), 7.33 (d, J=8.41 Hz, 2H), 7.09 (dd, J=8.41 Hz, 2.54 Hz, 1H), 2.56 (s, 3H). m/z (ESI, pos. ion) 248 (M+H)$^+$.

Step 2: 1-(6-fluoropyridin-3-yl)-1-(4-(methylthio) phenyl)ethanol (6-Fluoropyridin-3-yl)(4-(methylthio)phenyl)methanone (1.256 g, 5.079 mmol) was dissolved in THF (19 mL) and the flask was cooled in an ice water bath. Then, methylmagnesium bromide (3.0 M in diethyl ether, 3.40 mL, 10.2 mmol) was added via syringe over 5 min. The reaction was stirred at 0° C. under nitrogen for 20 min, and then was treated with saturated ammonium chloride (2.5 mL, added dropwise at first as gas evolution is observed). The reaction was quenched at 0° C. Then, the reaction was diluted with water (15 mL) and the layers were separated. The aqueous phase was extracted with DCM, and the organic phases were combined, dried over sodium sulfate, filtered, concentrated, and dried under high vacuum at room temperature overnight to give 1-(6-fluoropyridin-3-yl)-1-(4-(methylthio)phenyl)ethanol (1.375 g). $^1$H NMR (CDCl$_3$, 400 MHz) δ 8.26 (d, J=2.35 Hz, 1H), 7.82-7.76 (m, 1H), 7.35-7.30 (m, 2H), 7.25-7.20 (m, 2H), 6.86 (dd, J=8.61 Hz, 2.93 Hz, 1H), 2.48 (s, 3H), 2.30 (s, 1H), 1.96 (s, 3H). m/z (ESI, +ve ion) 264 (M+H)$^+$.

Step 3: 2-fluoro-5-(1-(4-(methylthio)phenyl)vinyl) pyridine 1-(6-Fluoropyridin-3-yl)-1-(4-(methylthio)phenyl)ethanol (1.261 g, 4.789 mmol) was dissolved in DCM (30 mL) and trifluoroacetic acid (1.0 mL, 13 mmol) was added, turning the solution dark green. The reaction was stirred at room temperature for 45 min and then was treated with saturated sodium bicarbonate (15 mL). The reaction was stirred for about 5 min, and then the layers were separated, and the aqueous phase was extracted with DCM. The organic phases were combined, dried over sodium sulfate, filtered, concentrated, and dried under high vacuum to give 2-fluoro-5-(1-(4-(methylthio)phenyl)vinyl)pyridine (1.183 g). $^1$H NMR (CDCl$_3$, 400 MHz) δ 8.23 (d, J=2.35 Hz, 1H), 7.71 (td, J=8.12 Hz, 2.54 Hz, 1H), 7.26-7.21 (m, 4H), 6.91 (dd, J=8.51 Hz, 2.64 Hz, 1H), 5.55 (s, 1H), 5.43 (s, 1H), 2.51 (s, 3H). m/z (ESI, +ve ion) 246 (M+H)$^+$.

Step 4: 2-fluoro-5-(1-(4-(methylthio)phenyl)ethyl) pyridine

2-Fluoro-5-(1-(4-(methylthio)phenyl)vinyl)pyridine (992 mg, 4.04 mmol) was dissolved in THF (12 mL) and water (4 mL) and the flask was cooled in an ice water bath under nitrogen. Then, ruthenium trichloride hydrate (212.4 mg, 0.9422 mmol) was added, and then sodium borohydride (393 mg, 10.4 mmol) was added portionwise over about 5 min. More THF (2 mL) was added, and the reaction was warmed to room temperature and stirred. After 2 hours and 15 minutes, more RuCl$_3$*H$_2$O (214 mg, 0.951 mmol) was added and the flask was again cooled in an ice water bath. Then, more sodium borohydride (384 mg, 10.2 mmol) was added, and the reaction was warmed to room temperature. The stirring was continued. Gas evolution was observed. After 50 min, more sodium borohydride (139 mg, 3.67 mmol) was added, and stirring was continued for 1 h. The reaction was diluted with water (20 mL) and DCM (30 mL). The suspension was filtered through a Celite® (diatomaceous earth) pad, which was washed repeatedly with DCM. The biphasic mixture was treated with saturated sodium bicarbonate (50 mL), and the layers were separated. The aqueous phase was extracted with DCM, and all the organic phases were combined, dried over sodium sulfate, filtered, concentrated, and purified on a silica gel filter (150 mL fritted funnel with about 2 inches of silica gel; DCM) to give 2-fluoro-5-(1-(4-(methylthio)phenyl) ethyl)pyridine (875 mg). $^1$H NMR (CDCl$_3$, 400 MHz) δ 8.10 (d, J=1.96 Hz, 1H), 7.56 (td, J=8.07 Hz, 2.64 Hz, 1H), 7.24-7.19 (m, 2H), 7.15-7.09 (m, 2H), 6.84 (dd, J=8.41 Hz, 2.93 Hz, 1H), 4.15 (q, J=7.24 Hz, 1H), 2.47 (s, 3H), 1.64 (d, J=7.24 Hz, 3H). m/z (ESI, pos. ion) 248 (M+H)$^+$.

Step 5: 2-fluoro-5-(1-(4-(methylthio)phenyl)ethyl) pyridin-3-ylboronic acid

2-Fluoro-5-(1-(4-(methylthio)phenyl)ethyl)pyridine (1.078 g, 4.359 mmol) and triisopropyl borate (2.50 mL, 10.9 mmol) were dissolved in THF (11.5 mL). In a separate flask, 2,2,6,6-tetramethylpiperidine (1.11 mL, 6.54 mmol) was dissolved in THF (12 mL) and the flask was cooled in an ice water bath. Then, n-butyllithium solution (1.6 M in hexanes, 3.8 mL, 6.1 mmol) was added via syringe, and the yellow solution was stirred under nitrogen for 15 min. Then, the contents were transferred via syringe to the other flask, which was pre-cooled in a dry ice/acetone bath. After completing the transfer, the reaction was stirred under nitrogen at −78° C. for 1 h. Then, the reaction was allowed to slowly warm up to room temperature while being stirred overnight. The reaction was treated with water (30 mL) and stirred for about 30 min. The layers were separated, and the organic phase was extracted with 1 N aqueous NaOH (15 mL). The organic phase was discarded, and the aqueous phase was treated with aqueous 5 N HCl to lower the pH to around 5-6. The aqueous phase was extracted with 10:1 DCM/MeOH. The extracts were combined, concentrated, and dried under high vacuum to afford 2-fluoro-5-(1-(4-(methylthio)phenyl)ethyl)pyridin-3-ylboronic acid (1.2342 g). $^1$H NMR (400 MHz, CDCl$_3$) δ 8.17-8.05 (m, 2H), 7.25-7.19 (m, 2H), 7.15-7.10 (m, 2H), 4.16 (q, J=7.37 Hz, 1H), 2.47 (s, 3H), 1.66 (d, J=7.24 Hz, 3H). m/z (ESI, +ve ion) 292 (M+H)$^+$.

Step 6: 4-(2-fluoro-5-(1-(4-(methylthio)phenyl) ethyl)pyridin-3-yl)-N,N-bis(4-methoxybenzyl)-6-methyl-1,3,5-triazin-2-amine 4-Chloro-N,N-bis(4-methoxybenzyl)-6-methyl-1,3,5-triazin-2-amine (1.4126 g, 3.6704 mmol), 2-fluoro-5-(1-(4-(methylthio)phenyl)ethyl)pyridin-3-ylboronic acid (1.2342 g, 4.2390 mmol), Am-Phos (140.4 mg, 0.1983 mmol), and potassium acetate (1.531 g, 15.60 mmol) were suspended in 1,4-dioxane (20 mL) and water (4 mL), and nitrogen was bubbled through the suspension for 15 s. Then, the flask was fitted with a reflux condenser and placed in a preheated oil bath (100° C.), and stirred under nitrogen overnight. Then, the reaction was cooled to room temperature, diluted with water (40 mL), and extracted with EtOAc. The organic extracts were combined, dried over sodium sulfate, filtered through a Celite® (diatomaceous earth) pad, concentrated, and purified on a silica gel filter (600 mL fritted filter with about 3 inches of silica gel; DCM to 100:1 DCM/MeOH to 75:1 DCM/MeOH). The fractions with product were collected, concentrated, and dried under high vacuum, first at room temperature, and then in a water bath (about 50° C.) to give 4-(2-fluoro-5-(1-(4-(methylthio)phenyl)ethyl)pyridin-3-yl)-N,N-bis(4-methoxybenzyl)-6-methyl-1,3,5-triazin-2-amine (1.797 g). $^1$H NMR (CDCl$_3$, 400 MHz) δ 8.34 (dd, J=8.90 Hz, 2.45 Hz, 1H), 8.15 (d, J=1.96 Hz, 1H), 7.24-7.17 (m, 6H), 7.16-7.11 (m, 2H), 6.86 (dd, J=10.17 Hz, 8.61 Hz, 4H), 4.82 (s, 2H), 4.78 (s, 2H), 4.20 (q, J=7.30 Hz, 1H), 3.82 (s, 3H), 3.81 (s, 3H), 2.53 (s, 3H), 2.45 (s, 3H), 1.67 (d, J=7.24 Hz, 3H). m/z (ESI, pos. ion) 596 (M+H)$^+$.

Step 7: 4-(2-fluoro-5-(1-(4-(methylsulfonyl)phenyl)ethyl)pyridin-3-yl)-N,N-bis(4-methoxybenzyl)-6-methyl-1,3,5-triazin-2-amine 4-(2-Fluoro-5-(1-(4-(methylthio)phenyl)ethyl)pyridin-3-yl)-N,N-bis(4-methoxybenzyl)-6-methyl-1,3,5-triazin-2-amine (1.797 g, 3.016 mmol) was dissolved in DCM (30 mL) and the reaction flask was cooled in an ice water bath under nitrogen. Then, 3-chlorobenzoperoxoic acid (1.668 g, 9.666 mmol) was added as a solution in DCM (52 mL), and the reaction was warmed to room temperature and stirred. After 30 min, the reaction was cooled in an ice water bath and treated with a mixture of saturated sodium bicarbonate (50 mL) and saturated sodium thiosulfate (15 mL). The biphasic mixture was warmed to room temperature and stirred. After 1 h, the layers were separated, and the aqueous phase was extracted with DCM. The organic phases were combined, dried over sodium sulfate, filtered, concentrated, and purified on a silica gel filter (150 mL fritted filter with about 2 inches of silica gel; DCM to 100:1 DCM/MeOH to 50:1 DCM/MeOH). The fractions with product were collected, concentrated, and dried under high vacuum to give 4-(2-fluoro-5-(1-(4-(methylsulfonyl)phenyl)ethyl)pyridin-3-yl)-N,N-bis(4-methoxybenzyl)-6-methyl-1,3,5-triazin-2-amine (1.517 g). $^1$H NMR (CDCl$_3$, 400 MHz) δ 8.34 (dd, J=8.90 Hz, 2.45 Hz, 1H), 8.17 (s, 1H), 7.88 (d, J=8.41 Hz, 2H), 7.42 (d, J=8.22 Hz, 2H), 7.21 (d, J=8.02 Hz, 4H), 6.86 (t, J=8.90 Hz, 4H), 4.82 (s, 2H), 4.78 (s, 2H), 4.34 (q, J=7.69 Hz, 1H), 3.82 (s, 3H), 3.81 (s, 3H), 3.02 (s, 3H), 2.54 (s, 3H), 1.74 (d, J=7.24 Hz, 3H). m/z (ESI, pos. ion) 628 (M+H)$^+$.

Step 8: N,N-bis(4-methoxybenzyl)-4-(2-(6-methoxypyridin-3-ylamino)-5-(1-(4-(methylsulfonyl)phenyl)ethyl)pyridin-3-yl)-6-methyl-1,3,5-triazin-2-amine 4-(2-Fluoro-5-(1-(4-(methylsulfonyl)phenyl)ethyl)pyridin-3-yl)-N,N-bis(4-methoxybenzyl)-6-methyl-1,3,5-triazin-2-amine (764.7 mg, 1.218 mmol) and 5-amino-2-methoxypyridine (162.9 mg, 1.312 mmol) were dissolved in THF (12 mL) and the flask was cooled in an ice water bath while being stirred under nitrogen. Then, lithium bis(trimethylsilyl)amide (1.0 M solution in tetrahydrofuran/ethyl benzene, 3.6 mL, 3.6 mmol) was added via syringe, and the reaction was stirred at 0° C. After 40 min, the reaction was treated with ice water (1.5 mL), diluted with DCM, dried over sodium sulfate, filtered, concentrated, and purified on a silica gel filter (150 mL fritted funnel with about 2 inches of silica gel; DCM to 100:1 DCM/MeOH to 75:1 DCM/MeOH to 40:1 DCM/MeOH). The fractions with product were collected, concentrated, and dried under high vacuum in a water bath (about 40° C.) to give N,N-bis(4-methoxybenzyl)-4-(2-(6-methoxypyridin-3-ylamino)-5-(1-(4-(methylsulfonyl)phenyl)ethyl)pyridin-3-yl)-6-methyl-1,3,5-triazin-2-amine (459.4 mg). $^1$H NMR (CDCl$_3$, 400 MHz) δ 11.57 (s, 1H), 8.65 (d, J=2.35 Hz, 1H), 8.25 (d, J=2.35 Hz, 1H), 8.14 (d, J=2.35 Hz, 1H), 7.89 (dd, J=8.71 Hz, 2.45 Hz, 1H), 7.81 (d, J=8.22 Hz, 2H), 7.40 (d, J=8.02 Hz, 2H), 7.24-7.14 (m, 4H), 6.90-6.81 (m, 4H), 6.70 (d, J=8.80 Hz, 1H), 4.87 (d, J=4.89 Hz, 2H), 4.77 (d, J=5.09 Hz, 2H), 4.23-4.16 (m, 1H), 3.92 (s, 3H), 3.82 (s, 3H), 3.80 (s, 3H), 2.98 (s, 3H), 2.57 (s, 3H), 1.66 (d, J=7.24 Hz, 3H). m/z (ESI, pos. ion) 732 (M+H)$^+$.

Step 9: 4-(2-(6-methoxypyridin-3-ylamino)-5-(1-(4-(methylsulfonyl)phenyl)ethyl)pyridin-3-yl)-6-methyl-1,3,5-triazin-2-amine N,N-bis(4-methoxybenzyl)-4-(2-(6-methoxypyridin-3-ylamino)-5-(1-(4-(methylsulfonyl)phenyl)ethyl)pyridin-3-yl)-6-methyl-1,3,5-triazin-2-amine (459.4 mg, 0.6277 mmol) was dissolved in trifluoroacetic acid (Aldrich, redistilled, 99+%, 7.5 mL) and the flask was fitted with a reflux condenser and put in a preheated oil bath (75° C.) and stirred overnight. Then, the reaction was cooled to room temperature, concentrated, diluted with DCM, and treated with saturated sodium bicarbonate and 5 N NaOH to raise the pH of the aqueous phase to about 6. The layers were separated, and the aqueous phase was extracted with DCM. The organic phases were combined, dried over sodium sulfate, filtered, concentrated, and purified on a silica gel column (25:1 DCM/MeOH to 20:1 DCM/MeOH). The fractions with product were collected, concentrated, treated with MeOH, and filtered. The solid was washed with MeOH, but was still not 95% pure by HPLC. So, the filtrate and solid were combined, concentrated, treated with EtOAc and acetone (which in combination dissolved the compound), concentrated, and purified by HPLC (10% to 100% MeCN/water with 0.1% TFA over 28 min; total flow rate of 100 mL/min) to give 4-(2-(6-methoxypyridin-3-ylamino)-5-(1-(4-(methylsulfonyl)phenyl)ethyl)pyridin-3-yl)-6-methyl-1,3,5-triazin-2-amine (192.4 mg). $^1$H NMR (CDCl$_3$, 400 MHz) δ 8.87 (s, 1H), 8.48 (s, 1H), 8.16 (d, J=1.57 Hz, 1H), 8.07 (d, J=8.02 Hz, 1H), 7.91 (d, J=8.22 Hz, 2H), 7.45 (d, J=8.22 Hz, 2H), 6.93 (d, J=9.00 Hz, 1H), 4.28 (q, J=7.56 Hz, 1H), 4.03 (s, 3H), 3.06 (s, 3H), 2.63 (s, 3H), 1.74 (d, J=7.04 Hz, 3H). m/z (ESI, pos. ion) 492 (M+H)$^+$.

Example 150

4-(2-(5-fluoro-6-methoxypyridin-3-ylamino)-5-(1-(4-(methylsulfonyl)phenyl)ethyl)pyridin-3-yl)-6-methyl-1,3,5-triazin-2-amine

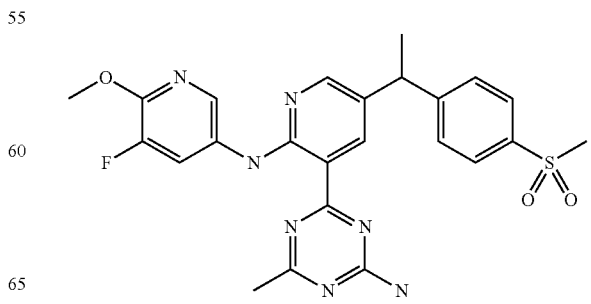

Step 1: 4-(2-(5-fluoro-6-methoxypyridin-3-ylamino)-5-(1-(4-(methylsulfonyl)phenyl)ethyl)pyridin-3-yl)-N,N-bis(4-methoxybenzyl)-6-methyl-1,3,5-triazin-2-amine 4-(2-Fluoro-5-(1-(4-(methylsulfonyl)phenyl)ethyl)pyridin-3-yl)-N,N-bis(4-methoxybenzyl)-6-methyl-1,3,5-triazin-2-amine (752 mg, 1.20 mmol) and 5-fluoro-6-methoxypyridin-3-amine (175.0 mg, 1.231 mmol) were dissolved in THF (12.0 mL) and the flask was cooled in an ice water bath under nitrogen. Then, lithium bis(trimethylsilyl)amide (1.0 M solution in tetrahydrofuran/ethylbenzene, 3.6 mL, 3.6 mmol) was added via syringe, and the reaction was stirred under nitrogen. After 15 min, the reaction was treated with ice water (1.5 mL) and diluted with DCM (150 mL). The solution was dried over sodium sulfate, filtered, concentrated, and purified on a silica gel filter (150 mL fritted filter with 2 inches of silica gel; DCM to 100:1 DCM/MeOH to 50:1 DCM/MeOH). The fractions with product were collected, concentrated, and dried under high vacuum to give 4-(2-(5-fluoro-6-methoxypyridin-3-ylamino)-5-(1-(4-(methylsulfonyl)phenyl)ethyl)pyridin-3-yl)-N,N-bis(4-methoxybenzyl)-6-methyl-1,3,5-triazin-2-amine (744.3 mg). $^1$H NMR (CDCl$_3$, 400 MHz) δ 11.82 (s, 1H), 8.66 (d, J=2.35 Hz, 1H), 8.17 (d, J=2.54 Hz, 1H), 8.03 (dd, J=12.13 Hz, 2.15 Hz, 1H), 7.95 (d, J=2.15 Hz, 1H), 7.81 (d, J=8.41 Hz, 2H), 7.40 (d, J=8.41 Hz, 2H), 7.24-7.14 (m, 4H), 7.90-7.81 (m, 4H), 4.87 (d, J=5.09 Hz, 2H), 4.77 (d, J=5.48 Hz, 2H), 4.21 (q, J=7.04 Hz, 1H), 4.01 (s, 3H), 3.82 (s, 3H), 3.81 (s, 3H), 2.98 (s, 3H), 2.58 (s, 3H), 1.67 (d, J=7.24 Hz, 3H). m/z (ESI, pos. ion) 750 (M+H)$^+$.

Step 2: 4-(2-(5-fluoro-6-methoxypyridin-3-ylamino)-5-(1-(4-(methylsulfonyl)phenyl)ethyl)pyridin-3-yl)-6-methyl-1,3,5-triazin-2-amine 4-(2-(5-Fluoro-6-methoxypyridin-3-ylamino)-5-(1-(4-(methylsulfonyl)phenyl)ethyl)pyridin-3-yl)-N,N-bis(4-methoxybenzyl)-6-methyl-1,3,5-triazin-2-amine (744 mg, 0.992 mmol) was dissolved in trifluoroacetic acid (Aldrich, redistilled, 99+%, 10 mL) and the flask was fitted with a reflux condenser and placed in a preheated oil bath (75° C.) and stirred overnight. Then, the reaction was cooled to room temperature, concentrated, diluted with DCM (30 mL), and treated with saturated sodium bicarbonate (30 mL) and with 5 N NaOH to raise the pH of the aqueous phase to about 7. The layers were separated, and the aqueous phase was extracted with DCM and with 10:1 DCM/MeOH). The organic extracts were combined, dried over sodium sulfate, filtered, concentrated, and purified on a silica gel filter (150 mL fritted filter with about 2 inches of silica gel; 100:1 DCM/MeOH to 75:1 DCM/MeOH to 50:1 DCM/MeOH). The fractions with product were collected, concentrated, and purified on HPLC (10% to 100% MeCN/water with 0.1% TFA over 28 min using a total flow rate of 100 mL/min) to give 4-(2-(5-fluoro-6-methoxypyridin-3-ylamino)-5-(1-(4-(methylsulfonyl)phenyl)ethyl)pyridin-3-yl)-6-methyl-1,3,5-triazin-2-amine (187.7 mg 36% yield). $^1$H NMR (CDCl$_3$, 400 MHZ) δ 11.60 (s, 1H), 8.73 (d, J=2.35 Hz, 1H), 8.24 (d, J=2.74 Hz, 1H), 8.06 (dd, J=11.93 Hz, 1.76 Hz, 1H), 8.01 (d, J=2.35 Hz, 1H), 7.90 (d, J=8.41 Hz, 2H), 7.45 (d, J=8.22 Hz, 2H), 4.30-4.23 (m, 1H), 4.04 (s, 3H), 2.64 (s, 3H), 1.74 (d, J=7.24 Hz, 3H). m/z (ESI, pos. ion) 510 (M+H)$^+$.

Example 151

4-(2-((6-methoxy-3-pyridinyl)amino)-5-(4-morpholinylcarbonyl)-3-pyridinyl)-6-methyl-1,3,5-triazin-2-amine

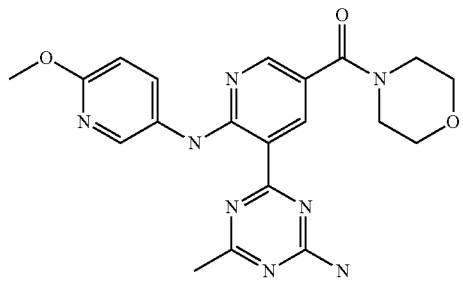 [SMILES: COc1ccc(Nc2ncc(C(=O)N3CCOCC3)cc2-c2nc(C)nc(N)n2)cn1]

Step 1: N,N-bis(4-methoxybenzyl)-4-(2-((6-methoxy-3-pyridinyl)amino)-5-(4-morpholinylcarbonyl)-3-pyridinyl)-6-methyl-1,3,5-triazin-2-amine A solution of 5-(4-(bis(4-methoxybenzyl)amino)-6-methyl-1,3,5-triazin-2-yl)-6-((6-methoxy-3-pyridinyl)amino)-3-pyridinecarbaldehyde (0.127 g, 0.220 mmol) in THF (2.00 mL) was treated with sodium cyanide (10.77 mg, 0.220 mmol), morpholine (0.096 mL, 1.099 mmol) and manganese (IV) oxide (0.287 g, 3.30 mmol) at ambient temperature. After 30 min, more manganese(IV) oxide (0.287 g, 3.30 mmol) was added and the mixture was stirred overnight at ambient temperature. The mixture was filtered through Celite® (diatomaceous earth) and the organic layer was washed with water followed by saturated NaCl (aq.) and then dried over anhydrous Na$_2$SO$_4$, filtered and concentrated to give N,N-bis(4-methoxybenzyl)-4-(2-((6-methoxy-3-pyridinyl)amino)-5-(4-morpholinylcarbonyl)-3-pyridinyl)-6-methyl-1,3,5-triazin-2-amine (0.128 g, 0.193 mmol, 88% yield) as a brown foam. $^1$H NMR (400 MHz, CDCl$_3$) δ 11.95 (s, 1H); 8.90 (d, J=2.54 Hz, 1H); 8.39 (d, J=2.35 Hz, 1H); 8.28 (d, J=2.74 Hz, 1H); 7.89 (dd, J=8.80, 2.74 Hz, 1H); 7.13-7.24 (m, 4H); 6.81-6.90 (m, 4H); 6.73 (d, J=8.80 Hz, 1H); 4.85 (s, 2H); 4.82 (s, 2H); 3.94 (s, 3H); 3.81 (s, 3H); 3.78 (s, 3H); 3.57-3.69 (m, 8H); 2.59 (s, 3H). m/z (ESI, +ve ion) 663.2 (M+H)$^+$.

Step 2: 4-(2-((6-methoxy-3-pyridinyl)amino)-5-(4-morpholinylcarbonyl)-3-pyridinyl)-6-methyl-1,3,5-triazin-2-amine A solution of N,N-b is (4-methoxybenzyl)-4-(2-((6-methoxy-3-pyridinyl)amino)-5-(4-morpholinylcarbonyl)-3-pyridinyl)-6-methyl-1,3,5-triazin-2-amine (0.128 g, 0.193 mmol) in TFA (2.00 mL) at ambient temperature was treated with triflic acid (0.051 mL, 0.579 mmol) and heated for 4 h at 80° C. The reaction mixture was concentrated, but not to dryness. A few ice cubes were added and saturated NaHCO$_3$ (aq.) was added until pH was about 7. The solid was collected by filtration, washed with water and CH$_2$Cl$_2$, and dried under vacuum to give 4-(2-((6-methoxy-3-pyridinyl)amino)-5-(4-morpholinylcarbonyl)-3-pyridinyl)-6-methyl-1,3,5-triazin- 2-amine (0.056 g, 0.133 mmol, 68.6% yield) as a brown solid. $^1$H NMR (400 MHz, d6-DMSO) δ 11.92 (s, 1H); 8.87 (s, 1H); 8.52 (s, 1H); 8.38 (s, 1H); 8.11-8.22 (m, 1H); 7.92 (br. s., 1H); 7.78 (br. s., 1H); 6.85 (d, J=8.80 Hz, 1H); 3.84 (s, 3H); 3.54-3.65 (m, 8H); 2.44 (s, 3H). m/z (ESI, +ve ion) 423.1 (M+H)$^+$.

Example 152

4-(2-((5-fluoro-6-methoxy-3-pyridinyl)amino)-5-((4-(methylsulfonyl)-1-piperazinyl)carbonyl)-3-pyridinyl)-6-methyl-1,3,5-triazin-2-amine

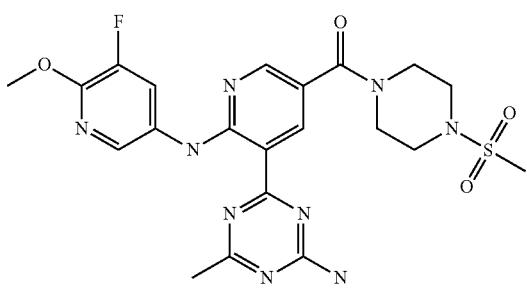

The title compound was prepared in an analogous manner to that described in Example 151 using 5-(4-(bis(4-methoxybenzyl)amino)-6-methyl-1,3,5-triazin-2-yl)-6-((5-fluoro-6-methoxy-3-pyridinyl)amino)-3-pyridinecarbaldehyde and 1-methanesulfonylpiperazine (Oakwood Products, West Columbia, S.C.), and the desired product 4-(2-((5-fluoro-6-methoxy-3-pyridinyl)amino)-5-((4-(methylsulfonyl)-1-piperazinyl)carbonyl)-3-pyridinyl)-6-methyl-1,3,5-triazin-2-amine was isolated as a yellow solid (52% for two steps). $^1$H NMR (400 MHz, d6-DMSO) δ 12.11 (s, 1H) 8.85-8.93 (m, 1H) 8.45 (dd, J=2.15, 0.39 Hz, 1H) 8.42 (d, J=2.35 Hz, 1H) 8.30-8.39 (m, 1H) 7.95 (br. s., 1H) 7.83 (br. s., 1H) 3.95 (s, 3H) 3.61-3.73 (m, 4H) 3.19 (t, 4H) 2.91 (s, 3H) 2.45 (s, 3H). m/z (ESI, +ve ion) 518.0 (M+H)$^+$.

Example 153

5-(4-amino-6-methyl-1,3,5-triazin-2-yl)-N-(2-methoxyethyl)-6-((6-methoxy-3-pyridinyl)amino)-3-pyridinecarboxamide

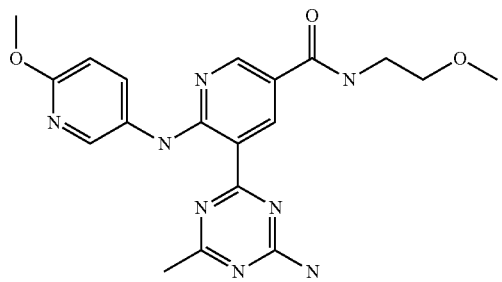 [SMILES: COCCNC(=O)c1cnc(Nc2ccc(OC)nc2)c(-c2nc(C)nc(N)n2)c1]

The title compound was prepared in an analogous manner to that described in Example 151 using 5-(4-(bis(4-methoxybenzyl)amino)-6-methyl-1,3,5-triazin-2-yl)-6-((6-methoxy-3-pyridinyl)amino)-3-pyridinecarbaldehyde and 2-methoxyethylamine (Sigma-Aldrich, St. Louis, Mo.), and the desired product 5-(4-amino-6-methyl-1,3,5-triazin-2-yl)-N-(2-methoxyethyl)-6-((6-methoxy-3-pyridinyl)amino)-3-pyridinecarboxamide was isolated as a yellow solid (8% for two steps). $^1$H NMR (400 MHz, CDCl$_3$) δ 12.08 (s, 1H); 9.19 (d, J=2.54 Hz, 1H); 8.78 (d, J=2.54 Hz, 1H); 8.35 (d, J=2.54 Hz, 1H); 8.12 (dd, J=8.80, 2.74 Hz, 1H); 6.79 (d, J=8.80 Hz, 1H); 6.72-6.76 (m, 1H); 3.95 (s, 3H); 3.66-3.72 (m, 2H); 3.63 (q, J=4.56 Hz, 2H); 3.38 (s, 3H); 2.55 (s, 3H). m/z (ESI, +ve ion) 411.0 (M+H)$^+$.

Example 154

4-((5-(4-amino-6-methyl-1,3,5-triazin-2-yl)-6-((6-methoxy-3-pyridinyl)amino)-3-pyridinyl)methyl)-3-morpholinone

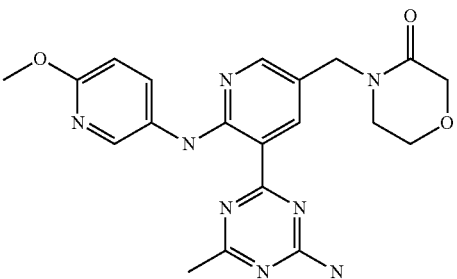 [SMILES: COc1ccc(Nc2ncc(CN3CCOCC3=O)cc2-c2nc(C)nc(N)n2)cn1]

Step 1: N45-(4-(bis(4-methoxybenzyl)amino)-6-methyl-1,3,5-triazin-2-yl)-6-((6-methoxy-3-pyridinyl)amino)-3-pyridinyl)methyl)-2-chloro-N-(2-hydroxyethyl)acetamide A mixture of 2-(((5-(4-(bis(4-methoxybenzyl)amino)-6-methyl-1,3,5-triazin-2-yl)-6-((6-methoxy-3-pyridinyl)amino)-3-pyridinyl)methyl)amino)ethanol (Example 225, Step 1; 0.118 g, 0.189 mmol), chloroacetyl chloride (0.023 mL, 0.284 mmol) and triethylamine (0.040 mL, 0.284 mmol) in THF (1 mL) was stirred at ambient temperature for 2 h. 2 M K$_2$CO$_3$ (0.2 mL, aq.) and MeOH (1 mL) were added. After 1 h, water was added to the mixture and it was extracted with EtOAc (3x). The combined organic layers were dried over anhydrous Na$_2$SO$_4$, filtered and concentrated to give N-((5-(4-(bis(4-methoxybenzyl)amino)-6-methyl-1,3,5-triazin-2-yl)-6-((6-methoxy-3-pyridinyl)amino)-3-pyridinyl)methyl)-2-chloro-N-(2-hydroxyethyl)acetamide (0.110 g, 0.157 mmol, 83% yield). m/z (ESI, +ve ion) 699.2 (M+H)$^+$.

Step 2: 4-((5-(4-(bis(4-methoxybenzyl)amino)-6-methyl-1,3,5-triazin-2-yl)-6-((6-methoxy-3-pyridinyl)amino)-3-pyridinyl)methyl)-3-morpholinone Sodium hydride (60% in mineral oil) (0.014 g, 0.346 mmol) was added to a mixture of N-((5-(4-(bis(4-methoxybenzyl)amino)-6-methyl-1,3,5-triazin-2-yl)-6-((6-methoxy-3-pyridinyl)amino)-3-pyridinyl)methyl)-2-chloro-N-(2-hydroxyethyl)acetamide (0.110 g, 0.157 mmol) in 3 mL of THF at 0° C. The reaction mixture was allowed to warm up to ambient temperature. After 1 h, water was added and the mixture was extracted with EtOAc (3x). The combined organic layers were dried over anhydrous Na$_2$SO$_4$, filtered and concentrated to give 4-((5-(4-(bis(4-methoxybenzyl)amino)-6-methyl-1,3,5-triazin-2-yl)-6-((6-methoxy-3-pyridinyl)amino)-3-pyridinyl)methyl)-3-morpholinone (0.101 g, 0.152 mmol, 97% yield) as a yellow foam. $^1$H NMR (400 MHz, CDCl$_3$) δ 11.66 (s, 1H); 8.71 (d, J=2.54 Hz, 1H); 8.23-8.27 (m, 1H); 8.20 (d, J=2.54 Hz, 1H); 7.89 (dd, J=8.80, 2.74 Hz, 1H); 7.15-7.24 (m, 4H); 6.80-6.90 (m, 4H); 6.70 (d, J=8.80 Hz, 1H); 4.86 (s, 2H); 4.81 (s, 2H); 4.55 (s, 2H); 4.10 (s, 2H); 3.92 (s, 3H); 3.81 (s, 3H); 3.78 (s, 3H); 3.74-3.77 (m, 2H); 3.23-3.28 (m, 2H); 2.57 (s, 3H). m/z (ESI, +ve ion) 663.2 (M+H)$^+$.

Step 3: 4-((5-(4-amino-6-methyl-1,3,5-triazin-2-yl)-6-((6-methoxy-3-pyridinyl)amino)-3-pyridinyl)methyl)-3-morpholinone A few drops of triflic acid were added to a solution of 4-((5-(4-(bis(4-methoxybenzyl)amino)-6-methyl-1,3,5-triazin-2-yl)-6-((6-methoxy-3-pyridinyl)amino)-3-pyridinyl)methyl)-3-morpholinone (0.115 g, 0.174 mmol) in 2 mL of TFA at RT. The mixture was heated to 80° C. for 1 h. The reaction was cooled and concentrated, but not to dryness. A few ice cubes were added and saturated NaHCO$_3$ (aq.) was added until pH=7. The yellow solid was filtered washed with water, CH$_2$Cl$_2$, MeOH and Et$_2$O and collected and dried under vacuum. The aqueous layer was extracted with 3/1 CHCl$_3$/n-BuOH (3×). The combined organic layers were dried over anhydrous Na$_2$SO$_4$, filtered and concentrated. The crude material was adsorbed onto a plug of silica gel and purified by chromatography through a Redi-Sep pre-packed silica gel column (4 g), eluting with a gradient of 0% to 10% MeOH in CH$_2$Cl$_2$. This material was combined with the yellow solid collected above to provide 4-((5-(4-amino-6-methyl-1,3,5-triazin-2-yl)-6-((6-methoxy-3-pyridinyl)amino)-3-pyridinyl)methyl)-3-morpholinone (0.040 g, 0.095 mmol, 54.6% yield) as a yellow solid. $^1$H NMR (400 MHz, d6-DMSO) δ 11.76 (s, 1H); 8.70 (dd, J=2.15, 0.39 Hz, 1H); 8.53 (dd, J=2.54, 0.39 Hz, 1H); 8.24 (dd, J=2.05, 0.49 Hz, 1H); 8.13-8.19 (m, 1H); 7.88 (br. s., 1H); 7.72 (br. s., 1H); 6.82 (d, J=8.80 Hz, 1H); 4.52 (s, 2H); 4.10 (s, 2H); 3.84 (s, 3H); 3.79-3.83 (m, 2H); 3.27-3.32 (m, 2H); 2.43 (s, 3H). m/z (ESI, +ve ion) 423.2 (M+H)$^+$.

Example 155

4-(2-(6-methoxypyridin-3-ylamino)-5-((1-(methylsulfonyl)piperidin-4-yl)methyl)pyridin-3-yl)-6-methyl-1,3,5-triazin-2-amine

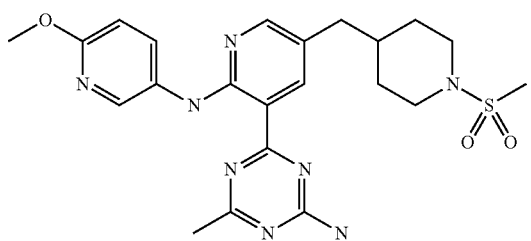

Step 1: 4-(5-chloro-2-fluoropyridin-3-yl)-N,N-bis(4-methoxybenzyl)-6-methyl-1,3,5-triazin-2-amine A mixture of 5-chloro-2-fluoropyridin-3-ylboronic acid (Combi Block, Inc., 2.507 g, 14.30 mmol), 4-chloro-N,N-bis(4-methoxybenzyl)-6-methyl-1,3,5-triazin-2-amine (5.24 g, 13.62 mmol), Amphos (bis-4-(di-tert-butylphosphanyl)-N,N-dimethylaniline-dichloropalladium, 0.482 g, 0.681 mmol) and potassium acetate (4.10 g, 41.8 mmol) in ethanol (100 mL) and water (10 mL) was purged with argon and heated at 100° C. overnight. The reaction mixture was cooled, concentrated to remove the EtOH and partitioned between water (50 mL) and EtOAc (50 mL). The aqueous phase was extracted with EtOAc (2×20 mL). The combined organic phases were washed with saturated aqueous sodium chloride (100 mL). The organic phase was dried over sodium sulfate, filtered and concentrated. The crude product was purified by ISCO chromatography (hexanes/EtOAc, 15 to 50%) to give 4-(5-chloro-2-fluoropyridin-3-yl)-N,N-bis(4-methoxybenzyl)-6-methyl-1,3,5-triazin-2-amine (3.62 g, 7.54 mmol, 55.4% yield) as a colorless sticky solid. m/z (ESI, +ve ion) 481.0 (M+H)$^+$.

Step 2: 4-((5-chloro-2-(6-methoxypyridin-3-ylamino)pyridin-3-yl)-N,N-bis(4-methoxybenzyl)-6-methyl-1,3,5-triazin-2-amine A solution of 6-methoxypyridin-3-amine (Sigma-Aldrich Inc., 1.405 g, 11.31 mmol) and 4-(5-chloro-2-fluoropyridin-3-yl)-N,N-bis(4-methoxybenzyl)-6-methyl-1,3,5-triazin-2-amine (3.62 g, 7.54 mmol) in THF (15.00 mL) was cooled to 0° C. in an ice bath and treated with 1.0 M LiHMDS in THF (22.63 mL, 22.63 mmol). The reaction mixture was quenched with a saturated solution of NH$_4$Cl at 0° C. and extracted with EtOAc (50 mL), dried over MgSO$_4$, filtered and concentrated. The crude residue was re diluted with DCM and concentrated with SiO2 and chromatographed through a Redi-Sep pre-packed silica gel column on the ISCO (40 g column, 20→100% EtOAc in hexanes) to give 4-(5-chloro-2-(6-methoxypyridin-3-ylamino)pyridin-3-yl)-N,N-bis(4-methoxybenzyl)-6-methyl-1,3,5-triazin-2-amine (3.77 g, 6.45 mmol, 86% yield) as a bright yellow crystalline solid. m/z (ESI, +ve ion) 584.1 (M+H)$^+$.

Step 3: tert-butyl 4-((5-(4-(bis(4-methoxybenzyl)amino)-6-methyl-1,3,5-triazin-2-yl)-6-(6-methoxypyridin-3-ylamino)pyridin-3-yl)methyl)piperidine-1-carboxylate tert-Butyl 4-methylenepiperidine-1-carboxylate (0.117 g, 0.592 mmol) was treated with 9-BBN (0.5 M in THF, 1.183 mL, 0.592 mmol) and the mixture was heated at reflux for 4 h. After cooling, the resulting solution was transferred into a stirred mixture of 4-(5-chloro-2-(6-methoxypyridin-3-ylamino)pyridin-3-yl)-N,N-bis(4-methoxybenzyl)-6-methyl-1,3,5-triazin-2-amine (0.288 g, 0.493 mmol), Pd$_2$(dba)$_3$ (0.023 g, 0.025 mmol), dicyclohexyl(2',4',6'-triisopropylbiphenyl-2-yl)phosphine (0.024 g, 0.049 mmol), and Na$_2$CO$_3$ (0.131 g, 1.233 mmol) in 1,4-dioxane (1.0 mL) and water (0.25 mL). The mixture was sealed and heated under microwave at 140° C. for 30 min. After cooling, the resulting mixture was passed through a short path of Celite® (diatomaceous earth), washing with EtOAc (3×10 mL). The combined organic phases were concentrated and purified by flash chromatography (short column, SiO$_2$, pure hexanes→30% EtOAc in hexanes) to give tert-butyl 4-((5-(4-(bis(4-methoxybenzyl)amino)-6-methyl-1,3,5-triazin-2-yl)-6-(6-methoxypyridin-3-ylamino)pyridin-3-yl)methyl)piperidine-1-carboxylate (0.261 g, 0.349 mmol, 70.9% yield) as a sticky yellow syrup. m/z (ESI, +ve ion) 747.2 (M+H)$^+$.

Step 4: N,N-bis(4-methoxybenzyl)-4-(2-(6-methoxy-pyridin-3-ylamino)-5-((1-(methylsulfonyl)piperidin-4-yl)methyl)pyridin-3-yl)-6-methyl-1,3,5-triazin-2-amine TFA (4.00 mL, 51.9 mmol) was slowly added to a slightly cooled stirred solution of tert-butyl 4-((5-(4-(bis(4-methoxybenzyl)amino)-6-methyl-1,3,5-triazin-2-yl)-6-(6-methoxypyridin-3-ylamino)pyridin-3-yl)methyl)piperidine-1-carboxylate (0.2611 g, 0.350 mmol) in DCM (5.00 mL, 78 mmol) and the mixture was stirred at room temperature for 1 h. The mixture was concentrated (under vacuum to remove as much TFA as possible). The sticky residue was taken up in DCM (10.00 mL) and TEA (0.487 mL, 3.50 mmol) followed by methanesulfonyl chloride (0.082 mL, 1.049 mmol) were slowly added at 0° C. The mixture was stirred for 1 h and then concentrated. The crude product was partitioned between 1 N NaOH$_{(aq)}$ and DCM (20 mL each). The separated aqueous layer was extracted with DCM (2×20 mL) and the combined organic layers were washed with brine, dried over Na$_2$SO$_4$, and concentrated to give the crude residue which was purified with flash column chromatography (ISCO Combiflash system, 10% to 50% ethyl acetate in hexanes) to give the desired product N,N-bis(4-methoxybenzyl)-4-(2-(6-methoxypyridin-3-ylamino)-5-((1-(methylsulfonyl)piperidin-4-yl)methyl)pyridin-3-yl)-6-methyl-1,3,5-triazin-2-amine (0.1923 g, 0.265 mmol, 76% yield) as a yellow film. m/z (ESI, +ve ion) 725.2 (M+H)$^+$.

Step 5: 4-(2-(6-methoxypyridin-3-ylamino)-5-((1-(methylsulfonyl)piperidin-4-yl)methyl)pyridin-3-yl)-6-methyl-1,3,5-triazin-2-amine A suspension of N,N-bis(4-methoxybenzyl)-4-(2-(6-methoxypyridin-3-ylamino)-5-((1-(methylsulfonyl)piperidin-4-yl)methyl)pyridin-3-yl)-6-methyl-1,3,5-triazin-2-amine (0.1923 g, 0.265 mmol) in TFA (1.022 mL, 13.26 mmol) was treated with a couple of drops of methanesulfonic acid (0.017 mL, 0.265 mmol) and the yellow solution was heated at 80° C. overnight. The volatile material was removed and the residue was carefully diluted with 5% 2 M NH$_3$ in MeOH/DCM. The solution was concentrated with SiO$_2$ and chromatographed through a Redi-Sep pre-packed silica gel column (pure DCM→10% MeOH in DCM w/NH$_3$). Following concentration of the eluent, the resulting yellow solid was washed with IPA to give 4-(2-(6-methoxypyridin-3-ylamino)-5-((1-(methylsulfonyl)piperidin-4-yl)methyl)pyridin-3-yl)-6-methyl-1,3,5-triazin-2-amine (88 mg, 0.182 mmol, 68.5% yield) as a yellow solid. $^1$H NMR (400 MHz, d6-DMSO) δ 11.66 (s, 1H); 8.60 (d, J=2.54 Hz, 1H); 8.54 (d, J=2.54 Hz, 1H); 8.17 (dd, J=8.90, 2.64 Hz, 1H); 8.14 (d, J=2.15 Hz, 1H); 7.84 (br. s., 1H); 7.71 (br. s., 1H); 6.81 (d, J=8.80 Hz, 1H); 3.84 (s, 3H); 3.45-3.62 (m, 2H); 2.82 (s, 3H); 2.61-2.72 (m, 2H); 2.43 (s, 3H); 1.67-1.68 (m, 2H); 1.46-1.64 (m, 1H); 1.15-1.32 (m, 2H). m/z (ESI, +ve ion) 485.2 (M+H)$^+$.

Example 156

4-(5-benzyl-2-(6-methoxypyridin-3-ylamino)pyridin-3-yl)-6-methyl-1,3,5-triazin-2-amine

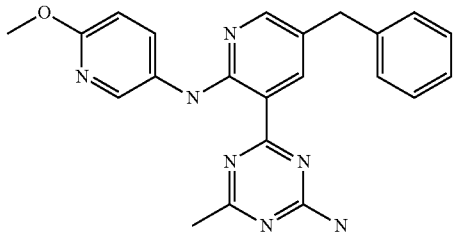 [SMILES: COc1ccc(Nc2ncc(Cc3ccccc3)cc2-c2nc(C)nc(N)n2)cn1]

Step 1: 4-(5-benzyl-2-(6-methoxypyridin-3-ylamino)pyridin-3-yl)-N,N-bis(4-methoxybenzyl)-6-methyl-1,3,5-triazin-2-amine A mixture of 2-benzyl-4,4,5,5-tetramethyl-1,3,2-dioxaborolane (Frontier Scientific Inc., 90 mg, 0.411 mmol), 4-(5-chloro-2-(6-methoxypyridin-3-ylamino)pyridin-3-yl)-N,N-bis(4-methoxybenzyl)-6-methyl-1,3,5-triazin-2-amine (160 mg, 0.274 mmol), Pd$_2$dba$_3$ (12.54 mg, 0.014 mmol), 2-(dicyclohexylphosphino)-2',4',6',-tri-i-propyl-1,1'-biphenyl (X-Phos, 13.06 mg, 0.027 mmol) (Strem Co.) was purged with argon and then treated with dioxane (2.50 mL), water (0.25 mL) and sodium carbonate (72.6 mg, 0.685 mmol) and heated under a microwave irradiation at 140° C. for 30 min. The mixture was filtered through a short plug of Celite® (diatomaceous earth), washed with EtOAc (×3), and concentrated. The crude product was adsorbed onto a plug of silica gel and chromatographed through a Redi-Sep pre-packed silica gel column (pure hexanes to 30% EtOAc in hexanes) to give 4-(5-benzyl-2-(6-methoxypyridin-3-ylamino)pyridin-3-yl)-N,N-bis(4-methoxybenzyl)-6-methyl-1,3,5-triazin-2-amine (110 mg, 62.8%) as a yellow syrup. m/z (ESI, +ve ion) 640.0 (M+H)$^+$.

Step 2: 4-(5-benzyl-2-(6-methoxypyridin-3-ylamino)pyridin-3-yl)-6-methyl-1,3,5-triazin-2-amine A mixture of 4-(5-benzyl-2-(6-methoxypyridin-3-ylamino)pyridin-3-yl)-N,N-bis(4-methoxybenzyl)-6-methyl-1,3,5-triazin-2-amine (110 mg, 0.172 mmol) in TFA (265 μL, 3.44 mmol) was treated with a couple of drops of trifluoromethanesulfonic acid (15.27 μL, 0.172 mmol) and the mixture was heated at 80° C. overnight. After cooling, the mixture was concentrated and the residue was dissolved in 5% MeOH/DCM and adsorbed onto a plug of silica gel and chromatographed through a Redi-Sep pre-packed silica gel column (pure DCM to 3% MeOH in DCM w/NH$_3$) to give 4-(5-benzyl-2-(6-methoxypyridin-3-ylamino)pyridin-3-yl)-6-methyl-1,3,5-triazin-2-amine (15 mg, 0.038 mmol, 21.84% yield) as a yellow solid. $^1$H NMR (400 MHz, d6-DMSO) δ 11.68 (s, 1H); 8.61 (d, J=2.15 Hz, 1H); 8.53 (d, J=2.54 Hz, 1H); 8.23 (d, J=2.15 Hz, 1H); 8.16 (dd, J=8.80, 2.74 Hz, 1H);

7.83 (br. s., 1H); 7.69 (br. s., 1H); 7.11-7.45 (m, 5H); 6.81 (d, J=8.80 Hz, 1H); 3.94 (s, 2H); 3.84 (s, 3H). m/z (ESI, +ve ion) 400.0 (M+H)+.

Example 157

4-(2-(6-methoxypyridin-3-ylamino)-5-((4-methylpiperazin-1-yl)methyl)pyridin-3-yl)-6-methyl-1,3,5-triazin-2-amine

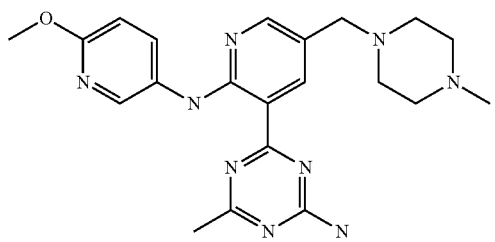

Step 1: N,N-bis(4-methoxybenzyl)-4-(2-(6-methoxypyridin-3-ylamino)-5-((4-methylpiperazin-1-yl)methyl)pyridin-3-yl)-6-methyl-1,3,5-triazin-2-amine A mixture of 4-(5-chloro-2-(6-methoxypyridin-3-ylamino)pyridin-3-yl)-N,N-bis(4-methoxybenzyl)-6-methyl-1,3,5-triazin-2-amine (160 mg, 0.274 mmol), 2-(dicyclohexylphosphino)-2',4',6',-tri-i-propyl-1,1'-biphenyl (X-Phos, 13.06 mg, 0.027 mmol), cesium carbonate (268 mg, 0.822 mmol), potassium 1-methyl-4-trifluoroboratomethylpiperazine (Frontier Scientific Co., 66.3 mg, 0.301 mmol) and palladium acetate (3.08 mg, 0.014 mmol) was purged with argon. The mixture was then treated with THF (1.0 mL) and water (0.1 mL) and heated under microwave irradiation at 140° C. for 30 min. The mixture was filtered through a short path of Celite® (diatomaceous earth), washed with EtOAc (×3), and concentrated. The crude product was adsorbed onto a plug of silica gel and chromatographed through a Redi-Sep pre-packed silica gel column (pure DCM to 5% MeOH in DCM) to give N,N-bis(4-methoxybenzyl)-4-(2-(6-methoxypyridin-3-ylamino)-5-((4-methylpiperazin-1-yl)methyl)pyridin-3-yl)-6-methyl-1,3,5-triazin-2-amine (161 mg, 0.243 mmol, 89% yield) as a yellow syrup. m/z (ESI, +ve ion) 662.0 (M+H)+.

Step 2: 4-(2-(6-methoxypyridin-3-ylamino)-5-((4-methylpiperazin-1-yl)methyl)pyridin-3-yl)-6-methyl-1,3,5-triazin-2-amine The title compound was prepared in an analogous manner to that described in Example 156, Step 2, from N,N-bis(4-methoxybenzyl)-4-(2-(6-methoxypyridin-3-ylamino)-5-((4-methylpiperazin-1-yl)methyl)pyridin-3-yl)-6-methyl-1,3,5-triazin-2-amine and isolated (96%) as a yellow solid. $^1$H NMR (400 MHz, d6-DMSO) δ 11.74 (s, 1H); 8.69 (d, J=2.15 Hz, 1H); 8.54 (d, J=2.74 Hz, 1H); 8.00-8.33 (m, 2H); 7.86 (br. s., 1H); 7.71 (br. s., 1H); 6.82 (d, J=8.80 Hz, 1H); 3.84 (s, 3H); 3.49-3.81 (m, 4H); 3.40 (s, 2H); 2.44 (s, 3H); 2.35 (m, 4H); 2.14 (s, 3H). m/z (ESI, +ve ion) 422.1 (M+H)+.

Example 158

(R)-4-(2-(6-methoxypyridin-3-ylamino)-5-((2-methyl-4-(methylsulfonyl)piperazin-1-yl)methyl)pyridin-3-yl)-6-methyl-1,3,5-triazin-2-amine

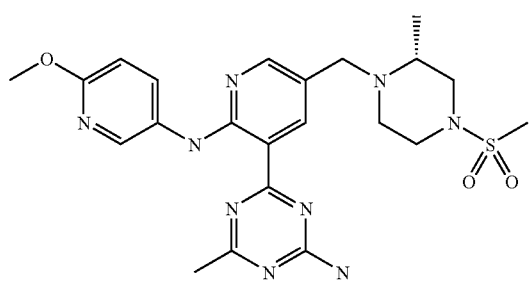

Step 1: potassium(R)-((4-(tert-butoxycarbonyl)-2-methylpiperazin-1-yl)methyl)trifluoroborate A mixture of potassium (bromomethyl)trifluoroborate (1.20 g, 5.38 mmol) and (R)-4-N-Boc-2-methyl-piperazine (1.166 g, 5.65 mmol) in THF (7.00 mL) was heated at 80° C. under nitrogen for 24 h. After cooling, the mixture was concentrated, re-dissolved in acetone (125 mL) and treated with K$_2$CO$_3$ (1 eq). The suspension was stirred for 30 min and filtered through a short plug of Celite® (diatomaceous earth), washing with additional acetone and the combined organic phases were concentrated to give potassium (R)-((4-(tert-butoxycarbonyl)-2-methylpiperazin-1-yl)methyl)trifluoroborate as a pale yellow foam (1.627 g, 94%). $^{19}$F-NMR (377 MHz, d6-acetone) δ −141.36.

Step 2: (R)-tert-butyl 4-((5-(4-(bis(4-methoxybenzyl)amino)-6-methyl-1,3,5-triazin-2-yl)-6-(6-methoxypyridin-3-ylamino)pyridin-3-yl)methyl)-3-methylpiperazine-1-carboxylate The title compound was prepared in an analogous manner to that described above in Example 157, Step 1, using potassium (R)-((4-(tert-butoxycarbonyl)-2-methylpiperazin-1-yl)methyl)trifluoroborate and 4-(5-chloro-2-(6-methoxypyridin-3-ylamino)pyridin-3-yl)-N,N-bis(4-methoxybenzyl)-6-methyl-1,3,5-triazin-2-amine to give (R)-tert-butyl 4-((5-(4-(bis(4-methoxybenzyl)amino)-6-methyl-1,3,5-triazin-2-yl)-6-(6-methoxypyridin-3-ylamino)pyridin-3-yl)methyl)-3-methylpiperazine-1-carboxylate (188 mg, 0.247 mmol, 74.3% yield) as a yellow syrup. m/z (ESI, +ve ion) 761.7 (M+H)+.

Step 3: (R)-4-(2-(6-methoxypyridin-3-ylamino)-5-((2-methyl-4-(methylsulfonyl)piperazin-1-yl)methyl)pyridin-3-yl)-6-methyl-1,3,5-triazin-2-amine The material isolated above from Step 1 was subjected to a sequence of transformations involving (1) deprotection of the BOC group; (2) N-piperazine sulfonamide formation; and (3) deprotection of the bis-PMB groups on the aminotriazine in an analogous manner to that described in Example 155 (Step 4 to Step 5) to give (R)-4-(2-(6-methoxypyridin-3-ylamino)-

5-((2-methyl-4-(methylsulfonyl)piperazin-1-yl)methyl)pyridin-3-yl)-6-methyl-1,3,5-triazin-2-amine (38 mg, 0.076 mmol, 85% yield) as a yellow solid. m/z (ESI, +ve ion) 499.9 (M+H)+.

Example 159 and Example 160

4-((5-(4-amino-6-methyl-1,3,5-triazin-2-yl)-6-(5-fluoro-6-methoxypyridin-3-ylamino)pyridin-3-yl)methyl)-N,N-dimethylpiperazine-1-carboxamide (Example 159) and 4-((5-(4-amino-6-methyl-1,3,5-triazin-2-yl)-6-(5-fluoro-6-hydroxypyridin-3-ylamino)pyridin-3-yl)methyl)-N,N-dimethylpiperazine-1-carboxamide (Example 160)

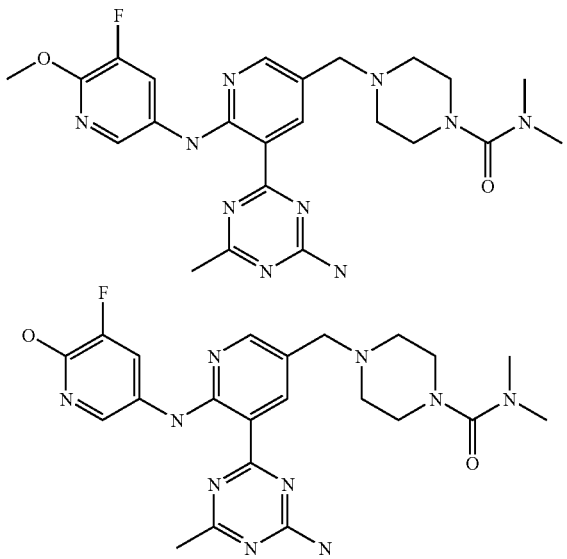

Step 1: tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)piperazine-1-carboxylate The title compound was prepared in an analogous manner to that described in Example 155, Step 2, using 5-fluoro-6-methoxypyridin-3-amine and tert-butyl 4-((5-(4-(bis(4-methoxybenzyl)amino)-6-methyl-1,3,5-triazin-2-yl)-6-fluoropyridin-3-yl)methyl)piperazine-1-carboxylate. tert-Butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)piperazine-1-carboxylate was isolated (90%) as a yellow solid. m/z (ESI, +ve ion) 765.8 (M+H)+.

Step 2: 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)-N,N-dimethylpiperazine-1-carboxamide A slightly cooled stirred solution of tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)piperazine-1-carboxylate (8.77 g, 11.45 mmol) in DCM (25.00 mL, 389 mmol) was treated with TFA (15.00 mL, 195 mmol) and the mixture was stirred at room temperature for 1 h. The mixture was concentrated and the residual sticky material was taken up in DCM (100 mL) and carefully quenched with saturated NaHCO$_3$($_{aq}$) until slightly basic. The aqueous layer was extracted with DCM (2×100 mL) and the combined organic layers were washed with brine, dried over Na$_2$SO$_4$, and concentrated to give 4-(2-(5-fluoro-6-methoxypyridin-3-ylamino)-5-(piperazin-1-ylmethyl)pyridin-3-yl)-N,N-bis(4-methoxybenzyl)-6-methyl-1,3,5-triazin-2-amine as a yellow solid. A portion of this solid (0.349 g, 0.524 mmol) was dissolved in DCM (5.00 mL, 78 mmol) and Et$_3$N (0.365 mL, 2.62 mmol) at −15° C. The mixture was treated slowly with dimethylcarbamic chloride (0.169 g, 1.573 mmol) and stirred for 1 h before warming up to room temperature overnight. The reaction mixture was concentrated, the crude product was adsorbed onto a plug of silica gel and chromatographed through a Redi-Sep pre-packed silica gel column (10 to 100% EtOAc in hexanes) to give 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)-N,N-dimethylpiperazine-1-carboxamide (0.3555 g, 92%) as a yellow solid (ESI, +ve ion) 736.7 (M+H)+.

Step 3: 4-((5-(4-amino-6-methyl-1,3,5-triazin-2-yl)-6-(5-fluoro-6-methoxypyridin-3-ylamino)pyridin-3-yl)methyl)-N,N-dimethylpiperazine-1-carboxamide and 4-((5-(4-amino-6-methyl-1,3,5-triazin-2-yl)-6-(5-fluoro-6-hydroxypyridin-3-ylamino)pyridin-3-yl)methyl)-N,N-dimethylpiperazine-1-carboxamide A stirred mixture of 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)-N,N-dimethylpiperazine-1-carboxamide (0.3555 g, 0.482 mmol) in TFA (1.859 mL, 24.12 mmol) was treated with methanesulfonic acid (0.031 mL, 0.482 mmol) and the solution was heated at 85° C. overnight. After cooling, the residue was carefully concentrated and diluted with 5% MeOH/DCM w/NH$_3$. The solution was concentrated with SiO$_2$ and chromatographed through a Redi-Sep pre-packed silica gel column (pure DCM to 10% MeOH in DCM) to give 4-((5-(4-amino-6-methyl-1,3,5-triazin-2-yl)-6-(5-fluoro-6-methoxypyridin-3-ylamino)pyridin-3-yl)methyl)-N,N-dimethylpiperazine-1-carboxamide (88 mg, 0.177 mmol, 36.7% yield). $^1$H NMR (400 MHz, d6-DMSO) δ 12.04 (s, 1H); 8.92 (br. s., 1H); 8.45 (s, 1H); 8.40 (br. s., 1H); 8.33 (d, J=11.35 Hz, 1H); 7.96 (br. s., 1H); 7.87 (br. s., 1H); 4.40 (br. s., 2H); 3.95 (s, 3H); 3.64 (d, J=14.87 Hz, 2H); 3.25-3.35 (m, 2H); 2.88-3.15 (m, 4H); 2.78 (s, 6H); 2.44 (s, 3H). m/z (ESI, +ve ion) 497.1 (M+H)+.

The column was further eluted with 20% MeOH in DCM, with NH$_3$ to give the side-product 4-((5-(4-amino-6-methyl-1,3,5-triazin-2-yl)-6-(5-fluoro-6-hydroxypyridin-3-ylamino)pyridin-3-yl)methyl)-N,N-dimethylpiperazine-1-carboxamide (51 mg, 0.106 mmol, 21.91% yield) as a yellow solid. $^1$H NMR (400 MHz, d6-DMSO) δ 11.94 (br. s., 1H); 11.39 (s, 1H); 8.69 (s, 1H); 8.20 (s, 1H); 7.92 (br. s., 1H); 7.85-7.91 (m, 1H); 7.80 (d, J=12.32 Hz, 1H); 7.72 (br. s., 1H);

3.44 (s, 2H); 3.09 (br. s., 4H); 2.72 (s, 6H); 2.42 (s, 3H); 2.30-2.40 (m, 4H). m/z (ESI, +ve ion) 483.1 (M+H)⁺.

Example 161

5-(3-(4-amino-6-methyl-1,3,5-triazin-2-yl)-5-((4-(methylsulfonyl)piperazin-1-yl)methyl)pyridin-2-ylamino)-3-fluoropyridin-2-ol

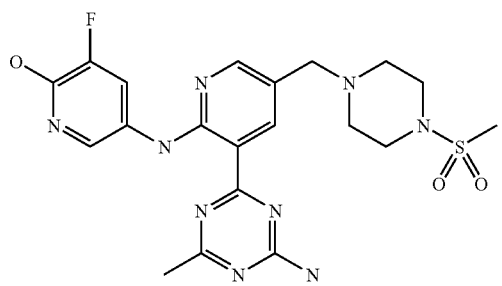 [SMILES: Cc1nc(N)nc(-c2cc(CN3CCN(S(C)(=O)=O)CC3)cnc2Nc2cnc(O)c(F)c2)n1]

The title compound was isolated as a side product (yellow solid) during the final step of Example 40. ¹H NMR (400 MHz, d6-DMSO) δ 11.99 (br. s., 1H); 11.39 (br. s., 1H); 8.70 (br. s., 1H); 8.20 (br. s., 1H); 7.91 (br. s., 2H); 7.80 (d, J=11.35 Hz, 1H); 7.73 (br. s., 1H); 3.48 (br. s., 2H); 3.10 (br. s., 4H); 2.86 (s, 3H); 2.44-2.49 (m, 4H); 2.42 (s, 3H). m/z (ESI, +ve ion) 489.8 (M+H)⁺.

Example 162

4-(2-(5-methoxypyridin-3-ylamino)-5-((4-(methylsulfonyl)piperazin-1-yl)methyl)pyridin-3-yl)-6-methyl-1,3,5-triazin-2-amine

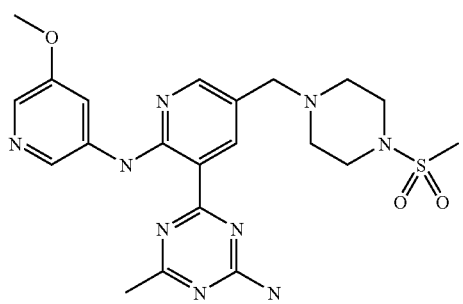 [SMILES: COc1cncc(Nc2ncc(CN3CCN(S(C)(=O)=O)CC3)cc2-c2nc(C)nc(N)n2)c1]

A stirred solution of 2-(2-fluoro-5-((4-(methylsulfonyl)piperazin-1-yl)methyl)pyridin-3-yl)-4-methyl-6-(methylthio)-1,3,5-triazine (200 mg, 0.485 mmol) and 5-methoxypyridin-3-amine (Astatech, Inc., 90 mg, 0.727 mmol) in DMF (5.00 mL, 1.000 mmol) was treated with 1.0 M LiHMDS in THF (1.939 mL, 1.939 mmol) at 0° C. and the mixture was stirred for 1 h. The reaction mixture was diluted with water (10 mL each) and ethyl acetate (15 mL). The separated aqueous layer was extracted with ethyl acetate (2×10 mL) and the combined organic layers were washed with brine, dried over Na₂SO₄, and concentrated to give the crude residue which was heated with 2.0 M ammonia in IPA (3.00 mL, 6.00 mmol) in a sealed tube at 90° C. overnight. After cooling, the mixture was adsorbed onto a plug of silica gel and chromatographed through a Redi-Sep pre-packed silica gel column (pure DCM to 5% MeOH in DCM) to give 4-(2-(5-methoxypyridin-3-ylamino)-5-((4-(methylsulfonyl)piperazin-1-yl)methyl)pyridin-3-yl)-6-methyl-1,3,5-triazin-2-amine (44 mg, 0.091 mmol, 18.69% yield) as a yellow solid. ¹H NMR (400 MHz, d6-DMSO) δ 12.13 (s, 1H); 8.74 (s, 1H); 8.55 (s, 1H); 8.31 (s, 1H); 8.19 (br. s., 1H); 7.93 (br. s., 2H); 7.78 (br. s., 1H); 3.86 (s, 3H); 3.52 (s, 2H); 3.11 (br. s., 4H); 2.87 (s, 3H); 2.46-2.50 (m, 4H); 2.46 (s, 3H). m/z (ESI, +ve ion) 486.1 (M+H)⁺.

Example 163

4-(2-(6-methoxypyridin-3-ylamino)-5-((4-(methylsulfonyl)piperazin-1-yl)methyl)pyridin-3-yl)-N,6-dimethyl-1,3,5-triazin-2-amine

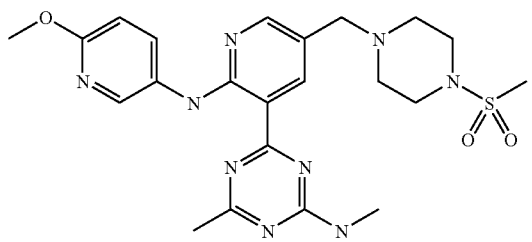

Methylamine was bubbled through a mixture of N-(6-methoxypyridin-3-yl)-3-(4-methyl-6-(methylthio)-1,3,5-triazin-2-yl)-5-((4-(methylsulfonyl)piperazin-1-yl)methyl)pyridin-2-amine (33 mg, 0.064 mmol) in IPA (1.50 mL, 19.47 mmol) for 15 min and then allowed to stand overnight. The resulting precipitate was collected by filtration and washed with a minimal amount of IPA to give 4-(2-(6-methoxypyridin-3-ylamino)-5-((4-(methylsulfonyl)piperazin-1-yl)methyl)pyridin-3-yl)-N,6-dimethyl-1,3,5-triazin-2-amine (17.1 mg, 1.761 mmol, 54.7% yield) as a yellow solid. ¹H NMR (400 MHz, d6-DMSO) mixture of rotamers δ 11.26-12.03 (m, 1H); 8.73 (d, J=13.69 Hz, 1H); 8.38-8.63 (m, 1H); 7.96-8.38 (m, 3H); 6.83 (d, J=8.41 Hz, 1H); 3.84 (br. s., 3H); 3.50 (d, J=12.72 Hz, 2H); 3.11 (br. s., 4H); 2.90-3.03 (m, 3H); 2.86 (br. s., 3H); 2.47-2.50 (m, 4H); 2.44 (br. s., 3H). m/z (ESI, +ve ion) 500.1 (M+H)⁺.

Example 164

4-(2-(3-(difluoromethoxy)phenylamino)pyridin-3-yl)-6-methyl-1,3,5-triazin-2-amine

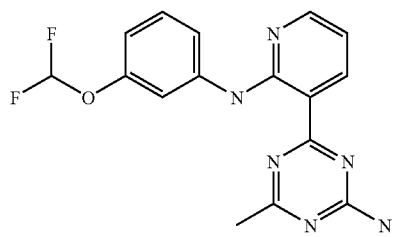 [SMILES: Cc1nc(N)nc(-c2cccnc2Nc2cccc(OC(F)F)c2)n1]

Step 1: 4-(2-(3-(difluoromethoxy)phenylamino)pyridin-3-yl)-N,N-bis(4-methoxybenzyl)-6-methyl-1,3,5-triazin-2-amine A solution of 3-(difluoromethoxy)aniline (0.038 mL, 0.303 mmol) (Aldrich) and 4-(2-fluoropyridin-3-yl)-N,N-bis (4-methoxybenzyl)-6-methyl-1,3,5-triazin-2-amine (0.09 g, 0.202 mmol) in THF (3.0 mL) at 0° C. was treated with LiHMDS 1.0 M in THF (0.606 mL, 0.606 mmol) (Aldrich) dropwise. The solution was stirred at 0° C. for 1.5 h and was then quenched with a saturated solution of NH$_4$Cl at 0° C. The mixture was extracted with EtOAc (15 mL), dried over MgSO$_4$, filtered and concentrated to give 4-(2-(3-(difluoromethoxy)phenylamino)pyridin-3-yl)-N,N-bis(4-methoxybenzyl)-6-methyl-1,3,5-triazin-2-amine (0.121 g, 0.207 mmol, 99% yield) as a brown oil. $^1$H NMR (400 MHz, CDCl$_3$) δ 12.12 (br. s., 1H); 8.84 (d, J=8.2 Hz, 1H); 8.35 (br. s., 1H); 7.72 (br. s., 1H); 7.31 (d, J=8.4 Hz, 1H); 7.20 (d, J=7.8 Hz, 5H); 7.11 (t, J=8.0 Hz, 4H); 6.84-6.90 (m, 4H); 6.80 (d, J=7.8 Hz, 1H); 6.71 (d, J=8.4 Hz, 1H); 6.65 (br. s., 1H); 6.45-6.54 (m, 10H); 6.42 (br. s., 4H); 6.28 (br. s., 1H); 4.84 (br. s., 4H); 3.80 (d, J=3.5 Hz, 7H); 2.60 (br. s., 3H). m/z (ESI, +ve ion) 585.1 (M+H)$^+$.

Step 2: 4-(2-(3-(difluoromethoxy)phenylamino)pyridin-3-yl)-6-methyl-1,3,5-triazin-2-amine A solution of 4-(2-(3-(difluoromethoxy)phenylamino)pyridin-3-yl)-N,N-bis(4-methoxybenzyl)-6-methyl-1,3,5-triazin-2-amine (0.121 g, 0.207 mmol) in TFA (8.0 mL) (Aldrich) was heated at 80° C. overnight using a hotplate and a metal heating block. The crude product was dissolved in 2.5 mL of DMSO, and was purified by reversed phase chromatography (Gilson; 10-90% CH$_3$CN in water with TFA additive: 0.1% v/v in each solvent). The fractions were combined and the CH$_3$CN was removed. DCM was added and the whole was washed with a saturated solution of NaHCO$_3$ (1×), brine (1×), dried over MgSO$_4$, filtered and concentrated to give 4-(2-(3-(difluoromethoxy)phenylamino)pyridin-3-yl)-6-methyl-1,3,5-triazin-2-amine (24 mg, 6.97 µmol, 3.37% yield) as a yellow amorphous solid. $^1$H NMR (400 MHz, CDCl$_3$) δ 12.17 (br. s., 1H); 8.80 (d, J=8.2 Hz, 1H); 8.41 (br. s., 1H); 7.97 (br. s., 1H); 7.83-7.90 (m, 1H); 7.78 (br. s., 1H); 7.62 (d, J=8.6 Hz, 1H); 7.31-7.40 (m, 1H); 6.93-7.01 (m, 1H); 6.78 (d, J=8.2 Hz, 1H); 2.45 (br. s., 3H). m/z (ESI, +ve ion) 345.1 (M+H)$^+$.

Example 165

N-(3-(4-amino-6-methyl-1,3,5-triazin-2-yl)pyridin-2-yl)-2-methylbenzo[d]oxazol-5-amine

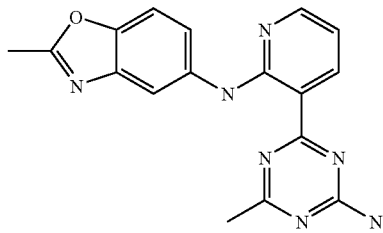 [SMILES: Cc1nc(N)nc(-c2cccnc2Nc2ccc3oc(C)nc3c2)n1]

Step 1: N-(3-(4-(bis(4-methoxybenzyl)amino)-6-methyl-1,3,5-triazin-2-yl)pyridin-2-yl)-2-methylbenzo[d]oxazol-5-amine The title compound was prepared in an analogous manner to that described in Example 164 using 2-methylbenzo[d]oxazol-5-amine (Bionet Research Intermediates) and 4-(2-fluoropyridin-3-yl)-N,N-bis(4-methoxybenzyl)-6-methyl-1,3,5-triazin-2-amine, and isolated as a brown oil (100%). $^1$H NMR (400 MHz, CDCl3) δ 11.94 (s, 1H); 8.31 (br. s., 1H); 8.04 (br. s., 1H); 7.31-7.42 (m, 1H); 7.27-7.30 (m, 2H); 7.14-7.24 (m, 3H); 6.79-6.96 (m, 5H); 4.84 (br. s., 4H); 3.80 (d, J=9.6 Hz, 6H); 2.62 (br. s., 3H); 2.59 (br. s., 4H). m/z (ESI, +ve ion) 574.0 (M+H)$^+$.

Step 2: N-(3-(4-amino-6-methyl-1,3,5-triazin-2-yl)pyridin-2-yl)-2-methylbenzo[d]oxazol-5-amine A solution of N-(3-(4-(bis(4-methoxybenzyl)amino)-6-methyl-1,3,5-triazin-2-yl)pyridin-2-yl)-2-methylbenzo[d]oxazol-5-amine (0.116 g, 0.202 mmol) in TFA (8.0 mL) (Aldrich) was heated at 80° C. overnight. The TFA was removed in vacuo. The crude product was dissolved in 4 mL of DMSO and was purified by reversed phase chromatography (Gilson; 10-90% CH$_3$CN in water with TFA additive: 0.1% v/v in each solvent). The fractions were combined and the CH$_3$CN was removed. DCM was added and the whole was washed with a saturated solution of NaHCO$_3$ (1×), brine (1×), dried over MgSO$_4$, filtered and concentrated. The compound and impurities had co-eluted. The material was purified by flash column chromatography using an ISCO Combiflash Companion (4 g column; 1-10% MeOH in DCM over 40 minutes). The compound and impurities co-eluted. The crude product was dissolved in 4 mL of DMSO. Purification by reversed phase chromatography (Gilson; 10-90% CH$_3$CN in water with NH$_4$OH additive: 0.1% v/v in each solvent) followed by drying in a Genevac Series II System gave N-(3-(4-amino-6-methyl-1,3,5-triazin-2-yl)pyridin-2-yl)-2-methylbenzo[d]oxazol-5-amine (1.079 mg, 3.24 µmol, 1.6% yield) as a yellow amorphous solid. $^1$H NMR (400 MHz, d6-DMSO) δ 12.04 (s, 1H); 8.79 (dd, J=7.7, 2.1 Hz, 1H); 8.37 (dd, J=4.7, 2.0 Hz, 1H); 8.33 (d, J=2.0 Hz, 1H); 7.86 (q, J=3.2 Hz, 1H); 7.70-7.77 (m, 1H); 7.62-7.68 (m, 1H); 7.54-7.60 (m, 1H); 6.91 (dd, J=7.8, 4.7 Hz, 1H); 2.60 (s, 3H); 2.45 (s, 4H). m/z (ESI, +ve ion) 334.1 (M+H)$^+$.

Example 166

4-(2-(3-fluoro-4-methoxyphenylamino)pyridin-3-yl)-6-methyl-1,3,5-triazin-2-amine

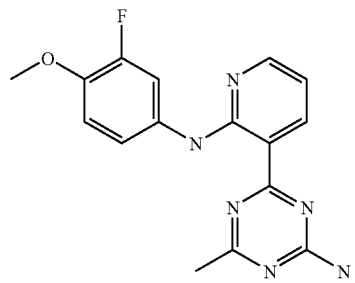 [SMILES: COc1ccc(Nc2ncccc2-c2nc(C)nc(N)n2)cc1F]

Step 1: 4-(2-(3-fluoro-4-methoxyphenylamino)pyridin-3-yl)-N,N-bis(4-methoxybenzyl)-6-methyl-1,3,5-triazin-2-amine The title compound was prepared in an analogous manner to that described in Example 164 using 3-fluoro-4-methoxyaniline (Aldrich) and 4-(2-fluoropyridin-3-yl)-N,N-bis(4-methoxybenzyl)-6-methyl-1,3,5-triazin-2-amine and isolated as a brown solid (100%). $^1$H NMR (400 MHz, d6-DMSO) δ 11.82 (br. s., 1H); 8.77 (d, J=7.0 Hz, 1H); 8.34 (br. s., 1H); 7.75 (d, J=14.1 Hz, 1H); 7.18-7.31 (m, 4H); 7.11-7.17 (m, 1H); 7.05 (t, J=9.8 Hz, 1H); 6.89 (t, J=7.4 Hz, 5H); 4.81 (d, J=8.6 Hz, 3H); 3.80 (br. s., 3H); 3.72 (d, J=10.4 Hz, 7H); 2.56 (br. s., 3H). m/z (ESI, +ve ion) 567.1 (M+H)$^+$.

Step 2: 4-(2-(3-fluoro-4-methoxyphenylamino)pyridin-3-yl)-6-methyl-1,3,5-triazin-2-amine A solution of 4-(2-(3-fluoro-4-methoxyphenylamino)pyridin-3-yl)-N,N-bis(4-methoxybenzyl)-6-methyl-1,3,5-triazin-2-amine (0.1253 g, 0.221 mmol) in TFA (8.0 mL) (Aldrich) was heated at 80° C. overnight. The TFA was removed in vacuo and the residue was treated with a saturated solution of NaHCO$_3$. The mixture was extracted with DCM (3×15 mL) and concentrated. The crude brown oil was dissolved in 2.5 mL of DMSO and purified by reversed phase chromatography (Gilson, 10-90% CH$_3$CN in water with NH$_4$OH additive: 0.1% v/v in each solvent). The fractions were concentrated in a Genevac Series II System to give 4-(2-(3-fluoro-4-methoxyphenylamino)pyridin-3-yl)-6-methyl-1,3,5-triazin-2-amine (3.3 mg, 10.11 μmol, 4.57% yield) as a yellow amorphous solid. $^1$H NMR (400 MHz, d6-DMSO) δ 11.91 (s, 1H); 8.77 (dd, J=7.8, 2.0 Hz, 1H); 8.35 (dd, J=4.7, 2.0 Hz, 1H); 7.94 (dd, J=14.2, 2.6 Hz, 1H); 7.48-7.53 (m, 1H); 7.11 (t, J=9.4 Hz, 1H); 6.90 (dd, J=7.8, 4.7 Hz, 1H); 3.82 (s, 3H); 2.43 (s, 3H). m/z (ESI, +ve ion) 327.1 (M+H)$^+$.

Example 167

4-(2-(4-fluoro-3-methoxyphenylamino)pyridin-3-yl)-6-methyl-1,3,5-triazin-2-amine

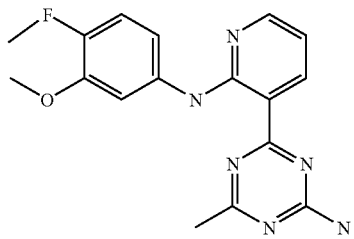

Step 1: 4-(2-(4-fluoro-3-methoxyphenylamino)pyridin-3-yl)-N,N-bis(4-methoxybenzyl)-6-methyl-1,3,5-triazin-2-amine The title compound was prepared in an analogous manner to that described in Example 164 using 4-fluoro-3-methoxyaniline (Combi-Blocks Inc.) and 4-(2-fluoropyridin-3-yl)-N,N-bis(4-methoxybenzyl)-6-methyl-1,3,5-triazin-2-amine, and isolated as a brown solid (100%). $^1$H NMR (400 MHz, d6-DMSO) δ 11.91 (br. s., 1H); 8.80 (br. s., 1H); 8.35 (br. s., 1H); 7.55 (br. s., 1H); 7.24 (br. s., 4H); 7.11 (d, J=1.2 Hz, 1H); 6.77-6.94 (m, 6H); 4.79 (br. s., 4H); 3.77 (br. s., 3H); 3.72 (d, J=10.6 Hz, 6H); 2.56 (br. s., 3H). m/z (ESI, +ve ion) 567.0 (M+H)$^+$.

Step 2: 4-(2-(4-fluoro-3-methoxyphenylamino)pyridin-3-yl)-6-methyl-1,3,5-triazin-2-amine A solution of 4-(2-(4-fluoro-3-methoxyphenylamino)pyridin-3-yl)-N,N-bis(4-methoxybenzyl)-6-methyl-1,3,5-triazin-2-amine (0.1196 g, 0.211 mmol) in TFA (8.0 mL) was heated at 80° C. overnight. The solution was cooled to room temperature and the TFA was removed in vacuo. The crude product was treated with a saturated solution of NaHCO$_3$, the aqueous layer was extracted with DCM (3×15 mL), the layers were separated, the combined organic layers were dried and concentrated. The crude brown oil was dissolved in 2.5 mL of DMSO and purified by reversed phase chromatography (Gilson, 10-90% CH$_3$CN in water with NH$_4$OH additive: 0.1% v/v in each solvent). The fractions were concentrated in a Genevac Series II System to give 4-(2-(4-fluoro-3-methoxyphenylamino)pyridin-3-yl)-6-methyl-1,3,5-triazin-2-amine (0.0025 g, 7.66 μmol, 3.63% yield) as a yellow amorphous solid. $^1$H NMR (400 MHz, d6-DMSO) δ 11.94 (s, 1H); 8.77 (dd, J=7.7, 1.9 Hz, 1H); 8.35 (dd, J=4.8, 1.9 Hz, 1H); 7.70-7.77 (m, 1H); 7.34 (s, 1H); 7.14 (dd, J=11.4, 8.9 Hz, 1H); 6.91 (dd, J=7.7, 4.8 Hz, 1H); 3.87 (s, 3H); 2.64-2.70 (m, 1H); 2.44 (s, 3H). m/z (ESI, +ve ion) 327.1 (M+H)$^+$.

Example 168

4-(2-(2,2-difluorobenzo[d][1,3]dioxol-5-ylamino)pyridin-3-yl)-6-methyl-1,3,5-triazin-2-amine

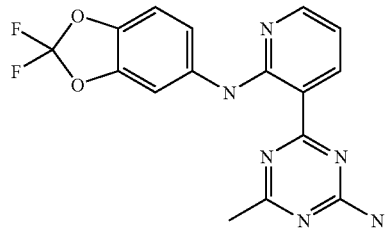 [SMILES: Cc1nc(N)nc(-c2cccnc2Nc2ccc3c(c2)OC(F)(F)O3)n1]

Step 1: 4-(2-(2,2-difluorobenzo[d][1,3]dioxol-5-ylamino)pyridin-3-yl)-N,N-bis(4-methoxybenzyl)-6-methyl-1,3,5-triazin-2-amine The title compound was prepared in an analogous manner to that described in Example 164 using 2,2-difluorobenzo[d][1,3]dioxol-5-amine (0.055 g, 0.320 mmol) (Apollo Scientific Limited) and 4-(2-fluoropyridin-3-yl)-N,N-bis(4-methoxybenzyl)-6-methyl-1,3,5-triazin-2-amine (0.095 g, 0.213 mmol), and isolated as a brown oil (100%). $^1$H NMR (400 MHz, d6-DMSO) δ 11.98 (br. s., 1H); 8.79 (d, J=7.6 Hz, 1H); 8.35 (br. s., 1H); 7.92 (br. s., 1H); 7.20-7.29 (m, 5H); 7.16 (d, J=8.4 Hz, 1H); 6.83-6.97 (m, 5H); 4.81 (d, J=7.4 Hz, 4H); 3.72 (d, J=12.7 Hz, 6H); 2.57 (br. s., 3H). m/z (ESI, +ve ion) 599.0 (M+H)$^+$.

Step 2: 4-(2-(2,2-difluorobenzo[d][1,3]dioxol-5-ylamino)pyridin-3-yl)-6-methyl-1,3,5-triazin-2-amine A solution of 4-(2-(2,2-difluorobenzo[d][1,3]dioxol-5-ylamino)pyridin-3-yl)-N,N-bis(4-methoxybenzyl)-6-methyl-1,3,5-triazin-2-amine (0.1352 g, 0.226 mmol) in TFA (8.0 mL) (Aldrich) was heated at 80° C. overnight. The solution was cooled to room temperature and the TFA was removed in vacuo. The residue was treated with a saturated solution of NaHCO$_3$, the aqueous layer was extracted with DCM (3×15 mL), the layers were separated, the combined organic layers were dried and concentrated. The crude brown oil was dissolved in 2.5 mL of DMSO and purified by reversed phase chromatography (Gilson, 10-90% CH$_3$CN in water with NH₄OH additive: 0.1% v/v in each solvent). The fractions were concentrated in a Genevac Series II System to give 4-(2-(2,2-difluorobenzo[d][1,3]dioxol-5-ylamino)pyridin-3-yl)-6-methyl-1,3,5-triazin-2-amine (3.1 mg, 8.65 µmol, 3.83% yield) as a yellow amorphous solid. ¹H NMR (400 MHz, d6-DMSO) δ 12.11 (s, 1H); 8.80 (dd, J=7.8, 2.0 Hz, 1H); 8.37 (dd, J=4.6, 2.1 Hz, 1H); 8.15 (d, J=2.2 Hz, 1H); 7.87 (br. s., 1H); 7.77 (br. s., 1H); 7.55 (dd, J=8.8, 2.2 Hz, 1H); 7.35 (d, J=8.8 Hz, 1H); 6.95 (dd, J=7.9, 4.6 Hz, 1H); 2.44 (s, 3H). m/z (ESI, +ve ion) 359.0 (M+H)⁺.

Example 169

5-(4-amino-6-methyl-1,3,5-triazin-2-yl)-6'-methoxy-N-(6-methoxypyridin-3-yl)-3,3'-bipyridin-6-amine

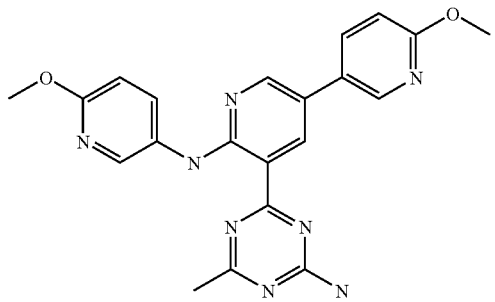

Step 1: 5-(4-(bis(4-methoxybenzyl)amino)-6-methyl-1,3,5-triazin-2-yl)-6'-methoxy-N-(6-methoxypyridin-3-yl)-3,3'-bipyridin-6-amine A mixture of 6-methoxypyridin-3-ylboronic acid (0.039 g, 0.256 mmol), 4-(5-chloro-2-(6-methoxypyridin-3-ylamino)pyridin-3-yl)-N,N-bis(4-methoxybenzyl)-6-methyl-1,3,5-triazin-2-amine (0.1244 g, 0.213 mmol), Pd₂dba₃ (7.80 mg, 8.52 µmol), and dicyclohexyl(2',4',6'-triisopropylbiphenyl-2-yl)phosphine (8.12 mg, 0.017 mmol) was purged with argon. The mixture were treated with dioxane (2.0 mL) and sodium carbonate (0.27 mL, 0.53 mmol) and heated in a Biotage Initiator microwave at 140° C. for 30 min. The cooled reaction mixture was treated with 1 N NaOH and extracted with EtOAc (30 mL), washed with brine, dried over MgSO₄, filtered and concentrated. The crude product was used directly in the next reaction. m/z (ESI, +ve ion) 657.0 (M+H)⁺.

Step 2: 5-(4-amino-6-methyl-1,3,5-triazin-2-yl)-6'-methoxy-N-(6-methoxypyridin-3-yl)-3,3'-bipyridin-6-amine A solution of 5-(4-(bis(4-methoxybenzyl)amino)-6-methyl-1,3,5-triazin-2-yl)-6'-methoxy-N-(6-methoxypyridin-3-yl)-3,3'-bipyridin-6-amine (0.163 g, 0.249 mmol) in TFA (8.0 mL) (Aldrich) was heated at 80° C. overnight. The solution was cooled to room temperature, the mixture was concentrated, the crude residue was treated with 2M NH₃ in MeOH and dry-packed with silica gel. Purification using an ISCO Combiflash Companion (40 g column; 1-20% MeOH in DCM over 25 min; product eluted with 10% MeOH) afforded 5-(4-amino-6-methyl-1,3,5-triazin-2-yl)-6'-methoxy-N-(6-methoxypyridin-3-yl)-3,3'-bipyridin-6-amine (0.0572 g, 0.137 mmol, 55.2% yield) as an orange colored amorphous solid. ¹H NMR (400 MHz, d6-DMSO) δ 11.81 (s, 1H); 8.98 (d, J=2.7 Hz, 1H); 8.62 (d, J=2.5 Hz, 1H); 8.56 (d, J=2.7 Hz, 1H); 8.47 (d, J=2.3 Hz, 1H); 8.20 (dd, J=8.8, 2.7 Hz, 1H); 8.00 (dd, J=8.6, 2.7 Hz, 1H); 7.90 (br. s., 1H); 7.76 (br. s., 1H); 6.94 (d, J=8.6 Hz, 1H); 6.85 (d, J=8.8 Hz, 1H); 3.90 (s, 3H); 3.86 (s, 3H); 2.46 (s, 3H). m/z (ESI, +ve ion) 417.0 (M+H)⁺.

Example 170

4-(2-(3,4-dimethoxyphenylamino)pyridin-3-yl)-6-methyl-1,3,5-triazin-2-amine

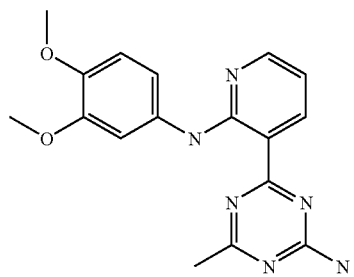 [SMILES: COc1ccc(Nc2ncccc2-c2nc(C)nc(N)n2)cc1OC]

Step 1: 4-(2-(3,4-dimethoxyphenylamino)pyridin-3-yl)-N,N-bis(4-methoxybenzyl)-6-methyl-1,3,5-triazin-2-amine The title compound was prepared in an analogous manner to that described in Example 164 using 3,4-dimethoxyaniline (Aldrich) and 4-(2-fluoropyridin-3-yl)-N,N-bis(4-methoxybenzyl)-6-methyl-1,3,5-triazin-2-amine, and isolated as a brown oil (100%). ¹H NMR (400 MHz, CDCl₃) δ 11.69 (s, 1H); 8.82 (dd, J=7.8, 2.0 Hz, 1H); 8.30 (dd, J=4.7, 1.8 Hz, 1H); 7.31 (d, J=2.2 Hz, 1H); 7.20 (d, J=8.2 Hz, 4H); 6.98 (dd, J=8.6, 2.3 Hz, 1H); 6.78-6.91 (m, 5H); 6.72 (dd, J=7.8, 4.7 Hz, 1H); 4.83 (s, 4H); 3.86 (s, 3H); 3.81 (s, 6H); 3.79 (s, 3H); 2.57 (s, 3H). m/z (ESI, +ve ion) 579.0 (M+H)⁺.

Step 2: 4-(2-(3,4-dimethoxyphenylamino)pyridin-3-yl)-6-methyl-1,3,5-triazin-2-amine A solution of 4-(2-(3,4-dimethoxyphenylamino)pyridin-3-yl)-N,N-bis(4-methoxybenzyl)-6-methyl-1,3,5-triazin-2-amine (0.255 g, 0.441 mmol) in TFA (8.0 mL) (Aldrich) was heated at 80° C. overnight. The solution was cooled to room temperature, the mixture was concentrated, the crude residue was treated with 2M NH₃ in MeOH and dry-packed with silica gel. Purification using an ISCO Combiflash Companion (12 g column; 1-25% MeOH in DCM over 30 min; product eluted with 11% MeOH) gave material of insufficient purity for testing. The residue was suspended in MeOH and the solid was removed by filtration to give 4-(2-(3,4-dimethoxyphenylamino)pyridin-3-yl)-6-methyl-1,3,5-triazin-2-amine (0.017 g, 0.049 mmol, 11.12% yield) as a brown amorphous solid. ¹H NMR (400 MHz, d6-DMSO) δ 11.77 (s, 1H); 8.75 (dd, J=7.7, 1.9 Hz, 1H); 8.31 (dd, J=4.5, 2.0 Hz, 1H); 7.79 (br. s., 1H); 7.70 (br. s., 1H); 7.47 (d, J=2.3 Hz, 1H); 7.30 (dd, J=8.7, 2.4 Hz, 1H); 6.91 (d, J=8.8 Hz, 1H); 6.84 (dd, J=7.8, 4.7 Hz, 1H); 3.79 (s, 3H); 3.74 (s, 3H); 2.44 (s, 3H). m/z (ESI, +ve ion) 339.0 (M+H)$^+$.

Example 171

N-(3-(4-amino-6-methyl-1,3,5-triazin-2-yl)pyridin-2-yl)-2-methylquinolin-6-amine

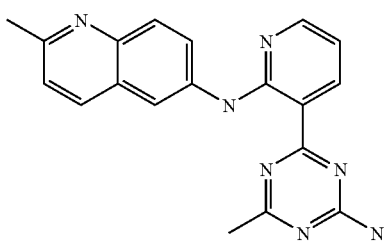 [SMILES: Cc1ccc2cc(Nc3ncccc3-c3nc(C)nc(N)n3)ccc2n1]

Step 1: N-(3-(4-(bis(4-methoxybenzyl)amino)-6-methyl-1,3,5-triazin-2-yl)pyridin-2-yl)-2-methylquinolin-6-amine The title compound was prepared in an analogous manner to that described in Example 164 using 2-methylquinolin-6-amine (Acros Organics) and 4-(2-fluoropyridin-3-yl)-N,N-bis(4-methoxybenzyl)-6-methyl-1,3,5-triazin-2-amine Purification using an ISCO Combiflash Companion (12 g column, 20-60% EtOAc in hexanes over 30 min, product eluted with 35-45% EtOAc) gave the title compound as a yellow amorphous solid (49.1%). $^1$H NMR (400 MHz, d6-DMSO) δ 12.19 (s, 1H); 8.84 (dd, J=7.8, 2.0 Hz, 1H); 8.45 (dd, J=4.7, 2.0 Hz, 1H); 8.39 (d, J=2.2 Hz, 1H); 8.08 (d, J=8.2 Hz, 1H); 7.78-7.83 (m, 1H); 7.71-7.77 (m, 1H); 7.34 (d, J=8.4 Hz, 1H); 7.26 (dd, J=8.6, 6.3 Hz, 4H); 6.98 (dd, J=7.8, 4.7 Hz, 1H); 6.90 (t, J=8.3 Hz, 4H); 4.84 (d, J=17.6 Hz, 4H); 3.72 (d, J=14.5 Hz, 6H); 2.62 (d, J=2.0 Hz, 6H). m/z (ESI, +ve ion) 584.0 (M+H)$^+$.

Step 2: N-(3-(4-amino-6-methyl-1,3,5-triazin-2-yl)pyridin-2-yl)-2-methylquinolin-6-amine A solution of N-(3-(4-(bis(4-methoxybenzyl)amino)-6-methyl-1,3,5-triazin-2-yl)pyridin-2-yl)-2-methylquinolin-6-amine (0.116 g, 0.199 mmol) in TFA (5.0 mL) (Aldrich) was heated at 80° C. overnight. The solution was cooled to room temperature, and the mixture was concentrated to about 50% of the original volume. The remaining mixture was pipetted carefully into a saturated solution of NaHCO$_3$, which had been cooled in an ice bath. The resulting precipitate was collected by filtration and washed with water. The solid was then suspended in IPA and the precipitate collected by filtration to give N-(3-(4-amino-6-methyl-1,3,5-triazin-2-yl)pyridin-2-yl)-2-methylquinolin-6-amine (0.0581 g, 0.169 mmol, 85% yield) as a yellow amorphous solid. $^1$H NMR (400 MHz, d6-DMSO) δ 12.30 (s, 1H); 8.83 (d, J=7.0 Hz, 1H); 8.62 (s, 1H); 8.45 (d, J=2.7 Hz, 1H); 8.15 (d, J=8.4 Hz, 1H); 8.03 (d, J=8.0 Hz, 1H); 7.82-7.93 (m, 2H); 7.80 (br. s., 1H); 7.36 (d, J=8.6 Hz, 1H); 6.99 (dd, J=7.3, 4.8 Hz, 1H); 2.63 (s, 3H); 2.48 (br. s., 3H). m/z (ESI, +ve ion) 344.0 (M+H)$^+$.

Example 172

5'-(4-amino-6-methyl-1,3,5-triazin-2-yl)-N-(6-methoxypyridin-3-yl)-2,3'-bipyridin-6'-amine

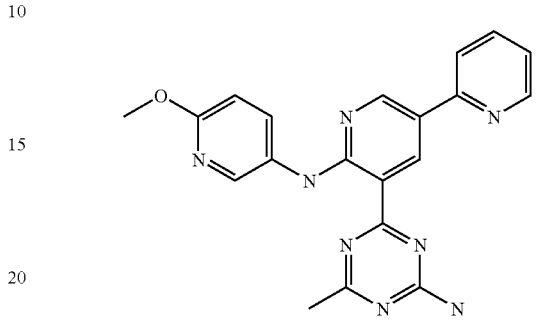

Step 1: 5'-(4-(bis(4-methoxybenzyl)amino)-6-methyl-1,3,5-triazin-2-yl)-N-(6-methoxypyridin-3-yl)-2,3'-bipyridin-6'-amine A mixture of 4-(5-chloro-2-(6-methoxypyridin-3-ylamino)pyridin-3-yl)-N,N-bis(4-methoxybenzyl)-6-methyl-1,3,5-triazin-2-amine (0.100 g, 0.171 mmol), dicyclohexyl(2',4',6'-triisopropylbiphenyl-2-yl)phosphine (4.08 mg, 8.56 μmol), tris(dibenzylideneacetone)dipalladium(0) (7.84 mg, 8.56 μmol) and 2-(tributylstannyl)pyridine (0.082 g, 0.223 mmol) (Alfa Aesar) was purged with argon and toluene (0.9 mL) was added. The tube was sealed and the mixture was heated at 110° C. The reaction mixture was cooled to room temperature, treated with water, extracted with DCM (2×15 mL), dried over MgSO$_4$, filtered and concentrated. The crude material was purified by flash chromatography using an ISCO Combiflash Companion (12 g column, 20-50% EtOAc in hexanes over 30 min; product eluted with about 30-35% EtOAc). $^1$H NMR (400 MHz, CDCl$_3$) δ 11.82 (s, 1H); 9.41 (d, J=2.5 Hz, 1H); 8.93 (d, J=2.3 Hz, 1H); 8.66 (d, J=4.9 Hz, 1H); 8.30 (d, J=2.7 Hz, 1H); 7.93 (dd, J=8.9, 2.6 Hz, 1H); 7.67-7.75 (m, 1H); 7.59-7.65 (m, 1H); 7.15-7.24 (m, 5H); 6.85 (dd, J=20.0, 8.6 Hz, 4H); 6.72 (d, J=8.8 Hz, 1H); 4.87 (d, J=17.2 Hz, 4H); 3.94 (s, 3H); 3.81 (s, 3H); 3.76 (s, 3H); 2.59 (s, 3H). m/z (ESI, +ve ion) 627.0 (M+H)$^+$.

Step 2: 5'-(4-amino-6-methyl-1,3,5-triazin-2-yl)-N-(6-methoxypyridin-3-yl)-2,3'-bipyridin-6'-amine A solution of 5'-(4-(bis(4-methoxybenzyl)amino)-6-methyl-1,3,5-triazin-2-yl)-N-(6-methoxypyridin-3-yl)-2,3'-bipyridin-6'-amine (0.0419 g, 0.067 mmol) in TFA (3.0 mL) (Aldrich) was heated at 80° C. overnight. The solution was cooled to room temperature and concentrated. The crude residue was treated with 2M NH$_3$ in MeOH and dry-packed with silica gel. Purification on an ISCO Combiflash Companion (12 g column, 1-15% MeOH in DCM over 25 min, product eluted with 10% MeOH)) gave 5'-(4-amino-6-methyl-1,3,5-triazin-2-N-(6-methoxypyridin-3-yl)-2,3'-bipyridin-6'-amine (0.0106 g, 0.027 mmol, 41.0% yield) as yellow amorphous solid. $^1$H NMR (400 MHz, d6-DMSO) δ 11.98 (s, 1H); 9.53 (d, J=2.5 Hz, 1H); 9.00 (d, J=2.5 Hz, 1H); 8.67 (d, J=5.3 Hz, 1H); 8.58 (d, J=2.7 Hz, 1H); 8.21 (dd, J=9.0, 2.9 Hz, 1H); 7.96 (t, J=7.8 Hz, 2H); 7.88 (td, J=7.6, 1.8 Hz, 1H); 7.76 (d, J=2.7 Hz, 1H); 7.33 (s, 1H); 6.86 (d, J=9.0 Hz, 1H); 3.86 (s, 3H); 2.47 (s, 3H). m/z (ESI, +ve ion) 387.0 (M+H)+.

Example 173

4-(2-(5-chloro-6-methoxypyridin-3-ylamino)pyridin-3-yl)-6-methyl-1,3,5-triazin-2-amine

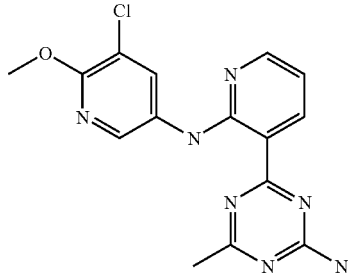

Step 1: 4-(2-(5-chloro-6-methoxypyridin-3-ylamino)pyridin-3-yl)-N,N-bis(4-methoxybenzyl)-6-methyl-1,3,5-triazin-2-amine The title compound was prepared in an analogous manner to that described in Example 164 using 5-chloro-6-methoxypyridin-3-amine and 4-(2-fluoropyridin-3-yl)-N,N-bis(4-methoxybenzyl)-6-methyl-1,3,5-triazin-2-amine, and isolated as a brown oil (100%). 1H NMR (400 MHz, d6-DMSO) δ 11.71 (s, 1H); 8.78 (dd, J=7.8, 2.2 Hz, 1H); 8.33 (dd, J=4.7, 2.0 Hz, 1H); 8.26 (d, J=2.5 Hz, 1H); 8.19 (d, J=2.3 Hz, 1H); 7.17-7.29 (m, 4H); 6.82-6.96 (m, 5H); 4.81 (d, J=6.5 Hz, 4H); 3.91 (s, 3H); 3.74 (s, 3H); 3.70 (s, 3H); 2.55-2.58 (m, 3H). m/z (ESI, +ve ion) 584.0 (M+H)+.

Step 2: 4-(2-(5-chloro-6-methoxypyridin-3-ylamino)pyridin-3-yl)-6-methyl-1,3,5-triazin-2-amine A solution of 4-(2-(5-chloro-6-methoxypyridin-3-ylamino)pyridin-3-yl)-N,N-bis(4-methoxybenzyl)-6-methyl-1,3,5-triazin-2-amine (0.3068 g, 0.525 mmol) in TFA (8.0 mL) (Aldrich) was heated at 80° C. overnight. The solution was cooled to room temperature, and concentrated to about 50% of the original volume. The remaining mixture was pipetted carefully into a saturated solution of NaHCO3, which had been cooled in an ice bath. The resulting precipitate was removed by filtration and washed with water. The solid was dissolved in DCM and MeOH, and dry packed with silica gel. Purification using an ISCO Combiflash Companion (12 g column, 1-6% MeOH in DCM over 40 min, product eluted with 4% MeOH) gave 4-(2-(5-chloro-6-methoxypyridin-3-ylamino)pyridin-3-yl)-6-methyl-1,3,5-triazin-2-amine (0.0434 g, 0.126 mmol, 24.03% yield) as a tan amorphous solid. 1H NMR (400 MHz, d6-DMSO) δ 11.89 (s, 1H); 8.80 (dd, J=7.8, 2.0 Hz, 1H); 8.51-8.56 (m, 2H); 8.35 (dd, J=4.7, 2.0 Hz, 1H); 7.92 (br. s., 1H); 7.76 (br. s., 1H); 6.94 (dd, J=7.8, 4.7 Hz, 1H); 3.93 (s, 3H); 2.43 (s, 3H). m/z (ESI, +ve ion) 344.0 (M+H)+.

Example 174

4-methyl-6-(2-(5-methylpyridin-3-ylamino)pyridin-3-yl)-1,3,5-triazin-2-amine

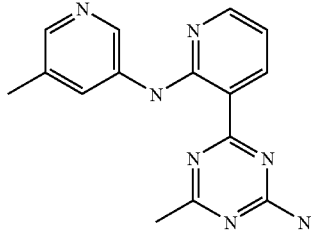 [SMILES: Cc1cncc(Nc2ncccc2-c2nc(C)nc(N)n2)c1]

Step 1: N,N-bis(4-methoxybenzyl)-4-methyl-6-(2-(5-methylpyridin-3-ylamino)pyridin-3-yl)-1,3,5-triazin-2-amine The title compound was prepared in an analogous manner to that described in Example 164 using 5-methylpyridin-3-amine (0.075 g, 0.690 mmol) (Aldrich) and 4-(2-fluoropyridin-3-yl)-N,N-bis(4-methoxybenzyl)-6-methyl-1,3,5-triazin-2-amine. Purification using an ISCO Combiflash Companion (12 g column, 30-70% EtOAc in hexanes over 30 min; the product eluted with 45% EtOAc) gave the title compound as a yellow amorphous solid (25.7%). 1H NMR (400 MHz, d6-DMSO) δ 11.93 (s, 1H); 8.81 (dd, J=7.8, 1.8 Hz, 1H); 8.61 (d, J=2.3 Hz, 1H); 8.39 (dd, J=4.7, 2.0 Hz, 1H); 8.02 (s, 1H); 7.93 (s, 1H); 7.25 (dd, J=10.2, 8.8 Hz, 4H); 6.85-7.00 (m, 5H); 4.82 (d, J=14.7 Hz, 4H); 3.74 (s, 3H); 3.71 (s, 3H); 2.59 (s, 3H); 2.26 (s, 3H). m/z (ESI, +ve ion) 534.0 (M+H)+.

Step 2: 4-methyl-6-(2-(5-methylpyridin-3-ylamino)pyridin-3-yl)-1,3,5-triazin-2-amine A solution of N,N-bis(4-methoxybenzyl)-4-methyl-6-(2-(5-methylpyridin-3-ylamino)pyridin-3-yl)-1,3,5-triazin-2-amine (0.063 g, 0.118 mmol) in TFA (3.0 mL) (Aldrich) was heated at 80° C. overnight. The solution was cooled to room temperature and was concentrated to about 50% of the original volume. The remaining mixture was pipetted carefully into a saturated solution of NaHCO3, which had been cooled in an ice bath. The resulting precipitate was removed by filtration and washed with water. The material was suspended in DMSO (5mL) and water (10 drops) was added. The solid was collected by filtration to give 4-methyl-6-(2-(5-methylpyridin-3-ylamino)pyridin-3-yl)-1,3,5-triazin-2-amine (0.0137 g, 0.047 mmol, 39.6% yield) as a yellow amorphous solid. 1H NMR (400 MHz, d6-DMSO) δ 11.96-12.04 (m, 1H); 8.81 (br. s., 2H); 8.39 (br. s., 1H); 8.23 (br. s., 1H); 8.05

(s, 1H); 7.89 (br. s., 1H); 7.77 (br. s., 1H); 6.96 (br. s., 1H); 2.45 (br. s., 3H); 2.32 (s, 3H). m/z (ESI, +ve ion) 294.0 (M+H)⁺.

Example 175

5-(4-amino-6-methyl-1,3,5-triazin-2-yl)-N-(5-fluoro-6-methoxypyridin-3-yl)-2,4'-bipyridin-6-amine

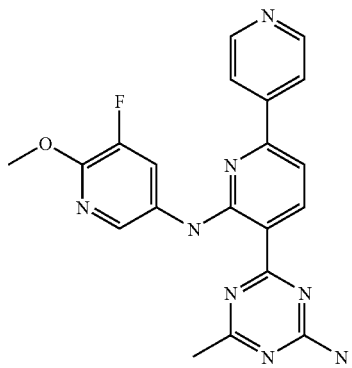 [SMILES: COc1ncc(Nc2nc(-c3ccncc3)ccc2-c2nc(C)nc(N)n2)cc1F]

Step 1: 5-(4-(bis(4-methoxybenzyl)amino)-6-methyl-1,3,5-triazin-2-yl)-N-(5-fluoro-6-methoxypyridin-3-yl)-2,4'-bipyridin-6-amine The title compound was prepared in an analogous manner to that described in Example 164 using 5-fluoro-6-methoxypyridin-3-amine (Anichem) and 4-(6-fluoro-2,4'-bipyridin-5-yl)-N,N-bis(4-methoxybenzyl)-6-methyl-1,3,5-triazin-2-amine. Purification using an ISCO Combiflash Companion (12 g column and sample loader, 30-100% EtOAc in hexanes over 20 min; the product eluted with 82% EtOAc) afforded the title compound as a brown oil (39.6%). ¹H NMR (400 MHz, d6-DMSO) δ 11.86 (s, 1H); 8.91 (d, J=8.2 Hz, 1H); 8.70-8.76 (m, 2H); 8.21 (d, J=2.2 Hz, 1H); 8.09 (dd, J=12.4, 2.2 Hz, 1H); 7.94-7.99 (m, 2H); 7.66 (d, J=8.0 Hz, 1H); 7.26 (dd, J=18.4, 8.6 Hz, 4H); 6.89 (dd, J=18.7, 8.7 Hz, 4H); 4.83 (d, J=9.2 Hz, 4H); 3.95 (s, 3H); 3.74 (s, 3H); 3.70 (s, 3H); 2.59 (s, 3H). m/z (ESI, +ve ion) 645.0 (M+H)⁺.

Step 2: 5-(4-amino-6-methyl-1,3,5-triazin-2-yl)-N-(5-fluoro-6-methoxypyridin-3-yl)-2,4'-bipyridin-6-amine A solution of 5-(4-(bis(4-methoxybenzyl)amino)-6-methyl-1,3,5-triazin-2-yl)-N-(5-fluoro-6-methoxypyridin-3-yl)-2,4'-bipyridin-6-amine (0.139 g, 0.216 mmol) in TFA (8.0 mL) (Aldrich) was heated at 80° C. overnight. The solution was cooled to room temperature and concentrated to about 50% of the original volume under a stream of argon. The remaining mixture was pipetted carefully into a saturated solution of NaHCO₃ which had been cooled in an ice bath. The resulting precipitate was removed by filtration and washed with water. The impure solid was suspended in IPA, and the suspension was subjected to filtration. The solid was washed with DMSO, followed by water to give 5-(4-amino-6-methyl-1,3,5-triazin-2-yl)-N-(5-fluoro-6-methoxypyridin-3-yl)-2,4'-bipyridin-6-amine (0.0565 g, 0.140 mmol, 64.8% yield). ¹H NMR (400 MHz, d6-DMSO) δ 12.03 (s, 1H); 8.93 (d, J=8.0 Hz, 1H); 8.75 (d, J=5.9 Hz, 2H); 8.54 (d, J=1.8 Hz, 1H); 8.32-8.38 (m, 1H); 8.00 (d, J=5.7 Hz, 2H); 7.95 (br. s., 1H); 7.81 (br. s., 1H); 7.67 (d, J=8.0 Hz, 1H); 3.97 (s, 3H); 2.46 (s, 3H). m/z (ESI, +ve ion) 405.0 (M+H)⁺.

Example 176

5-(4-amino-6-methyl-1,3,5-triazin-2-yl)-N-(5-fluoro-6-methoxypyridin-3-yl)-2,4'-bipyridin-6-amine

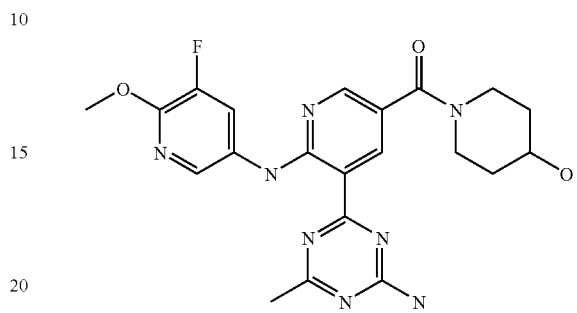

Step 1: (5-(4-(bis(4-methoxybenzyl)amino)-6-methyl-1,3,5-triazin-2-yl)-6-(5-fluoro-6-methoxypyridin-3-ylamino)pyridin-3-yl)(4-hydroxypiperidin-1-yl)methanone A solution of 5-(4-(bis(4-methoxybenzyl)amino)-6-methyl-1,3,5-triazin-2-yl)-6-(5-fluoro-6-methoxypyridin-3-ylamino)nicotinaldehyde (0.054 g, 0.091 mmol) in THF (1.0 mL) at room temperature was treated with sodium cyanide (4.44 mg, 0.091 mmol) (Sigma-Aldrich), piperidin-4-ol (0.046 g, 0.453 mmol) (Aldrich) and manganese (IV) oxide (0.118 g, 1.360 mmol) (Sigma-Aldrich). The mixture was stirred at room temperature. After 1 h the reaction was incomplete, so a few granules of NaCN, and another 15 equiv. of manganese(IV) oxide (0.118 g, 1.360 mmol) were added. The mixture was stirred at room temperature for 18 h, then filtered through Celite® (diatomaceous earth). The organic layer was washed with water, then brine, dried over MgSO₄, filtered and concentrated to give the title compound as a yellow film (85%). ¹H NMR (400 MHz, d6-DMSO) δ 11.86 (s, 1H); 8.77 (d, J=2.3 Hz, 1H); 8.38 (d, J=2.3 Hz, 1H); 8.02-8.11 (m, 2H); 7.23-7.32 (m, 2H); 7.19 (m, J=8.6 Hz, 2H); 6.91 (m, 2H); 6.83 (d, J=8.8 Hz, 2H); 4.72-4.87 (m, 5H); 3.90-3.95 (m, 3H); 3.66-3.76 (m, 8H); 3.17-3.28 (m, 2H); 2.58 (s, 3H); 1.71 (br. s., 2H); 1.36 (br. s., 2H). m/z (ESI, +ve ion) 695.0 (M+H)⁺.

Step 2: 5-(4-amino-6-methyl-1,3,5-triazin-2-yl)-N-(5-fluoro-6-methoxypyridin-3-yl)-2,4'-bipyridin-6-amine A solution of (5-(4-(bis(4-methoxybenzyl)amino)-6-methyl-1,3,5-triazin-2-yl)-6-(5-fluoro-6-methoxypyridin-3-ylamino)pyridin-3-yl)(4-hydroxypiperidin-1-yl)methanone (0.109 g, 0.157 mmol) in TFA (7.0 mL) (Aldrich) was heated at 80° C. overnight. The solution was cooled to room temperature and concentrated to about 50% of the original volume under a stream of argon. A few pieces of ice were added, and then a saturated solution of NaHCO₃ was added slowly until pH 7 was reached. The precipitate was isolated by filtration, and the filtercake was washed with water. The solid was suspended in 3 mL of MeOH and 1 mL of THF, then 0.5 mL of 1 N NaOH was added. The suspension was stirred at room temperature for 10 min. The solid was isolated by filtration and dried to give (5-(4-amino-6-methyl-1,3,5-triazin-2-yl)-6-(5-fluoro-6-methoxypyridin-3-ylamino)pyridin-3-yl)(4-hydroxypiperidin-1-yl)methanone (0.0406 g, 0.089 mmol, 56.9% yield) as an amorphous yellow solid. $^1$H NMR (400 MHz, d6-DMSO) δ 12.08 (s, 1H); 8.85 (d, J=2.3 Hz, 1H); 8.41 (dd, J=4.8, 2.2 Hz, 2H); 8.35 (dd, J=12.6, 2.2 Hz, 1H); 7.96 (br. s., 1H); 7.81 (br. s., 1H); 4.79 (d, J=3.7 Hz, 1H); 3.95 (s, 3H); 3.74 (s, 3H); 3.20-3.27 (m, 2H); 2.44 (s, 3H); 1.76 (br. s., 2H); 1.40 (br. s., 2H). m/z (ESI, +ve ion) 455.0 (M+H)$^+$.

Example 177

6-chloro-N,N-bis(4-methoxybenzyl)-2-methylpyrimidin-4-amine

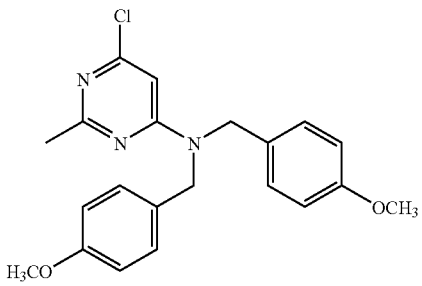 [SMILES: COc1ccc(CN(Cc2ccc(OC)cc2)c2cc(Cl)nc(C)n2)cc1]

Step 1: 6-chloro-N-(4-methoxybenzyl)-2-methylpyrimidin-4-amine

A mixture of 4,6-dichloro-2-methylpyrimidine (Aldrich) (1.45 g, 8.90 mmol), 4-methoxybenzylamine (Alfa Aesar) (1.278 mL, 9.78 mmol), and triethylamine (1.488 mL, 10.67 mmol) in DMF (10.0 mL) was stirred at 25° C. for 18 h. The resulting mixture was partitioned between EtOAc (300 mL) and half-saturated aqueous NaHCO$_3$ (80 mL). The organic layer was separated, sequentially washed with water (2×80 mL) and brine (80 mL), dried over sodium sulfate, filtered, and concentrated in vacuo. Chromatographic purification of the residue (ISCO, 120 g, 0 to100% EtOAc/Hexanes) furnished 6-chloro-N-(4-methoxybenzyl)-2-methylpyrimidin-4-amine (2.30 g, 8.72 mmol, 98% yield) as an off-white solid. $^1$H NMR (400 MHz, CDCl$_3$) δ 7.23 (d, J=8.41 Hz, 2H); 6.89 (d, J=8.61 Hz, 2H); 6.18 (s, 1H); 4.42 (br. s., 2H); 3.81 (s, 3H); 2.50 (s, 3H). m/z (ESI, +ve ion) 264.1 (M+H)$^+$.

Step 2: 6-chloro-N,N-bis(4-methoxybenzyl)-2-methylpyrimidin-4-amine

Sodium hydride (60 wt % in mineral oil) (0.340 g, 8.51 mmol) was added in one portion to a mixture of 6-chloro-N-(4-methoxybenzyl)-2-methylpyrimidin-4-amine (1.87 g, 7.09 mmol) and 1-(chloromethyl)-4-methoxybenzene (1.059 mL, 7.80 mmol) in DMF (50 mL) at 0° C. The resulting mixture was stirred at 0° C. for 5 min and then was warmed to 25° C. and stirred for 2 h. Water (200 mL) was then added, and the precipitated solid was collected by vacuum filtration, washed with water (150 mL), and dried in vacuo to furnish 6-chloro-N,N-bis(4-methoxybenzyl)-2-methylpyrimidin-4-amine (2.69 g, 7.01 mmol, 99% yield) as a white solid. $^1$H NMR (400 MHz, CDCl$_3$) δ 7.11 (d, J=7.24 Hz, 4H); 6.86 (d, J=7.24 Hz, 4H); 6.26 (s, 1H); 4.65 (br. s., 4H); 3.80 (s, 6H); 2.53 (s, 3H). m/z (ESI, +ve ion) 384.1 (M+H)$^+$.

Example 178

6-(2-(6-methoxypyridin-3-ylamino)-5-((4-(methylsulfonyl)piperazin-1-yl)methyl)pyridin-3-yl)-2-methylpyrimidin-4-amine

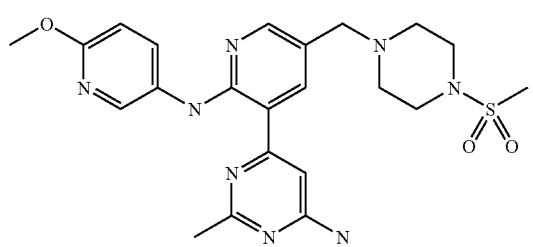

Step 1: tert-butyl 4-((5-(6-(bis(4-methoxybenzyl)amino)-2-methylpyrimidin-4-yl)-6-fluoropyridin-3-yl)methyl)piperazine-1-carboxylate 6-Chloro-N,N-bis(4-methoxybenzyl)-2-methylpyrimidin-4-amine (214.0 mg, 0.557 mmol), 5-((4-(tert-butoxycarbonyl)piperazin-1-yl)methyl)-2-fluoropyridin-3-ylboronic acid (Example 34, Step 3) (189 mg, 0.557 mmol), PdCl$_2$(AmPhos)$_2$ (Aldrich, St. Louis, Mo.) (19.74 mg, 0.028 mmol), and potassium acetate (164 mg, 1.672 mmol) in a mixture of ethanol (3.0 mL) and water (0.300 mL) was sparged with argon and then heated (microwave) at 100° C. in a 20 mL microwave vial for 20 min. The reaction mixture was then concentrated onto silica gel and chromatographically purified (ISCO, 24 g, 0 to 100% EtOAc/Hexanes) to provide tert-butyl 4-((5-(6-(bis(4-methoxybenzyl)amino)-2-methylpyrimidin-4-yl)-6-fluoropyridin-3-yl)methyl)piperazine-1-carboxylate (152.0 mg, 0.236 mmol, 42.4% yield) as a colorless oil. $^1$H NMR (400 MHz, CDCl$_3$) δ 8.44 (dd, J=9.39, 2.15 Hz, 1H); 8.14 (s, 1H); 7.17 (d, J=7.82 Hz, 4H); 6.86 (d, J=8.61 Hz, 5H); 4.74 (br. s., 4H); 3.79 (s, 6H); 3.55 (s, 2H); 3.42 (t, J=4.69 Hz, 4H); 2.62 (s, 3H); 2.37-2.43 (m, 4H); 1.45 (s, 9H). $^{19}$F NMR (377 MHz, CDCl$_3$) δ −71.01 (d, J=9.16 Hz, 1 F). m/z (ESI, +ve ion) 643.2 (M+H)$^+$.

Step 2: 6-(2-fluoro-5-((4-(methylsulfonyl)piperazin-1-yl)methyl)pyridin-3-yl)-N,N-bis(4-methoxybenzyl)-2-methylpyrimidin-4-amine 2,2,2-Trifluoroacetic acid (0.7 mL, 9.09 mmol) was added dropwise to tert-butyl 4-((5-(6-(bis(4-methoxybenzyl)amino)-2-methylpyrimidin-4-yl)-6-fluoropyridin-3-yl)methyl)piperazine-1-carboxylate (64.3 mg, 0.100 mmol) in dichloromethane (1.0 mL) at 25° C., and the resulting solution was stirred at 25° C. for 30 min. The reaction mixture was then concentrated in vacuo, and the residue was taken up in DCM (3.0 mL) and cooled to 0° C. Triethylamine (0.105 mL, 0.750 mmol) was added to the resulting solution, immediately followed by methanesulfonyl chloride (0.015 mL, 0.200 mmol). The resulting mixture was stirred at 0° C. for 20 min and then was concentrated onto silica gel and chromatographically purified (ISCO, 4 g, 0 to100% (10% MeOH-EtOAc)/hexanes) to provide 6-(2-fluoro-5-((4-(methylsulfonyl)piperazin-1-yl)methyl)pyridin-3-yl)-N,N-bis(4-methoxybenzyl)-2-methylpyrimidin-4-amine (54.5 mg, 0.088 mmol, 88% yield) as a colorless oil. ¹H NMR (400 MHz, CDCl₃) δ 8.45 (d, J=9.39 Hz, 1H); 8.14 (s, 1H); 7.17 (d, J=6.85 Hz, 4H); 6.86 (d, J=8.80 Hz, 5H); 4.74 (br. s., 4H); 3.79 (s, 6H); 3.60 (s, 2H); 3.25 (br. s., 4H); 2.78 (s, 3H); 2.62 (s, 3H); 2.58 (br. s., 4H). ¹⁹F NMR (377 MHz, CDCl₃) δ-70.62 (d, J=8.01 Hz, 1F). m/z (ESI, +ve ion) 621.1 (M+H)⁺.

Step 3: N,N-bis(4-methoxybenzyl)-6-(2-(6-methoxypyridin-3-ylamino)-5-((4-(methylsulfonyl)piperazin-1-yl)methyl)pyridin-3-yl)-2-methylpyrimidin-4-amine Lithium bis(trimethylsilyl)amide (Acros, Morris Plains, N.J.; 1.0M solution in THF/ethyl benezene) (0.599 mL, 0.599 mmol) was added dropwise to a solution of 6-(2-fluoro-5-((4-(methylsulfonyl)piperazin-1-yl)methyl)pyridin-3-yl)-N,N-bis(4-methoxybenzyl)-2-methylpyrimidin-4-amine (124.0 mg, 0.200 mmol) and 6-methoxypyridin-3-amine (0.037 mL, 0.300 mmol) in THF (3.0 mL) at 0° C., and the resulting dark brown solution was stirred at 0° C. for 1 h. Excess LiHMDS was quenched by the addition of sat. aq. NH₄Cl (5 mL), and the resulting mixture was partitioned between EtOAc (50 mL) and half-sat. aq. NH₄Cl (15 mL). The organic layer was separated, washed with brine (10 mL), dried over sodium sulfate, filtered, and concentrated in vacuo. Chromatographic purification of the residue (ISCO, 12 g, 0 to 10% MeOH/DCM) furnished N,N-bis(4-methoxybenzyl)-6-(2-(6-methoxypyridin-3-ylamino)-5-((4-(methylsulfonyl)piperazin-1-yl)methyl)pyridin-3-yl)-2-methylpyrimidin-4-amine (137.7 mg, 0.190 mmol, 95% yield) as a brown solid. ¹H NMR (400 MHz, CDCl₃) δ 11.67 (br. s., 1H); 8.36 (d, J=2.54 Hz, 1H); 8.06-8.11 (m, 2H); 7.54 (br. s., 1H); 7.18 (d, J=7.43 Hz, 4H); 6.84-6.90 (m, 4H); 6.75 (d, J=8.80 Hz, 1H); 6.56 (s, 1H); 4.77 (br. s., 4H); 3.93 (s, 3H); 3.80 (s, 6H); 3.42 (br. s., 2H); 3.19 (br. s., 4H); 2.76 (s, 3H); 2.65 (s, 3H); 2.50 (br. s., 4H). m/z (ESI, +ve ion) 561.2 (M-piperazine sulfonamide)⁺.

Step 4: 6-(2-(6-methoxypyridin-3-ylamino)-5-((4-(methylsulfonyl)piperazin-1-yl)methyl)pyridin-3-yl)-2-methylpyrimidin-4-amine A solution of N,N-bis(4-methoxybenzyl)-6-(2-(6-methoxypyridin-3-ylamino)-5-((4-(methylsulfonyl)piperazin-1-yl)methyl)pyridin-3-yl)-2-methylpyrimidin-4-amine (137.7 mg, 0.190 mmol) and trifluoromethanesulfonic acid (50 µL, 0.563 mmol) in TFA (2.5 mL) was stirred at 80° C. for 2.5 h. The mixture was subsequently cooled to 25° C. and concentrated in vacuo. Sat. aq. NaHCO₃ (25 mL) was carefully added to the residue (final pH about 8). The resulting suspension was sonicated for 2 min, and the precipitated solid was collected by vacuum filtration, washed with water (30 mL), and air-dried. The residue was taken up in MeOH, concentrated onto silica gel, and chromatographically purified (ISCO, 12 g, 0 to 10% MeOH/DCM) to yield 6-(2-(6-methoxypyridin-3-ylamino)-5-((4-(methylsulfonyl)piperazin-1-yl)methyl)pyridin-3-yl)-2-methylpyrimidin-4-amine (55.6 mg, 0.115 mmol, 60.4% yield) as a yellow solid. ¹H NMR (400 MHz, CDCl₃) δ 11.80 (br. s., 1H); 8.37 (d, J=2.74 Hz, 1H); 8.14 (d, J=1.96 Hz, 1H); 8.10 (dd, J=8.90, 2.84 Hz, 1H); 7.86 (br. s., 1H); 6.76 (d, J=8.80 Hz, 1H); 6.70 (br. s., 1H); 4.95 (br. s., 2H); 3.93 (s, 3H); 3.43-3.56 (m, 2H); 3.26 (br. s., 4H); 2.78 (s, 3H); 2.63 (s, 3H); 2.58 (br. s., 4H). m/z (ESI, +ve ion) 485.1 (M+H)⁺.

Example 179

(5-(4-amino-6-methyl-1,3,5-triazin-2-yl)-6-(6-methoxypyridin-3-ylamino)pyridin-3-yl)methanol

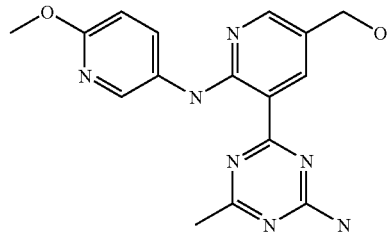 [SMILES: COc1ccc(Nc2ncc(CO)cc2-c2nc(C)nc(N)n2)cn1]

Step 1: (5-(4-(bis(4-methoxybenzyl)amino)-6-methyl-1,3,5-triazin-2-yl)-6-(6-methoxypyridin-3-ylamino)pyridin-3-yl)methanol Sodium borohydride (103 mg, 2.72 mmol) was added to a suspension of 5-(4-(bis(4-methoxybenzyl)amino)-6-methyl-1,3,5-triazin-2-yl)-6-(6-methoxypyridin-3-ylamino)nicotinaldehyde (Example 144, step 1) (522.8 mg, 0.905 mmol) in a mixture of methanol (5.0 mL) and DCM (5.0 mL) at 0° C. The resulting solution was stirred at 0° C. for 5 min and then was allowed to warm to 25° C. and stir for 45 min. Saturated aqueous ammonium chloride (10 mL) and water (20 mL) were subsequently added, and the resulting mixture was extracted with DCM (2×50 mL). The combined organic extracts were dried over sodium sulfate, filtered, and concentrated in vacuo to provide (5-(4-(bis(4-methoxybenzyl)amino)-6-methyl-1,3,5-triazin-2-yl)-6-(6-methoxypyridin-3-ylamino)pyridin-3-yl)methanol (504.5 mg, 0.870 mmol, 96% yield) as a yellow-orange solid. m/z (ESI, +ve ion) 580.2 (M+H)⁺.

Step 2: (5-(4-amino-6-methyl-1,3,5-triazin-2-yl)-6-(6-methoxypyridin-3-ylamino)pyridin-3-yl)methanol A solution of (5-(4-(bis (4-methoxybenzyl)amino)-6-methyl-1,3,5-triazin-2-yl)-6-(6-methoxypyridin-3-ylamino)pyridin-3-yl)methanol (100.7 mg, 0.174 mmol) and trifluoromethanesulfonic acid (0.07 mL, 0.788 mmol) in 2,2,2-trifluoroacetic acid (3.5 mL) was stirred at 75° C. for 1 h. The mixture was subsequently cooled to 25° C. and concentrated in vacuo. NaOH (1.0 N, aq.; 2.0 mL) was added, followed by MeOH (1.0 mL) (final pH>10), and the resulting mixture was stirred at 25° C. for 5 min. MeOH was removed in vacuo, and the resulting mixture was vacuum filtered. The collected solid was sequentially washed with water (20 mL) and ethyl ether (6 mL) and then dried in vacuo. Chromatographic purification of this solid (ISCO, 4 g, 0 to 10% MeOH/DCM) furnished (5-(4-amino-6-methyl-1,3,5-triazin-2-yl)-6-(6-methoxypyridin-3-ylamino)pyridin-3-yl)methanol (41.8 mg, 0.123 mmol, 70.9% yield) as a yellow solid. ¹H NMR (400 MHz, d4-MeOH) δ 8.94 (d, J=2.54 Hz, 1H); 8.48 (d, J=2.35 Hz, 1H), 8.25 (d, J=2.54 Hz, 1H); 8.07 (dd, J=8.80, 2.74 Hz, 1H);

6.85 (d, J=9.00 Hz, 1H); 4.60 (s, 2H); 3.94 (s, 3H); 3.38 (s, 2H); 2.52 (s, 3H). m/z (ESI, +ve ion) 340.1 (M+H)+.

Example 180

3-(6-amino-2-methylpyrimidin-4-yl)-N-(1H-indazol-4-yl)quinoxalin-2-amine

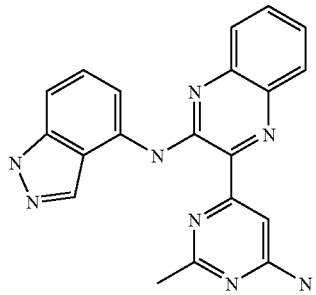 [SMILES: Cc1nc(N)cc(-c2nc3ccccc3nc2Nc2cccc3[nH]ncc23)n1]

Step 1: 4-chloro-2-methyl-6-(methylthio)pyrimidine

A mixture of 4,6-dichloro-2-methylpyrimidine (11.5 g, 70.6 mmol, Aldrich) and sodium methanethiolate (5.93 g, 85 mmol, Aldrich) in toluene (50 mL) was stirred at 25° C. for 24 h. The reaction mixture was concentrated in vacuo. The residue was diluted with EtOAc, washed with brine, and dried over Na$_2$SO$_4$. The crude product was purified by recrystallization from hexane to give 4-chloro-2-methyl-6-(methylthio)pyrimidine (5.5 g, 31.5 mmol, 44.6% yield) as white crystals. $^1$H NMR (400 MHz, CDCl$_3$) δ 7.01 (s, 1H); 2.64 (s, 3H); 2.56 (s, 3H). m/z (ESI, +ve ion) 175 (M+H)+.

Step 2: 4-iodo-2-methyl-6-(methylthio)pyrimidine

A mixture of 4-chloro-2-methyl-6-(methylthio)pyrimidine (5.3 g, 30.3 mmol) and hydriodic acid (67% solution, 5.71 mL, 76 mmol, Alfea Aesar, Avocado, Lancaster) in DCM (20 mL) was stirred at room temperature for 20 h and filtered. The collected solid was washed with DCM and then suspended in saturated NaHCO$_3$ and extracted with EtOAc (2×). The combined organic extracts were washed with brine, dried over Na$_2$SO$_4$, and concentrated to give 4-iodo-2-methyl-6-(methylthio)pyrimidine (7.3 g, 27.4 mmol, 90% yield) as a light yellow solid. $^1$H NMR (400 MHz, CDCl$_3$) δ 7.43 (s, 1H); 2.62 (s, 3H); 2.52 (s, 3H). m/z (ESI, +ve ion) 266 (M+H)+.

Step 3: 2-methyl-4-(methylthio)-6-(tributylstannyl)pyrimidine

A solution of 4-iodo-2-methyl-6-(methylthio)pyrimidine (2.35 g, 8.83 mmol) in THF (20 mL) was cooled to −78° C. and treated dropwise with isopropylmagnesium chloride (2 N solution in THF, 2 mL, 4.0 mmol, Aldrich). After 10 min, chlorotributylstannane (2.4 mL, 8.83 mmol, Aldrich) was added. The mixture was stirred at −78° C. for 1 h, then warmed to room temperature and stirred overnight. The mixture was concentrated in vacuo and purified by flash column chromatography with alumina, eluting with a gradient of 0-10% EtOAc in hexane, to give 2-methyl-4-(methylthio)-6-(tributylstannyl)pyrimidine (2.5 g, 5.82 mmol, 65.9% yield) as colorless oil. This was used as such without further purification. m/z (ESI, +ve ion) 430 (M+H)+.

Step 4: 2-chloro-3-(2-methyl-6-(methylthio)pyrimidin-4-yl)quinoxaline

A glass microwave reaction vessel was charged with 2-methyl-4-(methylthio)-6-(tributylstannyl)pyrimidine (1.6 g, 3.73 mmol), 2,3-dichloroquinoxaline (1.484 g, 7.45 mmol, Aldrich) and tetrakis(triphenylphosphine)palladium (0.431 g, 0.373 mmol, Strem Chemicals) in toluene (5 mL). Argon was bubbled through for 2 min. The reaction mixture was stirred and heated at 120° C. for 36 h. The mixture was cooled to room temperature, filtered through Celite® (diatomaceous earth) washing with 10% methanol-DCM, and the filtrate was concentrated. The crude product was purified by chromatography through a Redi-Sep pre-packed silica gel column (40 g), eluting with a gradient of 0-100% DCM-hexane to give 2-chloro-3-(2-methyl-6-(methylthio)pyrimidin-4-yl)quinoxaline (0.8 g, 2.64 mmol, 70.9% yield) as a white solid. $^1$H NMR (400 MHz, d6-DMSO) δ 8.23 (dd, J=8.02, 1.56 Hz, 1H); 8.13-8.19 (m, 1H); 7.96-8.05 (m, 2H); 7.73 (s, 1H); 2.67 (s, 3H); 2.61 (s, 3H). m/z (ESI, +ve ion) 303 (M+H)+.

Step 5: N-(1H-indazol-4-yl)-3-(2-methyl-6-(methylthio)pyrimidin-4-yl)quinoxalin-2-amine A glass microwave reaction vessel was charged with 1H-indazol-4-amine (220 mg, 1.651 mmol, Key Organics Limited/Bionet Research, United Kingdom), 1 drop of concentrated HCl, 2-chloro-3-(2-methyl-6-(methylthio)pyrimidin-4-yl)quinoxaline (250mg, 0.826 mmol), and ethanol (2 mL). The reaction mixture was stirred and heated in a Emrys Optmizer microwave reactor (Personal Chemistry, Biotage AB, Inc., Upssala, Sweden) at 160° C. for 1 h. The mixture was cooled to room temperature, then neutralized by 2 N NH$_3$ in MeOH, diluted with DCM and filterd through a Celite® (diatomaceous earth). The filtrate was concentrated in vacuo. The crude product was purified by chromatography through a Redi-Sep pre-packed silica gel column (40 g), eluting with a gradient of 0% to10% 2 M NH$_3$.MeOH in DCM to give N-(1H-indazol-4-yl)-3-(2-methyl-6-(methylthio)pyrimidin-4-yl)quinoxalin-2-amine (150 mg, 0.375 mmol, 45.5% yield) as an orange solid. $^1$H NMR (400 MHz, d6-DMSO) δ 13.23 (s, 1H); 12.59 (s, 1H); 8.50 (d, J=7.63 Hz, 1H); 8.42 (s, 1H); 8.31 (s, 1H); 8.03 (d, J=8.22 Hz, 1H); 7.74-7.85 (m, 2H); 7.59 (t, J=7.43 Hz, 1H); 7.41 (t, J=7.92 Hz, 1H); 7.27 (d, J=8.22 Hz, 1H); 2.91 (s, 3H); 2.68 (s, 3H). m/z (ESI, +ve ion) 400 (M+H)+.

Step 6: N-(1H-indazol-4-yl)-3-(2-methyl-6-(methylsulfinyl)pyrimidin-4-yl)quinoxalin-2-amine A 50 mL round-bottomed flask was charged with N-(1H-indazol-4-yl)-3-(2-methyl-6-(methylthio)pyrimidin-4-yl)quinoxalin-2-amine (150 mg, 0.375 mmol) in DCM-DMF(5:1, 6 mL). mCPBA (130 mg, 0.751 mmol, Aldrich) was added to this solution at 0° C., the mixture was stirred at 0° C. for 2 h, then warmed to room temperature and diluted with saturated NaHCO$_3$. The aqueous layer was extracted with DCM (3×), and the combined organic extracts were washed with brine, dried over MgSO$_4$, and concentrated in vacuo. The crude material was purified by chromatography through a Redi-Sep pre-packed silica gel column (40 g) eluting with a gradient of 2% to 10% 2M NH$_3$.MeOH in DCM to give N-(1H-indazol-4-yl)-3-(2-methyl-6-(methylsulfinyl)pyrimidin-4-yl)quinoxalin-2-amine (36 mg, 0.087 mmol, 23% yield) as an orange solid. m/z (ESI, +ve ion) 416 (M+H)+.

Step 7: 3-(6-amino-2-methylpyrimidin-4-yl)-N-(1H-indazol-4-yl)quinoxalin-2-amine A glass microwave reaction vessel was charged with N-(1H-indazol-4-yl)-3-(2-methyl-6-(methylsulfinyl)pyrimidin-4-yl)quinoxalin-2-amine (36 mg, 0.087 mmol) in dioxane (2 mL), ammonia was bubbled in for 5 minutes. The reaction mixture was stirred and heated at 100° C. for 4 h. More $NH_3$ was bubbled in and the mixture was heated for an additional 2 h. The mixture was cooled to room temperature and concentrated in vacuo. Prep TLC purification (5% MeOH in DCM as developed reagent) gave 3-(6-amino-2-methylpyrimidin-4-yl)-N-(1H-indazol-4-yl)quinoxalin-2-amine (10 mg, 0.027 mmol, 31.3% yield) as a yellow solid. $^1$H NMR (400 MHz, d6-DMSO) δ 13.22 (s, 2H); 8.52 (d, J=7.07 Hz, 1H); 8.31 (s, 1H); 7.95 (d, J=8.09 Hz, 1H); 7.82 (d, J=9.10 Hz, 1H); 7.72-7.80 (m, 1H); 7.64 (s, 1H); 7.55-7.62 (m, 1H); 7.34-7.46 (m, 2H); 7.26 (d, J=9.10 Hz, 1H); 2.70 (s, 3H). m/z (ESI, +ve ion) 369 (M+H)$^+$.

Example 181

N-(2-chloro-4-(3-(2-methyl-9H-purin-6-yl)pyridin-2-ylamino)phenyl)acetamide

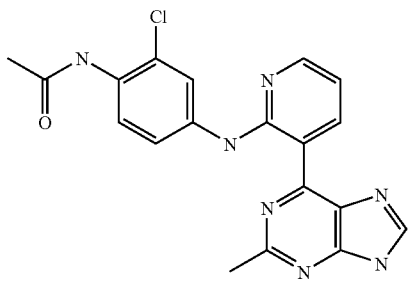 [SMILES: CC(=O)Nc1ccc(Nc2ncccc2-c2nc(C)nc3[nH]cnc23)cc1Cl]

Step 1: N-(2-chloro-4-(3-(2-methyl-9H-(tetrahydro-2H-pyran-2-yl)-9H-purin-6-yl)pyridin-2-ylamino)phenyl)acetamide A glass microwave reaction vessel was charged with 6-(2-fluoropyridin-3-yl)-2-methyl-9-(tetrahydro-2H-pyran-2-yl)-9H-purine (100 mg, 0.319 mmol) and N-(4-amino-2-chlorophenyl)acetamide (64.8 mg, 0.351 mmol, Aldrich) in THF (5 mL), argon was bubbled in for 2 min and the tube was sealed. The reaction mixture was cooled to 0° C., lithium bis(trimethylsilyl)amine (1 N in THF, 1 mL, 0.957 mmol) was added dropwise. The red solution was stirred at 0° C. for 1 h and then warmed to room temperature. The mixture was diluted with saturated $NaHCO_3$ and extracted with EtOAc (3×). The organic extract was washed with satd. NaCl and dried over $Na_2SO_4$. The solution was filtered and concentrated in vacuo. The crude material was purified by chromatography through a Redi-Sep pre-packed silica gel column (25 g) eluting with a gradient of 2% to 5% 2 M $NH_3$.MeOH in DCM to give N-(2-chloro-4-(3-(2-methyl-9-(tetrahydro-2H-pyran-2-yl)-9H-purin-6-yl)pyridin-2-ylamino)phenyl)acetamide (120 mg, 0.251 mmol, 79% yield) as a yellow solid. $^1$H NMR (400 MHz, d6-DMSO) δ 12.84 (s, 1H); 9.74 (dd, J=7.92, 1.86 Hz, 1H); 9.47 (s, 1H); 8.89 (s, 1H); 8.42 (dd, J=4.70, 1.76 Hz, 1H); 8.30 (d, J=2.35 Hz, 1H); 7.55-7.63 (m, 1H); 7.45-7.54 (m, 1H); 7.08 (dd, J=7.82, 4.69 Hz, 1H); 5.85 (dd, J=10.95, 2.15 Hz, 1H); 4.01-4.10 (m, 1H); 3.72-3.85 (m, 1H); 2.92 (s, 3H); 2.24-2.39 (m, 1H); 2.08 (s, 3H); 1.96-2.05 (m, 2H); 1.73-1.91 (m, 1H); 1.56-1.70 (m, 2H). m/z (ESI, +ve ion) 478 (M+H)$^+$.

Step 2: N-(2-chloro-4-(3-(2-methyl-9-(tetrahydro-2H-pyran-2-yl)-9H-purin-6-yl)pyridin-2-ylamino) phenyl)acetamide A mixture of N-(2-chloro-4-(3-(2-methyl-9-(tetrahydro-2H-pyran-2-yl)-9H-purin-6-yl)pyridin-2-ylamino)phenyl)acetamide (100 mg, 0.209 mmol) in DCM (3 mL) was cooled to 0° C., treated with trifluoroacetic acid (3 mL, 40.4 mmol), and the yellow solution was stirred at 0° C. for 1 h. The mixture was concentrated in vacuo, the residue was treated with 2 M $NH_3$ in MeOH and concentrated in vacuo. The crude product was purified by chromatography through a Redi-Sep pre-packed silica gel column (40 g), eluting with a gradient of 2% to 10% 2M $NH_3$.MeOH in DCM, to give N-(2-chloro-4-(3-(2-methyl-9H-purin-6-yl)pyridin-2-ylamino)phenyl)acetamide (70 mg, 0.178 mmol, 58.3% yield) as a yellow solid. $^1$H NMR (400 MHz, d6-DMSO) δ 13.62 (s, 1H); 13.01 (s, 1H); 9.80 (s, 1H); 9.47 (s, 1H); 8.38-8.43 (m, 1H); 8.31 (d, J=1.57 Hz, 1H); 7.54-7.60 (m, 1H); 7.47-7.52 (m, 1H); 7.07 (dd, J=7.82, 4.69 Hz, 1H); 2.88 (s, 3H); 2.07 (s, 3H). m/z (ESI, +ve ion) 394 (M+H)$^+$.

Example 182

N-(4-(3-(2-methyl-9H-purin-6-yl)pyridin-2-ylamino)phenyl)cyclopropanecarboxamide

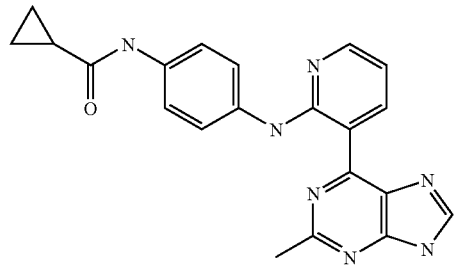 [SMILES: Cc1nc(-c2cccnc2Nc2ccc(NC(=O)C3CC3)cc2)c2nc[nH]c2n1]

Step 1: N-(4-(3-(2-methyl-9-(tetrahydro-2H-pyran-2-yl)-9H-purin-6-yl)pyridin-2-ylamino)phenyl)cyclopropanecarboxamide A glass microwave reaction vessel was charged with 6-(2-fluoropyridin-3-yl)-2-methyl-9-(tetrahydro-2H-pyran-2-yl)-9H-purine (100 mg, 0.319 mmol) and N-(4-aminophenyl)cyclopropanecarboxamide (56.2 mg, 0.319 mmol, Enamine Ltd, Ukraine) in THF (5 mL), argon was bubbled through for 2 min, and the tube was sealed. The reaction mixture was cooled to 0° C. and lithium bis(trimethylsilyl)amine (1 N in THF,1 mL, 1 mmol) was added dropwise. The red solution was stirred at 0° C. for 1 h and then warmed to room temperature. The mixture was quenched with saturated $NH_4Cl$ and extracted with EtOAc (3×). The organic extract was washed with satd NaCl and dried over $Na_2SO_4$. The solution was filtered and concentrated in vacuo. The crude material was purified by chromatography through a Redi-Sep pre-packed silica gel column (25 g) eluting with a gradient of 2% to 5% 2 M $NH_3$.MeOH in DCM to give N-(4-(3-(2-methyl-9-(tetrahydro-2H-pyran-2-yl)-9H-purin-6-yl)pyridin-2- ylamino)phenyl)cyclopropanecarboxamide (90 mg, 0.192 mmol, 60% yield) as a yellow solid. $^1$H NMR (400 MHz, d6-DMSO) δ 12.69 (s, 1H); 10.12 (s, 1H); 9.73 (dd, J=7.92, 1.86 Hz, 1H); 8.87 (s, 1H); 8.35 (dd, J=4.70, 1.76 Hz, 1H); 7.76 (d, J=9.00 Hz, 2H); 7.57 (d, J=8.80 Hz, 2H); 6.99 (dd, J=7.82, 4.69 Hz, 1H); 5.84 (dd, J=10.95, 1.76 Hz, 1H); 4.04 (d, J=12.63 Hz, 1H); 3.71-3.81 (m, 1H); 2.91 (s, 3H); 2.27-2.38 (m, 1H); 1.97-2.07 (m, 2H); 1.73-1.85 (m, 2H); 1.56-1.67 (m, 2H); 0.72-0.82 (m, 4H). m/z (ESI, +ve ion) 470 (M+H)$^+$.

Step 2: N-(4-(3-(2-methyl-9H-purin-6-yl)pyridin-2-ylamino)phenyl)cyclopropanecarboxamide A suspension of N-(4-(3-(2-methyl-9-(tetrahydro-2H-pyran-2-yl)-9H-purin-6-yl)pyridin-2-ylamino)phenyl)cyclopropanecarboxamide (80 mg, 0.170 mmol) in DCM (3 mL) was cooled to 0° C. and treated with trifluoroacetic acid (3 mL, 40.4 mmol). The yellow solution was stirred at 0° C. for 1 h. The mixture was concentrated in vacuo, the residue was neutralized with 2 M NH$_3$ in MeOH and then concentrated in vacuo. The crude product was purified by chromatography through a Redi-Sep pre-packed silica gel column (40 g) eluting with a gradient of 2% to 10% 2 M NH$_3$.MeOH in DCM to give N-(4-(3-(2-methyl-9H-purin-6-yl)pyridin-2-ylamino)phenyl)cyclopropanecarboxamide (20 mg, 0.052 mmol, 30.5% yield) as a yellow solid. $^1$H NMR (400 MHz, d6-DMSO) δ 13.47-13.72 (m, 1H); 12.82 (s, 1H); 10.10 (s, 1H); 9.78 (s, 1H); 8.59 (s, 1H); 8.33 (d, J=3.20 Hz, 1H); 7.75 (d, J=76.46 Hz, 2H); 7.58 (d, J=8.53 Hz, 2H); 6.94-7.03 (m, 1H); 2.87 (s, 3H); 1.72-1.82 (m, 4H); 0.72-0.84 (m, 4H). m/z (ESI, +ve ion) 386 (M+H)$^+$.

Example 183

N-(5-methoxypyridin-3-yl)-3-(2-methyl-9H-purin-6-yl)pyridin-2-amine

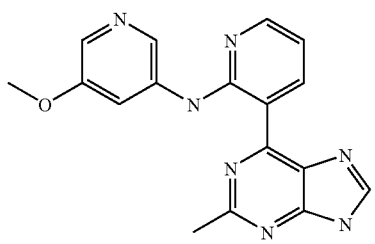 [SMILES: COc1cncc(Nc2ncccc2-c2nc(C)nc3[nH]cnc23)c1]

Step 1: N-(5-methoxypyridin-3-yl)-3-(2-methyl-9-(tetrahydro-2H-pyran-2-yl)-9H-purin-6-yl)pyridin-2-amine Argon was bubbled for 2 min through a glass microwave reaction vessel containing 6-(2-fluoropyridin-3-yl)-2-methyl-9-(tetrahydro-2H-pyran-2-yl)-9H-purine (100 mg, 0.319 mmol) and 5-methoxypyridin-3-amine (47.5 mg, 0.383 mmol, Astatech, Inc, Bristol, Pa.) in THF (5 mL), and the tube was sealed. The reaction mixture was cooled to 0° C. and lithium bis(trimethylsilyl)amine (1 N in THF, 1 mL, 0.957 mmol) was added dropwise. The red solution was stirred at 0° C. for 1 h and then warmed to room temperature. The mixture was quenched with saturated NH$_4$Cl and extracted with EtOAc (3×). The combined organic extracts were washed with satd. NaCl and dried over Na$_2$SO$_4$. The solution was filtered and concentrated in vacuo. The crude product was purified by chromatography through a Redi-Sep pre-packed silica gel column (25 g) eluting with a gradient of 2% to 5% 2 M NH$_3$.MeOH in DCM to give N-(5-methoxypyridin-3-yl)-3-(2-methyl-9-(tetrahydro-2H-pyran-2-yl)-9H-purin-6-yl)pyridin-2-amine (60 mg, 0.144 mmol, 45.0% yield) as an orange solid. m/z (ESI, +ve ion) 418 (M+H)$^+$.

Step 2: N-(5-methoxypyridin-3-yl)-3-(2-methyl-9H-purin-6-yl)pyridin-2-amine

A suspension of N-(5-methoxypyridin-3-yl)-3-(2-methyl-9-(tetrahydro-2H-pyran-2-yl)-9H-purin-6-yl)pyridin-2-amine (60 mg, 0.144 mmol) in DCM (3 mL) was cooled to 0° C., treated with trifluoroacetic acid (3 mL, 40.4 mmol), and the yellow solution was stirred at 0° C. for 1 h. The mixture was concentrated in vacuo, the residue was neutralized with 2 M NH$_3$ in MeOH and then concentrated in vacuo. The crude product was purified by chromatography through a Redi-Sep pre-packed silica gel column (40 g) eluting with a gradient of 2% to 10% 2 M NH$_3$.MeOH in DCM to give N-(5-methoxypyridin-3-yl)-3-(2-methyl-9H-purin-6-yl)pyridin-2-amine (30 mg, 0.090 mmol, 62.6% yield) as a yellow solid. $^1$H NMR (400 MHz, d6-DMSO) δ 13.66 (s, 1H); 13.09 (s, 1H); 9.84 (dd, J=7.82, 1.56 Hz, 1H); 8.63 (s, 1H); 8.46 (d, J=1.76 Hz, 1H); 8.41 (dd, J=4.69, 1.76 Hz, 1H); 8.20 (s, 1H); 7.95 (d, J=2.54 Hz, 1H); 7.10 (dd, J=7.82, 4.69 Hz, 1H); 3.87 (s, 3H); 2.89 (s, 3H). m/z (ESI, +ve ion) 334 (M+H)$^+$.

Example 184

4-(5-chloro-2-(6-methoxypyridin-3-ylamino)pyridin-3-yl)-6-methyl-1,3,5-triazin-2-amine

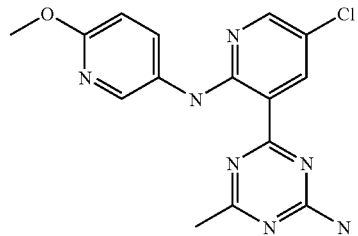 [SMILES: COc1ccc(Nc2ncc(Cl)cc2-c2nc(C)nc(N)n2)cn1]

Step 1: 4-(5-chloro-2-fluoropyridin-3-yl)-N,N-bis(4-methoxybenzyl)-6-methyl-1,3,5-triazin-2-amine A mixture of 5-chloro-2-fluoropyridin-3-ylboronic acid (1220 mg, 6.96 mmol) (Asymchem Laboratories, Inc.), 4-chloro-N,N-bis(4-methoxybenzyl)-6-methyl-1,3,5-triazin-2-amine (2300 mg, 5.98 mmol), and potassium acetate (1200 mg, 12.23 mmol) in dioxane (10 mL)-water (2.0 mL) was placed in a 100 mL flask under argon. A-Phos-PdCl$_2$ (150 mg, 0.212 mmol) was added and the mixture was heated to 95° C. under nitrogen. After 2 h, more boronic acid (600 mg) was added and the mixture was heated for another hour. The mixture was cooled to rt. Saturated NH$_4$Cl was added. The mixture was partitioned between water (5 mL) and EtOAc (30 mL). The organic layer was dried over Na$_2$SO$_4$ and concentrated. The residue was purified on silica gel using 10-50% EtOAc in hexane to give the desired product as a light yellow solid (2.3 g). LCMS (ES, pos.): calcd for C$_{25}$H$_{23}$ClFN$_5$O$_2$: 479.2; found: 480.1 (M+H)$^+$. $^1$H NMR (400 MHz, CDCl$_3$) δ 8.53 (dd, J=8.02, 2.74 Hz, 1H); 8.25 (d, J=1.37 Hz, 1H); 7.21

(d, J=8.41 Hz, 4H); 6.86 (t, J=8.22 Hz, 4H); 4.81 (d, J=7.24 Hz, 4H); 3.80 (2s, 6H); 2.54 (s, 3H).

Step 2: 4-(5-chloro-2-(6-methoxypyridin-3-ylamino) pyridin-3-yl)-N,N-bis(4-methoxybenzyl)-6-methyl-1,3,5-triazin-2-amine LiHMDS (1 M in THF, 1250 µL, 1.250 mmol) was added to a solution of 5-amino-2-methoxypyridine (123 mg, 0.990 mmol) and 4-(5-chloro-2-fluoropyridin-3-yl)-N,N-bis(4-methoxybenzyl)-6-methyl-1,3,5-triazin-2-amine (190 mg, 0.396 mmol) in THF (5 mL) under nitrogen at rt. A dark orange mixture formed. After 2 h, HCl (5 N, 0.3 mL) was added. The mixture was partitioned between EtOAc-water (10 mL each). The aqueous layer was extracted 3× with EtOAc. The combined organic layers were washed with water 3×, NaHCO$_3$ (satd), dried over MgSO$_4$, and concentrated. The residue was purified on silica (10-80% EtOAc in hexane) to give a yellow oil which, upon trituration with MeOH, resulted in a yellow solid (110 mg). LCMS (ES, pos.): calcd for C$_{31}$H$_{30}$ClN$_7$O$_3$: 583.2; found: 584.1 (M+H)$^+$. $^1$H NMR (400 MHz, CDCl$_3$) δ 11.64 (s, 1H); 8.73 (d, J=2.74 Hz, 1H); 8.25 (d, J=2.54 Hz, 1H); 8.19 (d, J=2.74 Hz, 1H); 7.83 (dd, J=9.00, 2.74 Hz, 1H); 7.19 (dd, J=16.43, 8.61 Hz, 4H); 6.78-6.92 (m, 4H); 6.70 (d, J=8.80 Hz, 1H); 4.86 (s, 2H); 4.81 (s, 2H); 3.92 (s, 3H); 3.80 (d, J=9.19 Hz, 6H); 2.57 (s, 3H).

Step 3: 4-(5-chloro-2-(6-methoxypyridin-3-ylamino) pyridin-3-yl)-6-methyl-1,3,5-triazin-2-amine A solution of 4-(5-chloro-2-(6-methoxypyridin-3-ylamino)pyridin-3-yl)-N,N-bis(4-methoxybenzyl)-6-methyl-1,3,5-triazin-2-amine (110 mg, 0.188 mmol) in TFA (10 mL) was heated at 80° C. for 16 h. The orange mixture was concentrated to a slurry, diluted with saturated NaHCO$_3$ (5 mL), and filtered. The solid was washed with water, MeOH, and (3:1) hexane-EtOAc to give the product as a brown solid (65 mg). LCMS (ES, pos.): calcd for C$_{15}$H$_{14}$ClN$_7$O: 343.1. found: 344.1 (M+H)$^+$. $^1$H NMR (400 MHz, d6-DMSO) δ 11.69 (br. s., 1H); 8.72 (br. s., 1H); 8.50 (d, J=3.33 Hz, 1H); 8.31 (br. s., 1H); 8.09 (br. s., 1H); 7.94 (br. s., 1H); 7.80 (br. s., 1H); 6.84 (br. s., 2H); 3.85 (br. s., 3H); 2.43 (br. s., 3H).

Example 185

4-(5-fluoro-2-(5-fluoro-6-methoxypyridin-3-ylamino)pyridin-3-yl)-6-methyl-1,3,5-triazin-2-amine

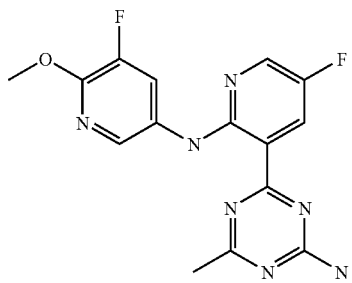 [SMILES: COc1ncc(Nc2ncc(F)cc2-c2nc(C)nc(N)n2)cc1F]

Step 1: 4-(2-chloro-5-fluoropyridin-3-yl)-N,N-bis(4-methoxybenzyl)-6-methyl-1,3,5-triazin-2-amine A mixture of 2-chloro-5-fluoropyridine-3-boronic acid (470 mg, 2.68 mmol) (Asymchem Laboratories, Inc.), 4-chloro-N,N-bis(4-methoxybenzyl)-6-methyl-1,3,5-triazin-2-amine (780 mg, 2.027 mmol), and potassium acetate (460 mg, 4.69 mmol) in dioxane (10 mL)-water (2 mL) was sparged with nitrogen for 10 min. Pd(Ph$_3$P)$_4$ (2342 mg, 2.027 mmol) was added. The mixture was heated at 100° C. for 60 min. The mixture was cooled to rt and diluted with EtOAc (100 mL) and water (30 mL). The organic phase was washed with water (2×20 mL) and filtered through a pad of MgSO$_4$. The organic residue was loaded onto a silica cartridge and eluded with 1:3 EtOAc-hexane to give the product (380 mg) contaminated with a small amount of Ph$_3$P. LCMS (ES, pos.): calcd for C$_{25}$H$_{23}$ClFN$_5$O$_2$: 479.2; found: 480.1 (M+H)$^+$. $^1$H NMR (400 MHz, CDCl$_3$) δ 8.33 (d, J=2.93 Hz, 1H); 7.94 (dd, J=8.02, 2.93 Hz, 1H); 7.20 (dd, J=15.45, 8.41 Hz, 4H); 6.86 (dd, J=12.13, 8.61 Hz, 4H); 4.81 (d, J=2.15 Hz, 4H); 3.81 (s, 3H); 3.80 (s, 3H); 2.55 (s, 3H).

Step 2: 4-(2-chloro-5-fluoropyridin-3-yl)-6-methyl-1,3,5-triazin-2-amine

A solution of 4-(2-chloro-5-fluoropyridin-3-yl)-N,N-bis(4-methoxybenzyl)-6-methyl-1,3,5-triazin-2-amine (570 mg, 1.188 mmol) in TFA (10 mL) was treated with TfOH (0.2 mL) and the mixture was heated to 80° C. After 24 h, the mixture was cooled to rt. Water (10 mL) was added. The mixture was filtered and the bluish solid was washed with water (3×5 mL). The aqueous phase was slowly neutralized with solid LiOH until pHabout8. The resulting slurry was filtered to give a white solid (85 mg). The filtrate was saturated with NaCl and the resulting slurry was filtered to give additional product (100 mg). LCMS (ES, pos.): calcd for C$_9$H$_7$ClFN$_5$: 239.0; found: 240.0 (M+H)$^+$. $^1$H NMR (400 MHz, d6-DMSO) δ 8.60 (d, J=2.74 Hz, 1H); 8.04-8.14 (m, 1H); 7.74 (br. s., 2H); 2.37 (s, 3H).

Step 3: 4-(5-fluoro-2-(5-fluoro-6-methoxypyridin-3-ylamino)pyridin-3-yl)-6-methyl-1,3,5-triazin-2-amine A solution of 4-(2-chloro-5-fluoropyridin-3-yl)-6-methyl-1,3,5-triazin-2-amine (100 mg, 0.417 mmol) and 5-fluoro-6-methoxypyridin-3-amine (120 mg, 0.844 mmol) (Anichem, NJ, USA) in THF (2.0 mL) was cooled in an ice bath under nitrogen. A THF solution of LiHMDS (1 M in THF, 2500 µL, 2.500 mmol) was added dropwise. After 5 min, the cooling bath was removed. After a total of 22 min, HCl (5 N, 0.5 mL) was added. After 5 min, EtOAc (10 mL) and saturated NH$_4$Cl (10 mL) were added. The organic layer was washed with water (2×5 mL). The combined aqueous layers were extracted with EtOAc (2×5 mL). The combined organic layers were dried over Na$_2$SO$_4$ and concentrated. The resulting residue was suspended in MeOH (5 mL) and filtered. The solid was washed with MeOH (2×2 mL), DCM (3×3 mL) and EtOAc (3×3 mL) to give the first batch of product as a brown solid. The combined washings were concentrated and purified on silica using 0-3% MeOH in DCM. The dark blue fraction contained the desired product (m/z 346) as a second batch. The combined product batches was suspended in ether (4 mL) and filtered to give the final product as a green solid (60 mg). LCMS (ES, pos.): calcd for C$_{15}$H$_{13}$F$_2$N$_7$O: 345.1. found: 346.2 (M+H)$^-$. $^1$H NMR (400 MHz, d6-DMSO) δ 11.78 (s, 1H); 8.56 (dd, J=9.78, 2.93 Hz, 1H); 8.38 (br. s., 2H); 8.28 (dd, J=12.81, 1.86 Hz, 1H); 7.97 (br. s., 1H); 7.84 (br. s., 1H);

3.93 (s, 3H); 2.44 (s, 3H). $^{19}$F NMR (377 MHz, d6-DMSO) δ −140.84 (s, 1 F); −139.70 (s, 1 F).

Example 186

4-(5-fluoro-2-(5-fluoropyridin-3-ylamino)pyridin-3-yl)-6-methyl-1,3,5-triazin-2-amine

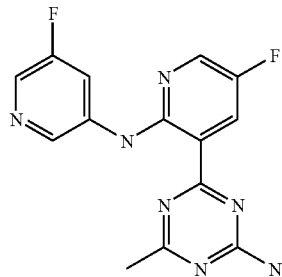 [SMILES: Cc1nc(N)nc(-c2cc(F)cnc2Nc2cncc(F)c2)n1]

A solution of 4-(2-chloro-5-fluoropyridin-3-yl)-6-methyl-1,3,5-triazin-2-amine (85 mg, 0.355 mmol) and 3-amino-5-fluoropyridine (118 mg, 1.053 mmol) in THF (3 mL) was cooled in an ice bath under nitrogen. After 5 min, a solution of LiHMDS (1 M in THF, 2500 µL, 2.500 mmol) was added. After 10 min, the cooling bath was removed. After 2 h, HCl (5 N, 0.5 mL) was added. EtOAc (10 mL) and saturated NH$_4$Cl (10 mL) were added. The mixture was vigorously stirred for 15 min. The resulting emulsion was filtered through a glass frit. The collected solid was dissolved in warm DMSO and purified by prep HPLC (30-75% MeCN/water/w 0.1% TFA over 20min). The collected product fractions were concentrated to dryness. Saturated NaHCO$_3$ (10 mL) was added. The mixture was neutralized with HCl (5 N) and filtered. The filtrate was extracted with iPrOH (5%) in CHCl$_3$ (3×5 mL). The combined organic layers were dried over Na$_2$SO$_4$ and concentrated to a yellow solid which was filtered as a suspension in ether to give the product as a yellow powder (18 mg). LCMS (ES, pos.): calcd for C$_{14}$H$_{11}$F$_2$N$_7$: 315.1; found: 316.1 (M+H)$^+$. $^1$H NMR (400 MHz, d6-DMSO) δ 12.18 (s, 1H); 8.82 (s, 1H); 8.62 (dd, J=9.78, 3.13 Hz, 1H); 8.44-8.53 (m, 2H); 8.18 (d, J=2.54 Hz, 1H); 8.04 (br. s., 1H); 7.90 (br. s., 1H); 2.46 (s, 3H). $^{19}$F NMR (377 MHz, d6-DMSO) δ −139.21 (s, 1 F); −127.41 (s, 1 F).

Example 187

5-(4-amino-6-methyl-1,3,5-triazin-2-yl)-6-(5-fluoro-6-methoxypyridin-3-ylamino)nicotinaldehyde

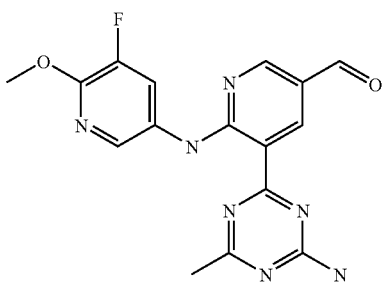 [SMILES: COc1ncc(Nc2ncc(C=O)cc2-c2nc(C)nc(N)n2)cc1F]

A solution of 5-(4-(bis(4-methoxybenzyl)amino)-6-methyl-1,3,5-triazin-2-yl)-6-(5-fluoro-6-methoxypyridin-3-ylamino)nicotinaldehyde (380 mg, 0.638 mmol) in DCM (5 mL) was treated with TFA (6.0 mL, 78 mmol) and then TfOH (0.050 mL, 0.563 mmol). The solution was heated at 80° C. under a condenser. After 2.5 h, more TfOH (0.050 mL, 0.563 mmol) was added. After 24 h, the mixture was concentrated. The residue was azeotroped with toluene (10 mL) once. The mixture was suspended in 1:1 DMSO-water (5 mL each) and filtered. The resulting solid was then suspended in saturated NaHCO$_3$ for several hours and filtered. The mother liquor was discarded. The resulting sludge was dissolved in hot DMSO and filtered. The filtrate was diluted with MeOH (2× v/v) and allowed to settle. The resulting suspension was filtered. The resulting solid was again dissolved in hot DMSO and diluted with MeOH. After 3 repetitions, the solid was about 95% pure product (50 mg). LCMS (ES, pos.): calcd for C$_{16}$H$_{14}$FN$_7$O$_2$: 355.1; found: 356.2 (M+H)$^+$. $^1$H NMR (400 MHz, d6-DMSO) δ 12.47 (br. s., 1H); 9.92 (s, 1H); 9.17 (br. s., 1H); 8.81 (br. s., 1H); 8.42 (br. s., 1H); 8.32 (d, J=13.11 Hz, 1H); 8.01 (br. s., 1H); 7.85 (d, J=0.78 Hz, 1H); 3.96 (s, 3H); 2.46 (br. s., 3H). $^{19}$F NMR (377 MHz, d6-DMSO) δ −139.31 (d, J=11.44 Hz, 1 F).

Example 188

4-(5-chloro-2-(tetrahydro-2H-pyran-4-ylamino)pyridin-3-yl)-6-methyl-1,3,5-triazin-2-amine

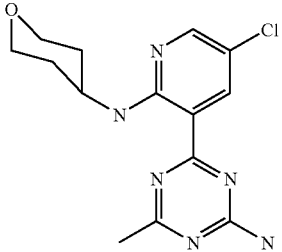 [SMILES: Cc1nc(N)nc(-c2cc(Cl)cnc2NC2CCOCC2)n1]

Step 1: 4-(5-chloro-2-(tetrahydro-2H-pyran-4-ylamino)pyridin-3-yl)-N,N-bis(4-methoxybenzyl)-6-methyl-1,3,5-triazin-2-amine A mixture of tetrahydro-2H-pyran-4-amine (130 mg, 1.285 mmol), 4-(5-chloro-2-fluoropyridin-3-yl)-N,N-bis(4-methoxybenzyl)-6-methyl-1,3,5-triazin-2-amine (345 mg, 0.719 mmol), and cesium carbonate (165 mg, 0.506 mmol) in THF (2.5 mL) was heated under microwave irradiation (100° C., 15 min; 120° C., 2×15 min). The mixture was partitioned between EtOAc (10 mL) and water (5 mL). The organic layer was washed with water, saturated NH$_4$Cl, dried over Na$_2$SO$_4$ and concentrated. The resulting solid was triturated with hot MeOH (10 mL) to give a yellow solid (300 mg). LCMS (ES, pos.): calcd for C$_{30}$H$_{33}$ClN$_6$O$_3$: 560.2; found: 561.2 (M+H)$^+$. $^1$H NMR (400 MHz, CDCl$_3$) δ 9.48 (d, J=7.24 Hz, 1H); 8.67 (d, J=2.54 Hz, 1H); 8.13 (d, J=2.54 Hz, 1H); 7.18 (t, J=9.10 Hz, 4H); 6.87 (d, J=8.61 Hz, 4H); 4.82 (s, 2H); 4.77 (s, 2H); 4.17-4.29 (m, 1H); 3.91 (dt, J=11.74, 3.62 Hz, 2H); 3.81 (s, 3H); 3.80 (s, 3H); 3.55 (td, J=11.25, 1.96 Hz, 2H); 2.52 (s, 3H); 1.96 (br. s., 2H); 1.33-1.48 (m, 2H).

Step 2: 4-(5-chloro-2-(tetrahydro-2H-pyran-4-ylamino)pyridin-3-yl)-6-methyl-1,3,5-triazin-2-amine A solution of 4-(5-chloro-2-(tetrahydro-2H-pyran-4-ylamino)pyridin-3-yl)-N,N-bis(4-methoxybenzyl)-6-methyl-1,3,5-triazin-2-amine (190 mg, 0.339 mmol) in TFA (5000 μL, 64.9 mmol), and TfOH (100 μL, 1.126 mmol) was heated at 80° C. for 3 h. The mixture was concentrated and stirred with saturated NaHCO$_3$ (10 mL) for 30 min. The suspension was filtered and washed with water (2×5 mL). The resulting solid was briefly rinsed with DCM (5 mL) and EtOAc (5 mL) to give the product as a yellow solid (68 mg). LCMS (ES, pos.): calcd for C$_{14}$H$_{12}$ClN$_6$O: 320.1. found: 321.2 (M+H)$^+$. $^1$H NMR (400 MHz, d6-DMSO) δ 9.61 (d, J=7.24 Hz, 1H); 8.58 (d, J=2.15 Hz, 1H); 8.23 (d, J=2.15 Hz, 1H); 7.68 (d, J=17.41 Hz, 2H); 4.21 (br. s., 1H); 3.88 (d, J=11.54 Hz, 2H); 3.47 (t, J=10.66 Hz, 2H); 2.38 (s, 3H); 1.92 (d., J=11.932H); 1.64 (q, J=9.59 Hz, 2H).

Example 189

4-(5-chloro-2-(5-fluoro-6-methoxypyridin-3-ylamino)pyridin-3-yl)-N-(2-methoxyethyl)-6-methyl-1,3,5-triazin-2-amine

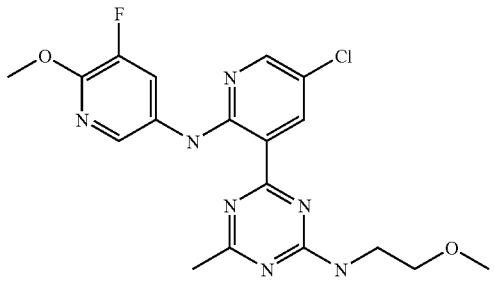

Step 1: 4-chloro-N-(2-methoxyethyl)-6-methyl-1,3,5-triazin-2-amine 2-methoxyethanamine (Aldrich, 0.350 g, 4.66 mmol) was added to a solution of 2,4-dichloro-6-methyl-1,3,5-triazine (0.80 g, 4.88 mmol) in dioxane (10 mL). Heat was generated. Hünig's base (1.0 mL, 5.73 mmol) was added and the mixture was stirred for 5 min. The mixture was partitioned between DCM (15 mL) and water. The organic phase was dried over Na$_2$SO$_4$ and concentrated. The resulting yellow oil was purified by chromatography on silica using EtOAc in hexane (20-80%) to give the desired product as a yellow solid (300 mg). LCMS (ES, pos.): calcd for C$_2$H$_{11}$ClN$_4$O: 202.1. found: 203.0 (M+H)$^+$. $^1$H NMR (400 MHz, CDCl$_3$) δ 5.93 (br. s., 1H); 3.60-3.70 (m, 2H); 3.49-3.58 (m, 2H); 3.38 (s, 3H); 2.42 (d, 3H).

Step 2: 4-(5-chloro-2-fluoropyridin-3-yl)-N-(2-methoxyethyl)-6-methyl-1,3,5-triazin-2-amine A mixture of 4-chloro-N-(2-methoxyethyl)-6-methyl-1,3,5-triazin-2-amine (300 mg, 1.480 mmol), 5-chloro-2-fluoropyridin-3-ylboronic acid (320 mg, 1.825 mmol), potassium acetate (298 mg, 3.04 mmol), and Am-phos PdCl$_2$ (47 mg, 0.066 mmol) in dioxane (10 mL) was heated at 100° C. under nitrogen. After 6 h, the mixture was cooled to rt and partitioned between water (10 mL) and EtOAc (20 mL). The organic layer was dried over Na$_2$SO$_4$ and concentrated. The oil was purified on silica using EtOAc in hexane (10-80%) to give the product as a yellow solid (130 mg). LCMS (ES, pos.): calcd for C$_{12}$H$_{13}$ClN$_5$O: 297.1. found: 298.1 (M+H)$^+$. $^1$H NMR (400 MHz, CDCl$_3$) δ 8.55 (ddd, J=16.24, 7.92, 2.64 Hz, 1H); 8.27 (br. s., 1H); 5.91 (br. s., 1H); 3.72 (quin, J=5.62 Hz, 2H); 3.59 (t, J=5.09 Hz, 2H); 3.40 (2s, 3H); 2.51 (2s, 3H).

Step 3: 4-(5-chloro-2-(5-fluoro-6-methoxypyridin-3-ylamino)pyridin-3-yl)-N-(2-methoxyethyl)-6-methyl-1,3,5-triazin-2-amine A mixture of 5-fluoro-6-methoxypyridin-3-amine (Anichem, N.J., USA, 100 mg, 0.704 mmol) and 4-(5-chloro-2-fluoropyridin-3-yl)-N-(2-methoxyethyl)-6-methyl-1,3,5-triazin-2-amine (130 mg, 0.437 mmol) in THF (5 mL) was cooled in an ice bath and LiHMDS (1.0 M, 1500 μL, 1.500 mmol) was added under nitrogen. After 5 min, the cooling bath was removed. After 10 min, the mixture was neutralized with HCl (5 N, 0.3 mL) and then partitioned between EtOAc (20 mL) and water (10 mL). The organic layer was washed with water (5 mL). The combined aqueous layers were extracted with EtOAc (2×5 mL). The combined organic layers were dried over Na$_2$SO$_4$ and concentrated. The resulting solid was triturated with EtOAc (5 mL) and filtered. The yellow solid was rinsed with ether (2×3 mL) to give the desired product as a yellow powder (115 mg). LCMS (ES, pos.): calcd for C$_{18}$H$_{19}$ClFN$_7$O$_2$: 419.1; found: 420.2 (M+H)$^+$. $^1$H NMR (400 MHz, d6-DMSO) mixture of rotamers δ 11.89, 11.67 (s, 1H); 8.73 (dd, J=6.75, 2.64 Hz, 1H); 8.14-8.58 (m, 4H); 3.94 (2s, 3H); 3.46-3.65 (m, 4H); 3.23, 3.29 (s, 3H); 2.46, 2.47 (s, 3H). $^{19}$F NMR (377 MHz, d6-DMSO) δ −139.65 (s); 139.26 (s).

Example 190

1-(5-(3-(4-amino-6-methyl-1,3,5-triazin-2-yl)pyridin-2-ylamino)pyridin-2-yl)-3-phenylurea

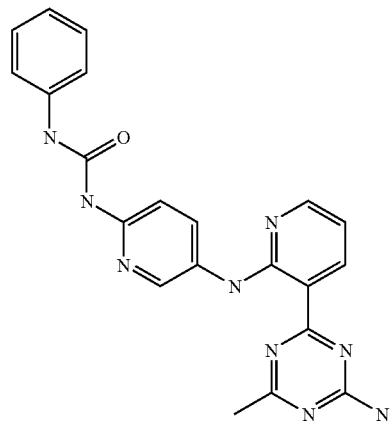 [SMILES: Cc1nc(N)nc(-c2cccnc2Nc2ccc(NC(=O)Nc3ccccc3)nc2)n1]

Step 1: tert-butyl 5-nitropyridin-2-ylcarbamate

A solution of 5-nitropyridin-2-amine (Aldrich) (3.05 g, 21.9 mmol), di-tert-butyl dicarbonate (Fluka) (5.76 g, 26.4 mmol) and N,N-dimethylpyridin-4-amine (Aldrich) (0.272 g, 2.23 mmol) in DCM (50 mL) was stirred at rt for 1 h. EtOAc was added and the resulting precipitate was collected and washed with DCM. The filtrate and wash were combined and concentrated, then EtOAc was added to the residue to induce more precipitate. The precipitates were combined to give tert-butyl 5-nitropyridin-2-ylcarbamate (3.52 g, 67% yield) as a yellow solid. $^1$H NMR (300 MHz, d6-DMSO) δ 10.70 (s, 1H); 9.09 (d, J=2.19 Hz, 1H); 8.54 (dd, J=9.35, 2.63 Hz, 1H); 8.02 (d, J=9.35 Hz, 1H); 1.50 (s, 9H).

Step 2: tert-butyl 5-aminopyridin-2-ylcarbamate

A mixture of tert-butyl 5-nitropyridin-2-ylcarbamate (3.76 g, 15.7 mmol) and Pd/C (Aldrich) (0.588 g, 5.52 mmol) in EtOH (100 mL) was evacuated under vacuum and refilled with hydrogen (6 times). The mixture was hydrogenated under balloon pressure of hydrogen at rt for 2.5 h. The reaction mixture was filtered through a pad of Celite® (diatomaceous earth) (eluent:EtOH) and concentrated to give tert-butyl 5-aminopyridin-2-ylcarbamate (3.22 g, 98% yield) as a cream color solid. $^1$H NMR (300 MHz, d6-DMSO) δ 9.06 (s, 1H); 7.62 (d, J=1.75 Hz, 1H); 7.40 (d, J=8.62 Hz, 1H); 6.94 (dd, J=8.70, 2.27 Hz, 1H); 4.93 (s, 2H); 1.44 (s, 9H). m/z (ESI, +ve ion) 210.2 (M+H)$^+$.

Step 3: tert-butyl 5-(3-(4-(bis(4-methoxybenzyl)amino)-6-methyl-1,3,5-triazin-2-yl)pyridin-2-ylamino)pyridin-2-ylcarbamate 4-(2-Fluoropyridin-3-yl)-N,N-bis(4-methoxybenzyl)-6-methyl-1,3,5-triazin-2-amine (0.150 g, 0.337 mmol) and tert-butyl 5-aminopyridin-2-ylcarbamate (0.0841 g, 0.402 mmol) were dissolved in THF (3 mL). The mixture was cooled to 0° C. and LiHMDS (Acros) (1.4 mL, 1.4 mmol) was added slowly. The dark red mixture was stirred at 0° C. for 1 h. The reaction mixture was partitioned between saturated aqueous ammonium chloride (20 mL) and EtOAc (20 mL). The aqueous phase was extracted with EtOAc (2×20 mL). The combined organic phases were dried over sodium sulfate, filtered and concentrated in vacuo. The crude product was purified by silica gel column chromatography (25 g, eluent: EtOAc in hexanes 0%-50%) to give tert-butyl 5-(3-(4-(bis(4-methoxybenzyl)amino)-6-methyl-1,3,5-triazin-2-yl)pyridin-2-ylamino)pyridin-2-ylcarbamate (0.145 g, 68% yield) as a yellow solid. $^1$H NMR (300 MHz, CDCl$_3$) δ 11.83 (s, 1H); 8.76-8.87 (m, 1H); 8.39-8.48 (m, 1H); 8.25-8.34 (m, 1H); 7.91-8.03 (m, 1H); 7.76-7.87 (m, 1H); 7.10-7.24 (m, 5H); 6.86 (t, J=7.09 Hz, 4H); 6.70-6.81 (m, 1H); 4.83 (br. s., 4H); 3.80 (d, J=5.70 Hz, 6H); 2.58 (s, 3H); 1.53 (s, 9H). m/z (ESI, +ve ion) 635.0 (M+H)$^+$.

Step 4: N5-(3-(4-(bis(4-methoxybenzyl)amino)-6-methyl-1,3,5-triazin-2-yl)pyridin-2-yl)pyridine-2,5-diamine A solution of tert-butyl 5-(3-(4-(bis(4-methoxybenzyl)amino)-6-methyl-1,3,5-triazin-2-yl)pyridin-2-ylamino)pyridin-2-ylcarbamate (0.145 g, 0.228 mmol) and TFA (Aldrich) (1.0 mL, 13 mmol) in DCM (3 mL) was stirred at rt for 1 h. The reaction mixture was partitioned between saturated aqueous sodium bicarbonate (40 mL) and DCM (20 mL). The aqueous phase was extracted with 25% iPrOH in CHCl$_3$+1% NH$_4$OH (2×40 mL). The combined organic phases were dried over sodium sulfate, filtered and concentrated in vacuo. The crude product was purified by silica gel chromatography (25 g, eluent: iPrOH (w/10% NH$_4$OH) in CHCl$_3$ 0%-10%) to give N5-(3-(4-(bis(4-methoxybenzyl)amino)-6-methyl-1,3,5-triazin-2-yl)pyridin-2-yl)pyridine-2,5-diamine (0.116 g, 95%) as an orange solid. $^1$H NMR (300 MHz, CDCl$_3$) δ 11.51 (s, 1H); 8.80 (dd, J=7.67, 1.53 Hz, 1H); 8.18-8.33 (m, 1H); 8.12 (d, J=1.75 Hz, 1H); 7.78 (dd, J=8.70, 2.27 Hz, 1H); 7.19 (t, J=8.84 Hz, 4H); 6.85 (t, J=8.84 Hz, 4H); 6.70 (dd, J=7.67, 4.75 Hz, 1H); 6.50 (d, J=8.77 Hz, 1H); 4.83 (d, J=6.58 Hz, 4H); 4.26 (br. s., 2H); 3.69-3.91 (m, 6H); 2.56 (s, 3H). m/z (ESI, +ve ion) 535.1 (M+H)$^-$.

Step 5: 1-(5-(3-(4-(bis(4-methoxybenzyl)amino)-6-methyl-1,3,5-triazin-2-yl)pyridin-2-ylamino)pyridin-2-yl)-3-phenylurea A solution of N5-(3-(4-(bis(4-methoxybenzyl)amino)-6-methyl-1,3,5-triazin-2-yl)pyridin-2-yl)pyridine-2,5-diamine (0.150 g, 0.281 mmol) and phenyl isocyanate (Fluka) (0.077 mL, 0.70 mmol) in THF (3 mL) was stirred at rt for 5 h. The resulting solid was collected by filtration to give 1-(5-(3-(4-(bis(4-methoxybenzyl)amino)-6-methyl-1,3,5-triazin-2-yl)pyridin-2-ylamino)pyridin-2-yl)-3-phenylurea (0.0707 g) as a yellow solid. The filtrate and wash were concentrated and purified by silica gel chromatography (25 g, eluent: EtOAc in hexanes 0%-30%) to give a second batch of the product (0.0924 g). The total yield was 0.1631 g, 89%. $^1$H NMR (300 MHz, CDCl$_3$) δ 11.83 (s, 1H); 11.66 (br. s., 1H); 8.80-8.89 (m, 1H); 8.41 (br. s., 1H); 8.27-8.36 (m, 1H); 7.88-7.99 (m, 1H); 7.62 (d, J=8.18 Hz, 2H); 7.31-7.41 (m, 3H); 7.15-7.24 (m, 4H); 7.03-7.12 (m, 1H); 6.75-6.93 (m, 5H); 6.64-6.73 (m, 1H); 4.85 (br. s., 4H); 3.79 (d, J=10.96 Hz, 6H); 2.61 (s, 3H). m/z (ESI, +ve ion) 654.0 (M+H)$^+$.

Step 6: 1-(5-(3-(4-amino-6-methyl-1,3,5-triazin-2-yl)pyridin-2-ylamino)pyridin-2-yl)-3-phenylurea A solution of 1-(5-(3-(4-(bis(4-methoxybenzyl)amino)-6-methyl-1,3,5-triazin-2-yl)pyridin-2-ylamino)pyridin-2-yl)-3-phenylurea (0.0707 g, 0.108 mmol) and trifluoromethanesulfonic acid (TCI) (0.02 mL, 0.225 mmol) in 1 mL of TFA was stirred at rt for 3 h then heated to 50° C. and stirred for 3 h. Then the mixture was heated at 75° C. overnight. Saturated sodium bicarbonate was added slowly to quench the reaction and the resulting precipitate was collected by filtration. The crude product was purified by preparative HPLC using Phenomenex, Gemni NX 5 micron C18 150×30 mm column (10%-90% CH$_3$CN w/0.1% TFA/H$_2$O w/0.1% TFA in 10 min). The resulting fraction was concentrated to dryness in vacuo. Saturated sodium bicarbonate was added to the residue and the resulting yellow precipitate was collected by filtration, washed with water and dried in a vacuum oven to give 1-(5-(3-(4-amino-6-methyl-1,3,5-triazin-2-yl)pyridin-2-ylamino)pyridin-2-yl)-3-phenylurea (0.0210 g, 47% yield) as a yellow solid. $^1$H NMR (400 MHz, d6-DMSO) δ 11.87 (s, 1H); 10.28 (br. s., 1H); 9.30 (s, 1H); 8.71-8.84 (m, 2H); 8.34 (dd, J=4.60, 1.86 Hz, 8.22 (dd, J=9.00, 2.74 Hz, 1H); 7.87 (br. s., 1H); 7.74 (br. s., 1H); 7.47-7.58 (m, 3H); 7.31 (t, J=7.92

Hz, 2H); 7.01 (t, J=7.43 Hz, 1H); 6.92 (dd, J=7.83, 4.69 Hz, 1H); 2.44 (s, 3H). m/z (ESI, +ve ion) 414.0 (M+H)+.

Example 191

1-(5-(3-(4-amino-6-methyl-1,3,5-triazin-2-yl)pyridin-2-ylamino)pyridin-2-yl)-3-(3-fluorophenyl)urea

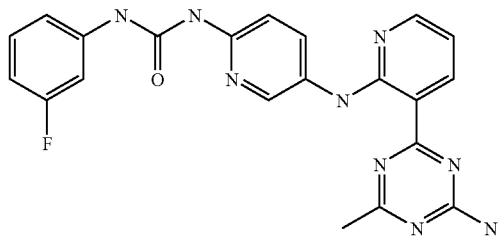 [SMILES: Cc1nc(N)nc(-c2cccnc2Nc2ccc(NC(=O)Nc3cccc(F)c3)nc2)n1]

Step 1: 1-(5-(3-(4-(bis(4-methoxybenzyl)amino)-6-methyl-1,3,5-triazin-2-yl)pyridin-2-ylamino)pyridin-2-yl)-3-(3-fluorophenyl)urea A solution of N5-(3-(4-(bis(4-methoxybenzyl)amino)-6-methyl-1,3,5-triazin-2-yl)pyridin-2-yl)pyridine-2,5-diamine (Example 190, Step 4, 0.156 g, 0.293 mmol) and 3-fluorophenyl isocyanate (0.084 mL, 0.73 mmol) in THF (3 mL) was stirred at rt for 5 h. The resulting precipitate was collected to give 1-(5-(3-(4-(bis(4-methoxybenzyl)amino)-6-methyl-1,3,5-triazin-2-yl)pyridin-2-ylamino)pyridin-2-yl)-3-(3-fluorophenyl)urea (0.0707 g) as a yellow solid. The filtrate and wash were concentrated and purified by silica gel chromatography (25 g, eluent: EtOAc in hexanes 0%-30%) to give a second batch of the product (0.1218 g). The combined yield was 0.1925 g (98%). $^1$H NMR (300 MHz, CDCl$_3$) δ 11.77-11.96 (m, 2H); 8.80-8.93 (m, 1H); 8.43 (br. s., 1H); 8.32 (br. s., 1H); 7.93 (br. s., 1H); 7.45-7.63 (m, 2H); 7.27-7.35 (m, 2H); 7.15-7.24 (m, 4H); 6.66-6.95 (m, 7H); 4.85 (br. s., 4H); 3.79 (d, J=10.08 Hz, 6H); 2.62 (s, 3H). m/z (ESI, +ve ion) 672.0 (M+H)+.

Step 2: 1-(5-(3-(4-amino-6-methyl-1,3,5-triazin-2-yl)pyridin-2-ylamino)pyridin-2-yl)-3-(3-fluorophenyl)urea A solution of 1-(5-(3-(4-(bis(4-methoxybenzyl)amino)-6-methyl-1,3,5-triazin-2-yl)pyridin-2-ylamino)pyridin-2-yl)-3-(3-fluorophenyl)urea (0.0824 g, 0.123 mmol) and trifluoromethanesulfonic acid (TCI) (0.02 mL, 0.225 mmol) in TFA (1 mL) was stirred at rt for 3 h, 50° C. for 3 h, then 75° C. for overnight. Saturated sodium bicarbonate was added slowly to quench the reaction and the resulting precipitate was collected by filtration. The crude product was purified by preparative HPLC using Phenomenex, Gemni NX 5 micron C18 150×30 mm column (10%-90% CH$_3$CN w/0.1% TFA/H$_2$O w/0.1% TFA in 10 min). The resulting fraction was concentrated to dryness in vacuo. Saturated sodium bicarbonate was added to the residue and the resulting yellow precipitate was collected by filtration, washed with water, and dried in a vacuum oven to give 1-(5-(3-(4-amino-6-methyl-1,3,5-triazin-2-yl)pyridin-2-ylamino)pyridin-2-yl)-3-(3-fluorophenyl)urea (0.0305 g, 58% yield) as a yellow solid. $^1$H NMR (400 MHz, d6-DMSO) δ 11.89 (s, 1H); 10.49 (br. s., 1H); 9.38 (s, 1H); 8.71-8.83 (m, 2H); 8.29-8.39 (m, 1H); 8.23 (dd, J=9.00, 2.35 Hz, 1H); 7.87 (br. s., 1H); 7.74 (br. s., 1H); 7.47-7.65 (m, 2H); 7.34 (q, J=7.89 Hz, 1H); 7.20 (d, J=8.02 Hz, 1H); 6.92 (dd, J=7.63, 4.69 Hz, 1H); 6.76-6.87 (m, 1H); 2.44 (s, 3H). m/z (ESI, +ve ion) 432.0 (M+H)+.

Example 192

1-(5-(3-(4-amino-6-methyl-1,3,5-triazin-2-yl)pyridin-2-ylamino)pyridin-2-yl)-3-isopropylurea

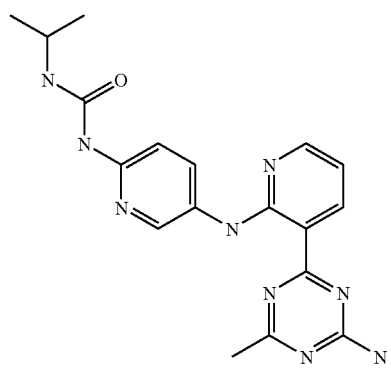 [SMILES: Cc1nc(N)nc(-c2cccnc2Nc2ccc(NC(=O)NC(C)C)nc2)n1]

Step 1: 1-(5-(3-(4-(bis(4-methoxybenzyl)amino)-6-methyl-1,3,5-triazin-2-yl)pyridin-2-ylamino)pyridin-2-yl)-3-isopropylurea A stirred solution of N5-(3-(4-(bis(4-methoxybenzyl)amino)-6-methyl-1,3,5-triazin-2-yl)pyridin-2-yl)pyridine-2,5-diamine (Example 190, Step 4, 0.124 g, 0.233 mmol) in THF (2 mL) was treated with 2-isocyanatopropane (Aldrich) (0.046 mL, 0.465 mmol) and the yellow solution was stirred at rt overnight. The mixture was concentrated and the crude product was purified by silica gel chromatography (25 g, eluent: iPrOH (w/10% NH$_4$OH) in CHCl$_3$ 0%-7.5%) to give 1-(5-(3-(4-(bis(4-methoxybenzyl)amino)-6-methyl-1,3,5-triazin-2-yl)pyridin-2-ylamino)pyridin-2-yl)-3-isopropylurea (0.1044 g, 72% yield) as a yellow solid. $^1$H NMR (300 MHz, CDCl$_3$) δ 11.74 (s, 1H); 8.98-9.14 (m, 1H); 8.83 (d, J=7.75 Hz, 1H); 8.35 (d, J=1.75 Hz, 1H); 8.24-8.33 (m, 1H); 7.84 (dd, J=8.77, 1.90 Hz, 1H); 7.35 (s, 1H); 7.20 (t, J=8.33 Hz, 4H); 6.86 (t, J=7.38 Hz, 4H); 6.77 (dd, J=7.75, 4.82 Hz, 1H); 6.65 (d, J=8.77 Hz, 1H); 4.84 (d, J=4.97 Hz, 4H); 4.01-4.18 (m, 1H); 3.80 (d, J=7.31 Hz, 6H); 2.60 (s, 3H); 1.28 (d, J=6.58 Hz, 6H). m/z (ESI, +ve ion) 620.0 (M+H)+.

Step 2: 1-(5-(3-(4-amino-6-methyl-1,3,5-triazin-2-yl)pyridin-2-ylamino)pyridin-2-yl)-3-isopropylurea A stirred solution of 1-(5-(3-(4-(bis(4-methoxybenzyl)amino)-6-methyl-1,3,5-triazin-2-yl)pyridin-2-ylamino)pyridin-2-yl)-3-isopropylurea (0.104 g, 0.168 mmol) in TFA (2 mL) was treated with trifluoromethanesulfonic acid (TCI) (0.02 mL, 0.2 mmol) and the reaction mixture was stirred at 70° C. for 2 h, then 80° C. for 2 h. TFA (2 mL) and trifluoromethanesulfonic acid (0.05 mL) were added. The heating was resumed at 75° C. for another 2 h. The mixture was cooled to rt, and some of the TFA was removed in vacuo. Sat'd NaHCO$_3$ was added slowly until effervescence was no longer observed. The aqueous phase was extracted with 25% iPrOH in CHCl$_3$+1% NH$_4$OH (3×10 mL). The combined organic phases were dried over sodium sulfate, filtered and concentrated in vacuo. The crude product was purified by silica gel chromatography (25 g, eluent: iPrOH (w/10% NH₄OH) in CHCl₃ 0%-10%) to give 1-(5-(3-(4-amino-6-methyl-1,3,5-triazin-2-yl)pyridin-2-ylamino)pyridin-2-yl)-3-isopropylurea (0.0312 g, 49% yield) as a yellow powder. ¹H NMR (300 MHz, d6-DMSO) δ 11.77 (s, 1H); 8.92 (s, 1H); 8.77 (d, J=7.75 Hz, 1H); 8.65 (br. s., 1H); 8.31 (br. s., 1H); 8.10 (br. s., 1H); 7.85 (br. s., 2H); 7.71 (br. s., 1H); 7.38 (d, J=8.92 Hz, 1H); 6.80-6.99 (m, 1H); 3.77-3.91 (m, 1H); 2.43 (s, 3H); 1.15 (d, J=6.28 Hz, 6H). m/z (ESI, +ve ion) 380.1 (M+H)⁺.

Example 193

N-(5-(3-(4-amino-6-methyl-1,3,5-triazin-2-yl)-5-chloropyridin-2-ylamino)pyridin-2-yl)acetamide

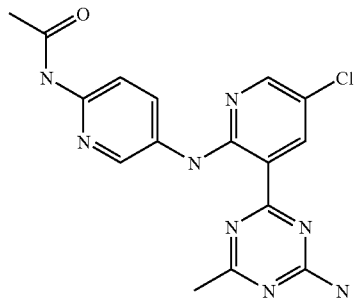 [SMILES: CC(=O)Nc1ccc(Nc2ncc(Cl)cc2-c2nc(C)nc(N)n2)cn1]

Step 1: tert-butyl 5-(3-(4-(bis(4-methoxybenzyl)amino)-6-methyl-1,3,5-triazin-2-yl)-5-chloropyridin-2-ylamino)pyridin-2-ylcarbamate A solution of 4-(5-chloro-2-fluoropyridin-3-yl)-N,N-bis(4-methoxybenzyl)-6-methyl-1,3,5-triazin-2-amine (0.723 g, 1.51 mmol) and tert-butyl 5-aminopyridin-2-ylcarbamate (Example 190, Step 2, 0.317 g, 1.52 mmol) in THF (5 mL) was treated dropwise with LiHMDS (4.52 mL, 4.52 mmol) at 0° C. The dark red mixture was stirred at 0° C. for 30 min. Water (0.2 mL) was added to quench the reaction. The reaction mixture was partitioned between saturated aqueous ammonium chloride (40 mL) and EtOAc (40 mL). The aqueous phase was extracted with EtOAc (20 mL). The combined organic phases were dried over sodium sulfate, filtered and concentrated in vacuo. The crude product was purified by column chromatography (50 g, eluent: EtOAc in hexanes 0%-35%) to give tert-butyl 5-(3-(4-(bis(4-methoxybenzyl)amino)-6-methyl-1,3,5-triazin-2-yl)-5-chloropyridin-2-ylamino)pyridin-2-ylcarbamate (0.697 g, 69% yield) as a yellow foam. ¹H NMR (300 MHz, CDCl₃) δ 11.77 (s, 1H); 8.74 (d, J=2.34 Hz, 1H); 8.39 (br. s., 1H); 8.22 (s, 1H); 7.79-7.94 (m, 2H); 7.28 (br. s., 1H); 7.19 (t, J=9.28 Hz, 4H); 6.86 (dd, J=8.18, 3.95 Hz, 4H); 4.83 (d, J=11.55 Hz, 4H); 3.80 (d, J=4.97 Hz, 6H); 2.58 (s, 3H); 1.53 (s, 9H). m/z (ESI, +ve ion) 669.2 (M+H)⁺.

Step 2: N5-(3-(4-(bis(4-methoxybenzyl)amino)-6-methyl-1,3,5-triazin-2-yl)-5-chloropyridin-2-yl)pyridine-2,5-diamine A solution of tert-butyl 5-(3-(4-(bis(4-methoxybenzyl)amino)-6-methyl-1,3,5-triazin-2-yl)-5-chloropyridin-2-ylamino)pyridin-2-ylcarbamate (0.827 g, 1.24 mmol) and TFA (5.0 mL, 64.9 mmol) in DCM (10 mL) was stirred at rt for 1.5 h. Toluene (3 mL) was added and the mixture was concentrated in vacuo. Saturated aqueous sodium bicarbonate (50 mL) was added carefully. The aqueous phase was extracted with 25% iPrOH in CHCl₃+1% NH₄OH (2×50 mL). The combined organic phases were dried over sodium sulfate, filtered and concentrated in vacuo to give N5-(3-(4-(bis(4-methoxybenzyl)amino)-6-methyl-1,3,5-triazin-2-yl)-5-chloropyridin-2-yl)pyridine-2,5-diamine (0.664 g, 94% yield) as a bright orange solid. ¹H NMR (300 MHz, CDCl₃) δ 11.46 (s, 1H); 8.72 (d, J=2.48 Hz, 1H); 8.17 (d, J=2.34 Hz, 1H); 8.06-8.13 (m, 1H); 7.64-7.75 (m, 1H); 7.18 (dd, J=12.57, 8.48 Hz, 4H); 6.86 (t, J=7.89 Hz, 4H); 6.49 (d, J=8.77 Hz, 1H); 4.83 (d, J=15.05 Hz, 4H); 4.31 (br. s., 2H); 3.80 (d, J=5.85 Hz, 6H); 2.56 (s, 3H). m/z (ESI, +ve ion) 569.2 (M+H)⁺.

Step 3: N-(5-(3-(4-(bis(4-methoxybenzyl)amino)-6-methyl-1,3,5-triazin-2-yl)-5-chloropyridin-2-ylamino)pyridin-2-yl)acetamide A solution of N5-(3-(4-(bis(4-methoxybenzyl)amino)-6-methyl-1,3,5-triazin-2-yl)-5-chloropyridin-2-yl)pyridine-2,5-diamine (0.0551 g, 0.097 mmol) and pyridine (0.05 mL, 0.618 mmol) in DMF (2 mL) was treated dropwise with acetic anhydride (Aldrich) (10.0 μl, 0.107 mmol) at 0° C. The orange solution was stirred at rt overnight. The mixture was concentrated in vacuo to reduce the solvent volume to about 1 mL. Water (2 mL) and brine (20 mL) were added and the aqueous phase was extracted with 25% iPrOH in CHCl₃+1% NH₄OH (2×20 mL). The combined organic phases were dried over sodium sulfate, filtered and concentrated in vacuo to give N-(5-(3-(4-(bis(4-methoxybenzyl)amino)-6-methyl-1,3,5-triazin-2-yl)-5-chloropyridin-2-ylamino)pyridin-2-yl)acetamide (0.060 g, 100% yield) as a yellow powder. ¹H NMR (300 MHz, CDCl₃) δ 11.88 (s, 1H); 8.75 (d, J=2.19 Hz, 1H); 8.47 (s, 1H); 8.24 (d, J=2.34 Hz, 1H); 8.06-8.16 (m, 1H); 7.86-7.95 (m, 1H); 7.83 (br. s, 1H); 7.19 (t, J=8.48 Hz, 4H); 6.87 (d, J=6.58 Hz, 4H); 4.84 (d, J=10.96 Hz, 4H); 3.80 (d, J=4.09 Hz, 6H); 2.59 (s, 3H); 2.20 (s, 3H). m/z (ESI, +ve ion) 611.2 (M+H)⁺.

Step 4: N-(5-(3-(4-amino-6-methyl-1,3,5-triazin-2-yl)-5-chloropyridin-2-ylamino)pyridin-2-yl)acetamide A solution of N-(5-(3-(4-(bis(4-methoxybenzyl)amino)-6-methyl-1,3,5-triazin-1,3,5-triazin-2-yl)-5-chloropyridin-2-ylamino)pyridin-2-yl)acetamide (0.060 g, 0.098 mmol) and trifluoromethanesulfonic acid (TCI) (40 μL, 0.450 mmol) in TFA (2 mL) was stirred at rt for 2.5 h. Then the mixture was stirred at 75° C. for 2 h. Most of the TFA was removed in vacuo and then the residue was taken up in a small amount of DCM. Solid NaHCO₃ was added in portions until no more effervescence was observed. Water was added and the resulting solid was collected by filtration. The crude product was purified by preparative HPLC using Phenomenex, Gemni 5 micron C18 100×30mm column (0%-10% CH₃CN w/0.1% TFA/H₂O w/0.1% TFA in 10 min). The fractions containing product formed a precipitate which was collected by filtration and dried in a vacuum oven to give N-(5-(3-(4-amino-6-methyl-1,3,5-triazin-2-yl)-5-chloropyridin-2-ylamino)pyridin-2-yl)acetamide (0.0173 g, 36% yield) as a yellow solid. ¹H NMR (300 MHz, d6-DMSO) δ 11.87 (s, 1H); 10.43 (s, 1H); 8.67-8.78 (m, 2H); 8.37 (br. s., 1H); 8.15-8.24 (m, 1H); 7.93-8.07 (m, 2H); 7.84 (br. s., 1H); 2.45 (s, 3H); 2.09 (s, 3H). m/z (ESI, +ve ion) 371.0 (M+H)+.

Example 194 methyl 5-(3-(4-amino-6-methyl-1,3,5-triazin-2-yl)-5-chloropyridin-2-ylamino)pyridin-2-ylcarbamate

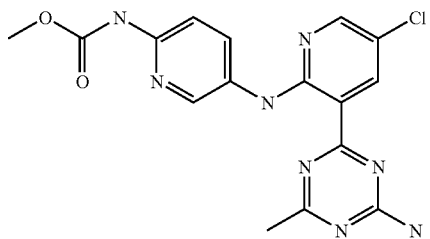 [SMILES: COC(=O)Nc1ccc(Nc2ncc(Cl)cc2-c2nc(C)nc(N)n2)cn1]

A solution of N5-(3-(4-(bis(4-methoxybenzyl)amino)-6-methyl-1,3,5-triazin-2-yl)-5-chloropyridin-2-yl)pyridine-2,5-diamine (Example 194, Step 2, 0.152 g, 0.266 mmol) and Et₃N (0.111 mL, 0.799 mmol) in DCM (3 mL) was treated with methyl chloroformate (Aldrich) (0.025 mL, 0.319 mmol) and the mixture was stirred at rt for 2 days during which time solvent was lost due to evaporation. The residue was taken into the mixed solvent (1:1 DCM/THF, 5 mL) and Et₃N (0.5 mL) and methyl chloroformate (0.1 mL) were added. The mixture was stirred at rt for 2 h. The resulting solid was collected and transferred to an Erlenmeyer flask using MeOH and DMSO. Water was added and the mixture was sonicated. The resulting orange solid was collected and this mixture was heated in TFA (2 mL) in the presence of trifluoromethanesulfonic acid (TCI) (0.2 mL) at rt for 30 min, then at 60° C. overnight. Solid sodium carbonate was added until effervescence subsided. Sodium bicarbonate was added slowly until no more effervescence was observed. The resulting solid was collected by filtration. The crude product was purified by preparative HPLC using Phenomenex, Gemini 5 micron C18 100×30mm column (1%-90% CH₃CN w/0.1% TFA/H₂O w/0.1% TFA in 15 min). The fractions containing product were collected and lyophilized to give an orange fluffy solid, which was taken into water and the resulting yellow precopitate was collected, washed with water and dried to give methyl 5-(3-(4-(bis(4-methoxybenzyl)amino)-6-methyl-1,3,5-triazin-2-yl)-5-chloropyridin-2-ylamino)pyridin-2-ylcarbamate (0.0074 g, 7% yield) as a yellow solid. ¹H NMR (400 MHz, d6-DMSO) δ 11.84 (s, 1H); 10.10 (s, 1H); 8.74 (d, J=2.74 Hz, 1H); 8.64 (d, J=2.54 Hz, 1H); 8.37 (d, J=2.74 Hz, 1H); 8.19 (dd, J=9.00, 2.74 Hz, 1H); 7.98 (br. s., 1H); 7.82-7.90 (m, 1H); 7.80 (d, J=8.80 Hz, 1H); 3.68 (s, 3H); 2.45 (s, 3H). m/z (ESI, +ve ion) 386.9 (M+H)+.

Example 195

1-(5-(3-(4-amino-6-methyl-1,3,5-triazin-2-yl)-5-chloropyridin-2-ylamino)pyridin-2-yl)-3-(4-(2-methoxyethoxy)phenyl)urea

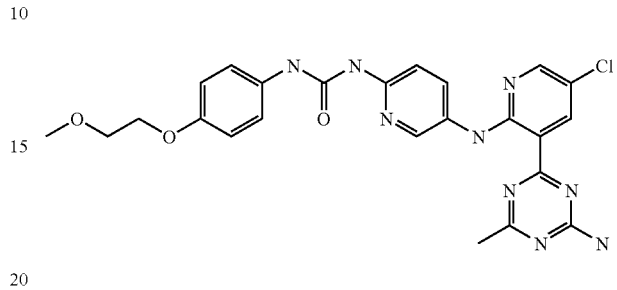

Step 1: 1-(2-methoxyethoxy)-4-nitrobenzene

A stirred solution of 4-nitrophenol (Fluka) (0.511 g, 3.67 mmol) in DMF (10 mL) was treated with 60% sodium hydride (Aldrich) (0.170 g, 4.25 mmol) added in portions at 0° C. The yellow mixture was stirred at that temperature for 10 min, then 2-bromoethyl methyl ether (Aldrich) (0.380 mL, 4.04 mmol) was added dropwise at 0° C. The mixture was stirred at that temperature for 5 min, warmed up to rt and stirred for 3.5 h then at 70° C. overnight. The reaction mixture was poured into ice-water (100 mL). The aqueous phase was extracted with EtOAc (2×70 mL). The combined organic phases were dried over sodium sulfate, filtered and concentrated in vacuo to give 1-(2-methoxyethoxy)-4-nitrobenzene (0.753 g, 105% yield) as an off-white solid. ¹H NMR (400 MHz, CDCl₃) δ 8.16-8.25 (m, 2H); 6.95-7.03 (m, 2H); 4.17-4.26 (m, 2H); 3.73-3.84 (m, 2H); 3.46 (s, 3H). m/z (ESI, +ve ion) 198.1 (M+H)+.

Step 2: 4-(2-methoxyethoxy)aniline

A mixture of 1-(2-methoxyethoxy)-4-nitrobenzene (0.724 g, 3.67 mmol) and 10% Pd/C (Aldrich) (0.201 g, 1.89 mmol) in EtOH (10 mL) was evacuated under vacuum and refilled with hydrogen (4 times). The mixture was hydrogenated under balloon pressure at rt for 1.5 h. The reaction mixture was filtered through a pad of Celite® (diatomaceous earth) (eluent:EtOH) and concentrated. The crude product was purified by silica gel chromatography (25 g, eluent: EtOAc in hexanes 0%-60%) to give 4-(2-methoxyethoxy)aniline (0.548 g, 89% yield) as a clear oil. ¹H NMR (400 MHz, CDCl₃) δ 6.73-6.82 (m, 2H); 6.58-6.68 (m, 2H); 4.01-4.08 (m, 2H); 3.67-3.76 (m, 2H); 3.29-3.52 (m, 5H). m/z (ESI, +ve ion) 168.1 (M+H)+.

Step 3: 4-nitrophenyl 4-(2-methoxyethoxy)phenylcarbamate

A solution of 4-(2-methoxyethoxy)aniline (0.397 g, 2.37 mmol) and pyridine (1 mL, 12.4 mmol) in DCM (3 mL) in was treated with 4-nitrophenyl chloroformate (Aldrich) (0.505 g, 2.51 mmol) added in portions (exothermic!). The pale yellow solution was stirred at RT for 5 h. The reaction mixture was partitioned between 0.5 N HCl (20 mL) and DCM (30 mL). The organic phase was washed with 0.5 N HCl (30 mL), saturated aqueous sodium bicarbonate (30 mL), water (30 mL) and saturated aqueous sodium chloride (30 mL). The organic phase was dried over sodium sulfate, filtered and concentrated in vacuo. The crude product was purified by silica gel chromatography (50 g, eluent: EtOAc in hexanes 10%-50%) to give 4-nitrophenyl 4-(2-methoxyethoxy)phenylcarbamate (0.57 g, 72% yield) as an off-white solid. $^1$H NMR (400 MHz, CDCl$_3$) δ 8.25-8.32 (m, 2H); 7.32-7.43 (m, 4H); 6.87-6.97 (m, 3H); 4.09-4.15 (m, 2H); 3.72-3.79 (m, 2H); 3.46 (s, 3H). m/z (ESI, +ve ion) 333.0 (M+H)$^+$.

Step 4: 1-(5-(3-(4-(bis(4-methoxybenzyl)amino)-6-methyl-1,3,5-triazin-2-yl)-5-chloropyridin-2-ylamino)pyridin-2-yl)-3-(4-(2-methoxyethoxy)phenyl)urea A mixture of N5-(3-(4-(bis(4-methoxybenzyl)amino)-6-methyl-1,3,5-triazin-2-yl)-5-chloropyridin-2-yl)pyridine-2,5-diamine (Example 4, step 2, 0.158 g, 0.277 mmol) and 4-nitrophenyl 4-(2-methoxyethoxy)phenylcarbamate (0.118 g, 0.354 mmol) in DCM (3 mL) was stirred at rt for 3 days. Et$_3$N (0.20 mL) was added followed by 4-nitrophenyl 4-(2-methoxyethoxy)phenylcarbamate (0.142 g, 0.428 mmol). The reaction mixture was stirred at rt for 2 h. The yellow solid was collected and washed with DCM to give 0.176 g of crude 1-(5-(3-(4-(bis(4-methoxybenzyl)amino)-6-methyl-1,3,5-triazin-2-yl)-5-chloropyridin-2-ylamino)pyridin-2-yl)-3-(4-(2-methoxyethoxy)phenyl)urea, which was taken into the next step without further purification.

Step 5: 1-(5-(3-(4-amino-6-methyl-1,3,5-triazin-2-yl)-5-chloropyridin-2-ylamino)pyridin-2-yl)-3-(4-(2-methoxyethoxy)phenyl)urea A solution of 1-(5-(3-(4-(bis(4-methoxybenzyl)amino)-6-methyl-1,3,5-triazin-2-yl)-5-chloropyridin-2-ylamino)pyridin-2-yl)-3-(4-(2-methoxyethoxy)phenyl)urea (0.176 g, 0.231 mmol) and trifluoromethanesulfonic acid (0.020 mL, 0.231 mmol) in TFA (2 mL) was stirred at rt for 30 min then warmed up to 60° C. and stirred overnight. After cooling to rt, solid sodium carbonate was added in portions until effervescence subsided. 25% iPrOH in CHCl$_3$ (+1% NH$_4$OH) was added to the residue, and the organic phase was washed with sodium bicarbonate. The material was not fully soluble in the organic layer so the organic layer containing solid was directly dried under vacuum (no drying agent was added). The crude product was purified by preparative HPLC using Phenomenex, Gemini 5 micron C18 100×30 mm column (1%-90% CH$_3$CN w/0.1% TFA/H$_2$O w/0.1% TFA in 15 min). The fractions containing product were collected and concentrated in vacuo. Sodium bicarbonate was added and the resulting solid was collected to give 1-(5-(3-(4-amino-6-methyl-1,3,5-triazin-2-yl)-5-chloropyridin-2-ylamino)pyridin-2-yl)-3-(4-(2-methoxyethoxy)phenyl)urea (0.0834 g, 69% yield) as a yellow solid. $^1$H NMR (400 MHz, d6-DMSO) δ 11.82 (br. s., 1H); 10.10 (br. s., 1H); 9.30 (br. s., 1H); 8.62-8.86 (m, 2H); 8.36 (d, J=2.54 Hz, 1H); 8.13 (br. s., 1H); 7.96 (br. s., 1H); 7.84 (br. s., 1H); 7.51 (br. s., 1H); 7.33-7.46 (m, 2H); 6.90 (d, J=8.41 Hz, 2H); 4.04 (br. s., 2H); 3.64 (d, J=3.72 Hz, 2H); 3.30 (d, J=5.87 Hz, 3H); 2.44 (d, J=5.48 Hz, 3H). m/z (ESI, +ve ion) 521.9 (M+H)$^+$.

Example 196

N-(5-(3-(4-amino-6-methyl-1,3,5-triazin-2-yl)-5-((4-(methylsulfonyl)piperazin-1-yl)methyl)pyridin-2-ylamino)pyridin-2-yl)acetamide

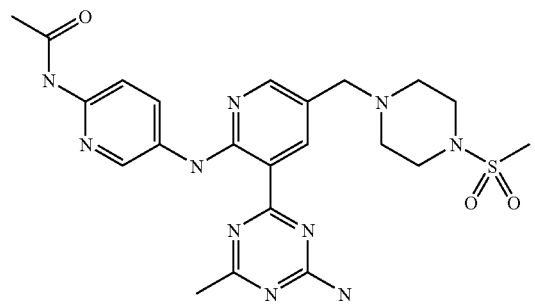 [SMILES: CC(=O)Nc1ccc(Nc2ncc(CN3CCN(S(C)(=O)=O)CC3)cc2-c2nc(C)nc(N)n2)cn1]

Step 1: tert-butyl 5-(3-(4-(bis(4-methoxybenzyl)amino)-6-methyl-1,3,5-triazin-2-yl)-5-((4-(methylsulfonyl)piperazin-1-yl)methyl)pyridin-2-ylamino)pyridin-2-ylcarbamate LiHMDS (Aldrich) (2.44 mL, 2.44 mmol) was added dropwise at 0° C. to a stirred solution of 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (0.507 g, 0.815 mmol) and tert-butyl 5-aminopyridin-2-ylcarbamate (0.204 g, 0.976 mmol) in THF (2 mL). The dark red mixture was stirred at 0° C. for 2 h. More LiHMDS (1.6 mL, 1.6 mmol) was added dropwise at 0° C. and stirring was continued for another 30 min. The reaction was quenched by adding 0.3 mL of sat'd NH$_4$Cl. The reaction mixture was partitioned between water (40 mL) and EtOAc (40 mL). The aqueous phase was extracted with EtOAc (2×30 mL). The combined organic layers were washed with saturated aqueous sodium chloride (40 mL), dried over sodium sulfate, filtered and concentrated in vacuo. The crude product was purified by silica gel chromatography (100 g, eluent: iPrOH (w/10% NH$_4$OH) in CHCl$_3$ 0%-10%) to give tert-butyl 5-(3-(4-(bis(4-methoxybenzyl)amino)-6-methyl-1,3,5-triazin-2-yl)-5-((4-(methylsulfonyl)piperazin-1-yl)methyl)pyridin-2-ylamino)pyridin-2-ylcarbamate (0.306 g, 46% yield). $^1$H NMR (400 MHz, CDCl$_3$) δ 11.76 (s, 1H); 8.71 (d, J=2.54 Hz, 1H); 8.42 (d, J=2.35 Hz, 1H); 8.23 (d, J=2.35 Hz, 1H); 7.94 (dd, J=9.00, 2.54 Hz, 1H); 7.83 (d, J=9.00 Hz, 1H); 7.15-7.25 (m, 5H); 6.86 (dd, J=11.15, 8.61 Hz, 4H); 4.83 (d, J=10.17 Hz, 4H); 3.76-3.85 (m, 6H); 3.50 (s, 2H); 3.18 (br. s., 4H); 2.71 (s, 3H); 2.59 (s, 3H); 2.55 (t, J=4.50 Hz, 4H); 1.53 (s, 9H).

Step 2: N5-(3-(4-(bis(4-methoxybenzyl)amino)-6-methyl-1,3,5-triazin-2-yl)-5-((4-(methylsulfonyl)piperazin-1-yl)methyl)pyridin-2-yl)pyridine-2,5-diamine tert-Butyl 5-(3-(4-(bis(4-methoxybenzyl)amino)-6-methyl-1,3,5-triazin-2-yl)-5-((4-(methylsulfonyl)piperazin-1-yl)methyl)pyridin-2-ylamino)pyridin-2-ylcarbamate (0.306 g, 0.377 mmol) was dissolved into DCM (5 mL total) in two 20 mL scintillation vials. TFA (2.5 mL total) was added and the solutions were stirred at rt for 3 h. The reaction mixtures were combined and poured into 20 mL of saturated aqueous sodium bicarbonate. The aqueous phase was extracted with 25% iPrOH in CHCl$_3$+1% NH$_4$OH (2×20 mL). The combined organic layers were dried over sodium sulfate, filtered and concentrated in vacuo. The crude product was purified by silica gel chromatography (25 g, eluent: iPrOH (w/10% NH$_4$OH) in CHCl$_3$ 0%-20%) to give N5-(3-(4-(bis(4-methoxybenzyl)amino)-6-methyl-1,3,5-triazin-2-yl)-5-((4-(methylsulfonyl)piperazin-1-yl)methyl)pyridin-2-yl)pyridine-2,5-diamine (0.221 g, 82% yield) as a yellow solid. $^1$H NMR (400 MHz, CDCl$_3$) δ 11.44 (br. s., 1H); 8.69 (br. s., 1H); 8.15-8.21 (m, 1H); 8.12 (br. s., 1H); 7.69-7.79 (m, 1H); 7.21 (d, J=8.61 Hz, 4H); 6.85 (dd, J=15.75, 8.51 Hz, 4H); 6.49 (d, J=8.80 Hz, 1H); 4.83 (d, J=15.85 Hz, 4H); 4.27 (br. s., 2H); 3.75-3.85 (m, 6H); 3.48 (br. s., 2H); 3.18 (br. s., 4H); 2.68-2.76 (m, 3H); 2.49-2.61 (m, 7H). m/z (ESI, +ve ion) 711.0 (M+H)$^+$.

Step 3: N-(5-(3-(4-(bis(4-methoxybenzyl)amino)-6-methyl-1,3,5-triazin-2-yl)-5-((4-(methylsulfonyl)piperazin-1-yl)methyl)pyridin-2-ylamino)pyridin-2-yl)acetamide Acetic anhydride (Aldrich) (0.13 mL, 1.4 mmol) was added slowly at 0° C. to a stirred solution of N5-(3-(4-(bis(4-methoxybenzyl)amino)-6-methyl-1,3,5-triazin-2-yl)-5-((4-(methylsulfonyl)piperazin-1-yl)methyl)pyridin-2-yl)pyridine-2,5-diamine (0.0864 g, 0.122 mmol) and pyridine (0.60 mL, 7.4 mmol) in DMF (2mL). The mixture was stirred at rt for 1.5 h. Water was added and the resulting solid was collected by filtration and washed with water and air-dried to give N-(5-(3-(4-(bis(4-methoxybenzyl)amino)-6-methyl-1,3,5-triazin-2-yl)-5-((4-(methylsulfonyl)piperazin-1-yl)methyl)pyridin-2-ylamino)pyridin-2-yl)acetamide (0.0857 g, 94% yield) as a yellow solid. $^1$H NMR (400 MHz, CDCl$_3$) δ 11.86 (s, 1H); 8.72 (d, J=2.15 Hz, 1H); 8.51 (d, J=2.54 Hz, 1H); 8.24 (d, J=2.35 Hz, 1H); 8.09 (s, 1H); 7.96 (d, J=2.15 Hz, 1H); 7.91 (s, 1H); 7.20 (dd, J=8.22, 6.26 Hz, 4H); 6.86 (t, J=8.61 Hz, 4H); 4.84 (d, J=8.80 Hz, 4H); 3.80 (d, J=7.43 Hz, 6H); 3.51 (s, 2H); 3.18 (br. s., 4H); 2.71 (s, 3H); 2.60 (s, 3H); 2.55 (t, J=4.21 Hz, 4H); 2.20 (s, 3H). m/z (ESI, +ve ion) 753.0 (M+H)$^-$.

Step 4: N-(5-(3-(4-amino-6-methyl-1,3,5-triazin-2-yl)-5-((4-(methylsulfonyl)piperazin-1-yl)methyl)pyridin-2-ylamino)pyridin-2-yl)acetamide N-(5-(3-(4-(bis(4-methoxybenzyl)amino)-6-methyl-1,3,5-triazin-2-yl)-5-((4-(methylsulfonyl)piperazin-1-yl)methyl)pyridin-2-ylamino)pyridin-2-yl)acetamide (0.0806 g, 0.107 mmol) and trifluoromethanesulfonic acid (0.02 mL, 0.2 mmol) were dissolved into TFA (2 mL). The pale yellow solution was stirred at rt for 30 min. Then the mixture was stirred at 65° C. for overnight. After cooling to rt, solid sodium carbonate was added followed by aq sodium bicarbonate. The resulting greenish solid was collected and the crude product was purified by preparative HPLC using Phenomenex, Gemni 5 micron C18 100×30mm column (1%-90% CH$_3$CN w/0.1% TFA/H$_2$O w/0.1% TFA in 10 min). The fractions containing product were collected and concentrated to dryness in vacuo. The yellow residue was taken up in aq. sat'd sodium bicarbonate and sonicated. The resulting yellow solid was collected and washed with water and dried in a vacuum oven overnight to give N-(5-(3-(4-amino-6-methyl-1,3,5-triazin-2-yl)-5-((4-(methylsulfonyl)piperazin-1-yl)methyl)pyridin-2-ylamino)pyridin-2-yl)acetamide (0.0361 g, 66% yield). $^1$H NMR (400 MHz, d6-DMSO) δ 11.90 (s, 1H); 10.35 (s, 1H); 8.74 (d, J=2.54 Hz, 1H); 8.71 (d, J=2.54 Hz, 1H); 8.21-8.28 (m, 2H); 8.02 (d, J=9.00 Hz, 1H); 7.89 (br. s., 1H); 7.74 (br. s., 1H); 3.49 (s, 2H); 3.10 (d, J=4.50 Hz, 4H); 2.86 (s, 3H); 2.44 (s, 3H); 2.07 (s, 3H). 4 protons on the piperazine were buried under the water peak and could not be integrated. m/z (ESI, +ve ion) 513.0 (M+H)$^+$.

Example 197

4-(2-(5-fluoro-6-methoxypyridin-3-ylamino)-6-methylpyridin-3-yl)-6-methyl-1,3,5-triazin-2-amine

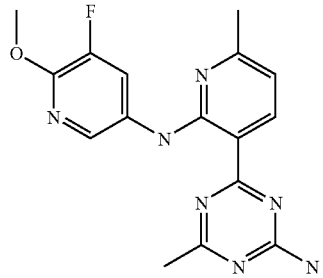 [SMILES: COc1ncc(Nc2nc(C)ccc2-c2nc(C)nc(N)n2)cc1F]

Step 1: 4-(2-fluoro-6-methylpyridin-3-yl)-N,N-bis(4-methoxybenzyl)-6-methyl-1,3,5-triazin-2-amine A mixture of 2-fluoro-6-picoline-3-boronic acid (Asynchem Laboratories, Inc.) (430 mg, 2.77 mmol), 4-chloro-N,N-bis(4-methoxybenzyl)-6-methyl-1,3,5-triazin-2-amine (970 mg, 2.52), potassium acetate (742 mg, 7.56 mmol) and bis(di-tert-butyl(4-dimethylaminophenyl)phosphine)dichloropalladium(II) (Aldrich) (89 mg, 0.126 mmol) in 8 mL of dioxane and 2 mL of water was heated in a microwave at 110° C. for 30 min. It was diluted with EtOAc and washed with 1 N NaOH. The organic layer was dried and concentrated. The residue was purified by chromatography through a Redi-Sep pre-packed silica gel column (12 g), eluting with a gradient of 25-50% EtOAc in hexanes to give 4-(2-fluoro-6-methylpyridin-3-yl)-N,N-bis(4-methoxybenzyl)-6-methyl-1,3,5-triazin-2-amine (939 mg, 2.043 mmol, 81% yield) as a yellow amorphous solid. $^1$H NMR (400 MHz, d6-DMSO) δ 8.53 (1H, m); 7.37 (1H, d, J=6.5 Hz); 7.24 (4H, dd, J=8.6, 1.2 Hz); 6.89 (4H, t, J=Hz); 4.75 (4H, d, J=6.5 Hz); 3.74 (3H, s); 3.72 (s, 3H); 2.51 (3H, s); 2.45 (3H, s). m/z (ESI, +ve ion) 460 (M+H)$^+$.

Step 2: 4-(2-(5-fluoro-6-methoxypyridin-3-ylamino)-6-methylpyridin-3-yl)-N,N-bis(4-methoxybenzyl)-6-methyl-1,3,5-triazin-2-amine A mixture of 4-fluoro-N,N-bis(4-methoxybenzyl)-6-methyl-1,3,5-triazin-2-amine (286 mg, 0.776 mmol) and 5-fluoro-6-methoxypyridin-3-amine (Anichem, Inc.) (199 mg, 1.397 mmol) in THF (6.0 mL) was purged with argon, cooled to 0° C., and treated slowly with LiHMDS (1.4 mL of 1 M solution in THF, 1.4 mmol). The resulting deep purple solution was stirred at 0° C. for 1 h then quenched with saturated NH$_4$Cl solution, and extracted twice with EtOAc. The combined organic extracts were dried over MgSO$_4$, filtered and concentrated. The residue was purified by chromatography through a Redi-Sep pre-packed silica gel column (12 g), eluting with a gradient of 25-50% EtOAc in hexanes to give the title compound (120 mg, 26%) as a yellow crystalline solid. $^1$H NMR (400 MHz, d6-DMSO) δ 11.89 (1H, s); 8.68 (1H, d, J=7.8 Hz); 8.18 (1H, d, J=2.3 Hz); 8.13 (1H, m); 7.23 (4H, m); 6.89 (4H, m); 6.81 (1H, d, J=2.3 Hz); 4.80 (4H, d, J=7.9 Hz); 3.93 (3H, s); 3.74 (3H, s); 3.70 (3H, s); 2.56 (3H, s); 2.43 (3H, s). m/z (ESI, +ve ion) 582 (M+H)$^+$.

Step 3: 4-(2-(5-fluoro-6-methoxypyridin-3-ylamino)-6-methylpyridin-3-yl)-6-methyl-1,3,5-triazin-2-amine A solution of 4-(2-(5-fluoropyridin-3-ylamino)-6-methylpyridin-3-yl)-N,N-bis(4-methoxybenzyl)-6-methyl-1,3,5-triazin-2-amine (118 mg, 0.214 mmol) in 2 mL of TFA was treated with 2 drops of triflic acid. The brown solution was heated in an oil bath at 80° C. for 8 h. The solution was concentrated and the residue was stirred in 5 mL of EtOAc and 2 mL of 0.5 N NaOH. The precipitated solid was collected by filtration, rinsed with 2×2 mL of water, followed by 2 mL of EtOAc and 2×2 mL of DCM. The yellow crystalline solid was collected and dried in a vacuum oven at 40° C. for 18 h to give 4-(2-(5-fluoropyridin-3-ylamino)-6-methylpyridin-3-yl)-6-methyl-1,3,5-triazin-2-amine (60 mg, 0.193 mmol, 90% yield). $^1$H NMR (400 MHz, d6-DMSO) δ 12.33 (1H, s); 8.66 (1H, s); 8.73 (1H, d, J=8.2 Hz); 8.60 (1H, d, J=12.9 Hz); 8.16 (1H, s); 7.90 (1H, br.); 7.75 (1H, br.); 6.91 (1H, d, J=8.0 Hz); 2.48 (3H, s); 2.44 (3H, s). m/z (ESI, +ve ion) 312 (M+H)$^+$.

Example 198

4-(2-(5-fluoro-6-methoxypyridin-3-ylamino)-6-(morpholinomethyl)pyridin-3-yl)-6-methyl-1,3,5-triazin-2-amine

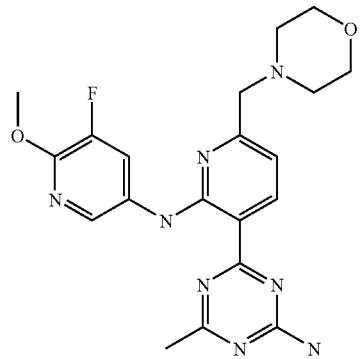 [SMILES: COc1ncc(Nc2nc(CN3CCOCC3)ccc2-c2nc(C)nc(N)n2)cc1F]

Step 1:
4-((5-bromo-6-fluoropyridin-2-yl)methyl)morpholine

A solution of 3-bromo-2-fluoro-6-methylpyridine (1.44 g, 7.58 mmol) (Waterstone Technology) in carbon tetrachloride (15 mL) was treated with N-bromosuccinimide (1.42 g, 7.96 mmol) and dibenzoyl peroxide (184 mg, 0.758 mmol) and heated in an oil bath at 80° C. for 2 h, when LCMS detected a mixture of starting material, mono- and bis-brominated products. The reaction mixture was cooled to RT and filtered through a fritted funnel The filtrate was concentrated and the resulting brown oil was purified on a Redi-Sep pre-packed silica gel column (40 g) eluting with a gradient of 1-20% EtOAc in hexanes to give a thick oil containing a mixture of starting material, mono- and bis-brominated products. The residue was dissolved in 5 mL of DMF at 0° C., treated with morpholine (0.715 mL, 8.21 mmol) and potassium carbonate (1.1 g, 7.70 mmol), and stirred at 0° C. for 45 min. Icy water (10 mL) was added and stirred at RT for 15 min. The off-white solid was filtered, rinsed with 2×5 mL of water and collected. The solid was dried in a vacuum oven at 40° C. for 48 h to yield 268 mg of 4-((5-bromo-6-fluoropyridin-2-yl)methyl)morpholine. The filtrate was transferred to a separatory funnel and extracted with 2×50 mL of EtOAc. The EtOAc solution was washed with brine, dried and concentrated. The residue was purified on a Redi-Sep pre-packed silica gel column (40 g) eluting with a gradient of 50-75% EtOAc in hexanes to give 432 mg of 4-((5-bromo-6-fluoropyridin-2-yl)methyl)morpholine. $^1$H NMR (400 MHz, d6-DMSO) δ 8.26 (1H, m); 7.36 (1H, dd, J=7.8, 1.4 Hz); 3.58 (4H, t, J=4.3 Hz); 3.52 (2H, s); 2.41 (4H, t, J=4.3 Hz). m/z (ESI, +ve ion) 275/277 (M+H)$^+$.

Step 2: 4-(2-fluoro-6-(morpholinomethyl)pyridin-3-yl)-N,N-bis(4-methoxybenzyl)-6-methyl-1,3,5-triazin-2-amine A mixture of 4-((5-bromo-6-fluoropyridin-2-yl)methyl)morpholine (277 mg, 1.007 mmol), 1,1'-bis(diphenylphosphino)ferrocene-palladium dichloride (49.3 mg, 0.060 mmol), bis(pinacolato)diboron (307 mg, 1.208 mmol) and potassium acetate (198 mg, 2.014 mmol) in 2 mL of dioxane was heated in a microwave at 125° C. for 20 min. Water (0.7 mL), KOAc (100 mg), 4-chloro-N,N-bis(4-methoxybenzyl)-6-methyl-1,3,5-triazin-2-amine (504 mg, 1.309 mmol) and Am-Phos (35 mg) were added and the mixture was heated in a microwave at 102° C. for 35 min. It was diluted with 5 mL of EtOAc and washed with 1 mL of 0.5 N NaOH. The EtOAc layer was concentrated and purified on a Redi-Sep pre-packed silica gel column (12 g) eluting with a gradient of 50-75% EtOAc in hexanes to give 4-(2-fluoro-6-(morpholinomethyl)pyridin-3-yl)-N,N-bis(4-methoxybenzyl)-6-methyl-1,3,5-triazin-2-amine (115 mg, 21% yield) as a brown amorphous solid. $^1$H NMR (400 MHz, d6-DMSO) δ 8.60 (1H, dd, J=9.8, 1.8 Hz); 7.55 (1H, d, J=7.4 Hz); 7.24 (4H, d, J=8.2 Hz); 6.89 (4H, t, J=8.1 Hz); 4.76 (4H, d, J=7.4 Hz); 3.74 (3H, s); 3.72 (3H, s); 3.60 (6 H, m); 2.44 (7H, m). m/z (ESI, +ve ion) 545 (M+H)$^+$.

Step 3: 4-(2-(5-fluoro-6-methoxypyridin-3-ylamino)-6-(morpholinomethyl)pyridin-3-yl)-6-methyl-1,3,5-triazin-2-amine The title compound was prepared in an analogous manner to that described in Example 197 (starting from Step 2) using 4-(2-fluoro-6-(morpholinomethyl)pyridin-3-yl)-N,N-bis(4-methoxybenzyl)-6-methyl-1,3,5-triazin-2-amine. $^1$H NMR (400 MHz, d6-DMSO) δ 12.00 (1H, s); 8.77 (1H, d, J=8.0 Hz); 8.52 (1H, d, J=11.2 Hz); 8.51 (1H, s); 7.87 (1H, s); 7.73

(1H, s); 7.01 (1H, d, J=8.0 Hz); 3.94 (3H, s); 3.63 (4H, m); 3.59 (2 H, s); 2.48 (4H, m); 2.42 (3H, s). m/z (ESI, +ve ion) 427 (M+H)⁺.

Example 199

4-(2-(5-fluoro-6-methoxypyridin-3-ylamino)-6-((2,2,2-trifluoroethoxy)methyl)pyridin-3-yl)-6-methyl-1,3,5-triazin-2-amine

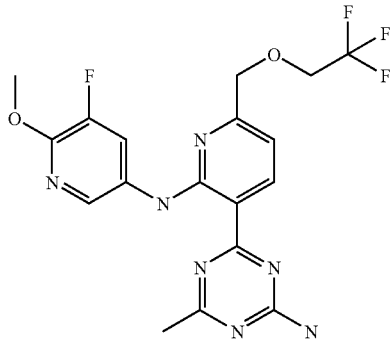 [SMILES: COc1ncc(Nc2nc(COCC(F)(F)F)ccc2-c2nc(C)nc(N)n2)cc1F]

Step 1: 3-bromo-2-fluoro-6-((2,2,2-trifluoroethoxy)methyl)pyridine

The title compound was prepared in an analogous manner to that described in Example 198 (Step 1) using 3-bromo-2-fluoro-6-methylpyridine (1.44 g, 7.58 mmol) (Waterstone Technology) and 2,2,2-trifluoroethanol. ¹H NMR (400 MHz, d6-DMSO) δ 8.34 (1H, t, J=8.5 Hz); 7.34 (1H, d, J=7.9 Hz); 4.69 (2 H, s); 4.22 (2 H, q, J=9.5 Hz). m/z (ESI, +ve ion) 288/290 (M+H)⁺.

Step 2. 4-(2-(5-fluoro-6-methoxypyridin-3-ylamino)-6-((2,2,2-trifluoroethoxy)methyl)pyridin-3-yl)-6-methyl-1,3,5-triazin-2-amine The title compound was prepared in an analogous manner to that described in Example 198 (starting from step 2) using 3-bromo-2-fluoro-6-((2,2,2-trifluoroethoxy)methyl)pyridine. ¹H NMR (400 MHz, d6-DMSO) δ 12.00 (1H, s); 8.83 (1H, d, J=8.0 Hz); 8.47 (1H, d, J=2.1 Hz); 8.41 (1H, dd, J=12.8, 2.2 Hz); 7.89 (1H, br.); 7.75 (1H, br.); 6.97 (1H, d, J=8.0 Hz); 4.74 (2 H, s); 4.24 (2 H, q, J=9.4 Hz); 3.93 (3H, s); 2.43 (3H, s). m/z (ESI, +ve ion) 440 (M+H)⁺.

Example 200

4-(2-(5-fluoropyridin-3-ylamino)-6-methylpyridin-3-yl)-6-methyl-1,3,5-triazin-2-amine

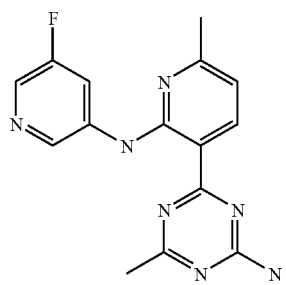 [SMILES: Cc1ccc(-c2nc(C)nc(N)n2)c(Nc2cncc(F)c2)n1]

The title compound was prepared in an analogous manner to that described in Example 197 starting from 2-fluoro-6-picoline-3-boronic acid (Asynchem Laboratories, Inc.) and 3-amino-5-fluoropyridine (Matrix Scientific). ¹H NMR (400 MHz, d6-DMSO) δ 12.33 (1H, s); 8.66 (1H, s); 8.73 (1H, d, J=8.2 Hz); 8.60 (1H, d, J=12.9 Hz); 8.16 (1H, s); 7.90 (1H, br.); 7.75 (1H, br.); 6.91 (1H, d, J=8.0 Hz); 2.48 (3H, s); 2.44 (3H, s). m/z (ESI, +ve ion) 312 (M+H)⁺.

Example 201

4-(2-(6-methoxypyridin-3-ylamino)-5-(thiomorpholinomethyl)pyridin-3-yl)-6-methyl-1,3,5-triazin-2-amine

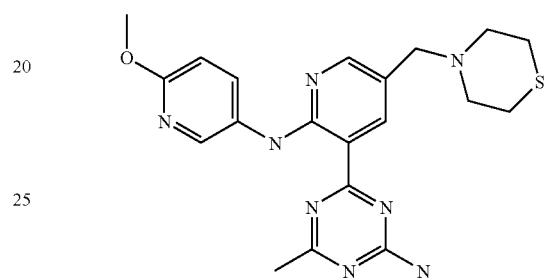

Step 1: 4((6-fluoropyridin-3-yl)methyl)thiomorpholine

A solution of 5-(bromomethyl)-2-fluoropyridine (3.61 g, 19.00 mmol) in anhydrous DMF (22 mL) at 0° C. was treated with thiomorpholine (2.254 g, 21.85 mmol) (TCI America) in 3 mL of DMF and potassium carbonate (3.28 g, 23.75 mmol). The suspension was slowly warmed to RT and stirred at RT for 2 h. The reaction was quenched with 30 mL of ice water, stirred at RT for 30 min, and the solid was collected by filtration, and rinsed with water followed by ether to give 4-((6-fluoropyridin-3-yl)methyl)thiomorpholine (3.33 g, 15.69 mmol, 83% yield) as an off-white crystalline solid. ¹H NMR (400 MHz, d6-DMSO) δ 8.12 (s, 1H); 7.89 (td, J=8.20, 2.2 Hz, 1H); 7.14 (dd, J=8.10, 2.80 Hz, 1H); 3.53 (s, 2H); 2.63-2.59 (br. 8H). m/z (ESI, +ve ion) 213 (M+H)⁺.

Step 2: 2-fluoro-5-(thiomorpholinomethyl)pyridin-3-ylboronic acid

A solution of diisopropylamine (0.767 mL, 5.43 mmol) in 2 mL of THF at −40° C. was treated with n-butyllithium (3.4 ml of 1.6 M solution in hexanes, 5.43 mmol) and stirred at this temperature for 30 min. The solution was cooled to −78° C. and treated dropwise via cannula with a solution of 4-((6-fluoropyridin-3-yl)methyl)thiomorpholine (922 mg, 4.34 mmol) in THF (2+2 mL) over 10 min. The brown mixture was stirred at −78° C. for 90 min and then treated dropwise via syringe with a solution of triisopropyl borate (1.49 mL, 6.51 mmol) in THF (1 mL). The mixture was stirred at −78° C. for 30 min. The cooling bath was removed, and the reaction mixture was allowed to warm up to RT. The mixture was quenched with 1.0 N NaOH (5 mL) and stirred for an additional 30 min. The mixture was transferred to a separatory funnel and extracted with 5 mL of ether. The ether layer was discarded, and the aqueous layer was carefully acidified with 2.5 N aqueous HCl until acidic (pH 4 about 5) and the resulting cloudy mixture was diluted with EtOAc (50 mL). The separated aqueous layer was extracted with EtOAc (2×15 mL) and the combined organic extracts were washed with brine, dried (Na$_2$SO$_4$), filtered, and concentrated to give 2-fluoro-5-(thiomorpholinomethyl)pyridin-3-ylboronic acid (790 mg, 3.08 mmol, 71.0% yield) as an off-white crystalline solid. $^1$H NMR (400 MHz, d4-MeOH) δ 8.11 (1H, d, J=2.5 Hz); 8.00 (1H, dd, J=8.0, 2.5 Hz); 3.75 (2H, s.); 2.91 (4H, m); 2.73 (4H, br. s.). m/z (ESI, +ve ion) 257 (M+H)$^+$.

Step 3: 4-(2-fluoro-5-(thiomorpholinomethyl)pyridin-3-yl)-N,N-bis(4-methoxybenzyl)-6-methyl-1,3,5-triazin-2-amine A mixture of 4-chloro-N,N-bis(4-methoxybenzyl)-6-methyl-1,3,5-triazin-2-amine (312 mg, 0.811 mmol), 2-fluoro-5-(thiomorpholinomethyl)pyridin-3-ylboronic acid (249 mg, 0.973 mmol), Am-Phos (40 mg, 0.057 mmol), and potassium acetate (239 mg, 2.432 mmol) in EtOH (3.5 mL) and water (1.5 mL) was heated in a microwave at 100° C. for 30 min. The mixture was partitioned between EtOAc (20 mL) and 1 N NaOH (3 mL). The separated EtOAc layer was washed with brine, concentrated and purified on a Redi-Sep pre-packed silica gel column (40 g) eluting with a gradient of 30-70% EtOAc in hexanes to give 4-(2-fluoro-5-(thiomorpholinomethyl)pyridin-3-yl)-N,N-bis(4-methoxybenzyl)-6-methyl-1,3,5-triazin-2-amine (306 mg, 67.3% yield) as a yellow viscous oil. $^1$H NMR (400 MHz) δ 8.47 (dd, J=9.3, 1.9 Hz, 1H); 8.28 (s, 1H); 7.24 (d, J=8.4 Hz, 4H); 6.90 (t, J=8.5 Hz, 4H); 4.76 (d, J=4.9 Hz, 4H); 3.74 (s, 3H); 3.73 (s, 3H); 3.60 (s, 2H); 2.66-2.58 (m, 8H); 2.47 (s, 3H). m/z (ESI, +ve ion) 561 (M+H)$^+$.

Step 4: N,N-bis(4-methoxybenzyl)-4-(2-(6-methoxypyridin-3-ylamino)-5-(thiomorpholinomethyl)pyridin-3-yl)-6-methyl-1,3,5-triazin-2-amine A solution of 4-(2-fluoro-5-(thiomorpholinomethyl)pyridin-3-yl)-N,N-bis(4-methoxybenzyl)-6-methyl-1,3,5-triazin-2-amine (390 mg, 0.696 mmol) and 6-methoxypyridin-3-amine (130 mg, 1.043 mmol) in 3 mL of THF at 0° C. was treated with LiHMDS (2.08 mL of 1.0 M solution in THF, 2.08 mmol).

After stirring at 0° C. for 10 min, the mixture was quenched with saturated NH$_4$Cl solution and extracted with EtOAc. The organic layer was washed with brine, dried and concentrated. The brown residue was stirred with 30 mL of EtOAc. The solid was collected by filtration and rinsed with 5 mL of EtOAc. The yellow crystalline solid was dried in a vacuum oven at 45° C. for 18 h to give the title compound (403 mg, 87% yield). $^1$H NMR (400 MHz, d6-DMSO) δ 11.50 (s, 1H); 8.65 (d, J=2.3 Hz, 1H); 8.30 (d, J=2.6 Hz, 1H); 8.17 (s, 1H); 7.88 (dd, J=8.3, 2.7 Hz, 1H); 7.25 (m, 4H); 6.91 (m, 4H); 6.75 (d, J=8.8 Hz, 1H); 4.85 (s, 2H); 4.80 (s, 2H); 3.82 (s, 3H); 3.74 (s, 3H); 3.70 (s, 3H); 3.46 (s, 2H); 3.31 (br., 4H); 2.60 (m, 4H); 2.56 (s, 3H). m/z (ESI, +ve ion) 665 (M+H)$^+$.

Step 5: 4-(2-(6-methoxypyridin-3-ylamino)-5-(thiomorpholinomethyl)pyridin-3-yl)-6-methyl-1,3,5-triazin-2-amine A solution of N,N-bis(4-methoxybenzyl)-4-(2-(6-methoxypyridin-3-ylamino)-5-(thiomorpholinomethyl)pyridin-3-yl)-6-methyl-1,3,5-triazin-2-amine (86 mg, 0.129 mmol) in 2 mL of TFA was treated with 2 drops of triflic acid. The brown solution was heated in an oil bath at 80° C. for 5 h. The volatiles were removed on and the dark residue was basified with 1 N NaOH and extracted with EtOAc twice followed by DCM once. The combined organic extracts were concentrated and purified on a Redi-Sep pre-packed silica gel column (12 g) eluting with a gradient of 2-6% MeOH in DCM to give 4-(2-(6-methoxypyridin-3-ylamino)-5-(thiomorpholinomethyl)pyridin-3-yl)-6-methyl-1,3,5-triazin-2-amine (30 mg, 55% yield) as an orange crystalline solid. $^1$H NMR (400 MHz, d6-DMSO) δ 11.75 (1H, s); 8.68 (1H, d, J=2.4 Hz); 8.54 (1H, d, J=2.7 Hz); 8.18 (1H, d, J=2.5 Hz); 8.16 (1H, d J=2.9 Hz); 7.87 (1H, br. s); 7.73 (1H, br. s); 6.82 (1H, d, J=9.0 Hz); 3.84 (3H, s); 3.46 (2 H, s); 2.67-2.60 (8H, m); 2.44 (3H, s). m/z (ESI, +ve ion) 425 (M+H)$^+$.

Example 202

4-(2-(6-methoxypyridin-3-ylamino)-5-(1-sulfoxidemorpholinomethyl)pyridin-3-yl)-6-methyl-1,3,5-triazin-2-amine

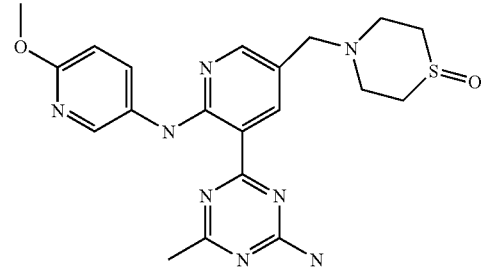 [SMILES: COc1ccc(Nc2ncc(CN3CCS(=O)CC3)cc2-c2nc(C)nc(N)n2)cn1]

Step 1: N,N-bis(4-methoxybenzyl)-4-(2-(6-methoxypyridin-3-ylamino)-5-(1-sulfoxidemorpholinomethyl)pyridin-3-yl)-6-methyl-1,3,5-triazin-2-amine A solution of N,N-bis(4-methoxybenzyl)-4-(2-(6-methoxypyridin-3-ylamino)-5-(thiomorpholinomethyl)pyridin-3-yl)-6-methyl-1,3,5-triazin-2-amine (100 mg, 0.150 mmol) in 0.5 mL of DCM and 0.25 mL of TFA at 0° C. was treated dropwise with a solution of PTFA (prepared by the addition of 0.3 mL of hydrogen peroxide (30% wt.) (17 mg, 0.15 mmol) to 0.47 mL of TFA). After stirring at 0-5° C. for 30 min, the mixture was diluted with DCM, washed with 1 N NaOH followed by brine. The DCM layer was dried and concentrated. The residue was purified on a Redi-Sep pre-packed silica gel column (12 g) eluting with a gradient of 2-10% MeOH in DCM to give the title compound (66 mg, 64% yield) as a brown amorphous solid. $^1$H NMR (400 MHz, d6-DMSO) δ 11.50 (s, 1H); 8.67 (d, J=2.1 Hz, 1H); 8.30 (d, J=2.7 Hz, 1H); 8.21 (d, J=2.7 Hz, 1H); 7.87 (dd, J=8.8, 2.8 Hz, 1H); 7.25 (m, 4H); 6.90 (m, 4H); 6.75 (d, J=8.8 Hz, 1H); 4.84 (s, 2H); 4.80 (s, 2H); 3.82 (s, 3H); 3.74 (s, 3H); 3.70 (s, 3H); 3.53 (s, 2H); 2.86 (m, 4H); 2.60 (m, 4H); 2.56 (s, 3H). m/z (ESI, +ve ion) 681 (M+H)$^+$.

Step 2: 4-(2-(6-methoxypyridin-3-ylamino)-5-(1-sulfoxidemorpholinomethyl)pyridin-3-yl)-6-methyl-1,3,5-triazin-2-amine A solution of N,N-bis(4-methoxybenzyl)-4-(2-(6-methoxypyridin-3-ylamino)-5-(1-sulfoxidemorpholinomethyl)pyridin-3-yl)-6-methyl-1,3,5-triazin-2-amine (66 mg, 0.097 mmol) in 2 mL of TFA was treated with 2 drops of triflic acid.

The brown solution was heated in an oil bath at 80° C. for 5 h. The volatiles were removed under reduced pressure. The dark residue was treated with 1 N NaOH and extracted with DCM (2×10 mL) followed by EtOAc (10 mL). The combined organic extracts were dried and concentrated. The residue was purified on a Redi-Sep pre-packed silica gel column (12 g), eluting with a gradient of 2-10% MeOH in DCM to give the title compound (20 mg, 47% yield) as a yellow crystalline solid. $^1$H NMR (400 MHz, d6-DMSO) δ 11.76 (1H, s); 8.71 (1H, d, J=2.3 Hz); 8.54 (1H, d, J=2.5 Hz); 8.22 (1H, d, J=2.3 Hz); 8.18 (1H, m); 7.88 (1H, br. s); 7.73 (1H, br. s); 6.82 (1H, d, J=8.8 Hz); 3.84 (3H, s); 3.53 (2 H, s); 2.87 (4H, m); 2.74 (2 H, m); 2.67 (2H, m); 2.44 (3H, s). m/z (ESI, +ve ion) 441 (M+H)$^+$.

Example 203

N-(3-(4-amino-6-methyl-1,3,5-triazin-2-yl)-5-((4-(methylsulfonyl)piperazin-1-yl)methyl)pyridin-2-yl)-3-methyl-3H-imidazo[4,5-B]pyridin-6-amine

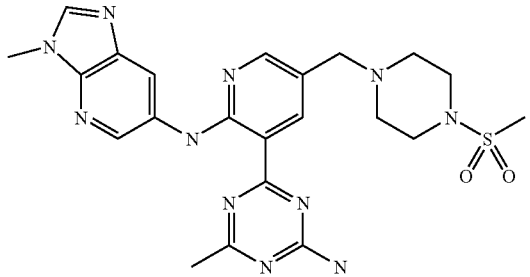

The title compound was prepared in an analogous manner to that described in Example 197 (starting from Step 2) using 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (388 mg, 0.624 mmol) and 3-methyl-3H-imidazo[4,5-b]pyridin-6-amine (Adesis) as starting materials. $^1$H NMR (400 MHz, d6-DMSO) δ 12.00 (s, 1H); 8.73 (d, J=2.3 Hz, 1H); 8.67 (m, 2H); 8.36 (s, 1H); 8.26 (d, J=2.5 Hz, 1H); 7.93 (br, 1H); 7.74 (br, 1H); 3.84 (s, 3H); 3.50 (s, 2H); 3.11 (m, 4H); 2.87 (s, 3H); 2.48-2.49 (m, 4H); 2.49 (m, 3H). m/z (ESI, +ve ion) 510 (M+H)$^+$.

Example 204

((3S)-1-(6-(((6-methoxy-3-pyridinyl)amino)-5-(2-methyl-9H-purin-6-yl)-3-pyridinyl)-3-pyrrolidinyl)methanol

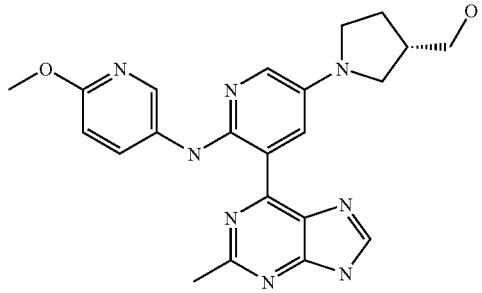 [SMILES: COc1ccc(Nc2ncc(N3CC[C@H](CO)C3)cc2-c2nc(C)nc3[nH]cnc23)cn1]

The title compound was synthesized following an analogous procedure to Example 97, substituting (S)-3-hydroxymethylpyrrolidine (Aldrich) for morpholine. $^1$H NMR (400 MHz, d6-DMSO) δ 13.56 (br. s., 1H); 12.14 (br. s., 1H); 9.25 (br. s., 1H); 8.61 (d, J=0.59 Hz, 1H); 8.49 (br. s., 1H); 8.13 (br. s., 1H); 7.79 (br. s., 1H); 6.80 (dd, J=8.51, 1.08 Hz, 1H); 4.75 (br. s., 1H); 3.83 (s, 3H); 3.41-3.53 (m, 6H); 3.11 (t, J=7.82 Hz, 1H); 2.84 (d, J=0.59 Hz, 3H); 2.08 (br. s., 1H); 1.77 (dt, J=13.35, 6.72 Hz, 1H). m/z (ESI, +ve ion) 433.38 (M+H)$^+$.

Example 205

(3S)-1-(6-(((6-methoxy-3-pyridinyl)amino)-5-(2-methyl-9H-purin-6-yl)-3-pyridinyl)-3-pyrrolidinol

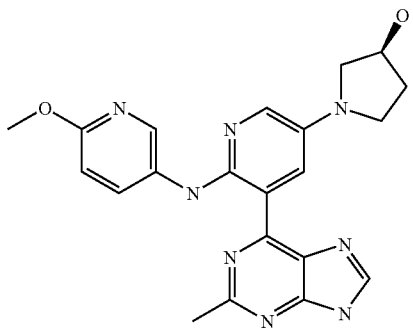 [SMILES: COc1ccc(Nc2ncc(N3CC[C@H](O)C3)cc2-c2nc(C)nc3[nH]cnc23)cn1]

The title compound was synthesized following an analogous procedure to Example 97, substituting (R)-(+)-3-pyrrolidinol (Aldrich) for morpholine. $^1$H NMR (400 MHz, d6-DMSO) δ 13.56 (br. s., 1H); 12.11 (br. s., 1H); 9.25 (s, 1H); 8.61 (s, 1H); 8.49 (br. s., 1H); 8.15 (d, J=9.19 Hz, 1H); 7.80 (br. s., 1H); 6.80 (d, J=0.39 Hz, 1H); 4.99 (d, J=0.39 Hz, 1H); 4.46 (br. s., 1H); 3.83 (s, 3H); 3.30-3.54 (m, 4H); 3.16 (d, J=9.98 Hz, 1H); 2.84-2.85 (br. s., 3H); 2.06-2.16 (m, 1H). m/z (ESI, +ve ion) 419.2 (M+H)$^+$.

Example 206

(3R)-1-(6-(((6-methoxy-3-pyridinyl)amino)-5-(2-methyl-9H-purin-6-yl)-3-pyridinyl)-3-pyrrolidinol

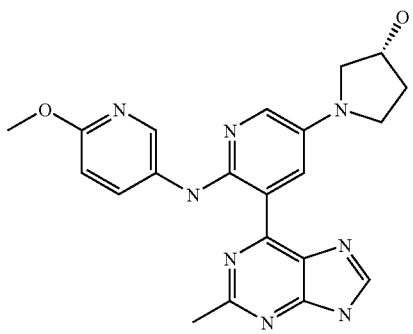 [SMILES: COc1ccc(Nc2ncc(N3CC[C@@H](O)C3)cc2-c2nc(C)nc3[nH]cnc23)cn1]

The title compound was synthesized following an analogous procedure to Example 97, substituting (S)-3-hydroxypyrrolidine (Aldrich) for morpholine. $^1$H NMR (400 MHz, d6-DMSO) δ 13.55 (s, 1H); 12.10 (s, 1H); 9.25 (d, J=2.74 Hz, 1H); 8.61 (s, 1H); 8.49 (d, J=1.17 Hz, 1H); 8.15 (dd, J=8.51, 2.64 Hz, 1H); 7.81 (br. s., 1H); 6.79 (d, J=8.80 Hz, 1H); 4.99 (d, J=4.11 Hz, 1H); 4.45 (d, J=1.56 Hz, 1H); 3.83 (s, 3H); 3.50 (dd, J=9.88, 5.38 Hz, 1H); 3.29-3.45 (m, 2H); 3.17 (d, J=1.17 Hz, 1H); 2.85 (s, 3H); 2.09-2.16 (m, 1H); 1.88-1.97 (m, 1H). m/z (ESI, +ve ion) 419.2 (M+H)⁺.

Example 207 tert-butyl 4-((5-(4-(bis(4-methoxybenzyl)amino)-6-methyl-1,3,5-triazin-2-yl)-6-(2-methoxypyrimidin-5-ylamino)pyridin-3-yl)methyl)piperazine-1-carboxylate

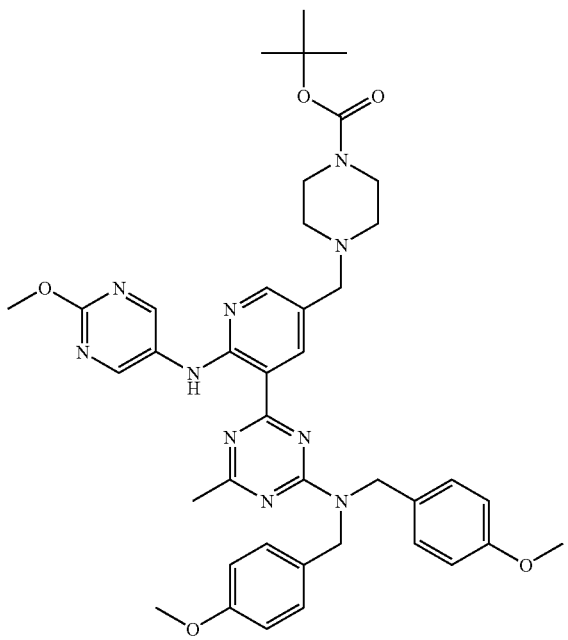

A solution of tert-butyl 4-((5-(4-(bis(4-methoxybenzyl)amino)-6-methyl-1,3,5-triazin-2-yl)-6-fluoropyridin-3-yl)methyl)piperazine-1-carboxylate (0.500 g, 0.777 mmol) and 2-methoxypyrimidin-5-amine (0.117 g, 0.932 mmol) (ACES PHARMA) in tetrahydrofuran (10 mL, 123 mmol) was stirred at 0° C. and treated dropwise via syringe with lithium bis(trimethylsilyl)amide (1.0 M solution in tetrahydrofuran; 2.330 mL, 2.330 mmol). The solution was stirred at 0° C. for 1 h. The solution was quenched with water (10 mL) and diluted with water (15 mL) and EtOAc (100 mL). The organic layer was separated and dried over Na₂SO₄, filtered and concentrated in vacuo to give tert-butyl 4-((5-(4-(bis(4-methoxybenzyl)amino)-6-methyl-1,3,5-triazin-2-yl)-6-(2-methoxypyrimidin-5-ylamino)pyridin-3-yl)methyl)piperazine-1-carboxylate (0.420 mg, 0.561 mmol, 72% yield). m/z (ESI, +ve ion) 749.4 (M+H)⁺.

Example 208

N,N-bis(4-methoxybenzyl)-4-(2-(2-methoxypyrimidin-5-ylamino)-5-((4-(methylsulfonyl)piperazin-1-yl)methyl)pyridin-3-yl)-6-methyl-1,3,5-triazin-2-amine

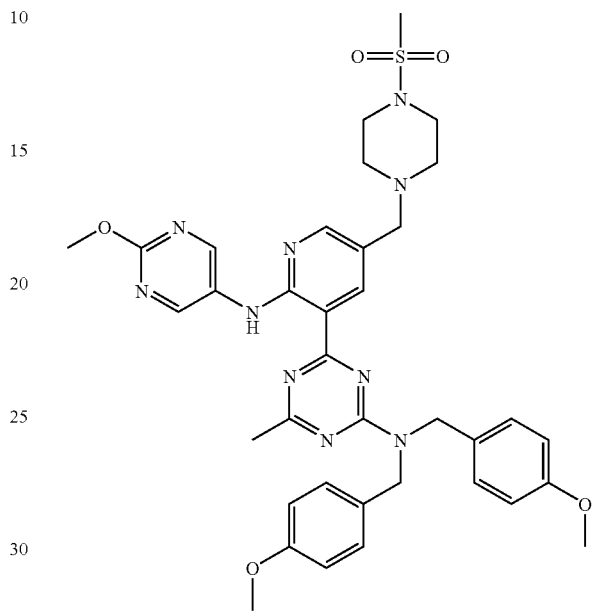

TFA (4.00 mL, 51.9 mmol) was added slowly to an ice-bath cooled stirred solution of tert-butyl 4-((5-(4-(bis(4-methoxybenzyl)amino)-6-methyl-1,3,5-triazin-2-yl)-6-(2-methoxypyrimidin-5-ylamino)pyridin-3-yl)methyl)piperazine-1-carboxylate (413 mg, 0.551 mmol) in dichloromethane (5.00 mL, 78 mmol) and the resulting mixture was stirred at room temperature for 1 h. The mixture was concentrated under vacuum to remove as much TFA as possible. The sticky residue was taken up in dichloromethane (5.00 mL) to which triethylamine (0.384 mL, 2.76 mmol) and methanesulfonyl chloride (0.129 mL, 1.654 mmol) were slowly added at 0° C. The mixture was stirred at 0° C. for 1 h and concentrated. The crude product was partitioned between 1 N NaOH(aq) and dichloromethane (20 mL each), and the separated aqueous layer was extracted with dichloromethane (2×20 mL). The combined organic layers were washed with brine, dried over Na₂SO₄, and concentrated to give the crude product which was purified by flash column chromatography (ISCO Combiflash system, pure DCM to 3% MeOH in DCM w/NH₃) to give N,N-bis(4-methoxybenzyl)-4-(2-(2-methoxypyrimidin-5-ylamino)-5-((4-(methylsulfonyl)piperazin-1-yl)methyl)

pyridin-3-yl)-6-methyl-1,3,5-triazin-2-amine (277 mg, 0.381 mmol, 69.1% yield) as a brown foam. m/z (ESI, +ve ion) 727.2 (M+H)⁺.

Example 209

4-(2-(2-methoxypyrimidin-5-ylamino)-5-((4-(methylsulfonyl)piperazin-1-yl)methyl)pyridin-3-yl)-6-methyl-1,3,5-triazin-2-amine

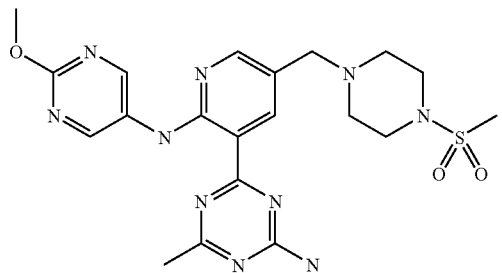 [SMILES: COc1ncc(Nc2ncc(CN3CCN(S(C)(=O)=O)CC3)cc2-c2nc(C)nc(N)n2)cn1]

A mixture of N,N-bis(4-methoxybenzyl)-4-(2-(2-methoxypyrimidin-5-ylamino)-5-((4-(methylsulfonyl)piperazin-1-yl)methyl)pyridin-3-yl)-6-methyl-1,3,5-triazin-2-amine (301 mg, 0.414 mmol) in trifluoroacetic acid (638 nL, 8.28 mmol) was treated with a couple of drops of trifluoromethanesulfonic acid and the mixture was heated at 80° C. overnight. After cooling, the mixture was concentrated and the residue was dissolved in 5% (2 M NH₃ in MeOH)/DCM (5 mL) and the crude product was adsorbed onto a plug of silica gel and chromatographed through a Redi-Sep pre-packed silica gel column (pure DCM→3% MeOH in DCM). The isolated yellow solid was dissolved in DMSO and was subjected to a reversed phase preparative HPLC purification (10% MeCN in H₂O to 100% MeCN w/0.1% (v/v) TFA). The product fraction was basified with saturated NaHCO₃(aq), extracted with dichloromethane (3×20 mL) and the combined organic layers were dried over Na₂SO₄, filtered, and concentrated to give 4-(2-(2-methoxypyrimidin-5-ylamino)-5-((4-(methylsulfonyl)piperazin-1-yl)methyl)pyridin-3-yl)-6-methyl-1,3,5-triazin-2-amine (65 mg, 0.134 mmol, 32.3% yield) as a bright yellow solid. ¹H NMR (400 MHz, d6-DMSO) δ 11.78 (s, 1H); 9.03 (s, 2H); 8.73 (d, J=1.56 Hz, 1H); 8.23 (d, J=1.76 Hz, 1H); 7.91 (br. s., 1H); 7.75 (br. s., 1H); 3.91 (s, 3H); 3.50 (s, 2H); 3.11 (br. s., 4H); 2.86 (s, 3H); 2.46-2.49 (m, 4H); 2.44 (s, 3H). m/z (ESI, +ve ion) 486.8 (M+H)⁺.

Example 210

4-((5-(4-(bis(4-methoxybenzyl)amino)-6-methyl-1,3,5-triazin-2-yl)-6-((6-methoxy-3-pyridinyl)amino)-3-pyridinyl)methyl)-N,N-dimethyl-1-piperazinesulfonamide

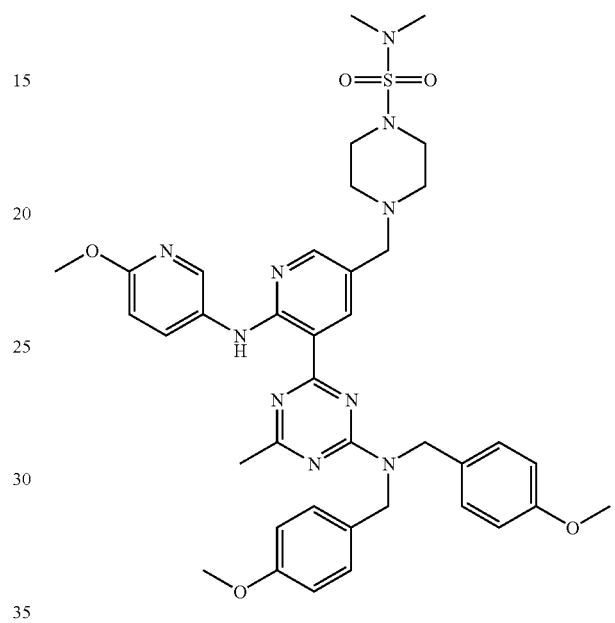

The title compound was synthesized following an analogous procedure to Example 85, Step 2, substituting dimethylsulfamoyl chloride (0.259 mL, 2.408 mmol) (Aldrich) for methanesulfonyl chloride. m/z (ESI, +ve ion) 755.3 (M+H)⁺.

Example 211

4-((5-(4-amino-6-methyl-1,3,5-triazin-2-yl)-6-((6-methoxy-3-pyridinyl)amino)-3-pyridinyl)methyl)-N,N-dimethyl-1-piperazinesulfonamide

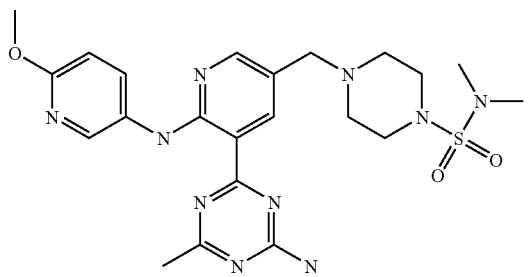 [SMILES: COc1ccc(Nc2ncc(CN3CCN(S(=O)(=O)N(C)C)CC3)cc2-c2nc(C)nc(N)n2)cn1]

A solution of 4-((5-(4-(bis(4-methoxybenzyl)amino)-6-methyl-1,3,5-triazin-2-yl)-6-(6-methoxypyridin-3-ylamino)pyridin-3-yl)methyl)-N,N-dimethylpiperazine-1-sulfonamide (0.210 g, 0.278 mmol) in trifluoroacetic acid (5 mL, 67.3 mmol) and trifluoromethanesulfonic acid (0.2 mL, 0.278 mmol) was stirred at 80° C. for 2 h. The dark solution was cooled down to room temperature and concentrated to a slurry. The slurry was neutralized to pH 8 with aqueous NaHCO₃. The precipitate was dissolved in DCM/MeOH and adsorbed onto a plug of silica gel and chromatographed through a Redi-Sep pre-packed silica gel column (40 g) eluting with a gradient of 5% to 10% 2 M NH₃.MeOH in CH₂Cl₂ to give 4-((5-(4-amino-6-methyl-1,3,5-triazin-2-yl)-6-(6-methoxypyridin-3-ylamino)pyridin-3-yl)methyl)-N,N-dimethylpiperazine-1-sulfonamide (0.110 g, 0.214 mmol, 77% yield). ¹H NMR (400 MHz, d6-DMSO) δ 11.75 (s, 1H); 8.70 (d, J=2.15 Hz, 1H); 8.55 (d, J=0.39 Hz, 1H); 8.19 (d, J=2.54 Hz, 2H); 8.17 (dd, J=8.90, 2.84 Hz, 1H); 7.86 (d, J=0.98 Hz, 1H); 7.71 (d, J=1.76 Hz, 1H); 6.82 (d, J=8.80 Hz, 1H); 3.84 (s, 3H); 3.47 (s, 2H); 3.31 (s, 2H); 3.16 (d, J=4.89 Hz, 3H); 2.75 (s, 6H); 2.47 (s, 2H); 2.44 (s, 3H). m/z (ESI, +ve ion) 515.2 (M+H)⁺.

Example 212

(5-(4-(bis(4-methoxybenzyl)amino)-6-methyl-1,3,5-triazin-2-yl)-6-((6-methoxy-3-pyridinyl)amino)-3-pyridinyl)methanol

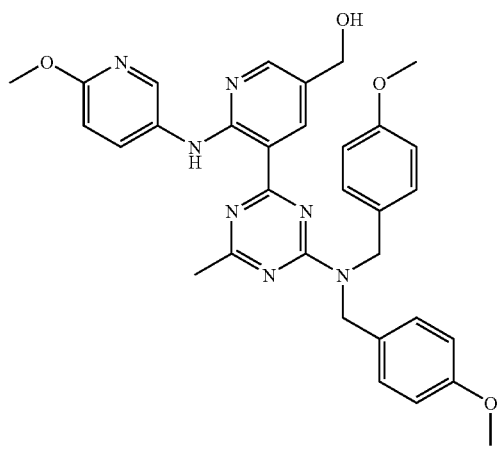

A suspension of 5-(4-(bis(4-methoxybenzyl)amino)-6-methyl-1,3,5-triazin-2-yl)-6-(6-methoxypyridin-3-ylamino) nicotinaldehyde (1.0 g, 1.731 mmol) in dichloromethane (20 mL, 306 mmol) and methanol (20 mL, 494 mmol) was stirred at 0° C. and treated in portions with sodium borohydride powder (Aldrich) (0.211 g, 5.57 mmol). The resulting suspension was warmed up to room temperature and stirred for 1 h. The reaction mixture was treated with saturated NH₄Cl (10 mL), diluted with water (40 mL) and stirred at room temperature for 2 h. The reaction mixture was diluted with water (10 mL) and extracted with dichloromethane (3×50 mL). The combined organic extracts were dried over Na₂SO₄, filtered and concentrated in vacuo to give (5-(4-(bis(4-methoxybenzyl)amino)-6-methyl-1,3,5-triazin-2-yl)-6-(6-methoxypyridin-3-ylamino)pyridin-3-yl)methanol (0.850 g, 1.466 mmol, 85yield). m/z (ESI, +ve ion) 580.2 (M+H)⁺.

Example 213

(5-(4-(bis(4-methoxybenzyl)amino)-6-methyl-1,3,5-triazin-2-yl)-6-(6-methoxypyridin-3-ylamino)pyridin-3-yl)methyl methanesulfonate

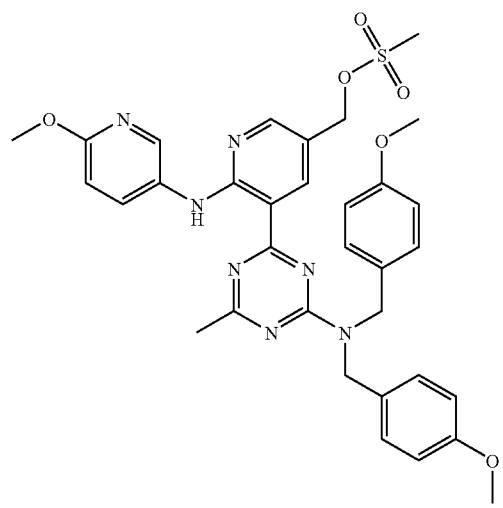

A suspension of (5-(4-(bis(4-methoxybenzyl)amino)-6-methyl-1,3,5-triazin-2-yl)-6-(6-methoxypyridin-3-ylamino) pyridin-3-yl)methanol (1.0 g, 1.725 mmol) in dichloromethane (25 mL, 1.725 mmol) was stirred at 0° C. and treated in one portion with triethylamine (1.092 mL, 7.85 mmol) and methanesulfonyl chloride (0.497 mL, 6.42 mmol). The resulting solution was stirred under nitrogen for 30 min. The reaction mixture was diluted with dichloromethane (10 mL) and treated with water (10 mL). The layers were separated and the aqueous layer was extracted with dichloromethane (2×50 mL) and dried over Na₂SO₄, filtered and concentrated in vacuo to give (5-(4-(bis(4-methoxybenzyl) amino)-6-methyl-1,3,5-triazin-2-yl)-6-(6-methoxypyridin- 3-ylamino)pyridin-3-yl)methyl methanesulfonate (0.935 g, 1.422 mmol, 82% yield). m/z (ESI, +ve ion) 658.2 (M+H)⁺

Example 214

1-((5-(4-(bis(4-methoxybenzyl)amino)-6-methyl-1,3,5-triazin-2-yl)-6-(6-methoxypyridin-3-ylamino)pyridin-3-yl)methyl)piperidin-4-ol

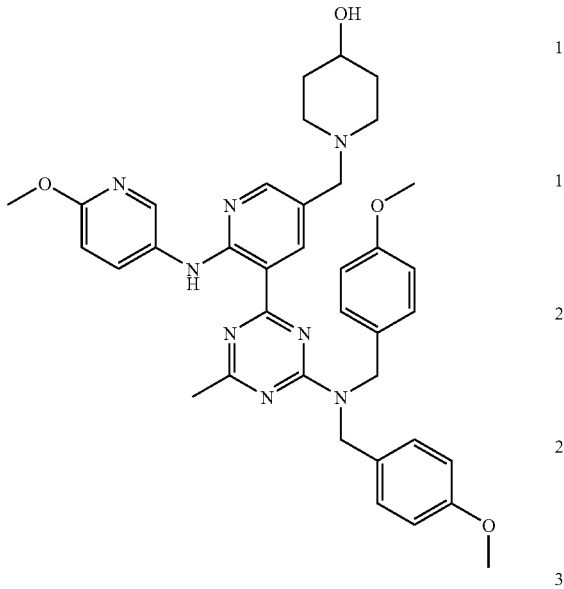

A suspension of (5-(4-(bis(4-methoxybenzyl)amino)-6-methyl-1,3,5-triazin-2-yl)-6-(6-methoxypyridin-3-ylamino)pyridin-3-yl)methyl methanesulfonate (0.510 g, 0.775 mmol), 4-hydroxypiperidine (0.254 g, 2.51 mmol) and triethylamine (0.491 mL, 3.53 mmol) in dichloromethane (25 mL) was stirred at room temperature overnight. The reaction mixture was diluted with water (20 mL) and extracted with dichloromethane (3×25 mL). The combined organic extracts were dried over Na₂SO₄, filtered and concentrated. The crude product was adsorbed onto a plug of silica gel and chromatographed through a Redi-Sep pre-packed silica gel column (40 g) eluting with a gradient of 5% to 20% 2 M NH₃.MeOH in CH₂Cl₂ to give 1-((5-(4-(bis(4-methoxybenzyl)amino)-6-methyl-1,3,5-triazin-2-yl)-6-(6-methoxypyridin-3-ylamino)pyridin-3-yl)methyl)piperidin-4-ol (0.385 g, 0.581 mmol, 74.9% yield). m/z (ESI, +ve ion) 663.3 (M+H)⁺.

Example 215

1-((5-(4-amino-6-methyl-1,3,5-triazin-2-yl)-6-(6-methoxypyridin-3-ylamino)pyridin-3-yl)methyl)piperidin-4-ol

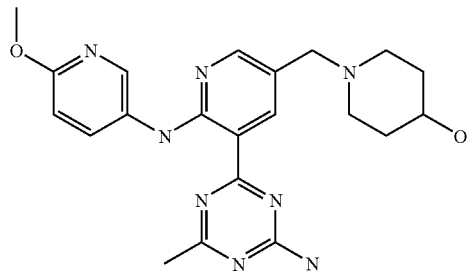 [SMILES: COc1ccc(Nc2ncc(CN3CCC(O)CC3)cc2-c2nc(C)nc(N)n2)cn1]

The title compound was synthesized from 1-((5-(4-(bis(4-methoxybenzyl)amino)-6-methyl-1,3,5-triazin-2-yl)-6-(6-methoxypyridin-3-ylamino)pyridin-3-yl)methyl)piperidin-4-ol (Example 213) following an analogous procedure to Example 209. ¹H NMR (400 MHz, d6-DMSO) δ 11.75 (s, 1H); 8.68 (d, J=0.78 Hz, 1H); 8.54 (d, J=2.74 Hz, 1H); 8.18 (d, J=2.74 Hz, 1H); 8.16 (t, J=2.35 Hz, 1H); 7.87 (d, J=1.37 Hz, 1H); 7.71 (br. s., 1H); 6.80-6.83 (d, J=9.00 Hz, 1H); 4.54 (d, J=4.11 Hz, 1H); 3.84 (s, 3H); 3.38 (br. s., 3H); 2.67 (dd, J=4.60, 2.64 Hz, 2H); 2.44 (s, 3H); 1.99 (m, 2H); 1.69 (d, J=3.33 Hz, 2H); 1.38 (d, J=10.76 Hz, 2H). m/z (ESI, +ve ion) 423.2 (M+H)⁺.

Example 216

(R)-(1-((5-(4-(bis(4-methoxybenzyl)amino)-6-methyl-1,3,5-triazin-2-yl)-6-(6-methoxypyridin-3-ylamino)pyridin-3-yl)methyl)pyrrolidin-3-yl)methanol

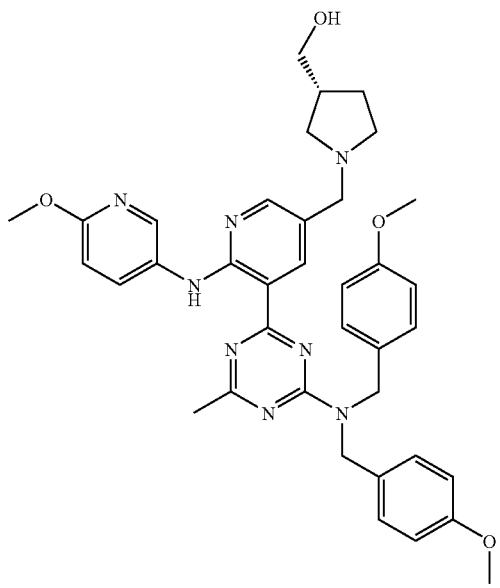

A mixture of 5-(4-(bis(4-methoxybenzyl)amino)-6-methyl-1,3,5-triazin-2-yl)-6-(6-methoxypyridin-3-ylamino) nicotinaldehyde (0.310 g, 0.537 mmol) and (R)-pyrrolidin-3-yl-methanol (0.163 mL, 1.610 mmol) in dichloromethane (0.035 mL, 0.537 mmol) and methanol (0.022 mL, 0.537 mmol) was treated with sodium triacetoxyborohydride (0.341 g, 1.610 mmol). The solution was stirred at room temperature overnight. The crude product was adsorbed onto a plug of silica gel and chromatographed through a Redi-Sep pre-packed silica gel column (40 g) eluting with a gradient of 5% to 10% 2 M NH₃.MeOH in CH₂Cl₂ to give (R)-(1-((5-(4-(bis(4-methoxybenzyl)amino)-6-methyl-1,3,5-triazin-2-yl)-6-(6-methonol ylamino)pyridin-3-yl)methyl)pyrrolidin-3-yl)methanol (0.188 g, 0.284 mmol, 52.9% yield). m/z (ESI, +ve ion) 663.2 (M+H)⁺.

Example 217

(R)-(1-((5-(4-amino-6-methyl-1,3,5-triazin-2-yl)-6-(6-methoxypyridin-3-ylamino)pyridin-3-yl)methyl)pyrrolidin-3-yl)methanol

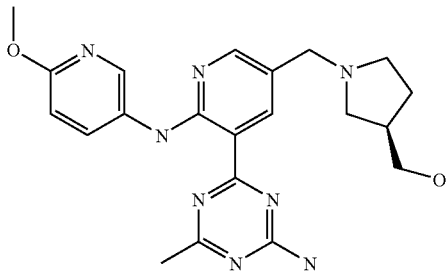 [SMILES: COc1ccc(Nc2ncc(CN3CC[C@@H](CO)C3)cc2-c2nc(C)nc(N)n2)cn1]

The title compound was synthesized from (R)-(1-((5-(4-(bis(4-methoxybenzyl)amino)-6-methyl-1,3,5-triazin-2-yl)-6-(6-methoxypyridin-3-ylamino)pyridin-3-yl)methyl)pyrrolidin-3-yl)methanol (Example 216) following an analogous procedure to Example 209. $^1$H NMR (400 MHz, d6-DMSO) δ 11.83 (s, 1H); 10.01-10.12 (dd, J=5.28, 2.35 Hz, 1H); 8.91 (dd, J=5.28, 2.35 Hz, 1H); 8.54 (dd, J=2.54, 0.39 Hz, 1H); 8.42 (dd, J=3.72, 2.35 Hz, 1H); 8.15 (dd, J=8.90, 2.84 Hz, 1H); 7.93 (d, J=1.17 Hz, 1H); 7.82 (d, J=0.78 Hz, 1H); 6.85 (d, J=9.00 Hz, 1H); 4.38 (dd, J=6.85, 0.39 Hz, 2H); 3.85 (s, 3H); 3.31-3.51 (m, 4H); 3.07-3.29 (m, 2H); 2.55-2.86 (m, 1H); 2.44 (s, 3H); 1.92-2.14 (m, 1H); 1.61-1.82 (m, 1H). m/z (ESI, +ve ion) 423.2 (M+H)$^+$.

Example 218

(S)-N,N-bis(4-methoxybenzyl)-4-(2-(6-methoxypyridin-3-ylamino)-5-((3-methylmorpholino)methyl)pyridin-3-yl)-6-methyl-1,3,5-triazin-2-amine

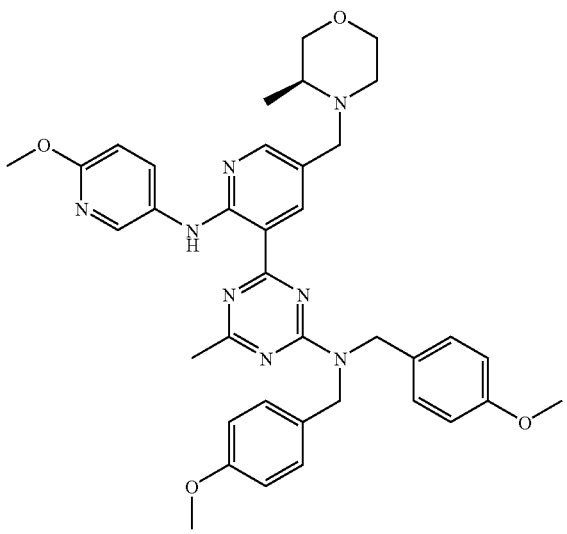

4 Å molecular sieves were added to a mixture of 5-(4-(bis(4-methoxybenzyl)amino)-6-methyl-1,3,5-triazin-2-yl)-6-(6-methoxypyridin-3-ylamino)nicotinaldehyde (0.300 g, 0.519 mmol) and 3(S)-3-methylmorpholine (0.158 mL, 1.558 mmol) in toluene (50 mL, 470 mmol) and the mixture was stirred under N$_2$ at reflux for 3 h. The mixture was filtered through Celite® (diatomaceous earth) and concentrated in vacuo to give a yellow oil. The oil was dissolved in methanol (50 mL, 1234 mmol) at 0° C. and the stirred solution was treated with sodium cyanoborohydride (0.082 mL, 1.558 mmol). Glacial acetic acid (0.500 mL, 8.66 mmol) was added slowly. The mixture was allowed to warm up to room temperature and stirred for 3 h. The reaction was quenched with 20% NaOH aqueous solution (5 mL) and water (2 mL), extracted with EtOAc and dried over K$_2$CO$_3$, and concentrated in vacuo. The crude product was adsorbed onto a plug of silica gel and chromatographed through a Redi-Sep prepacked silica gel column (40 g) eluting with gradient of 20% to 50% EtOAc/hexane to give (S)-N,N-bis(4-methoxybenzyl)-4-(2-(6-methoxypyridin-3-ylamino)-5-((3-methylmorpholino)methyl)pyridin-3-yl)-6-methyl-1,3,5-triazin-2-amine (0.095 g, 0.143 mmol, 27.6% yield). m/z (ESI, +ve ion) 663.3 (M+H)$^+$.

Example 219

(S)-4-(2-(6-methoxypyridin-3-ylamino)-5-((3-methylmorpholino)methyl)pyridin-3-yl)-6-methyl-1,3,5-triazin-2-amine

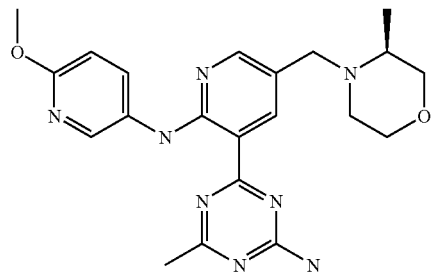 [SMILES: COc1ccc(Nc2ncc(CN3CCOC[C@@H]3C)cc2-c2nc(C)nc(N)n2)cn1]

The title compound was synthesized from (S)-N,N-bis(4-methoxybenzyl)-4-(2-(6-methoxypyridin-3-ylamino)-5-((3-methylmorpholino)methyl)pyridin-3-yl)-6-methyl-1,3,5-triazin-2-amine following an analogous procedure to Example 209. $^1$H NMR (400 MHz, CDCl$_3$) δ 11.71 (br. s., 1H); 8.85 (br. s., 1H); 8.35 (dd, J=2.35, 0.39 Hz, 1H); 8.21 (d, J=0.59 Hz, 1H); 8.09 (d, J=8.80 Hz, 1H); 6.77 (d, J=8.80 Hz, 1H); 5.70 (br. s., 2H); 3.94 (s, 3H); 3.64-3.84 (m, 3H); 3.49 (s, 2H); 2.62 (s, 1H); 2.44 (s, 3H); 1.24-1.26 (m, 3H); 1.20-1.22 (s, 3H). m/z (ESI, +ve ion) 423.2 (M+H)$^+$.

Example 220

4-(5-(azetidin-1-ylmethyl)-2-(6-methoxypyridin-3-ylamino)pyridin-3-yl)-6-methyl-1,3,5-triazin-2-amine

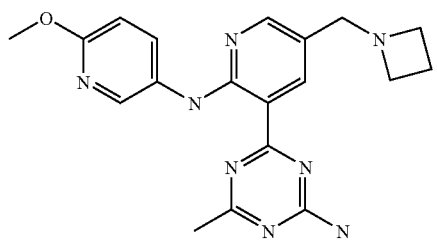 [SMILES: COc1ccc(Nc2ncc(CN3CCC3)cc2-c2nc(C)nc(N)n2)cn1]

Step 1: 4-(5-(azetidin-1-ylmethyl)-2-(6-methoxypyridin-3-ylamino)pyridin-3-yl)-N,N-bis(4-methoxybenzyl)-6-methyl-1,3,5-triazin-2-amine 5-(4-(Bis(4-methoxybenzyl)amino)-6-methyl-1,3,5-triazin-2-yl)-6-(6-methoxypyridin-3-ylamino)nicotinaldehyde (228 mg, 0.395 mmol) and sodium triacetoxyborohydride (125 mg, 0.592 mmol) were added to a solution of azetidine hydrochloride (Aldrich, St. Louis, Mo.) (48.0 mg, 0.513 mmol) in methanol (2 mL), DCM (2 mL) and diisopropylethylamine (103 µL, 0.592 mmol). The reaction mixture was stirred at ambient temperature for 2 h. More sodium triacetoxyborohydride was added and the mixture was allowed to stir at ambient temperature for 30 min. The reaction mixture was concentrated and diluted with 150 mL of DCM, added to a separatory funnel, partitioned with water, washed 2 times with 50 mL of sodium bicarbonate (saturated, aqueous), separated, diluted with a small amount of methanol to make the solution clear, dried over sodium sulfate, and concentrated to give 4-(5-(azetidin-1-ylmethyl)-2-(6-methoxypyridin-3-ylamino)pyridin-3-yl)-N,N-bis(4-methoxybenzyl)-6-methyl-1,3,5-triazin-2-amine (150 mg, 61.4% yield). m/z (ESI, +ve ion) 619.2 (M+H)$^+$.

Step 2: 4-(5-(azetidin-1-ylmethyl)-2-(6-methoxypyridin-3-ylamino)pyridin-3-yl)-6-methyl-1,3,5-triazin-2-amine A solution of 4-(5-(azetidin-1-ylmethyl)-2-(6-methoxypyridin-3-ylamino)pyridin-3-yl)-N,N-bis(4-methoxybenzyl)-6-methyl-1,3,5-triazin-2-amine (150 mg, 0.242 mmol) in TFA (2424 µL) was treated with trifluoromethanesulfonic acid (63.5 µL, 0.727 mmol) and stirred at 80° C. for 1 h. The reaction mixture was concentrated and diluted with 100 mL of DCM, added to a separatory funnel, partitioned with sodium bicarbonate (saturated, aqueous), washed 2 times with 75 mL of sodium bicarbonate (saturated, aqueous), separated, diluted with a small amount of methanol to make the solution clear, dried over sodium sulfate, and concentrated to give crude product. The crude product was purified via flash chromatography (silica gel) with 100% DCM to 8% 2 M ammonia in MeOH/DCM to give 4-(5-(azetidin-1-ylmethyl)-2-(6-methoxypyridin-3-ylamino)pyridin-3-yl)-6-methyl-1,3,5-triazin-2-amine (11 mg, 11.99% yield). $^1$H NMR (400 MHz, CDCl$_3$) δ 11.75 (s, 1H); 8.90 (d, J=2.35 Hz, 1H); 8.37 (d, J=2.74 Hz, 1H); 8.17 (d, J=2.35 Hz, 1H); 8.08 (dd, J=8.90, 2.64 Hz, 1H); 6.77 (d, J=8.80 Hz, 1H); 3.94 (s, 3H); 3.76 (s, 2H); 3.53 (t, J=7.34 Hz, 4H); 2.53 (s, 3H); 2.28 (quin, J=7.38 Hz, 2H). m/z (ESI, +ve ion) 379.1 (M+H)$^+$.

Example 221

4-(2-(6-methoxypyridin-3-ylamino)-5-(pyrrolidin-1-ylmethyl)pyridin-3-yl)-6-methyl-1,3,5-triazin-2-amine

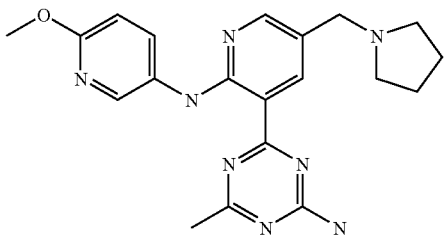 [SMILES: COc1ccc(Nc2ncc(CN3CCCC3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde and pyrrolidine (Aldrich, St. Louis, Mo.). $^1$H NMR (400 MHz, CDCl$_3$) δ 11.64 (s, 1H); 8.71 (d, J=2.35 Hz, 1H); 8.36 (d, J=2.54 Hz, 1H); 8.20 (d, J=2.35 Hz, 1H); 8.13 (dd, J=8.80, 2.74 Hz, 1H); 6.76 (d, J=8.80 Hz, 1H); 6.33 (br. s., 2H); 3.94 (s, 3H); 3.58 (s, 2H); 2.57 (br. s., 4H); 2.54 (s, 3H); 1.80-1.90 (m, 4H). m/z (ESI, +ve ion) 392.9 (M+H)$^+$.

Example 222

4-(2-(6-methoxypyridin-3-ylamino)-5-(piperidin-1-ylmethyl)pyridin-3-yl)-6-methyl-1,3,5-triazin-2-amine

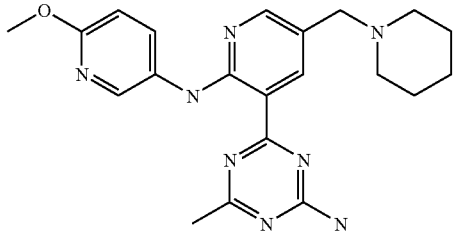 [SMILES: COc1ccc(Nc2ncc(CN3CCCCC3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (264 mg, 0.457 mmol) and piperidine (Aldrich, St. Louis, Mo.) (67.7 µL, 0.686 mmol). $^1$H NMR (400 MHz, CDCl$_3$) δ 11.64 (s, 1H); 8.72 (d, J=2.35 Hz, 1H); 8.35 (d, J=2.54 Hz, 1H); 8.21 (d, J=2.35 Hz, 1H); 8.14 (dd, J=8.90, 2.84 Hz, 1H); 6.77 (d, J=9.00 Hz, 1H); 5.56 (br. s., 2H); 3.94 (s, 3H); 3.45 (s, 2H); 2.56 (s, 3H); 2.41

(br. s., 3H); 1.60 (dt, J=10.95, 5.48 Hz, 5H); 1.39-1.46 (m, 2H). m/z (ESI, +ve ion) 407.0 (M+H)+.

Example 223

4-(2-(6-methoxypyridin-3-ylamino)-5-(3-(methylsulfonyl)azetidin-1-yl)methyl)pyridin-3-yl)-6-methyl-1,3,5-triazin-2-amine

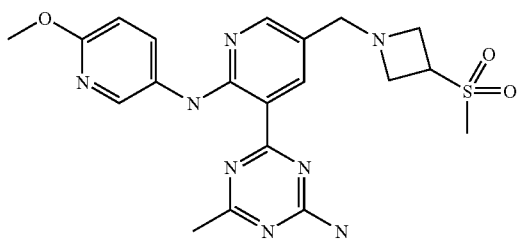 [SMILES: COc1ccc(Nc2ncc(CN3CC(S(C)(=O)=O)C3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.200 g, 0.346 mmol) and 3-(methylsulfonyl)azetidine (PharmaBlock, Carrboro, N.C.) (0.070 g, 0.519 mmol). $^1$H NMR (400 MHz, d6-DMSO) δ 11.81 (s, 1H); 8.88 (br. s., 1H); 8.54 (d, J=2.74 Hz, 1H); 8.38 (d, J=1.76 Hz, 1H); 8.13 (dd, J=8.90, 2.64 Hz, 1H); 7.77-7.94 (m, 2H); 6.85 (d, J=8.80 Hz, 1H); 4.09-4.58 (m, 7H); 3.85 (s, 3H); 3.12 (s, 3H); 2.44 (s, 3H). m/z (ESI, +ve ion) 456.8 (M+H)+.

Example 224

4-(2-(6-methoxypyridin-3-ylamino)-5-((4-(methylsulfonyl)piperidin-1-yl)methyl)pyridin-3-yl)-6-methyl-1,3,5-triazin-2-amine

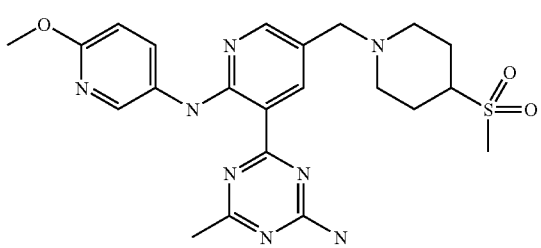 [SMILES: COc1ccc(Nc2ncc(CN3CCC(S(C)(=O)=O)CC3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.200 g, 0.346 mmol) and 4-(methylsulfonyl)piperidine (PharmaBlock, Carrboro, N.C.) (0.085 g, 0.519 mmol). $^1$H NMR (400 MHz, CDCl$_3$) δ 11.67 (s, 1H); 8.71 (d, J=2.15 Hz, 1H); 8.36 (d, J=2.54 Hz, 1H); 8.18 (d, J=2.35 Hz, 1H); 8.11 (dd, J=9.00, 2.74 Hz, 1H); 6.77 (d, J=8.80 Hz, 1H); 5.76 (s, 2H); 3.94 (s, 3H); 3.49 (s, 2H); 3.10 (d, J=11.35 Hz, 2H); 2.80-2.86 (m, 4H); 2.55 (s, 3H); 2.00-2.18 (m, 4H); 1.84-2.00 (m, 3H). m/z (ESI, +ve ion) 484.9 (M+H)+.

Example 225

2-((5-(4-amino-6-methyl-1,3,5-triazin-2-yl)-6-(6-methoxypyridin-3-ylamino)pyridin-3-yl)methylamino)ethanol

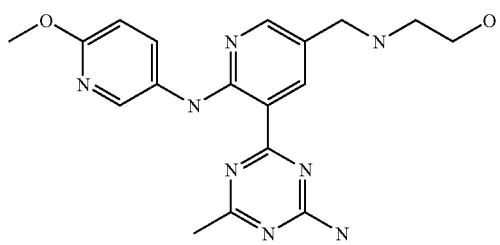 [SMILES: COc1ccc(Nc2ncc(CNCCO)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.200 g, 0.346 mmol) and ethanolamine (Aldrich, St. Louis, Mo.) (0.031 mL, 0.519 mmol). $^1$H NMR (400 MHz, d6-DMSO) δ 11.79 (s, 1H); 8.89 (d, J=2.35 Hz, 1H); 8.55 (d, J=2.54 Hz, 1H); 8.34 (d, J=2.35 Hz, 1H); 8.13 (dd, J=8.90, 2.64 Hz, 1H); 7.74-7.93 (m, 1H); 6.84 (d, J=9.00 Hz, 1H); 5.08 (br. s., 1H); 4.08 (s, 2H); 3.82-3.88 (m, 3H); 3.63 (q, J=4.96 Hz, 2H); 2.95 (t, J=5.09 Hz, 2H); 2.44 (s, 3H). m/z (ESI, +ve ion) 383.1 (M+H)+.

Example 226

(R)-2-((5-(4-amino-6-methyl-1,3,5-triazin-2-yl)-6-(6-methoxypyridin-3-ylamino)pyridin-3-yl)methylamino)propan-1-ol

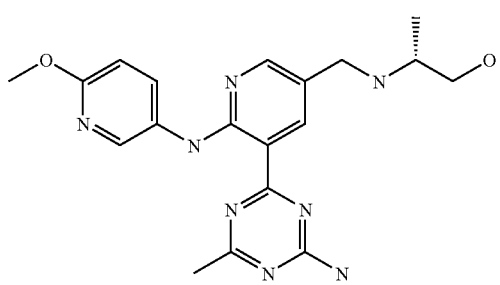 [SMILES: COc1ccc(Nc2ncc(CN[C@H](C)CO)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.230 g, 0.398 mmol) and (R)-2-aminopropanol (Aldrich, St. Louis, Mo.) (0.047 mL, 0.597 mmol). $^1$H NMR (400 MHz, d6-DMSO) δ 11.82 (s, 1H); 8.93 (d, J=2.35 Hz, 1H); 8.60-8.80 (m, 2H); 8.56 (d, J=2.54 Hz, 1H); 8.38 (d, J=2.54 Hz, 1H); 8.13 (dd, J=8.90, 2.84 Hz, 1H); 7.76-7.95 (m, 2H); 6.85 (d, J=8.80 Hz, 1H);

4.17 (t, J=5.67 Hz, 2H); 3.85 (s, 3H); 3.50-3.56 (m, 2H); 3.22-3.32 (m, 1H); 2.44 (s, 3H); 1.26 (d, J=6.65 Hz, 3H). m/z (ESI, +ve ion) 397.1 (M+H)+.

Example 227

4-(5-((2-methoxyethylamino)methyl)-2-(6-methoxy-pyridin-3-ylamino)pyridin-3-yl)-6-methyl-1,3,5-triazin-2-amine

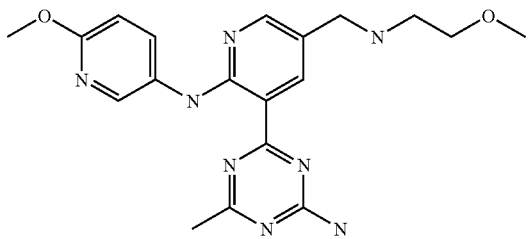

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.24 g, 0.415 mmol) and 2-methoxyethanamine (Aldrich, St. Louis, Mo.) (0.054 mL, 0.623 mmol). $^1$H NMR (400 MHz, CDCl$_3$) δ 11.63 (s, 1H); 8.78 (d, J=2.54 Hz, 1H); 8.35 (d, J=2.54 Hz, 1H); 8.24 (d, J=2.54 Hz, 1H); 8.12 (dd, J=8.80, 2.74 Hz, 1H); 6.77 (d, J=8.80 Hz, 1H); 5.63 (s, 2H); 3.94 (s, 3H); 3.78 (s, 2H); 3.52-3.57 (m, 2H); 3.36 (s, 3H); 2.80-2.86 (m, 2H); 2.55 (s, 3H). m/z (ESI, +ve ion) 397.0 (M+H)+.

Example 228

(RAC)-4-(2-(6-methoxypyridin-3-ylamino)-5-((3-methylsulfonyl)pyrrolidin-1-yl)methyl)pyridin-3-yl)-6-methyl-1,3,5-triazin-2-amine

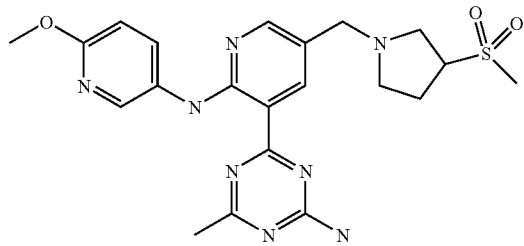 [SMILES: COc1ccc(Nc2ncc(CN3CCC(S(C)(=O)=O)C3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.23 g, 0.398 mmol) and 3-(methylsulfonyl)pyrrolidine (PharmaBlock, Carrboro, N.C.) (0.089 g, 0.597 mmol). $^1$H NMR (400 MHz, CDCl$_3$) δ 11.63 (s, 1H); 8.73 (d, J=2.35 Hz, 1H); 8.36 (d, J=2.54 Hz, 1H); 8.21 (d, J=2.15 Hz, 1H); 8.10 (dd, J=8.80, 2.74 Hz, 1H); 6.78 (d, J=8.80 Hz, 1H); 5.55 (br. s., 2H); 3.94 (s, 3H); 3.56-3.68 (m, 3H); 2.99-3.05 (m, 1H); 2.88-2.95 (m, 1H); 2.87 (s, 3H); 2.76-2.84 (m, 1H); 2.61-2.70 (m, 1H); 2.56 (s, 3H); 2.25-2.35 (m, 2H). m/z (ESI, +ve ion) 470.9 (M+H)+.

Example 229

1-((5-(4-amino-6-methyl-1,3,5-triazin-2-yl)-6-(6-methoxypyridin-3-ylamino)pyridin-3-yl)methyl)azetidin-3-ol

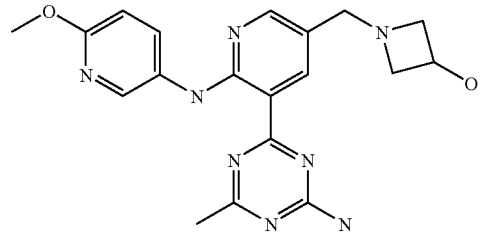 [SMILES: COc1ccc(Nc2ncc(CN3CC(O)C3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.22 g, 0.381 mmol) and 3-hydroxyazetidine hydrochloride (Oakwood Products, Inc., West Columbia, S.C.) (0.063 g, 0.571 mmol). $^1$H NMR (400 MHz, CDCl$_3$) δ 11.46 (s, 1H); 8.53 (br. s., 1H); 8.36 (d, J=2.54 Hz, 1H); 8.14 (d, J=2.15 Hz, 1H); 8.09 (dd, J=8.90, 2.64 Hz, 1H); 6.77 (d, J=8.80 Hz, 1H); 4.46-4.55 (m, 1H); 3.94 (s, 3H); 3.64 (s, 2H); 3.59 (t, J=7.73 Hz, 2H); 3.30-3.40 (m, 2H); 2.56 (s, 3H). m/z (ESI, +ve ion) 395.0 (M+H)+.

Example 230

2-((5-(4-amino-6-methyl-1,3,5-triazin-2-yl)-6-(6-methoxypyridin-3-ylamino)pyridin-3-yl)methyl)-2,5,7-triazaspiro[3.4]octane-6,8-dione

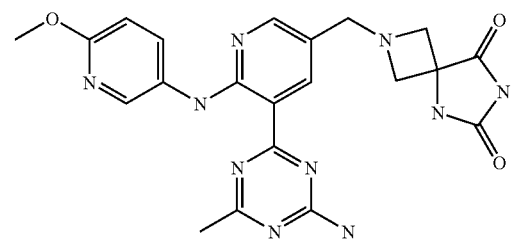 [SMILES: COc1ccc(Nc2ncc(CN3CC4(C3)NC(=O)NC4=O)cc2-c2nc(C)nc(N)n2)cn1]

Step 1: 2-benzhydryl-2,5,7-triazaspiro[3.4]octane-6,8-dione

Potassium cyanide (0.151 g, 2.32 mmol), ammonium carbonate (0.445 g, 4.64 mmol), and 1-benzhydrylazetidin-3-one (WO2007109334) (0.500 g, 2.11 mmol) were combined in 10 mL 2:1 EtOH/H$_2$O and heated at 60° C. for 3 days in a sealed tube. The reaction mixture was cooled and concentrated in vacuo to remove EtOH. Additional water was added, and the solids were collected by filtration, rinsing with water and a minimal volume of MeOH. This gave 441 mg of a white solid. The material was suspended in 10 mL MeOH and sonicated for 10 min. The solid was collected and rinsed with MeOH to give 2-benzhydryl-2,5,7-triazaspiro[3.4]octane-6,8-dione (0.283 g, 43.7% yield) as a white solid. m/z (ESI, +ve ion) 308.1 (M+H)⁺.

Step 2: 2,5,7-triazaspiro[3.4]octane-6,8-dione acetate

A mixture of 2-benzhydryl-2,5,7-triazaspiro[3.4]octane-6,8-dione (0.258 g, 0.839 mmol) and 10% palladium on carbon (0.179 g, 0.168 mmol) in 4 mL MeOH was treated with acetic acid (0.0961 mL, 1.68 mmol) and the slurry was stirred under a balloon containing hydrogen overnight. The reaction was filtered, rinsed with MeOH, and concentrated in vacuo to give an oil. Concentration from benzene gave a solid which was suspended in diethylether, sonicated, filtered, and dried in vacuo to give 2,5,7-triazaspiro[3.4]octane-6,8-dione acetate (0.117 g, 69.3% yield) as a white solid.

Step 3: 2-((5-(4-amino-6-methyl-1,3,5-triazin-2-yl)-6-(6-methoxypyridin-3-ylamino)pyridin-3-yl)methyl)-2,5,7-triazaspiro[3.4]octane-6,8-dione The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (109 mg, 0.189 mmol) and 2,5,7-triazaspiro[3.4]octane-6,8-dione acetate (56.9 mg, 0.283 mmol). ¹H NMR (400 MHz, d6-DMSO) δ 11.75 (s, 1H); 10.71 (br. s., 1H); 8.72 (br. s., 1H); 8.60 (s, 1H); 8.54 (d, J=2.54 Hz, 1H); 8.20 (br. s., 1H); 8.16 (dd, J=9.00, 2.74 Hz, 1H); 7.90 (br. s., 1H); 7.75 (br. s., 1H); 6.82 (d, J=8.80 Hz, 1H); 3.84 (s, 3H); 2.44 (s, 3H). m/z (ESI, +ve ion) 463.1 (M+H)⁺.

Example 231

4-(5-((3-aminoazetidin-1-yl)methyl)-2-(6-methoxypyridin-3-ylamino)pyridin-3-yl)-6-methyl-1,3,5-triazin-2-amine

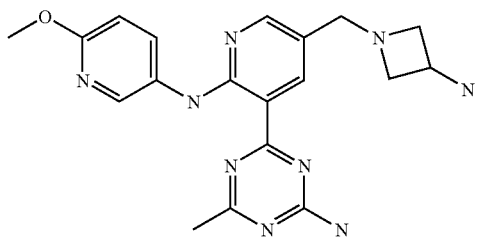 [SMILES: COc1ccc(Nc2ncc(CN3CC(N)C3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (0.56 g, 0.969 mmol) and tert-butyl azetidin-3-ylcarbamate (Astatech, Bristol, Pa.) (0.250 g, 1.454 mmol). ¹H NMR (400 MHz, d4-MeOH) δ 8.85 (d, 1H); 8.46 (d, J=2.54 Hz, 1H); 8.18 (d, J=2.35 Hz, 1H); 8.01 (dd, J=8.80, 2.74 Hz, 1H); 6.81 (d, J=8.80 Hz, 1H); 3.91 (s, 3H); 3.83-3.88 (m, 1H); 3.82 (s, 2H); 3.75 (t, J=7.92 Hz, 2H); 3.36-3.40 (m, 2H); 2.47 (s, 3H). m/z (ESI, +ve ion) 394.0 (M+H)⁺.

Example 232

N-(1-((5-(4-amino-6-methyl-1,3,5-triazin-2-yl)-6-(6-methoxypyridin-3-ylamino)pyridin-3-yl)methyl)azetidin-3-yl)methanesulfonamide

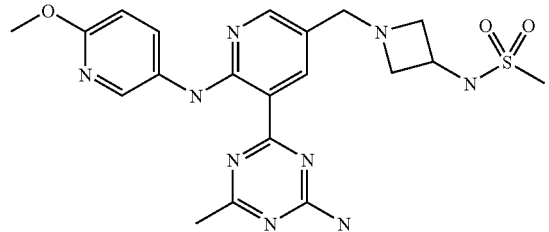

A solution of 4-(5-((3-amino azetidin-1-yl)methyl)-2-(6-methoxypyridin-3-ylamino)pyridin-3-yl)-6-methyl-1,3,5-triazin-2-amine (106 mg, 0.269 mmol) and triethylamine (56.2 µL, 0.404 mmol) in DCM (2.7 mL) was treated with MsCl (20.85 µL, 0.269 mmol) and stirred at ambient temperature for 3 h. The reaction mixture was diluted with 100 mL of DCM, added to a separatory funnel, partitioned with sodium bicarbonate (saturated, aqueous), washed 2 times with 50 mL of sodium bicarbonate (saturated, aqueous), separated, dried over sodium sulfate, and concentrated. The crude product was purified via flash chromatography (silica gel) with 100% DCM to 6% 2 M ammonia in MeOH/DCM to give N-(1-((5-(4-amino-6-methyl-1,3,5-triazin-2-yl)-6-(6-methoxypyridin-3-ylamino)pyridin-3-yl)methyl)azetidin-3-yl)methanesulfonamide (10 mg, 7% yield) as yellow solid. m/z (ESI, +ve ion) 472.1 (M+H)⁺.

Example 233

4-(5-((5,6-dihydro-[1,2,4]triazolo[1,5-a]pyrazin-7(8H)-yl)methyl)-2-(6-methoxypyridin-3-ylamino)pyridin-3-yl)-6-methyl-1,3,5-triazin-2-amine

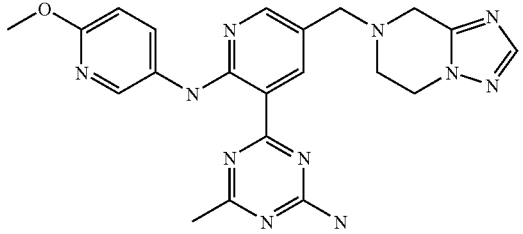 [SMILES: COc1ccc(Nc2ncc(CN3CCn4ncnc4C3)cc2-c2nc(C)nc(N)n2)cn1]

The title compound was synthesized following an analogous procedure to Example 220 using 5-(4-(bis(4-methoxybenzyl)amino)-6-methyl-1,3,5-triazin-2-yl)-6-(6-methoxypyridin-3-ylamino)nicotinaldehyde (178 mg, 0.308 mmol) and 5,6,7,8-tetrahydro-[1,2,4]triazolo[1,5-a]pyrazine (GeneTech, Indianapolis, Ind.) (57.4 mg, 0.462 mmol). ¹H NMR (400 MHz, CDCl₃) δ 11.70 (s, 1H); 8.78 (d, J=2.54 Hz, 1H); 8.36 (d, J=2.74 Hz, 1H); 8.25 (d, J=2.35 Hz, 1H); 8.10 (dd, J=8.80, 2.74 Hz, 1H); 7.87 (s, 1H); 6.78 (d, J=8.61 Hz, 1H); 5.59 (s, 2H); 4.20 (t, J=5.38 Hz, 2H); 3.94 (s, 3H); 3.84 (s, 2H); 3.73 (s, 2H); 3.00 (t, J=5.48 Hz, 2H); 2.56 (s, 3H). m/z (ESI, +ve ion) 445.9 (M+H)$^+$.

Example 234

5-(1,3-dioxolan-2-yl)-2-fluoro-3-(4,4,5,5-tetramethyl-1,3,2-dioxaborolan-2-yl)pyridine

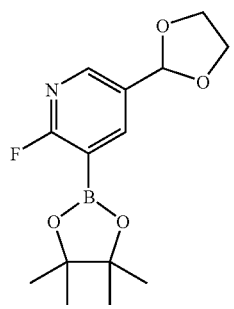 [SMILES: CC1(C)OB(c2cc(C3OCCO3)cnc2F)OC1(C)C]

Step 1: 5-(1,3-dioxolan-2-yl)-2-fluoropyridine

6-Fluoronicotinaldehyde (21.96 g, 176 mmol) was suspended in toluene (340 mL) and ethylene glycol (10.4 mL, 186 mmol) and p-toluenesulfonic acid (Acros, 15% in acetic acid, 1.10 mL) were added. The flask was fitted with a Dean-Stark head and a reflux condenser, and placed in a preheated oil bath (120° C.) and the reaction was stirred. After 45 minutes, the reaction was cooled to room temperature. The reaction was diluted with saturated sodium bicarbonate (50 mL), water (150 mL) and EtOAc (150 mL). The layers were separated and the aqueous phase was extracted with EtOAc. The organic phases were combined, dried over sodium sulfate, filtered, concentrated, and purified on a silica gel filter (600 mL fritted filter with about 3 inches of silica gel; DCM to 100:1 to 50:1 DCM/MeOH to 40:1 DCM/MeOH) to give 19.055 g of 5-(1,3-dioxolan-2-yl)-2-fluoropyridine. m/z (ESI, +ve ion) 170 (M+H)$^+$.

Step 2:
5-(1,3-dioxolan-2-yl)-2-fluoropyridin-3-ylboronic acid 5-(1,3-Dioxolan-2-yl)-2-fluoropyridine (18.803 g, 111 mmol) was dissolved in THF (300 mL) in a 1 L round-bottom flask, and the flask was cooled in a dry ice/acetone bath under nitrogen. Then, lithium diisopropylamide (2.0 M in heptane/tetrahydrofuran/ethylbenzene; Acros) (89 mL, 178 mmol) was added via syringe over 20 min. After 75 min, triisopropyl borate (40.8 mL, 178 mmol) was added via syringe over 5 minutes, and then the reaction was allowed to slowly warm up to room temperature while being stirred under nitrogen. After 4.5 h, the reaction mixture was treated with 1 N NaOH (300 mL). The layers were separated, and the organic phase was discarded. The aqueous phase was treated with concentrated HCl and 5 N aqueous HCl to lower the pH to about 5. Then, the aqueous phase was extracted with 10:1 DCM/MeOH. The aqueous phase was treated with 5 N HCl during the extractions to maintain the pH at 5-6. Brine was also added to the aqueous phase to aid extraction. The extracts were combined, concentrated, and dried under high vacuum to give 14.56 g of product. m/z (ESI, +ve ion) 214 (M+H)$^+$.

Step 3: 5-(1,3-dioxolan-2-yl)-2-fluoro-3-(4,4,5,5-tetramethyl-1,3,2-dioxaborolan-2-yl)pyridine 5-(1,3-Dioxolan-2-yl)-2-fluoropyridin-3-ylboronic acid (14.56 g, 68.4 mmol) was suspended in PhMe (300 mL) and anhydrous magnesium sulfate (41.223 g, 342 mmol) and pinacol (8.27 g, 70.0 mmol) were added. The reaction was stirred under nitrogen at room temperature over the weekend. The suspension was filtered, and the solid was washed with EtOAc. The filtrate was washed with brine (2×200 mL), and the organic phase was dried over sodium sulfate, filtered, concentrated and dried to give 19.19 g of 5-(1,3-dioxolan-2-yl)-2-fluoro-3-(4,4,5,5-tetramethyl-1,3,2-dioxaborolan-2-yl)pyridine as a light yellow powder. $^1$H NMR (CDCl$_3$, 400 MHz) δ 8.39 (d, J=2.54 Hz, 1H); 8.28 (dd, J=8.02 Hz, 2.54 Hz, 1H); 5.84 (s, 1H); 4.17-4.04 (m, 4H); 1.37 (s, 12H).

Example 235

2-((5-(4-amino-6-methyl-1,3,5-triazin-2-yl)-6-(6-methoxypyridin-3-ylamino)pyridin-3-yl)(hydroxy)methyl)-4-bromo-N,N-dimethylbenzenesulfonamide

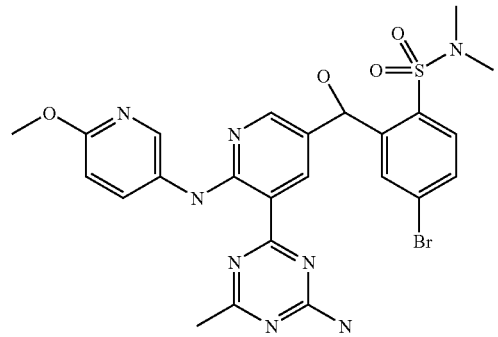

Step 1: 2-((5-(4-(bis(4-methoxybenzyl)amino)-6-methyl-1,3,5-triazin-2-yl)-6-(6-methoxypyridin-3-ylamino)pyridin-3-yl)(hydroxy)methyl)-4-bromo-N,N-dimethylbenzenesulfonamide A solution of 4-bromo-N,N-dimethylbenzenesulfonamide (Aldrich; 152 mg, 0.575 mmol) in THF (1.0 mL) was cooled to −78° C. and treated dropwise with n-butyllithium (1.60 M solution in hexanes) (359 μL, 0.575 mmol). The resulting pale solution was allowed to slowly warm to 0° C. over 30 min to give a dark brown solution which was then added dropwise to a suspension of 5-(4-(bis(4-methoxybenzyl)amino)-6-methyl-1,3,5-triazin-2-yl)-6-(6-methoxypyridin-3-ylamino) nicotinaldehyde (110.7 mg, 0.192 mmol) in THF (2.0 mL) cooled to −78° C. The mixture was stirred for 2 h, slowly allowing to warm to 0° C., and the resulting yellow suspension was quenched (water) and extracted into DCM from saturated aqueous NaHCO$_3$. The extracts were dried (MgSO$_4$), concentrated and purified by flash chromatography (0 to 10 to 20 to 30 to 40% EtOAc in DCM) to give recovered 5-(4-(bis(4-methoxybenzyl)amino)-6-methyl-1,3,5-triazin-2-yl)-6-(6-methoxypyridin-3-ylamino)nicotinaldehyde (54.6 mg, 49%, eluting off with 20% EtOAc/DCM) followed by 2-((5-(4-(bis(4-methoxybenzyl)amino)-6-methyl-1,3,5-triazin-2-yl)-6-(6-methoxypyridin-3-ylamino)pyridin-3-yl)(hydroxy)methyl)-4-bromo-N,N-dimethylbenzenesulfonamide (30.0 mg, 0.036 mmol, 18.60% yield) (eluting off with 30% EtOAc/DCM) followed by 4-((5-(4-(bis(4-methoxybenzyl)amino)-6-methyl-1,3,5-triazin-2-yl)-6-(6-methoxypyridin-3-ylamino)pyridin-3-yl)(hydroxy)methyl)-N,N-dimethylbenzenesulfonamide (38.3 mg, 0.050 mmol, 26.2% yield) (eluting off with 40% EtOAc/DCM).

Step 2: 2-((5-(4-amino-6-methyl-1,3,5-triazin-2-yl)-6-(6-methoxypyridin-3-ylamino)pyridin-3-yl)(hydroxy)methyl)-4-bromo-N,N-dimethylbenzenesulfonamide A solution of 2-((5-(4-(bis(4-methoxybenzyl)amino)-6-methyl-1,3,5-triazin-2-yl)-6-(6-methoxypyridin-3-ylamino)pyridin-3-yl)(hydroxy)methyl)-4-bromo-N,N-dimethylbenzenesulfonamide (30.0 mg, 0.036 mmol) in DCM (0.5 mL) was treated with TFA (0.5 mL) followed by triethylsilane (0.3 mL). The mixture was stirred at 72° C. for 16 h. An additional 1 mL of TFA was added, the mixture was placed in a sealed tube, and heated at 100° C. for 4 h to give a much darker orange solution. The mixture was concentrated, neutralized with 2 N NH$_3$/MeOH, concentrated and purified by prep HPLC to give 2-((5-(4-amino-6-methyl-1,3,5-triazin-2-yl)-6-(6-methoxypyridin-3-ylamino)pyridin-3-yl)(hydroxy)methyl)-4-bromo-N,N-dimethylbenzenesulfonamide (20 mg, 0.033 mmol, 93% yield) as a yellow solid. m/z (ESI, +ve ion) 601/603 (M+H)$^+$.

Example 236

4-((5-(4-amino-6-methyl-1,3,5-triazin-2-yl)-6-(6-methoxypyridin-3-ylamino)pyridin-3-yl)(hydroxy)methyl)-N,N-dimethylbenzenesulfonamide

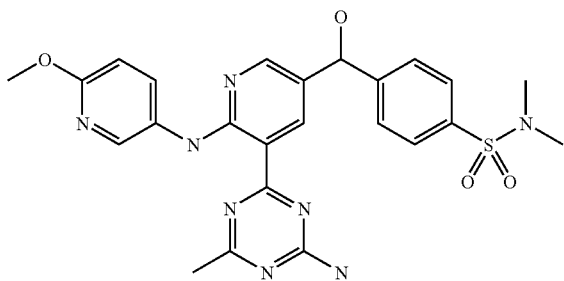

Step 1: 4-((5-(4-(bis(4-methoxybenzyl)amino)-6-methyl-1,3,5-triazin-2-yl)-6-(6-methoxypyridin-3-ylamino)pyridin-3-yl)(hydroxy)methyl)-N,N-dimethylbenzenesulfonamide A suspension of Mg turnings (49 mg) in THF (0.5 mL) was treated with 1,2-dibromoethane (25 µL) and allowed to stand for 5 min. Effervescence was observed. The suspension was the stirred and a solution of 4-bromo-N,N-dimethylbenzenesulfonamide (500 mg, 1.893 mmol) in THF (3.4 mL total volume) was added. The suspension was stirred for 1 h, after which time most of the Mg had dissolved to give about a 0.48 M solution of (4-(N,N-dimethylsulfamoyl)phenyl)magnesium bromide in THF.
(4-(N,N-Dimethylsulfamoyl)phenyl)magnesium bromide (0.48 M in THF) (2545 µL, 1.222 mmol) was added to 5-(4-(bis(4-methoxybenzyl)amino)-6-methyl-1,3,5-triazin-2-yl)-6-(6-methoxypyridin-3-ylamino)nicotinaldehyde (176.4 mg, 0.305 mmol) to give a deep orange solution. The solution was stirred for 16 h and then quenched with MeOH (1.0 mL). The product was extracted into DCM from water, dried (MgSO$_4$), and purified by flash chromatography (0 to 10% to 20% to 30% EtOAc/DCM) to give 4-((5-(4-(bis(4-methoxybenzyl)amino)-6-methyl-1,3,5-triazin-2-yl)-6-(6-methoxypyridin-3-ylamino)pyridin-3-yl)(hydroxy)methyl)-N,N-dimethylbenzenesulfonamide (171.5 mg, 0.225 mmol, 73.6% yield) as a yellow solid. $^1$H NMR (400 MHz, d6-DMSO) δ 11.51 (s, 1H); 8.74 (s, 1H); 8.30 (dd, J=4.11, 2.54 Hz, 2H); 7.85 (d, J=2.35 Hz, 1H); 7.55-7.72 (m, 4H); 7.26 (d, J=8.22 Hz, 2H); 7.19 (d, J=8.41 Hz, 2H); 6.90 (d, J=8.41 Hz, 2H); 6.83 (d, J=8.61 Hz, 2H); 6.74 (d, J=9.00 Hz, 1H); 6.19 (d, J=3.91 Hz, 1H); 5.86 (d, J=4.11 Hz, 1H); 4.68-4.91 (m, 4H); 3.82 (s, 3H); 3.74 (s, 3H); 3.70 (s, 3H); 2.56 (s, 6H); 2.54 (s, 3H). m/z (ESI, +ve ion) 763.1 (M+H)$^+$.

Step 2: 4-((5-(4-amino-6-methyl-1,3,5-triazin-2-yl)-6-(6-methoxypyridin-3-ylamino)pyridin-3-yl)(hydroxy)methyl)-N,N-dimethylbenzenesulfonamide A solution of 445-(4-(bis(4-methoxybenzyl)amino)-6-methyl-1,3,5-triazin-2-yl)-6-(6-methoxypyridin-3-ylamino)pyridin-3-yl)(hydroxy)methyl)-N,N-dimethylbenzenesulfonamide (38.3 mg, 0.050 mmol) in TFA (1.0 mL) was heated at 100° C. in a sealed tube for 5 h. The dark solution was concentrated and purified by prep HPLC to give 4-((5-(4-amino-6-methyl-1,3,5-triazin-2-yl)-6-(6-methoxypyridin-3-ylamino)pyridin-3-yl)(hydroxy)methyl)-N,N-dimethylbenzenesulfonamide trifluoroacetate (25 mg, 0.039 mmol, 78% yield). The sample was recrystallized from dioxane and dried to give a yellow solid. $^1$H NMR (400 MHz, d6-DMSO) δ 11.79 (s, 1H); 10.37 (br. s., 1H); 9.20 (d, J=2.35 Hz, 1H); 8.60 (d, J=2.54 Hz, 1H); 8.49 (d, J=2.54 Hz, 1H); 8.12 (dd, J=8.80, 2.74 Hz, 1H); 7.85-8.00 (m, 3H); 7.78 (br. s., 1H); 7.56 (td, J=7.58, 1.27 Hz, 1H); 7.35-7.46 (m, 1H); 6.83 (d, J=8.80 Hz, 1H); 6.61 (d, J=9.39 Hz, 1H); 3.84 (s, 3H); 2.84 (d, J=4.50 Hz, 3H); 2.76 (d, J=4.69 Hz, 3H); 2.46 (s, 3H). $^{19}$F NMR (376 MHz, d6-DMSO) δ −74.57 (br. s., 3 F). m/z (ESI, +ve ion) 523 (M+H)$^+$.

Example 237

4-(amino(5-(4-amino-6-methyl-1,3,5-triazin-2-yl)-6-(6-methoxypyridin-3-ylamino)pyridin-3-yl)methyl)-N,N-dimethylbenzenesulfonamide

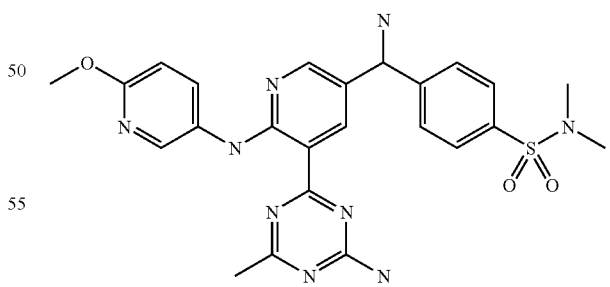

Step 1: (5-(4-(bis(4-methoxybenzyl)amino)-6-methyl-1,3,5-triazin-2-yl)-6-(6-methoxypyridin-3-ylamino)pyridin-3-yl)(4-(N,N-dimethylsulfamoyl)phenyl)methyl methanesulfonate A solution of 4-((5-(4-(bis(4-methoxybenzyl)amino)-6-methyl-1,3,5-triazin-2-yl)-6-(6-methoxypyridin-3-ylamino)

pyridin-3-yl)(hydroxy)methyl)-N,N-dimethylbenzenesulfonamide (12.9 mg, 0.017 mmol) in DCM (0.2 mL) was treated with pyridine (20 μL, 0.25 mmol) followed by methanesulfonyl chloride (20 μL, 0.258 mmol). The mixture was allowed to stand overnight. Some crystals formed. The crystals were colorless and insoluble in DCM, but soluble in water. The mixture was diluted with DCM (10 mL) and washed with saturated aqueous NaHCO$_3$ (5 mL). The DCM layer was dried and concentrated to give a yellow solid which was soluble in DCM, but insoluble in EtOAc and sparingly soluble in dioxane. The crude product was taken on directly to the next step.

Step 2: 4-(amino(5-(4-(bis(4-methoxybenzyl)amino)-6-methyl-1,3,5-triazin-2-yl)-6-(6-methoxypyridin-3-ylamino)pyridin-3-yl)methyl)-N,N-dimethylbenzenesulfonamide A solution of (5-(4-(bis(4-methoxybenzyl)amino)-6-methyl-1,3,5-triazin-2-yl)-6-(6-methoxypyridin-3-ylamino)pyridin-3-yl)(4-(N,N-dimethylsulfamoyl)phenyl)methyl methanesulfonate (14.22 mg, 0.017 mmol) in DCM (0.1 mL) was treated with 0.5 M NH$_3$ in dioxane (2 mL). The mixture was allowed to stand overnight, after which time partial conversion to the amine was observed by LCMS. The mixture was then sealed and heated and 80° C. for 2 h, after which time the starting material was consumed. The mixture was concentrated and taken on directly to the next step.

Step 3: 4-(amino(5-(4-amino-6-methyl-1,3,5-triazin-2-yl)-6-(6-methoxypyridin-3-ylamino)pyridin-3-yl)methyl)-N,N-dimethylbenzenesulfonamide A solution of 4-(amino(5-(4-(bis(4-methoxybenzyl)amino)-6-methyl-1,3,5-triazin-2-yl)-6-(6-methoxypyridin-3-ylamino)pyridin-3-yl)methyl)-N,N-dimethylbenzenesulfonamide (12.88 mg, 0.017 mmol) in TFA (1 mL) was heated at 100° C. in a sealed tube for 4 h, after which time reaction was complete. The mixture was concentrated and purified by prep HPLC to give 4-(amino(5-(4-amino-6-methyl-1,3,5-triazin-2-yl)-6-(6-methoxypyridin-3-ylamino)pyridin-3-yl)methyl)-N,N-dimethylbenzenesulfonamide trifluoroacetate (3.2 mg). m/z (ESI, +ve ion) 522 (M+H)$^+$.

Example 238

3-(4-amino-6-methyl-1,3,5-triazin-2-yl)-N-(6-methoxypyridin-3-yl)quinolin-2-amine

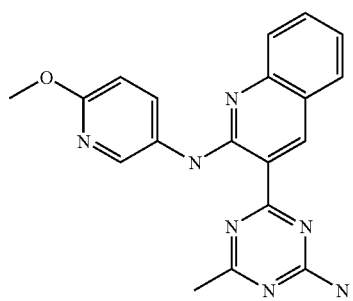 [SMILES: COc1ccc(Nc2nc3ccccc3cc2-c2nc(C)nc(N)n2)cn1]

Step 1: 4-(2-chloroquinolin-3-yl)-N,N-bis(4-methoxybenzyl)-6-methyl-1,3,5-triazin-2-amine A 10 mL reaction vial was charged with 4-iodo-N,N-bis(4-methoxybenzyl)-6-methyl-1,3,5-triazin-2-amine (0.36 g, 0.75 mmol, Example 115), 2-chloroquinolin-3-ylboronic acid (0.31 g, 1.50 mmol, Aldrich, St. Louis, Mo.), sodium carbonate (0.16 g, 1.50 mmol), tetrakis(triphenylphosphine)palladium (0) (43 mg, 0.04 mmol, Strem, Newburyport, Mass.), DME (4 mL), and water (1 mL). The vial was sealed and purged with argon for several minutes. The reaction mixture was stirred at 90° C. for 5 h and then allowed to cool to room. The organic phase was taken and the solvents removed under vacuum. The crude material was adsorbed onto a plug of silica gel and purified by chromatography through a Redi-Sep pre-packed silica gel column (12 g) eluting with a gradient of 0% to 1% 2 M NH$_3$.MeOH in CH$_2$Cl$_2$. The title compound was obtained as a yellow solid (90% pure) and used without further purification. m/z (ESI, +ve ion) 511.8 (M+H)$^+$.

Step 2: 3-(4-(bis(4-methoxybenzyl)amino)-6-methyl-1,3,5-triazin-2-yl)-N-(6-methoxypyridin-3-yl)quinolin-2-amine A mixture of 5-amino-2-methoxypyridine (0.08 mL, 0.61 mmol, Aldrich, St. Louis, Mo.) and 4-(2-chloroquinolin-3-yl)-N,N-bis(4-methoxybenzyl)-6-methyl-1,3,5-triazin-2-amine (210 mg, 0.410 mmol) in THF (3 mL) was cooled to 0° C. and LiHMDS (1 M in THF, 1.23 mL, 1.23 mmol) was added. The reaction mixture was stirred at 0° C. for 1 h, diluted with an aqueous satd solution of NH$_4$Cl (5 mL) and extracted with EtOAc (20 mL). The organic extract was washed with water and dried over Na$_2$SO$_4$. The solution was filtered and concentrated in vacuo, and the residue was adsorbed onto a plug of silica gel. Purification by chromatography through a Redi-Sep pre-packed silica gel column (12 g) eluting with a gradient of 2% to 3% 2 M NH$_3$.MeOH in CH$_2$Cl$_2$ gave the title compound as an orange solid (65% pure) that was used without further purification. m/z (ESI, +ve ion) 599.8 (M+H)$^+$.

Step 3: 3-(4-amino-6-methyl-1,3,5-triazin-2-yl)-N-(6-methoxypyridin-3-yl)quinolin-2-amine A solution of 3-(4-(bis(4-methoxybenzyl)amino)-6-methyl-1,3,5-triazin-2-yl)-N-(6-methoxypyridin-3-yl)quinolin-2-amine (0.16 g, 0.26 mmol) in TFA (3 mL) was treated with a couple of drops of trifluoromethane sulfonic acid. The reaction mixture was stirred at 90° C. for 18 h, allowed to cool to room temperature, and the solvent was removed in vacuo. Purification by reverse-phase preparative HPLC using a Phenomenex Gemini column, 10 micron, C18, 100 Å, 150×30 mm, 0.1% TFA in CH$_3$CN/H$_2$O, gradient 10% to 90% over 18 min gave 3-(4-amino-6-methyl-1,3,5-triazin-2-yl)-N-(6-methoxypyridin-3-yl)quinolin-2-amine (31 mg, 0.09 mmol, 33% yield) as a yellow solid. $^1$H NMR (400 MHz, d6-DMSO) δ 11.99 (br. s., 1H); 9.33 (s, 1H); 8.88 (br. s., 1H); 8.42 (d, J=7.43 Hz, 1H); 7.77-8.09 (m, 3H); 7.67 (br. s., 2H); 7.33 (br.

s., 1H); 6.87 (d, J=8.80 Hz, 1H); 3.87 (s, 3H); 2.49 (s, 3H). m/z (ESI, +ve ion) 359.9 (M+H)+.

Example 239

4-(2-(6-methoxypyridin-3-ylamino)phenyl)-6-methyl-1,3,5-triazin-2-amine

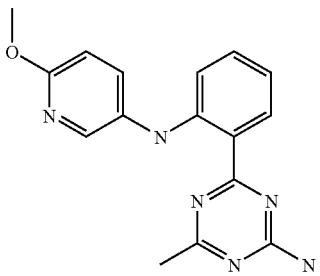 [SMILES: COc1ccc(Nc2ccccc2-c2nc(C)nc(N)n2)cn1]

Step 1: 4-(2-aminophenyl)-N,N-bis(4-methoxybenzyl)-6-methyl-1,3,5-triazin-2-amine A 20 mL reaction vial was charged with 2-(4,4,5,5-tetramethyl-1,3,2-dioxaborolan-2-yl)aniline (0.31 g, 1.42 mmol, Oakwood Products, West Columbia, S.C.), tetrakis(triphenylphosphine)palladium (0) (63 mg, 0.06 mmol, Newburyport, Mass.), 4-chloro-N,N-bis(4-methoxybenzyl)-6-methyl-1,3,5-triazin-2-amine (0.42 g, 1.10 mmol), sodium carbonate (0.29 g, 2.73 mmol), DME (5 mL), and water (1.5 mL). The vial was sealed and purged with argon for several minutes. The reaction mixture was stirred at 90° C. for 2 h and allowed to cool to room temperature. The reaction mixture was diluted with water (10 mL) and extracted with EtOAc (20 mL). The organic extract was washed with water and dried over Na2SO4. The solution was filtered and concentrated in vacuo to give the crude material. The crude material was adsorbed onto silica gel and purified by chromatography through a Redi-Sep pre-packed silica gel column (40 g) eluting with a gradient of 0% to 1% MeOH in CH2Cl2 to give the title compound as a light yellow oil. m/z (ESI, +ve ion) 441.9 (M+H)+.

Step 2: N,N-bis(4-methoxybenzyl)-4-(2-(6-methoxypyridin-3-ylamino)phenyl)-6-methyl-1,3,5-triazin-2-amine A mixture of 4-(2-aminophenyl)-N,N-bis(4-methoxybenzyl)-6-methyl-1,3,5-triazin-2-amine (0.54 g, 1.22 mmol), copper acetate (0.33 g, 1.83 mmol, Aldrich, St. Louis, Mo.), 6-methoxypyridin-3-ylboronic acid (0.56 g mg, 3.67 mmol, Boron Molecular, Research Triangle Park, N.C.) and diisopropylethylamine (0.85 mL, 4.89 mmol) in DCM (15 mL) was stirred at room temperature for 16 h, filtered through a pad of Celite® (diatomaceous earth), and the solvent was removed in vacuo. The crude material was adsorbed onto silica gel and purified by chromatography through a Redi-Sep pre-packed silica gel column (40 g) eluting with a gradient of 0% to 2% 2 M NH3.MeOH in CH2Cl2, to give the title compound as a dark yellow oil. m/z (ESI, +ve ion) 548.8 (M+H)+.

Step 3: 4-(2-(6-methoxypyridin-3-ylamino)phenyl)-6-methyl-1,3,5-triazin-2-amine

A solution of N,N-bis(4-methoxybenzyl)-4-(2-(6-methoxypyridin-3-ylamino)phenyl)-6-methyl-1,3,5-triazin-2-amine (0.38 g, 0.70 mmol) in TFA (3 mL) was treated with several drops of trifluoromethane sulfonic acid and heated at 80° C. for 3 h. The solvent was removed in vacuo and the residue was purified by reverse phase preparative HPLC using a Phenomenex Gemini column, 10 micron, C18, 100 Å, 150×30 mm, 0.1% TFA in MeCN/H2O gradient to give 4-(2-(6-methoxypyridin-3-ylamino)phenyl)-6-methyl-1,3,5-triazin-2-amine (47 mg, 0.15 mmol, 22% yield) as a yellow solid. 1H NMR (400 MHz, d6-DMSO) δ 10.92 (s, 1H); 8.44 (dd, J=8.12, 1.66 Hz, 1H); 8.12 (d, J=2.74 Hz, 1H); 7.68 (dd, J=8.80, 2.74 Hz, 2H); 7.53 (br. s., 1H); 7.28 (ddd, J=8.46, 6.99, 1.57 Hz, 1H); 6.88 (dd, J=12.81, 8.51 Hz, 2H); 6.69-6.82 (m, 1H); 3.86 (s, 3H); 2.38 (s, 3H). m/z (ESI, +ve ion) 309.0 (M+H)+.

Example 240

N-(3-(4-amino-6-methyl-1,3,5-triazin-2-yl)-5-((4-(methylsulfonyl)piperazin-1-yl)methyl)pyridin-2-yl)benzo[d]thiazol-5-amine

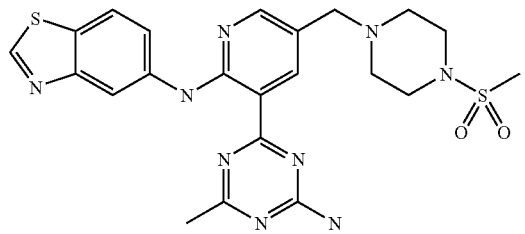 [SMILES: Cc1nc(N)nc(-c2cc(CN3CCN(S(C)(=O)=O)CC3)cnc2Nc2ccc3scnc3c2)n1]

Step 1: N-(3-(4-(bis(4-methoxybenzyl)amino)-6-methyl-1,3,5-triazin-2-yl)-5-((4-(methylsulfonyl)piperazin-1-yl)methyl)pyridin-2-yl)benzo[d]thiazol-5-amine A mixture of 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (Example 128; 60.0 mg, 0.097 mmol) and benzo[d]thiazol-5-amine (29.0 mg, 0.193 mmol) (Maybridge, Trevillet, UK) in THF (1.0 mL) at 0° C. was treated with LiHMDS (1.0 M in THF, Aldrich, St. Louis, Mo.) (483 µL, 0.483 mmol) dropwise via syringe. The reaction was stirred at 0° C. for 15 min, then was quenched with sat. aq. NH4Cl (3 mL). The aqueous layer was extracted with EtOAc (3×20 mL) and the combined organic layers were dried (MgSO4), filtered and concentrated in vacuo. The residue was purified by flash chromatography on silica eluting with a gradient of 10-35% EtOAc in DCM with 1% MeOH to give N-(3-(4-(bis(4-methoxybenzyl)amino)-6-methyl-1,3,5-triazin-2-yl)-5-((4-(methylsulfonyl)piperazin-1-yl)methyl)pyridin-2-yl)benzo[d]thiazol-5-amine (51.0 mg, 0.068 mmol, 70.3% yield) as an orange solid. 1H NMR (400 MHz, CDCl3) δ 9.16 (1H, br. s.); 8.99 (1H, s); 8.40-8.54 (2H, m); 7.84 (1H, d, J=8.8 Hz); 7.58 (1H, d, J=8.6 Hz); 7.12-7.25 (4H, m); 6.77-6.92 (4H, m); 4.93 (2H, s); 4.89 (2H, s); 4.15 (2H, s); 3.79 (12H, d, J=18.0 Hz); 3.35-3.51 (2H, m); 2.87-2.97 (2H, m); 2.85 (3H, s); 2.69 (3H, s). m/z (ESI, positive ion) 752 (M+H)+.

Step 2: N-(3-(4-amino-6-methyl-1,3,5-triazin-2-yl)-5-((4-(methylsulfonyl)piperazin-1-yl)methyl)pyridin-2-yl)benzo[d]thiazol-5-amine A microwave vial (5 mL) was charged with N-(3-(4-(bis(4-methoxybenzyl)amino)-6-methyl-1,3,5-triazin-2-yl)-5-

((4-(methylsulfonyl)piperazin-1-yl)methyl)pyridin-2-yl) benzo[d]thiazol-5-amine (45.0 mg, 0.060 mmol) in trifluoroacetic acid (Aldrich, St. Louis, Mo.) (1.50 mL, 20.19 mmol). The mixture was heated in a microwave at 120° C. for 45 min, and then the solvent was removed in vacuo. The residue was purified with reverse phase preperative HPLC using a Phenomenex Gemini columb, 5 micron, C18, 100 Å, 150×30 mm (eluting with 10% to 55% MeCN/water with 0.1% TFA over 30 minutes with a total flow rate of 45 mL/min) to give N-(3-(4-amino-6-methyl-1,3,5-triazin-2-yl)-5-((4-(methylsulfonyl)piperazin-1-yl)methyl)pyridin-2-yl)benzo[d]thiazol-5-amine (16.0 mg, 0.031 mmol, 52.3% yield) as a yellow solid after solvent removal and neutralization. $^1$H NMR (400 MHz, d6-DMSO) δ 12.23 (1H, s); 9.35 (1H, s); 8.90 (1H, d, J=1.8 Hz); 8.76 (1H, d, J=2.0 Hz); 8.34 (1H, d, J=2.0 Hz); 8.06 (1H, d, J=8.8 Hz); 7.91 (1H, br. s.); 7.72-7.86 (2H, m); 3.53 (2H, s); 3.12 (4H, d, J=4.1 Hz); 2.87 (3H, s); 2.48 (7H, br. s.). m/z (ESI, +ve ion) 512 (M+H)$^+$.

Example 241

N-(3-(4-amino-6-methyl-1,3,5-triazin-2-yl)-5-((4-(methylsulfonyl)piperazin-1-yl)methyl)pyridin-2-yl)benzo[d]thiazol-6-amine

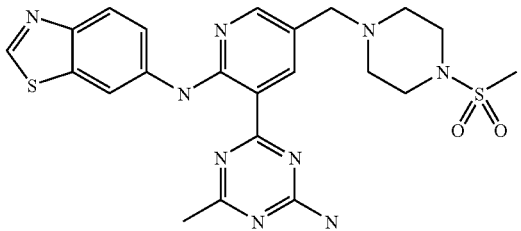 [SMILES: Cc1nc(N)nc(-c2cc(CN3CCN(S(C)(=O)=O)CC3)cnc2Nc2ccc3ncsc3c2)n1]

The title compound was prepared in an analogous manner to that described in Example 240 using benzo[d]thiazol-6-amine in Step 1, and isolated as a yellow solid. $^1$H NMR (400 MHz, d6-DMSO) δ 12.30 (1H, s); 9.21 (1H, s); 8.87 (1H, d, J=1.4 Hz); 8.76 (1H, d, J=2.0 Hz); 8.33 (1H, d, J=2.2 Hz); 8.01 (1H, d, J=8.8 Hz); 7.90 (2H, dd, J=9.3, 1.7 Hz); 7.79 (1H, br. s.); 3.52 (2H, s); 3.12 (4H, br. s.); 2.87 (3H, s); 2.48 (7H, br. s.). m/z (ESI, +ve ion) 512 (M+H)$^+$.

Example 242

4-(2-(5-fluoropyridin-3-ylamino)-5-((4-(methylsulfonyl)piperazin-1-yl)methyl)pyridin-3-yl)-6-methyl-1,3,5-triazin-2-amine

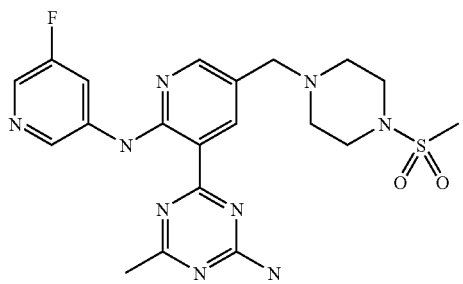 [SMILES: Cc1nc(N)nc(-c2cc(CN3CCN(S(C)(=O)=O)CC3)cnc2Nc2cncc(F)c2)n1]

The title compound was prepared in an analogous manner to that described in Example 240 using 3-amino-5-fluoropyridine (SynChem, Elk Grove Village, Ill.) in Step 1, and isolated as a yellow solid. $^1$H NMR (400 MHz, d6-DMSO) δ 12.33 (1H, s); 8.82 (1H, s); 8.77 (1H, s); 8.56 (1H, d, J=12.1 Hz); 8.35 (1H, s); 8.17 (1H, d, J=2.0 Hz); 7.97 (1H, br. s.); 7.81 (1H, br. s.); 3.54 (2H, s); 3.12 (4H, br. s.); 2.87 (3H, s); 2.46 (7H, br. s.). m/z (ESI, positive ion) 474 (M+H)$^+$.

Example 243

4-(2-(1H-pyrazol-4-ylamino)-5-((4-(methylsulfonyl)piperazin-1-yl)methyl)pyridin-3-yl)-6-methyl-1,3,5-triazin-2-amine

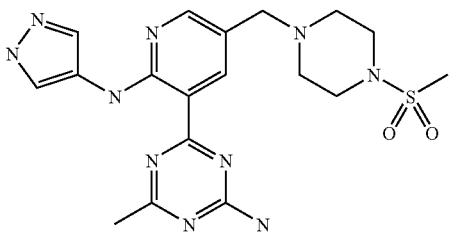 [SMILES: Cc1nc(N)nc(-c2cc(CN3CCN(S(C)(=O)=O)CC3)cnc2Nc2cn[nH]c2)n1]

Step 1: 1-(4-methoxybenzyl)-4-nitro-1H-pyrazole

A solution of 4-nitro-1H-pyrazole (500 mg, 4.42 mmol; Bionet Research, Cornwall, UK) in DMF (5 mL) was treated with potassium carbonate (400 μL, 6.63 mmol) and 4-methoxybenzyl chloride (600 μL, 4.42 mmol). The reaction was stirred at room temperature for 2 h, then diluted with DCM (200 mL) and washed with water (4×40 mL). The organic layer was then dried (MgSO$_4$), filtered and concentrated in vacuo to give the crude product, which was used in the next step without further purification.

Step 2: 1-(4-methoxybenzyl)-1H-pyrazol-4-amine

A solution of 1-(4-methoxybenzyl)-4-nitro-1H-pyrazole (1031 mg, 4.42 mmol) in EtOH (25 mL) and sat. aq. NH$_4$Cl (15 mL) in a sealed tube (125 mL) was treated with iron (1234 mg, 22.10 mmol, Aldrich, St. Louis, Mo.). The mixture was stirred at 105° C. for 1 h, then cooled to room temperature. The mixture was diluted with EtOAc (200 mL) and filtered through a plug of Celite® (diatomaceous earth). The filtrate was separated and the organic layer was dried (MgSO$_4$), filtered and concentrated in vacuo. The residue was filtered through a plug of silica gel (eluting with DCM:EtOAc:MeOH=25:25:1) to give 1-(4-methoxybenzyl)-1H-pyrazol-4-amine (560 mg, 2.76 mmol, 62.3% yield) as a brown solid. m/z (ESI, positive ion) 204 (M+H)$^+$.

Step 3: 4-(2-(1H-pyrazol-4-ylamino)-5-((4-(methylsulfonyl)piperazin-1-yl)methyl)pyridin-3-yl)-6-methyl-1,3,5-triazin-2-amine The title compound was prepared in an analogous manner to that described in Example 240 using 1-(4-methoxybenzyl)-1H-pyrazol-4-amine in Step 1 and isolated as a yellow solid. $^1$H NMR (400 MHz, d6-DMSO) δ 12.46 (1H, br. s.); 11.59 (1H, s); 8.67 (1H, d, J=2.0 Hz); 8.24 (1H, d, J=2.2 Hz); 7.92-8.07 (2H, m); 7.83 (1H, br. s.); 7.69 (1H, br. s.); 3.47

(2H, s); 3.11 (4H, br. s.); 2.86 (3H, s); 2.46-2.48 (4H, m); 2.43 (3H, s). m/z (ESI, +ve ion) 445 (M+H)+.

Example 244

4-(2-(1H-pyrazol-3-ylamino)-5-((4-(methylsulfonyl)piperazin-1-yl)methyl)pyridin-3-yl)-6-methyl-1,3,5-triazin-2-amine

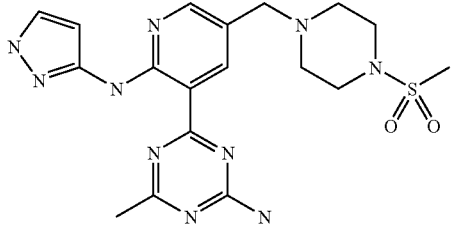 [SMILES: Cc1nc(N)nc(-c2cc(CN3CCN(S(C)(=O)=O)CC3)cnc2Nc2cc[nH]n2)n1]

The title compound was prepared in an analogous manner to that described in Example 240 using 1-(4-methoxybenzyl)-1H-pyrazol-3-amine (prepared in an analogous manner to that described in Example 243 using 3-nitro-1H-pyrazole (Maybridge, Trevillett, UK) in step 1) in step 1 and isolated as a yellow solid. $^1$H NMR (400 MHz, d6-DMSO) δ 12.21 (1H, d, J=1.0 Hz); 12.04 (1H, s); 8.67 (1H, s); 8.23 (1H, s); 7.69 (2H, br. s.); 7.62 (1H, s); 6.76 (1H, s); 3.47 (2H, s); 3.10 (4H, br. s.); 2.87 (3H, s); 2.46-2.49 (4H, m); 2.44 (3H, s). m/z (ESI, positive ion) 445 (M+H)+.

Example 245

N-(3-(4-amino-6-methyl-1,3,5-triazin-2-yl)-5-((4-(methylsulfonyl)piperazin-1-yl)methyl)pyridin-2-yl)-6-fluoro-1H-indazol-4-amine

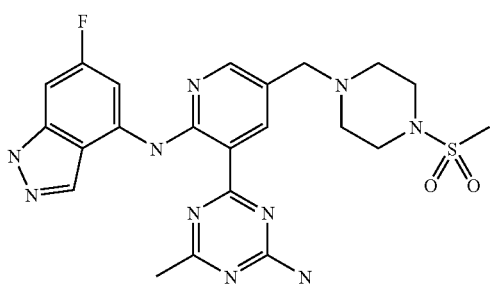 [SMILES: Cc1nc(N)nc(-c2cc(CN3CCN(S(C)(=O)=O)CC3)cnc2Nc2cc(F)cc3[nH]ncc23)n1]

The title compound was prepared in an analogous manner to that described in Example 240 using 6-fluoro-1-(4-methoxybenzyl)-1H-indazol-4-amine (prepared in an analogous manner to that described in Example 243 using 6-fluoro-4-nitro-1H-indazole (Aldrich, St. Louis, Mo.) in Step 1) in Step 1 and isolated as a yellow solid. $^1$H NMR (400 MHz, d6-DMSO) δ 13.19 (1H, br. s.); 12.51 (1H, s); 8.77 (1H, s); 8.41 (1H, s); 8.15-8.29 (2H, m); 7.83 (2H, br. s.); 6.90 (1H, d, J=8.8 Hz); 3.55 (2H, s); 3.12 (4H, br. s.); 2.87 (3H, s); 2.59 (4H, s). m/z (ESI, positive ion) 513 (M+H)+.

Example 246

4-(2-(5-fluoro-6-methoxypyridin-3-ylamino)pyridin-3-yl)-6-methyl-1,3,5-triazin-2-amine

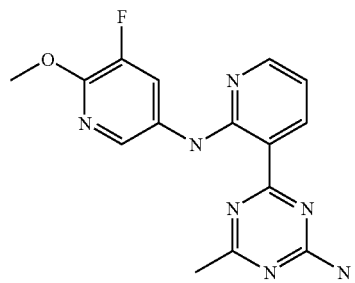 [SMILES: COc1ncc(Nc2ncccc2-c2nc(C)nc(N)n2)cc1F]

Step 1: 4-(2-(5-fluoro-6-methoxypyridin-3-ylamino)pyridin-3-yl)-N,N-bis(4-methoxybenzyl)-6-methyl-1,3,5-triazin-2-amine A solution of THF (3 mL) containing 5-fluoro-6-methoxypyridin-3-amine (87 mg, 0.613 mmol) (Anichem) and 4-(2-fluoropyridin-3-yl)-N,N-bis(4-methoxybenzyl)-6-methyl-1,3,5-triazin-2-amine (Example 52; 182 mg, 0.409 mmol) was cooled to 0° C. in an ice bath and treated dropwise with 1 M LiHMDS (1.226 mL, 1.226 mmol). The solution was stirred at this temperature for 1.5 h and quenched with a saturated solution of NH$_4$Cl. The product was extracted with EtOAc (15 mL), dried over MgSO$_4$, filtered and concentrated to give crude 4-(2-(5-fluoro-6-methoxypyridin-3-ylamino)pyridin-3-yl)-N,N-bis(4-methoxybenzyl)-6-methyl-1,3,5-triazin-2-amine (269.7 mg, 0.475 mmol) as a bright yellow amorphous solid which was used in the next step without further purification. m/z (ESI, +ve ion) 568.0 (M+H)+. $^1$H NMR (400 MHz, CDCl$_3$) δ 11.94 (1H, s); 8.82 (1H, dd, J=7.8, 2.0 Hz); 8.29 (1H, dd, J=4.8, 2.1 Hz); 8.05 (1H, dd, J=12.3, 2.2 Hz); 7.97 (1H, d, J=2.3 Hz); 7.20 (4H, dd, J=10.6, 8.6 Hz); 6.86 (4H, t, J=9.0 Hz); 6.78 (1H, dd, J=7.8, 4.7 Hz); 4.84 (2H, br. s.); 4.83 (2H, br. s.); 4.01 (3H, s); 3.81 (3H, s); 3.79 (3H, s); 2.58 (3H, s).

Step 2: 4-(2-(5-fluoro-6-methoxypyridin-3-ylamino)pyridin-3-yl)-6-methyl-1,3,5-triazin-2-amine 4-(2-(5-Fluoro-6-methoxypyridin-3-ylamino)pyridin-3-yl)-N,N-bis(4-methoxybenzyl)-6-methyl-1,3,5-triazin-2-amine (232 mg, 0.409 mmol) was treated with TFA (8.0 mL) (Aldrich) and heated at 75° C. with a reflux condenser for 17 h. The TFA was removed in vacuo and the crude product was treated with 2 M NH$_3$ in MeOH resulting in a suspension that was filtered and washed with water to give the desired product in ca. 80% purity. It was then resuspended in MeOH and filtered and washed with 1 N NaOH (aq), MeOH and hexanes and dried to give an olive-colored amorphous solid. It was further purified on the ISCO (12 g column, 1-25% MeOH in DCM) to give 4-(2-(5-fluoro-6-methoxypyridin-3-ylamino)pyridin-3-yl)-6-methyl-1,3,5-triazin-2-amine (68.6 mg, 0.210 mmol, 51.3% yield) as a fibrous, yellow amorphous solid. m/z (ESI, +ve ion) 328.1 (M+H)+. $^1$H NMR (400 MHz, d6-DMSO) δ 11.95 (1H, s); 8.80 (1H, dd, J=7.8, 2.0 Hz); 8.42

(1H, d, J=2.3 Hz); 8.33-8.40 (2H, m); 7.91 (1H, br. s.); 7.77 (1H, br. s.); 6.94 (1H, dd, J=7.8, 4.7 Hz); 3.94 (3H, s); 2.43 (3H, s).

Example 247

4-(2-(6-methoxypyridin-3-ylamino)-5-(1-methyl-1H-pyrazol-4-yl)pyridin-3-yl)-6-methyl-1,3,5-triazin-2-amine

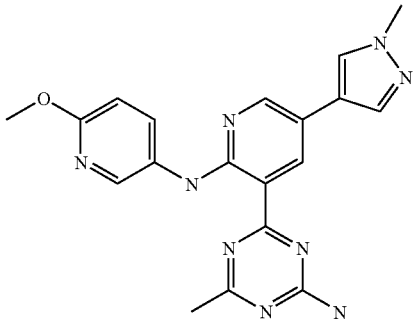 [SMILES: COc1ccc(Nc2ncc(-c3cnn(C)c3)cc2-c2nc(C)nc(N)n2)cn1]

Step 1: 4-(5-chloro-2-fluoropyridin-3-yl)-N,N-bis(4-methoxybenzyl)-6-methyl-1,3,5-triazin-2-amine A mixture of 5-chloro-2-fluoropyridin-3-ylboronic acid (454 mg, 2.59 mmol) (Combi-Blocks Inc.), 4-chloro-N,N-bis(4-methoxybenzyl)-6-methyl-1,3,5-triazin-2-amine (950 mg, 2.468 mmol), Amphos 2 (87 mg, 0.123 mmol) and potassium acetate (744 mg, 7.58 mmol) (Aldrich) in EtOH (15 mL) and water (1.5 mL) was purged with argon and heated in a microwave reactor at 100° C. for 30 min. The reaction mixture was concentrated to remove the EtOH and partitioned between water (20 mL) and EtOAc (20 mL). The aqueous phase was further extracted with EtOAc (20 mL). The combined organic phases were washed with saturated aqueous sodium chloride (40 mL). The organic phase was dried over sodium sulfate, filtered and concentrated. The crude product was purified on the ISCO (40 g column, eluent: 30-80% EtOAc in hexanes) to give 4-(5-chloro-2-fluoropyridin-3-yl)-N,N-bis(4-methoxybenzyl)-6-methyl-1,3,5-triazin-2-amine (913 mg, 1.902 mmol, 77% yield) as a pale yellow sticky solid. The material was used in the next step without further purification. m/z (ESI, +ve ion) 480.1 (M+H)$^+$. $^1$H NMR (400 MHz, CDCl$_3$) δ 8.53 (1H, dd, J=7.9, 2.6 Hz); 8.25 (1H, dd, J=2.6, 1.3 Hz); 7.21 (4H, d, J=8.6 Hz); 6.80-6.90 (4H, m); 4.82 (2H, s); 4.80 (2H, s); 3.81 (3H, s); 3.80 (3H, s); 2.54 (3H, s).

Step 2: 4-(5-chloro-2-(6-methoxypyridin-3-ylamino)pyridin-3-yl)-N,N-bis(4-methoxybenzyl)-6-methyl-1,3,5-triazin-2-amine A solution of 6-methoxypyridin-3-amine (354 mg, 2.85 mmol) (Aldrich) and 4-(5-chloro-2-fluoropyridin-3-yl)-N,N-bis(4-methoxybenzyl)-6-methyl-1,3,5-triazin-2-amine (913 mg, 1.902 mmol) in THF (15 mL) was cooled to 0° C. in an ice bath and treated dropwise with 1 M LiHMDS (5.71 mL, 5.71 mmol). After stirring for 1 h at this temperature, the reaction mixture was quenched with a saturated solution of NH$_4$Cl at 0° C. and extracted with EtOAc (50 mL), dried over MgSO$_4$, filtered and concentrated. Purification on the ISCO (40 g column, 20-100% EtOAc in hexanes) gave 4-(5-chloro-2-(6-methoxypyridin-3-ylamino)pyridin-3-yl)-N,N-bis(4-methoxybenzyl)-6-methyl-1,3,5-triazin-2-amine (717.3 mg, 1.228 mmol, 64.6% yield) as a bright yellow crystalline solid. m/z (ESI, +ve ion) 584.1 (M+H)$^+$. $^1$H NMR (400 MHz, CDCl$_3$) δ 11.65 (1H, s); 8.73 (1H, d, J=2.7 Hz); 8.26 (1H, d, J=2.7 Hz); 8.19 (1H, d, J=2.7 Hz); 7.83 (1H, dd, J=8.8, 2.7 Hz); 7.19 (4H, dd, J=16.2, 8.6 Hz); 6.86 (4H, dd, J=10.4, 8.8 Hz); 6.70 (1H, d, J=8.8 Hz); 4.86 (2H, s); 4.81 (2H, s); 3.93 (3H, s); 3.81 (3H, s); 3.79 (3H, s); 2.57 (3H, s).

Step 3: N,N-bis(4-methoxybenzyl)-4-(2-(6-methoxypyridin-3-ylamino)-5-(1-methyl-1H-pyrazol-4-yl)pyridin-3-yl)-6-methyl-1,3,5-triazin-2-amine A mixture of 1-methyl-4-(4,4,5,5-tetramethyl-1,3,2-dioxaborolan-2-yl)-1H-pyrazole (41.5 mg, 0.199 mmol) (Aldrich), 4-(5-chloro-2-(6-methoxypyridin-3-ylamino)pyridin-3-yl)-N,N-bis(4-methoxybenzyl)-6-methyl-1,3,5-triazin-2-amine (97 mg, 0.166 mmol), Pd$_2$dba$_3$ (6.08 mg, 6.64 μmol) (Strem Chemicals), and 2-(dicyclohexylphosphino)-2',4',6',-tri-i-propyl-1,1'-biphenyl (6.33 mg, 0.013 mmol) (Strem Chemicals) was purged with argon, treated with dioxane (2 mL) and 1 M aqueous sodium carbonate (0.415 mL, 0.415 mmol), and heated in a microwave at 140° C. for 30 min. The reaction mixture was treated with 1 N NaOH and extracted with EtOAc (30 mL), washed with brine and dried over MgSO$_4$, filtered and concentrated to give N,N-bis(4-methoxybenzyl)-4-(2-(6-methoxypyridin-3-ylamino)-5-(1-methyl-1H-pyrazol-4-yl)pyridin-3-yl)-6-methyl-1,3,5-triazin-2-amine (140 mg, 0.222 mmol) which was used in the next step without further purification. m/z (ESI, +ve ion) 630.0 (M+H)$^+$. $^1$H NMR (400 MHz, CDCl$_3$) δ 11.60 (1H, s); 8.83 (1H, d, J=2.5 Hz); 8.41 (1H, d, J=2.5 Hz); 8.27 (1H, d, J=2.7 Hz); 7.89 (1H, dd, J=8.8, 2.7 Hz); 7.68 (1H, s); 7.52 (1H, s); 7.21 (4H, dd, J=13.5, 8.6 Hz); 6.86 (4H, dd, J=13.1, 8.6 Hz); 6.71 (1H, d, J=9.0 Hz); 4.88 (2H, s); 4.82 (2H, s); 3.93 (3H, s); 3.93 (3H, s); 3.81 (3H, s); 3.78 (3H, s); 2.59 (3H, s).

Step 4: 4-(2-(6-methoxypyridin-3-ylamino)-5-(1-methyl-1H-pyrazol-4-yl)pyridin-3-yl)-6-methyl-1,3,5-triazin-2-amine N,N-bis(4-methoxybenzyl)-4-(2-(6-methoxypyridin-3-ylamino)-5-(1-methyl-1H-pyrazol-4-yl)pyridin-3-yl)-6-methyl-1,3,5-triazin-2-amine (140 mg, 0.222 mmol) was treated with TFA (10 mL) and heated at 80° C. with a reflux condenser for 18 h. The TFA was removed in vacuo and the residue was treated with 2 M NH$_3$ in MeOH to pH 7 and dry-packed with silica gel. Purification on the ISCO (12 g column, 1-20% MeOH in DCM) gave 4-(2-(6-methoxypyridin-3-ylamino)-5-(1-methyl-1H-pyrazol-4-yl)pyridin-3-yl)-6-methyl-1,3,5-triazin-2-amine (71.7 mg, 0.184 mmol, 83% yield) as an orange crystalline solid. m/z (ESI, +ve ion) 390.0 (M+H)$^+$. $^1$H NMR (400 MHz, d6-DMSO) δ 11.69 (1H, s); 8.87 (1H, d, J=2.5 Hz); 8.55 (2H, t, J=3.1 Hz); 8.18 (1H, dd, J=8.8, 2.7 Hz); 8.12 (1H, s); 7.90 (1H, s); 7.82 (1H, s); 7.77 (1H, s); 6.84 (1H, d, J=8.8 Hz); 3.88 (3H, s); 3.85 (3H, s); 2.46 (3H, s).

Example 248

4-(2-(5,6-difluoropyridin-3-ylamino)pyridin-3-yl)-6-methyl-1,3,5-triazin-2-amine

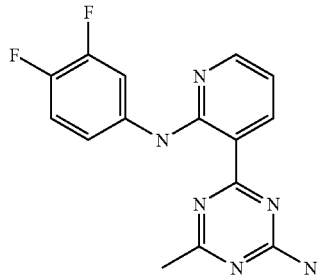 [SMILES: Cc1nc(N)nc(-c2cccnc2Nc2ccc(F)c(F)c2)n1]

The title compound was prepared in an analogous manner to that described in Example 246 using 4-(2-fluoropyridin-3-yl)-N,N-bis(4-methoxybenzyl)-6-methyl-1,3,5-triazin-2-amine and 3,4-difluoroaniline (Aldrich), and was isolated as an orange amorphous solid (59%). m/z (ESI, +ve ion) 315.0 (M+H)+. 1H NMR (400 MHz, d6-DMSO) δ 12.11 (1H, s); 8.80 (1H, dd, J=7.8, 2.0 Hz); 8.39 (1H, dd, J=4.7, 2.0 Hz); 8.19 (1H, ddd, J=13.8, 7.5, 2.5 Hz); 7.89 (1H, br. s.); 7.78 (1H, br. s); 7.55-7.62 (1H, m); 7.32-7.41 (1H, m); 6.97 (1H, dd, J=7.8, 4.7 Hz); 2.44 (3H, s).

Example 249

4-(2-(6-methoxypyridin-3-ylamino)-5-(1,2,3,6-tetrahydropyridin-4-yl)pyridin-3-yl)-6-methyl-1,3,5-triazin-2-amine

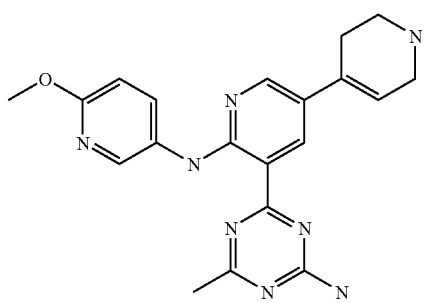 [SMILES: COc1ccc(Nc2ncc(C3=CCNCC3)cc2-c2nc(C)nc(N)n2)cn1]

The title compound was prepared in an analogous manner to that described in Example 247 using 4-(5-chloro-2-(6-methoxypyridin-3-ylamino)pyridin-3-yl)-N,N-bis(4-methoxybenzyl)-6-methyl-1,3,5-triazin-2-amine and tert-butyl 4-(4,4,5,5-tetramethyl-1,3,2-dioxaborolan-2-yl)-5,6-dihydropyridine-1(2H)-carboxylate, and was isolated as a bright yellow amorphous solid (13%). m/z (ESI, +ve ion) 391.1 (M+H)+. 1H NMR (400 MHz, d6-DMSO) δ 11.74 (1H, br. s.); 8.81 (1H, br. s.); 8.54 (1H, br. s.); 8.40 (1H, br. s.); 8.17 (1H, br. s.); 7.88 (1H, br. s.); 7.73 (1H, br. s.); 6.83 (1H, br. s.); 6.17 (1H, d, J=1.0 Hz); 3.84 (3H, s); 2.93 (2H, br. s.); 2.44 (4H, br. s.); 1.56 (4H, s).

Example 250

4-(2-(6-methoxypyridin-3-ylamino)-5-(1H-pyrazol-4-yl)pyridin-3-yl)-6-methyl-1,3,5-triazin-2-amine

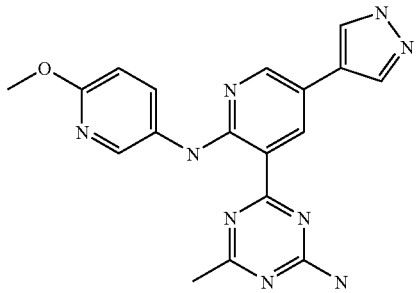 [SMILES: COc1ccc(Nc2ncc(-c3cn[nH]c3)cc2-c2nc(C)nc(N)n2)cn1]

The title compound was prepared in an analogous manner to that described in Example 247 using 4-(5-chloro-2-(6-methoxypyridin-3-ylamino)pyridin-3-yl)-N,N-bis(4-methoxybenzyl)-6-methyl-1,3,5-triazin-2-amine and 4-(4,4,5,5-tetramethyl-1,3,2-dioxaborolan-2-yl)-1H-pyrazole (Strem Chemicals), and was isolated as an orange amorphous solid (95%). m/z (ESI, +ve ion) 376.1 (M+H)+. 1H NMR (400 MHz, d6-DMSO) δ 12.98 (1H, br. s.); 11.70 (1H, s); 8.89 (1H, br. s.); 8.59 (2H, br. s.); 8.17 (2H, br. s.); 7.87 (2H, br. s.); 7.74 (1H, br. s.); 6.84 (1H, s); 3.85 (3H, s); 2.46 (3H, br. s.).

Example 251

5-(4-amino-6-methyl-1,3,5-triazin-2-yl)-N-(6-methoxypyridin-3-yl)-6'-methyl-3,3'-bipyridin-6-amine

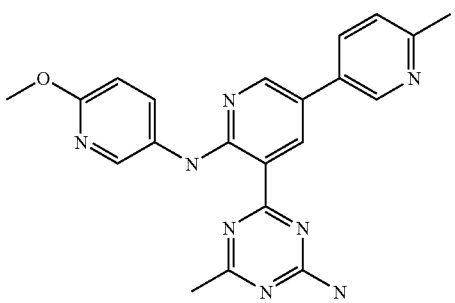

The title compound was prepared in an analogous manner to that described in Example 247 using 4-(5-chloro-2-(6-methoxypyridin-3-ylamino)pyridin-3-yl)-N,N-bis(4-methoxybenzyl)-6-methyl-1,3,5-triazin-2-amine and 6-methylpyridin-3-ylboronic acid (40.5 mg, 0.296 mmol) (Frontier Scientific), and was isolated as a yellow crystalline solid (56%). m/z (ESI, +ve ion) 401.0 (M+H)+. 1H NMR (400 MHz, d6-DMSO) δ 11.85 (1H, s); 9.03 (1H, d, J=2.7 Hz); 8.77 (1H, d, J=2.2 Hz); 8.67 (1H, d, J=2.5 Hz); 8.56 (1H, d, J=2.7 Hz); 8.20 (1H, dd, J=8.8, 2.7 Hz); 7.99 (1H, dd, J=8.1, 2.2 Hz); 7.91 (1H, br. s.); 7.77 (1H, br. s.); 7.38 (1H, d, J=8.2 Hz); 6.85 (1H, d, J=8.8 Hz); 3.86 (3H, s); 2.52 (3H, s); 2.46 (3H, s).

Example 252

4-(2-(6-methoxypyridin-3-ylamino)-5-(pyridazin-4-yl)pyridin-3-yl)-6-methyl-1,3,5-triazin-2-amine

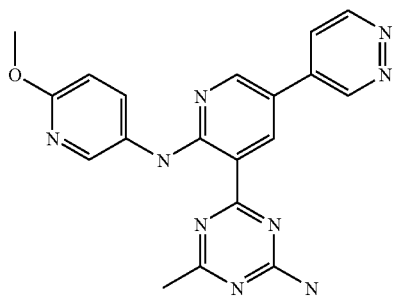 [SMILES: COc1ccc(Nc2ncc(-c3ccnnc3)cc2-c2nc(C)nc(N)n2)cn1]

Step 1: N,N-bis(4-methoxybenzyl)-4-(2-(6-methoxy-pyridin-3-ylamino)-5-(pyridazin-4-yl)pyridin-3-yl)-6-methyl-1,3,5-triazin-2-amine 4-(5-chloro-2-(6-methoxypyridin-3-ylamino)pyridin-3-yl)-N,N-bis(4-methoxybenzyl)-6-methyl-1,3,5-triazin-2-amine (190 mg, 0.325 mmol), dicyclohexyl(2',4',6'-triisopropylbiphenyl-2-yl)phosphine (15.51 mg, 0.033 mmol) (Strem Chemicals), tris(dibenzylideneacetone)dipalladium(0) (14.89 mg, 0.016 mmol) (Strem Chemicals) and 4-(tributylstannyl)pyridazine (156 mg, 0.423 mmol) (Synthonix) were weighed in a vial, purged with argon, and then treated with toluene (1.6 mL). The vial was sealed and heated at 110° C. in an oil bath for 21 h. The reaction mixture was treated with water and extracted with EtOAc (2×30 mL), washed with brine (20 mL) and dried over MgSO$_4$, filtered and concentrated. The residue was purified by flash chromatography using an ISCO Combiflash Companion (12 g column, 20-100% EtOAc in hexanes) to give N,N-bis(4-methoxybenzyl)-4-(2-(6-methoxypyridin-3-ylamino)-5-(pyridazin-4-yl)pyridin-3-yl)-6-methyl-1,3,5-triazin-2-amine (157.1 mg, 0.250 mmol, 77% yield) as a bright yellow crystalline solid. m/z (ESI, +ve ion) 628.0 (M+H)$^+$. $^1$H NMR (400 MHz, CDCl$_3$) δ 11.96 (1H, s); 9.44 (1H, d, J=1.4 Hz); 9.16 (1H, d, J=5.1 Hz); 9.10 (1H, d, J=2.7 Hz); 8.64 (1H, d, J=2.7 Hz); 8.30 (1H, d, J=2.5 Hz); 7.88 (1H, dd, J=8.7, 2.6 Hz); 7.58 (1H, dd, J=5.4, 2.6 Hz); 7.23 (2H, d, J=8.6 Hz); 7.17 (2H, d, J=8.8 Hz); 6.87 (4H, dd, J=12.7, 8.6 Hz); 6.75 (1H, d, J=8.8 Hz); 4.91 (2H, s); 4.83 (2H, s); 3.95 (3H, s); 3.81 (3H, s); 3.78 (3H, s); 2.62 (3H, s).

Step 2: 4-(2-(6-methoxypyridin-3-ylamino)-5-(pyridazin-4-yl)pyridin-3-yl)-6-methyl-1,3,5-triazin-2-amine N,N-bis(4-methoxybenzyl)-4-(2-(6-methoxypyridin-3-ylamino)-5-(pyridazin-4-yl)pyridin-3-yl)-6-methyl-1,3,5-triazin-2-amine (140 mg, 0.223 mmol) was treated with TFA (10 mL) and fitted with a reflux condenser and heated at 80° C. for 15 h. The TFA was removed in vacuo and the residue was pipetted into an ice-cooled saturated solution of NaHCO$_3$ resulting in a yellow suspension which was collected by filtration on a sintered glass frit. The resulting yellow solid was washed with water and MeOH dry-packed on silica gel and attempted purification on the ISCO (12 g column, 1-40% MeOH in DCM (also tried 25% 2M NH3 in MeOH in DCM)) could not liberate the desired product from silica gel. The silica gel was washed with DMSO (20 mL) and filtered through 0.45 µm acrodiscs and the DMSO removed in a Genevac over the weekend to give 4-(2-(6-methoxypyridin-3-ylamino)-5-(pyridazin-4-yl)pyridin-3-yl)-6-methyl-1,3,5-triazin-2-amine (9.5 mg, 0.025 mmol, 10.99% yield) as a bright yellow amorphous solid. m/z (ESI, +ve ion) 388.1 (M+H)$^+$. $^1$H NMR (400 MHz, d6-DMSO) δ 11.99 (1H, s); 9.66 (1H, s); 9.25 (1H, s); 9.21 (1H, d, J=2.3 Hz); 8.91 (1H, d, J=2.3 Hz); 8.55 (1H, d, J=2.7 Hz); 8.16-8.20 (1H, m); 7.98-8.02 (1H, m); 7.92 (1H, s); 7.81 (1H, s); 6.88 (1H, d, J=8.8 Hz); 3.87 (3H, s); 2.54 (3H, s).

Example 253

5-(4-amino-6-methyl-1,3,5-triazin-2-yl)-5'-fluoro-N-(6-methoxypyridin-3-yl)-3,3'-bipyridin-6-amine

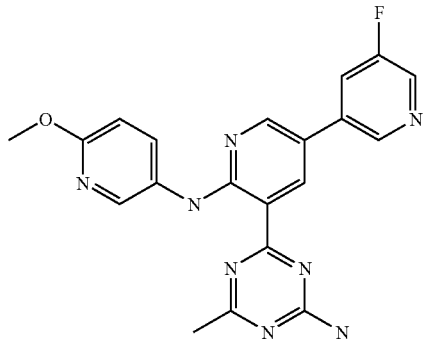 [SMILES: COc1ccc(Nc2ncc(-c3cncc(F)c3)cc2-c2nc(C)nc(N)n2)cn1]

The title compound was prepared in an analogous manner to that described in Example 247 using 4-(5-chloro-2-(6-methoxypyridin-3-ylamino)pyridin-3-yl)-N,N-bis(4-methoxybenzyl)-6-methyl-1,3,5-triazin-2-amine and 5-fluoropyridin-3-ylboronic acid (Combi-Blocks Inc.), and was isolated as an orange crystalline solid (22%). m/z (ESI, +ve ion) 405.0 (M+H)$^+$. $^1$H NMR (400 MHz, d6-DMSO) δ 11.90 (1H, s); 9.09 (1H, d, J=2.7 Hz); 8.80 (1H, s); 8.75 (1H, d, J=2.7 Hz); 8.56 (2H, t, J=2.5 Hz); 8.19 (1H, dd, J=8.9, 2.8 Hz); 8.10 (1H, br. s.); 7.92 (1H, br. s.); 7.77 (1H, br. s.); 6.86 (1H, d, J=9.0 Hz); 3.86 (3H, s), 2.47 (3H, s).

Example 254

5-(4-amino-6-methyl-1,3,5-triazin-2-yl)-N-(6-methoxypyridin-3-yl)-2,3'-bipyridin-6-amine

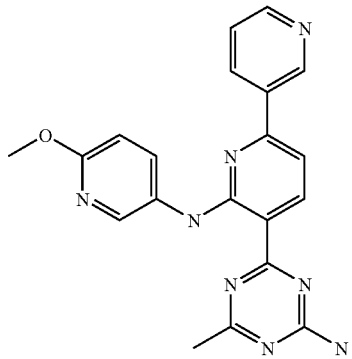 [SMILES: COc1ccc(Nc2nc(-c3cccnc3)ccc2-c2nc(C)nc(N)n2)cn1]

Step 1: 6-fluoro-2,3'-bipyridine

A mixture of 2-chloro-6-fluoro-pyridine (0.436 mL, 3.31 mmol) (Oakwood,), 3-pyridylboronic acid (448 mg, 3.65 mmol) (Combi-Blocks Inc.), and tetrakis(triphenylphosphine)palladium (0) (77 mg, 0.066 mmol) (Strem Chemicals) was purged with argon and dioxane (10 mL) and a 1 M solution of sodium carbonate (4.97 mL, 4.97 mmol) were added. The mixture was heated in a microwave at 110° C. for 30 min. The cooled reaction mixture was treated with 1 N NaOH and extracted with EtOAc (30 mL), washed with brine and dried over MgSO$_4$, filtered and concentrated. Purification on the ISCO (12 g column, 70-100% EtOAc in hexanes) gave 6-fluoro-2,3'-bipyridine (581 mg, 3.34 mmol, 99% yield) as a pale yellow crystalline solid. m/z (ESI, +ve ion) 175.1 (M+H)$^+$. $^1$H NMR (400 MHz, CDCl$_3$) δ 9.20 (1H, d, J=1.6 Hz); 8.67 (1H, d, J=3.9 Hz); 8.34 (1H, d, J=8.0 Hz); 7.90 (1H, q, J=8.0 Hz); 7.67 (1H, dd, J=7.5, 2.4 Hz); 7.42 (1H, dd, J=7.9, 4.8 Hz); 6.94 (1H, dd, J=8.0, 2.9 Hz).

Step 2: 6-fluoro-2,3'-bipyridin-5-ylboronic acid

A stirred solution of diisopropylamine (0.531 ml, 3.79 mmol) (Aldrich) in THF (4 mL) was treated with 1.6 M n-butyllithium in hexanes (2.368 ml, 3.79 mmol) (Aldrich) at −40° C. and the pale yellow solution was stirred for 1 h and then cooled to −78° C. A solution of 6-fluoro-2,3'-bipyridine (550 mg, 3.16 mmol) in THF (5 mL) was added by cannula slowly over 2 min. The resulting bright orange solution was stirred at −78° C. for 1.5 h and then a solution of triisopropyl borate (1.089 m$_l$, 4.74 mmol) (Aldrich) in THF (4 mL) was added slowly. The resulting mixture was stirred at −78° C. for 30 min and then the cooling bath was removed. After the reaction mixture had warmed up to room temperature, the yellow heterogeneous mixture was quenched with 1 N NaOH (aq) (10 mL) and stirred for 30 min. The separated aqueous layer was removed and carefully acidified with 5 N HCl until acidic (pH 5about6) and the resulting cloudy mixture was extracted with EtOAc (20 mL). Most of the product remained in the aqueous phase so the water was removed on the freeze-dryer overnight resulting in a white fluffy product contaminated with salt. m/z (ESI, +ve ion) 219.1 (M+H)$^+$. $^1$H NMR (400 MHz, MeOH) δ 9.22 (1H, s); 8.62 (1H, d, J=4.5 Hz); 8.51 (1H, d, J=8.0 Hz); 8.12 (1H, t, J=7.9 Hz); 7.89 (1H, dd, J=7.3, 2.8 Hz); 7.59 (1H, dd, J=8.0, 4.9 Hz).

Step 3: 4-(6-fluoro-2,3'-bipyridin-5-yl)-N,N-bis(4-methoxybenzyl)-6-methyl-1,3,5-triazin-2-amine A mixture of 6-fluoro-2,3'-bipyridin-5-ylboronic acid (555 mg, 2.55 mmol), 4-chloro-N,N-bis(4-methoxybenzyl)-6-methyl-1,3,5-triazin-2-amine (700 mg, 1.819 mmol), Amphos 2 (64.4 mg, 0.091 mmol) (Aldrich) and potassium acetate (548 mg, 5.58 mmol) (Aldrich) in dioxane (12 mL) and water (3.0 mL) was purged with argon and heated in a microwave reactor at 120° C. for 30 min. The reaction mixture was treated with 1 N NaOH (15 mL) and extracted with EtOAc (50 mL), washed with brine and dried over MgSO$_4$, filtered and concentrated. The crude product was purified on the ISCO (40 g column, 40-100% EtOAc in hexanes) to give 4-(6-fluoro-2,3'-bipyridin-5-yl)-N,N-bis(4-methoxybenzyl)-6-methyl-1,3,5-triazin-2-amine (490.3 mg, 0.938 mmol, 51.6% yield) as a bright yellow crystalline solid. m/z (ESI, +ve ion) 523.0 (M+H)$^+$. $^1$H NMR (400 MHz, CDCl$_3$) δ 9.26 (1H, d, J=1.8 Hz); 8.67-8.72 (2H, m); 8.40 (1H, dt, J=8.0, 2.0 Hz); 7.77 (1H, dd, J=7.8, 1.6 Hz); 7.43 (1H, dd, J=8.0, 5.3 Hz); 7.20-7.25 (4H, m); 6.83-6.90 (4H, m); 4.83 (4H, s); 3.82 (3H, s); 3.80 (3H, s); 2.56 (3H, s).

Step 4: 5-(4-(bis(4-methoxybenzyl)amino)-6-methyl-1,3,5-triazin-2-yl)-N-(6-methoxypyridin-3-yl)-2,3'-bipyridin-6-amine A solution of 4-(6-fluoro-2,3'-bipyridin-5-yl)-N,N-bis(4-methoxybenzyl)-6-methyl-1,3,5-triazin-2-amine (230 mg, 0.440 mmol) and 5-amino-2-methoxypyridine (0.082 mL, 0.660 mmol) (Aldrich) in THF (6.0 mL) was cooled to 0° C. in an ice bath and treated with 1 M LiHMDS (1.320 mL, 1.320 mmol) (Aldrich) resulting in a deep purple solution which was stirred at 0° C. for 30 min. The reaction was quenched by the addition of a saturated solution of NH$_4$Cl and extracted with EtOAc (20 mL), washed with brine and dried over MgSO$_4$, filtered and concentrated. The crude material was used in the next step without further purification. m/z (ESI, +ve ion) 627.0 (M+H)$^+$. $^1$H NMR (400 MHz, CDCl$_3$) δ 11.89 (1H, s); 9.25 (1H, d, J=1.6 Hz); 8.91 (1H, d, J=8.2 Hz); 8.64 (1H, dd, J=4.8, 1.7 Hz); 8.37 (1H, d, J=2.5 Hz); 8.31 (1H, dt, J=8.0, 2.0 Hz); 8.01 (1H, dd, J=8.9, 2.6 Hz); 7.66 (1H, d, J=2.7 Hz); 7.39 (1H, dd, J=7.8, 4.7 Hz); 7.18-7.25 (4H, m); 7.03 (1H, dd, J=8.6, 2.9 Hz); 6.82-6.91 (4H, m); 4.85 (4H, s); 3.86 (3H, s); 3.81 (3H, s); 3.79 (3H, s); 2.60 (3H, s).

Step 5: 5-(4-amino-6-methyl-1,3,5-triazin-2-yl)-N-(6-methoxypyridin-3-yl)-2,3'-bipyridin-6-amine A solution of 5-(4-(bis(4-methoxybenzyl)amino)-6-methyl-1,3,5-triazin-2-yl)-N-(6-methoxypyridin-3-yl)-2,3'-bipyridin-6-amine (276 mg, 0.440 mmol) in TFA (10 mL) was heated to 75° C. for 15 h. about 80% of the TFA was removed in vacuo and the crude oily residue was pipetted into an ice cooled solution of NaHCO$_3$. The resulting suspension was collected by filtration and was washed with water and MeOH. The solid was then dry-packed on silica gel and purified on the ISCO (12 g column, 1-25% MeOH in DCM) to give partially purified product. This was suspended in MeOH and filtered, and the filtercake was dry-packed with silica gel and purified on the ISCO (12 g column, 3-15% MeOH in DCM) to give 5-(4-amino-6-methyl-1,3,5-triazin-2-yl)-N-(6-methoxypyridin-3-yl)-2,3'-bipyridin-6-amine (17.2 mg, 0.045 mmol, 10.11% yield) as a brown amorphous solid. m/z (ESI, +ve ion) 387.0 (M+H)$^+$. $^1$H NMR (400 MHz, d6-DMSO) δ 11.86 (1H, s); 9.26 (1H, d, J=2.0 Hz); 8.88 (1H, d, J=8.0 Hz); 8.66 (2H, d, J=2.9 Hz); 8.41 (1H, dt, J=8.1, 1.8 Hz); 8.21 (1H, dd, J=8.9, 2.6 Hz); 7.89 (1H, br. s.); 7.74 (1H, br. s.); 7.58 (1H, d, J=8.0 Hz); 7.52-7.56 (1H, m); 6.90 (1H, d, J=9.0 Hz); 3.87 (3H, s); 2.45 (3H, s).

Example 255

5-(4-amino-6-methyl-1,3,5-triazin-2-yl)-N-(5-fluoro-6-methoxypyridin-3-yl)-2,3'-bipyridin-6-amine

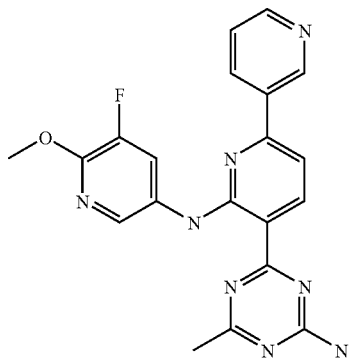

The title compound was prepared in an analogous manner to that described in Example 254 using 4-(6-fluoro-2,3'-bipyridin-5-yl)-N,N-bis(4-methoxybenzyl)-6-methyl-1,3,5-triazin-2-amine and 5-fluoro-6-methoxypyridin-3-amine (Anichem), and was isolated as an orange amorphous solid (5.7%). m/z (ESI, +ve ion) 405.0 (M+H)$^+$. $^1$H NMR (400 MHz, d6-DMSO) δ 12.03 (1H, s); 9.27 (1H, d, J=2.0 Hz); 8.91 (1H, d, J=8.2 Hz); 8.67 (1H, dd, J=4.8, 1.5 Hz); 8.55 (1H, d, J=2.2 Hz); 8.39-8.43 (1H, m); 8.36 (1H, dd, J=12.7, 2.3 Hz); 7.93 (1H, br. s.); 7.79 (1H, br. s.); 7.62 (1H, d, J=8.2 Hz); 7.57 (1H, dd, J=7.9, 4.8 Hz); 3.96 (3H, s); 2.45 (3H, s).

Example 256

4-(5-(3,6-dihydro-2H-pyran-4-yl)-2-(6-methoxypyridin-3-ylamino)pyridin-3-yl)-6-methyl-1,3,5-triazin-2-amine

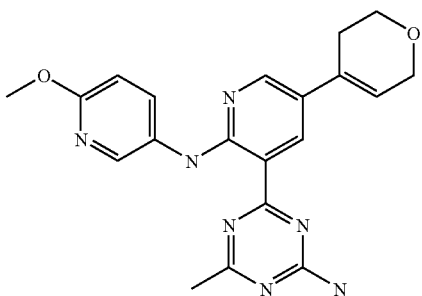

The title compound was prepared in an analogous manner to that described in Example 247 using 4-(5-chloro-2-(6-methoxypyridin-3-ylamino)pyridin-3-yl)-N,N-bis(4-methoxybenzyl)-6-methyl-1,3,5-triazin-2-amine and 2-(3,6-dihydro-2H-pyran-4-yl)-4,4,5,5-tetramethyl-1,3,2-dioxaborolane (Frontier Scientific), and was isolated as a yellow amorphous solid (35%). m/z (ESI, +ve ion) 392.0 (M+H)$^+$. $^1$H NMR (400 MHz, d6-DMSO) δ 11.76 (1H, s); 8.83 (1H, d, J=2.5 Hz); 8.54 (1H, d, J=2.7 Hz); 8.44 (1H, d, J=2.5 Hz); 8.17 (1H, dd, J=8.8, 2.7 Hz); 7.87 (1H, br. s.); 7.73 (1H, br. s.); 6.83 (1H, d, J=8.8 Hz); 6.22 (1H, br. s.); 4.24 (2H, d, J=2.5 Hz); 3.82-3.87 (5H, m); 2.47 (2H, m); 2.44 (3H, s).

Example 257

4-(5-chloro-2-(5-fluoropyridin-3-ylamino)pyridin-3-yl)-6-methyl-1,3,5-triazin-2-amine

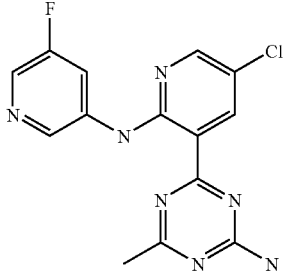 [SMILES: Cc1nc(N)nc(-c2cc(Cl)cnc2Nc2cncc(F)c2)n1]

The title compound was prepared in an analogous manner to that described in Example 246 using 4-(5-chloro-2-fluoropyridin-3-yl)-N,N-bis(4-methoxybenzyl)-6-methyl-1,3,5-triazin-2-amine and 5-fluoropyridin-3-amine (Matrix Scientific), and was isolated as an orange amorphous solid (10%). m/z (ESI, +ve ion) 332.0 (M+H)$^+$. $^1$H NMR (400 MHz, d6-DMSO) δ 12.27 (1H, s); 8.77-8.84 (2H, m); 8.44-8.51 (2H, m); 8.21 (1H, d, J=2.5 Hz); 8.05 (1H, br. s.); 7.91 (1H, br. s.); 2.47 (3H, s).

Example 258

4-(2-(5-fluoropyridin-3-ylamino)-5-(1-methyl-1H-pyrazol-4-yl)pyridin-3-yl)-6-methyl-1,3,5-triazin-2-amine

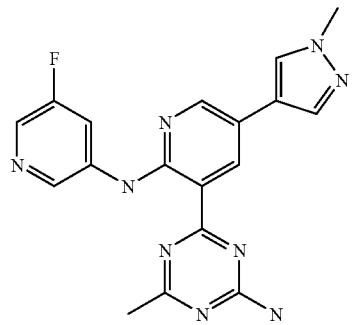 [SMILES: Cc1nc(N)nc(-c2cc(-c3cnn(C)c3)cnc2Nc2cncc(F)c2)n1]

The title compound was prepared in an analogous manner to that described in Example 247 using 4-(5-chloro-2-fluoropyridin-3-yl)-N,N-bis(4-methoxybenzyl)-6-methyl-1,3,5-triazin-2-amine and 1-methyl-4-(4,4,5,5-tetramethyl-1,3,2-dioxaborolan-2-yl)-1H-pyrazole (Aldrich), and was isolated as a dark brown amorphous solid (82%). m/z (ESI, +ve ion) 378.0 (M+H)$^+$. $^1$H NMR (400 MHz, d6-DMSO) δ 12.27 (1H, br. s.); 8.93 (1H, br. s.); 8.84 (1H, br. s.); 8.71 (1H, br. s.); 8.58 (1H, br. s.); 8.17 (2H, br. s.); 8.00 (1H, br. s.); 7.87 (2H, br. s.); 3.90 (3H, br. s.); 2.50 (3H, s).

Example 259

4-(2-(5-fluoro-6-methoxypyridin-3-ylamino)-6-(2-methoxyethoxy)pyridin-3-yl)-6-methyl-1,3,5-triazin-2-amine

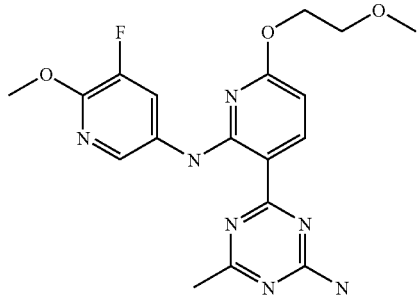

Step 1: 2-fluoro-6-(2-methoxyethoxy)pyridine

Sodium hydride (60 wt % dispersion in mineral oil, 2.51 g, 62.8 mmol) (Aldrich) was added to a stirred mixture of anhydrous 2-methoxyethanol (Aldrich, 2.87 mL, 36.4 mmol) and DMF (30 mL) at 0° C. After 30 min of stirring at 0° C. the reaction mixture turned into a white solid. It was then treated with 2,6-difluoropyridine (3.00 mL, 33.1 mmol) (Aldrich) and allowed to warm to room temperature over 1.5 h. The reaction was quenched with a saturated aqueous solution of NaHCO$_3$ and stirred for 1 h, partitioned between EtOAc and the layers were separated. The organic layer was washed with saturated aqueous NaHCO$_3$, brine, dried (MgSO$_4$), filtered, and the filtrate was concentrated. The residue was purified by flash chromatography on silica gel (40 g column, 0-5% EtOAc in hexanes) to give 2-fluoro-6-(2-methoxyethoxy)pyridine (3.0769 g, 17.98 mmol, 54% yield) as a viscous, clear colorless oil. m/z (ESI, +ve ion) 172.1 (M+H)$^+$. $^1$H NMR (400 MHz, CDCl$_3$) δ 7.64 (1H, q, J=8.2 Hz); 6.67 (1H, dd, J=8.0, 1.0 Hz); 6.46 (1H, dd, J=7.8, 2.3 Hz); 4.41-4.47 (2H, m); 3.70-3.76 (2H, m); 3.44 (3H, s).

Step 2: 2-fluoro-6-(2-methoxyethoxy)pyridin-3-ylboronic acid

2-Fluoro-6-(2-methoxyethoxy)pyridine (1.13 g, 6.60 mmol) in THF (5 mL) was cooled to −60° C. and treated with lithium diisopropylamide, 2.0 M solution in heptane/tetrahydrofuran/ethylbenzene (4.95 mL, 9.90 mmol) (Aldrich) and stirred at −60° C. for 1 h. The mixture was then treated with triisopropyl borate (2.277 mL, 9.90 mmol) (Aldrich) and allowed to warm to RT over 30 min. It was then quenched by the addition of a saturated solution of ammonium chloride and stirred for 30 min. The reaction mixture was extracted with EtOAc (3×25 mL), dried over MgSO$_4$, filtered and concentrated. Purification on the ISCO (12 g column, 5-100% EtOAc) gave a mixture of 2-fluoro-6-(2-methoxyethoxy)pyridin-3-ylboronic acid (226 mg, 1.051 mmol, 15.92% yield) and 6-fluoro-2-(2-methoxyethoxy)-pyridin-3-ylboronic acid as a semi-crystalline solid. m/z (ESI, +ve ion) 216.1 (M+H)$^+$.

Step 3: 4-(2-(5-fluoro-6-methoxypyridin-3-ylamino)-6-(2-methoxyethoxy)pyridin-3-yl)-6-methyl-1,3,5-triazin-2-amine The title compound was prepared in an analogous manner to that described in Example 254 using 4-(2-fluoro-6-(2-methoxyethoxy)pyridin-3-yl)-N,N-bis(4-methoxybenzyl)-6-methyl-1,3,5-triazin-2-amine and 5-fluoro-6-methoxypyridin-3-amine (Anichem), and was isolated as yellow amorphous powder (4.9%). m/z (ESI, +ve ion) 402.0 (M+H)$^+$. $^1$H NMR (400 MHz, d4-MeOH) δ 12.15 (1H, br. s.); 8.77 (1H, d, J=8.6 Hz); 8.32 (1H, br. s.); 8.15 (1H, br. s.); 6.30 (1H, s); 3.98 (3H, s); 3.72 (2H, br. s.); 3.37 (4H, s); 2.44 (4H, s).

Example 260

N-(3-(4-amino-6-methyl-1,3,5-triazin-2-yl)-5-((4-(methylsulfonyl)piperazin-1-yl)methyl)pyridin-2-yl)-1H-benzo[d]imidazol-5-amine

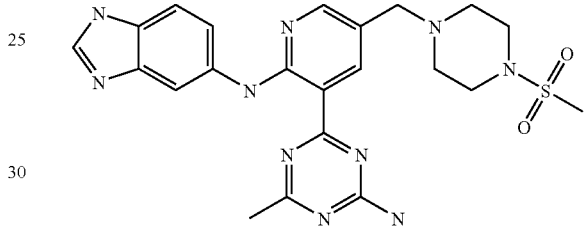

The title compound was prepared in an analogous manner to that described in Example 246 using 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine and a mixture of 1-(4-methoxybenzyl)-1H-benzo[d]imidazol-5-amine and 1-(4-methoxybenzyl)-1H-benzo[d]imidazol-6-amine regioisomers, and was isolated as yellow amorphous solid (5.5%). m/z (ESI, +ve ion) 495.2 (M+H)$^+$. $^1$H NMR (400 MHz, d6-DMSO) δ 12.29 (1H, br. s.); 12.04 (1H, br. s.); 8.72 (1H, d, J=2.5 Hz); 8.39 (1H, br. s.); 8.25 (1H, d, J=2.3 Hz); 8.11 (1H, s); 7.80-7.86 (1H, m); 7.72 (1H, br. s.); 7.51 (1H, br. s.); 7.37 (1H, br. s.); 3.50 (2H, s); 3.11 (4H, d, J=4.5 Hz); 2.87 (3H, s); 2.50 (4H, s); 2.47 (3H, s).

Example 261

N-(3-(4-amino-6-methyl-1,3,5-triazin-2-yl)-5-(piperazin-1-ylmethyl)pyridin-2-yl)-1H-benzo[d]imidazol-5-amine

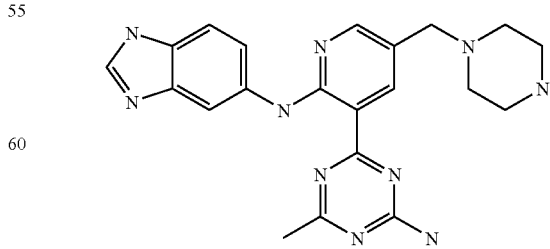

The title compound was also formed during the synthesis of N-(3-(4-amino-6-methyl-1,3,5-triazin-2-yl)-5-((4-(methylsulfonyl)piperazin-1-yl)methyl)pyridin-2-yl)-1H-benzo[d]imidazol-5-amine (Example 260), and was isolated as a yellow amorphous solid (3.1%). m/z (ESI, +ve ion) 417.2 (M+H)+. $^1$H NMR (400 MHz, d4-MeOH) δ 8.84 (1H, d, J=2.3 Hz); 8.23 (1H, d, J=1.6 Hz); 8.17 (1H, d, J=2.3 Hz); 8.08 (1H, s); 7.55 (1H, d, J=8.8 Hz); 7.36 (1H, dd, J=8.7, 1.7 Hz); 3.48 (2H, s); 2.83 (4H, t, J=4.9 Hz); 2.63 (2H, s); 2.49 (6H, s).

Example 262

4-(5-(difluoromethoxy)-2-(6-methoxypyridin-3-ylamino)pyridin-3-yl)-6-methyl-1,3,5-triazin-2-amine

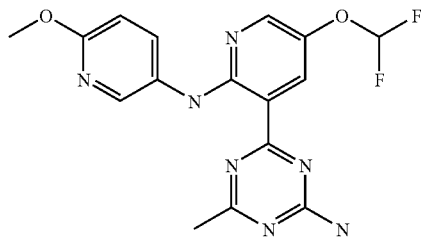 [SMILES: COc1ccc(Nc2ncc(OC(F)F)cc2-c2nc(C)nc(N)n2)cn1]

Step 1: 5-(benzyloxy)-2-fluoropyridine

A solution of 2-fluoro-5-hydroxypyridine (Combi-block) (1.00 g, 8.84 mmol) in DMF (12 mL) was treated with sodium hydride, 60% dispersion in mineral oil (Alfa-Aesar) (0.88 g, 22.1 mmol) at rt under $N_2$. After stirring for 40 min, benzyl chloride (Aldrich) (3.05 mL, 26.5 mmol) and tetrabutylammonium iodide (Aldrich) (0.33 g, 0.88 mmol) were added, and the reaction mixture was stirred for a further 2 h. Water (2 mL) was added to quench the reaction, and the reaction mixture was partitioned between EtOAc and sat. $NaHCO_3$. The aqueous layer was extracted with EtOAc (2×15 mL). The combined organic extracts were washed with sat. $NaHCO_3$, brine, dried over $MgSO_4$ and concentrated. The residue was purified by column chromatography (120 g, 10% to 20% actone in hexanes) to give the product as a colorless liquid (1.32 g). m/z (ESI, +ve ion) 204.0 (M+H)+. $^1$H NMR (300 MHz, $CDCl_3$) δ 7.91 (br. s., 1H); 7.32-7.51 (m, 6H); 6.86 (dd, J=8.84, 3.29 Hz, 1H); 5.10 (s, 2H).

Step 2: 5-(benzyloxy)-2-fluoropyridin-3-ylboronic acid

A solution of diisopropylamine (Aldrich) (0.33 mL, 2.16 mmol) in THF (5 mL) was cooled to 0° C. and treated with n-butyllithium (Aldrich) (0.94 mL, 2.36 mmol). The resulting mixture was stirred at 0° C. for 30 min and then cooled to −78° C. 5-(Benzyloxy)-2-fluoropyridine (Aldrich) (0.200 g, 0.982 mmol) in THF (3 mL) was added dropwise and the solution was stirred at −78° C. for 40 min before being treated with triisopropyl borate (Aldrich) (0.50 mL, 2.16 mmol) in THF (2 mL). After the addition, the cooling bath was removed and the reaction mixture slowly warmed up to rt and and was stirred for 1 h. The reaction mixture was quenched with 5% NaOH (10 mL). The aqueous layer was separated and acidified to pH 5 using 5 N HCl. The resulting mixture was extracted with EtOAc (2×15 mL). The combined organic extracts were dried over $MgSO_4$ and concentrated to give the crude product as yellow solid (0.210 g). m/z (ESI, +ve ion) 248.0 (M+H)+. $^1$H NMR (300 MHz, d4-MeOH) δ 6.60 (br. s., 1H); 6.36 (br. s., 1H); 6.00-6.24 (m, 5H); 3.87 (s, 2H).

Step 3: 4-(5-(benzyloxy)-2-fluoropyridin-3-yl)-N,N-bis(4-methoxybenzyl)-6-methyl-1,3,5-triazin-2-amine A mixture of 4-chloro-N,N-bis(4-methoxybenzyl)-6-methyl-1,3,5-triazin-2-amine (0.150 g, 0.390 mmol), 5-(benzyloxy)-2-fluoropyridin-3-ylboronic acid (0.107 g, 0.432 mmol), Amphos (Aldrich) (0.014 g, 0.020 mmol), potassium acetate (Strem) (0.119 g, 1.22 mmol), EtOH (3 mL), and water (0.3 mL) was sealed under $N_2$ and heated in a microwave at 100° C. for 20 min. The reaction mixture was partitioned between EtOAc and water. The aqueous layer was extracted with EtOAc (2×10 mL). The combined organic layers were dried over $MgSO_4$ and concentrated. The crude product was purified by column chromatography (40 g, 10% to 20% EtOAc in hexanes) to give the product as a white solid (0.090 g). m/z (ESI, +ve ion) 552.0 (M+H)+. $^1$H NMR (300 MHz, $CDCl_3$) δ 8.17 (d, J=7.31 Hz, 1H); 8.01 (br. s., 1H); 7.31-7.48 (m, 5H); 7.23 (d, J=7.89 Hz, 4H); 6.87 (t, J=7.60 Hz, 4H); 5.13 (s, 2H); 4.81 (d, J=6.28 Hz, 3H); 3.81 (d, J=8.33 Hz, 6H); 2.55 (s, 3H).

Step 4: 5-(4-(bis(4-methoxybenzyl)amino)-6-methyl-1,3,5-triazin-2-yl)-6-fluoropyridin-3-ol A solution of 4-(5-(benzyloxy)-2-fluoropyridin-3-yl)-N,N-bis(4-methoxybenzyl)-6-methyl-1,3,5-triazin-2-amine (0.080 g, 0.145 mmol) in EtOAc (8 mL) under $N_2$ gas was treated with 10% palladium on carbon (Aldrich) (7.72 mg, 0.073 mmol). The reaction mixture was purged with $N_2$ and then stirred at rt under $H_2$ for 2 h. The reaction mixture was passed through Celite® (diatomaceous earth). The filtrate was concentrated. The crude product was purified by column chromatography (12 g, 20% to 30% acetone in hexanes) to give the product as a white solid (0.050 g). m/z (ESI, +ve ion) 462.0 (M+H)+. $^1$H NMR (300 MHz, $CDCl_3$) δ 8.03 (dd, J=7.60, 3.07 Hz, 1H); 7.89 (br. s., 1H); 7.23 (d, J=6.43 Hz, 4H); 6.87 (t, J=7.53 Hz, 4H); 5.78 (br. s., 1H); 4.82 (s, 4H); 3.81 (d, J=4.82 Hz, 6H); 2.55 (s, 3H).

Step 5: 4-(5-(difluoromethoxy)-2-fluoropyridin-3-yl)-N,N-bis(4-methoxybenzyl)-6-methyl-1,3,5-triazin-2-amine A solution of 5-(4-(bis(4-methoxybenzyl)amino)-6-methyl-1,3,5-triazin-2-yl)-6-fluoropyridin-3-ol (0.050 g, 0.108 mmol) in DMF (3 mL) was treated with sodium 2-chloro-2,2-difluoroacetate (Aldrich) (0.033 g, 0.217 mmol) and cesium carbonate (Aldrich) (0.053 g, 0.163 mmol). The reaction mixture was heated at 100° C. under $N_2$ for 2 h. The reaction mixture was cooled to rt and partitioned between EtOAc and water. The organic layer was washed with sat. $NaHCO_3$, water, brine, dried over $MgSO_4$ and concentrated. The crude product was purified by column chromatography (12 g, 10% to 20% EtOAc in hexanes) to give the product as a white solid (0.030 g). m/z (ESI, +ve ion) 512.0 (M+H)+. $^1$H NMR (300 MHz, $CDCl_3$) δ 8.39 (d, J=7.45 Hz, 1H); 8.18 (br. s., 1H); 7.23 (d, J=7.89 Hz, 4H); 6.87 (t, J=7.60 Hz, 4H); 6.23-6.83 (m, 1H); 4.82 (d, J=8.04 Hz, 4H); 3.81 (d, J=4.82 Hz, 6H); 2.55 (s, 3H).

Step 6: 4-(5-(difluoromethoxy)-2-(6-methoxypyridin-3-ylamino)pyridin-3-yl)-N,N-bis(4-methoxybenzyl)-6-methyl-1,3,5-triazin-2-amine A solution of 4-(5-(difluoromethoxy)-2-fluoropyridin-3-yl)-N,N-bis(4-methoxybenzyl)-6-methyl-1,3,5-triazin-2- amine (0.030 g, 0.059 mmol) and 5-amino-2-methoxypyridine (Aldrich) (8.06 µL, 0.065 mmol), in THF (1 mL) was cooled to 0° C. under N₂ and treated with lithium bis(trimethylsilyl)amide, 1.0 M solution in tetrahydriofuran (Aldrich) (0.039 mL, 0.235 mmol). The dark red mixture was stirred at 0° C. for 1 h and then partitioned between EtOAc and sat. NH₄Cl. The aqueous layer was extracted with EtOAc (2×10 mL). The combined organic layers were washed with water, brine, dried over MgSO₄ and concentrated. The crude product was purified by column chromatography (12 g, 10% to 20% EtOAc in hexanes) to give the product as a yellow solid (0.022 g). m/z (ESI, +ve ion) 616.0 (M+H)⁺. ¹H NMR (300 MHz, CDCl₃) δ 11.65 (s, 1H); 8.63 (br. s., 1H); 8.26 (s, 1H); 8.17 (br. s., 1H); 7.89 (d, J=8.77 Hz, 1H); 7.11-7.25 (m, 4H); 6.78-6.95 (m, 4H); 6.72 (d, J=8.77 Hz, 1H); 6.11-6.69 (m, 1H); 4.74-4.93 (m, 4H); 3.94 (s, 3H); 3.81 (d, J=8.48 Hz, 6H); 2.59 (s, 3H).

Step 7: 4-(5-(difluoromethoxy)-2-(6-methoxypyridin-3-ylamino)pyridin-3-yl)-6-methyl-1,3,5-triazin-2-amine A solution of 4-(5-(difluoromethoxy)-2-(6-methoxypyridin-3-ylamino)pyridin-3-yl)-N,N-bis(4-methoxybenzyl)-6-methyl-1,3,5-triazin-2-amine (0.022 g, 0.036 mmol) in trifluoroacetic acid (Aldrich) (0.531 mL, 7.15 mmol) and trifluoromethane sulfonic acid (TCI) (3.16 µL, 0.036 mmol) was heated at 80° C. for 20 min. The reaction mixture was concentrated and the residue was first diluted with sat. NaHCO₃ (8 mL) then extracted with CHCl₃ (3×10 mL). The combined organic layers were dried over MgSO₄ and concentrated. The crude product was purified by column chromatography (12 g, 10% to 20% acetone in hexanes) to give the product as a yellow solid (0.010 g). m/z (ESI, +ve ion) 376.0 (M+H)⁺. ¹H NMR (300 MHz, CDCl₃) δ 11.65 (s, 1H); 8.67 (br. s., 1H); 8.35 (br. s., 1H); 8.20 (br. s., 1H); 8.09 (d, J=9.94 Hz, 1H); 6.79 (d, J=8.92 Hz, 1H); 6.11-6.75 (m, 1H); 5.41 (br. s., 2H); 3.95 (s, 3H); 2.58 (s, 3H).

Example 263

4-(3-(4-amino-6-methyl-1,3,5-triazin-2-yl)pyridin-2-ylamino)pyridin-2(1H)-one

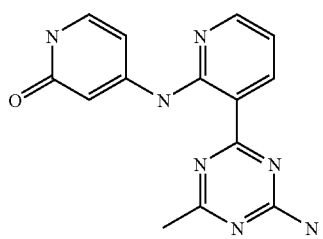 [SMILES: Cc1nc(N)nc(-c2cccnc2Nc2cc[nH]c(=O)c2)n1]

Step 1: 2-(4-methoxybenzyloxy)pyridin-4-amine

A solution of 4-amino-2-chloropyridine (Aldrich) (1.000 g, 7.78 mmol) in 4-methoxybenzyl alcohol (Fluka) (9.66 mL, 78 mmol) was treated with sodium hydroxide (J. T. Baker) (0.584 mL, 31.1 mmol) and tetrabutylammonium iodide (Aldrich) (0.287 g, 0.778 mmol). The resulting mixture was heated at 160° C. under N₂ for 2 h. The reaction mixture was partitioned between EtOAc and water. The aqueous layer was extracted with EtOAc (2×15 mL). The combined organic layers were dried over MgSO₄ and concentrated. The crude product was purified by column chromatography (120 g, 20% to 30% acetone in hexanes) to give the product as a white solid (1.32 g). m/z (ESI, +ve ion) 231.1 (M+H)⁺. ¹H NMR (300 MHz, CDCl₃) δ 7.85 (d, J=5.70 Hz, 1H); 7.38 (d, J=8.18 Hz, 2H); 6.91 (d, J=8.48 Hz, 2H); 6.22 (d, J=7.02 Hz, 1H); 5.99 (s, 1H); 5.27 (s, 2H); 4.04 (br. s., 2H); 3.82 (s, 3H).

Step 2: N,N-bis(4-methoxybenzyl)-4-(2-(2-(4-methoxybenzyloxy)pyridin-4-ylamino)pyridin-3-yl)-6-methyl-1,3,5-triazin-2-amine A solution of 2-(4-methoxybenzyloxy)pyridin-4-amine (0.500 g, 2.171 mmol) in THF (10 mL) was cooled to 0° C. under N₂. Lithium bis(trimethylsilyl)amide, 1.0 M solution in tetrahydrofuran (Aldrich) (6.51 mL, 6.51 mmol) was added dropwise and the mixture was stirred at 0° C. for 30 min. 4-(2-Fluoropyridin-3-yl)-N,N-bis(4-methoxybenzyl)-6-methyl-1,3,5-triazin-2-amine (1.161 g, 2.61 mmol) was added to this reaction mixture. After the addition, the resulting mixture was stirred at 0° C. for 10 min and then removed from the ice bath and stirred for 2 h at rt. The reaction was quenched with water. The resulting mixture was partitioned between EtOAc and sat. NH4Cl. The organic layer was washed with water, brine, dried over MgSO₄ and concentrated. The crude product was purified by column chromatography (120 g, 20% to 30% EtOAc in hexanes) to give the product as a white solid (0.950 g). m/z (ESI, +ve ion) 656.0 (M+H)⁺. ¹H NMR (300 MHz, CDCl₃) δ 12.36 (s, 1H); 8.85 (d, J=7.75 Hz, 1H); 8.40 (d, J=4.38 Hz, 1H); 7.98 (d, J=5.41 Hz, 1H); 7.50 (s, 1H); 7.43 (d, J=8.33 Hz, 2H); 7.21 (d, J=8.18 Hz, 4H); 7.02 (d, J=4.38 Hz, 1H); 6.73-6.98 (m, 7H); 5.32 (s, 2H); 4.85 (br. s., 4H); 3.69-3.96 (m, 9H); 2.62 (s, 3H).

Step 3: 4-(3-(4-amino-6-methyl-1,3,5-triazin-2-yl)pyridin-2-ylamino)pyridin-2(1H)-one A solution of N,N-bis(4-methoxybenzyl)-4-(2-(2-(4-methoxybenzyloxy)pyridin-4-ylamino)pyridin-3-yl)-6-methyl-1,3,5-triazin-2-amine (0.120 g, 0.183 mmol) in trifluoroacetic acid (Aldrich) (1.631 mL, 21.96 mmol) and trifluoromethane sulfonic acid (TCI) (0.810 mL, 9.15 mmol) was heated at 80° C. in a sealed tube for 1 h. The reaction mixture was neutralized with sat. NaHCO₃. The precipitate was collected by filtration. The precipitate was purified by prep HPLC to give the product as a white solid (0.010 g). m/z (ESI, +ve ion) 296.1 (M+H)⁺. ¹H NMR (300 MHz, d6-DMSO) δ 12.14 (s, 1H); 10.94 (br. s., 1H); 8.81 (d, J=6.87 Hz, 1H); 8.46 (d, J=4.09 Hz, 1H); 7.66-8.04 (m, 2H); 7.24 (d, J=7.31 Hz, 1H); 7.19 (s, 1H); 7.08 (dd, J=7.97, 4.75 Hz, 1H); 6.53 (d, J=5.70 Hz, 1H); 2.44 (s, 3H).

Example 264

N-(5-(3-(4-amino-6-methyl-1,3,5-triazin-2-yl)pyridin-2-ylamino)-2-chloropyridin-3-yl)-4-fluorobenzenesulfonamide

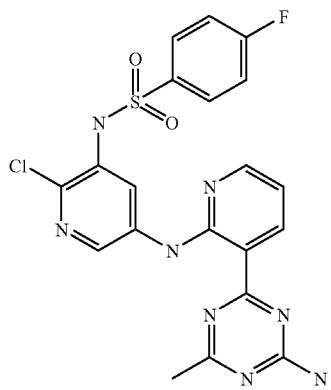 [SMILES: Cc1nc(N)nc(-c2cccnc2Nc2cnc(Cl)c(NS(=O)(=O)c3ccc(F)cc3)c2)n1]

Step 1: N-(2-chloro-5-(diphenylmethyleneamino)pyridin-3-yl)-4-fluorobenzenesulfonamide A mixture of N-(5-bromo-2-chloropyridin-3-yl)-4-fluorobenzenesulfonamide (Inogent, Inc.) (1.000 g, 2.74 mmol), palladium (II) acetate (Aldrich) (0.035 g, 0.156 mmol), (diphenylphosphino)xanthene (Acros) (0.176 g, 0.304 mmol), sodium tert-butoxide (Fluka) (0.620 g, 6.45 mmol), toluene (10 mL), and benzophenone imine (Aldrich) (0.459 mL, 2.74 mmol) was heated at 100° C. in a sealed tube for 6 h. The reaction mixture was partitioned between EtOAc and Tris HCl (1 M, pH 7). The aqueous layer was extracted with EtOAc (2×10 mL). The combined organic layers were dried over $MgSO_4$ and concentrated. The crude product was purified by column chromatography (120 g, 10% to 20% acetone in hexanes) to give the product as a yellow solid (0.520 g). m/z (ESI, +ve ion) 466.0 (M+H)$^+$. $^1$H NMR (300 MHz, CDCl$_3$) δ 7.75 (d, J=7.45 Hz, 2H); 7.61 (d, J=2.05 Hz, 1H); 7.50-7.59 (m, 3H); 7.40-7.49 (m, 3H); 7.35 (br. s., 3H); 7.03-7.17 (m, 4H); 6.73 (br. s., 1H).

Step 2: N-(5-amino-2-chloropyridin-3-yl)-4-fluorobenzenesulfonamide

A solution of N-(2-chloro-5-(diphenylmethyleneamino)pyridin-3-yl)-4-fluorobenzenesulfonamide (0.520 g, 1.116 mmol) in THF (8 mL) and hydrochloric acid, 2 N (J. T. Baker) (0.837 mL, 1.674 mmol) was stirred at rt in a sealed tube for 30 min. The reaction mixture was partitioned between EtOAc and sat. NaHCO$_3$. The aqueous layer was extracted with EtOAc (2×10 mL). The combined organic layers were dried over MgSO$_4$ and concentrated. The crude product was purified by column chromatography (80 g, 20% to 40% acetone in hexanes) to give the product as a yellow solid (0.270 g). m/z (ESI, +ve ion) 302.0 (M+H)$^+$. $^1$H NMR (300 MHz, CDCl$_3$) δ 7.80 (dd, J=8.77, 4.97 Hz, 2H); 7.61 (d, J=2.63 Hz, 1H); 7.34 (d, J=2.48 Hz, 1H); 7.16 (t, J=8.48 Hz, 2H); 6.82 (br. s., 1H); 3.84 (br. s., 2H).

Step 3: N-(5-(3-(4-amino-6-methyl-1,3,5-triazin-2-yl)pyridin-2-ylamino)-2-chloropyridin-3-yl)-4-fluorobenzenesulfonamide A solution of N-(5-amino-2-chloropyridin-3-yl)-4-fluorobenzenesulfonamide (0.124 g, 0.409 mmol) in THF (5 mL) was cooled to 0° C. under N$_2$. Lithium bis(trimethylsilyl)amide, 1.0 M solution in tetrahydrofuran (Aldrich) (1.706 mL, 1.706 mmol) was added dropwise and the mixture was stirred at 0° C. for 30 min. 4-(2-Fluoropyridin-3-yl)-6-methyl-1,3,5-triazin-2-amine (0.070 g, 0.341 mmol) was added and the mixture was stirred at 0° C. for 10 min. The reaction mixture was then stirred at rt for 20 h. The reaction was quenched with sat. NH$_4$Cl and the resulting mixture was partitioned between sat. NaHCO$_3$ and CHCl$_3$. The aqueous layer was extracted with CHCl$_3$ (2×15 mL). The combined organic layers were dried over MgSO$_4$ and concentrated. The crude product was purified by prep HPLC. Fractions containing the product were combined and concentrated. The residue was basified using sat. NaHCO$_3$ (10 mL). The aqueous layer was extracted with CHCl$_3$ (3×15 mL). The combined organic layers were dried over MgSO$_4$ and concentrated to give the product as a yellow solid (0.050 g). m/z (ESI, +ve ion) 486.8 (M+H)$^+$. $^1$H NMR (300 MHz, CDCl$_3$) δ 12.38 (s, 1H); 8.74-9.01 (m, 2H); 8.44 (d, J=3.22 Hz, 1H); 8.39 (d, J=2.34 Hz, 1H); 7.95 (dd, J=8.62, 5.12 Hz, 2H); 7.15 (t, J=8.48 Hz, 2H); 6.86-7.03 (m, 2H); 5.43 (br. s., 2H); 2.60 (s, 3H).

Example 265

N5-(3-(4-amino-6-methyl-1,3,5-triazin-2-yl)pyridin-2-yl)-2-chloropyridine-3,5-diamine

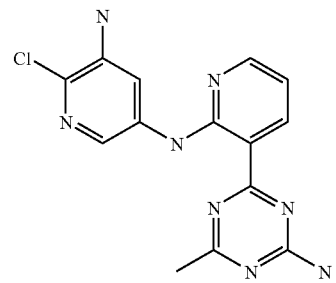 [SMILES: Cc1nc(N)nc(-c2cccnc2Nc2cnc(Cl)c(N)c2)n1]

Step 1: N-(5-(3-(4-(bis(4-methoxybenzyl)amino)-6-methyl-1,3,5-triazin-2-yl)pyridin-2-ylamino)-2-chloropyridin-3-yl)-4-fluorobenzenesulfonamide A mixture of N-(5-amino-2-chloropyridin-3-yl)-4-fluorobenzenesulfonamide (0.08 g, 0.265 mmol) in THF (5 mL) was cooled to 0° C. under N$_2$. Lithium bis(trimethylsilyl)amide, 1.0 M solution in tetrahydrofuran (Aldrich) (0.795 mL, 0.795 mmol) was added dropwise and the mixture was stirred at 0° C. for 30 min before 4-(2-fluoropyridin-3-yl)-N,N-bis(4-methoxybenzyl)-6-methyl-1,3,5-triazin-2-amine (0.142 g, 0.318 mmol) was added. The resulting mixture was stirred at 0° C. for 10 min then removed from the ice bath and stirred for 3 h. The reaction mixture was quenched with water. The resulting mixture was partitioned between EtOAc and sat. NH$_4$Cl. The aqueous layer was extracted with EtOAc (2×10 mL). The combined organic layers were washed with water, brine, dried over MgSO$_4$ and concentrated. The crude product was purified by column chromatography (40 g, 20% to 30% acetone in hexanes) to give the product as a yellow solid (0.090 g). m/z (ESI, +ve ion) 727.1 (M+H)$^+$. $^1$H NMR (300 MHz, CDCl$_3$) δ 12.48 (s, 1H); 8.78-8.95 (m, 2H); 8.41 (d, J=3.51 Hz, 1H); 8.27 (s, 1H); 7.93 (dd, J=8.62, 4.97 Hz, 2H); 7.22 (d, J=6.58 Hz, 4H); 7.14 (t, J=8.48 Hz, 2H); 6.77-6.97 (m, 6H); 4.85 (d, J=3.36 Hz, 4H); 3.81 (d, J=5.12 Hz, 6H); 2.61 (s, 3H).

Step 2: N5-(3-(4-amino-6-methyl-1,3,5-triazin-2-yl)pyridin-2-yl)-2-chloropyridine-3,5-diamine A solution of N-(5-(3-(4-(bis(4-methoxybenzyl)amino)-6-methyl-1,3,5-triazin-2-yl)pyridin-2-ylamino)-2-chloropyridin-3-yl)-4-fluorobenzenesulfonamide (0.087 g, 0.120 mmol) in trifluoroacetic acid (Aldrich) (0.622 mL, 8.37 mmol) and trifluoromethane sulfonic acid (TCI) (0.265 mL, 2.99 mmol).was heated at 80° C. in a sealed tube for 20 min. The reaction mixture was first neutralized with sat. NaHCO$_3$ and then extracted with CHCl$_3$ (3×15 mL). The combined organic layers were washed with water, brine, dried over MgSO$_4$ and concentrated. The crude product was purified by column chromatography (40 g, 20% to 30% acetone in hexanes) to give the product as a white solid (0.025 g). m/z (ESI, +ve ion) 329.0 (M+H)$^+$. $^1$H NMR (300 MHz, d6-DMSO) δ 12.01 (s, 1H); 8.79 (d, J=7.16 Hz, 1H); 8.37 (d, J=4.39 Hz, 1H); 7.96 (s, 2H); 7.61-7.88 (m, 2H); 6.96 (dd, J=7.89, 4.82 Hz, 1H); 5.48 (s, 2H); 2.45 (s, 3H).

Example 266

N-(4-(3-(4-amino-6-methyl-1,3,5-triazin-2-yl)-5-chloropyridin-2-ylamino)-2-fluorophenyl)acetamide

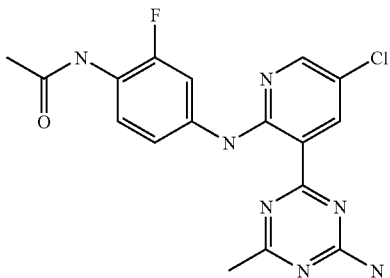 [SMILES: CC(=O)Nc1ccc(Nc2ncc(Cl)cc2-c2nc(C)nc(N)n2)cc1F]

A mixture of N-(4-amino-2-fluorophenyl)acetamide (0.084 g, 0.501 mmol) in THF (5 mL) was cooled to 0° C. under N$_2$. Lithium bis(trimethylsilyl)amide, 1.0 M solution in tetrahydrofuran (Aldrich) (0.487 mL, 2.504 mmol) was added and the mixture was stirred at 0° C. for 30 min before 4-(5-chloro-2-fluoropyridin-3-yl)-6-methyl-1,3,5-triazin-2-amine (0.100 g, 0.417 mmol) was added. The resulting mixture was stirred at 0° C. for 10 min and then removed from the ice bath and stirred for 2 h. The reaction was quenched with sat. NH$_4$Cl. The resulting mixture was partitioned between pH 7 buffer (1 M TRIS-HCl) and CHCl$_3$. The aqueous layer was extracted with CHCl$_3$ (2×15 mL). The combined organic layers were dried over MgSO$_4$ and concentrated. The crude product was purified by prep HPLC. Fractions containing the product were combined and the solvent was removed in vacuo. The residue was basified using sat. NaHCO$_3$ (10 mL). The aqueous layer was extracted with CHCl$_3$ (3×15 mL). The combined organic layers were dried over MgSO$_4$ and concentrated to give the product as a brown solid (40 mg). m/z (ESI, +ve ion) 388.0 (M+H)$^+$. $^1$H NMR (400 MHz, d6-DMSO) δ 12.08 (s, 1H); 9.63 (s, 1H); 8.75 (d, J=2.74 Hz, 1H); 8.43 (d, J=2.74 Hz, 1H); 7.93-8.06 (m, 2H); 7.88 (br. s., 1H); 7.71 (t, J=8.80 Hz, 1H); 7.45 (dd, J=8.80, 1.76 Hz, 1H); 2.45 (s, 3H); 2.06 (s, 3H).

Example 267

N-(4-(3-(4-amino-6-methyl-1,3,5-triazin-2-yl)-5-((4-(methylsulfonyl)piperazin-1-yl)methyl)pyridin-2-ylamino)-2-fluorophenyl)acetamide

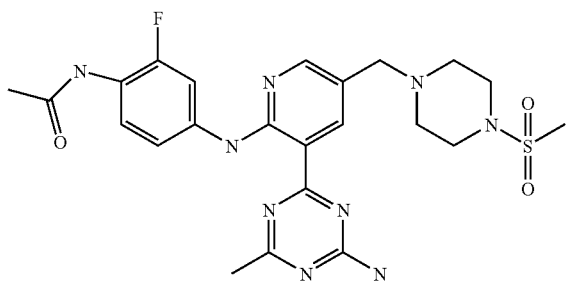 [SMILES: CC(=O)Nc1ccc(Nc2ncc(CN3CCN(S(C)(=O)=O)CC3)cc2-c2nc(C)nc(N)n2)cc1F]

Step 1: N-(4-(3-(4-(bis(4-methoxybenzyl)amino)-6-methyl-1,3,5-triazin-2-yl)-5-((4-(methylsulfonyl)piperazin-1-yl)methyl)pyridin-2-ylamino)-2-fluorophenyl)acetamide A mixture of N-(4-amino-2-fluorophenyl)acetamide (0.110 g, 0.654 mmol) in THF (5 mL) was cooled to 0° C. under N$_2$. Lithium bis(trimethylsilyl)amide, 1.0 M solution in tetrahydrofuran (Aldrich) (0.636 mL, 3.27 mmol) was added and the mixture was stirred at 0° C. for 30 min before 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (0.447 g, 0.720 mmol) was added. The resulting mixture was stirred at 0° C. for 10 min, and then the ice bath was removed and and stirring was continued for 2 h. The reaction was quenched with sat. NH$_4$Cl. The resulting mixture was partitioned between pH 7 buffer (1 M TRIS-HCl) and CHCl$_3$. The aqueous layer was extracted with CHCl$_3$ (2×15 mL). The combined organic layers were dried over MgSO$_4$ and concentrated. The crude product was purified by column chromatography (40 g, 3% MeOH and 12% EtOAc in DCM) to give the product as a yellow solid (0.125 g). m/z (ESI, +ve ion) 770.0 (M+H)$^+$. $^1$H NMR (300 MHz, CDCl$_3$) δ 11.99 (br. s., 1H); 8.73 (s, 1H); 8.28 (s, 1H); 8.02-8.16 (m, 1H); 7.91 (s, 1H); 7.22 (d, J=7.45 Hz, 5H); 6.96 (d, J=8.33 Hz, 1H); 6.88 (d, J=8.18 Hz, 4H); 4.86 (br. s., 4H); 3.81 (d, J=2.92 Hz, 6H); 3.52 (s, 2H); 3.19 (br. s., 4H); 2.72 (s, 3H); 2.61 (s, 3H); 2.48-2.59 (m, 4H); 2.21 (s, 3H).

Step 2: N-(4-(3-(4-amino-6-methyl-1,3,5-triazin-2-yl)-5-((4-(methylsulfonyl)piperazin-1-yl)methyl)pyridin-2-ylamino)-2-fluorophenyl)acetamide A solution of N-(4-(3-(4-(bis(4-methoxybenzyl)amino)-6-methyl-1,3,5-triazin-2-yl)-5-((4-(methylsulfonyl)piperazin-1-yl)methyl)pyridin-2-ylamino)-2-fluorophenyl)acetamide (0.125 g, 0.162 mmol) in trifluoroacetic acid (Aldrich) (1.206 mL, 16.24 mmol) and trifluoromethane sulfonic acid (TCI) (0.431 mL, 4.87 mmol) was stirred at rt in a sealed tube for 1 h. The reaction mixture was first neutralized with sat. NaHCO$_3$ and then extracted with CHCl$_3$ (3×15 mL). The combined organic layers were dried over MgSO₄ and concentrated. The crude product was purified by column chromatography (120 g, 3% MeOH in DCM) to give the product as a yellow solid (0.070 g). m/z (ESI, +ve ion) 530. (M+H)⁺. ¹H NMR (300 MHz, CDCl₃) δ 12.03 (s, 1H); 8.73 (s, 1H); 8.31 (s, 1H); 8.19 (t, J=8.70 Hz, 1H); 8.07 (d, J=13.74 Hz, 1H); 7.15 (d, J=9.50 Hz, 1H); 5.44 (br. s., 2H); 3.54 (s, 2H); 3.27 (br. s., 4H); 2.79 (s, 3H); 2.60 (s, 7H); 2.22 (s, 3H).

Example 268

N-(4-(3-(4-amino-6-methyl-1,3,5-triazin-2-yl)-5-((4-(methylsulfonyl)piperazin-1-yl)methyl)pyridin-2-ylamino)phenyl)acetamide

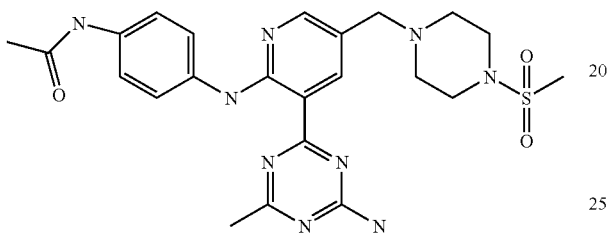

Step 1: N-(4-(3-(4-(bis(4-methoxybenzyl)amino)-6-methyl-1,3,5-triazin-2-yl)-5-((4-(methylsulfonyl)piperazin-1-yl)methyl)pyridin-2-ylamino)phenyl)acetamide A solution of 4′-aminoacetanilide (0.097 g, 0.643 mmol) in THF (5 mL) was cooled to 0° C. under N₂. Lithium bis(trimethylsilyl)amide, 1.0 M solution in tetrahydrofuran (Aldrich) (0.313 mL, 1.608 mmol) was added and the mixture was stirred at 0° C. for 30 min before 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (0.200 g, 0.322 mmol) was added. The resulting mixture was stirred at 0° C. for 10 min, and then the ice bath was removed and stirring was continued for 2 h. The reaction was quenched with sat. NH₄Cl. The resulting mixture was partitioned between pH 7 buffer (1 M TRIS-HCl) and CHCl₃. The aqueous layer was extracted with CHCl₃ (2×10 mL). The combined organic layers were dried over MgSO₄ and concentrated. The crude product was purified by column chromatography (40 g, 3% MeOH and 12% EtOAc in DCM) to give the product as a yellow solid (0.140 g). m/z (ESI, +ve ion) 752.0 (M+H)⁺. ¹H NMR (300 MHz, CDCl₃) δ 11.82 (s, 1H); 8.72 (s, 1H); 8.24 (s, 1H); 7.54 (d, J=8.48 Hz, 2H); 7.40 (d, J=8.62 Hz, 2H); 7.22 (d, J=7.75 Hz, 4H); 7.07 (br. s., 1H); 6.87 (dd, J=8.18, 4.09 Hz, 4H); 4.85 (d, J=4.68 Hz, 4H); 3.81 (d, J=3.95 Hz, 6H); 3.51 (s, 2H); 3.19 (br. s., 4H); 2.71 (s, 3H); 2.60 (s, 3H); 2.44-2.58 (m, 4H); 2.18 (s, 3H).

Step 2: N-(4-(3-(4-amino-6-methyl-1,3,5-triazin-2-yl)-5-((4-(methylsulfonyl)piperazin-1-yl)methyl)pyridin-2-ylamino)phenyl)acetamide A solution of N-(4-(3-(4-(bis(4-methoxybenzyl)amino)-6-methyl-1,3,5-triazin-2-yl)-5-((4-(methylsulfonyl)piperazin-1-yl)methyl)pyridin-2-ylamino)phenyl)acetamide (0.140 g, 0.186 mmol) in trifluoroacetic acid (Aldrich) (1.383 mL, 18.62 mmol) and trifluoromethane sulfonic acid (TCI) (0.494 mL, 5.59 mmol) was stirred at rt in a sealed tube for 1 h. The reaction mixture was first neutralized with sat. NaHCO₃ then extracted with CHCl₃ (2×10 mL). The combined organic layers were dried over MgSO₄ and concentrated. The crude product was purified by column chromatography (120 g, 4% MeOH in DCM) to give the product as a yellow solid (0.070 g). m/z (ESI, +ve ion) 512.0 (M+H)⁺. ¹H NMR (300 MHz, CDCl₃) δ 11.85 (s, 1H); 8.72 (s, 1H); 8.28 (d, J=0.73 Hz, 1H); 7.68 (s, 2H); 7.48 (d, J=8.48 Hz, 2H); 7.12 (br. s., 1H); 5.43 (br. s., 2H); 3.53 (s, 2H); 3.26 (br. s., 4H); 2.78 (s, 3H); 2.59 (s, 7H); 2.19 (s, 3H).

Example 269

(R,S)-1-(5-(4-amino-6-methyl-1,3,5-triazin-2-yl)-6-(6-methoxypyridin-3-ylamino)pyridin-3-yl)-2,2,2-trifluoroethanol

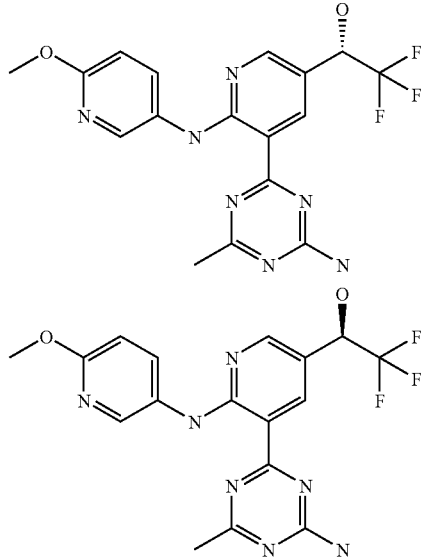

A stirred solution of 5-(4-(bis(4-methoxybenzyl)amino)-6-methyl-1,3,5-triazin-2-yl)-6-(6-methoxypyridin-3-ylamino)nicotinaldehyde (130 mg, 0.225 mmol) in DMF (2.00 mL, 25.8 mmol) was treated with CsF (34.2 mg, 0.225 mmol) followed by trimethyl(trifluoromethyl)silane (96 mg, 0.675 mmol) at 0° C. for 10 min and then allowed to warm to room temperature for 2 h. The reaction mixture was diluted with NH₄Cl(aq) and water (10 mL each) and diluted with ethyl acetate (5 mL). The separated aqueous layer was extracted with ethyl acetate (2×10 mL) and the combined organic layers were washed with brine, dried over Na₂SO₄, and concentrated. The residue was taken up in TFA (3 mL) and a couple drops of TfOH were added. The mixture was heated at 75° C. for 4 h and then cooled to RT and concentrated. The residue was re-dissolved in 5% MeOH in DCM (w/NH₃), concentrated with SiO₂, and purified by chromatography through a Redi-Sep pre-packed silica gel column (pure DCM→5% MeOH in DCM) to give the product (9.3 mg, 10%) as a yellow solid. m/z (ESI, +ve ion) 408 (M+H)⁻. ¹H NMR (400 MHz, d6-DMSO) δ 11.87 (s, 1H); 8.92 (d, J=2.15 Hz, 1H); 8.53 (d, J=2.74 Hz, 1H); 8.35 (d, J=2.35 Hz, 1H); 8.15 (dd, J=8.80, 2.74 Hz, 1H); 7.92 (br. s., 1H); 7.76 (br.

s., 1H); 6.93 (d, J=5.48 Hz, 1H); 6.84 (d, J=8.80 Hz, 1H); 5.09-5.35 (m, 1H); 3.85 (s, 3H); 2.44 (s, 3H).

Example 270

(S)-4-(2-(5-fluoro-6-methoxypyridin-3-ylamino)-5-((2-methyl-4-(methylsulfonyl)piperazin-1-yl)methyl)pyridin-3-yl)-6-methyl-1,3,5-triazin-2-amine

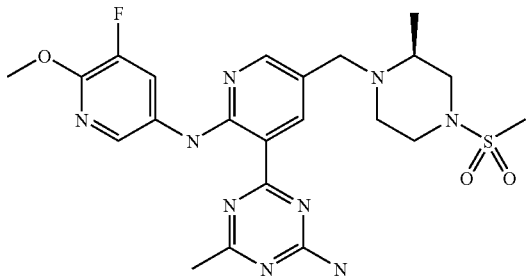

Step 1. potassium (S)-((4-(tert-butoxycarbonyl)-2-methylpiperazin-1-yl)methyl)trifluoroborate A mixture of potassium (bromomethyl)trifluoroborate (Aldrich, 1.20 g, 5.38 mmol) and (S)-tert-butyl 3-methylpiperazine-1-carboxylate (Aldrich, 1.131 g, 5.65 mmol) in THF (7.00 mL) was heated at 80° C. under nitrogen for 24 h. The mixture was allowed to cool to ambient temperature and was then concentrated in vacuo. The residue was re-dissolved in acetone (125 mL) and treated with $K_2CO_3$ (1 eq). The suspension was stirred for 30 min and then filtered through a short plug of Celite® (diatomaceous earth). The filter cake was washed with additional acetone, and the combined organic filtrates were concentrated to give the crude product as a colorless foam (1.51 g, 88%). The pure material was obtained as a beige powder by adding acetone-ether (2:1) to the foam and then slowly adding hexanes while sonicating the mixture. $^{19}$F-NMR (377 MHz, $d_6$-acetone) δ −141.28.

Step 2. 4-(5-chloro-2-fluoropyridin-3-yl)-N,N-bis(4-methoxybenzyl)-6-methyl-1,3,5-triazin-2-amine A mixture of 5-chloro-2-fluoropyridin-3-ylboronic acid (Combi Blocks, 2.507 g, 14.30 mmol), 4-chloro-N,N-bis(4-methoxybenzyl)-6-methyl-1,3,5-triazin-2-amine (5.24 g, 13.62 mmol), bis-(di-tert-butyl(4-dimethylaminophenyl)phosphine)dichloropalladium(II) (0.482 g, 0.681 mmol), and potassium acetate (4.10 g, 41.8 mmol) in ethanol (100 mL) and water (10 mL) was degassed and stirred under $N_2$ at 100° C. for 16 h. The reaction mixture was then cooled to ambient temperature, concentrated in vacuo, and the residue was partitioned between water (50 mL) and EtOAc (50 mL). The aqueous phase was extracted with EtOAc (2×20 mL), and the combined organic layers were washed with saturated aqueous sodium chloride (100 mL). The organic phase was dried over sodium sulfate, filtered and concentrated. Chromatographic purification of the residue (silica gel, 15 to 50% EtOAc/hexanes) gave 4-(5-chloro-2-fluoropyridin-3-yl)-N,N-bis(4-methoxybenzyl)-6-methyl-1,3,5-triazin-2-amine (3.62 g, 7.54 mmol, 55.4% yield). m/z (ESI, +ve ion) 480 (M+H)$^+$.

Step 3. (S)-tert-butyl 4-((5-(4-(bis(4-methoxybenzyl)amino)-6-methyl-1,3,5-triazin-2-yl)-6-fluoropyridin-3-yl)methyl)-3-methylpiperazine-1-carboxylate A mixture of 4-(5-chloro-2-fluoropyridin-3-yl)-N,N-bis(4-methoxybenzyl)-6-methyl-1,3,5-triazin-2-amine (8.99 g, 18.73 mmol), potassium (S)-((4-(tert-butoxycarbonyl)-2-methylpiperazin-1-yl)methyl)trifluoroborate (6.00 g, 18.73 mmol), diacetoxypalladium (0.210 g, 0.937 mmol), dicyclohexyl(2',4',6'-triisopropylbiphenyl-2-yl)phosphine (0.893 g, 1.873 mmol), and cesium carbonate (18.31 g, 56.2 mmol) in THF (100 mL) and water (10.0 mL) was heated at 80° C. overnight. After cooling to ambient temperature, the mixture was passed through a short plug of Celite® (diatomaceous earth), washing with EtOAc (3×30 mL). The combined organic filtrates were concentrated and purified by flash chromatography (silica gel, 5% to 50% ethyl acetate/hexanes) to give (S)-tert-butyl 4-((5-(4-(bis(4-methoxybenzyl)amino)-6-methyl-1,3,5-triazin-2-yl)-6-fluoropyridin-3-yl)methyl)-3-methylpiperazine-1-carboxylate (10.39 g, 15.80 mmol, 84% yield) as a pale-yellow foam. m/z (ESI, +ve ion) 658 (M+H)$^+$.

Step 4. (S)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine A stirred solution of (S)-tert-butyl 4-((5-(4-(bis(4-methoxybenzyl)amino)-6-methyl-1,3,5-triazin-2-yl)-6-fluoropyridin-3-yl)methyl)-3-methylpiperazine-1-carboxylate (10.386 g, 15.79 mmol) in DCM (25.0 mL, 389 mmol) was cooled in an ice bath and slowly treated with TFA (25.0 mL, 324 mmol). The resulting mixture was stirred at room temperature for 1 h and then concentrated. The sticky residue was taken up in DCM (100 mL) and cooled to −45° C. TEA (22.0 mL, 158 mmol) was then added via additional funnel, followed by slow addition of methanesulfonyl chloride (6.15 mL, 79 mmol) in DCM (20 mL). The heterogeneous mixture was stirred at −30° C. for 30 min and then quenched with water and $NH_4Cl$(aq) (50 mL each). The organic layer was separated, and the aqueous layer was extracted with DCM (2×50 mL). The combined organic layers were then washed with brine, dried over $Na_2SO_4$, and concentrated to give (S)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (13.6 g crude) as a pale-yellow foam, which was taken directly to the next step without further purification. m/z (ESI, +ve ion) 636 (M+H)$^+$.

Step 5. (S)-4-(2-(5-fluoro-6-methoxypyridin-3-ylamino)-5-((2-methyl-4-(methylsulfonyl)piperazin-1-yl)methyl)pyridin-3-yl)-N,N-bis(4-methoxybenzyl)-6-methyl-1,3,5-triazin-2-amine A mixture of 5-fluoro-6-methoxypyridin-3-amine (3.34 g, 23.53 mmol) and (S)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (13.6 g crude from previous step) in THF (150 mL) at −10° C. was treated dropwise with LiHMDS (1.0 M in THF, Aldrich; 64.2 mL, 64.2 mmol) and the mixture was stirred for 30 min. The reaction was quenched with water and saturated $NH_4Cl$(aq) (100 mL each) and diluted with EtOAc (50 mL). The organic layer was separated, and precipitated solids were collected by filtration. The filtered organic layer was then concentrated to minimal volume, and the precipitated brownish-yellow solid was collected by filtration and washed with a minimal amount of EtOAc. All collected solids were then combined, slurried in isopropanol, collected by filtration, and dried in vacuo to give (S)-4-(2-(5-fluoro-6-methoxypyridin-3-ylamino)-5-((2-methyl-4-(methylsulfonyl)piperazin-1-yl)methyl)pyridin-3-yl)-N,N-bis(4-methoxybenzyl)-6-methyl-1,3,5-triazin-2-amine (9.678 g, 81% over 2 steps) as a yellow solid. m/z (ESI, +ve ion) 758 (M+H)$^-$.

Step 6. (S)-4-(2-(5-fluoro-6-methoxypyridin-3-ylamino)-5-((2-methyl-4-(methylsulfonyl)piperazin-1-yl)methyl)pyridin-3-yl)-6-methyl-1,3,5-triazin-2-amine A solution of (S)-4-(2-(5-fluoro-6-methoxypyridin-3-ylamino)-5-((2-methyl-4-(methylsulfonyl)piperazin-1-yl)methyl)pyridin-3-yl)-N,N-bis(4-methoxybenzyl)-6-methyl-1,3,5-triazin-2-amine (9.6775 g, 12.77 mmol) in TFA (65 mL) was treated dropwise with trifluoromethanesulfonic acid (5.67 mL, 63.8 mmol) and the mixture was stirred for 1 h at 70° C. The volatile material was removed in vacuo, and the residual sticky oil was cooled to 0° C. (external ice bath). About 100 g ice was added, and the mixture was carefully quenched with 1 N NaOH(aq) until slightly basic. The mixture was stirred overnight, and the resulting yellow precipitate was collected by filtration and washed with isopropanol (100 mL). The collected yellow solid was purified by column chromatography (silica gel, 0% to 5% (2.0M ammonia in MeOH)/DCM, followed by repurification on silica gel, DCM to 40% EtOAc/DCM to EtOAc) to provide a yellow solid. This solid was washed with hot toluene several times to give (S)-4-(2-(5-fluoro-6-methoxypyridin-3-ylamino)-5-((2-methyl-4-(methylsulfonyl)piperazin-1-yl)methyl)pyridin-3-yl)-6-methyl-1,3,5-triazin-2-amine (3.808 g, 58%) as a yellow solid. m/z (ESI, +ve ion) 518 (M+H)$^+$; $^1$H NMR (400 MHz, d$_6$-DMSO) δ 11.95 (s, 1H), 8.67-8.75 (m, 1H), 8.41 (s, 1H), 8.38 (d, J=12.91 Hz, 1H), 8.27 (s, 1H), 7.90 (br s, 1H), 7.76 (br s, 1H), 3.93 (s, 3H), 3.91 (br s, 1H), 3.12-3.30 (m, 3H), 2.90 (d, J=14.28 Hz, 1H), 2.85 (s, 3H), 2.65-2.78 (m, 2H), 2.55-2.64 (m, 1H), 2.44 (s, 3H), 2.13-2.28 (m, 1H), 1.16 (d, J=6.06 Hz, 3H).

Example 271

4-(2-(5-fluoro-6-methoxypyridin-3-ylamino)-5-((S)-1-((S)-2-methyl-4-(methylsulfonyl)piperazin-1-yl)ethyl)pyridin-3-yl)-6-methyl-1,3,5-triazin-2-amine

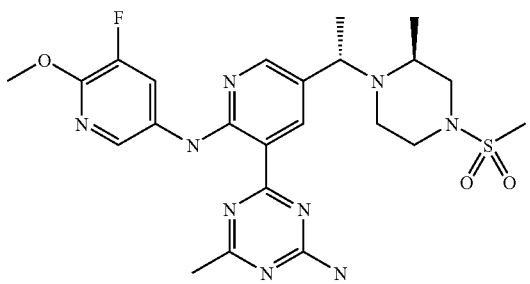

Step 1: 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone A stirred mixture of 4-(5-chloro-2-(5-fluoro-6-methoxypyridin-3-ylamino)pyridin-3-yl)-N,N-bis(4-methoxybenzyl)-6-methyl-1,3,5-triazin-2-amine (Example 313, Step 2; 0.6020 g, 1.000 mmol), X-Phos-Pd(OAc)$_2$ re-milled mix (1:1, 0.070 g, 0.100 mmol), and cesium fluoride (0.129 mL, 3.50 mmol) in 1,4-dioxane (5.00 mL, 58.5 mmol) was treated with tributyl(1-ethoxyvinyl)stannane (0.507 mL, 1.500 mmol) under nitrogen. The mixture was sealed and heated at 110° C. for 16 h. The reaction mixture was then cooled to room temperature and passed through a short plug of Celite® (diatomaceous earth). The filter cake was washed with EtOAc (3×20 mL) and the combined filtrates were concentrated in vacuo. The residue was loaded onto a short column of silica gel, tin byproducts were eluted with DCM, and the desired product was then eluted with 5% MeOH/DCM to give a mixture of desired product and a small amount of dechlorinated product. Chromatographic purification of this mixture (silica gel, 0% to 30% EtOAc/hexanes) gave 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone (0.482 g, 0.791 mmol, 79% yield) as a light yellow solid. m/z (ESI, positive ion) 610 (M+H)$^+$.

Step 2: 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol A stirred solution of 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone (0.1350 g, 0.221 mmol) in THF (5.00 mL) was treated with sodium borohydride (0.042 g, 1.107 mmol) at 0° C. and the resulting mixture was stirred for 10 min before being allowed to warm to room temperature for 1 h. The resulting suspension was quenched with 1 N aqueous NaOH, the organic layer was separated, and the aqueous layer was extracted with ethyl acetate (2×10 mL). The combined organic layers were then washed with brine, dried over Na$_2$SO$_4$, and concentrated to give 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol, which was used directly without further purification.

Step 3: 1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl methanesulfonate A solution of 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol (0.4361 g, 0.713 mmol) in DCM (10.00 mL) at 0° C. was treated with Et$_3$N (0.298 mL, 2.139 mmol) and methanesulfonyl chloride (0.139 mL, 1.782 mmol).

The resulting mixture was stirred at 0° C. for 2 h and then quenched with water (10 mL). The aqueous layer was extracted with DCM (2×5 mL), and the combined organic layers were sequentially washed with 1 N HCl(aq), saturated aqueous NaHCO$_3$, and brine. The combined organic layers were then dried over Na$_2$SO$_4$ and concentrated to give crude 1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl methanesulfonate as a yellow residue which was used directly without further purification.

Step 4: (S)-tert-butyl 4-((S)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate and (S)-tert-butyl 4-((R)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate A stirred solution of crude 1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl methanesulfonate (0.492 g, 0.713 mmol) in CH₃CN (10.00 mL, 191 mmol) was treated with 2,2,6,6-tetramethylpiperidine (0.182 mL, 1.070 mmol) and (S)-tert-butyl 3-methylpiperazine-1-carboxylate (Aldrich, st. Louis, Mo., 0.186 g, 0.927 mmol) and the mixture was heated at reflux overnight. The mixture was then allowed to cool to room temperature, and the resulting suspension was diluted with water and DCM (20 mL each). The organic layer was separated, and the aqueous layer was extracted with DCM (2×20 mL). All organic layers were then combined, washed with brine, dried over Na₂SO₄, and concentrated. The residue was purified by flash column chromatography (silica gel, 0% to 15% ethyl acetate/DCM, followed elution with 5% MeOH/DCM) to give the two separated diasteromers (S)-tert-butyl 4-((S)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (first eluting diastereomer; 101 mg, 17.8%) and (S)-tert-butyl 4-((R)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (second eluting diastereomer; 101 mg, 17.8%). Absolute stereochemistries of the two diastereomers were determined by co-crystal structure of Example 272 (derived from the second eluting distereomer) in complex with PI3Kγ at 2.9 Å resolution. m/z (ESI, +ve ion) 794 (M+H)⁺.

Step 5: 4-(2-(5-fluoro-6-methoxypyridin-3-ylamino)-5-((S)-1-((S)-2-methyl-4-(methylsulfonyl)piperazin-1-yl)ethyl)pyridin-3-yl)-6-methyl-1,3,5-triazin-2-amine A solution of (S)-tert-butyl 4-((S)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (0.101 g, 0.127 mmol) (the first-eluting diastereomer from Example 271, Step 4) in DCM (3.00 mL, 46.6 mmol) was treated with TFA (3.00 mL, 38.9 mmol) and the resulting mixture was stirred at room temperature for 30 min before being concentrated to give a brown oil. This oil was re-dissolved in DCM (3.00 mL) and sequentially treated with Et₃N (0.089 mL, 0.636 mmol) and methanesulfonyl chloride (0.030 mL, 0.382 mmol) (slow addition) at −15° C., and the resulting mixture was stirred for 1 h. The reaction mixture was then quenched with saturated aqueous NaHCO₃ and water. The separated aqueous layer was extracted with DCM (2×) and the combined organic layers were dried over Na₂SO₄ and concentrated. The crude product was treated with TFA (2.00 mL) and heated at 80° C. overnight. The resulting mixture was allowed to cool to room temperature and was then concentrated in vacuo. The crude product was adsorbed onto silica gel and chromatographically purified (silica gel, 0% to 5% MeOH/DCM) to give 4-(2-(5-fluoro-6-methoxypyridin-3-ylamino)-5-((S)-1-((S)-2-methyl-4-(methylsulfonyl)piperazin-1-yl)ethyl)pyridin-3-yl)-6-methyl-1,3,5-triazin-2-amine (29 mg, 0.055 mmol, 42.9% yield) as a yellow solid. m/z (ESI, +ve ion) 532 (M+H)⁺. ¹H NMR (400 MHz, d6-DMSO) δ 11.95 (s, 1H); 8.74 (d, J=2.54 Hz, 1H); 8.27-8.46 (m, 3H); 7.90 (br. s., 1H); 7.77 (br. s., 1H); 3.99-4.09 (m, 1H); 3.93 (s, 3H); 3.20-3.30 (m, 1H); 2.94-3.11 (m, 2H); 2.84 (s, 3H); 2.75-2.84 (m, 2H); 2.45 (s, 3H); 2.40 (dd, 1H); 2.29-2.35 (m, 1H); 1.28 (d, J=6.65 Hz, 3H); 1.15 (d, J=6.26 Hz, 3H).

Example 272

4-(2-(5-fluoro-6-methoxypyridin-3-ylamino)-5-((R)-1-((S)-2-methyl-4-(methylsulfonyl)piperazin-1-yl)ethyl)pyridin-3-yl)-6-methyl-1,3,5-triazin-2-amine

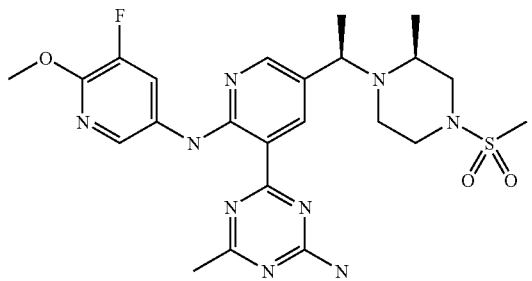

The title compound was prepared from (S)-tert-butyl 4-((R)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (second eluting diastereomer from Example 271, Step 4) in 59% yield as a yellow solid following an analogous procedure to Example 271, Step 5. Absolute stereochemistries at the chiral centers were confirmed by co-crystal structure of Example 272 in complex with PI3Kγ at 2.9 Å resolution. m/z (ESI, +ve ion) 532 (M+H)⁺. ¹H NMR (400 MHz, d₆-DMSO) δ 11.93 (s, 1H); 8.72 (d, J=2.35 Hz, 1H); 8.35-8.45 (m, 2H); 8.32 (d, J=2.35 Hz, 1H); 7.89 (br. s., 1H); 7.76 (br. s., 1H); 3.96-4.08 (m, 1H); 3.93 (s, 3H); 3.07-3.15 (m, 2H); 3.05 (dd, J=10.86, 2.84 Hz, 1H); 2.73-2.90 (m, 5H); 2.51-2.55 (m, 2H); 2.44 (s, 3H); 1.37 (d, J=6.85 Hz, 3H); 1.07 (d, J=6.06 Hz, 3H).

Example 272 was also prepared by the following sequence of reaction conditions:

Step 1. tert-butyl(3S)-4-((1R)-1-(6-fluoro-3-pyridinyl)ethyl)-3-methyl-1-piperazinecarboxylate A mixture of 5-(1-bromoethyl)-2-fluoropyridine (Example 146, Step 2; 8.95 g, 43.9 mmol) and (S)-tert-butyl 3-methylpiperazine-1-carboxylate (9.22 g, 46.1 mmol) (CNH Technologies Inc.) in acetonitrile (200 mL) was treated with K₂CO₃ (7.27 g, 52.6 mmol) and KI (1.456 g, 8.77 mmol). The mixture was placed into a pre-heated (70° C.) oil bath and allowed to stir under an inert atmosphere overnight. The heating bath was then removed and the reaction mixture was allowed to cool to ambient temperature. The reaction mixture was diluted with chloroform (200 mL) and water (300 mL). The organic layer was separated, and the aqueous layer was extracted with chloroform (1×100 mL). The combined organic layers were then washed with a saturated brine solution, dried over Na₂SO₄, filtered, and concentrated. The crude material was adsorbed onto silica gel and purified by column chromatography (120 g silica gel, 0% to 40% EtOAc/hexanes) to provide tert-butyl(3S)-4-((1R)-1-(6-fluoro-3-pyridinyl)ethyl)-3-methyl-1-piperazinecarboxylate (5.02 g, 15.52 mmol, 35.4% yield) (lower R_f diastereomer) as a viscous yellow-orange oil. m/z (ESI, +ve) 324.1 (M+H)⁺. ¹H NMR (400 MHz, CDCl₃) δ 8.09-8.14 (m, 1H); 7.75 (td, J=8.0, 2.2 Hz, 1H); 6.90 (dd, J=8.5, 2.8 Hz, 1H); 3.94 (br. s., 1H, =); 3.55

(br. s., 1H); 3.37 (br. s., 2H); 3.20 (br. s., 1H); 2.71 (ddd, J=11.3, 7.6, 3.5 Hz, 1H); 2.43 (dd, J=9.6, 5.5 Hz, 2H); 1.43 (s, 9H); 1.38 (d, J=6.8 Hz, 3H); 0.99 (d, J=6.3 Hz, 3H).

Step 2. (5-((1R)-1-((2S)-4-(tert-butoxycarbonyl)-2-methyl-1-piperazinyl)ethyl)-2-fluoro-3-pyridinyl) boronic acid n-Butyllithium (2.5 M in hexanes; 7.23 mL, 18.07 mmol) was added dropwise to a solution of diisopropylamine (2.55 mL, 18.07 mmol) in 8 mL of THF at −40° C. The mixture was stirred for 1 h at −40° C. This solution was cannulated into a 3-necked 250-mL round-bottomed flask that contained a solution of tert-butyl(3S)-4-((1R)-1-(6-fluoro-3-pyridinyl) ethyl)-3-methyl-1-piperazinecarboxylate (4.87 g, 15.06 mmol) in 60 mL of THF at −78° C. After 15 min at −78° C., triisopropyl borate (Aldrich; 6.92 mL, 30.1 mmol) was added, and the resulting mixture was stirred at −78° C. for 15 min and then allowed to warm to ambient temperature. The reaction mixture was subsequently treated with 1 M NaOH (80 mL) and allowed to stir for 20 min. The aqueous layer was separated and the organic layer was discarded. The aqueous layer was treated with 10% HCl (aq) until a pH of about 5 to 6 was achieved. The resulting mixture was diluted with EtOAc (20 mL) and the mixture was extracted with 8:2 EtOAc/MeOH (200 mL). The combined organic extracts were dried over $Na_2SO_4$, filtered and concentrated to give (5-((1R)-1-((2S)-4-(tert-butoxycarbonyl)-2-methyl-1-piperazinyl)ethyl)-2-fluoro-3-pyridinyl)boronic acid (5.01 g, 13.64 mmol, 91% yield) as an off-white solid. m/z (ESI, +ve) 368.1 (M+H)⁻.

Step 3. tert-butyl(3S)-4-((1R)-1-(5-(4-(bis(4-methoxybenzyl)amino)-6-methyl-1,3,5-triazin-2-yl)-6-fluoro-3-pyridinyl)ethyl)-3-methyl-1-piperazinecarboxylate A 1-L round-bottomed flask was charged with (5-((1R)-1-((2S)-4-(tert-butoxycarbonyl)-2-methyl-1-piperazinyl) ethyl)-2-fluoro-3-pyridinyl)boronic acid (11.90 g, 32.4 mmol), 4-chloro-N,N-bis(4-methoxybenzyl)-6-methyl-1,3,5-triazin-2-amine (Example 51; 13.72 g, 35.6 mmol), KOAc (10.18 g, 104 mmol), dioxane (180 mL), and water (36.0 mL). Nitrogen gas was bubbled through the mixture for 10 min. Bis-(di-tert-butyl(4-dimethylaminophenyl)phosphine) dichloropalladium(II) (2.295 g, 3.24 mmol) was added and a reflux condensor was attached to the flask. The mixture was heated at 100° C. under nitrogen overnight (17 h). After cooling to ambient temperature, water was added and the mixture was extracted with EtOAc (3×200 mL). The combined organic extracts were dried over anhydrous $Na_2SO_4$, filtered, and concentrated. The crude material was adsorbed onto silica gel and purified by column chromatography (330 g of silica gel, 5% to 75% EtOAc/hexanes) to give tert-butyl (3S)-4-((1R)-1-(5-(4-(bis(4-methoxybenzyl)amino)-6-methyl-1,3,5-triazin-2-yl)-6-fluoro-3-pyridinyl)ethyl)-3-methyl-1-piperazinecarboxylate (13.35 g, 19.87 mmol, 61.3% yield) as a light-yellow foam. m/z (ESI, +ve) 672.2 (M+H)⁺. ¹H NMR (400 MHz, CDCl₃) δ 8.39-8.46 (m, 1H) 8.19-8.24 (m, 1H) 7.19-7.25 (m, 4H) 6.83-6.90 (m, 4H) 4.82 (d, J=11.93 Hz, 4H) 3.97-4.07 (m, 1H) 3.81 (s, 3H) 3.80 (br s, 1H) 3.79 (s, 3H) 3.31-3.44 (m, 2H) 3.08-3.18 (m, 1H) 2.69-2.77 (m, 1H) 2.55 (s, 3H) 2.42-2.48 (m, 2H) 1.39-1.46 (m, 12H) 1.00 (d, J=6.26 Hz, 3H).

Step 4. 4-(2-fluoro-5-((1R)-1-((2S)-2-methyl-4-(methylsulfonyl)-1-piperazinyl)ethyl)-3-pyridinyl)-N,N-bis(4-methoxybenzyl)-6-methyl-1,3,5-triazin-2-amine A solution of tert-butyl(3S)-4-((1R)-1-(5-(4-(bis(4-methoxybenzyl)amino)-6-methyl-1,3,5-triazin-2-yl)-6-fluoro-3-pyridinyl)ethyl)-3-methyl-1-piperazinecarboxylate (9.17 g, 13.65 mmol) in $CH_2Cl_2$ (136 mL) at 0° C. was treated with TFA (52.6 mL, 682 mmol) (added over 10 min). The ice bath was then removed and the reaction mixture stirred at ambient temperature for 90 min. The solvent was removed in vacuo with a heating bath at 25° C., providing a viscous oil, which was cooled to 0° C. and diluted with 150 mL of $CH_2Cl_2$. Ice was added to the resulting solution, followed by solid $NaHCO_3$ with rapid stirring until effervescence ceased. The resulting mixture was diluted with water (100 mL) and $CH_2Cl_2$ (150 mL). The organic layer was separated, and the aqueous layer was extracted with $CH_2Cl_2$ (2×). All organic layers were then combined, dried over sodium sulfate, and filtered through a 0.45 μm ZAPCAP filter (Whatman, Schleicher & Schuell). The filtrate was then concentrated to about 150 mL and cooled to 0° C. $NEt_3$ (7.61 mL, 54.6 mmol) was added, followed by methanesulfonyl chloride (2.11 mL, 27.3 mmol). After 1 h at 0° C., saturated aqueous $NaHCO_3$ was added and the resulting mixture was extracted with $CH_2Cl_2$ (3×). The combined organic extracts were dried over $Na_2SO_4$, filtered, and concentrated. The crude material was loaded onto a silica gel column (330 g) as a solution in $CH_2Cl_2$ and purified by column chromatography (20% to 100% (10% MeOH/EtOAc)/hexanes), which gave 4-(2-fluoro-5-((1R)-1-((2S)-2-methyl-4-(methylsulfonyl)-1-piperazinyl)ethyl)-3-pyridinyl)-N,N-bis(4-methoxybenzyl)-6-methyl-1,3,5-triazin-2-amine (7.45 g, 11.47 mmol, 84% yield) as an off-white foam. m/z (ESI, +ve) 650.2 (M+H)⁺. ¹H NMR (400 MHz, CDCl₃) δ 8.41-8.47 (m, 1H); 8.21-8.25 (m, 1H); 7.20-7.25 (m, 4H); 6.83-6.89 (m, 4H); 4.81 (d, J=8.61 Hz, 4H); 4.02 (q, J=6.78 Hz, 1H); 3.81 (s, 3H); 3.79 (s, 3H); 3.28-3.35 (m, 1H); 3.12-3.20 (m, 1H); 3.05-3.10 (m, 1H); 2.92-2.99 (m, 1H); 2.87 (ddd, J=11.44, 7.92, 3.33 Hz, 1H); 2.70 (s, 3H) 2.60-2.68 (m, 2H) 2.55 (s, 3H) 1.43 (d, J=6.85 Hz, 3H) 1.08 (d, J=6.46 Hz, 3H).

Step 5. 4-(2-((5-fluoro-6-methoxy-3-pyridinyl) amino)-5-((1R)-1-((2S)-2-methyl-4-(methylsulfonyl)-1-piperazinyl)ethyl)-3-pyridinyl)-N,N-bis(4-methoxybenzyl)-6-methyl-1,3,5-triazin-2-amine Lithium bis(trimethylsilyl)amide (1.0 M solution in THF, Aldrich; 9.23 mL, 9.23 mmol) was added dropwise over 5 min to a mixture of 4-(2-fluoro-5-((1R)-1-((2S)-2-methyl-4-(methylsulfonyl)-1-piperazinyl)ethyl)-3-pyridinyl)-N,N-bis (4-methoxybenzyl)-6-methyl-1,3,5-triazin-2-amine (2.000 g, 3.08 mmol) and 5-fluoro-6-methoxypyridin-3-amine (Anichem, Inc., 0.656 g, 4.62 mmol) in THF (30.8 mL) at 0° C., and the resulting reddish-brown solution was stirred at 0° C. for 1 h. Saturated $NH_4Cl$ (aq., 50 mL) was added and the reaction mixture was partitioned between EtOAc (100 mL) and half-saturated $NH_4Cl$ (aq., 50 mL). The organic layer was separated, and the aqueous layer was extracted with EtOAc (2×100 mL). The combined organic extracts were washed with brine, dried over $Na_2SO_4$, filtered, and concentrated. The crude material was adsorbed onto silica gel and purified by column chromatography (80 g of silica gel, 0% to 100% EtOAc/hexanes) gave 4-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-N,N-bis(4-methoxybenzyl)-6-methyl-1,3,5-triazin-2-amine (1.90 g, 2.461 mmol, 80% yield) as a yellow solid. m/z (ESI, +ve) 771.8 (M+H)⁺. ¹H NMR (400 MHz, CDCl₃) δ 11.89 (s, 1H); 8.69-8.73 (m, 1H); 8.20-8.24 (m, 1H); 8.08 (dt, J=12.37, 1.05 Hz, 1H); 7.95-7.98 (m, 1H); 7.18-7.24 (m, 4H); 6.82-6.90 (m, 4H); 4.78-4.88 (m, 4H); 4.01 (s, 3H); 3.97-4.01 (m, 1H); 3.81 (s, 3H); 3.78 (s, 3H); 3.18-3.20 (m, 1H); 3.08-3.15 (m, 2H); 2.75-2.87 (m, 2H); 2.67 (s, 3H); 2.56-2.63 (m, 1H); 2.59 (s, 3H); 2.43-2.51 (m, 1H); 1.40 (d, J=6.85 Hz, 3H); 1.07 (d, J=6.26 Hz, 3H).

Step 6. 4-(2-((5-fluoro-6-methoxy-3-pyridinyl) amino)-5-((1R)-1-((2S)-2-methyl-4-(methylsulfonyl)-1-piperazinyl)ethyl)-3-pyridinyl)-6-methyl-1,3, 5-triazin-2-amine A solution of 4-(2-((5-fluoro-6-methoxy-3-pyridinyl) amino)-5-((1R)-1-((2S)-2-methyl-4-(methylsulfonyl)-1-piperazinyl)ethyl)-3-pyridinyl)-N,N-bis(4-methoxybenzyl)-6-methyl-1,3,5-triazin-2-amine (4.76 g, 6.17 mmol) in TFA (30.8 mL) was treated with trifluoromethanesulfonic acid (3.12 mL, 35.1 mmol) via a glass pipette. The reaction mixture was stirred at 70° C. for 2 h. The mixture was then allowed to cool to ambient temperature and was concentrated. The brown residue was cooled in an ice bath, and ice followed by 1 M NaOH (aq., 60 mL) were added to bring the pH of the resulting mixture to about 9. The resulting yellow-brown slurry was extracted with $CH_2Cl_2$ (3×75 mL), and the combined organic extracts were dried over $Na_2SO_4$ and concentrated. The crude product was adsorbed onto silica gel and purified by column chromatography (330 g of silica gel, 5% to 100% (10% MeOH in EtOAc)/hexanes) to give 2.87 g of a dark-yellow solid. This solid was suspended in 25 mL of EtOAc and stirred overnight at ambient temperature. The yellow solid was filtered and washed with EtOAc and then dried under high vaccum while heated to 50° C. to give 4-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-6-methyl-1,3,5-triazin-2-amine (2.15 g, 4.19 mmol, 68% yield) as a bright-yellow solid. m/z (ESI, +ve) 532.0 (M+H)$^+$. $^1$H NMR (400 MHz, d$_6$-DMSO) δ 11.93 (s, 1H) 8.72 (dd, J=2.05, 0.49 Hz, 1H) 8.36-8.43 (m, 2H) 8.32 (dd, J=1.96, 0.59 Hz, 1H) 7.88 (br. s, 1H) 7.74 (br. s, 1H) 3.96-4.01 (m, 1H) 3.94 (s, 3H) 3.12 (t, J=5.09 Hz, 2H) 3.04 (d, J=0.39 Hz, 1H) 2.77-2.89 (m, 5H) 2.45 (s, 3H) 1.37 (d, J=6.85 Hz, 3H) 1.07 (d, J=6.26 Hz, 3H).

Example 273

2-(5-(4-amino-6-methyl-1,3,5-triazin-2-yl)-6-(5-fluoro-6-methoxypyridin-3-ylamino)pyridin-3-yl)propan-2-ol

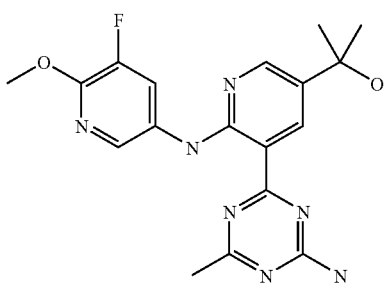 [SMILES: COc1ncc(Nc2ncc(C(C)(C)O)cc2-c2nc(C)nc(N)n2)cc1F]

Step 1: 1-(5-(4-amino-6-methyl-1,3,5-triazin-2-yl)-6-(5-fluoro-6-methoxypyridin-3-ylamino)pyridin-3-yl) ethanone A solution of 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone (Example 271; 332 mg, 0.54 mmol) in TFA (3 mL) was treated with TfOH (0.1 mL). The solution was heated at 80° C. in an oil bath for 4 h, allowed to cool to room temperature, and concentrated. The dark residue was treated with a few ice cubes followed by sat. NaHCO$_3$ while rapidly stirring. The precipitated yellow solid was collected by filtration and rinsed with water (5 mL). The yellow solid was purified by flash chromatography eluting with 1-15% MeOH in DCM to give 1-(5-(4-amino-6-methyl-1,3, 5-triazin-2-yl)-6-(5-fluoro-6-methoxypyridin-3-ylamino) pyridin-3-yl)ethanone (140 mg, 69%) as a bright yellow crystalline solid. m/z (ESI, +ve ion) 460 (M+H)$^+$. $^1$H NMR (400 MHz, d6-DMSO) δ 12.38 (br., 1H); 9.26 (d, J=2.2 Hz, 1H); 8.96 (d, J=2.2 Hz, 1H); 8.42 (s, 1H); 8.35 (dd, J=12.3, 1.6 Hz, 1H); 8.00 (s, 1H); 7.83 (s, 1H); 3.96 (s, 3H); 2.57 (s, 3H); 2.46 (s, 3H).

Step 2: 2-(5-(4-amino-6-methyl-1,3,5-triazin-2-yl)-6-(5-fluoro-6-methoxypyridin-3-ylamino)pyridin-3-yl) propan-2-ol A suspension of 1-(5-(4-amino-6-methyl-1,3,5-triazin-2-yl)-6-(5-fluoro-6-methoxypyridin-3-ylamino)pyridin-3-yl) ethanone (140 mg, 0.38 mmol) in THF (2 mL) at 0° C. was treated with methylmagnesium bromide (1.9 mL of 1.4 M in toluene/THF=75/25, 2.65 mmol). The reaction mixture was stirred at 0° C. for 5 min followed by RT for 30 min and then quenched with sat. NH$_4$Cl solution and extracted with EtOAc. The organic layer was concentrated and purified on a silica gel column eluting with 5-10% MeOH in DCM to give 2-(5-(4-amino-6-methyl-1,3,5-triazin-2-yl)-6-(5-fluoro-6-methoxypyridin-3-ylamino)pyridin-3-yl)propan-2-ol (50 mg, 34%) as a yellow crystalline solid. m/z (ESI, +ve ion) 386.0 (M+H)$^+$. $^1$H NMR (400 MHz, d6-DMSO) δ 11.91 (br., 1H); 8.95 (d, J=2.6 Hz, 1H); 8.43-8.37 (m, 3H); 7.89 (s, 1H); 7.73 (s, 1H); 5.15 (s, 1H); 3.93 (s, 3H); 2.45 (s, 3H); 1.47 (s, 6H).

Example 274

2-fluoro-5-(1-morpholinoethyl)pyridin-3-ylboronic acid

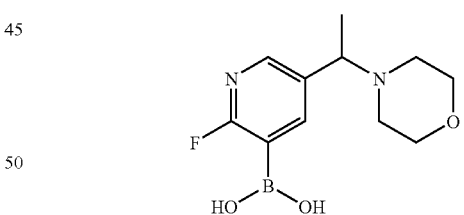

Step 1: 1-(6-fluoropyridin-3-yl)ethanol

A solution of 6-fluoronicotinaldehyde (1.12 g, 8.95 mmol, Frontier Scientific, Cat: #F1911, Batch: #RP09-2154) in THF (11.0 mL) was treated dropwise with methylmagnesium bromide (1.4 M solution in PhMe/THF (75:25), 7.03 mL, 9.85 mmol, Aldrich) and allowed to stir at RT for 20 min. The reaction mixture was quenched by the addition of a saturated solution of NH$_4$Cl (aq.) and allowed to stir for 10 min. The reaction mixture was extracted with EtOAc (2×60 mL), dried over MgSO$_4$, filtered and concentrated. Purification on the ISCO (12 g column, 25-70% EtOAc in hexanes) gave the title compound (1.05 g, 83% yield) as a pale yellow viscous oil. $^1$H NMR (400 MHz, CDCl$_3$) δ 8.20 (d, J=2.0 Hz, 1H); 7.85 (td, J=8.1, 2.5 Hz, 1H); 6.93 (dd, J=8.4, 2.9 Hz, 1H); 4.98 (qd, J=6.5, 3.9 Hz, 1H); 1.53 (d, J=6.5 Hz, 3H). m/z (ESI, +ve) 142.1 (M+H)$^-$.

Step 2: 4-(1-(6-fluoropyridin-3-yl)ethyl)morpholine

A solution of 1-(6-fluoropyridin-3-yl)ethanol (1.05 g, 7.44 mmol) in DCM (20.0 mL) was cooled in an ice bath and treated dropwise with methanesulfonyl chloride (0.863 mL, 11.16 mmol, Aldrich) and Et$_3$N (2.074 mL, 14.88 mmol, Aldrich, Cat: #471283-100ML, Batch: #29296KJ) at 0° C. and stirred for 30 min. The resulting light yellow suspension was quenched with water and extracted with DCM (2×25 mL), dried over MgSO$_4$, filtered and concentrated to give the mesylated alcohol intermediate as a light yellow viscous oil. This was treated with DCM (20.0 mL), THF (3 mL), morpholine (2.59 mL, 29.8 mmol, Aldrich) and Et$_3$N (4.0 mL) and allowed to stir at RT for 24 h. The reaction mixture was treated with water and extracted with DCM (2×50 mL), dried over MgSO$_4$, filtered and concentrated. Purification on the ISCO (40 g column, 5-100% EtOAc in hexanes) gave the title compound (1.14 g, 73.0% yield) as a viscous yellow oil. $^1$H NMR (400 MHz, CDCl$_3$) δ 8.12 (d, J=2.2 Hz, 1H); 7.79 (td, J=8.1, 2.3 Hz, 1H); 6.90 (dd, J=8.4, 2.9 Hz, 1H); 3.63-3.74 (m, 4H); 3.40 (q, J=6.7 Hz, 1H); 2.49 (d, J=4.9 Hz, 2H); 2.29-2.39 (m, 2H); 1.35 (d, J=6.7 Hz, 3H). m/z (ESI, +ve) 211.1 (M+H)$^+$.

Step 3: 2-fluoro-5-(1-morpholinoethyl)pyridin-3-ylboronic acid

A solution of LDA was prepared by addition of n-butyl-lithium (1.6 M in hexanes, 9.60 mL, 15.35 mmol) to a solution of diisopropylamine (2.152 mL, 15.35 mmol) in THF (20 mL) at −40° C. The LDA solution was cooled to −78° C. and a solution of 4-(1-(6-fluoropyridin-3-yl)ethyl)morpholine (2.69 g, 12.79 mmol) in THF (15 mL) was added slowly over 20 min. The deep-red mixture was stirred at −78° C. for 1.5 h. A solution of triisopropyl borate (4.41 mL, 19.19 mmol) in THF (10 mL) was added slowly. The resulting mixture was stirred at −78° C. for 30 min and then the cooling bath was removed. After the reaction mixture had warmed up to room temperature, the tan mixture was quenched with 1 N NaOH (aq) (15 mL). The separated aqueous layer was removed and the flask was rinsed with 1 N NaOH(aq) (2×20 mL) and the organic layer was extracted with 1 N NaOH (2×10 mL). The aqueous layer was collected and carefully acidified with 5 N HCl until acidic (pH 5 to about 6). The aqueous layer was frozen and the water was removed by lyophilization. The mixture was diluted with 1:1 MeOH/DCM and placed into a sonicator for 5 min. The mixture was filtered through a fine-fritted funnel The filtrate was concentrated in vacuo to give 2-fluoro-5-(1-morpholinoethyl)pyridin-3-ylboronic acid (3.120 g, 12.28 mmol, 96% yield) as a yellow solid. $^1$H NMR (400 MHz, d4-MeOH) δ 8.00 (dd, J=8.22, 2.54 Hz, 1H); 7.88 (d, J=2.35 Hz, 1H); 3.68 (t, J=4.69 Hz, 4H); 3.40-3.54 (m, 1H); 2.56 (d, J=10.76 Hz, 2H); 2.35-2.50 (m, 2H); 1.41 (t, J=6.65 Hz, 3H). m/z (ESI, +ve) 255.1 (M+H)$^+$.

Examples 275 and 276

6-(2-((5-fluoro-6-methoxy-3-pyridinyl)amino)-5-((1S)-1-(4-morpholinyl)ethyl)-3-pyridinyl)-2-methyl-4-pyrimidinamine and 6-(2-((5-fluoro-6-methoxy-3-pyridinyl)amino)-5-((1R)-1-(4-morpholinyl)ethyl)-3-pyridinyl)-2-methyl-4-pyrimidinamine

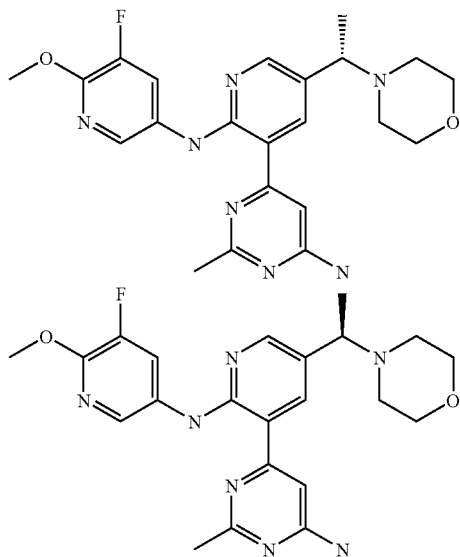

Step 1: 6-(2-fluoro-5-(1-(4-morpholinyl)ethyl)-3-pyridinyl)-N,N-bis(4-methoxybenzyl)-2-methyl-4-pyrimidinamine A mixture of (2-fluoro-5-(1-(4-morpholinyl)ethyl)-3-pyridinyl)boronic acid (1.100 g, 4.33 mmol), 6-chloro-N,N-bis(4-methoxybenzyl)-2-methyl-4-pyrimidinamine (Example 117; 1.828 g, 4.76 mmol), bis(di-tert-butyl(4-dimethylaminophenyl)phosphine)dichloropalladium(II) (0.245 g, 0.346 mmol) and potassium acetate (1.275 g, 12.99 mmol) in dioxane (3.2 mL) and water (0.533 mL) was stirred and heated in an Initiator microwave reactor (Personal Chemistry, Biotage AB, Inc., Upssala, Sweden) at 120° C. for 15 min. The reaction mixture was diluted with EtOAc and water. The layers were separated and the aqueous layer was extracted with EtOAc (2×). The combined organic layers were dried over anhydrous Na$_2$SO$_4$, filtered and concentrated. The crude material was adsorbed onto silica gel and purified by chromatography through a Redi-Sep pre-packed silica gel column (120 g) eluting with a gradient of 0% to 100% EtOAc in hexane to give 6-(2-fluoro-5-(1-(4-morpholinyl)ethyl)-3-pyridinyl)-N,N-bis(4-methoxybenzyl)-2-methyl-4-pyrimidinamine (0.570 g, 1.022 mmol, 23.61% yield) as a light-yellow oil. $^1$H NMR (400 MHz, CDCl$_3$) δ 8.38-8.45 (m, 1H); 8.14-8.19 (m, 1H); 7.17 (d, J=8.61 Hz, 4H); 6.82-6.88 (m, 5H); 4.75 (br s, 4H); 3.79 (s, 6H); 3.69 (ddd, J=5.62, 3.77, 1.76 Hz, 4H); 3.48 (q, J=6.72 Hz, 1H); 2.62 (s, 3H); 2.46-2.56 (m, 2H); 2.33-2.42 (m, 2H); 1.39 (d, J=6.65 Hz, 3H). m/z (ESI, +ve) 558.2 (M+H)$^+$.

Step 2: 6-(2-((5-fluoro-6-methoxy-3-pyridinyl) amino)-5-(1-(4-morpholinyl)ethyl)-3-pyridinyl)-N, N-bis(4-methoxybenzyl)-2-methyl-4-pyrimidinamine Lithium bis(trimethylsilyl)amide (1.0 M solution in hexane, 0.592 mL, 0.592 mmol) was added to a solution of 6-(2-fluoro-5-(1-(4-morpholinyl)ethyl)-3-pyridinyl)-N,N-bis(4-methoxybenzyl)-2-methyl-4-pyrimidinamine (0.110 g, 0.197 mmol) and 5-fluoro-6-methoxypyridin-3-amine (0.042 g, 0.296 mmol, Anichem, North Brunswick, N.J.) in THF (1.5 mL) at −10° C. After 1 h, more lithium bis(trimethylsilyl)amide (1.0 M solution in hexane, 0.592 mL, 0.592 mmol) and 5-fluoro-6-methoxypyridin-3-amine (0.042 g, 0.296 mmol) were added. After a further 1 h, saturated $NH_4Cl$ (aq.) was added. The mixture was extracted with EtOAc (3×). The combined organic layers were dried over anhydrous $Na_2SO_4$, filtered and concentrated. The crude material was adsorbed onto a plug of silica gel and purified by chromatography through a Redi-Sep pre-packed silica gel column (12 g), eluting with a gradient of 0% to 100% EtOAc in hexane to give 6-(2-((5-fluoro-6-methoxy-3-pyridinyl)amino)-5-(1-(4-morpholinyl)ethyl)-3-pyridinyl)-N,N-bis(4-methoxybenzyl)-2-methyl-4-pyrimidinamine (0.104 g, 0.153 mmol, 78% yield) as a brown oil. $^1$H NMR (400 MHz, $CDCl_3$) δ 11.92 (s, 1H); 8.26 (dd, J=12.72, 2.35 Hz, 1H); 8.11 (d, J=2.15 Hz, 1H); 8.02 (d, J=2.35 Hz, 1H); 7.56-7.61 (m, 1H); 7.18 (dd, J=8.61, 0.98 Hz, 4H); 6.82-6.91 (m, 4H); 6.53 (s, 1H); 4.80 (br s, 4H); 4.01 (s, 3H); 3.79 (s, 6H); 3.62 (t, J=4.69 Hz, 4H); 3.30 (q, J=6.65 Hz, 1H); 2.66 (s, 3H); 2.39-2.47 (m, 2H); 2.30-2.37 (m, 2H); 1.31 (d, J=6.85 Hz, 3H). m/z (ESI, +ve) 680.2 $(M+H)^+$.

Step 3: 6-(2-((5-fluoro-6-methoxy-3-pyridinyl) amino)-5-((1S)-1-(4-morpholinyl)ethyl)-3-pyridinyl)-2-methyl-4-pyrimidinamine and 6-(2-((5-fluoro-6-methoxy-3-pyridinyl)amino)-5-(1R)-1-(4-morpholinyl)ethyl)-3-pyridinyl)-2-methyl-4-pyrimidinamine A solution of 6-(2-((5-fluoro-6-methoxy-3-pyridinyl)amino)-5-(1-(4-morpholinyl)ethyl)-3-pyridinyl)-N,N-bis(4-methoxybenzyl)-2-methyl-4-pyrimidinamine (0.272 g, 0.400 mmol) in TFA (3 mL) was treated with a few drops of triflic acid and heated at 80° C. for 3 h. After cooling to RT, the reaction mixture was concentrated. A few ice cubes were added and saturated $NaHCO_3$ (aq.) was added until pH of about 7. The aqueous layer was extracted with $CH_2Cl_2$/n-BuOH (3×). The combined organic layers were dried over anhydrous $Na_2SO_4$, filtered and concentrated. The residue was adsorbed onto a plug of silica gel and purified by chromatography through a Redi-Sep pre-packed silica gel column (12 g), eluting with a gradient of 0% to 30% MeOH in $CH_2Cl_2$ to give 120 mg of 6-(2-((5-fluoro-6-methoxy-3-pyridinyl) amino)-5-(1-(4-morpholinyl)ethyl)-3-pyridinyl)-2-methyl-4-pyrimidinamine as a mixture of enantiomers as a yellow solid. $^1$H NMR (400 MHz, d6-DMSO) δ 12.21 (s, 1H); 8.33 (dd, J=13.01, 2.25 Hz, 1H); 8.12-8.21 (m, 2H); 7.96 (d, J=2.15 Hz, 1H); 7.04 (s, 2H); 6.79 (s, 1H); 3.92 (s, 3H); 3.57 (t, J=4.79 Hz, 4H); 3.43 (q, J=6.65 Hz, 1H); 2.51 (s, 3H); 2.38-2.47 (m, 2H); 2.27-2.36 (m, 2H); 1.34 (d, J=6.65 Hz, 3H). m/z (ESI, +ve) 440.1 $(M+H)^+$.

The enantiomers were separated by SFC chromatography using a Chiral pak AD-H column (250×21 mm, 5 μm), 40° C. column temperature, eluting with a mobile phase of 80/20 liquid $CO_2$/EtOH (0.2% DEA) at a flow rate of 70 mL/min and an outlet pressure of 100 bar. These conditions provided each enantiomer in >99% ee (based on peak area at 215 nm) using the following SFC conditions: Chiral pak AD-H column (150×4.6 mm, 5 μm), 40° C. column temperature, eluting with a mobile phase of 80/20 liquid $CO_2$/EtOH (0.2% DEA) at a flow rate of 4.0 mL/min and a outlet pressure of 100 bar. Absolute stereochemistries of the two enantiomers were inferred by analogy to Example 146.

Example 277

4-(5-(2-aminopropan-2-yl)-2-(6-methoxypyridin-3-ylamino)pyridin-3-yl)-6-methyl-1,3,5-triazin-2-amine

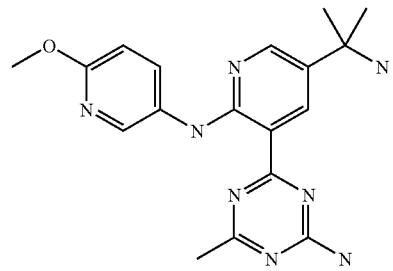 [SMILES: COc1ccc(Nc2ncc(C(C)(C)N)cc2-c2nc(C)nc(N)n2)cn1]

Step 1: N,N-bis(4-methoxybenzyl)-4-(2-(6-methoxy-pyridin-3-ylamino)-5-(prop-1-en-2-yl)pyridin-3-yl)-6-methyl-1,3,5-triazin-2-amine A mixture of isopropenylboronic acid pinacol ester (0.119 mL, 0.633 mmol, Aldrich, St. Louis, Mo.), potassium carbonate (0.175 g, 1.267 mmol), $(Amphos)_2PdCl_2$ (0.022 g, 0.032 mmol) and 4-(5-chloro-2-(6-methoxypyridin-3-ylamino)pyridin-3-yl)-N,N-bis(4-methoxybenzyl)-6-methyl-1,3,5-triazin-2-amine (Example 155, 0.185 g, 0.317 mmol) in 4:1 dioxane/water (2.5 mL) was heated in a sealed tube for 24 h. The reaction was cooled and partitioned between water and DCM. The aqueous layer was extracted with DCM (3×), and the combined organic layers were dried over anhydrous sodium sulfate, filtered, and concentrated in vacuo. The crude material was purified by silica gel chromatography (25 g column) using 0-30% EtOAc/hexane. The product-containing fractions were concentrated to give N,N-bis(4-methoxybenzyl)-4-(2-(6-methoxypyridin-3-ylamino)-5-(prop-1-en-2-yl)pyridin-3-yl)-6-methyl-1,3,5-triazin-2-amine (0.171 g, 0.290 mmol, 92% yield) as an orange solid. m/z (ESI, +ve ion) 590 $(M+H)^+$. $^1$H NMR (400 MHz, $CDCl_3$) δ 11.71 (br. s., 1H); 8.94 (s, 1H); 8.44 (d, J=2.5 Hz, 1H); 8.27 (d, J=2.3 Hz, 1H); 7.91 (br. s., 1H); 7.22 range (m, 4H); 6.86 range (m, 4H); 6.73 (d, J=9.0 Hz, 1H); 5.33 (s, 1H); 5.01 (s, 1H); 4.89 (s, 2H); 4.82 (s, 2H); 3.94 (s, 3H); 3.82 (s, 3H); 3.79 (s, 3H); 2.59 (s, 3H); 2.13 (s, 3H).

Step 2: 4-(5-(2-azidopropan-2-yl)-2-(6-methoxypyridin-3-ylamino)pyridin-3-yl)-N,N-bis(4-methoxybenzyl)-6-methyl-1,3,5-triazin-2-amine A slurry of sodium azide (0.075 g, 1.160 mmol) and N,N-bis(4-methoxybenzyl)-4-(2-(6-methoxypyridin-3-ylamino)-5-(prop-1-en-2-yl)pyridin-3-yl)-6-methyl-1,3,5-triazin-2-amine (0.171 g, 0.290 mmol) in $CHCl_3$ (1 mL) at −15° C. was treated with a solution of trifluoroacetic acid (0.223 mL, 2.90 mmol) in $CHCl_3$ (1 mL) added via syringe over 10 min. The cooling reaction mixture was allowed to gradually warm to room temperature and stirred overnight. The reaction was sealed and heated at 60° C. After 2 h, the reaction was poured onto ice and basified with 10 N NaOH. The reaction was partitioned between water and DCM. The aqueous layer was extracted with DCM (3×), and the combined organic layers were dried over anhydrous sodium sulfate, filtered, and concentrated in vacuo to give 4-(5-(2-azidopropan-2-yl)-2-(6-methoxypyridin-3-ylamino)pyridin-3-yl)-N,N-bis(4-methoxybenzyl)-6-methyl-1,3,5-triazin-2-amine (0.184 g, 0.291 mmol, 100% yield). m/z (ESI, +ve ion) 633 (M+H)+. 1H NMR (400 MHz, CDCl3) δ 11.67 (br. s., 1H); 8.90 (d, J=2.7 Hz, 1H); 8.38 (d, J=2.5 Hz, 1H); 8.26 (d, J=2.5 Hz, 1H); 7.91 (dd, J=8.8, 2.7 Hz, 1H); 7.18-7.26 (m, 4H); 6.81-6.94 (m, 4H); 6.73 (d, J=8.8 Hz, 1H); 4.90 (s, 2H); 4.81 (s, 2H); 3.94 (s, 3H); 3.82 (s, 3H); 3.78 (s, 3H); 2.59 (s, 3H); 1.64 (s, 6H).

Step 3: 4-(5-(2-aminopropan-2-yl)-2-(6-methoxypyridin-3-ylamino)pyridin-3-yl)-N,N-bis(4-methoxybenzyl)-6-methyl-1,3,5-triazin-2-amine 4-(5-(2-Azidopropan-2-yl)-2-(6-methoxypyridin-3-ylamino)pyridin-3-yl)-N,N-bis(4-methoxybenzyl)-6-methyl-1,3,5-triazin-2-amine (0.184 g, 0.291 mmol) and 10% palladium on carbon (0.186 g, 0.174 mmol) were combined in a flask and flushed with nitrogen. THF (5 mL) was added and the reaction was stirred under a H2 atmosphere for 1.5 h. The reaction was filtered through Celite® (diatomaceous earth) rinsing with DCM, and the filtrate was concentrated in vacuo to give 4-(5-(2-aminopropan-2-yl)-2-(6-methoxypyridin-3-ylamino)pyridin-3-yl)-N,N-bis(4-methoxybenzyl)-6-methyl-1,3,5-triazin-2-amine (0.176 g, 0.290 mmol, 100% yield). m/z (ESI, +ve ion) 607 (M+H)+. 1H NMR (400 MHz, CDCl3) δ 11.55 (s, 1H); 8.92 (d, J=2.7 Hz, 1H); 8.48 (d, J=2.5 Hz, 1H); 8.23 (d, J=2.5 Hz, 2H); 7.91 (dd, J=8.8, 2.7 Hz, 1H); 7.15-7.25 (m, 4H); 6.78-6.95 (m, 4H); 6.69 (d, J=8.8 Hz, 1H); 4.89 (s, 2H); 4.81 (s, 2H); 3.92 (s, 3H); 3.81 (s, 3H); 3.77 (s, 3H); 2.58 (s, 3H); 1.53 (s, 6H).

Step 4: 4-(5-(2-aminopropan-2-yl)-2-(6-methoxypyridin-3-ylamino)pyridin-3-yl)-6-methyl-1,3,5-triazin-2-amine A solution of 4-(5-(2-aminopropan-2-yl)-2-(6-methoxypyridin-3-ylamino)pyridin-3-yl)-N,N-bis(4-methoxybenzyl)-6-methyl-1,3,5-triazin-2-amine (0.025 g, 0.041 mmol) in TFA (1 mL) was treated with triflic acid (0.029 mL, 0.330 mmol), sealed, and heated at 80° C. for 2 h. The reaction was cooled and treated with ice and 10 N NaOH until basic. The reaction was partitioned between water and DCM. The aqueous layer was extracted with DCM (3×) and the combined organic extracts were dried over anhydrous sodium sulfate, filtered, and concentrated in vacuo. This material was dissolved in DMSO and purified by prep HPLC (5-50% MeCN/H2O with 0.1% TFA). Product-containing fractions were concentrated in vacuo to give 4-(5-(2-aminopropan-2-yl)-2-(6-methoxypyridin-3-ylamino)pyridin-3-yl)-6-methyl-1,3,5-triazin-2-amine 2,2,2-trifluoroacetate (9 mg, 0.019 mmol, 45.5% yield) as an orange solid. m/z (ESI, +ve ion) 367 (M+H)+. 1H NMR (400 MHz, d6-DMSO) δ 11.76 (s, 1H); 8.93 (d, J=2.7 Hz, 1H); 8.54 (d, J=2.5 Hz, 1H); 8.50 (d, J=2.7 Hz, 1H); 8.37 (br. s., 3H); 8.13 (dd, J=8.8, 2.7 Hz, 1H); 7.90 (br. s., 1H); 7.80 (br. s., 1H); 6.84 (d, J=9.0 Hz, 1H); 3.85 (s, 3H); 2.45 (s, 3H); 1.68 (s, 6H).

Example 278

4-(5-(2-aminopropan-2-yl)-2-(5-fluoro-6-methoxypyridin-3-ylamino)pyridin-3-yl)-6-methyl-1,3,5-triazin-2-amine

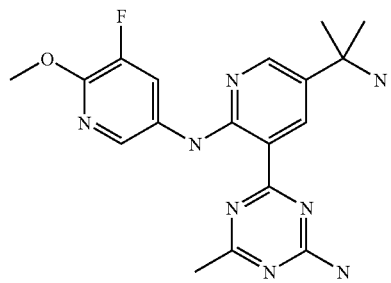 [SMILES: COc1ncc(Nc2ncc(C(C)(C)N)cc2-c2nc(C)nc(N)n2)cc1F]

The title compound was prepared in an analogous manner to that described in Example 277, using 4-(5-chloro-2-(5-fluoro-6-methoxypyridin-3-ylamino)pyridin-3-yl)-N,N-bis(4-methoxybenzyl)-6-methyl-1,3,5-triazin-2-amine (Example 313) in Step 1, to give 4-(5-(2-aminopropan-2-yl)-2-(5-fluoro-6-methoxypyridin-3-ylamino)pyridin-3-yl)-6-methyl-1,3,5-triazin-2-amine as a yellow solid (52%, 3 steps). m/z (ESI, +ve ion) 385 (M+H)+. 1H NMR (400 MHz, d6-DMSO) δ 11.90 (s, 1H); 8.98 (d, J=2.5 Hz, 1H); 8.53 (d, J=2.5 Hz, 1H); 8.40 (s, 2H); 8.37 (d, J=2.2 Hz, 1H); 7.88 (br. s., 1H); 7.73 (br. s., 1H); 3.93 (s, 3H); 2.44 (s, 3H); 1.42 (s, 6H).

Example 279

4-(2-(6-methoxypyridin-3-ylamino)-5-(2-(4-(methylsulfonyl)piperazin-1-yl)propan-2-yl)pyridin-3-yl)-6-methyl-1,3,5-triazin-2-amine

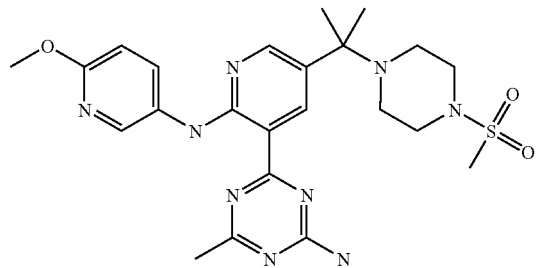 [SMILES: COc1ccc(Nc2ncc(C(C)(C)N3CCN(S(C)(=O)=O)CC3)cc2-c2nc(C)nc(N)n2)cn1]

Step 1. N,N-bis(4-methoxybenzyl)-4-(2-(6-methoxypyridin-3-ylamino)-5-(2-(4-(methylsulfonyl)piperazin-1-yl)propan-2-yl)pyridin-3-yl)-6-methyl-1,3,5-triazin-2-amine 4-(5-(2-aminopropan-2-yl)-2-(6-methoxypyridin-3-ylamino)pyridin-3-yl)-N,N-bis(4-methoxybenzyl)-6-methyl-1,3,5-triazin-2-amine (Example 277, 0.176 g, 0.290 mmol) and 2,2'-(methylsulfonylazanediyl)bis(ethane-2,1-diyl)dimethanesulfonate (Tetrahedron 1985, 41, 1959-1964; 0.118 g, 0.348 mmol) were combined in DIPEA (2 mL) in a sealed vial and heated at 130° C. overnight. The reaction was partitioned between saturated NaHCO$_3$ and DCM. The aqueous layer was extracted with DCM (3×) and the combined organic layers were dried over anhydrous sodium sulfate, filtered, and concentrated in vacuo. The material was treated with DCM and purified by silica gel chromatography (25 g column) using 0-100% EtOAc/hexane to give N,N-bis(4-methoxybenzyl)-4-(2-(6-methoxypyridin-3-ylamino)-5-(2-(4-(methylsulfonyl)piperazin-1-yl)propan-2-yl)pyridin-3-yl)-6-methyl-1,3,5-triazin-2-amine (0.034 g, 0.045 mmol, 15.55% yield). m/z (ESI, +ve ion) 754 (M+H)$^+$.

Step 2: 4-(2-(6-methoxypyridin-3-ylamino)-5-(2-(4-(methylsulfonyl)piperazin-1-yl)propan-2-yl)pyridin-3-yl)-6-methyl-1,3,5-triazin-2-amine A solution of N,N-bis(4-methoxybenzyl)-4-(2-(6-methoxypyridin-3-ylamino)-5-(2-(4-(methylsulfonyl)piperazin-1-yl)propan-2-yl)pyridin-3-yl)-6-methyl-1,3,5-triazin-2-amine (0.034 g, 0.045 mmol) in trifluoroacetic acid (1 mL) was treated with triflic acid (0.032 mL, 0.361 mmol). The light yellow reaction was sealed and heated at 80° C. After 30 min the reaction was cooled with ice and basified with 10 N NaOH, then partitioned between water and DCM. The aqueous layer was extracted with DCM (3×) and the combined organic layers were dried over anhydrous sodium sulfate, filtered, and concentrated in vacuo. This material was dissolved in DMSO and purified by prep HPLC (5-70% MeCN/H$_2$O with 0.1% TFA). Product-containing fractions were concentrated, then treated with sat'd aq. NaHCO$_3$ and DCM. The aq. layer was extracted with DCM (3×) and the combined organic layers were dried over sodium sulfate, filtered, and concentrated in vacuo to give 4-(2-(6-methoxypyridin-3-ylamino)-5-(2-(4-(methylsulfonyl)piperazin-1-yl)propan-2-yl)pyridin-3-yl)-6-methyl-1,3,5-triazin-2-amine (0.006 g, 0.012 mmol, 25.9% yield) as a yellow solid. m/z (ESI, +ve ion) 514 (M+H)$^+$. $^1$H NMR (400 MHz, d6-DMSO) δ 11.70 (s, 1H); 8.83 (d, J=2.5 Hz, 1H); 8.53 (d, J=2.7 Hz, 1H); 8.45 (d, J=2.5 Hz, 1H); 8.19 (dd, J=8.9, 2.8 Hz, 1H); 7.61-7.93 (m, 2H); 6.81 (d, J=9.0 Hz, 1H); 3.84 (s, 3H); 3.01-3.16 (m, 4H); 2.86 (s, 3H); 2.48-2.63 (m, 4H); 2.44 (s, 3H); 1.36 (s, 6H).

Example 280

4-(2-(5-fluoro-6-methoxypyridin-3-ylamino)-5-(2-(4-(methylsulfonyl)piperazin-1-yl)propan-2-yl)pyridin-3-yl)-6-methyl-1,3,5-triazin-2-amine

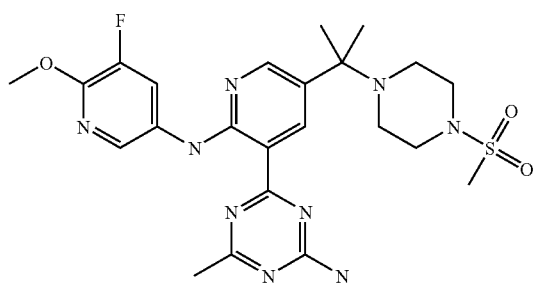 [SMILES: COc1ncc(Nc2ncc(C(C)(C)N3CCN(S(C)(=O)=O)CC3)cc2-c2nc(C)nc(N)n2)cc1F]

The title compound was prepared as a yellow solid (29% yield, 2 steps) in an analogous manner to that described in Example 279 using 4-(5-(2-aminopropan-2-yl)-2-(5-fluoro-6-methoxypyridin-3-ylamino)pyridin-3-yl)-6-methyl-1,3,5-triazin-2-amine (Example 279) in Step 1. m/z (ESI, +ve ion) 532 (M+H)$^+$. $^1$H NMR (400 MHz, d6-DMSO) δ 11.91 (s, 1H); 8.86 (d, J=2.5 Hz, 1H); 8.51 (d, J=2.5 Hz, 1H); 8.37-8.45 (m, 2H); 7.88 (br. s., 1H); 7.74 (br. s., 1H); 3.93 (s, 3H); 3.09 (m, 4H); 2.86 (s, 3H); 2.51-2.58 (m, 4H); 2.44 (s, 3H); 1.37 (s, 6H).

Example 281

4-(2-(5-fluoro-6-methoxypyridin-3-ylamino)-5-(2-morpholinopropan-2-yl)pyridin-3-yl)-6-methyl-1,3,5-triazin-2-amine

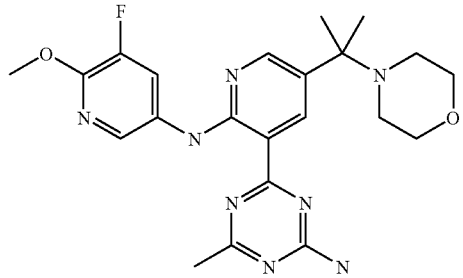 [SMILES: COc1ncc(Nc2ncc(C(C)(C)N3CCOCC3)cc2-c2nc(C)nc(N)n2)cc1F]

Step 1: 2-(5-(4-(bis(4-methoxybenzyl)amino)-6-methyl-1,3,5-triazin-2-yl)-6-(5-fluoro-6-methoxypyridin-3-ylamino)pyridin-3-yl)-2-morpholinopropanenitrile A solution of 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone (Example 271, 0.564 g, 0.925 mmol) and morpholine (0.201 mL, 2.313 mmol) in DCM (4.5 mL) was treated with tetraisopropoxytitanium (0.678 mL, 2.313 mmol). The reaction was sealed and stirred rapidly overnight. Cyanodiethylaluminum (1.0 M in toluene; 2.313 mL, 2.313 mmol) was added and the reaction was resealed and stirred overnight. EtOAc was added followed by sat'd NaHCO$_3$ (cautiously). An exotherm and effervescence was observed, so the reaction was poured onto ice and treated with EtOAc and sat'd aq. NaHCO$_3$. The aqueous layer was extracted with EtOAc (2×). The combined organic layers were dried over sodium sulfate, filtered, and concentrated in vacuo to give 2-(5-(4-(bis(4-methoxybenzyl)amino)-6-methyl-1,3,5-triazin-2-yl)-6-(5-fluoro-6-methoxypyridin-3-ylamino)pyridin-3-yl)-2-morpholinopropanenitrile (0.650 g, 0.921 mmol, 100% yield) as a yellow solid. m/z (ESI, +ve ion) 706 (M+H)$^+$. $^1$H NMR (400 MHz, CDCl$_3$) δ 11.99 (br. s., 1H); 9.00 (d, J=2.5 Hz, 1H); 8.50 (d, J=2.5 Hz, 1H); 8.03 (dd, J=12.1, 2.2 Hz, 1H); 7.97 (d, J=2.2 Hz, 1H); 7.17-7.26 (m, 4H); 6.82-6.93 (m, 4H); 4.73-5.01 (m, 4H); 4.03 (s, 3H); 3.82 (s, 3H); 3.79 (s, 3H); 3.61-3.71 (m, 4H); 2.64-2.76 (m, 2H); 2.60 (s, 3H); 2.44-2.54 (m, 2H); 1.75 (s, 3H).

Step 2: 4-(2-(5-fluoro-6-methoxypyridin-3-ylamino)-5-(2-morpholinopropan-2-yl)pyridin-3-yl)-N,N-bis(4-methoxybenzyl)-6-methyl-1,3,5-triazin-2-amine A solution of 2-(5-(4-(bis(4-methoxybenzyl)amino)-6-methyl-1,3,5-triazin-2-yl)-6-(5-fluoro-6-methoxypyridin-3-ylamino)pyridin-3-yl)-2-morpholinopropanenitrile (0.500 g, 0.708 mmol) in THF (2 mL) at 0° C. was treated with methylmagnesium bromide (3.0 M in diethyl ether; 1.181 mL, 3.54 mmol). The cooling bath was removed after 10 min, and the reaction was allowed to warm to ambient temperature. After 2 h total, the reaction was cooled to 0° C. and quenched with EtOAc (1 mL) followed by ice and sat'd aq. NH₄Cl. The reaction was partitioned between satd NH₄Cl and DCM. The aqueous layer was extracted with DCM (3×) and the combined organic extracts were dried over anhydrous sodium sulfate, filtered, and concentrated in vacuo. The material was treated with DCM and purified by silica gel chromatography using 10-80% EtOAc/hexane. The product-containing fractions were concentrated to give 4-(2-(5-fluoro-6-methoxypyridin-3-ylamino)-5-(2-morpholinopropan-2-yl)pyridin-3-yl)-N,N-bis(4-methoxybenzyl)-6-methyl-1,3,5-triazin-2-amine (0.363 g, 0.522 mmol, 73.7% yield) as a yellow solid. m/z (ESI, +ve ion) 695 (M+H)⁺. ¹H NMR (400 MHz, CDCl₃) δ 11.86 (s, 1H); 8.96 (d, J=2.5 Hz, 1H); 8.47 (d, J=2.5 Hz, 1H); 8.13 (dd, J=12.5, 2.2 Hz, 1H); 7.91-8.01 (m, 1H); 7.17-7.26 (m, 4H); 6.75-6.96 (m, 4H); 4.89 (s, 2H); 4.84 (s, 2H); 4.02 (s, 3H); 3.82 (s, 3H); 3.79 (s, 3H); 3.55-3.65 (m, 4H); 2.59 (s, 3H); 2.42-2.51 (m, 4H); 1.35 (s, 6H).

Step 3: 4-(2-(5-fluoro-6-methoxypyridin-3-ylamino)-5-(2-morpholinopropan-2-yl)pyridin-3-yl)-6-methyl-1,3,5-triazin-2-amine 4-(2-(5-Fluoro-6-methoxypyridin-3-ylamino)-5-(2-morpholinopropan-2-yl)pyridin-3-yl)-N,N-bis(4-methoxybenzyl)-6-methyl-1,3,5-triazin-2-amine (0.363 g, 0.522 mmol) in TFA (3 mL) was treated with trifluoromethanesulfonic acid (0.232 mL, 2.61 mmol). The reaction was sealed and heated at 80° C. for 30 min, cooled, and poured onto ice. The mixture was basified with 10 N NaOH and the reaction was partitioned between water and DCM. The aqueous layer was extracted with DCM (3×) and the combined organic extracts were dried over anhydrous sodium sulfate, filtered, and concentrated in vacuo. This material was dissolved in DMSO and purified by prep HPLC (10-55% MeCN/H₂O with 0.1% TFA). Product-containing fractions were treated with sat'd aq. NaHCO₃ and DCM. The aq. layer was extracted with DCM (3×) and the combined organic extracts were dried over sodium sulfate, filtered, and concentrated in vacuo to give 4-(2-(5-fluoro-6-methoxypyridin-3-ylamino)-5-(2-morpholinopropan-2-yl)pyridin-3-yl)-6-methyl-1,3,5-triazin-2-amine (0.069 g, 0.152 mmol, 29.1% yield). m/z (ESI, +ve ion) 455 (M+H)⁺. ¹H NMR (400 MHz, d6-DMSO) δ 11.91 (s, 1H); 8.90 (d, J=2.5 Hz, 1H); 8.48 (d, J=2.5 Hz, 1H); 8.33-8.44 (m, 2H); 7.88 (br. s., 1H); 7.73 (br. s., 1H); 3.93 (s, 3H); 3.57 (br. s., 4H); 2.44 (s, 3H); 2.36-2.43 (m, 4H); 1.35 (s, 6H).

Example 282

4-(2-(6-methoxypyridin-3-ylamino)-5-(1-(4-(methylsulfonyl)piperazin-1-yl)cyclopropyl)pyridin-3-yl)-6-methyl-1,3,5-triazin-2-amine

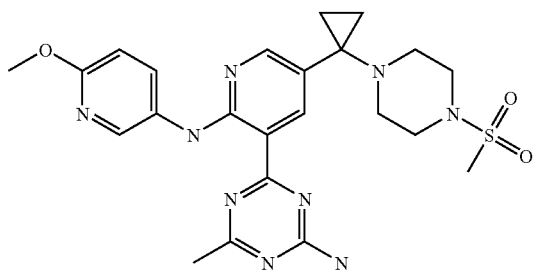

Step 1: (5-(4-(bis(4-methoxybenzyl)amino)-6-methyl-1,3,5-triazin-2-yl)-6-(6-methoxypyridin-3-ylamino)pyridin-3-yl)(4-(methylsulfonyl)piperazin-1-yl)methanone A mixture of 5-(4-(bis(4-methoxybenzyl)amino)-6-methyl-1,3,5-triazin-2-yl)-6-(6-methoxypyridin-3-ylamino)nicotinaldehyde (Example 144, 1.00 g, 1.731 mmol), activated manganese (IV) oxide (<5 micron; 4.52 g, 51.9 mmol), sodium cyanide (0.053 mL, 1.731 mmol) and 1-(methylsulfonyl)piperazine (0.711 g, 4.33 mmol) in THF (15 mL) was stirred rapidly under nitrogen for 72 h. The reaction was filtered through Celite® (diatomaceous earth) rinsing with 10% MeOH/DCM followed by EtOAc. The filtrate was concentrated and adsorbed onto 5 g silica gel and passed through an 80 g column using 20-100% EtOAc/hexanes to give (5-(4-(bis(4-methoxybenzyl)amino)-6-methyl-1,3,5-triazin-2-yl)-6-(6-methoxypyridin-3-ylamino)pyridin-3-yl)(4-(methylsulfonyl)piperazin-1-yl)methanone (0.352 g, 0.476 mmol, 27.5% yield) as a yellow foam. m/z (ESI, +ve ion) 740 (M+H)⁺. ¹H NMR (400 MHz, CDCl₃) δ 12.02 (s, 1H); 8.91 (d, J=2.3 Hz, 1H); 8.42 (d, J=2.5 Hz, 1H); 8.29 (d, J=2.5 Hz, 1H); 7.90 (dd, J=8.8, 2.7 Hz, 1H); 7.11-7.24 (m, 4H); 6.80-6.94 (m, 4H); 6.75 (d, J=9.0 Hz, 1H); 4.85 (s, 2H); 4.82 (s, 2H); 3.95 (s, 3H); 3.82 (s, 3H); 3.80 (s, 3H); 3.71-3.78 (m, 4H); 3.17-3.25 (m, 4H); 2.70 (s, 3H); 2.60 (s, 3H).

Step 2: 4-(2-(6-methoxypyridin-3-ylamino)-5-(1-(4-(methylsulfonyl)piperazin-1-yl)cyclopropyl)pyridin-3-yl)-6-methyl-1,3,5-triazin-2-amine A solution of (5-(4-(bis(4-methoxybenzyl)amino)-6-methyl-1,3,5-triazin-2-yl)-6-(6-methoxypyridin-3-ylamino)pyridin-3-yl)(4-(methylsulfonyl)piperazin-1-yl)methanone (0.163 g, 0.220 mmol) and titanium (IV) isopropoxide (0.194 mL, 0.661 mmol) in THF (2 mL) at 0° C. under nitrogen was treated dropwise with ethylmagnesium bromide (1.0 M solution in tert-butyl methyl ether; 1.322 mL, 1.322 mmol). The reaction was warmed to ambient temperature and an additional 3 equiv. EtMgBr was added. After 1 h, the reaction was quenched with ice and DCM, and was filtered through Celite® (diatomaceous earth) rinsing with copious amounts of DCM. The reaction was partitioned between water and DCM. The aqueous layer was extracted with DCM (3×) and the combined organic extracts were dried over anhydrous sodium sulfate, filtered, and concentrated in vacuo to give an orange solid. The solid was taken up in TFA (1.5 mL) and 20 drops TfOH was added from a Pasteur pipette. The resulting mixture was sealed and heated at 80° C. for 1 h. The reaction was cooled in an ice bath and treated with ice and 10 N NaOH until basic. The reaction was partitioned between water and DCM. The aqueous layer was extracted with DCM (3×) and the combined organic extracts were dried over anhydrous sodium sulfate, filtered, and concentrated in vacuo. This material was dissolved in DMSO and purified by prep HPLC (5-50% MeCN/$H_2O$ with 0.1% TFA). Product-containing fractions were concentrated to give 4-(2-(6-methoxypyridin-3-ylamino)-5-(1-(4-(methylsulfonyl)piperazin-1-yl)cyclopropyl)pyridin-3-yl)-6-methyl-1,3,5-triazin-2-amine 2,2,2-trifluoroacetate (0.0063 g, 10.07 µmol, 4.57% yield) as an orange solid. m/z (ESI, +ve ion) 512 (M+H)$^+$. $^1$H NMR (400 MHz, d6-DMSO) δ 11.80 (s, 1H); 8.68 (d, J=2.3 Hz, 1H); 8.52 (d, J=2.5 Hz, 1H); 8.27 (d, J=2.2 Hz, 1H); 8.16 (dd, J=8.8, 2.7 Hz, 1H); 7.90 (br. s., 1H); 7.74 (br. s., 1H); 6.83 (d, J=8.8 Hz, 1H); 3.85 (s, 3H); 3.01-3.23 (m, 4H); 2.84 (s, 3H); 2.60-2.79 (m, 4H); 2.44 (s, 3H); 1.00-1.13 (m, 2H); 0.84-0.97 (m, 2H).

Example 283

6-(3-(5-fluoro-6-methoxypyridin-3-ylamino)-6-(1-(4-(methylsulfonyl)piperazin-1-yl)ethyl)pyrazin-2-yl)-2-methylpyrimidin-4-amine

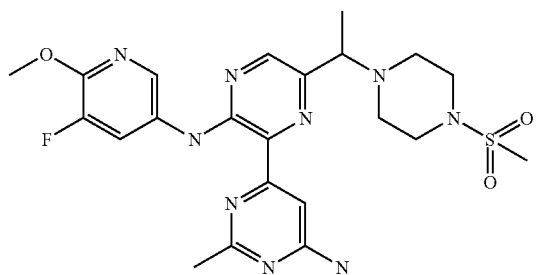

Step 1. 3-bromo-5-chloro-N-(5-fluoro-6-methoxypyridin-3-yl)pyrazin-2-amine

A mixture of 3-bromo-5-chloropyrazin-2-amine (780 mg, 3.74 mmol, Ark Phar. Inc., Libertyville, Ill.), 5-fluoro-6-methoxypyridin-3-ylboronic acid (1919 mg, 11.23 mmol, Anichem), N,N-diisopropylethylamine (1.953 mL, 11.23 mmol, Aldrich, St. Louis, Mo.) and copper (II) acetate (1.12 g, 5.61 mmol, Aldrich, St. Louis, Mo.) in dichloromethane (30 mL) was stirred at room temperature for 72 h. The reaction mixture was diluted with water (20 mL) and extracted with EtOAc (2×40 mL). The combined organic extracts were washed with saturated NaCl (20 mL) and dried over $Na_2SO_4$. The solution was filtered and concentrated in vacuo to give the crude material as a light-yellow solid. The crude product was purified by silica gel chromatography, eluting with 20% EtOAc/hexanes to give 3-bromo-5-chloro-N-(5-fluoro-6-methoxypyridin-3-yl)pyrazin-2-amine (218 mg, 0.654 mmol, 17.47% yield). $^1$H NMR (300 MHz, CDCl$_3$) δ 4.03 (s, 3H) 7.00 (s, 1H) 7.82 (dd, J=11.25, 1.75 Hz, 1H) 8.04 (d, J=9.06 Hz, 2H). m/z (ESI, +ve ion) 331.9 (M+H)$^+$.

Step 2. 5-chloro-N-(5-fluoro-6-methoxypyridin-3-yl)-3-(2-methyl-6-(methylthio)pyrimidin-4-yl)pyrazin-2-amine A glass microwave reaction vessel was charged with 3-bromo-5-chloro-N-(5-fluoro-6-methoxypyridin-3-yl)pyrazin-2-amine (216 mg, 0.648 mmol,), 2-methyl-4-(methylthio)-6-(tributylstannyl)pyrimidine (334 mg, 0.777 mmol), copper (I) iodide (25 mg, 0.130 mmol, Aldrich, St. Louis, Mo.), cesium fluoride (197 mg, 1.295 mmol, Alfa Aesar) and tetrakis(triphenylphosphine)palladium (74.8 mg, 0.065 mmol, Strem) in dioxane (3 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (5 mL) and extracted with $CH_2Cl_2$ (2×30 mL). The combined organic extracts were washed with saturated NaCl (5 mL) and dried over $Na_2SO_4$. The solution was filtered and concentrated in vacuo to give the crude material as a yellow solid. The crude product was purified by silica gel chromatography, eluting with 5% EtOAc/$CH_2Cl_2$ to give 5-chloro-N-(5-fluoro-6-methoxypyridin-3-yl)-3-(2-methyl-6-(methylthio)pyrimidin-4-yl)pyrazin-2-amine (176 mg, 0.448 mmol, 69.2% yield). $^1$H NMR (300 MHz, CDCl$_3$) δ 2.63 (s, 3H) 2.79 (s, 3H) 4.04 (s, 3H) 8.01-8.29 (m, 4H) 12.45 (s, 1H). m/z (ESI, +ve ion) 393.0 (M+H)$^+$.

Step 3. 1-(5-(5-fluoro-6-methoxypyridin-3-ylamino)-6-(2-methyl-6-(methylthio)pyrimidin-4-yl)pyrazin-2-yl)ethanone A mixture of 5-chloro-N-(5-fluoro-6-methoxypyridin-3-yl)-3-(2-methyl-6-(methylthio)pyrimidin-4-yl)pyrazin-2-amine (151 mg, 0.384 mmol), dicyclohexyl(2',4',6'-triisopropylbiphenyl-2-yl)phosphine (36.6 mg, 0.077 mmol, Aldrich, St. Louis, Mo.), palladium diacetate (8.63 mg, 0.038 mmol, Aldrich, St. Louis, Mo.), copper(I) iodide (15 mg, 0.077 mmol, Aldrich, St. Louis, Mo.), cesium fluoride (117 mg, 0.769 mmol, Alfa Aesar) and tributyl(1-ethoxyvinyl)tin (0.195 mL, 0.577 mmol, Aldrich, St. Louis, Mo.) in dioxane (3 mL) was stirred at 100° C. for 18 h. The mixture was cooled down to room temperature. The reaction mixture was diluted with water (10 mL) and extracted with $CH_2Cl_2$ (2×30 mL). The combined organic extracts were washed with saturated NaCl (10 mL) and dried over $Na_2SO_4$. The solution was filtered and concentrated in vacuo to give the crude material as a yellow solid. The crude product was purified by silica gel chromatography, eluting with 10% EtOAc/$CH_2Cl_2$ to give 1-(5-(5-fluoro-6-methoxypyridin-3-ylamino)-6-(2-methyl-6-(methylthio)pyrimidin-4-yl)pyrazin-2-yl)ethanone (102 mg, 0.255 mmol, 66.3% yield). $^1$H NMR (300 MHz, CDCl$_3$) δ 2.66 (s, 3H) 2.71 (s, 3H) 2.81 (s, 3H) 4.05 (s, 3H) 8.04-8.33 (m, 3H) 8.92 (s, 1H) 12.99 (s, 1H). m/z (ESI, +ve ion) 401.0 (M+H)$^+$.

Step 4. 1-(5-(5-fluoro-6-methoxypyridin-3-ylamino)-6-(2-methyl-6-(methylsulfinyl)pyrimidin-4-yl)pyrazin-2-yl)ethanone A mixture of 1-(5-(5-fluoro-6-methoxypyridin-3-ylamino)-6-(2-methyl-6-(methylthio)pyrimidin-4-yl)pyrazin-2-yl)ethanone (52 mg, 0.130 mmol) and 3-chloroperoxybenzoic acid (44.8 mg, 0.260 mmol, Aldrich, St. Louis, Mo.) in dioxane (1 mL) was stirred at room temperature for 2 h. The mixture was taken on directly to the next step without work-up.

Step 5. 1-(6-(6-amino-2-methylpyrimidin-4-yl)-5-(5-fluoro-6-methoxypyridin-3-ylamino)pyrazin-2-yl)ethanone The reaction mixture from the previous step was treated with ammonia (0.5 mL, 23.11 mmol, J. T. Baker) (30% in water) and the mixture was stirred at 100° C. for 5 h. The solvent was removed in vacuo and the residue was purified by silica gel chromatography eluting with 5% EtOAc/hexanes to give 1-(6-(6-amino-2-methylpyrimidin-4-yl)-5-(5-fluoro-6-methoxypyridin-3-ylamino)pyrazin-2-yl)ethanone (18 mg, 0.049 mmol, 37.5% yield). $^1$H NMR (300 MHz, CDCl$_3$) δ 2.67 (s, 3H) 2.70 (s, 3H) 4.05 (s, 3H) 5.08 (s, 2H) 7.53 (s, 1H) 8.16 (d, J=2.19 Hz, 1H) 8.25 (dd, J=11.91, 2.12 Hz, 1H) 8.91 (s, 1H) 13.36 (s, 1H). m/z (ESI, +ve ion) 370.0 (M+H)$^+$.

Step 6. 6-(3-(5-fluoro-6-methoxypyridin-3-ylamino)-6-(1-(4-(methylsulfonyl)piperazin-1-yl)ethyl)pyrazin-2-yl)-2-methylpyrimidin-4-amine A mixture of 1-(methylsulfonyl)piperazine (13.34 mg, 0.081 mmol, Apollo), 1-(6-(6-amino-2-methylpyrimidin-4-yl)-5-(5-fluoro-6-methoxypyridin-3-ylamino)pyrazin-2-yl)ethanone (15 mg, 0.041 mmol) and titanium(iv) isopropoxide (0.048 mL, 0.162 mmol, Aldrich, St. Louis, Mo.) in tetrahydrofuran (0.5 mL) was stirred at 75° C. for 25 h. The mixture was cooled down to 20° C. and CH$_2$Cl$_2$ (1 mL) was added followed by sodium triacetoxyborohydride (34.4 mg, 0.162 mmol). The reaction mixture was stirred at room temperature for 5 h. The reaction mixture was diluted with ammonia (3 mL, 30% in water) and extracted with CH$_2$Cl$_2$ (2×20 mL). The combined organic extracts were washed with saturated NaCl (5 mL) and dried over Na$_2$SO$_4$. The solution was filtered and concentrated in vacuo to give the crude material as a yellow solid. The crude product was purified by silica gel chromatography eluting with 5% MeOH/CH$_2$Cl$_2$ to give 6-(3-(5-fluoro-6-methoxypyridin-3-ylamino)-6-(1-(4-(methylsulfonyl)piperazin-1-yl)ethyl)pyrazin-2-yl)-2-methylpyrimidin-4-amine (4.8 mg, 9.27 μmol, 23% yield). $^1$H NMR (300 MHz, CDCl$_3$) δ 1.44 (d, J=6.58 Hz, 3H) 2.46-2.69 (m, 7H) 2.77 (s, 3H) 3.23 (t, J=4.24 Hz, 4H) 3.55 (q, J=6.77 Hz, 1H) 4.03 (s, 3H) 5.42 (s, 2H) 8.04 (d, J=2.19 Hz, 1H) 8.20-8.37 (m, 2H) 8.70 (d, J=1.90 Hz, 1H) 11.90 (s, 1H). m/z (ESI, +ve ion) 518.2 (M+H)$^+$.

Example 284

2-(6-(6-amino-2-methylpyrimidin-4-yl)-5-(5-fluoro-6-methoxypyridin-3-ylamino)pyrazin-2-yl)propan-2-ol

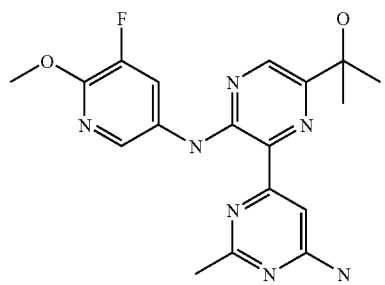 [SMILES: COc1ncc(Nc2ncc(C(C)(C)O)nc2-c2cc(N)nc(C)n2)cc1F]

A mixture of 1-(6-(6-amino-2-methylpyrimidin-4-yl)-5-(5-fluoro-6-methoxypyridin-3-ylamino)pyrazin-2-yl)etha-none (11 mg, 0.030 mmol) and methylmagnesium bromide, 3.0 M solution in diethyl ether (10.65 μL, 0.089 mmol, Aldrich, St. Louis, Mo.) in tetrahydrofuran (1 mL) was stirred at 0° C. for 30 min. The reaction mixture was diluted with saturated NH$_4$Cl (5 mL) and extracted with CH$_2$Cl$_2$ (2×10 mL). The organic extracts were washed with saturated NaCl 5 mL) and dried over Na$_2$SO$_4$. The solution was filtered and concentrated in vacuo to give the crude material as a yellow solid. The crude product was purified by silica gel chromatography eluting with 5% MeOH/CH$_2$Cl$_2$ to give 2-(6-(6-amino-2-methylpyrimidin-4-yl)-5-(5-fluoro-6-methoxypyridin-3-ylamino)pyrazin-2-yl)propan-2-ol (8.5 mg, 0.022 mmol, 74.1% yield). $^1$F1 NMR (300 MHz, CDCl$_3$) δ 1.63 (s, 6H) 2.66 (s, 3H) 3.66 (s, 1H) 4.03 (s, 3H) 5.01 (s, 2H) 7.45 (s, 1H) 8.11 (d, J=1.90 Hz, 1H) 8.22 (dd, J=12.13, 2.05 Hz, 1H) 8.39 (s, 1H) 12.66 (s, 1H). m/z (ESI, +ve ion) 386.1 (M+H)$^+$.

Example 285

1-(6-(6-amino-2-methylpyrimidin-4-yl)-5-(6-methoxypyridin-3-ylamino)pyrazin-2-yl)ethanone

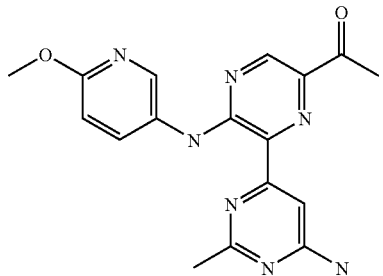 [SMILES: COc1ccc(Nc2ncc(C(C)=O)nc2-c2cc(N)nc(C)n2)cn1]

Step 1. 3-bromo-5-chloro-N-(6-methoxypyridin-3-yl)pyrazin-2-amine

A mixture of 3-bromo-5-chloropyrazin-2-amine (624 mg, 2.99 mmol, Ark Phar. Inc), 6-methoxypyridin-3-ylboronic acid (1374 mg, 8.98 mmol, Combi. Blocks), copper (II) acetate (896 mg, 4.49 mmol, Aldrich, St. Louis, Mo.), and N,N-diisopropylethylamine (2.083 mL, 11.97 mmol, Aldrich, St. Louis, Mo.) in dichloromethane (20 mL) was stirred at room temperature for 48 h. The mixture was filtered through a pad of Celite® (diatomaceous earth) and washed with EtOAc. The solvent was removed in vacuo and the residue was purified by silica gel chromatography eluting with 10% EtOAc/hexanes to give 3-bromo-5-chloro-N-(6-methoxypyridin-3-yl)pyrazin-2-amine (165 mg, 0.523 mmol, 17.47% yield). $^1$H NMR (300 MHz, CDCl$_3$) δ 3.95 (s, 3H) 6.79 (d, J=8.77 Hz, 1H) 6.92 (s, 1H) 7.77 (dd, J=8.84, 2.41 Hz, 1H) 8.01 (s, 1H) 8.29 (d, J=2.05 Hz, 1H). m/z (ESI, +ve ion) 316.9 (M+H)$^+$.

Step 2. 5-chloro-N-(6-methoxypyridin-3-yl)-3-(2-methyl-6-(methylthio)pyrimidin-4-yl)pyrazin-2-amine A glass microwave reaction vessel was charged with 3-bromo-5-chloro-N-(6-methoxypyridin-3-yl)pyrazin-2-amine (83 mg, 0.263 mmol), copper (I) iodide (10 mg, 0.053 mmol, Aldrich), cesium fluoride (80 mg, 0.526 mmol, Alfa Aesar), tetrakis(triphenylphosphine)palladium(0) (30.4 mg, 0.026 mmol) and 2-methyl-4-(methylthio)-6-(tributylstannyl)pyrimidine (113 mg, 0.263 mmol) in dioxane (2 mL). The reaction mixture was stirred and heated in a Emrys Optimizer microwave reactor (Personal Chemistry, Biotage AB, Inc., Upssala, Sweden) at 140° C. for 30 min. The reaction mixture was diluted with water (10 mL) and extracted with $CH_2Cl_2$ (2×30 mL). The combined organic extracts were washed with saturated NaCl (10 mL) and dried over $Na_2SO_4$. The solution was filtered and concentrated in vacuo to give the crude material as a yellow solid. The crude product was purified by silica gel chromatography eluting with 10% EtOAc/hexanes to give 5-chloro-N-(6-methoxypyridin-3-yl)-3-(2-methyl-6-(methylthio)pyrimidin-4-yl)pyrazin-2-amine (72 mg, 0.192 mmol, 73.0% yield). $^1$H NMR (300 MHz, $CDCl_3$) δ 2.63 (s, 3H) 2.78 (s, 3H) 3.95 (s, 3H) 6.79 (d, J=8.77 Hz, 1H) 8.01 (dd, J=8.70, 2.12 Hz, 1H) 8.17 (d, J=5.55 Hz, 2H) 8.39 (s, 1H) 12.21 (s, 1H). m/z (ESI, +ve ion) 375.0 $(M+H)^+$.

Step 3. 1-(5-(6-methoxypyridin-3-ylamino)-6-(2-methyl-6-(methylthio)pyrimidin-4-yl)pyrazin-2-yl)ethanone A mixture of 5-chloro-N-(6-methoxypyridin-3-yl)-3-(2-methyl-6-(methylthio)pyrimidin-4-yl)pyrazin-2-amine (30 mg, 0.080 mmol), 2-(dicyclohexylphosphino)-2',4',6',-triisopropyl-biphenyl (7.63 mg, 0.016 mmol, Aldrich), copper (I) iodide (17 mg, 0.016 mmol, Aldrich), palladium diacetate (1.8 mg, 8.00 μmol, Aldrich), cesium fluoride (15 mg, 0.160 mmol, Alfa Aesar) and tributyl(1-ethoxyvinyl)tin (0.041 mL, 0.120 mmol, Aldrich) in dioxane (2 mL) was stirred at 100° C. for 18 h. The reaction mixture was diluted with water (5 mL) and extracted with EtOAc (2×20 mL). The combined organic extracts were washed with saturated NaCl (5 mL) and dried over $Na_2SO_4$. The solution was filtered and concentrated in vacuo to give the crude material as a yellow solid. The crude product was purified by silica gel chromatography, eluting with 10% EtOAc/$CH_2Cl_2$ to give 1-(5-(6-methoxypyridin-3-ylamino)-6-(2-methyl-6-(methylthio)pyrimidin-4-yl)pyrazin-2-yl)ethanone (19 mg, 0.050 mmol, 62.1% yield). $^1$H NMR (300 MHz, $CDCl_3$) δ 2.66 (s, 3H) 2.71 (s, 3H) 2.80 (s, 3H) 3.96 (s, 3H) 6.82 (d, J=8.92 Hz, 1H) 8.14 (dd, J=8.92, 2.78 Hz, 1H) 8.25 (s, 1H) 8.45 (d, J=2.63 Hz, 1H) 8.91 (s, 1H) 12.79 (s, 1H). m/z (ESI, +ve ion) 383.0 $(M+H)^+$.

Step 4. 1-(5-(6-methoxypyridin-3-ylamino)-6-(2-methyl-6-(methylsulfinyl)pyrimidin-4-yl)pyrazin-2-yl)ethanone A mixture of 1-(5-(6-methoxypyridin-3-ylamino)-6-(2-methyl-6-(methylthio)pyrimidin-4-yl)pyrazin-2-yl)ethanone (25 mg, 0.065 mmol) and 3-chloroperoxybenzoic acid (22.5 mg, 0.131 mmol, Aldrich) in dioxane (1 mL) was stirred at room temperature for 2 h. The reaction mixture was taken on directly to the next step without work-up.

Step 5. 1-(6-(6-amino-2-methylpyrimidin-4-yl)-5-(6-methoxypyridin-3-ylamino)pyrazin-2-yl)ethanone The reaction mixture from the previous step was treated with ammonia (0.5 mL, 30% in water, J. T. Baker). The reaction mixture was stirred at 100° C. for 4 h. The solvent was removed in vacuo and the residue was purified by silica gel chromatography eluting with 5% MeOH/$CH_2Cl_2$ to give 1-(6-(6-amino-2-methylpyrimidin-4-yl)-5-(6-methoxypyridin-3-ylamino)pyrazin-2-yl)ethanone (16 mg, 0.046 mmol, 69.8% yield). $^1$H NMR (300 MHz, $CDCl_3$) δ 2.66 (s, 3H) 2.70 (s, 3H) 3.96 (s, 3H) 5.10 (s, 2H) 6.81 (d, J=8.77 Hz, 1H) 7.53 (s, 1H) 8.09 (s, 1H) 8.15 (dd, J=8.62, 2.34 Hz, 1H) 8.46 (d, J=2.48 Hz, 1H) 8.88 (s, 1H) 13.14 (s, 1H). m/z (ESI, +ve ion) 352.1 $(M+H)^+$.

Example 286

6-(3-(6-methoxypyridin-3-ylamino)-6-(1-(4-(methylsulfonyl)piperazin-1-yl)ethyl)pyrazin-2-yl)-2-methylpyrimidin-4-amine

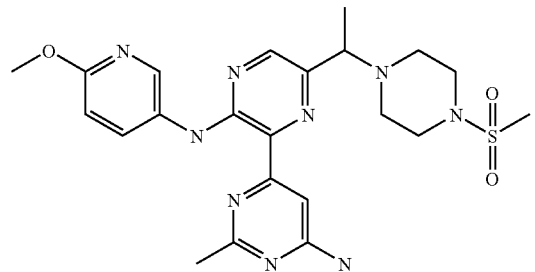

A mixture of 1-(methylsulfonyl)piperazine (5.61 mg, 0.034 mmol, Apollo), 1-(6-(6-amino-2-methylpyrimidin-4-yl)-5-(6-methoxypyridin-3-ylamino)pyrazin-2-yl)ethanone (6 mg, 0.017 mmol) and tetraisopropoxytitanium (19.41 mg, 0.068 mmol, Aldrich) in tetrahydrofuran (0.5 mL) was stirred at 75° C. for 48 h. The mixture was cooled down to 20° C. and $CH_2Cl_2$ (1 mL) was added followed by sodium triacetoxyborohydride (14.48 mg, 0.068 mmol). The reaction mixture was stirred at room temperature for 5 h. Ammonia (1 mL, 30% in water) was added and the mixture was extracted with $CH_2Cl_2$ (2×10 mL). The combined organic extracts were washed with saturated NaCl (5 mL) and dried over $Na_2SO_4$. The solution was filtered and concentrated in vacuo to give the crude material as a yellow solid. The crude product was purified by silica gel chromatography eluting with 5% MeOH/$CH_2Cl_2$ to give 6-(3-(6-methoxypyridin-3-ylamino)-6-(1-(4-(methylsulfonyl)piperazin-1-yl)ethyl)pyrazin-2-yl)-2-methylpyrimidin-4-amine (5.2 mg, 10.41 μmol, 61.0% yield). $^1$H NMR (300 MHz, $CDCl_3$) δ 1.48 (d, J=6.87 Hz, 3H) 2.64 (s, 3H) 2.78 (s, 4H) 3.14-3.40 (m, 4H) 3.81 (q, J=6.72 Hz, 1H) 5.10 (s, 2H) 6.78 (d, J=8.77 Hz, 1H) 7.46 (s, 1H) 8.08

(dd, J=8.84, 2.70 Hz, 1H) 8.20 (s, 1H) 8.43 (d, J=2.63 Hz, 1H). m/z (ESI, +ve ion) 500.1 (M+H)+.

Example 287

(R)-N-(3-(4-amino-6-methyl-1,3,5-triazin-2-yl)-5-(1-(4-(methylsulfonyl)piperazin-1-yl)ethyl)pyridin-2-yl)-5-fluoroquinolin-7-amine

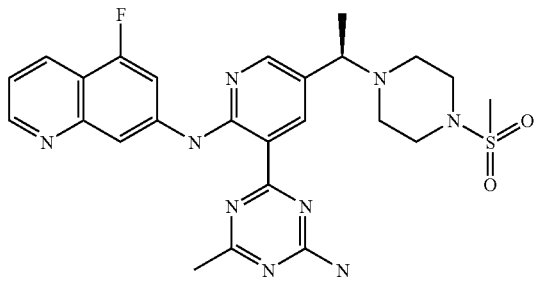 [SMILES: Cc1nc(N)nc(-c2cc([C@@H](C)N3CCN(S(C)(=O)=O)CC3)cnc2Nc2cc(F)c3cccnc3c2)n1]

Step 1. (E)-2-(3,3-diethoxyprop-1-enyl)-1-fluoro-3-nitrobenzene

A glass microwave reaction vessel was charged with 3,3-diethoxy-1-propenylboronic acid pinacol ester (0.154 mL, 0.600 mmol, Frontier Scientific), 2-bromo-1-fluoro-3-nitrobenzene (110 mg, 0.500 mmol, Aldrich), dichloro 1,1'-bis (diphenylphosphino)ferrocene palladium (II) (40.8 mg, 0.050 mmol, Strem) and cesium carbonate (326 mg, 1.00 mmol, Aldrich) in dioxane (3 mL) and water (0.5 mL). The reaction mixture was stirred and heated in an Emrys Optimizer microwave reactor (Personal Chemistry, Biotage AB, Inc., Upssala, Sweden) at 120° C. for 20 min. The reaction mixture was diluted with water (10 mL) and extracted with EtOAc (2×20 mL). The combined organic extracts were washed with saturated NaCl (5 mL) and dried over $Na_2SO_4$. The solution was filtered and concentrated in vacuo to give the crude material. The crude product was purified by silica gel chromatography eluting with 10% EtOAc/hexanes to give (E)-2-(3,3-diethoxyprop-1-enyl)-1-fluoro-3-nitrobenzene (82 mg, 0.305 mmol, 60.9% yield). $^1$H NMR (300 MHz, $CDCl_3$) δ 1.26 (t, J=7.02 Hz, 6H) 3.45-3.81 (m, 4H) 5.09 (d, J=4.09 Hz, 1H) 6.16-6.37 (m, 1H) 6.76 (d, J=17.25 Hz, 1H) 7.29-7.53 (m, 2H) 7.57-7.75 (m, 1H). m/z (ESI, +ve ion) 270 (M+H)+.

Step 2. (E)-3-(4-bromo-2-fluoro-6-nitrophenyl)acrylaldehyde

A mixture of (E)-2-(3,3-diethoxyprop-1-enyl)-1-fluoro-3-nitrobenzene (63.5 mg, 0.22 mmol), 1,3-dibromo-5,5-dimethylhydantoin (63.5 mg, 0.222 mmol, Aldrich) and sulfuric acid, 95% (0.5 mL, 7.14 mmol) was stirred at room temperature for 4 h. Ice (5 g) was added and the mixture was extracted with EtOAc (2×20 mL). The combined organic extracts were washed with saturated NaCl (6 mL) and dried over $Na_2SO_4$. The solution was filtered and concentrated in vacuo to give the crude material as a yellow oil. The crude product was purified by silica gel chromatography eluting with 20% EtOAc/hexanes to give (E)-3-(4-bromo-2-fluoro-6-nitrophenyl)acrylaldehyde (46 mg, 0.168 mmol, 39.3% yield). $^1$H NMR (300 MHz, $CDCl_3$) δ 7.47-7.58 (m, 1H) 7.58-7.71 (m, 1H) 8.10 (d, J=8.33 Hz, 1H) 8.15 (s, 1H) 9.50 (s, 1H). m/z (ESI, +ve ion) 273 (M+H)+.

Step 3. 7-bromo-5-fluoroquinoline

A glass microwave reaction vessel was charged with (E)-3-(4-bromo-2-fluoro-6-nitrophenyl)acrylaldehyde (35 mg, 0.128 mmol), iron powder (0.018 mL, 2.55 mmol, Aldrich) and ammonium chloride (6.83 mg, 0.128 mmol, Aldrich) in ethanol (1 mL). The reaction mixture was stirred and heated in an Emrys Optimizer microwave reactor (Personal Chemistry, Biotage AB, Inc., Upssala, Sweden) at 120° C. for 5 min. The mixture was filtered through a pad of Celite® (diatomaceous earth), washed with EtOAc. The solvent was removed in vacuo and the residue was purified by silica gel chromatography eluting with 20% EtOAc/hexanes to give 7-bromo-5-fluoroquinoline (16 mg, 0.071 mmol, 55.4% yield). $^1$H NMR (300 MHz, $CDCl_3$) δ 7.20-7.34 (m, 1H) 7.59-7.74 (m, 1H) 7.90 (d, J=8.48 Hz, 1H) 8.58 (d, J=1.61 Hz, 1H) 8.95 (d, J=2.34 Hz, 1H). m/z (ESI, +ve ion) 227.9 (M+H)+.

Step 4. N-(diphenylmethylene)-5-fluoroquinolin-7-amine

A mixture of 7-bromo-5-fluoroquinoline (128 mg, 0.566 mmol), benzophenone imine (0.143 mL, 0.849 mmol, Aldrich), $Pd(dba)_2$ (32.6 mg, 0.057 mmol, Strem), 2,2'-bis(diphenylphosphino)-1,1'-binaphthyl (70.5 mg, 0.113 mmol, Aldrich) and sodium 2-methylpropan-2-olate (82 mg, 0.849 mmol, Aldrich) in toluene (4 mL) was stirred at 110° C. for 5 h. The mixture was cooled down to room temperature. The reaction mixture was diluted with saturated $NH_4Cl$ (10 mL) and extracted with EtOAc (2×40 mL). The combined organic extracts were washed with saturated NaCl (10 mL) and dried over $Na_2SO_4$. The solution was filtered and concentrated in vacuo to give the crude material as a light-yellow solid, which was used for the next step without purification.

Step 5. 5-fluoroquinolin-7-amine

A mixture of N-(diphenylmethylene)-5-fluoroquinolin-7-amine (185 mg, 0.566 mmol) and hydrochloric acid (1.132 mL, 1.132 mmol) in THF (5 mL) was stirred at room temperature for 3 h. The reaction mixture was diluted with saturated $NaHCO_3$ (5 mL) and extracted with EtOAc (2×30 mL). The organic extract was washed with saturated NaCl (5 mL) and dried over $Na_2SO_4$. The solution was filtered and concentrated in vacuo to give the crude material as a light-yellow oil. The crude product was purified by silica gel chromatography eluting with 80% EtOAc/hexanes to give 5-fluoroquinolin-7-amine (82 mg, 0.506 mmol, 89% yield). $^1$H NMR (300 MHz, $CDCl_3$) δ 4.02 (s, 2H) 7.11 (dd, J=9.65, 8.18 Hz, 1H) 7.29-7.40 (m, 1H) 7.45 (d, J=2.48 Hz, 1H) 7.76 (d, J=8.48 Hz, 1H) 8.53 (d, J=2.78 Hz, 1H). m/z (ESI, +ve ion) 163.1 (M+H)+.

Step 6. (R)-N-(3-(4-(bis(4-methoxybenzyl)amino)-6-methyl-1,3,5-triazin-2-yl)-5-(1-(4-(methylsulfonyl) piperazin-1-yl)ethyl)pyridin-2-yl)-5-fluoroquinolin-7-amine A mixture of (R)-4-(2-fluoro-5-(1-(4-(methylsulfonyl) piperazin-1-yl)ethyl)pyridin-3-yl)-N,N-bis(4-methoxybenzyl)-6-methyl-1,3,5-triazin-2-amine (Example 146, Step 6) (140 mg, 0.220 mmol), 5-fluoroquinolin-7-amine (35.7 mg, 0.220 mmol) and lithium bis(trimethylsilyl)amide (1.0 M in THF; 0.661 mL, 0.661 mmol, Aldrich) in THF (3 mL) was stirred at 0° C. for 1 h. The reaction mixture was diluted with saturated NH₄Cl (10 mL) and extracted with EtOAc (2×30 mL). The organic extract was washed with saturated NaCl (10 mL) and dried over Na₂SO₄. The solution was filtered and concentrated in vacuo to give the crude material as yellow oil. The crude product was purified by silica gel chromatography eluting with EtOAc to give (R)-N-(3-(4-(bis(4-methoxybenzyl)amino)-6-methyl-1,3,5-triazin-2-yl)-5-(1-(4-(methylsulfonyl)piperazin-1-yl)ethyl)pyridin-2-yl)-5-fluoroquinolin-7-amine (122 mg, 0.157 mmol, 71.2% yield). ¹H NMR (300 MHz, CDCl₃) δ 1.40 (d, J=6.72 Hz, 3H) 2.57 (dd, J=11.91, 4.17 Hz, 4H) 2.65 (s, 3H) 2.67 (s, 3H) 3.07-3.24 (m, 4H) 3.81 (s, 3H) 4.76-4.98 (m, 4H) 6.86 (dd, J=12.28, 8.62 Hz, 4H) 7.11-7.25 (m, 9H) 7.38-7.52 (m, 1H) 7.82 (d, J=8.48 Hz, 1H) 8.42 (d, J=2.19 Hz, 1H) 8.77 (d, J=2.34 Hz, 1H) 8.91 (d, J=2.49 Hz, 1H) 9.14 (d, J=2.05 Hz, 1H) 12.57 (s, 1H). m/z (ESI, +ve ion) 778.1 (M+H)⁺.

Step 7. (R)-N-(3-(4-amino-6-methyl-1,3,5-triazin-2-yl)-5-(1-(4-(methylsulfonyl)piperazin-1-yl)ethyl)pyridin-2-yl)-5-fluoroquinolin-7-amine A glass microwave reaction vessel was charged with (R)-N-(3-(4-(bis(4-methoxybenzyl)amino)-6-methyl-1,3,5-triazin-2-yl)-5-(1-(4-(methylsulfonyl)piperazin-1-yl)ethyl)pyridin-2-yl)-5-fluoroquinolin-7-amine (82 mg, 0.105 mmol) and trifluoroacetic acid (1 mL, 13.46 mmol, Aldrich). The reaction mixture was stirred and heated in an oil bath at 75° C. for 14 h. The solvent was removed in vacuo. The residue was treated with 10% MeOH/CH₂Cl₂ (40 mL). The reaction mixture was washed with sat. NaHCO₃ (10 mL), saturated NaCl (10 mL) and dried over Na₂SO₄. The solution was filtered and concentrated in vacuo to give the crude material as a yellow solid. The crude product was purified by silica gel chromatography eluting with 5% MeOH/CH₂Cl₂ to give (R)-N-(3-(4-amino-6-methyl-1,3,5-triazin-2-yl)-5-(1-(4-(methylsulfonyl)piperazin-1-yl)ethyl)pyridin-2-yl)-5-fluoroquinolin-7-amine (33 mg, 0.061 mmol, 58.2% yield). ¹H NMR (300 MHz, CDCl₃) δ 1.47 (d, J=6.72 Hz, 3H) 2.52-2.72 (m, 7H) 2.78 (s, 3H) 3.25 (t, J=4.17 Hz, 4H) 3.60 (q, J=6.53 Hz, 1H) 5.49 (s, 2H) 7.12-7.24 (m, 1H) 7.39-7.54 (m, 1H) 7.83 (d, J=8.33 Hz, 1H) 8.48 (d, J=2.19 Hz, 1H) 8.77 (d, J=2.05 Hz, 1H) 8.96 (d, J=2.34 Hz, 1H) 9.25 (d, J=1.90 Hz, 1H) 12.51 (s, 1H). m/z (ESI, +ve ion) 538.1 (M+H)⁺.

Example 288

N-(3-(4-amino-6-methyl-1,3,5-triazin-2-yl)-5-(1-morpholinoethyl)pyridin-2-yl)benzo[d]thiazol-5-amine

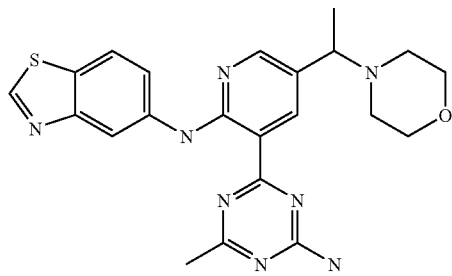 [SMILES: Cc1nc(N)nc(-c2cc(C(C)N3CCOCC3)cnc2Nc2ccc3scnc3c2)n1]

Step 1.
2-fluoro-5-(1-morpholinoethyl)pyridin-3-ylboronic acid

A stirred solution of diisopropylamine (2.152 mL, 15.35 mmol) in tetrahydrofuran (20 mL) was treated with n-butyllithium 1.6M in Hexanes (9.60 mL, 15.35 mmol) at −40° C. The yellow solution was stirred at the same temperature for 1 h and then cooled to −78° C. A solution of 4-(1-(6-fluoropyridin-3-yl)ethyl)morpholine (2.69 g, 12.79 mmol) in THF (15 mL) was added via cannula over 20 min. The deep-red mixture was stirred at the same temperature for 1.5 h. Then a solution of triisopropyl borate (4.41 mL, 19.19 mmol) in THF (10 mL) was added slowly into the mixture. The resulting mixture was stirred at the same temperature for 30 min and then the cooling bath was removed. After the reaction mixture had warmed to room temperature, the tan mixture was quenched with 1 N NaOH (aq) (15 mL) and stirred. The separated aqueous layer was removed and the flask was rinsed with 1 N NaOH (aq) (2×20 mL) and the organic layer was extracted with 1 N NaOH (2×10 mL). The aqueous layer was collected and carefully acidified with 5 N HCl until acidic (pH 5 about 6) and the resulting cloudy mixture was extracted with EtOAc (3×30 mL). The combined organic phases were dried over sodium sulfate, filtered and concentrated in vacuo. The product remained in the aqueous layer. The aqueous layer was frozen and the water removed by lyophilization. The mixture was diluted with 1:1 MeOH/DCM and placed into a sonicator for 5 min. The mixture was filtered through a fine-fritted funnel and the filtrate was concentrated in vacuo to give 2-fluoro-5-(1-morpholinoethyl)pyridin-3-ylboronic acid (3.120 g, 12.28 mmol, 96% yield) as a yellow solid. ¹H NMR (400 MHz, d₄-MeOH) δ 8.00 (dd, J=8.22, 2.54 Hz, 1H) 7.88 (d, J=2.35 Hz, 1H) 3.68 (t, J=4.69 Hz, 4H) 3.40-3.54 (m, 1H) 2.56 (d, J=10.76 Hz, 2H) 2.35-2.50 (m, 2H) 1.41 (t, J=6.65 Hz, 3H). m/z (ESI, +ve ion) 255.1 (M+H)⁺.

Step 2. 4-(2-fluoro-5-(1-morpholinoethyl)pyridin-3-yl)-N,N-bis(4-methoxybenzyl)-6-methyl-1,3,5-triazin-2-amine A glass microwave reaction vessel was charged with 4-chloro-N,N-bis(4-methoxybenzyl)-6-methyl-1,3,5-triazin-2-amine (0.433 g, 1.126 mmol), 2-fluoro-5-(1-morpholinoethyl)pyridin-3-ylboronic acid (0.260 g, 1.023 mmol), potassium acetate (0.308 g, 3.14 mmol), Am-Phos (0.051 g, 0.082 mmol), dioxane (3 mL) and water (0.5 mL, 27.8 mmol). The reaction mixture was stirred and heated in a CEM Explorer Microwave Unit for 10 min at 120° C., while 100 Watts of energy was supplied via Powermax® (simultaneous heating while cooling technology). The reaction mixture was diluted with sat. sodium bicarbonate (10 mL) and extracted with chloroform (3×10 mL). The organic extracts were combined and dried over sodium sulfate. The solution was filtered and concentrated in vacuo to give the crude material as a yellow oil. The crude product was adsorbed onto a plug of silica gel and chromatographed through a silica gel column (40 gram), eluting with 50% ethyl acetate/hexanes to give 4-(2-fluoro-5-(1-morpholinoethyl)pyridin-3-yl)-N,N-bis(4-methoxybenzyl)-6-methyl-1,3,5-triazin-2-amine (0.300 g, 0.537 mmol, 52.5% yield) as a light-yellow oil. ¹H NMR (400 MHz, d₆-DMSO) δ 8.46 (d, J=9.59 Hz, 1H) 8.31 (d, J=1.57 Hz, 1H) 7.25 (d, J=7.63 Hz, 4H) 6.90 (dd, J=10.27, 8.71 Hz, 4H) 4.77 (d, J=13.30 Hz, 3H) 3.66-3.79 (m, 6H)

3.47-3.61 (m, 5H) 3.36 (s, 4H) 3.18 (d, J=5.09 Hz, 1H) 2.49-2.53 (m, 3H) 2.40 (s, 2H) 2.14-2.34 (m, 2H). m/z (ESI, +ve ion) 559.2 (M+H)$^+$.

Step 3. N-(3-(4-amino-6-methyl-1,3,5-triazin-2-yl)-5-(1-morpholinoethyl)pyridin-2-yl)benzo[d]thiazol-5-amine A mixture of 4-(2-fluoro-5-(1-morpholinoethyl)pyridin-3-yl)-N,N-bis(4-methoxybenzyl)-6-methyl-1,3,5-triazin-2-amine (0.300 g, 0.537 mmol) and benzo[d]thiazol-5-amine (0.202 g, 1.343 mmol) in THF (10 mL) was chilled to 0° C. in an ice bath. Then sodium bis(trimethylsilyl)amide (1.0 M solution in THF, Aldrich; 2.148 mL, 2.148 mmol) was added into the mixture via syringe. After the addition, the ice bath was removed and the mixture was allowed to stir under an inert atmosphere for 1 h. The reaction mixture was diluted with water (30 mL) and the organic layer was extracted with chloroform (3×20 mL). The combined organic extracts were dried over sodium sulfate, filtered and concentrated in vacuo. This gave the crude bis-PMB protected product as a tan oil. This crude material was treated with trifluoroacetic acid (1.8 mL) and trifluoromethanesulfonic acid (0.2 mL). The reaction mixture was placed into a pre-heated bath (70° C.) and allowed to stir under inert atmosphere for 10 min. The mixture was removed from the heat source and allowed to cool to ambient temperature. The mixture was concentrated in vacuo. The crude residue was diluted with DCM (10 mL), and then sodium carbonate (1.5 g) was added to the mixture with stirring. The mixture was filtered and concentrated in vacuo. The crude was purified by reverse phase HPLC (Varian, 5-70% acetonitrile in water with trifluoroacetic acid as additive 0.1% v/v in each solvent) to give N-(3-(4-amino-6-methyl-1,3,5-triazin-2-yl)-5-(1-morpholinoethyl)pyridin-2-yl)benzo[d]thiazol-5-amine (0.015 g, 0.033 mmol, 6.23% yield) as a tan solid. $^1$H NMR (400 MHz, d$_6$-DMSO) δ 12.24 (s, 1H) 9.36 (s, 1H) 8.92 (s, 1H) 8.75 (s, 1H) 8.36 (s, 1H) 8.06 (d, J=8.61 Hz, 1H) 7.92 (s, 1H) 7.82 (d, J=8.61 Hz, 2H) 3.57 (s, 4H) 3.29-3.46 (m, 1H) 2.50 (d, J=7.82 Hz, 5H) 2.34 (s, 2H) 1.36 (d, J=6.46 Hz, 3H). m/z (ESI, +ve ion) 449.1 (M+H)$^+$.

Example 289

4-(1-(5-(4-amino-6-methyl-1,3,5-triazin-2-yl)-6-(benzo[d]thiazol-5-ylamino)pyridin-3-yl)ethyl)-N,N-dimethylpiperazine-1-carboxamide

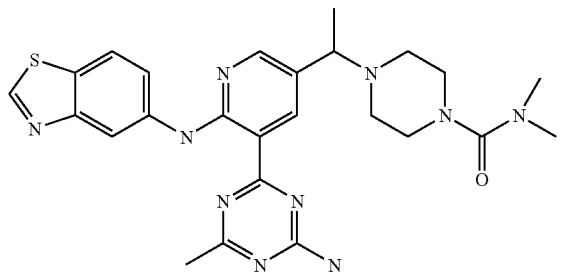 [SMILES: Cc1nc(N)nc(-c2cc(C(C)N3CCN(C(=O)N(C)C)CC3)cnc2Nc2ccc3scnc3c2)n1]

Step 1. 5-(1-bromoethyl)-2-fluoropyridine

A mixture of 6-fluoronicotinaldehyde (10.000 g, 80 mmol) in THF (300 mL) was chilled to −10° C. in a dry ice/acetone bath, then methylmagnesium bromide (3 M soln. in diethyl ether, Aldrich; 27.4 mL, 82 mmol) was added into the reaction mixture via addition funnel After the addition, the ice bath was removed and the reaction mixture was allowed to stir under inert atmosphere 45 min. The mixture was chilled to −10° C. in a dry ice/acetone bath, then methanesulfonyl chloride (6.50 mL, 84 mmol) was slowly added into the reaction mixture via syringe. After the addition, the ice bath was removed and the reaction mixture was allowed to stir under an inert atmosphere for 2 h. The reaction mixture was quenched with water (100 mL) and diluted with chloroform (300 mL). The organic layer was extracted with chloroform (3×50 mL). The combined organic extracts were dried over sodium sulfate, filtered and concentrated in vacuo to give 5-(1-bromoethyl)-2-fluoropyridine (16.31 g, 80 mmol, 100% yield) as a tan oil. This material was carried into the next step of the synthesis immediately to prevent decomposition. $^1$H NMR (400 MHz, CDCl$_3$) δ 8.25 (d, J=2.35 Hz, 1H) 7.93 (td, J=8.02, 2.54 Hz, 1H) 6.90-7.11 (m, 1H) 5.21 (q, J=6.85 Hz, 1H) 2.06 (d, J=7.04 Hz, 3H). m/z (ESI, +ve ion) 205.9 (M+H)$^+$.

Step 2. tert-butyl 4-(1-(6-fluoropyridin-3-yl)ethyl)piperazine-1-carboxylate

A mixture of 5-(1-bromoethyl)-2-fluoropyridine (17.65 g, 87 mmol) and tert-butyl piperazine-1-carboxylate (16.92 g, 91 mmol) in acetonitrile (300 mL). was treated with potassium carbonate (14.35 g, 104 mmol) and potassium iodide (2.87 g, 17.30 mmol). The mixture was placed into a pre-heated (70° C.) bath and allowed to stir under inert atmosphere overnight. The reaction mixture was diluted with chloroform (200 mL) and water (100 mL). The organic layer was extracted with chloroform (3×50 mL). The combined organic extracts were dried over sodium sulfate, filtered and concentrated in vacuo. The crude material was adsorbed onto a plug of silica gel and purified by chromatography through a silica-gel column (330 g) eluting with 50% ethyl acetate/hexanes to give tert-butyl 4-(1-(6-fluoropyridin-3-yl)ethyl)piperazine-1-carboxylate (17.27 g, 55.8 mmol, 64.5% yield) as a yellow oil. m/z (ESI, +ve ion) 310.1 (M+H)$^+$.

Step 3. 5-(1-(4-(tert-butoxycarbonyl)piperazin-1-yl)ethyl)-2-fluoropyridin-3-ylboronic acid A solution of tert-butyl 4-(1-(6-fluoropyridin-3-yl)ethyl)piperazine-1-carboxylate (8.41 g, 27.2 mmol) in tetrahydrofuran (100 mL) was chilled to −78° C. in a dry ice/acetone bath. Then n-butyllithium (1.6 M in hexanes; Aldrich; 18.69 mL, 29.9 mmol) was added via cannula into the mixture. The deep red solution was stirred at the same temperature for 1 h, then triisopropyl borate (7.50 mL, 32.6 mmol) was added into the mixture. The resulting mixture was stirred at the same temperature (−78° C.) for 30 min, then the ice bath was removed. After the reaction mixture warmed up to room temperature, the tan mixture was quenched with 1 N NaOH (aq) (50 mL) and stirred 10 min. The separated aqueous layer was collected and the round-bottomed flask was rinsed with 1 N NaOH(aq) (2×10 mL). The aqueous layer was carefully acidified with 10% HCl until acidic (about pH 5 to 6) and the resulting cloudy mixture was extracted with 3:1 dichloromethane/methanol (3×20 mL). The combined organic extracts were dried over sodium sulfate, filtered and concentrated in vacuo. This gave 5-(1-(4-(tert-butoxycarbonyl)piperazin-1-yl)ethyl)-2-fluoropyridin-3-ylboronic acid (5.507 g, 15.59 mmol, 57.4% yield) as tan solid. $^1$H NMR (400 MHz, d$_6$-DMSO) δ 7.79-8.70 (m, 2H) 3.66 (t, J=6.36 Hz, 1H) 3.34 (s, 4H) 2.56 (s, 3H) 2.39 (s, 4H) 1.26-1.51 (m, 12H). m/z (ESI, +ve ion) 354.2 (M+H)$^+$.

Step 4. tert-butyl 4-(1-(5-(4-(bis(4-methoxybenzyl) amino)-6-methyl-1,3,5-triazin-2-yl)-6-fluoropyridin-3-yl)ethyl)piperazine-1-carboxylate A glass microwave reaction vessel was charged with 4-chloro-N,N-bis(4-methoxybenzyl)-6-methyl-1,3,5-triazin-2-amine (2.140 g, 5.56 mmol) and 5-(1-(4-(tert-butoxycarbonyl)piperazin-1-yl)ethyl)-2-fluoropyridin-3-ylboronic acid (4.12 g, 11.68 mmol) in dioxane (25 mL). Then A-Phos (0.394 g, 0.556 mmol), potassium acetate (1.637 g, 16.68 mmol) and water (3 mL) were added into the reaction mixture. The reaction mixture was stirred and heated in a CEM Voyager Microwave (Large Scale Unit) at 120° C. for 20 min (160 watts, Powermax feature on). The mixture was diluted with dichloromethane (20 mL), water (20 mL) and brine solution (10 mL). The organic layer was collected by extracting with dichloromethane (3×15 mL). The combined organic extracts were dried over sodium sulfate, filtered and concentrated in vacuo. This gave the crude product as a tan oil. The crude material was adsorbed onto a plug of silica gel and purified by chromatography through silica-gel column (220 g), eluting with 100% ethyl acetate to give tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (3.65 g, 5.55 mmol, 99% yield) as a tan solid. $^1$H NMR (400 MHz, d$_6$-DMSO) δ 8.47 (dd, J=9.39, 2.35 Hz, 1H) 8.31 (d, J=1.57 Hz, 1H) 7.26 (dd, J=8.61, 3.33 Hz, 4H) 6.90 (dd, J=12.42, 8.71 Hz, 4H) 4.78 (d, J=12.91 Hz, 4H) 3.74 (d, J=8.02 Hz, 6H) 3.70 (d, J=6.85 Hz, 1H) 3.28 (d, J=6.06 Hz, 4H) 2.50-2.53 (m, 3H) 2.21-2.39 (m, 4H) 1.37 (d, J=1.76 Hz, 15H). m/z (ESI, +ve ion) 658.3 (M+H)$^+$.

Step 5. N-(3-(4-(bis(4-methoxybenzyl)amino)-6-methyl-1,3,5-triazin-2-yl)-5-(1-(piperazin-1-yl)ethyl) pyridin-2-yl)benzo[d]thiazol-5-amine A glass microwave reaction vessel (80 mL) was charged with tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (3.65 g, 5.55 mmol) and trifluoroacetic acid (6.41 mL, 83 mmol) in dichloroethane (30 mL). The reaction mixture was stirred and heated in a CEM Voyager Model (Large-Scale Unit) Microwave at 80° C. for 5 min (100 watts, Powermax feature on). The mixture was added to a round bottom flask and concentrated in vacuo. The crude residue was diluted with THF (10 mL), then benzo[d]thiazol-5-amine (0.539 g, 3.59 mmol) was added to the reaction mixture with stirring. The mixture was chilled to 0° C. in an ice bath, then sodium bis(trimethylsilyl)amide (1.0 M in THF, Aldrich; 5.74 mL, 5.74 mmol) was added slowly via syringe into the mixture. After the addition, the ice bath was removed and the mixture allowed to stir under inert atmosphere for 1 h. The reaction mixture was diluted with sat. sodium bicarbonate (10 mL) and extracted with chloroform (3×15 mL). The combined organic extracts were dried over sodium sulfate, filtered and concentrated in vacuo to give a tan oil. The crude material was adsorbed onto a plug of silica gel and purified by chromatography through a silica-gel column (80 g) eluting with a 20% mixture of 10:1 methanol and ammonium hydroxide/dichloromethane to give N-(3-(4-(bis(4-methoxybenzyl)amino)-6-methyl-1,3,5-triazin-2-yl)-5-(1-(piperazin-1-yl)ethyl)pyridin-2-yl)benzo[d]thiazol-5-amine (0.651 g, 0.946 mmol, 66.0% yield) as a tan oil. $^1$H NMR (400 MHz, CDCl$_3$) δ 12.06 (s, 1H) 8.96 (s, 1H) 8.74 (d, J=2.54 Hz, 1H) 8.63 (d, J=1.96 Hz, 1H) 8.31 (d, J=2.35 Hz, 1H) 8.12 (d, J=1.76 Hz, 1H) 7.78 (td, J=8.12, 2.35 Hz, 1H) 7.60 (dd, J=8.61, 1.96 Hz, 1H) 7.14-7.28 (m, 4H) 6.80-6.91 (m, 4H) 4.76-4.91 (m, 4H) 3.72-3.82 (m, 6H) 3.37-3.51 (m, 1H) 2.86 (dt, J=12.67, 4.72 Hz, 4H) 2.40-2.55 (m, 4H) 2.62 (s, 3H) 2.32-2.40 (m, 1H). m/z (ESI, +ve ion) 688.2 (M+H)$^-$.

Step 6. 4-(1-(5-(4-amino-6-methyl-1,3,5-triazin-2-yl)-6-(benzo[d]thiazol-5-ylamino)pyridin-3-yl) ethyl)-N,N-dimethylpiperazine-1-carboxamide A mixture of N-(3-(4-(bis(4-methoxybenzyl)amino)-6-methyl-1,3,5-triazin-2-yl)-5-(1-(piperazin-1-yl)ethyl)pyridin-2-yl)benzo[d]thiazol-5-amine (0.300 g, 0.436 mmol) in dichloromethane (10 mL) was chilled to 0° C. in an ice bath, then triethylamine (0.304 mL, 2.181 mmol) was added to the mixture. After 10 min, dimethylcarbamic chloride (Aldrich; 0.141 g, 1.308 mmol) was added into the mixture dropwise via syringe. After the addition, the ice bath was removed and the mixture was allowed to stir under inert atmosphere overnight. The mixture was diluted with chloroform (20 mL) and water (10 mL). The organic layer was extracted with chloroform (3×10 mL). The combined combined organic extracts were dried over sodium sulfate, filtered and concentrated in vacuo. The crude material was adsorbed onto a plug of silica gel and purified by chromatography through a SiliCycle SiliaSep pre-packed silica-gel column (40 g), eluting with 20% MeOH in CH$_2$Cl$_2$ to give the urea as a tan oil. This material was diluted with trifluoroacetic acid (1.803 mL, 23.40 mmol) and stirred 5 min. Then trifluoromethanesulfonic acid (0.214 mL, 2.406 mmol) was added to the mixture. The reaction mixture was placed into a pre-heated (70° C.) bath and allowed to stir under inert atmosphere for 10 min. The heating bath was removed and the mixture was allowed to cool to ambient temperature. The mixture was concentrated in vacuo. The residue was diluted with dichloromethane (10 mL), then sodium carbonate (2.0 g) was added into the mixture with stirring. After 5 min, methanol (5 mL) was added into the mixture and allowed to stir 20 min. The mixture was filtered and concentrated in vacuo. The mixture was recrystallized from ethyl acetate/ethyl ether. This gave 4-(1-(5-(4-amino-6-methyl-1,3,5-triazin-2-yl)-6-(benzo[d]thiazol-5-ylamino) pyridin-3-yl)ethyl)-N,N-dimethylpiperazine-1-carboxamide (0.070 g, 0.135 mmol, 61.7% yield) as a yellow solid. $^1$H NMR (400 MHz, d$_6$-DMSO) δ 12.24 (s, 1H) 9.36 (s, 1H) 8.92 (s, 1H) 8.92 (s, 1H) 8.37 (s, 1H) 7.91 (s, 1H) 8.05 (s, 1H) 7.83 (s, 2H) 3.53 (m, 1H) 3.10 (s, 4H) 2.70 (s, 6H) 2.43-2.55 (m, 3H) 2.36 (d, J=4.50 Hz, 4H) 1.38 (d, J=6.06 Hz, 3H). m/z (ESI, +ve ion) 519.1 (M+H)$^+$.

Example 290

N-(3-(4-amino-6-methyl-1,3,5-triazin-2-yl)-5-(1-(4-(methylsulfonyl)piperazin-1-yl)ethyl)pyridin-2-yl) benzo[d]thiazol-5-amine

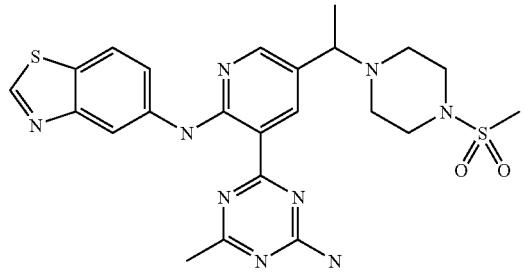 [SMILES: Cc1nc(N)nc(-c2cc(C(C)N3CCN(S(C)(=O)=O)CC3)cnc2Nc2ccc3scnc3c2)n1]

Step 1. N-(3-(4-amino-6-methyl-1,3,5-triazin-2-yl)-5-(1-(4-(methylsulfonyl)piperazin-1-yl)ethyl)pyridin-2-yl)benzo[d]thiazol-5-amine A stirred mixture of N-(3-(4-(bis(4-methoxybenzyl)amino)-6-methyl-1,3,5-triazin-2-yl)-5-(1-(piperazin-1-yl)ethyl)pyridin-2-yl)benzo[d]thiazol-5-amine (0.350 g, 0.509 mmol) in dichloromethane (10 mL) was treated with triethylamine (0.355 mL, 2.54 mmol). After 10 min, methanesulfonyl chloride (Aldrich; 0.119 mL, 1.526 mmol) was added into the mixture slowly via syringe. After the addition, the reaction mixture was placed into a pre-heated (70° C.) bath and allowed to stir under inert atmosphere for 1.5 h. The heating bath was removed and the mixture was allowed to cool to ambient temperature. The mixture was diluted with chloroform (20 mL) and water (10 mL) and the organic layer was extracted with chloroform (3×10 mL). The combined organic extracts were dried (magnesium sulfate), filtered and concentrated in vacuo. The crude material was adsorbed onto a plug of silica gel and purified by chromatography through a silica-gel column (40 g) eluting with 20% methanol/dichloromethane to give the bis-PMB protected material as a tan oil. This material was diluted with trifluoroacetic acid (1.8 mL, 23.36 mmol) and allowed to stir 5 min. Then trifluoromethanesulfonic acid (0.2 mL, 2.252 mmol) was added into the mixture. The mixture was placed into a pre-heated (70° C.) bath and allowed to stir under inert atmosphere for 10 min. The heating bath was removed and the mixture was allowed to cool to ambient temperature. The mixture was concentrated in vacuo. The mixture was diluted with dichloromethane (10 mL) and sodium carbonate (1.00 g) was added into the mixture, then allowed to stir for 5 min. Then methanol (3 mL) was added into the mixture and allowed to stir 20 min. The mixture was filtered and the filtrate was concentrated in vacuo. The crude product was recrystallized from ethyl acetate/diethyl ether to give N-(3-(4-amino-6-methyl-1,3,5-triazin-2-yl)-5-(1-(4-(methylsulfonyl)piperazin-1-yl)ethyl)pyridin-2-yl)benzo[d]thiazol-5-amine (0.035 g, 0.067 mmol, 17.71% yield) as a tan solid. $^{1}$H NMR (400 MHz, d$_6$-DMSO) δ 12.23 (s, 1H) 9.36 (s, 1H) 8.92 (s, 1H) 8.74 (s, 1H) 8.39 (s, 1H) 8.05 (s, 1H) 7.91 (s, 1H) 7.79 (m, 2H) 3.59 (m, 1H) 3.10 (s, 4H) 2.86 (s, 3H) 2.50 (d, J=8.80 Hz, 4H) 1.99 (s, 3H) 1.38 (d, J=6.06 Hz, 3H). m/z (ESI, +ve ion) 526.0 (M+H)$^+$.

Examples 291 and 292

(R)-4-(2-(5-fluoro-6-methoxypyridin-3-ylamino)-5-(1-morpholinoethyl)pyridin-3-yl)-6-methyl-1,3,5-triazin-2-amine and (S)-4-(2-(5-fluoro-6-methoxypyridin-3-ylamino)-5-(1-morpholinoethyl)pyridin-3-yl)-6-methyl-1,3,5-triazin-2-amine

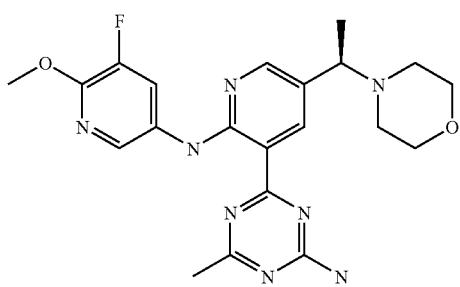

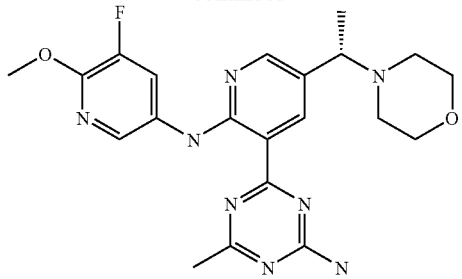

A mixture of isomers of 4-(2-(5-fluoro-6-methoxypyridin-3-ylamino)-5-(1-morpholinoethyl)pyridin-3-yl)-6-methyl-1,3,5-triazin-2-amine was prepared following an analogous procedure to Example 288, substituting 2-methoxy-3-fluoro-5-aminopyridine in place of benzo[d]thiazol-5-amine in Step 2. The isomers were separated using chiral SFC preparative chromatography. The following conditions were used:
Column: Chiralcel OJ-H (3×15 cm)
A: Liquid CO$_2$
B: 25% 1:1 heptane:ethanol (0.2% DEA), isocratic
Flow Rate: 80 mL/min, 220 nm.

The two separate peaks containing the two enantiomers were collected, concentrated, and dried under high vacuum to give the two enantiomers. The absolute stereochemistries were not determined First Eluting Peak: (Isomer 1; Example 291)
$^{1}$H NMR (400 MHz, CDCl$_3$) δ 11.90 (s, 1H) 8.73 (d, J=2.35 Hz, 1H) 8.29 (td, J=6.16, 2.15 Hz, 2H) 8.04 (d, J=2.15 Hz, 1H) 5.52 (s, 2H) 4.02 (s, 3H) 3.71 (t, J=4.60 Hz, 4H) 3.40 (q, J=6.72 Hz, 1H) 2.57 (s, 3H) 2.51 (s, 2H) 2.39-2.45 (m, 2H) 1.41 (d, J=6.65 Hz, 3H). m/z (ESI, +ve ion) 441.1 (M+H)$^+$.

Second Eluting Peak: (Isomer 2; Example 292)
$^{1}$H NMR (400 MHz, CDCl$_3$) δ 11.91 (s, 1H) 8.72 (d, J=2.35 Hz, 1H) 8.26-8.31 (m, 2H) 8.04 (d, J=2.35 Hz, 1H) 5.65 (s, 2H) 4.03 (s, 3H) 3.69-3.76 (m, 4H) 3.39 (q, J=6.65 Hz, 1H) 2.49-2.60 (m, 5H) 2.39-2.48 (m, 2H) 1.42 (d, J=6.65 Hz, 3H). m/z (ESI, +ve ion) 441.1 (M+H)$^+$.

Example 293

N-(3-(4-amino-6-methyl-1,3,5-triazin-2-yl)-5-((R)-1-((S)-2-methyl-4-(methylsulfonyl)piperazin-1-yl)ethyl)pyridin-2-yl)benzo[d]thiazol-5-amine

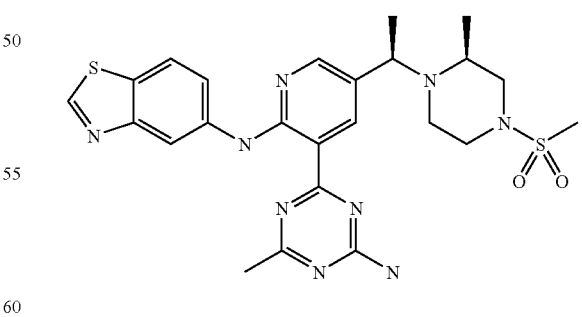

Step 1. N-(3-(4-amino-6-methyl-1,3,5-triazin-2-yl)-5-((R)-1-((S)-2-methylpiperazin-1-yl)ethyl)pyridin-2-yl)benzo[d]thiazol-5-amine A mixture of (S)-tert-butyl 4-((R)-1-(5-(4-(bis(4-methoxybenzyl)amino)-6-methyl-1,3,5-triazin-2-yl)-6-fluoropyridin-3-yl)ethyl)-3-methylpiperazine-1-carboxylate (0.300 g, 0.447 mmol) and benzo[d]thiazol-5-amine (0.101 g, 0.670 mmol) in THF (10 mL was chilled to 0° C. in an ice bath, then sodium bis(trimethylsilyl)amide (1.0 M in THF, Aldrich; 1.563 mL, 1.563 mmol) was added slowly via syringe into the mixture. After the addition, the ice bath was removed and the mixture was allowed to stir under inert atmosphere for 1 h. The reaction mixture was diluted with sat. sodium bicarbonate (10 mL) and extracted with chloroform (3×15 mL). The combined organic extracts were dried over sodium sulfate, filtered and concentrated in vacuo to give the crude material as a tan oil. The crude material was adsorbed onto silica gel and purified by chromatography through a silica-gel column (40 g) eluting with 100% ethyl acetate to give the bis-PMB protected material (0.056 g) as a tan oil. The crude residue was diluted with trifluoroacetic acid (0.9 mL) and trifluoromethanesulfonic acid (0.1 mL). The mixture was placed into a pre-heated (70° C.) bath and allowed to stir under inert atmosphere 10 min. The mixture was removed from the heating bath and allowed to cool to ambient temperature. The mixture was concentrated in vacuo. The mixture was diluted with DCM (10 mL) and stirred, while sodium carbonate (1.0 g) was added slowly into the mixture. After 2 min, methanol (3 mL) was added into the mixture and allowed to stir an additional 20 min. The mixture was filtered through a fine-fritted funnel The organic layer was concentrated in vacuo. This gave N-(3-(4-amino-6-methyl-1,3,5-triazin-2-yl)-5-((R)-1-((S)-2-methylpiperazin-1-yl)ethyl)pyridin-2-yl)benzo[d]thiazol-5-amine (0.206 g, 0.446 mmol, 100% yield) as a yellow solid. $^1$H NMR (300 MHz, CDCl$_3$) δ 12.06 (s, 1H) 8.98 (s, 1H) 8.74 (d, 1H) 8.66 (s, 1H) 8.31 (d, 1H) 7.36 range (m, 1H) 5.44 (s, 2H) 2.61 (s, 9H) 1.52 (s, 3H) 1.25 (s, 6H). m/z (ESI, +ve ion) 462.1 (M+H)$^+$.

Step 2. N-(3-(4-amino-6-methyl-1,3,5-triazin-2-yl)-5-((R)-1-((S)-2-methyl-4-(methylsulfonyl)piperazin-1-yl)ethyl)pyridin-2-yl)benzo[d]thiazol-5-amine A mixture of N-(3-(4-amino-6-methyl-1,3,5-triazin-2-yl)-5-((R)-1-((S)-2-methylpiperazin-1-yl)ethyl)pyridin-2-yl)benzo[d]thiazol-5-amine (0.100 g, 0.217 mmol) in THF (5 mL) was chilled to 0° C. in an ice bath, then sodium carbonate (0.115 g, 1.083 mmol) was added to the mixture while stirring. After 10 min, methanesulfonyl chloride (0.051 mL, 0.650 mmol) was added into the mixture slowly via syringe. After the addition, the ice bath was removed and the mixture was allowed to stir under inert atmosphere overnight. The mixture was diluted with chloroform (20 mL) and water (10 mL). The organic layer was extracted with chloroform (3×10 mL). The combined organic extracts were dried (magnesium sulfate), filtered and concentrated in vacuo. The crude material was adsorbed onto silica gel and purified by chromatography through a silica-gel column (25 g), eluting with a 20% mixture of 10:1 methanol/ammonium hydroxide in dichloromethane to give N-(3-(4-amino-6-methyl-1,3,5-triazin-2-yl)-5-((R)-1-((S)-2-methyl-4-(methylsulfonyl)piperazin-1-yl)ethyl)pyridin-2-yl)benzo[d]thiazol-5-amine (0.012 g, 0.022 mmol, 10.26% yield) as a yellow solid. $^1$H NMR (400 MHz, CDCl$_3$) δ 12.02 (s, 1H) 8.92 (s, 1H) 8.65 (s, 1H) 8.60 (s, 1H) 8.26 (d, J=2.35 Hz, 1H) 7.79-7.83 (m, 1H) 7.72 (dd, J=8.61, 1.56 Hz, 1H) 5.55 (s, 2H) 4.05 (q, J=7.04 Hz, 1H) 3.21 (s, 2H) 3.11 (s, 1H) 2.87 (s, 2H) 2.61-2.73 (m, 4H) 2.47-2.60 (m, 4H) 1.34-1.46 (m, 3H) 1.02-1.22 (m, 3H). m/z (ESI, +ve ion) 540.0 (M+H)$^+$.

Example 294

4-(1-(5-(4-amino-6-methyl-1,3,5-triazin-2-yl)-6-(5-fluoro-6-methoxypyridin-3-ylamino)pyridin-3-yl)ethyl)-N,N-dimethylpiperazine-1-carboxamide

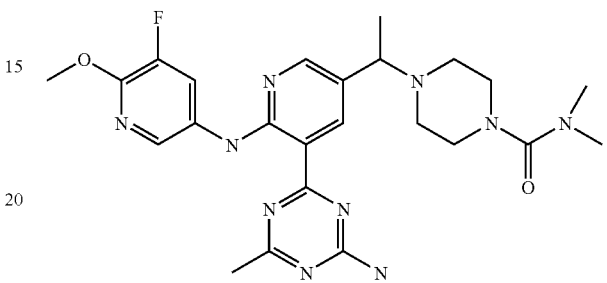

Step 1. tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate A glass microwave reaction vessel was charged with 4-chloro-N,N-bis(4-methoxybenzyl)-6-methyl-1,3,5-triazin-2-amine (0.300 g, 0.780 mmol) and 5-(1-(4-(tert-butoxycarbonyl)piperazin-1-yl)ethyl)-2-fluoropyridin-3-ylboronic acid (0.385 g, 1.091 mmol) in dioxane (3 mL). Then A-Phos (0.055 g, 0.078 mmol), potassium acetate (0.230 g, 2.339 mmol) and water (0.5 mL) were added into the reaction mixture. The reaction mixture was stirred and heated in a CEM Explorer Microwave at 120° C. for 10 min (120 watts, Powermax feature on). The mixture was diluted with dichloromethane (10 mL), water (10 mL) and brine (5 mL). The organic layer was collected by extracting with dichloromethane (3×10 mL). The combined organic extracts were dried (magnesium sulfate), filtered and concentrated in vacuo to give the crude material as tan oil. The crude material was adsorbed onto silica gel and purified by chromatography through a silica-gel column (40 g) eluting with 100% ethyl acetate to give tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (0.513 g, 0.780 mmol, 100% yield) as a tan solid. $^1$H NMR (400 MHz, CDCl$_3$) δ 8.19-8.32 (m, 1H) 7.91 (d, J=8.02 Hz, 1H) 7.22 (dd, J=8.61, 2.93 Hz, 4H) 6.83-6.97 (m, 4H) 4.82 (d, J=9.39 Hz, 4H) 3.76-3.83 (m, 6H) 3.67-3.71 (m, 3H) 3.40 (s, 4H) 3.01 (s, 1H) 2.55 (s, 3H) 2.45 (s, 2H) 2.37 (s, 2H) 2.04-2.07 (m, 3H) 1.38-1.53 (m, 9H). m/z (ESI, +ve ion) 658.3 (M+H)$^+$.

Step 2. 4-(2-(5-fluoro-6-methoxypyridin-3-ylamino)-5-(1-(piperazin-1-yl)ethyl)pyridin-3-yl)-6-methyl-1,3,5-triazin-2-amine A mixture of tert-butyl 4-(1-(5-(4-(bis(4-methoxybenzyl)amino)-6-methyl-1,3,5-triazin-2-yl)-6-fluoropyridin-3-yl)ethyl)piperazine-1-carboxylate (0.518 g, 0.788 mmol) and 5-fluoro-6-methoxypyridin-3-amine (0.280 g, 1.969 mmol) in THF (10 mL) was chilled to 0° C. in an ice bath, then sodium bis(trimethylsilyl)amide (1.0 M in THF, Aldrich; 3.15 mL, 3.15 mmol) was added slowly via syringe into the mixture. After the addition, the ice bath was removed and the mixture was allowed to stir under inert atmosphere for 1 h. The reaction mixture was diluted with sat. sodium bicarbonate (10 mL) and extracted with chloroform (3×15 mL). The combined organic extracts were dried over sodium sulfate, filtered and concentrated in vacuo to give the crude material as tan oil. The crude material was adsorbed onto silica gel and purified by chromatography through a silica-gel column (80 g) eluting with a 20% mixture of 10:1 methanol/ammonium hydroxide in dichloromethane to give the intermediate as a tan oil. The residue was diluted with trifluoroacetic acid (5 mL, 64.9 mmol) and trifluoromethanesulfonic acid (0.5 mL, 5.63 mmol) with stirring. The flask was placed into a preheated (70° C.) bath and allowed to stir 10 min. The heating bath was removed and the mixture allowed to cool to ambient temperature. The mixture was concentrated in vacuo. The crude residue was diluted with DCM (10 mL), then sodium carbonate (0.500 g) was added into the mixture with stirring. After 2 min, methanol (2 mL) was added into the mixture and allowed to stir 20 min. The mixture was filtered and the filtrate was concentrated in vacuo. The crude material was adsorbed onto silica gel and purified by chromatography through a silica-gel column (40 g), eluting with a 20% mixture of 10:1 methanol/ammonium hydroxide in dichloromethane to give 4-(2-(5-fluoro-6-methoxypyridin-3-ylamino)-5-(1-(piperazin-1-yl)ethyl)pyridin-3-yl)-6-methyl-1,3,5-triazin-2-amine (0.141 g, 0.321 mmol, 31.3% yield) as a tan solid. m/z (ESI, +ve ion) 440.1 (M+H)⁺.

Step 3. 4-(1-(5-(4-amino-6-methyl-1,3,5-triazin-2-yl)-6-(5-fluoro-6-methoxypyridin-3-ylamino)pyridin-3-yl)ethyl)-N,N-dimethylpiperazine-1-carboxamide A mixture of 4-(2-(5-fluoro-6-methoxypyridin-3-ylamino)-5-(1-(piperazin-1-yl)ethyl)pyridin-3-yl)-6-methyl-1,3,5-triazin-2-amine (0.141 g, 0.321 mmol) in dichloromethane (5 mL) was chilled to 0° C. in an ice bath, then triethylamine (0.224 mL, 1.604 mmol) was added to the mixture while stirring. After 10 min, dimethylcarbamic chloride (Aldrich; 0.104 g, 0.962 mmol) was added into the mixture slowly via syringe. After the addition, the ice bath was removed and the mixture was allowed to stir under inert atmosphere overnight. The mixture was diluted with chloroform (20 mL) and water (10 mL). The organic layer was extracted with chloroform (3×10 mL). The combined organic extracts were dried (magnesium sulfate), filtered and concentrated in vacuo. The crude material was adsorbed onto silica gel and purified by chromatography through a silica-gel column (25 g) eluting with a 20% mixture of 10:1 methanol/ammonium hydroxide in dichloromethane to give 4-(1-(5-(4-amino-6-methyl-1,3,5-triazin-2-yl)-6-(5-fluoro-6-methoxypyridin-3-ylamino)pyridin-3-yl)ethyl)-N,N-dimethylpiperazine-1-carboxamide (0.070 g, 0.137 mmol, 42.7% yield) as a tan solid. ¹H NMR (400 MHz, CDCl₃) δ 12.34 (s, 1H) 9.40 (d, J=2.15 Hz, 1H) 8.17-8.23 (dd, 1H) 8.12 (d, J=2.54 Hz, 1H) 8.09 (d, J=2.15 Hz, 1H) 4.04 (s, 3H) 3.10-3.98 (m, 9H) 2.85 (s, 6H) 2.56 (s, 3H) 1.88 (d, J=6.85 Hz, 3H). m/z (ESI, +ve ion) 533 (M+Na)⁺.

Example 295

N-(5-fluoro-6-methoxypyridin-3-yl)-5-((R)-1-((S)-2-methyl-4-(methylsulfonyl)piperazin-1-yl)ethyl)-3-(2-methyl-9H-purin-6-yl)pyridin-2-amine

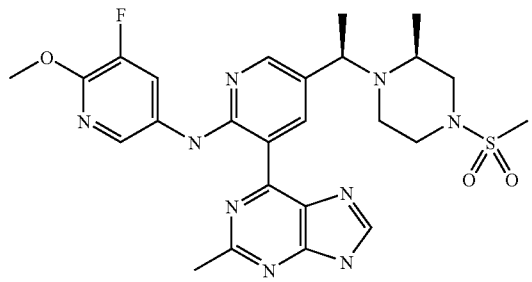

Step 1. (3S)-tert-butyl 4-((1R)-1-(6-fluoro-5-(2-methyl-9-(tetrahydro-2H-pyran-2-yl)-9H-purin-6-yl)pyridin-3-yl)ethyl)-3-methylpiperazine-1-carboxylate A glass microwave reaction vessel was charged with 6-chloro-2-methyl-9-(tetrahydro-2H-pyran-2-yl)-9H-purine (0.200 g, 0.791 mmol) and 5-((R)-1-((S)-4-(tert-butoxycarbonyl)-2-methylpiperazin-1-yl)ethyl)-2-fluoropyridin-3-ylboronic acid (0.407 g, 1.108 mmol) in dioxane (3 mL). Then A-Phos (0.056 g, 0.079 mmol), potassium acetate (0.233 g, 2.374 mmol) and water (0.5 mL) was added into the reaction mixture. The reaction mixture was stirred and heated in a CEM Explorer Microwave at 120° C. for 10 min (120 watts, Powermax feature on). The mixture was diluted with dichloromethane (10 mL), water (10 mL) and brine solution (5 mL). The organic layer was collected by extracting with dichloromethane (3×10 mL). The combined organic extracts were dried over sodium sulfate, filtered and concentrated in vacuo to give the crude material as tan oil. The crude material was adsorbed onto silica gel and purified by chromatography through a silica-gel column (40 g) eluting with 100% ethyl acetate, then with 10% methanol in dichloromethane to give (3S)-tert-butyl 4-((1R)-1-(6-fluoro-5-(2-methyl-9-(tetrahydro-2H-pyran-2-yl)-9H-purin-6-yl)pyridin-3-yl)ethyl)-3-methylpiperazine-1-carboxylate (0.342 g, 0.634 mmol, 80% yield) as a tan solid. ¹H NMR (400 MHz, CDCl₃) δ 8.26-8.35 (m, 3H) 5.86 (dd, J=10.37, 2.35 Hz, 1H) 4.19 (d, J=11.74 Hz, 2H) 3.83 (d, J=2.54 Hz, 1H) 2.89 (s, 3H) 2.54 (d, J=2.93 Hz, 2H) 2.16 (s, 1H) 2.11 (s, 1H) 2.07 (d, J=17.80 Hz, 1H) 1.81 (d, J=11.54 Hz, 2H) 1.59-1.75 (m, 3H) 1.39-1.49 (m, 15H) 1.02 (d, J=5.67 Hz, 3H). m/z (ESI, +ve ion) 540.2 (M+H).

Step 2. (3S)-tert-butyl 4-((1R)-1-(6-(5-fluoro-6-methoxypyridin-3-ylamino)-5-(2-methyl-9-(tetrahydro-2H-pyran-2-yl)-9H-purin-6-yl)pyridin-3-yl)ethyl)-3-methylpiperazine-1-carboxylate A mixture of (3S)-tert-butyl 4-((1R)-1-(6-fluoro-5-(2-methyl-9-(tetrahydro-2H-pyran-2-yl)-9H-purin-6-yl)pyridin-3-yl)ethyl)-3-methylpiperazine-1-carboxylate (0.323 g, 0.599 mmol) and 5-fluoro-6-methoxypyridin-3-amine (0.170 g, 1.197 mmol) in THF (15 mL) was chilled to −20° C. in a diluted dry ice/acetone bath, then lithium bis(trimethylsilyl) amide (1.0 M in THF, Aldrich; 1.796 mL, 1.796 mmol) was added slowly via syringe into the reaction mixture. After the addition, the ice bath was removed and the mixture was allowed to stir under inert atmosphere for 1 h. The mixture was diluted with chloroform (20 mL) and water (10 mL). The organic layer was extracted with chloroform (3×10 mL). The combined organic extracts were dried over sodium sulfate, filtered and concentrated in vacuo. The crude material was adsorbed onto silica gel and purified by chromatography through a silica-gel column (80 g) eluting with 100% EtOAc to give (3S)-tert-butyl 4-((1R)-1-(6-(5-fluoro-6-methoxypyridin-3-ylamino)-5-(2-methyl-9-(tetrahydro-2H-pyran-2-yl)-9H-purin-6-yl)pyridin-3-yl)ethyl)-3-methylpiperazine-1-carboxylate (0.155 g, 0.234 mmol, 39.1% yield) as a tan solid. $^1$H NMR (400 MHz, CDCl$_3$) δ 12.63 (s, 1H) 9.71 (d, J=2.15 Hz, 1H) 8.32 (dd, J=12.52, 2.15 Hz, 1H) 8.22 (s, 1H) 8.17 (d, J=2.35 Hz, 1H) 8.03 (d, J=2.15 Hz, 1H) 5.80 (dd, J=10.56, 2.15 Hz, 1H) 4.12 (s, 2H) 3.96 (s, 3H) 3.76 (d, J=2.54 Hz, 1H) 3.53 (m, 1H) 3.23 (m, 1H) 2.84 (s, 5H) 2.41 (m, 1H) 2.08 (s, 1H) 2.03 (s, 1H) 1.97 (s, 1H) 1.64 (s, 3H) 1.58 (s, 2H) 1.45 (d, J=6.85 Hz, 3H) 1.32 (s, 9H) 1.07 (d, J=5.87 Hz, 3H). m/z (ESI, +ve ion) 662.2 (M+H)$^+$.

Step 3. N-(5-fluoro-6-methoxypyridin-3-yl)-5-((R)-1-((S)-2-methyl-4-(methylsulfonyl)piperazin-1-yl)ethyl)-3-(2-methyl-9H-purin-6-yl)pyridin-2-amine A mixture of (3S)-tert-butyl 4-((1R)-1-(6-(5-fluoro-6-methoxypyridin-3-ylamino)-5-(2-methyl-9-(tetrahydro-2H-pyran-2-yl)-9H-purin-6-yl)pyridin-3-yl)ethyl)-3-methylpiperazine-1-carboxylate (0.180 g, 0.272 mmol) and trifluoroacetic acid (0.314 mL, 4.08 mmol) in DCM (10 mL) was treated with trifluoromethanesulfonic acid (0.01 mL) and allowed to stir under inert atmosphere for 1 h. The mixture was concentrated in vacuo, then THF (10 mL) was added to the residue and stirred 5 min. Then sodium carbonate (0.500 g) was added to the mixture and allowed to stir under inert atmosphere an additional 5 min. Then methanesulfonyl chloride (0.064 mL, 0.816 mmol) was added slowly via syringe into the mixture. The mixture was allowed to stir under inert atmosphere overnight. The mixture was diluted with DCM (20 mL), water (20 mL) and brine solution (10 mL). The organic layer was extracted with DCM (3×15 mL). The combined organic extracts were dried over sodium sulfate, filtered and concentrated in vacuo. The crude material was recrystallized from methanol and dichloromethane to give N-(5-fluoro-6-methoxypyridin-3-yl)-5-((R)-1-((S)-2-methyl-4-(methylsulfonyl)piperazin-1-yl)ethyl)-3-(2-methyl-9H-purin-6-yl)pyridin-2-amine (0.007 g, 0.013 mmol, 4.63% yield) as a tan solid. $^1$H NMR (400 MHz, CDCl$_3$) δ 12.69 (s, 1H) 9.84 (s, 1H) 8.38 (dd, J=12.42, 2.05 Hz, 1H) 8.28 (d, J=2.15 Hz, 1H) 8.22 (s, 1H) 8.11 (d, J=2.15 Hz, 1H) 7.26 (s, 8H) 4.16 (dq, J=14.18, 6.94 Hz, 1H) 4.04 (s, 3H) 3.30 (s, 2H) 3.14-3.21 (m, 1H) 2.93-3.06 (m, 4H) 2.85 (dd, J=10.76, 7.24 Hz, 1H) 2.69-2.78 (m, 4H) 2.55-2.64 (m, 1H) 1.54 (d, J=6.85 Hz, 3H) 1.13-1.32 (m, 3H). m/z (ESI, +ve ion) 556.1 (M+H)$^+$.

Example 296

N-(5-fluoro-6-methoxypyridin-3-yl)-5-((S)-1-((S)-2-methyl-4-(methylsulfonyl)piperazin-1-yl)ethyl)-3-(2-methyl-9H-purin-6-yl)pyridin-2-amine

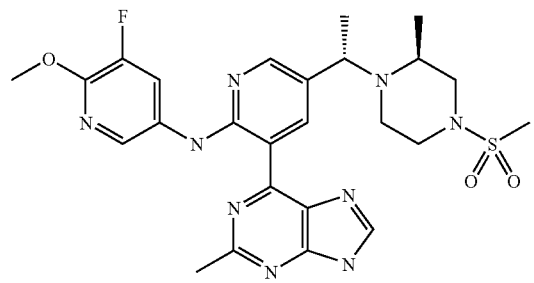

The title compound was prepared in an analogous manner to that described in the Example 295 using 5-((S)-1-((S)-4-(tert-butoxycarbonyl)-2-methylpiperazin-1-yl)ethyl)-2-fluoropyridin-3-ylboronic acid, 6-chloro-2-methyl-9-(tetrahydro-2H-pyran-2-yl)-9H-purine, and 5-fluoro-6-methoxypyridin-3-amine, and was isolated as a tan solid (38%). $^1$H NMR (400 MHz, CDCl$_3$) δ 9.60 (s, 1H) 8.24 (d, J=1.37 Hz, 2H) 8.11 (s, 1H) 7.97 (s, 1H) 4.01 (s, 5H) 3.76 (s, 4H) 2.89 (s, 5H) 2.61 (s, 4H) 1.88 (s, 3H) 1.70 (s, 3H). m/z (ESI, +ve ion) 556.1 (M+H)$^+$.

Example 297

(R)-N-(5-fluoro-6-methoxypyridin-3-yl)-3-(2-methyl-9H-purin-6-yl)-5-(1-(4-(methylsulfonyl)piperazin-1-yl)ethyl)pyridin-2-amine

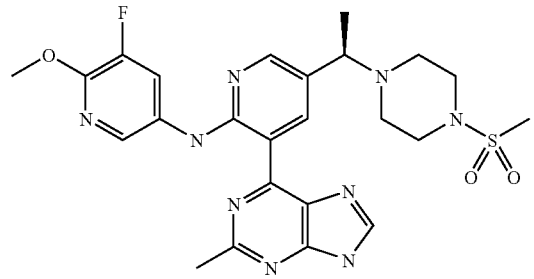

Step 1. tert-butyl 4-((1R)-1-(6-fluoro-5-(2-methyl-9-(tetrahydro-2H-pyran-2-yl)-9H-purin-6-yl)pyridin-3-yl)ethyl)piperazine-1-carboxylate A glass microwave reaction vessel was charged with 6-chloro-2-methyl-9-(tetrahydro-2H-pyran-2-yl)-9H-purine (0.250 g, 0.989 mmol) and (R)-5-(1-(4-(tert-butoxycarbonyl)piperazin-1-yl)ethyl)-2-fluoropyridin-3-ylboronic acid (0.489 g, 1.385 mmol) in dioxane (3 mL). Then A-Phos (0.070 g, 0.099 mmol), potassium acetate (0.291 g, 2.97 mmol) and water (0.5 mL) were added into the reaction mixture. The reaction mixture was stirred and heated in a CEM Explorer Microwave at 120° C. for 10 min (120 watts, Powermax feature on). The mixture was diluted with dichloromethane (10 mL), water (10 mL) and brine solution (5 mL). The organic layer was collected by extracting with dichloromethane (3×10 mL). The combined organic extracts were dried over sodium sulfate, filtered and concentrated in vacuo to give the crude material as a tan oil. The crude material was adsorbed onto a plug of silica gel and purified by chromatography through a silica-gel column (40 g) eluting with 100% ethyl acetate to give tert-butyl 4-((1R)-1-(6-fluoro-5-(2-methyl-9-(tetrahydro-2H-pyran-2-yl)-9H-purin-6-yl)pyridin-3-yl)ethyl)piperazine-1-carboxylate (0.400 g, 0.761 mmol, 77% yield) as a light-yellow solid. $^1$H NMR (400 MHz, CDCl$_3$) δ 8.20-8.29 (m, 3H) 5.78 (dd, J=10.37, 2.35 Hz, 1H) 3.76 (s, 1H) 3.55 (d, J=6.65 Hz, 1H) 3.34 (s, 5H) 2.82 (s, 3H) 2.33 (d, J=5.09 Hz, 5H) 1.95-2.13 (m, 3H) 1.56-1.81 (m, 5H) 1.33-1.40 (m, 9H). m/z (ESI, +ve ion) 526.2 (M+H)$^+$.

Step 2. tert-butyl 4-((1R)-1-(6-(5-fluoro-6-methoxypyridin-3-ylamino)-5-(2-methyl-9-(tetrahydro-2H-pyran-2-yl)-9H-purin-6-yl)pyridin-3-yl)ethyl)piperazine-1-carboxylate A mixture of tert-butyl 4-((1R)-1-(6-fluoro-5-(2-methyl-9-(tetrahydro-2H-pyran-2-yl)-9H-purin-6-yl)pyridin-3-yl)ethyl)piperazine-1-carboxylate (0.673 g, 1.280 mmol) in THF (15 mL) under inert atmosphere was treated with a solution of 5-fluoro-6-methoxypyridin-3-amine (0.364 g, 2.56 mmol) in THF (10 mL) via syringe. The mixture was chilled to −20° C. in a diluted dry ice/acetone bath, then sodium bis(trimethylsilyl)amide (1.0 M in THF, Aldrich; 3.84 mL, 3.84 mmol) was added slowly via syringe into the reaction mixture. After the addition, the ice bath was removed and the mixture was allowed to stir under inert atmosphere for 1 h. The mixture was diluted with chloroform (20 mL) and water (10 mL). The organic layer was extracted with chloroform (3×10 mL). The combined organic extracts were dried over sodium sulfate, filtered and concentrated in vacuo. The crude material was adsorbed onto a plug of silica gel and purified by chromatography through a silica-gel column (80 g) eluting with 100% ethyl acetate to give tert-butyl 4-((1R)-1-(6-(5-fluoro-6-methoxypyridin-3-ylamino)-5-(2-methyl-9-(tetrahydro-2H-pyran-2-yl)-9H-purin-6-yl)pyridin-3-yl)ethyl)piperazine-1-carboxylate (0.459 g, 0.709 mmol, 55.3% yield) as a tan solid. $^1$H NMR (400 MHz, CDCl$_3$) δ 12.61 (s, 1H) 9.65 (t, J=1.96 Hz, 1H) 8.31 (dd, J=12.52, 2.35 Hz, 1H) 8.18-8.23 (m, 2H) 8.03 (d, J=2.35 Hz, 1H) 5.80 (dd, J=10.47, 2.05 Hz, 1H) 3.96 (s, 3H) 3.76 (s, 1H) 3.55 (d, J=6.85 Hz, 1H) 3.36 (s, 4H) 2.85 (s, 3H) 2.40 (d, J=3.33 Hz, 4H) 2.07 (s, 1H) 2.02 (s, 1H) 1.97 (s, 1H) 1.54-1.81 (m, 2H) 1.41 (d, J=6.65 Hz, 3H) 1.36 (s, 9H) 1.19 (s, 1H) 0.90 (d, J=6.65 Hz, 1H). m/z (ESI, +ve ion) 648.2 (M+H)$^+$.

Step 3. (R)-N-(5-fluoro-6-methoxypyridin-3-yl)-3-(2-methyl-9H-purin-6-yl)-5-(1-(4-(methylsulfonyl)piperazin-1-yl)ethyl)pyridin-2-amine A mixture of tert-butyl 4-((1R)-1-(6-(5-fluoro-6-methoxypyridin-3-ylamino)-5-(2-methyl-9-(tetrahydro-2H-pyran-2-yl)-9H-purin-6-yl)pyridin-3-yl)ethyl)piperazine-1-carboxylate (0.450 g, 0.695 mmol) and trifluoroacetic acid (0.803 mL, 10.42 mmol) in DCM (25 mL) was treated with trifluoromethanesulfonic acid (0.01 mL) and allowed to stir under inert atmosphere for 1 h. The mixture was concentrated in vacuo. The residue was diluted with DCM (10 mL), then sodium carbonate (2.50 g) was added to the mixture and allowed to stir 10 min. Then methanesulfonyl chloride (0.271 mL, 3.47 mmol) was added slowly via syringe into the mixture. The mixture was allowed to stir under inert atmosphere overnight. The mixture was diluted with dichloromethane (20 mL), water (20 mL) and brine solution (10 mL). The organic layer was extracted with dichloromethane (3×15 mL). The combined organic extracts were dried over sodium sulfate, filtered and concentrated in vacuo. The crude material was purified by reverse-phase preparative HPLC using a Phenomenex Luna column, 10 micron, C18(2), 100 Å, 250×50 mm, (Varian, 5-70% acetonitrile in water with trifluoroacetic acid additive 0.1% v/v in each solvent) and then further purified by normal phase silica-gel chromatography on an Interchim puriflash (25 g) column eluting with 10% methanol in dichloromethane to give N-(5-fluoro-6-methoxypyridin-3-yl)-3-(2-methyl-9H-purin-6-yl)-5-((R)-1-(4-(methylsulfonyl)piperazin-1-yl)ethyl)pyridin-2-amine (0.010 g, 0.018 mmol, 2.66% yield) as a light-yellow solid. $^1$H NMR (400 MHz, CDCl$_3$) δ 12.69 (s, 1H) 9.77 (d, J=1.96 Hz, 1H) 8.39 (dd, J=12.52, 2.15 Hz, 1H) 8.32 (d, J=2.15 Hz, 1H) 8.21 (s, 1H) 8.11 (d, J=2.15 Hz, 1H) 4.04 (s, 3H) 3.67-3.73 (m, 1H) 3.26 (t, J=4.69 Hz, 4H) 2.94 (s, 3H) 2.77 (s, 3H) 2.62-2.71 (m, 4H) 1.51 (d, J=6.65 Hz, 3H). m/z (ESI, +ve ion) 542.1 (M+H)$^+$.

Example 298

1-(5-(4-amino-6-methyl-1,3,5-triazin-2-yl)-6-(5-fluoro-6-methoxypyridin-3-ylamino)pyridin-3-yl)cyclopropanol

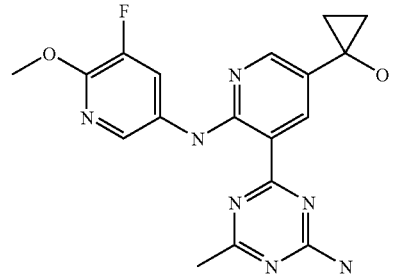

Step 1. methyl 5-(4-(bis(4-methoxybenzyl)amino)-6-methyl-1,3,5-triazin-2-yl)-6-(5-fluoro-6-methoxypyridin-3-ylamino)nicotinate A slurry of 5-(4-(bis(4-methoxybenzyl)amino)-6-methyl-1,3,5-triazin-2-yl)-6-(5-fluoro-6-methoxypyridin-3-ylamino)nicotinaldehyde (Example 143, 0.200 g, 0.336 mmol), manganese dioxide (0.584 g, 6.72 mmol), methanol (0.068 mL, 1.679 mmol), acetic acid (0.029 mL, 0.504 mmol), and sodium cyanide (0.082 g, 1.679 mmol) in 4 mL THF was stirred rapidly overnight. Manganese dioxide (0.584 g, 6.72 mmol) was added, the reaction was sealed, and stirred rapidly for 3 days. The reaction was filtered through Celite® (diatomaceous earth), rinsing with 10% MeOH/DCM. The residue was adsorbed onto 2 g silica gel, dried, and purified by silica gel chromatography (40 g column) using 0-100% EtOAc/hexane. The product-containing fractions were concentrated to afford methyl 5-(4-(bis(4-methoxybenzyl)amino)-6-methyl-1,3,5-triazin-2-yl)-6-(5-fluoro-6-methoxypyridin-3-ylamino)nicotinate (0.107 g, 0.171 mmol, 50.9% yield) as a orange solid. m/z (ESI, +ve ion) 626 (M+H)$^+$. $^1$H NMR (400 MHz, CDCl$_3$) δ 12.33 (br. s., 1H), 9.41 (d, J=2.3 Hz, 1H), 8.92 (d, J=2.3 Hz, 1H), 7.98 (d, J=2.3

Hz, 1H,) 7.90-7.97 (m, 1H), 7.16-7.25 (m, 4H), 6.82-6.92 (m, 4H), 4.90 (s, 2H), 4.84 (s, 2H,) 4.04 (s, 3H), 3.92 (s, 3H), 3.82 (s, 3H), 3.79 (s, 3H), 2.61 (s, 3H).

Step 2. methyl 5-(4-amino-6-methyl-1,3,5-triazin-2-yl)-6-(5-fluoro-6-methoxypyridin-3-ylamino)nicotinate A solution of methyl 5-(4-(bis(4-methoxybenzyl)amino)-6-methyl-1,3,5-triazin-2-yl)-6-(5-fluoro-6-methoxypyridin-3-ylamino)nicotinate (0.965 g, 1.542 mmol) and triflic acid (0.685 mL, 7.71 mmol), in 6 mL TFA was heated in a flask fitted with a reflux condenser and drying tube at 80° C. for 30 min. The dark red reaction was cooled and triflic acid (0.685 mL, 7.71 mmol) was added, and the reaction was reheated to 80° C. After 30 min, the reaction was judged complete. The reaction was cooled to 0° C., and ice was added, along with solid sodium bicarbonate, in portions, with rapid stirring. DCM was added. Upon complete quenching of acid, the thick mixture was extracted with 3×10% iPrOH/DCM, 2×10% iPrOH/EtOAc (EtOAc layers were washed 1×brine). The combined organic extracts were dried over sodium sulfate, filtered, and concentrated in vacuo. The solid was suspended in diethyl ether, sonicated, and filtered, rinsing with 3× diethyl ether to give methyl 5-(4-amino-6-methyl-1,3,5-triazin-2-yl)-6-(5-fluoro-6-methoxypyridin-3-ylamino)nicotinate (0.400 g, 1.038 mmol, 67.3% yield) as an orange solid. m/z (ESI, +ve ion) 386 (M+H)$^+$. $^1$H NMR (400 MHz, d$_6$-DMSO) δ 12.37 (s, 1H), 9.26 (d, J=2.3 Hz, 1H), 8.83 (d, J=2.3 Hz, 1H), 8.41 (d, J=2.3 Hz, 1H), 8.31 (dd, J=12.4, 2.2 Hz, 1H), 8.01 (br. s., 1H), 7.84 (br. s., 1H), 3.95 (s, 3H), 3.88 (s, 3H), 2.46 (s, 3H).

Step 3. 1-(5-(4-amino-6-methyl-1,3,5-triazin-2-yl)-6-(5-fluoro-6-methoxypyridin-3-ylamino)pyridin-3-yl)cyclopropanol To a slurry of methyl 5-(4-amino-6-methyl-1,3,5-triazin-2-yl)-6-(5-fluoro-6-methoxypyridin-3-ylamino)nicotinate (0.400 g, 1.038 mmol) and titanium(iv) isopropoxide (0.365 mL, 1.246 mmol) in 8 mL THF at ambient temperature was added ethylmagnesium bromide 1.0 M solution in THF (5.61 mL, 5.61 mmol) over 2-3 min. The reaction became dark brown and warm, with bubbling. The reaction was cooled briefly with an ice bath and then allowed to stir at ambient temperature. After 1 h, an additional 2.4 equiv 1.0 M ethylmagnesium bromide in THF was added at ambient temperature. After 30 min, the reaction was cooled to 0° C. and quenched with ice and sat'd aq. NH$_4$Cl. The reaction was partitioned between sat'd aqueous NH$_4$Cl and DCM. The aqueous layer was extracted with DCM 3 times, and ethyl acetate once, and the combined organics were dried over anhydrous sodium sulfate, filtered, and concentrated in vacuo. Purification by RPHPLC (Gradient, Acetonitrile+ 0.1% TFA/water+0.1% TFA) provided 0.070 g of a sticky orange film. The material was treated with sat'd aq. NaHCO$_3$ and 10% iPrOH/DCM. The aq. layer was extracted 3×10% iPrOH/DCM and combined organics dried over sodium sulfate, filtered, and concentrated in vacuo to give 1-(5-(4-amino-6-methyl-1,3,5-triazin-2-yl)-6-(5-fluoro-6-methoxypyridin-3-ylamino)pyridin-3-yl)cyclopropanol (0.027 g, 0.070 mmol, 7% yield) as a yellow solid. m/z (ESI, +ve ion) 384 (M+H)$^+$. $^1$H NMR (400 MHz, d6-DMSO) δ 11.90 (s, 1H), 8.82 (d, J=2.5 Hz, 1H), 8.29-8.48 (m, 2H), 8.20 (d, J=2.5 Hz, 1H), 7.91 (br. s., 1H), 7.75 (br. s., 1H), 6.03 (s, 1H), 3.93 (s, 3H), 2.44 (s, 3H), 1.04-1.13 (m, 2H), 0.86-0.98 (m, 2H).

Example 299

4-(2-(5-fluoro-6-methoxypyridin-3-ylamino)-5-(1-(isopropylamino)ethyl)pyridin-3-yl)-6-methyl-1,3,5-triazin-2-amine

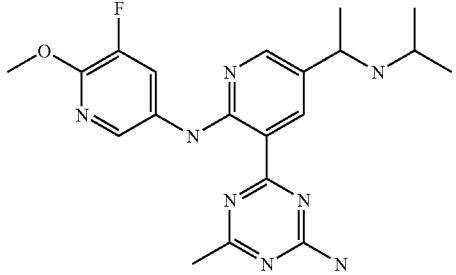 [SMILES: COc1ncc(Nc2ncc(C(C)NC(C)C)cc2-c2nc(C)nc(N)n2)cc1F]

A mixture of 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone (Example 271, 0.270 g, 0.443 mmol), titanium (iv) isopropoxide (0.519 mL, 1.772 mmol) and isopropylamine (0.152 mL, 1.772 mmol) in 3 mL THF was sealed and heated to 60° C. overnight. The reaction was cooled, diluted with 3 mL DCM and treated with sodium triacetoxyborohydride (0.375 g, 1.772 mmol). After 1 h, sodium cyanoborohydride (0.111 g, 1.772 mmol) was added. After 3 h, the reaction was complete. The reaction was treated with ice, water, conc. NH$_4$OH, and DCM. The organic layer was removed. Upon attempted extraction, only an emulsion was possible, so the material was filtered through celite. The aq. layer was extracted 1×DCM. The combined organics were dried over sodium sulfate, filtered, and concentrated in vacuo to give 0.331 g of an orange oil containing impure 4-(2-(5-fluoro-6-methoxypyridin-3-ylamino)-5-(1-(isopropylamino)ethyl)pyridin-3-yl)-N,N-b is (4-methoxybenzyl)-6-methyl-1,3,5-triazin-2-amine m/z (ESI, +ve ion) 653 (M+H)$^+$. The impure material was treated with 2 mL TFA and triflic acid (0.197 mL, 2.214 mmol) in a sealed vessel, and was heated to 80° C. for 30 min. The reaction was cooled and poured onto ice, and basified with 10 N NaOH. The material was extracted with DCM, three times, and 10% iPrOH/DCM once. The combined organics were dried over sodium sulfate, filtered, and concentrated in vacuo. The resulting solid was suspended in MeOH and filtered, rinsing with MeOH. The solid was dried in vacuo to give 4-(2-(5-fluoro-6-methoxypyridin-3-ylamino)-5-(1-(isopropylamino)ethyl)pyridin-3-yl)-6-methyl-1,3,5-triazin-2-amine (0.145 g, 0.352 mmol, 79% yield) as an orange solid. m/z (ESI, +ve ion) 413 (M+H)$^+$. $^1$H NMR (400 MHz, d$_6$-DMSO) δ 11.91 (s, 1H), 8.77 (br. s., 1H), 8.28-8.49 (m, 3H), 7.89 (br. s., 1H), 7.74 (br.

s., 1H), 3.93 (s, 3H), 3.76-3.91 (m, 1H), 3.26-3.32 (m, 1H), 2.44 (s, 3H), 1.27 (br. s., 3H), 0.84-1.08 (m, 6H).

Example 300

4-(5-(1-aminocyclopropyl)-2-(5-fluoro-6-methoxy-pyridin-3-ylamino)pyridin-3-yl)-6-methyl-1,3,5-triazin-2-amine

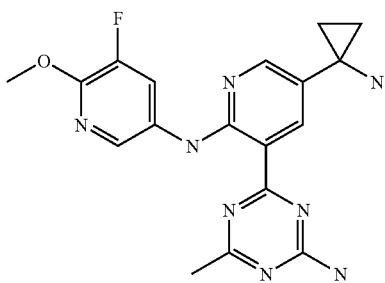 [SMILES: COc1ncc(Nc2ncc(C3(N)CC3)cc2-c2nc(C)nc(N)n2)cc1F]

Step 1. 5-(4-(bis(4-methoxybenzyl)amino)-6-methyl-1,3,5-triazin-2-yl)-6-(5-fluoro-6-methoxypyridin-3-ylamino)nicotinonitrile A dark brown solution of hydroxyammonium chloride (0.700 g, 10.07 mmol), 5-(4-(bis(4-methoxybenzyl)amino)-6-methyl-1,3,5-triazin-2-yl)-6-(5-fluoro-6-methoxypyridin-3-ylamino)nicotinaldehyde (Example 143, 2.00 g, 3.36 mmol) and pyridine (0.815 mL, 10.07 mmol) in 15 mL DMF was allowed to stir 2 h. The reaction was partitioned between water and EtOAc. The organic layer was washed with water 2 times, saturated aqueous NaCl once, and the organics were dried over anhydrous sodium sulfate, filtered, and concentrated in vacuo to give an orange solid, 2.0 g. This was treated with acetic anhydride (15.84 mL, 168 mmol), and the flask fitted with a water-cooled reflux condenser, and placed in an oil bath. The reaction was heated to reflux for 5 h, and then the reaction was cooled and stirred overnight. The slurry was treated with 80 mL MeOH, filtered and dried in vacuo to give 5-(4-(bis(4-methoxybenzyl)amino)-6-methyl-1,3,5-triazin-2-yl)-6-(5-fluoro-6-methoxypyridin-3-ylamino)nicotinonitrile (1.50 g, 2.53 mmol, 75% yield) as a green-brown solid. m/z (ESI, +ve ion) 593 (M+H)+. 1H NMR (400 MHz, CDCl3) δ 12.46 (s, 1H), 8.99 (d, J=2.3 Hz, 1H), 8.52 (d, J=2.3 Hz, 1H), 7.99 (d, J=2.3 Hz, 1H), 7.92 (dd, J=11.7, 2.2 Hz, 1H), 7.12-7.25 (m, 4H), 6.82-6.94 (m, 4H), 4.88 (s, 2H), 4.82 (s, 2H), 4.04 (s, 3H), 3.82 (s, 3H), 3.81 (s, 3H), 2.61 (s, 3H).

Step 2. 4-(5-(1-aminocyclopropyl)-2-(5-fluoro-6-methoxypyridin-3-ylamino)pyridin-3-yl)-6-methyl-1,3,5-triazin-2-amine 2,2,2-trifluoroacetate To a dark brown slurry of 5-(4-(bis(4-methoxybenzyl)amino)-6-methyl-1,3,5-triazin-2-yl)-6-(5-fluoro-6-methoxypyridin-3-ylamino)nicotinonitrile (0.210 g, 0.354 mmol) in 7 mL THF was added titanium (IV) isopropoxide (0.125 mL, 0.425 mmol), and the reaction was cooled to −78° C. Ethylmagnesium bromide 1.0 M solution in THF (2.268 mL, 2.268 mmol) was added slowly dropwise and the reaction was allowed to stir 1 h at −78° C. The reaction was allowed to warm to ambient temperature. After 2 h, boron trifluoride diethyl etherate (0.108 mL, 0.850 mmol) was added. After 1 h, boron trifluoride diethyl etherate (0.108 mL, 0.850 mmol) was again added. After 1 h, the reaction was quenched by addition of 1 N NaOH, and treated with EtOAc. The aq. layer was extracted 3× EtOAc, and 1×DCM. The combined organics were dried over sodium sulfate, filtered, and concentrated in vacuo. The resulting impure mixture was combined with additional impure material for the next reaction. 0.334 g of an impure mixture containing 4-(5-(1-aminocyclopropyl)-2-(5-fluoro-6-methoxypyridin-3-ylamino)pyridin-3-yl)-N,N-bis(4-methoxybenzyl)-6-methyl-1,3,5-triazin-2-amine was dissolved in 2 mL TFA and treated with triflic acid (0.238 mL, 2.68 mmol), and the reaction was sealed and heated to 80° C. for 0.5 h. The reaction was cooled, poured onto ice, treated with 10 N NaOH until basic. The aqueous was extracted 3×DCM, 1×10% iPrOH/DCM, dried over sodium sulfate, filtered, and concentrated in vacuo. This material was dissolved in DMSO/TFA and purified by reverse phase HPLC, 10-60% ACN/H2O (+0.1% TFA); product-containing fractions were concentrated in vacuo to give 4-(5-(1-aminocyclopropyl)-2-(5-fluoro-6-methoxypyridin-3-ylamino)pyridin-3-yl)-6-methyl-1,3,5-triazin-2-amine 2,2,2-trifluoroacetate (0.010 g, 0.020 mmol, 3.76% yield) as an orange solid. m/z (ESI, +ve ion) 383 (M+H)+. 1H NMR (400 MHz, d6-DMSO) δ 12.03 (s, 1H), 8.94 (d, J=2.5 Hz, 1H), 8.53 (br. s., 3H), 8.38-8.49 (m, 2H), 8.30 (dd, J=12.7, 2.2 Hz, 1H), 7.96 (br. s., 1H), 7.84 (br. s., 1H), 3.94 (s, 3H), 2.46 (s, 3H), 1.26-1.35 (m, 2H), 1.14-1.23 (m, 2H).

Example 301

4-(5-(3-aminopentan-3-yl)-2-(5-fluoro-6-methoxy-pyridin-3-ylamino)pyridin-3-yl)-6-methyl-1,3,5-triazin-2-amine

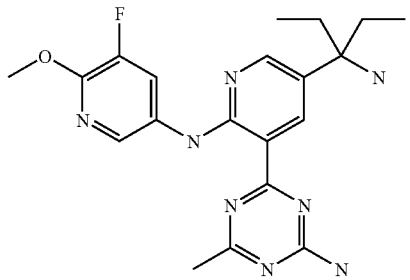 [SMILES: CCC(N)(CC)c1cnc(Nc2cnc(OC)c(F)c2)c(-c2nc(C)nc(N)n2)c1]

To a slurry of 5-(4-(bis(4-methoxybenzyl)amino)-6-methyl-1,3,5-triazin-2-yl)-6-(5-fluoro-6-methoxypyridin-3-ylamino)nicotinonitrile (Example 143, 0.205 g, 0.346 mmol) in 7 mL THF at 0° C. was added tetraisopropoxytitanium (0.122 mL, 0.415 mmol) followed by ethylmagnesium bromide 1.0 M in THF (2.214 mL, 2.214 mmol). The reaction became dark brown. After 30 min, boron trifluoride diethyl etherate (0.210 mL, 1.660 mmol) was added. The reaction was warmed to ambient temperature, and after 15 min, quenched with 10 N NaOH. The aqueous was extracted 3× EtOAc. The combined extracts were dried over sodium sulfate, filtered, and concentrated in vacuo to give 0.234 g. This material treated with 2 mL TFA and triflicacid (0.154 mL, 1.730 mmol). The reaction was sealed, and heated to 80° C. for 30 min. The reaction was cooled and pour onto ice, basified with 10 N NaOH and extracted 3×DCM. The combined organics were dried over anhydrous sodium sulfate, filtered, and concentrated. The resulting material was treated with DMSO and TFA purified by RPHPLC, 10-60% ACN/H2O (+0.1% TFA); Product-containing fractions were concentrated and treated with sat'd aq. NaHCO₃ and DCM. The aqueous layer was extracted 3×10% IPA/DCM and combined organics dried over sodium sulfate, filtered, and concentrated in vacuo to give 4-(5-(3-aminopentan-3-yl)-2-(5-fluoro-6-methoxypyridin-3-ylamino)pyridin-3-yl)-6-methyl-1,3,5-triazin-2-amine (0.018 g, 0.044 mmol, 12.62% yield) as a yellow solid. m/z (ESI, +ve ion) 413 (M+H)⁺. ¹H NMR (400 MHz, d₆-DMSO) δ 11.92 (s, 1H), 8.88 (d, J=2.5 Hz, 1H), 8.35-8.46 (m, 3H), 7.88 (br. s., 1H), 7.72 (br. s., 1H), 3.93 (s, 3H), 2.44 (s, 3H), 1.53-1.84 (m, 4H), 0.69 (t, J=7.3 Hz, 6H).

Example 302

(R)-4-(2-(5-isopropyl-6-methoxypyridin-3-ylamino)-5-(1-(4-(methylsulfonyl)piperazin-1-yl)ethyl)pyridin-3-yl)-6-methyl-1,3,5-triazin-2-amine

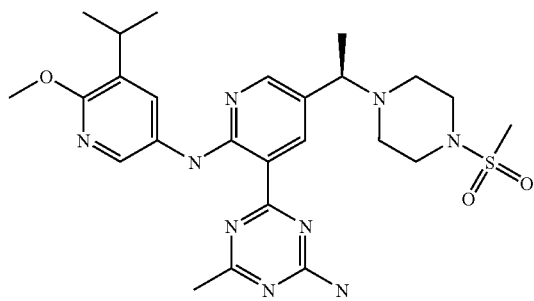 [SMILES: COc1ncc(Nc2ncc([C@@H](C)N3CCN(S(C)(=O)=O)CC3)cc2-c2nc(C)nc(N)n2)cc1C(C)C]

Step 1. 3-bromo-2-methoxy-5-nitropyridine

To a cloudy mixture of 3-bromo-2-chloro-5-nitropyridine (Atlantic Scitech, Linden, N.J., 5.10 g, 21.48 mmol) in 50 mL anhydrous methanol at 0° C. (ice/water bath) was added sodium methoxide 5.4 M in methanol (7.96 mL, 43.0 mmol) dropwise by addition funnel The reaction became clear then a thick precipitate formed. The ice/water bath was removed and the reaction warmed to ambient temperature, quenched with water and sat'd aq. NH₄Cl and DCM. The aqueous layer was extracted with DCM 2 times, and the combined organics were dried over anhydrous sodium sulfate, filtered, and concentrated in vacuo to give 3-bromo-2-methoxy-5-nitropyridine (5.07 g, 21.76 mmol, quantitative yield) as a light yellow solid. m/z (ESI, +ve ion) 233 (M+H)⁺. ¹H NMR (400 MHz, CDCl₃) δ 9.02 (d, J=2.3 Hz, 1H), 8.63 (d, J=2.5 Hz, 1H), 4.15 (s, 3H).

Step 2. 5-isopropyl-6-methoxypyridin-3-amine

Argon was bubbled through a slurry of potassium carbonate (4.45 g, 32.2 mmol), potassium isopropenyltrifluoroborate (3.18 g, 21.46 mmol), bis(4-(di-tert-butylphosphino)-N,N-dimethylbenzenamine)palladium dichloride (Aldrich, St. Louis, Mo., 0.152 g, 0.215 mmol), and 3-bromo-2-methoxy-5-nitropyridine (2.50 g, 10.73 mmol) in 50 mL dioxane and 20 mL water for 5 min. The reaction was sealed and heated to 80° C. for 1 h. The dark red reaction was cooled and partitioned between water and DCM. The aqueous layer was extracted with DCM 3 times, and the combined organics were dried over anhydrous sodium sulfate, filtered, and concentrated in vacuo, to give a red solid, which was used without further purification. The solid was treated 10% palladium on carbon (50% water wet) (2.62 g, 2.464 mmol) and 75 mL MeOH and was fitted with hydrogen balloon and stirred rapidly for 3 h. The reaction was flushed with nitrogen, filtered through Celite® (diatomaceous earth), rinsing with 400 mL MeOH, and concentrated in vacuo to give 5-isopropyl-6-methoxypyridin-3-amine (1.81 g, 10.89 mmol, quantitative yield) as a brown oil. m/z (ESI, +ve ion) 167 (M+H)⁺. ¹H NMR (400 MHz, CDCl₃) δ 7.51 (d, J=2.9 Hz, 1H), 6.94 (d, J=2.7 Hz, 1H), 3.90 (s, 3H), 3.13 (m, 1H), 1.14-1.22 (m, 6H).

Step 3. (R)-4-(2-(5-isopropyl-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine To a solution of (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (Examples 145 and 146) 0.380 g, 0.598 mmol) and 5-isopropyl-6-methoxypyridin-3-amine (0.149 g, 0.897 mmol) in 3 mL THF at 0° C. was added lithium bis(trimethylsilyl)amide 1.0 M in THF (2.69 mL, 2.69 mmol) dropwise via syringe over 1 min. The dark red reaction was allowed to stir 30 min and was quenched by addition of saturated aq. NH₄Cl. The reaction was partitioned between water and DCM. The aqueous layer was extracted with DCM 3 times, and the combined organics were dried over anhydrous sodium sulfate, filtered, and concentrated in vacuo. The material was treated with DCM and purified by silica gel chromatography (80 g column) using 20-100% EtOAc/hexane followed by 10% MeOH/EtOAc to elute the desired product. The product-containing fractions were concentrated to afford (R)-4-(2-(5-isopropyl-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (0.097 g, 0.124 mmol, 21% yield) as a red oil. m/z (ESI, +ve ion) 782 (M+H)⁺. ¹H NMR (400 MHz, CDCl₃) δ 11.59 (s, 1H), 8.70 (d, J=2.2 Hz, 1H), 8.15-8.29 (m, 2H), 7.77 (d, J=2.5 Hz, 1H), 7.15-7.25 (m, 4H), 6.77-6.96 (m, 4H), 4.71-4.97 (m, 4H), 3.95 (s, 3H), 3.82 (s, 3H), 3.79 (s, 3H), 3.53 (q, J=6.8 Hz, 1H), 3.11-3.20 (m, 5H), 2.69 (s, 3H), 2.47-2.63 (m, 7H), 1.38 (d, J=6.7 Hz, 3H), 1.21 (d, J=6.8 Hz, 6H).

Step 4. (R)-4-(2-(5-isopropyl-6-methoxypyridin-3-ylamino)-5-(1-(4-(methylsulfonyl)piperazin-1-yl)ethyl)pyridin-3-yl)-6-methyl-1,3,5-triazin-2-amine A dark red solution of (R)-4-(2-(5-isopropyl-6-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (0.097 g, 0.124 mmol) and trifluoromethanesulfonic acid (0.055 mL, 0.620 mmol) in 1 mL TFA was sealed and heated to 80° C. for 30 min. The reaction was cooled with ice, then quenched with 10 N NaOH until basic, and partitioned between water and DCM. The aqueous layer was extracted with DCM 2 times, and the combined organics were dried over anhydrous sodium sulfate, filtered, and concentrated in vacuo. This material was dissolved in DMSO (plus a few drops TFA) and purified by RPHPLC, 10-80% ACN/H₂O (plus 0.1% TFA); product-containing fractions were concentrated to dryness, then treated with sat'd aq. NaHCO₃ and DCM. The aq. layer was extracted 3×DCM and combined organics dried over sodium sulfate, filtered, and concentrated in vacuo to give (R)-4-(2-(5-isopropyl-6-methoxypyridin-3-ylamino)-5-(1-(4-(methylsulfonyl)piperazin-1-yl)ethyl)pyridin-3-yl)-6-methyl-1,3,5-triazin-2-amine as a yellow solid (0.021 g, 0.039 mmol, 31% yield).

m/z (ESI, +ve ion) 542 (M+H)⁺. ¹H NMR (400 MHz, CDCl₃) δ 11.58 (br. s., 1H), 8.69 (br. s., 1H), 8.17-8.34 (m, 2H), 7.92 (br. s., 1H), 5.38 (br. s., 2H), 3.97 (s, 3H), 3.47-3.62 (m, 1H), 3.11-3.31 (m, 5H), 2.77 (br. s., 3H), 2.49-2.68 (m, 7H), 1.44 (d, J=6.1 Hz, 3H), 1.27 (d, J=6.8 Hz, 6H).

Example 303

4-(5-(ethylsulfonyl)-2-(5-fluoro-6-methoxypyridin-3-ylamino)pyridin-3-yl)-6-methyl-1,3,5-triazin-2-amine

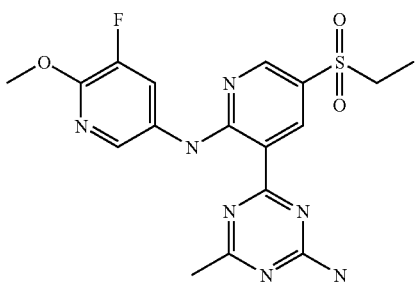 [SMILES: CCS(=O)(=O)c1cnc(Nc2cnc(OC)c(F)c2)c(-c2nc(C)nc(N)n2)c1]

Step 1. 4-(5-(ethylsulfinyl)-2-(5-fluoro-6-methoxy-pyridin-3-ylamino)pyridin-3-yl)-N,N-bis(4-methoxybenzyl)-6-methyl-1,3,5-triazin-2-amine Argon was bubbled through a slurry of 4-(5-chloro-2-(5-fluoro-6-methoxypyridin-3-ylamino)pyridin-3-yl)-N,N-bis(4-methoxybenzyl)-6-methyl-1,3,5-triazin-2-amine (Example 313, Step 2) 0.318 g, 0.528 mmol) (R)-1-[(S)-2-(Dicyclohexylphosphino)ferrocenyl]ethyldi-tert-butylphosphine (Aldrich, St. Louis, Mo., 0.029 g, 0.053 mmol) diacetoxypalladium (0.012 g, 0.053 mmol), and sodium ethanethiolate (0.156 g, 1.849 mmol) in 3 mL DME for 1 min. The reaction was sealed and heated to 110° C. overnight. The reaction was refreshed with (R)-1-[(S)-2-(Dicyclohexylphosphino)ferrocenyl]ethyldi-tert-butylphosphine (0.029 g, 0.053 mmol), diacetoxypalladium (0.012 g, 0.053 mmol), and sodium ethanethiolate (0.156 g, 1.849 mmol), flushed with argon, sealed, and reheated overnight. The reaction was cooled and adsorbed onto 2 g silica gel from DCM, and purified by silica gel chromatography, 40 g, 0-50% EA/hexanes. The product containing fractions were combined and concentrated to give 0.249 g yellow solid. The material was adsorbed onto 1.5 g silica gel from DCM, and purified by silica gel chromatography, 40 g, 0 to 5% EtOAc/DCM to give 4-(5-(ethylsulfinyl)-2-(5-fluoro-6-methoxypyridin-3-ylamino)pyridin-3-yl)-N,N-bis(4-methoxybenzyl)-6-methyl-1,3,5-triazin-2-amine (0.090 g, 0.140 mmol, 27% yield). m/z (ESI, +ve ion) 644 (M+H)⁺. ¹H NMR (400 MHz, CDCl₃) δ 11.75 (br. s., 1H), 8.76 (d, J=2.5 Hz, 1H), 8.18-8.24 (m, 1H), 8.02 (d, J=2.3 Hz, 1H), 7.88-7.98 (m, 1H), 7.12-7.24 (m, 4H), 6.81-6.94 (m, 4H), 4.87 (s, 2H), 4.82 (s, 2H), 4.04 (s, 3H), 3.82 (s, 3H), 3.80 (s, 3H), 2.91 (q, J=7.4 Hz, 2H), 2.59 (s, 3H), 1.37 (t, J=7.3 Hz, 3H).

Step 2. 4-(5-(ethylsulfonyl)-2-(5-fluoro-6-methoxy-pyridin-3-ylamino)pyridin-3-yl)-N,N-bis(4-methoxybenzyl)-6-methyl-1,3,5-triazin-2-amine To a slurry of 4-(5-(ethylsulfinyl)-2-(5-fluoro-6-methoxypyridin-3-ylamino)pyridin-3-yl)-N,N-bis(4-methoxyben-zyl)-6-methyl-1,3,5-triazin-2-amine (0.090 g, 0.140 mmol) in 2 mL MeOH, 2 mL dioxane, and 1 mL water was added potassium peroxymonosulfate sulfate (0.172 g, 0.280 mmol). The bright yellow slurry was stirred rapidly overnight. The reaction was partitioned between satd NaHCO₃ and DCM. The aqueous layer was extracted with DCM 3 times, and the combined organics were dried over anhydrous sodium sulfate, filtered, and concentrated in vacuo. The material was treated with DCM and purified by silica gel chromatography (25 g column) using 20 to 100% EtOAc/hexane. The product-containing fractions were concentrated to afford 4-(5-(ethylsulfonyl)-2-(5-fluoro-6-methoxypyridin-3-ylamino)pyridin-3-yl)-N,N-bis(4-methoxybenzyl)-6-methyl-1,3,5-triazin-2-amine (0.066 g, 0.100 mmol, 71.6% yield) as a yellow solid. m/z (ESI, +ve ion) 660 (M+H)⁺. ¹H NMR (400 MHz, CDCl₃) δ 11.91 (s, 1H), 8.80 (d, J=2.7 Hz, 1H), 8.43 (d, J=2.7 Hz, 1H), 8.15-8.33 (m, 2H), 7.14-7.25 (m, 4H), 6.80-6.93 (m, 4H), 4.87 (s, 2H), 4.83 (s, 2H), 4.02 (s, 3H), 3.82 (s, 3H), 3.79 (s, 3H), 3.07-3.22 (m, 1H), 2.82-2.94 (m, 1H), 2.62 (s, 3H), 1.28 (t, J=7.4 Hz, 3H).

Step 3. 4-(5-(ethylsulfonyl)-2-(5-fluoro-6-methoxy-pyridin-3-ylamino)pyridin-3-yl)-6-methyl-1,3,5-triazin-2-amine A solution of 4-(5-(ethylsulfonyl)-2-(5-fluoro-6-methoxy-pyridin-3-ylamino)pyridin-3-yl)-N,N-bis(4-methoxybenzyl)-6-methyl-1,3,5-triazin-2-amine (0.066 g, 0.100 mmol) in trifluoromethanesulfonic acid (0.089 mL, 1.000 mmol) and 1.5 mL TFA was sealed and heated to 70° C. for 30 min, cooled, and treated with ice and 10 N NaOH until basic. The reaction was partitioned between water and DCM. The aqueous layer was extracted with DCM 5 times, and the combined organics were dried over anhydrous sodium sulfate, filtered, and concentrated in vacuo. The resulting yellow solid was suspended in 1 mL EtOAc, filtered, rinsing 2× diethyl ether, and dried in vacuo to give 4-(5-(ethylsulfonyl)-2-(5-fluoro-6-methoxypyridin-3-ylamino)pyridin-3-yl)-6-methyl-1,3,5-triazin-2-amine (0.029 g, 0.069 mmol, 69% yield) as a yellow solid. m/z (ESI, +ve ion) 420 (M+H)⁺. ¹H NMR (400 MHz, d₆-DMSO) δ 11.87 (s, 1H), 8.73 (d, J=2.7 Hz, 1H), 8.52 (d, J=2.7 Hz, 1H), 8.41 (d, J=2.5 Hz, 1H), 8.33 (d, J=2.7 Hz, 1H), 7.98 (br. s., 1H), 7.83 (br. s., 1H), 3.95 (s, 3H), 3.06-3.21 (m, 1H), 2.73-2.89 (m, 1H), 2.44 (s, 3H), 1.09 (t, J=7.3 Hz, 3H).

Example 304

N-(5-((3-(6-amino-2-methyl-4-pyrimidinyl)-2-pyridinyl)amino)-2-chloro-3-pyridinyl)methanesulfonamide

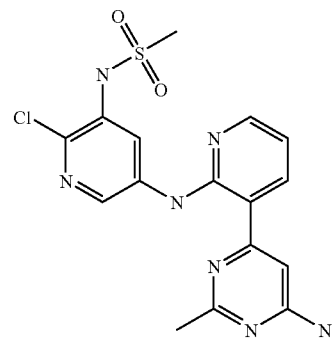 [SMILES: Cc1nc(N)cc(-c2cccnc2Nc2cnc(Cl)c(NS(C)(=O)=O)c2)n1]

Step 1: 6-(2-fluoro-3-pyridinyl)-2-methyl-4-pyrimidinamine

A mixture of 6-chloro-2-methyl-4-pyrimidinamine (SynChem, Inc., Des Plaines, Ill.) (0.500 g, 3.48 mmol), 2-fluoropyridin-3-ylboronic acid (0.589 g, 4.18 mmol), PdCl$_2$ (dppf) complex with dichloromethane (0.199 g, 0.244 mmol) and 2 M Na$_2$CO$_3$ (aq., 5.22 mL, 10.45 mmol) in dioxane (17 mL) was stirred at 110° C. overnight. After cooling to RT, water was added and the mixture was filtered through Celite® (diatomaceous earth). The mixture was extracted with EtOAc (3×). The combined organic layers were dried over anhydrous Na$_2$SO$_4$, filtered and concentrated. The crude material was adsorbed onto a plug of silica gel and purified by chromatography through a silica gel column (40 g), eluting with a gradient of 0% to 5% MeOH in CH$_2$Cl$_2$, to provide 6-(2-fluoro-3-pyridinyl)-2-methyl-4-pyrimidinamine (0.173 g, 0.85 mmol, 24% yield) as an off-white solid. m/z (ESI, +ve) 205.1 (M+H)$^+$. $^1$H NMR (400 MHz, d$_6$-DMSO) δ 8.52-8.62 (m, 1H); 8.27-8.34 (m, 1H); 7.44-7.61 (m, 2H); 7.00 (br. s., 1H); 6.75-6.83 (m, 1H); 2.39 (s, 3H).

Step 2: N-(5-((3-(6-amino-2-methyl-4-pyrimidinyl)-2-pyridinyl)amino)-2-chloro-3-pyridinyl)methanesulfonamide To a solution of N-(5-amino-2-chloro-3-pyridinyl)methanesulfonamide (Example 330, Step 2) (0.085 g, 0.384 mmol) in THF (5.0 mL) at 0° C. was added NaHMDS (2 M solution in THF) (0.959 mL, 1.918 mmol). After the addition, the reaction mixture continued to stir at 0° C. under N$_2$ for 30 minutes. 6-(2-fluoro-3-pyridinyl)-2-methyl-4-pyrimidinamine (0.094 g, 0.460 mmol) was added into the reaction mixture and the reaction mixture continued to stir at 0° C. for 10 minutes and was then slowly warmed up at RT. After 1 hour at RT, more NaHMDS (2 M solution in THF) (0.50 mL, 1.0 mmol) was added. After 1 more hour, the reaction mixture was partitioned between pH 7 buffer (1 M TRIS-HCl) and CH$_2$Cl$_2$. The layers were separated and the aqueous layer was extracted with CH$_2$Cl$_2$ (3×). The combined organic layers were dried over Na$_2$SO$_4$, filtered and concentrated. The crude product was purified by HPLC to afford N-(5-((3-(6-amino-2-methyl-4-pyrimidinyl)-2-pyridinyl)amino)-2-chloro-3-pyridinyl)methanesulfonamide (0.0190 g, 0.047 mmol, 12.20% yield). m/z (ESI, +ve) 406.1 (M+H)$^+$. $^1$H NMR (400 MHz, d$_6$-DMSO) δ 12.68 (s, 1H); 9.66 (s, 1H); 8.61 (d, J=2.74 Hz, 1H); 8.41 (d, J=2.54 Hz, 1H); 8.32 (dd, J=4.89, 1.76 Hz, 1H); 8.10-8.14 (m, 1H); 7.09 (s, 2H); 7.02 (dd, J=7.82, 4.69 Hz, 1H); 6.78 (s, 1H); 3.13 (s, 3H); 2.52 (s, 3H).

Example 305

6-(2-((5-fluoro-6-methoxy-3-pyridinyl)amino)-5-((1R)-1-(4-(methylsulfonyl)-1-piperazinyl)ethyl)-3-pyridinyl)-2-methyl-4-pyrimidinamine

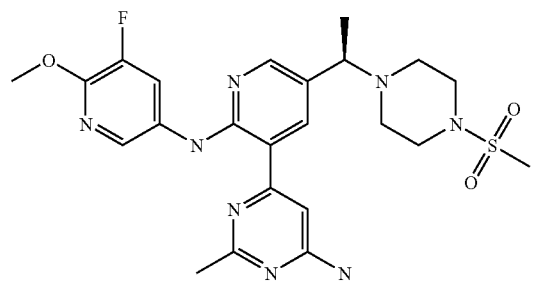

Step 1: tert-butyl 4-((1R)-1-(5-(6-(bis(4-methoxybenzyl)amino)-2-methyl-4-pyrimidinyl)-6-fluoro-3-pyridinyl)ethyl)-1-piperazinecarboxylate 6-chloro-N,N-bis(4-methoxybenzyl)-2-methylpyrimidin-4-amine (Example 177) (0.766 g, 1.996 mmol), (5-((1R)-1-(4-(tert-butoxycarbonyl)-1-piperazinyl)ethyl)-2-fluoro-3-pyridinyl)boronic acid (Example 146, Step 4) (0.705 g, 1.996 mmol), PdCl$_2$AmPhos (0.071 g, 0.100 mmol), and KOAc (0.588 g, 5.99 mmol) in a mixture of dioxane (16.6 mL) and water (3.3 mL) was sparged with nitrogen and then heated at 100° C. for 2.5 h. The yellow reaction mixture was subsequently partitioned between CH$_2$Cl$_2$ (60 mL) and water (50 mL). The organic layer was separated, and the aqueous layer was extracted with CH$_2$Cl$_2$ (2×50 mL). The combined organic extracts were then dried over Na$_2$SO$_4$ and concentrated. The crude material was adsorbed onto a plug of silica gel and purified by chromatography through a silica gel column (80 g), eluting with a gradient of 0% to 100% EtOAc in hexane, to provide tert-butyl 4-((1R)-1-(5-(6-(bis(4-methoxybenzyl)amino)-2-methyl-4-pyrimidinyl)-6-fluoro-3-pyridinyl)ethyl)-1-piperazinecarboxylate (0.570 g, 0.868 mmol, 43.5% yield) as light-yellow foam. m/z (ESI, +ve) 657.2 (M+H)$^+$. $^1$H NMR (400 MHz, CDCl$_3$) δ 8.43 (d, J=8.22 Hz, 1H); 8.18 (s, 1H); 7.18 (d, J=7.24 Hz, 4H); 6.82-6.89 (m, 5H); 4.75 (br. s., 4H); 3.79 (s, 6H); 3.60 (d, J=7.04 Hz, 1H); 3.43 (br. s., 4H); 2.63 (s, 3H); 2.30-2.53 (m, 4H); 1.44 (s, 12H).

Step 2: 6-(2-fluoro-5-((1R)-1-(1-piperazinyl)ethyl)-3-pyridinyl)-N,N-bis(4-methoxybenzyl)-2-methyl-4-pyrimidinamine A mixture of tert-butyl 4-((1R)-1-(5-(6-(bis(4-methoxybenzyl)amino)-2-methyl-4-pyrimidinyl)-6-fluoro-3-pyridinyl)ethyl)-1-piperazinecarboxylate (0.57 g, 0.87 mmol) in CH$_2$Cl$_2$ (4.3 mL) at 0° C. was treated with TFA (1.29 mL, 17.36 mmol). The reaction mixture was allowed to warm up to RT. After 90 minutes the reaction mixture was concentrated and the residue was dissolved in CH$_2$Cl$_2$ and saturated NaHCO$_3$ (aq.). The layers were separated and the aqueous layer was extracted with CH$_2$Cl$_2$ (2×). The combined organic layers were dried over anhydrous Na$_2$SO$_4$, filtered and concentrated to give 6-(2-fluoro-5-((1R)-1-(1-piperazinyl)ethyl)-3-pyridinyl)-N,N-bis(4-methoxybenzyl)-2-methyl-4-pyrimidinamine (0.41 g, 0.74 mmol, 85% yield). m/z (ESI, +ve) 557.2 (M+H)+. 1H NMR (400 MHz, CDCl3) δ 8.41 (dd, J=9.29, 2.45 Hz, 1H); 8.14-8.18 (m, 1H); 7.18 (d, J=7.43 Hz, 4H); 6.86 (d, J=8.61 Hz, 4H); 6.83 (br. s, 1H); 4.74 (br. s., 4H); 3.79 (s, 6H); 3.57 (q, J=6.78 Hz, 1H); 2.96 (m, 4H); 2.62 (s, 3H); 2.57 (br. s., 2H); 2.44-2.51 (m, 2H); 1.40 (d, J=6.85 Hz, 3H).

Step 3: 6-(2-fluoro-5-((1R)-1-(4-(methylsulfonyl)-1-piperazinyl)ethyl)-3-pyridinyl)-N,N-bis(4-methoxybenzyl)-2-methyl-4-pyrimidinamine A solution of 6-(2-fluoro-5-((1R)-1-(1-piperazinyl)ethyl)-3-pyridinyl)-N,N-bis(4-methoxybenzyl)-2-methyl-4-pyrimidinamine (0.448 g, 0.805 mmol) in CH2Cl2 (4 mL) at −20° C. was treated with NEt3 (1.122 mL, 8.05 mmol) followed by methanesulfonyl chloride (0.190 mL, 2.414 mmol). The mixture stirred at −20° C. for 30 minutes and then 1 M NaOH (aq.) and CH2Cl2 were added. The layers were separated and the aqueous layer was extracted with CH2Cl2 (2×). The crude material was adsorbed onto a plug of silica gel and purified by chromatography through a silica gel column (12 g), eluting with a gradient of 75% to 100% EtOAc in hexane, to provide 6-(2-fluoro-5-((1R)-1-(4-(methylsulfonyl)-1-piperazinyl)ethyl)-3-pyridinyl)-N,N-bis(4-methoxybenzyl)-2-methyl-4-pyrimidinamine (0.317 g, 0.499 mmol, 62.1% yield) as a white foam. m/z (ESI, +ve) 635.2 (M+H)+. 1H NMR (400 MHz, CDCl3) δ 8.46 (d, J=9.00 Hz, 1H); 8.18 (s, 1H); 7.17 (d, J=7.63 Hz, 4H); 6.83-6.89 (m, 5H); 4.74 (br. s., 4H); 3.80 (s, 6H); 3.65 (m, 1H); 3.18-3.30 (m, 4H); 2.77 (s, 3H); 2.64 (s, 5H); 2.50-2.58 (m, 2H); 1.44 (d, J=6.65 Hz, 3H).

Step 4: 6-(2-((5-fluoro-6-methoxy-3-pyridinyl)amino)-5-((1R)-1-(4-(methylsulfonyl)-1-piperazinyl)ethyl)-3-pyridinyl)-N,N-bis(4-methoxybenzyl)-2-methyl-4-pyrimidinamine Lithium bis(trimethylsilyl)amide (1.0 M solution in THF) (1.42 mL, 1.42 mmol) was added to a solution of 6-(2-fluoro-5-((1R)-1-(4-(methylsulfonyl)-1-piperazinyl)ethyl)-3-pyridinyl)-N,N-bis(4-methoxybenzyl)-2-methyl-4-pyrimidinamine (0.300 g, 0.47 mmol) and 5-fluoro-6-methoxypyridin-3-amine (Anichem, Inc. North Brunswick, N.J.) (0.101 g, 0.71 mmol) in THF (1.5 mL) at −10° C. More lithium bis(trimethylsilyl)amide (1.0 M solution in THF) (1.42 mL, 1.42 mmol) and 5-fluoro-6-methoxypyridin-3-amine (0.101 g, 0.71 mmol) were added and the reaction mixture was stirred for another hour. Saturated NH4Cl (aq.) was added and the mixture was extracted with EtOAc (3×). The combined organic layers were dried over anhydrous Na2SO4, filtered and concentrated. The crude material was adsorbed onto a plug of silica gel and purified by chromatography through a Redi-Sep pre-packed silica gel column (40 g), eluting with a gradient of 0% to 100% EtOAc in hexane, to provide 6-(2-((5-fluoro-6-methoxy-3-pyridinyl)amino)-5-((1R)-1-(4-(methylsulfonyl)-1-piperazinyl)ethyl)-3-pyridinyl)-N,N-bis(4-methoxybenzyl)-2-methyl-4-pyrimidinamine (0.200 g, 0.264 mmol, 55.9% yield) as a brown foam. m/z (ESI, +ve) 757.2 (M+H)+. 1H NMR (400 MHz, CDCl3) δ 11.92 (br. s., 1H) 8.24 (dd, J=12.52, 2.15 Hz, 1H) 8.13 (d, J=1.57 Hz, 1H) 8.03 (d, J=2.15 Hz, 1H) 7.50 (br. s., 1H) 7.19 (d, J=6.46 Hz, 4H) 6.87 (d, J=8.61 Hz, 5H) 6.52 (br. s., 1H) 4.79 (br. s., 4H) 4.01 (s, 3H) 3.79 (s, 6H) 3.44 (br. s., 4H) 3.17 (br. s., 4H) 2.75 (s, 3H) 2.66 (s, 3H) 2.40-2.59 (m, 4H) 1.34 (br. s., 3H)

Step 5: 6-(2-((5-fluoro-6-methoxy-3-pyridinyl)amino)-5-((1R)-1-(4-(methylsulfonyl)-1-piperazinyl)ethyl)-3-pyridinyl)-2-methyl-4-pyrimidinamine A solution of 6-(2-((5-fluoro-6-methoxy-3-pyridinyl)amino)-5-((1R)-1-(4-(methylsulfonyl)-1-piperazinyl)ethyl)-3-pyridinyl)-N,N-bis(4-methoxybenzyl)-2-methyl-4-pyrimidinamine (0.200 g, 0.264 mmol) in TFA (2 mL) at RT was treated with a few drops of triflic acid. The solution was heated to 80° C. for 90 minutes. The reaction mixture was allowed to cool to RT and was then concentrated. A few ice cubes were added and then saturated NaHCO3 (aq.) was added followed by CH2Cl2. The mixture was filtered and the layers were separated. The aqueous layer was extracted with CH2Cl2 (2×). The combined organic layers were dried over anhydrous Na2SO4, filtered and concentrated. The crude material was adsorbed onto a plug of silica gel and purified by chromatography through a silica gel column (12 g), eluting with a gradient of 0% to 3% MeOH in CH2Cl2, to provide 6-(2-((5-fluoro-6-methoxy-3-pyridinyl)amino)-5-((1R)-1-(4-(methylsulfonyl)-1-piperazinyl)ethyl)-3-pyridinyl)-2-methyl-4-pyrimidinamine (0.110 g, 0.213 mmol, 81% yield) as a yellow solid. m/z (ESI, +ve) 517.1 (M+H)+. 1H NMR (400 MHz, d6-DMSO) δ 12.17 (br. s, 1H); 8.35 (dd, J=13.01, 2.25 Hz, 1H); 8.22 (d, J=2.15 Hz, 1H); 8.17 (d, J=2.35 Hz, 1H); 7.95-7.98 (m, 1H); 7.04 (s, 2H); 6.80 (s, 1H); 3.94 (s, 3H); 3.61 (q, J=6.78 Hz, 1H); 3.11 (t, J=4.99 Hz, 4H); 2.87 (s, 3H); 2.53-2.58 (m, 5H); 2.43-2.50 (m, 2H); 1.38 (d, J=6.85 Hz, 3H).

Example 306

6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-2-methyl-4-pyrimidinamine

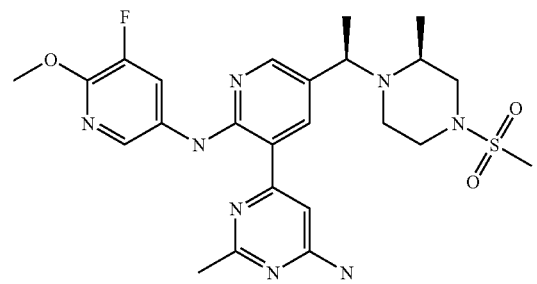

Step 1: tert-butyl(3S)-4-((1R)-1-(5-(6-(bis(4-methoxybenzyl)amino)-2-methyl-4-pyrimidinyl)-6-fluoro-3-pyridinyl)ethyl)-3-methyl-1-piperazinecarboxylate A glass microwave reaction vessel was charged with (5-((1R)-1-((2S)-4-(tert-butoxycarbonyl)-2-methyl-1-piperazinyl)ethyl)-2-fluoro-3-pyridinyl)boronic acid (Example 272, Step 2) (0.530 g, 1.443 mmol), 6-chloro-N,N-bis(4-methoxybenzyl)-2-methylpyrimidin-4-amine (Example 177) (0.554 g, 1.443 mmol), PdCl2(AmPhos)2 (0.102 g, 0.144 mmol) and KOAc (0.425 g, 4.33 mmol). The tube was sealed and evacuated under vacuum and back-filled with nitrogen. Dioxane (3.75 mL) and water (0.375 mL) was added and Ar (g) was bubbled through the mixture for 5 minutes. The reaction mixture was stirred and heated in a Initiator microwave reactor (Personal Chemistry, Biotage AB, Inc., Upssala, Sweden) at 120° C. for 20 minutes. The crude material was adsorbed onto a plug of silica gel and purified by chromatography through a silica gel column (40 g), eluting with a gradient of 0% to 100% EtOAc in hexane, to provide tert-butyl (3S)-4-((1R)-1-(5-(6-(bis(4-methoxybenzyl)amino)-2-methyl-4-pyrimidinyl)-6-fluoro-3-pyridinyl)ethyl)-3-methyl-1-piperazinecarboxylate (0.240 g, 0.358 mmol, 24.79% yield) as a yellow oil. m/z (ESI, +ve) 671.3 (M+H)$^+$. $^1$H NMR (400 MHz, CDCl$_3$) δ 8.40 (dd, J=9.39, 2.54 Hz, 1H); 8.13 (d, J=1.37 Hz, 1H); 7.18 (d, J=8.02 Hz, 4H); 6.80-6.90 (m, 5H); 4.50-5.03 (m, 4H); 4.03 (d, J=5.28 Hz, 1H); 3.73-3.84 (m, 6H); 3.24-3.57 (m, 3H); 3.08-3.22 (m, 1H); 2.69-2.81 (m, 1H); 2.61 (s, 3H); 2.29-2.51 (m, 2H); 1.37-1.48 (m, 12H); 1.02 (d, J=6.26 Hz, 3H).

Step 2: 6-(2-fluoro-5-((1R)-1-((2S)-2-methyl-1-piperazinyl)ethyl)-3-pyridinyl)-N,N-bis(4-methoxybenzyl)-2-methyl-4-pyrimidinamine A solution of tert-butyl (3S)-4-((1R)-1-(5-(6-(bis(4-methoxybenzyl)amino)-2-methyl-4-pyrimidinyl)-6-fluoro-3-pyridinyl)ethyl)-3-methyl-1-piperazinecarboxylate (0.240 g, 0.358 mmol) in CH$_2$Cl$_2$ (5 mL) at 0° C. was treated with TFA (0.53 mL, 7.16 mmol). The reaction was allowed to warm up to RT and stir for 2 hours. The reaction mixture was concentrated, resuspended in CH$_2$Cl$_2$ and treated with aqueous NaHCO$_3$ (sat.). The layers were separated and the aqueous layer was extracted with CH$_2$Cl$_2$ (2×). The combined organic layers were dried over anhydrous Na$_2$SO$_4$, filtered and concentrated to give 6-(2-fluoro-5-((1R)-1-((2S)-2-methyl-1-piperazinyl)ethyl)-3-pyridinyl)-N,N-bis(4-methoxybenzyl)-2-methyl-4-pyrimidinamine (0.200 g, 0.350 mmol, 98% yield) as a light yellow oil. m/z (ESI, +ve) 571.3 (M+H)$^+$. $^1$H NMR (400 MHz, CDCl$_3$) δ 8.39 (dd, J=9.39, 2.35 Hz, 1H); 8.12 (s, 1H); 7.18 (d, J=7.82 Hz, 4H); 6.79-6.89 (m, 5H); 4.74 (br. s., 4H); 4.16 (q, J=6.98 Hz, 1H); 3.79 (s, 6H); 2.80-2.99 (m, 4H); 2.53-2.63 (m, 4H); 2.23-2.41 (m, 2H); 1.47 (s, 3H); 1.08 (d, J=6.26 Hz, 3H).

Step 3: 6-(2-fluoro-5-((1R)-1-((2 S)-2-methyl-4-(methylsulfonyl)-1-piperazinyl)ethyl)-3-pyridinyl)-N,N-bis(4-methoxybenzyl)-2-methyl-4-pyrimidinamine A solution of 6-(2-fluoro-5-((1R)-1-((2S)-2-methyl-1-piperazinyl)ethyl)-3-pyridinyl)-N,N-bis(4-methoxybenzyl)-2-methyl-4-pyrimidinamine (0.200 g, 0.350 mmol) in CH$_2$Cl$_2$ (3 mL) at −20° C. was treated with NEt$_3$ (0.488 mL, 3.50 mmol) followed by methanesulfonyl chloride (0.083 mL, 1.051 mmol). The mixture stirred at −20° C. for 30 minutes. 1 M NaOH (aq.) and CH$_2$Cl$_2$ were then added. The layers were separated and the aqueous layer was extracted with CH$_2$Cl$_2$ (2×). The combined organic layers were dried over anhydrous Na$_2$SO$_4$, filtered and concentrated. The crude material was adsorbed onto a plug of silica gel and purified by chromatography through a silica gel column (12 g), eluting with a gradient of 60% to 100% EtOAc in hexane, to provide 6-(2-fluoro-5-((1R)-1-((2S)-2-methyl-4-(methylsulfonyl)-1-piperazinyl)ethyl)-3-pyridinyl)-N,N-bis(4-methoxybenzyl)-2-methyl-4-pyrimidinamine (0.130 g, 0.200 mmol, 57.2% yield) as a white foam. m/z (ESI, +ve) 649.2 (M+H)$^+$. $^1$H NMR (400 MHz, CDCl$_3$) δ 8.42 (dd, J=9.29, 2.45 Hz, 1H); 8.14 (d, J=1.17 Hz, 1H); 7.18 (d, J=7.82 Hz, 4H); 6.81-6.89 (m, 5H); 4.74 (br. s., 4H); 4.04 (q, J=6.78 Hz, 1H); 3.79 (s, 6H); 3.28-3.37 (m, 1H); 3.16-3.24 (m, 1H); 3.12 (dd, J=10.95, 2.93 Hz, 1H); 2.85-3.01 (m, 2H); 2.77 (s, 3H); 2.63-2.70 (m, 2H); 2.62 (s, 3H); 1.44 (d, J=6.85 Hz, 3H); 1.10 (d, J=6.26 Hz, 3H).

Step 4: 6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-N,N-bis(4-methoxybenzyl)-2-methyl-4-pyrimidinamine A solution of 6-(2-fluoro-5-((1R)-1-((2S)-2-methyl-4-(methylsulfonyl)-1-piperazinyl)ethyl)-3-pyridinyl)-N,N-bis(4-methoxybenzyl)-2-methyl-4-pyrimidinamine (0.130 g, 0.200 mmol) and 5-fluoro-6-methoxypyridin-3-amine (0.043 g, 0.301 mmol) in THF (2.00 mL) at −10° C. was treated with lithium bis(trimethylsilyl)amide (1.0 M solution in THF) (0.60 mL, 0.60 mmol). After 30 minutes, more lithium bis(trimethylsilyl)amide, (1.0 M solution in THF) (0.60 mL, 0.60 mmol) was added and the reaction mixture stirred for another 30 minutes at −10° C. Saturated NH$_4$Cl (aq.) was added and the mixture was extracted with CH$_2$Cl$_2$ (3×). The combined organic layers were dried over anhydrous Na$_2$SO$_4$, filtered and concentrated. The crude material was adsorbed onto a plug of silica gel and purified by chromatography through a silica gel column (4 g), eluting with a gradient of 0% to 100% EtOAc in hexane, to provide 6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-N,N-bis(4-methoxybenzyl)-2-methyl-4-pyrimidinamine (0.050 g, 0.065 mmol, 32.4% yield) as a brown oil. m/z (ESI, +ve) 771.2 (M+H)$^+$.

Step 5: 6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-2-methyl-4-pyrimidinamine A mixture of 6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-N,N-bis(4-methoxybenzyl)-2-methyl-4-pyrimidinamine (0.050 g, 0.065 mmol) in TFA (1 mL) was treated with triflic acid (5.76 μL, 0.065 mmol) and heated to 80° C. for 1 h. The reaction mixture was concentrated and then ice cubes were added to the brown residue. Saturated NaHCO$_3$ (aq.) was added followed by CH$_2$Cl$_2$. The layers were separated and the aqueous layer was extracted with CH$_2$Cl$_2$ (2×). The combined organic layers were dried over anhydrous Na$_2$SO$_4$, filtered and concentrated. The crude material was adsorbed onto a plug of silica gel and purified by chromatography through a silica gel column (4 g), eluting with a gradient of 0% to 5% MeOH in CH$_2$Cl$_2$, to provide 6-(2-((5-fluoro-6-methoxy-3-pyridinyl)amino)-5-((1R)-1-((2S)-2-methyl-4-(methylsulfonyl)-1-piperazinyl)ethyl)-3-pyridinyl)-2-methyl-4-pyrimidinamine (0.010 g, 0.019 mmol, 29.1% yield) as a brown solid. m/z (ESI, +ve) 531.2 (M+H)$^+$. $^1$H NMR (400 MHz, d$_6$-DMSO) δ 12.14 (s, 1H); 8.36 (dd, J=12.91, 2.35 Hz, 1H); 8.22-8.25 (m, 1H); 8.16 (d, J=2.35 Hz, 1H); 7.95 (dd, J=1.96, 0.39 Hz, 1H); 7.04 (s, 2H); 6.79 (s, 1H); 4.02 (q, J=6.65 Hz, 1H); 3.94 (s, 3H); 3.05-3.20

(m, 2H); 2.77-2.95 (m, 5H); 2.53 (br. s., 3H); 2.45 (dd, J=11.35, 5.28 Hz, 1H); 1.40 (d, J=6.65 Hz, 3H); 1.10 (d, J=6.26 Hz, 3H).

Example 307

N-(5-((3-(6-amino-2-methyl-4-pyrimidinyl)-2-pyrazinyl)amino)-2-chloro-3-pyridinyl)methanesulfonamide

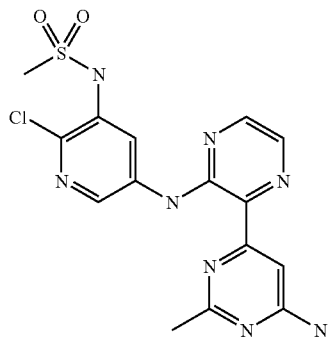 [SMILES: Cc1nc(N)cc(-c2nccnc2Nc2cnc(Cl)c(NS(C)(=O)=O)c2)n1]

Step 1:
6-(3-fluoro-2-pyrazinyl)-2-methyl-4-pyrimidinamine

A microwave tube was charged with 6-chloro-2-methyl-4-pyrimidinamine (SynChem, Inc., Des Plaines, Ill.) (0.223 g, 1.550 mmol), PdCl$_2$ (10.99 mg, 0.062 mmol), tri-t-butylphosphonium tetrafluoroborate (0.036 g, 0.124 mmol), CuI (0.024 g, 0.124 mmol) and CsF (0.471 g, 3.10 mmol). The tube was sealed and evacuated under vaccuum and back-filled with N$_2$ (g) 5 times. Argon was bubbled through the tube and 2-fluoro-3-(tributylstannyl)pyrazine (F. Toudic et al. Tetrahedron, 2003, 29, 6375-6384; 1.80 g, 4.65 mmol) in DMF (4 mL) was added and Ar (g) was bubbled through the solution for 5 minutes. The mixture was heated to 60° C. and stirred for 18 h. Water and EtOAc was added and the mixture was filtered through Celite® (diatomaceous earth). The layers were separated and the aqueous layer was extracted with EtOAc (2x). The combined organic layers were dried over anhydrous Na$_2$SO$_4$, filtered and concentrated. The crude material was adsorbed onto a plug of silica gel and purified by chromatography through a silica gel column (40 g), eluting with a gradient of 0% to 3% MeOH in CH$_2$Cl$_2$. The product was further purified by HPLC (10 to 90% CH$_3$CN and H$_2$O with 0.1% NH$_4$OH, flow rate equal to about 45 mL/min) to afford 6-(3-fluoro-2-pyrazinyl)-2-methyl-4-pyrimidinamine (0.077 g, 0.375 mmol, 24.21% yield) as a white solid. m/z (ESI, +ve) 206.1 (M+H)$^+$. $^1$H NMR (400 MHz, CDCl$_3$) δ 9.54 (d, J=4.50 Hz, 1H); 8.53 (d, J=8.22 Hz, 1H); 7.26 (s, 1H); 5.58 (br. s., 2H); 2.63 (s, 3H).

Step 2: N-(5-((3-(6-amino-2-methyl-4-pyrimidinyl)-2-pyrazinyl)amino)-2-chloro-3-pyridinyl)methanesulfonamide To a solution of N-(5-amino-2-chloropyridin-3-yl)methanesulfonamide (Example 330, Step 2) (0.091 g, 0.413 mmol) in THF (2.5 mL) at 0° C. was added NaHMDS (1.0 M solution in THF) (1.876 mL, 1.876 mmol). After the addition, the reaction mixture continued to stir at 0° C. under N$_2$ for 30 min. 6-(3-fluoropyrazin-2-yl)-2-methylpyrimidin-4-amine (0.077 g, 0.375 mmol) was added into the reaction mixture. The reaction mixture continued to stir at 0° C. for 10 min and was then slowly warmed up to RT. After 1 hour, the reaction mixture was partitioned between pH 7 buffer (1M TRIS-HCl) and CH$_2$Cl$_2$. The aqueous layer was extracted with CH$_2$Cl$_2$ (3x). The combined organic layers were dried over Na$_2$SO$_4$, filtered and concentrated. The crude product was purified by HPLC (10-90% CH$_3$CN and H$_2$O with 0.1% NH$_4$OH, flow rate equal to about 5 mL/min). The fractions containing the desired product were concentrated under a vacuum. The material was further purified by chromatography through a silica gel column (4 g), eluting with a gradient of 0% to 10% MeOH in CH$_2$Cl$_2$, to provide N-(5-((3-(6-amino-2-methyl-4-pyrimidinyl)-2-pyrazinyl)amino)-2-chloro-3-pyridinyl)methanesulfonamide (0.0080 g, 0.020 mmol, 5.24% yield) as a yellow solid. m/z (ESI, +ve) 407.0 (M+H)$^+$. $^1$H NMR (400 MHz, d$_6$-DMSO) δ 10.12 (s, 1H); 8.85 (s, 2H); 8.35 (s, 1H); 8.23-8.30 (m, 1H); 7.22 (s, 1H); 6.87 (br. s., 1H); 3.14 (s, 3H); 2.42 (s, 3H).

Example 308

4-(2-(6-methoxypyridin-3-ylamino)-5-(1-(3-(methylsulfonyl)azetidin-1-yl)ethyl)pyridin-3-yl)-6-methyl-1,3,5-triazin-2-amine

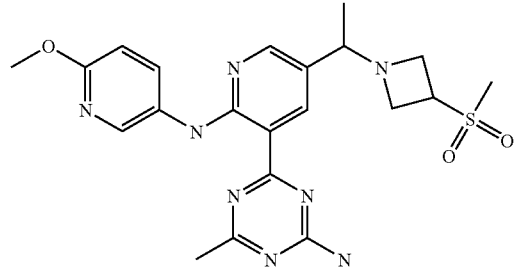 [SMILES: COc1ccc(Nc2ncc(C(C)N3CC(S(C)(=O)=O)C3)cc2-c2nc(C)nc(N)n2)cn1]

Step 1. 1-(5-(4-(bis(4-methoxybenzyl)amino)-6-methyl-1,3,5-triazin-2-yl)-6-(6-methoxypyridin-3-ylamino)pyridin-3-yl)ethanol Methylmagnesium bromide (1.4 M in 3:1 toluene/THF) (Aldrich, St. Louis, Mo.; 1.787 mL, 2.502 mmol) was added (dropwise, over 10 min) to a yellow-brown solution of 5-(4-(bis(4-methoxybenzyl)amino)-6-methyl-1,3,5-triazin-2-yl)-6-(6-methoxypyridin-3-ylamino)nicotinaldehyde (Example 144, Step 1; 451.7 mg, 0.782 mmol) in THF (5.0 mL) at 0° C., and the resulting brown solution was stirred at 0° C. for 1 h. Saturated ammonium chloride (10 ml) and water (10 ml) were then added, THF was removed in vacuo, and the resulting mixture was extracted with EtOAc (2x60 mL). The combined organic extracts were dried over sodium sulfate, filtered, and concentrated in vacuo. Trituration of the residue with hexanes (10 mL) furnished 1-(5-(4-(bis(4-methoxybenzyl)amino)-6-methyl-1,3,5-triazin-2-yl)-6-(6-methoxypyridin-3-ylamino)pyridin-3-yl)ethanol (331.1 mg, 0.558 mmol, 71.3% yield) as a yellow-brown solid. m/z (ESI, +ve) 594.2 (M+H)$^+$.

Step 2. 1-(5-(4-(bis(4-methoxybenzyl)amino)-6-methyl-1,3,5-triazin-2-yl)-6-(6-methoxypyridin-3-ylamino)pyridin-3-yl)ethyl methanesulfonate Methanesulfonyl chloride (0.164 mL, 2.119 mmol) was added to a solution of 1-(5-(4-(bis(4-methoxybenzyl)amino)-

6-methyl-1,3,5-triazin-2-yl)-6-(6-methoxypyridin-3-ylamino)pyridin-3-yl)ethanol (331.1 mg, 0.558 mmol) and triethylamine (0.350 mL, 2.510 mmol) in CH$_2$Cl$_2$ (7.5 mL) at 0° C., and the resulting mixture was stirred at 0° C. for 30 min. The reaction mixture was then partitioned between CH$_2$Cl$_2$ (40 mL) and water (30 mL). The organic layer was separated, and the aqueous layer was extracted with CH$_2$Cl$_2$ (30 mL). The combined organic extracts were dried over sodium sulfate, filtered, and concentrated in vacuo to provide 1-(5-(4-(bis(4-methoxybenzyl)amino)-6-methyl-1,3,5-triazin-2-yl)-6-(6-methoxypyridin-3-ylamino)pyridin-3-yl)ethyl methanesulfonate (356.1 mg, 0.530 mmol, 95% yield) as a yellow-brown solid, which was used directly in Step 3.

Step 3. N,N-bis(4-methoxybenzyl)-4-(2-(6-methoxypyridin-3-ylamino)-5-(1-(3-(methylsulfonyl)azetidin-1-yl)ethyl)pyridin-3-yl)-6-methyl-1,3,5-triazin-2-amine Triethylamine (0.327 mL, 2.345 mmol) and 3-(methylsulfonyl)azetidine (PharmaBlock, Carrboro, N.C.; 241 mg, 1.786 mmol) were sequentially added to a solution of 1-(5-(4-(bis(4-methoxybenzyl)amino)-6-methyl-1,3,5-triazin-2-yl)-6-(6-methoxypyridin-3-ylamino)pyridin-3-yl)ethyl methanesulfonate (375 mg, 0.558 mmol) in CH$_2$Cl$_2$ (5.5 mL) and the resulting mixture was stirred at 25° C. for 21 h. The reaction mixture was then concentrated in vacuo and chromatographically purified (silica gel, 0 to 100% (10% MeOH-EtOAc)/hexanes) to furnish N,N-bis(4-methoxybenzyl)-4-(2-(6-methoxypyridin-3-ylamino)-5-(1-(3-(methylsulfonyl)azetidin-1-yl)ethyl)pyridin-3-yl)-6-methyl-1,3,5-triazin-2-amine (141.0 mg, 0.198 mmol, 35.5% yield) as a yellow oil. m/z (ESI, +ve) 711.3 (M+H)$^+$.

Step 4. 4-(2-(6-methoxypyridin-3-ylamino)-5-(1-(3-(methylsulfonyl)azetidin-1-yl)ethyl)pyridin-3-yl)-6-methyl-1,3,5-triazin-2-amine 2,2,2-trifluoroacetate An orange solution of N,N-bis(4-methoxybenzyl)-4-(2-(6-methoxypyridin-3-ylamino)-5-(1-(3-(methylsulfonyl)azetidin-1-yl)ethyl)pyridin-3-yl)-6-methyl-1,3,5-triazin-2-amine (70.0 mg, 0.098 mmol) and trifluoromethanesulfonic acid (0.030 mL, 0.338 mmol) in TFA (1.5 mL) was stirred at 75° C. for 18 h. The resulting mixture was subsequently cooled to 25° C. and concentrated in vacuo. The residue was taken up in DMSO (2.0 mL) and purified by rpHPLC (Phenomenex Luna 5 μm C18 30×150 mm, 35 mL/min, 5 to 100% CH$_3$CN/H$_2$O (plus 0.1% TFA, both solvents) to provide 4-(2-(6-methoxypyridin-3-ylamino)-5-(1-(3-(methylsulfonyl)azetidin-1-yl)ethyl)pyridin-3-yl)-6-methyl-1,3,5-triazin-2-amine 2,2,2-trifluoroacetate (43.6 mg, 0.075 mmol, 76% yield) as an orange solid. $^1$H NMR (400 MHz, d$_4$-MeOH) δ 9.10 (d, J=2.5 Hz, 1H), 8.70 (d, J=2.7 Hz, 1H), 8.40 (d, J=2.5 Hz, 1H), 8.19 (dd, J=9.0, 2.7 Hz, 1H), 7.07 (d, J=9.0 Hz, 1H), 4.65 (q, J=6.7 Hz, 1H), 4.54-4.61 (m, 1H), 4.38-4.53 (m, 4H), 4.02 (s, 3H), 3.05 (s, 3H), 2.66 (s, 3H), 2.52 (s, 3H), 1.67 (d, J=6.8 Hz, 3H). $^{19}$F NMR (376 MHz, d$_4$-MeOH) δ −79.11 (s, 3F). m/z (ESI, +ve) 471.3 (M+H)$^+$.

Example 309

(R)-4-(2-(6-chloropyridin-3-ylamino)-5-(1-(4-(methylsulfonyl)piperazin-1-yl)ethyl)pyridin-3-yl)-6-methyl-1,3,5-triazin-2-amine

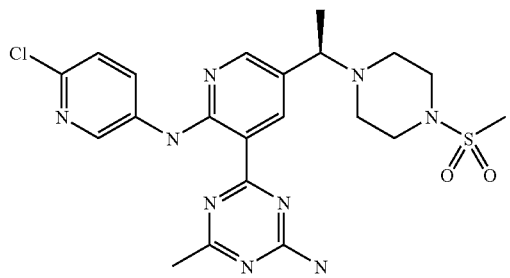 [SMILES: Cc1nc(N)nc(-c2cc([C@@H](C)N3CCN(S(C)(=O)=O)CC3)cnc2Nc2ccc(Cl)nc2)n1]

Step 1. (R)-4-(2-(6-chloropyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine Sodium bis(trimethylsilyl)amide (1.0M in THF) (Aldrich, St. Louis, Mo.; 0.777 mL, 0.777 mmol) was added to a mixture of (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (Example 146, Step 6) 141.2 mg, 0.222 mmol) and 6-chloropyridin-3-amine (Aldrich, St. Louis, Mo.; 57.1 mg, 0.444 mmol) in THF (2.5 mL) at 0° C., and the resulting dark brown solution was stirred at 0° C. for 30 min. Excess sodium bis(trimethylsilyl)amide was then quenched with saturated aqueous NH$_4$Cl (2 mL), and the reaction mixture was partitioned between EtOAc (50 mL) and saturated aqueous NH$_4$Cl (20 mL). The organic layer was separated, and the aqueous layer was extracted with EtOAc (2×20 mL). The combined organic extracts were sequentially washed with brine, dried over sodium sulfate, filtered, and concentrated in vacuo. Chromatographic purification of the residue (silica gel, 0 to 100% EtOAc/hexanes) furnished (R)-4-(2-(6-chloropyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (125.0 mg, 0.168 mmol, 76% yield) as a yellow-brown oil. $^1$H NMR (400 MHz, CDCl$_3$) δ 12.12 (s, 1H), 8.74 (d, J=2.2 Hz, 1H), 8.50 (s, 1H), 8.28 (s, 1H), 8.18-8.24 (m, 1H), 7.21 (td, J=5.7, 2.4 Hz, 5H), 6.89 (s, 2H), 6.85 (d, J=8.6 Hz, 2H), 4.74-4.93 (m, 4H), 3.81 (s, 3H), 3.79 (s, 3H), 3.52-3.59 (m, 1H), 3.15 (br. s., 4H), 2.67 (s, 3H), 2.60 (s, 3H), 2.47-2.58 (m, 4H), 1.38 (d, J=6.7 Hz, 3H). m/z (ESI, +ve) 744.2 (M+H)$^+$.

Step 2. (R)-4-(2-(6-chloropyridin-3-ylamino)-5-(1-(4-(methylsulfonyl)piperazin-1-yl)ethyl)pyridin-3-yl)-6-methyl-1,3,5-triazin-2-amine A brown solution of (R)-4-(2-(6-chloropyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (125.0 mg, 0.168 mmol) and trifluoromethanesulfonic acid (0.15 mL, 1.689 mmol) in TFA (1.5 mL) was stirred at 75° C. for 1.5 h. The mixture was subsequently cooled to 25° C. and concentrated in vacuo. The residue was taken up in CH$_2$Cl$_2$ (50 mL), and the resulting solution was washed with saturated aqueous sodium bicarbonate (40 mL). The organic layer was separated, and the aqueous layer was extracted with CH$_2$Cl$_2$ (2×30 mL). All organic layers were then combined, dried over sodium sulfate, filtered, and concentrated in vacuo. Chromatographic purification of the residue (silica gel, 0 to 10% MeOH/CH$_2$Cl$_2$) furnished (R)-4-(2-(6-chloropyridin-3-ylamino)-5-(1-(4-(methylsulfonyl)piperazin-1-yl)ethyl)pyridin-3-yl)-6-methyl-1,3,5-triazin-2-amine (52.8 mg, 0.105 mmol, 62.4% yield) as a yellow solid. $^1$H NMR (400 MHz, d$_6$-DMSO) δ 12.16 (s, 1H), 8.88 (d, J=2.7 Hz, 1H), 8.74 (d, J=2.5 Hz, 1H), 8.48 (dd, J=8.7, 2.8 Hz, 1H), 8.35 (d, J=2.3 Hz, 1H), 7.45 (d, J=8.8 Hz, 1H), 3.59 (q, J=6.8 Hz, 1H), 3.09 (t, J=4.5 Hz, 4H), 2.86 (s, 3H), 2.56 (br. s., 2H), 2.46 (s, 3H), 2.41-2.45 (m, 2H), 1.36 (d, J=6.7 Hz, 3H). m/z (ESI, +ve) 504.1 (M+H)$^+$.

Example 310

(R)-N-(3-(4-amino-6-methyl-1,3,5-triazin-2-yl)-5-(1-(4-(methylsulfonyl)piperazin-1-yl)ethyl)pyridin-2-yl)quinolin-7-amine 2,2,2-trifluoroacetate

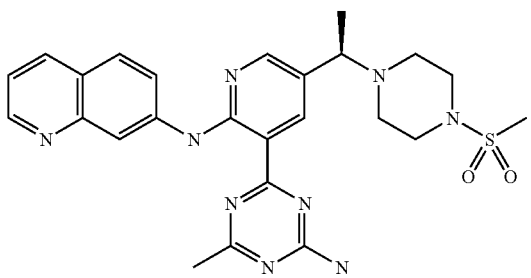 [SMILES: Cc1nc(N)nc(-c2cc([C@@H](C)N3CCN(S(C)(=O)=O)CC3)cnc2Nc2ccc3cccnc3c2)n1]

Step 1. (R)-N-(3-(4-(bis(4-methoxybenzyl)amino)-6-methyl-1,3,5-triazin-2-yl)-5-(1-(4-(methylsulfonyl)piperazin-1-yl)ethyl)pyridin-2-yl)quinolin-7-amine Sodium bis(trimethylsilyl)amide (1.0 M in THF) (Aldrich, St. Louis, Mo.; 0.863 mL, 0.863 mmol) was added to a mixture of (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (Example 146, Step 6; 156.7 mg, 0.246 mmol) and quinolin-7-amine (Ark Pharm, Libertyville, Ill.; 71.1 mg, 0.493 mmol) in THF (2.5 mL) at 0° C., and the resulting dark brown solution was stirred at 0° C. for 2 h. Excess sodium bis(trimethylsilyl)amide was then quenched with saturated aqueous NH$_4$Cl (2 mL), and the reaction mixture was partitioned between EtOAc (50 mL) and saturated aqueous NH$_4$Cl (20 mL). The organic layer was separated, and the aqueous layer was extracted with EtOAc (2×20 mL). The combined organic extracts were sequentially washed with brine, dried over sodium sulfate, filtered, and concentrated in vacuo. Chromatographic purification of the residue (silica gel, 0 to 6% MeOH/CH$_2$Cl$_2$) furnished (R)-N-(3-(4-(bis(4-methoxybenzyl)amino)-6-methyl-1,3,5-triazin-2-yl)-5-(1-(4-(methylsulfonyl)piperazin-1-yl)ethyl)pyridin-2-yl)quinolin-7-amine (189 mg, 0.249 mmol, 101% yield) as a yellow-orange foam, which was used directly in Step 2. m/z (ESI, +ve) 760.3 (M+H)$^+$.

Step 2. (R)-N-(3-(4-amino-6-methyl-1,3,5-triazin-2-yl)-5-(1-(4-(methylsulfonyl)piperazin-1-yl)ethyl)pyridin-2-yl)quinolin-7-amine 2,2,2-trifluoroacetate A brown solution of (R)-N-(3-(4-(bis(4-methoxybenzyl)amino)-6-methyl-1,3,5-triazin-2-yl)-5-(1-(4-(methylsulfonyl)piperazin-1-yl)ethyl)pyridin-2-yl)quinolin-7-amine (170.8 mg, 0.225 mmol) and trifluoromethanesulfonic acid (0.2 mL, 2.252 mmol) (10% v/v with TFA) in TFA (2.0 mL) was stirred at 75° C. for 1.5 h. The reaction mixture was subsequently cooled to 25° C. and concentrated in vacuo. The residue was taken up in CH$_2$Cl$_2$ (50 mL), and the resulting solution was washed with saturated aqueous sodium bicarbonate (40 mL). The organic layer was separated, and the aqueous layer was extracted with CH$_2$Cl$_2$ (2×30 mL). All organic layers were then combined, dried over sodium sulfate, filtered, and concentrated in vacuo. The residue was taken up in DMSO (2.0 mL) and purified by rpHPLC (Phenomenex Luna 5 μm C18, 30×150 mm, 45 mL/min, 10 to 100% CH$_3$CN/H$_2$O (plus 0.1% TFA, both solvents)) to provide (R)-N-(3-(4-amino-6-methyl-1,3,5-triazin-2-yl)-5-(1-(4-(methylsulfonyl)piperazin-1-yl)ethyl)pyridin-2-yl)quinolin-7-amine 2,2,2-trifluoroacetate (52.0 mg, 0.082 mmol, 36.5% yield) as a yellow-orange solid. $^1$H NMR (400 MHz, d$_4$-MeOH) δ 9.52 (d, J=1.8 Hz, 1H), 9.18 (d, J=2.5 Hz, 1H), 8.99 (d, J=8.2 Hz, 1H), 8.96 (dd, J=5.6, 1.3 Hz, 1H), 8.68 (d, J=2.5 Hz, 1H), 8.25 (d, J=9.2 Hz, 1H), 8.04 (dd, J=9.0, 2.0 Hz, 1H), 7.83 (dd, J=8.0, 5.7 Hz, 1H), 4.70 (q, J=7.0 Hz, 1H), 3.55 (br. s., 4H), 2.94 (s, 3H), 2.65 (s, 4H), 2.58 (s, 3H), 1.89 (d, J=6.8 Hz, 3H). $^{19}$F NMR (376 MHz, d$_4$-MeOH) δ −77.36 (s, 3F). m/z (ESI, +ve) 520.2 (M+H)$^+$.

Example 311

2-(5-(4-amino-6-methyl-1,3,5-triazin-2-yl)-6-(5-fluoro-6-methoxypyridin-3-ylamino)pyridin-3-yl)-2-methylpropan-1-ol

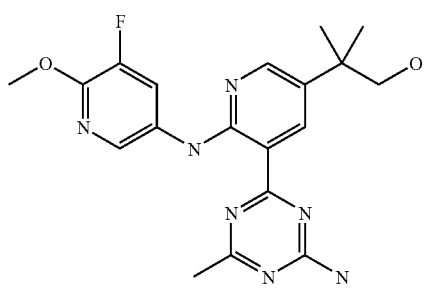 [SMILES: COc1ncc(Nc2ncc(C(C)(C)CO)cc2-c2nc(C)nc(N)n2)cc1F]

Step 1. tert-butyl 2-(6-fluoropyridin-3-yl)acetate (2-tert-Butoxy-2-oxoethyl)zinc(II) chloride (0.5M in ethyl ether) (Rieke Metals, Inc., Lincoln, Nebr.; 73.9 mL, 36.9 mmol) was added to a mixture of 5-bromo-2-fluoropyridine (Acros, Morris Plains, N.J.; 2.92 mL, 28.4 mmol) and bis(di-tert-butyl(4-dimethylaminophenyl)phosphine)dichloropalladium(II) (Aldrich, St. Louis, Mo.; 0.201 g, 0.284 mmol) in THF (150 mL) and the resulting yellow solution was stirred at 65° C. for 1.5 h in a flask fitted with an air-cooled reflux condenser. Water (200 μL) was added to the reaction, and the resulting mixture was concentrated onto silica gel and chromatographically purified (silica gel, 0 to 30% EtOAc/hexanes) to provide tert-butyl 2-(6-fluoropyridin-3-yl)acetate (2.43 g, 11.50 mmol, 40.5% yield) as a yellow oil. $^1$H NMR (400 MHz, CDCl$_3$) δ 8.09 (s, 1H), 7.74 (td, J=8.0, 2.5 Hz, 1H), 6.90 (dd, J=8.4, 2.9 Hz, 1H), 3.52 (s, 2H), 1.44 (s, 9H). m/z (ESI, +ve) 212.1 (M+H)$^+$.

Step 2. tert-butyl 2-(6-fluoropyridin-3-yl)-2-methylpropanoate

Potassium tert-butoxide (2.71 g, 24.16 mmol) was added to a mixture of tert-butyl 2-(6-fluoropyridin-3-yl)acetate (2.43 g, 11.50 mmol) and iodomethane (1.511 mL, 24.16 mmol) in THF (100 mL) at −78° C., and the resulting yellow-orange mixture was stirred at −78° C. for 7 h, then allowed to warm to 25° C. and stir for 20 h. The resulting off-white suspension was subsequently concentrated onto silica gel and chromatographically purified (silica gel, 0 to 20% EtOAc/Hexanes) to provide tert-butyl 2-(6-fluoropyridin-3-yl)-2-methylpropanoate (2.07 g, 8.65 mmol, 75% yield) as a colorless oil. $^1$H NMR (400 MHz, CDCl$_3$) δ 8.20 (d, J=2.3 Hz, 1H), 7.73-7.79 (m, 1H), 6.88 (dd, J=8.6, 3.1 Hz, 1H), 1.56 (s, 6H), 1.38 (s, 9H). $^{19}$F NMR (377 MHz, CDCl$_3$) δ −71.44 (d, J=4.8 Hz, 1 F). m/z (ESI, +ve) 240.2 (M+H)$^+$.

Step 3. 2-(6-fluoropyridin-3-yl)-2-methylpropan-1-ol

Lithium aluminum hydride (1.0M in THF) (Aldrich, St. Louis, Mo.; 12.98 mL, 12.98 mmol) was added to a solution of tert-butyl 2-(6-fluoropyridin-3-yl)-2-methylpropanoate (2.07 g, 8.65 mmol) in THF (34 mL) at 0° C. (gas evolution), and the resulting solution was stirred at 0° C. for 5 min. EtOAc (15 mL) was then added at 0° C. to quench excess lithium aluminum hydride, followed by 10% aqueous Na/K tartrate (150 mL). The resulting mixture was stirred at 25° C. for 10 min and then partitioned between EtOAc (200 mL) and water (50 mL). The organic layer was separated, and the aqueous layer was extracted with EtOAc (150 mL). The combined organic extracts were washed with brine (150 mL), dried over sodium sulfate, filtered, and concentrated in vacuo to provide 2-(6-fluoropyridin-3-yl)-2-methylpropan-1-ol (1.46 g, 8.63 mmol, 100% yield) as a colorless oil. $^1$H NMR (400 MHz, CDCl$_3$) δ 8.22 (br. s., 1H), 7.78-7.84 (m, 1H), 6.89 (dd, J=8.6, 3.1 Hz, 1H), 3.63 (s, 2H), 1.36 (s, 6H). $^{19}$F NMR (377 MHz, CDCl$_3$) δ −72.21 (br. s., 1 F). m/z (ESI, +ve) 170.2 (M+H)$^+$.

Step 4. 5-(1-(tert-butyldimethylsilyloxy)-2-methylpropan-2-yl)-2-fluoropyridine Tert-butyldimethylsilyl trifluoromethanesulfonate (2.180 mL, 9.49 mmol) was added to a solution of 2-(6-fluoropyridin-3-yl)-2-methylpropan-1-ol (1.46 g, 8.63 mmol) and N,N-diisopropylethylamine (3.31 mL, 18.98 mmol) in CH$_2$Cl$_2$ (43.1 mL) at 0° C., and the resulting mixture stirred at 0° C. for 30 min. The reaction mixture was subsequently concentrated onto silica gel and chromatographically purified (silica gel, 0 to 15% EtOAc/hexanes) to provide 5-(1-(tert-butyldimethylsilyloxy)-2-methylpropan-2-yl)-2-fluoropyridine (2.22 g, 7.83 mmol, 91% yield) as a colorless oil. $^1$H NMR (400 MHz, CDCl$_3$) δ 8.20 (d, J=2.0 Hz, 1H), 7.79 (td, J=8.2, 2.7 Hz, 1H), 6.85 (dd, J=8.6, 2.9 Hz, 1H), 3.51 (s, 2H), 1.31 (s, 6H), 0.83 (s, 9H), −0.06 (s, 6H). $^{19}$F NMR (377 MHz, CDCl$_3$) δ −73.08 (d, J=6.0 Hz, 1 F). m/z (ESI, +ve) 284.3 (M+H)$^+$.

Step 5. 5-(1-(tert-butyldimethylsilyloxy)-2-methylpropan-2-yl)-2-fluoropyridin-3-ylboronic acid n-Butyllithium (1.66 M in hexane) (Aldrich, St. Louis, Mo.; 0.429 mL, 0.712 mmol) was added (dropwise over 1 min) to a solution of 5-(1-(tert-butyldimethylsilyloxy)-2-methylpropan-2-yl)-2-fluoropyridine (183.5 mg, 0.647 mmol) in THF (3.3 mL) at −78° C., and the resulting yellow solution was stirred at −78° C. for 1 h. Tri-isopropyl borate (Aldrich, St. Louis, Mo.; 0.179 mL, 0.777 mmol) was then added, and the resulting mixture was stirred at −78° C. for 1 h. The reaction mixture was subsequently partitioned between EtOAc (50 mL) and water (30 mL) (1N HCl (about 200 µL) was added to bring the pH of the aqueous layer to 6.5). The organic layer was separated, and the aqueous layer was extracted with EtOAc (30 mL). The combined organic extracts were dried over sodium sulfate, filtered, and concentrated in vacuo to provide 5-(1-(tert-butyldimethylsilyloxy)-2-methylpropan-2-yl)-2-fluoropyridin-3-ylboronic acid (228.0 mg, 0.697 mmol, 108% yield) as a colorless oil. m/z (ESI, +ve) 328.3 (M+H)$^+$.

Step 6. 4-(5-(1-(tert-butyldimethylsilyloxy)-2-methylpropan-2-yl)-2-fluoropyridin-3-yl)-6-methyl-1,3,5-triazin-2-amine A yellow solution of 5-(1-(tert-butyldimethylsilyloxy)-2-methylpropan-2-yl)-2-fluoropyridin-3-ylboronic acid (177 mg, 0.541 mmol), 4-chloro-6-methyl-1,3,5-triazin-2-amine (Example 9; 78 mg, 0.541 mmol), bis(di-tert-butyl(4-dimethylaminophenyl)phosphine)dichloropalladium(II) (Aldrich, St. Louis, Mo.; 19.15 mg, 0.027 mmol), and potassium acetate (159 mg, 1.622 mmol) in a mixture of dioxane (4.0 mL) and water (1.0 mL) was stirred under argon at 100° C. for 2 h. The yellow reaction mixture was subsequently partitioned between CH$_2$Cl$_2$ (80 mL) and water (50 mL). The organic layer was separated, and the aqueous layer was extracted with CH$_2$Cl$_2$ (2×30 mL). The combined organic extracts were then dried over sodium sulfate and concentrated onto silica gel. Chromatographic purification (silica gel, 0 to 60% EtOAc/hexanes) provided 4-(5-(1-(tert-butyldimethylsilyloxy)-2-methylpropan-2-yl)-2-fluoropyridin-3-yl)-6-methyl-1,3,5-triazin-2-amine (73.0 mg, 0.186 mmol, 34.5% yield) as a white solid. $^1$H NMR (400 MHz, CDCl$_3$) δ 8.56 (dd, J=9.2, 2.5 Hz, 1H), 8.33 (d, J=1.4 Hz, 1H), 5.65 (br. s., 2H), 3.57 (s, 2H), 2.54 (s, 3H), 1.37 (s, 6H), 0.84 (s, 9H), −0.03 (s, 6H). $^{19}$F NMR (377 MHz, CDCl$_3$) δ −70.17 (d, J=9.2 Hz, 1 F). m/z (ESI, +ve) 392.3 (M+H)$^+$.

Step 7. 4-(5-(1-(tert-butyldimethylsilyloxy)-2-methylpropan-2-yl)-2-(5-fluoro-6-methoxypyridin-3-ylamino)pyridin-3-yl)-6-methyl-1,3,5-triazin-2-amine Sodium bis(trimethylsilyl)amide (1.0M in THF) (Aldrich, St. Louis, Mo.; 0.447 mL, 0.447 mmol) was added to an orange-brown solution of 4-(5-(1-(tert-butyldimethylsilyloxy)-2-methylpropan-2-yl)-2-fluoropyridin-3-yl)-6-methyl-1,3,5-triazin-2-amine (73.0 mg, 0.186 mmol) and 5-fluoro-6-methoxypyridin-3-amine (Anichem, North Brunswick, N.J.; 31.8 mg, 0.224 mmol) in THF (2.0 mL) at 0° C., and the resulting brown solution was stirred at 0° C. for 1 h. Excess sodium bis(trimethylsilyl)amide was carefully quenched with saturated aqueous NH$_4$Cl (5 mL), and the resulting mixture was partitioned between CH$_2$Cl$_2$ (50 mL) and half-saturated aqueous NH$_4$Cl (30 mL). The aqueous layer was extracted with CH$_2$Cl$_2$ (30 mL), and the combined organic extracts were dried over sodium sulfate, filtered, and concentrated in vacuo. Chromatographic purification of the residue (silica gel, 0 to 70% EtOAc/hexanes) furnished 4-(5-(1-(tert-butyldimethylsilyloxy)-2-methylpropan-2-yl)-2-(5-fluoro-6-methoxypyridin-3-ylamino)pyridin-3-yl)-6-methyl-1,3,5-triazin-2-amine (88.8 mg, 0.173 mmol, 93% yield) as a yellow-orange solid. m/z (ESI, +ve) 514.0 (M+H)+.

Step 8. 2-(5-(4-amino-6-methyl-1,3,5-triazin-2-yl)-6-(5-fluoro-6-methoxypyridin-3-ylamino)pyridin-3-yl)-2-methylpropan-1-ol Tetra(N-butyl)ammonium fluoride (1.0M in THF) (Fluka, St. Louis, Mo.; 0.432 mL, 0.432 mmol) was added to an orange solution of 4-(5-(1-(tert-butyldimethylsilyloxy)-2-methylpropan-2-yl)-2-(5-fluoro-6-methoxypyridin-3-ylamino)pyridin-3-yl)-6-methyl-1,3,5-triazin-2-amine (88.8 mg, 0.173 mmol) in THF (2.0 mL) at 0° C., and the resulting mixture was stirred at 0° C. for 10 min, then at 25° C. for 3 h. The reaction mixture was subsequently concentrated onto silica gel and chromatographically purified (silica gel, 0 to 100% EtOAc/hexanes) to provide 2-(5-(4-amino-6-methyl-1,3,5-triazin-2-yl)-6-(5-fluoro-6-methoxypyridin-3-ylamino)pyridin-3-yl)-2-methylpropan-1-ol (44.0 mg, 0.110 mmol, 63.7% yield) as a yellow solid. $^1$H NMR (400 MHz, d$_6$-DMSO) δ 11.87 (s, 1H), 8.81 (d, J=2.7 Hz, 1H), 8.37-8.43 (m, 3H), 7.86 (br. s., 1H), 7.72 (br. s., 1H), 4.75 (br. s., 1H), 3.93 (s, 3H), 3.43 (s, 2H), 2.44 (s, 3H), 1.27 (s, 6H). $^{19}$F NMR (377 MHz, d$_6$-DMSO) δ -139.89 to -139.79 (m, 1 F). m/z (ESI, +ve) 400.3 (M+H)+.

Example 312

2-(5-(4-amino-6-methyl-1,3,5-triazin-2-yl)-6-(5-fluoro-6-methoxypyridin-3-ylamino)pyridin-3-yl)propan-1-ol

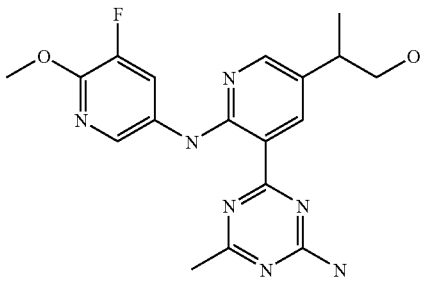 [SMILES: COc1ncc(Nc2ncc(C(C)CO)cc2-c2nc(C)nc(N)n2)cc1F]

Step 1. 2-fluoro-5-(PROP-1-EN-2-yl)pyridine

A burgundy-colored solution of 5-bromo-2-fluoropyridine (Acros, Morris Plains, N.J.; 1.737 mL, 16.88 mmol), potassium trifluoro(prop-1-en-2-yl)borate (Aldrich, St. Louis, Mo.; 3.75 g, 25.3 mmol), bis(di-tert-butyl(4-dimethylaminophenyl)phosphine)dichloropalladium(II) (Aldrich, St. Louis, Mo.; 0.239 g, 0.338 mmol), and potassium carbonate (7.00 g, 50.6 mmol) in a mixture of dioxane (40 mL) and water (10.00 mL) was stirred at 80° C. for 2.5 h. The reaction mixture was then cooled to 25° C. and partitioned between CH$_2$Cl$_2$ (300 mL) and water (100 mL). The aqueous layer was extracted with CH$_2$Cl$_2$ (2×100 mL), and the combined organic layers were dried over sodium sulfate, filtered, and concentrated onto silica gel. Chromatographic purification (silica gel, 0 to 20% EtOAc/hexanes) furnished 2-fluoro-5-(prop-1-en-2-yl)pyridine (2.06 g, 15.02 mmol, 89% yield) as a colorless oil. $^1$H NMR (400 MHz, CDCl3) δ ppm 8.29 (d, J=2.5 Hz, 1H), 7.81-7.89 (m, 1H), 6.89 (dd, J=8.5, 3.0 Hz, 1H), 5.36 (s, 1H), 5.16 (s, 1H), 2.15 (s, 3H). $^{19}$F NMR (377 MHz, CDCl$_3$) δ -70.28 (br. s., 1 F). m/z (ESI, +ve) 138.1 (M+H)+.

Step 2. 2-(6-fluoropyridin-3-yl)propan-1-ol

Borane tetrahydrofuran complex (1.0M in THF) (Aldrich, St. Louis, Mo.; 15.75 mL, 15.75 mmol) was added to a solution of 2-fluoro-5-(prop-1-en-2-yl)pyridine (1.44 g, 10.50 mmol) in THF (70 mL) at 0° C. and the resulting mixture was stirred under argon at 25° C. for 1.5 h. The resulting mixture was then cooled to 0° C., and sodium hydroxide (2.5N, aqueous; 5.25 mL, 13.12 mmol) and hydrogen peroxide (30%, aq.) (Columbus Chemical Industries, Columbus, Wis.; 1.877 mL, 18.37 mmol) were sequentially added (gas evolution), and the resulting light-yellow solution was stirred at 60° C. for 1.25 h. The reaction mixture was then partially concentrated in vacuo (to remove THF) and partitioned between EtOAc (300 mL) and half-saturated aqueous NaHCO$_3$ (100 mL). The organic layer separated, and the aqueous layer was extracted with EtOAc (2×100 mL). The combined organic extracts were washed with brine (200 mL), dried over sodium sulfate, filtered, and concentrated in vacuo. Chromatographic purification of the residue (silica gel, 0 to 100% EtOAc/hexanes) furnished 2-(6-fluoropyridin-3-yl)propan-1-ol (0.951 g, 6.13 mmol, 58.4% yield) as a colorless oil. $^1$H NMR (400 MHz, CDCl$_3$) δ 8.10 (d, J=2.0 Hz, 1H), 7.68 (td, J=8.0, 2.5 Hz, 1H), 6.90 (dd, J=8.4, 2.9 Hz, 1H), 3.67-3.79 (m, 2H), 3.00 (sxt, J=6.8 Hz, 1H), 1.31 (d, J=7.0 Hz, 3H). $^{19}$F NMR (377 MHz, CDCl3) δ ppm -71.31 (br. s., 1 F). m/z (ESI, +ve) 156.2 (M+H)+.

Step 3. 5-(1-(tert-butyldimethylsilyloxy)propan-2-yl)-2-fluoropyridine

Tert-butyldimethylsilyl trifluoromethanesulfonate (2.160 mL, 9.41 mmol) was added to a solution of 2-(6-fluoropyridin-3-yl)propan-1-ol (1.39 g, 8.96 mmol) and N,N-diisopropylethylamine (3.35 mL, 19.26 mmol) in CH$_2$Cl$_2$ (45 mL) at 0° C., and the resulting mixture stirred at 0° C. for 2.5 h. The reaction mixture was subsequently concentrated onto silica gel and chromatographically purified (silica gel, 0 to 20% EtOAc/hexanes) to provide 5-(1-(tert-butyldimethylsilyloxy)propan-2-yl)-2-fluoropyridine (1.89 g, 7.01 mmol, 78% yield) as a colorless oil. $^1$H NMR (400 MHz, CDCl$_3$) δ 8.06 (d, J=2.2 Hz, 1H), 7.65 (td, J=8.1, 2.5 Hz, 1H), 6.86 (dd, J=8.4, 2.9 Hz, 1H), 3.58-3.69 (m, 2H), 2.93 (sxt, J=6.7 Hz, 1H), 1.28 (d, J=7.0 Hz, 3H), 0.84 (s, 9H), -0.04 (s, 3H), -0.05 (s, 3H). $^{19}$F NMR (377 MHz, CDCl$_3$) δ -72.06 (d, J=6.0 Hz, 1 F). m/z (ESI, +ve) 270.3 (M+H)+.

Step 4. 5-(1-(tert-butyldimethylsilyloxy)propan-2-yl)-2-fluoropyridin-3-ylboronic acid n-Butyllithium (1.55M in hexane) (Aldrich, St. Louis, Mo.; 4.98 mL, 7.72 mmol) was added (dropwise over 5 min) to a solution of 5-(1-(tert-butyldimethylsilyloxy)propan-2-yl)-2-fluoropyridine (1.89 g, 7.01 mmol) in THF (35 mL) at -78° C., and the resulting yellow solution was stirred at -78° C. for 1 h. Triisopropyl borate (Aldrich, St. Louis, Mo.; 1.935 mL, 8.42 mmol) was then added, and the resulting mixture was stirred at -78° C. for 1 h. The reaction mixture was subsequently partitioned between EtOAc (250 mL) and water (90 mL) (1N aq. HCl (12.0 mL) was added to bring the pH to about 6.5). The organic layer was separated, and the aqueous layer was extracted with EtOAc (2×100 mL). The combined organic extracts were dried over sodium sulfate, filtered, and concentrated in vacuo to provide 5-(1-(tert-butyldimethylsilyloxy)propan-2-yl)-2-fluoropyridin-3-ylboronic acid (2.25 g, 7.18 mmol, 102% yield) as a colorless oil, which was used directly in the subsequent step. m/z (ESI, +ve) 314.2 (M+H)$^+$.

Step 5. 4-(5-(1-(tert-butyldimethylsilyloxy)propan-2-yl)-2-fluoropyridin-3-yl)-6-methyl-1,3,5-triazin-2-amine A yellow solution of 5-(1-(tert-butyldimethylsilyloxy)propan-2-yl)-2-fluoropyridin-3-ylboronic acid (1.79 g, 5.71 mmol), 4-chloro-6-methyl-1,3,5-triazin-2-amine (Example 9; 0.826 g, 5.71 mmol), bis(di-tert-butyl(4-dimethylaminophenyl)phosphine)dichloropalladium(II) (Aldrich, St. Louis, Mo.; 0.202 g, 0.286 mmol), and potassium acetate (1.682 g, 17.14 mmol) in a mixture of dioxane (50 mL) and water (12.50 mL) was stirred under argon at 100° C. for 2 h. The yellow reaction mixture was subsequently partitioned between $CH_2Cl_2$ (200 mL) and half-saturated brine (100 mL). The organic layer was separated, and the aqueous layer was extracted with $CH_2Cl_2$ (2×100 mL). The combined organic extracts were dried over sodium sulfate and concentrated onto silica gel. Chromatographic purification (silica gel, 0 to 70% EtOAc/hexanes) provided 4-(5-(1-(tert-butyldimethylsilyloxy)propan-2-yl)-2-fluoropyridin-3-yl)-6-methyl-1,3,5-triazin-2-amine (1.11 g, 2.94 mmol, 51.5% yield) as a colorless oil. $^1$H NMR (400 MHz, CDCl$_3$) δ 8.44 (dd, J=9.3, 2.4 Hz, 1H), 8.19 (d, J=1.4 Hz, 1H), 5.49 (br. s., 2H), 3.63-3.76 (m, 2H), 2.96-3.07 (m, 1H), 2.55 (s, 3H), 1.34 (d, J=7.0 Hz, 3H), 0.85 (s, 9H), −0.02 (s, 3H), −0.03 (s, 3H). $^{19}$F NMR (377 MHz, CDCl$_3$) δ −68.99 (d, J=6.0 Hz, 1 F). m/z (ESI, +ve) 378.3 (M+H)$^+$.

Step 6. 4-(5-(1-(tert-butyldimethylsilyloxy)propan-2-yl)-2-(5-fluoro-6-methoxypyridin-3-ylamino)pyridin-3-yl)-6-methyl-1,3,5-triazin-2-amine Sodium bis(trimethylsilyl)amide (1.0M in THF) (Aldrich, St. Louis, Mo.; 1.279 mL, 1.279 mmol) was added to an orange-brown solution of 4-(5-(1-(tert-butyldimethylsilyloxy)propan-2-yl)-2-fluoropyridin-3-yl)-6-methyl-1,3,5-triazin-2-amine (201.2 mg, 0.533 mmol) and 5-fluoro-6-methoxypyridin-3-amine (Anichem, North Brunswick, N.J.; 91 mg, 0.640 mmol) in THF (5.0 mL) at 0° C., and the resulting brown solution was stirred at 0° C. for 1.5 h. Additional sodium bis(trimethylsilyl)amide (1.0M in THF) (Aldrich, St. Louis, Mo.; 0.300 mL, 0.300 mmol) was then added, and the resulting mixture was stirred at 0° C. for 30 min. Excess sodium bis(trimethylsilyl)amide was carefully quenched with saturated aqueous NH$_4$Cl (5 mL), and the resulting mixture was partitioned between $CH_2Cl_2$ (50 mL) and half-saturated aqueous NH$_4$Cl (30 mL). The aqueous layer was extracted with $CH_2Cl_2$ (30 mL), and the combined organic extracts were dried over sodium sulfate, filtered, and concentrated in vacuo. Chromatographic purification of the residue (silica gel, 0 to 70% EtOAc/hexanes) furnished 4-(5-(1-(tert-butyldimethylsilyloxy)propan-2-yl)-2-(5-fluoro-6-methoxypyridin-3-ylamino)pyridin-3-yl)-6-methyl-1,3,5-triazin-2-amine (241.0 mg, 0.482 mmol, 91% yield) as a yellow-orange solid. $^1$H NMR (400 MHz, CDCl$_3$) δ 11.82 (s, 1H), 8.73 (d, J=2.5 Hz, 1H), 8.26 (dd, J=12.3, 2.2 Hz, 1H), 8.22 (d, J=2.3 Hz, 1H), 8.04 (d, J=2.3 Hz, 1H), 5.40 (br. s., 2H), 4.02 (s, 3H), 3.67 (dd, J=6.2, 2.8 Hz, 2H), 2.91 (q, J=6.5 Hz, 1H), 2.57 (s, 3H), 1.32 (d, J=7.0 Hz, 3H), 0.87 (s, 9H), 0.00 (s, 3H), −0.01 (s, 3H). $^{19}$F NMR (377 MHz, CDCl$_3$) δ −139.42 (s, 1 F). m/z (ESI, +ve) 500.3 (M+H)$^+$.

Step 7. 2-(5-(4-amino-6-methyl-1,3,5-triazin-2-yl)-6-(5-fluoro-6-methoxypyridin-3-ylamino)pyridin-3-yl)propan-1-ol Tetra(N-butyl)ammonium fluoride (1.0M in THF) (Fluka, St. Louis, Mo.; 1.206 mL, 1.206 mmol) was added to an orange solution of 4-(5-(1-(tert-butyldimethylsilyloxy)propan-2-yl)-2-(5-fluoro-6-methoxypyridin-3-ylamino)pyridin-3-yl)-6-methyl-1,3,5-triazin-2-amine (241.0 mg, 0.482 mmol) in THF (5.0 mL) at 25° C., and the resulting mixture was stirred at 25° C. for 2 h. The reaction mixture was subsequently concentrated onto silica gel and chromatographically purified (silica gel, 0 to 100% EtOAc/hexanes) to provide 2-(5-(4-amino-6-methyl-1,3,5-triazin-2-yl)-6-(5-fluoro-6-methoxypyridin-3-ylamino)pyridin-3-yl)propan-1-ol (139.0 mg, 0.361 mmol, 74.8% yield) as a yellow solid. $^1$H NMR (400 MHz, d$_6$-DMSO) δ 11.88 (s, 1H), 8.66 (d, J=2.5 Hz, 1H), 8.41 (d, J=2.2 Hz, 1H), 8.35-8.40 (m, 1H), 8.25 (d, J=2.5 Hz, 1H), 7.88 (br. s., 1H), 7.74 (br. s., 1H), 4.70 (br. s., 1H), 3.93 (s, 3H), 3.49 (d, J=6.5 Hz, 2H), 2.83 (sxt, J=6.9 Hz, 1H), 2.44 (s, 3H), 1.22 (d, J=7.0 Hz, 3H). $^{19}$F NMR (376 MHz, d$_6$-DMSO) δ −139.83 (d, J=13.0 Hz, 1 F). m/z (ESI, +ve) 386.2 (M+H)$^+$.

Step 8. (R)-2-(5-(4-amino-6-methyl-1,3,5-triazin-2-yl)-6-(5-fluoro-6-methoxypyridin-3-ylamino)pyridin-3-yl)propan-1-ol and (S)-2-(5-(4-amino-6-methyl-1,3,5-triazin-2-yl)-6-(5-fluoro-6-methoxypyridin-3-ylamino)pyridin-3-yl)propan-1-ol A mixture of isomers of 2-(5-(4-Amino-6-methyl-1,3,5-triazin-2-yl)-6-(5-fluoro-6-methoxypyridin-3-ylamino)pyridin-3-yl)propan-1-ol was separated into its constituent enantiomers by super-critical fluid chromatography (SFC) using the following conditions:

Column: Chiralpak® IC (21×250 mm, 5 µm)

Mobile Phase: 78:22 (A:B)

A: Liquid $CO_2$

B: Methanol (0.2% diethylamine)

Flow Rate: 50 mL/min

Oven/column temperature: 40° C.

1.1 mg/injection (repeat injection)

The two separate peaks containing the two enantiomers were collected, concentrated in vacuo, and dried under high vacuum to afford the two enantiomers. Absolute stereochemistry was not determined.

First Eluting Peak:

$^1$H NMR (400 MHz, CDCl$_3$) δ 11.84 (s, 1H), 8.72 (d, J=2.2 Hz, 1H), 8.22-8.30 (m, 2H), 8.03 (d, J=2.0 Hz, 1H), 5.38 (br. s., 2H), 4.02 (s, 3H), 3.75 (d, J=6.8 Hz, 2H), 2.93-3.01 (m, 1H), 2.57 (s, 3H), 1.33 (d, J=6.8 Hz, 3H). $^{19}$F NMR (377 MHz, CDCl$_3$) δ −138.86 (d, J=12.6 Hz, 1 F). m/z (ESI, +ve) 386.2 (M+H)$^+$.

Second Eluting Peak:

$^1$H NMR (400 MHz, CDCl$_3$) δ 11.85 (br. s., 1H), 8.81 (d, J=1.2 Hz, 1H), 8.27 (d, J=1.8 Hz, 1H), 8.13 (dd, J=13.1, 2.2 Hz, 1H), 8.03 (d, J=2.0 Hz, 1H), 5.61 (br. s., 2H), 4.03 (s, 3H), 3.69-3.82 (m, 2H), 2.95-3.03 (m, 1H), 2.59 (s, 3H), 1.33 (d, J=7.0 Hz, 3H). m/z (ESI, +ve) 386.2 (M+H)$^+$.

Chiral SFC analysis revealed both of the separated enantiomers to have ee's of >98%.

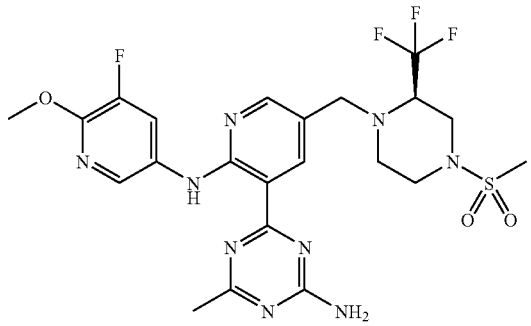

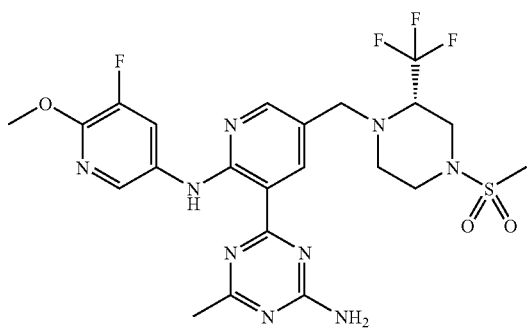

Example 313

4-(2-(5-fluoro-6-methoxypyridin-3-ylamino)-5-((4-(methylsulfonyl)-2-(trifluoromethyl)piperazin-1-yl)methyl)pyridin-3-yl)-6-methyl-1,3,5-triazin-2-amine

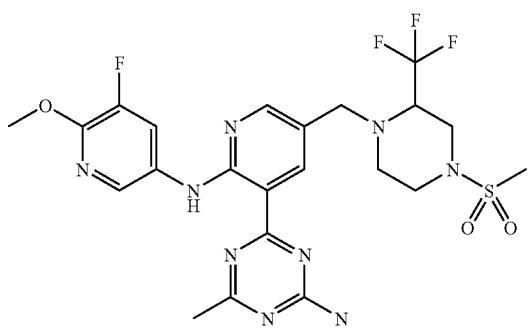

Step 1. 4-(5-chloro-2-fluoropyridin-3-yl)-N,N-bis(4-methoxybenzyl)-6-methyl-1,3,5-triazin-2-amine A mixture of 5-chloro-2-fluoropyridin-3-ylboronic acid (Combi Blocks, 2.507 g, 14.30 mmol), 4-chloro-N,N-bis(4-methoxybenzyl)-6-methyl-1,3,5-triazin-2-amine (Example 51; 5.24 g, 13.62 mmol), bis-(di-tert-butyl(4-dimethylaminophenyl)phosphine)dichloropalladium(II) (Aldrich; 0.482 g, 0.681 mmol) and potassium acetate (4.10 g, 41.8 mmol) in ethanol (100 mL) and water (10 mL) was degassed and stirred under $N_2$ at 100° C. for 16 h. The reaction mixture was cooled, concentrated, and the residue was partitioned between water (50 mL) and EtOAc (50 mL). The aqueous phase was extracted with EtOAc (2×20 mL) and the combined organic layers were washed with saturated aqueous sodium chloride (100 mL). The organic phase was dried over sodium sulfate, filtered and concentrated. Chromatographic purification of the residue (silica gel, 15% to 50% EtOAc/hexanes) provided 4-(5-chloro-2-fluoropyridin-3-yl)-N,N-bis(4-methoxybenzyl)-6-methyl-1,3,5-triazin-2-amine (3.62 g, 7.54 mmol, 55.4% yield). m/z (ESI, +ve ion) 480 $(M+H)^+$.

Step 2. 4-(5-chloro-2-(5-fluoro-6-methoxypyridin-3-ylamino)pyridin-3-yl)-N-bis(4-methoxybenzyl)-6-methyl-1,3,5-triazin-2-amine A stirred mixture of 5-fluoro-6-methoxypyridin-3-amine (Anichem, North Brunswick, N.J.; 0.834 g, 5.87 mmol) and 4-(5-chloro-2-fluoropyridin-3-yl)-N,N-bis(4-methoxybenzyl)-6-methyl-1,3,5-triazin-2-amine (1.8776 g, 3.91 mmol) in THF (50.0 mL, 610 mmol) was treated dropwise with LiHMDS (1.0 M in THF, 16.74 mL, 16.74 mmol) at −15° C. (ice-salt bath) and stirred for 40 min. The reaction was then quenched with water and saturated $NH_4Cl$ (aq) (25 mL each) and diluted with EtOAc (25 mL). Organic layer was separated, and the aqueous layer was extracted with ethyl acetate (2×50 mL). The combined organic layers were then washed with brine, dried over $Na_2SO_4$, and concentrated. Chromatographic purification of the residue (silica gel, 0% to 1% MeOH/DCM) followed by washing of the purified product with isopropanol gave 4-(5-chloro-2-(5-fluoro-6-methoxypyridin-3-ylamino)-N,N-bis(4-methoxybenzyl)-6-methyl-1,3,5-triazin-2-amine (2.07 g, 3.44 mmol, 88% yield). $^1H$ NMR (400 MHz, $CDCl_3$) δ 8.77 (d, J=2.54 Hz, 1H); 8.23 (d, J=2.54 Hz, 1H); 7.95 (d, J=1.96 Hz, 1H); 7.90 (d, J=12.13 Hz, 1H); 7.18 (dd, J=17.41, 8.41 Hz, 4H); 6.86 (t, J=8.12 Hz, 4H); 4.86 (s, 2H); 4.82 (s, 2H); 4.01 (s, 3H); 3.81 (s, 3H); 3.79 (s, 3H); 2.60 (s, 3H).

Step 3. 4-(2-(5-fluoro-6-methoxypyridin-3-ylamino)-5-((4-(methylsulfonyl)-2-(trifluoromethyl)piperazin-1-yl)methyl)pyridin-3-yl)-6-methyl-1,3,5-triazin-2-amine The title compound was prepared from 4-(5-chloro-2-(5-fluoro-6-methoxypyridin-3-ylamino)pyridin-3-yl)-N,N-bis(4-methoxybenzyl)-6-methyl-1,3,5-triazin-2-amine and tert-butyl 3-(trifluoromethyl)piperazine-1-carboxylate (Anichem, Inc.) via similar steps as previously described in Example 270, Step 1, and Step 4 to Step 5 and isolated as a yellow solid. m/z (ESI, +ve ion) 572 $(M+H)^+$. $^1H$ NMR (400 MHz, $CDCl_3$) δ 11.93 (s, 1H) 8.74 (d, J=2.35 Hz, 1H) 8.28 (d, J=2.35 Hz, 1H) 8.25 (dd, J=12.23, 2.25 Hz, 1H) 8.04 (d, J=2.15 Hz, 1H) 5.45 (br. s., 2H) 4.03 (s, 3H) 3.85-3.97 (m, 2H) 3.80 (dd, J=12.42, 2.25 Hz, 1H) 3.44-3.54 (m, 1H) 3.33-

3.40 (m, 1H) 3.27 (dd, J=12.32, 1.76 Hz, 1H) 2.97-3.16 (m, 2H) 2.83 (s, 3H) 2.63-2.73 (m, 1H) 2.58 (s, 3H).

Example 314

1-(5-(4-amino-6-methyl-1,3,5-triazin-2-yl)-6-(5-fluoro-6-methoxypyridin-3-ylamino)pyridin-3-yl)-2,2,2-trifluoroethanol

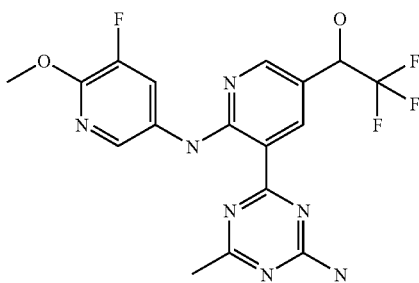 [SMILES: COc1ncc(Nc2ncc(C(O)C(F)(F)F)cc2-c2nc(C)nc(N)n2)cc1F]

The title compound was prepared and isolated as a yellow solid from 1-(5-(4-(bis(4-methoxybenzyl)amino)-6-methyl-1,3,5-triazin-2-yl)-6-fluoropyridin-3-yl)-2,2,2-trifluoroethanol following an analogous procedure to Example 269. m/z (ESI, +ve ion) 426 (M+H)⁺. ¹H NMR (400 MHz, d₆-DMSO) δ 12.06 (s, 1H) 8.95 (s, 1H) 8.41 (d, J=1.76 Hz, 2H) 8.35 (d, J=12.52 Hz, 1H) 7.97 (br. s., 1H) 7.81 (br. s., 1H) 6.97 (d, J=5.48 Hz, 1H) 4.97-5.51 (m, 1H) 3.94 (s, 3H) 2.45 (s, 3H).

Example 315

(S)-4-(2-(5-fluoro-6-methoxypyridin-3-ylamino)-5-((3-methylmorpholino)methyl)pyridin-3-yl)-6-methyl-1,3,5-triazin-2-amine

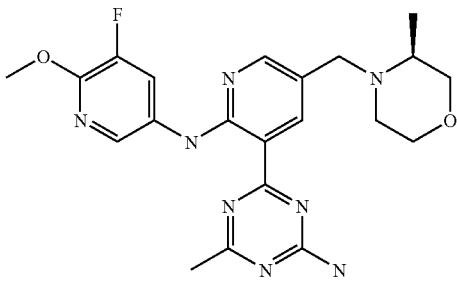 [SMILES: COc1ncc(Nc2ncc(CN3CCOC[C@@H]3C)cc2-c2nc(C)nc(N)n2)cc1F]

(S)-3-methylmorpholine (Aldrich, 0.105 g, 1.041 mmol) and 5-(4-(bis(4-methoxybenzyl)amino)-6-methyl-1,3,5-triazin-2-yl)-6-(5-fluoro-6-methoxypyridin-3-ylamino)nicotinaldehyde (Example 143, Step 2; 0.310 g, 0.520 mmol) were suspended in THF (3 mL) and titanium (IV) ethoxide (0.60 mL, 2.90 mmol) was added. The mixture was sealed and heated at 70° C. overnight. The light brown solution was cooled to 0° C. and excess sodium cyanoborohydride (0.327 g, 5.20 mmol) was added, and the mixture was stirred at 0° C. for 2 h. The resulting solution was quenched with a couple drop of MeOH followed by water. DCM was added to the entire mass and vigorously stirred for 10 min. The mixture was filtered and passed through a short path of Celite® (diatomaceous earth). The filter cake was washed with DCM (3×10 mL). The combined organic phases were concentrated to give a crude residue. Flash column chromatographic purification (short column, SiO₂, 100% DCM to 5% MeOH in DCM) provided (S)-4-(2-(5-fluoro-6-methoxypyridin-3-ylamino)-5-((3-methylmorpholino)methyl)pyridin-3-yl)-N,N-bis(4-methoxybenzyl)-6-methyl-1,3,5-triazin-2-amine (375 mg) as a yellow solid, which was deprotected under similar conditions according to the procedure reported previously (Example 178, Step 4) to afford the title compound (199 mg, 82%) as a yellow solid. m/z (ESI, +ve ion) 441 (M+H)⁺. ¹H NMR (400 MHz, CDCl₃) δ (rotatomer mixtures) 12.09 (br. s., 1H) 9.01 (br. s., 1H) 8.15-8.56 (m, 2H) 8.05 (br. s., 1H) 7.26 (br. s., 1H) 4.88-6.53 (m, 1H) 4.32 (br. s., 1H) 4.03 (br. s., 3H) 3.84 (br. s., 4H) 3.57 (br. s., 2H) 2.91 (br. s., 2H) 2.55 (br. s., 3H) 1.21 (d, J=5.28 Hz, 3H).

Example 316

(R)-4-(2-(5-fluoro-6-methoxypyridin-3-ylamino)-5-((2-methyl-4-(methylsulfonyl)piperazin-1-yl)methyl)pyridin-3-yl)-6-methyl-1,3,5-triazin-2-amine

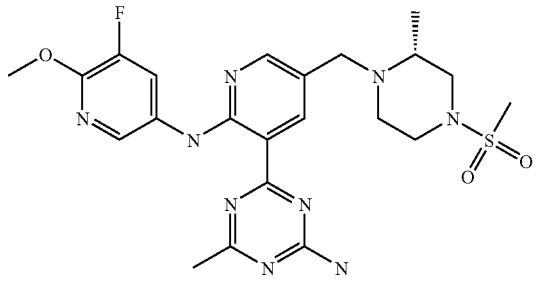 [SMILES: COc1ncc(Nc2ncc(CN3CCN(S(C)(=O)=O)C[C@H]3C)cc2-c2nc(C)nc(N)n2)cc1F]

Step 1. (R)-tert-butyl 4-((5-(4-(bis(4-methoxybenzyl)amino)-6-methyl-1,3,5-triazin-2-yl)-6-fluoropyridin-3-yl)methyl)-3-methylpiperazine-1-carboxylate In a 5 mL microwave tube was weighed 4-(5-chloro-2-fluoropyridin-3-yl)-N,N-bis(4-methoxybenzyl)-6-methyl-1,3,5-triazin-2-amine (1.00 g, 2.084 mmol; Example 313, Step 1), 2-(dicyclohexylphosphino)-2',4',6',-tri-i-propyl-1,1'-biphenyl (0.099 g, 0.208 mmol), cesium carbonate (2.037 g, 6.25 mmol), potassium (R)-((4-(tert-butoxycarbonyl)-2-methylpiperazin-1-yl)methyl)trifluoroborate (prepared similarly according to Example 270, Stepl, from (R)-4-N-boc-2-methyl-piperazine (Sigma Adrich, Inc.), 0.701 g, 2.188 mmol,), palladium acetate (0.023 g, 0.104 mmol) followed by purging with argon. The solids were then treated with THF (10.00 mL), water (1.0 mL) and heated under a microwave irradiation at 85° C. overnight. The mixture was filtered through a short path of Celite® (diatomaceous earth), washed with ethyl acetate (3×), and concentrated. The crude product was adsorbed onto a plug of silica gel and chromatographed through a silica gel column (100% DCM to 5% MeOH in DCM) to obtain the desired product (R)-tert-butyl 4-((5-(4-(bis(4-methoxybenzyl)amino)-6-methyl-1,3,5-triazin-2-yl)-6-fluoropyridin-3-yl)methyl)-3-methylpiperazine-1-carboxylate (1.01 g, 1.535 mmol, 73.7% yield) as a yellow foam. m/z (ESI, +ve ion) 658 (M+H)⁺.

Step 2. (R)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine To a slightly cooled stirred solution of (R)-tert-butyl 4-((5-(4-(bis(4-methoxybenzyl)amino)-6-methyl-1,3,5-triazin-2- yl)-6-fluoropyridin-3-yl)methyl)-3-methylpiperazine-1-carboxylate (1.01 g, 1.535 mmol) in DCM (5.0 mL, 78 mmol) was added slowly TFA (4.00 mL, 51.9 mmol) and the mixture was stirred at room temperature for 1 h. The mixture was concentrated and the sticky residue was taken up in a solution of DCM (10.0 mL) to which TEA (2.140 mL, 15.35 mmol) and methanesulfonyl chloride (0.598 mL, 7.68 mmol) was slowly added subsequently at 0° C. The mixture was stirred at the same temperature for 1 h, concentrated, and the crude product was partitioned between 1 N NaOH(aq) and DCM (20 mL each). The separated aqueous layer was extracted with DCM (2×20 mL) and the combined organic layers were washed with brine, dried over $Na_2SO_4$, and concentrated to give a crude residue which was purified by flash column chromatography (ISCO Combiflash system, 10% ethyl acetate/hexanes to 70% ethyl acetates in hexanes) to obtain the desired product (R)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (0.4779 g, 0.752 mmol, 49.0% yield) as a pale yellow foam. m/z (ESI, +ve ion) 636 $(M+H)^+$.

Step 3. (R)-4-(2-(5-fluoro-6-methoxypyridin-3-ylamino)-5-((2-methyl-4-(methylsulfonyl)piperazin-1-yl)methyl)pyridin-3-yl)-N,N-bis(4-methoxybenzyl)-6-methyl-1,3,5-triazin-2-amine To a stirred mixture of 5-fluoro-6-methoxypyridin-3-amine (0.118 g, 0.827 mmol) and (R)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (0.4779 g, 0.752 mmol) in THF (10.00 mL) was added LiHMDS, 1.0 M in THF (Aldrich; 2.255 mL, 2.255 mmol) dropwise at −10° C. and the mixture was stirred at the same temperature for 30 min.

The reaction was quenched with water and saturated $NH_4Cl$(aq) (25 mL each) and diluted with EtOAc (25 mL). The separated aqueous layer was extracted with ethyl acetate (2×50 mL) and the combined organic layers were washed with brine, dried over $Na_2SO_4$ and concentrated to give a crude residue which was purified by flash column chromatography (ISCO Combiflash system, 0% to 1% DCM in MeOH) followed by washing with IPA to obtain the desired product (R)-4-(2-(5-fluoro-6-methoxypyridin-3-ylamino)-5-((2-methyl-4-(methylsulfonyl)piperazin-1-yl)methyl)pyridin-3-yl)-N,N-bis(4-methoxybenzyl)-6-methyl-1,3,5-triazin-2-amine (0.377 g, 0.497 mmol, 66.2% yield).

Step 4. (R)-4-(2-(5-fluoro-6-methoxypyridin-3-ylamino)-5-((2-methyl-4-(methylsulfonyl)piperazin-1-yl)methyl)pyridin-3-yl)-6-methyl-1,3,5-triazin-2-amine The title compound was prepared from (R)-4-(2-(5-fluoro-6-methoxypyridin-3-ylamino)-5-((2-methyl-4-(methylsulfonyl)piperazin-1-yl)methyl)pyridin-3-yl)-N,N-bis(4-methoxybenzyl)-6-methyl-1,3,5-triazin-2-amine via a similar deprotection step as previously described in Example 178, Step 4, using trifluoroacetic acid and trifluoromethanesulfonic acid, and isolated as a yellow solid. m/z (ESI, +ve ion) 518 $(M+H)^+$. $^1H$ NMR (400 MHz, $d_6$-DMSO) 811.95 (s, 1H) 8.71 (d, J=2.35 Hz, 1H) 8.41 (d, J=2.15 Hz, 1H) 8.33-8.40 (m, 1H) 8.27 (d, J=2.15 Hz, 1H) 7.90 (br. s., 1H) 7.76 (br. s., 1H) 3.93 (s, 3H) 3.91 (s, 1H) 3.13-3.30 (m, 3H) 2.87-2.95 (m, 1H) 2.85 (s, 3H) 2.53-2.79 (m, 3H) 2.44 (s, 3H) 2.14-2.28 (m, 1H) 1.16 (d, J=6.26 Hz, 3H).

Example 317

(S)-4-(2-(6-chloro-5-methoxypyridin-3-ylamino)-5-((2-methyl-4-(methylsulfonyl)piperazin-1-yl)methyl)pyridin-3-yl)-6-methyl-1,3,5-triazin-2-amine

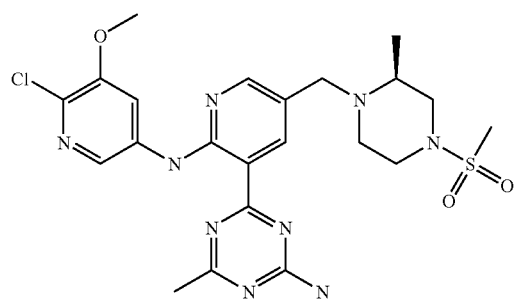 [SMILES: COc1cc(Nc2ncc(CN3CCN(S(C)(=O)=O)C[C@@H]3C)cc2-c2nc(C)nc(N)n2)cnc1Cl]

The title compound was prepared from 6-chloro-5-methoxypyridin-3-amine (Small Molecules, Inc.) and (S)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (preparation similar as reported in Example 316, Steps 1 to 2; from (S)-tert-butyl 3-methylpiperazine-1-carboxylate (Sigma Aldrich, Inc.)) via similar steps as previously described in Example 316 and isolated as a yellow solid. m/z (ESI, +ve ion) 534 $(M+H)^+$. $^1H$ NMR (400 MHz, $d_6$-DMSO) δ 11.99-12.52 (m, 1H) 8.76-9.96 (m, 1H) 8.15-8.63 (m, 3H) 6.57-8.07 (m, 2H) 4.09-5.06 (m, 2H) 3.94 (s, 3H) 3.59-3.86 (m, 2H) 2.86-3.35 (m, 7H) 2.46 (s, 3H) 0.96-1.58 (m, 4H).

Example 318

(S)-4-(2-(6-chloropyridin-3-ylamino)-5-((2-methyl-4-(methylsulfonyl)piperazin-1-yl)methyl)pyridin-3-yl)-6-methyl-1,3,5-triazin-2-amine

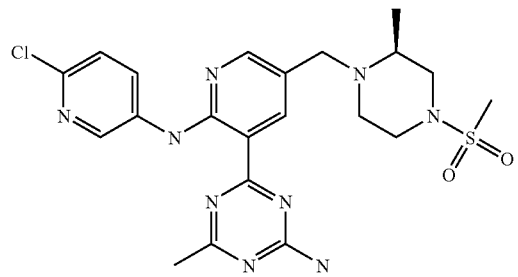 [SMILES: Cc1nc(N)nc(-c2cc(CN3CCN(S(C)(=O)=O)C[C@@H]3C)cnc2Nc2ccc(Cl)nc2)n1]

The title compound was prepared from 6-chloropyridin-3-amine (Sigma Aldrich, Inc.) and (S)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (preparation similar as reported in Example 316, Steps 1 to 2; from (S)-tert-butyl 3-methylpiperazine-1-carboxylate (Sigma Aldrich, Inc.)) via similar steps as previously described in Example 316 and isolated as a yellow solid. m/z (ESI, +ve ion) 504 $(M+H)^+$. $^1H$ NMR (400 MHz, d6-DMSO) δ 12.16 (s, 1H) 8.88 (d, J=2.74 Hz, 1H) 8.73 (d, J=2.35 Hz, 1H) 8.47 (dd, J=8.71, 2.84 Hz, 1H) 8.31 (d, J=2.35 Hz, 1H) 7.93 (br. s., 1H) 7.78 (br. s., 1H) 7.45 (d, J=8.61 Hz, 1H) 3.94 (d, J=13.11 Hz, 1H) 3.07-3.29 (m, 3H) 2.86-2.97 (m, 1H) 2.85 (s, 3H) 2.64-2.79 (m, 2H) 2.54-2.64 (m, 1H) 2.45 (s, 3H) 2.14-2.29 (m, 1H) 1.16 (d, J=6.06 Hz, 3H).

Example 319

(S)-4-(2-(2-methoxypyrimidin-5-ylamino)-5-((2-methyl-4-(methylsulfonyl)piperazin-1-yl)methyl)pyridin-3-yl)-6-methyl-1,3,5-triazin-2-amine

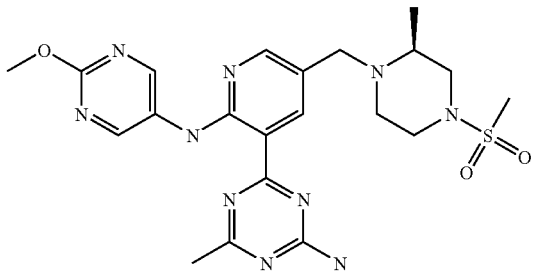 [SMILES: COc1ncc(Nc2ncc(CN3CCN(S(C)(=O)=O)C[C@@H]3C)cc2-c2nc(C)nc(N)n2)cn1]

The title compound was prepared from 2-methoxypyrimidin-5-amine (Aces Pharma, Inc.) and (S)-4-(2-fluoro-5-((2-methyl-4-(methylsulfonyl)piperazin-1-yl)methyl)pyridin-3-yl)-N,N-bis(4-methoxybenzyl)-6-methyl-1,3,5-triazin-2-amine (preparation similar as reported in Example 316, Steps 1 to 2; from (S)-tert-butyl 3-methylpiperazine-1-carboxylate (Sigma Aldrich, Inc.)) via similar steps as previously described in Example 316 and isolated as a yellow solid. m/z (ESI, +ve ion) 501 (M+H)$^+$. $^1$H NMR (400 MHz, d$_6$-DMSO) δ 11.77 (s, 1H) 9.03 (s, 2H) 8.71 (d, J=1.96 Hz, 1H) 8.24 (d, J=2.15 Hz, 1H) 7.90 (br. s., 1H) 7.74 (br. s., 1H) 3.91 (s, 3H) 3.24 (d, J=13.50 Hz, 2H) 2.86-2.96 (m, 1H) 2.85 (s, 3H) 2.55-2.79 (m, 4H) 2.44 (s, 3H) 2.11-2.37 (m, 2H) 1.16 (d, J=6.26 Hz, 3H).

Example 320

2-(5-(4-amino-6-methyl-1,3,5-triazin-2-yl)-6-(6-methoxypyridin-3-ylamino)pyridin-3-yl)-1,1,1-trifluoropropan-2-ol

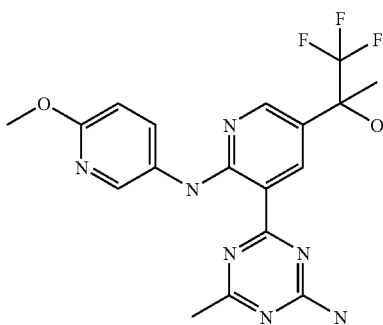 [SMILES: COc1ccc(Nc2ncc(C(C)(O)C(F)(F)F)cc2-c2nc(C)nc(N)n2)cn1]

Step 1. 1-(5-(4-(bis(4-methoxybenzyl)amino)-6-methyl-1,3,5-triazin-2-yl)-6-(6-methoxypyridin-3-ylamino)pyridin-3-yl)-2,2,2-trifluoroethanone To a stirred solution of 1-(5-(4-(bis(4-methoxybenzyl)amino)-6-methyl-1,3,5-triazin-2-yl)-6-(6-methoxypyridin-3-ylamino)pyridin-3-yl)-2,2,2-trifluoroethanol (preparation described previously in Example 269) (104 mg, 0.161 mmol) and 4 Å molecular sieves in dichloromethane (3.00 mL) was added TPAP (Sigma Aldrich, Inc., 5.64 mg, 0.016 mmol), NMO (Sigma Aldrich, Inc.), 24.45 mg, 0.209 mmol) at room temperature and the mixture was stirred at the same temperature for 1 h and then concentrated. The dark residue was rediluted with ethyl acetate and filtered through a short path of Celite® (diatomaceous earth)/SiO$_2$. The filtered solid was washed with ethyl acetate (3×10 mL). The combined organic phases were concentrated to give a yellow crude residue 1-(5-(4-(bis(4-methoxybenzyl)amino)-6-methyl-1,3,5-triazin-2-yl)-6-(6-methoxypyridin-3-ylamino)pyridin-3-yl)-2,2,2-trifluoroethanone which was used directly for the next step without further purification.

Step 2. 2-(5-(4-amino-6-methyl-1,3,5-triazin-2-yl)-6-(6-methoxypyridin-3-ylamino)pyridin-3-yl)-1,1,1-trifluoropropan-2-ol To a stirred mixture of crude 1-(5-(4-(bis(4-methoxybenzyl)amino)-6-methyl-1,3,5-triazin-2-yl)-6-(6-methoxypyridin-3-ylamino)pyridin-3-yl)-2,2,2-trifluoroethanone (71 mg, 0.110 mmol) in TFA (1.5 mL, 19.47 mmol) was added trifluoromethanesulfonic acid (0.15 mL, 1.689 mmol) and the dark brown solution was stirred at 70° C. for 2 h. After cooling, the resulting deep reddish brown solution was concentrated with SiO$_2$ and the residue was purified by flash column chromatography (ISCO Combiflash system, DCM to 5% MeOH/NH$_3$ in DCM) to give semi-pure ketone, which was dried under vacuum and used directly in the next step.

The semi-pure ketone isolated above was dissolved in THF (2.00 mL, 24.41 mmol), cooled to 0° C. and an excess amount of methylmagnesium bromide, 3.0 M in ether (2.00 mL, 6.00 mmol) was added slowly. The mixture was stirred at 0° C. for another 1 h and carefully quenched with 1 N HCl, water and ethyl acetate (0.5, 2.0, 5.0 mL each). The separated aqueous layer was extracted with ethyl acetate (2×10 mL) and the combined organic layers were washed with brine, dried over Na$_2$SO$_4$, and concentrated to give the crude residue which was purified by flash column chromatography (DCM to 5% MeOH/NH$_3$ in DCM) followed by washing with a minimum amount of iPrOH to afford 2-(5-(4-amino-6-methyl-1,3,5-triazin-2-yl)-6-(6-methoxypyridin-3-ylamino)pyridin-3-yl)-1,1,1-trifluoropropan-2-ol (8.4 mg, 0.020 mmol, 18% yield) as a yellow solid. m/z (ESI, +ve ion) 422 (M+H)$^+$. $^1$H NMR (400 MHz, d$_6$-DMSO) δ 11.84 (m, 1H) 9.01 (br. s., 1H) 8.52 (br. s., 1H) 8.43 (br. s., 1H) 8.16 (d, J=8.41 Hz, 1H) 7.89 (br. s., 1H) 7.72 (br. s., 1H) 6.83 (d, J=8.02 Hz, 1H) 6.71 (s, 1H) 3.85 (s, 3H) 2.44 (s, 3H) 1.72 (br. s., 3H).

Example 321

4-(2-(6-methoxypyridin-3-ylamino)-5-(2,2,2-trifluoro-1-(4-(methylsulfonyl)piperazin-1-yl)ethyl)pyridin-3-yl)-6-methyl-1,3,5-triazin-2-amine

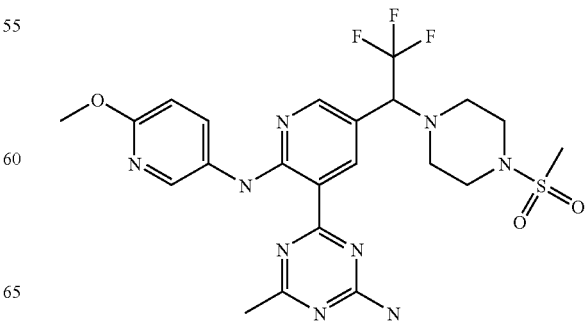

The title compound was prepared similarly as described in Example 325 from 1-(5-(4-(bis(4-methoxybenzyl)amino)-6-methyl-1,3,5-triazin-2-yl)-6-fluoropyridin-3-yl)-2,2,2-trifluoroethanol and 6-methoxypyridin-3-amine and isolated as a yellow solid. m/z (ESI, +ve ion) 554 (M+H)+. 1H NMR (400 MHz, CD3OD) δ 9.09 (d, J=1.96 Hz, 1H) 8.92 (d, J=2.54 Hz, 1H) 8.29-8.43 (m, 2H) 7.39 (d, J=9.19 Hz, 1H) 4.64 (q, J=9.00 Hz, 1H) 4.15 (s, 3H) 3.25 (t, J=4.79 Hz, 4H) 2.84-2.90 (m, 2H) 2.83 (s, 3H) 2.72-2.81 (m, 2H) 2.59 (s, 3H), 3 exchangeable protons not observed.

Examples 322 and 323

(R)-1-(5-(4-amino-6-methyl-1,3,5-triazin-2-yl)-6-(6-methoxypyridin-3-ylamino)pyridin-3-yl)-2,2,2-trifluoroethanol and (S)-1-(5-(4-amino-6-methyl-1,3,5-triazin-2-yl)-6-(6-methoxypyridin-3-ylamino)pyridin-3-yl)-2,2,2-trifluoroethanol

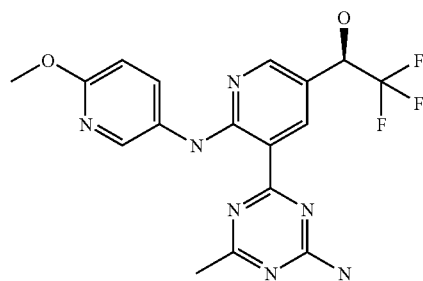

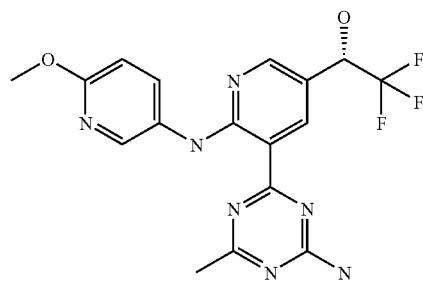

The preparation of a mixture of isomers has been described previously (Example 269). The individual enantiomers (R)-1-(5-(4-amino-6-methyl-1,3,5-triazin-2-yl)-6-(6-methoxypyridin-3-ylamino)pyridin-3-yl)-2,2,2-trifluoroethanol and (S)-1-(5-(4-amino-6-methyl-1,3,5-triazin-2-yl)-6-(6-methoxypyridin-3-ylamino)pyridin-3-yl)-2,2,2-trifluoroethanol were separated and provided by chiral column chromatography (preparative SFC, ODH column (21×250 mm, 5 um), 20% methanol with 0.2% DEA in supercritical CO2) as yellow solids.

Example 324

4-(5-(1-amino-2,2,2-trifluoroethyl)-2-(6-methoxypyridin-3-ylamino)pyridin-3-yl)-6-methyl-1,3,5-triazin-2-amine

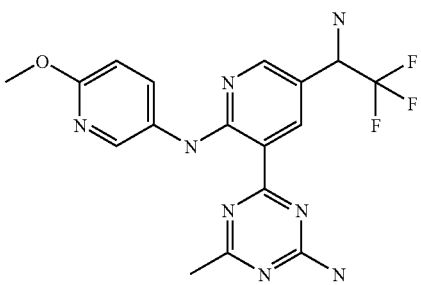 [SMILES: COc1ccc(Nc2ncc(C(N)C(F)(F)F)cc2-c2nc(C)nc(N)n2)cn1]

Step 1. 4-(5-(1-chloro-2,2,2-trifluoroethyl)-2-(6-methoxypyridin-3-ylamino)pyridin-3-yl)-N,N-bis(4-methoxybenzyl)-6-methyl-1,3,5-triazin-2-amine To a solution of 1-(5-(4-(bis(4-methoxyb enzyl)amino)-6-methyl-1,3,5-triazin-2-yl)-6-(6-methoxypyridin-3-ylamino)pyridin-3-yl)-2,2,2-trifluoroethanol (0.172 g, 0.266 mmol) in dichloromethane (3.00 mL, 0.266 mmol) was added triethylamine (0.093 mL, 0.664 mmol) and methanesulfonyl chloride (0.042 mL, 0.531 mmol) at 0° C. and the mixture was stirred at the same temperature for 1.5 h. The reaction was quenched with saturated NH4Cl and water at 0° C., and the separated aqueous layer was extracted with DCM (2×10 mL) and the combined organic layers were dried over Na2SO4, and concentrated and dried under vacuum to give the crude 4-(5-(1-chloro-2,2,2-trifluoroethyl)-2-(6-methoxypyridin-3-ylamino)pyridin-3-yl)-N,N-bis(4-methoxybenzyl)-6-methyl-1,3,5-triazin-2-amine (0.177 g, 0.0266 mmol), which was used directly in the next step without further purification.

Step 2. 4-(5-(1-amino-2,2,2-trifluoroethyl)-2-(6-methoxypyridin-3-ylamino)pyridin-3-yl)-N,N-bis(4-methoxybenzyl)-6-methyl-1,3,5-triazin-2-amine 4-(5-(1-Chloro-2,2,2-trifluoroethyl)-2-(6-methoxypyridin-3-ylamino)pyridin-3-yl)-N,N-bis(4-methoxybenzyl)-6-methyl-1,3,5-triazin-2-amine (0.177 g, 0.266 mmol) was dissolved in MeCN (6.00 mL) and saturated ammonium hydroxide aqueous solution (0.6 mL, 4.31 mmol) was added at room temperature and the mixture was stirred at the same temperature for 5 h. The reaction mixture was concentrated and the crude product was adsorbed onto silica gel and chromatographed through a silica gel column (100% DCM to 5% MeOH (w/NH3 in DCM) to obtain 4-(5-(1-amino-2,2,2-trifluoroethyl)-2-(6-methoxypyridin-3-ylamino)pyridin-3-yl)-N,N-bis(4-methoxybenzyl)-6-methyl-1,3,5-triazin-2-amine 4-(5-(1-chloro-2,2,2-trifluoroethyl)-2-(6-methoxypyridin-3-ylamino)pyridin-3-yl)-N,N-bis(4-methoxybenzyl)-6-methyl-1,3,5-triazin-2-amine (0.165 g, 96%) as a brown foam.

Step 3. 4-(5-(1-amino-2,2,2-trifluoroethyl)-2-(6-methoxypyridin-3-ylamino)pyridin-3-yl)-6-methyl-1,3,5-triazin-2-amine The title compound was prepared similarly as described previously in Example 178, Step 4 using trifluoroacetic acid and trifluoromethanesulfonic acid; by deprotection of 4-(5-(1-amino-2,2,2-trifluoroethyl)-2-(6-methoxypyridin-3-ylamino)pyridin-3-yl)-N,N-bis(4-methoxybenzyl)-6-methyl-1,3,5-triazin-2-amine (0.165 g, 0.255 mmol) and isolated (69 mg, 66%) as a yellow solid. m/z (ESI, +ve ion) 407 (M+H)$^+$. $^1$H NMR (400 MHz, CD$_3$OD) δ 9.22 (br. s., 1H) 8.89 (br. s., 1H) 8.47 (br. s., 1H) 8.40 (d, J=7.83 Hz, 1H) 7.27 (d, J=9.39 Hz, 1H) 5.47 (q, J=7.37 Hz, 1H) 4.10 (s, 3H) 2.54 (s, 3H); 5 exchangeable protons not observed.

The individual enantiomers (R)-4-(5-(1-amino-2,2,2-trifluoroethyl)-2-(6-methoxypyridin-3-ylamino)pyridin-3-yl)-6-methyl-1,3,5-triazin-2-amine and (S)-4-(5-(1-amino-2,2,2-trifluoroethyl)-2-(6-methoxypyridin-3-ylamino)pyridin-3-yl)-6-methyl-1,3,5-triazin-2-amine were separated and provided by chiral column chromatography (preparative SFC, OJH column (21×250 mm, 5 um), 15% methanol with 0.2% DEA in supercritical CO$_2$) as yellow solids.

Example 325

4-(2-(5-fluoro-6-methoxypyridin-3-ylamino)-5-(2,2,2-trifluoro-1-(4-(methylsulfonyl)piperazin-1-yl)ethyl)pyridin-3-yl)-6-methyl-1,3,5-triazin-2-amine compound

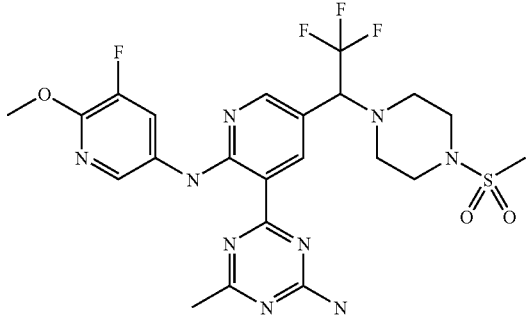

Step 1. 1-(5-(4-(bis(4-methoxybenzyl)amino)-6-methyl-1,3,5-triazin-2-yl)-6-fluoropyridin-3-yl)-2,2,2-trifluoroethanol To a stirred solution of 5-(4-(bis(4-methoxybenzyl)amino)-6-methyl-1,3,5-triazin-2-yl)-6-fluoronicotinaldehyde (3.7810 g, 7.99 mmol; Example 143, Step 1-2) in THF (50.00 mL) was added trimethyl(trifluoromethyl)silane (TCI America, Inc.; 1.703 g, 11.98 mmol) followed by CsF (0.243 g, 1.597 mmol) at 0° C. and the mixture was stirred at the same temperature for 10 min before warming to room temperature and stirring for 3.5 h. The reaction was quenched with 1 N HCl and stirred for another 30 min, and then EtOAc (10 mL) was added. The separated aqueous layer was extracted with ethyl acetate (2×20 mL) and the combined organic layers were washed with brine, dried over Na$_2$SO$_4$, and concentrated to give a brown foam residue as the desired product 1-(5-(4-(bis(4-methoxybenzyl)amino)-6-methyl-1,3,5-triazin-2-yl)-6-fluoropyridin-3-yl)-2,2,2-trifluoroethanol (4.69 g, 8.63 mmol, 108% yield) which was used directly for the next step.

Step 2. 1-(5-(4-(bis(4-methoxybenzyl)amino)-6-methyl-1,3,5-triazin-2-yl)-6-(5-fluoro-6-methoxypyridin-3-ylamino)pyridin-3-yl)-2,2,2-trifluoroethanol To a stirred mixture of 5-fluoro-6-methoxypyridin-3-amine (2.427 g, 17.07 mmol) and 1-(5-(4-(bis(4-methoxybenzyl)amino)-6-methyl-1,3,5-triazin-2-yl)-6-fluoropyridin-3-yl)-2,2,2-trifluoroethanol (4.64 g, 8.54 mmol) in THF (50.00 mL, 610 mmol) was added LiHMDS (1.0 M in THF, Aldrich; 42.7 mL, 42.7 mmol) dropwise at −10° C. and the mixture was stirred at the same temperature for 30 min. The reaction was quenched with water and saturated NH$_4$Cl (aq) (25 mL each) and diluted with EtOAc (25 mL). The separated aqueous layer was extracted with ethyl acetate (2×50 mL) and the combined organic layers were washed with brine, dried over Na$_2$SO$_4$, and concentrated to give a crude residue which was purified by flash column chromatography (ISCO Combiflash system, 0% to 50% ethyl acetate in hexanes) to obtain the desired product 1-(5-(4-(bis(4-methoxybenzyl)amino)-6-methyl-1,3,5-triazin-2-yl)-6-(5-fluoro-6-methoxypyridin-3-ylamino)pyridin-3-yl)-2,2,2-trifluoroethanol (5.1428 g, 7.73 mmol, 91% yield) as a brown foam.

Step 3. 4-(5-(1-chloro-2,2,2-trifluoroethyl)-2-(5-fluoro-6-methoxypyridin-3-ylamino)pyridin-3-yl)-N,N-bis(4-methoxybenzyl)-6-methyl-1,3,5-triazin-2-amine To a solution of (5-(4-(bis(4-methoxybenzyl)amino)-6-methyl-1,3,5-triazin-2-yl)-6-(5-fluoro-6-methoxypyridin-3-ylamino)pyridin-3-yl)-2,2,2-trifluoroethanol (1.03 g, 1.547 mmol) in dichloromethane (20 mL, 1.547 mmol) was added triethylamine (0.539 mL, 3.87 mmol) and methanesulfonyl chloride (0.244 mL, 3.09 mmol) at 0° C. and the mixture was stirred at the same temperature for 3 h, and warmed up to room temperature and stirred for another 2 h. The reaction was quenched with saturated aqueous NH$_4$Cl solution and water at room temperature, and the separated aqueous layer was extracted with DCM (2×50 mL) and the combined organic layers were dried over Na$_2$SO$_4$ and concentrated and dried under vacuum to give the crude product. m/z (ESI, +ve ion) 684 (M+H)$^+$. The material was used directly without further purification.

Step 4. tert-butyl 4-(1-(5-(4-(bis(4-methoxybenzyl)amino)-6-methyl-1,3,5-triazin-2-yl)-6-(5-fluoro-6-methoxypyridin-3-ylamino)pyridin-3-yl)-2,2,2-trifluoroethyl)piperazine-1-carboxylate A solution of 4-(5-(1-chloro-2,2,2-trifluoroethyl)-2-(5-fluoro-6-methoxypyridin-3-ylamino)pyridin-3-yl)-N,N-bis(4-methoxybenzyl)-6-methyl-1,3,5-triazin-2-amine (1.059 g, 1.548 mmol) in CH$_3$CN (10.00 mL) was treated with 1-N-Boc-piperazine (Aldrich, 0.577 g, 3.10 mmol) and triethylamine (1.079 mL, 7.74 mmol) and the mixture was heated at 100° C. for 3 h. The reaction mixture was concentrated and the crude product was adsorbed onto a plug of silica gel and chromatographed through a silica gel column (100% DCM to 5% MeOH (w/NH$_3$ in DCM) to give tert-butyl 4-(1-(5-(4-(bis(4-methoxybenzyl)amino)-6-methyl-1,3,5-triazin-2-yl)-6-(5-fluoro-6-methoxypyridin-3-ylamino)pyridin-3-yl)-2,2,2-trifluoroethyl)piperazine-1-carboxylate (1.24 g, 1.487 mmol, 96% yield) as a brown foam. m/z (ESI, +ve ion) 834 (M+H)$^+$.

Step 5. 4-(2-(5-fluoro-6-methoxypyridin-3-ylamino)-5-(2,2,2-trifluoro-1-(4-(methyl sulfonyl)piperazin-1-yl)ethyl)pyridin-3-yl)-6-methyl-1,3,5-triazin-2-amine The title compound was prepared from tert-butyl 4-(1-(5-(4-(bis(4-methoxybenzyl)amino)-6-methyl-1,3,5-triazin-2-yl)-6-(5-fluoro-6-methoxypyridin-3-ylamino)pyridin-3-yl)-

2,2,2-trifluoroethyl)piperazine-1-carboxylate via the similar deprotection step as previously described in Example 178, Step 4 using trifluoroacetic acid and trifluoromethanesulfonic acid and isolated (quantitative) as a yellow solid. m/z (ESI, +ve ion) 572 (M+H)+. 1H NMR (400 MHz, d6-DMSO) δ 11.96 (s, 1H) 8.84 (d, J=2.15 Hz, 1H) 8.40 (d, J=2.35 Hz, 1H) 8.29-8.39 (m, 2H) 8.03 (br. s., 1H) 7.88 (br. s., 1H) 4.86 (q, J=9.45 Hz, 1H) 3.95 (s, 3H) 3.13 (t, J=4.60 Hz, 4H) 2.86 (s, 3H) 2.69-2.78 (m, 2H) 2.58-2.69 (m, 2H) 2.45 (s, 3H).

The individual enantiomers (R)-4-(2-(5-fluoro-6-methoxypyridin-3-ylamino)-5-(2,2,2-trifluoro-1-(4-(methylsulfonyl)piperazin-1-yl)ethyl)pyridin-3-yl)-6-methyl-1,3,5-triazin-2-amine and (S)-(2-(5-fluoro-6-methoxypyridin-3-ylamino)-5-(2,2,2-trifluoro-1-(4-(methylsulfonyl)piperazin-1-yl)ethyl)pyridin-3-yl)-6-methyl-1,3,5-triazin-2-amine were separated and provided by chiral column chromatography (Preparative SFC, AD column (21×250 mm, 10 um), eluent: 30% iPOH with 0.2% DEA as additive is supercritical fluid $CO_2$) as yellow solids.

Example 326

N-(3-(4-amino-6-methyl-1,3,5-triazin-2-yl)-5-((4-(methylsulfonyl)piperazin-1-yl)methyl)pyridin-2-yl)ISOquinolin-7-amine

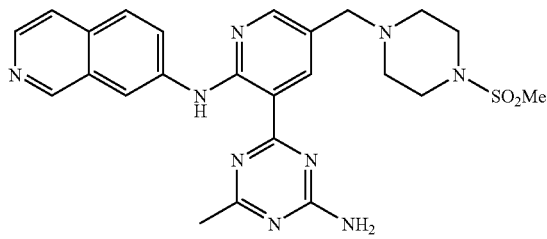 [SMILES: Cc1nc(N)nc(-c2cc(CN3CCN(S(C)(=O)=O)CC3)cnc2Nc2ccc3ccncc3c2)n1]

Step 1. N-(3-(4-(bis(4-methoxybenzyl)amino)-6-methyl-1,3,5-triazin-2-yl)-5-((4-(methylsulfonyl)piperazin-1-yl)methyl)pyridin-2-yl)ISOquinolin-7-amine A glass microwave reaction vessel was charged with 4-(2-fluoro-5-((4-(methylsulfonyl)piperazin-1-yl)methyl)pyridin-3-yl)-N,N-bis(4-methoxybenzyl)-6-methyl-1,3,5-triazin-2-amine (400 mg, 0.643 mmol) and isoquinolin-7-amine (139 mg, 0.965 mmol) (Ark Pharm, Inc, Libertyville, Ill.) in dioxane (2 mL) and the reaction mixture was cooled at 0° C. To this solution, sodium bis(trimethylsilyl)amide (1.0N in THF, 2 mL, 2 mmol) was mixed. The red solution was stirred at 0° C. for 1 h and 25° C. for 16 h. The reaction mixture was diluted with saturated $NH_4Cl$ and extracted with EtOAc (3×). The organic extract was washed with saturated NaCl and dried over $MgSO_4$. The solution was filtered and concentrated under a vacuum. The crude material was adsorbed onto a plug of silica gel and purified by chromatography through a silica gel column (40 g), eluting with a gradient of 0% to 5% 2M $NH_3$.MeOH in DCM, to provide N-(3-(4-(bis(4-methoxybenzyl)amino)-6-methyl-1,3,5-triazin-2-yl)-5-((4-(methylsulfonyl)piperazin-1-yl)methyl)pyridin-2-yl)isoquinolin-7-amine (150 mg, 31.3% yield) as a yellow solid. m/z (ESI, positive ion): 746 (M+H)+. 1H NMR (400 MHz, DMSO-d6): δ ppm 2.63 (s, 3H) 2.82 (s, 3H) 3.06-3.10 (m, 4H) 3.57 (s, 2H) 3.70 (s, 3H) 3.75 (s, 3H) 4.86 (s, 4H) 6.84-6.97 (m, 4H) 7.30 (t, J=6.85 Hz, 4H) 7.72 (d, J=5.48 Hz, 1H) 7.74-7.79 (m, 1H) 7.82-7.88 (m, 1H) 8.35 (d, J=5.67 Hz, 1H) 8.39 (d, J=2.35 Hz, 1H) 8.58 (d, J=1.76 Hz, 1H) 8.75 (d, J=2.35 Hz, 1H) 9.13 (s, 1H) 12.19 (s, 1H).

Step 2. N-(3-(4-amino-6-methyl-1,3,5-triazin-2-yl)-5-((4-(methylsulfonyl)piperazin-1-yl)methyl)pyridin-2-yl)ISOquinolin-7-amine To a 25 mL, round-bottomed flask was added N-(3-(4-(bis(4-methoxybenzyl)amino)-6-methyl-1,3,5-triazin-2-yl)-5-((4-(methylsulfonyl)piperazin-1-yl)methyl)pyridin-2-yl)isoquinolin-7-amine (150 mg, 0.201 mmol) and 5% TfOH-TFA (5 mL). The reaction mixture was stirred at 70° C. for 30 minutes and cooled to room temperature. After removal of TFA in high vacuum, the residue was treated with saturated $NaHCO_3$, the obtained suspension was filtered to provide the crude product as a yellow solid. After air drying, the solid was treated with MeOH-DCM-ether and filtered to provide N-(3-(4-amino-6-methyl-1,3,5-triazin-2-yl)-5-((4-(methylsulfonyl)piperazin-1-yl)methyl)pyridin-2-yl)isoquinolin-7-amine (100 mg, 98% yield) as a yellow solid. m/z (ESI positive ion): 506 (M+H)+. 1H NMR (400 MHz, DMSO-d6): δ ppm 2.88 (s, 3H) 3.09-3.16 (m, 4H) 3.29-3.36 (m, 7H) 3.56 (s, 2H) 7.74 (d, J=5.67 Hz, 1H) 7.83 (br s, 1H) 7.93 (d, J=8.80 Hz, 2H) 8.07 (dd, J=8.90, 2.05 Hz, 1H) 8.36 (d, J=5.67 Hz, 1H) 8.40 (d, J=2.15 Hz, 1H) 8.79 (d, J=2.35 Hz, 1H) 8.87 (d, J=1.56 Hz, 1H) 9.21 (s, 1H) 12.42 (s, 1H).

Example 327

4-(5-(1-aminoethyl)-2-(5-fluoro-6-methoxypyridin-3-ylamino)pyridin-3-yl)-6-methyl-1,3,5-triazin-2-amine

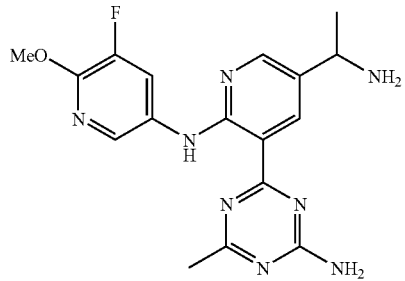 [SMILES: COc1ncc(Nc2ncc(C(C)N)cc2-c2nc(C)nc(N)n2)cc1F]

Step 1. 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol To a 150 mL round-bottomed flask was added 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanone (1 g, 1.640 mmol) and sodium borohydrate (0.06 g, 1.640 mmol) in DCM (10 mL)-MeOH (10 mL). The suspension was stirred at room temperature for 16 h. The solution was quenched by saturated $NH_4Cl$, extracted the aqueous with DCM (3×), the combined organic was dried over $MgSO_4$, concentrated in vacuum to provide 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol (0.9 g, 90% yield) as a yellow solid. m/z (ESI positive ion) m/z: 612 (M+H)+. 1H NMR (400 MHz, DMSO-d6): δ ppm 1.36 (d, J=6.46 Hz, 3H) 2.57 (s, 3H) 3.74 (s, 3H) 3.91 (s, 3H)

4.75 (dd, J=6.26, 4.50 Hz, 1H) 4.83 (d, J=12.32 Hz, 4H) 5.25 (d, J=4.30 Hz, 1H) 6.82-6.97 (m, 4H) 7.19-7.35 (m, 4H) 7.98-8.14 (m, 2H) 8.30 (d, J=2.35 Hz, 1H) 8.78 (d, J=2.35 Hz, 1H) 11.68 (s, 1H).

Step 2. 4-(5-(1-azidoethyl)-2-(5-fluoro-6-methoxy-pyridin-3-ylamino)pyridin-3-yl)-N,N-bis(4-methoxy-benzyl)-6-methyl-1,3,5-triazin-2-amine A glass microwave reaction vessel was charged with 1-(5-(4-(bis(4-methoxybenzyl)amino)-6-methyl-1,3,5-triazin-2-yl)-6-(5-fluoro-6-methoxypyridin-3-ylamino)pyridin-3-yl)ethanol (0.9 g, 1.635 mmol) in toluene (15 mL). The tube was sealed under inert atmosphere. To this suspension, diphenyl azidophosphate (0.9 mL, 4.2 mmol) and 1,8-diazabicyclo[5.4.0]undec-7-ene (0.64 mL, 4.3 mmol) were mixed, the solution was stirred for 16 h. The mixture was diluted with EtOAc, washed by saturated NH₄Cl and brine, concentrated under a vacuum to provide 4-(5-(1-azidoethyl)-2-(5-fluoro-6-methoxypyridin-3-ylamino)pyridin-3-yl)-N,N-bis(4-methoxybenzyl)-6-methyl-1,3,5-triazin-2-amine (1.1 g, 92% purity, 100% yield) as a yellow solid, which was used in next step without further purification. MS (ESI positive ion) m/z: 637 (M+1).

Step 3. 4-(5-(1-aminoethyl)-2-(5-fluoro-6-methoxy-pyridin-3-ylamino)pyridin-3-yl)-N,N-bis(4-methoxy-benzyl)-6-methyl-1,3,5-triazin-2-amine To a 50 mL round-bottomed flask was added 4-(5-(1-azi-doethyl)-2-(5-fluoro-6-methoxypyridin-3-ylamino)pyridin-3-yl)-N,N-bis(4-methoxybenzyl)-6-methyl-1,3,5-triazin-2-amine (1 g, 1.571 mmol) in THF (10 mL). Under nitrogen protection, 10% Pd—C (0.5 g) was mixed, the suspension was stirred under a hydrogen balloon for 16 h. The mixture was filtered through a Celite® (diatomaceous earth) pad, washed the pad with EtOAc, the filtrate was concentrated in vacuum to provide 4-(5-(1-aminoethyl)-2-(5-fluoro-6-methoxypyridin-3-ylamino)pyridin-3-yl)-N,N-bis(4-methoxybenzyl)-6-methyl-1,3,5-triazin-2-amine (0.8 g, 83% yield) as a black solid. m/z (ESI positive ion) m/z: 611(M+H)⁺.

Step 4. 4-(5-(1-aminoethyl)-2-(5-fluoro-6-methoxy-pyridin-3-ylamino)pyridin-3-yl)-6-methyl-1,3,5-triazin-2-amine To a 25 mL round-bottomed flask was added 4-(5-(1-ami-noethyl)-2-(5-fluoro-6-methoxypyridin-3-ylamino)pyridin-3-yl)-N,N-bis(4-methoxybenzyl)-6-methyl-1,3,5-triazin-2-amine (150 mg, 0.246 mmol) and 7% TfOH-TFA (5 mL). The solution was heated at 70° C. for 20 minutes. The mixture was cooled to 0° C. and neutralized with 10N NaOH. The obtained suspension was filtered to provide 4-(5-(1-aminoethyl)-2-(5-fluoro-6-methoxypyridin-3-ylamino)pyridin-3-yl)-6-methyl-1,3,5-triazin-2-amine (80 mg, 88% yield) as a yellow solid. m/z (ESI positive ion): 371 (M+H)⁺. ¹H NMR 400 MHz, DMSO-d₆): δ ppm 1H NMR (400 MHz, DMSO-d₆) δ ppm 1.07 (d, J=6.26 Hz, 3H) 1.75 (br s, 2H) 2.23 (s, 3H) 3.81-3.86 (m, 1H) 7.60 (d, J=61.62 Hz, 2H) 8.09-8.25 (m, 3H) 8.61 (s, 1H) 11.68 (s, 1H).

Example 328

N-(5-(3-(4-amino-6-methyl-1,3,5-triazin-2-yl)-5-(tetrahydro-2H-pyran-4-yl)pyridin-2-ylamino)-2-chloropyridin-3-yl)methanesulfonamide

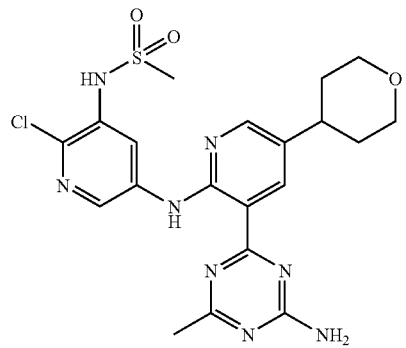 [SMILES: Cc1nc(N)nc(-c2cc(C3CCOCC3)cnc2Nc2cnc(Cl)c(NS(C)(=O)=O)c2)n1]

Step 1. 4-(5-(3,6-dihydro-2H-pyran-4-yl)-2-fluoro-pyridin-3-yl)-N,N-bis(4-methoxybenzyl)-6-methyl-1,3,5-triazin-2-amine A mixture of 2-(3,6-dihydro-2H-pyran-4-yl)-4,4,5,5-tet-ramethyl-1,3,2-dioxaborolane (320 mg, 1.523 mmol) (Frontier Scientific), 4-(5-chloro-2-fluoropyridin-3-yl)-N,N-bis(4-methoxybenzyl)-6-methyl-1,3,5-triazin-2-amine (600 mg, 1.250 mmol), potassium carbonate (400 mg, 2.89 mmol), and Amphos-PdCl₂ (50 mg, 0.071 mmol) in dioxane (8 mL) was sparged with argon for 5 min. The mixture was heated at 110° C. under nitrogen. After 14 h, x-phos and Pd₂dba₃ (40 mg each) were added. After 3 h, more x-phos, Pd₂dba₃ and boronic ester were added. After 16 h, the mixture was cooled to room temperature, and partitioned between EtOAc (40 mL) and water (20 mL). The aqueous phase was extracted with EtOAc once. The combined organic phase was washed with water (3×), dried over Na₂SO₄ and concentrated. The residue was purified on silica gel (5 to 30% EtOAc). The dechlorinated fraction came out as the first major peak, followed by the product as the next major peak. The product was collected as a pink solid (130 mg). m/z (ESI, positive ion): 528.2 (M+H)⁺. ¹H NMR (400 MHz, CDCl₃-d) δ ppm 2.49-2.58 (m, 5H) 3.79 (s, 3H) 3.91 (s, 3H) 3.95 (t, J=5.38 Hz, 2H) 4.31-4.36 (m, 2H) 4.82 (d, J=8.61 Hz, 4H) 6.20 (br. s., 1H) 6.86 (dd, J=11.15, 8.61 Hz, 4H) 7.22 (d, J=6.85 Hz, 4H) 8.31 (d, J=1.96 Hz, 1H) 8.50 (dd, J=9.00, 2.54 Hz, 1H).

Step 2. 4-(2-fluoro-5-(tetrahydro-2H-pyran-4-yl)pyridin-3-yl)-N,N-bis(4-methoxybenzyl)-6-methyl-1,3,5-triazin-2-amine The solid 4-(5-(3,6-dihydro-2H-pyran-4-yl)-2-fluoropyri-din-3-yl)-N,N-bis(4-methoxybenzyl)-6-methyl-1,3,5-tri-azin-2-amine (130 mg, 0.246 mmol) from step 1 was dissolved in THF (30 mL) and mixed with palladium hydroxide on carbon (20%, 80 mg). The mixture was purged with hydrogen through vacuum/back-fill (3×) and stirred under a hydrogen balloon. After 15 h, the mixture was heated to about 50° C. for 2 h. The mixture was cooled to room temperature and filtered through a pad of Celite® (diatomaceous earth). The filtrate was concentrated to a yellow film. m/z (ESI, positive ion): 530.2 (M+H)+.

Step 3. 4-(2-fluoro-5-(tetrahydro-2H-pyran-4-yl) pyridin-3-yl)-6-methyl-1,3,5-triazin-2-amine The crude product from step 2 was dissolved in TFA (2500 µL, 32.4 mmol). TfOH (50 µL, 0.563 mmol) was added. The mixutre was heated at 66° C. After 16 h, the residue was transferred to a cold solution of $Na_2CO_3$ (saturated) and extracted with DCM. The organic phase was dried over $Na_2SO_4$ and concentrated. The residue was purified on silica (1 to 5% MeOH in EtOAc) to give the product as a yellow solid (55 mg, 77%). This material was mixed with toluene and concentrated to dryness before use. m/z (ESI, positive ion): 290.1 (M+H)+. $^1$H NMR (400 MHz, $CDCl_3$) δ ppm 1.77-1.95 (m, 4H) 2.55 (s, 3H) 2.83-2.96 (m, 1H) 3.56 (td, J=11.40, 2.84 Hz, 2H) 4.07-4.18 (m, 2H) 5.82 (br. s., 2 H, NH2) 8.20 (s, 1H) 8.39 (dd, J=9.00, 2.54 Hz, 1H).

Step 4. N-(5-(3-(4-amino-6-methyl-1,3,5-triazin-2-yl)-5-(tetrahydro-2H-pyran-4-yl)pyridin-2-ylamino)-2-chloropyridin-3-yl)methanesulfonamide To a solution of N-(5-amino-2-chloropyridin-3-yl)methanesulfonamide (60 mg, 0.271 mmol) and 4-(2-fluoro-5-(tetrahydro-2H-pyran-4-yl)pyridin-3-yl)-6-methyl-1,3,5-triazin-2-amine (55 mg, 0.190 mmol) in anhydrous DMF (1 mL) cooled in an ice bath was added solid NaHMDS (210 mg, 1.088 mmol) under nitrogen. The resulting orange mixture was stirred with cooling. After 1.5 h, HCl (5 N, 0.25 mL, 1.25 mmol) was added to the mixture. The resulting mixutre was diluted with water (5 mL) and acidified with HCl, 5 N) to about pH 5. The resulting slurry was filtered and washed with water (3×3 mL). The solid was washed with EtOAc to afford the product as a brown solid. The mother liquid was chromatographed on silica gel (0-5% MeOH in EtOAc) to give additional product. The combined product was about 30 mg (32%). m/z (ESI, positive ion): 491.1 (M+H)+. $^1$H NMR (400 MHz, DMSO-$d_6$) δ ppm 1.60-1.82 (m, 4H) 2.46 (s, 3H) 2.84 (t, J=11.35 Hz, 1H) 3.12 (s, 3H) 3.46 (t, J=10.76 Hz, 2H) 3.97 (d, J=12.13 Hz, 2H) 7.78 (br. s., 1H) 7.92 (br. s., 1H) 8.33 (s, 1H) 8.64 (d, J=3.33 Hz, 2H) 8.72 (s, 1H) 9.64 (br. s., 1H) 12.17 (s, 1H).

Example 329

N-(5-(3-(4-amino-6-methyl-1,3,5-triazin-2-yl)-5-chloropyridin-2-ylamino)-2-methoxypyridin-3-yl) methanesulfonamide

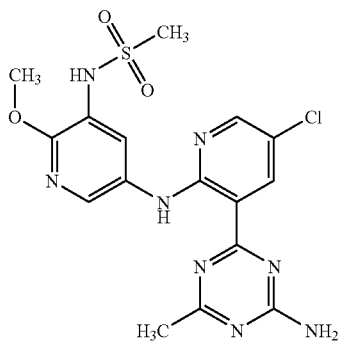 [SMILES: COc1ncc(Nc2ncc(Cl)cc2-c2nc(C)nc(N)n2)cc1NS(C)(=O)=O]

Step 1. 4-(5-chloro-2-fluoropyridin-3-yl)-6-methyl-1,3,5-triazin-2-amine

To a 20 mL microwave reaction tube was added 4-chloro-6-methyl-1,3,5-triazin-2-amine (Example 9, 1.00 g, 6.94 mmol), 5-chloro-2-fluoropyridin-3-ylboronic acid (Combi-Blocks, 1.62 g, 9.22 mmol), potassium acetate (Aldrich, 2.07 g, 21.1 mmol) and Am-Phos (Aldrich, 0.247 g, 0.349 mmol) in EtOH (12 mL) and water (1.2 mL). The mixture was degassed by bubbling argon through for 5 min. The tube was heated in an microwave reactor (Biotage) at 100° C. for 20 min. The reaction mixture was partitioned between water (100 mL) and 25% IPA in chloroform with 1% $NH_4OH$ (60 mL). The aqueous phase was extracted with 25% IPA in chloroform with 1% $NH_4OH$ (2×50 mL). The combined organic phases were washed with saturated aqueous sodium chloride (40 mL). The organic phase was dried over sodium sulfate, filtered and concentrated in vacuo. Adding DCM to the residue resulted in precipitate formation. The solid was collected via filtration and washed with MeOH to afford 4-(5-chloro-2-fluoropyridin-3-yl)-6-methyl-1,3,5-triazin-2-amine (0.937 g) as a light yellow powder. The filtrate and the wash were combined and concentrated, then purified by column chromatography (eluent: iPrOH (w/10% $NH_4OH$) in $CHCl_3$ 0.25% to 6.25%) followed by washing with MeOH to afford additional product (0.149 g) as a white solid. The total yield is 1.08 g (65%). $^1$H NMR (400 MHz, DMSO-$d_6$) δ ppm 8.54 (dd, J=8.02, 2.74 Hz, 1H) 8.46-8.51 (m, 1H) 7.73 (s, 2H) 2.37 (s, 3H). m/z (ESI, positive ion) m/z: 240.1 (M+H)+.

Step 2. N-(5-bromo-2-methoxypyridin-3-yl)methanesulfonamide

To a 20 mL scintillation vial, 5-bromo-3-iodo-2-methoxypyridine (Alfa Aesar, 2.02 g, 6.43 mmol), methanesulfonamide (Fluka, 0.645 g, 6.78 mmol), copper (I) iodide (Strem, 0.122 g, 0.643 mmol), cesium carbonate (Aldrich, 5.27 g, 16.1 mmol) and water (0.60 ml, 33.3 mmol) were mixed into DMF (6 mL). The reaction mixture was stirred at 105° C. for overnight. Then the mixture was heated in a microwave reactor (Biotage) at 120° C. for 30 min. The reaction mixture was partitioned between Tris-HCl buffer (1 M, pH 7.0) (20 mL) and EtOAc (20 mL). The aq phase was extracted with EtOAc (2×20 mL). The combined organic phases were washed with saturated aq NaCl (40 mL). The organic phase was dried over sodium sulfate, filtered and concentrated in vacuo to afford the crude product, which was purified by silica gel column chromatography (100 g, eluent: EtOAc in hexanes 0% to 50%) to afford N-(5-bromo-2-methoxypyridin-3-yl)methanesulfonamide (1.06 g, 59% yield) as a white solid. $^1$H NMR (300 MHz, $CDCl_3$) δ ppm 7.97 (d, J=2.19 Hz, 1H) 7.90 (d, J=2.19 Hz, 1H) 6.72 (br. s., 1H) 4.00 (s, 3H) 3.04 (s, 3H). m/z (ESI, positive ion): 280.8, 282.8 [M+1, M+3].

Step 3. N-(5-(diphenylmethyleneamino)-2-methoxypyridin-3-yl)methanesulfonamide

To a 5 mL microwave reaction tube was added N-(5-bromo-2-methoxypyridin-3-yl)methanesulfonamide (0.208 g, 0.739 mmol), xantphos (Acros, 0.044 g, 0.077 mmol), $Pd_2dba_3$ (Aldrich, 0.034 g, 0.037 mmol), NaOtBu (Aldrich, 0.178 g, 1.85 mmol) and diphenylmethanimine (Aldrich, 0.130 mL, 0.776 mmol) in DMF (3 mL). The mixture was degassed by bubbling argon through for 5 min. The tube was heated in a microwave reactor (Biotage) at 120° C. for 30 min. The reaction mixture was partitioned between tris-HCl buffer (1 M, pH 7.0) (20 mL) and EtOAc (10 mL). The aqueous phase was extracted with EtOAc (20 mL). The combined organic phases were washed with saturated aqueous sodium chloride (20 mL). The organic phase was dried over sodium sulfate, filtered and concentrated in vacuo. The crude product was purified by silica gel column chromatography (50 g, eluent: EtOAc in hexanes 20% to 80%) to afford N-(5-(diphenylmethyleneamino)-2-methoxypyridin-3-yl)methanesulfonamide (0.109 g, 39% yield) as a light yellow solid. $^1$H NMR (400 MHz, CDCl$_3$) δ ppm 7.69-7.74 (m, 2H) 7.53 (d, J=2.35 Hz, 1H) 7.46-7.51 (m, 1H) 7.38-7.44 (m, 2H) 7.30-7.36 (m, 3H) 7.12-7.18 (m, 3H) 6.60 (s, 1H) 3.94 (s, 3H) 2.69 (s, 3H).

Step 4. N-(5-amino-2-methoxypyridin-3-yl)methanesulfonamide

To a 150 mL round-bottomed flask, N-(5-(diphenylmethyleneamino)-2-methoxypyridin-3-yl)methanesulfonamide (0.100 g, 0.262 mmol) and 1 N hydrochloric acid (0.30 mL, 0.30 mmol) were mixed into THF (2 mL). The yellow mixture was stirred at room temperature for 20 min. The reaction mixture was partitioned between tris-HCl buffer (1 M, pH 7.0) (10 mL) and EtOAc (10 mL). The aqueous phase was extracted with EtOAc (10 mL). The aqueous phase was acidified to about pH 5 and the aqueous phase was extracted with EtOAc (10 mL). The combined organic phases were dried over sodium sulfate, filtered and concentrated in vacuo. The crude product was purified by silica gel column chromatography (25 g, eluent: EtOAc in hexanes 50%-100%) to afford N-(5-amino-2-methoxypyridin-3-yl)methanesulfonamide (0.028 g, 49% yield) as a yellow solid. $^1$H NMR (400 MHz, CDCl$_3$) δ ppm 7.43 (d, J=2.54 Hz, 1H) 7.27 (d, J=2.74 Hz, 1H) 6.66 (br. s., 1H) 3.93 (s, 3H) 3.46 (br. s., 2H) 2.99 (s, 3H). m/z (ESI, positive ion) 218.0 (M+H)$^+$.

Step 5. N-(5-(3-(4-amino-6-methyl-1,3,5-triazin-2-yl)-5-chloropyridin-2-ylamino)-2-methoxypyridin-3-yl)methanesulfonamide To a stirred solution of N-(5-amino-2-methoxypyridin-3-yl)methanesulfonamide (Step 4, 0.028 g, 0.13 mmol) and 4-(5-chloro-2-fluoropyridin-3-yl)-6-methyl-1,3,5-triazin-2-amine (Step 1, 0.0364 g, 0.152 mmol) in DMF (1 mL) in 5 mL microwave vial, NaHMDS (Aldrich, 1 M in THF, 0.52 mL, 0.52 mmol) was added dropwise at 0° C. The solution was stirred at 0° C. for 1.5 h. The reaction mixture was poured into sat'd NH$_4$Cl (15 mL) and stirred. The resulting solid was collected via filtration. The crude product was purified by preparative HPLC (column: Phenomenex, Gemni 5 micron C18 100×30 mm, 10%-90% CH$_3$CN w/0.1% TFA/H$_2$O w/0.1% TFA in 10 min). The corresponding fractions were combined and concentrated. Sat'd NaHCO$_3$ was added to the residue and sonicated. The resulting yellow solid was collected and washed with water and with MeOH to afford 5 N-(5-(3-(4-amino-6-methyl-1,3,5-triazin-2-yl)-5-chloropyridin-2-ylamino)-2-methoxypyridin-3-yl)methanesulfonamide (12.9 mg, 23% yield) as bright yellow solid. $^1$H NMR (400 MHz, DMSO-d$_6$) δ ppm 11.76 (s, 1H) 9.27 (s, 1H) 8.72 (d, J=2.54 Hz, 1H) 8.32 (dd, J=10.47, 2.45 Hz, 2H) 8.09 (d, J=2.15 Hz, 1H) 7.77-8.01 (m, 2H) 3.91 (s, 3H) 3.05 (s, 3H) 2.44 (s, 3H). m/z (ESI, positive ion): 436.9 (M+H)$^+$.

Example 330

N-(5-(3-(4-amino-6-methyl-1,3,5-triazin-2-yl)-5-methoxypyridin-2-ylamino)-2-chloropyridin-3-yl)methanesulfonamide

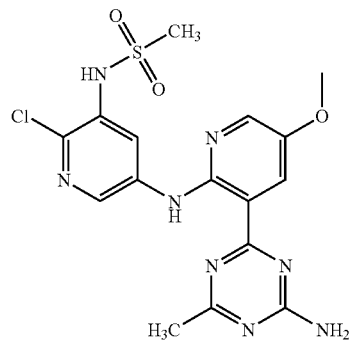 [SMILES: COc1cnc(Nc2cnc(Cl)c(NS(C)(=O)=O)c2)c(-c2nc(C)nc(N)n2)c1]

Step 0. N-(5-bromo-2-chloropyridin-3-yl)-N-(methylsulfonyl)methanesulfonamide To a stirred solution of 5-bromo-2-chloropyridin-3-amine (3.04 g, 14.7 mmol) of pyridine (20 mL) in 150-mL round-bottom flask, methanesulfonyl chloride (2.83 ml, 36.6 mmol) was added dropwise at 0° C. The ice bath was removed and the light brown solution was stirred at RT for overnight. Water (100 mL) was added and the precipitate was formed. The mixture was stirred at RT to break up lumps. The cream color solid was collected via filtration and washed with water several times then air dried to afford N-(5-bromo-2-chloropyridin-3-yl)-N-(methylsulfonyl)methanesulfonamide (5.16 g, 96.9% yield) as a cream colored powder. $^1$H NMR (300 MHz, DMSO-d$_6$) δ ppm 3.65 (s, 6H), 8.69 (d, J=2.3 Hz, 1H), 8.75 (d, J=2.3 Hz, 1H). m/z (ESI, positive ion): 362.8 [M+H]$^+$.

Step 1. N-(2-chloro-5-(diphenylmethyleneamino)pyridin-3-yl)methanesulfonamide To a 20 mL microwave reaction tube was added N-(5-bromo-2-chloropyridin-3-yl)-N-(methylsulfonyl)methanesulfonamide (Step 0) 1.11 g, 3.04 mmol), xantphos (0.179 g, 0.308 mmol), NaOtBu (1.18 g, 12.3 mmol), Pd$_2$dba$_3$ (0.139 g, 0.152 mmol) and diphenylmethanimine (0.62 mL, 3.7 mmol) in DMF (10 mL). The mixture was degassed by bubbling argon through for 10 min. The tube was heated in Initiator microwave reactor (Biotage) at 120° C. for 30 min. The reaction mixture was partitioned between tris-HCl buffer (1 M, pH 7.0) (80 mL) and EtOAc (50 mL). The aqueous phase was extracted with EtOAc (2×60 mL). The combined organic phases were washed with water (200 mL) and saturated aqueous sodium chloride (150 mL). The organic phase was dried over sodium sulfate, filtered and concentrated in vacuo. The crude product was purified by silica gel column chromatography (100 g, eluent: EtOAc in hexanes 0% to 50%) to afford N-(2-chloro-5-(diphenylmethyleneamino)pyridin-3-yl)methanesulfonamide (0.90 g, 77% yield) as a light brown solid. $^1$H NMR (400 MHz, CDCl$_3$) δ ppm 7.72-7.77 (m, 3H)

7.50-7.56 (m, 1H) 7.43 (t, J=7.53 Hz, 2H) 7.32-7.37 (m, 3H) 7.28-7.31 (m, 1H) 7.11-7.16 (m, 2H) 6.66 (s, 1H) 2.78 (s, 3H).

Step 2.
N-(5-amino-2-chloropyridin-3-yl)methanesulfonamide

To a 1 L round-bottomed flask, N-(2-chloro-5-(diphenylmethyleneamino)pyridin-3-yl)methanesulfonamide (0.90 g, 2.3 mmol) and 1 N hydrochloric acid (2.5 mL, 2.5 mmol) were mixed into THF (10 mL). The mixture was stirred at room temperature for 20 min. The reaction mixture was partitioned between saturated aqueous sodium bicarbonate (40 mL) and EtOAc (30 mL). The aqueous phase was extracted with EtOAc (30 mL). The combined organic phases were dried over sodium sulfate, filtered and concentrated in vacuo to afford 0.586 g of brown residue. This material was purified by silica gel column chromatography (25 g, eluent: EtOAc in hexanes 30% to 100%) to afford 0.144 g of light yellow solid. The pH of original aqueous phase was adjusted to about pH 5 and extracted with EtOAc to afford 0.34 g of additional crude product, which was purified by silica gel column chromatography (25 g, eluent: EtOAc in hexanes 40% to 100%) to afford 0.275 g of white crystalline solid, yielding total of 0.419 g of N-(5-amino-2-chloropyridin-3-yl)methanesulfonamide (81% yield). $^1$H NMR (400 MHz, DMSO-$d_6$) δ ppm 9.34 (s, 1H) 7.56 (d, J=2.54 Hz, 1H) 7.08 (d, J=2.54 Hz, 1H) 5.64 (s, 2H) 3.04 (s, 3H). m/z (ESI, positive ion): 221.9 (M+H)$^+$.

Step 3. 2-fluoro-5-methoxypyridine

To a 20 mL microwave vial, 6-fluoropyridin-3-ol (Alfa Aesar, 1.04 g, 9.18 mmol), potassium carbonate (1.90 g, 13.8 mmol) and methyl iodide (Aldrich, 0.689 mL, 11.0 mmol) were mixed into DMF (6 mL). The brown mixture was stirred at 45° C. for 2.5 h. The mixture was diluted with water and the aqueous phase was extracted with EtOAc (3×20 mL). The combined organic phases were washed with saturated aqueous sodium chloride (30 mL). The organic phase was dried over sodium sulfate, filtered and concentrated in vacuo to afford 2-fluoro-5-methoxypyridine (1.08 g, 92% yield) as a light brown oil. This material was used in the next reaction without further purification. $^1$H NMR (400 MHz, CDCl$_3$) δ ppm 7.79-7.85 (m, 1H) 7.33 (td, J=6.02, 3.23 Hz, 1H) 6.86 (dd, J=8.90, 3.42 Hz, 1H) 3.85 (s, 3H). m/z (ESI, positive ion): 128.1 (M+H)$^+$.

Step 4. 2-fluoro-5-methoxypyridin-3-ylboronic acid

To a 100 mL round-bottomed flask, diisopropylamine (Aldrich, 1.40 mL, 9.99 mmol) was dissolved into THF (6 mL). nBuLi (Aldrich, 2.5 M in hexanes, 3.60 mL, 8.99 mmol) was added slowly at 0° C. The mixture was stirred at 0° C. for 30 min then cooled to −78° C. 2-fluoro-5-methoxypyridine (0.520 g, 4.09 mmol) in 4 mL of THF was added slowly, and the mixture was stirred at that temperature for 40 min. Triisopropyl borate (Aldrich, 2.07 mL, 8.99 mmol) in a total of 4 mL of THF was added slowly and the mixture was stirred at −78° C. for 5 min. The cold bath was removed and the reaction mixture was stirred at room temperature for 1 h. 1 N NaOH (20 mL) was added to the mixture to quench the reaction. The layers were separated and the aqueous phase was treated with 5 N HCl to adjust the pH to around 5. The aqueous phase was extracted with EtOAc (2×20 mL). The combined organic phases were dried over sodium sulfate, filtered and concentrated in vacuo to afford 0.593 g of tan color solid. This material was used in the next step without further purification.

Step 5. 4-(2-fluoro-5-methoxypyridin-3-yl)-6-methyl-1,3,5-triazin-2-amine

To a 20 mL microwave reaction tube was added 4-chloro-6-methyl-1,3,5-triazin-2-amine (Example 9, 1.02 g, 7.05 mmol), 2-fluoro-5-methoxypyridin-3-ylboronic acid (1.67 g, 9.77 mmol), Am-Phos (Aldrich, 0.255 g, 0.360 mmol) and potassium acetate (Aldrich, 2.11 g, 21.5 mmol) in EtOH (10 mL) and water (1 mL). The mixture was degassed by bubbling argon through for 5 min. The tube was heated in a microwave reactor (Biotage) at 100° C. for 20 min. The reaction mixture was partitioned between water (200 mL) and EtOAc (200 mL). Layers were separated and insoluble material was collected (precipitate 1). The aqueous phase was further extracted with 10% isopropanol in chloroform (3×100 mL). Each organic phase was dried over sodium sulfate, filtered and concentrated in vacuo. Upon addition of DCM to the crude product, precipitate came out and the solid was collected via filtration. The first precipitate (precipitate 1) and the solid from extraction were all desired product (1.17 g, 70.3%). $^1$H NMR (400 MHz, CDCl$_3$) δ ppm 8.08 (dd, J=7.53, 3.23 Hz, 1H) 7.97 (dd, J=3.03, 1.86 Hz, 1H) 5.47 (br. s., 2H) 3.92 (s, 3H) 2.54 (s, 3H). m/z (ESI, positive ion): 236.0 (M+H)$^+$.

Step 6. N-(5-(3-(4-amino-6-methyl-1,3,5-triazin-2-yl)-5-methoxypyridin-2-ylamino)-2-chloropyridin-3-yl)methanesulfonamide To a 5 mL microwave vial, 4-(2-fluoro-5-methoxypyridin-3-yl)-6-methyl-1,3,5-triazin-2-amine (0.0550 g, 0.234 mmol) and N-(5-amino-2-chloropyridin-3-yl)methanesulfonamide (Step 2, 0.0579 g, 0.261 mmol) were dissolved into DMF (1 mL). NaHMDS (Aldrich, 1 M in THF, 0.935 mL, 0.935 mmol) was added slowly at 0° C. and the dark red mixture was stirred at that temperature for 40 min. The mixture was poured into sat'd NH$_4$Cl (20 mL) and stirred for 5 min. The resulting solid was collected via filtration, washed with water and purified by preparative HPLC using a Phenomenex Gemini 5 micron C18 100×30 mm column (1%-90% CH$_3$CN w/0.1% TFA/H$_2$O w/0.1% TFA in 10 min). The fractions were combined and concentrated. The residue was taken into sat'd NaHCO$_3$. The aqueous pH was adjusted to pH 4-5 and the resulting solid was collected to give N-(5-(3-(4-amino-6-methyl-1,3,5-triazin-2-yl)-5-methoxypyridin-2-ylamino)-2-chloropyridin-3-yl)methanesulfonamide (0.0146 g, 14% yield) as a yellow solid. $^1$H NMR (400 MHz, DMSO-$d_6$) δ ppm 11.97 (br. s., 1H) 9.62 (br. s., 1H) 8.61 (d, J=14.08 Hz, 2H) 8.41 (br. s., 1H) 8.20 (br. s., 1H) 7.68-8.09 (m, 2H) 3.86 (br. s., 3H) 3.13 (br. s., 3H) 2.45 (br. s., 3H). m/z (ESI, positive ion) m/z: 436.9 (M+H)$^+$.

Example 331

N'-(5-((3-(4-amino-6-methyl-1,3,5-triazin-2-yl)-5-methoxy-2-pyridinyl)amino)-2-chloro-3-pyridinyl)-N,N-dimethylsulfamide

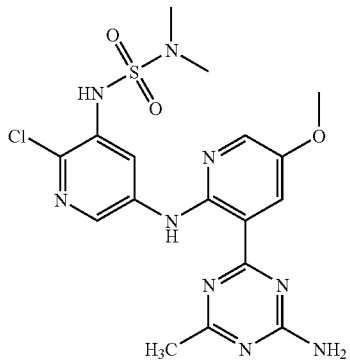 [SMILES: COc1cnc(Nc2cnc(Cl)c(NS(=O)(=O)N(C)C)c2)c(-c2nc(C)nc(N)n2)c1]

To a stirred solution of N'-(5-amino-2-chloro-3-pyridinyl)-N,N-dimethylsulfamide (Example 384, Step 2, 0.0697 g, 0.278 mmol) and 4-(2-fluoro-5-methoxypyridin-3-yl)-6-methyl-1,3,5-triazin-2-amine (Example 330, Step 5, 0.0595 g, 0.253 mmol) in DMF (1 mL) in 5 mL microwave vial, NaHMDS (Aldrich, 1 M in THF, 1.02 mL, 1.02 mmol) was added dropwise at 0° C. The dark red solution was stirred at that temperature for 45 min. Sat'd NH$_4$Cl (0.2 mL) was added to quench the reaction. The reaction mixture was poured into sat'd NH$_4$Cl (20 mL) and the mixture was stirred for 5 min. The resulting brown precitipate was collected and the crude product was purified by preparative HPLC using a Phenomenex, Gemni 5 micron C18 100×30 mm column (1% to 90% CH$_3$CN w/0.1% TFA/H$_2$O w/0.1% TFA in 10 min). The corresponding fractions were collected and concentrated in vacuo. The residue was collected and washed with water and small amount of MeOH to afford N'-(5-((3-(4-amino-6-methyl-1,3,5-triazin-2-yl)-5-methoxy-2-pyridinyl)amino)-2-chloro-3-pyridinyl)-N,N-dimethylsulfamide (0.0240 g, 20% yield) as a yellow solid. $^1$H NMR (400 MHz, DMSO-d$_6$) δ ppm 12.00 (br. s., 1H) 9.53 (br. s., 1H) 8.77 (br. s., 1H) 8.52 (br. s., 1H) 8.35-8.46 (m, 1H) 8.19 (br. s., 1H) 7.71-8.03 (m, 2H) 3.86 (br. s., 3H) 2.79 (br. s., 6H) 2.46 (br. s., 3H). m/z (ESI, positive ion) m/z: 466.0 (M+H)$^+$.

Example 332

N-(5-(3-(4-amino-6-methyl-1,3,5-triazin-2-yl)-5-(morpholinomethyl)pyridin-2-ylamino)-2-chloropyridin-3-yl)methanesulfonamide

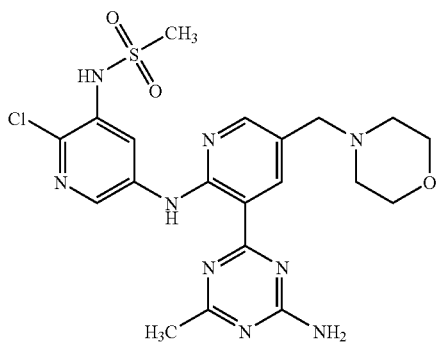 [SMILES: Cc1nc(N)nc(-c2cc(CN3CCOCC3)cnc2Nc2cnc(Cl)c(NS(C)(=O)=O)c2)n1]

Step 1. 4-(2-fluoro-5-(morpholinomethyl)pyridin-3-yl)-6-methyl-1,3,5-triazin-2-amine To a 20 mL microwave reaction tube was added 2-fluoro-5-(morpholinomethyl)pyridin-3-ylboronic acid (Example 129, Step 3) (2.00 g, 8.33 mmol), 4-chloro-6-methyl-1,3,5-triazin-2-amine (Example 9, 0.501 g, 3.47 mmol), Am-Phos (Aldrich, 0.124 g, 0.175 mmol) and potassium acetate (Aldrich, 1.14 g, 11.6 mmol) in EtOH (10 mL) and water (1 mL). The mixture was degassed by bubbling argon through for 10 min. The tube was heated in a microwave reactor (Biotage) at 100° C. for 20 min. After the reaction mixture was cooled to room temperature, insoluble material was removed via filtration. The filtrate was partitioned between saturated aqueous sodium chloride (60 mL) and 10% isopropanol in chloroform (60 mL). The aqueous phase was extracted with 10% isopropanol in chloroform (2×60 mL). The combined organic phases were dried over sodium sulfate, filtered and concentrated in vacuo. The crude product was purified by silica gel column chromatography (100 g, eluent: iPrOH in CHCl$_3$ 0% to 25%) to afford 4-(2-fluoro-5-(morpholinomethyl)pyridin-3-yl)-6-methyl-1,3,5-triazin-2-amine (0.27 g, 26% yield) as a white foam. $^1$H NMR (400 MHz, CDCl$_3$) δ ppm 8.46 (dd, J=9.00, 2.35 Hz, 1H) 8.27 (s, 1H) 5.83 (br. s., 2H) 3.70-3.75 (m, 4H) 3.56 (s, 2H) 2.54 (s, 3H) 2.44-2.50 (m, 4H). m/z (ESI, positive ion): 305.0 (M+H)$^+$.

Step 2. N-(5-(3-(4-amino-6-methyl-1,3,5-triazin-2-yl)-5-(morpholinomethyl)pyridin-2-ylamino)-2-chloropyridin-3-yl)methanesulfonamide To a stirred solution of 4-(2-fluoro-5-(morpholinomethyl)pyridin-3-yl)-6-methyl-1,3,5-triazin-2-amine (0.0602 g, 0.198 mmol) and N-(5-amino-2-chloropyridin-3-yl)methanesulfonamide (Example 330, step 2, 0.0494 g, 0.223 mmol) in DMF (1 mL) in a 5 mL microwave vial, NaHMDS (Aldrich, 1 M in THF, 0.80 mL, 0.80 mmol) was added dropwise at 0° C. The mixture was stirred at 0° C. for 45 min. The reaction mixture was partitioned between saturated aqueous ammonium chloride (30 mL) and 25% isopropanol in chloroform (20 mL). The aq phase was acidified to a pH of about 3 to 4 then extracted with 25% isopropanol in chloroform (2×30 mL). The combined organic phases were dried over sodium sulfate, filtered and concentrated in vacuo to afford a brown residue. Upon addition of MeOH to the residue, a tan precipitate came out. The solid was collected via filtration and washed with MeOH to afford N-(5-(3-(4-amino-6-methyl-1,3,5-triazin-2-yl)-5-(morpholinomethyl)pyridin-2-ylamino)-2-chloropyridin-3-yl)methanesulfonamide (0.0774 g, 77% yield) as a tan solid. $^1$H NMR (400 MHz, DMSO-d$_6$) δ ppm 12.26 (s, 1H) 9.66 (br. s., 1H) 8.76 (s, 1H) 8.67 (t, J=2.45 Hz, 2H) 8.31 (d, J=1.56 Hz, 1H) 7.74-8.01 (m, 2H) 3.43-3.66 (m, 6H) 3.14 (s, 3H) 2.38-2.48 (m, 7H). m/z (ESI, pos. ion): 505.9 (M+H)$^+$.

Example 333

N'-(5-((3-(4-amino-6-methyl-1,3,5-triazin-2-yl)-5-(4-morpholinylmethyl)-2-pyridinyl)amino)-2-chloro-3-pyridinyl)-N,N-dimethylsulfamide

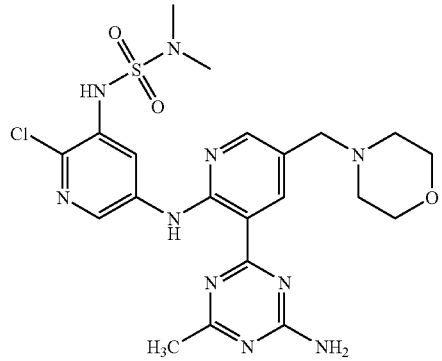 [SMILES: Cc1nc(N)nc(-c2cc(CN3CCOCC3)cnc2Nc2cnc(Cl)c(NS(=O)(=O)N(C)C)c2)n1]

To a stirred solution of 4-(2-fluoro-5-(morpholinomethyl) pyridin-3-yl)-6-methyl-1,3,5-triazin-2-amine (Example 384, Step 2, 0.0614 g, 0.202 mmol) and N'-(5-amino-2-chloro-3-pyridinyl)-N,N-dimethylsulfamide (KY, 0.050 g, 0.199 mmol) in DMF (1 mL) in 5 mL microwave vial, NaHMDS (Aldrich, 1 M in THF, 0.80 mL, 0.80 mmol) was added dropwise at 0° C. The mixture was stirred at 0° C. for 45 min.

The reaction mixture was partitioned between saturated aqueous ammonium chloride (30 mL) and 25% isopropanol in chloroform (20 mL). The aqueous phase was acidified to a pH of about 3 to 4 then extracted with 25% isopropanol in chloroform (2×30 mL). The combined organic phases were dried over sodium sulfate, filtered and concentrated in vacuo. The crude product was purified by silica gel column chromatography (25 g, eluent: iPrOH in CHCl$_3$ 0%-25%) to afford N'-(5-((3-(4-amino-6-methyl-1,3,5-triazin-2-yl)-5-(4-morpholinylmethyl)-2-pyridinyl)amino)-2-chloro-3-pyridinyl)-N,N-dimethylsulfamide (0.0437 g, 44% yield) as a yellow solid. $^1$H NMR (400 MHz, DMSO-d$_6$) δ ppm 12.28 (s, 1H) 9.57 (s, 1H) 8.82 (s, 1H) 8.76 (d, J=2.35 Hz, 1H) 8.53 (d, J=2.35 Hz, 1H) 8.29 (d, J=2.35 Hz, 1H) 7.74-7.98 (m, 2H) 3.57 (t, J=4.21 Hz, 4H) 3.48 (s, 2H) 2.79 (s, 6H) 2.46 (s, 3H) 2.35-2.43 (m, 4H). m/z (ESI, positive ion): 535.0 (M+H)$^+$.

Example 334

N-(5-(3-(4-amino-6-methyl-1,3,5-triazin-2-yl)-5-methoxypyridin-2-ylamino)-2-chloropyridin-3-yl)morpholine-4-sulfonamide

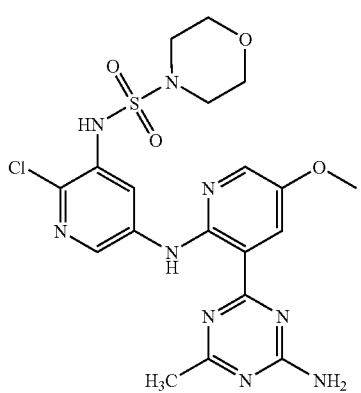 [SMILES: COc1cnc(Nc2cnc(Cl)c(NS(=O)(=O)N3CCOCC3)c2)c(-c2nc(C)nc(N)n2)c1]

Step 1. N-(2-chloro-5-(diphenylmethyleneamino)pyridin-3-yl)morpholine-4-sulfonamide To a 20 mL microwave reaction tube was added N-(5-bromo-2-chloropyridin-3-yl)morpholine-4-sulfonamide (Example 366, Step 3) 0.510 g, 1.43 mmol), xantphos (0.0839 g, 0.145 mmol), Pd$_2$dba$_3$ (0.0646 g, 0.071 mmol), NaOtBu (Aldrich, 0.418 g, 4.35 mmol) and diphenylmethanimine (Aldrich, 0.264 mL, 1.57 mmol) in DMF (6 mL). The mixture was degassed by bubbling argon through for 5 min. The tube was heated in a microwave reactor (Biotage) at 120° C. for 30 min. The reaction mixture was partitioned between saturated aqueous ammonium chloride (40 mL) and EtOAc (40 mL). The aqueous phase was extracted with EtOAc (2×40 mL). The combined organic phases were washed with water (80 mL) and saturated aqueous sodium chloride (80 mL). The organic phase was dried over sodium sulfate, filtered and concentrated in vacuo. The crude product was purified by silica gel column chromatography (100 g, eluent: EtOAc in hexanes 0% to 70%) to afford N-(2-chloro-5-(diphenylmethyleneamino)pyridin-3-yl)morpholine-4-sulfonamide in 2 fractions (total 0.42 g, 72% yield) as a yellow solid (0.26 g) and a light brown solid (0.21 g). $^1$H NMR (400 MHz, CDCl$_3$) δ ppm 7.73 (d, J=7.43 Hz, 2H) 7.62 (d, J=2.35 Hz, 1H) 7.49-7.55 (m, 1H) 7.43 (t, J=7.53 Hz, 2H) 7.31-7.37 (m, 4H) 7.11-7.16 (m, 2H) 6.63 (br. s., 1H) 3.60-3.65 (m, 4H) 3.03-3.09 (m, 4H).

Step 2. N-(5-amino-2-chloropyridin-3-yl)morpholine-4-sulfonamide

The two batches of N-(2-chloro-5-(diphenylmethyleneamino)pyridin-3-yl)morpholine-4-sulfonamide (total 0.47 g, 1.0 mmol) were placed in two 150 mL round-bottomed flasks. To each flask were added 1 N hydrochloric acid (0.6 mL each, total 1.2 mL) and 3 mL THF (3 mL each, total 6 mL). After stirring at room temperature for 10 min, the two reaction mixtures were combined and most of THF was removed in vacuo, and the residue was partitioned between saturated aqueous ammonium chloride (30 mL) and 25% isopropanol in chloroform (30 mL). The aqueous phase was extracted with 25% isopropanol in chloroform (2×20 mL). The combined organic phases were dried over sodium sulfate, filtered and concentrated in vacuo. The crude product was purified by silica gel column chromatography (25 g, eluent: iPrOH in CHCl$_3$ 0% to 10%) to afford N-(5-amino-2-chloropyridin-3-yl)morpholine-4-sulfonamide (0.233 g, 77% yield) as a light brown solid. $^1$H NMR (400 MHz, CDCl$_3$) δ ppm 7.64 (d, J=2.74 Hz, 1H) 7.30 (d, J=2.74 Hz, 1H) 6.68 (br. s., 1H) 3.83 (br. s., 2H) 3.66-3.71 (m, 4H) 3.22-3.27 (m, 4H). m/z (ESI, positive ion): 293.0 (M+H)$^+$.

Step 3. N-(5-(3-(4-amino-6-methyl-1,3,5-triazin-2-yl)-5-methoxypyridin-2-ylamino)-2-chloropyridin-3-yl)morpholine-4-sulfonamide To a stirred solution of N-(5-amino-2-chloropyridin-3-yl)morpholine-4-sulfonamide (0.0819 g, 0.280 mmol) and 4-(2-fluoro-5-methoxypyridin-3-yl)-6-methyl-1,3,5-triazin-2-amine (Example 330 step 5, 0.0621 g, 0.264 mmol) in DMF (1 mL) in 5 mL microwave vial, NaHMDS (Aldrich, 1 M in THF, 1.06 mL, 1.06 mmol) was added dropwise at 0° C. The mixture was stirred at 0° C. for 45 min. The reaction mixture was partitioned between saturated aqueous ammonium chloride (30 mL) and 25% isopropanol in chloroform (20 mL). The aqueous phase was acidified to pH 3 to 4 then extracted with 25% isopropanol in chloroform (2×30 mL). The combined organic phases were dried over sodium sulfate, filtered and concentrated in vacuo. The crude product was purified by preparative HPLC using a Phenomenex, Gemni 5 micron C18 100×30 mm column (1% to 90% CH$_3$CN w/0.1% TFA/H$_2$O w/0.1% TFA in 10 min). The fraction was collected and the solvent was evaporated to give a red solid. The solid was partitioned between tris-HCl buffer (1 M, pH 7.0) and 25% IPA in CHCl$_3$. The aqueous phase was acidified to pH about 3 then extracted with 25% IPA in CHCl$_3$. The combined organic phases were dried over sodium sulfate, filtered and concentrated in vacuo. This material was dissolved in about 1 mL DMSO and about 2 mL of water was added. The resulting solid was collected via filtration and washed with copious amount of water and dried to afford N-(5-(3-(4-amino-6-methyl-1,3,5-triazin-2-yl)-5-methoxypyridin-2-ylamino)-2-chloropyridin-3-yl)morpholine-4-sulfonamide (0.015 g, 11% yield) as a dark yellow solid. $^1$H NMR (400 MHz, DMSO-d$_6$) δ ppm 12.01 (br. s., 1H) 9.73 (br. s., 1H) 8.79 (br. s., 1H) 8.52 (br. s., 1H) 8.38-8.47 (m, 1H) 8.18 (br. s., 1H)

7.76-7.99 (m, 2H) 3.86 (br. s., 3H) 3.57-3.66 (m, 4H) 3.09-3.21 (m, 4H) 2.45 (br. s., 3H). m/z (ESI, positive ion): 508.0 (M+H)+.

Example 335

N-(5-(3-(4-amino-6-methyl-1,3,5-triazin-2-yl)-5-(2-methoxyethoxy)pyridin-2-ylamino)-2-chloropyridin-3-yl)methanesulfonamide

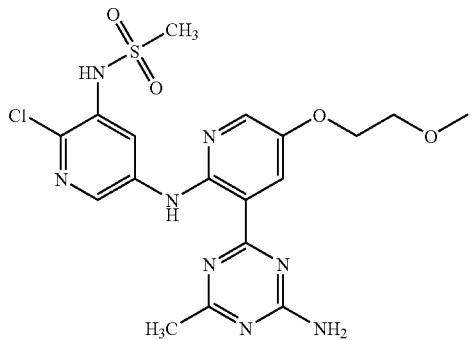 [SMILES: COCCOc1cnc(Nc2cnc(Cl)c(NS(C)(=O)=O)c2)c(-c2nc(C)nc(N)n2)c1]

Step 1. 2-fluoro-5-(2-methoxyethoxy)pyridine

To a 20 mL microwave vial, 6-fluoropyridin-3-ol (Alfa Aesar, 1.04 g, 9.24 mmol), 2-bromoethyl methyl ether (Aldrich, 1.04 mL, 11.1 mmol) and potassium carbonate (1.97 g, 14.2 mmol) were mixed into DMF (8 mL). The suspention was stirred at 45° C. for 1 h. The temperature was raised to 55° C. for 45 min. 2-Bromoethyl methyl ether (0.50 mL) was added and the mixture was stirred at 40° C. for overnight. The reaction mixture was poured into about 50 mL water and the aqueous phase was extracted with diethyl ether (2×40 mL). The aqueous phase was saturated with solid NaCl and extracted with diethyl ether (2×40 mL). The combined organic phases were washed with saturated aqueous sodium bicarbonate (2×50 mL). The organic phase was dried over sodium sulfate, filtered and concentrated in vacuo. The light brown oil was placed under an air stream for 30 min to remove residual ether to afford 2-fluoro-5-(2-methoxyethoxy)pyridine (1.64 g, 100% yield) as an amber oil. $^1$H NMR (400 MHz, CDCl$_3$) δ ppm 7.84-7.87 (m, 1H) 7.37 (ddd, J=9.05, 6.21, 3.13 Hz, 1H) 6.85 (dd, J=8.80, 3.52 Hz, 1H) 4.13-4.17 (m, 2H) 3.74-3.78 (m, 2H) 3.45 (s, 3H). m/z (ESI, positive ion): 172.1 (M+H)+.

Step 2.
2-fluoro-5-(2-methoxyethoxy)pyridin-3-ylboronic acid

To a stirred solution of diisopropylamine (Aldrich, 3.03 mL, 21.2 mmol) in THF (30 mL) in 250 mL round-bottomed flask, nBuLi (Aldrich, 2.5 M in hexanes, 8.12 mL, 20.3 mmol) was added slowly at 0° C. The mixture was stirred at 0° C. for 30 min. The mixture was cooled to −78° C. and 2-fluoro-5-(2-methoxyethoxy)pyridine (1.58 g, 9.23 mmol) in a total of 5 mL THF was added slowly. The orange mixture was stirred at that temperature for 30 min then triisopropyl borate (Aldrich, 4.72 mL, 20.3 mmol) in a total of 5 mL of THF was added slowly. The mixture was stirred at −78° C. for 10 min, then the cold bath was removed and the mixture was stirred at room temperature for 1 h. 1N NaOH (about 70 mL) was added and the layers were separated. The aqueous phase was washed with EtOAc (50 mL) and acidified to about pH 5 with 5 N HCl. The aq phase was extracted with EtOAc (4×50 mL). The combined organic phases were washed with saturated aqueous sodium chloride (50 mL). The organic phase was dried over sodium sulfate, filtered and concentrated in vacuo to afford 2-fluoro-5-(2-methoxyethoxy)pyridin-3-ylboronic acid (1.76 g, 89% yield) as a pale yellow residue. This material was used without further purification.

Step 3. 4-(2-fluoro-5-(2-methoxyethoxy)pyridin-3-yl)-6-methyl-1,3,5-triazin-2-amine To a 20 mL microwave reaction tube was added 2-fluoro-5-(2-methoxyethoxy)pyridin-3-ylboronic acid (1.06 g, 4.95 mmol), 4-chloro-6-methyl-1,3,5-triazin-2-amine (Example 9, 0.508 g, 3.51 mmol), Am-Phos (Aldrich, 0.125 g, 0.176 mmol) and potassium acetate (Aldrich, 1.04 g, 10.6 mmol) in EtOH (10 mL) and water (1 mL). The mixture was degassed by bubbling argon through for 5 min. The tube was heated in a microwave reactor (Biotage) at 100° C. for 20 min. The reaction mixture was partitioned between water (50 mL) and EtOAc (50 mL). The aqueous phase was extracted with EtOAc (2×50 mL) and 10% IPA in CHCl$_3$ (3×50 mL). The combined organic phases were dried over sodium sulfate, filtered and concentrated in vacuo. The residue was treated with DCM and the resulting solid was collected to afford 4-(2-fluoro-5-(2-methoxyethoxy)pyridin-3-yl)-6-methyl-1,3,5-triazin-2-amine (0.234 g) as an off-white solid. The filtrate was concentrated and purified by silica gel column chromatography (100 g, eluent: iPrOH in CHCl$_3$ 0% to 12.5%) to afford additional material (0.399 g) as a pale yellow solid. Total yield was 0.632 g, 64%. $^1$H NMR (400 MHz, CDCl$_3$) δ ppm 8.14 (dd, J=7.63, 3.13 Hz, 1H) 8.01 (dd, J=2.93, 1.76 Hz, 1H) 5.56 (br. s., 2H) 4.19-4.27 (m, 2H) 3.75-3.81 (m, 2H) 3.46 (s, 3H) 2.53 (s, 3H).

Step 4. N-(5-(3-(4-amino-6-methyl-1,3,5-triazin-2-yl)-5-(2-methoxyethoxy)pyridin-2-ylamino)-2-chloropyridin-3-yl)methanesulfonamide To a stirred mixture of 4-(2-fluoro-5-(2-methoxyethoxy)pyridin-3-yl)-6-methyl-1,3,5-triazin-2-amine (0.105 g, 0.376 mmol) and N-(5-amino-2-chloropyridin-3-yl)methanesulfonamide (Example 330 step 2, 0.0977 g, 0.441 mmol) in DMF (1 mL) in 5 mL microwave vial, NaHMDS (Aldrich, 1 M in THF, 1.20 mL, 1.20 mmol) was added slowly at 0° C. The dark brown mixture was stirred at 0° C. for 30 min. Additional NaHMDS (0.5 mL) was added at 0° C. and the stirring was continued at 0° C. for 30 min. The reaction mixture was poured into 30 mL of sat'd NH$_4$Cl and stirred for 30 min. The resulting yellow solid was collected via filtration and washed with copious amount of water and air-dried to afford N-(5-(3-(4-amino-6-methyl-1,3,5-triazin-2-yl)-5-(2-methoxyethoxy)pyridin-2-ylamino)-2-chloropyridin-3-yl)methanesulfonamide (0.120 g, 66% yield) as a yellow solid. $^1$H NMR (400 MHz, DMSO-d$_6$) δ ppm 11.96 (s, 1H) 9.62 (s, 1H) 8.61 (d, J=19.95 Hz, 2H) 8.44 (d, J=2.74 Hz, 1H) 8.21 (d, J=2.54 Hz, 1H) 7.75-8.01 (m, 2H) 4.12-4.27 (m, 2H) 3.69 (d, J=4.30 Hz, 2H) 3.33 (br. s., 3H) 3.13 (s, 3H) 2.45 (s, 3H). m/z (ESI, positive ion): 481.0 (M+H)+.

Example 336

N-(5-(3-(4-amino-6-methyl-1,3,5-triazin-2-yl)-5-(2-methoxyethoxy)pyridin-2-ylamino)-2-methoxypyridin-3-yl)methanesulfonamide

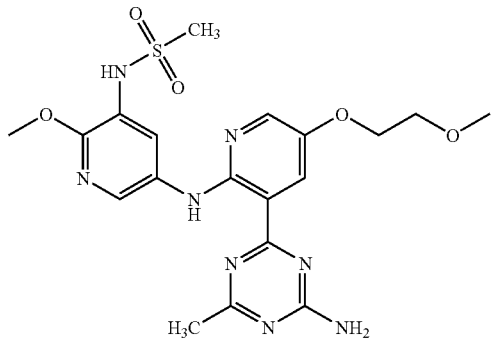

To a 5 mL microwave vial, 4-(2-fluoro-5-(2-methoxyethoxy)pyridin-3-yl)-6-methyl-1,3,5-triazin-2-amine (Example 335 step 3, 0.0647 g, 0.232 mmol) and N-(5-amino-2-methoxypyridin-3-yl)methanesulfonamide (Example 329 step 4, 0.0636 g, 0.293 mmol) were mixed into DMF (1 mL). NaHMDS (Aldrich, 1 M in THF, 0.95 mL, 0.95 mmol) was added dropwise at 0° C. The dark red mixture was stirred at 0° C. for 30 min. Buffer (pH 5.0, citric acid/NaOH) (10 mL) was added and the mixture was stirred for 30 min. The resulting solid was collected via filtration and washed with MeOH to give 0.0414 g of brown solid. The filtrate was concentrated and purified by silica gel column chromatography (25 g, eluent: iPrOH in CHCl$_3$ 2.5% to 12.5%) to afford 0.0122 g of dark orange solid. The previous brown solid and this material were combined and taken into methanol and sonicated. Evaporation of MeOH afforded N-(5-(3-(4-amino-6-methyl-1,3,5-triazin-2-yl)-5-(2-methoxyethoxy)pyridin-2-ylamino)-2-methoxypyridin-3-yl)methanesulfonamide (0.0366 g, 33% yield) as a brown solid.

$^1$H NMR (400 MHz, DMSO-d$_6$) δ ppm 11.53 (s, 1H) 9.18 (s, 1H) 8.41 (d, J=3.13 Hz, 1H) 8.32 (d, J=2.35 Hz, 1H) 8.17 (d, J=2.54 Hz, 1H) 8.13 (d, J=3.13 Hz, 1H) 7.66-7.92 (m, 2H) 4.15 (dd, J=5.28, 3.72 Hz, 2H) 3.90 (s, 3H) 3.67 (dd, J=5.18, 3.81 Hz, 2H) 3.31-3.32 (m, 3H) 3.05 (s, 3H) 2.44 (s, 3H). m/z (ESI, positive ion): 476.9 (M+H)+.

Example 337

N-(5-(3-(4-amino-6-methyl-1,3,5-triazin-2-yl)-5-(morpholinomethyl)pyridin-2-ylamino)-2-methoxypyridin-3-yl)methanesulfonamide

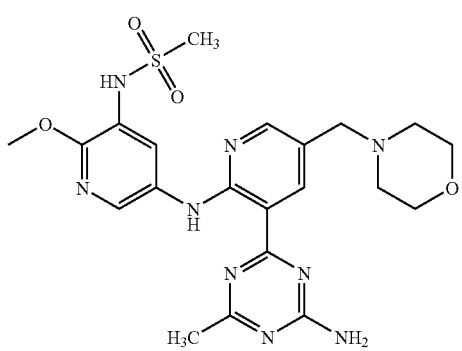 [SMILES: COc1ncc(Nc2ncc(CN3CCOCC3)cc2-c2nc(C)nc(N)n2)cc1NS(C)(=O)=O]

To a 5 mL microwave vial, 4-(2-fluoro-5-(morpholinomethyl)pyridin-3-yl)-6-methyl-1,3,5-triazin-2-amine (Example 332, step 1, 0.0684 g, 0.225 mmol) and N-(5-amino-2-methoxypyridin-3-yl)methanesulfonamide (Example 330 step 4, 0.0584 g, 0.269 mmol) were mixed into DMF (1 mL). NaHMDS (Aldrich, 1 M in THF, 0.90 mL, 0.90 mmol) was added dropwise at 0° C. The dark red mixture was stirred at 0° C. for 30 min. Buffer (pH 5.0, citric acid/NaOH) (10 mL) was added and the mixture was stirred at 0° C. for 30 min. The resulting solid was collected via filtration and washed with water. The filtrate was extracted with 10% isopropanol in chloroform (2×20 mL). The combined organic phases were dried over sodium sulfate, filtered and concentrated in vacuo to afford 0.0902 g of yellow solid. This material and the previously collected solid were combined and washed with DCM and MeOH then was purified by preparative HPLC using a Phenomenex, Gemni 5 micron C18 100×30 mm column (1% to 90% CH$_3$CN w/0.1% TFA/H$_2$O w/0.1% TFA in 20 min). The fractions were collected and concentrated. To the residue, buffer (pH 5.0, citric acid/NaOH) (about 2 to 3 mL) was added, then pH 7 buffer was added to bring the pH close to 6. The resulting solid was collected via filtration and washed with copious amount of water, then dried in a vaccum oven overnight to afford N-(5-(3-(4-amino-6-methyl-1,3,5-triazin-2-yl)-5-(morpholinomethyl)pyridin-2-ylamino)-2-methoxypyridin-3-yl)methanesulfonamide (0.0734 g, 65% yield) as a yellow solid. $^1$H NMR (400 MHz, DMSO-d$_6$) δ ppm 11.90 (s, 1H) 9.26 (s, 1H) 8.89 (s, 1H) 8.43 (br. s., 1H) 8.32 (d, J=2.35 Hz, 1H) 8.23 (d, J=2.35 Hz, 1H) 7.91 (br. s., 1H) 7.81 (br. s., 1H) 4.36 (br. s., 2H) 3.94-4.01 (m, 2H) 3.93 (s, 3H) 3.67 (br. s., 2H) 3.26-3.30 (m, 2H) 3.11 (br. s., 2H) 3.05 (s, 3H) 2.44 (s, 3H). m/z (ESI, positive ion): 502.0 (M+H)+.

Example 338

N-(2-chloro-5-(3-(2-methyl-9H-purin-6-yl)pyridin-2-ylamino)pyridin-3-yl)methanesulfonamide

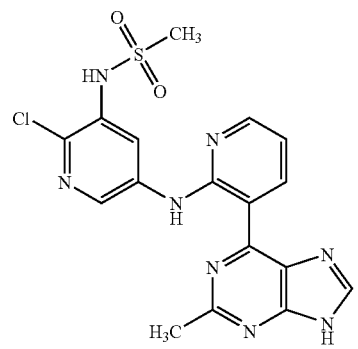 [SMILES: Cc1nc(-c2cccnc2Nc2cnc(Cl)c(NS(C)(=O)=O)c2)c2nc[nH]c2n1]

To a stirred solution of 6-(2-fluoropyridin-3-yl)-2-methyl-9-(tetrahydro-2H-pyran-2-yl)-9H-purine (Example 4, 0.0895 g, 0.286 mmol) and N-(5-amino-2-chloropyridin-3-yl)methanesulfonamide (Example 330, Step 2, 0.0772 g, 0.348 mmol) in THF (1 mL) in 5 mL microwave vial, LiHMDS (1.14 mL, 1.14 mmol) was added dropwise at 0° C. The dark red mixture was stirred at 0° C. for 30 min. The reaction was quenched by adding saturated aqueous sodium chloride (0.2 mL). The reaction mixture was partitioned between buffer (pH 5.0, citric acid/NaOH) (30 mL) and EtOAc (30 mL). The aqueous phase was extracted with EtOAc (30 mL). The combined organic phases were washed with water (40 mL) and saturated aqueous sodium chloride (40 mL). The organic phase was dried over sodium sulfate, filtered and concentrated in vacuo. The residue was taken into THF (5 mL) and 5 N HCl (1 mL) was added. The yellow mixture was stirred at room temperature for 30 min. The reaction mixture was concentrated and the crude product was purified by preparative HPLC using a Phenomenex, Gemni 5 micron C18 100×30 mm column (1% to 90% CH$_3$CN w/0.1% TFA/H$_2$O w/0.1% TFA in 10 min). The pure fractions were collected and lyophilized to afford N-(2-chloro-5-(3-(2-methyl-9H-purin-6-yl)pyridin-2-ylamino)pyridin-3-yl)methanesulfonamide (TFA salt, 0.0185 g, 11% yield) as an orange solid. $^1$H NMR (400 MHz, DMSO-d$_6$) δ ppm 13.12 (br. s., 1H) 9.79 (d, J=7.63 Hz, 1H) 9.67 (s, 1H) 8.74 (d, J=2.54 Hz, 1H) 8.63 (s, 1H) 8.50 (d, J=2.54 Hz, 1H) 8.41 (dd, J=4.69, 1.96 Hz, 1H) 7.14 (dd, J=7.92, 4.79 Hz, 1H) 3.13-3.18 (m, 3H) 2.86-2.90 (m, 3H). Note: one proton was missing from the NMR spectrum. m/z (ESI, positive ion): 430.9 (M+H)$^+$ as parent ion.

Example 339

N-(2-chloro-5-(3-(2-methyl-9H-purin-6-yl)-5-(1-morpholinoethyl)pyridin-2-ylamino)pyridin-3-yl)methanesulfonamide

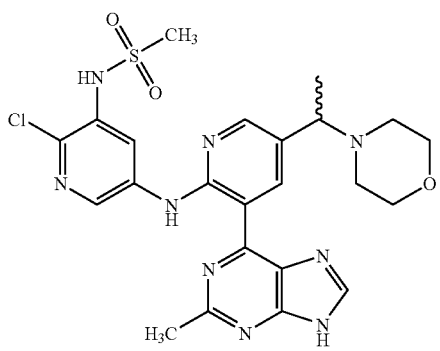 [SMILES: Cc1nc(-c2cc(C(C)N3CCOCC3)cnc2Nc2cnc(Cl)c(NS(C)(=O)=O)c2)c2nc[nH]c2n1]

Step 1. 1-(6-fluoropyridin-3-yl)ethanol

To a stirred mixture of 6-fluoronicotinaldehyde (Frontier Science, 3.14 g, 25.1 mmol) in THF (40 mL) in 250 mL round-bottomed flask, methylmagnesium bromide (Aldrich, 3 M in diethyl ether, 9.21 mL, 27.6 mmol) was added dropwise at about 5 to 10° C. The mixture was stirred at about 5° C. for 30 min. A mixture of water (30 mL) and saturated aqueous ammonium chloride (30 mL) was added slowly and EtOAc (20 mL) was added. The layers were separated. The aqueous phase was extracted with EtOAc (2×60 mL). The combined organic phases were dried over sodium sulfate, filtered and concentrated in vacuo. The crude product was purified by silica gel column chromatography (100 g, eluent: EtOAc in hexanes 20% to 70%) to afford (2.30 g, 65% yield) as a clear oil. $^1$H NMR (400 MHz, CDCl$_3$) δ ppm 8.19 (d, J=1.76 Hz, 1H) 7.85 (td, J=8.07, 2.45 Hz, 1H) 6.92 (dd, J=8.41, 2.93 Hz, 1H) 4.94-5.02 (m, 1H) 2.00 (d, J=3.72 Hz, 1H) 1.53 (d, J=6.46 Hz, 3H). m/z (ESI, positive ion): 142.1 (M+H)$^+$.

Step 2. 4-(1-(6-fluoropyridin-3-yl)ethyl)morpholine

To a stirred solution of 1-(6-fluoropyridin-3-yl)ethanol (2.30 g, 16.3 mmol) and Et$_3$N (4.52 mL, 32.6 mmol) in DCM (50 mL) in 500 mL round-bottomed flask, methanesulfonyl chloride (Aldrich, 1.30 mL, 16.8 mmol) was added dropwise at 0° C. The mixture was stirred at 0° C. for 30 min. Water (50 mL) was added and the layers were separated. The aqueous phase was extracted with DCM (2×30 mL). The combined organic phases were dried over sodium sulfate, filtered and concentrated in vacuo to afford cloudy viscous pale yellow oil. To this intermediate, DCM (40 mL), Et$_3$N (9 mL) and morpholine (5.68 mL, 65.2 mmol) were added and the mixture was stirred at room temperature overnight. THF (5 mL) was added and the stirring was resumed. After overnight stirring, water (60 mL) was added and the layers were separated. The aqueous phase was extracted with EtOAc (2×60 mL). The combined organic phases were dried over sodium sulfate, filtered and concentrated in vacuo. The crude product was purified by silica gel column chromatography (100 g, eluent: iPrOH in CHCl$_3$ 0% to 5%) to give 4-(1-(6-fluoropyridin-3-yl)ethyl)morpholine (2.92 g, 85% yield) as a pale yellow oil. $^1$H NMR (400 MHz, chloroFORM-d) δ ppm 8.12 (s, 1H) 7.79 (td, J=8.12, 2.35 Hz, 1H) 6.90 (dd, J=8.41, 2.93 Hz, 1H) 3.68 (t, J=4.60 Hz, 4H) 3.36-3.44 (m, 1H) 2.44-2.56 (m, 2H) 2.30-2.40 (m, 2H) 1.35 (d, J=6.65 Hz, 3H). m/z (ESI, positive ion): 211.1 (M+H)$^+$.

Step 3. 4-(1-(6-fluoro-5-(4,4,5,5-tetramethyl-1,3,2-dioxaborolan-2-yl)pyridin-3-yl)ethyl)morpholine To a stirred solution of diisopropylamine (Aldrich, redistilled, 99.95%, 0.813 mL, 5.80 mmol) in THF (10 mL) in 150 mL round-bottomed flask, nBuLi (Aldrich, 2.5 M in hexanes, 2.32 mL, 5.80 mmol) was added dropwise at 0° C. The mixture was stirred at 0° C. for 30 min. The mixture was cooled to −78° C. and 4-(1-(6-fluoropyridin-3-yl)ethyl)morpholine (1.02 g, 4.84 mmol) in a total of 3 mL of THF was added dropwise. The mixture was stirred at −78° C. for 45 min. Triisopropyl borate (Aldrich, 1.39 mL, 6.04 mmol) in a total of 3 mL THF was added dropwise at that temperature, then the cold bath was removed. The mixture was stirred at room temperature for 1 h 20 min. Pinacol (0.773 g, 6.54 mmol) in a total of 5 mL THF was added at once and the mixture was stirred at room temperature for 10 min. Acetic acid (0.291 mL, 5.08 mmol) in a total of 3 mL THF was added at once and the mixture was stirred at room temperature for 2 h. The mixture was filtered through a pad of Celite® (diatomaceous earth), and extracted with 1 N NaOH (2×50 mL). The aqueous phase was treated with 4 N HCl until a pH of about 6 to 7 while an ice-water bath was applied, then extracted with EtOAc (3×50 mL). The combined organic phases were dried over sodium sulfate, filtered and concentrated in vacuo to afford crude 4-(1-(6-fluoro-5-(4,4,5,5-tetramethyl-1,3,2-dioxaborolan-2-yl)pyridin-3-yl)ethyl)morpholine (1.22 g, 75% yield) as a light brown viscous oil. This material was used in the next reaction without further purification.

Step 4. 4-(1-(6-fluoro-5-(2-methyl-9-(tetrahydro-2H-pyran-2-yl)-9H-purin-6-yl)pyridin-3-yl)ethyl)morpholine To a 5 mL microwave reaction tube was added 4-(1-(6-fluoro-5-(4,4,5,5-tetramethyl-1,3,2-dioxaborolan-2-yl)pyridin-3-yl)ethyl)morpholine (0.523 g, 1.55 mmol), 6-chloro-2-methyl-9-(tetrahydro-2H-pyran-2-yl)-9H-purine (Example 3, 0.322 g, 1.28 mmol), Am-Phos (Aldrich, 0.0531 g, 0.075 mmol) and potassium acetate (Aldrich, 0.379 g, 3.87 mmol) in 1,4-dioxane (4 mL) and water (0.4 mL). The mixture was degassed by bubbling argon through for 5 min. The tube was heated in a microwave reactor (Biotage) at 100° C. for 15 min. The reaction mixture was partitioned between water (40 mL) and EtOAc (40 mL). The layers were separated and saturated $NH_4Cl$ (30 mL) was added to the aqueous phase. The aqueous phase was extracted with EtOAc (2×40 mL). The combined organic phases were washed with saturated aqueous sodium chloride (100 mL). The organic phase was dried over sodium sulfate, filtered and concentrated in vacuo. The crude product was purified by silica gel column chromatography (50 g, eluent: EtOAc in hexanes 20% to 70% then IPA/$CHCl_3$ 0% to 12.5%) to afford 4-(1-(6-fluoro-5-(2-methyl-9-(tetrahydro-2H-pyran-2-yl)-9H-purin-6-yl)pyridin-3-yl)ethyl)morpholine (0.30 g, 55% yield) as an off-white solid. $^1$H NMR (400 MHz, $CDCl_3$) δ ppm 8.27-8.37 (m, 3H) 5.86 (d, J=10.37 Hz, 1H) 4.15-4.24 (m, 1H) 3.78-3.88 (m, 1H) 3.64-3.75 (m, 4H) 3.53 (q, J=6.72 Hz, 1H) 2.89 (s, 3H) 2.50-2.60 (m, 2H) 2.38-2.48 (m, 2H) 2.01-2.22 (m, 3H) 1.69-1.91 (m, 3H) 1.43 (d, J=6.65 Hz, 3H). m/z (ESI, positive ion): 427.1 (M+H)$^+$.

Step 5. N-(2-chloro-5-(3-(2-methyl-9-(tetrahydro-2H-pyran-2-yl)-9H-purin-6-yl)-5-(1-morpholinoethyl)pyridin-2-ylamino)pyridin-3-yl)methanesulfonamide To a stirred solution of 4-(1-(6-fluoro-5-(2-methyl-9-(tetrahydro-2H-pyran-2-yl)-9H-purin-6-yl)pyridin-3-yl)ethyl)morpholine (0.157 g, 0.368 mmol) and N-(5-amino-2-chloropyridin-3-yl)methanesulfonamide (Example 330 step 2, 0.103 g, 0.462 mmol) in THF (2 mL) in 20 mL microwave vial, NaHMDS (Aldrich, 1 M in THF, 1.47 mL, 1.47 mmol) was added dropwise at 0° C. The dark red mixture was stirred at 0° C. for 30 min. The mixture was partitioned between a mixture of saturated aqueous sodium chloride (10 mL)/buffer (pH 5.0, citric acid/NaOH) (10 mL) and EtOAc (20 mL). The aqueous phase was extracted with EtOAc (2×20 mL). The combined organic phases were dried over sodium sulfate, filtered and concentrated in vacuo. The crude product was purified by silica gel column chromatography (50 g, eluent: iPrOH in $CHCl_3$ 0% to 10%) to afford N-(2-chloro-5-(3-(2-methyl-9-(tetrahydro-2H-pyran-2-yl)-9H-purin-6-yl)-5-(1-morpholinoethyl)pyridin-2-ylamino)pyridin-3-yl)methanesulfonamide (0.169 g, 73% yield) as a yellow solid. $^1$H NMR (400 MHz, $CDCl_3$) δ ppm 13.18 (s, 1H) 9.78 (d, J=1.96 Hz, 1H) 8.83 (d, J=2.54 Hz, 1H) 8.63 (d, J=2.54 Hz, 1H) 8.36 (d, J=2.35 Hz, 1H) 8.31 (s, 1H) 6.76 (br. s., 1H) 5.85-5.90 (m, 1H) 4.17-4.24 (m, 1H) 3.79-3.88 (m, 1H) 3.73 (t, J=4.50 Hz, 4H) 3.51-3.59 (m, 1H) 3.14 (s, 3H) 2.94 (s, 3H) 2.45-2.62 (m, 4H) 2.01-2.22 (m, 3H) 1.66-1.93 (m, 3H) 1.48 (d, J=6.65 Hz, 3H). m/z (ESI, positive ion): 628.0 (M+H)$^+$.

Step 6. N-(2-chloro-5-(3-(2-methyl-9H-purin-6-yl)-5-(1-morpholinoethyl)pyridin-2-ylamino)pyridin-3-yl)methanesulfonamide To a 20 mL scintillation vial, N-(2-chloro-5-(3-(2-methyl-9-(tetrahydro-2H-pyran-2-yl)-9H-purin-6-yl)-5-(1-morpholinoethyl)pyridin-2-ylamino)pyridin-3-yl)methanesulfonamide (0.165 g, 0.263 mmol) and 5 N hydrochloric acid (0.5 mL, 2.5 mmol) were mixed into THF (3 mL). The solution was stirred at room temperature for 30 min. 10 mL of buffer (pH 5, citric acid/NaOH) was added and the pH was further adjusted to about 5 by adding a few drops of 6 N NaOH. The aqueous phase was extracted with 10% isopropanol in chloroform (3×20 mL). The combined organic phases were dried over sodium sulfate, filtered and concentrated in vacuo. The crude product was purified by preparative HPLC using a Phenomenex, Gemni 5 micron C18 100×30 mm column (1% to 90% $CH_3CN$ w/0.1% TFA/$H_2O$ w/0.1% TFA in 10 min). The corresponding fractions were collected and concentrated down to dryness. The residue was treated with about 5 mL of pH 5 buffer and pH 7 buffer were added to adjust pH to about 6. The aqueous phase was extracted with 10% isopropanol in chloroform (3×20 mL). The combined organic phases were dried over sodium sulfate, filtered and concentrated in vacuo to afford 0.101 g of yellow solid. $^1$H NMR (400 MHz, DMSO-$d_6$) δ ppm 13.65 (br. s., 1H) 13.11 (br. s., 1H) 9.82 (br. s., 1H) 9.68 (br. s., 1H) 8.71 (d, J=1.96 Hz, 1H) 8.66 (s, 1H) 8.53 (s, 1H) 8.34 (d, J=1.17 Hz, 1H) 3.50-3.67 (m, 5H) 3.15 (s, 3H) 2.88 (s, 3H) 2.35-2.46 (m, 2H) 1.42 (d, J=6.65 Hz, 3H). Note: 2 protons were buried under DMSO peak and could not be integrated. m/z (ESI, positive ion): 544.0 (M+H)$^+$.

Example 340

N'-(2-chloro-5-((3-(2-methyl-9H-purin-6-yl)-5-(1-(4-morpholinyl)ethyl)-2-pyridinyl)amino)-3-pyridinyl)-N,N-dimethylsulfamide

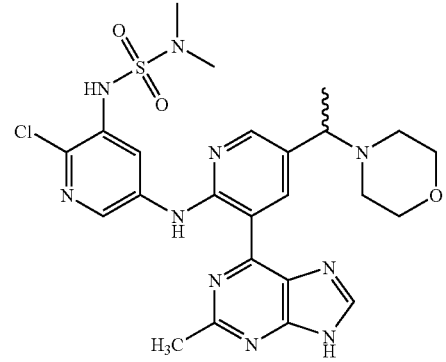 [SMILES: Cc1nc(-c2cc(C(C)N3CCOCC3)cnc2Nc2cnc(Cl)c(NS(=O)(=O)N(C)C)c2)c2nc[nH]c2n1]

Step 1. N'-(2-chloro-5-((3-(2-methyl-9-(tetrahydro-2H-pyran-2-yl)-9H-purin-6-yl)-5-(1-(4-morpholinyl)ethyl)-2-PYRID INYL)amino)-3-pyridinyl)-N,N-dimethylsulfamide To a stirred solution of 4-(1-(6-fluoro-5-(2-methyl-9-(tetrahydro-2H-pyran-2-yl)-9H-purin-6-yl)pyridin-3-yl)ethyl)morpholine (Example 339 step 4, 0.0475 g, 0.111 mmol) and N'-(5-amino-2-chloro-3-pyridinyl)-N,N-dimethylsulfamide (Example 384, Step 2 0.0380 g, 0.152 mmol) in THF (1 mL) in 20 mL scintillation vial, NaHMDS (Aldrich, 1 M in THF, 0.445 mL, 0.445 mmol) was added dropwise at 0° C. The dark red mixture was stirred at 0° C. for 30 min. The reaction mixture was partitioned between buffer (pH 5.0, citric acid/NaOH) (20 mL) and EtOAc (20 mL) resulted in having insoluble materials. The biphase mixture was filtered and the solid was collected and washed with water to afford N'-(2-chloro-543-(2-methyl-9-(tetrahydro-2H-pyran-2-yl)-9H-purin-6-yl)-5-(1-(4-morpholinyl)ethyl)-2-pyridinyl)amino)-3-pyridinyl)-N,N-dimethylsulfamide (0.0472 g, 65% yield) as a yellow solid. $^1$H NMR (400 MHz, chloroFORM-d) δ ppm 13.12 (s, 1H) 9.76 (s, 1H) 8.86 (d, J=2.35 Hz, 1H) 8.50 (d, J=1.96 Hz, 1H) 8.32 (s, 2H) 6.79 (br. s., 1H) 5.87 (d, J=8.22 Hz, 1H) 4.16-4.26 (m, 1H) 3.79-3.90 (m, 1H) 3.73 (br. s., 4H) 3.55 (br. s., 1H) 2.87-3.04 (m, 9H) 2.50 (br. s., 4H) 1.98-2.21 (m, 3H) 1.69-1.92 (m, 3H) 1.48 (d, J=6.46 Hz, 3H). m/z (ESI, positive ion): 657.0 (M+H)$^+$.

Step 2. N'-(2-chloro-5-((3-(2-methyl-9H-purin-6-yl)-5-(1-(4-morpholinyl)ethyl)-2-pyridinyl)amino)-3-pyridinyl)-N,N-dimethylsulfamide To a 20 mL scintillation vial, N'-(2-chloro-5-((3-(2-methyl-9-(tetrahydro-2H-pyran-2-yl)-9H-purin-6-yl)-5-(1-(4-morpholinyl)ethyl)-2-pyridinyl)amino)-3-pyridinyl)-N,N-dimethylsulfamide (0.047 g, 0.072 mmol) and 5 N hydrochloric acid (0.5 mL, 2.5 mmol) were mixed into THF (2 mL). The solution was stirred at room temperature for 30 min. Buffer (pH 5, citric acid/NaOH) (10 mL) was added and the pH was further adjusted to about 5 using a few drops of 6 N NaOH. The aqueous phase was extracted with 10% isopropanol in chloroform (2×20 mL). The combined organic phases were dried over sodium sulfate, filtered and concentrated in vacuo to afford N'-(2-chloro-5-((3-(2-methyl-9H-purin-6-yl)-5-(1-(4-morpholinyl)ethyl)-2-pyridinyl)amino)-3-pyridinyl)-N,N-dimethylsulfamide (0.0237 g, 58% yield) as a yellow powder. $^1$H NMR (400 MHz, chloroFORM-d) δ ppm 13.10 (s, 1H) 11.17 (br. s., 1H) 9.81 (br. s., 1H) 8.86 (d, J=2.15 Hz, 1H) 8.51 (d, J=2.35 Hz, 1H) 8.34 (d, J=1.37 Hz, 1H) 8.22 (s, 1H) 6.81 (br. s., 1H) 3.74 (br. s., 4H) 3.56 (d, J=6.65 Hz, 1H) 2.96 (s, 9H) 2.44-2.66 (m, 4H) 1.50 (d, J=6.65 Hz, 3H). m/z (ESI, positive ion): 573.0 (M+H)$^+$.

Example 341

(R)-4-(2-(6-chloro-5-methoxypyridin-3-ylamino)-5-(1-(4-(methylsulfonyl)piperazin-1-yl)ethyl)pyridin-3-yl)-6-methyl-1,3,5-triazin-2-amine

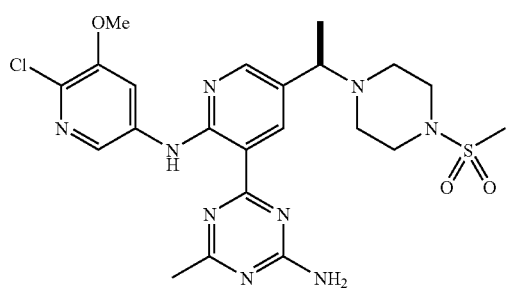 [SMILES: COc1cc(Nc2ncc([C@@H](C)N3CCN(S(C)(=O)=O)CC3)cc2-c2nc(C)nc(N)n2)cnc1Cl]

Step 1. (R)-4-(2-(6-chloro-5-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine At 0° C., a solution of (R)-4-(2-fluoro-5-(1-(4-(methylsulfonyl)piperazin-1-yl)ethyl)pyridin-3-yl)-N,N-bis(4-methoxybenzyl)-6-methyl-1,3,5-triazin-2-amine (Example 146, Step 6) (155 mg, 0.244 mmol) and 6-chloro-5-methoxypyridin-3-amine (Small Molecules, Inc) (77 mg, 0.488 mmol) in 1 mL of THF was treated with sodium bis(trimethylsilyl)amide (0.853 mL of 1.0 M solution in THF, 0.853 mmol) and the dark red solution was stirred at that temperature for 1 h. It was quenched with 4 mL of saturated aqueous ammonium chloride solution and extracted with EtOAc (2×20 mL). The combined organic phases were washed with brine (10 mL), dried over sodium sulfate, filtered and concentrated. The residue was loaded on a silica gel column and eluted with 50-100% EtOAc in DCM to give the title compound (140 mg, 74% yield) as an orange amorphous solid. $^1$H NMR (400 MHz, DMSO-d6) δ ppm 12.11 (s, 1H), 8.70 (d, J=2.40 Hz, 1H), 8.37 (d, J=2.30 Hz, 1H), 8.18 (dd, J=8.8, 2.40 Hz, 2H), 7.28 (m, 4H), 6.90 (m, 4H), 4.85-4.81 (m, 4H), 3.87 (s, 3H), 3.74 (s, 3H), 3.70 (s, 3H), 3.60 (m, 1H), 3.04 (m, 4H), 2.78 (s, 3H), 2.59 (s, 3H), 2.47 (m, 4H), 1.34 (m, 3H). m/z (ESI, positive ion) 774.9 (M+H)$^+$.

Step 2. (R)-4-(2-(6-chloro-5-methoxypyridin-3-ylamino)-5-(1-(4-(methylsulfonyl)piperazin-1-yl)ethyl)pyridin-3-yl)-6-methyl-1,3,5-triazin-2-amine A solution of (R)-4-(2-(6-chloro-5-methoxypyridin-3-ylamino)-5-(1-(4-(methylsulfonyl)piperazin-1-yl)ethyl)pyridin-3-yl)-N,N-bis(4-methoxybenzyl)-6-methyl-1,3,5-triazin-2-amine (130 mg, 0.168 mmol) in 3 mL of TFA was treated with 0.1 mL of trifluoromethanesulfonic acid. It was heated in an oil bath at 80° C. for 3 h. The dark solution was concentrated and the residue was treated with ice cube followed by 0.5 N NaOH until the pH was about 8. The mixture was extracted with 2×30 mL of EtOAc followed by 2×15 mL of DCM. The combined organic solution was dried and concentrated. The residue was loaded on a silica gel column and eluted with 1 to 10% MeOH in DCM to give (R)-4-(2-(6-chloro-5-methoxypyridin-3-ylamino)-5-(1-(4-(methylsulfonyl)piperazin-1-yl)ethyl)pyridin-3-yl)-6-methyl-1,3,5-triazin-2-amine (70 mg, 78% yield) as a yellow crystalline solid. $^1$H NMR (400 MHz, DMSO-d6) δ ppm 12.22 (s, 1H), 8.74 (d, J=2.4 Hz, 1H), 8.44 (d, J=2.2 Hz, 1H), 8.36 (dd, J=10.4, 2.2 Hz, 2H), 7.95 (br., 1H), 7.83 (br., 1H), 3.94 (s, 3H), 3.60 (m, 1H), 3.09 (m, 4H), 2.86 (s, 3H), 2.46 (s, 3H), 2.44 (m, 4H), 1.36 (d, J=6.7 Hz, 3H). m/z (ESI, positive ion) 534.2 (M+H)$^+$.

Example 342

2-(5-(4-amino-6-methyl-1,3,5-triazin-2-yl)-6-(6-chloro-5-methoxypyridin-3-ylamino)pyridin-3-yl)propan-2-ol

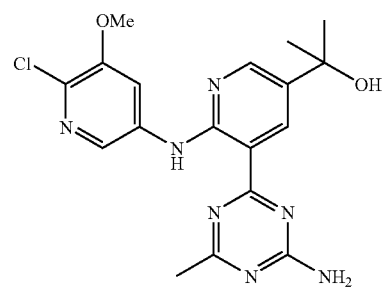 [SMILES: COc1cc(Nc2ncc(C(C)(C)O)cc2-c2nc(C)nc(N)n2)cnc1Cl]

Step 1. 4-(5-(1-ethoxyvinyl)-2-fluoropyridin-3-yl)-6-methyl-1,3,5-triazin-2-amine A mixture of 4-(5-chloro-2-fluoropyridin-3-yl)-6-methyl-1,3,5-triazin-2-amine (273 mg, 1.14 mmol), X-Phos (50 mg, 0.11 mmol), diacetoxypalladium (24 mg, 0.11 mmol), cesium fluoride (519 mg, 3.42 mmol) and tributyl(1-ethoxyvinyl) stannane (0.54 mL, 1.60 mmol) in 1,4-dioxane (4 mL) and DMF (1 mL) was heated in a microwave at 120° C. for 1 h. The reaction mixture was passed through a short path of a neutral alumina column, eluted with 50 mL of DCM followed by 150 mL of EtOAc. The fractions containing the desired mass [m/z (ESI, positive ion) 276.0 (M+H)⁺] were collected and concentrated to give the title compound (203 mg, 64.7% yield) as an off white crystalline solid. ¹H NMR (400 MHz, DMSO-d₆) δ ppm 8.60 (2 H, m), 7.67 (2 H, m), 4.93 (1 H, d, J=3.1 Hz), 4.67 (1 H, d, J=3.1 Hz), 3.95 (2H, m), 2.38 (3 H, s), 1.11 (3 H, m). m/z (ESI, positive ion) 276.0 (M+H)⁺.

Step 2. 1-(5-(4-amino-6-methyl-1,3,5-triazin-2-yl)-6-(6-chloro-5-methoxypyridin-3-ylamino)pyridin-3-yl)ethanone To a mixture of 4-(5-(1-ethoxyvinyl)-2-fluoropyridin-3-yl)-6-methyl-1,3,5-triazin-2-amine (100 mg, 0.363 mmol) and 6-chloro-5-methoxypyridin-3-amine (Small Molecules, Inc) (86 mg, 0.545 mmol) in 1 mL of THF and 0.3 mL of DMF at 0° C. was added sodium bis(trimethylsilyl)amide (1.09 mL of 1.0 M solution in THF, 1.09 mmol) dropwise and the dark red solution was stirred at this temperature for 30 min. It was quenched with 4 mL of 0.5 N HCl and stirred at RT for 10 min. The mixture was treated with 1 N NaOH to pH of about 8. It was extracted twice with EtOAc (30 mL). The combined organic phases were washed with brine and dried over Na₂SO₄. It was concentrated to half of its volume, the precipitated tan solid was filtered through a fritted funnel, rinsed with 2 mL of ether, collected and dried to give 1-(5-(4-amino-6-methyl-1,3,5-triazin-2-yl)-6-(6-chloro-5-methoxypyridin-3-ylamino)pyridin-3-yl)ethanone (90 mg, 64% yield). ¹H NMR (400 MHz, DMSO-d6) δ ppm 12.63 (s, 1H), 9.29 (s, 1H), 9.03 (s, 1H), 8.47 (s, 1H), 8.30 (s, 1H), 8.06 (br., 1H), 7.90 (br., 1H), 3.96 (s, 3H), 2.60 (s, 3H), 2.47 (s, 3H). m/z (ESI, positive ion) 386.0 (M+H)⁺.

Step 3. 2-(5-(4-amino-6-methyl-1,3,5-triazin-2-yl)-6-(6-chloro-5-methoxypyridin-3-ylamino)pyridin-3-yl)propan-2-ol A solution of 1-(5-(4-amino-6-methyl-1,3,5-triazin-2-yl)-6-(6-chloro-5-methoxypyridin-3-ylamino)pyridin-3-yl)ethanone (85 mg, 0.220 mmol) in 2 mL of THF at 0° C. was treated with methylmagnesium bromide (0.73 mL of 3.0 M solution in ether, 2.20 mmol) and stirred at this temperature for 15 min. It was quenched with ice cold saturated NH₄Cl solution and extracted twice with EtOAc. The combined organic solution was concentrated and the residue was purified on a silica gel column and eluted with 50 to 100% EtOAc in DCM to give the title compound (23 mg, 26% yield) as a yellow crystalline solid. ¹H NMR (400 MHz, DMSO-d₆) δ ppm 12.19 (br., 1H), 8.97 (d, J=2.6 Hz, 1H), 8.50 (d, J=2.6 Hz, 1H), 8.44 (d, J=2.3 Hz, 1H), 8.37 (d, J=2.4 Hz, 1H), 7.95 (s, 1H), 7.80 (s, 1H), 5.21 (s, 1H), 3.94 (s, 3H), 2.47 (s, 3H), 1.49 (s, 6H). m/z (ESI, positive ion) 402.0 (M+H)⁺.

Example 343

4-(5-(3,6-dihydro-2H-pyran-4-yl)-2-(5-fluoro-6-methoxypyridin-3-ylamino)pyridin-3-yl)-6-methyl-1,3,5-triazin-2-amine

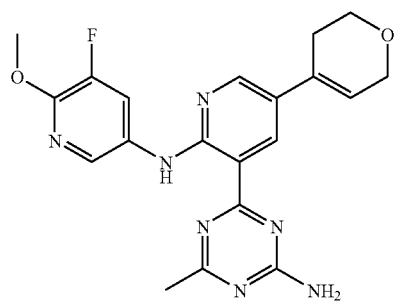 [SMILES: COc1ncc(Nc2ncc(C3=CCOCC3)cc2-c2nc(C)nc(N)n2)cc1F]

Step 1. 4-(5-(3,6-dihydro-2H-pyran-4-yl)-2-fluoropyridin-3-yl)-N,N-bis(4-methoxybenzyl)-6-methyl-1,3,5-triazin-2-amine A mixture of 4-(5-chloro-2-fluoropyridin-3-yl)-N,N-bis(4-methoxybenzyl)-6-methyl-1,3,5-triazin-2-amine (2.0 g, 4.17 mmol), 2-(3,6-dihydro-2H-pyran-4-yl)-4,4,5,5-tetramethyl-1,3,2-dioxaborolane (Frontier Scientific) (1.051 g, 5.00 mmol), Pd₂(dba)₃ (0.191 g, 0.208 mmol), dicyclohexyl(2',4',6'-triisopropylbiphenyl-2-yl)phosphine (0.199 g, 0.417 mmol) and 2 N Na₂CO₃ (5.21 mL, 10.42 mmol) in 10 mL of dioxane was heated in a microwave at 130° C. for 30 min. The reaction mixture was partitioned between 10 mL of 0.5 N NaOH and 50 mL of EtOAc. The organic layer was separated and washed with brine, dried and concentrated. The residue was purified on a silica gel column and eluted with 25 to 75% EtOAc in hexanes to give the title compound (1.19 g, 54% yield) as an off white crystalline solid. ¹H NMR (400 MHz, DMSO-d6) δ ppm 8.51-8.47 (m, 2H), 7.24 (t, J=9.2 Hz, 4H), 6.90 (m, 4H), 6.38 (m, 1H), 4.78 (s, 2H), 4.76 (s, 2H), 4.24 (d, J=2.7 Hz, 2H), 3.84 (m, 2H), 3.74 (s, 3H), 3.72 (s, 3H), 2.51 (m, 2H), 2.47 (s, 3H). m/z (ESI, positive ion) 528.0 (M+H)⁺.

Step 2. 4-(5-(3,6-dihydro-2H-pyran-4-yl)-2-(5-fluoro-6-methoxypyridin-3-ylamino)pyridin-3-yl)-N,N-bis(4-methoxybenzyl)-6-methyl-1,3,5-triazin-2-amine A mixture of 4-(5-(3,6-dihydro-2H-pyran-4-yl)-2-fluoropyridin-3-yl)-N,N-bis(4-methoxybenzyl)-6-methyl-1,3,5-triazin-2-amine (191 mg, 0.362 mmol) and 6-fluoro-5-methoxypyridin-3-amine (77 mg, 0.543 mmol) in 1.5 mL of THF at 0° C. was treated with sodium bis(trimethylsilyl)amide (0.90 mL of 1.0 M solution in tetrahydrofuran, 0.90 mmol) and stirred at this temperature for 15 min. It was quenched with 4 mL of saturated aqueous ammonium chloride solution and extracted with EtOAc (2×20 mL). The combined organic phases were washed with brine (10 mL), dried over sodium sulfate, filtered and concentrated. The residue was loaded on a silica gel column and eluted with 50-100% EtOAc in DCM to give the title compound (167 mg, 71.0% yield) as an orange amorphous solid. ¹H NMR (400 MHz, DMSO-d6) δ ppm 11.73 (s, 1H), 8.70 (d, J=2.5 Hz, 1H), 8.46 (d, J=2.3 Hz, 1H), 8.10 (m, 2H), 7.30 (d, J=8.6 Hz, 2H), 7.21 (d, J=8.4 Hz, 2H), 6.91 (d, J=8.6 Hz, 2H), 6.85 (d, J=8.6 Hz, 2H), 6.18 (s, 1H), 4.87 (s, 2H), 4.80 (s, 2H), 4.21 (m, 2H), 3.92 (s, 3H), 3.82 (m, 2H), 3.74 (s, 3H), 3.69 (s, 3H), 2.57 (s, 3H), 2.40 (m, 2H). m/z (ESI, positive ion) 650.3 (M+H)+.

Step 3. 4-(5-(3,6-dihydro-2H-pyran-4-yl)-2-(5-fluoro-6-methoxypyridin-3-ylamino)pyridin-3-yl)-6-methyl-1,3,5-triazin-2-amine A solution of 4-(5-(3,6-dihydro-2H-pyran-4-yl)-2-(5-fluoro-6-methoxypyridin-3-ylamino)pyridin-3-yl)-N,N-bis(4-methoxybenzyl)-6-methyl-1,3,5-triazin-2-amine (140 mg, 0.215 mmol) in 3 mL of TFA was treated with 0.15 mL of trifluoromethanesulfonic acid and heated at 80° C. in an oil bath for 3 h. It was concentrated and the dark residue was stirred in 15 mL of EtOAc then treated with 5 mL of 1 N NaOH. The aqueous layer was extracted with 2×10 mL of DCM. The combined EtOAc extracts and DCM extracts were concentrated. The residue was purified on a silica gel column and eluted with 35-100% EtOAc in DCM to give 4-(5-(3,6-dihydro-2H-pyran-4-yl)-2-(5-fluoro-6-methoxypyridin-3-ylamino)pyridin-3-yl)-6-methyl-1,3,5-triazin-2-amine (70 mg, 79% yield) as a yellow crystalline solid. 1H NMR (400 MHz, DMSO-d6) δ ppm 11.95 (s, 1H), 8.85 (d, J=2.6 Hz, 1H), 8.49 (d, J=2.5 Hz, 1H), 8.41-8.35 (m, 2H), 7.91 (br., 1H), 7.76 (br., 1H), 6.24 (m, 1H), 4.24 (m, 2H), 3.94 (s, 3H), 3.84 (m, 2H), 2.45 (s, 5H). m/z (ESI, positive ion) 410.0 (M+H)+.

Example 344

4-(2-(5-fluoro-6-methoxypyridin-3-ylamino)-5-(tetrahydro-2H-pyran-4-yl)pyridin-3-yl)-6-methyl-1,3,5-triazin-2-amine

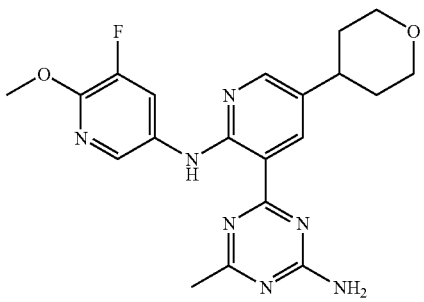 [SMILES: COc1ncc(Nc2ncc(C3CCOCC3)cc2-c2nc(C)nc(N)n2)cc1F]

Step 1. 4-(2-fluoro-5-(tetrahydro-2H-pyran-4-yl)pyridin-3-yl)-N,N-bis(4-methoxybenzyl)-6-methyl-1,3,5-triazin-2-amine A solution of 4-(5-(3,6-dihydro-2H-pyran-4-yl)-2-fluoropyridin-3-yl)-N,N-bis(4-methoxybenzyl)-6-methyl-1,3,5-triazin-2-amine (300 mg, 0.569 mmol) in 5 mL of EtOH and 5 mL of EtOAc was placed with palladium hydroxide (20% wt.) (80 mg, 0.114 mmol) and hydrogenated with a balloon full of hydrogen. After 18 h, the mixture was filtered through a pad of Celite® (diatomaceous earth) and rinsed with 2×10 mL of EtOAc. The filtrate was concentrated and the residue was purified on a silica gel column and eluted with 20-65% EtOAc in hexanes to provide 4-(2-fluoro-5-(tetrahydro-2H-pyran-4-yl)pyridin-3-yl)-N,N-bis(4-methoxybenzyl)-6-methyl-1,3,5-triazin-2-amine (230 mg, 76% yield) as an off white amorphous solid. 1H NMR (400 MHz, DMSO-d6) δ ppm 8.36 (dd, J=9.4, 1.6 Hz, 1H), 8.30 (d, J=1.9 Hz, 1H), 7.24 (m, 4H), 6.90 (m, 4H), 4.79 (s, 2H), 4.75 (s, 2H), 3.94 (m, 2H), 3.74 (s, 3H), 3.72 (s, 3H), 3.45 (m, 2H), 2.95 (m, 1H), 2.47 (s, 3H), 1.70 (m, 4H). m/z (ESI, positiive ion) 530.3 (M+H)+.

Step 2. 4-(2-(5-fluoro-6-methoxypyridin-3-ylamino)-5-(tetrahydro-2H-pyran-4-yl)pyridin-3-yl)-N,N-bis(4-methoxybenzyl)-6-methyl-1,3,5-triazin-2-amine A mixture of 4-(2-fluoro-5-(tetrahydro-2H-pyran-4-yl)pyridin-3-yl)-N,N-bis(4-methoxybenzyl)-6-methyl-1,3,5-triazin-2-amine (210 mg, 0.397 mmol) and 5-fluoro-6-methoxypyridin-3-amine (85 mg, 0.595 mmol) in 1.5 mL of THF at 0° C. was treated with sodium bis(trimethylsilyl)amide (0.99 mL of 1.0 M solution in tetrahydrofuran, 0.99 mmol). It was stirred at this temperature for 15 min, then quenched with sat NH4Cl (5 mL) and extracted with 2×10 mL of EtOAc. The combined organic solution was dried with sodium sulfate and concentrated. The residue was purified on a silica gel column and eluted with 10-30% EtOAc in DCM to give the title compound (220 mg, 85% yield) as a brown amorphous solid. 1H NMR (400 MHz, DMSO-d6) δ ppm 11.65 (s, 1H), 8.56 (d, J=2.6 Hz, 1H), 8.26 (d, J=2.4 Hz, 1H), 8.07 (m, 2H), 7.29 (d, J=8.6 Hz, 2H), 7.22 (d, J=8.4 Hz, 2H), 6.91 (d, J=8.6 Hz, 2H), 6.85 (d, J=8.6 Hz, 2H), 4.87 (s, 2H), 4.80 (s, 2H), 3.96 (m, 2H), 3.91 (s, 3H), 3.74 (s, 3H), 3.69 (s, 3H), 3.45 (m, 2H), 2.78 (m, 1H), 2.57 (s, 3H), 1.67 (m, 4H). m/z (ESI, positive ion) 652.0 (M+H)+.

Step 3. 4-(2-(5-fluoro-6-methoxypyridin-3-ylamino)-5-(tetrahydro-2H-pyran-4-yl)pyridin-3-yl)-N,N-bis(4-methoxybenzyl)-6-methyl-1,3,5-triazin-2-amine A solution of 4-(2-(5-fluoro-6-methoxypyridin-3-ylamino)-5-(tetrahydro-2H-pyran-4-yl)pyridin-3-yl)-N,N-bis(4-methoxybenzyl)-6-methyl-1,3,5-triazin-2-amine (210 mg, 0.322 mmol) in 3 mL of TFA was treated with 0.15 mL of triflic acid and heated at 80° C. in an oil bath for 3 h. It was concentrated and the residue was cooled with an ice bath, treated with 5 mL of 1 N NaOH. The precipitated brown solid was filtered, rinsed with 3×3 mL of water, followed 3×10 mL of EtOAc. The brown solid was collected and dried in a vacuum oven at 50° C. for 24 h to afford the title compound (120 mg, 91% yield). 1H NMR (400 MHz, DMSO-d6) δ ppm 11.86 (s, 1H), 8.70 (s, 1H), 8.45-8.30 (m, 3H), 7.88 (br., 1H), 7.74 (br., 1H), 3.95 (m, 2H), 3.93 (s, 3H), 3.47 (m, 2H), 2.81 (m, 1H), 2.46 (s, 3H), 1.72 (m, 4H). m/z (ESI, positive ion) 412.1 (M+H)+.

Example 345

2-(5-(6-amino-2-methylpyrimidin-4-yl)-6-(5-fluoro-6-methoxypyridin-3-ylamino)pyridin-3-yl)propan-2-ol

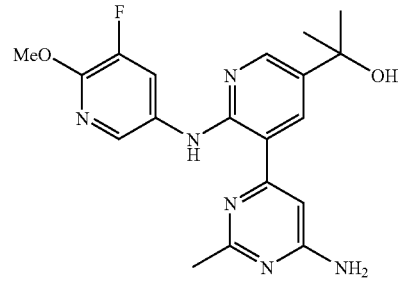 [SMILES: COc1ncc(Nc2ncc(C(C)(C)O)cc2-c2cc(N)nc(C)n2)cc1F]

Step 1. 6-(5-chloro-2-fluoropyridin-3-yl)-2-methylpyrimidin-4-amine

A mixture of 6-chloro-2-methylpyrimidin-4-amine (1.03 g, 7.17 mmol) (SynChem Inc,), 5-chloro-2-fluoropyridin-3-ylboronic acid (1.572 g, 8.97 mmol) (Combi-Blocks Inc.), PdCl$_2$AmPhos (0.254 g, 0.359 mmol) and potassium acetate (2.11 g, 21.52 mmol) in 8 mL of dioxane, 1 mL of EtOH and 4 mL of water in a sealed glass tube was heated in a microwave at 105° C. for 45 min. Crude liquid chromatography/mass spectropscopy indicated the reaction was not completed. To the reaction mixture was added 83 mg of Pd(PPh$_3$)$_4$, 300 mg of 5-chloro-2-fluoropyridin-3-ylboronic acid and 0.3 mL of 2 N Na$_2$CO$_3$. It was heated in a microwave at 115° C. for 20 min. The precipitated yellow solid was filtered, washed with 3 mL of 1 N NaOH, followed by 3 mL of water and 5 mL of EtOAc. The yellow crystalline solid was dried in a vacuum oven at 45° C. for 18 h to provide 6-(5-chloro-2-fluoropyridin-3-yl)-2-methylpyrimidin-4-amine (1.18 g, 68% yield). $^1$H NMR (400 MHz, DMSO-d6) δ ppm 8.59 (dd, J=8.4, 2.7 Hz, 1H), 8.40 (m, 1H), 7.08 (br, 2H), 6.82 (d, J=1.8 Hz, 1H), 2.40 (s, 3H). m/z (ESI, positive ion) 238.9 (M+H)$^+$.

Step 2. 6-(5-(1-ethoxyvinyl)-2-fluoropyridin-3-yl)-2-methylpyrimidin-4-amine To a 5 mL microwave reaction tube was added 6-(5-chloro-2-fluoropyridin-3-yl)-2-methylpyrimidin-4-amine (227 mg, 0.95 mmol), palladium acetate (10 mg, 0.048 mmol), X-phos (40 mg, 0.09 mmol), cesium fluoride (433 mg, 2.85 mmol) and tributyl(1-ethoxyvinyl)stannane (0.45 mL, 1.33 mmol) in 1,4-dioxane (4 mL) and DMF (1 mL). The glass tube was sealed and heated in a microwave at 120° C. for 1 h. The reaction mixture was passed through a short path of neutral alumina column, eluted with 50 mL of DCM followed by 150 mL of EtOAc and 50 mL of 5% MeOH in EtOAc. The desired fractions were collected, concentrated to give 6-(5-(1-ethoxyvinyl)-2-fluoropyridin-3-yl)-2-methylpyrimidin-4-amine (208 mg, 80% yield) as an off white crystalline solid. m/z (ESI, positive ion) 275.1 (M+H)$^+$.

Step 3. 1-(5-(6-amino-2-methylpyrimidin-4-yl)-6-(5-fluoro-6-methoxypyridin-3-ylamino)pyridin-3-yl)ethanone A mixture of 6-(5-(1-ethoxyvinyl)-2-fluoropyridin-3-yl)-2-methylpyrimidin-4-amine (208 mg, 0.76 mmol) and 5-fluoro-6-methoxypyridin-3-amine (162 mg, 1.14 mmol) in 1.5 mL of THF at 0° C. was added sodium bis(trimethylsilyl)amide (1 M in THF) (2.28 mL, 2.28 mmol) dropwise at 0° C. and the dark red solution was stirred at this temperature for 30 min. It was quenched with 4 mL of 0.5 N HCl and stirred for 10 min. The mixture was basified with 1 N NaOH to pH of 8 and stirred with 10 mL of EtOAc for 5 min. The precipitated brown solid was filtered, washed with 2×2 mL of water followed by 2×2 mL of EtOAc. The brown solid was dried in a vacuum oven at 45° C. for 18 h to give 1-(5-(6-amino-2-methylpyrimidin-4-yl)-6-(5-fluoro-6-methoxypyridin-3-ylamino)pyridin-3-yl)ethanone (90 mg, 32% yield). $^1$H NMR (400 MHz, DMSO-d6) δ ppm 12.93 (s, 1H), 8.90 (s, 1H), 8.50 (s, 1H), 8.37 (s, 1H), 8.24 (s, 1H), 7.10 (br., 2H), 6.93 (s, 1H), 3.95 (s, 3H), 2.60 (s, 3H), 1.58 (s, 3H). m/z (ESI, positive ion) 369.0 (M+H)$^+$.

Step 4. 2-(5-(6-amino-2-methylpyrimidin-4-yl)-6-(5-fluoro-6-methoxypyridin-3-ylamino)pyridin-3-yl)propan-2-ol A suspension of 1-(5-(6-amino-2-methylpyrimidin-4-yl)-6-(5-fluoro-6-methoxypyridin-3-ylamino)pyridin-3-yl)ethanone (88 mg, 0.24 mmol) in 2 mL of THF at 0° C. was treated with methylmagnesium bromide (0.55 mL of 3.0 M solution in diethyl ether, 1.67 mmol). It was stirred at 0° C. for 15 min, and quenched with 5 mL of sat. NH$_4$Cl. The mixture was extracted with 2×15 mL of EtOAc. The organic extracts were dried and concentrated. The crude material was purified on a silica gel column and eluted with 20-70% EtOAc in DCM to give 2-(5-(6-amino-2-methylpyrimidin-4-yl)-6-(5-fluoro-6-methoxypyridin-3-ylamino)pyridin-3-yl)propan-2-ol (58 mg, 63% yield) as a yellow crystalline solid. $^1$H NMR (400 MHz, DMSO-d$_6$) δ ppm 12.23 (s, 1H), 8.35 (m, 1H), 8.32 (d, J=2.2 Hz, 1H), 8.17 (m, 2H), 7.02 (br, 2H), 6.03 (s, 1H), 5.18 (s, 1H), 3.92 (s, 3H), 2.47 (s, 3H), 1.48 (s, 6H). m/z (ESI, positive ion) 385.2 (M+H)$^+$.

Example 346

2-(5-(4-amino-6-methyl-1,3,5-triazin-2-yl)-6-(5-fluoro-6-methoxypyridin-3-ylamino)pyridin-3-yl)-2-methylpropanoic acid

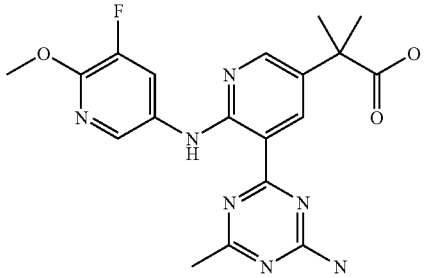 [SMILES: COc1ncc(Nc2ncc(C(C)(C)C(=O)O)cc2-c2nc(C)nc(N)n2)cc1F]

Step 1. 2-(5-bromo-2-fluoropyridin-3-yl)-6-methyl-1,3,6,2-dioxazaborocane-4,8-dione 5-Bromo-2-fluoropyridin-3-ylboronic acid (14.87 g, 67.7 mmol) (Frontier Scientific) and 2,2'-(methylazanediyl)diacetic acid (10.95 g, 74.4 mmol) (Aldrich) were dissolved in toluene (242 mL) and DMSO (97 mL) and the resulting mixture was heated at reflux under a Dean Stark trap for 2 h. After water (>2.5 mL) was collected in the trap, the reaction mixture was concentrated in vacuo to remove toluene, and water was slowly added to the resulting solution until the desired product precipitated as a white solid. This solid was collected by vacuum filtration, washed with water, and dried in a vacuum oven to give the title compound (82% yield) as a fluffy white solid. m/z (ESI, +ve ion) 330.8/332.9 (M+H)$^+$.

Step 2 tert-butyl 2-(6-fluoro-5-(6-methyl-4,8-dioxo-1,3,6,2-dioxazaborocan-2-yl)pyridin-3-yl)acetate To 2-(5-bromo-2-fluoropyridin-3-yl)-6-methyl-1,3,6,2-dioxazaborocane-4,8-dione (2.79 g, 8.43 mmol) was added dioxane (84 mL), bis-(di-tert-butyl(4-dimethylaminophenyl)phosphine)dichloropalladium(II) (0.299 g, 0.422 mmol) and (2-tert-butoxy-2-oxoethyl)zinc(II) chloride in ether (25.3 mL, 12.65 mmol) (Rieke Metals), and the resulting mixture was sparged with nitrogen for 5 min at ambient temperature. The reaction mixture was then heated to 80° C. for 2 h. The reaction mixture was subsequently cooled to ambient temperature, adsorbed onto silica gel, and purified via flash chromatography (silica gel) with 100% DCM to 5% MeOH/DCM to give the title compound (62% yield) as a beige solid. m/z (ESI, +ve ion) 367.2 (M+H)$^+$.

Step 3. tert-butyl 2-(5-(4-(bis(4-methoxybenzyl) amino)-6-methyl-1,3,5-triazin-2-yl)-6-fluoropyridin-3-yl)acetate To 4-chloro-N,N-bis(4-methoxybenzyl)-6-methyl-1,3,5-triazin-2-amine (0.783 g, 2.035 mmol) (Example 51), tert-butyl 2-(6-fluoro-5-(6-methyl-4,8-dioxo-1,3,6,2-dioxazaborocan-2-yl)pyridin-3-yl)acetate (1.49 g, 4.07 mmol), and bis-(di-tert-butyl(4-dimethylaminophenyl)phosphine) dichloropalladium(II) (0.072 g, 0.102 mmol) was added dioxane (20 mL) and potassium carbonate in water (3.05 mL, 6.10 mmol), and the resulting mixture was heated at 80° C. for 1 h. The reaction mixture was then added to a separatory funnel and partitioned between EtOAc (100 mL) and sodium bicarbonate (saturated, aqueous). The organic layer was separated, washed 2 times with 75 mL of sodium bicarbonate (saturated, aqueous), dried over sodium sulfate, filtered, and concentrated in vacuo. Chromatographic purification of the residue (silica gel; 0% to 40% EtOAc/hexanes) gave the title compound (37% yield). m/z (ESI, +ve ion) 560.4 (M+H)$^+$.

Step 4. tert-butyl 2-(5-(4-(bis(4-methoxybenzyl) amino)-6-methyl-1,3,5-triazin-2-yl)-6-fluoropyridin-3-yl)-2-methylpropanoate A solution of tert-butyl 2-(5-(4-(bis(4-methoxybenzyl) amino)-6-methyl-1,3,5-triazin-2-yl)-6-fluoropyridin-3-yl) acetate (430 mg, 0.768 mmol) in tetrahydrofuran (7.6 mL) was cooled to −78° C., and LiHMDS in THF (845 µL, 0.845 mmol) was added. After stirring the resulting solution at −78° C. for 30 min, the reaction mixture was allowed to warm to ambient temperature. The reaction solution was then again cooled to −78° C., and iodomethane in THF (1.0 M; 768 µL, 0.768 mmol) was added. The resulting mixture was stirred at −78° C. for 6 h to effect the first methyl addition (confirmed by LCMS monitoring). The reaction mixture was diluted with 100 mL of EtOAc, added to a separatory funnel, partitioned with sodium bicarbonate (saturated, aqueous), washed 2 times with 50 mL of sodium bicarbonate (saturated, aqueous), separated, dried over sodium sulfate, and concentrated in vacuo to give the mono-methyl addition product. This material was then dissolved in tetrahydrofuran (7.6 mL) and cooled to −78° C. LiHMDS in THF (1.0 M, Aldrich; 845 µL, 0.845 mmol) was added, and the resulting mixture was stirred for 30 min before iodomethane in THF (1.0 M; 768 µL, 0.768 mmol) was added. The resulting mixture was stirred at −78° C. for 6 h, and the reaction mixture was then diluted with 150 mL of EtOAc, added to a separatory funnel, partitioned with sodium bicarbonate (saturated, aqueous), washed 2 times with 50 mL of sodium bicarbonate (saturated, aqueous), separated, dried over sodium sulfate, and concentrated in vacuo. Chromaographic purification of the residue (silica gel) with 100% hexanes to 50% EtOAc/hexanes to give the title compound (41% yield). m/z (ESI, +ve ion) 588.4 (M+H)$^+$.

Step 5. tert-butyl 2-(5-(4-(bis(4-methoxybenzyl) amino)-6-methyl-1,3,5-triazin-2-yl)-6-(5-fluoro-6-methoxypyridin-3-ylamino)pyridin-3-yl)-2-methylpropanoate Tert-butyl 2-(5-(4-(bis(4-methoxybenzyl)amino)-6-methyl-1,3,5-triazin-2-yl)-6-fluoropyridin-3-yl)-2-methylpropanoate (185 mg, 0.315 mmol) and 5-fluoro-6-methoxypyridin-3-amine (Aldrich; 67.1 mg, 0.472 mmol) were dissolved in tetrahydrofuran (3.1 mL) and the resulting mixture was cooled to −60° C. and sodium bis(trimethylsilyl)amide, 1 M in THF (Aldrich; 944 µL, 0.944 mmol) was added. The resulting mixture was stirred at −60° C. for 1 h, and the reaction mixture was then diluted with 100 mL of EtOAc, added to a separatory funnel, partitioned with sodium bicarbonate (saturated, aqueous), washed 2 times with 50 mL of sodium bicarbonate (saturated, aqueous), separated, dried over sodium sulfate, and concentrated in vacuo. Chromatographic purification of the residue (silica gel) with 100% hexanes to 50% EtOAc/hexanes to give the title compound (11% yield) as a yellow oil. m/z (ESI, +ve) 709.8 (M+H)$^+$.

Step 6. 2-(5-(4-amino-6-methyl-1,3,5-triazin-2-yl)-6-(5-fluoro-6-methoxypyridin-3-ylamino)pyridin-3-yl)-2-methylpropanoic acid Tert-butyl 2-(5-(4-(bis(4-methoxybenzyl)amino)-6-methyl-1,3,5-triazin-2-yl)-6-(5-fluoro-6-methoxypyridin-3-ylamino)pyridin-3-yl)-2-methylpropanoate (25 mg, 0.035 mmol) was dissolved in TFA (344 µL), trifluoromethanesulfonic acid (15.48 mg, 0.103 mmol) was added, and the resulting mixture was stirred at 80° C. for 4 h. The reaction mixture was subsequently concentrated in vacuo and the residue was taken up in 100 mL of EtOAc, added to a separatory funnel, partitioned with sodium bicarbonate (saturated, aqueous), washed 2 times with 50 mL of sodium bicarbonate (saturated, aqueous), separated, dried over sodium sulfate, filtered, and concentrated in vacuo. Chromatographic purification of the residue (silica gel, 0% to 100% EtOAc/hexanes) gave impure product which was further purified by preparatory TLC (2 plates; silica gel). TLC plates were loaded with the impure material and eluted in 10% MeOH/DCM to give the title compound (70% yield) following extraction of the product-containing bands with methanol, filtration, and concentration in vacuo. $^1$H NMR (400 MHz, d$_4$-MeOH) δ 9.00 (d, J=2.74 Hz, 1H) 8.58 (s, 1H) 8.39 (d, J=2.54 Hz, 1H) 8.16-8.24 (m, 2H) 4.01 (s, 3H) 2.52 (s, 3H) 1.59 (s, 6H). m/z (ESI, +ve) 414.0 (M+H)$^+$. m/z (ESI, +ve ion) 414.0 (M+H)$^+$.

Example 347

1-(5-(4-amino-6-methyl-1,3,5-triazin-2-yl)-6-(5-fluoro-6-methoxypyridin-3-ylamino)pyridin-3-yl)-2-methylpropane-1,2-diol

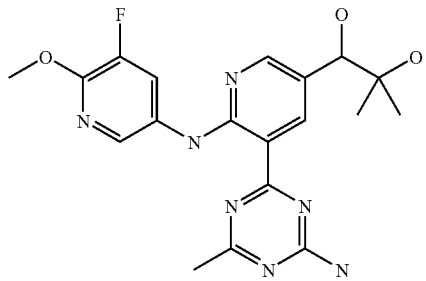 [SMILES: COc1ncc(Nc2ncc(C(O)C(C)(C)O)cc2-c2nc(C)nc(N)n2)cc1F]

Step 1. 4-(5-chloro-2-(5-fluoro-6-methoxypyridin-3-ylamino)pyridin-3-yl)-6-methyl-1,3,5-triazin-2-amine 4-(5-chloro-2-(5-fluoro-6-methoxypyridin-3-ylamino)pyridin-3-yl)-N,N-bis(4-methoxybenzyl)-6-methyl-1,3,5-triazin-2-amine (1.35 g, 2.242 mmol) (Example 313, Step 2) was dissolved in TFA (22 mL), trifluoromethanesulfonic acid (0.587 mL, 6.73 mmol) was added, and the resulting mixture was stirred at 80° C. for 2 h. The reaction mixture was then concentrated, and the residue was taken up in 400 mL of EtOAc, added to a separatory funnel, partitioned with sodium bicarbonate (saturated, aqueous), washed 4 times with 150 mL of sodium bicarbonate (saturated, aqueous), separated, and concentrated via rotovap to give the title compound as an insoluble yellow solid which was used without further purification. m/z (ESI, +ve ion) 362.0 (M+H)$^+$.

Step 2. 4-(2-(5-fluoro-6-methoxypyridin-3-ylamino)-5-(2-methylprop-1-enyl)pyridin-3-yl)-6-methyl-1,3,5-triazin-2-amine To 4-(5-chloro-2-(5-fluoro-6-methoxypyridin-3-ylamino)pyridin-3-yl)-6-methyl-1,3,5-triazin-2-amine (0.85 g, 2.350 mmol) was added dioxane (23.50 mL), potassium carbonate in water (3.52 mL, 7.05 mmol), 4,4,5,5-tetramethyl-2-(2-methylprop-1-enyl)-1,3,2-dioxaborolane (0.723 mL, 3.52 mmol) (Frontier Scientific), and bis-(di-tert-butyl(4-dimethylaminophenyl)phosphine)dichloropalladium(II) (Aldrich; 0.083 g, 0.117 mmol). The resulting mixture was sparged with nitrogen and then stirred at 80° C. for 16 h. The reaction mixture was subsequently diluted with 150 mL of EtOAc, added to a separatory funnel, partitioned with sodium bicarbonate (saturated, aqueous), washed 2 times with 150 mL of sodium bicarbonate (saturated, aqueous), separated, dried over sodium sulfate, and concentrated in vacuo. Chromatographic purification of the residue (silica gel, 0% to 100% EtOAc/hexanes) gave the title compound (88% yield) as a yellow solid. m/z (ESI, +ve ion) 382.2 (M+H)$^+$.

Step 3. 4-(5-(3,3-dimethyloxiran-2-yl)-2-(5-fluoro-6-methoxypyridin-3-ylamino)pyridin-3-yl)-6-methyl-1,3,5-triazin-2-amine A solution of 4-(2-(5-fluoro-6-methoxypyridin-3-ylamino)-5-(2-methylprop-1-enyl)pyridin-3-yl)-6-methyl-1,3,5-triazin-2-amine (380 mg, 0.996 mmol) in DCM (9.9 mL) was cooled to 0° C., and 3-chlorobenzoperoxoic acid (268 mg, 1.196 mmol) was then added. The resulting mixture was stirred at 0° C. for 1.5 h and then allowed to warm to ambient temperature and stir for 2 h. The reaction mixture was then diluted with 200 mL of EtOAc, added to a separatory funnel and partitioned with sodium bicarbonate (saturated, aqueous). The organic layer was washed 1 time with 150 mL of sodium bicarbonate (saturated, aqueous), separated, dried over sodium sulfate, and concentrated in vacuo to give the title compound. m/z (ESI, +ve ion) 398.2 (M+H)$^+$.

Step 4. 1-(5-(4-amino-6-methyl-1,3,5-triazin-2-yl)-6-(5-fluoro-6-methoxypyridin-3-ylamino)pyridin-3-yl)-2-methylpropane-1,2-diol 4-(5-(3,3-Dimethyloxiran-2-yl)-2-(5-fluoro-6-methoxypyridin-3-ylamino)pyridin-3-yl)-6-methyl-1,3,5-triazin-2-amine (5 mg, 0.013 mmol) was dissolved in conc. hydrochloric acid (252 nL, 1.258 mmol) and stirred at 25° C. for 30 min. The reaction mixture was then added to a separatory funnel and partitioned between DCM (100 mL) and 1 N NaOH (aqueous). The organic layer was separated, washed 2 times with 50 mL of 1 N NaOH (aqueous), dried over sodium sulfate, and concentrated in vacuo. The combined aqueous layers were subsequently extracted with EtOAc (3×80 mL), and the combined extracts were concentrated in vacuo. The combined crude products were subsequently dissolved in methanol (about 20 mg/mL) and purified by preparative HPLC (Phenomenex Luna 5 μM C18, 30×150 mm, 10-100% MeCN/H$_2$O with 0.1% TFA modifier) to give the title compound. $^1$H NMR (400 MHz, d$_4$-MeOH) δ 9.25 (d, J=1.96 Hz, 1H) 8.17 (d, J=2.15 Hz, 1H) 8.09 (d, J=2.15 Hz, 1H) 7.92 (dd, J=11.35, 1.96 Hz, 1H) 4.49 (s, 1H) 4.04 (s, 3H) 2.50 (s, 3H) 1.23 (s, 3H) 1.15 (s, 3H). m/z (ESI, +ve ion) 416.0 (M+H)$^+$.

Example 348

2-(5-(4-amino-6-methyl-1,3,5-triazin-2-yl)-6-(6-methoxy-5-(trifluoromethyl)pyridin-3-ylamino)pyridin-3-yl)propan-2-ol

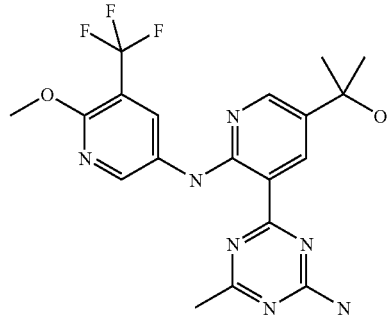 [SMILES: COc1ncc(Nc2ncc(C(C)(C)O)cc2-c2nc(C)nc(N)n2)cc1C(F)(F)F]

Step 1.
6-methoxy-5-(trifluoromethyl)pyridin-3-amine

To 5-Iodo-2-methoxy-3-(trifluoromethyl)pyridine (0.97 g, 3.20 mmol) (ECA International Product List) was added DMF (8.0 mL), (9,9-dimethyl-9H-xanthene-4,5-diyl)bis(diphenylphosphine) (0.093 g, 0.160 mmol), Pd$_2$(dba)$_3$ (0.147 g, 0.160 mmol), diphenylmethanimine (0.806 mL, 4.80 mmol), and sodium 2-methylpropan-2-olate (1.231 g, 12.80 mmol), and the resulting mixture was heated at 120° C. for 30 min. The reaction mixture was then diluted with 100 mL of EtOAc, added to a separatory funnel, partitioned with 1 N HCl (aqueous), and washed 2 times with 50 mL of sodium bicarbonate (saturated, aqueous). The organic layer was separated, dried over sodium sulfate, and concentrated in vacuo. Chromatographic purification of the residue (silica gel, 0% to 5% (2 M ammonia in MeOH)/DCM) provided the title compound (34% yield). m/z (ESI, +ve ion) 193.2 (M+H)$^+$.

Step 2. 2-(5-(4-amino-6-methyl-1,3,5-triazin-2-yl)-6-(6-methoxy-5-(trifluoromethyl)pyridin-3-ylamino)pyridin-3-yl)propan-2-ol The title compound was synthesized as a yellow solid following an analogous procedure to Example 356, Steps 1, 2, 4, and 5, substituting 6-methoxy-5-(trifluoromethyl)pyridin-3-amine (145 mg, 0.755 mmol) in Step 4. $^1$H NMR (400 MHz, d$_4$-MeOH) δ 9.04 (d, J=2.54 Hz, 1H) 8.59 (d, J=2.35

Hz, 1H) 8.54 (d, J=2.35 Hz, 1H) 8.43 (d, J=2.54 Hz, 1H) 4.02 (s, 3H) 2.51 (s, 3H) 1.60 (s, 6H). m/z (ESI, +ve ion) 436.0 (M+H)⁺.

Example 349

1-(5-(4-amino-6-methyl-1,3,5-triazin-2-yl)-6-(5-fluoro-6-methoxypyridin-3-ylamino)pyridin-3-yl)ethanol

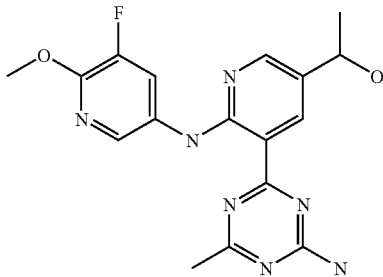 [SMILES: COc1ncc(Nc2ncc(C(C)O)cc2-c2nc(C)nc(N)n2)cc1F]

Step 1. 1-(5-(4-amino-6-methyl-1,3,5-triazin-2-yl)-6-(5-fluoro-6-methoxypyridin-3-ylamino)pyridin-3-yl)ethanone The title compound was synthesized following an analogous procedure to Example 356, Steps 1, 2, and 4 substituting 5-fluoro-6-methoxypyridin-3-amine (247 mg, 1.738 mmol) (AniChem) in Step 4. m/z (ESI, +ve ion) 370.0 (M+H)⁺.

Step 2. 1-(5-(4-amino-6-methyl-1,3,5-triazin-2-yl)-6-(5-fluoro-6-methoxypyridin-3-ylamino)pyridin-3-yl)ethanol 1-(5-(4-Amino-6-methyl-1,3,5-triazin-2-yl)-6-(5-fluoro-6-methoxypyridin-3-ylamino)pyridin-3-yl)ethanone (250 mg, 0.677 mmol) was dissolved in THF (1.35 mL), sodium borohydride (128 mg, 3.38 mmol) was added, and the resulting mixture was stirred at ambient temperature for 2 h. The reaction mixture was then quenched with water and added to a separatory funnel The reaction mixture was then partitioned between EtOAc (100 mL) and ammonium chloride (saturated, aqueous). The organic layer was separated, washed 2 times with 75 mL of ammonium chloride (saturated, aqueous), dried over sodium sulfate, and concentrated in vacuo. Chromatographic purification of the residue (silica gel, 0% to 5% (2 M ammonia in MeOH)/DCM) gave the title compound (40% yield) as a yellow solid. ¹H NMR (400 MHz, CDCl₃) δ 11.90 (s, 1H) 8.87 (s, 1H) 8.34 (d, J=2.15 Hz, 1H) 8.20-8.30 (m, 1H) 8.05 (d, J=1.76 Hz, 1H) 5.41 (br. s., 2H) 4.95 (q, J=6.52 Hz, 1H) 4.03 (s, 3H) 2.57 (s, 3H) 1.83 (br. s., 1H) 1.58 (br. s., 3H). m/z (ESI, +ve ion) 372.0 (M+H)⁺.

Example 350

2-(5-(4-amino-6-methyl-1,3,5-triazin-2-yl)-6-(5,6-dimethoxypyridin-3-ylamino)pyridin-3-yl)propan-2-ol

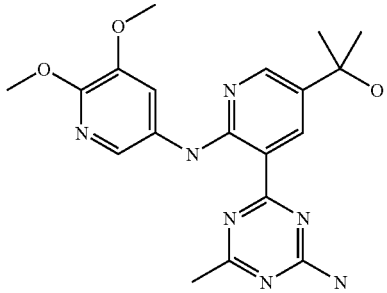 [SMILES: COc1cc(Nc2ncc(C(C)(C)O)cc2-c2nc(C)nc(N)n2)cnc1OC]

The title compound was synthesized as a yellow solid following an analogous procedure to Example 356, Steps 1, 2, 4, and 5, substituting 5,6-dimethoxypyridin-3-amine (92 mg, 0.597 mmol) (WO2008124083) in Step 4. ¹H NMR (400 MHz, CDCl₃) δ 11.72 (s, 1H) 8.95 (d, J=2.54 Hz, 1H) 8.46 (d, J=2.74 Hz, 1H) 7.97 (s, 1H) 7.79 (d, J=2.15 Hz, 1H) 5.49 (s, 2H) 4.02 (s, 3H) 3.93 (s, 3H) 2.56 (s, 3H) 1.87 (br. s., 1H) 1.64 (s, 6H). m/z (ESI, +ve ion) 398.0 (M+H)⁺.

Example 351

1-(5-(4-amino-6-methyl-1,3,5-triazin-2-yl)-6-(5-fluoro-6-methoxypyridin-3-ylamino)pyridin-3-yl)-2-hydroxy-2-methylpropyl 3-chlorobenzoate

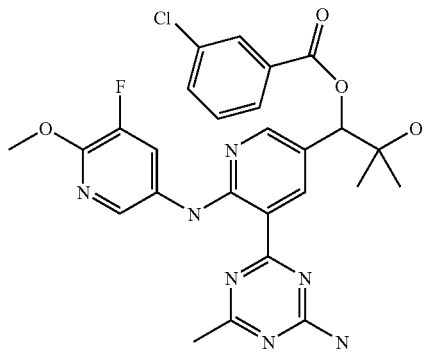 [SMILES: COc1ncc(Nc2ncc(C(OC(=O)c3cccc(Cl)c3)C(C)(C)O)cc2-c2nc(C)nc(N)n2)cc1F]

The title compound was isolated from Example 347, Step 3 after it was purified via flash chromatography (silica gel, 0% to 4% (2 M ammonia in MeOH)/DCM). ¹H NMR (400 MHz, d₄-MeOH) δ 11.82 (s, 1H) 8.96 (d, J=2.15 Hz, 1H) 8.36 (d, J=1.96 Hz, 1H) 8.16 (s, 1H) 8.03-8.12 (m, 4H) 7.57-7.66 (m, 1H) 7.43-7.53 (m, 1H) 5.81 (s, 1H) 3.91 (s, 3H) 2.41 (s, 3H) 1.34 (s, 3H) 1.28 (s, 3H). m/z (ESI, +ve ion) 554.2 (M+H)⁺.

Example 352

2-(5-(4-amino-6-methyl-1,3,5-triazin-2-yl)-6-(5-fluoropyridin-3-ylamino)pyridin-3-yl)propan-2-ol

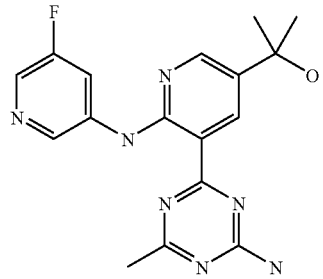 [SMILES: Cc1nc(N)nc(-c2cc(C(C)(C)O)cnc2Nc2cncc(F)c2)n1]

The title compound was synthesized as a yellow solid following an analogous procedure to Example 356, Steps 1, 2, 4, and 5, substituting 3-amino-5-fluoropyridine (73.9 mg, 0.659 mmol) (Matrix Scientific) in Step 4. ¹H NMR (400 MHz, d₆-DMSO) δ 12.31 (s, 1H) 9.00 (d, J=2.54 Hz, 1H) 8.80 (s, 1H) 8.58 (d, J=12.32 Hz, 1H) 8.52 (d, J=2.54 Hz, 1H) 8.14 (d, J=2.54 Hz, 1H) 7.95 (br. s., 1H) 7.78 (br. s., 1H) 5.20 (s, 1H) 2.47 (s, 3H) 1.49 (s, 6H). m/z (ESI, +ve ion) 356.0 (M+H)⁺.

Example 353

2-(5-(4-amino-6-methyl-1,3,5-triazin-2-yl)-6-(5-methoxypyridin-3-ylamino)pyridin-3-yl)propan-2-ol

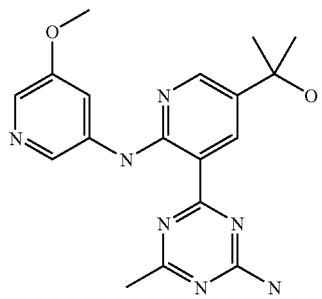 [SMILES: COc1cncc(Nc2ncc(C(C)(C)O)cc2-c2nc(C)nc(N)n2)c1]

The title compound was synthesized as a yellow solid following an analogous procedure to Example 356, Steps 1, 2, 4, and 5, substituting 5-methoxy-pyridin-3-ylamine (94 mg, 0.757 mmol) (J & W PharmLab) in Step 4. $^1$H NMR (400 MHz, d$_4$-MeOH) δ 9.06 (d, J=2.54 Hz, 1H) 8.53 (s, 1H) 8.43 (s, 1H) 8.20-8.28 (m, 1H) 7.86 (d, J=2.74 Hz, 1H) 3.93 (s, 3H) 2.53 (s, 3H) 1.62 (s, 6H). m/z (ESI, +ve ion) 368.0 (M+H)$^+$.

Example 354

2-(5-(4-amino-6-methyl-1,3,5-triazin-2-yl)-6-(6-methoxy-5-methylpyridin-3-ylamino)pyridin-3-yl)propan-2-ol

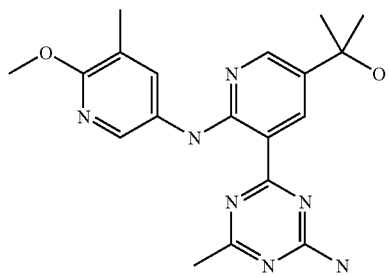 [SMILES: COc1ncc(Nc2ncc(C(C)(C)O)cc2-c2nc(C)nc(N)n2)cc1C]

The title compound was synthesized as a yellow solid following an analogous procedure to Example 356, Steps 1, 2, 4, and 5, substituting 6-methoxy-5-methylpyridin-3-amine hydrochloride (126 mg, 0.719 mmol) (Asymchem) in Step 4. $^1$H NMR (400 MHz, CDCl$_3$) δ 11.51 (s, 1H) 8.93 (d, J=2.54 Hz, 1H) 8.43 (d, J=2.54 Hz, 1H) 8.15 (d, J=2.54 Hz, 1H) 7.91 (d, J=1.96 Hz, 1H) 5.57 (s, 2H) 3.96 (s, 3H) 2.54 (s, 3H) 2.22 (s, 3H) 1.98 (br. s., 1H) 1.63 (s, 6H). m/z (ESI, +ve ion) 382.1 (M+H)$^+$.

Example 355

2-(5-(4-amino-6-methyl-1,3,5-triazin-2-yl)-6-(5-(methylsulfonyl)pyridin-3-ylamino)pyridin-3-yl)propan-2-ol

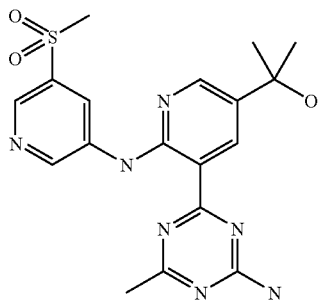 [SMILES: Cc1nc(N)nc(-c2cc(C(C)(C)O)cnc2Nc2cncc(S(C)(=O)=O)c2)n1]

The title compound was synthesized as a yellow solid following an analogous procedure to Example 356, substituting methanesulfinic acid, sodium salt (0.743 g, 7.28 mmol) (Acros Organics) in Step 3. $^1$H NMR (400 MHz, d$_6$-DMSO) δ 9.14-9.16 (m, 1H) 9.11-9.14 (m, 1H) 9.01 (d, J=2.54 Hz, 1H) 8.64 (d, J=1.96 Hz, 1H) 8.53 (d, J=2.54 Hz, 1H) 5.22 (s, 1H) 3.33 (s, 3H) 2.48 (s, 3H) 1.50 (s, 6H). m/z (ESI, +ve ion) 416.1 (M+H)$^+$.

Example 356

2-(5-(4-amino-6-methyl-1,3,5-triazin-2-yl)-6-(5-(phenylsulfonyl)pyridin-3-ylamino)pyridin-3-yl)propan-2-ol

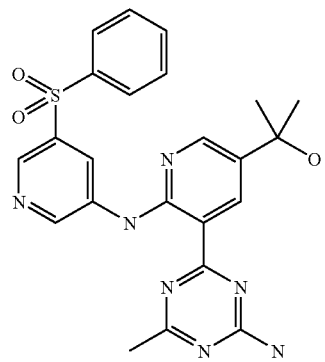 [SMILES: Cc1nc(N)nc(-c2cc(C(C)(C)O)cnc2Nc2cncc(S(=O)(=O)c3ccccc3)c2)n1]

Step 1. 4-(5-chloro-2-fluoropyridin-3-yl)-6-methyl-1,3,5-triazin-2-amine

To a 4-(5-Chloro-2-fluoropyridin-3-yl)-N,N-bis(4-methoxybenzyl)-6-methyl-1,3,5-triazin-2-amine (3.87 g, 8.06 mmol) (Example 313, Step 1) was dissolved in TFA (81 mL), trifluoromethanesulfonic acid (2.1 mL, 24 mmol) was added, and the resulting mixture was stirred at 80° C. for 2 h. The reaction mixture was then concentrated in vacuo. The residue was partitioned between EtOAc (150 mL) and sodium bicarbonate (saturated, aqueous). The organic layer was the separated, washed 2 times with 100 mL of sodium bicarbonate (saturated, aqueous), dried over sodium sulfate, and concentrated in vacuo. Chromatographic purification of the residue (silica gel, 0% to 40% EtOAc/hexanes) provided the title compound (51% yield). m/z (ESI, +ve ion) 240.1 (M+H)$^+$.

Step 2. 4-(5-(1-ethoxyvinyl)-2-fluoropyridin-3-yl)-6-methyl-1,3,5-triazin-2-amine To 4-(5-chloro-2-fluoropyridin-3-yl)-6-methyl-1,3,5-triazin-2-amine (1.34 g, 5.59 mmol) was added DMF (8 mL), dioxane (48 mL), cesium fluoride (2.55 g, 16.78 mmol), X-Phos (0.258 g, 0.559 mmol), palladium (II) acetate (0.126 g, 0.559 mmol), and tributyl(1-ethoxyvinyl)stannane (2.64 mL, 7.83 mmol) (Aldrich), and the resulting mixture was stirred at 110° C. for 1.5 h. The reaction mixture was cooled to ambient temperature and purified via flash chromatography (neutral alumina) with 100% DCM (to remove the stannane), then 100% EtOAc to give the title compound (>99% yield). m/z (ESI, +ve ion) 276.0 (M+H)$^+$.

Step 3. 5-(phenylsulfonyl)pyridin-3-amine

To 5-bromopyridin-3-amine (1.59 g, 9.19 mmol) (Aldrich) was added benzenesulfinic acid, sodium salt (1.810 g, 11.03 mmol) (Sigma-Aldrich), copper(I) iodide (0.175 g, 0.919 mmol), (S)-pyrrolidine-2-carboxylic acid (0.212 g, 1.838 mmol), sodium hydroxide (0.074 g, 1.838 mmol), and DMSO (18 mL), and the resulting mixture was stirred at 100° C. for 3 days. The reaction mixture was then diluted with 200 mL of EtOAc, added to a separatory funnel, and partitioned with sodium bicarbonate (saturated, aqueous). The organic layer was separated, washed 4 times with 150 mL of sodium bicarbonate (saturated, aqueous), dried over sodium sulfate, and concentrated in vacuo. Chromatographic purification of the residue (silica gel, 0% to 3% (2 M ammonia in MeOH)/DCM) furnished the title compound (11% yield). m/z (ESI, +ve ion) 235.3 (M+H)+.

Step 4. 1-(5-(4-amino-6-methyl-1,3,5-triazin-2-yl)-6-(5-(phenylsulfonyl)pyridin-3-ylamino)pyridin-3-yl)ethanone 4-(5-(1-Ethoxyvinyl)-2-fluoropyridin-3-yl)-6-methyl-1,3,5-triazin-2-amine (255 mg, 0.925 mmol) and 5-(phenylsulfonyl)pyridin-3-amine (260 mg, 1.110 mmol) were dissolved in THF (9.2 mL) and the resulting mixture was cooled to 0° C. and NaHMDS in THF (1.0 M, Aldrich; 2775 µL, 2.77 mmol) was added. The reaction mixture was stirred at 0° C. for 1.5 h. The reaction mixture was then diluted with 100 mL of EtOAc, added to a separatory funnel, and partitioned with ammonium chloride (saturated, aqueous). The organic layer was separated, washed 2 times with 50 mL of ammonium chloride (saturated, aqueous), dried over sodium sulfate, and concentrated in vacuo. Chromatographic purification of the residue (silica gel, 0% to 3% (2 M ammonia in MeOH)/DCM) gave the title compound (44% yield) as a yellow amorphous solid. m/z (ESI, +ve ion) 462.2 (M+H)+.

Step 5. 2-(5-(4-amino-6-methyl-1,3,5-triazin-2-yl)-6-(5-(phenylsulfonyl)pyridin-3-ylamino)pyridin-3-yl)propan-2-ol To cerium(III) chloride (304 mg, 1.235 mmol) was added THF (4.1 mL) and the resulting mixture was heated to 40° C. for 1 h. The reaction mixture was then cooled to −78° C. and methylmagnesium bromide in ether (3.0 M, Aldrich; 1372 µL, 4.12 mmol) was added. The resulting mixture was stirred at −78° C. for 15 min. 1-(5-(4-Amino-6-methyl-1,3,5-triazin-2-yl)-6-(5-(phenylsulfonyl)pyridin-3-ylamino)pyridin-3-yl)ethanone (190 mg, 0.412 mmol) in THF (4.1 mL) was then added, and the resulting mixture was stirred at −78° C. for 4 h. The reaction mixture was subsequently diluted with 100 mL of EtOAc, added to a separatory funnel, and partitioned with sodium bicarbonate (saturated, aqueous). The organic layer was separated, washed 2 times with 50 mL of sodium bicarbonate (saturated, aqueous), dried over sodium sulfate, and concentrated in vacuo. Chromatographic purification of the residue (silica gel, 0% to 3% (2 M ammonia in MeOH)/DCM) provided the title compound (36% yield) as a light yellow solid. $^1$H NMR (400 MHz, d$_6$-DMSO) δ 12.38 (s, 1H) 9.18-9.23 (m, 1H) 9.06 (d, J=2.35 Hz, 1H) 9.00 (d, J=2.35 Hz, 1H) 8.67 (d, J=2.15 Hz, 1H) 8.53 (d, J=2.54 Hz, 1H) 8.02-8.08 (m, 2H) 7.98 (br. s., 1H) 7.79 (br. s., 1H) 7.71-7.77 (m, 1H) 7.64-7.71 (m, 2H) 5.22-5.26 (m, 1H) 2.46 (s, 3H) 1.51 (s, 6H). m/z (ESI, +ve ion) 478.1 (M+H)+.

Example 357

4-((5-(4-amino-6-methyl-1,3,5-triazin-2-yl)-6-(5-fluoro-6-methoxypyridin-3-ylamino)pyridin-3-yl)methyl)-N-isopropyl-N-methylpiperazine-1-carboxamide

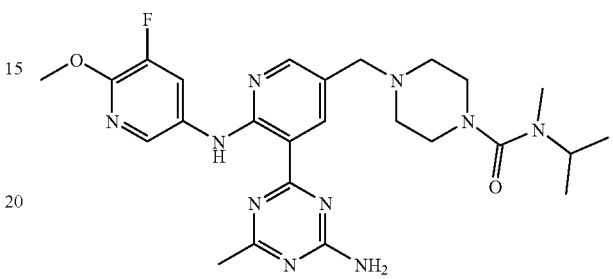

Step 1. N-isopropyl-N-methyl-1H-imidazole-1-carboxamide

To a 50 mL round-bottomed flask was added 1,1'-carbonyldiimidazole (1.663 g, 10.25 mmol), (Fluka Chemie) DCM (25 mL). The solution was stirred at 0° C. using a water bath and treated in one portion with n-isopropylmethylamine (0.5 mL, 6.84 mmol) (Aldrich). The water bath was removed, and the solution was stirred at room temperature. After 2 hours all starting material was consumed. The reaction mixture was diluted with DCM (10 mL) and quenched with water. The organic layer was separated, dried over sodium sulfate and concentrated to afford N-isopropyl-N-methyl-1H-imidazole-1-carboxamide (0.920 g, 5.50 mmol, 80% yield).

Step 2. 1-(isopropyl(methyl)carbamoyl)3-methyl-1H-imidazol-3-ium iodide

To a 50 mL round-bottomed flask was added N-isopropyl-N-methyl-1H-imidazole-1-carboxamide (0.550 g, 3.29 mmol), acetonitrile (29 mL, 3.29 mmol), iodomethane (0.817 mL, 13.16 mmol). The resulting solution was stirred at room temperature overnight. The solvent was removed under vacuum to afford 1-(isopropyl(methyl)carbamoyl)3-methyl-1H-imidazol-3-ium iodide.

Step 3. 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)-N-isopropyl-N-methylpiperazine-1-carboxamide To a 50 mL round-bottomed flask was added 4-(2-(5-fluoro-6-methoxypyridin-3-ylamino)-5-(piperazin-1-ylmethyl)pyridin-3-yl)-N,N-bis(4-methoxybenzyl)-6-methyl-1,3,5-triazin-2-amine (0.350 g, 0.526 mmol), 1-(isopropyl(methyl)carbamoyl)-3-methyl-1H-imidazol-3-ium (0.479 g, 2.63 mmol), DCM (25 mL, 0.526 mmol), triethylamine (0.366 mL, 2.63 mmol). After 1 hour the mixture was washed with 1.0 N HCl (2×5 mL) and brine, the organic layer was dried over sodium sulfate, filtered and concentrated under a vacuum to give 4-((5-(4-(bis(4-methoxybenzyl)amino)-6-methyl-1,3,5-triazin-2-yl)-6-(5-fluoro-6-methoxypyridin-3- ylamino)pyridin-3-yl)methyl)-N-isopropyl-N-methylpiperazine-1-carboxamide, which was treated with trifluoroacetic acid (5 mL, 67.3 mmol), trifluoromethanesulfonic acid (0.2 mL, 0.278 mmol). The solution was stirred at 80° C. for one hour. The dark solution was cooled down to room temperature and concentrated to slurry. The slurry was neutralized to pH 8 with NaHCO₂. The precipitate was dissolved in DCM/MeOH and adsorbed onto a plug of silica gel and chromatographed through a silica gel column (40 g), eluting with a gradient of 5% to 10% 2 M NH₃.MeOH in DCM, to provide 4-((5-(4-amino-6-methyl-1,3,5-triazin-2-yl)-6-(5-fluoro-6-methoxypyridin-3-ylamino)pyridin-3-yl)methyl)-N-isopropyl-N-methylpiperazine-1-carboxamide (0.033 g, 0.063 mmol, 26.7% yield). m/z (ESI, Positive ion) 525.2 (M+H)⁺. ¹H NMR (400 MHz, DMSO-d₆) δ ppm 1.07 (d, J=6.85 Hz, 6H) 2.44 (s, 3H) 2.64 (s, 3H) 2.97 (dd, J=5.38, 4.60 Hz, 4H) 3.09 (d, J=7.24 Hz, 1H) 3.25 (d, J=4.89 Hz, 4H) 3.95 (s, 3H) 4.12 (s, 2H) 7.83 (br. s., 1H) 7.96 (br. s., 1H) 8.33-8.37 (d, 1H) 8.40 (s, 1H) 8.44 (s, 1H) 8.87 (dd, J=2.15, 0.39 Hz, 1H) 12.01 (s, 1H).

Example 358

4-((5-(4-amino-6-methyl-1,3,5-triazin-2-yl)-6-(5-fluoro-6-methoxypyridin-3-ylamino)pyridin-3-yl)methyl)-N-methyl-N-(2,2,2-trifluoroethyl)piperazine-1-carboxamide

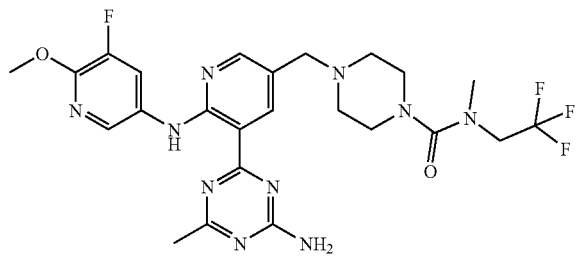 [SMILES: COc1ncc(Nc2ncc(CN3CCN(C(=O)N(C)CC(F)(F)F)CC3)cc2-c2nc(C)nc(N)n2)cc1F]

The title compound was synthesized following an analogous procedure to Example 357, substituting 2,2,2-trifluoro-N-methylethanamine (Accela ChemBio Inc.) for n-isopropylmethylamine (0.035 g, 0.064 mmol, 50.4% yield). m/z (ESI, positive ion): 547.2 (M+H)⁺. ¹H NMR (400 MHz, CDCl₃) ppm 2.48 (b, 3H) 2.56 (s, 3H) 2.99 (s, 3H) 3.36 (b, 4H) 3.53 (b, 3H) 3.91 (d, J=9.19 Hz, 2H) 3.94 (s, 3H) 6.78 (d, J=9.00 Hz, 1H) 8.12 (dd, J=9.00, 2.74 Hz, 1H) 8.23 (dd, J=2.15, 0.39 Hz, 1H) 8.35 (s, 2H) 8.35 (d, J=0.39 Hz, 1H) 8.75 (s, 1H) 11.68 (s, 1H).

Example 359

4-((5-(4-amino-6-methyl-1,3,5-triazin-2-yl)-6-(6-methoxypyridin-3-ylamino)pyridin-3-yl)methyl)-N-cyclopropyl-N-methylpiperazine-1-carboxamide

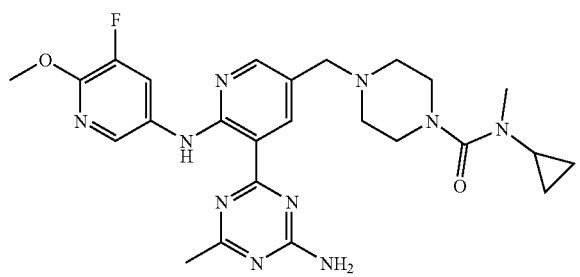 [SMILES: COc1ncc(Nc2ncc(CN3CCN(C(=O)N(C)C4CC4)CC3)cc2-c2nc(C)nc(N)n2)cc1F]

The title compound was synthesized following an analogous procedure to Example 357, substituting N-methylcyclopropanamine ((Accela ChemBio Inc.) for n-isopropylmethylamine (0.152 g, 0.301 mmol, 82% yield). m/z (ESI, positive ion): 505.2 (M+H)⁺. ¹H NMR (400 MHz, CDCl₃) ppm 0.56-0.65 (m, 2H) 0.65-0.76 (m, 2H) 2.55 (s, 4H) 2.55 (s, 3H) 2.82 (s, 3H) 3.53 (br. s., 4H) 3.68 (br. s., 3H) 3.94 (s, 3H) 5.72 (br. s., 2H) 6.78 (d, J=8.80 Hz, 1H) 8.11-8.16 (d, 1H) 8.26 (s, 1H) 8.35 (s, 1H) 8.85 (s, 1H) 11.76 (br. s., 1H).

Example 360

4-(2-(5-fluoro-6-methoxypyridin-3-ylamino)-5-((R)-1-((R)-2-methyl-4-(methylsulfonyl)piperazin-1-yl)ethyl)pyridin-3-yl)-6-methyl-1,3,5-triazin-2-amine

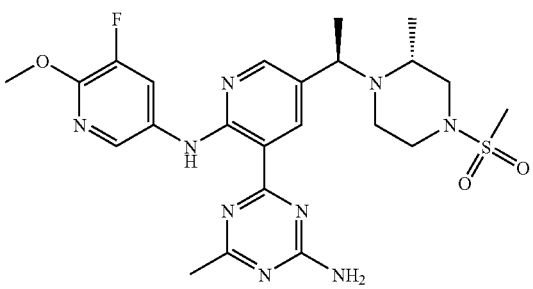 [SMILES: COc1ncc(Nc2ncc([C@@H](C)N3CCN(S(C)(=O)=O)C[C@H]3C)cc2-c2nc(C)nc(N)n2)cc1F]

Step 1. 5-(1-bromoethyl)-2-fluoropyridine

To a 250 mL round-bottomed flask was added 2-fluoro-5-formylpyridine (5.10 mL, 40.8 mmol), (Frontier Scientific), and tetrahydrofuran (100 mL, 1233 mmol). The solution was stirred at −10° C. using an ice bath and treated dropwise via addition funnel with methylmagnesium bromide (14.27 mL, 42.8 mmol), (Aldrich). After the addition, the ice bath was removed and the mixture was stirred at ambient temperature. After 30 minutes the reaction was complete. The mixture was stirred at −10° C. and treated dropwise via syringe with methanesulfonyl chloride (3.41 mL, 44.0 mmol), (Aldrich). After the addition, the water bath was removed and the mixture was stirred at ambient temperature and progress was followed with LC/MS. The reaction mixture was quenched with water (50 ml) and diluted with DCM (150 ml). The aqueous layer was extracted with DCM (3×50 mL) dried over sodium sulfate, filtered and concentrated in vacuum to give 5-(1-bromoethyl)-2-fluoropyridine (7.16 g, 35.1 mmol, 86% yield).

Step 2. (3R)-tert-butyl 4-(1-(6-fluoropyridin-3-yl)ethyl)-3-methylpiperazine-1-carboxylate To a 100 mL round-bottomed flask was added 5-(1-bromoethyl)-2-fluoropyridine (3.9 g, 19.11 mmol), acetonitrile (75 mL, 1435 mmol), (R)-4-N-boc-2-methyl-piperazine (4.02 g, 20.07 mmol), (Aldrich), potassium carbonate (1.384 mL, 22.94 mmol), (Aldrich), potassium iodide (0.205 mL, 3.82 mmol), (Fluka). The reaction mixture was stirred at 70° C. overnight. The reaction mixture was diluted with water (50 mL) and DCM (50 mL) and extracted with DCM (3×50 mL) dried over sodium sulfate, filtered and concentrated under a vacuum to give (3R)-tert-butyl 4-(1-(6-fluoropyridin-3-yl)ethyl)-3-methylpiperazine-1-carboxylate (3.05 g, 9.43 mmol, 49.3% yield). The crude product was adsorbed onto a plug of silica gel and chromatographed through a silica gel column (80 g), eluting with a gradient of 0% to 50% EtOAc in hexane, to provide (3R)-tert-butyl 4-(1-(6-fluoropyridin-3-yl)ethyl)-3-methylpiperazine-1-carboxylate (3.05 g, 9.43 mmol, 49.3% yield).

Step 3. 5-(1-((R)-4-(tert-butoxycarbonyl)-2-methylpiperazin-1-yl)ethyl)-2-fluoropyridin-3-ylboronic acid To a 150-mL round-bottomed flask was added (3R)-tert-butyl 4-(1-(6-fluoropyridin-3-yl)ethyl)-3-methylpiperazine-1-carboxylate (3.0 g, 9.28 mmol), and tetrahydrofuran (100 mL, 9.28 mmol). The solution was stirred at −78° C. and treated dropwise via syringe with butyllithium solution, 2.5 m in hexanes (4.08 mL, 10.20 mmol) (Aldrich). The solution was stirred at −78° C. for 1 hr and treated in one portion with triisopropyl borate (2.55 mL, 11.13 mmol) (Aldrich). The mixture was stirred at −78° C. for 1 hour. NaOH (1.0 N (30 mL) was added and the solution was stirred at room temperature for 30 minutes. The aqueous layer was separated and the organic layer was extracted with additional NaOH (1.0N, 30 mL). The combined aqueous layer was carefully acidified with 5N HCl (12 mL) to a final pH of about 4 to 5. The reaction mixture was extracted with EtOAc (3×100 mL) and the organic extract was dried over sodium sulfate, filtered and concentrated under a vacuum to give 5-(1-((R)-4-(tert-butoxycarbonyl)-2-methylpiperazin-1-yl)ethyl)-2-fluoropyridin-3-ylboronic acid (2.5 g, 6.81 mmol, 73.4% yield).

Step 4. (3R)-tert-butyl 4-(1-(5-(4-(bis(4-methoxybenzyl)amino)-6-methyl-1,3,5-triazin-2-yl)-6-fluoropyridin-3-yl)ethyl)-3-methylpiperazine-1-carboxylate A glass microwave reaction vessel was charged with 5-(1-((R)-4-(tert-butoxycarbonyl)-2-methylpiperazin-1-yl)ethyl)-2-fluoropyridin-3-ylboronic acid (1.4 g, 3.81 mmol),4-chloro-N,N-bis(4-methoxybenzyl)-6-methyl-1,3,5-triazin-2-amine (1.467 g, 3.81 mmol),1,4-dioxane (10 mL, 3.81 mmol), potassium acetate (1.122 g, 11.44 mmol), water (1 mL, 3.81 mmol), and amphos (0.270 g, 0.381 mmol). The reaction mixture was stirred and heated in a microwave reactor (Personal Chemistry, Biotage AB, Inc., Upssala, Sweden) at 120° C. for 20 min (watts, Powermax feature, ramp time min) LC/MS showed desired product, starting triazine and debornated product. The reaction mixture was diluted with water (20 mL) and DCM (25 mL) and the aqueous layer was extracted with DCM (3×50 mL) dried over sodium sulfate, filtered and concentrated in vacuum. The crude product was adsorbed onto a plug of silica gel and chromatographed through a silica gel column (40 g), eluting with a gradient of 0% to 50% EtOAc in hexane, to provide (3R)-tert-butyl 4-(1-(5-(4-(bis(4-methoxybenzyl)amino)-6-methyl-1,3,5-triazin-2-yl)-6-fluoropyridin-3-yl)ethyl)-3-methylpiperazine-1-carboxylate (1.26 g, 1.876 mmol, 49.2% yield).

Step 5. (R)-tert-butyl 4-((R)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate and (R)-tert-butyl 4-((S)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate To a 250 mL round-bottomed flask was added (3R)-tert-butyl 4-(1-(5-(4-(bis(4-methoxybenzyl)amino)-6-methyl-1,3,5-triazin-2-yl)-6-fluoropyridin-3-yl)ethyl)-3-methylpiperazine-1-carboxylate (1.0 g, 1.489 mmol), 5-fluoro-6-methoxypyridin-3-amine (0.317 g, 2.233 mmol) (Anichem), tetrahydrofuran (20 mL, 247 mmol). The solution was stirred at −40° C. and treated dropwise via addition funnel with lithium bis(trimethylsily)amide (Aldrich) (4.47 mL, 4.47 mmol). The solution was stirred at −40° C. for 30 minutes and quenched with water and NH₄Cl (20 ml) each and diluted with EtOAc (20 mL) and the aqueous layer was extracted with EtOAc (2×20 mL). The organic extract was washed with saturated NaCl (20 mL) and dried over sodium sulfate, filtered and concentrated in vacuum. The crude product was adsorbed onto a plug of silica gel and chromatographed through a silica gel column (40 g), eluting with a gradient of 5% to 50% EtOAc in hexane, to provide (R)-tert-butyl 4-((R)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (0.45 g, 0.567 mmol, 38.1% yield), and (R)-tert-butyl 4-((S)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (0.35 g, 0.441 mmol, 29.6% yield).

Step 6. 4-(2-(5-fluoro-6-methoxypyridin-3-ylamino)-5-((R)-1-((R)-2-methyl-4-(methylsulfonyl)piperazin-1-yl)ethyl)pyridin-3-yl)-N,N-bis(4-methoxybenzyl)-6-methyl-1,3,5-triazin-2-amine To a 100 mL round-bottomed flask was added (R)-tert-butyl 4-((R)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate (0.200 g, 0.252 mmol), dichloromethane (5 mL, 78 mmol), trifluoroacetic acid (5 mL, 67.3 mmol). The solution was stirred for 1 hr. The solution was concentrated down and the residue was dissolved in DCM and slowly washed with NaHCO₃, to get rid off the TFA. The DCM solution was dried over sodium sulfate, filtered and concentrated. The residue was dried under a high vacuum overnight. The residue was dissolved in DCM, cooled down in a dry ice/IPA cooling bath and treated with triethylamine (0.349 mL, 2.52 mmol), and methanesulfonyl chloride (0.098 mL, 1.260 mmol).The solution was stirred at −50° C. for 30 minutes. The solvent was removed under a vacuum and the crude product was washed with water (30 mL), stirred, and sonicated. The resulting suspension was collected, washed with water, and dried in a vacuum oven overnight to give 4-(2-(5-fluoro-6-methoxypyridin-3-ylamino)-5-((R)-1-((R)-2-methyl-4-(methylsulfonyl)piperazin-1-yl)ethyl)pyridin-3-yl)-N,N-bis(4-methoxybenzyl)-6-methyl-1,3,5-triazin-2-amine (0.150 g, 0.194 mmol, 77% yield).

Step 7. 4-(2-(5-fluoro-6-methoxypyridin-3-ylamino)-5-((R)-1-((R)-2-methyl-4-(methylsulfonyl)piperazin-1-yl)ethyl)pyridin-3-yl)-6-methyl-1,3,5-triazin-2-amine To a 50-mL round-bottomed flask was added 4-(2-(5-fluoro-6-methoxypyridin-3-ylamino)-5-((R)-1-((R)-2-methyl-4-(methylsulfonyl)piperazin-1-yl)ethyl)pyridin-3-yl)-N,N-bis(4-methoxybenzyl)-6-methyl-1,3,5-triazin-2-amine (0.130 g, 0.168 mmol), 2,2,2-trifluoroacetic acid (5 mL, 0.842 mmol), and trifluoromethanesulfonic acid (0.2 mL, 0.168 mmol).The solution was stirred at 70° C. for 30 minutes. The volatiles were removed under a vacuum and the residue was cooled in ice bath and neutralized with 1 N NaOH. The mixture was stirred at room temperature overnight and the precipitate was filtered and washed with water. The precipitate was purified with preparative TLC using 5% (MeOH in DCM). The sample dried overnight under high vacuum to give 4-(2-(5-fluoro-6-methoxypyridin-3- ylamino)-5-((R)-1-((R)-2-methyl-4-(methylsulfonyl)piperazin-1-yl)ethyl)pyridin-3-yl)-6-methyl-1,3,5-triazin-2-amine (0.047 g, 0.088 mmol, 52.5% yield). m/z (ESI, positive ion) 532.2 (M+H)⁺. ¹H NMR (400 MHz, DMSO-d₆) δ ppm 1.07 (d, J=6.26 Hz, 3H) 1.38 (d, J=6.65 Hz, 3H) 2.45 (m, 4H) −2.55 (m, 1H) 2.84 (s, 5H) 3.01-3.18 (m, 3H) 3.94 (s, 3H) 4.00 (d, J=6.85 Hz, 1H) 7.74-7.78 (m, 1H) 7.88-7.92 (m, 1H) 8.31-8.34 (m, 1H) 8.37-8.43 (m, 2H) 8.70-8.74 (m, 1H) 11.93 (s, 1H).

Example 361

4-(2-(5-fluoro-6-methoxypyridin-3-ylamino)-5-((S)-1-((R)-2-methyl-4-(methylsulfonyl)piperazin-1-yl)ethyl)pyridin-3-yl)-6-methyl-1,3,5-triazin-2-amine

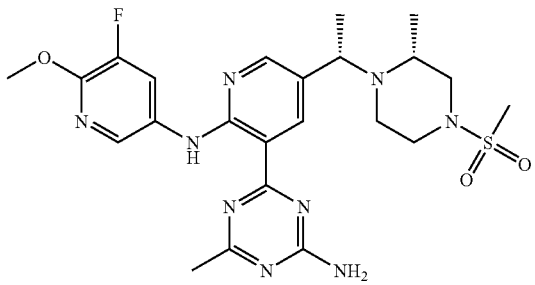

The title compound was prepared in an analogous manner to that described above in Example 360, Steps 6 and 7, using (R)-tert-butyl 4-((S)-1-(5-(4-(bis(4-methoxybenzyl)amino)-6-methyl-1,3,5-triazin-2-yl)-6-(5-fluoro-6-methoxypyridin-3-ylamino)pyridin-3-yl)ethyl)-3-methylpiperazine-1-carboxylate instead of 4-(2-(5-fluoro-6-methoxypyridin-3-ylamino)-5-((R)-1-((R)-2-methyl-4-(methylsulfonyl)piperazin-1-yl)ethyl)pyridin-3-yl)-N,N-bis(4-methoxybenzyl)-6-methyl-1,3,5-triazin-2-amine (0.031 g, 0.058 mmol, 47.4% yield). m/z (ESI, positive ion): 532.2 (M+H)⁺. ¹H NMR (400 MHz, DMSO-d₆) δ ppm 1.16 (d, J=6.46 Hz, 3H) 1.27 (br. s., 3H) 2.45 (s, 4H) 2.52 (m, 1H) 2.85 (s, 5H) 3.04 (s, 3H) 3.94 (s, 3H) 4.04 (d, J=6.85 Hz, 1H) 7.76 (m, 1H) 7.90 (m, 1H) 8.37 (m, 1H) 8.41 (m, 2H) 8.75 (br. s., 1H) 11.95 (s, 1H).

Example 362

4-(2-(2-methoxypyrimidin-5-ylamino)-5-((R)-1-((S)-2-methyl-4-(methylsulfonyl)piperazin-1-yl)ethyl)pyridin-3-yl)-6-methyl-1,3,5-triazin-2-amine

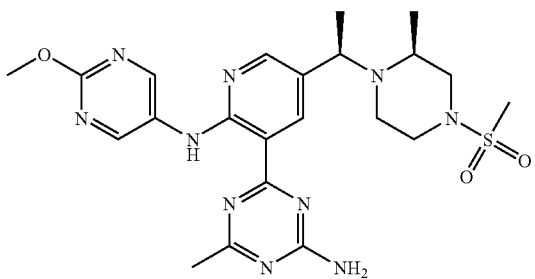 [SMILES: COc1ncc(Nc2ncc([C@@H](C)N3CCN(S(C)(=O)=O)C[C@@H]3C)cc2-c2nc(C)nc(N)n2)cn1]

The title compound was prepared in an analogous manner to that described above in Example 360, Steps 6 and 7, using (S)-tert-butyl 3-methylpiperazine-1-carboxylate (Aldrich) in Step 1 (Scheme 6) instead of (R)-4-N-boc-2-methyl-piperazine and 2-methoxypyrimidin-5-amine instead of 5-fluoro-6-methoxypyridin-3-amine in Step 5. (0.023 g, 0.045 mmol, 33.7% yield). m/z (ESI, positive ion): 515.2 (M+H)⁺. ¹H NMR (400 MHz, DMSO-d₆) δ ppm 1.07 (d, J=6.26 Hz, 3H) 1.38 (d, J=6.85 Hz, 3H) 2.45 (s, 3H) 2.53-2.57 (m, 1H) 2.78-2.89 (m, 2H) 2.84 (s, 4H) 3.02-3.17 (m, 3H) 3.32 (s, 1H) 3.91-4.03 (m, 1H) 3.94 (s, 4H) 7.73-7.78 (m, 1H) 7.87-7.92 (m, 1H) 8.30-8.34 (m, 1H) 8.37-8.43 (m, 2H) 8.70-8.74 (m, 1H) 11.93 (s, 1H).

Example 363

4-(2-(6-chloropyridin-3-ylamino)-5-((R)-1-((S)-2-methyl-4-(methylsulfonyl)piperazin-1-yl)ethyl)pyridin-3-yl)-6-methyl-1,3,5-triazin-2-amine

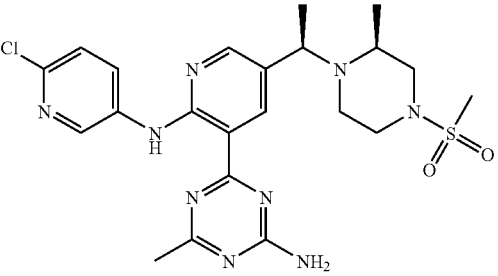 [SMILES: Cc1nc(N)nc(-c2cc([C@@H](C)N3CCN(S(C)(=O)=O)C[C@@H]3C)cnc2Nc2ccc(Cl)nc2)n1]

The title compound was prepared in an analogous manner to that described above in Example 362, using 5-amino-2-chloropyridine instead of 2-methoxypyrimidin-5-amine in step 5. (0.041 g, 0.079 mmol, 30.0% yield). m/z 518.2 (M+H)⁺. ¹H NMR (400 MHz, DMSO-d₆) δ ppm 1.06-1.07 (d, J=6.06 Hz, 3H) 1.37-1.38 (d, J=6.65 Hz, 3H) 2.46 (br, 3H) 2.55 (br., 2H) 2.84 (d, J=9.78 Hz, 5H) 3.04-3.06 (t, J=5.48 Hz, 1H) 3.13 (br., 2H) 4.01 (d, J=6.85 Hz, 1H) 7.46-7.46 (d, J=8.61 Hz, 1H) 7.80 (br. S., 1H) 7.94 (br. S., 1H) 8.37 (br. s., 1H) 8.48-8.51 (d, J=8.61 Hz, 1H) 8.75 (br. s., 1H) 8.86-8.89 (br., s, 1H) 12.15 (s, 1H).

Example 364

(R)-4-(2-(5-fluoro-6-methoxypyridin-3-ylamino)-5-((3-methyl-4-(methylsulfonyl)piperazin-1-yl)methyl)pyridin-3-yl)-6-methyl-1,3,5-triazin-2-amine

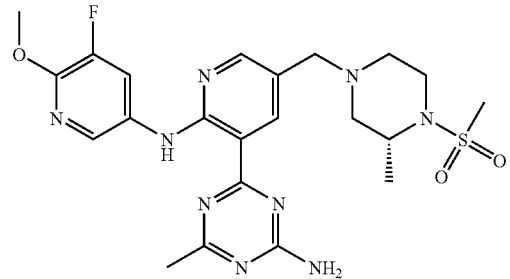 [SMILES: COc1ncc(Nc2ncc(CN3CCN(S(C)(=O)=O)[C@H](C)C3)cc2-c2nc(C)nc(N)n2)cc1F]

Step 1. (R)-tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)-2-methylpiperazine-1-carboxylate To a 15 mL round-bottomed flask was added 5-(4-(bis(4-methoxybenzyl)amino)-6-methyl-1,3,5-triazin-2-yl)-6-(5-fluoro-6-methoxypyridin-3-ylamino)nicotinaldehyde (0.438 g, 0.735 mmol), (R)-tert-butyl 2-methylpiperazine-1-carboxylate (0.368 g, 1.838 mmol), tetrahydrofuran (0.053 g, 0.735 mmol), titanium (iv) ethoxide (0.761 mL, 3.68 mmol) (Aldrich). The flask was sealed and the solution was stirred at 70° C. overnight. The solution was stirred at 0° C. and treated in one portion with sodium cyanotrihydridoborate (0.462 g, 7.35 mmol) (Aldrich). The suspension was stirred at 0° C. for two hours. The suspension was quenched with drops of MeOH and water, then DCM. The suspension was stirred for 10 minutes vigorously and was filtered through Celite® (diatomaceous earth) and the filtrated cake was washed with DCM. The organic phase was concentrated to afford (R)-tert-butyl 4-((5-(4-(bis(4-methoxybenzyl)amino)-6-methyl-1,3,5-triazin-2-yl)-6-(5-fluoro-6-methoxypyridin-3-ylamino)pyridin-3-yl)methyl)-2-methylpiperazine-1-carboxylate (0.425 g, 0.545 mmol, 74.1% yield).

Step 2 (R)-4-(2-(5-fluoro-6-methoxypyridin-3-ylamino)-5-((3-methyl-4-(methylsulfonyl)piperazin-1-yl)methyl)pyridin-3-yl)-N,N-bis(4-methoxybenzyl)-6-methyl-1,3,5-triazin-2-amine The title compound was prepared in an analogous manner to that described above in Example 360, Step 6. (0.164 g, 0.216 mmol, 46.9% yield).

Step 3. (R)-4-(2-(5-fluoro-6-methoxypyridin-3-ylamino)-5-((3-methyl-4-(methylsulfonyl)piperazin-1-yl)methyl)pyridin-3-yl)-6-methyl-1,3,5-triazin-2-amine The title compound was prepared in an analogous manner to that described above in Example 360, Step 7. (0.030 g, 0.058 mmol, 27.5% yield). m/z (ESI, positive ion) 518.2 (M+H)+. $^1$H NMR (400 MHz, DMSO-$d_6$) δ ppm 1.26 (d, J=6.65 Hz, 3H) 2.10 (d, J=3.52 Hz, 1H) 2.16-2.22 (m, 1H) 2.44 (s, 3H) 2.59-2.61 (d, J=9.59 Hz, 1H) 2.77-2.81 (d, 1H) 2.93 (s, 3H) 3.15-3.23 (m, 1H) 3.42 (d, J=12.91 Hz, 2H) 3.51 (s, 1H) 3.94 (br, 4H) 7.77 (br. s., 1H) 7.88-7.93 (br, 1H) 8.25-8.28 (s, 1H) 8.35-8.36 (s, 1H) 8.38-8.40 (m, 1H) 8.43 (d, J=2.35 Hz, 1H) 8.74-8.77 (s, 1H) 11.93 (s, 1H).

Example 365

N-(5-(3-(4-amino-6-methyl-1,3,5-triazin-2-yl)pyridin-2-ylamino)-2-chloropyridin-3-yl)cyclopropanesulfonamide

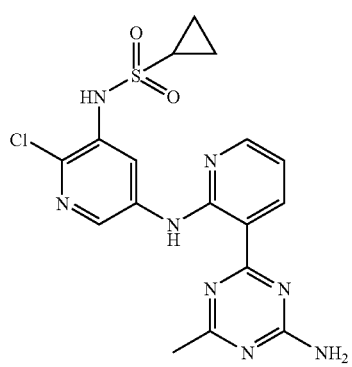 [SMILES: Cc1nc(N)nc(-c2cccnc2Nc2cnc(Cl)c(NS(=O)(=O)C3CC3)c2)n1]

Step 1. N-(5-bromo-2-chloropyridin-3-yl)-N-(cyclopropylsulfonyl)cyclopropanesulfonamide To a solution of 5-bromo-2-chloropyridin-3-amine (1.000 g, 4.82 mmol) in pyridine (10 mL) was added cyclopropanesulfonyl chloride (0.540 mL, 5.30 mmol). The resulting mixture was heated to 100° C. under $N_2$ for 20 h. Reaction was cooled to rt and was poured into the beaker which filled with EtOAc (50 ml) and hand stirred for 10 minutes. The organic layer was decanted into a round-bottom flask. The original mixture (black paste) was dissolved into DCM (3 ml) followed by adding EtOAc (20 ml) and hand stirred for 10 min and decanted to the same round-bottom flask that was mentioned earlier. The combined organic layers were concentrated in vacuo. The crude product was purified by column chromatography (80 g, 10% to 20% EtOAc in hexanes) to afford the product as a light brownish solid (880 mg). MS (ESI pos. ion) m/z: 414.8. $^1$H NMR (300 MHz, CDCl$_3$) δ ppm 1.25 (dd, J=7.67, 4.02 Hz, 4H) 1.32 (d, J=3.95 Hz, 4H) 3.14-3.32 (m, 2H) 7.97 (d, J=1.90 Hz, 1H) 8.53 (d, J=1.90 Hz, 1H).

Step 2. N-(2-chloro-5-(diphenylmethyleneamino)pyridin-3-yl)cyclopropanesulfonamide To a 20 mL microwave vial was added N-(5-bromo-2-chloropyridin-3-yl)-N-(cyclopropylsulfonyl)cyclopropanesulfonamide (0.880 g, 2.117 mmol), 4,5-bis(diphenylphosphino)-9,9-dimethylxanthene (Acros) (0.122 g, 0.212 mmol), tris(dibenzylideneacetone)dipalladium (0) (Strem) (0.097 g, 0.106 mmol), sodium tert-butoxide (Fluka) (0.814 g, 8.47 mmol), DMF (10 mL), and benzophenone imine (Aldrich) (0.426 mL, 2.54 mmol). The resulting mixture was degassed by bubbling $N_2$ for 5 min. It was sealed off and microwave heated at 130° C. for 20 min. The resulting mixture was partitioned between EtOAc and sat. NH$_4$Cl (25 mL). The aqueous layer was extracted with EtOAc (2×10 mL). The combined organic layers were dried over MgSO$_4$ and concentrated. The crude product was purified by column chromatography (80 g, 10% to 20% acetone in hexanes) to afford the desired product as a yellow foam-like solid (300 mg). MS (ESI pos. ion) m/z: 412.0. $^1$H NMR (300 MHz, CDCl$_3$) δ ppm 0.89 (d, J=7.02 Hz, 2H) 1.03 (d, J=3.07 Hz, 2H) 6.60 (br. s., 1H) 7.14 (d, J=3.65 Hz, 2H) 7.34 (d, J=6.28 Hz, 4H) 7.39-7.48 (m, 2H) 7.49-7.56 (m, 1H) 7.68-7.80 (m, 3H).

Step 3. N-(5-amino-2-chloropyridin-3-yl)cyclopropanesulfonamide

To a solution of N-(2-chloro-5-(diphenylmethyleneamino)pyridin-3-yl)cyclopropanesulfonamide (0.300 g, 0.728 mmol) in THF (5 mL) was added hydrochloric acid. In (1.092 mL, 1.092 mmol). The reaction was stirred at rt in closed system. After 30 min, LC/MS showed no sign of starting materials with desired product mass as the major peak. The reaction mixture was partitioned between EtOAc and sat. NaHCO$_3$. The aqueous layer was extracted with more EtOAc (2×10 mL). The combined organic layer were dried over MgSO$_4$ and concentrated. The crude product was purified by column chromatography (40 g, 3% MeOH in DCM) to afford the desired product as a yellow solid (170 mg). MS (ESI pos. ion) m/z: 248.0. $^1$H NMR (300 MHz, CDCL$_3$) δ ppm 1.04 (d, J=6.58 Hz, 2H) 1.13-1.32 (m, 2H) 2.51 (t, J=4.60 Hz, 1H) 3.85 (br. s., 2H) 6.63 (br. s., 1H) 7.35 (s, 1H) 7.68 (s, 1H).

Step 4. N-(5-(3-(4-amino-6-methyl-1,3,5-triazin-2-yl)pyridin-2-ylamino)-2-chloropyridin-3-yl)cyclopropanesulfonamide To a 15 mL RB flask was added N-(5-amino-2-chloropyridin-3-yl)cyclopropanesulfonamide (0.050 g, 0.202 mmol), 4-(2-fluoropyridin-3-yl)-6-methyl-1,3,5-triazin-2-amine (0.050 g, 0.242 mmol), and DMF (2.0 mL). The mixture was cooled to 0° C. under $N_2$. Sodium bis(trimethylsilyl)amide, 1.0 m solution in THF (Aldrich) (0.807 mL, 0.807 mmol) was then added to the solution in one portion. The now brugundy color mixture was stirred at 0° C. for 10 min then warmed up to rt for 30 min. The reaction mixture was poured into the beaker which had filled with 15 mL sat. $NH_4Cl$. The resulting mixture was stirred at rt for 15 h. The ppt in the solution mixture was collected by filtration. The solid was rinsed with water and dried opened to the air for 4 h. This crude product was purified by column chromatography (40 g, 3% MeOH in DCM) to afford the desired product as a yellow solid (60.0 mg). MS (ESI pos. ion) m/z: 433.0. $^1$H NMR (300 MHz, $CDCl_3$) δ ppm 0.97-1.14 (m, 2H) 1.33 (dd, J=4.60, 1.83 Hz, 2H) 2.51-2.69 (m, 4H) 5.42 (br. s., 2H) 6.75 (s, 1H) 6.92 (dd, J=7.82, 4.90 Hz, 1H) 8.32-8.45 (m, 1H) 8.56 (d, J=2.34 Hz, 1H) 8.76 (d, J=2.34 Hz, 1H) 8.87 (dd, J=7.89, 1.75 Hz, 1H) 12.36 (s, 1H).

Example 366

N-(5-(3-(4-amino-6-methyl-1,3,5-triazin-2-yl)pyridin-2-ylamino)-2-chloropyridin-3-yl)morpholine-4-sulfonamide

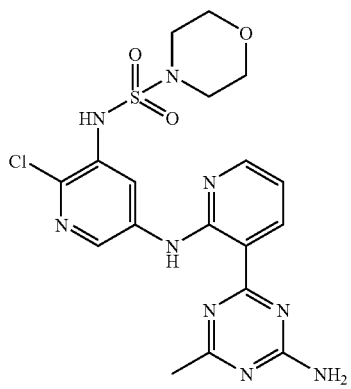 [SMILES: Cc1nc(N)nc(-c2cccnc2Nc2cnc(Cl)c(NS(=O)(=O)N3CCOCC3)c2)n1]

Step 1. N-(5-bromo-2-chloropyridin-3-yl)morpholine-4-sulfonamide

To a solution of 5-bromo-2-chloropyridin-3-amine (Small Molecules, Inc.) (1.000 g, 4.82 mmol) in pyridine (8 mL) was added 4-dimethylaminopyridine (Aldrich) (0.147 g, 1.205 mmol) and morpholine (Aldrich) (0.546 mL, 6.27 mmol). The reaction mixture was cooled to −30° C. and allowed the mixture to stir for 10 minutes. Then sulfuryl chloride (Aldrich) (0.586 mL, 7.23 mmol) was added dropwise into the reaction mixture. After the addition, the mixture was allowed to stir an additional 20 min. in the cooling bath then was allowed to warm to rt and continued to stir under $N_2$ for 20 h. The reaction mixture was poured into the beaker which filled with EtOAc (50 mL) and hand stirred for 10 minutes. The organic layer was decanted into a round-bottom flask. The original mixture (black paste) was dissolved into DCM (3 ml) followed by adding EtOAc (20 mL) and hand stirred for 10 min and decanted to the same round-bottom flask that was mentioned earlier. The combined organic layers were concentrated in-vacuo. The crude product was purified by column chromatography (80 g, 10% to 20% acetone in hexanes) to obtain the desired product as light yellow solid (800 mg). MS (ESI pos. ion) m/z: 356.8. $^1$H NMR (300 MHz, $CDCl_3$) δ ppm 3.15-3.41 (m, 4H) 3.60-3.83 (m, 4H) 6.79 (br. s., 1H) 8.08 (s, 1H) 8.23 (s, 1H).

Step 2. N-(2-chloro-5-(diphenylmethyleneamino)pyridin-3-yl)morpholine-4-sulfonamide To a 20 mL microwave vial was added N-(5-bromo-2-chloropyridin-3-yl)morpholine-4-sulfonamide (0.500 g, 1.40 mmol), 4,5-bis(diphenylphosphino)-9,9-dimethylxanthene (Acros) (0.048 g, 0.084 mmol), tris(dibenzylideneacetone)dipalladium (o) (Strem) (0.015 g, 0.017 mmol), sodium tert-butoxide (Fluka) (0.268 g, 2.8 mmol), toluene (10 mL), and benzophenone imine (Aldrich) (0.260 mL, 1.54 mmol). The resulting mixture was sealed off and microwave heated at 110° C. for 20 min. Reaction mixture was partitioned between EtOAc and Tris HCl 1M pH7. The aqueous layer was extracted with EtOAc (2×10 mL). The combined organic layers were dried over $MgSO_4$ and concentrated. The crude product was purified by column chromatography (24 g, 10% to 20% EtOAc in hexanes) to afford the desired product as a yellow foam (150.0 mg). MS (ESI pos. ion) m/z: 457.0. $^1$H NMR (300 MHz, $CDCl_3$) δ ppm 3.07 (d, J=4.38 Hz, 4H) 3.63 (d, J=4.38 Hz, 4H) 6.62 (br. s., 1H) 7.14 (d, J=3.95 Hz, 2H) 7.35 (d, J=5.85 Hz, 4H) 7.40-7.49 (m, 2H) 7.49-7.58 (m, 1H) 7.63 (s, 1H) 7.74 (d, J=7.16 Hz, 2H).

Step 3. N-(5-amino-2-chloropyridin-3-yl)morpholine-4-sulfonamide

To a solution of N-(2-chloro-5-(diphenylmethyleneamino)pyridin-3-yl)morpholine-4-sulfonamide (0.150 g, 0.328 mmol) in THF (3 mL) was added hydrochloric acid, 2 n (JT Baker) (0.020 mL, 0.657 mmol). The reaction was stirred at rt in closed system for 20 min. The reaction mixture was partitioned between EtOAc and sat. $NaHCO_3$. The aqueous layer was extracted with EtOAc (2×10 mL). The combined organic layer were dried over $MgSO_4$ and concentrated. The crude product was purified by column chromatography (24 g, 3% MeOH in DCM) to afford the desired product as a white foam-like solid (70.0 mg). MS (ESI pos. ion) m/z: 293.0. $^1$H NMR (300 MHz, $CDCl_3$) δ ppm 3.16-3.32 (m, 4H) 3.61-3.74 (m, 4H) 3.84 (br. s., 2H) 6.67 (br. s., 1H) 7.31 (d, J=2.34 Hz, 1H) 7.64 (d, J=2.19 Hz, 1H).

Step 4. N-(5-(3-(4-amino-6-methyl-1,3,5-triazin-2-yl)pyridin-2-ylamino)-2-chloropyridin-3-yl)morpholine-4-sulfonamide To a 15 mL RB flask was added N-(5-amino-2-chloropyridin-3-yl)morpholine-4-sulfonamide (0.065 g, 0.222 mmol), 4-(2-fluoropyridin-3-yl)-6-methyl-1,3,5-triazin-2-amine (0.055 g, 0.266 mmol), and DMF (3.0 mL). The mixture was cooled to 0° C. under $N_2$. sodium bis(trimethylsilyl)amide, 1.0 m in THF (Aldrich) (0.888 mL, 0.888 mmol) was added to the solution in one portion. The now dark brown mixture was stirred at 0° C. for 10 min then warmed up to rt and stirred for 1 h. The reaction mixture was quenched with sat. $NH_4Cl$ and extracted with $CHCl_3$ (3×10 mL). The combined organic layers were dried over $MgSO_4$ and concentrated. The crude product was purified by column chromatography (24 g, 3% MeOH in DCM) to afford the desired product as a yellow solid (42.0 mg). MS (ESI pos. ion) m/z: 478.0. $^1$H NMR (300 MHz, DMSO-$d_6$) δ ppm 2.45 (s, 3H) 3.15 (br. s., 4H) 3.61 (br. s., 4H) 7.03 (dd, J=7.53, 4.60 Hz, 1H) 7.79 (br. s., 1H) 7.91 (br. s., 1H) 8.38 (d, J=3.36 Hz, 1H) 8.51 (s, 1H) 8.82 (d, J=5.41 Hz, 2H) 9.78 (s, 1H) 12.26 (s, 1H).

Example 367

N-(5-(3-(4-amino-6-methyl-1,3,5-triazin-2-yl)pyridin-2-ylamino)-2-chloropyridin-3-yl)-N-isopropyl-N-methylaminosulfamide

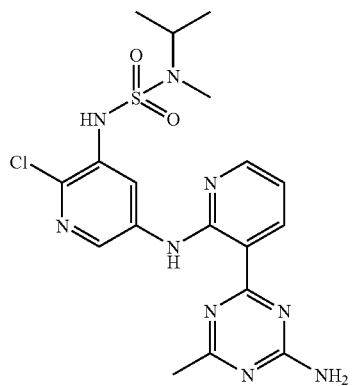 [SMILES: Cc1nc(N)nc(-c2cccnc2Nc2cnc(Cl)c(NS(=O)(=O)N(C)C(C)C)c2)n1]

Step 1. N-(5-bromo-2-chloropyridin-3-yl)-N-isopropyl-N-methylaminosulfamide

To a solution of 5-bromo-2-chloropyridin-3-amine (Small Molecules, Inc.) (1.000 g, 4.82 mmol) in pyridine (8 mL) was added n-isopropylmethylamine (Aldrich) (0.651 mL, 6.27 mmol) and 4-dimethylaminopyridine (Aldrich) (0.147 g, 1.205 mmol). The reaction mixture was cooled to −30° C. and allowed the mixture to stir for 10 minutes. Sulfuryl chloride (Aldrich) (0.586 mL, 7.23 mmol) was added dropwise into the mixture. After the addition, the mixture was allowed to stir for additional 20 min. in the cooling bath then was allowed to warm to rt and continued to stir under $N_2$ for 20 h. The reaction mixture was poured into the beaker which filled with EtOAc (30 ml) and hand-stirred for 10 minutes. The organic layer was decanted into a round-bottom flask. The original mixture (black paste) was dissolved into DCM (3 ml) followed by adding EtOAc (20 ml) and hand-stirred for 10 min and decanted to the same round-bottom flask that was mentioned earlier. The combined organic layers were concentrated in-vacuo. The crude product was purified by column chromatography (120 g, 10% to 20% EtOAc in hexanes) to obtain the desired porduct as light brown solid (660 mg). MS (ESI pos. ion) m/z: 342.1. $^1$H NMR (300 MHz, CDCl$_3$) δ ppm 1.00-1.26 (m, 6H) 2.76 (s, 3H) 4.19 (dt, J=13.37, 6.61 Hz, 1H) 6.85 (br. s., 1H) 7.94 (d, J=2.19 Hz, 1H) 8.17 (d, J=2.19 Hz, 1H).

Step 2. N-(2-chloro-5-(diphenylmethyleneamino)pyridin-3-yl)-N-isopropyl-N-methylaminosulfamide To a 20 mL microwave vial, which was degassed by bubbling $N_2$, was added N-(5-bromo-2-chloropyridin-3-yl)-N-isopropyl-N-methylaminosulfamide (0.660 g, 1.926 mmol), 4,5-bis(diphenylphosphino)-9,9-dimethylxanthene (0.111 g, 0.193 mmol), tris(dibenzylideneacetone)dipalladium (o) (0.088 g, 0.096 mmol), sodium tert-butoxide (0.740 g, 7.70 mmol), DMF (12 mL), and benzophenone imine (0.356 mL, 2.119 mmol). The resulting mixture was sealed off and microwave heated at 140° C. for 20 min. The resulting mixture was partitioned between EtOAc and sat. NH$_4$Cl (25 mL). The aqueous layer was extracted with EtOAc (2×10 mL). The combined organic layers were dried over MgSO$_4$ and concentrated. The crude product was purified by column chromatography (80 g, 10% to 20% EtOAc in hexanes) to afford the desired product as a yellow foam-like solid (270 mg). MS (ESI pos. ion) m/z: 442.8. $^1$H NMR (300 MHz, CDCl$_3$) δ ppm 1.04 (d, J=6.72 Hz, 6H) 2.66 (s, 3H) 3.99 (dt, J=13.52, 6.69 Hz, 1H) 6.70 (br. s., 1H) 7.13 (d, J=5.26 Hz, 2H) 7.28-7.37 (m, 4H) 7.39-7.47 (m, 2H) 7.49-7.59 (m, 2H) 7.74 (d, J=7.02 Hz, 2H).

Step 3. N-(5-bromo-2-chloropyridin-3-yl)-N-isopropyl-N-methylaminosulfamide

To a solution of N-(2-chloro-5-(diphenylmethyleneamino)pyridin-3-yl)-N-isopropyl-N-methylaminosulfamide (0.250 g, 0.564 mmol) in THF (3 mL) was added hydrochloric acid, 2n (0.423 mL, 0.847 mmol). The reaction was stirred at rt in closed system for 20 min. The reaction mixture was partitioned between EtOAc and sat. NaHCO$_3$. The aqueous layer was extracted with EtOAc (2×10 mL). The combined organic layer were dried over MgSO$_4$ and concentrated. The crude product was purified by column chromatography (24 g, 3% MeOH in DCM) to afford the desired product as a white foam-like solid (110.0 mg). MS (ESI pos. ion) m/z: 279.0. $^1$H NMR (300 MHz, CDCl$_3$) δ ppm 1.10 (d, J=6.72 Hz, 6H) 2.75 (s, 3H) 3.80 (br. s., 2H) 4.14 (dt, J=13.34, 6.70 Hz, 1H) 6.74 (br. s., 1H) 7.21 (d, J=2.63 Hz, 1H) 7.59 (d, J=2.63 Hz, 1H).

Step 4. N-(5-(3-(4-amino-6-methyl-1,3,5-triazin-2-yl)pyridin-2-ylamino)-2-chloropyridin-3-yl)-N-isopropyl-N-methylaminosulfamide To a 15 mL RB flask was added N-(5-bromo-2-chloropyridin-3-yl)-N-isopropyl-N-methylaminosulfamide (0.050 g, 0.179 mmol), 4-(2-fluoropyridin-3-yl)-6-methyl-1,3,5-triazin-2-amine (0.044 g, 0.215 mmol) and DMF (3.0 mL). The mixture was cooled to 0° C. under $N_2$. Sodium bis(trimethylsilyl)amide, 1.0 m solution in THF (Aldrich) (0.717 mL, 0.717 mmol) was then added to the solution in one portion. The now dark brown mixture was stirred at 0° C. for 10 min then warmed up to rt for 30 min. The reaction mixture was poured into the beaker which had filled with 15 mL sat. NH$_4$Cl. The resulting mixture was stirred for 1 h. The ppt was collected by filtration; the ppt was rinsed with water and dried opened to the air and later dried in the vacuum oven for 20 h to afford the product as light brown solid (71 mg). MS (ESI pos. ion) m/z: 464.0. $^1$H NMR (300 MHz, DMSO-$d_6$) δ ppm 1.03 (d, J=6.58 Hz, 6H) 2.45 (s, 3H) 2.72 (s, 3H) 4.07 (dt, J=13.23, 6.54 Hz, 1H) 7.03 (dd, J=7.82, 4.75 Hz, 1H) 7.79 (br.

s., 1H) 7.91 (br. s., 1H) 8.30-8.41 (m, 1H) 8.44 (d, J=2.19 Hz, 1H) 8.77-8.85 (m, 1H) 8.88 (d, J=2.19 Hz, 1H) 9.46 (s, 1H) 12.28 (s, 1H).

Example 368

N5-(3-(4-amino-6-methyl-1,3,5-triazin-2-yl)-5-methoxypyridin-2-yl)-2-chloropyridine-3,5-diamine

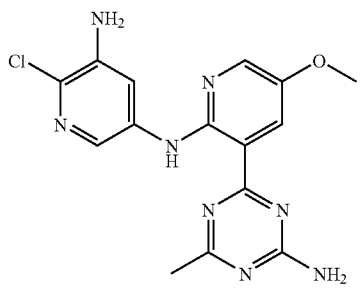 [SMILES: COc1cnc(Nc2cnc(Cl)c(N)c2)c(-c2nc(C)nc(N)n2)c1]

Step 1. di-tert-butyl 5-bromo-2-chloropyridin-3-ylcarbamate

To a solution of 5-bromo-2-chloropyridin-3-amine (1.000 g, 4.82 mmol) in DMF (8 mL) at 0° C. was added sodium hydride, 60% dispersion in mineral oil (Lancaster) (0.272 mL, 6.27 mmol) portionwise. After stirred for 20 min, di-tert-butyl dicarbonate (Fluka) (2.52 g, 11.57 mmol) was then added. After the addition, ice bath was removed. The reaction mixture was warmed up and stirred at rt under $N_2$ for 3 h. The reaction mixture was poured into the beaker which had filled with sat. $NH_4Cl$ and stirred for 2 hours. The precipitate in the solution mixture was collected by filtration. The solid was rinsed with water and dried opened to the air for 20 h to afford the product as light brown solid (1.6 g). MS (ESI pos. ion) m/z: 407.0. $^1$H NMR (300 MHz, $CDCl_3$) δ ppm 1.44 (s, 18H) 7.73 (d, J=2.19 Hz, 1H) 8.43 (d, J=2.19 Hz, 1H).

Step 2. tert-butyl 2-chloro-5-(diphenylmethyleneamino)pyridin-3-ylcarbamate

To a 20 mL microwave vial was added di-tert-butyl 5-bromo-2-chloropyridin-3-ylcarbamate (0.500 g, 1.226 mmol), 4,5-bis(diphenylphosphino)-9,9-dimethylxanthene (Acros) (0.071 g, 0.123 mmol), tris(dibenzylideneacetone)dipalladium (0) (Strem) (0.056 g, 0.061 mmol), sodium tert-butoxide (Fluka) (0.471 g, 4.91 mmol), DMF (12 mL), and benzophenone imine (Aldrich) (0.226 mL, 1.349 mmol). The resulting mixture was degassed by bubbling $N_2$ for 5 min. It was sealed off and microwave heated at 130° C. for 20 min. Reaction mixture was partitioned between EtOAc and sat. $NH_4Cl$. The aqueous layer was extracted with EtOAc (2×10 mL). The combined organic layers were dried over $MgSO_4$ and concentrated. The crude product was purified by column chromatography (80 g, 10% to 20% EtOAc in hexanes) to afford the desired product as a yellow film (280 mg). MS (ESI pos. ion) m/z: 408.0. $^1$H NMR (300 MHz, $CDCl_3$) δ ppm 1.52 (s, 9H) 6.87 (br. s., 1H) 7.15 (d, J=3.36 Hz, 2H) 7.29-7.35 (m, 3H) 7.37-7.46 (m, 3H) 7.47-7.54 (m, 1H) 7.75 (d, J=7.16 Hz, 2H) 8.05 (d, J=2.05 Hz, 1H).

Step 3. tert-butyl 5-amino-2-chloropyridin-3-ylcarbamate

To a solution of tert-butyl 2-chloro-5-(diphenylmethyleneamino)pyridin-3-ylcarbamate (0.280 g, 0.686 mmol) in THF (5 mL) was added hydrochloric acid, 1n (JT Baker) (0.031 mL, 1.030 mmol). The reaction was stirred at rt in closed system for 20 min. The reaction mixture was partitioned between EtOAc/sat. $NaHCO_3$. The aqueous layer was extracted with EtOAc (2×10 mL). The combined organic layer were dried over $MgSO_4$ and concentrated. The crude product was purified by column chromatography (24 g, 3% MeOH in DCM) to afford the desired product as a white foam-like solid (135.0 mg). MS (ESI pos. ion) m/z: 244.1. $^1$H NMR (300 MHz, $CDCl_3$) δ ppm 1.54 (s, 9H) 3.73 (br. s., 2H) 6.93 (br. s., 1H) 7.52 (d, J=2.63 Hz, 1H) 7.94 (d, J=2.63 Hz, 1H).

Step 4. tert-butyl 5-(3-(4-amino-6-methyl-1,3,5-triazin-2-yl)-5-methoxypyridin-2-ylamino)-2-chloropyridin-3-ylcarbamate To a 15 mL RB flask was added tert-butyl 5-amino-2-chloropyridin-3-ylcarbamate (0.130 g, 0.533 mmol), 4-(2-fluoro-5-methoxypyridin-3-yl)-6-methyl-1,3,5-triazin-2-amine (Example 330 step 5) (0.151 g, 0.640 mmol), and DMF (2.0 mL). The mixture was cooled to 0° C. under $N_2$. Sodium bis(trimethylsilyl)amide, 1.0 m in THF (Aldrich) (2.134 mL, 2.134 mmol) was then added to the solution in one portion. The now burgundy color mixture was stirred at 0° C. for 10 min then warmed up to rt and stirred for 30 min. The reaction mixture was poured into the beaker which had filled with 15 mL sat. $NH_4Cl$. The resulting mixture was stirred at rt for 5 h. The ppt in the solution mixture was collected by filtration. The solid was rinsed with water and dried opened to the air for 4 h. This crude product was purified by column chromatography (40 g, 3% MeOH in DCM) to afford the desired product as a yellow solid (210 mg). MS (ESI pos. ion) m/z: 459.0. $^1$H NMR (300 MHz, DMSO-$d_6$) δ ppm 1.47 (s, 9H) 2.45 (s, 3H) 3.85 (s, 3H) 7.80 (br. s., 1H) 7.94 (br. s., 1H) 8.20 (d, J=3.07 Hz, 1H) 8.42 (d, J=3.07 Hz, 1H) 8.58 (d, J=2.34 Hz, 1H) 8.63 (d, J=2.34 Hz, 1H) 8.75 (s, 1H) 11.91 (s, 1H).

Step 5. N5-(3-(4-amino-6-methyl-1,3,5-triazin-2-yl)-5-methoxypyridin-2-yl)-2-chloropyridine-3,5-diamine To a 20 mL scintillation vial which contained tert-butyl 5-(3-(4-amino-6-methyl-1,3,5-triazin-2-yl)-5-methoxypyridin-2-ylamino)-2-chloropyridin-3-ylcarbamate (0.210 g, 0.458 mmol) in DCM (5 mL) was added trifluoroacetic acid (Aldrich) (0.170 mL, 2.288 mmol). The resulting mixture was capped and stirred at rt in closed system for 1 h. The reaction mixture was first neutralized with sat. $NaHCO_3$ then extracted with $CHCl_3$ (3×10 mL). The combined organic layers were dried over $MgSO_4$ and concentrated. The crude product was purified using the column chromatography (40 g, 3% to 5% MeOH in DCM) to afford the desired product as a yellow solid (135 mg). MS (ESI pos. ion) m/z: 359.0. Calc'd exact mass for $C_{15}H_{15}ClN_8O$: 358.1. $^1$H NMR (400 MHz, DMSO-$d_6$) δ ppm 2.45 (s, 3H) 3.84 (s, 3H) 5.43 (s, 2H) 7.78 (br. s., 1H) 7.86 (br. s., 1H) 7.89 (d, J=2.35 Hz, 1H) 7.94 (d, J=2.15 Hz, 1H) 8.16 (d, J=3.13 Hz, 1H) 8.40 (d, J=3.13 Hz, 1H) 11.75 (s, 1H).

Example 369

N-(5-(3-(4-amino-6-methyl-1,3,5-triazin-2-yl)-5-(1-morpholinoethyl)pyridin-2-ylamino)-2-chloropyridin-3-yl)methanesulfonamide

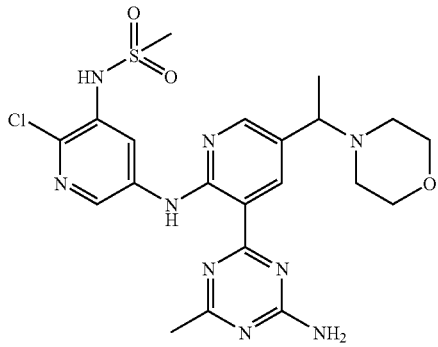

Step 1.
2-fluoro-5-(1-morpholinoethyl)pyridin-3-ylboronic acid

To a solution of diisopropylamine (Aldrich) (0.640 mL, 4.57 mmol) in THF (10 mL) at −40° C. in 100 mL 3-neck round-bottom flask was added butyllithium solution, 1.6 m in hexanes (Aldrich) (2.85 mL, 4.57 mmol) dropwise via the addition funnel After the addition, it was continued to stir at −40° C. for 20 min then cooled to −78° C. To this reaction mixture was added 4-(1-(6-fluoropyridin-3-yl)ethyl)morpholine (Example 339 step 3) (0.800 g, 3.81 mmol) in THF (10 mL) dropwise via the addition funnel It was continued to stir at −78° C. after the addition. After 1 h, triisopropyl borate (Aldrich) (1.309 mL, 5.71 mmol) was added into the reaction mixture dropwise via the addition funnel After the addition, it was continued to stir at −78° C. for 20 min then removed the cooling bath and slowly warmed up to rt and stirred for 1 h. The reaction mixture was quenched with 1N NaOH (15 mL). The aqueous layer was extracted with EtOAc (2×15 mL)—the organic layer was discard; the aqueous layer was acidified to a pH of about 5 to 6 using 5 N HCl. The resulting mixture was extracted with EtOAc (2×15 mL) and CHCl$_3$ (2×15 mL). The combined organic layers were dried over MgSO$_4$ and concetrated to afford the product as a light brown amorphous solid (780 mg). MS (ESI pos. ion) m/z: 255.1. $^1$H NMR (400 MHz, CDCl$_3$) δ ppm 1.38 (dd, J=11.44, 6.75 Hz, 3H) 2.36 (d, J=4.30 Hz, 2H) 2.45-2.60 (m, 2H) 3.35-3.47 (m, 1H) 3.63-3.77 (m, 4H) 8.15 (dd, J=9.00, 2.35 Hz, 1H) 8.19-8.27 (m, 2H) 8.33 (d, J=9.00 Hz, 1H).

Step 2. 4-(2-fluoro-5-(1-morpholinoethyl)pyridin-3-yl)-6-methyl-1,3,5-triazin-2-amine To a 20 mL microwave vial was added 4-chloro-6-methyl-1,3,5-triazin-2-amine (0.300 g, 2.075 mmol), 2-fluoro-5-(1-morpholinoethyl)pyridin-3-ylboronic acid (0.580 g, 2.283 mmol), Amphos (Aldrich) (0.073 g, 0.104 mmol), potassium acetate (Aldrich) (0.611 g, 6.23 mmol), EtOH (9 mL), and water (0.9 mL). The resulting mixture was degassed by bubbling N$_2$ for 5 min then sealed off and microwave heated at 100° C. for 20 min. The reaction mixture was partitioned between 25% IPA in CHCl$_3$ (1% NH$_4$OH) (30 mL) and water (50 mL). The aqueous layer was extracted with more 25% IPA in CHCl$_3$ (2×10 mL). The combined organic layers were dried over MgSO$_4$ and concentrated. The crude product was purified by column chromatography (40 g, 3% MeOH in DCM) to afford the desired product as a white solid (200 mg). MS (ESI pos. ion) m/z: 319.1. $^1$H NMR (300 MHz, CDCl$_3$) δ ppm 1.42 (d, J=6.58 Hz, 3H) 2.32-2.47 (m, 2H) 2.49-2.63 (m, 5H) 3.50 (q, J=6.33 Hz, 1H) 3.71 (t, J=4.38 Hz, 4H) 5.49 (br. s., 2H) 8.29 (s, 1H) 8.46 (dd, J=9.13, 2.27 Hz, 1H).

Step 3. N-(5-(3-(4-amino-6-methyl-1,3,5-triazin-2-yl)-5-(1-morpholinoethyl)pyridin-2-ylamino)-2-chloropyridin-3-yl)methanesulfonamide To a 15 mL round-bottom flask was added 4-(2-fluoro-5-(1-morpholinoethyl)pyridin-3-yl)-6-methyl-1,3,5-triazin-2-amine (0.100 g, 0.314 mmol), N-(5-amino-2-chloropyridin-3-yl)methanesulfonamide (0.084 g, 0.377 mmol), and DMF (2.0 mL). The mixture was cooled to 0° C. under N$_2$. Sodium bis(trimethylsilyl)amide, 1.0 m in THF (0.254 mL, 1.256 mmol) was then added to the solution in one portion. The now brugundy color mixture was stirred at 0° C. for 10 min then warmed up to rt and stir for 1 h. The reaction mixture was extracted with EtOAc (2×10 mL), CHCl$_3$ (2×10 mL). The combined organic layer were dried over MgSO$_4$ and concentrated. The crude product was purified by column chromatography (40 g, 3% MeOH in DCM) to afford the desired product as a yellow solid (100 mg). MS (ESI pos. ion) m/z: 520.1. $^1$H NMR (300 MHz, DMSO-d$_6$) δ ppm 1.34 (d, J=6.58 Hz, 3H) 2.33 (br. s., 2H) 2.46 (s, 5H) 3.13 (s, 3H) 3.46 (d, J=4.82 Hz, 1H) 3.57 (br. s., 4H) 7.69-8.00 (m, 2H) 8.32 (s, 1H) 8.66 (d, J=2.48 Hz, 2H) 8.74 (s, 1H) 9.65 (br. s., 1H).

Separation of Isomers

A mixture of isomers of N-(2-chloro-5-(3-(6-amino-2-methylpyrimidin-4-yl)-5-(1-morpholinoethyl)pyridin-2-ylamino)pyridin-3-yl)-N,N-dimethylaminosulfamide were separated using chiral SFC preparative chromatography. The following conditions were used:

Column: IC (21 mm×25 cm)

Mobile Phase: 65:35 (A:B)

A: Liquid CO$_2$

B: Isopropanol (0.2% diethylamine)

Flow Rate: 70 mL/min

Oven/column temp: 40° C.

The two separate peaks contained the two enantiomers were collected, concentrated, and dried under high vacuum to afford the two enantiomers. The absolute stereochemistry was not determined (See Examples 72)

Example 370

N-(5-(3-(4-amino-6-methyl-1,3,5-triazin-2-yl)-5-(1-morpholinoethyl)pyridin-2-ylamino)-2-chloropyridin-3-yl)-N,N-dimethylaminosulfamide

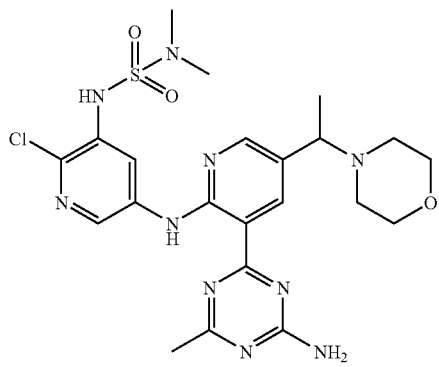 [SMILES: Cc1nc(N)nc(-c2cc(C(C)N3CCOCC3)cnc2Nc2cnc(Cl)c(NS(=O)(=O)N(C)C)c2)n1]

To a 15 mL round-bottom flask was added 4-(2-fluoro-5-(1-morpholinoethyl)pyridin-3-yl)-6-methyl-1,3,5-triazin-2-amine (0.100 g, 0.314 mmol), N-(5-bromo-2-chloropyridin-3-yl)-N,N-dimethylaminosulfamide (0.095 g, 0.377 mmol), and DMF (2.0 mL). The mixture was cooled to 0° C. under $N_2$. Sodium bis(trimethylsilyl)amide, 1.06 m solution in THF (Aldrich) (0.244 mL, 1.256 mmol) was added to the solution in one portion. The now burgundy color mixture was stirred at 0° C. for 10 min then warmed up to rt and stirred for 1 h. The reaction mixture was poured into the beaker which had filled with 15 mL sat. $NH_4Cl$. The resulting mixture was stirred at rt for 2 h. The ppt in the solution mixture was collected by filtration. The solid was rinsed with water and dried in the vacuum oven for 15 h. This crude product was purified by column chromatography (24 g, 3% MeOH in DCM) to afford the desired product as a yellow solid (120 mg). MS (ESI pos. ion) m/z: 548.9. $^1$H NMR (400 MHz, DMSO-$d_6$) δ ppm 1.34 (d, J=6.46 Hz, 3H) 2.33 (br. s., 2H) 2.46 (s, 5H) 2.79 (s, 6H) 3.46 (br. s., 1H) 3.56 (br. s., 4H) 7.79 (br. s., 1H) 7.94 (br. s., 1H) 8.31 (d, J=2.35 Hz, 1H) 8.54 (d, J=2.54 Hz, 1H) 8.75 (d, J=2.15 Hz, 1H) 8.83 (d, J=2.35 Hz, 1H) 9.59 (s, 1H) 12.29 (s, 1H).

Separation of Isomers

A mixture of isomers of N-(2-chloro-5-(3-(6-amino-2-methylpyrimidin-4-yl)-5-(1-morpholinoethyl)pyridin-2-ylamino)pyridin-3-yl)-N,N-dimethylaminosulfamide were separated using chiral SFC preparative chromatography. The following conditions were used:

Column: OZ—H (21 mm×25 cm)
Mobile Phase: 50:50 (A:B)
A: Liquid $CO_2$
B: MeOH (0.2% diethylamine)
Flow Rate: 60 mL/min
Oven/column temp: 35° C.

The two separate peaks contained the two enantiomers were collected, concentrated, and dried under high vacuum to afford the two enantiomers. The absolute stereochemistry was not determined (ee examples 373 and 374).

Example 371 and 372

(5-(3-(4-amino-6-methyl-1,3,5-triazin-2-yl)-5-(1-morpholinoethyl)pyridin-2-ylamino)-2-chloropyridin-3-yl)methanesulfonamide; and)-N-(5-(3-(4-amino-6-methyl-1,3,5-triazin-2-yl)-5-(1-morpholinoethyl)pyridin-2-ylamino)-2-chloropyridin-3-yl)methanesulfonamide

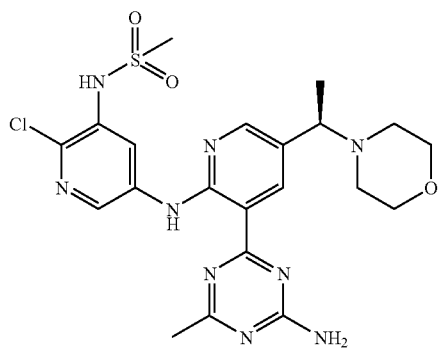 [SMILES: Cc1nc(N)nc(-c2cc([C@@H](C)N3CCOCC3)cnc2Nc2cnc(Cl)c(NS(C)(=O)=O)c2)n1]

MS (ESI pos. ion) m/z: 520.1. $^1$H NMR (300 MHz, DMSO-$d_6$) δ ppm 1.34 (d, J=6.58 Hz, 3H) 2.33 (br. s., 2H) 2.46 (s, 5H) 3.13 (s, 3H) 3.46 (d, J=4.82 Hz, 1H) 3.57 (br. s., 4H) 7.69-8.00 (m, 2H) 8.32 (s, 1H) 8.66 (d, J=2.48 Hz, 2H) 8.74 (s, 1H) 9.65 (br. s., 1H).

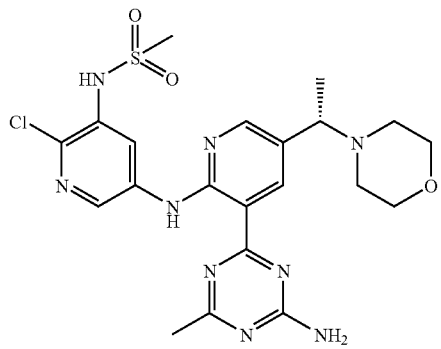 [SMILES: Cc1nc(N)nc(-c2cc([C@H](C)N3CCOCC3)cnc2Nc2cnc(Cl)c(NS(C)(=O)=O)c2)n1]

MS (ESI pos. ion) m/z: 520.1. $^1$H NMR (400 MHz, CDCl$_3$) δ ppm 1.43 (br. s., 3H) 2.33-2.58 (m, 3H) 2.60 (s, 4H) 3.14 (s, 3H) 3.43 (br. s., 1H) 3.73 (br. s., 4H) 5.51 (br. s., 2H) 6.78 (br.

s., 1H) 8.38 (d, J=1.76 Hz, 1H) 8.56 (d, J=2.35 Hz, 1H) 8.78 (d, J=2.35 Hz, 2H) 12.40 (br. s., 1H).

Example 373 and 374

(R)-N-(5-(3-(4-amino-6-methyl-1,3,5-triazin-2-yl)-5-(1-morpholinoethyl)pyridin-2-ylamino)-2-chloropyridin-3-yl)-N,N-dimethylaminosulfamide; and (S)-N-(5-(3-(4-amino-6-methyl-1,3,5-triazin-2-yl)-5-(1-morpholinoethyl)pyridin-2-ylamino)-2-chloropyridin-3-yl)-N,N-dimethylaminosulfamide

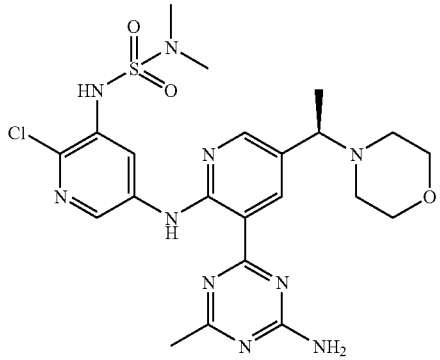 [SMILES: Cc1nc(N)nc(-c2cc([C@@H](C)N3CCOCC3)cnc2Nc2cnc(Cl)c(NS(=O)(=O)N(C)C)c2)n1]

MS (ESI pos. ion) m/z: 548.9. $^1$H NMR (300 MHz, CDCl$_3$) δ ppm 1.36-1.50 (m, 3H) 2.36-2.47 (m, 2H) 2.47-2.57 (m, 2H) 2.61 (s, 3H) 2.96 (s, 6H) 3.42 (d, J=6.72 Hz, 1H) 3.72 (t, J=4.38 Hz, 4H) 5.49 (br. s., 2H) 8.33 (d, J=2.34 Hz, 1H) 8.43 (d, J=2.34 Hz, 1H) 8.78 (d, J=2.19 Hz, 1H) 8.82 (d, J=2.48 Hz, 1H) 12.35 (s, 1H).

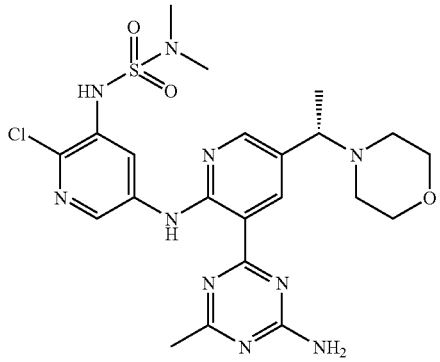 [SMILES: Cc1nc(N)nc(-c2cc([C@H](C)N3CCOCC3)cnc2Nc2cnc(Cl)c(NS(=O)(=O)N(C)C)c2)n1]

MS (ESI pos. ion) m/z: 548.9. $^1$H NMR (300 MHz, CDCl$_3$) δ ppm 1.43 (br. s., 3H) 2.30-2.57 (m, 4H) 2.61 (s, 3H) 2.96 (s, 6H) 3.41 (br. s., 1H) 3.73 (br. s., 4H) 5.50 (br. s., 2H) 6.78 (br. s., 1H) 8.34 (br. s., 1H) 8.42 (d, J=2.34 Hz, 1H) 8.81 (d, J=2.34 Hz, 2H) 12.36 (br. s., 1H).

Example 375

N-(5-(3-(6-amino-2-methylpyrimidin-4-yl)pyridin-2-ylamino)-2-chloropyridin-3-yl)-N,N-dimethylaminosulfamide

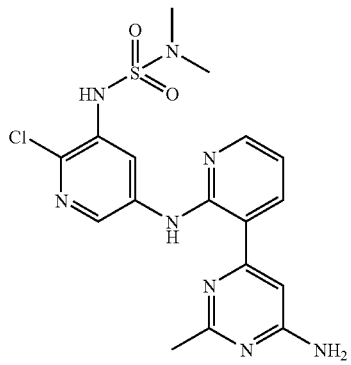 [SMILES: Cc1nc(N)cc(-c2cccnc2Nc2cnc(Cl)c(NS(=O)(=O)N(C)C)c2)n1]

Step 1.
6-(2-fluoropyridin-3-yl)-2-methylpyrimidin-4-amine

To a 20 mL microwave vials was added 4-Amino-6-chloro-2-methylpyrimidine (SynChem) (0.500 g, 3.48 mmol), 2-fluoro-3-pyridineboronic acid (Aldrich) (0.687 g, 4.88 mmol), Amphos (Aldrich) (0.123 g, 0.174 mmol), potassium acetate (Aldrich) (0.653 mL, 10.45 mmol), EtOH (12 mL), and water (1.2 mL). The vial was degassed by bubbling N$_2$ for 5 min then sealed off and microwave heated at 100° C. for 20 min. The reaction mixture was partitioned between EtOAc and water. The aqueous layer was extracted with EtOAc (2×10 mL). The combined organic layers were dried over MgSO$_4$ and concentrated. The crude product was purified by column chromatography (80 g, 20% to 40% acetone in hexanes) to afford the desired product as a yellow solid (600 mg). MS (ESI pos. ion) m/z: 205.1. $^1$H NMR (300 MHz, CDCl$_3$) δ ppm 2.59 (s, 3H) 4.96 (br. s., 2H) 6.89 (s, 1H) 7.34 (ddd, J=7.34, 4.93, 1.90 Hz, 1H) 8.27 (dd, J=3.00, 1.53 Hz, 1H) 8.66 (ddd, J=9.76, 7.64, 2.05 Hz, 1H).

Step 2. N-(5-(3-(6-amino-2-methylpyrimidin-4-yl)pyridin-2-ylamino)-2-chloropyridin-3-yl)-N,N-dimethylaminosulfamide To a 5 mL microwave vial was added 6-(2-fluoropyridin-3-yl)-2-methylpyrimidin-4-amine (0.450 g, 2.204 mmol), N-(5-bromo-2-chloropyridin-3-yl)-N,N-dimethylaminosulfamide (0.608 g, 2.424 mmol), hydrochloric acid 5.0 normal solution (JT Baker) (0.134 mL, 4.41 mmol), and EtOH (10 mL). The resulting mixture was sealed off and microwave heated at 160° C. for 20 min. Solvent was concentrated. The crude product was purified by column chromatography (40 g, 20% to 40% acetone in hexanes) to afford the desired product as a light brown solid (60 mg). MS (ESI pos. ion) m/z: 434.9. $^1$H NMR (300 MHz, DMSO-d$_6$) δ ppm 2.52 (s, 3H) 2.79 (s, 6H) 6.78 (s, 1H) 7.01 (dd, J=7.67, 4.90 Hz, 1H) 7.06 (br. s., 2H) 8.12 (d, J=7.75 Hz, 1H) 8.31 (d, J=4.68 Hz, 1H) 8.51 (d, J=2.19 Hz, 1H) 8.56 (s, 1H) 9.57 (s, 1H) 12.69 (s, 1H).

Example 376

N-(5-(3-(4-amino-6-methyl-1,3,5-triazin-2-yl)-5-(2-methoxyethoxy)pyridin-2-ylamino)-2-methylpyridin-3-yl)methanesulfonamide

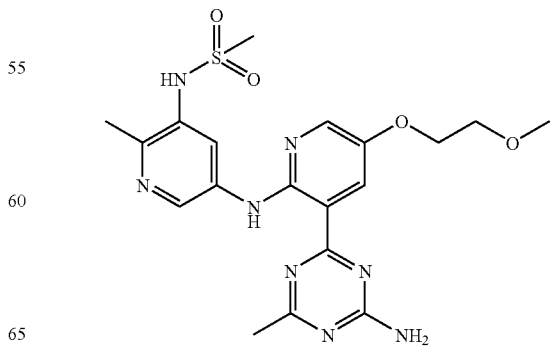

Step 1. N-(5-bromo-2-methylpyridin-3-yl)-N-(methylsulfonyl)methanesulfonamide To a solution of 5-bromo-2-methylpyridin-3-amine (PharmaBlock) (2.000 g, 10.69 mmol) in pyridine (15.0 mL) was added 4-dimethylaminopyridine (Aldrich) (0.131 g, 1.069 mmol) and methanesulfonyl chloride (2.5 mL, 32.1 mmol). The resulting mixture was heated to 100° C. under $N_2$ for 2 h. Reaction was cooled to rt. The reaction mixture was poured into the beaker which filled with EtOAc (50 ml) and hand stirred for 10 minutes. The organic layer was decanted into a round-bottom flask. The original mixture (black paste) was dissolved into DCM (3 ml) followed by adding EtOAc (20 ml) and hand stirred for 10 min and decanted to the same round-bottom flask that was mentioned earlier. The combined organic layers were concentrated in-vacuo. The crude product was purified by column chromatography (120 g, 10% to 20% acetone in hexanes) to afford the desired product as light brown solid (1.1 g). MS (ESI pos. ion) m/z: 342.8. $^1$H NMR (300 MHz, $CDCl_3$) δ ppm 2.64 (s, 3H) 3.47 (s, 6H) 7.73 (d, J=2.05 Hz, 1H) 8.67 (d, J=2.05 Hz, 1H).

Step 2. N-(5-(diphenylmethyleneamino)-2-methylpyridin-3-yl)methanesulfonamide To two 20 mL microwave vials were added N-(5-bromo-2-methylpyridin-3-yl)-N-(methylsulfonyl)methanesulfonamide (1.300 g, 3.79 mmol) (780 mg each), 4,5-bis(diphenylphosphino)-9,9-dimethylxanthene (Acros) (0.219 g, 0.379 mmol) (121 mg each), tris(dibenzylideneacetone)dipalladium (o) (Strem) (0.173 g, 0.189 mmol) (104 mg each), sodium tert-butoxide (Fluka) (1.092 g, 11.36 mmol) (655 mg), DMF (12 mL each vial), and benzophenone imine (Aldrich) (0.699 mL, 4.17 mmol) (0.420 mL each). Both resulting mixtures were degassed by bubbling $N_2$ for 5 min then sealed off and microwave heated at 130° C. for 20 min. LC/MS showed no sign of starting material mass with desired product mass as the major peak on both vials. Both reaction mixtures were combined and partitioned between EtOAc and sat. $NH_4Cl$. The aqueous layer was extracted with EtOAc (2×15 mL). The combined organic layers were dried over $MgSO_4$ and concentrated. The crude product was purified by column chromatography (120 g, 20% to 40% acetone in hexanes) to afford the desired product as a yellow foam-like solid (430 mg). MS (ESI pos. ion) m/z: 365.8. $^1$H NMR (300 MHz, $CDCl_3$) δ ppm 2.43 (s, 3H) 2.75 (s, 3H) 6.07 (br. s., 1H) 7.09-7.21 (m, 3H) 7.29-7.37 (m, 3H) 7.38-7.47 (m, 2H) 7.48-7.56 (m, 1H) 7.75 (d, J=7.02 Hz, 2H) 7.92 (d, J=2.19 Hz, 1H).

Step 3. N-(5-amino-2-methylpyridin-3-yl)methanesulfonamide

To a solution of N-(5-(diphenylmethyleneamino)-2-methylpyridin-3-yl)methanesulfonamide (0.430 g, 1.177 mmol) in THF (10 mL) was added hydrochloric acid (JT Baker) (1.765 mL, 1.765 mmol) (1N). The reaction was stirred at rt in closed system for 20 min. The reaction mixture was partitioned between EtOAc and sat. $NaHCO_3$. The aqueous layer was extracted with EtOAc (2×10 mL). The combined organic layer were dried over $MgSO_4$ and concentrated. The crude product was purified by column chromatography (40 g, 5% to 10% MeOH in DCM) to afford the desired product as a brown solid (70.0 mg). MS (ESI pos. ion) m/z: 202.1. $^1$H NMR (300 MHz, $CDCl_3$) δ ppm 2.42 (s, 3H) 3.03 (s, 3H) 3.70 (br. s., 2H) 6.15 (br. s., 1H) 7.20 (d, J=2.34 Hz, 1H) 7.87 (d, J=2.34 Hz, 1H).

Step 4. N-(5-(3-(4-amino-6-methyl-1,3,5-triazin-2-yl)-5-(2-methoxyethoxy)pyridin-2-ylamino)-2-methylpyridin-3-yl)methanesulfonamide To a 15 mL round-bottom flask was added 4-(2-fluoro-5-(2-methoxyethoxy)pyridin-3-yl)-6-methyl-1,3,5-triazin-2-amine (Example 335 Step 3) (0.050 g, 0.179 mmol), N-(5-amino-2-methylpyridin-3-yl)methanesulfonamide (0.043 g, 0.215 mmol), and DMF (2.0 mL). The mixture was cooled to 0° C. under $N_2$. Sodium bis(trimethylsilyl)amide, 1.0 m in THF (Aldrich) (0.145 mL, 0.716 mmol) was then added to the solution in one portion. The now dark burgundy color mixture was stirred at 0° C. for 10 min then warmed up to rt and stirred for 1 h. The reaction mixture was partitioned between sat. $NH_4Cl$ and $CHCl_3$. The aqueous layer was extracted with more $CHCl_3$ (2×10 mL). The combined organic layers were dried over $MgSO_4$ and concentrated. The crude product was purified by column chromatography (16 g, 5% to 10% MeOH in DCM) to afford the desired product as a yellow solid (25 mg). MS (ESI pos. ion) m/z: 461.0. $^1$H NMR (300 MHz, DMSO-$d_6$) δ ppm 2.45 (d, J=2.63 Hz, 6H) 2.52 (s, 3H) 3.06 (s, 3H) 3.61-3.73 (m, 2H) 4.09-4.23 (m, 2H) 7.77 (br. s., 1H) 7.89 (br. s., 1H) 8.17 (d, J=2.92 Hz, 1H) 8.33 (d, J=1.75 Hz, 1H) 8.42 (d, J=3.07 Hz, 1H) 8.65 (s, 1H) 9.29 (br. s., 1H) 11.76 (s, 1H).

Example 377

N-(5-(3-(4-amino-6-methyl-1,3,5-triazin-2-yl)pyridin-2-ylamino)-2-methylpyridin-3-yl)methanesulfonamide

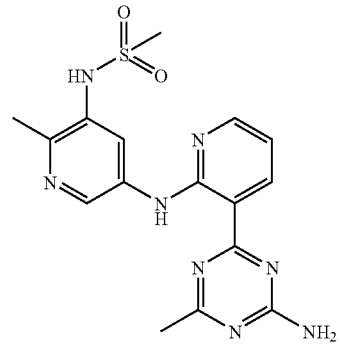 [SMILES: Cc1nc(N)nc(-c2cccnc2Nc2cnc(C)c(NS(C)(=O)=O)c2)n1]

To a 15 mL round-bottom flask was added 4-(2-fluoropyridin-3-yl)-6-methyl-1,3,5-triazin-2-amine (0.045 g, 0.219 mmol), N-(5-amino-2-methylpyridin-3-yl)methanesulfonamide (0.049 g, 0.241 mmol), and DMF (2.0 mL). The mixture was cooled to 0° C. under $N_2$. Sodium bis(trimethylsilyl)amide, 1.0 m in THF (Aldrich) (0.178 mL, 0.877 mmol) was then added to the solution in one portion. The now burgundy color mixture was stirred at 0° C. for 10 min then warmed up to rt and stirred for 1 h. The reaction mixture was quenched with sat. $NH_4Cl$ and partitioned between water and $CHCl_3$. The aqueous layer was extracted with more $CHCl_3$ (2×10 mL). The combined organic layers were dried over $MgSO_4$ and concentrated. The crude product was purified by column chromatography (16 g, 5% to 10% MeOH in DCM) to afford the desired product as a yellow solid (35 mg). MS (ESI pos. ion) m/z: 387.0. $^1$H NMR (300 MHz, DMSO-$d_6$) δ ppm 2.46 (d, J=9.06 Hz, 6H) 3.06 (s, 3H) 3.33 (s, 3H) 6.96 (dd, J=7.60, 4.68 Hz, 1H) 7.75 (br. s., 1H) 7.87 (br. s., 1H) 8.27-8.41 (m, 2H) 8.67 (d, J=2.05 Hz, 1H) 8.79 (dd, J=7.82, 1.53 Hz, 1H) 9.30 (br. s., 1H) 12.03 (s, 1H).

Example 378

N-(5-(3-(4-amino-6-methyl-1,3,5-triazin-2-yl)-5-chloropyridin-2-ylamino)-2-methylpyridin-3-yl)methanesulfonamide

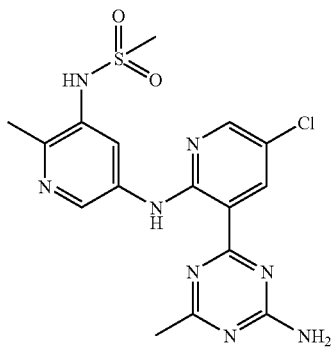 [SMILES: Cc1nc(N)nc(-c2cc(Cl)cnc2Nc2cnc(C)c(NS(C)(=O)=O)c2)n1]

To a 15 mL round-bottom flask was added 4-(5-chloro-2-fluoropyridin-3-yl)-6-methyl-1,3,5-triazin-2-amine (0.050 g, 0.209 mmol), N-(5-amino-2-methylpyridin-3-yl)methanesulfonamide (0.046 g, 0.230 mmol), and DMF (2.0 mL). The mixture was cooled to 0° C. under $N_2$. Sodium bis(trimethylsilyl)amide, 1.0 m in THF (0.169 mL, 0.835 mmol) was then added to the solution in one portion. The now burgundy color mixture was stirred at 0° C. for 10 min then warmed up to rt and stirred for 1 h. The reaction mixture was quenched with sat. $NH_4Cl$ and partitioned between water and $CHCl_3$. The aqueous layer was extracted with more $CHCl_3$ (2×10 mL). The combined organic layers were dried over $MgSO_4$ and concentrated. The crude product was purified by column chromatography (40 g, 3% MeOH in DCM) to afford the desired product as a yellow solid (100 mg). MS (ESI pos. ion) m/z: 421.0. $^1$H NMR (300 MHz, DMSO-$d_6$) δ ppm 2.45 (s, 6H) 3.06 (s, 3H) 7.84 (br. s., 1H) 7.97 (br. s., 1H) 8.24 (d, J=2.05 Hz, 1H) 8.38 (d, J=2.63 Hz, 1H) 8.64 (d, J=2.19 Hz, 1H) 8.75 (d, J=2.63 Hz, 1H) 9.32 (br. s., 1H) 11.98 (s, 1H).

Example 379

N-(2-chloro-5-(3-(6-amino-2-methylpyrimidin-4-yl)-5-(1-morpholinoethyl)pyridin-2-ylamino)pyridin-3-yl)-N,N-dimethylaminosulfamide

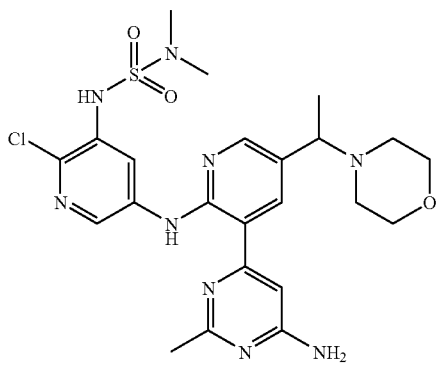 [SMILES: Cc1nc(N)cc(-c2cc(C(C)N3CCOCC3)cnc2Nc2cnc(Cl)c(NS(=O)(=O)N(C)C)c2)n1]

Step 1. 4-chloro-2-methyl-6-(methylthio)pyrimidine

To a solution of 4,6-dichloro-2-methylpyrimidine (Aldrich) (2.000 g, 12.27 mmol) in THF (25 mL) was added sodium thiomethoxide (Aldrich) (0.903 g, 12.88 mmol). The reaction mixture was stirred at rt under $N_2$ for 3 h. The reaction mixture was partitioned between EtOAc and water. The aqueous layer was extracted with EtOAc (2×15 mL). The combined organic layers were dried over $MgSO_4$ and concentrated. The crude product was purified by column chromatography (120 g, 5% to 10% acetone in hexanes) to afford the product as white solid (1.3 g). MS (ESI pos. ion) m/z: 174.9. $^1$H NMR (300 MHz, $CDCl_3$) δ ppm 2.57 (s, 3H) 2.65 (s, 3H) 7.02 (s, 1H).

Step 2. 4-(1-(6-fluoro-5-(2-methyl-6-(methylthio)pyrimidin-4-yl)pyridin-3-yl)ethyl)morpholine To a 20 mL microwave vials was added 4-chloro-2-methyl-6-(methylthio)pyrimidine (0.175 g, 1.002 mmol), 2-fluoro-5-(1-morpholinoethyl)pyridin-3-ylboronic acid (Example 339 Step 3) (0.305 g, 1.202 mmol), trans-dichlorobis(triphenylphosphine)palladium (II) (Strem) (0.056 g, 0.080 mmol), sodium carbonate (JT Baker) (0.531 mg, 5.01 mmol), DME (10 mL), and water (2.5 mL). The vial was degassed by bubbling $N_2$ for 5 min then sealed off and microwave heated at 90° C. for 20 min. The reaction mixture was partitioned between EtOAc and water. The aqueous layer was extracted with EtOAc (2×10 mL). The combined organic layers were dried over $MgSO_4$ and concentrated. The crude product was purified by column chromatography (40 g, 10% to 20% acetone in hexanes) to afford the product as white solid (275 mg). MS (ESI pos. ion) m/z: 349.1. $^1$H NMR (300 MHz, $CDCl_3$) δ ppm 1.43 (d, J=6.72 Hz, 3H) 2.33-2.46 (m, 2H) 2.48-2.58 (m, 2H) 2.61 (s, 3H) 2.74 (s, 3H) 3.52 (q, J=6.58 Hz, 1H) 3.71 (t, J=4.46 Hz, 4H) 7.55 (s, 1H) 8.25 (s, 1H) 8.56 (dd, J=9.43, 2.27 Hz, 1H).

Step 3. N-(2-chloro-5-(3-(2-methyl-6-(methylthio)pyrimidin-4-yl)-5-(1-morpholinoethyl)pyridin-2-ylamino)pyridin-3-yl)-N,N-dimethylaminosulfamide To a flame dry 15 mL round-bottom flask was added 4-(1-(6-fluoro-5-(2-methyl-6-(methylthio)pyrimidin-4-yl)pyridin-3-yl)ethyl)morpholine (0.150 g, 0.430 mmol), N-(5-amino-2-chloropyridin-3-yl)-N,N-dimethylaminosulfamide (0.130 g, 0.517 mmol), and THF (3.0 mL). The mixture was cooled to 0° C. under $N_2$. Sodium bis(trimethylsilyl)amide, 1.0 m in THF (Aldrich) (1.837 mL, 1.837 mmol) was added to the solution in one portion. The now dark burgundy color mixture was stirred at 0° C. for 10 min then warmed up to rt and stirred for 1 h. The reaction mixture was quenched with sat. $NH_4Cl$. The reaction mixture was partitioned between water and $CHCl_3$. The aqueous layer was extracted with $CHCl_3$ (2×10 mL). The combined organic layers were dried over $MgSO_4$ and concentrated. The crude product was purified by column chromatography (40 g, 20% to 30% acetone in hexanes) to afford the product as a yellow solid (160 mg). MS (ESI pos. ion) m/z: 578.9. $^1$H NMR (300 MHz, $CDCl_3$) δ ppm 1.41 (d, J=6.58 Hz, 3H) 2.34-2.46 (m, 2H) 2.52 (br. s., 2H) (s, 3H) 2.81 (s, 3H) 2.95 (s, 6H) 3.38 (d, J=6.43 Hz, 1H) 3.71 (d, J=4.09 Hz, 4H) 6.78 (s, 1H) 7.45 (s, 1H) 8.00 (d, J=1.61 Hz, 1H) 8.25 (s, 1H) 8.40 (d, J=2.34 Hz, 1H) 8.78 (d, J=2.34 Hz, 1H) 12.38 (s, 1H).

Step 4. N-(2-chloro-5-(3-(2-methyl-6-(methylsulfonyl)pyrimidin-4-yl)-5-(1-morpholinoethyl)pyridin-2-ylamino)pyridin-3-yl)-N,N-dimethylaminosulfamide To a 20 mL scintillation vial, which contained N-(2-chloro-5-(3-(2-methyl-6-(methylthio)pyrimidin-4-yl)-5-(1-morpholinoethyl)pyridin-2-ylamino)pyridin-3-yl)-N,N-dimethylaminosulfamide (0.125 g, 0.216 mmol), was added Oxone® (potassium, peroxymonosulfate, Aldrich) (0.265 mL, 0.432 mmol), and MeOH/water (1:1, 6 mL). The resulting mixture was capped and stirred at rt in closed system for 1 h. The reaction mixture was partitioned between water/CHCl$_3$. The aqueous layer was extracted more with CHCl$_3$ (2×10 mL). The combined organic layers were dried over MgSO$_4$ and concentrated. The crude product was purified by column chromatography (24 g, DCM:EtOAc:MeOH=70%:27%:3%) to afford the product as a yellow solid (110 mg). MS (ESI pos. ion) m/z: 610.8. $^1$H NMR (300 MHz, CDCl$_3$) δ ppm 1.42 (d, J=6.58 Hz, 3H) 2.35-2.47 (m, 2H) 2.48-2.62 (m, 2.95 (s, 6H) 3.00 (s, 3H) 3.34 (s, 3H) 3.37-3.47 (m, 1H) 3.72 (t, J=3.95 Hz, 4H) 6.79 (br. s., 1H) 8.21 (s, 1H) 8.35 (d, J=7.60 Hz, 2H) 8.44 (d, J=2.34 Hz, 1H) 8.77 (d, J=2.34 Hz, 1H) 12.22 (s, 1H).

Step 5. N-(2-chloro-5-(3-(6-amino-2-methylpyrimidin-4-yl)-5-(1-morpholinoethyl)pyridin-2-ylamino)pyridin-3-yl)-N,N-dimethylaminosulfamide To a 20 mL microwave vials was added N-(2-chloro-5-(3-(2-methyl-6-(methylsulfonyl)pyrimidin-4-yl)-5-(1-morpholinoethyl)pyridin-2-ylamino)pyridin-3-yl)-N,N-dimethylaminosulfamide (0.100 g, 0.164 mmol), ammonium hydroxide 30% (JT Baker) (0.425 mL, 3.27 mmol), and dioxane (3 mL). The vial was sealed and heated at 95° C. in closed system for 1 h. Solvent was concentrated. The crude product was purified by column chromatography (16 g, 3% to 10% MeOH in DCM) to afford the product as light yellow solid (80 mg). MS (ESI pos. ion) m/z: 548.0. $^1$H NMR (400 MHz, CDCl$_3$) δ ppm 1.41 (br. s., 3H) 2.42 (br. s., 2H) 2.53 (br. s., 2H) 2.67 (s, 3H) 2.95 (s, 6H) 3.37 (br. s., 1H) 3.72 (br. s., 4H) 5.00 (br. s., 2H) 6.64-6.84 (m, 2H) 7.96 (br. s., 1H) 8.21 (br. s., 1H) 8.39 (d, J=2.15 Hz, 1H) 8.79 (d, J=2.35 Hz, 1H) 12.52 (br. s., 1H).

Separation OS Isomers

A mixture of isomers of N-(2-chloro-5-(3-(6-amino-2-methylpyrimidin-4-yl)-5-(1-morpholinoethyl)pyridin-2-ylamino)pyridin-3-yl)-N,N-dimethylaminosulfamide were separated using chiral SFC preparative chromatography. The following conditions were used:

Column; OZ—H (21 mm×25 cm)

Mobile Phase: 40:60 (A:B)

A: Liquid CO$_2$

B: MeOH (0.2% diethylamine)

Flow Rate: 45 mL/min

Oven/column temp: 40° C.

The two separate peaks contained the two enantiomers were collected, concentrated, and dried under high vacuum to afford the two enantiomers. The absolute stereochemistry was not determined (See examples 381 and 381)

Example 380

N-(5-(3-(6-amino-2-methylpyrimidin-4-yl)-5-vinylpyridin-2-ylamino)-2-chloropyridin-3-yl)methanesulfonamide

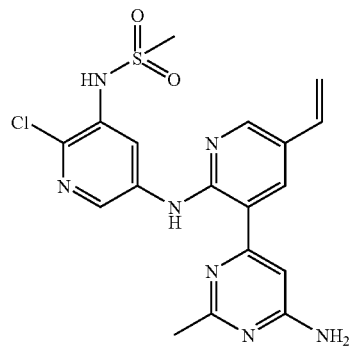 [SMILES: C=Cc1cnc(Nc2cnc(Cl)c(NS(C)(=O)=O)c2)c(-c2cc(N)nc(C)n2)c1]

Step 1. N-(2-chloro-5-(3-(2-methyl-6-(methylthio)pyrimidin-4-yl)-5-(1-morpholinoethyl)pyridin-2-ylamino)pyridin-3-yl)methanesulfonamide To a flame dry 15 mL round-bottom flask was added 4-(1-(6-fluoro-5-(2-methyl-6-(methylthio)pyrimidin-4-yl)pyridin-3-yl)ethyl)morpholine (0.160 g, 0.459 mmol), N-(5-amino-2-chloropyridin-3-yl)methanesulfonamide (0.122 g, 0.551 mmol), and THF (4.0 mL). The mixture was cooled to 0° C. under N$_2$. Sodium bis(trimethylsilyl)amide, 1.0 m in THF (Aldrich) (1.837 mL, 1.837 mmol) was then added to the solution in one portion. The now dark burgundy color mixture was stirred at 0° C. for 10 min then warmed up to rt and stirred for 1 h. The reaction mixture was quenched with sat. NH$_4$Cl. The reaction mixture was partitioned between water and CHCl$_3$. The aqueous layer was extracted with CHCl$_3$ (2×10 mL). The combined organic layers were dried over MgSO$_4$ and concentrated. The crude product was purified by column chromatography (40 g, DCM:EtOAc:MeOH=65%:32%:3%) to afford the product as a yellow solid (175 mg). MS (ESI pos. ion) m/z: 550.0. $^1$H NMR (300 MHz, CDCl$_3$) δ ppm 1.41 (d, J=6.58 Hz, 3H) 2.34-2.48 (m, 2H) 2.49-2.60 (m, 2H) 2.66 (s, 3H) 2.81 (s, 3H) 3.13 (s, 3H) 3.39 (d, J=6.58 Hz, 1H) 3.72 (t, J=4.38 Hz, 4H) 6.75 (br. s., 1H) 7.45 (s, 1H) 8.01 (d, J=1.90 Hz, 1H) 8.30 (d, J=1.90 Hz, 1H) 8.52 (d, J=2.48 Hz, 1H) 8.76 (d, J=2.48 Hz, 1H) 12.43 (s, 1H).

Step 2. N-(5-(3-(6-amino-2-methylpyrimidin-4-yl)-5-vinylpyridin-2-ylamino)-2-chloropyridin-3-yl)methanesulfonamide To a 20 mL scintillation vial, which contained N-(2-chloro-5-(3-(2-methyl-6-(methylthio)pyrimidin-4-yl)-5-(1-morpholinoethyl)pyridin-2-ylamino)pyridin-3-yl)methanesulfonamide (0.150 g, 0.273 mmol), was added 3-chloroperoxybenzoic acid (0.188 g, 0.654 mmol) and DCM (8 mL). The resulting mixture was capped and stirred at rt in closed system for 1 h. The reaction mixture was partitioned between water and CHCl$_3$. The aqueous layer was extracted more with CHCl$_3$ (2×10 mL). The combined organic layers were dried over MgSO₄ and concentrated. The crude product was purified by column chromatography (24 g, 5% to 20% MeOH in DCM) to afford the product as a yellow solid (100 mg). This intermediate was then added into the 5 mL microwave along with ammonium hydroxide 30% (0.142 mL, 3.64 mmol), and dioxane (2 mL). The vial was sealed and heated at 95° C. in closed system for 1 h. Solvent was concentrated. The crude product was purified by column chromatography (24 g, 3% to 10% MeOH in DCM) to afford the product as yellow solid (30 mg). MS (ESI pos. ion) m/z: 431.9. ¹H NMR (300 MHz, DMSO-d₆) δ ppm 2.52 (s, 3H) 3.13 (s, 3H) 5.27 (d, J=11.11 Hz, 1H) 5.89 (d, J=17.54 Hz, 1H) 6.76 (dd, J=17.76 Hz, 1H) 6.89 (s, 1H) 7.05 (br. s., 2H) 8.24 (s, 1H) 8.42 (s, 2H) 8.60 (d, J=2.05 Hz, 1H) 9.63 (s, 1H) 12.66 (s, 1H).

Example 381 and 382

(R)-N-(2-chloro-5-(3-(6-amino-2-methylpyrimidin-4-yl)-5-(1-morpholinoethyl)pyridin-2-ylamino)pyridin-3-yl)-N,N-dimethylaminosulfamide; and (S-)N-(2-chloro-5-(3-(6-amino-2-methylpyrimidin-4-yl)-5-(1-morpholinoethyl)pyridin-2-ylamino)pyridin-3-yl)-N,N-dimethylaminosulfamide

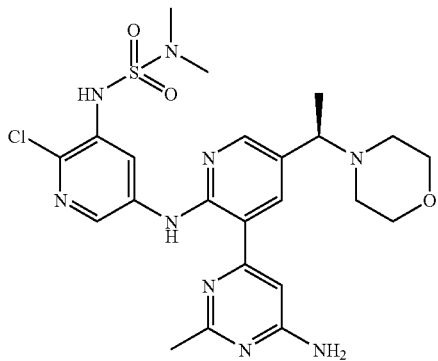 [SMILES: Cc1nc(N)cc(-c2cc([C@@H](C)N3CCOCC3)cnc2Nc2cnc(Cl)c(NS(=O)(=O)N(C)C)c2)n1]

MS (ESI pos. ion) m/z: 548.0. ¹H NMR (400 MHz, CDCl₃) δ ppm 1.31-1.51 (m, 3H) 2.45 (br. s., 2H) 2.55 (br. s., 2H) 2.66 (s, 3H) 2.95 (s, 6H) 3.39 (br. s., 1H) 3.73 (br. s., 4H) 5.02 (br. s., 2H) 6.77 (br. s., 2H) 7.98 (br. s., 1H) 8.21 (s, 1H) 8.40 (d, J=2.35 Hz, 1H) 8.79 (d, J=2.35 Hz, 1H) 12.54 (br. s., 1H).

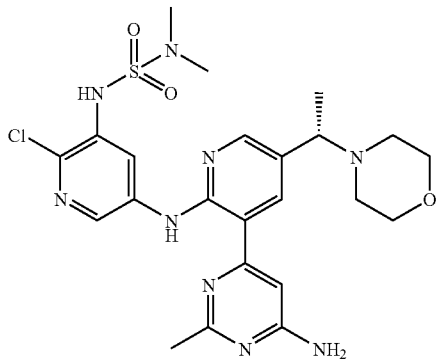 [SMILES: Cc1nc(N)cc(-c2cc([C@H](C)N3CCOCC3)cnc2Nc2cnc(Cl)c(NS(=O)(=O)N(C)C)c2)n1]

MS (ESI pos. ion) m/z: 548.0. ¹H NMR (400 MHz, CDCl₃) δ ppm 1.44 (br. s., 3H) 2.45 (br. s., 2H) 2.56 (br. s., 2H) 2.66 (s, 3H) 2.95 (s, 6H) 3.40 (br. s., 1H) 3.74 (br. s., 4H) 5.02 (br. s., 2H) 6.77 (br. s., 2H) 8.00 (br. s., 1H) 8.21 (d, J=2.15 Hz, 1H) 8.39 (d, J=2.35 Hz, 1H) 8.79 (d, J=2.35 Hz, 1H) 12.55 (br. s., 1H).

Example 383

4-(5-((1,1-dioxidohexahydro-5H-isothiazolo[2,3-a]pyrazin-5-yl)methyl)-2-((5-fluoro-6-methoxy-3-pyridinyl)amino)-3-pyridinyl)-6-methyl-1,3,5-triazin-2-amine

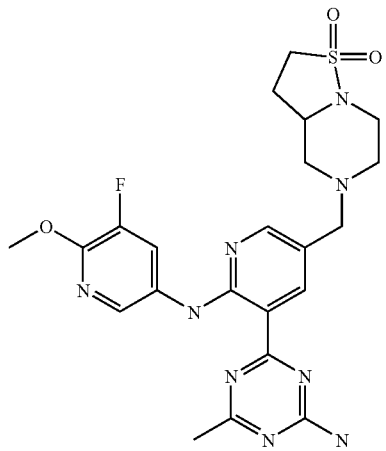 [SMILES: COc1ncc(Nc2ncc(CN3CCN4C(CCS4(=O)=O)C3)cc2-c2nc(C)nc(N)n2)cc1F]

Step 1. 4-(5-(((1,1-dioxidohexahydro-5H-isothiazolo[2,3-a]pyrazin-5-yl)methyl)-2-((5-fluoro-6-methoxy-3-pyridinyl)amino)-3-pyridinyl)-N,N-bis(4-methoxybenzyl)-6-methyl-1,3,5-triazin-2-amine To a stirred mixture of hexahydro-2H-isothiazolo[2,3-a]pyrazine 1,1-dioxide (ref: WO2007028654, 0.180 g, 1.021 mmol) in THF (2.50 mL, 30.5 mmol) was added 5-(4-(bis(4-methoxybenzyl)amino)-6-methyl-1,3,5-triazin-2-yl)-6-(5-fluoro-6-methoxypyridin-3-ylamino)nicotinaldehyde (preparation previously described, 0.3042 g, 0.511 mmol) and titanium (IV) ethoxide (0.529 mL, 2.55 mmol) and the mixture was heated at 70° C. overnight. The resulting mixture was cooled to 0° C. and excess sodium cyanoborohydride (0.160 g, 2.55 mmol) was added and the entire mixture was stirred at the same temperature for 1 h prior to being quenched with MeOH (1.0 mL). The mixture was concentrated and adsorbed onto a plug of silica gel and chromatographed through a silica gel column (100% DCM to 70% ethyl acetate in DCM to obtain the desired product 4-(5-((1,1-dioxidohexahydro-5H-isothiazolo[2,3-a]pyrazin-5-yl)methyl)-2-((5-fluoro-6-methoxy-3-pyridinyl)amino)-3-pyridinyl)-N,N-bis(4-methoxybenzyl)-6-methyl-1,3,5-triazin-2-amine (0.297 g, 77%) as a yellow syrup. m/z (ESI, +ve ion) 756 (M+H)⁺.

Step 2. 4-(5-((1,1-dioxidohexahydro-5H-isothiazolo[2,3-a]pyrazin-5-yl)methyl)-2-((5-fluoro-6-methoxy-3-pyridinyl)amino)-3-pyridinyl)-6-methyl-1,3,5-triazin-2-amine The title compound was prepared from 4-(5-((1,1-dioxidohexahydro-5H-isothiazolo[2,3-a]pyrazin-5-yl)methyl)-2-((5-fluoro-6-methoxy-3-pyridinyl)amino)-3-pyridinyl)-N,N-bis(4-methoxybenzyl)-6-methyl-1,3,5-triazin-2-amine via the similar deprotection protocol as described previously in Example 178, Step 4, using trifluoroacetic acid and trifluoromethanesulfonic acid and isolated (61 mg, 30%) as a yellow solid. m/z (ESI, +ve ion) 516 (M+H)+. 1H NMR (400 MHz, d$_6$-DMSO) δ 11.95 (s, 1H) 8.73 (d, J=2.15 Hz, 1H) 8.42 (d, J=2.15 Hz, 1H) 8.37 (dd, J=12.81, 2.05 Hz, 1H) 8.26 (d, J=2.15 Hz, 1H) 7.91 (br. s., 1H) 7.76 (br. s., 1H) 3.93 (s, 3H) 3.45-3.62 (m, 1H) 3.00-3.30 (m, 5H) 2.80-3.00 (m, 2H) 2.62-2.74 (m, 1H) 2.44 (s, 3H) 2.23-2.36 (m, 1H) 2.06-2.16 (m, 1H) 1.81-1.96 (m, 2H).

Example 384

N'-(5-((3-(4-amino-6-methyl-1,3,5-triazin-2-yl)-5-chloro-2-pyridinyl)amino)-2-chloro-3-pyridinyl)-N,N-dimethylsulfamide

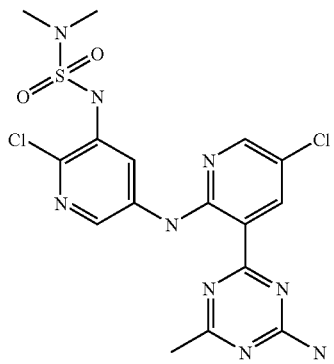 [SMILES: Cc1nc(N)nc(-c2cc(Cl)cnc2Nc2cnc(Cl)c(NS(=O)(=O)N(C)C)c2)n1]

Step 1. N-(2-chloro-5-(diphenylmethyleneamino)pyridin-3-yl)-N,N-dimethylaminosulfamide To a 20 mL microwave vial, which was degassed by bubbling N$_2$, was added N-(5-bromo-2-chloropyridin-3-yl)-N,N-dimethylaminosulfamide (WO2009155121A2; 0.500 g, 1.589 mmol), 4,5-bis(diphenylphosphino)-9,9-dimethylxanthene (Strem; 0.092 g, 0.159 mmol), tris(dibenzylideneacetone)dipalladium (0) (Strem; 0.073 g, 0.079 mmol), sodium tert-butoxide (0.458 g, 4.77 mmol), DMF (8 mL), and benzophenone imine (Aldrich; 0.293 mL, 1.748 mmol). The resulting mixture was sealed off and microwave heated at 130° C. for 20 min. The resulting mixture was partitioned between EtOAc and sat. NH$_4$Cl (25 mL). Water (5 mL) was added to dissolve NH$_4$Cl that precipitated out between the organic and aqueous layers (pH was between 5 to 6 for the aqueous layer). The aqueous layer was extracted with more EtOAc (2×10 mL). The combined organic layers were dried over MgSO$_4$ and concentrated. The crude product was purified by column chromatography (80 g silica, 10% to 20% acetone in hexanes) to afford the desired product as a yellow foam-like solid (280 mg). 1H NMR (300 MHz, CDCl$_3$) δ 2.71 (s, 6H) 6.62 (br. s., 1H) 7.14 (d, J=3.80 Hz, 2H) 7.33 (d, J=2.78 Hz, 4H) 7.39-7.47 (m, 2H) 7.49-7.57 (m, 1H) 7.62 (s, 1H) 7.74 (d, J=7.45 Hz, 2H).

Step 2. N'-(5-amino-2-chloro-3-pyridinyl)-N,N-dimethylsulfamide

To a solution of N-(2-chloro-5-(diphenylmethyleneamino)pyridin-3-yl)-N,N-dimethylaminosulfamide (0.300 g, 0.723 mmol) in THF (5 mL) was added 1 N hydrochloric acid (1.085 mL, 1.085 mmol). The reaction was stirred at ambient temperature in a closed system. After 30 min, the reaction mixture was partitioned between EtOAc/sat. NaHCO$_3$. The aqueous layer was extracted with more EtOAc (2×10 mL). The combined organic layers were dried over MgSO$_4$ and concentrated. The crude product was purified by column chromatography (40 g silica, 3% MeOH in DCM) to afford the desired product as a yellow solid (170 mg). 1H NMR (300 MHz, CDCl$_3$) δ 2.87 (s, 6H) 3.82 (br. s., 2H) 6.67 (br. s., 1H) 7.30 (d, J=2.05 Hz, 1H) 7.62 (d, J=2.05 Hz, 1H).

Step 3. N'-(5-((3-(4-amino-6-methyl-1,3,5-triazin-2-yl)-5-chloro-2-pyridinyl)amino)-2-chloro-3-pyridinyl)-N,N-dimethylsulfamide To a 100-mL round-bottomed flask was added 4-(5-chloro-2-fluoropyridin-3-yl)-6-methyl-1,3,5-triazin-2-amine (Example 356, Step 1; 960 mg, 4.01 mmol), N'-(5-amino-2-chloro-3-pyridinyl)-N,N-dimethylsulfamide (1004 mg, 4.01 mmol) and lithium bis(trimethylsilyl)amide (Aldrich; 3352 mg, 20.03 mmol) in tetrahydrofuran (20 mL) at 0° C. After the addition, the reaction mixture was stirred at 0° C. for 20 min. The reaction mixture was diluted with satd NH$_4$Cl (30 mL) and extracted with CH$_2$Cl$_2$ (3×200 mL). The organic extract was washed with satd NaCl (30 mL) and dried over Na$_2$SO$_4$. The solution was filtered and concentrated in vacuo to give the crude material as a yellow solid. The crude product was purified by silica gel chromatography eluting with 5% MeOH/CH$_2$Cl$_2$ to give N'-(5-((3-(4-amino-6-methyl-1,3,5-triazin-2-yl)-5-chloro-2-pyridinyl)amino)-2-chloro-3-pyridinyl)-N,N-dimethylsulfamide (1.29 g, 2.74 mmol, 68.5% yield) as a yellow solid. m/z (ESI, +ve ion) 470.0 (M+H)+. 1H NMR (400 MHz, CDCl$_3$) δ 2.61 (s, 3H) 2.95 (s, 6H) 5.48 (br. s., 2H) 6.80 (s, 1H) 8.31 (d, J=2.74 Hz, 1H) 8.38 (d, J=2.54 Hz, 1H) 8.74 (d, J=2.54 Hz, 1H) 8.85 (d, J=2.74 Hz, 1H) 12.35 (s, 1H).

The following assays can be used to determine the degree of activity of individual compounds as PI3 kinase and/or mTOR inhibitors as well as assess selectivity over other kinases.

Recombinant Expression Of PI3K Enzymes

Full length p110 subunits of PI3K α, β and δ, N-terminally labeled with polyHis tag, can be co-expressed with p85 with Baculo virus expression vectors in sf9 insect cells. P110/p85 heterodimers can be purified by sequential Ni-NTA, Q-HP, Superdex-100 chromatography. Purified α, β and δ isozymes can be stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, can be expressed with Baculo virus in Hi5 insect cells. The γ isozyme can be purified by sequential Ni-NTA, Superdex-200, Q-HP chromatography. The γ isozyme can be stored frozen at −80° C. in NaH$_2$PO$_4$, pH 8, 0.2M NaCl, 1% ethylene glycol, 2 mM β-mercaptoethanol.

|  | Alpha | Beta | Delta | Gamma |
|---|---|---|---|---|
| 50 mM Tris | pH 8 | pH 7.5 | pH 7.5 | pH 8 |
| MgCl$_2$ | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 hr | 2 hr | 2 hr | 1 hr |
| [Enzyme] | 15 nM | 40 nM | 15 nM | 50 nM |

In Vitro PI3K Alphascreen® Assay

The PI3K AlphaScreen® assay (Perkinelmer, Waltham, Mass.) measures the activity of a panel of four phosphoinositide 3-kinases: PI3Kα, PI3Kβ, PI3Kγ, and PI3Kδ. Each of these enzymes phosphorylates the 3'-hydroxyl group on phosphatidylinositiol (4,5)-bisphosphate ($PIP_2$) to produce phosphatidylinositol (3,4,5)-trisphosphate ($PIP_3$). This phosphorylation activity is measured using a GST-tagged $PIP_3$ binding protein (Echelon Biosciences, Salt Lake City, Utah), an anti-GST-tagged Acceptor bead, and streptavidin-Donor bead. The interaction of biotinylated-$PIP_3$ analog ($IP_4$) and the $PIP_3$ binding protein brings both Acceptor and Donor beads together producing, upon excitation of the Donor beads at 680 nm, a singlet oxygen species leading to the luminescent AlphaScreen® signal. When $PIP_3$ is produced via phophorylation of PIP2 by a PI3K, PIP3 competes with biotinylated-$PIP_3$ analog ($IP_4$) for binding to the $PIP_3$ binding protein. In the absence of this interaction, proximity of the Donor and Acceptor beads is decreased, producing a loss of luminescent signal which is inversely proportional to PI3K activity. An inhibitor reduces activity of the enzyme, resulting in less $PIP_3$ production and greater luminescence.

The enzyme reaction buffer is made using sterile water (Baxter, Deerfield, Ill.) and 50 mM Tris HCl pH 7, 14 mM $MgCl_2$, 2 mM sodium cholate, and 100 mM NaCl. 2 mM DTT is added fresh the day of the experiment. The AlphaScreen® reaction buffer is made using sterile water and 10 mM Tris HCl pH 7.5, 150 mM NaCl, 0.10% Tween 20, and 30 mM EDTA. 1 mM DTT is added fresh the day of the experiment.

The source plates for this assay are 384-well Greiner clear polypropylene plates containing test compounds at 5 mM and diluted 1:2 over 22 points. Columns 23 and 24 contain only DMSO as these are designated for positive and negative controls. Source plates are replicated into 384-well Optiplates (Perkinelmer, Waltham, Mass.), 0.5 µL/well, to make assay-ready plates.

The different PI3K isoforms are each diluted in enzyme reaction buffer to 2× working solutions. PI3Kα is diluted to 1.6 nM, PI3Kβ is diluted to 0.8 nM, PI3Kγ is diluted to 15 nM, and PI3Kδ is diluted to 1.6 nM. Two different 2× substrate solutions are made in enzyme reaction buffer. In one solution, PI(4,5)P2 (Echelon Biosciences, Salt Lake City, Utah) is diluted to 10 µM and ATP is diluted to 20 µM. This solution is used in the assays testing PI3Kα and PI3Kβ. In a second solution, PI(4,5)P2 is diluted to 10 µM and ATP is diluted to 8 µM. This solution is used in the assays testing PI3Kγ and PI3Kδ.

The AlphaScreen® reaction solutions are made using beads from the anti-GST AlphaScreen® kit (Perkinelmer, Waltham, Mass.). Two solutions are made in Alphascreen reaction buffer to 4× working concentrations. In one solution, biotinylated-$IP_4$ (Echelon Biosciences, Salt Lake City, Utah) is diluted to 40 nM and streptavadin-Donor Beads are diluted to 80 µg/mL. In the second solution, $PIP_3$-binding protein (Echelon Biosciences, Salt Lake City, Utah) is diluted to 40 nM and anti-GST-Acceptor Beads are diluted to 80 µg/mL. 10 µL/well of enzyme reaction buffer is added to Column 24 of the assay ready plates in place of enzyme. This is done for plates in the PI3Kα, β, and δ assays.

Using a 384-well dispensing Multidrop (Titertek, Huntsville, Ala.), 10 µL/well of 2× enzyme (PI3Kα, β, δ) is added to Columns 1-23 of the appropriate assay ready plates (for PI3Kγ 10 µL is added to Columns 1-24). 10 µL/well of the appropriate substrate solution (the solution with 20 µM ATP for PI3Kα and β assays, and the solution with 8 µM ATP for PI3Kγ and δ assays) is then added to Columns 1-24 of the plates. Plates are then incubated at room temperature for 20 minutes.

In the dark, 10 µL/well of the Donor Bead solution is added to Columns 1-24 of the plates to quench the enzyme reaction. The plates are incubated at room temperature for 30 minutes. Still in the dark, 10 µL/well of the Acceptor Bead solution is also added to Columns 1-24 of the plates. The plates are then incubated in the dark for 1.5 hours. The plates are read on an Envision Multilabel Plate Reader (Perkinelmer, Waltham, Mass.) with a 680 nm excitation filter and a 520-620 nm emission filter.

Activity data for the compounds tested in the assay is provided in Table 1 under the column heading PI3Kα AlphaScreen®.

pAkt Aplhascreen (U87 Cell)

The pAkt AlphaScreen® assay (Perkinelmer, Waltham, Mass.) determines whether there is phosphorylation of Akt at Serine 473 by recruitment of a phosphospecific antibody. This assay was performed using U87 MG cells. The U87 growth media consists of MEM (Gibco, Carlsbad, Calif.) supplemented with 10% FBS (Gibco,), 1× Non-Essential Amino Acids (Gibco,) and 1× Penicillin/Streptomycin/Glutamine (Gibco). The cells were maintained weekly using 0.05% Trypsin (Gibco) and replated in 150 mm TC-Treated Culture Dishes (Corning, Corning, N.Y.).

The first day of the assay, the adherent cells were trypsinized, media was added to the loose cells and cells were mixed to a homogenous mixture. 0.5 ml of the homogenous mixture was counted on the Beckman Coulter® Vi-CELL™ XR (Fullerton, Calif.). 50 frames of cells were counted and the number of viable cells was determined. The cells were then diluted to 0.25 million cells per ml, and centrifuged at 200 rcf for 5 minutes. The media was removed and the cells were reconstituted in fresh media for plating. The cells were plated at 20 µl per well on the Perkinelmer® FlexDrop PLUS in Low Volume 384 Well White Tissue Culture Plates (Corning) with a final cell density of 5K cells per well. The plates were incubated overnight at 37° Celsius, 5% $CO_2$.

On the second day, the compound plates were prepared, the cells were treated with compound and the pAkt reaction mix was added to the cell lysate. 384 well compound plates were prepared containing 1 µl of compound per well starting at 5 mM and diluted 1:2 across the row, resulting in a 22 well serial dilution. 39 µl of growth media was added to the compound plate in rows 1-22 using the Perkinelmer® FlexDrop PLUS resulting in a DMSO concentration of 2.5%. The cell plates and diluted compound plates were put onto the VELOCITY11™ VPREP™ 384 ST where the compound plate was mixed and 5 µl of serially diluted compound or controls was added to the cell plate. The final concentration of the compounds was 25 µM serially diluted to 11.9 pM in 0.5% DMSO. The cell plates were then incubated with compound for two hours at 37° Celsius, 5% $CO_2$. After two hours, the media in the cell plates was aspirated using the BioTek® ELx405HT plate washer (Winooski, Vt.) removing the majority of media and compound without disturbing the adherent U87 cells. The following assay reagents are components of the SureFire® Akt (Ser 473) Phosphorylation 50K Point Kit (TGR BioSciences, Adelaide, Austalia) and an IgG Detection Kit (Perkinelmer, Waltham, Mass.). 5 µl of 1× Lysis Buffer was added to each well using the Perkinelmer® FlexDrop PLUS. The plates were then incubated at room temperature on a shaker for ten minutes. The AlphaScreen® reaction was prepared under low light conditions (subdued or green light) including p-Akt (Ser 473) Reaction Buffer, Dilution Buffer, Activation Buffer, Acceptor Beads and Donor Beads at a ratio of 40:20:10:1:1 respectively. The AlphaScreen® reaction was added to the cell lysate at 6 µl per well using the Perkinelmer® FlexDrop PLUS. The plates were placed in a humid environment to reduce edge effects and incubated overnight at room temperature with restricted air flow in the dark.

On the final day of the experiment, the plates were read on the Perkinelmer® EnVision™ 2103 Multilable Reader using the standard AlphaScreen® readout. The POC is calculated and the data is analyzed to report the $IC_{50}$ IP for pAkt at Serine 473.

Activity data for the compounds tested in the PI3K cell based Akt assay is provided in Table 1 under the column heading U87

The compounds of the present invention may inhibit mTOR, PI3K or both. The assay below can be used to determine if a compound inhibits mTOR. Thus, one aspect of the present invention concerns compounds that inhibit PI3K and mTOR. In another aspect, the present invention concerns compounds that primarily inhibit mTOR. In another aspect, the present invention concerns compounds that primarily inhibit PI3K. The present invention also contemplates the use of such compounds for the treatment of the diseases and conditions, such as cancer, disclosed herein.

In Vitro MTOR Assay

The Invitrogen (Carlsbad, Calif.) mammalian target of rapamycin (mTOR) Lanthascreen assay can be used to quantitate mTOR kinase activity in an in vitro setting. Active mTOR phosphorylates eukaryotic translation initiation factor 4E binding protein 1 (4E-BP1) on residue threonine 46. This phosphorylation event can be detected with a phospho-specific terbium (Tb) labeled Ab, in turn bringing the Tb label in close proximity to the GFP tagged 4E-BP1 and allowing for time-resolved fluorescence resonance energy transfer (TR-FRET), which correlates 4E-BP1 phosphorylation levels with mTOR kinase activity.

Enzyme reaction buffer can be prepared in deionized water containing 50 mM HEPES (pH 7.5), 0.01% Polysorbate 20, 1 mM EGTA, and 10 mM $MnCl_2$.

Dilutions of the compound to be tested can be prepared in 96-well polypropylene plates (Fisher Scientific, Waltham, Mass.). One row represents a 10-point dose of compound diluted 1:3 in enzyme reaction buffer and 20% dimethyl sulfoxide (DMSO). The top concentration for all compounds is 36 µM. Wells 6 and 12 can serve as the no compound (DMSO only) and high compound controls.

An mTOR substrate solution can prepared in enzyme reaction buffer containing 1600 nM green fluorescent protein tagged eukaryotic translation initiation factor 4E binding protein 1 (GFP-4E-BP1) (Invitrogen, Carlsbad, Calif.) and 28 uM adenosine triphosphate (ATP) (Calbiochem, Gibbstown, N.J.).

mTOR enzyme (Invitrogen, Carlsbad, Calif.) can be diluted in enzyme reaction buffer to a working concentration of 100 ng/mL.

The enzyme assay can be run in 384 well low volume assay plates (Corning, Corning, N.Y.). 2.5 uL of substrate solution containing GFP-4E-BP1 and ATP can be added to appropriate wells in the assay plate followed by 2.5 µL of compound dilutions. 5 µL of appropriately diluted mTOR enzyme can be added and the reaction allowed to proceed for 1 hour at room temperature. Final reagent concentrations in the enzyme assay are 50 ng/mL mTOR, 400 nM GFP-4E-BP1, and 7 µM ATP.

The enzyme assay can be terminated upon the addition of 10 µL of 20 mM EDTA and 4 nM Tb-labeled anti-phospho-4E-BP1 [T46] antibody (Invitrogen, Carlsbad, Calif.). The assay plate can then be incubated at room temperature for 1 hour and results read on a Tecan Safire II plate reader (Tecan, Männedorf, Switzerland).

Activity data for the compounds tested in the assay is provided in Table 1 under the column heading mTOR.

B-RAF Homogenous Time Resolved Fluorescence (HTRF) Kinase Assay

A Homogeneous Time Resolved Fluorescence (HTRF) kinase assay was established to assay the ability of compounds to inhibit human mutant B-raf kinase activity on the substrate MEK1. For $IC_{50}$ generation, the assay begins when 1 µL of a 50× compound dose curve in DMSO is added to 60 pM of recombinant HuBraf V600E in a final volume of 40 µl kinase reaction buffer. After a 60-minute incubation at room temperature, the kinase reaction is initiated with the addition of 10 µl substrate mix, resulting in a final concentration of 10 µM ATP (Km=about 20 µMM), 100 nM His-Avitag-MEK1 (Δ32-51, D190N kinase dead) (Km about 200 nM) in a final reaction volume of 50 µl. The final concentration of the kinase reaction buffer is 50 mM Tris-HCl pH 7.5, 10 mM $MgCl_2$, 0.5% glucose, 0.5 mM DTT, 0.01% BSA. The kinase reaction proceeds for 60 minutes at room temperature until the reaction is quenched by the addition of 10 µl Stop/Detection buffer composed of kinase reaction buffer with the addition of Tween-20 (for a final concentration 0.1%), Hexokinase (0.01 unit), Streptavidin-Allophycocyanin (final 10 nM), and Europium labeled anti-Phospho-MEK1/2 (ser217/221 from Cell Signaling Technology, Danvers, Mass.) antibody (final 300 pM). The detection reaction proceeds for one hour and is read on a RubyStar (BMG Labtech, Durham, N.C.) counter. $IC_{50}$s for the test compounds are generated using Excel-XLfit software. For single concentration percent of control (POC;= 100-percent inhibition) assays, compounds were assayed as above at a single test concentration of 10 µM test compound. All assay data is reported as the mean of at least 2 separate $IC_{50}$ or POC determinations, with N-(3-chlorophenyl)-4-methyl-3-(3-(pyrimidin-4-yl)pyridin-2-ylamino)benzamide (WO 2005113494A2) used as a positive control.

Data for the compounds tested in the assay is provided in Table 2 titled Mutant B-raf HTRF Assay.

Kinase Panel Screen

Compounds were profiled using a LabChip® EZ Reader II platform and a ProfilerPro Kinase Selectivity Assay Kit (Caliper Lifesciences Inc., Hopkinton, Mass.). Compounds were tested at a concentration of 1 µM in duplicate, with mean data reported as percent of control (POC).

The data obtained from this kinse screen is set forth in Table 3 below titled Kinase Panel Screen.

The data below shows that the $R^2$ group, particularly when methyl, in the compounds of Formula I, or the pharmaceutically acceptable salts thereof, unexpectedly and surprisingly provides for lipid kinase activity over protein kinase activity.

TABLE 1

| Example | PI3Kα AlphaScreen ® Ki µM | mTOR $IC_{50}$ µM | U87Cell $IC_{50}$ µM |
|---|---|---|---|
| 16 | >1.5 | 1.686 | |
| 17 | >1.5 | 17.548 | |
| 18 | 22.621 | >50 | >25 |
| 19 | 5.618 | >50 | 2.369 |
| 20 | 7.277 | 5.124 | 5.122 |
| 21 | 3.139 | >50 | >25 |
| 22 | 0.187 | 7.156 | 0.146 |
| 23 | 0.013 | 0.201 | 0.060 |
| 24 | 0.033 | >50 | 0.227 |

TABLE 1-continued

| Example | PI3Kα AlphaScreen® Ki μM | mTOR IC$_{50}$ μM | U87Cell IC$_{50}$ μM |
|---|---|---|---|
| 25 | 0.107 | 7.734 | 0.356 |
| 26 | 0.024 | 0.535 | 0.296 |
| 27 | 0.130 | >50 | 0.810 |
| 29 | 0.802 | >50 | 3.013 |
| 30 | 0.008 | 0.178 | 0.030 |
| 31 | 0.242 | >50 | 0.305 |
| 32 | 0.191 | >50 | 0.587 |
| 33 | 0.055 | >10 | 0.042 |
| 34 | 1.577 | >10 | >10 |
| 35 | 0.009 | 4.763 | 0.016 |
| 36 | 0.004 | >10 | 0.022 |
| 37 | 0.129 | >10 | 0.237 |
| 38 | 0.017 | >10 | 0.145 |
| 39 | 0.055 | >10 | 0.046 |
| 40 | 0.009 | >10 | 0.006 |
| 41 | 0.061 | >10 | 0.239 |
| 44 | 0.104 | >10 | 0.126 |
| 46 | 0.130 | 6.992 | 0.079 |
| 47 | 0.036 | >50 | 0.197 |
| 48 | 0.247 | >10 | 0.828 |
| 49 | 0.500 | 14.240 | 1.153 |
| 50 | 1.334 | 5.953 | 3.073 |
| 54 | 0.160 | >10 | 0.674 |
| 55 | 1.411 | >50 | 6.462 |
| 56 | 0.181 | 0.621 | 0.727 |
| 57 | 0.036 | 0.534 | 0.344 |
| 58 | 0.062 | 0.292 | 0.245 |
| 61 | 0.720 | >10 | 3.629 |
| 64 | 0.050 | >10 | >10 |
| 65 | 0.119 | | |
| 66 | 0.062 | 0.426 | 0.173 |
| 71 | 0.402 | >50 | 1.190 |
| 72 | 0.033 | 2.752 | 8.534 |
| 73 | 0.083 | >10 | 0.554 |
| 74 | 0.011 | >10 | 0.089 |
| 75 | 0.023 | 0.248 | 0.179 |
| 76 | 0.044 | 0.924 | 0.195 |
| 77 | 0.035 | 0.353 | 0.167 |
| 78 | 0.022 | >10 | 0.479 |
| 79 | 0.009 | >10 | 0.072 |
| 80 | 0.033 | >10 | 0.305 |
| 81 | 0.042 | >10 | 0.509 |
| 82 | 0.025 | >10 | 0.226 |
| 83 | 0.045 | >10 | 0.700 |
| 84 | 0.097 | >10 | 1.910 |
| 85 | 0.019 | >10 | 0.133 |
| 86 | 0.018 | 0.346 | 0.063 |
| 87 | 0.043 | 1.874 | 0.209 |
| 88 | 0.007 | >10 | 0.045 |
| 89 | 0.042 | 0.612 | 0.146 |
| 90 | 0.009 | 0.743 | 0.129 |
| 91 | 0.057 | >10 | 0.378 |
| 92 | 0.033 | 0.714 | 0.916 |
| 93 | 0.104 | 3.537 | 0.929 |
| 94 | 0.181 | 4.138 | 1.227 |
| 95 | 0.077 | >10 | 0.272 |
| 96 | 0.035 | >10 | 0.412 |
| 97 | 0.107 | >10 | 0.441 |
| 98 | 0.079 | >10 | 0.297 |
| 99 | 0.023 | 0.186 | 0.204 |
| 100 | 0.029 | 1.149 | 0.192 |
| 101 | 0.040 | 2.701 | 0.293 |
| 102 | 0.462 | 0.035 | 0.088 |
| 103 | 0.002 | 0.245 | 0.028 |
| 104 | 0.003 | >10 | 0.130 |
| 105 | 0.009 | 0.270 | 0.159 |
| 106 | 0.012 | 0.084 | 0.140 |
| 107 | 0.359 | >50 | 1.544 |
| 108 | 2.725 | >50 | 1.215 |
| 109 | 1.914 | >50 | 0.821 |
| 110 | 0.264 | >10 | 2.415 |
| 111 | 0.252 | >10 | 1.172 |
| 112 | 0.098 | >10 | 0.450 |
| 113 | 0.038 | >10 | >10 |
| 114 | 0.327 | >10 | 0.660 |
| 115 | 0.868 | >10 | 1.765 |
| 116 | 0.059 | >10 | 0.589 |
| 117 | 0.018 | >10 | >10 |
| 118 | 0.113 | >10 | 0.172 |
| 119 | 0.018 | >10 | 0.653 |
| 120 | 0.097 | >10 | 0.148 |
| 121 | 0.045 | >10 | 0.190 |
| 122 | 0.051 | >10 | 0.725 |
| 123 | 0.102 | >10 | >10 |
| 124 | 0.282 | >10 | >10 |
| 125 | 0.504 | >10 | >10 |
| 126 | 0.145 | >10 | 0.240 |
| 127 | 0.011 | >10 | 0.249 |
| 128 | 0.007 | >10 | 0.021 |
| 129 | 0.100 | 1.344 | 0.083 |
| 130 | 0.020 | >10 | 0.014 |
| 131 | 0.012 | 0.268 | 0.351 |
| 132 | 0.012 | 0.129 | 0.147 |
| 133 | 0.031 | 0.251 | 0.278 |
| 134 | 0.217 | >10 | 1.247 |
| 135 | 0.120 | >10 | 0.435 |
| 136 | 0.054 | 0.556 | 0.124 |
| 137 | 0.040 | 0.550 | 0.181 |
| 138 | 0.048 | 1.397 | 0.172 |
| 139 | 0.005 | >10 | 0.185 |
| 140 | 0.006 | 0.476 | 0.034 |
| 141 | 0.002 | >10 | 0.011 |
| 142 | 0.002 | >10 | 0.006 |
| 143 | 0.002 | >10 | 0.006 |
| 144 | 0.007 | 2.201 | 0.026 |
| 145 | 0.008 | 1.719 | 0.008 |
| 146 | 0.006 | 3.249 | 0.007 |
| 147 | 0.004 | >10 | 0.007 |
| 148 | 0.004 | >10 | 0.005 |
| 149 | 0.005 | >10 | 0.053 |
| 150 | 0.001 | >10 | 0.011 |
| 151 | 0.064 | 5.390 | 0.143 |
| 152 | 0.010 | >10 | 0.037 |
| 153 | 0.021 | >10 | 0.110 |
| 154 | 0.033 | 3.030 | 0.079 |
| 155 | 0.009 | >10 | 0.054 |
| 156 | 0.065 | >10 | 0.697 |
| 157 | 0.258 | >10 | 0.227 |
| 158 | 0.007 | 3.284 | 0.016 |
| 159 | 0.011 | >10 | 0.011 |
| 160 | 0.505 | >10 | 3.172 |
| 161 | 0.036 | >10 | 0.073 |
| 162 | 0.009 | >10 | 0.030 |
| 163 | 0.007 | >10 | 0.030 |
| 164 | 0.963 | >10 | >10 |
| 165 | 0.178 | >10 | 2.589 |
| 166 | 0.177 | >10 | 0.902 |
| 167 | 0.457 | >10 | 1.162 |
| 168 | 0.610 | >10 | >10 |
| 169 | 0.017 | >10 | 0.105 |
| 170 | 0.560 | >10 | 0.596 |
| 171 | 0.611 | >10 | >10 |
| 172 | 0.006 | >10 | 0.058 |
| 173 | 0.060 | >10 | 0.353 |
| 174 | 0.455 | >10 | >10 |
| 175 | 0.063 | >10 | >10 |
| 176 | 0.044 | >10 | 0.134 |
| 178 | 0.006 | >10 | 0.050 |
| 179 | 0.063 | 2.475 | 0.088 |
| 180 | 0.124 | >10 | 1.569 |
| 181 | 0.754 | >10 | 0.562 |
| 182 | 0.344 | 0.050 | 0.092 |
| 183 | 0.026 | >10 | 0.446 |
| 184 | 0.070 | >10 | 0.394 |
| 185 | 0.022 | >10 | 0.199 |
| 186 | 0.851 | >10 | >10 |
| 187 | 0.013 | >10 | 0.018 |
| 188 | 2.082 | >10 | >10 |
| 189 | 0.409 | >10 | >10 |
| 190 | 0.002 | 5.320 | 0.891 |

TABLE 1-continued

| Example | PI3Kα AlphaScreen® Ki μM | mTOR IC$_{50}$ μM | U87Cell IC$_{50}$ μM |
|---|---|---|---|
| 191 | 0.004 | >10 | 2.133 |
| 192 | 0.691 | >10 | 0.941 |
| 193 | 0.080 | >10 | 0.100 |
| 194 | 0.153 | >10 | >10 |
| 195 | 0.016 | >10 | >10 |
| 196 | 0.052 | 1.115 | 0.322 |
| 197 | 0.033 | >10 | 0.211 |
| 198 | 0.276 | >10 | 0.219 |
| 199 | 0.068 | >10 | 0.227 |
| 200 | 0.180 | >10 | >10 |
| 201 | 0.094 | >10 | 0.066 |
| 202 | 0.147 | >10 | 0.124 |
| 203 | 0.016 | >10 | 0.562 |
| 204 | 0.040 | >10 | 0.434 |
| 205 | 0.047 | 0.839 | 0.384 |
| 206 | 0.068 | 0.594 | 0.387 |
| 209 | 0.008 | 1.138 | 0.062 |
| 211 | 0.017 | >10 | 0.023 |
| 215 | 0.199 | >10 | 0.350 |
| 217 | 0.278 | >10 | 0.389 |
| 219 | 0.093 | >10 | 0.295 |
| 220 | 0.160 | >10 | 0.622 |
| 221 | 0.266 | >10 | 0.219 |
| 222 | 0.153 | >10 | 0.137 |
| 223 | 0.006 | >10 | 0.028 |
| 224 | 0.022 | >10 | 0.046 |
| 225 | 0.135 | >10 | 0.275 |
| 226 | 0.354 | >10 | 0.573 |
| 227 | 0.283 | >10 | 0.151 |
| 228 | 0.016 | 3.578 | 0.038 |
| 229 | 0.059 | >10 | 0.276 |
| 230 | 0.068 | >10 | 2.474 |
| 231 | 0.446 | >10 | 0.404 |
| 232 | 0.039 | 3.739 | 0.078 |
| 233 | 0.041 | 4.801 | 0.058 |
| 235 | 0.023 | 0.726 | >10 |
| 236 | 0.004 | 4.767 | >10 |
| 237 | 0.018 | >10 | 0.046 |
| 238 | 0.045 | >10 | 0.245 |
| 239 | 0.396 | >10 | 3.453 |
| 240 | 0.008 | 0.849 | 0.043 |
| 241 | 0.043 | >10 | 0.087 |
| 242 | 0.015 | >10 | 0.023 |
| 243 | 0.163 | 1.749 | 1.524 |
| 244 | 1.459 | 0.389 | 1.486 |
| 245 | 0.008 | >10 | 0.019 |
| 246 | 0.019 | >10 | 0.042 |
| 247 | 0.008 | >10 | 0.034 |
| 248 | 0.442 | >10 | 2.295 |
| 249 | 0.021 | 2.614 | 0.088 |
| 250 | 0.011 | >10 | 0.046 |
| 251 | 0.008 | >10 | 0.029 |
| 252 | 0.060 | >10 | 0.151 |
| 253 | 0.012 | >10 | 0.280 |
| 254 | 0.067 | >10 | 0.583 |
| 255 | 0.004 | >10 | 0.037 |
| 256 | 0.005 | >10 | 0.047 |
| 257 | 0.426 | >10 | >10 |
| 258 | 0.014 | >10 | 0.192 |
| 259 | 0.081 | >10 | 0.190 |
| 260 | 0.016 | 0.501 | 1.033 |
| 261 | 0.069 | 2.213 | 2.722 |
| 262 | 0.047 | >10 | 0.180 |
| 263 | 0.643 | >10 | >10 |
| 264 | 0.005 | 0.389 | 0.150 |
| 265 | 0.324 | 0.471 | 0.349 |
| 266 | 0.155 | 0.463 | 1.105 |
| 267 | 0.369 | 0.623 | 0.486 |
| 268 | 0.103 | 0.161 | 0.739 |
| 269 | 0.033 | 0.581 | 0.089 |
| 270 | 0.002 | >10 | 0.007 |
| 271 | 0.003 | >10 | 0.003 |
| 272 | 0.001 | >10 | 0.001 |
| 273 | 0.004 | >10 | 0.013 |
| 275 | 0.032 | >10 | 0.018 |
| 276 | 0.017 | >10 | 0.091 |
| 277 | 0.056 | 0.517 | 0.170 |
| 278 | 0.045 | >10 | 0.024 |
| 279 | 0.011 | 1.778 | 0.034 |
| 280 | 0.002 | >10 | 0.014 |
| 281 | 0.006 | >10 | 0.016 |
| 282 | 0.007 | >10 | 0.026 |
| 283 | 0.003 | >10 | 0.004 |
| 284 | 0.031 | >10 | 0.063 |
| 285 | 0.103 | >10 | >10 |
| 286 | 0.011 | 1.950 | 0.111 |
| 287 | 0.020 | >10 | 0.204 |
| 288 | 0.045 | 0.239 | 0.033 |
| 289 | 0.060 | 0.326 | 0.111 |
| 290 | 0.024 | 0.202 | 0.045 |
| 291 | 0.037 | >10 | 0.007 |
| 292 | 0.044 | 4.015 | 0.020 |
| 293 | 0.004 | 0.252 | 0.024 |
| 294 | 0.012 | >10 | 0.090 |
| 295 | 0.003 | >10 | 0.006 |
| 296 | 0.018 | >10 | 0.051 |
| 297 | 0.001 | >10 | 0.009 |
| 298 | 0.004 | 0.242 | 0.023 |
| 299 | 0.061 | >10 | 0.045 |
| 300 | 0.074 | >10 | 0.017 |
| 301 | 0.110 | 4.875 | 0.070 |
| 302 | 0.024 | >10 | 0.203 |
| 303 | 0.807 | >10 | >10 |
| 304 | 0.029 | 0.444 | 0.146 |
| 305 | 0.002 | >10 | 0.001 |
| 306 | 0.001 | >10 | 0.003 |
| 307 | 0.260 | 3.882 | >10 |
| 308 | 0.019 | 1.892 | 0.060 |
| 309 | 0.044 | 2.674 | 0.046 |
| 310 | 0.036 | 0.127 | 0.065 |
| 311 | 0.008 | >10 | 0.037 |
| 312 | 0.002 | >10 | 0.022 |
| 312 | 0.009 | >10 | 0.031 |
| 312 First eluting | 0.007 | >10 | 0.025 |
| 312 Second eluting | | | |
| 313 | 0.007 | >10 | >10 |
| 314 | 0.017 | 2.231 | 0.034 |
| 315 | 0.027 | >10 | 0.031 |
| 316 | 0.002 | >10 | 0.001 |
| 317 | 0.018 | >10 | 0.012 |
| 318 | 0.032 | >10 | 0.044 |
| 319 | 0.021 | 1.579 | 0.052 |
| 320 | 0.124 | 0.263 | 0.061 |
| 321 | 0.034 | 3.093 | 0.080 |
| 322 | 0.086 | 0.599 | 0.051 |
| 323 | 0.034 | 0.379 | 0.046 |
| 324 | 0.059 | 1.085 | 0.106 |
| 325 | 0.006 | >10 | 0.026 |
| 326 | 0.068 | >10 | 0.057 |
| 327 | 0.069 | 0.917 | 0.146 |
| 328 | 0.002 | 0.026 | 0.001 |
| 329 | 0.010 | >10 | 0.095 |
| 330 | 0.007 | 0.050 | 0.004 |
| 331 | 0.014 | 0.064 | 0.006 |
| 332 | 0.004 | 0.154 | 0.005 |
| 333 | 0.007 | 0.523 | 0.004 |
| 334 | 0.011 | 0.585 | 0.008 |
| 335 | 0.005 | 0.051 | 0.008 |
| 336 | 0.055 | 1.416 | 0.036 |
| 337 | 0.098 | >10 | 0.021 |
| 338 | 0.005 | 0.017 | 0.046 |
| 339 | 0.003 | 0.046 | 0.045 |

TABLE 1-continued

| Example | PI3Kα AlphaScreen ® Ki μM | mTOR IC$_{50}$ μM | U87Cell IC$_{50}$ μM |
|---|---|---|---|
| 340 | 0.004 | 0.081 | 0.014 |
| 341 | 0.019 | >10 | 0.017 |
| 342 | 0.025 | 0.474 | 0.008 |
| 343 | 0.005 | >10 | 0.015 |
| 344 | 0.005 | >10 | 0.014 |
| 345 | 0.013 | >10 | 0.035 |
| 346 | 0.377 | >10 | >10 |
| 347 | 0.075 | >10 | 0.108 |
| 348 | 0.207 | >10 | 0.146 |
| 349 | 0.059 | >10 | 0.013 |
| 350 | 0.019 | 5.490 | 0.007 |
| 351 | 0.009 | >10 | 0.070 |
| 352 | 0.023 | 2.540 | 0.097 |
| 353 | 0.015 | 2.125 | 0.071 |
| 354 | 0.012 | 5.999 | 0.037 |
| 355 | 0.191 | >10 | 1.156 |
| 356 | 0.058 | 7.120 | 0.766 |
| 357 | 0.014 | >10 | 0.083 |
| 358 | 0.024 | 1.745 | 0.121 |
| 359 | 0.045 | 2.990 | 0.090 |
| 360 | 0.011 | >10 | 0.012 |
| 361 | 0.024 | >10 | 0.031 |
| 362 | 0.002 | 1.209 | 0.010 |
| 363 | 0.015 | >10 | 0.031 |
| 364 | 0.005 | >10 | 0.007 |
| 365 | 0.006 | 0.345 | 0.048 |
| 366 | 0.014 | 0.416 | 0.040 |
| 367 | 0.044 | 0.420 | 0.246 |
| 368 | 0.270 | 0.262 | 0.117 |
| 369 | 0.008 | 0.472 | 0.009 |
| 370 | 0.010 | 0.700 | 0.003 |
| 371 | 0.007 | 0.322 | 0.019 |
| 372 | 0.005 | 0.339 | 0.004 |
| 373 | 0.006 | 0.315 | 0.001 |
| 374 | 0.015 | 0.388 | 0.007 |
| 375 | 0.152 | 3.298 | 0.175 |
| 376 | 0.071 | 1.942 | 0.267 |
| 377 | 0.279 | >10 | 0.364 |
| 378 | 0.085 | >10 | 0.095 |
| 379 | 0.012 | 3.847 | 0.046 |
| 380 | 0.059 | 0.264 | 0.016 |
| 381 | 0.018 | 5.394 | 0.040 |
| 382 | 0.015 | 3.190 | 0.023 |
| 383 | 0.007 | >10 | 0.008 |
| 384 | 0.002 | 0.163 | 0.024 |

TABLE 2

Mutant B-raf HTRFAssay
Percent of Control (POC) at 10 μM compound concentration

| Example | POC Mean n = 2 | IC$_{50}$ |
|---|---|---|
| 16 | 42 | >1 |
| 17 | 38 | >1 |
| 18 | 3 | 0.15 |
| 19 | 7 | 0.142 |
| 20 | 72 | |
| 22 | 118 | |
| 23 | 100 | |
| 24 | 94 | |
| 25 | 95 | |
| 26 | 84 | |
| 27 | 110 | |
| 30 | 92 | |
| 31 | 97 | |
| 32 | 107 | |
| 33 | 94 | |
| 35 | 98 | |
| 41 | 96 | |
| 44 | 94 | |
| 46 | 68 | |
| 47 | 91 | |
| 48 | 100 | |
| 50 | 87 | |
| 55 | 103 | |
| 56 | 58 | >1 |
| 57 | 87 | |
| 58 | 97 | |
| 61 | 66 | |
| 64 | 107 | |
| 65 | 85 | |
| 66 | 103 | |
| 71 | 75 | |
| 72 | 77 | |
| 73 | 108 | |
| 74 | 111 | |
| 75 | 94 | |
| 76 | 108 | |
| 84 | 97 | |
| 85 | 90 | |
| 89 | 102 | |
| 90 | 99 | |
| 97 | 96 | |
| 107 | 62 | >1 |
| 109 | 35 | >1 |

TABLE 3

Kinase Panel Screen
POC (Percent of control) at 1 μM compound concentration

| Example | MAPKAPK2 | AURORAA | PKC zeta | RSK1 | PRAK | ERK1 | PKD2 |
|---|---|---|---|---|---|---|---|
| 18 | 93 | 84 | 102 | 96 | 95 | 104 | 97 |
| 19 | 90 | 24 | 98 | 87 | 84 | 93 | 97 |
| 20 | 100 | 96 | 99 | 97 | 99 | 96 | 100 |
| 22 | 98 | 102 | 98 | 100 | 106 | 99 | 99 |
| 23 | 99 | 112 | 102 | 103 | 97 | 104 | 104 |
| 27 | 101 | 78 | 99 | 89 | 98 | 100 | 102 |
| 30 | 103 | 100 | 110 | 103 | 112 | 93 | 98 |
| 35 | 100 | 100 | 98 | 93 | 96 | 99 | 97 |
| 46 | 98 | 31 | 198 | 100 | 111 | 92 | 106 |
| 47 | 101 | 85 | 102 | 105 | 103 | 103 | 113 |
| 57 | 99 | 99 | 100 | 97 | 100 | 100 | 97 |
| 58 | 96 | 94 | 142 | 94 | 84 | 101 | 92 |
| 74 | 100 | 102 | 94 | 100 | 97 | 99 | 99 |
| 89 | 100 | 108 | 109 | 99 | 99 | 100 | 100 |
| 103 | 100 | 100 | 98 | 100 | 103 | 101 | 87 |

| Example | CK1 delta | CHK1 | ABL | FYN | LYN | CHK2 | cMET |
|---|---|---|---|---|---|---|---|
| 18 | 35 | 97 | 77 | 86 | 81 | 94 | 104 |
| 19 | 72 | 83 | 19 | 33 | 50 | 18 | 89 |

TABLE 3-continued

Kinase Panel Screen
POC (Percent of control) at 1 μM compound concentration

| | | | | | | | |
|---|---|---|---|---|---|---|---|
| 20 | 93 | 104 | 99 | 101 | 92 | 103 | 106 |
| 22 | 91 | 103 | 103 | 103 | 108 | 102 | 106 |
| 23 | 70 | 105 | 97 | 96 | 101 | 101 | 104 |
| 27 | 43 | 103 | 104 | 98 | 91 | 97 | 95 |
| 30 | 95 | 96 | 98 | 97 | 100 | 106 | 101 |
| 35 | 102 | 101 | 93 | 95 | 107 | 100 | 102 |
| 46 | 91 | 98 | 97 | 101 | 96 | 101 | 104 |
| 47 | 69 | 92 | 81 | 87 | 55 | 99 | 102 |
| 57 | 55 | 106 | 94 | 103 | 95 | 98 | 100 |
| 58 | 104 | 101 | 99 | 103 | 100 | 99 | 103 |
| 74 | 97 | 101 | 103 | 104 | 97 | 98 | 102 |
| 89 | 98 | 99 | 107 | 99 | 96 | 97 | 102 |
| 103 | 120 | 107 | 95 | 97 | 97 | 94 | 94 |

| Example | LCK | SRC | GSK3 beta | ERK2 | PKA alpha | AKT2 | INSR |
|---|---|---|---|---|---|---|---|
| 18 | 72 | 93 | 92 | 96 | 97 | 93 | 90 |
| 19 | 70 | 23 | 79 | 94 | 70 | 110 | 88 |
| 20 | 101 | 95 | 95 | 101 | 97 | 92 | 97 |
| 22 | 97 | 101 | 94 | 103 | 97 | 97 | 96 |
| 23 | 97 | 99 | 96 | 103 | 99 | 112 | 98 |
| 27 | 101 | 89 | 80 | 97 | 84 | 95 | 71 |
| 30 | 102 | 103 | 104 | 102 | 100 | 105 | 102 |
| 35 | 94 | 97 | 102 | 104 | 96 | 101 | 99 |
| 46 | 96 | 96 | 95 | 116 | 102 | 110 | 98 |
| 47 | 61 | 79 | 97 | 104 | 16 | 74 | 99 |
| 57 | 96 | 93 | 101 | 97 | 100 | 98 | 94 |
| 58 | 98 | 102 | 101 | 103 | 96 | 96 | 104 |
| 74 | 98 | 99 | 100 | 101 | 102 | 96 | 96 |
| 89 | 101 | 101 | 100 | 106 | 99 | 93 | 97 |
| 103 | 92 | 89 | 96 | 94 | 99 | 89 | 95 |

| Example | p38 alpha | AKT1 | MSK1 | PKC beta2 | ROCK2 | CDK2 | MST2 |
|---|---|---|---|---|---|---|---|
| 18 | 86 | 103 | 97 | 91 | 98 | 91 | 96 |
| 19 | 86 | 94 | 106 | 94 | 104 | 90 | 82 |
| 20 | 93 | 105 | 93 | 104 | 101 | 96 | 95 |
| 22 | 101 | 102 | 103 | 96 | 94 | 107 | 98 |
| 23 | 104 | 103 | 112 | 92 | 101 | 106 | 101 |
| 27 | 104 | 98 | 94 | 166 | 95 | 84 | 84 |
| 30 | 99 | 102 | 90 | 94 | 98 | 101 | 98 |
| 35 | 100 | 98 | 110 | 90 | 101 | 103 | 101 |
| 46 | 96 | 93 | 103 | 96 | 94 | 97 | 96 |
| 47 | 91 | 50 | 76 | 100 | 93 | 93 | 101 |
| 57 | 100 | 102 | 101 | 97 | 95 | 95 | 95 |
| 58 | 98 | 106 | 98 | 161 | 100 | 99 | 100 |
| 74 | 101 | 109 | 98 | 94 | 101 | 96 | 98 |
| 89 | 100 | 102 | 91 | 94 | 101 | 96 | 98 |
| 103 | 92 | 94 | 101 | 100 | 106 | 100 | 98 |

| Example | PKGa2 | PAK2 | IGF1R | FGFR1 | MARK1 | CAMK2 | PIM2 |
|---|---|---|---|---|---|---|---|
| 18 | 90 | 96 | 64 | 62 | 112 | 90 | 101 |
| 19 | 93 | 105 | 94 | 51 | 95 | 84 | 105 |
| 20 | 98 | 103 | 93 | 94 | 108 | 111 | 105 |
| 22 | 93 | 99 | 97 | 96 | 109 | 118 | 97 |
| 23 | 87 | 96 | 101 | 99 | 97 | 108 | 99 |
| 27 | 90 | 99 | 41 | 94 | 102 | 116 | 106 |
| 30 | 98 | 105 | 80 | 99 | 98 | 103 | 99 |
| 35 | 99 | 104 | 96 | 90 | 92 | 101 | 98 |
| 46 | 95 | 95 | 78 | 98 | 102 | 105 | 99 |
| 47 | 80 | 99 | 82 | 94 | 107 | 126 | 104 |
| 57 | 98 | 95 | 77 | 95 | 99 | 109 | 94 |
| 58 | 97 | 102 | 92 | 94 | 146 | 103 | 94 |
| 74 | 92 | 94 | 93 | 99 | 111 | 106 | 92 |
| 89 | 87 | 97 | 98 | 97 | 92 | 108 | 93 |
| 103 | 98 | 98 | 91 | 100 | 131 | 95 | 96 |

| Example | BTK | TAK1 | DYRK1a | CAMK4 | AMPK | FLT3 | HGK |
|---|---|---|---|---|---|---|---|
| 18 | 99 | 97 | 59 | 71 | 83 | 106 | 92 |
| 19 | 75 | 90 | 66 | 77 | 57 | 25 | 50 |
| 20 | 98 | 99 | 102 | 100 | 93 | 120 | 94 |
| 22 | 99 | 99 | 96 | 95 | 92 | 105 | 97 |
| 23 | 100 | 102 | 93 | 98 | 98 | 106 | 99 |
| 27 | 99 | 102 | 92 | 56 | 83 | 73 | 91 |
| 30 | 97 | 99 | 93 | 94 | 91 | 99 | 96 |

TABLE 3-continued

Kinase Panel Screen
POC (Percent of control) at 1 μM compound concentration

| 35 | 97 | 98 | 98 | 98 | 98 | 103 | 97 |
| 46 | 98 | 98 | 96 | 96 | 91 | 99 | 104 |
| 47 | 93 | 106 | 82 | 91 | 87 | 89 | 91 |
| 57 | 98 | 97 | 91 | 93 | 92 | 92 | 93 |
| 58 | 102 | 107 | 93 | 95 | 99 | 112 | 104 |
| 74 | 99 | 98 | 100 | 95 | 100 | 122 | 94 |
| 89 | 102 | 93 | 88 | 109 | 91 | 95 | 95 |
| 103 | 97 | 115 | 83 | 95 | 102 | 85 | 85 |

| Example | KDR | cRAF | p70S6K | SGK1 | SYK |
|---|---|---|---|---|---|
| 18 | 89 | 1 | 98 | 97 | 63 |
| 19 | 29 | 56 | 91 | 88 | 15 |
| 20 | 93 | 59 | 104 | 95 | 107 |
| 22 | 106 | 98 | 74 | 99 | 96 |
| 23 | 105 | 108 | 112 | 102 | 110 |
| 27 | 81 | 95 | 91 | 85 | 83 |
| 30 | 102 | 95 | 97 | 93 | 106 |
| 35 | 102 | 94 | 94 | 93 | 102 |
| 46 | 90 | 91 | 90 | 89 | 104 |
| 47 | 86 | 56 | 60 | 89 | 95 |
| 57 | 90 | 100 | 94 | 92 | 100 |
| 58 | 93 | 99 | 98 | 97 | 86 |
| 74 | 97 | 101 | 98 | 108 | 97 |
| 89 | 92 | 99 | 89 | 92 | 80 |
| 103 | 91 | 100 | 109 | 96 | 99 |

Blank = not determined

It is noted that if an assay is run more than once the number above represents an average of the results from each experiment.

What is claimed:

1. A compound of Formula II, or a pharmaceutically acceptable salt thereof,

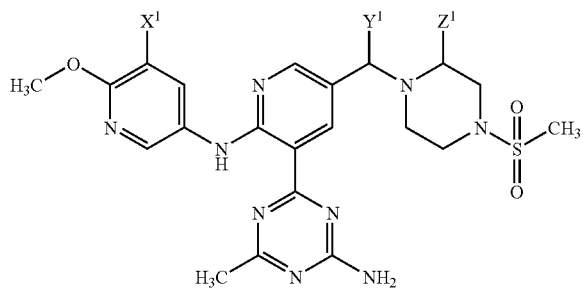

II wherein $X^1$ is fluorine or hydrogen;

$Y^1$ is hydrogen or methyl; and $Z^1$ is hydrogen or methyl.

2. A compound in accordance with claim 1, or a pharmaceutically acceptable salt thereof, wherein $X^1$ is fluorine; $Y^1$ is hydrogen or methyl; and $Z^1$ is hydrogen or methyl.

3. A compound of Formula IIa, or a pharmaceutically acceptable salt thereof,

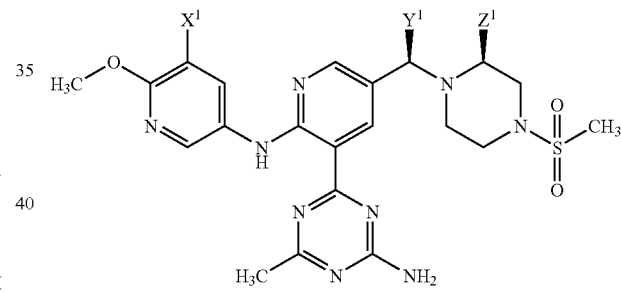

IIa wherein $X^1$ is fluorine or hydrogen;

$Y^1$ is hydrogen or methyl; and $Z^1$ is hydrogen or methyl.

4. A compound in accordance with claim 3, or a pharmaceutically acceptable salt thereof, wherein $X^1$ is fluorine; $Y^1$ is hydrogen or methyl; and $Z^1$ is hydrogen or methyl.

5. The compound 4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine, or a pharmaceutically acceptable salt thereof.

6. The compound (S)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine, or a pharmaceutically acceptable salt thereof.

7. The compound (R)-4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine, or a pharmaceutically acceptable salt thereof.

8. A pharmaceutical composition comprising: a compound in accordance with any one of claims 1 to 4 or 5 to 7, or a pharmaceutically acceptable salt thereof, and a pharmaceutically acceptable excipient.

* * * * *